US011957687B2

(12) United States Patent
Vacca

(10) Patent No.: US 11,957,687 B2
(45) Date of Patent: Apr. 16, 2024

(54) MODULATORS OF HSD17B13 AND METHODS OF USE THEREOF

(71) Applicant: REGENERON PHARMACEUTICALS, INC., Tarrytown, NY (US)

(72) Inventor: Joseph Vacca, Telford, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 39 days.

(21) Appl. No.: 17/622,454

(22) PCT Filed: Jul. 1, 2020

(86) PCT No.: PCT/US2020/040542
§ 371 (c)(1),
(2) Date: Dec. 23, 2021

(87) PCT Pub. No.: WO2021/003295
PCT Pub. Date: Jan. 7, 2021

(65) Prior Publication Data
US 2023/0094341 A1 Mar. 30, 2023

Related U.S. Application Data

(60) Provisional application No. 62/869,752, filed on Jul. 2, 2019.

(51) Int. Cl.
| | |
|---|---|
| A61K 31/5377 | (2006.01) |
| A61K 31/4412 | (2006.01) |
| A61K 31/4427 | (2006.01) |
| A61K 31/443 | (2006.01) |
| A61K 31/4433 | (2006.01) |
| A61K 31/4436 | (2006.01) |
| A61K 31/4439 | (2006.01) |
| A61K 31/444 | (2006.01) |
| A61K 31/4545 | (2006.01) |
| A61K 31/4709 | (2006.01) |
| A61K 31/4725 | (2006.01) |
| A61K 31/496 | (2006.01) |
| A61K 31/497 | (2006.01) |
| A61K 31/506 | (2006.01) |
| A61K 31/513 | (2006.01) |
| A61P 1/16 | (2006.01) |
| C07D 213/82 | (2006.01) |
| C07D 239/36 | (2006.01) |
| C07D 239/56 | (2006.01) |
| C07D 295/135 | (2006.01) |
| C07D 401/12 | (2006.01) |
| C07D 405/12 | (2006.01) |
| C07D 405/14 | (2006.01) |
| C07D 409/12 | (2006.01) |
| C07D 409/14 | (2006.01) |

(Continued)

(52) U.S. Cl.
CPC ...... *A61K 31/5377* (2013.01); *A61K 31/4412* (2013.01); *A61K 31/4427* (2013.01); *A61K 31/443* (2013.01); *A61K 31/4433* (2013.01); *A61K 31/4436* (2013.01); *A61K 31/4439* (2013.01); *A61K 31/444* (2013.01); *A61K 31/4545* (2013.01); *A61K 31/4709* (2013.01); *A61K 31/4725* (2013.01); *A61K 31/496* (2013.01); *A61K 31/497* (2013.01); *A61K 31/506* (2013.01); *A61K 31/513* (2013.01); *A61P 1/16* (2018.01); *C07D 213/82* (2013.01); *C07D 239/36* (2013.01); *C07D 239/56* (2013.01); *C07D 295/135* (2013.01); *C07D 401/12* (2013.01); *C07D 405/12* (2013.01); *C07D 405/14* (2013.01); *C07D 409/12* (2013.01); *C07D 409/14* (2013.01); *C07D 498/04* (2013.01); *C07D 513/04* (2013.01)

(58) Field of Classification Search
None
See application file for complete search history.

(56) References Cited

U.S. PATENT DOCUMENTS

| | | |
|---|---|---|
| 2014/0073634 A1 | 3/2014 | Jones et al. |
| 2014/0128365 A1 | 5/2014 | Robl et al. |

(Continued)

FOREIGN PATENT DOCUMENTS

| | | |
|---|---|---|
| EP | 1352650 A1 | 10/2003 |
| EP | 1987717 A1 | 11/2008 |

(Continued)

OTHER PUBLICATIONS

Andrea Chicca et al., "Polypharmacological profile of 1, 2-dihydro-2-oxo-pyridine-3carboxamides in the endocannabinoid system", European Journal of Medicinal Chemistry, vol. 154, Jun. 2018 (Jun. 2018), pp. 155-171, XP055729409, NL.

Hang Shi et al., "Ligand Promoted meta-C-H Chlorination of Anilines and Phenols", Journal of the American Chemical Society, vol. 138, No. 45, Nov. 8, 2016, pp. 14876-14879, XP055729669, US.

Database Registry [Online] Chemical Abstracts Service, Columbus, Ohio, US; Aug. 18, 2011, XP002800420, retrieved from STN Database accession No. 1319339-98-4 abstract.

(Continued)

*Primary Examiner* — Zinna Northington Davis
(74) *Attorney, Agent, or Firm* — Troutman Pepper Hamilton Sanders LLP

(57) ABSTRACT

The disclosure relates to compounds and pharmaceutical compositions capable of modulating the hydroxysteroid 17-beta dehydrogenase (HSD17B) family member proteins including inhibiting the HSD17B member proteins, e.g. HSD17B13. The disclosure further relates to methods of treating liver diseases, disorders, or conditions with the compounds and pharmaceutical compositions disclosed herein, in which the HSD17B family member protein plays a role.

14 Claims, No Drawings

(51) Int. Cl.
*C07D 498/04* (2006.01)
*C07D 513/04* (2006.01)

(56) References Cited

U.S. PATENT DOCUMENTS

| | | | |
|---|---|---|---|
| 2014/0221411 A1 | 8/2014 | Kim et al. | |
| 2015/0238491 A1 | 8/2015 | Dilly et al. | |
| 2016/0150782 A1* | 6/2016 | Arve .................... | C07D 213/82 546/284.7 |

FOREIGN PATENT DOCUMENTS

| | | |
|---|---|---|
| EP | 2832726 A1 | 2/2015 |
| WO | 03/022835 A1 | 3/2003 |
| WO | 2005/042492 A1 | 5/2005 |
| WO | 2005/042493 A1 | 5/2005 |
| WO | 2007/096647 A2 | 8/2007 |
| WO | 2015/004040 A1 | 1/2015 |
| WO | 2015/169971 A1 | 11/2015 |
| WO | 2016/096942 A1 | 6/2016 |
| WO | 2020/051207 A2 | 3/2020 |

OTHER PUBLICATIONS

Database Registry [Online] Chemical Abstracts Service, Columbus, Ohio, US; Aug. 24, 2011, XP002800419, retrieved from STN Database accession No. 1322579-16-7 abstract.
Database Registry [Online] Chemical Abstracts Service, Columbus, Ohio, US; Oct. 27, 2008, XP002800421, retrieved from STN Database accession No. 1066903-86-3 abstract.
Miscellaneous Communication dated Mar. 3, 2022 for U.S. Appl. No. 16/978,947, filed Sep. 8, 2020 // 2 pages.
Third Party Submission Under 35 USC Section 122(e) and 37 CFR Section 1.290 dated Feb. 25, 2022 for U.S. Appl. No. 16/978,947, filed Sep. 8, 2020 // 30 pages.

* cited by examiner

MODULATORS OF HSD17B13 AND METHODS OF USE THEREOF

CROSS-REFERENCE TO RELATED APPLICATIONS

This application is a U.S. National Phase of International Patent Application No. PCT/US2020/040542, filed on Jul. 1, 2020, which claims priority to U.S. Provisional Application No. 62/869,752 filed on Jul. 2, 2019, all of which the entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Dec. 6, 2023, is named 250298_00311_SL.txt and is 36,702 bytes in size.

FIELD

The present disclosure relates to compounds and pharmaceutical compositions capable of modulating the hydroxysteroid 17-beta dehydrogenase (HSD17B) family member proteins (e.g., HSD17B13), including inhibiting the HSD17B member proteins (e.g., HSD17B13), and methods of treating liver diseases, disorders, or conditions in which the HSD17B family member protein (e.g., HSD17B13) plays a role.

BACKGROUND

Chronic liver disease and cirrhosis are leading causes of morbidity and mortality in the United States, accounting for 38,170 deaths (1.5% of total deaths) in 2014 (Kochanek et al., Nat'l. Vital Stat. Rep., 2016, 65, 1-122). The most common etiologies of cirrhosis in the U.S. are alcoholic liver disease, chronic hepatitis C, and nonalcoholic fatty liver disease (NAFLD), together accounting for about 80% of patients awaiting liver transplant between 2004 and 2013 (Wong et al., Gastroenterology, 2015, 148, 547-555). The estimated prevalence of NAFLD in the U.S. is between 19 and 46 percent (Browning et al., Hepatology, 2004, 40, 1387-1395; Lazo et al., Am. J. Epidemiol., 2013, 178, 38-45; and Williams et al., Gastroenterology, 2011, 140, 124-131) and is rising over time (Younossi et al., Clin. Gastroenterol. Hepatol., 2011, 9, 524-530), likely in conjunction with increased rates of obesity, its primary risk factor (Cohen et al., Science, 2011, 332, 1519-1523). While significant advances have been made in the treatment of hepatitis C, there are currently no evidence-based treatments for alcoholic or nonalcoholic liver disease and cirrhosis.

Thus, there exists a strong unmet need for developing effective treatments for liver diseases.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY

As discussed herein, there is a strong need to develop effective treatments for liver diseases in general, and alcoholic or nonalcoholic liver disease and cirrhosis in particular. The present disclosure addresses these and other needs by providing new compounds, pharmaceutical compositions, and methods of treatment based on such compounds and pharmaceutical compositions.

Various non-limiting aspects and embodiments are described below.

In one aspect, the present disclosure provides a compound according to formula (I'):

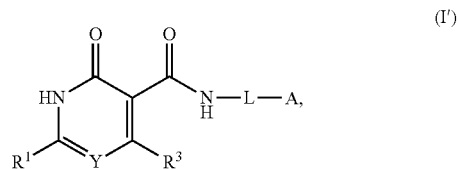

or a pharmaceutically acceptable salt thereof, wherein:
A is A', A", CR$^4$(Ar)$_2$, or Ar;
wherein:
A' is

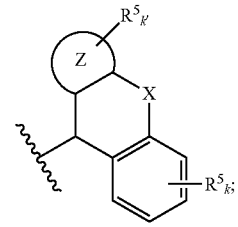

A" is

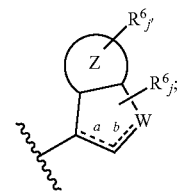

Z is phenyl, Het, or a C$_4$-C$_8$ cycloalkyl; and
Ar is independently at each occurrence a phenyl, naphthyl, or a C$_4$-C$_8$ cycloalkyl, any of which is optionally substituted with one or more R$^8$ or Het;
Het is a 6-membered heterocycle comprising from 1 to 3 heteroatoms independently selected from N and O, wherein Het is optionally substituted with one or more of C$_{1-3}$ alkyl, C$_{1-3}$ alkenyl, halogen, —OH or =O;
L is a bond, —(CH$_2$)$_n$—, —(CHB)$_n$—, —CH$_2$CHB—, or —CHBCH$_2$—;
wherein:
B is benzyl or C$_{1-12}$ alkyl optionally comprising 1-4 O atoms, either of which is optionally substituted by —OH or —OCH$_3$;
n is 1 or 2; and wherein:
when A is phenyl, phenyl is optionally substituted by one or more R$^7$ and not by R$^8$;
when L is a bond, A is CR$^4$(Ar)$_2$, R$^1$ is methyl, Y is CR$^2$ and R$^2$ is H, R$^3$ is H, and CR$^4$(Ar)$_2$ has only one R$^8$ group, then R$^8$ is not —F;

when L is a bond, A is CR⁴(Ar)₂, R¹ is ethyl, Y is CR²
and R² is Me, R³ is H, and CR⁴(Ar)₂ has only one R⁸
group, then R⁸ is not —OMe;

when L is a bond, A is CR⁴(Ar)₂, R¹ is CF₃, Y is CR²
and R² is H, R³ is H, and one Ar has two R⁸ groups,
then the R⁸ groups are not both -Me;

when L is —(CH₂)$_n$—, A is CR⁴(Ar)₂, R⁴ is H, and R¹
is CF₃, then at least one Ar is substituted with at least
one R⁸;

when L is —(CH₂)$_n$—, A is phenyl, and R¹ is CF₃, then
at least one R⁷ is a phenoxy that is optionally
substituted with a halogen; and when L is —(CHB)$_n$—, B is C$_{1-4}$ alkyl, A is phenyl and
R⁴ is H, then R⁷ is present and is not —Cl, —F,
—CN, C$_{1-4}$ alkyl, or C$_{1-4}$ alkoxy;

k and k' are independently from 0 to 4;
j and j' are independently from 0 to 4;
W is =CH—, =C(R⁶)—, —CH₂—, —CH(R⁶)—,
—(C=O)—, —CH₂CH₂—, —CH(R⁶)—CH₂—,
—O—, —O—CH₂—, —O—CH(R⁶)—, —(NH)—,
—N(R⁶)—, —CH₂—NH—, —CH₂—N(R⁶)—, or
—S—;
a and b are independently a single bond or a double bond;
wherein: when W is —CH₂—, or when W is
—O—CH₂—, R¹ is CF₃, Y is CH, and R³ is H, then
A" is substituted with at least one R⁶ which is not
—OH;
X is a bond, —CH₂—, —CH₂—CH₂—, —CH₂—O—,
—CH=CH—, —(C=O)—, —O—, —NR$^{\#}$—, —S—,
—(S=O)—, or —(SO₂)—;
Y is N, —CR², or —COR²;
R¹ is H, —(CH₂)$_{0-3}$—NH₂, —(CH₂)$_{0-3}$—NHR$^{\#}$,
—(CH₂)$_{0-3}$—N(R$^{\#}$)₂, C$_{1-4}$ alkyl, C$_{1-4}$ haloalkyl, phenyl, benzyl, or —(CH₂)$_{0-3}$—X—(CH₂)$_{0-3}$-phenyl,
wherein phenyl is optionally substituted with one or
more R⁵ groups;
R² is H, halogen, —(CH₂)$_{0-3}$—NH₂, —(CH₂)$_{0-3}$—NHR$^{\#}$,
—(CH₂)$_{0-3}$—N(R$^{\#}$)₂, C$_{1-12}$ alkyl, C$_{1-12}$ alkenyl, C$_{6-12}$
aryl, C$_{1-12}$ aralkyl, C$_{1-12}$ arylalkyl, C$_{1-4}$ haloalkyl, C$_{3-7}$
cycloalkyl, or a 5-7-membered heterocycle with 1 to 4
heteroatoms independently selected from O, N and S or
combinations thereof, any of which is optionally substituted by one or more of —OH, C$_{1-4}$ alkyl, C$_{1-4}$
alkoxy, =O, phenyl, or benzyl;
R³ is H, C$_{1-4}$ alkyl, or C$_{1-4}$ haloalkyl;
wherein:
when Y is N, at least one of R¹ and R³ is not H, and
when Y is CR², at least one of R¹, R², and R³ is not
H;
R⁴ is H, C$_{1-4}$ alkyl, or C$_{1-4}$ haloalkyl;
R⁵ is independently at each occurrence halogen, —CN,
=O, —OH, —NH₂, —(CH₂)$_{1-3}$—OR$^{\#}$, —NH—
(C=O)—R*, —NH—(C=O)O—R*, —NH—
(SO₂)—R*, —(CH₂)$_{1-3}$—NR$^{\#}$₂, —NHR$^{\#}$, —N(R$^{\#}$)₂,
C$_{1-4}$ alkoxy, phenoxy, C$_{1-12}$ alkyl, C$_{1-12}$ heteroalkyl
comprising 1 to 3 hetero atoms selected from —O—,
—S—, or —NH—, C$_{1-12}$ alkenyl, C$_{1-12}$ alkynyl, C$_{1-4}$
haloalkyl, C$_{1-4}$ haloalkoxy, C$_{6-12}$ aryl, a 3-7-membered
heterocycle with 1 to 4 heteroatoms selected from O, N
and S or combinations thereof, or wherein two adjacent
R⁵ groups form a 5-7 membered ring that optionally
contains 1 to 3 heteroatoms selected from O, N, and S;
any of which is optionally substituted with R*;
R⁶ is independently at each occurrence halogen, —OH,
=O, —CN, —(CH₂)$_{0-3}$—NH₂, —(CH₂)$_{0-3}$—NHR$^{\#}$,
—(CH₂)$_{0-3}$—N(R$^{\#}$)₂, —(CH₂)$_{0-3}$—NHCOOR$^{\#}$,
—(CH₂)$_{0-3}$—COOR$^{\#}$, C$_{1-4}$ alkoxy, C$_{1-4}$ alkyl, C$_{1-12}$
alkenyl; C$_{1-4}$ haloalkyl, C$_{1-4}$ heteroalkyl with 1 or 2
methylene replaced with —O— or —S—, or C$_{6-12}$ aryl,
any of which is optionally substituted with R*;
R⁷ is independently at each occurrence halogen, —CN,
=O, —OH, —(CH₂)$_{1-3}$—OR$^{\#}$, —NH—(C=O)—R*,
—NH—(SO₂)—R*, —(CH₂)$_{1-3}$—NR$^{\#}$₂, —NHR$^{\#}$,
—N(R$^{\#}$)₂, C$_{1-4}$ alkoxy, phenoxy, C$_{1-12}$ alkyl, C$_{1-12}$
alkenyl, C$_{1-4}$ haloalkyl, or C$_{6-12}$ aryl, any of which is
optionally substituted with R*;
R⁸ is independently at each occurrence halogen, —CN,
=O, —OH, —(CH₂)$_{0-3}$—SH, —(CH₂)$_{0-3}$—SR*,
—(SO₂)—R*, —NH₂, —(CH₂)$_{1-3}$—OR, —NH—
(C=O)—R*, —NH—(SO₂)—R*, —(CH₂)$_{1-3}$—NR$^{\#}$₂,
—NHR$^{\#}$, or —N(R$^{\#}$)₂, C$_{1-4}$ alkoxy, phenoxy, C$_{1-12}$
alkyl, C$_{1-12}$ alkenyl, C$_{1-12}$ alkynyl, C$_{1-4}$ haloalkyl, C$_{1-4}$
haloalkoxy, C$_{6-12}$ aryl, a 4-7-membered heterocycle
with 1 to 4 heteroatoms selected from O, N and S or
combinations thereof, or wherein two adjacent R⁸
groups form a 5-7 membered ring that optionally
contains 1 to 3 heteroatoms selected from O, N, and S;
any of which is optionally substituted with R*;
R* is halogen, —OH, C$_{1-3}$ alkyl, C$_{1-3}$ haloalkyl, phenyl,
or benzyl, any of which is optionally substituted with a
halogen; and
R$^{\#}$ is C$_{1-3}$ alkyl, C$_{1-3}$ haloalkyl, C$_{3-6}$ cycloalkyl, phenyl, or
benzyl, any of which is optionally substituted with a
halogen.

In one aspect, the present disclosure provides a compound having the structure of formula (I):

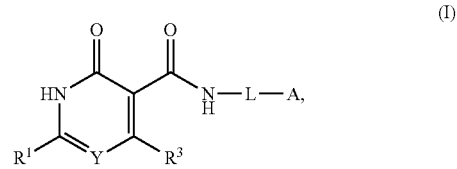

or a pharmaceutically acceptable salt thereof, wherein:
A is A', A", CR⁴(Ar)₂, or phenyl that is optionally
substituted with one or more R⁷; wherein:
A' is

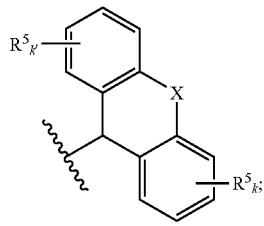

A" is

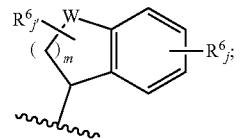

and
Ar is independently at each occurrence a phenyl that is
optionally substituted with one or more R⁸ or Het where Het is a 6-membered heterocycle comprising from 1 to 3 nitrogen atoms, wherein Het is optionally substituted with one or more of halogen, —OH or =O;

L is a bond, —(CH$_2$)$_n$—, —(CHB)$_n$—, —CH$_2$CHB—, or —CHBCH$_2$—;

wherein:

B is C$_{1-12}$ alkyl or benzyl;

n is 1 or 2; and when L is a bond, A is CR$^4$(Ar)$_2$, R$^1$ is methyl, Y is CR$^2$ and R$^2$ is H, R$^3$ is H, and CR$^4$(Ar)$_2$ has only one R$^8$ group, then R$^8$ is not —F;

when L is a bond, A is CR$^4$(Ar)$_2$, R$^1$ is ethyl, Y is CR$^2$ and R$^2$ is Me, R$^3$ is H, and CR$^4$(Ar)$_2$ has only one R$^8$ group, then R$^8$ is not —OMe;

when L is a bond, A is CR$^4$(Ar)$_2$, R$^1$ is CF$_3$, Y is CR$^2$ and R$^2$ is H, R$^3$ is H, and one Ar has two R$^8$ groups, then the R$^8$ groups are not both -Me;

when L is —(CH$_2$)$_n$—, A is CR$^4$(Ar)$_2$, R$^4$ is H, and R$^1$ is CF$_3$, then at least one Ar is substituted with at least one R$^8$;

when L is —(CH$_2$)$_n$—, A is phenyl, and R$^1$ is CF$_3$, then at least one R$^7$ is a phenoxy that is optionally substituted with a halogen; and when L is —(CHB)$_n$—, B is C$_{1-4}$ alkyl, A is phenyl and R$^4$ is H, then at least one R$^7$ is present and is not —Cl, —F, —CN, C$_{1-4}$ alkyl, or C$_{1-4}$ alkoxy;

m is 1 or 2;

k and k' are independently from 0 to 4;

j and j' are independently from 0 to 4;

W is —CH$_2$—, —O—, —(NH)—, or —S—;

wherein:

when W is —CH$_2$— and m is 1, or when W is —O— and m is 2, then A" is substituted with at least one R$^6$;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, —COR$^2$ or —CNHR$^2$;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl;

wherein:

when Y is N, at least one of R$^1$ and R$^3$ is not H, and when Y is CR$^2$, at least one of R$^1$, R$^2$, and R$^3$ is not H;

R$^4$ is H, C$_{1-4}$ alkyl, or C$_{1-4}$ haloalkyl;

R$^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^5$ groups form a 5-7 membered ring that optionally contains 1 to 3 heteroatoms selected from O, N, and S; any of which is optionally substituted with R*;

R$^6$ is independently at each occurrence halogen, C$_{1-4}$ alkoxy, C$_{1-12}$ alkyl, C$_{1-12}$ alkenyl, C$_{1-4}$ haloalkyl, or C$_{6-12}$ aryl, any of which is optionally substituted with R*;

R$^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, —N(R$^\#$)$_2$, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;

R$^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups form a 5-7 membered ring that optionally contains 1 to 3 heteroatoms selected from O, N, and S; any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In one embodiment, the compound is according to formula (II'):

or a pharmaceutically acceptable salt thereof, wherein:

X is O or S;

Z is a 6-membered heterocycle comprising 1 to 2 N heteroatoms, or a C$_4$-C$_8$ cycloalkyl;

R$^5$ is independently at each occurrence C$_{1-3}$ alkyl, C$_{1-3}$ alkenyl, C$_{1-3}$ alkoxy, C$_{1-3}$ haloalkyl, halogen, —CN, or —OH; and k and k' are independently from 0 to 2.

In one embodiment, the compound is according to formula (II):

(II)

or a pharmaceutically acceptable salt thereof, wherein k, k', X, Y, R$^1$, R$^2$, R$^3$, and R$^5$ are as defined above.

In one embodiment, the compound is according to formula (IIa):

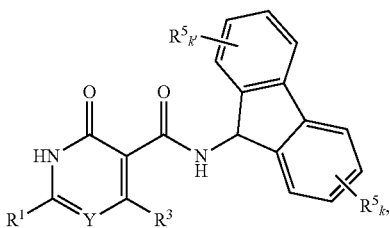

(IIa)

or a pharmaceutically acceptable salt thereof, wherein k, k', Y, $R^1$, $R^2$, $R^3$, and $R^5$ are as defined above.

In one embodiment, the compound is according to formula (IIb):

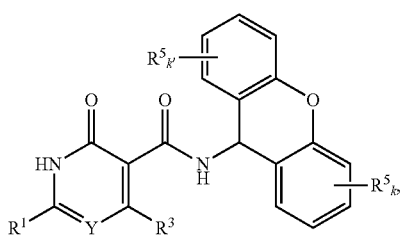

(IIb)

or a pharmaceutically acceptable salt thereof, wherein k, k', Y, $R^1$, $R^2$, $R^3$, and $R^5$ are as defined above.

In one embodiment, the compound is according to formula (IIc):

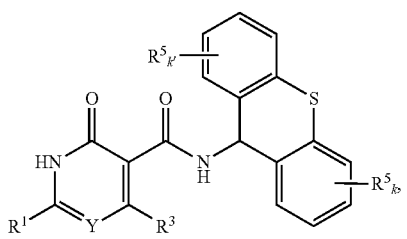

(IIc)

or a pharmaceutically acceptable salt thereof, wherein k, k', Y, $R^1$, $R^2$, $R^3$, and $R^5$ are as defined above.

In one embodiment, the compound is according to formula (IId):

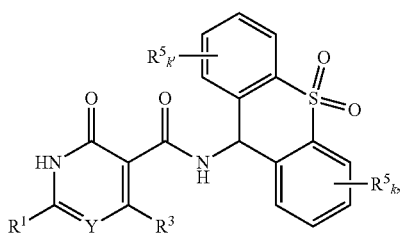

(IId)

or a pharmaceutically acceptable salt thereof, wherein k, k', Y, $R^1$, $R^2$, $R^3$, and $R^5$ are as defined above.

In one embodiment, the compound is according to formula (III'):

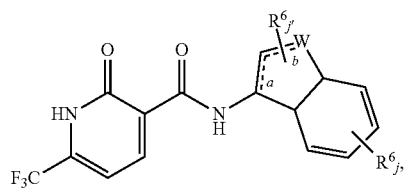

(III')

or a pharmaceutically acceptable salt thereof, wherein:
  W is =CH—, =C($R^6$)—, —CH($R^6$)—, —(NH)—, —N($R^6$)—, —O—, or —S—;
  j and j' are independently from 0 to 2;
  a is a double bond and b is a single bond, or a is a single bond and b is a double bond; and
  $R^6$ is independently at each occurrence —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-12}$ alkyl, $C_{1-12}$ alkenyl; $C_{1-4}$ haloalkyl, $C_{1-4}$ heteroalkyl, or $C_{6-12}$ aryl, any of which is optionally substituted with R*,
  wherein R# and R* are as defined above.

In one embodiment, the compound is according to formula (III):

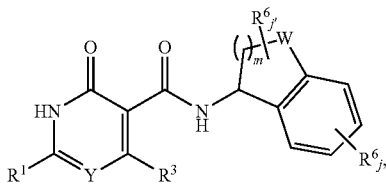

(III)

or a pharmaceutically acceptable salt thereof, wherein j, j', W, Y, m, $R^1$, $R^2$, $R^3$, and $R^6$ are as defined above.

In one embodiment, the compound is according to formula (IV):

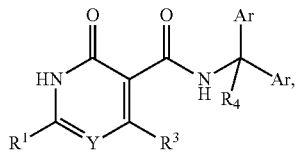

(IV)

or a pharmaceutically acceptable salt thereof, wherein Y, $R^1$, $R^2$, $R^3$, $R^4$, and Ar are as defined above.

In one embodiment, the compound is according to formula (IVa):

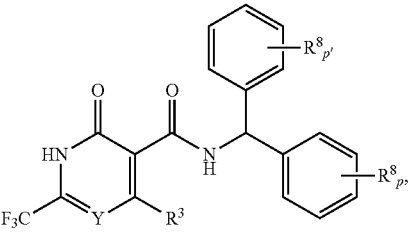

(IVa)

or a pharmaceutically acceptable salt thereof, wherein Y, $R^3$, and $R^8$ are as defined above, and wherein p and p' are independently 0 or 1.

In one embodiment, the compound is according to formula (IVe):

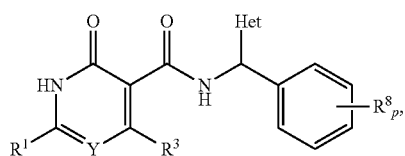

(IVe)

or a pharmaceutically acceptable salt thereof, wherein Het, Y, $R^1$, $R^2$, $R^3$, and $R^8$ are as defined above, and wherein p is from 0 to 5.

In one embodiment, the compound is according to formula (IVf):

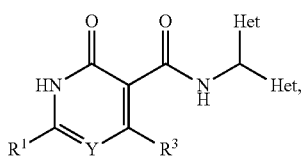

(IVf)

or a pharmaceutically acceptable salt thereof, wherein Het, Y, $R^1$, $R^2$, and $R^3$ are as defined above.

In one embodiment, the compound is according to formula (V')

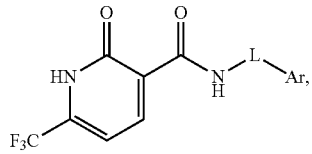

(V')

or a pharmaceutically acceptable salt thereof, wherein L and Ar are as defined above.

In one embodiment, the compound is according to formula (V):

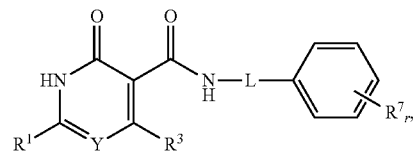

(V)

or a pharmaceutically acceptable salt thereof, wherein r is from 0 to 5; and L, Y, $R^1$, $R^2$, $R^3$, and $R^7$ are as defined above.

In one embodiment, the compound is according to formula (Va):

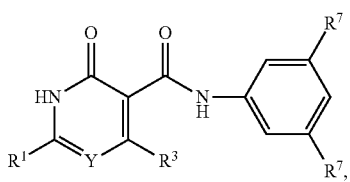

(Va)

or a pharmaceutically acceptable salt thereof, wherein Y, $R^1$, $R^2$, $R^3$, and $R^7$ are as defined above.

In one embodiment, the compound is according to formula (Vb):

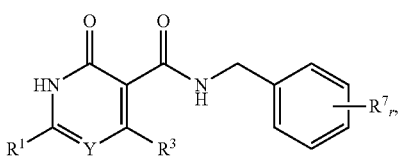

(Vb)

or a pharmaceutically acceptable salt thereof, wherein r, Y, $R^1$, $R^2$, $R^3$, and $R^7$ are as defined above.

In one embodiment, the compound is according to formula (VI):

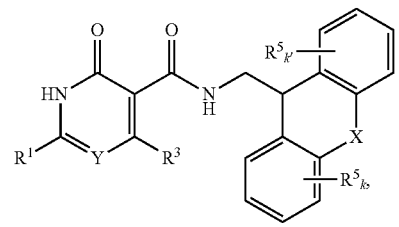

(VI)

or a pharmaceutically acceptable salt thereof, wherein k, k' Y, $R^1$, $R^2$, $R^3$, and $R^5$ are as defined above.

In one embodiment, the compound is according to formula (VII):

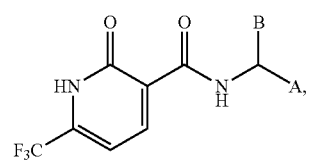

(VII)

or a pharmaceutically acceptable salt thereof, wherein A, B, are as defined above.

In one embodiment, the compound is according to formula (VIIa):

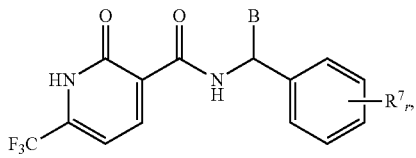
(VIIa)

or a pharmaceutically acceptable salt thereof, wherein r and R⁷ are as defined above.

In one embodiment, the compound is according to formula (VIII):

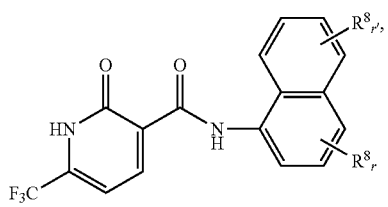
(VIII)

or a pharmaceutically acceptable salt thereof, wherein:
r and r' are independently from 0 to 4;
R⁸ is independently at each occurrence halogen, —CN, =O, —OH, —(CH₂)₀₋₃—SH, —(CH₂)₀₋₃—SR*, —(SO₂)—R*, —NH₂, —(CH₂)₁₋₃—OR#, —NH—(C=O)—R*, —NH—(SO₂)—R*, —(CH₂)₁₋₃—NR#₂, —NHR#, or —N(R#)₂, C₁₋₄ alkoxy, phenoxy, C₁₋₁₂ alkyl, C₁₋₁₂ alkenyl, C₁₋₁₂ alkynyl, C₁₋₄ haloalkyl, C₁₋₄ haloalkoxy, C₆₋₁₂ aryl, a 4-7-membered heterocycle with 1 to 4 heteroatoms selected from O, N and S or combinations thereof, or wherein two adjacent R⁸ groups form a 5-7 membered ring that optionally contains 1 to 3 heteroatoms selected from O, N, and S; any of which is optionally substituted with R*, wherein R# and R* are as defined above.

In one embodiment, the compound is one of the following or a pharmaceutically acceptable salt thereof:

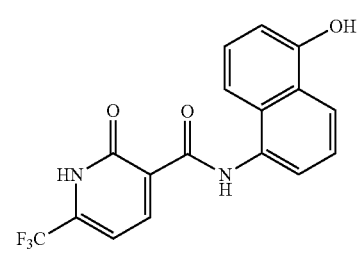

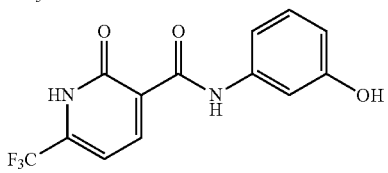

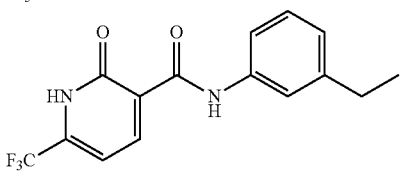

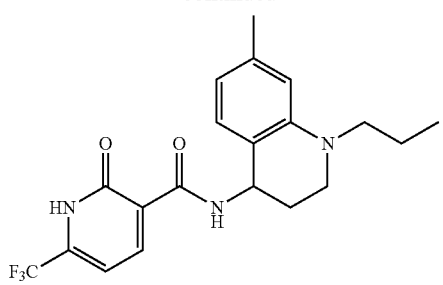

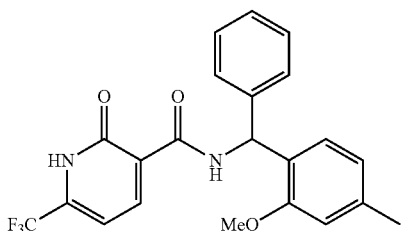

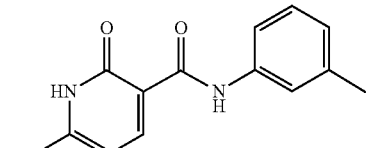

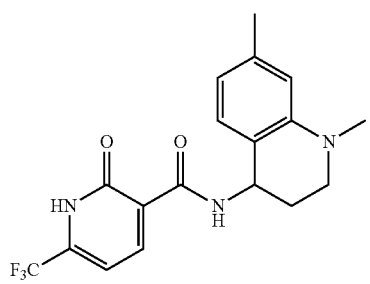

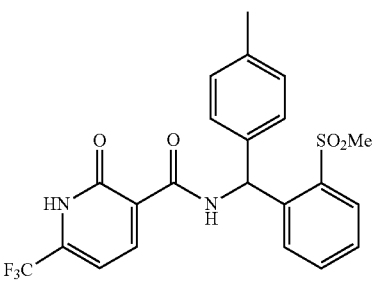

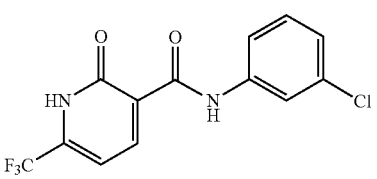

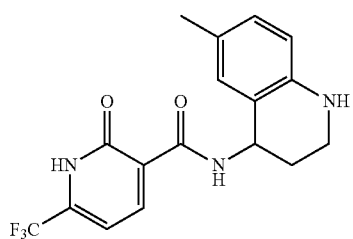

13
-continued
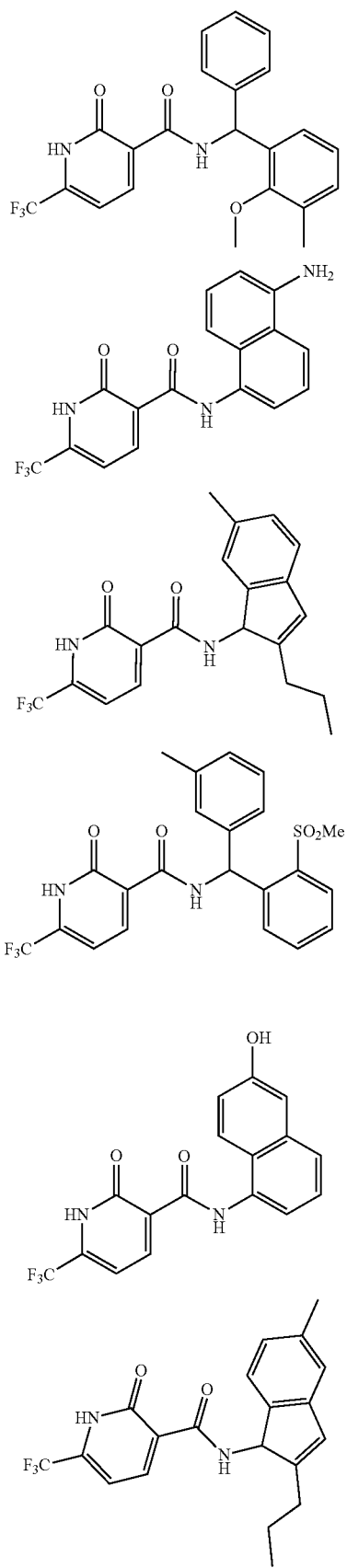
14
-continued
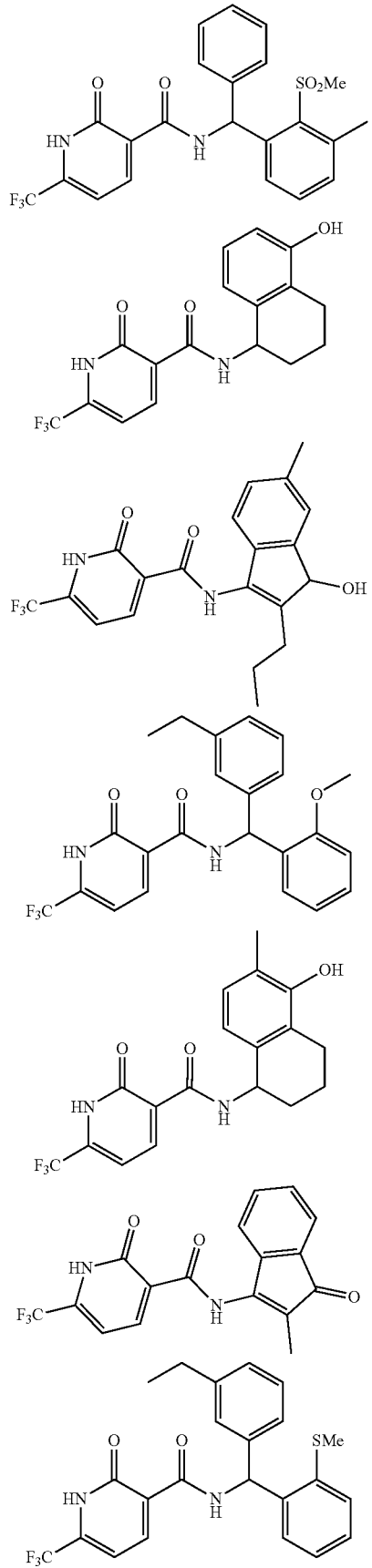

-continued
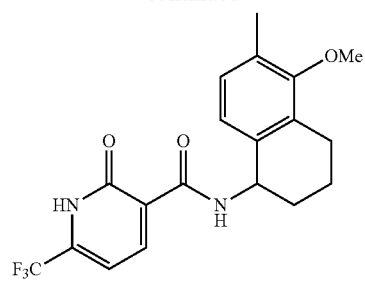
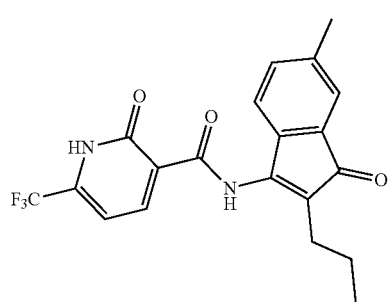
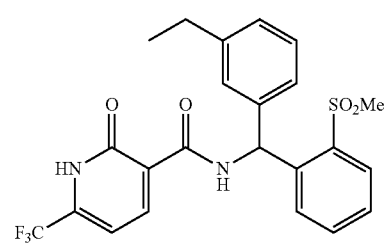
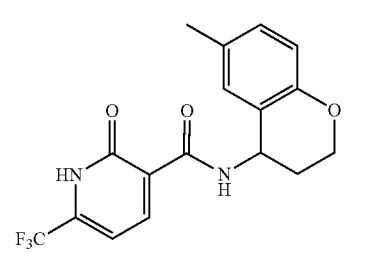
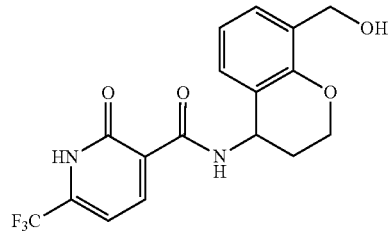
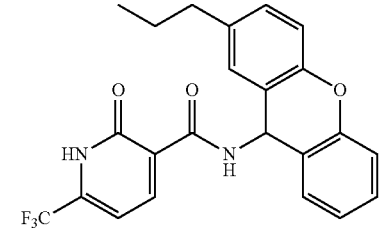
-continued
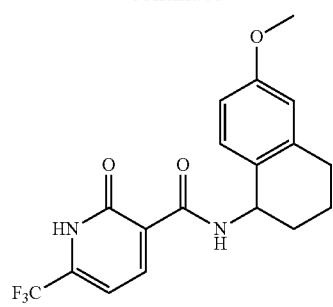
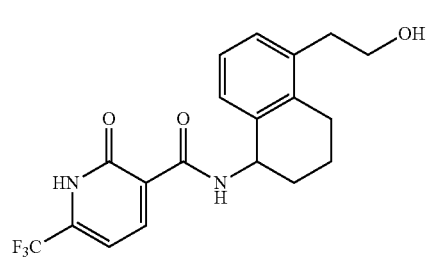
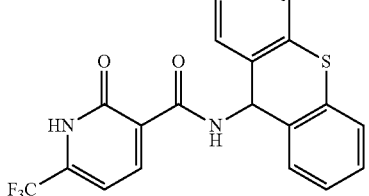
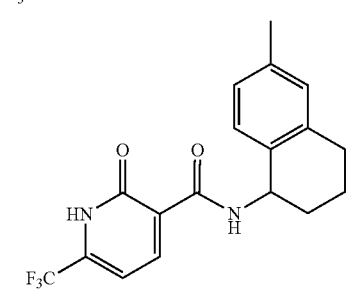
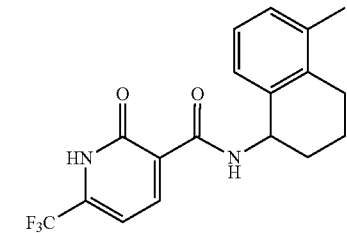
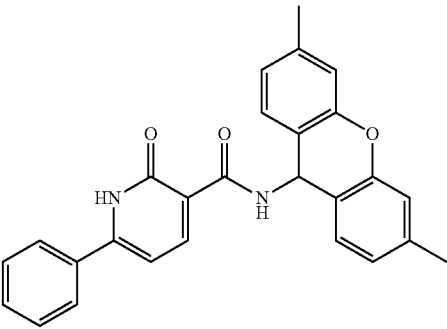

-continued
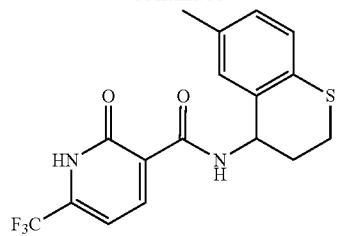
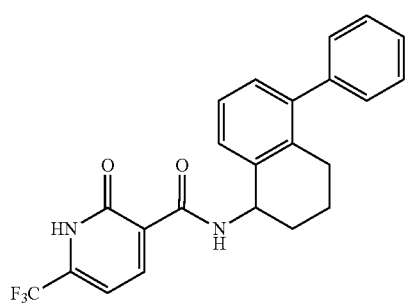
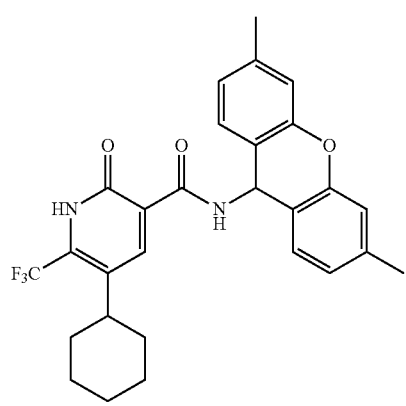
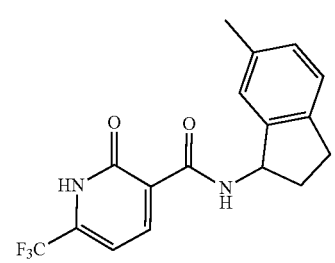
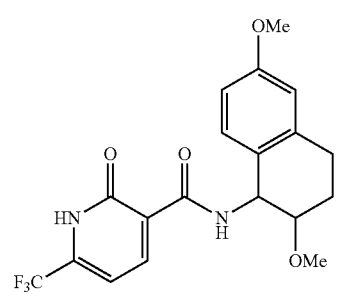
-continued
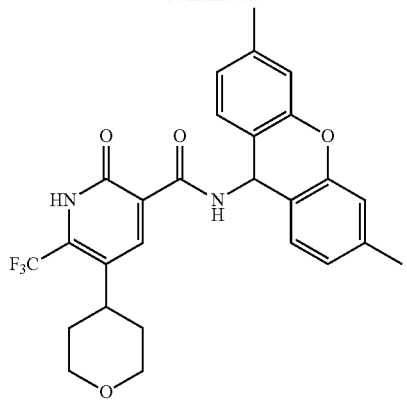
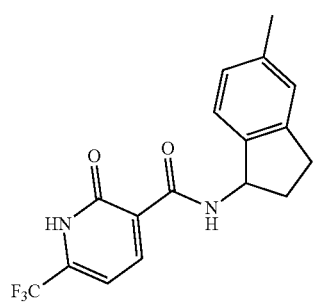
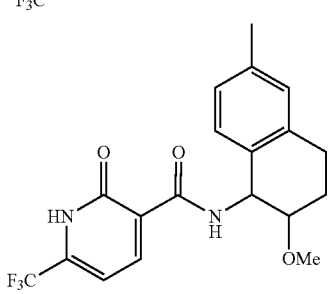
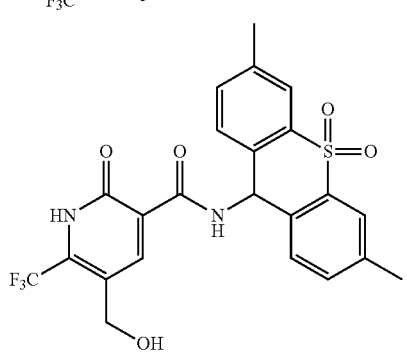
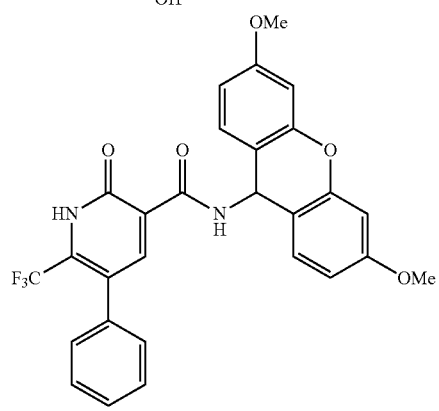

-continued
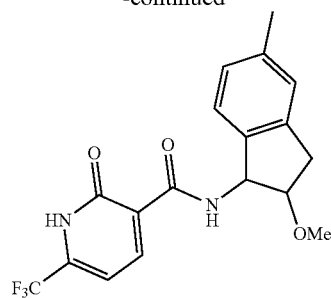
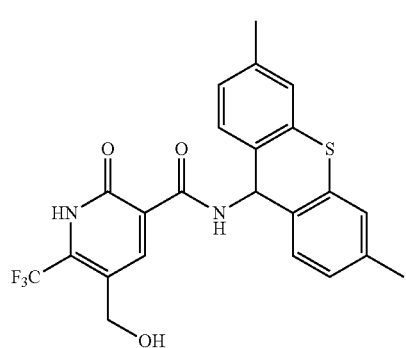
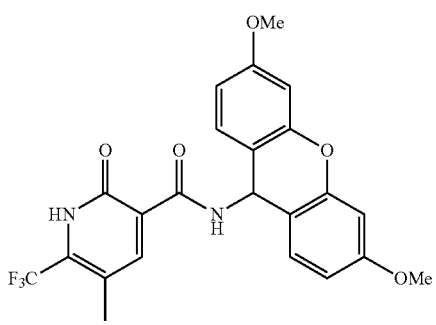
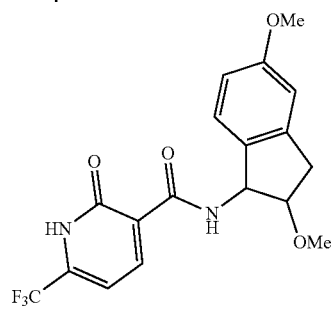
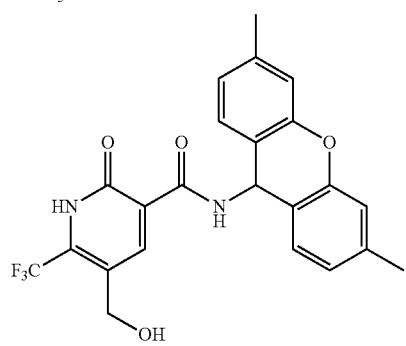
-continued
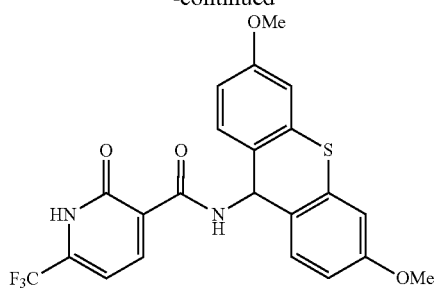
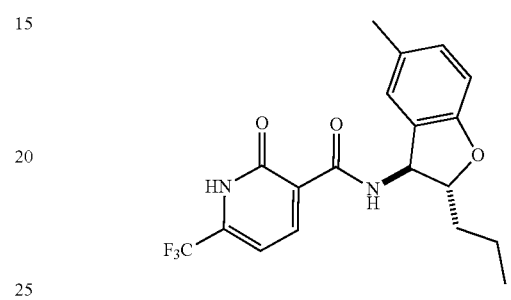
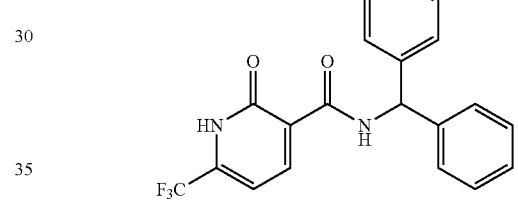
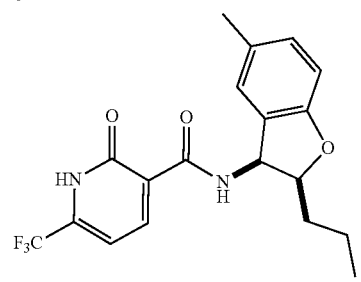
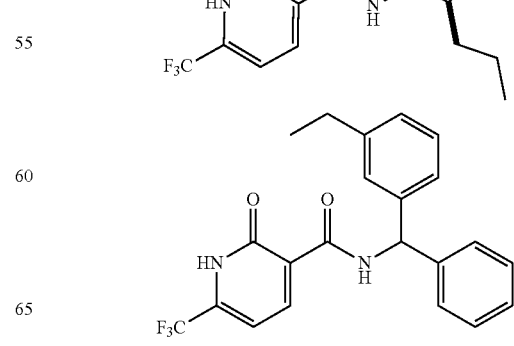

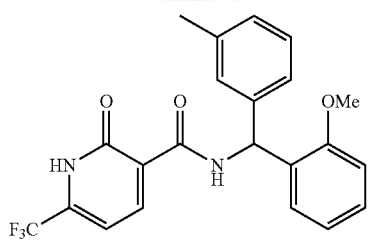
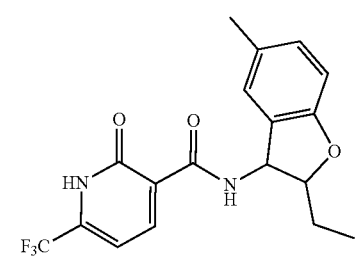
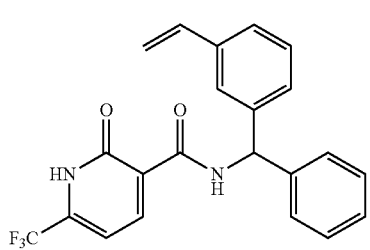
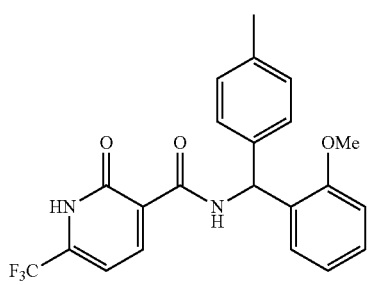
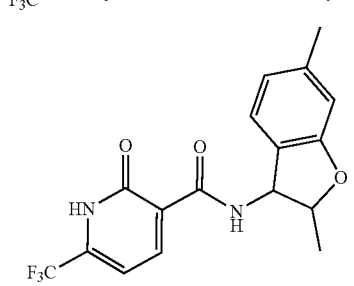
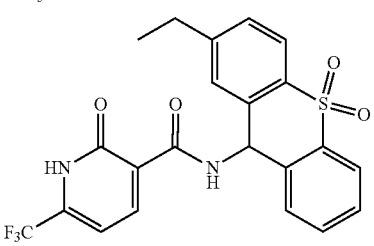
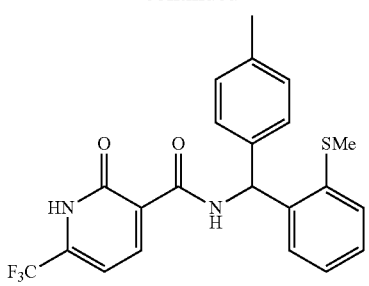
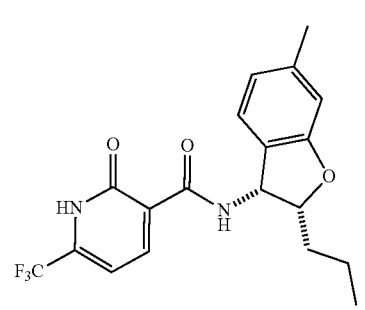
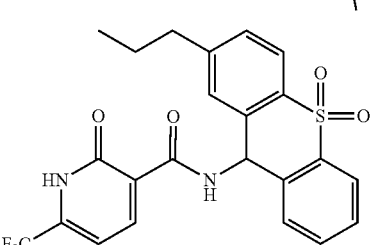
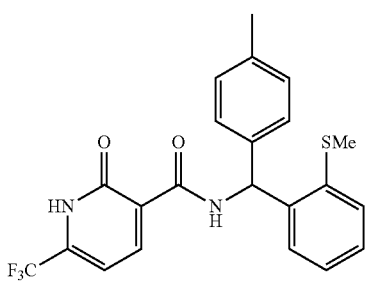
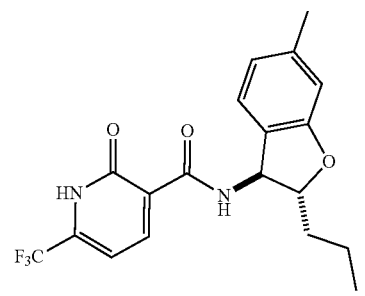
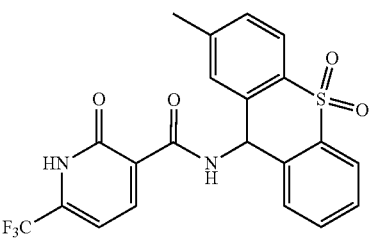

-continued
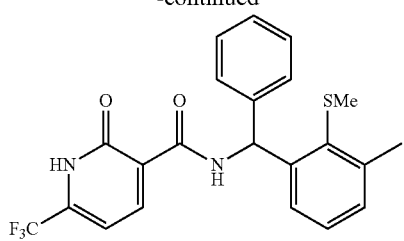
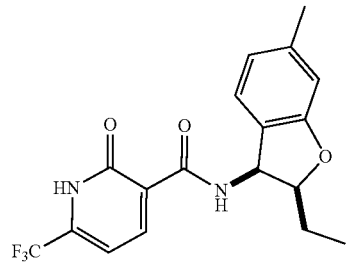
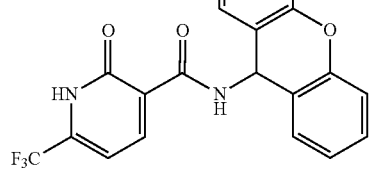
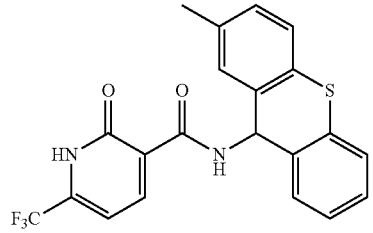
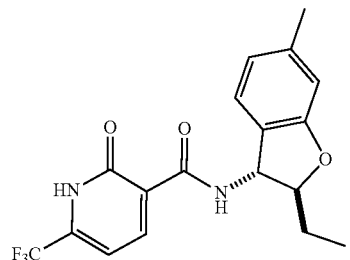
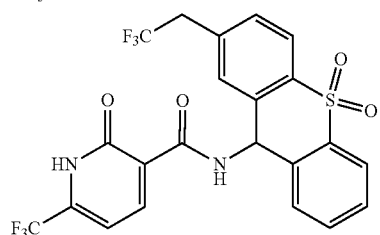
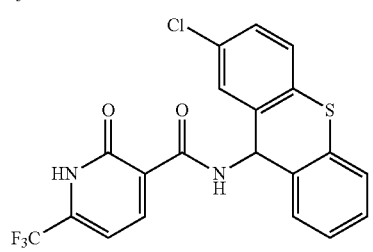
-continued
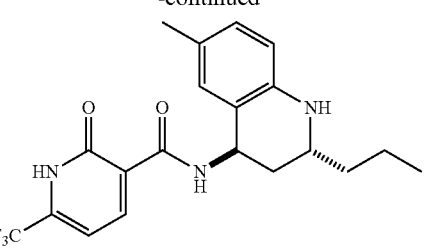
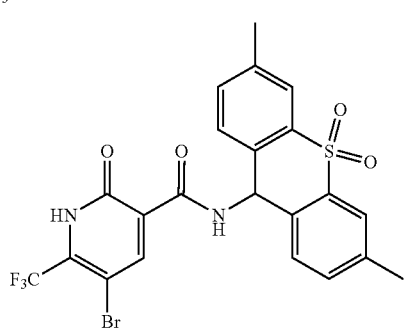
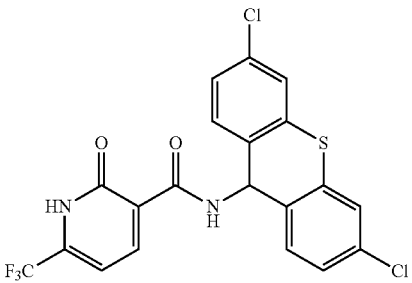
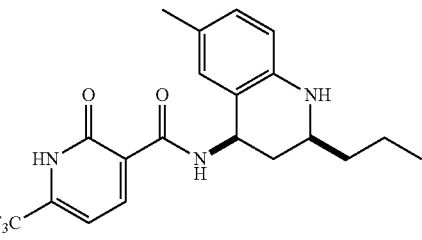
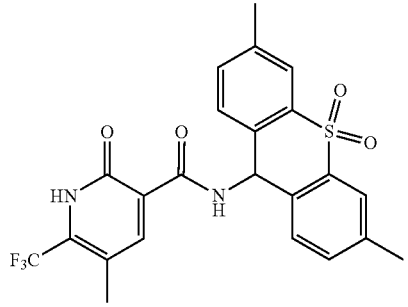
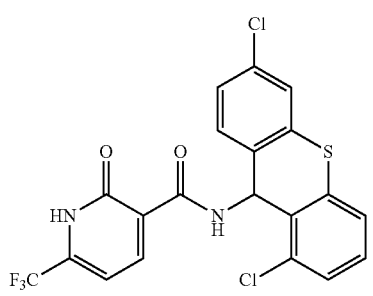

-continued
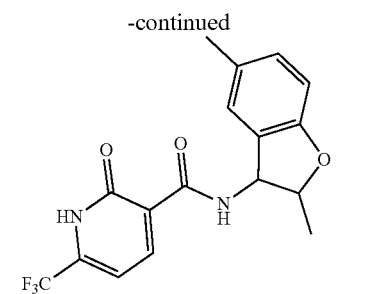
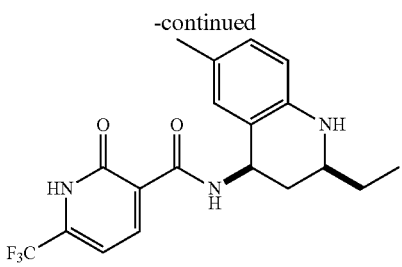
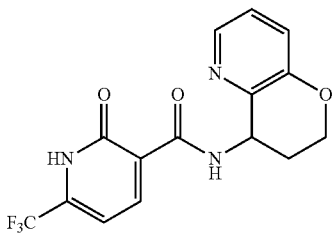
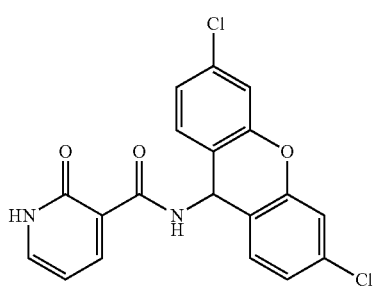
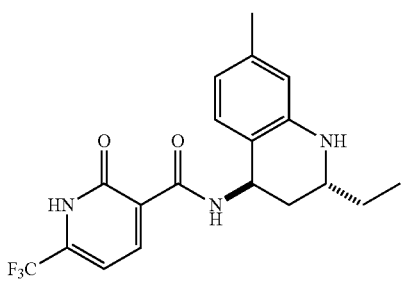
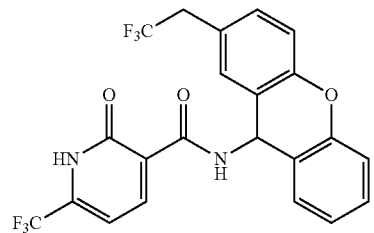
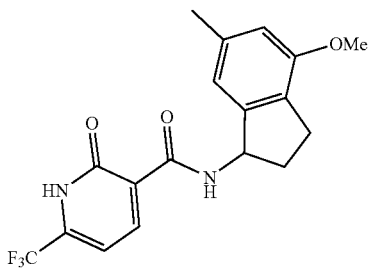

-continued
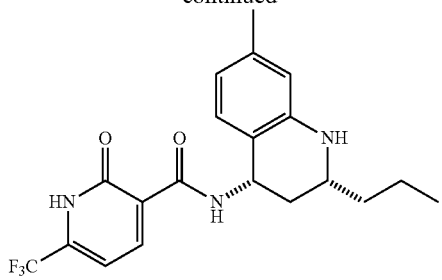
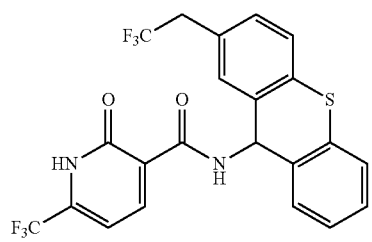
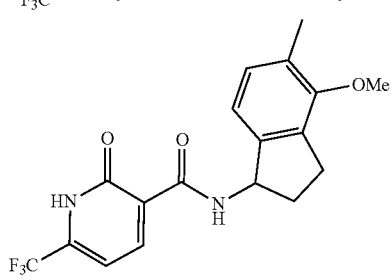
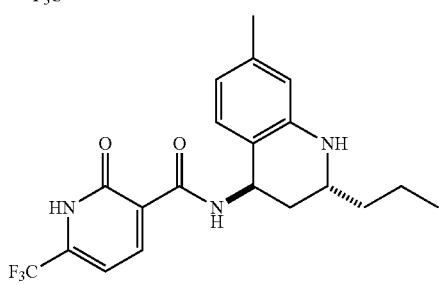
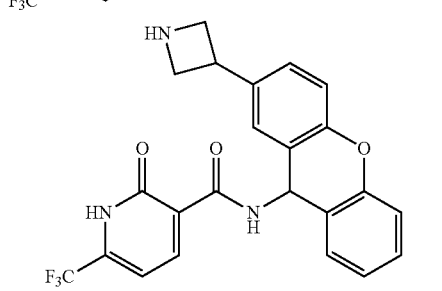
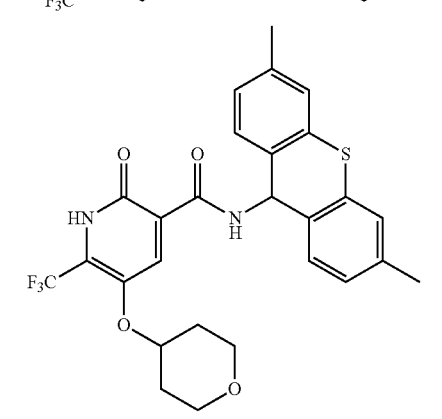
-continued
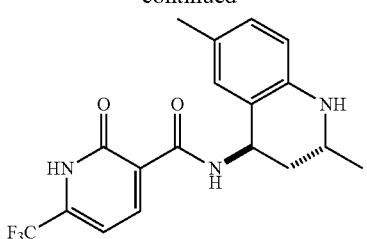
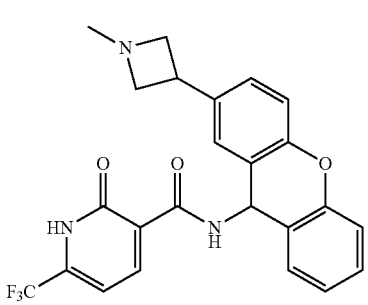
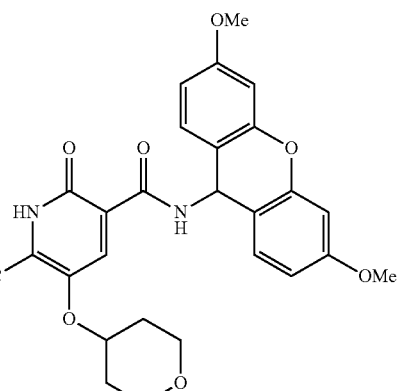
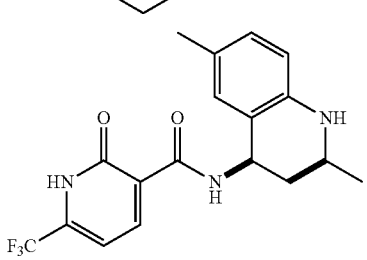
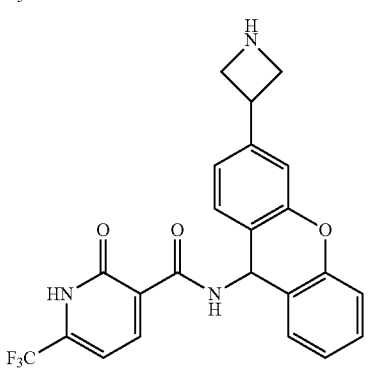

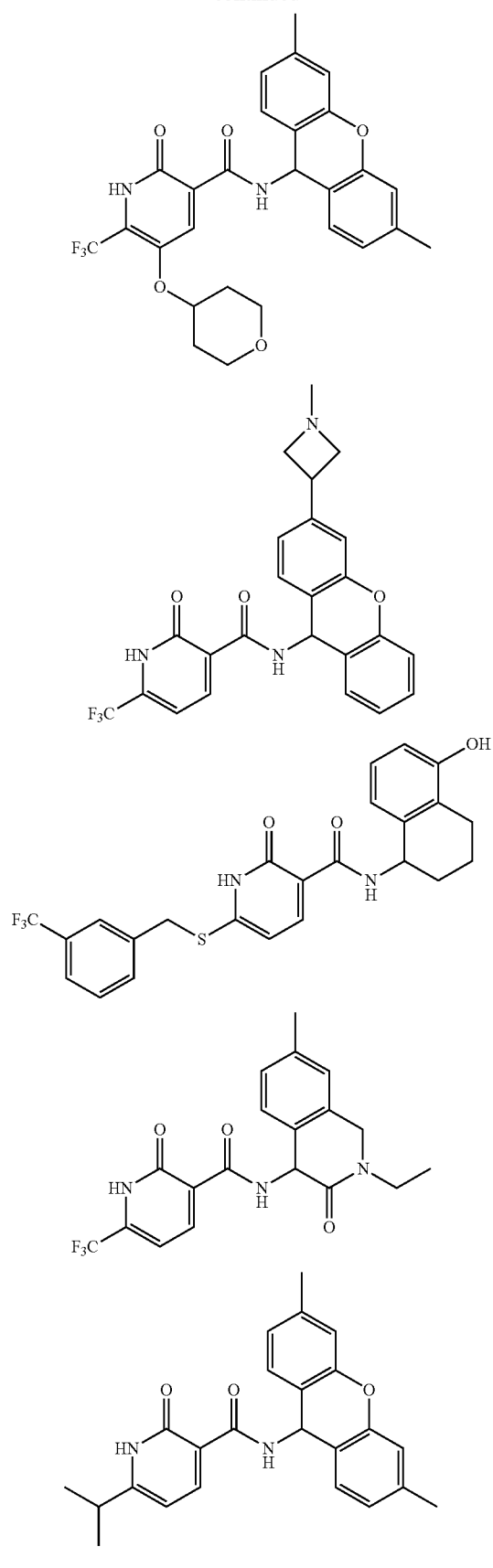
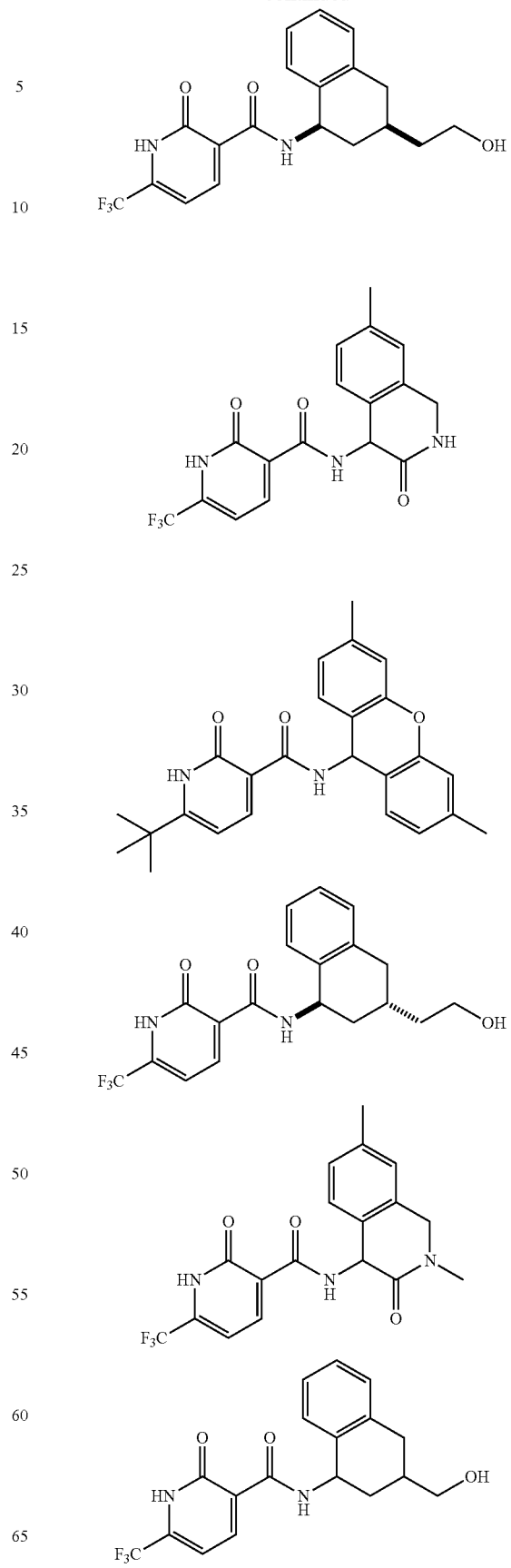

31
-continued
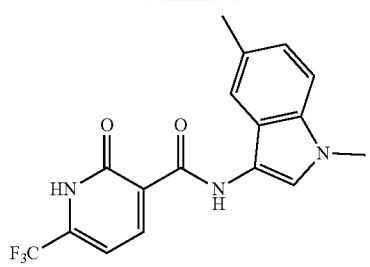
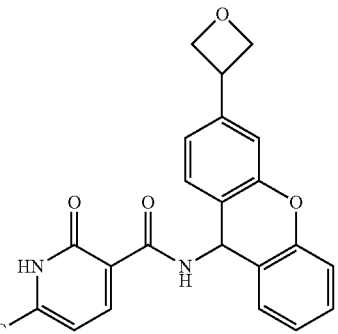
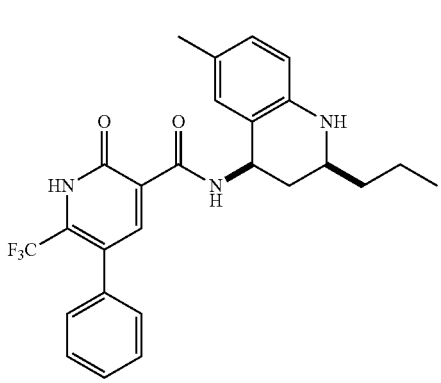
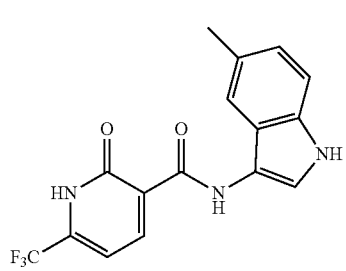
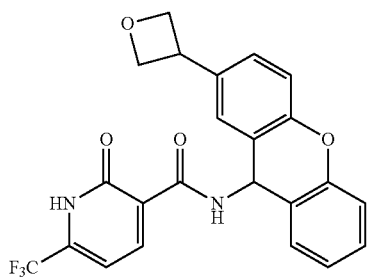
32
-continued
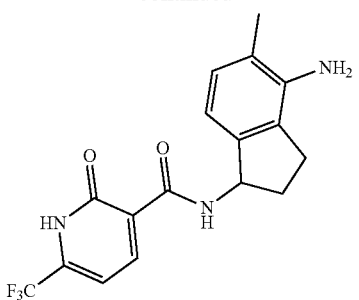
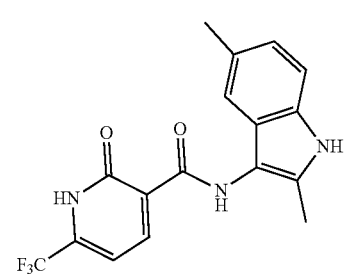
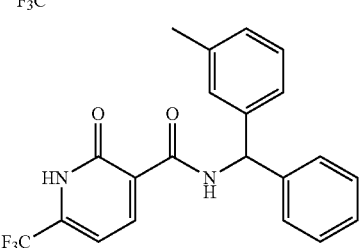
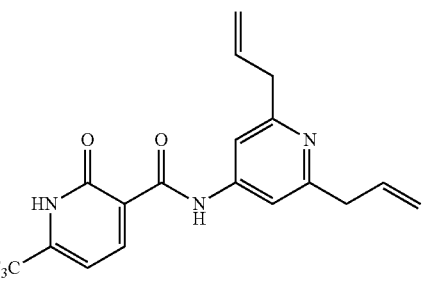
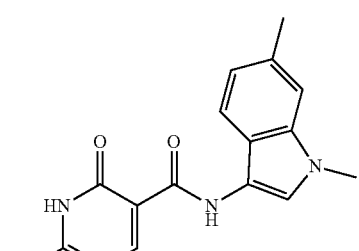
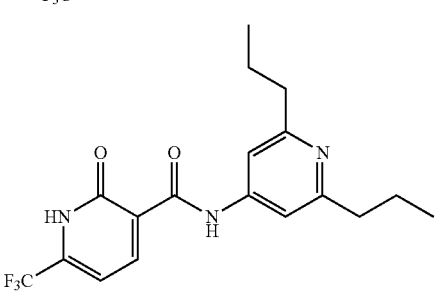

-continued
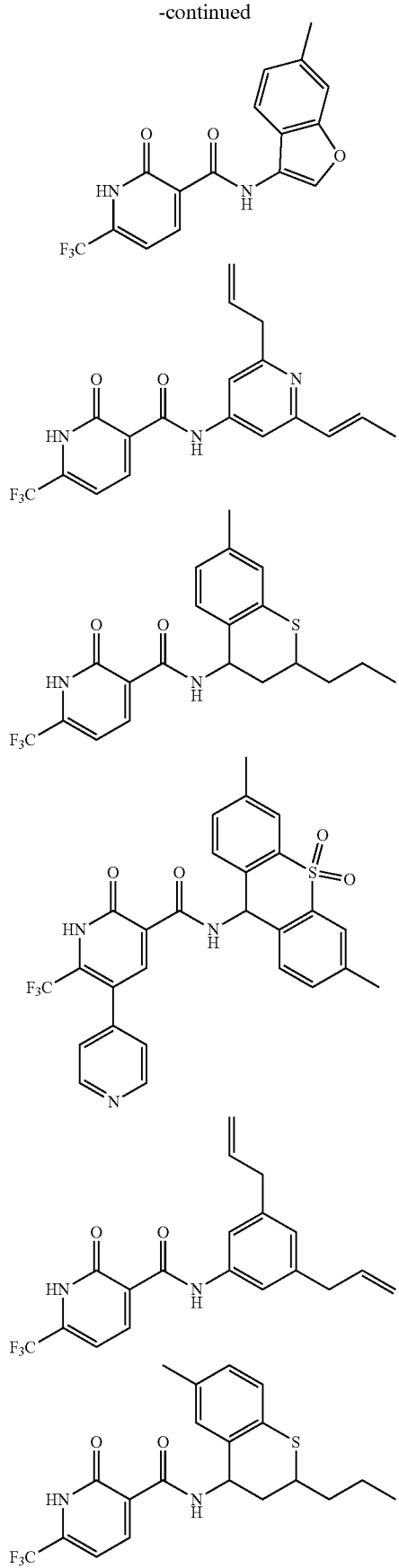
-continued
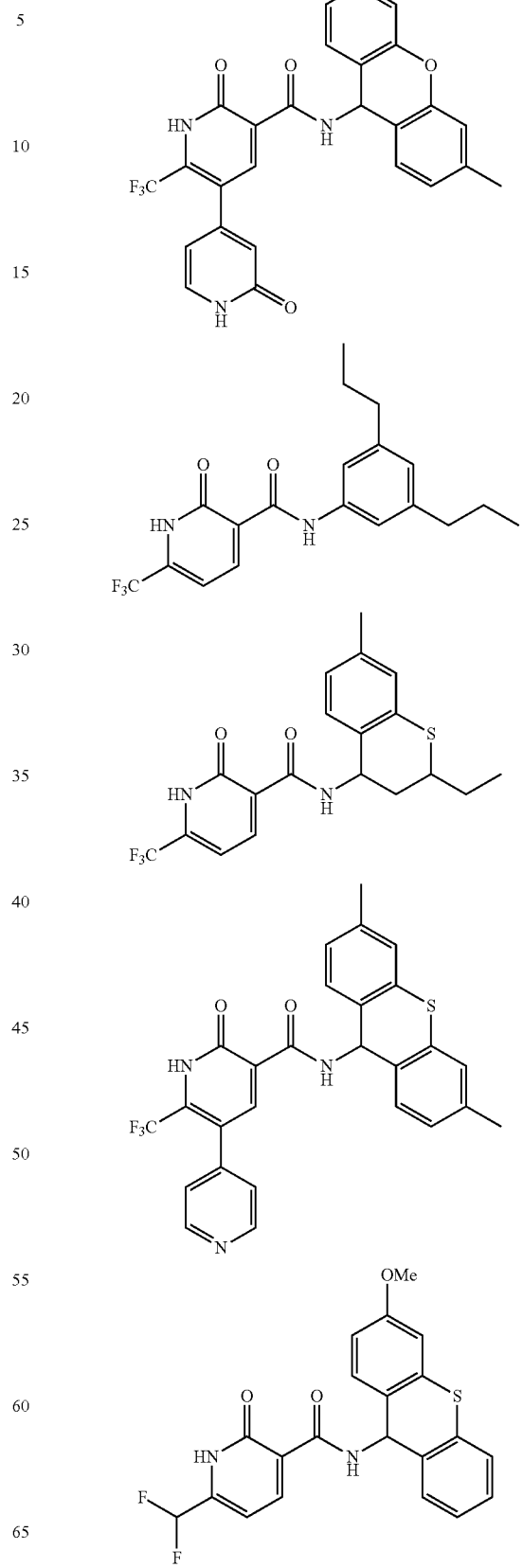

-continued
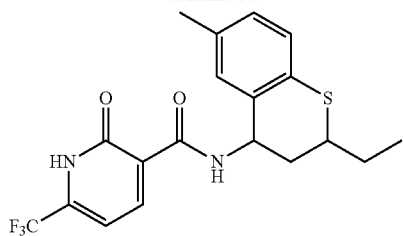
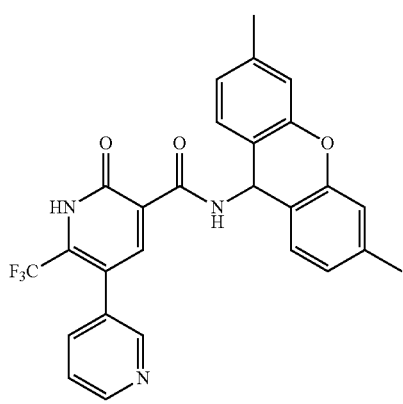
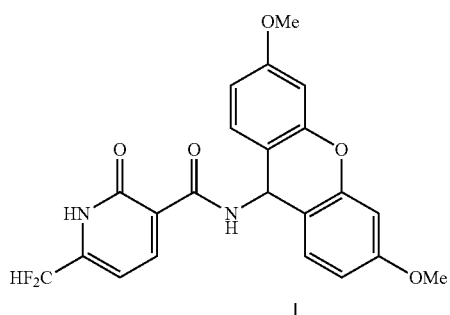
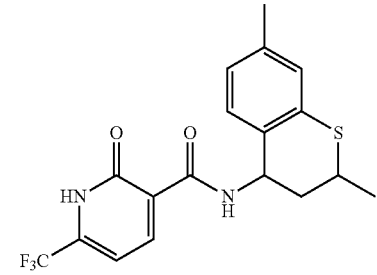
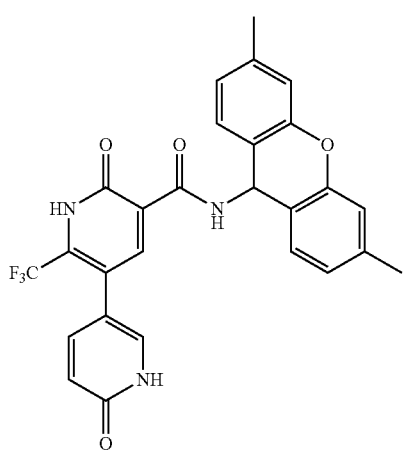
-continued
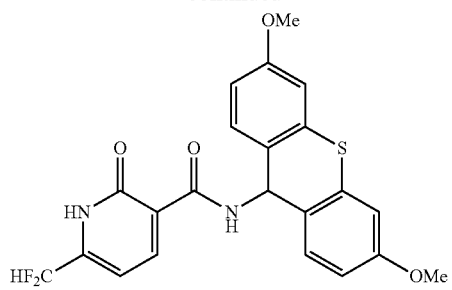
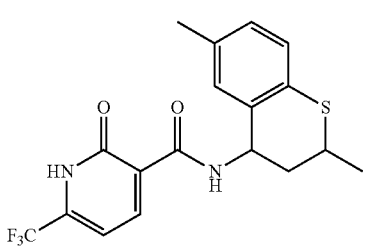
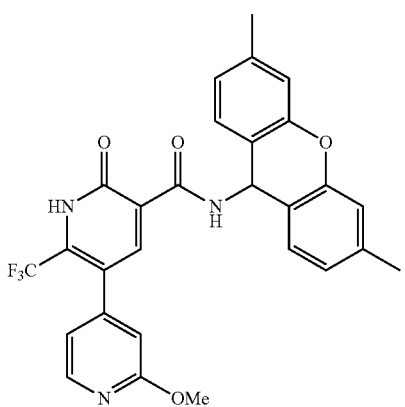
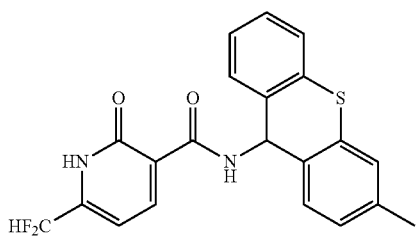
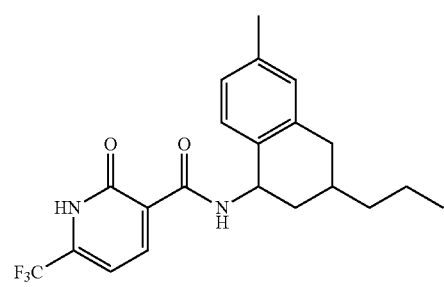

37
-continued
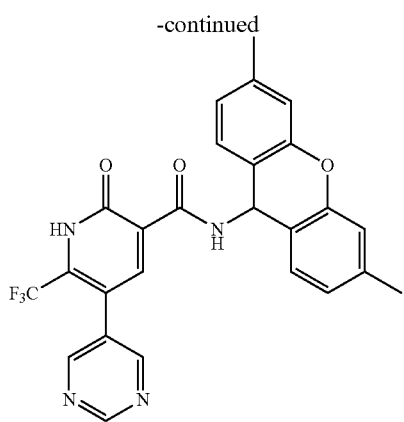
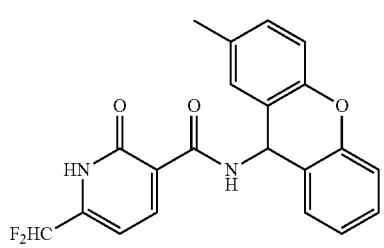
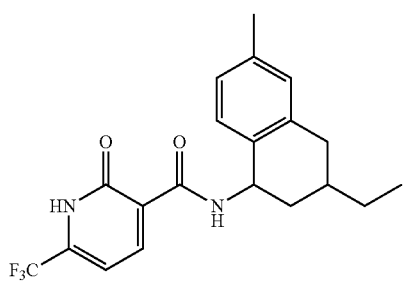
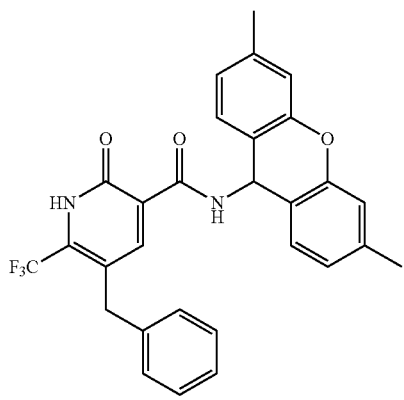
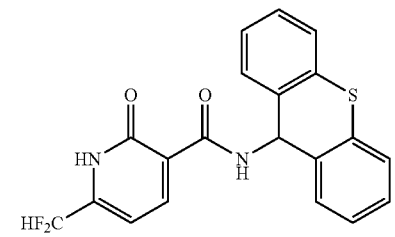
38
-continued
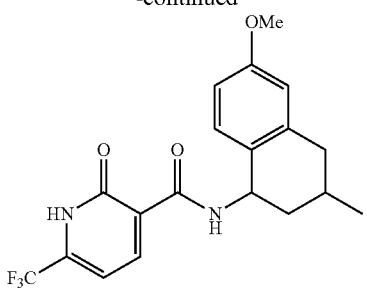
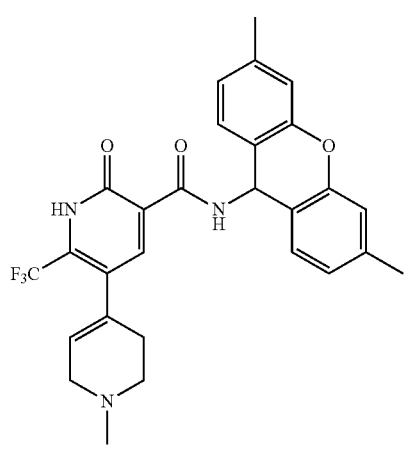
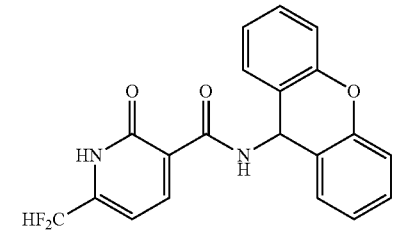
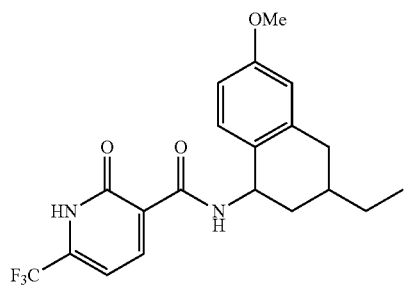
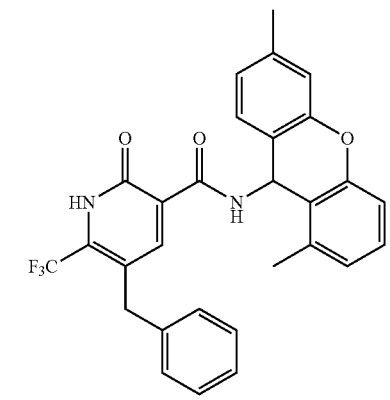

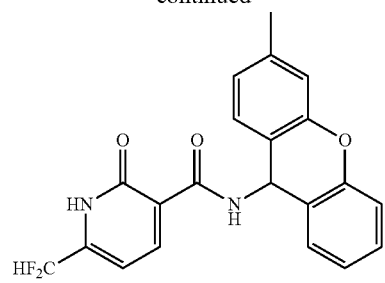
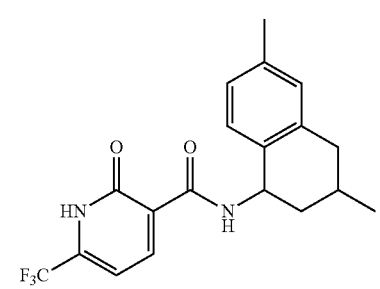
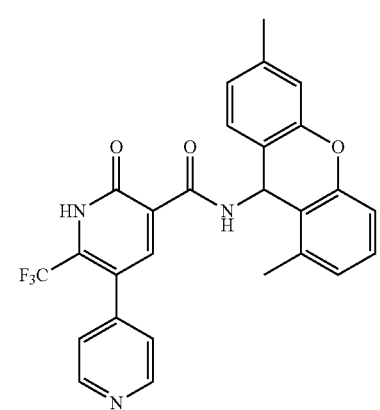
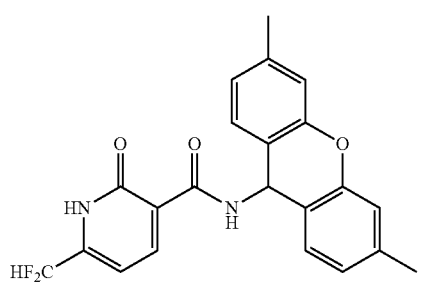
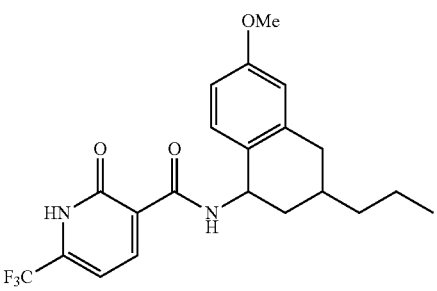
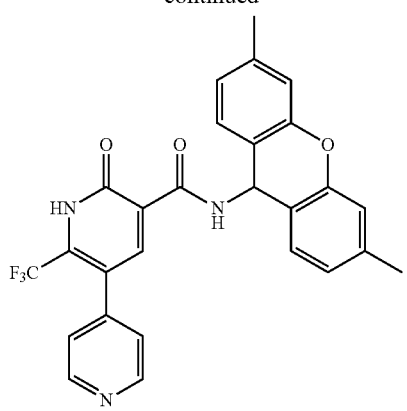
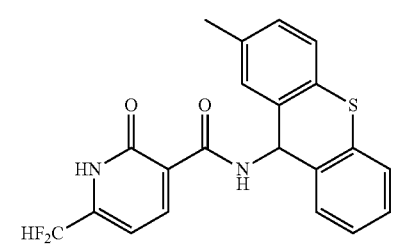
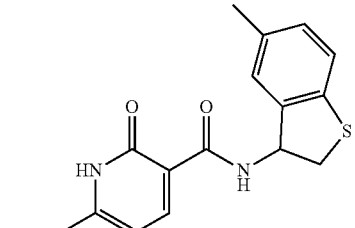
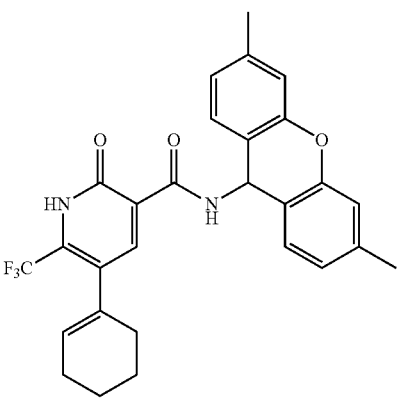
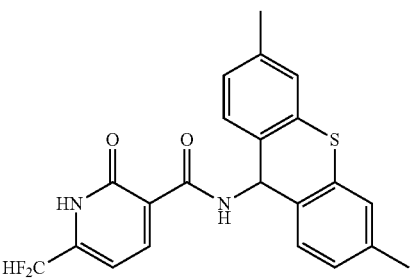

-continued
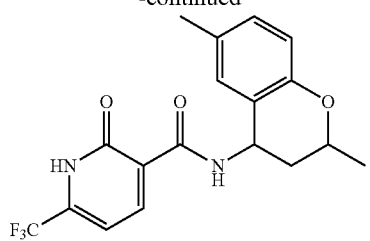
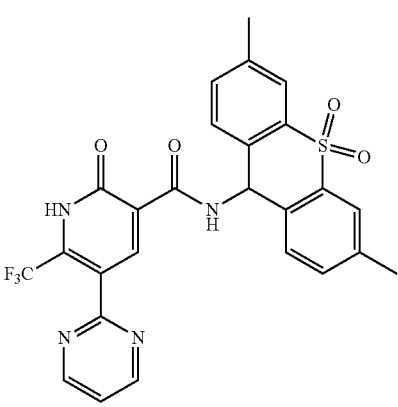
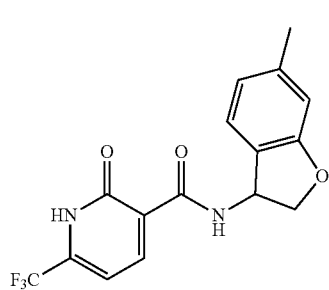
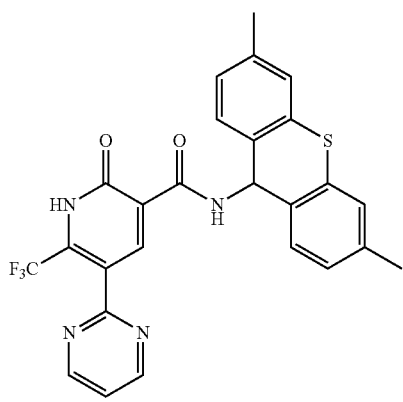
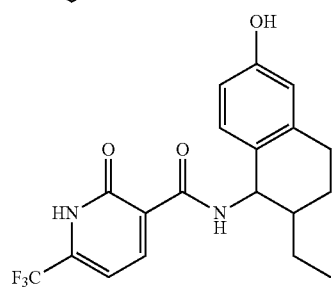
-continued
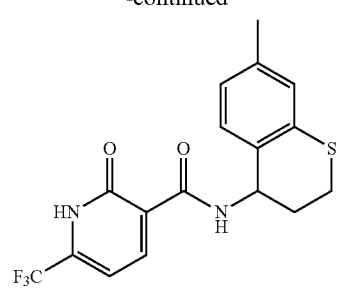
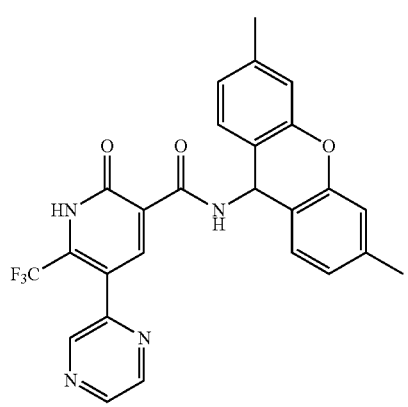
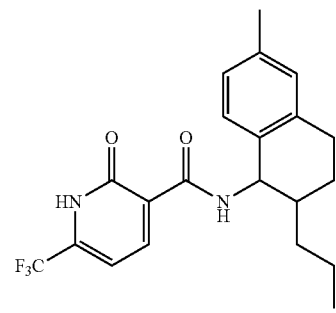
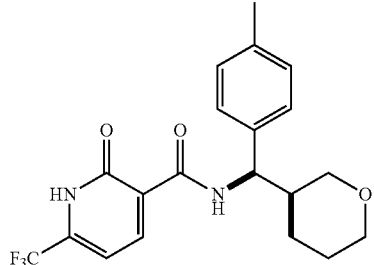
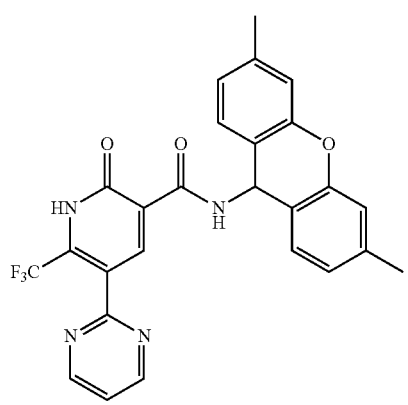

-continued
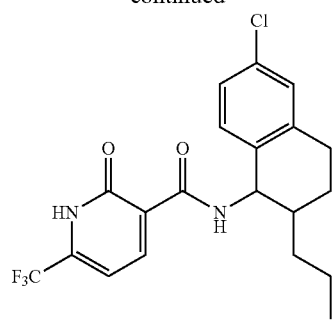
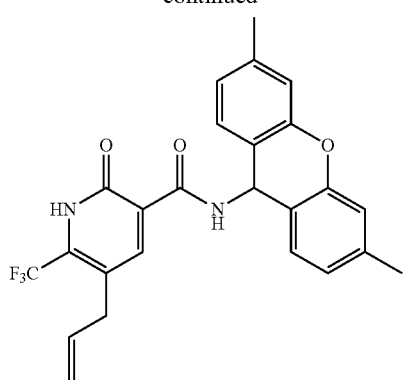
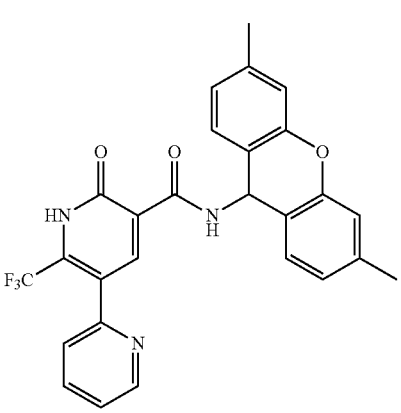
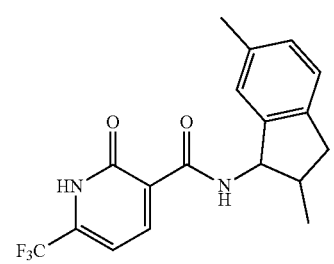
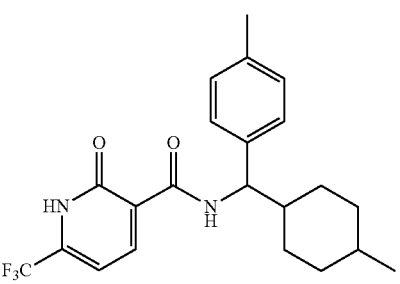
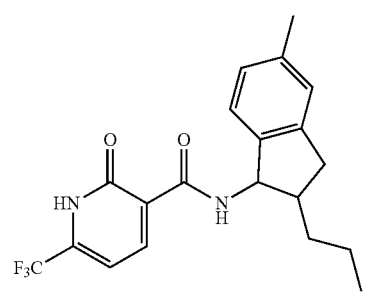
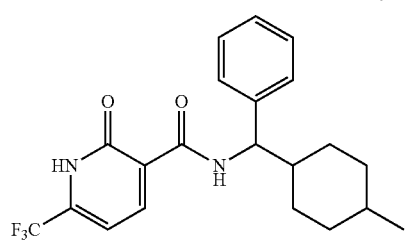
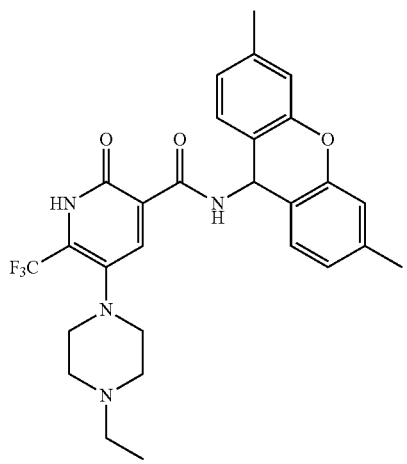

-continued
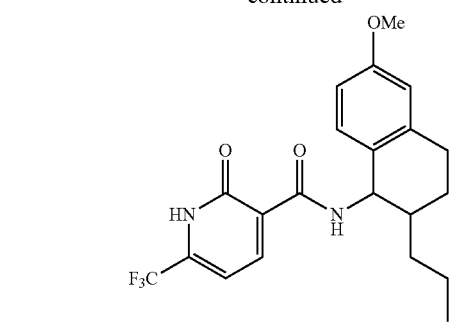
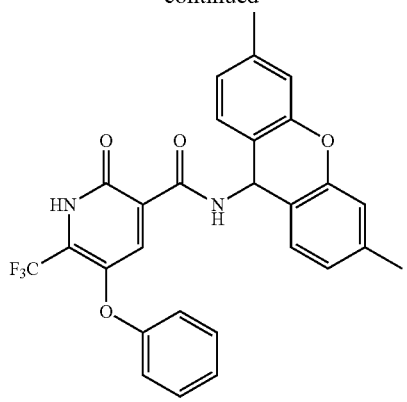
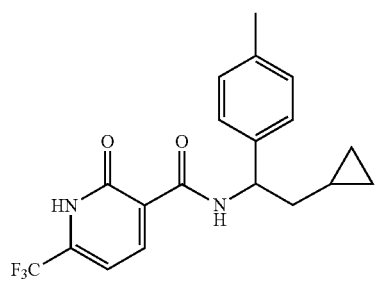
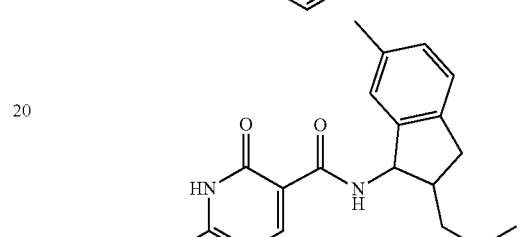
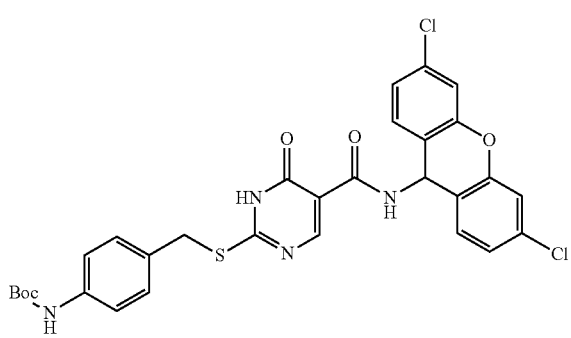
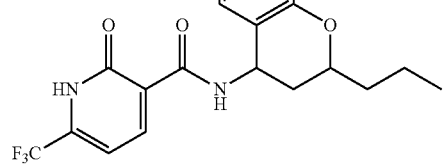
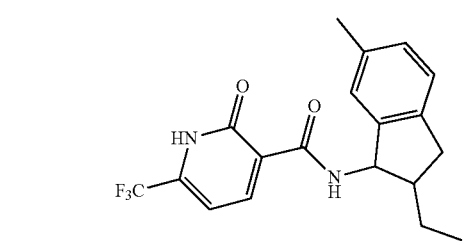
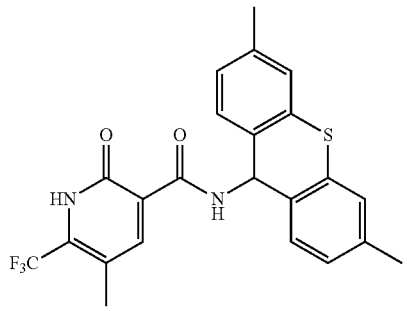
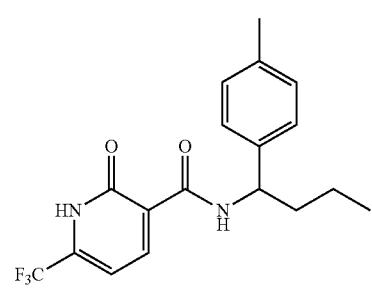
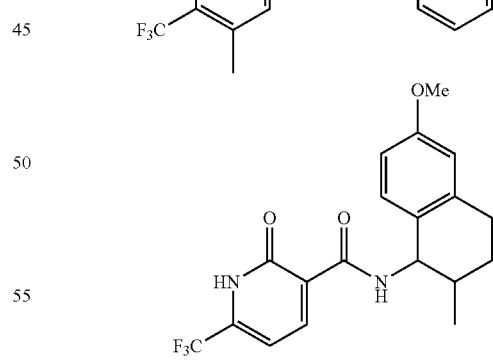
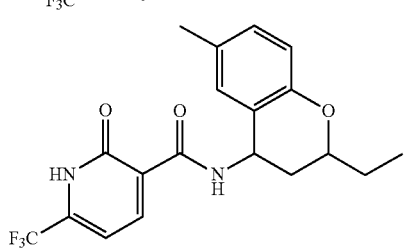

47
-continued
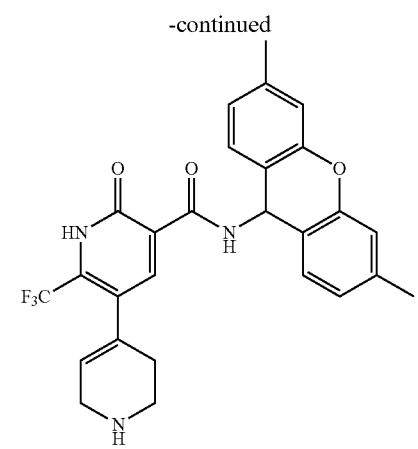
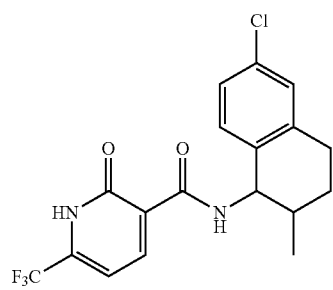
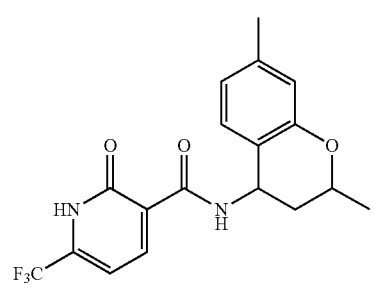
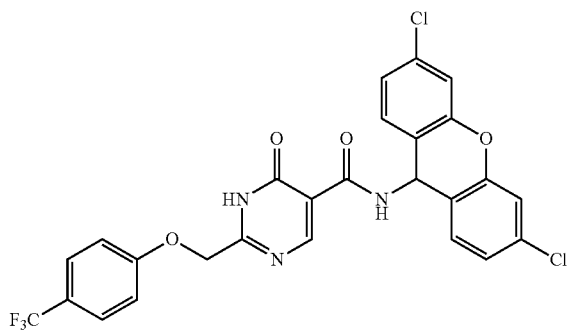
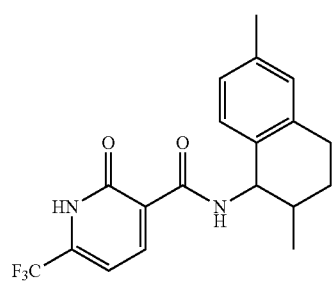
48
-continued
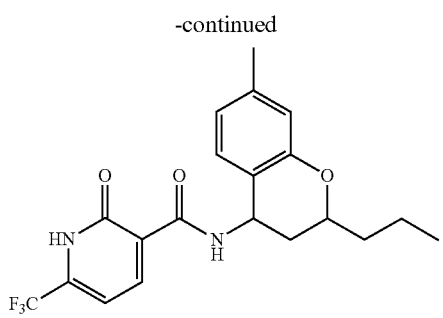
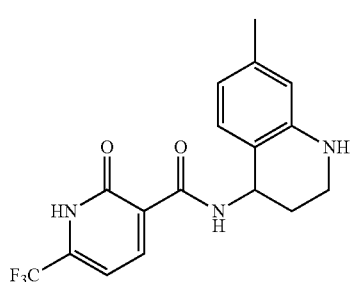
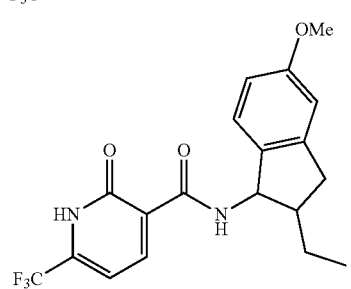
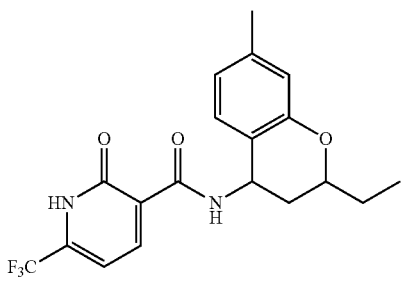
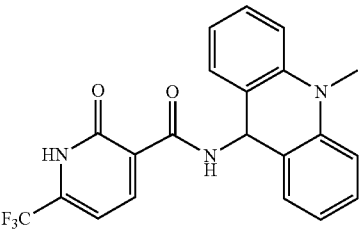
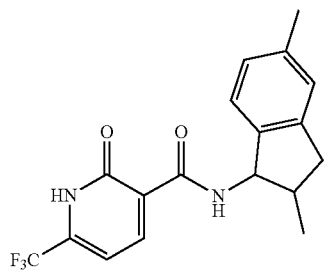

49
-continued
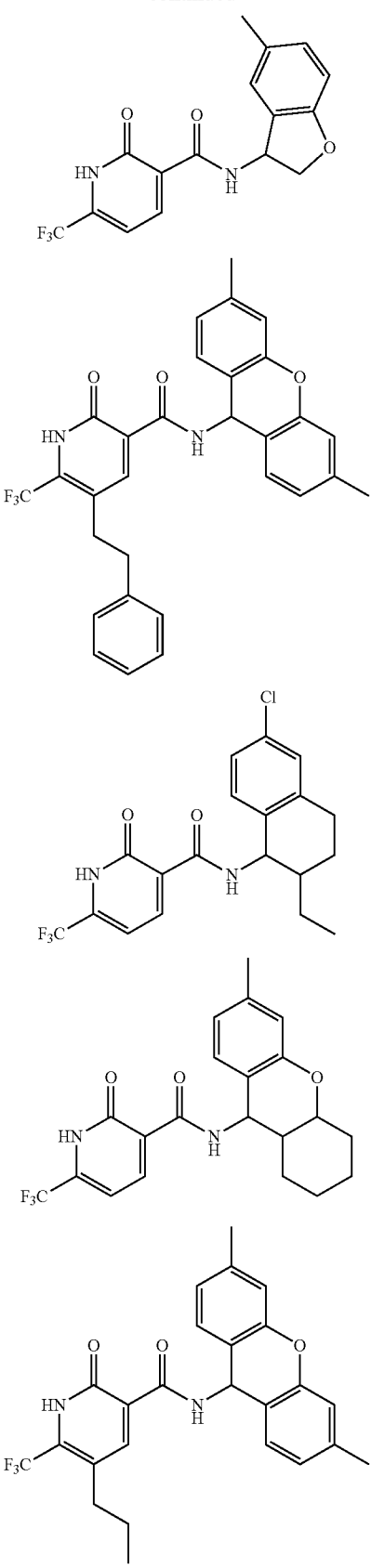
50
-continued
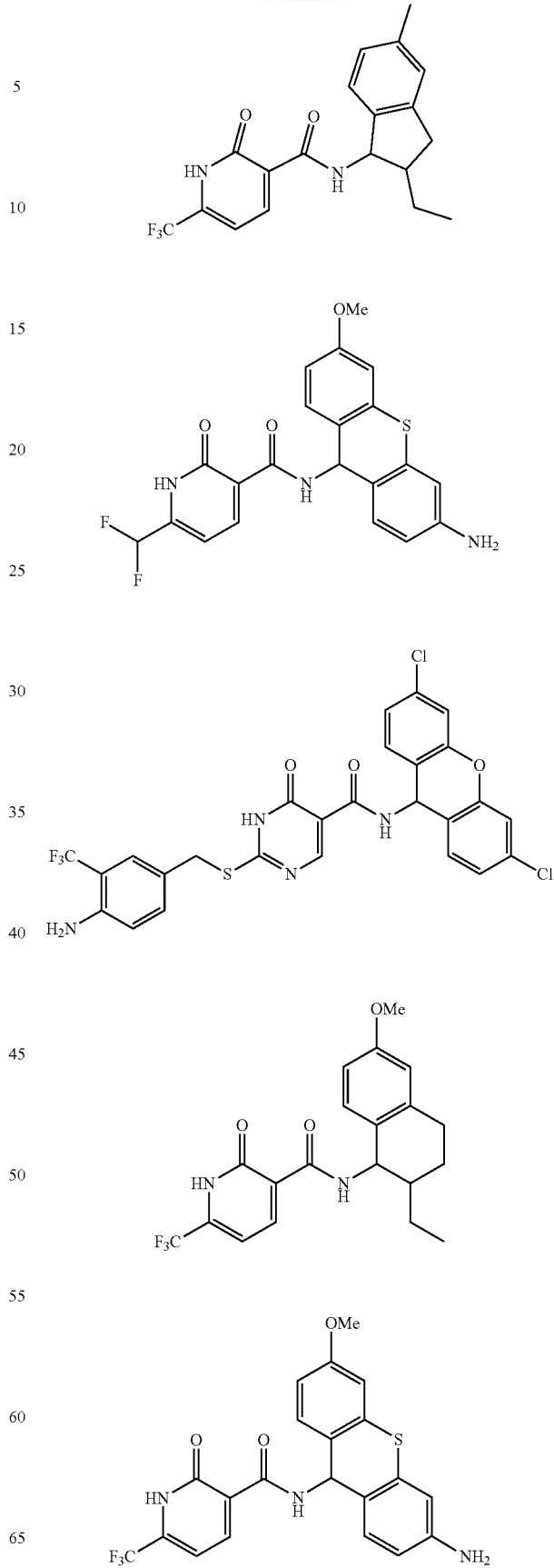

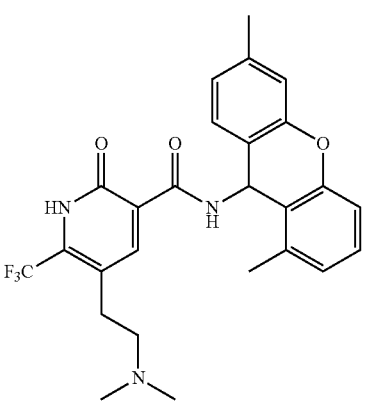
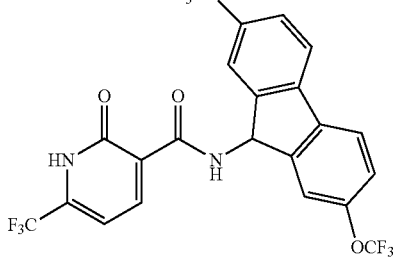
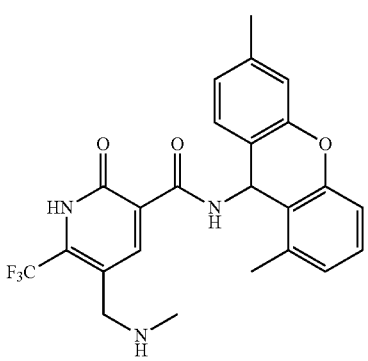
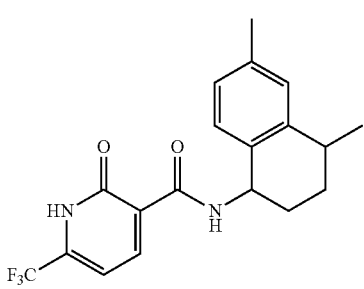
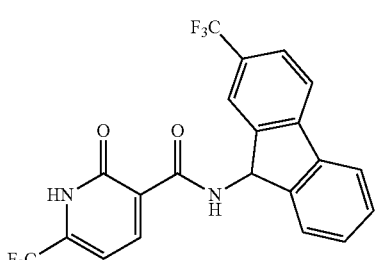
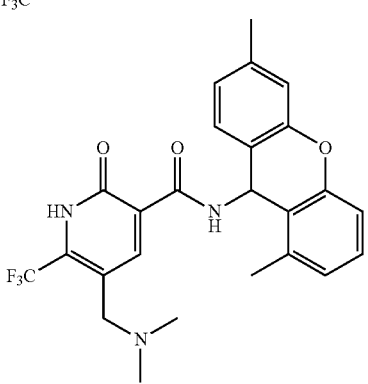

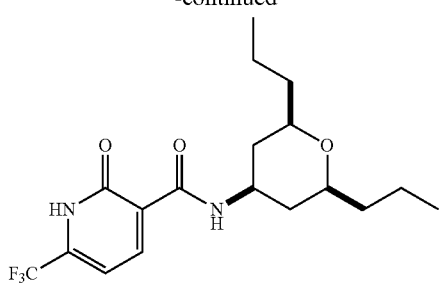
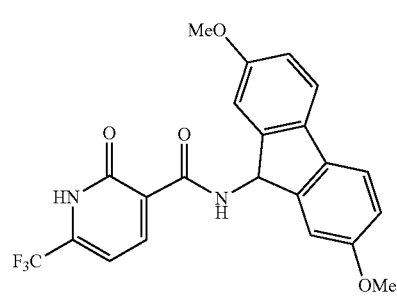
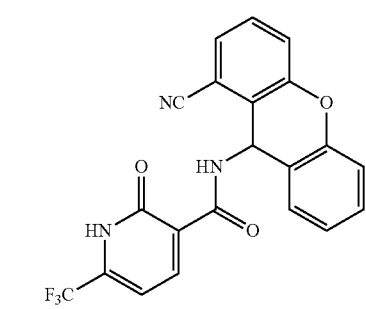
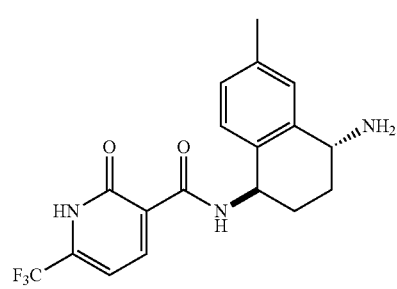
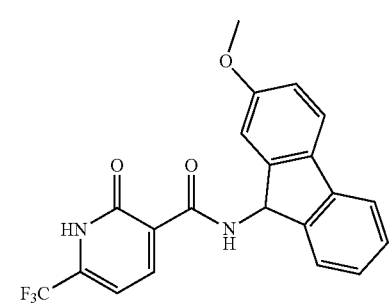
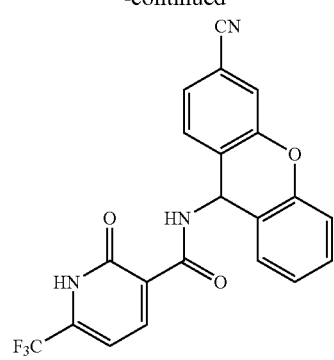
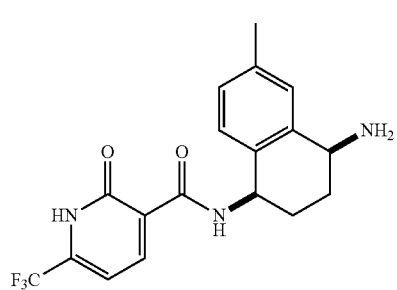
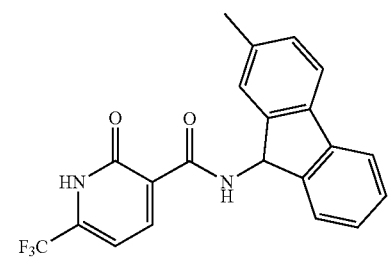
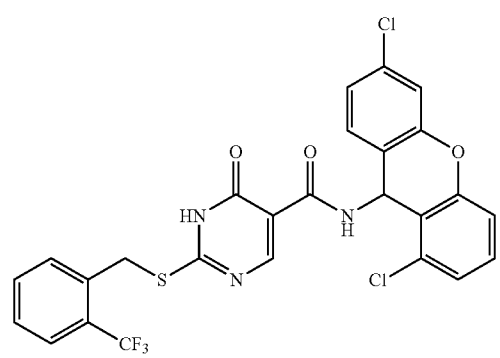
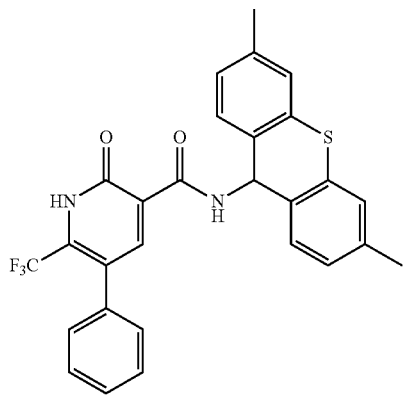

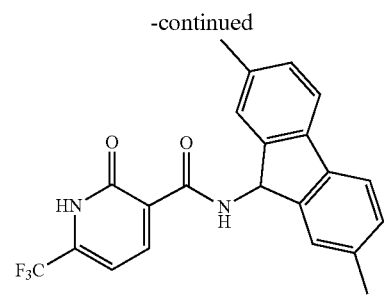
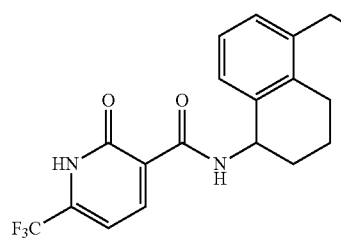
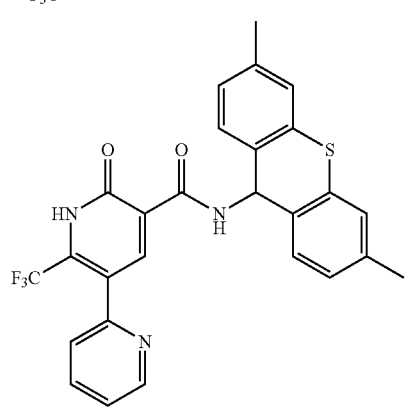
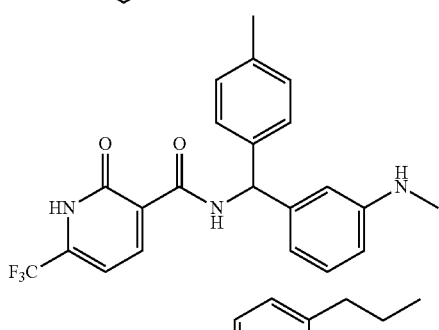
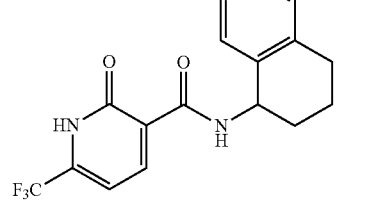
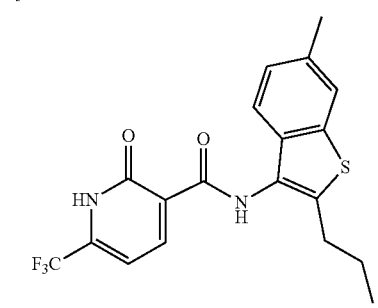
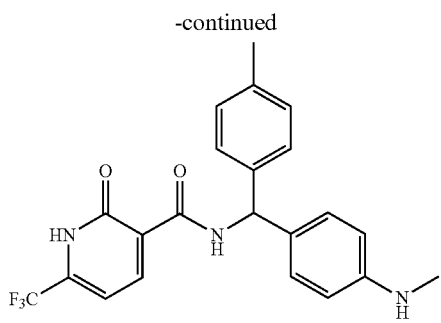
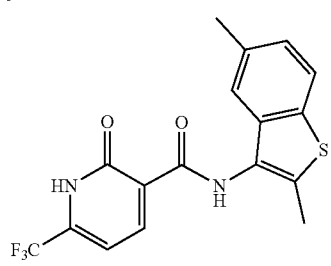

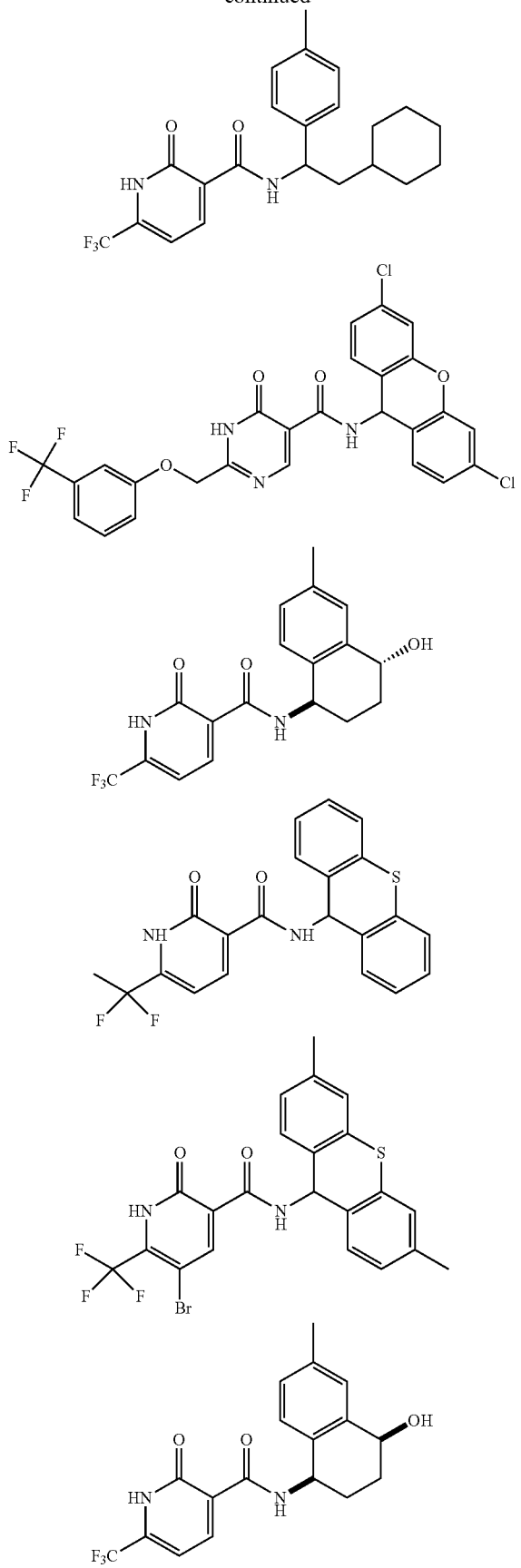
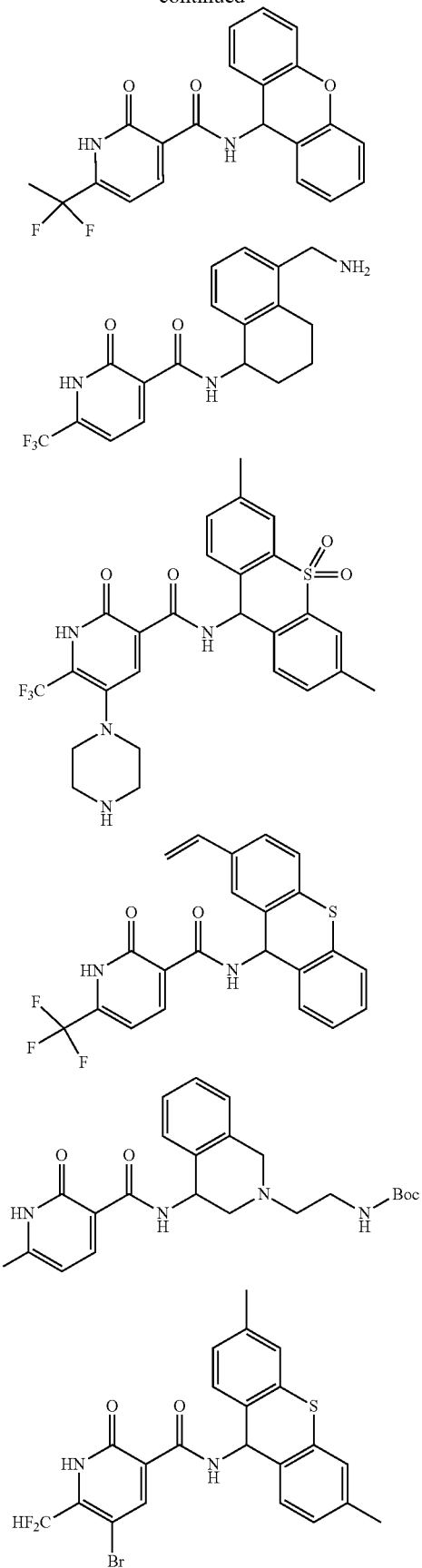

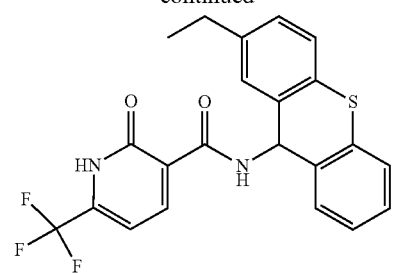
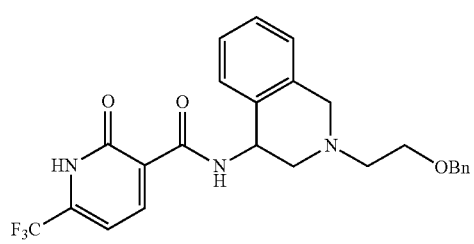
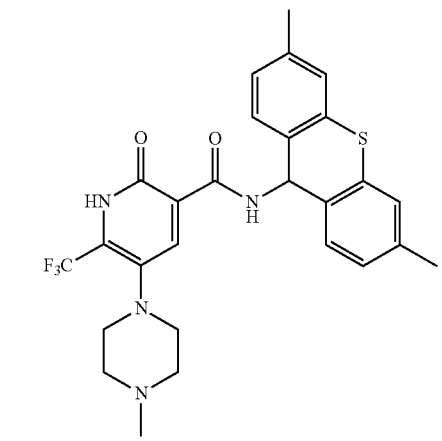
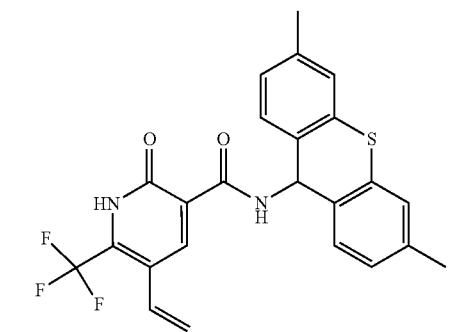
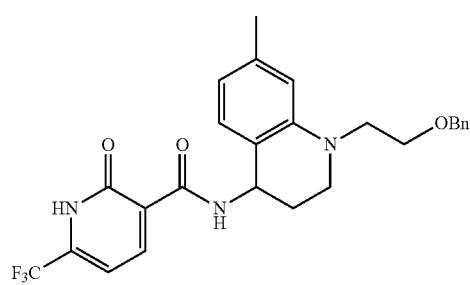
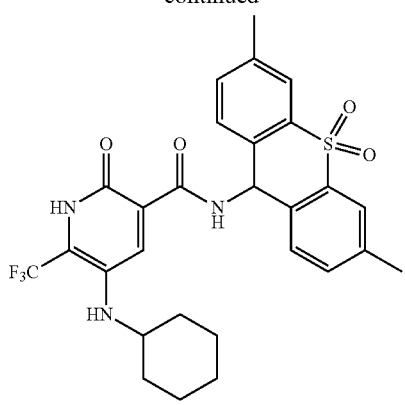
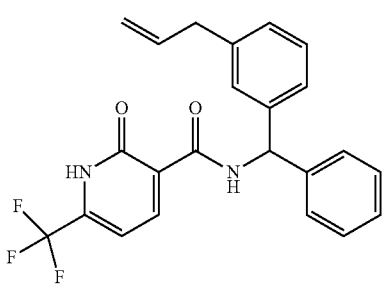
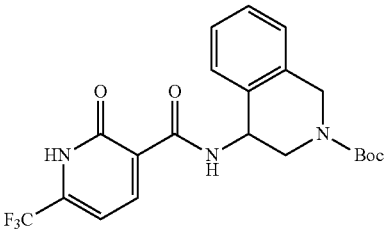
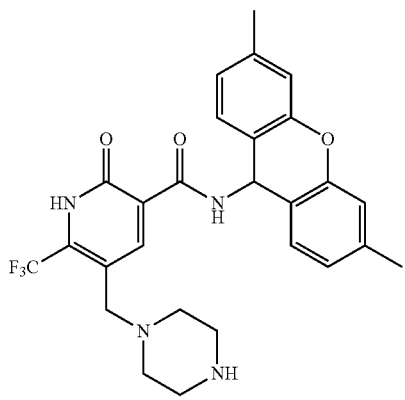
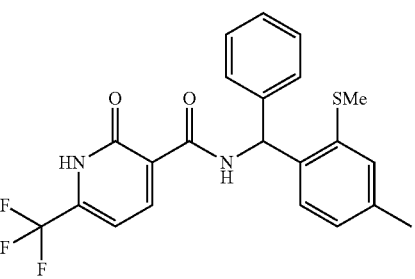

-continued
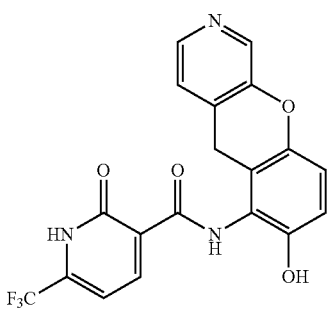
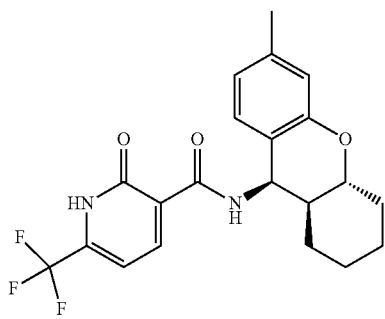
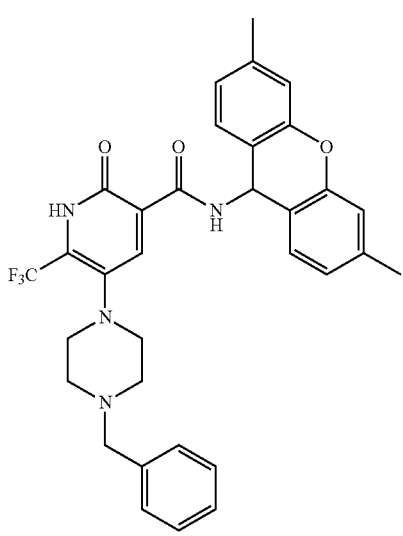
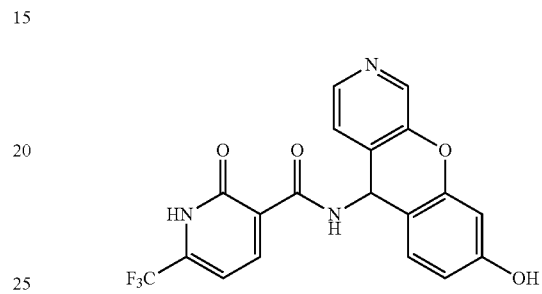
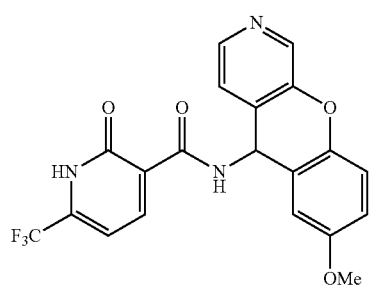
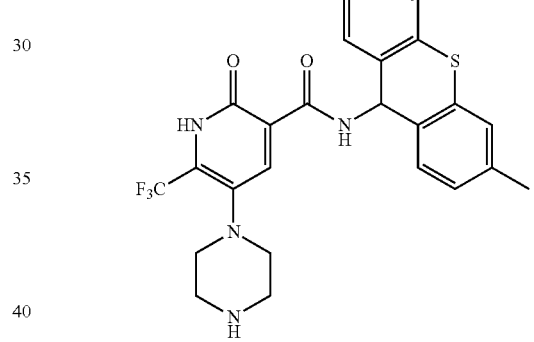
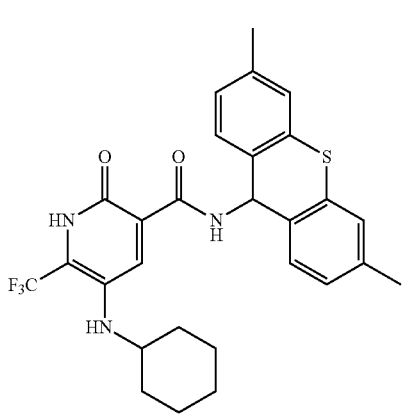
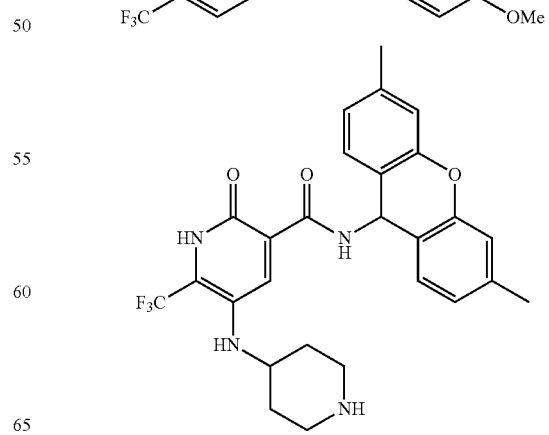

-continued
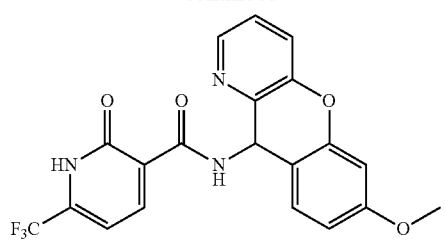
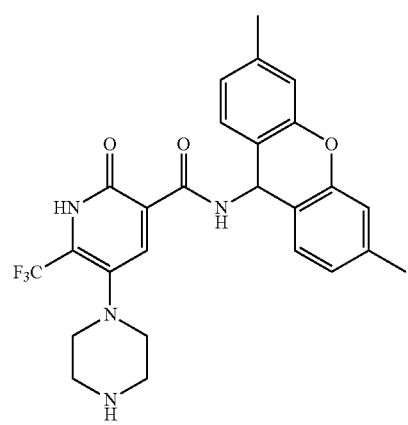
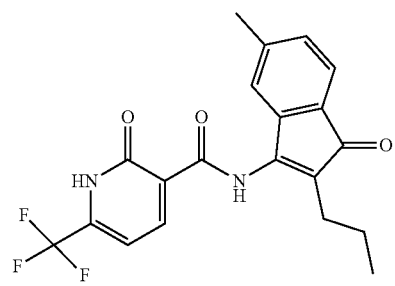
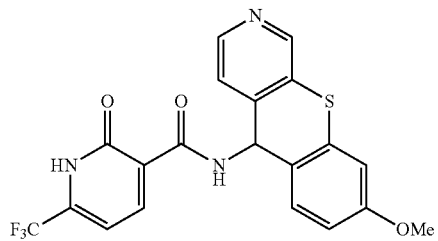
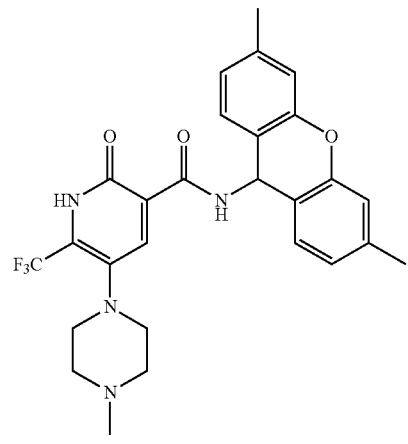
-continued
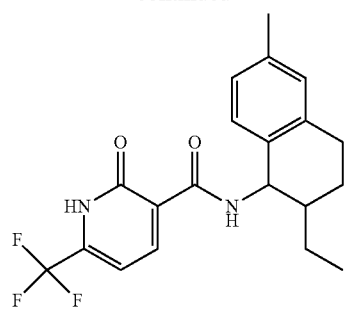
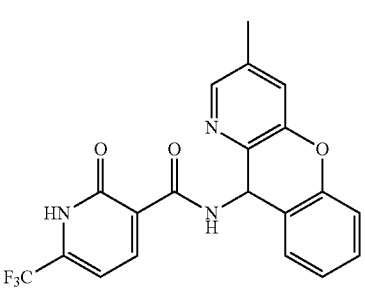
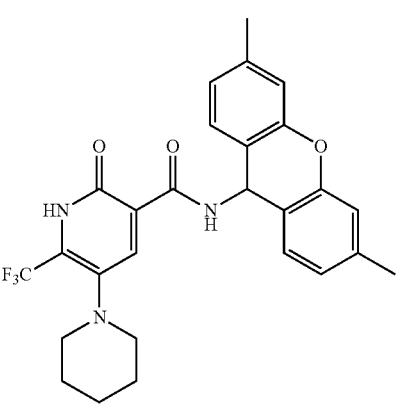
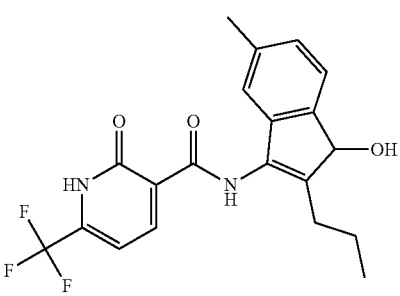
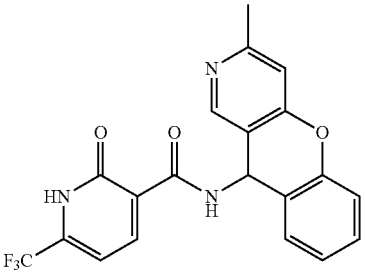

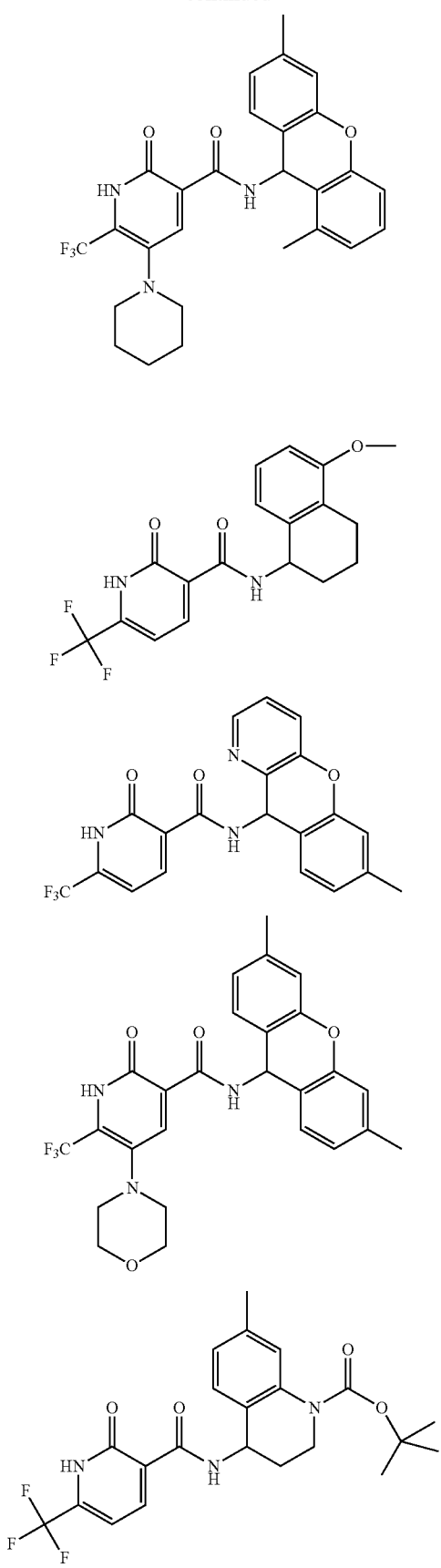
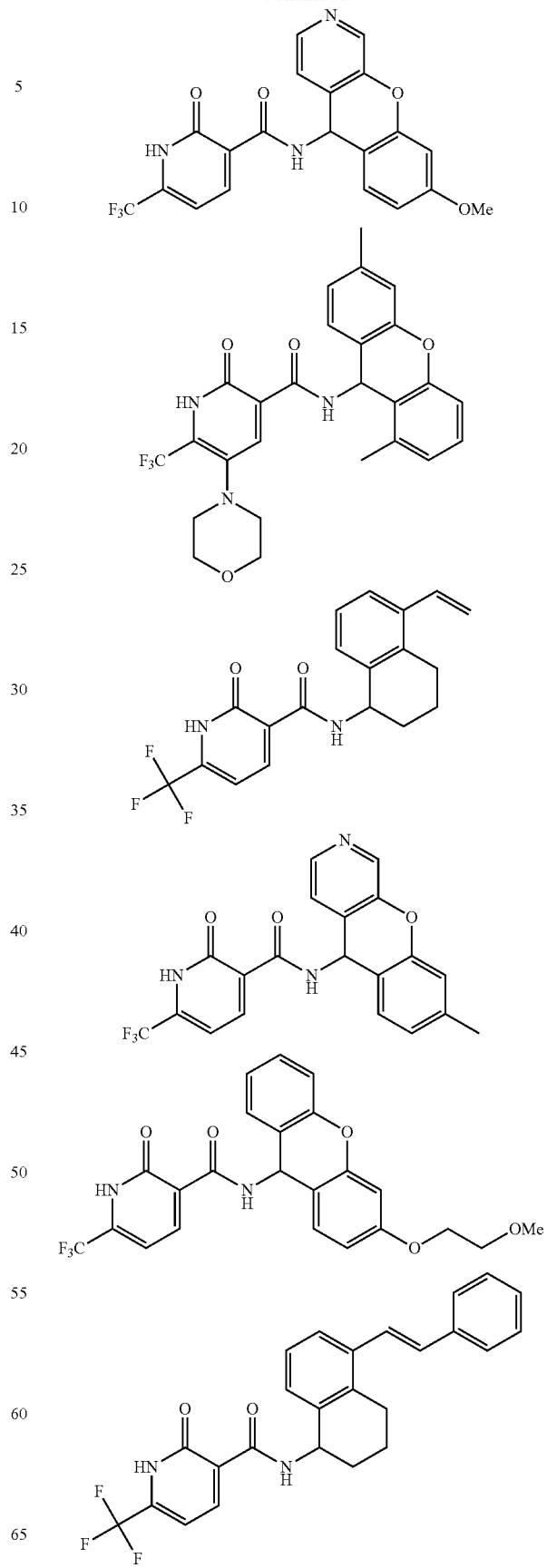

-continued
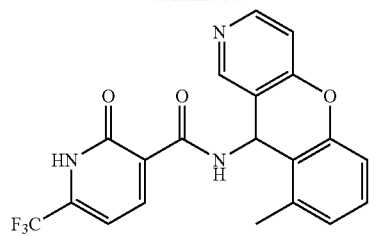
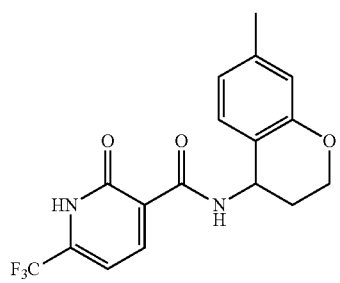
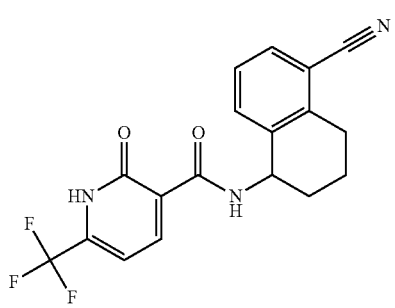
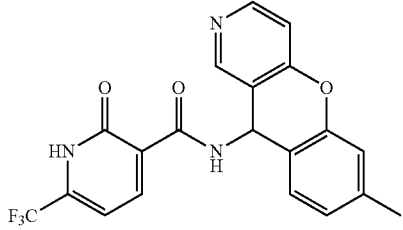
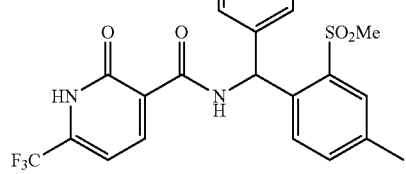
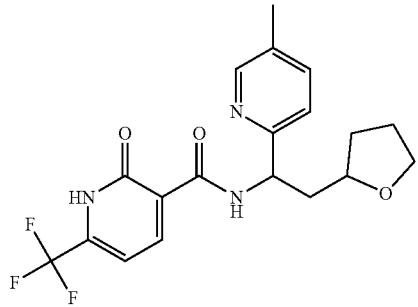
-continued
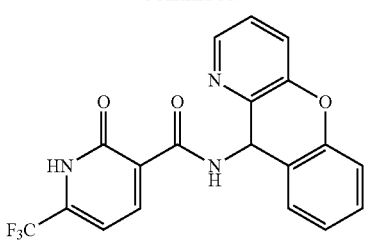
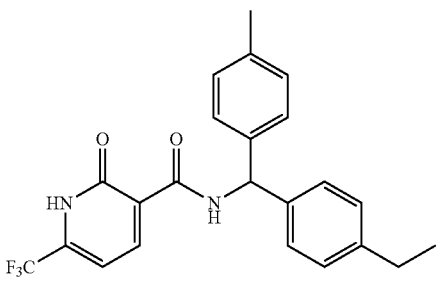
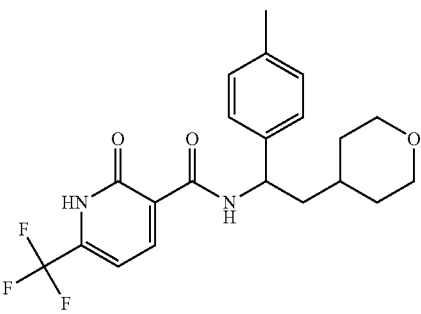
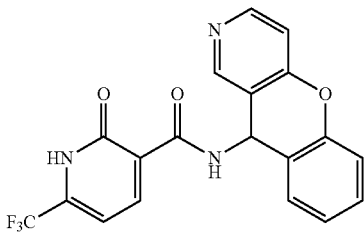
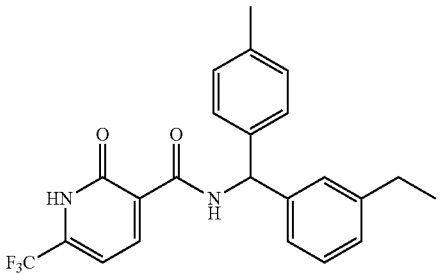
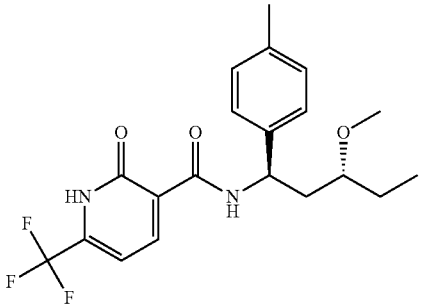

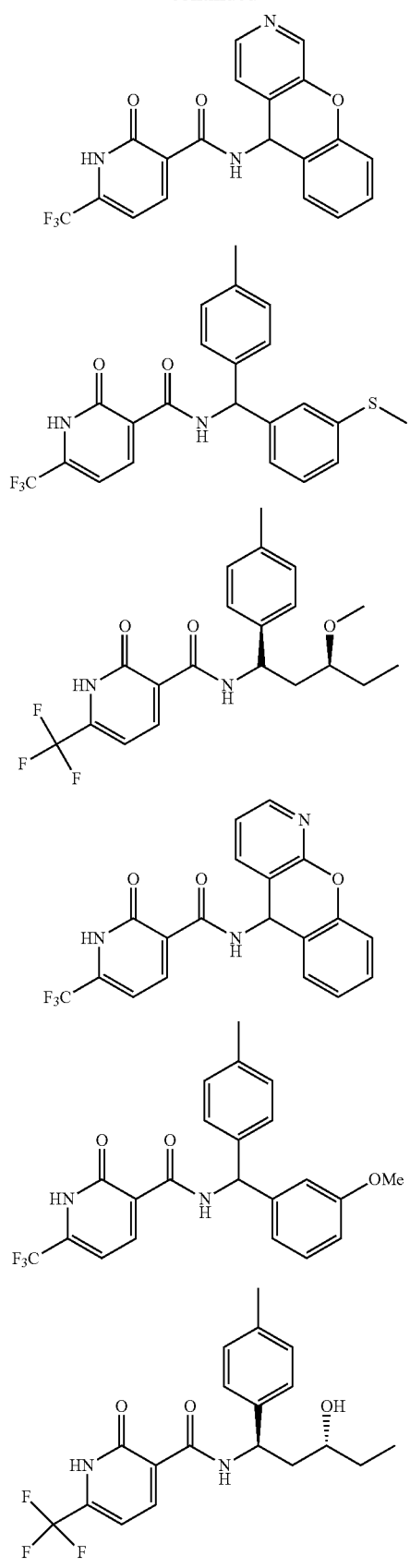
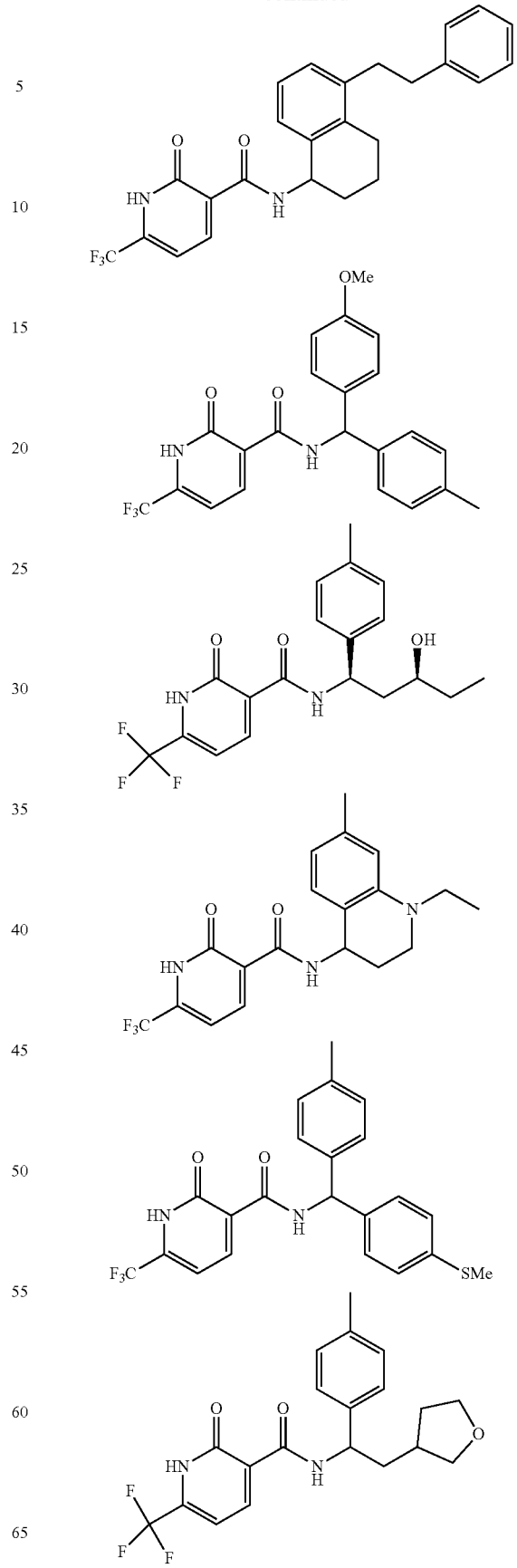

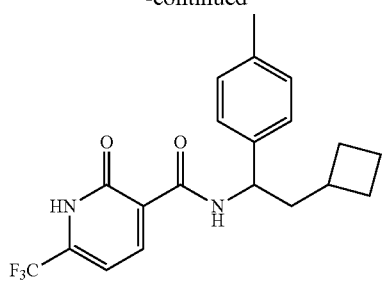
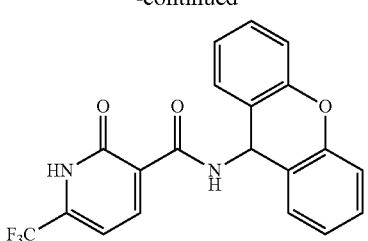
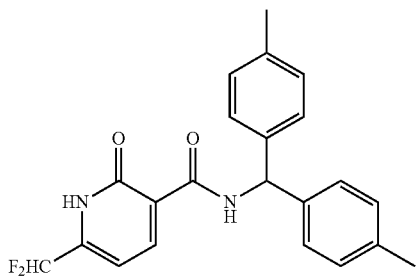
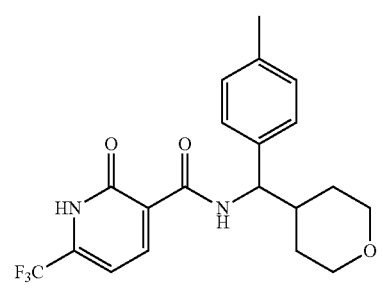
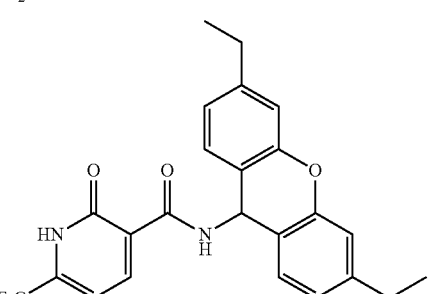
In one embodiment, the compound is one of the following or a pharmaceutically acceptable salt thereof:
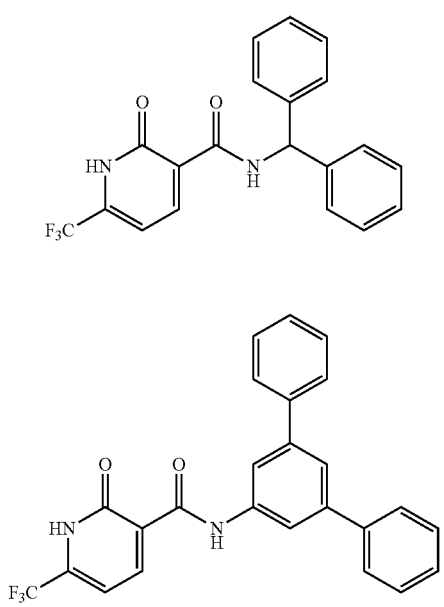
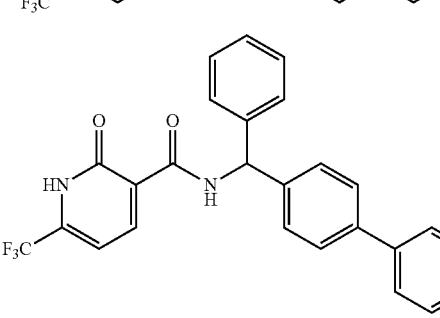
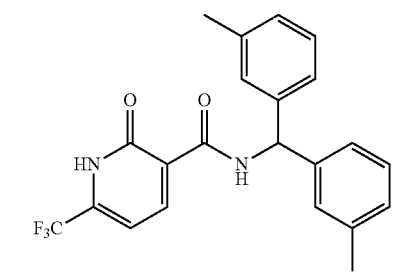
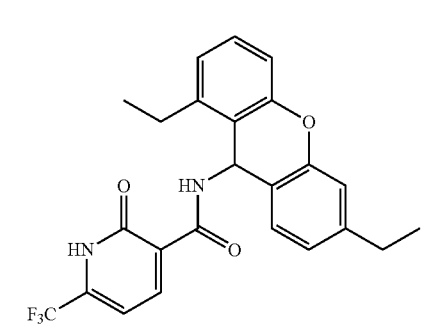
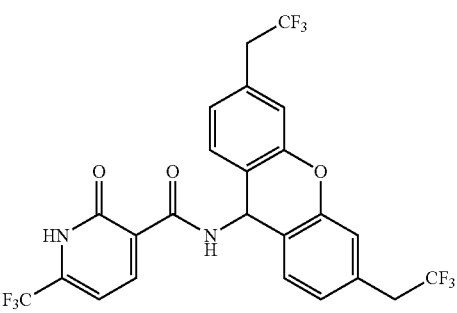

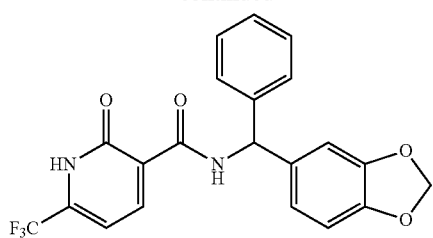
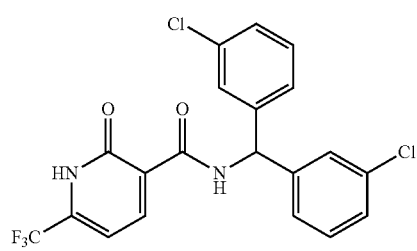
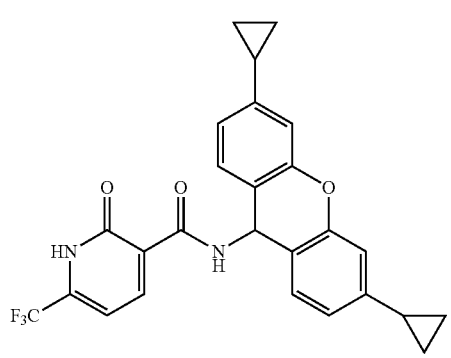
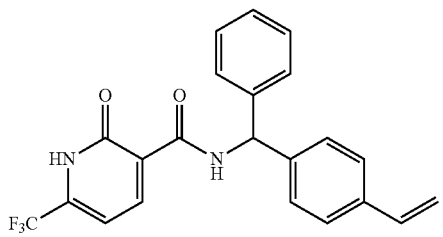
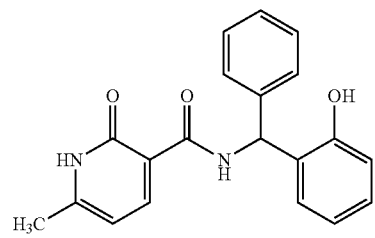
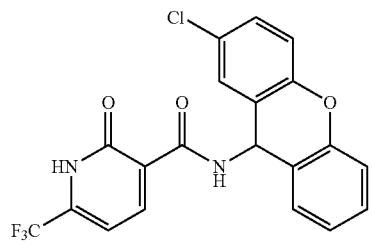
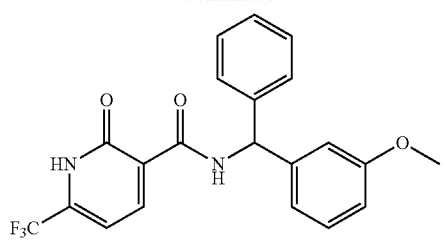
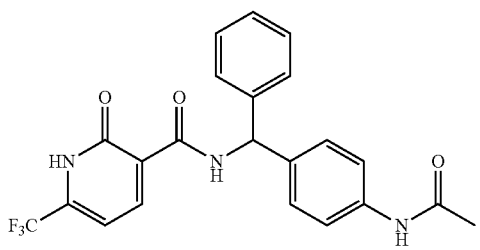
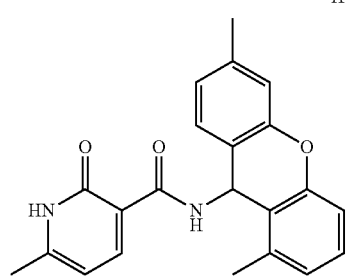
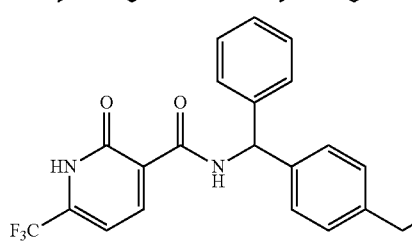
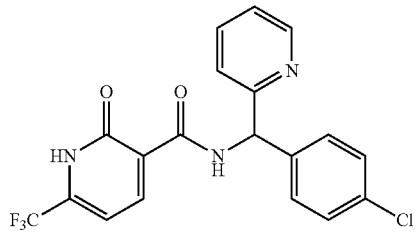
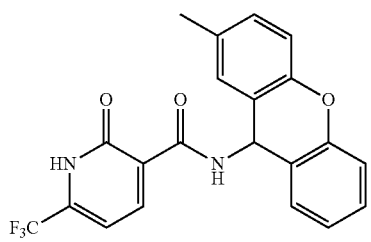
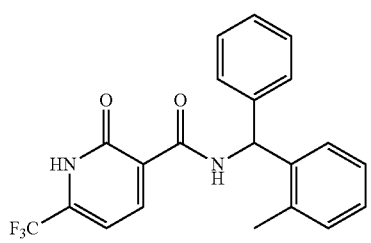

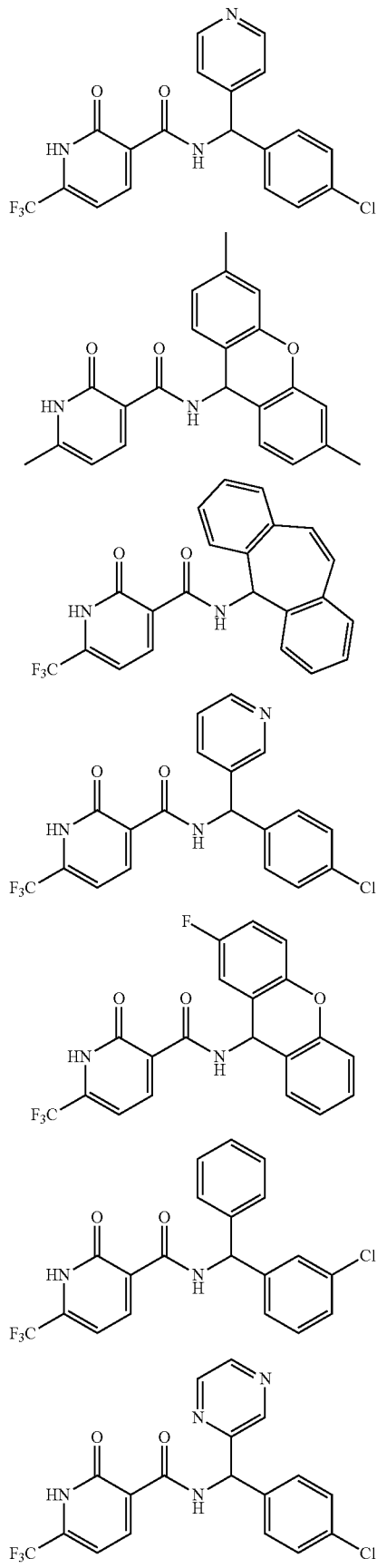
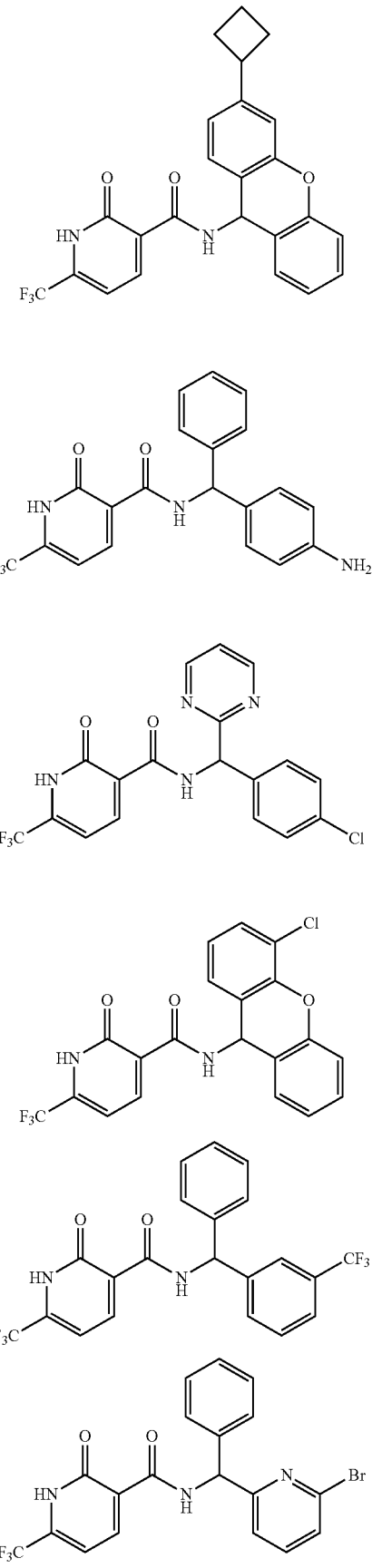

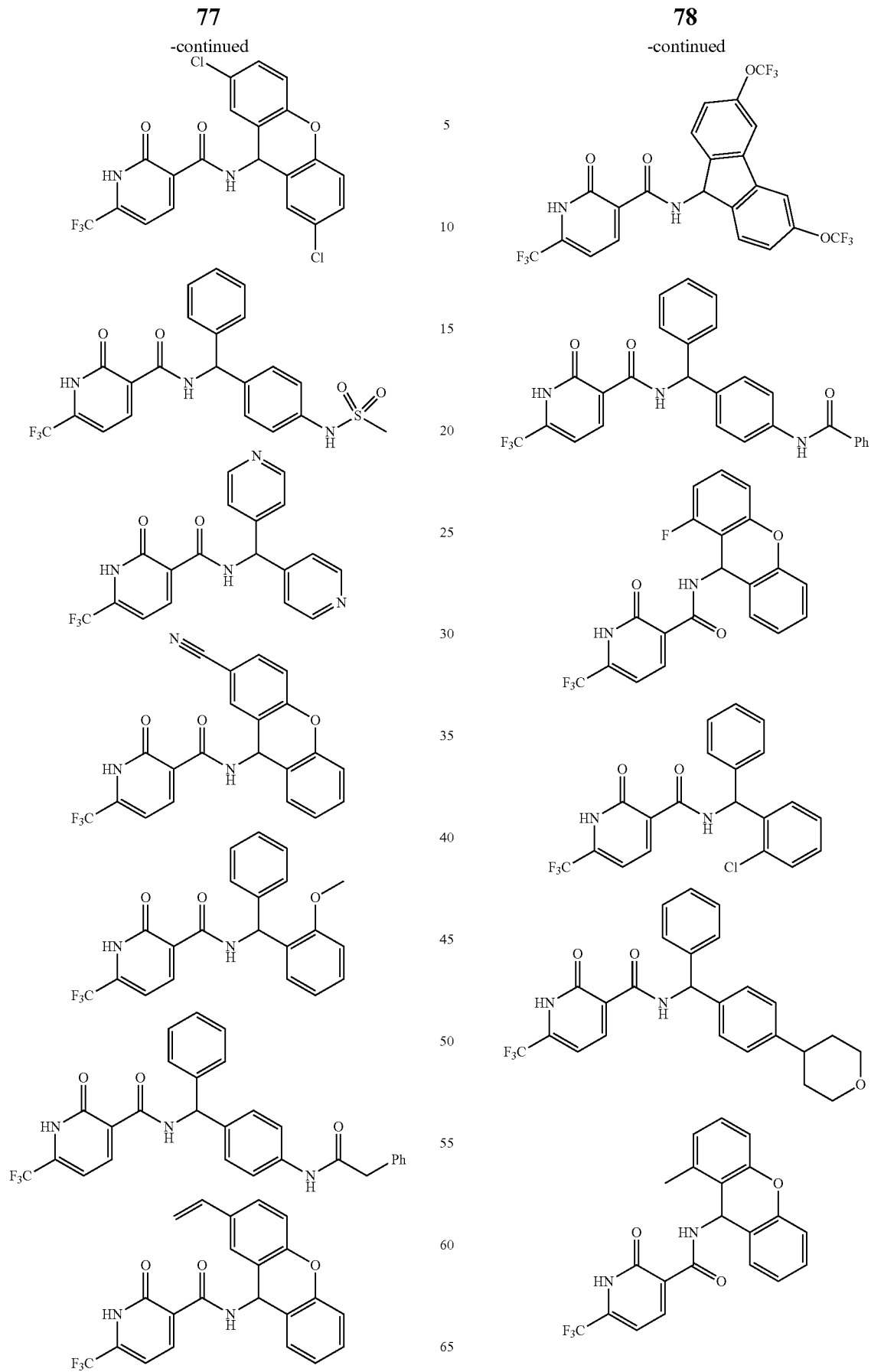

-continued
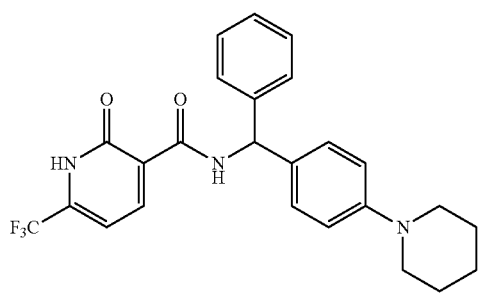
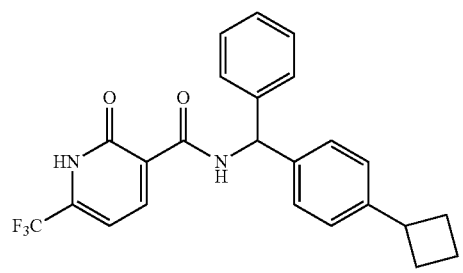
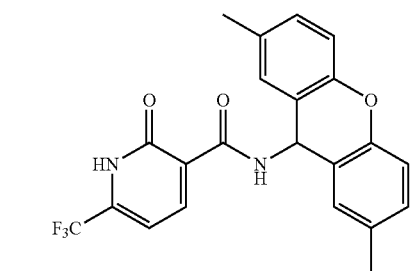
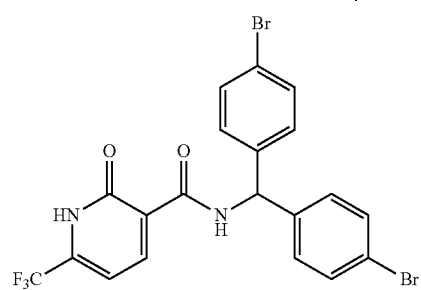
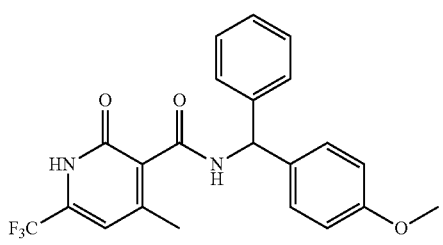
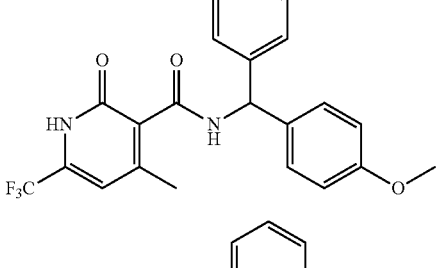
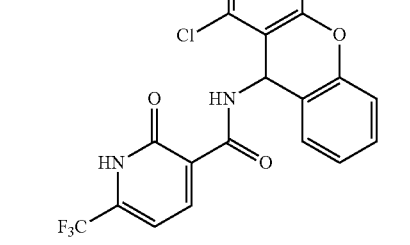
-continued
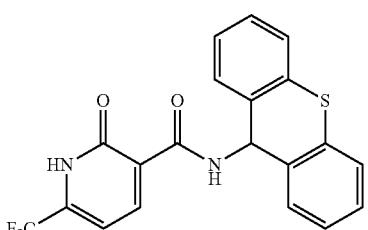
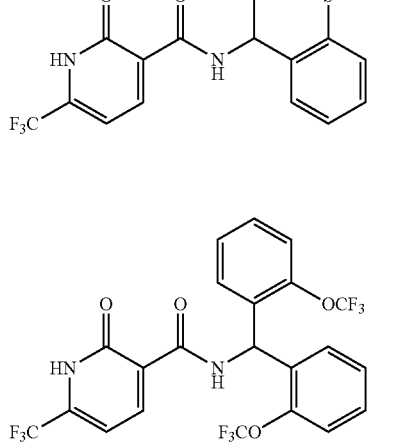
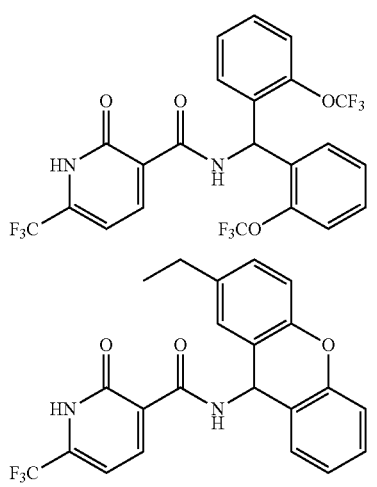
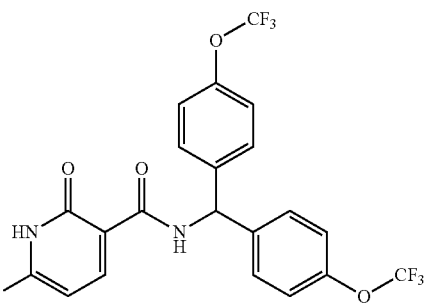
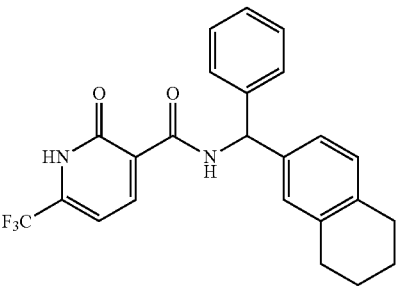
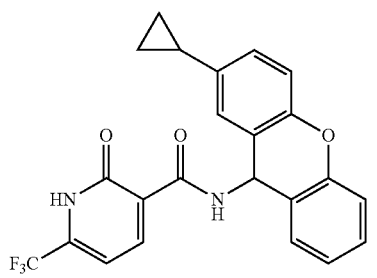

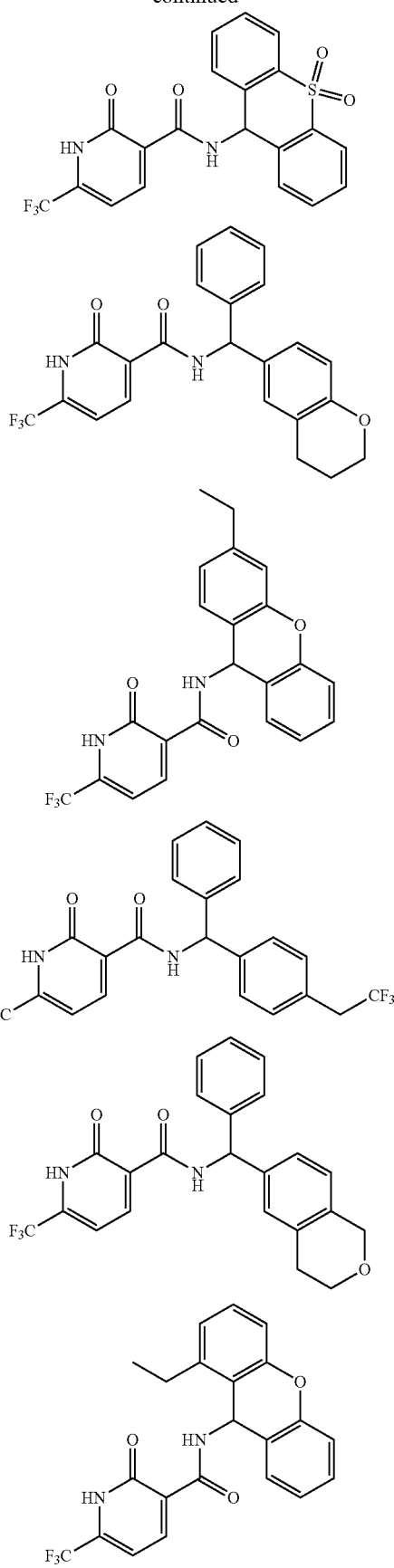
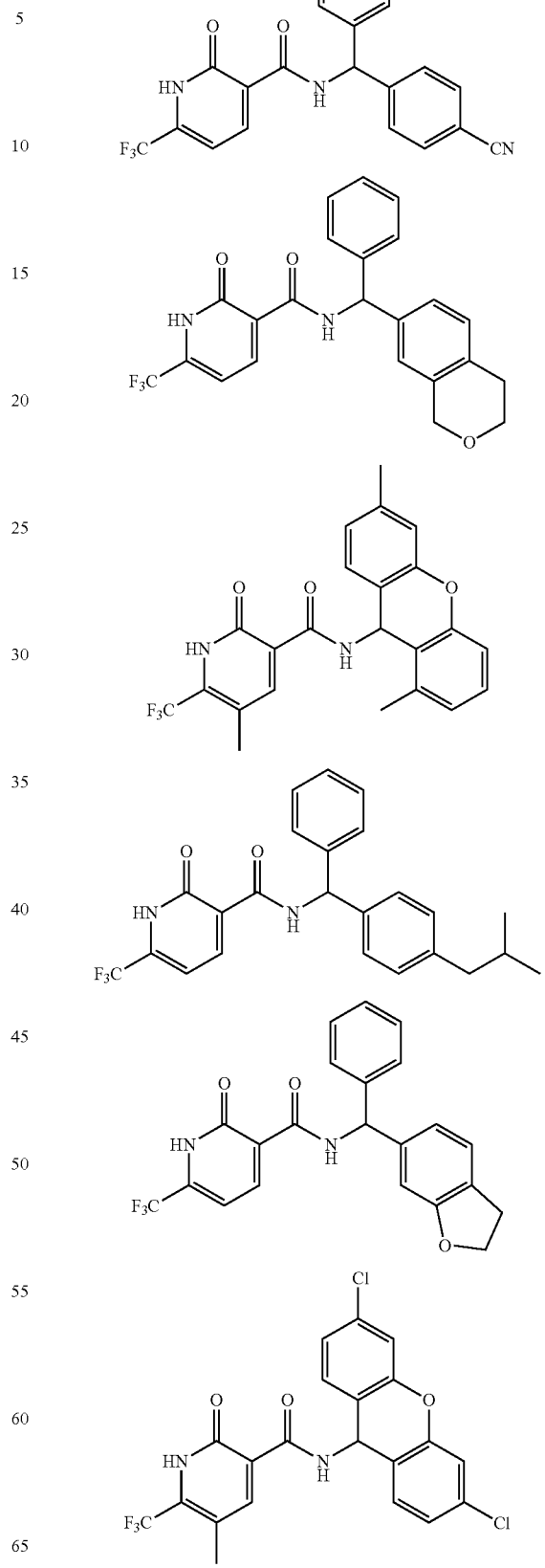

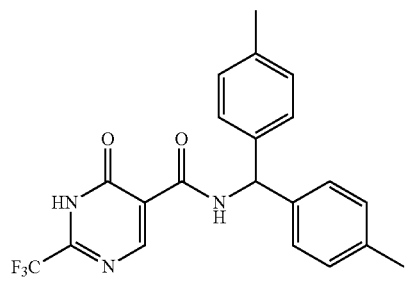
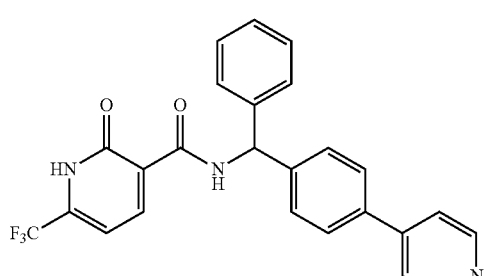
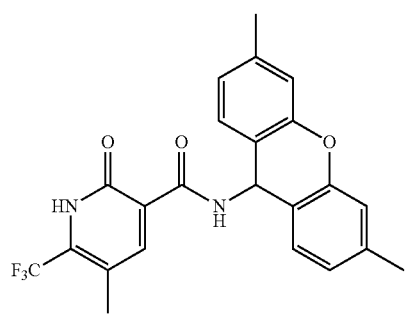
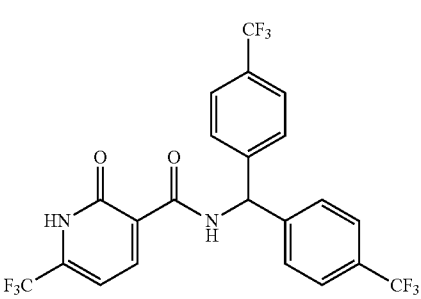
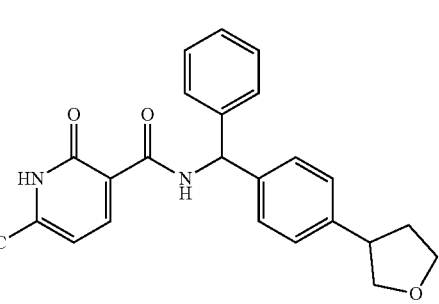
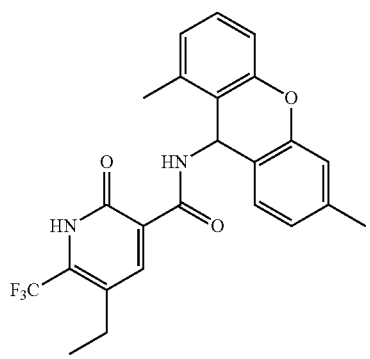
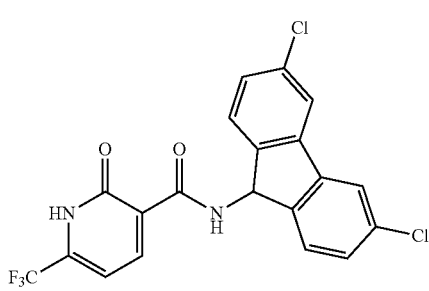
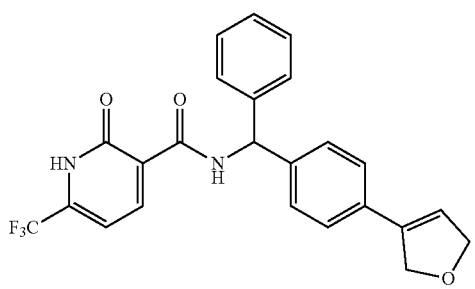
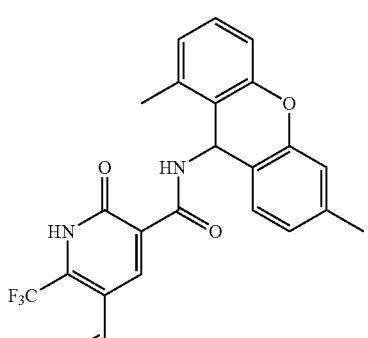
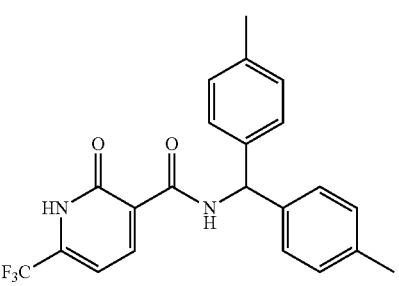

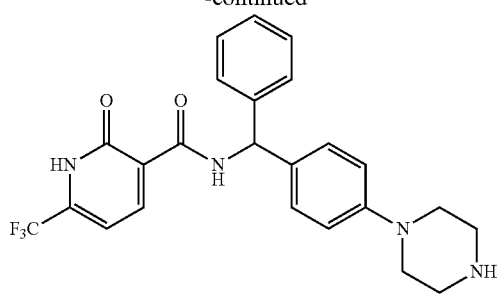
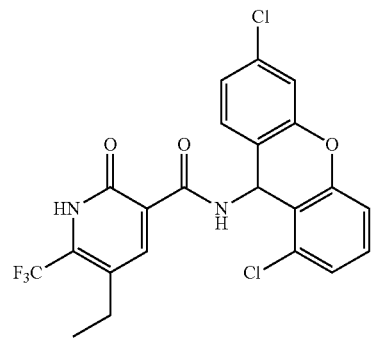
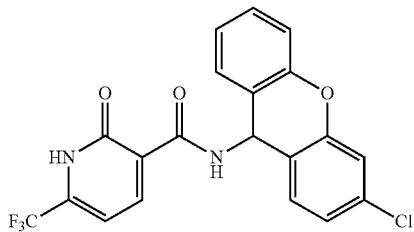
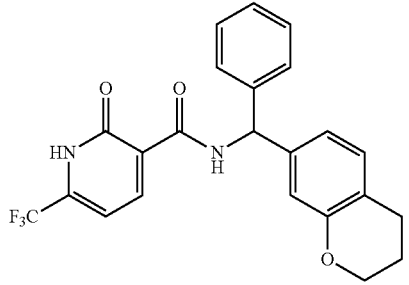
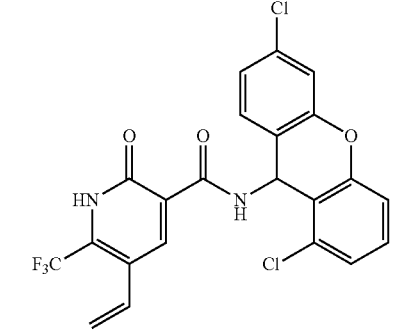
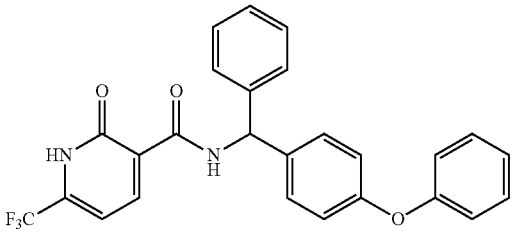
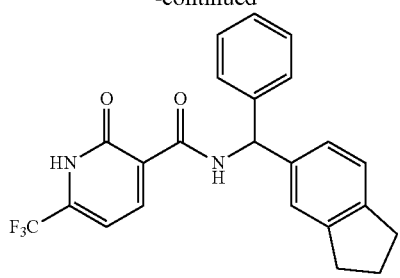
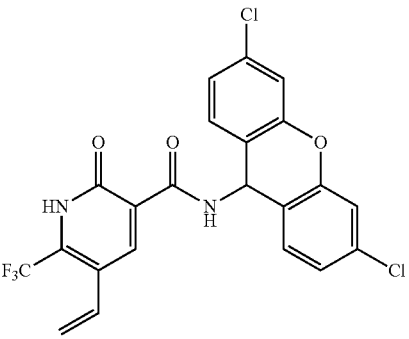
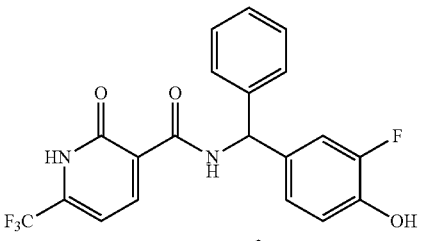
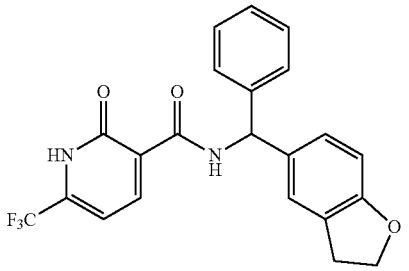
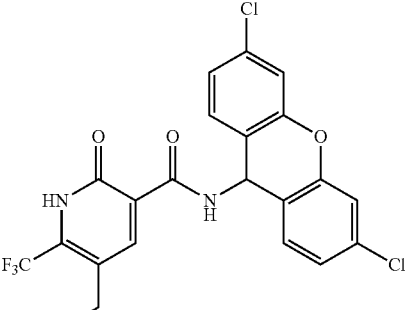
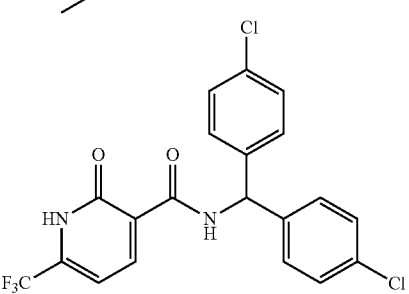

-continued
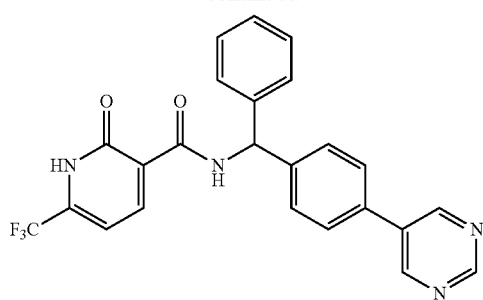
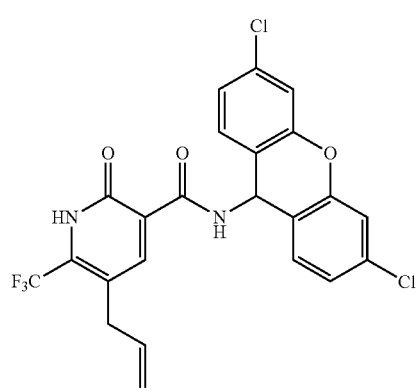
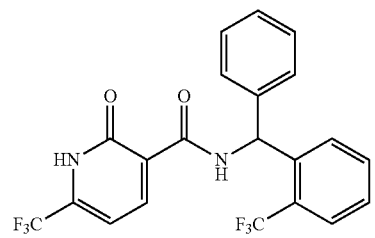
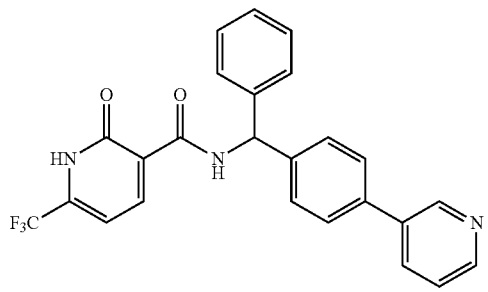
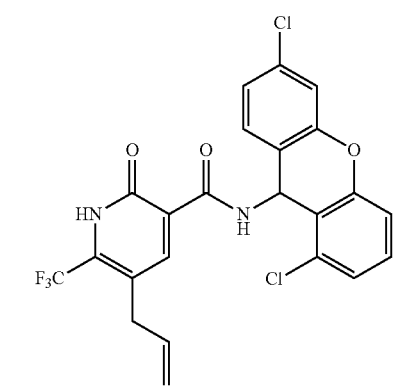
-continued
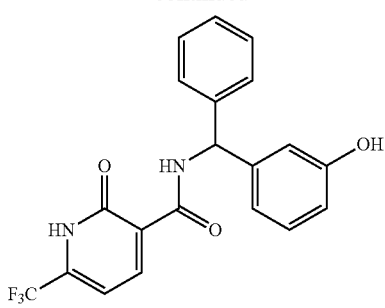
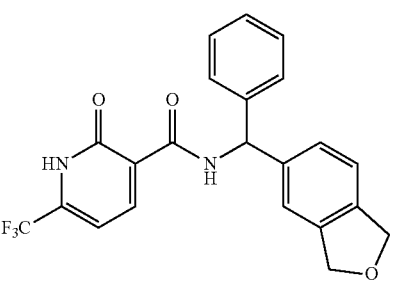
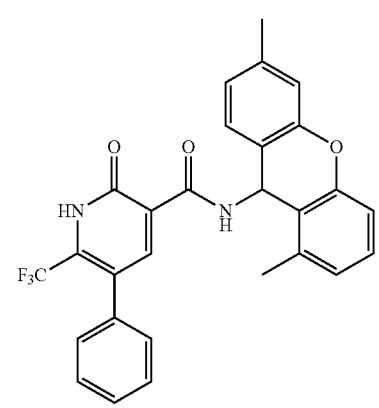
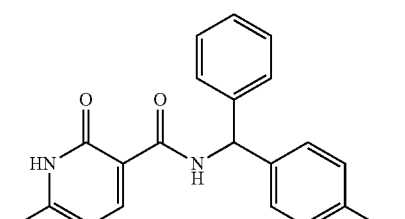
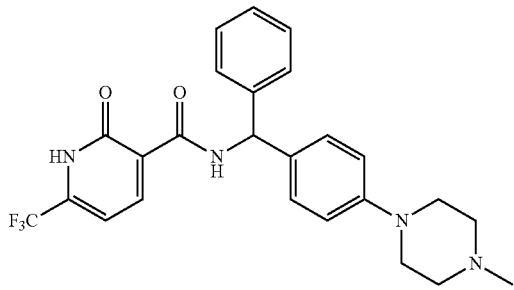

89
-continued
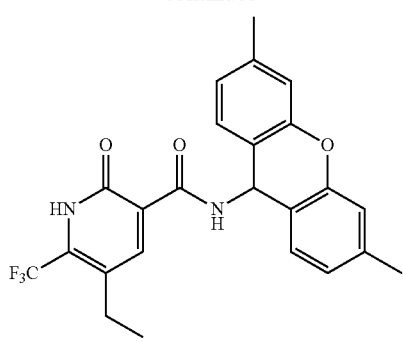
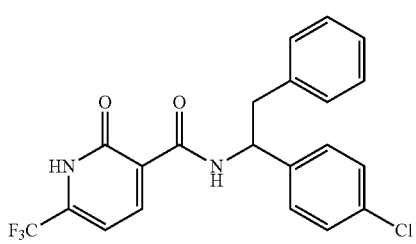
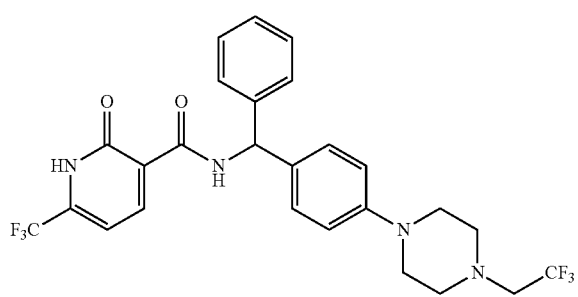
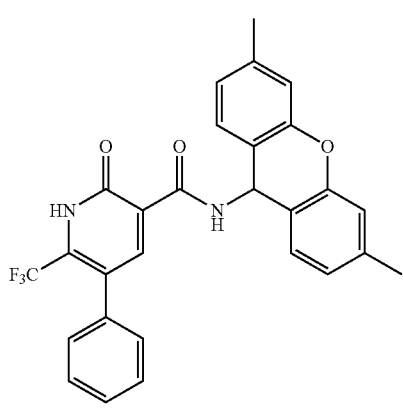
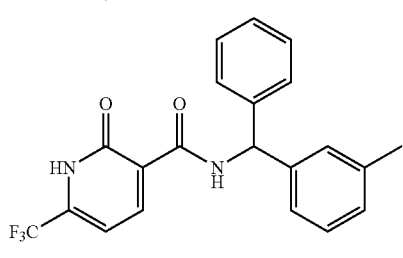
90
-continued
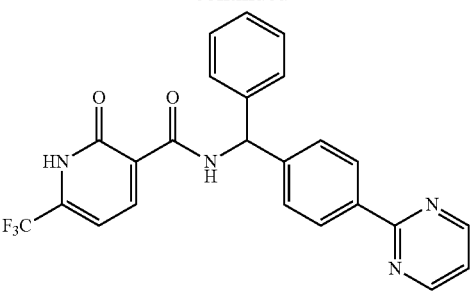
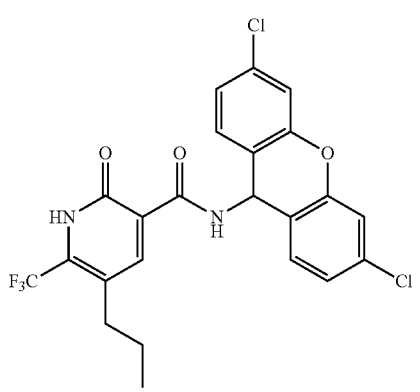
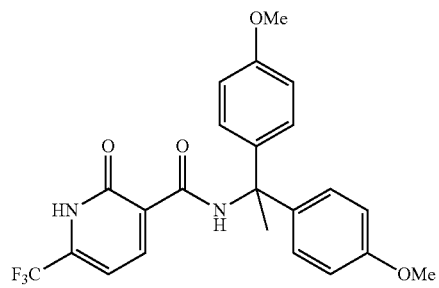
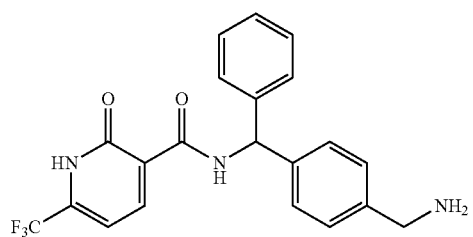
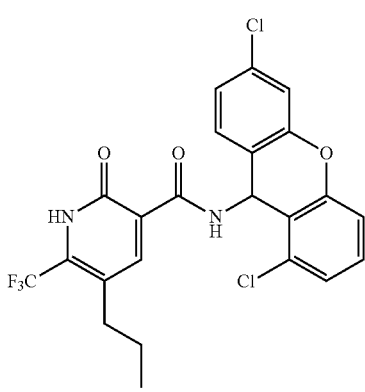

-continued
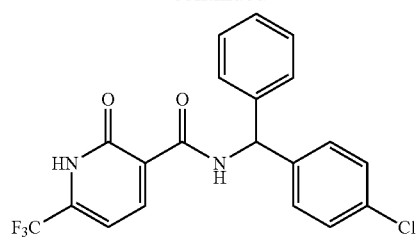
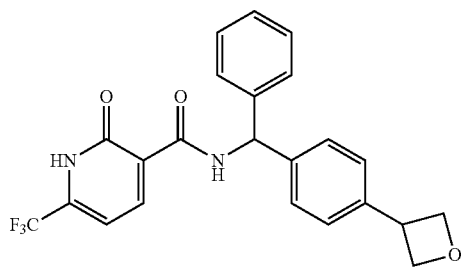
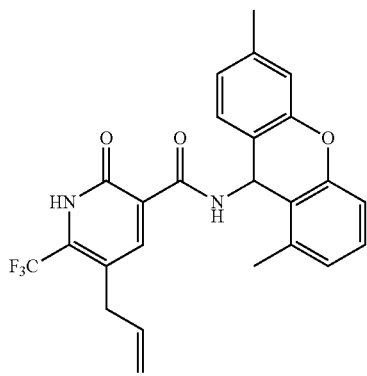
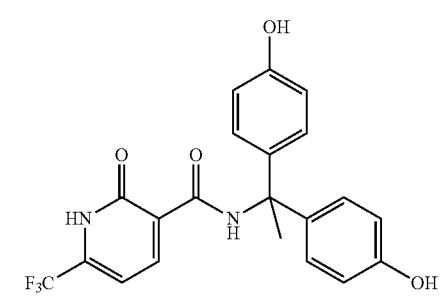
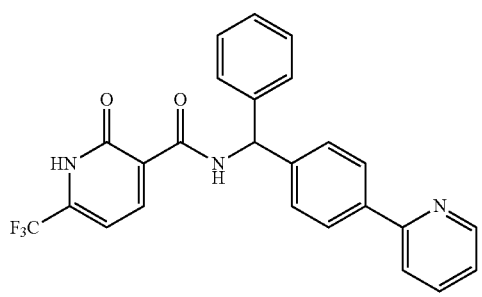
-continued
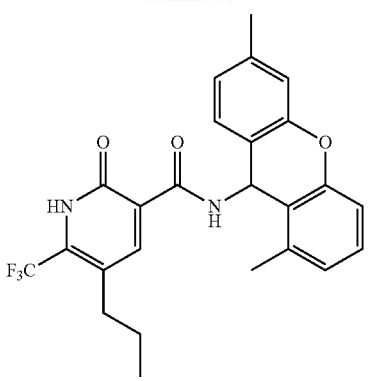
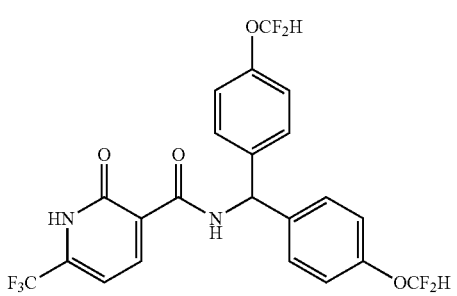
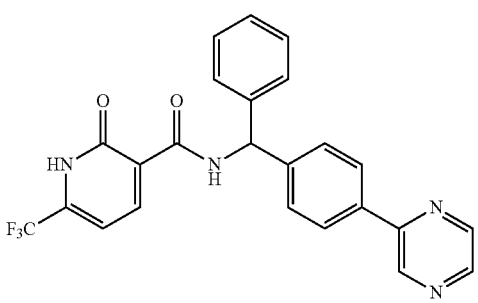
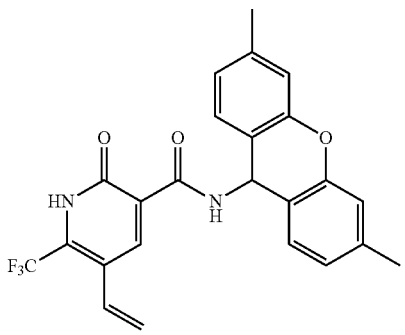
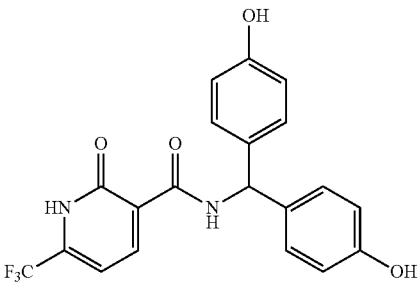

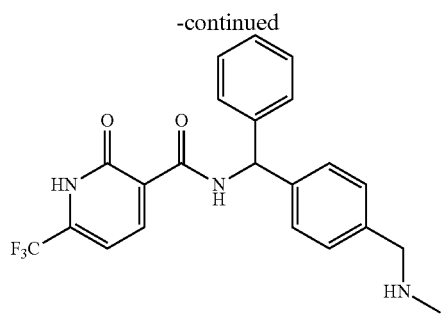
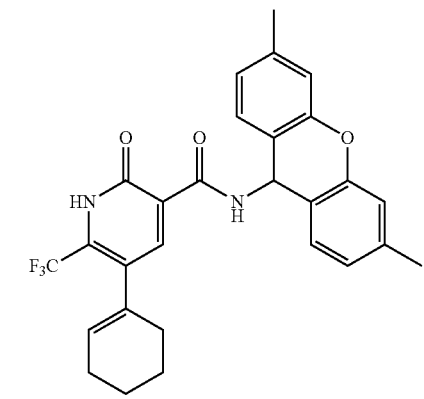
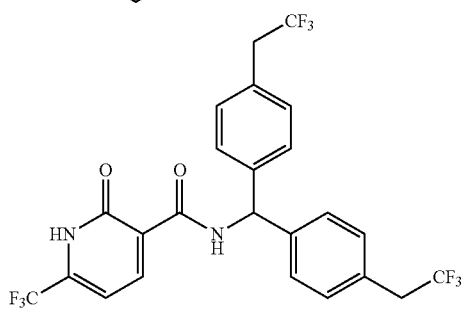
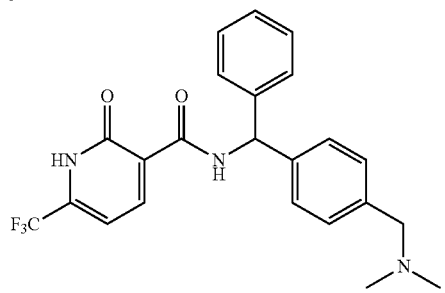
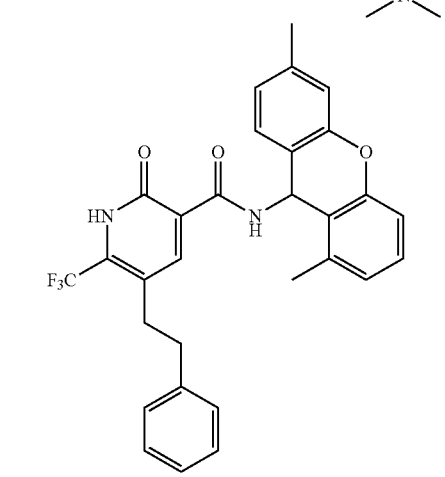
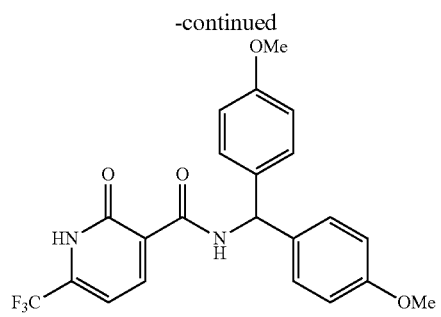
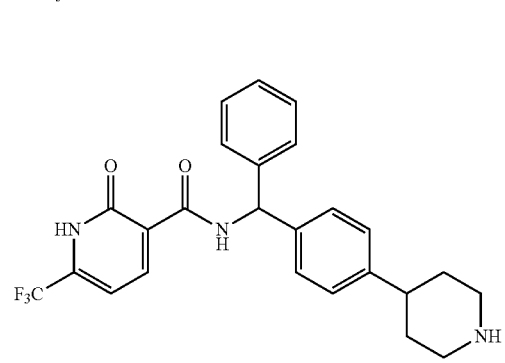
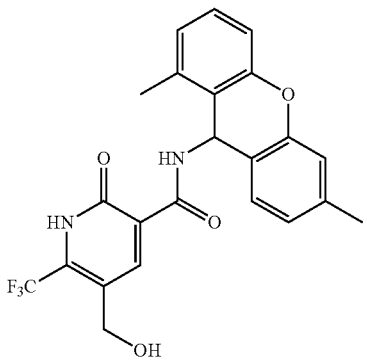
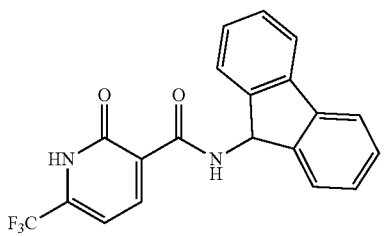
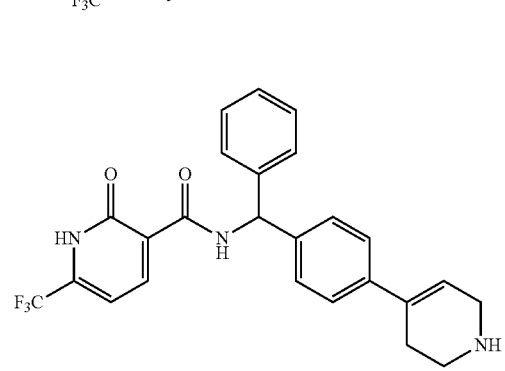

95
-continued
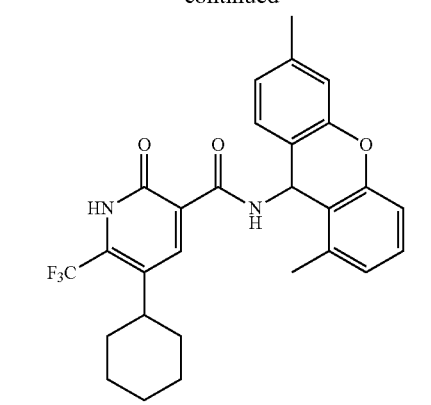
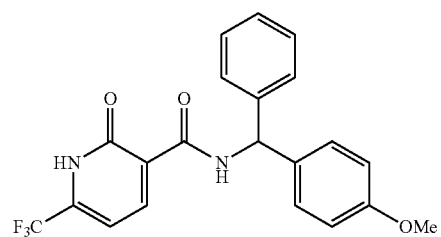
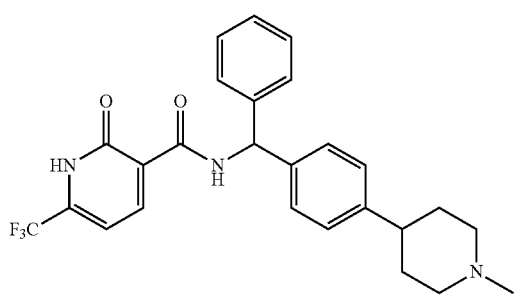
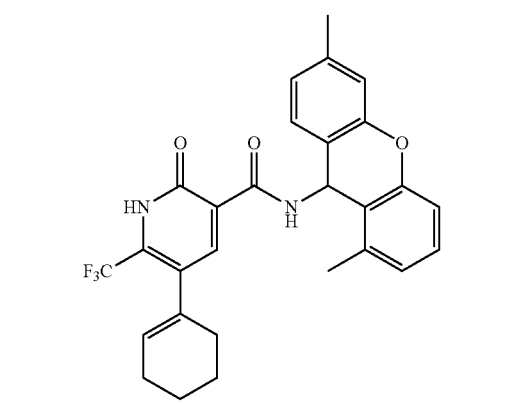
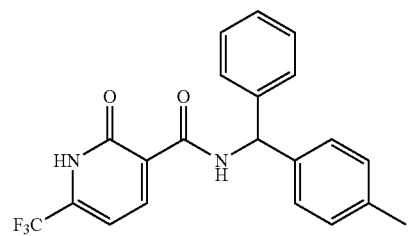
96
-continued
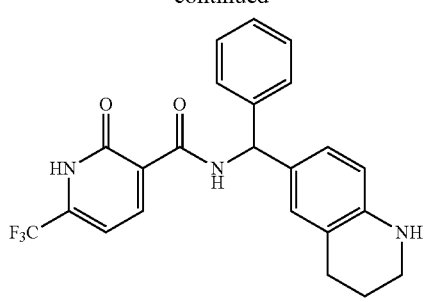
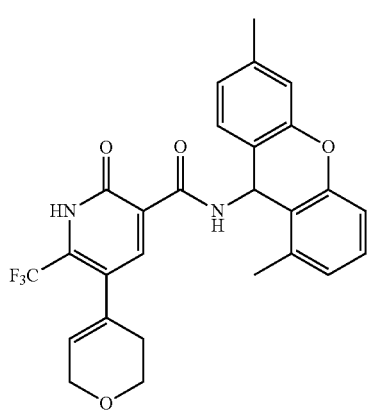
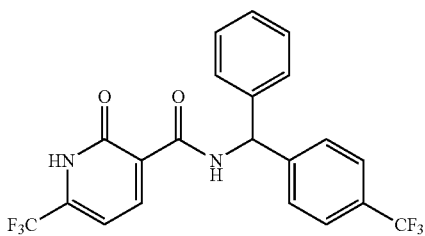
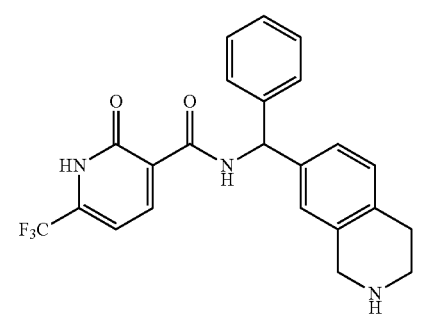
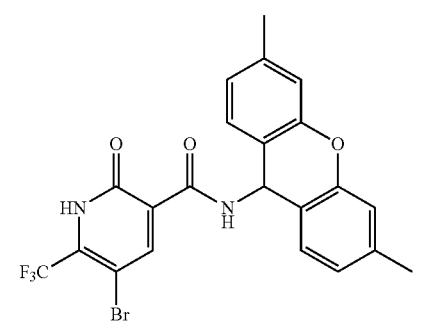

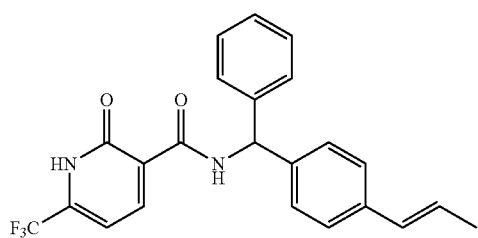
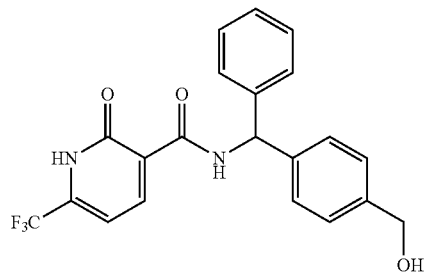
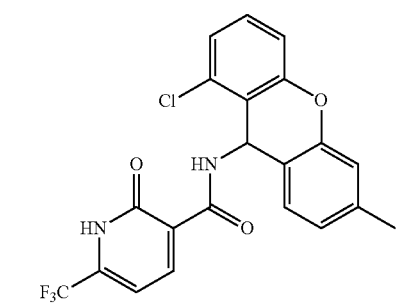
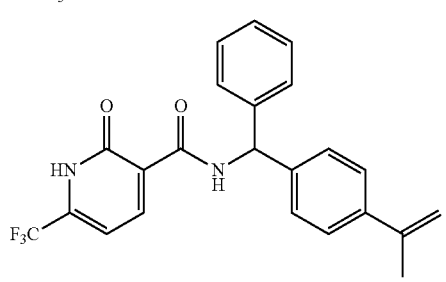
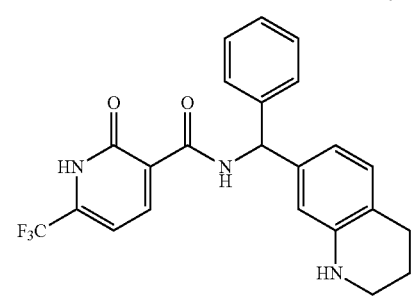
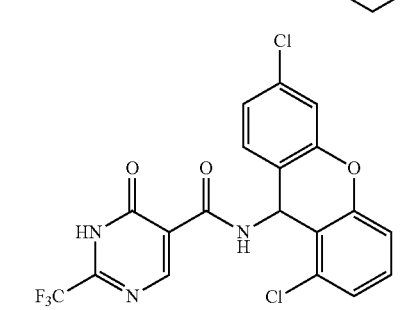
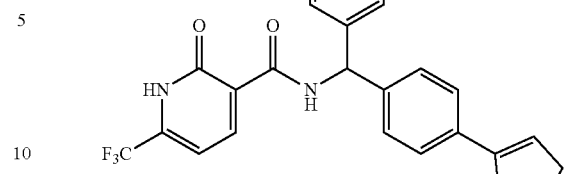
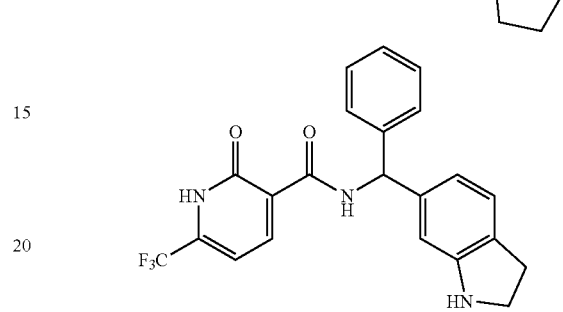

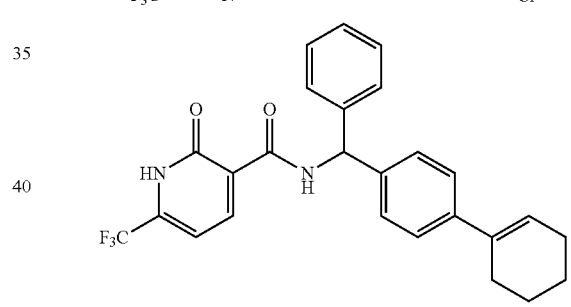
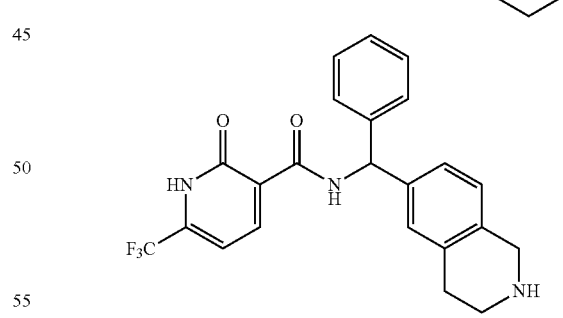
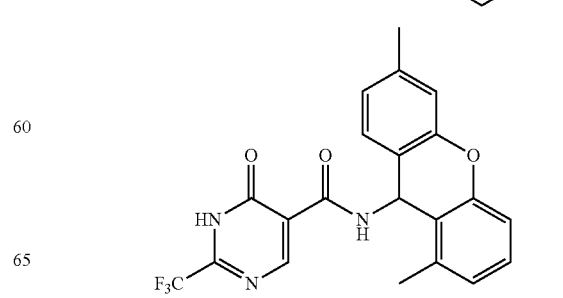

-continued
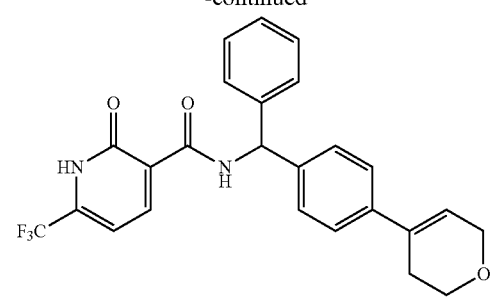
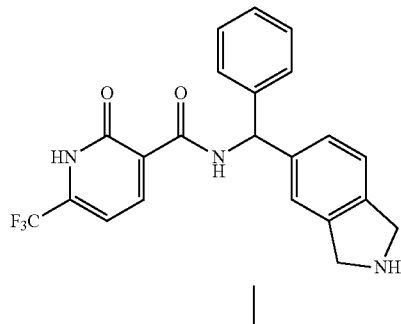
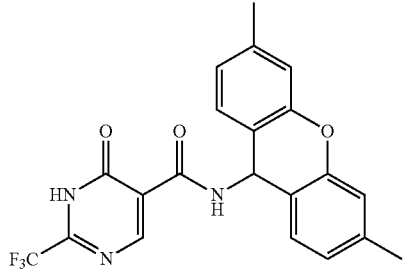
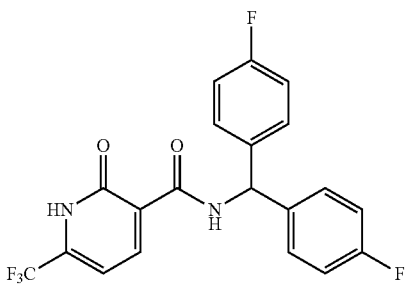
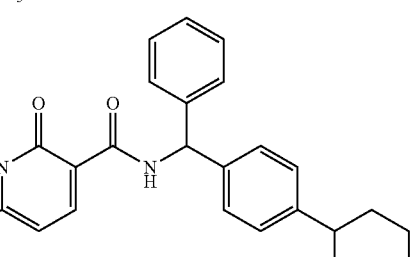
-continued
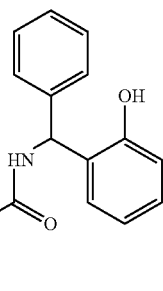
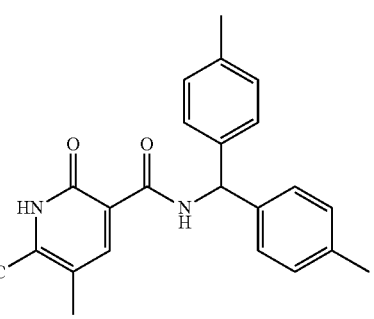
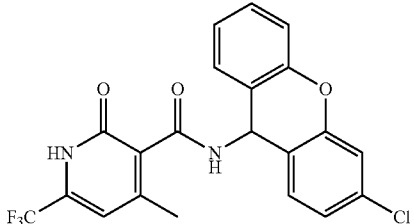
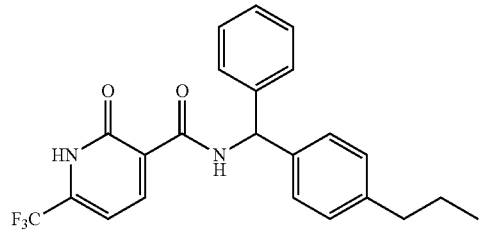
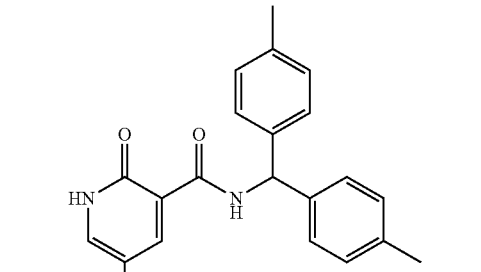
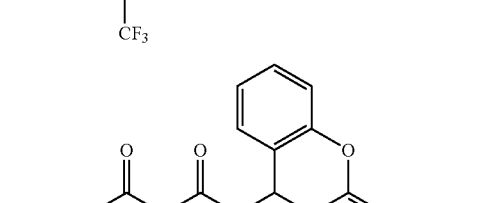

-continued
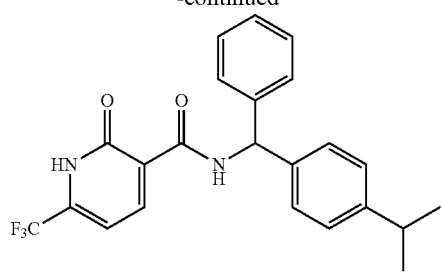
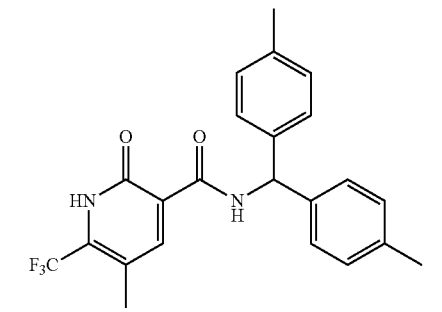
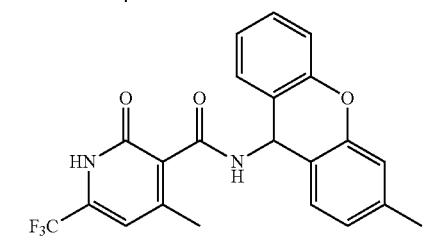
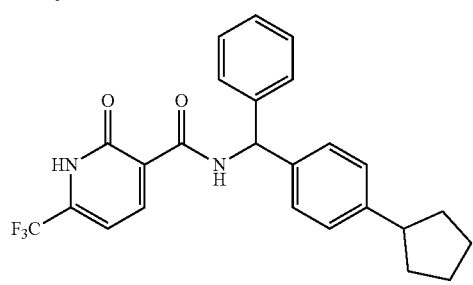
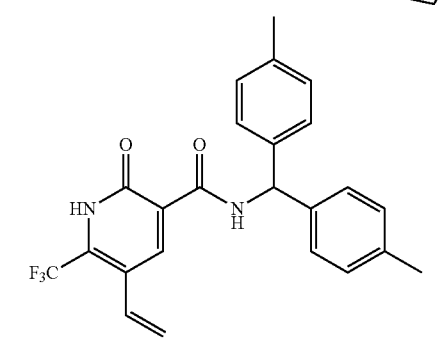
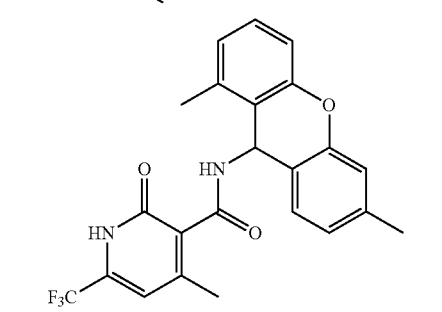
-continued
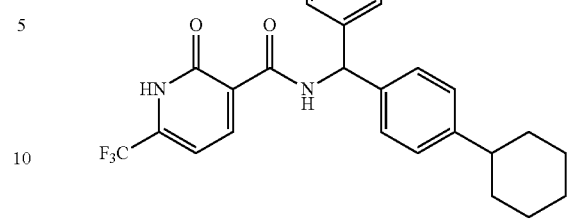
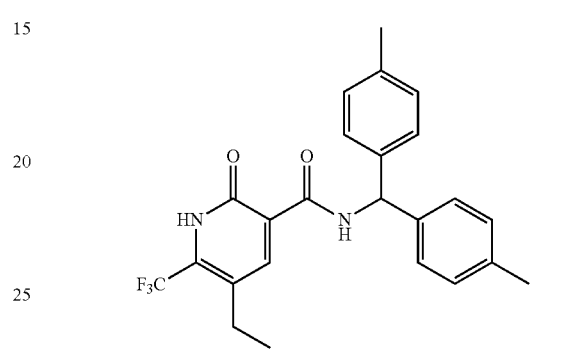
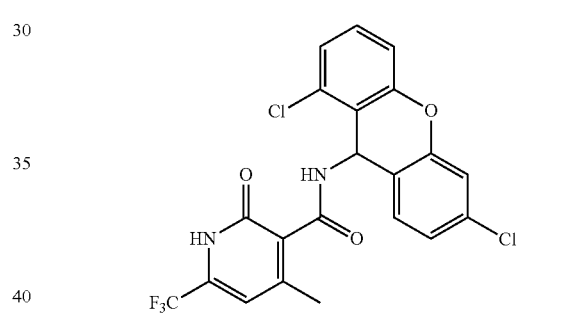
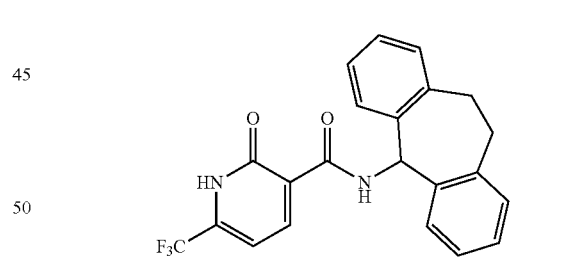
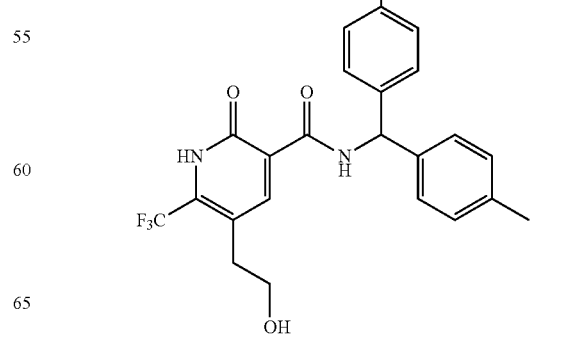

-continued
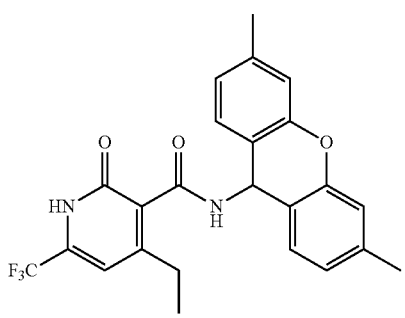
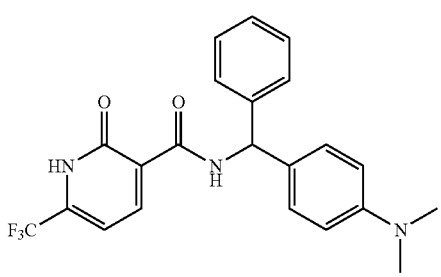
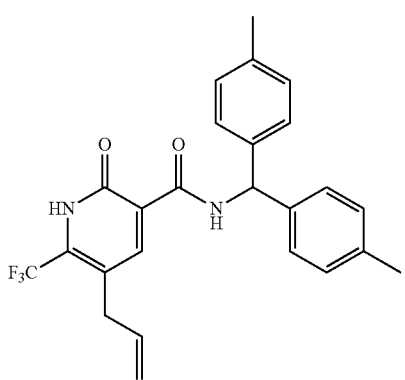
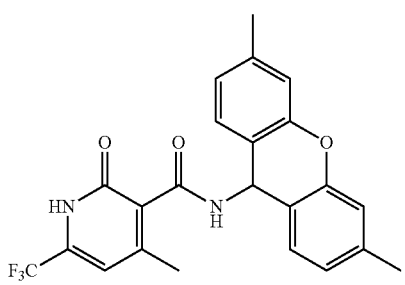
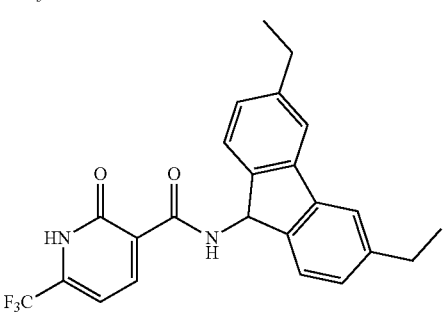
-continued
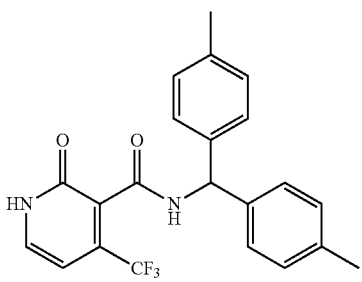
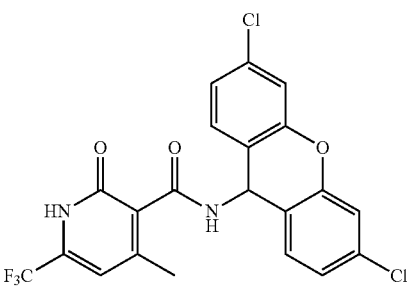
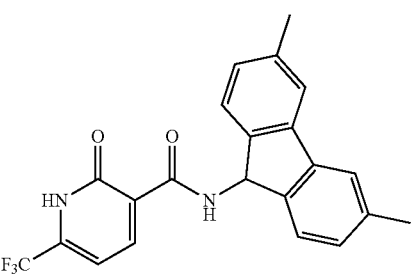
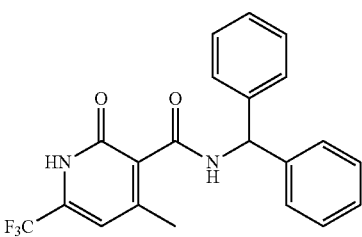
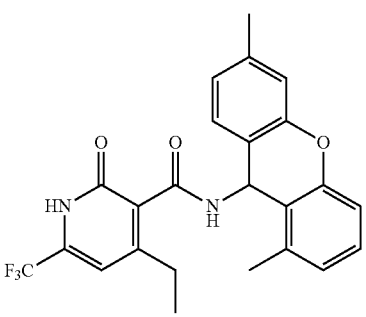
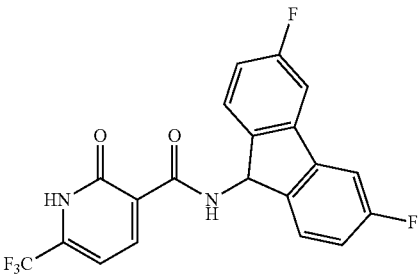

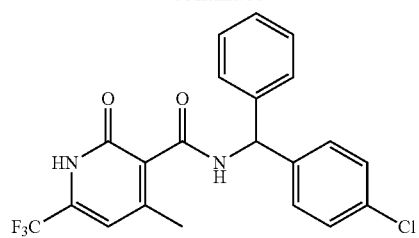
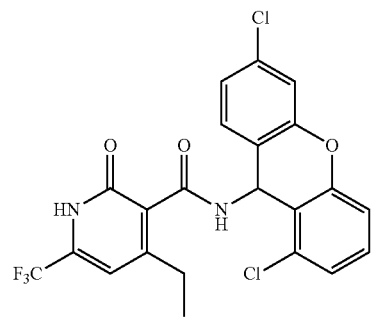
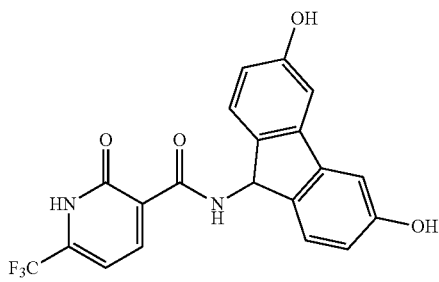
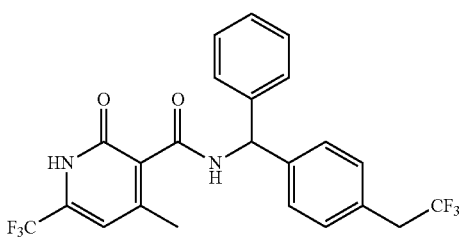
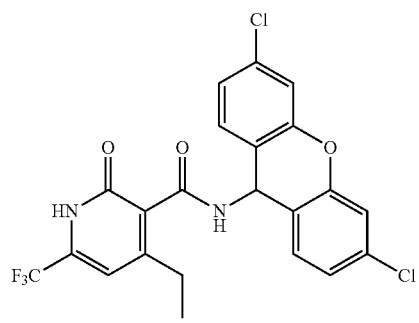
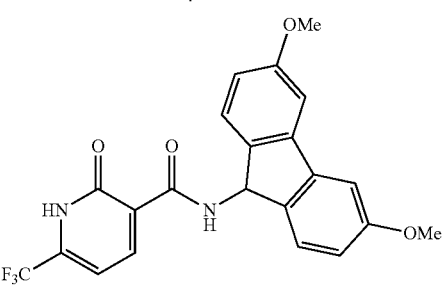
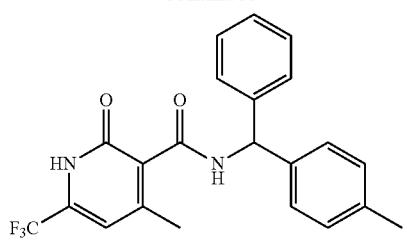
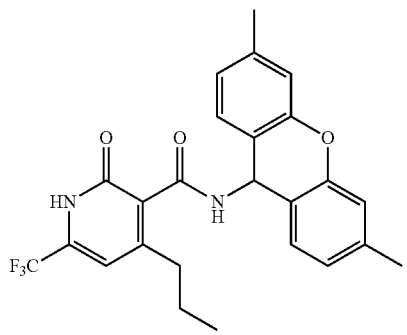
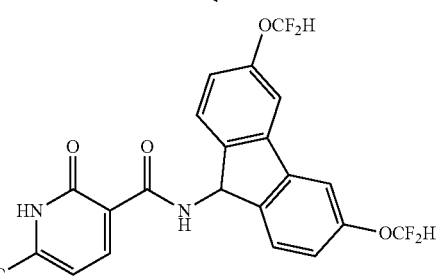
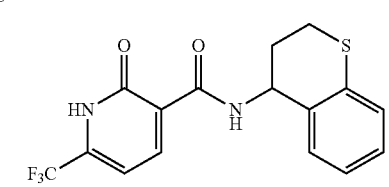
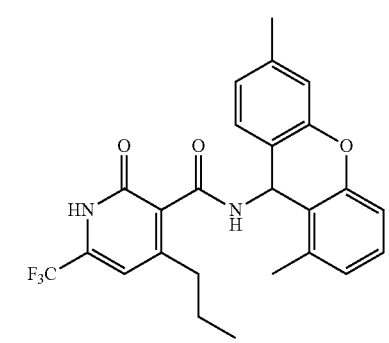
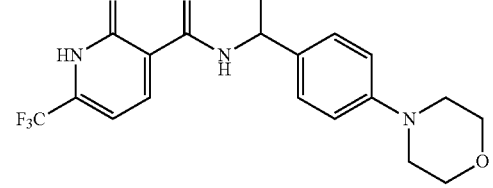

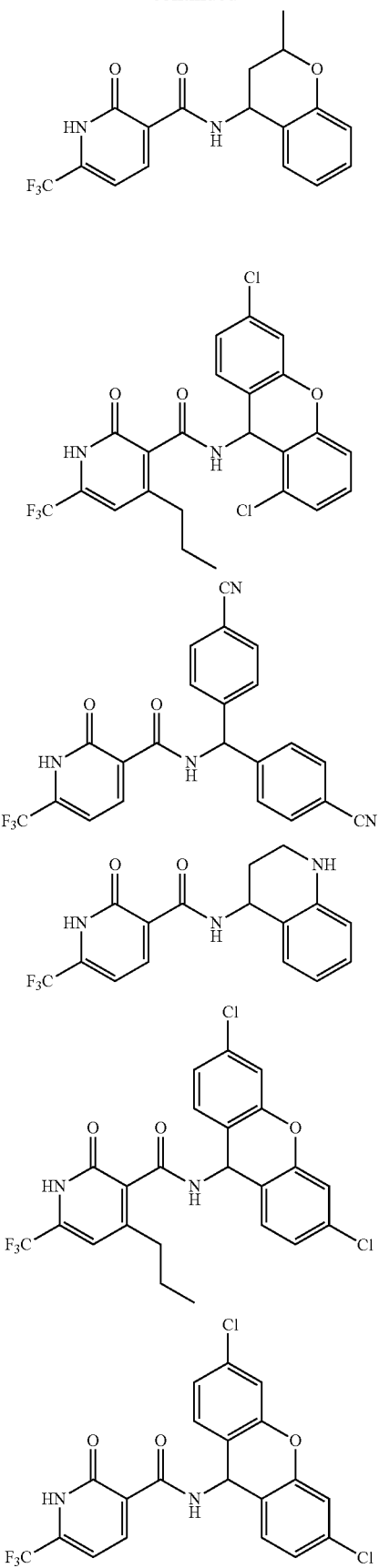
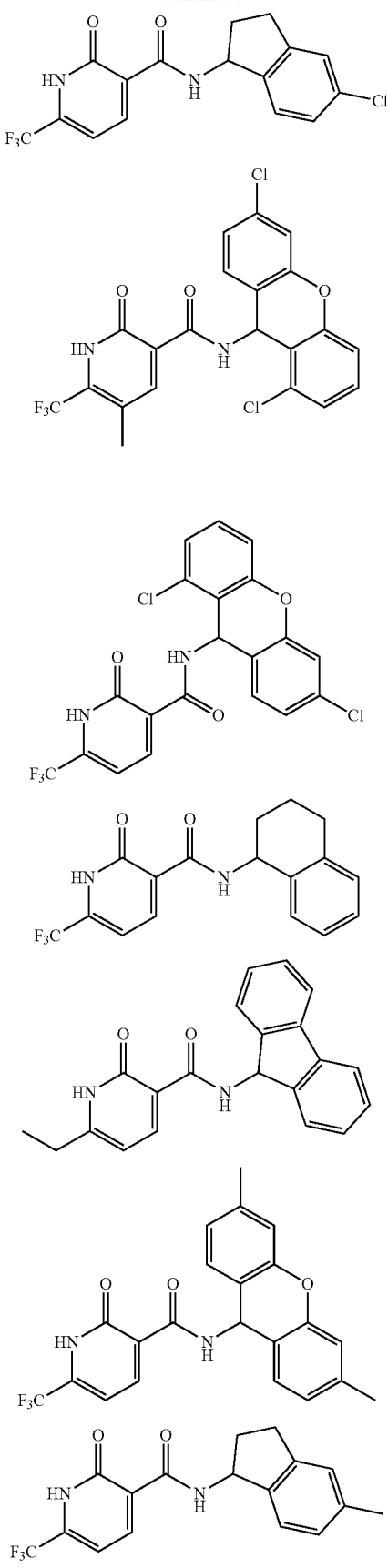

-continued
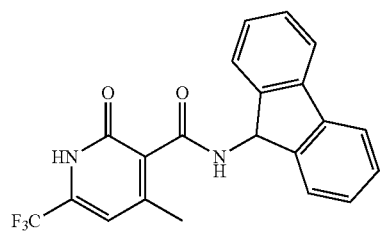
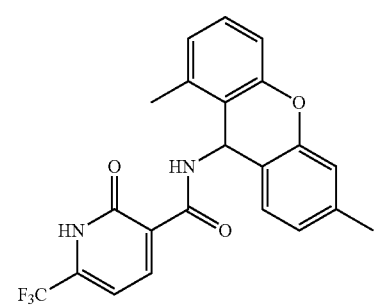
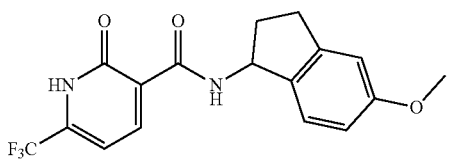
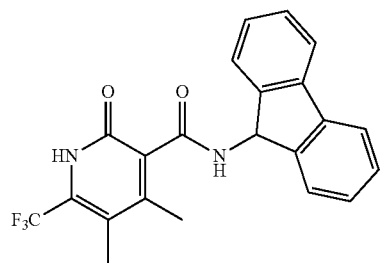
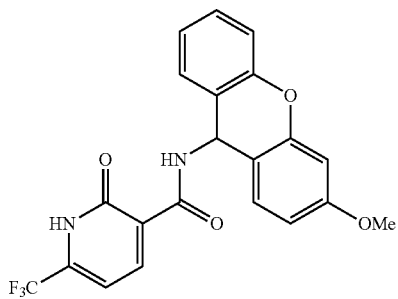
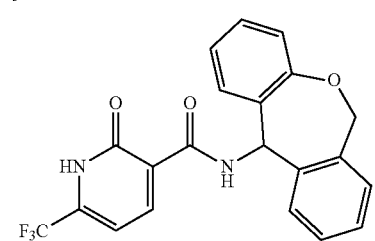
-continued
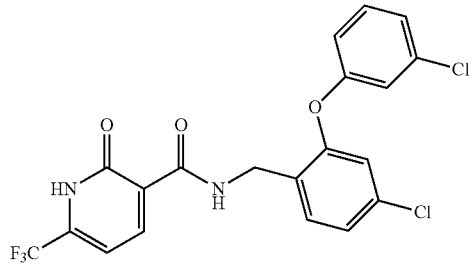
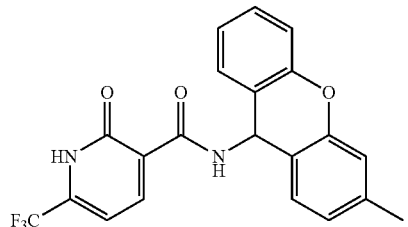
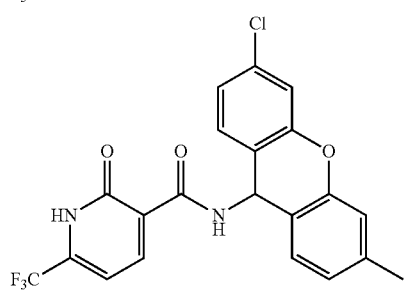
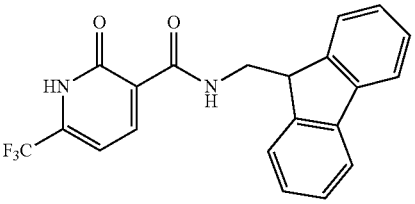
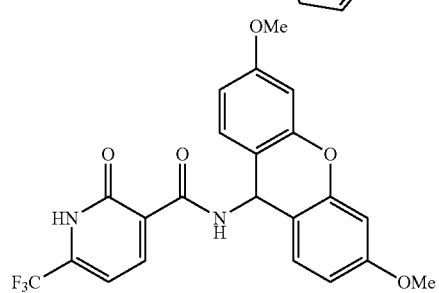
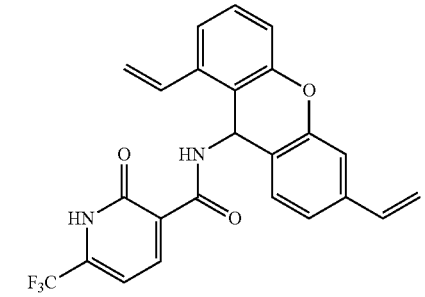
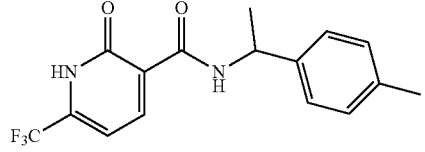

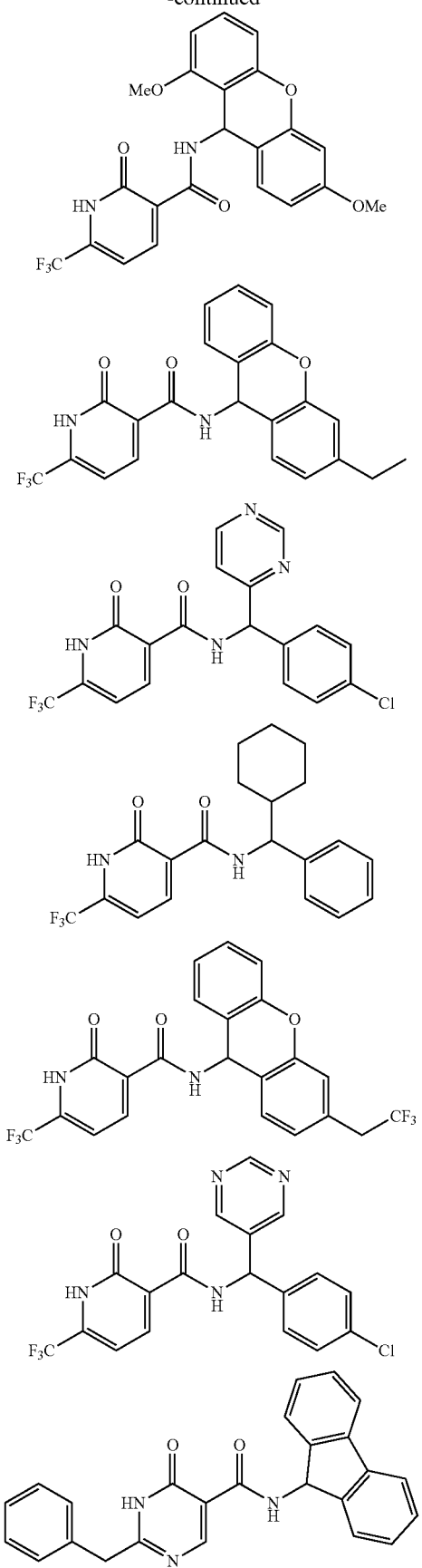

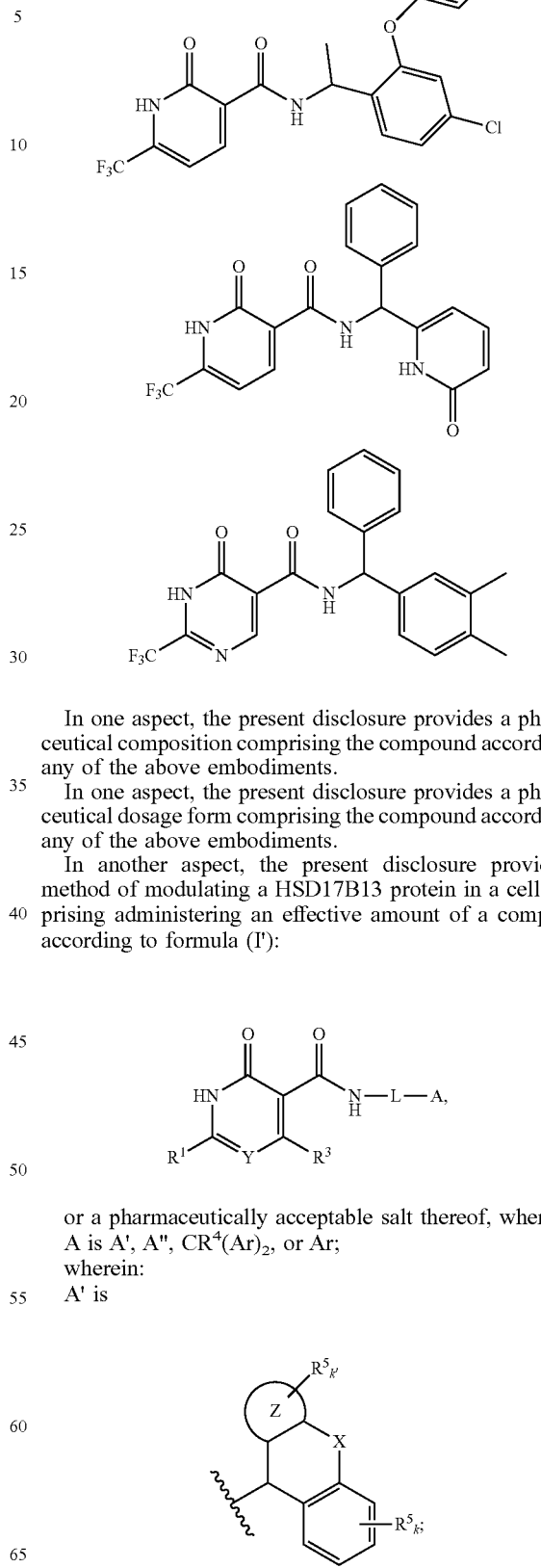

In one aspect, the present disclosure provides a pharmaceutical composition comprising the compound according to any of the above embodiments.

In one aspect, the present disclosure provides a pharmaceutical dosage form comprising the compound according to any of the above embodiments.

In another aspect, the present disclosure provides a method of modulating a HSD17B13 protein in a cell comprising administering an effective amount of a compound according to formula (I'):

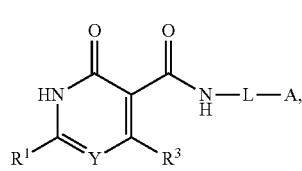

(I')

or a pharmaceutically acceptable salt thereof, wherein:
A is A', A", CR$^4$(Ar)$_2$, or Ar;
wherein:
A' is

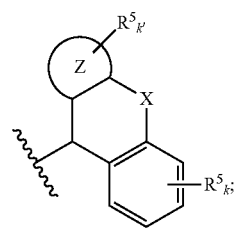

A" is

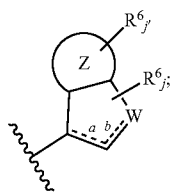

Z is phenyl, Het, or a $C_4$-$C_8$ cycloalkyl; and

Ar is independently at each occurrence a phenyl, naphthyl, or a $C_4$-$C_8$ cycloalkyl, any of which is optionally substituted with one or more $R^8$ or Het;

Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;

L is a bond, —$(CH_2)_n$—, —$(CHB)_n$—, —$CH_2CHB$—, or —$CHBCH_2$—;

wherein:

B is benzyl or $C_{1-12}$ alkyl optionally comprising 1-4 O atoms, either of which is optionally substituted by —OH or —$OCH_3$;

n is 1 or 2;

k and k' are independently from 0 to 4;

j and j' are independently from 0 to 4;

W is =CH—, =C($R^6$)—, —$CH_2$—, —CH($R^6$)—, —(C=O)—, —$CH_2CH_2$—, —CH($R^6$)—$CH_2$—, —O—, —O—$CH_2$—, —O—CH($R^6$)—, —(NH)—, —N($R^6$)—, —$CH_2$—NH—, —$CH_2$—N($R^6$)—, or —S—;

a and b are independently a single bond or a double bond;

X is a bond, —$CH_2$—, —$CH_2$—$CH_2$—, —$CH_2$—O—, —CH=CH—, —(C=O)—, —O—, —$NR^{\#}$—, —S—, —(S=O)—, or —$(SO_2)$—;

Y is N, —$CR^2$, or —$COR^2$;

$R^1$ is H, —$(CH_2)_{0-3}$—$NH_2$, —$(CH_2)_{0-3}$—$NHR^{\#}$, —$(CH_2)_{0-3}$—$N(R^{\#})_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;

$R^2$ is H, halogen, —$(CH_2)_{0-3}$—$NH_2$, —$(CH_2)_{0-3}$—$NHR^{\#}$, —$(CH_2)_{0-3}$—$N(R^{\#})_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$ is independently at each occurrence halogen, —CN, =O, —OH, —$NH_2$, —$(CH_2)_{1-3}$—$OR^{\#}$, —NH—(C=O)—$R^*$, —NH—(C=O)O—$R^*$, —NH—$(SO_2)$—$R^*$, —$(CH_2)_{1-3}$—$NR^{\#}_2$, —$NHR^{\#}$, —$N(R^{\#})_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with $R^*$;

$R^6$ is independently at each occurrence halogen, —OH, =O, —CN, —$(CH_2)_{0-3}$—$NH_2$, —$(CH_2)_{0-3}$—$NHR^{\#}$, —$(CH_2)_{0-3}$—$N(R^{\#})_2$, —$(CH_2)_{0-3}$—$NHCOOR^{\#}$, —$(CH_2)_{0-3}$—$COOR^{\#}$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with $R^*$;

$R^7$ is independently at each occurrence halogen, —CN, =O, —OH, —$(CH_2)_{1-3}$—$OR^{\#}$, —NH—(C=O)—$R^*$, —NH—$(SO_2)$—$R^*$, —$(CH_2)_{1-3}$—$NR^{\#}_2$, —$NHR^{\#}$, —$N(R^{\#})_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with $R^*$;

$R^8$ is independently at each occurrence halogen, —CN, =O, —OH, —$(CH_2)_{0-3}$—SH, —$(CH_2)_{0-3}$—$SR^*$, —$(SO_2)$—$R^*$, —$NH_2$, —$(CH_2)_{1-3}$—$OR^{\#}$, —NH—(C=O)—$R^*$, —NH—$(SO_2)$—$R^*$, —$(CH_2)_{1-3}$—$NR^{\#}_2$, —$NHR^{\#}$, or —$N(R^{\#})_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with $R^*$;

$R^*$ is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, $C_{3-6}$ cycloalkyl, phenyl, or benzyl, any of which is optionally substituted with a halogen.

In another aspect, the present disclosure provides a method of modulating a HSD17B13 protein in a cell comprising administering an effective amount of a compound according to formula (I):

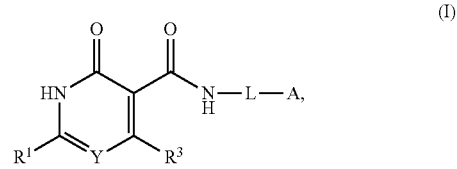

(I)

or a pharmaceutically acceptable salt thereof, wherein:

A is A', A", $CR^4(Ar)_2$, or a phenyl that is optionally substituted with one or more $R^7$; wherein:

A' is

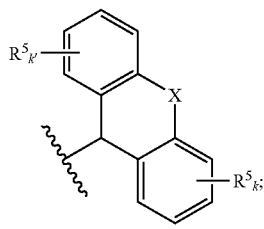

A" is

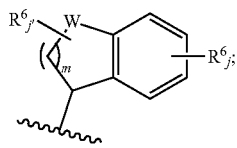

and

Ar is independently at each occurrence a phenyl that is optionally substituted with one or more $R^8$ or Het, where Het is a 6-membered heterocycle comprising from 1 to 3 nitrogen atoms, wherein Het is optionally substituted with one or more of halogen, —OH or =O;

L is a bond, —$(CH_2)_n$—, —$(CHB)_n$—, —$CH_2CHB$—, or —$CHBCH_2$—;

wherein:
B is $C_{1-12}$ alkyl or benzyl; and
n is 1 or 2;
m is 1 or 2;
k and k' are independently from 0 to 4;
j and j' are independently from 0 to 4;
W is —$CH_2$—, —O—, —(NH)—, or —S—;
wherein:
X is a bond, —$CH_2$—, —$CH_2$—$CH_2$—, —$CH_2$—O—, —CH=CH—, —(C=O)—, —O—, —$NR^\#$—, —S—, —(S=O)—, or —$(SO_2)$—;
Y is N, —$CR^2$, —$COR^2$ or —$CNHR^2$;
$R^1$ is H, $C_{1-4}$ alkyl, $C_{1-4}$ haloalkyl, or benzyl;
$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;
$R^3$ is H, $C_{1-4}$ alkyl, or $C_{1-4}$ haloalkyl;
wherein:
$R^4$ is H, $C_{1-4}$ alkyl, or $C_{1-4}$ haloalkyl;
$R^5$, $R^6$, $R^7$, and $R^8$ are each optional and independently at each occurrence halogen, —CN, =O, —OH, —$NH_2$, —$(CH_2)_{1-3}$—$OR^\#$, —NH—(C=O)—$R^*$, —NH—$(SO_2)$—$R^*$, —$(CH_2)_{1-3}$—$NR^\#_2$, —$NHR^\#$, —$N(R^\#)_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$, $R^6$, $R^7$, or $R^8$ groups form a 5-7 membered ring that optionally contains 1 to 3 heteroatoms selected from O, N, and S; any of which is optionally substituted with $R^*$;
$R^*$ is halogen, —OH, $C_{1-3}$ alkyl, $C_{1-3}$ haloalkyl, phenyl, or benzyl, any of which is optionally substituted with a halogen; and
$R^\#$ is $C_{1-3}$ alkyl, $C_{1-3}$ haloalkyl, phenyl, or benzyl, any of which is optionally substituted with a halogen.

In one embodiment, modulating the HSD17B13 protein comprises inhibiting the HSD17B13 protein.

In one embodiment, the compound does not modulate one or more of HSD17B1, HSD17B2, HSD17B3, HSD17B4, HSD17B5, HSD17B6, HSD17B7, HSD17B8, HSD17B9, HSD17B10, HSD17B11, HSD17B12, or HSD17B14.

In one embodiment, the compound does not modulate one or more of HSD17B1, HSD17B2, HSD17B4, and HSD17B10.

In one embodiment, the HSD17B13 comprises the amino acid sequence of SEQ ID NO: 1 or SEQ ID NO: 6.

In one embodiment, the HSD17B1 comprises the amino acid sequence of SEQ ID NO: 2 or SEQ ID NO: 7.

In one embodiment, the HSD17B2 comprises the amino acid sequence of SEQ ID NO: 3 or SEQ ID NO: 8.

In one embodiment, the HSD17B4 comprises the amino acid sequence of SEQ ID NO: 4 or SEQ ID NO: 9.

In one embodiment, the HSD17B10 comprises the amino acid sequence of SEQ ID NO: 5 or SEQ ID NO: 10.

In one embodiment, the cell is a mammalian cell.
In one embodiment, the cell is a human cell.
In one embodiment, the cell is a liver cell.
In one embodiment, the cell is ex vivo or in vivo.
In one embodiment, the compound inhibits the HSD17B13 protein with an IC50 of less than 10 µmol.
In one embodiment, the compound inhibits the HSD17B13 protein with an IC50 of less than 1 µmol.
In one embodiment, the compound inhibits the HSD17B13 protein with an IC50 of less than 0.5 µmol.
In one embodiment, the compound inhibits the HSD17B13 protein with an IC50 of less than 0.1 µmol.

In another aspect, the present disclosure provides a method of treating a liver disease in a subject having liver disease comprising administering to the subject an effective amount of a compound according to formula (I'):

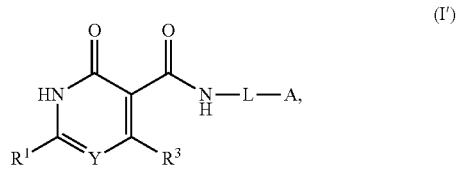

or a pharmaceutically acceptable salt thereof, wherein:
A is A', A", $CR^4(Ar)_2$, or Ar;
wherein:
A' is

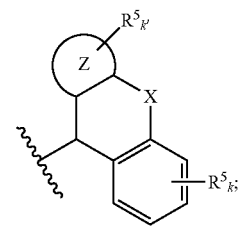

A" is

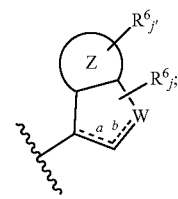

Z is phenyl, Het, or a $C_4$-$C_8$ cycloalkyl; and
Ar is independently at each occurrence a phenyl, naphthyl, or a $C_4$-$C_8$ cycloalkyl, any of which is optionally substituted with one or more $R^8$ or Het;
Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;

L is a bond, —$(CH_2)_n$—, —$(CHB)_n$—, —$CH_2CHB$—, or —$CHBCH_2$—;

B is benzyl or $C_{1-12}$ alkyl optionally comprising 1-4 O atoms, either of which is optionally substituted by —OH or —$OCH_3$;

n is 1 or 2; and k and k' are independently from 0 to 4;

j and j' are independently from 0 to 4;

W is =CH—, =$C(R^6)$—, —$CH_2$—, —$CH(R^6)$—, —(C=O)—, —$CH_2CH_2$—, —$CH(R^6)$—$CH_2$—, —O—, —O—$CH_2$—, —O—$CH(R^6)$—, —(NH)—, —$N(R^6)$—, —$CH_2$—NH—, —$CH_2$—$N(R^6)$—, or —S—;

wherein: a and b are independently a single bond or a double bond;

X is a bond, —$CH_2$—, —$CH_2$—$CH_2$—, —$CH_2$—O—, —CH=CH—, —(C=O)—, —O—, —$NR^\#$—, —S—, —(S=O)—, or —$(SO_2)$—;

Y is N, —$CR^2$, or —$COR^2$;

$R^1$ is H, —$(CH_2)_{0-3}$—$NH_2$, —$(CH_2)_{0-3}$—$NHR^\#$, —$(CH_2)_{0-3}$—$N(R^\#)_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;

$R^2$ is H, halogen, —$(CH_2)_{0-3}$—$NH_2$, —$(CH_2)_{0-3}$—$NHR^\#$, —$(CH_2)_{0-3}$—$N(R^\#)_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$ is independently at each occurrence halogen, —CN, =O, —OH, —$NH_2$, —$(CH_2)_{1-3}$—$OR^\#$, —NH—(C=O)—R*, —NH—(C=O)O—R*, —NH—$(SO_2)$—R*, —$(CH_2)_{1-3}$—$NR^\#_2$, —$NHR^\#$, —$N(R^\#)_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

$R^6$ is independently at each occurrence halogen, —OH, =O, —CN, —$(CH_2)_{0-3}$—$NH_2$, —$(CH_2)_{0-3}$—$NHR^\#$, —$(CH_2)_{0-3}$—$N(R^\#)_2$, —$(CH_2)_{0-3}$—$NHCOOR^\#$, —$(CH_2)_{0-3}$—$COOR^\#$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with R*;

$R^7$ is independently at each occurrence halogen, —CN, =O, —OH, —$(CH_2)_{1-3}$—$OR^\#$, —NH—(C=O)—R*, —NH—$(SO_2)$—R*, —$(CH_2)_{1-3}$—$NR^\#_2$, —$NHR^\#$, —$N(R^\#)_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;

$R^8$ is independently at each occurrence halogen, —CN, =O, —OH, —$(CH_2)_{0-3}$—SH, —$(CH_2)_{0-3}$—SR*, —$(SO_2)$—R*, —$NH_2$, —$(CH_2)_{1-3}$—$OR^\#$, —NH—(C=O)—R*, —NH—$(SO_2)$—R*, —$(CH_2)_{1-3}$—$NR^\#_2$, —$NHR^\#$, or —$N(R^\#)_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, $C_{3-6}$ cycloalkyl, phenyl, or benzyl, any of which is optionally substituted with a halogen.

In another aspect, the present disclosure provides a method of treating a liver disease in a subject having liver disease comprising administering to the subject an effective amount of a compound according to formula (I):

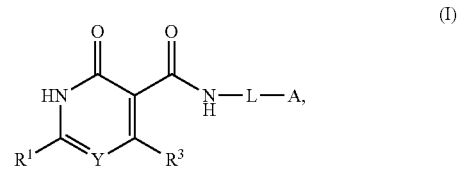

(I)

or a pharmaceutically acceptable salt thereof, wherein:

A is A', A", $CR^4(Ar)_2$, or a phenyl that is optionally substituted with one or more $R^7$; wherein:

A' is

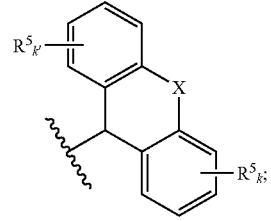

A" is

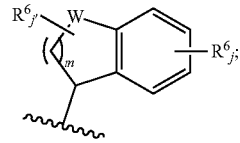

and

Ar is independently at each occurrence a phenyl that is optionally substituted with one or more $R^8$ or Het, where Het is a 6-membered heterocycle comprising from 1 to 3 nitrogen atoms, wherein Het is optionally substituted with one or more of halogen, —OH or =O;

L is a bond, —$(CH_2)_n$—, —$(CHB)_n$—, —$CH_2CHB$—, or —$CHBCH_2$—;

wherein:

B is $C_{1-12}$ alkyl or benzyl; and n is 1 or 2;

m is 1 or 2;

k and k' are independently from 0 to 4;

j and j' are independently from 0 to 4;

W is —$CH_2$—, —O—, —(NH)—, or —S—;

wherein:

X is a bond, —$CH_2$—, —$CH_2$—$CH_2$—, —$CH_2$—O—, —CH=CH—, —(C=O)—, —O—, —$NR^\#$—, —S—, —(S=O)—, or —($SO_2$)—;

Y is N, —$CR^2$, —$COR^2$ or —$CNHR^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$, $R^6$, $R^7$, and $R^8$ are each optional and independently at each occurrence halogen, —CN, =O, —OH, —$NH_2$, —$(CH_2)_{1-3}$—$OR^\#$, —NH—(C=O)—R*, —NH—($SO_2$)—R*, —$(CH_2)_{1-3}$—$NR^\#_2$, —$NHR^\#$, —$N(R^\#)_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$, $R^6$, $R^7$, or $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, phenyl, or benzyl, any of which is optionally substituted with a halogen.

In one embodiment, the liver disease is an alcoholic liver disease.

In one embodiment, the alcoholic liver disease comprises one or more of cirrhosis, steatosis, or hepatocellular carcinoma resulting from alcohol consumption.

In one embodiment, the liver disease is a non-alcoholic liver disease.

In one embodiment, the non-alcoholic liver disease comprises one or more of nonalcoholic fatty liver disease (NAFLD) or non-alcoholic steatohepatitis (NASH).

In one embodiment, the non-alcoholic liver disease comprises one or more of cirrhosis, steatosis, or hepatocellular carcinoma not caused by alcohol consumption.

In one embodiment, the subject is homozygous or heterozygous for functional HSD17B13.

In one embodiment, the subject expresses a patatin like phospholipase domain containing 3 (PNPLA3) protein comprising an I148M variation.

In another aspect, the present disclosure provides a method of treating a subject who is not a carrier of the HSD17B13 rs72613567 variant and has or is susceptible to developing a chronic liver disease, comprising administering to the subject an effective amount of a compound according to formula (I'):

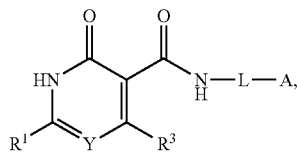

(I')

or a pharmaceutically acceptable salt thereof, wherein:
A is A', A", $CR^4(Ar)_2$, or Ar;

wherein:
A' is

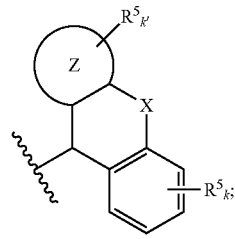

A" is

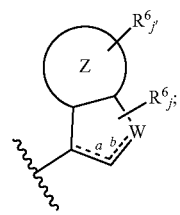

Z is phenyl, Het, or a $C_4$-$C_8$ cycloalkyl; and

Ar is independently at each occurrence a phenyl, naphthyl, or a $C_4$-$C_8$ cycloalkyl, any of which is optionally substituted with one or more $R^8$ or Het;

Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;

L is a bond, —$(CH_2)_n$—, —$(CHB)_n$—, —$CH_2CHB$—, or —$CHBCH_2$—;

B is benzyl or $C_{1-12}$ alkyl optionally comprising 1-4 O atoms, either of which is optionally substituted by —OH or —$OCH_3$;

n is 1 or 2;

k and k' are independently from 0 to 4;

j and j' are independently from 0 to 4;

W is =CH—, =C($R^6$)—, —$CH_2$—, —CH($R^6$)—, —(C=O)—, —$CH_2CH_2$—, —CH($R^6$)—$CH_2$—, —O—, —O—$CH_2$—, —O—CH($R^6$)—, —(NH)—, —N($R^6$)—, —$CH_2$—N($R^6$)—, or —S—;

a and b are independently a single bond or a double bond;

X is a bond, —$CH_2$—, —$CH_2$—$CH_2$—, —$CH_2$—O—, —CH=CH—, —(C=O)—, —O—, —$NR^\#$—, —S—, —(S=O)—, or —($SO_2$)—;

Y is N, —$CR^2$, or —$COR^2$;

$R^1$ is H, —$(CH_2)_{0-3}$—$NH_2$, —$(CH_2)_{0-3}$—$NHR^\#$, —$(CH_2)_{0-3}$—$N(R^\#)_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;

$R^2$ is H, halogen, —$(CH_2)_{0-3}$—$NH_2$, —$(CH_2)_{0-3}$—$NHR^\#$, —$(CH_2)_{0-3}$—$N(R^\#)_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$ is independently at each occurrence halogen, —CN, =O, —OH, —$NH_2$, —$(CH_2)_{1-3}$—$OR^\#$, —NH—

(C=O)—R*, —NH—(C=O)O—R*, —NH—(SO₂)—R*, —(CH₂)₁₋₃—NR$^\#$₂, —NHR$^\#$, —N(R$^\#$)₂, C$_{1-4}$ alkoxy, phenoxy, C$_{1-12}$ alkyl, C$_{1-12}$ heteroalkyl comprising 1 to 3 hetero atoms selected from —O—, —S—, or —NH—, C$_{1-12}$ alkenyl, C$_{1-12}$ alkynyl, C$_{1-4}$ haloalkyl, C$_{1-4}$ haloalkoxy, C$_{6-12}$ aryl, a 3-7-membered heterocycle with 1 to 4 heteroatoms selected from O, N and S or combinations thereof, or wherein two adjacent R⁵ groups form a 5-7 membered ring that optionally contains 1 to 3 heteroatoms selected from O, N, and S; any of which is optionally substituted with R*;

R⁶ is independently at each occurrence halogen, —OH, =O, —CN, —(CH₂)₀₋₃—NH₂, —(CH₂)₀₋₃—NHR$^\#$, —(CH₂)₀₋₃—N(R$^\#$)₂, —(CH₂)₀₋₃—NHCOOR$^\#$, —(CH₂)₀₋₃—COOR$^\#$, C$_{1-4}$ alkoxy, C$_{1-12}$ alkyl, C$_{1-12}$ alkenyl; C$_{1-4}$ haloalkyl, C$_{1-4}$ heteroalkyl with 1 or 2 methylene replaced with —O— or —S—, or C$_{6-12}$ aryl, any of which is optionally substituted with R*;

R⁷ is independently at each occurrence halogen, —CN, =O, —OH, —(CH₂)₁₋₃—OR$^\#$, —NH—(C=O)—R*, —NH—(SO₂)—R*, —(CH₂)₁₋₃—NR$^\#$₂, —NHR$^\#$, —N(R$^\#$)₂, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;

R⁸ is independently at each occurrence halogen, —CN, =O, —OH, —(CH₂)₀₋₃—SH, —(CH₂)₀₋₃—SR*, —(SO₂)—R*, —NH₂, —(CH₂)₁₋₃—OR$^\#$, —NH—(C=O)—R*, —NH—(SO₂)—R*, —(CH₂)₁₋₃—NR$^\#$₂, —NHR$^\#$, or —N(R$^\#$)₂, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R⁸ groups form a 5-7 membered ring that optionally contains 1 to 3 heteroatoms selected from O, N, and S; any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, C$_{3-6}$ cycloalkyl, phenyl, or benzyl, any of which is optionally substituted with a halogen.

In another aspect, the present disclosure provides a method of treating a subject who is not a carrier of the HSD17B13 rs72613567 variant and has or is susceptible to developing a chronic liver disease, comprising administering to the subject an effective amount of a compound according to formula (I):

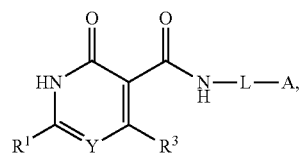

(I)

or a pharmaceutically acceptable salt thereof, wherein:

A is A', A", CR⁴(Ar)₂, or a phenyl that is optionally substituted with one or more R⁷; wherein:

A' is

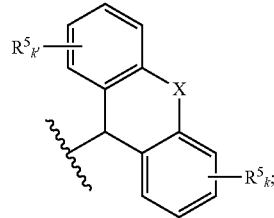

A" is

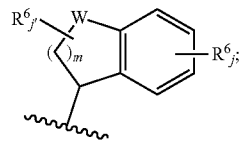

and

Ar is independently at each occurrence a phenyl that is optionally substituted with one or more R⁸ or Het, where Het is a 6-membered heterocycle comprising from 1 to 3 nitrogen atoms, wherein Het is optionally substituted with one or more of halogen, —OH or =O;

L is a bond, —(CH₂)$_n$—, —(CHB)$_n$—, —CH₂CHB—, or —CHBCH₂—;

B is C$_{1-12}$ alkyl or benzyl; and n is 1 or 2;

m is 1 or 2;

k and k' are independently from 0 to 4;

j and j' are independently from 0 to 4;

W is —CH₂—, —O—, —(NH)—, or —S—;

X is a bond, —CH₂—, —CH₂—CH₂—, —CH₂—O—, —CH=CH—, —(C=O)—, —O—, —NR$^\#$—, —S—, —(S=O)—, or —(SO₂)—;

Y is N, —CR², —COR² or —CNHR²;

R¹ is H, C$_{1-4}$ alkyl, C$_{1-4}$ haloalkyl, or benzyl;

R² is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R³ is H, C$_{1-4}$ alkyl, or C$_{1-4}$ haloalkyl;

R⁴ is H, C$_{1-4}$ alkyl, or C$_{1-4}$ haloalkyl;

R⁵ is independently at each occurrence halogen, —CN, =O, —OH, —NH₂, —(CH₂)₁₋₃—OR$^\#$, —NH—(C=O)—R*, —NH—(SO₂)—R*, —(CH₂)₁₋₃—NR$^\#$₂, —NHR$^\#$, —N(R$^\#$)₂, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R⁵ groups form a 5-7 membered ring that optionally contains 1 to 3 heteroatoms selected from O, N, and S; any of which is optionally substituted with R*;

R⁶ is independently at each occurrence halogen, —OH, C$_{1-4}$ alkoxy, C$_{1-12}$ alkyl, C$_{1-12}$ alkenyl, C$_{1-4}$ haloalkyl, or C$_{6-12}$ aryl, any of which is optionally substituted with R*;

R⁷ is independently at each occurrence halogen, —CN, =O, —OH, —(CH₂)₁₋₃—OR$^\#$, —NH—(C=O)—R*, —NH—(SO₂)—R*, —(CH₂)₁₋₃—NR$^\#$₂, —NHR$^\#$, —N(R$^\#$)₂, C$_{1-4}$ alkoxy, phenoxy, C$_{1-12}$ alkyl, C$_{1-12}$ alkenyl, $C_{1-4}$ haloalkyl, or $C_{6-12}$ aryl, any of which is optionally substituted with R*;

$R^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, phenyl, or benzyl, any of which is optionally substituted with a halogen.

In one embodiment, the liver disease is an alcoholic liver disease.

In one embodiment, the alcoholic liver disease comprises one or more of cirrhosis, steatosis, or hepatocellular carcinoma resulting from alcohol consumption.

In one embodiment, the liver disease is a non-alcoholic liver disease.

In one embodiment, the non-alcoholic liver disease comprises one or more of nonalcoholic fatty liver disease (NAFLD) or non-alcoholic steatohepatitis (NASH).

In one embodiment, the non-alcoholic liver disease comprises one or more of cirrhosis, steatosis, or hepatocellular carcinoma not caused by alcohol consumption.

In one embodiment, the subject is homozygous or heterozygous for functional HSD17B13.

In one embodiment, any of the above methods further comprises administering a second therapeutic agent.

In one embodiment, the compound is administered to the subject orally, topically, intranasally, intravenously, intramuscularly, or subcutaneously.

In one embodiment, the compound is a compound of Table 3.

These and other aspects will become apparent to those skilled in the art after a reading of the following detailed description, including the appended claims.

DETAILED DESCRIPTION

Detailed embodiments are disclosed herein; however, it is to be understood that the disclosed embodiments are merely illustrative of the disclosure that can be embodied in various forms. In addition, each of the examples given in connection with the various embodiments of the disclosure is intended to be illustrative, and not restrictive. Therefore, specific structural and functional details disclosed herein are not to be interpreted as limiting, but merely as a representative basis for teaching one skilled in the art to variously employ the present disclosure.

Unless defined otherwise, all technical and scientific terms used herein have the same meaning as commonly understood by one of ordinary skill in the art to which this disclosure belongs.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that can be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal," as used herein, refers to humans, veterinary animals (e.g., cats, dogs, cows, horses, sheep, pigs, etc.) and experimental animals used to model diseases (e.g., mice, rats, rabbits, dogs, monkeys). In one embodiment, the subject is a human.

As used herein the term "effective" applied to dose or amount refers to that quantity of a compound or pharmaceutical composition that is sufficient to result in a desired activity upon administration to a subject. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase "pharmaceutically acceptable," as used in connection with compositions of the disclosure, refers to molecular entities and other ingredients of such compositions that are physiologically tolerable and, in certain embodiments, do not typically produce untoward reactions when administered to a mammal (e.g., a human). As used herein, in certain embodiments, the term "pharmaceutically acceptable" means approved by a regulatory agency of the Federal or a state government or listed in the U.S. Pharmacopeia or other generally recognized pharmacopeia for use in mammals, and more particularly in humans.

Ranges can be expressed herein as from "about" or "approximately" one particular value and/or to "about" or "approximately" another particular value. When such a range is expressed, another embodiment includes from the one particular value and/or to the other particular value. As used herein, the term "about," when used in reference to a particular recited numerical value, means that the value can vary from the recited value by no more than 10%. For example, as used herein, the expression "about 100" includes 90 and 110 and all values in between (e.g., 91, 92, 93, 94, etc.).

By "comprising" or "containing" or "including" is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

The term "aliphatic" or "aliphatic group," as used herein, means a straight-chain (i.e., unbranched), branched, or cyclic (also referred to herein as "carbocycle," "cycloaliphatic" or "cycloalkyl") hydrocarbon chain that is completely saturated or that contains one or more units of unsaturation, or a monocyclic hydrocarbon, bicyclic hydrocarbon, tricyclic hydrocarbon, or polycyclic hydrocarbon that is completely saturated or that contains one or more units of unsaturation, but which is not aromatic, that is attached to the rest of the molecule. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched alkyl, alkenyl, alkynyl groups and hybrids thereof such as (cycloalkyl)alkyl, (cycloalkenyl)alkyl or (cycloalkyl)alkenyl.

In some embodiments, an aliphatic group is a cycloaliphatic group. The term "cycloaliphatic," as used herein, refers to saturated or partially unsaturated cyclic aliphatic monocyclic, bicyclic, or polycyclic ring systems, as described herein, having from 3 to 14 carbons. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic," can also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a cycloaliphatic group is tricyclic. In some embodiments, a cycloaliphatic group is polycyclic. In some embodiments, "cycloaliphatic" (or "carbocycle" or "cycloalkyl") refers to a monocyclic $C_{3-6}$ hydrocarbon, or a $C_{8-10}$ bicyclic hydrocarbon that is completely saturated or that contains one or more units of unsaturation, but which is not aromatic, that has a single point of attachment to the rest of the molecule, or a $C_{9-16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and can include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 1-20 carbon atoms in its backbone (e.g., $C_{1-20}$ for straight chain, $C_{2-20}$ for branched chain), and alternatively, about 1-10 carbon atoms, or about 1 to 6 carbon atoms. In some embodiments, a cycloalkyl ring has from about 3-10 carbon atoms in their ring structure where such rings are monocyclic or bicyclic, and alternatively about 5, 6 or 7 carbons in the ring structure. In some embodiments, a cycloalkyl group is a cyclopropyl, a cyclobutyl, a cyclopentyl, or a cyclohexyl group. In some embodiments, an alkyl group can be a lower alkyl group, wherein a lower alkyl group comprises 1-4 carbon atoms (e.g., $C_{1-4}$ for straight chain lower alkyls). When used in the context of a divalent alkyl group, it is to be understood that "alkyl" refers to an alkylene group.

As used herein, the term "alkenyl" refers to an alkyl group, as defined herein, including straight-chain alkenyl groups, branched-chain alkenyl groups, and cycloalkenyl groups having one or more double bonds. In certain embodiments, a straight chain or branched chain alkenyl has about 1-20 carbon atoms in its backbone (e.g., $C_{2-20}$ for straight chain, $C_{3-20}$ for branched chain), and alternatively, about 2-10 carbon atoms, or about 2 to 6 carbon atoms. In some embodiments, an alkenyl group has 1, 2, 3, 4, 5, or 6 double bonds. In some embodiments, a cycloalkenyl ring has from about 3-10 carbon atoms in the ring structure where such rings are monocyclic or bicyclic, and alternatively about 5, 6 or 7 carbons in the ring structure, and 1, 2, or 3 double bonds. In some embodiments, a cycloalkenyl group is a cyclopropenyl, a cyclobutenyl, a cyclobutadienyl, a cyclopentenyl, a cyclopentadienyl, a cyclohexenyl, or a cyclohexadienyl group. In some embodiments, an alkenyl group can be a lower alkenyl group, wherein a lower alkenyl group comprises 2-4 carbon atoms (e.g., $C_{2-4}$ for straight chain lower alkenyls). In one embodiment, a cycloalkenyl group has six carbon atoms and one double bond.

As used herein, the term "alkynyl" refers to an alkyl group, as defined herein, including straight-chain alkynyl groups, branched-chain alkynyl groups, and cycloalkynyl groups having one or more triple bonds. In certain embodiments, a straight chain or branched chain alkynyl has about 2-20 carbon atoms in its backbone (e.g., $C_{2-20}$ for straight chain, $C_{3-20}$ for branched chain), and alternatively, about 2-10 carbon atoms, or about 2 to 6 carbon atoms. In some embodiments, an alkynyl group has 1, 2, 3, 4, 5, or 6 triple bonds. In some embodiments, a cycloalkynyl ring has from about 6-12 carbon atoms in the ring structure where such rings are monocyclic or bicyclic, and alternatively about 8, 9, or 10 carbons in the ring structure, and 1, 2, or 3 triple bonds. In some embodiments, an alkynyl group can be a lower alkynyl group, wherein a lower alkynyl group comprises 2-4 carbon atoms (e.g., $C_{2-4}$ for straight chain lower alkynyls).

The term "heteroalkyl" is given its ordinary meaning in the art and refers to alkyl groups as described herein in which one or more carbon atoms is replaced with a heteroatom (e.g., oxygen, nitrogen, sulfur, and the like). In some embodiments, a heteroalkyl group can have one or more of methylene groups replaced with —O—, —S—, or —NH—, in which the hydrogen of —NH— is optionally substituted. Examples of heteroalkyl groups include, but are not limited to, alkoxy, poly(ethylene glycol)-, alkyl-substituted amino, tetrahydrofuranyl, piperidinyl, morpholinyl, etc.

The term "haloalkyl" is given its ordinary meaning in the art and refers to alkyl groups as described herein in which one or more hydrogen atoms is replaced by a halogen atom, i.e., F, Cl, Br, or I. In some embodiments a haloalkyl group can be a perfluoroalkyl group, i.e., a group where all hydrogen atoms are replaced with fluoride atoms. In some embodiments a haloalkyl group can be a halomethyl group, i.e., a $C_1$ group with 1, 2, or 3 halogen atoms, e.g., —CF$_3$, —CF$_2$H, —CH$_2$F, —CH$_2$Cl, —CH$_2$Br; —CH$_2$I. In some embodiments a haloalkyl group can be, e.g., —CF$_3$, —CF$_2$H, —CH$_2$F, —CH$_2$Cl, —CH$_2$Br; —CH$_2$I, —CH$_2$CF$_3$, CH$_2$CH$_2$F, —CH$_2$CH$_2$Br, —CH$_2$CH$_2$Cl, —CH$_2$CH$_2$I, etc.

The term "haloalkoxy" is given its ordinary meaning in the art and refers to alkoxy groups as described herein, i.e. alkyl groups bonded to an oxygen atom, in which one or more hydrogen atoms is replaced by a halogen atom, i.e., F, Cl, Br, or I. In some embodiments a haloalkoxy group can be a perfluoroalkoxy group, i.e., a group where all hydrogen atoms are replaced with fluoride atoms. In some embodiments a haloalkoxy group can be, e.g., —OCF$_3$, —OCF$_2$H, —OCH$_2$F, —OCH$_2$Cl, —OCH$_2$Br; —OCH$_2$I, —OCH$_2$CF$_3$, —OCH$_2$CH$_2$F, —OCH$_2$CH$_2$Br, —OCH$_2$CH$_2$Cl, —OCH$_2$CH$_2$I, etc.

The term "aryl" used alone or as part of a larger moiety as in "aralkyl," "aralkoxy," "aryloxy" or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" can be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which can bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The term "aralkyl" refers to alkyl groups as described herein in which one or more hydrogen atoms is substituted by aryl groups, where the radical or point of attachment is on the alkyl group. The alkyl part of an aralkyl group is optionally substituted as described in the term "alkyl" above. The aryl part of the aralkyl group is optionally substituted as described in ther term "alkyl" above.

The term "alkylaryl" referes to aryl groups as described herein in which one or more hydrogen atoms is substituted by alkyl groups, where the radical or point of attachment is on the aryl group. The aryl part of the alkylaryl group is optionally substituted as described in the term "aryl" above. The alkyl part of an alkylaryl group is optionally substituted as described in the term "alkyl" above.

The terms "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quatemized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group can be monocyclic, bicyclic, tricyclic, tetracyclic, and/or otherwise polycyclic. The term "heteroaryl" can be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is saturated, partially unsaturated, or aromatic, and having, in addition to carbon atoms, one or more, e.g., one to four, heteroatoms, as defined above. As used herein, the term "heterocycle" encompasses heteroaryl groups, as defined above. In one embodiment, a heterocycle can be a saturated, partially unsaturated, or aromatic, 5-7 membered monocyclic moiety comprising from 1 to 3 nitrogen atoms, e.g., a pyrrole, an imidazole, a pyrazole, a pyrazole, a triazole, a piperidine, a piperazine, a pyridazine, a pyridine, 2H-pyridine, a pyridone, a pyrimidine, or a pyrazine, including monovalent or divalent radicals thereof. When used in reference to a ring atom of a heterocycle, the term "nitrogen" includes a substituted nitrogen. In one embodiment, a heterocycle can be a saturated, partially unsaturated, or aromatic, 5-7 membered monocyclic moiety comprising from 1 to 3 oxygen atoms, e.g., a tetrahydrofuran (i.e., oxolane), a furan, a dihydrofuran, a dioxolane, a tetrahydropyran (i.e., oxane), a pyran, a dihydropyran, a dioxane, a dioxine, a trioxane, an oxepane, or an oxepine, including monovalent or divalent radicals thereof. In one embodiment, a heterocycle can be thiophene, oxazole, thiazole, or morpholine, including monovalent or divalent radicals thereof.

A heterocyclic ring can be attached, e.g., to its pendant group, at any heteroatom or carbon atom that results in a stable structure. Examples of such saturated or partially unsaturated heterocyclic radicals include, without limitation, tetrahydropyranyl, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as phenyl, indolinyl, 3H-indolyl, chromanyl, phenanthridinyl, or tetrahydroquinolinyl. A heterocyclyl group can be monocyclic, bicyclic, tricyclic, tetracyclic, and/or otherwise polycyclic. The term "heterocyclylalkyl" refers to an alkyl group substituted by a heterocyclyl.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon, including any oxidized form of nitrogen, sulfur, phosphorus, or silicon; the quaternized form of any basic nitrogen. In some embodiments, a heteroatom can be a substitutable nitrogen of a heterocyclic ring.

The term "unsaturated," as used herein, means that a moiety has one or more units of unsaturation.

The term "halogen" means F, Cl, Br, or I atom, and/or its radical or substituent, namely —F, —Cl, —Br, or —I.

As described herein, in certain embodiments, certain compounds of the disclosure can be indicated to comprise "optionally substituted" moieties. When indicated, in general, the term "substituted," whether preceded by the term "optionally" or not, means that one or more hydrogens of the designated moiety are replaced with a suitable substituent. Unless otherwise indicated, an "optionally substituted" group can have a suitable substituent at each substitutable position of the group, and when more than one position in any given structure can be substituted with more than one substituent selected from a specified group, the substituent can be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

As used herein, a substituent, e.g., —B, can be represented as a

where ∿∿∿ denotes a point of attachment.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure (e.g., keto- and enol tautomeric forms). For example, compounds including carbonyl —CH$_2$(C=O)— or —NH(C=O)— groups (keto forms) can undergo tautomerization to form hydroxyl —CH=C(OH)— or —N=C(OH)— groups (enol forms). Both keto and enol forms, individually as well as mixtures thereof, are included within the scope of the present disclosure. In particular, the definition of the compounds according to the disclosure includes the tautomeric structures of hydroxypyridinecarboxamides, as shown below:

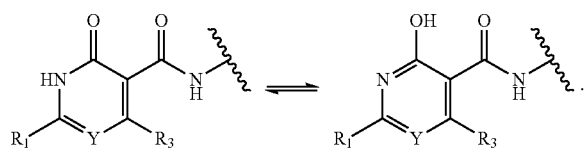

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}$C— or $^{13}$C- or $^{14}$C-enriched carbon are within the scope of this disclosure.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Unless otherwise stated, all crystalline forms of the compounds of the disclosure and salts thereof are also within the scope of the disclosure. The compounds of the disclosure can be isolated in various amorphous and crystalline forms, including without limitation forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

As used herein, "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (PXRD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

In some embodiments, the compounds of the disclosure are substantially isolated. By "substantially isolated" is meant that a particular compound is at least partially isolated from impurities. For example, in some embodiments a compound of the disclosure comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated compound including, for example, other crystalline forms and other substances.

The present disclosure also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, H$_2$SO$_4$) or organic acid (such as acetic acid, benzoic acid, trifluoroacetic acid salts of basic residues such as amines); alkali (such as Li, Na, K, Mg, Ca) or organic (such as trialkylammonium) salts of acidic residues such can be synthesized from the parent compound which contains a basic or acidic as carboxylic acids; and the like. The salts of the present application moiety conventional chemical methods. Generally, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile (ACN) can be used.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Berge, S M et al, *Journal of Pharmaceutical Science*, 1977, 66, 1, 1-19. By way of an example, in an embodiment of the disclosure pharmaceutically acceptable salts can comprise a suitable anion selected from F$^-$, Cl$^-$, Br$^-$, I$^-$, OH$^-$, $^-$BF$_4$, CF$_3$SO$_3^-$, monobasic sulfate, dibasic sulfate, monobasic phosphate, dibasic phosphate, or tribasic phosphate, NO$_3^-$, PF$_6^-$, NO$_2^-$, carboxylate, C$_e$F$_f$SO$_3^-$, (where e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, oxalate, palmitate, pamoate, pantothenate, polygalacturonate, propionate, salicylate, stearate, subacetate, succinate, tartrate, teoclate, tosylate, or triethiiodide. By way of another example, in an embodiment of the disclosure pharmaceutically acceptable salts can comprise a suitable cation selected from aluminum, arginine, benzathine, calcium, chloroprocaine, choline, diethanolamine, ethanolamine, ethylenediamine, lysine, magnesium, histidine, lithium, meglumine, potassium, procaine, sodium, triethylamince, or zinc. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene Protective Groups in Organic Synthesis*, 4th Ed., John Wiley & Sons: New York, 2006. In one non-limiting embodiment, protecting groups can include 1-chloroethyl carbonyl (ACE), acetoyl, benzyl (Bn), benzyloxy carbonyl (CBz), formyl, methyl carbonyl, trifluoroacetyl, t-butoxy carbonyl (Boc), and fluorenylmethyloxycarbonyl (Fmoc).

Compounds of the Disclosure

In one aspect, the present disclosure provides a compound according to formula (I'):

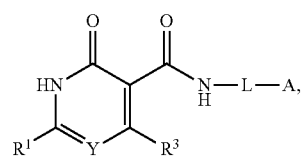

or a pharmaceutically acceptable salt thereof, wherein:
A is A', A", CR$^4$(Ar)$_2$, or Ar;
wherein:
A' is

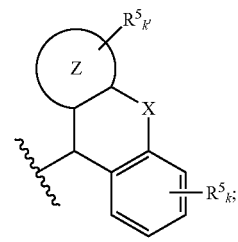

A" is

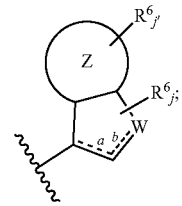

Z is phenyl, Het, or a C$_4$-C$_8$ cycloalkyl; and
Ar is independently at each occurrence a phenyl, naphthyl, or a C$_4$-C$_8$ cycloalkyl, any of which is optionally substituted with one or more R$^8$ or Het;
Het is a 6-membered heterocycle comprising from 1 to 3 heteroatoms independently selected from N and O, wherein Het is optionally substituted with one or more of C$_{1-3}$ alkyl, C$_{1-3}$ alkenyl, halogen, —OH or =O;
L is a bond, —(CH$_2$)$_n$—, —(CHB)$_n$—, —CH$_2$CHB—, or —CHBCH$_2$—;
B is benzyl or C$_{1-12}$ alkyl optionally comprising 1-4 O atoms, either of which is optionally substituted by —OH or —OCH$_3$;
n is 1 or 2; and wherein:
when A is phenyl, phenyl is optionally substituted by one or more R$^7$ and not by R$^8$;
when L is a bond, A is CR$^4$(Ar)$_2$, R$^1$ is methyl, Y is CR$^2$ and R$^2$ is H, R$^3$ is H, and CR$^4$(Ar)$_2$ has only one R$^8$ group, then R$^8$ is not —F;
when L is a bond, A is CR$^4$(Ar)$_2$, R$^1$ is ethyl, Y is CR$^2$ and R$^2$ is Me, R$^3$ is H, and CR$^4$(Ar)$_2$ has only one R$^8$ group, then R$^8$ is not —OMe;
when L is a bond, A is CR$^4$(Ar)$_2$, R$^1$ is CF$_3$, Y is CR$^2$ and R$^2$ is H, R$^3$ is H, and one Ar has two R$^8$ groups, then the R$^8$ groups are not both -Me;
when L is —(CH$_2$)$_n$—, A is CR$^4$(Ar)$_2$, R$^4$ is H, and R$^1$ is CF$_3$, then at least one Ar is substituted with at least one R$^8$;
when L is —(CH$_2$)$_n$—, A is phenyl, and R$^1$ is CF$_3$, then at least one R$^7$ is a phenoxy that is optionally substituted with a halogen; and when L is —(CHB)$_n$—, B is C$_{1-4}$ alkyl, A is phenyl and R$^4$ is H, then R$^7$ is present and is not —Cl, —F, —CN, C$_{1-4}$ alkyl, or C$_{1-4}$ alkoxy;

k and k' are independently from 0 to 4;

j and j' are independently from 0 to 4;

W is =CH—, =C(R$^6$)—, —CH$_2$—, —CH(R$^6$)—, —(C=O)—, —CH$_2$CH$_2$—, —CH(R$^6$)—CH$_2$—, —O—, —O—CH$_2$—, —O—CH(R$^6$)—, —(NH)—, —N(R$^6$)—, —CH$_2$—NH—, —CH$_2$—N(R$^6$)—, or —S—;

a and b are independently a single bond or a double bond;

wherein:
when W is —CH$_2$—, or when W is —O—CH$_2$—, R$^1$ is CF$_3$, Y is CH, and R$^3$ is H,
then A" is substituted with at least one R$^6$ which is not —OH;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, or —COR$^2$;

R$^1$ is H, —(CH$_2$)$_{0-3}$—NH$_2$, —(CH$_2$)$_{0-3}$—NHR$^\#$, —(CH$_2$)$_{0-3}$—N(R$^\#$)$_2$, C$_{1-4}$ alkyl, C$_{1-4}$ haloalkyl, phenyl, benzyl, or —(CH$_2$)$_{0-3}$—X—(CH$_2$)$_{0-3}$-phenyl, wherein phenyl is optionally substituted with one or more R$^5$ groups;

R$^2$ is H, halogen, —(CH$_2$)$_{0-3}$—NH$_2$, —(CH$_2$)$_{0-3}$—NHR$^\#$, —(CH$_2$)$_{0-3}$—N(R$^\#$)$_2$, C$_{1-12}$ alkyl, C$_{1-12}$ alkenyl, C$_{6-12}$ aryl, C$_{1-12}$ aralkyl, C$_{1-12}$ arylalkyl, C$_{1-4}$ haloalkyl, C$_{3-7}$ cycloalkyl, or a 5-7-membered heterocycle with 1 to 4 heteroatoms independently selected from O, N and S or combinations thereof, any of which is optionally substituted by one or more of —OH, C$_{1-4}$ alkyl, C$_{1-4}$ alkoxy, =O, phenyl, or benzyl;

R$^3$ is H, C$_{1-4}$ alkyl, or C$_{1-4}$ haloalkyl;

wherein:
when Y is N, at least one of R$^1$ and R$^3$ is not H, and when Y is CR$^2$, at least one of R$^1$, R$^2$, and R$^3$ is not H;

R$^4$ is H, C$_{1-4}$ alkyl, or C$_{1-4}$ haloalkyl;

R$^5$ is independently at each occurrence halogen, —CN, =O, —OH, —NH$_2$, —(CH$_2$)$_{1-3}$—OR$^\#$, —NH—(C=O)—R*, —NH—(C=O)O—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ heteroalkyl comprising 1 to 3 hetero atoms selected from —O—, —S—, or —NH—, C$_{1-12}$ alkenyl, C$_{1-12}$ alkynyl, C$_{1-4}$ haloalkyl, C$_{1-4}$ haloalkoxy, C$_{6-12}$ aryl, a 3-7-membered heterocycle with 1 to 4 heteroatoms selected from O, N and S or combinations thereof, or wherein two adjacent R$^5$ groups form a 5-7 membered ring that optionally contains 1 to 3 heteroatoms selected from O, N, and S; any of which is optionally substituted with R*;

R$^6$ is independently at each occurrence halogen, —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, C$_{1-4}$ alkoxy, C$_{1-12}$ alkyl, C$_{1-12}$ alkenyl; C$_{1-4}$ haloalkyl, C$_{1-4}$ heteroalkyl with 1 or 2 methylene replaced with —O— or —S—, or C$_{6-12}$ aryl, any of which is optionally substituted with R*;

R$^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;

R$^8$ is independently at each occurrence halogen, —CN, =O, —OH, —(CH$_2$)$_{0-3}$—SH, —(CH$_2$)$_{0-3}$—SR*, —(SO$_2$)—R*, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups form a 5-7 membered ring that optionally contains 1 to 3 heteroatoms selected from O, N, and S; any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, C$_{3-6}$ cycloalkyl, phenyl, or benzyl, any of which is optionally substituted with a halogen.

In another aspect, the present disclosure provides a compound according to formula (I'), wherein Z is pyridyl.

In another aspect, the present disclosure provides a compound according to formula (I'), wherein R$^1$, R$^5$, and R$^8$ are each independently a 5 membered heterocycle comprising 1 N atom or 1 O atom, a 5 membered heterocycle comprising 2 N atoms or 2 O atoms, a 5 membered heterocycle comprising 1 N atom and 1 O atom, a 6 membered heterocycle comprising 1 N atom or 1 O atom, a 6 membered heterocycle comprising 2 N atoms or 2 O atoms, or a 6 membered heterocycle comprising 1 N atom and 1 O atom.

In another aspect, the present disclosure provides a compound according to formula (I'), wherein R$^1$, R$^5$, and R$^8$ are each independently a pyrrole, imidazole, pyrazole, pyrazole, triazole, tetrahydrofuran, furan, pyridone, oxazole, piperidine, piperazine, pyridine, pyrimidine, pyrazine, tetrahydropyran, pyran, or dioxane radical.

In another aspect, the present disclosure provides a compound according to formula (I'), wherein R$^5$ and R$^8$ are each independently a 6 membered hetercycle having 1 or 2 nitrogen atoms wherein each of the nitrogen atoms is optionally bonded to hydrogen or R*.

In one embodiment, the present disclosure provides a compound according to formula (I'), wherein R$^1$, R$^5$, and R$^8$ are each independently a tetrahydropyran (i.e., oxane), pyridine, tetrhydrofuran (i.e., oxolane), piperazine, piperidine, 2H-pyridine, pyridone, dihydropyridine, pyrazine, pyrimidine, dihydrofuran, dihydropyran, or morpholine radical.

In one aspect, the present disclosure provides a compound according to formula (I):

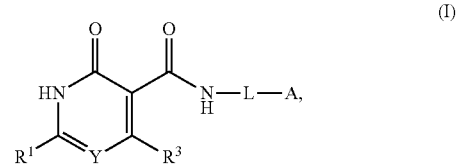

(I)

or a pharmaceutically acceptable salt thereof wherein:

A is A', A", CR$^4$(Ar)$_2$, or a phenyl that is optionally substituted with one or more R$^7$;

wherein:

A' is

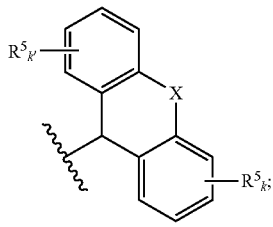

A" is

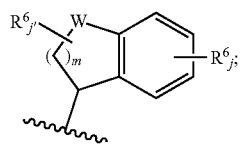

and

Ar is independently at each occurrence a phenyl that is optionally substituted with one or more $R^8$ or Het, where Het is a 6-membered heterocycle comprising from 1 to 3 nitrogen atoms, wherein Het is optionally substituted with one or more of halogen, —OH or =O;

L is a bond, —(CH$_2$)$_n$—, —(CHB)$_n$—, —CH$_2$CHB—, or —CHBCH$_2$—;

wherein:

B is $C_{1-12}$ alkyl or benzyl;

n is 1 or 2; and when L is a bond, A is $CR^4(Ar)_2$, $R^1$ is methyl, Y is $CR^2$ and $R^2$ is H, $R^3$ is H, and $CR^4(Ar)_2$ has only one $R^8$ group, then $R^8$ is not —F;

when L is a bond, A is $CR^4(Ar)_2$, $R^1$ is ethyl, Y is $CR^2$ and $R^2$ is Me, $R^3$ is H, and $CR^4(Ar)_2$ has only one $R^8$ group, then $R^8$ is not —OMe;

when L is a bond, A is $CR^4(Ar)_2$, $R^1$ is $CF_3$, Y is $CR^2$ and $R^2$ is H, $R^3$ is H, and one Ar has two $R^8$ groups, then the $R^8$ groups are not both -Me;

when L is —(CH$_2$)$_n$—, A is $CR^4(Ar)_2$, $R^4$ is H, and $R^1$ is $CF_3$, then at least one Ar is substituted with at least one $R^8$;

when L is —(CH$_2$)$_n$—, A is phenyl, and $R^1$ is $CF_3$, then at least one $R^7$ is a phenoxy that is optionally substituted with a halogen; and when L is —(CHB)$_n$—, B is $C_{1-4}$ alkyl, A is phenyl and $R^4$ is H, then at least one $R^7$ is present and is not —Cl, —F, —CN, $C_{1-4}$ alkyl, or $C_{1-4}$ alkoxy;

m is 1 or 2;

k and k' are independently from 0 to 4;

j and j' are independently from 0 to 4;

W is —CH$_2$—, —O—, —(NH)—, or —S—;

wherein:

when W is —CH$_2$— and m is 1, or when W is —O— and m is 2, then A" is substituted with at least one $R^6$;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

$R^3$ is H, $C_{1-4}$ alkyl, or $C_{1-4}$ haloalkyl;

wherein:

when Y is N, at least one of $R^1$ and $R^3$ is not H, and when Y is $CR^2$, at least one of $R^1$, $R^2$, and $R^3$ is not H;

$R^4$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

$R^6$ is independently at each occurrence halogen, $C_{1-4}$ alkoxy, $C_{1-12}$ alkyl, $C_{1-12}$ alkenyl, $C_{1-4}$ haloalkyl, or $C_{6-12}$ aryl, any of which is optionally substituted with R*;

$R^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;

$R^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;

R* is H, halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, phenyl, or benzyl, any of which is optionally substituted with a halogen.

In certain embodiments of the compound according to formula (I) or formula (I'), $R^1$ is H, methyl, ethyl, —CF$_3$, —CF$_2$H or benzyl; $R^2$ is H, Br, methyl, ethyl, vinyl, allyl, phenyl, cyclohexyl, cyclohex-1-en-1-yl, 2-hydroxyethyl, —CF$_3$, or —CF$_2$H; $R^3$ is H, methyl, ethyl, or propyl; and $R^4$ is H or methyl.

In another aspect, the present disclosure provides a compound according to formula (II')

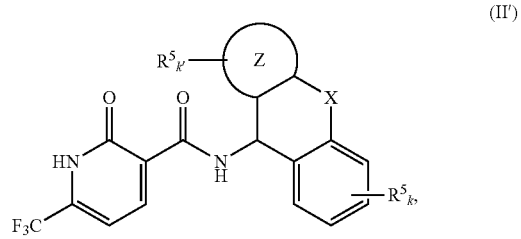

(II')

or a pharmaceutically acceptable salt thereof, wherein:

X is O or S;

Z is a 6-membered heterocycle comprising 1 to 2 N heteroatoms, or a $C_4$-$C_8$ cycloalkyl;

$R^5$ is independently at each occurrence $C_{1-3}$ alkyl, $C_{1-3}$ alkenyl, $C_{1-3}$ alkoxy, $C_{1-3}$ haloalkyl, halogen, —CN, or —OH; and k and k' are independently from 0 to 2.

In another aspect, the present disclosure provides a compound according to formula (II'), wherein X is O or S; Z is a $C_4$-$C_8$ cycloalkyl; $R^5$ is independently at each occurrence $C_{1-3}$ alkyl, $C_{1-3}$ alkenyl, $C_{1-3}$ alkoxy, $C_{1-3}$ haloalkyl, halogen, —CN, or —OH; and k and k' are independently from 0 to 2.

In another aspect, the present disclosure provides a compound according to formula (II):

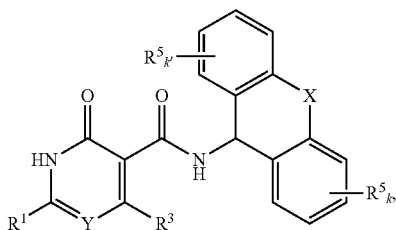

(II)

or a pharmaceutically acceptable salt thereof wherein:

k and k' are independently from 0 to 4;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, each of which is optionally substituted by —OH;

$R^3$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, phenyl, or benzyl, any of which is optionally substituted with a halogen.

In certain embodiments of the compound according to formula (II), or formula (II'), $R^1$ is H, methyl, ethyl, —CF$_3$, —CF$_2$H or benzyl; $R^2$ is H, Br, methyl, ethyl, vinyl, allyl, phenyl, cyclohexyl, cyclohex-1-en-1-yl, 2-hydroxyethyl, —CF$_3$, or —CF$_2$H; $R^3$ is H, methyl, ethyl, or propyl; and $R^5$ is independently at each occurrence —Cl, —F, —OH, methyl, ethyl, vinyl, trifluoromethyl, trifluoroethyl, methoxy, difluoromethoxy, or trifluoromethoxy.

In another aspect, the present disclosure provides a compound according to formula (IIa):

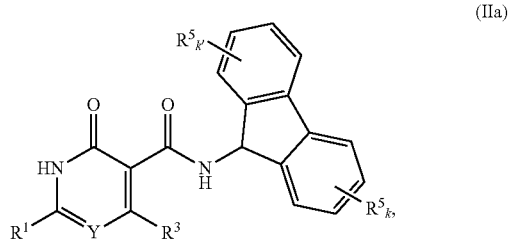

(IIa)

or a pharmaceutically acceptable salt thereof wherein:

k and k' are independently from 0 to 2;

Y is N, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, each of which is optionally substituted by —OH;

$R^3$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, or a 4-7-membered heterocycle with 1 to 4 heteroatoms selected from O, N and S or combinations thereof; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, phenyl, or benzyl, any of which is optionally substituted with a halogen.

In certain embodiments of the compound according to formula (IIa), $R^1$ is methyl, ethyl, —CF$_3$, or benzyl; $R^2$ is H, methyl, or ethyl; $R^3$ is H or methyl; and $R^5$ is independently at each occurrence —Cl, —F, —OH, methyl, ethyl, vinyl, trifluoromethyl, trifluoroethyl, methoxy, difluoromethoxy, or trifluoromethoxy.

In certain embodiments of the compound according to formula (IIa), $R^5$ is independently at each occurrence $C_{1-4}$ alkyl, $C_{1-4}$ alkenyl, $C_{1-4}$ alkoxy, $C_{1-4}$ haloalkyl, —OH or halogen. In further embodiments, $R^1$ is —CF$_3$, Y is CH, and $R^3$ is H.

In another aspect, the present disclosure provides a compound according to formula (IIb):

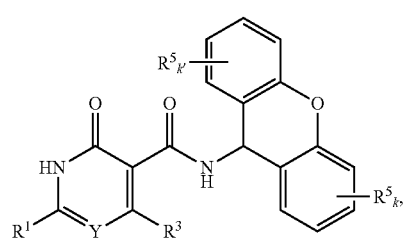

(IIb)

or a pharmaceutically acceptable salt thereof wherein:

k and k' are independently from 0 to 2;

Y, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

$R^3$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, or a 4-7-membered heterocycle with 1 to 4 heteroatoms selected from O, N and S or combinations thereof; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, phenyl, or benzyl, any of which is optionally substituted with a halogen.

In another aspect, the present disclosure provides a compound according to formula (IIb), wherein $R^5$ is independently at each occurrence $C_{1-3}$ alkyl, $C_{1-3}$ alkenyl, $C_{1-4}$ alkoxy, $C_{1-4}$ haloalkyl, —CN, NH$_2$, —OH, halogen, or 3-5 membered heterocycle with 1-4 heteroatoms selected from 0 and N or combinations thereof, where N may be further substituted by $C_{1-3}$ alkyl.

In another aspect, the present disclosure provides a compound according to formula (IIb), wherein $R^1$ is —H, —CH$_3$, —CH$_2$F, —CHF$_2$, —CF$_3$, —CH(CH$_3$)$_2$, phenyl, —S—CH$_2$-phenyl, or —(CH$_2$)—O-phenyl wherein phenyl is optionally substituted with one or more R*, —CF$_3$, —NH$_2$, or —NH—(C=O)O—R*; and wherein $R^3$ is H.

In certain embodiments of the compound according to formula (IIb), $R^1$ is methyl, ethyl, or —CF$_3$; $R^2$ is H, methyl, or ethyl; $R^3$ is H, methyl, ethyl, or propyl; and $R^5$ is independently at each occurrence —Cl, —F, —OH, methyl, ethyl, vinyl, trifluoromethyl, trifluoroethyl, methoxy, difluoromethoxy, or trifluoromethoxy.

In another aspect, the present disclosure provides a compound according to formula (IIb1):

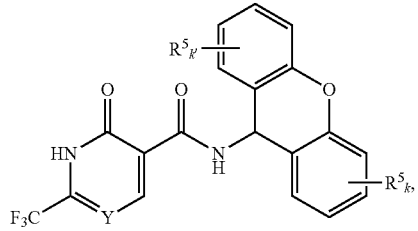

(IIb1)

or a pharmaceutically acceptable salt thereof wherein:

k and k' are independently from 0 to 2;

Y is N, —CR$^2$, —COR$^2$ or —CNHR$^2$;

$R^2$ is H, halogen, $C_{1-6}$ alkyl, $C_{1-6}$ alkenyl, phenyl, benzyl, $C_{1-4}$ haloalkyl, or a 5-7-membered heterocycle with 1 to 4 heteroatoms selected from O, N and S or combinations thereof, any of which is optionally substituted by —OH;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, or a 4-7-membered heterocycle with 1 to 4 heteroatoms selected from O, N and S or combinations thereof; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, phenyl, or benzyl, any of which is optionally substituted with a halogen.

In one embodiment, the present disclosure provides a compound according to formula (IIb1) wherein $R^2$ is H, methyl, or ethyl; and $R^5$ is independently at each occurrence —F, —OH, methyl, ethyl, vinyl, trifluoromethyl, trifluoroethyl, methoxy, difluoromethoxy, or trifluoromethoxy.

In another aspect, the present disclosure provides a compound according to formula (IIb1'):

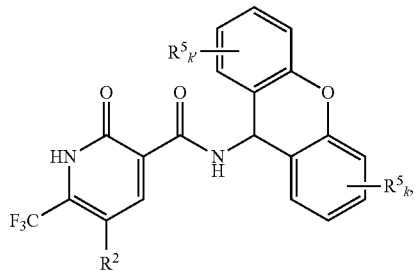

(IIb1')

or a pharmaceutically acceptable salt thereof wherein:

k and k' are independently from 0 to 2;

$R^2$ is H, halogen, $C_{1-6}$ alkyl, $C_{1-6}$ alkenyl, phenyl, benzyl, $C_{1-4}$ haloalkyl, or a 5-7-membered heterocycle with 1 to 4 heteroatoms selected from O, N and S or combinations thereof, any of which is optionally substituted by —OH;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, or a 4-7-membered heterocycle with 1 to 4 heteroatoms selected from O, N and S or combinations thereof; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$ is $C_{1-3}$ alkyl, $C_{1-3}$ haloalkyl, phenyl, or benzyl, any of which is optionally substituted with a halogen.

In one embodiment, the present disclosure provides a compound according to formula (IIb1') where in $R^5$ is independently at each occurrence halogen, —OH, —(CH$_2$)$_{1-3}$—OR$^\#$, $C_{1-4}$ alkoxy, phenoxy, $C_{1-4}$ alkyl, $C_{1-4}$ alkenyl, $C_{1-4}$ alkynyl, $C_{1-4}$ haloalkyl, $C_{1-4}$ haloalkoxy, phenyl, benzyl; any of which is optionally substituted with R*.

In another embodiment, the present disclosure provides a compound according to formula (IIb1') wherein $R^2$ is H, methyl, or ethyl; and $R^5$ is independently at each occurrence —Cl, —F, —OH, methyl, ethyl, vinyl, trifluoromethyl, trifluoroethyl, methoxy, difluoromethoxy, or trifluoromethoxy.

In another aspect, the present disclosure provides a compound according to formula (IIb1"):

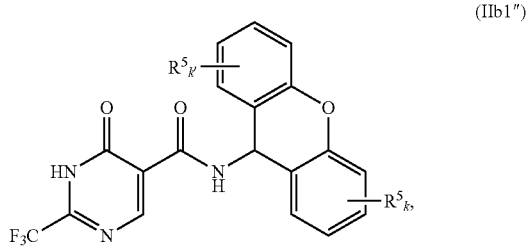

(IIb1″)

or a pharmaceutically acceptable salt thereof wherein:

k and k' are independently from 0 to 2;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, or a 4-7-membered heterocycle with 1 to 4 heteroatoms selected from O, N and S or combinations thereof; any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In one embodiment, the present disclosure provides a compound according to formula (IIb1″) where in $R^5$ is independently at each occurrence halogen, —OH, —(CH$_2$)$_{1-3}$—OR$^\#$, C$_{1-4}$ alkoxy, phenoxy, C$_{1-4}$ alkyl, C$_{1-4}$ alkenyl, C$_{1-4}$ alkynyl, C$_{1-4}$ haloalkyl, C$_{1-4}$ haloalkoxy, phenyl, benzyl; any of which is optionally substituted with R*.

In another embodiment, the present disclosure provides a compound according to formula (IIb1″) where in $R^5$ is independently at each occurrence —Cl, —F, —Br, —OH, methyl, ethyl, propyl, butyl (e.g., t-butyl or iso-butyl), trifluoromethyl, trifluoroethyl methoxy, ethoxy, difluoromethoxy, or trifluoromethoxy.

In another aspect, the present disclosure provides a compound according to formula (IIb2):

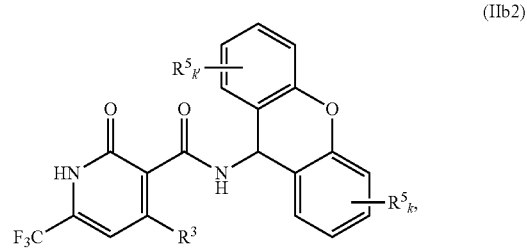

(IIb2)

or a pharmaceutically acceptable salt thereof wherein:

k and k' are independently at each occurrence from 0 to 2;

$R^3$ is C$_{1-4}$ alkyl;

$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, or a 4-7-membered heterocycle with 1 to 4 heteroatoms selected from O, N and S or combinations thereof; any of which is optionally substituted with R*;

R* is H, halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In another aspect, the present disclosure provides a compound according to formula (IIb2) wherein $R^5$ is independently at each occurrence halogen, —OH, —(CH$_2$)$_{1-3}$—OR$^\#$, C$_{1-4}$ alkoxy, phenoxy, C$_{1-4}$ alkyl, C$_{1-4}$ alkenyl, C$_{1-4}$ alkynyl, C$_{1-4}$ haloalkyl, C$_{1-4}$ haloalkoxy, phenyl, benzyl; any of which is optionally substituted with R*.

In another aspect, the present disclosure provides a compound according to formula (IIb2) where in $R^5$ is independently at each occurrence halogen, —OH, —OMe, —Othyl, or C$_{1-4}$ alkyl.

In another aspect, the present disclosure provides a compound according to formula (IIc):

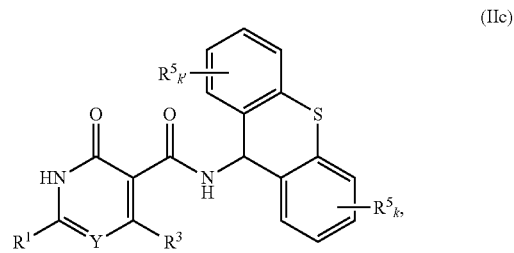

(IIc)

or a pharmaceutically acceptable salt thereof, wherein k, k', Y, $R^1$, $R^2$, $R^3$, and $R^5$ are as defined above.

In another aspect, the present disclosure provides a compound according to formula (IIc) wherein $R^5$ is independently at each occurrence C$_{1-3}$ alkyl, C$_{1-3}$ alkenyl, C$_{1-3}$ heterocycle where one or more heteroatom is independently O or N, C$_{1-4}$ alkoxy, C$_{1-4}$ haloalkyl, —CN, —NH$_2$, —OH, or halogen.

In a further aspect, the present disclosure provides a compound according to formula (IIc) wherein $R^1$ is —CF$_3$ or —CHF$_2$; Y is CH or COR$^2$; and $R^3$ is H.

In a further aspect, the present disclosure provides a compound according to formula (IIc) wherein $R^2$ is C$_{1-3}$ alkyl optionally substituted by —OH, C$_{1-3}$ haloalkyl, C$_{1-3}$ alkenyl, non-aromatic heterocycle having 1-2 heteroatoms selected from N or O, aromatic heterocycle having 1-3 N heteroatoms or —(CH$_2$)$_{0-3}$—NHR$^\#$.

In another aspect, the present disclosure provides a compound according to formula (IId):

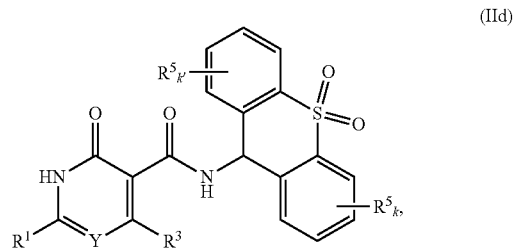

(IId)

or a pharmaceutically acceptable salt thereof, wherein k, k', Y, $R^1$, $R^2$, $R^3$, and $R^5$ are as defined above.

In a further aspect, the present disclosure provides a compound according to formula (IId) wherein $R^5$ is independently at each occurrence C$_{1-3}$ alkyl, C$_{1-3}$ alkenyl, C$_{1-3}$ heterocycle where one or more heteroatom is independently O or N, $C_{1-4}$ alkoxy, $C_{1-4}$ haloalkyl, —CN, —NH$_2$, —OH or halogen.

In a further aspect, the present disclosure provides a compound according to formula (IId) wherein R$^1$ is —CF$_3$ or —CHF$_2$; Y is CH or CR$^2$; and R$^3$ is H.

In a further aspect, the present disclosure provides a compound according to formula (IId) wherein R$^2$ is $C_{1-3}$ alkyl optionally substituted by —OH, or $C_{1-3}$ haloalkyl.

In another aspect, the present disclosure provides a compound according to formula (III'):

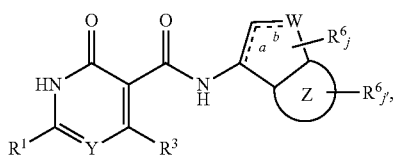

(III')

or a pharmaceutically acceptable salt thereof, wherein j, j', a, b, W, Y, Z, R$^1$, R$^2$, R$^3$, and R$^6$ are as defined above.

In a further aspect, the present disclosure provides a compound according to formula (III'), wherein:
W is =CH—, =C(R$^6$)—, —CH$_2$—, —CH(R$^6$)—, —CH$_2$CH$_2$—, —CH(R$^6$)—CH$_2$—, —(C=O)—, —O—CH$_2$—, —O—CH(R$^6$)—, —(NH)—, —N(R$^6$)—, —CH$_2$—NH—, —CH$_2$—N(R$^6$)—, —O—, or —S—;
a and b are independently a single bond or a double bond;
Z is a 6-membered heterocycle comprising 1 to 2 N heteroatoms;
Y is CH;
R$^1$ is CF$_3$ or —S—(CH$_2$)$_{0-3}$-phenyl, wherein phenyl is optionally substituted with one or more R$^5$ groups;
R$^3$ is H;
R$^6$ is independently at each occurrence halogen, —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with R*; and
j and j' are independently from 0 to 2.

In a further aspect, the present disclosure provides a compound according to formula (III'), wherein:
W is —CH$_2$—, —CH(R$^6$)—, (NH)—, —N(R$^6$)—, —O—, or —S—;
a and b are each a single bond;
Z is a 6-membered aromatic heterocycle comprising 1 N heteroatom;
Y is CH; R$^1$ is CF$_3$; R$^3$ is H;
R$^6$ is independently at each occurrence halogen, —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-3}$ alkyl, $C_{1-3}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with R*; and
j and j' are independently from 0 to 2.

In another aspect, the present disclosure provides a compound according to formula (III'), wherein W is —CH$_2$—, —CH(R$^6$)—, —(NH)—, —N(R$^6$)—, —O—, or —S—, a and b are each a single bond, or wherein W is =CH—, =C(R$^6$)—, —CH(R$^6$)—, —(NH)—, —N(R$^6$)—, —O—, or —S—, a is a double bond and b is a single bond or a is a single bond and b is a double bond.

In certain embodiments, the present disclosure provides a compound according to formula (III'), wherein:
when W is =CH— or C(R$^6$)—, then a is a single bond and b is a double bond;
when W is —CH$_2$—, —CH(R$^6$)—, —(C=O)—, —O—, —S—, —(NH)—, or —N(R$^6$)—, then a is double bond and b is a single bond or both a and b are single bonds; or
when W is —CH$_2$CH$_2$—, —CH(R$^6$)—CH$_2$—, —O—CH$_2$—, —O—CH(R$^6$)—, —CH$_2$—NH—, or —CH$_2$—N(R$^6$)—, then one of a or b is a single bond or both a and b are single bonds.

In another aspect, the present disclosure provides a compound according to formula (III'a):

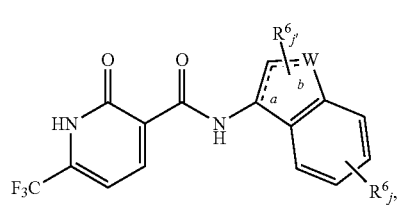

(III'a)

or a pharmaceutically acceptable salt thereof, wherein:
W is =CH—, =C(R$^6$)—, —CH(R$^6$)—, —(NH)—, —N(R$^6$)—, —O—, or —S—;
j and j' are independently from 0 to 2;
a is a double bond and b is a single bond or a is a single bond and b is a double bond; and
R$^6$ is independently at each occurrence —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-12}$ alkyl, $C_{1-12}$ alkenyl; $C_{1-4}$ haloalkyl, $C_{1-4}$ heteroalkyl, or $C_{6-12}$ aryl, any of which is optionally substituted with R*.

In another aspect, the present disclosure provides a compound according to formula (III):

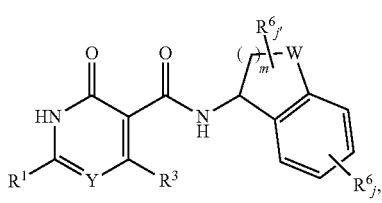

(III)

or a pharmaceutically acceptable salt thereof, wherein:
j and j' are independently from 0 to 4;
m is 1 or 2;
W is —CH$_2$—, —O—, —(NH)—, or —S—;
wherein:
when W is —CH$_2$— and m is 1, or when W is —O— and m is 2, then A" is substituted with at least one R$^6$;
Y is N, —CR$^2$, —COR$^2$ or —CNHR$^2$;
R$^1$ is H, $C_{1-4}$ alkyl, $C_{1-4}$ haloalkyl, or benzyl;
R$^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

R³ is H, C₁₋₄ alkyl, or C₁₋₄ haloalkyl;

R⁶ is independently at each occurrence halogen, C₁₋₄ alkoxy, C₁₋₁₂ alkyl, C₁₋₁₂ alkenyl, C₁₋₄ haloalkyl, or C₆₋₁₂ aryl, any of which is optionally substituted with R*;

R* is halogen, —OH, C₁₋₃ alkyl, C₁₋₃ haloalkyl, phenyl, or benzyl, any of which is optionally substituted with a halogen; and R# is C₁₋₃ alkyl, C₁₋₃ haloalkyl, phenyl, or benzyl, any of which is optionally substituted with a halogen.

In another aspect, the present disclosure provides a compound according to formula (IIIa):

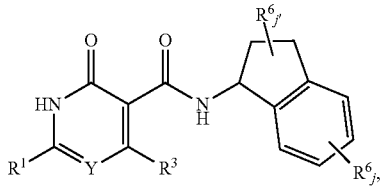

(IIIa)

or a pharmaceutically acceptable salt thereof, wherein:

j and j' are independently at each occurrence from 0 to 4, wherein at least one of j or j' is not 0;

Y is N, —CR², —COR² or —CNHR²;

R¹ is H, C₁₋₄ alkyl, C₁₋₄ haloalkyl, or benzyl;

R² is H; halogen; C₁₋₁₂ alkyl; C₁₋₁₂ alkenyl; C₆₋₁₂ aryl; C₁₋₁₂ aralkyl; C₁₋₄ haloalkyl, or a 5-7-membered heterocycle with 1 to 4 heteroatoms selected from O, N and S or combinations thereof, each of which is optionally substituted by —OH;

R³ is H; C₁₋₄ alkyl, or C₁₋₄ haloalkyl;

R⁶ is independently at each occurrence halogen, C₁₋₄ alkoxy, C₁₋₁₂ alkyl, C₁₋₁₂ alkenyl, C₁₋₄ haloalkyl, or C₆₋₁₂ aryl, any of which is optionally substituted with R*;

R* is halogen, —OH, C₁₋₃ alkyl, C₁₋₃ haloalkyl, phenyl, or benzyl, any of which is optionally substituted with a halogen; and R# is C₁₋₃ alkyl, C₁₋₃ haloalkyl, phenyl, or benzyl, any of which is optionally substituted with a halogen.

In another aspect, the present disclosure provides a compound according to formula (IIIa1):

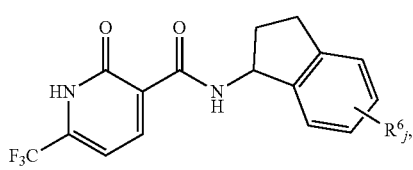

(IIIa1)

or a pharmaceutically acceptable salt thereof, wherein:

j is from 1 to 4;

R⁶ is independently at each occurrence halogen, C₁₋₄ alkoxy, C₁₋₁₂ alkyl, C₁₋₁₂ alkenyl, C₁₋₄ haloalkyl, or C₆₋₁₂ aryl, any of which is optionally substituted with R*;

R* is halogen, —OH, C₁₋₃ alkyl, C₁₋₃ haloalkyl, phenyl, or benzyl, any of which is optionally substituted with a halogen; and R# is C₁₋₃ alkyl, C₁₋₃ haloalkyl, phenyl, or benzyl, any of which is optionally substituted with a halogen.

In one embodiment, the present disclosure provides a compound according to formula (IIIa1), wherein R⁶ is independently at each occurrence halogen, C₁₋₄ alkoxy, C₁₋₃ alkyl, C₁₋₃ alkenyl, or C₁₋₄ haloalkyl.

In another aspect, the present disclosure provides a compound according to formula (IIIb):

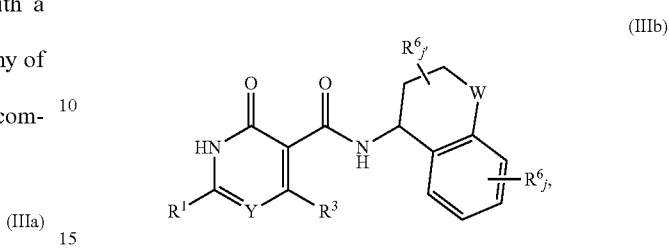

(IIIb)

or a pharmaceutically acceptable salt thereof, wherein:

j and j' are independently from 0 to 4;

W is —CH₂—, —(NH)—, or —S—;

Y is N, —CR², —COR² or —CNHR²;

R¹ is H, C₁₋₄ alkyl, C₁₋₄ haloalkyl, or benzyl;

R² is H, halogen, C₁₋₁₂ alkyl, C₁₋₁₂ alkenyl, C₆₋₁₂ aryl, C₁₋₁₂ aralkyl, C₁₋₄ haloalkyl, or a 5-7-membered heterocycle with 1 to 4 heteroatoms selected from O, N and S or combinations thereof, any of which is optionally substituted by —OH;

R³ is H; C₁₋₄ alkyl, or C₁₋₄ haloalkyl;

R⁶ is independently at each occurrence halogen; —OH, C₁₋₄ alkoxy; C₁₋₁₂ alkyl; C₁₋₁₂ alkenyl; C₁₋₄ haloalkyl, or C₆₋₁₂ aryl, any of which is optionally substituted with R*; and R* is halogen, —OH, C₁₋₃ alkyl, C₁₋₃ haloalkyl, phenyl, or benzyl, any of which is optionally substituted with a halogen.

In one embodiment, the present disclosure provides a compound according to formula (IIIb) wherein j and j' are each 0.

In another aspect, the present disclosure provides a compound according to formula (IIIb1):

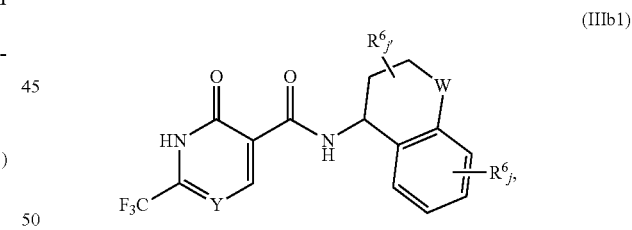

(IIIb1)

or a pharmaceutically acceptable salt thereof, wherein:

j and j' are independently at each occurrence from 0 to 4;

W is —CH₂—, —(NH)—, or —S—;

Y is N, —CR², —COR² or —CNHR²;

R⁶ is optional and independently at each occurrence halogen, —OH, C₁₋₄ alkoxy, C₁₋₁₂ alkyl, C₁₋₁₂ alkenyl, C₁₋₄ haloalkyl, or C₆₋₁₂ aryl, any of which is optionally substituted with R*;

R* is halogen, —OH, C₁₋₃ alkyl, C₁₋₃ haloalkyl, phenyl, or benzyl, any of which is optionally substituted with a halogen.

In one embodiment, the present disclosure provides a compound according to formula (IIIb1) wherein j and j' are each 0.

In another aspect, the present disclosure provides a compound according to formula (IIIc):

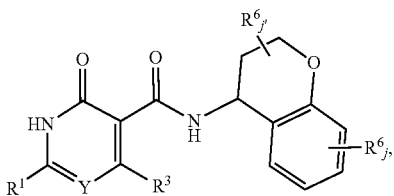

(IIIc)

or a pharmaceutically acceptable salt thereof, wherein:

j and j' are independently from 0 to 4, wherein at least one j or j' is not 0;

Y is N, —CR$^2$, —COR$^2$ or —CNHR$^2$;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl;

R$^6$ is independently at each occurrence halogen, —OH, C$_{1-4}$ alkoxy, C$_{1-12}$ alkyl, C$_{1-12}$ alkenyl, C$_{1-4}$ haloalkyl, or C$_{6-12}$ aryl, any of which is optionally substituted with R*; and R* is halogen, —OH, C$_{1-3}$ alkyl, C$_{1-3}$ haloalkyl, phenyl, or benzyl, any of which is optionally substituted with a halogen.

In another aspect, the present disclosure provides a compound according to formula (IIIc1):

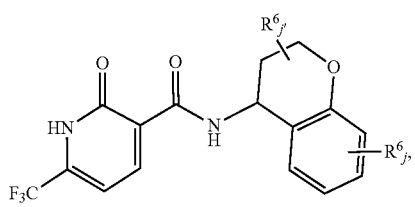

(IIIc1)

or a pharmaceutically acceptable salt thereof, wherein:

j and j' are independently from 0 to 4, wherein at least one j or j' is not 0;

R$^6$ is independently at each occurrence halogen; —OH, C$_{1-4}$ alkoxy; C$_{1-12}$ alkyl; C$_{1-12}$ alkenyl; C$_{1-4}$ haloalkyl, or C$_{6-12}$ aryl, any of which is optionally substituted with R*; and R* is halogen, —OH, C$_{1-3}$ alkyl, C$_{1-3}$ haloalkyl, phenyl, or benzyl, any of which is optionally substituted with a halogen.

In another aspect, the present disclosure provides a compound according to formula (IV):

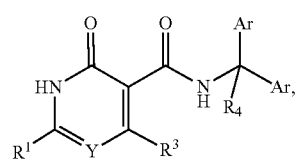

(IV)

or a pharmaceutically acceptable salt thereof, wherein

Ar is independently at each occurrence a phenyl that is optionally substituted with one or more R$^8$ or Het, where Het is a 6-membered heterocycle comprising from 1 to 3 nitrogen atoms, wherein Het is optionally substituted with one or more of halogen, —OH or =O;

Y is N, —CR$^2$, —COR$^2$ or —CNHR$^2$;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, each of which is optionally substituted by —OH;

R$^3$ is H, C$_{1-4}$ alkyl, or C$_{1-4}$ haloalkyl, wherein:

when Y is N, at least one of R$^1$ and R$^3$ is not H, and when Y is CR$^2$, then at least one of R$^1$, R$^2$, and R$^3$ is not H;

R$^4$ is H, C$_{1-4}$ alkyl, or C$_{1-4}$ haloalkyl;

R$^8$ is optional and is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#$$_2$, —NHR$^\#$, or —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups form a 5-7 membered ring that optionally contains 1 to 3 heteroatoms selected from O, N, and S; where any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen;

wherein:

when R$^1$ is C$_{1-3}$ alkyl, Y is CR$^2$ and R$^2$ is H, R$^3$ is H, and only one R$^8$ group is present, then R$^8$ is not —F, —OMe or -OEt;

when R$^1$ is ethyl, Y is CR$^2$ and R$^2$ is Me, R$^3$ is H, and only one R$^8$ group is present, then R$^8$ is not —OMe;

when R$^1$ is CF$_3$, Y is CR$^2$ and R$^2$ is H, R$^3$ is H, and only two R$^8$ groups are present, then the R$^8$ groups are not both -Me.

In another aspect, the present disclosure provides a compound according to formula (IVa):

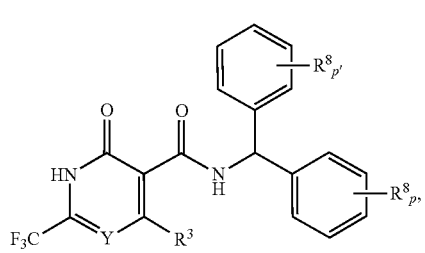

(IVa)

or a pharmaceutically acceptable salt thereof, wherein;

p and p' are independently 0 or 1;

Y is N, —CR$^2$, —COR$^2$ or —CNHR$^2$;

R$^2$ is H, halogen, C$_{1-3}$ alkyl, C$_{1-12}$ alkenyl, C$_{1-4}$ haloalkyl;

R$^3$ is H, C$_{1-4}$ alkyl, or C$_{1-4}$ haloalkyl;

R$^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—, NR$^\#$$_2$, —NHR$^\#$, or —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, phenyl, or benzyl, any of which is optionally substituted with a halogen.

In another aspect, the present disclosure provides a compound according to formula (IVa1'):

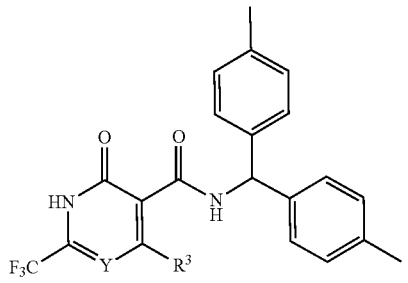

(IVa1')

or a pharmaceutically acceptable salt thereof, wherein
Y is N, —$CR^2$, —$COR^2$ or —$CNHR^2$;
$R^2$ is H, halogen, $C_{1-12}$ alky, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH; and
$R^3$ is H, $C_{1-4}$ alkyl, or $C_{1-4}$ haloalkyl.

In another aspect, the present disclosure provides a compound according to formula (IVa2):

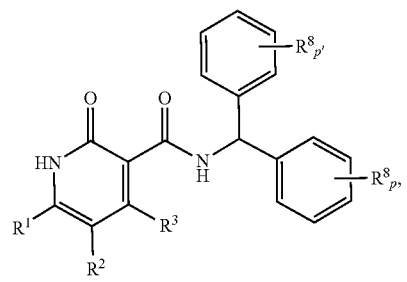

(IVa2)

or a pharmaceutically acceptable salt thereof, wherein
p and p' are independently from 0 to 5;
$R^1$ is H, methyl, CH(hal)$_2$, or CH$_2$(hal);
$R^2$ is H, methyl, C(hal)$_3$, CH(hal)$_2$, or CH$_2$(hal);
$R^3$ is H, methyl, C(hal)$_3$, CH(hal)$_2$, or CH$_2$(hal);
where hal is a halogen; and
wherein at least one of $R^1$, $R^2$ or $R^3$ comprises a hal;
$R^8$ is independently at each occurrence halogen, —CN, —OH, —NH$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, and a 4-7-membered heterocycle with 1 to 4 heteroatoms selected from O, N and S or combinations thereof; wherein any of which is optionally substituted with R*, and
R* is halogen, —OH, $C_{1-3}$ alkyl, $C_{1-3}$ haloalkyl, phenyl, or benzyl, any of which is optionally substituted with a halogen.

In another aspect, the present disclosure provides a compound according to formula (IVa2'):

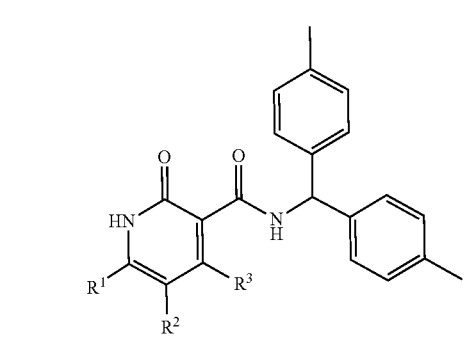

(IVa2')

or a pharmaceutically acceptable salt thereof, wherein
$R^1$ is H, methyl, CH(hal)$_2$, or CH$_2$(hal);
$R^2$ is H, methyl, C(hal)$_3$, CH(hal)$_2$, or CH$_2$(hal);
$R^3$ is H, methyl, C(hal)$_3$, CH(hal)$_2$, or CH$_2$(hal);
where hal is a halogen, and
wherein at least one of $R^1$, $R^2$, and $R^3$ comprises a hal.

In another aspect, the present disclosure provides a compound according to formula (IVb):

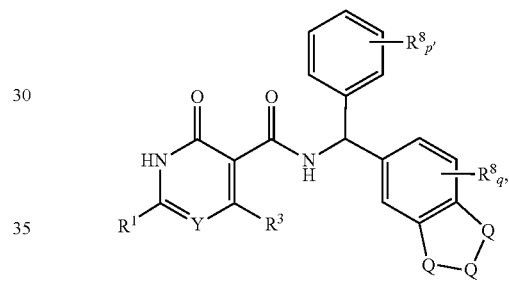

(IVb)

or a pharmaceutically acceptable salt thereof, wherein:
p is from 0 to 5;
q is from 0 to 3;
Y is N, —$CR^2$, —$COR^2$ or —$CNHR^2$;
Q is independently at each occurrence —CH—, —CH$_2$—; —NH—, or —O—;
$R^1$ is H; $C_{1-4}$ alkyl; $C_{1-4}$ haloalkyl, or benzyl;
$R^2$ is H; halogen; $C_{1-12}$ alkyl; $C_{1-12}$ alkenyl; $C_{6-12}$ aryl; $C_{1-12}$ aralkyl; $C_{1-4}$ haloalkyl, or a 5-7-membered heterocycle with 1 to 4 heteroatoms selected from O, N and S or combinations thereof, each of which is optionally substituted by —OH;
$R^3$ is H, $C_{1-4}$ alkyl, or $C_{1-4}$ haloalkyl;
$R^8$ is independently at each occurrence halogen, —CN, =O, —OH, —NH$_2$, —(CH$_2$)$_{1-3}$—OR$^{\#}$, —NH—(C=O)—R*, —NH—(SO$_2$)—R*, —(CH$_2$)$_{1-3}$—NR$^{\#}_2$, —NHR$^{\#}$, or —N(R$^{\#}$)$_2$, $C_{1-4}$ alkoxy, phenoxy, $C_{1-12}$ alkyl, $C_{1-12}$ alkenyl, $C_{2-12}$ alkynyl, $C_{1-4}$ haloalkyl, $C_{1-4}$ haloalkoxy, $C_{6-12}$ aryl, and a 4-7-membered heterocycle with 1 to 4 heteroatoms selected from O, N and S or combinations thereof; wherein any of which is optionally substituted with R*;
R* is halogen, —OH, $C_{1-3}$ alkyl, $C_{1-3}$ haloalkyl, phenyl, or benzyl, any of which is optionally substituted with a halogen; and
$R^{\#}$ is $C_{1-3}$ alkyl, $C_{1-3}$ haloalkyl, phenyl, or benzyl, any of which is optionally substituted with a halogen.

In another aspect, the present disclosure provides a compound according to formula (IVb1):

(IVb1)

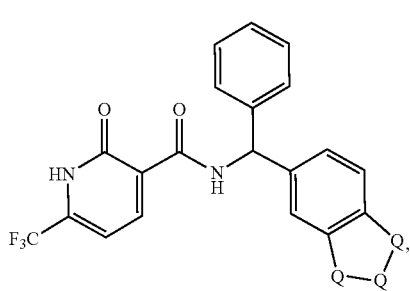

or a pharmaceutically acceptable salt thereof, wherein Q is independently at each occurrence —CH—, —CH$_2$—, —NH—, or —O—.

In another aspect, the present disclosure provides a compound according to formula (IVc):

(IVc)

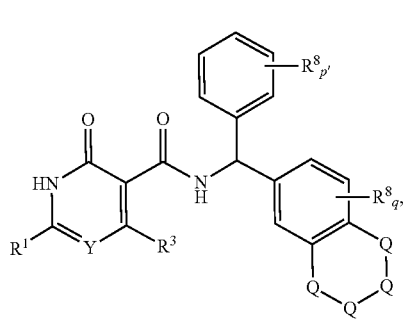

or a pharmaceutically acceptable salt thereof, wherein:

p is from 0 to 5;

q is from 0 to 3;

Y is N, —CR$^2$, —COR$^2$ or —CNHR$^2$;

Q is independently at each occurrence —CH—, —CH$_2$—, —NH—, or —O—;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl;

R$^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, C$_{1-4}$ alkoxy, phenoxy, C$_{1-12}$ alkyl, C$_{1-12}$ alkenyl, C$_{2-12}$ alkynyl, C$_{1-4}$ haloalkyl, C$_{1-4}$ haloalkoxy, C$_{6-12}$ aryl, and a 4-7-membered heterocycle with 1 to 4 heteroatoms selected from O, N and S or combinations thereof; wherein any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In another aspect, the present disclosure provides a compound according to formula (IVc1):

(IVc1)

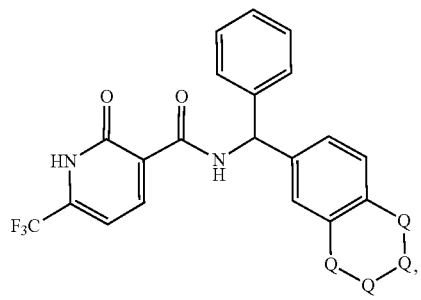

or a pharmaceutically acceptable salt thereof, wherein Q is independently at each occurrence —CH—, —CH$_2$—, —NH—, or —O—.

In another aspect, the present disclosure provides a compound according to formula (IVd):

(IVd)

or a pharmaceutically acceptable salt thereof, wherein p and p' are independently from 0 to 5;

Y is N, —CR$^2$, —COR$^2$ or —CNHR$^2$;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl;

R$^4$ is C$_{1-4}$ alkyl, or C$_{1-4}$ haloalkyl;

R$^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, C$_{1-4}$ alkoxy, phenoxy, C$_{1-12}$ alkyl, C$_{1-12}$ alkenyl, C$_{2-12}$ alkynyl, C$_{1-4}$ haloalkyl, C$_{1-4}$ haloalkoxy, C$_{6-12}$ aryl, and a 4-7-membered heterocycle with 1 to 4 heteroatoms selected from O, N and S or combinations thereof; wherein any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In another aspect, the present disclosure provides a compound according to formula (IVd1):

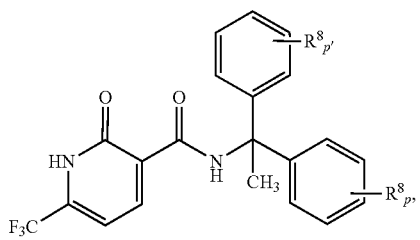

(IVd1)

or a pharmaceutically acceptable salt thereof, wherein p and p' are independently from 0 to 5;

$R^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups optionally form a 5-7 membered ring that optionally contains 1 to 3 heteroatoms selected from O, N, and S; any of which is optionally substituted with R*;

R* is halogen, —OH, C$_{1-3}$ alkyl, C$_{1-3}$ haloalkyl, phenyl, or benzyl, any of which is optionally substituted with a halogen; and R$^\#$ is C$_{1-3}$ alkyl, C$_{1-3}$ haloalkyl, phenyl, or benzyl, any of which is optionally substituted with a halogen.

In another aspect, the present disclosure provides a compound according to formula (IVe):

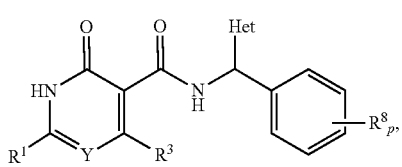

(IVe)

or a pharmaceutically acceptable salt thereof, wherein p is from 0 to 5;

Y is N, —CR$^2$, —COR$^2$ or —CNHR$^2$;

Het is a 6-membered heterocycle comprising from 1 to 3 nitrogen atoms, wherein Het is optionally substituted with one or more of halogen, —OH or =O;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl;

R$^8$ is independently at each occurrence halogen, —CN, =O, —OH, —NH$_2$, C$_{1-4}$ alkoxy, phenoxy, C$_{1-4}$ alkyl, C$_{2-4}$ alkenyl, C$_{2-4}$ alkynyl, C$_{1-2}$ haloalkyl, or C$_{1-2}$ haloalkoxy.

In another aspect, the present disclosure provides a compound according to formula (IVe1):

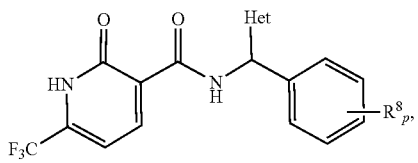

(IVe1)

or a pharmaceutically acceptable salt thereof, wherein p is from 0 to 5;

Het is a 6-membered heterocycle comprising from 1 to 3 nitrogen atoms, wherein Het is optionally substituted with one or more of halogen, —OH or =O, and R$^8$ is independently at each occurrence halogen, —OH, —NH$_2$, C$_{1-4}$ alkoxy, phenoxy or C$_{1-4}$ alkyl.

In another aspect, the present disclosure provides a compound according to formula (IVf):

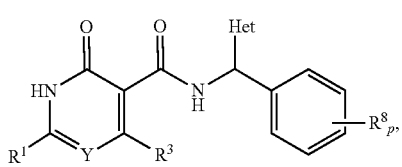

(IVf)

or a pharmaceutically acceptable salt thereof, wherein

Y is N, —CR$^2$, —COR$^2$ or —CNHR$^2$;

Het is a 6-membered heterocycle comprising from 1 to 3 nitrogen atoms, wherein Het is optionally substituted with one or more of halogen, —OH or =O;

R$^1$ is H, C$_{1-4}$ alkyl, C$_{1-4}$ haloalkyl, or benzyl;

R$^2$ is H, halogen, C$_{1-12}$ alkyl, C$_{1-12}$ alkenyl, C$_{6-12}$ aryl, C$_{1-12}$ aralkyl, C$_{1-4}$ haloalkyl, or a 5-7-membered heterocycle with 1 to 4 heteroatoms selected from O, N and S or combinations thereof, any of which is optionally substituted by —OH;

R$^3$ is H, C$_{1-4}$ alkyl, or C$_{1-4}$ haloalkyl.

In another aspect, the present disclosure provides a compound according to formula (IVf1):

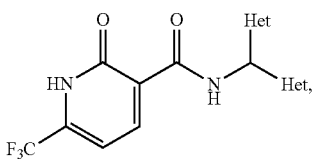

(IVf1)

or a pharmaceutically acceptable salt thereof, wherein Het is a 6-membered heterocycle comprising from 1 to 3 nitrogen atoms, wherein Het is optionally substituted with one or more of halogen, —OH or =O.

In another aspect, the present disclosure provides a compound according to formula (V'):

(V')

[Chemical structure showing a pyridinone with F₃C substituent and C(O)NH-L-Ar group]

or a pharmaceutically acceptable salt thereof, wherein L and Ar are as defined above.

In another aspect, the present disclosure provides a compound according to formula (V'), wherein: L is a bond; Ar is a radical of pyridine or oxane; and $R^8$ is independently at each occurrence $C_{1-4}$ alkyl, $C_{1-4}$ alkenyl, or $C_{1-4}$ haloalkyl, any of which is optionally substituted with R*.

In another aspect, the present disclosure provides a compound according to formula (V):

(V)

[Chemical structure]

or a pharmaceutically acceptable salt thereof, wherein:
r is from 0 to 5;
L is $-(CH_2)_n-$, $-(CHB)_n-$, $-CH_2CHB-$, or $-CHBCH_2-$; wherein:
B is $C_{1-12}$ alkyl or benzyl;
n is 1 or 2; and
when L is $-(CH_2)_n-$ and $R^1$ is $CF_3$, then at least one $R^7$ is a phenoxy that is optionally substituted with a halogen;
when L is $-(CHB)_n-$ and B is methyl, then at least one $R^7$ is present, and
when L is $-(CHB)_n-$ and B is $C_{2-12}$ alkyl, then $R^7$ is not halogen; $-CN$; $C_{1-12}$ alkyl; or $C_{1-4}$ alkoxy;
Y is N, $-CR^2$, $-COR^2$ or $-CNHR^2$;
$R^1$ is H, $C_{1-4}$ alkyl, $C_{1-4}$ haloalkyl, or benzyl;
$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by $-OH$;
$R^3$ is H, $C_{1-4}$ alkyl, or $C_{1-4}$ haloalkyl;
wherein:
when Y is N, at least one of $R^1$ and $R^3$ is not H, and when Y is $CR^2$, at least one of $R^1$, $R^2$ and $R^3$ is not H;
$R^7$ is independently at each occurrence halogen, $-CN$, $=O$, $-OH$, $-(CH_2)_{1-3}-OR^\#$, $-NH-(C=O)-R^*$, $-NH-(SO_2)-R^*$, $-(CH_2)_{1-3}-NR^\#_2$, $-NHR^\#$, $-N(R^\#)_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;
R* is halogen, $-OH$, $C_{1-3}$ alkyl, $C_{1-3}$ haloalkyl, phenyl, or benzyl, any of which is optionally substituted with a halogen; and
$R^\#$ is $C_{1-3}$ alkyl, $C_{1-3}$ haloalkyl, phenyl, or benzyl, any of which is optionally substituted with a halogen.

In another aspect, the present disclosure provides a compound according to formula (Va):

(Va)

[Chemical structure]

or a pharmaceutically acceptable salt thereof, wherein:
Y is N, $-CR^2$, $-COR^2$ or $-CNHR^2$;
$R^1$H; $C_{1-4}$ alkyl; $C_{1-4}$ haloalkyl, or benzyl;
$R^2$ is H; halogen; $C_{1-12}$ alkyl; $C_{1-12}$ alkenyl; $C_{6-12}$ aryl; $C_{1-12}$ aralkyl; $C_{1-4}$ haloalkyl, or a 5-7-membered heterocycle with 1 to 4 heteroatoms selected from O, N and S or combinations thereof, each of which is optionally substituted by $-OH$;
$R^3$ is H; $C_{1-4}$ alkyl, or $C_{1-4}$ haloalkyl; wherein:
when Y is N, at least one of $R^1$ and $R^3$ is not H, and when Y is $CR^2$, at least one of $R^1$, $R^2$ and $R^3$ is not H;
$R^7$ is independently at each occurrence halogen; $-CN$; $=O$; $-OH$; $-(CH_2)_{1-3}-OR^\#$; $-NH-(C=O)-R^*$; $-NH-(SO_2)-R^*$; $-(CH_2)_{1-3}-NR^\#_2$; $-NHR^\#$, $-N(R^\#)_2$; $C_{1-4}$ alkoxy; phenoxy; $C_{1-12}$ alkyl; $C_{1-12}$ alkenyl; $C_{1-4}$ haloalkyl; or $C_{6-12}$ aryl, wherein any of which is optionally substituted with R*;
R* is halogen, $-OH$, $C_{1-3}$ alkyl, $C_{1-3}$ haloalkyl, phenyl, or benzyl, any of which is optionally substituted with a halogen; and
$R^\#$ is $C_{1-3}$ alkyl, $C_{1-3}$ haloalkyl, phenyl, or benzyl, any of which is optionally substituted with a halogen.

In another aspect, the present disclosure provides a compound according to formula (Va1):

(Va1)

[Chemical structure]

or a pharmaceutically acceptable salt thereof, wherein:
at least one $R^7$ is present and is independently at each occurrence halogen; $-OH$; $C_{1-4}$ alkyl; $C_{2-6}$ alkenyl; $C_{1-4}$ haloalkyl; $C_{1-4}$ alkoxy; phenoxy; or phenyl, wherein any of which is optionally substituted with R*;
R* is halogen, $-OH$, $C_{1-3}$ alkyl, $C_{1-3}$ haloalkyl, phenyl, or benzyl, any of which is optionally substituted with a halogen; and
$R^\#$ is $C_{1-3}$ alkyl, $C_{1-3}$ haloalkyl, phenyl, or benzyl, any of which is optionally substituted with a halogen.

In another aspect, the present disclosure provides a compound according to formula (Vb):

(Vb)

[Chemical structure]

or a pharmaceutically acceptable salt thereof, wherein:
r is from 1 to 5;
Y is N, —CR², —COR² or —CNHR²;
R¹H, C₁₋₄ alkyl, C₁₋₄ haloalkyl, or benzyl;
R² is H, halogen, C₁₋₁₂ alkyl, C₁₋₁₂ alkenyl, C₆₋₁₂ aryl, C₁₋₁₂ aralkyl, C₁₋₄ haloalkyl, or a 5-7-membered heterocycle with 1 to 4 heteroatoms selected from O, N and S or combinations thereof, each of which is optionally substituted by —OH;
R³ is H, C₁₋₄ alkyl, or C₁₋₄ haloalkyl; wherein:
when Y is N, at least one of R¹ and R³ is not H, and
when Y is CR², at least one of R¹, R², and R³ is not H; at least one R⁷ is phenoxy further substituted by a halogen, where additional R⁷ groups are optionally present and are independently at each occurrence halogen; —OH; C₁₋₄ alkyl; C₂₋₆ alkenyl; C₁₋₄ haloalkyl; C₁₋₄ alkoxy; phenyl, phenoxy; or C₆₋₁₂ aryl, wherein any of which is optionally substituted with R*;
R* is halogen, —OH, C₁₋₃ alkyl, C₁₋₃ haloalkyl, phenyl, or benzyl, any of which is optionally substituted with a halogen; and
R# is C₁₋₃ alkyl, C₁₋₃ haloalkyl, phenyl, or benzyl, any of which is optionally substituted with a halogen.

In another aspect, the present disclosure provides a compound according to formula (Vb1):

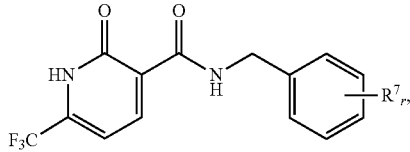

(Vb1)

or a pharmaceutically acceptable salt thereof, wherein:
r is from 1 to 5;
at least one R⁷ is phenoxy further substituted by a halogen, where additional R⁷ groups are optionally present and are independently at each occurrence halogen, —CN, ═O, —OH, —(CH₂)₁₋₃—OR#, —NH—(C═O)—R*, —NH—(SO₂)—R*, —(CH₂)₁₋₃—NR#₂, —NHR#, —N(R#)₂, C₁₋₄ alkoxy, phenoxy, C₁₋₁₂ alkyl, C₁₋₁₂ alkenyl, C₁₋₄ haloalkyl, or C₆₋₁₂ aryl, any of which is optionally substituted with R*;
R* is halogen, —OH, C₁₋₃ alkyl, C₁₋₃ haloalkyl, phenyl, or benzyl, any of which is optionally substituted with a halogen; and
R# is C₁₋₃ alkyl, C₁₋₃ haloalkyl, phenyl, or benzyl, any of which is optionally substituted with a halogen.

In another aspect, the present disclosure provides a compound according to formula (VI):

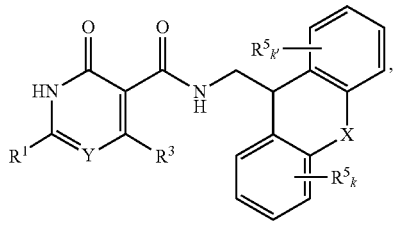

(VI)

or a pharmaceutically acceptable salt thereof, wherein:
k and k' are independently from 0 to 4;

X is a bond, —CH₂—, —CH₂—CH₂—, —CH₂—O—, —CH═CH—, —(C═O)—, —O—, —NR#—, —S—, —(S═O)—, or —(SO₂)—;
R¹ is H, C₁₋₄ alkyl, C₁₋₄ haloalkyl, or benzyl;
R² is H, halogen, C₁₋₁₂ alkyl, C₁₋₁₂ alkenyl, C₆₋₁₂ aryl, C₁₋₁₂ aralkyl, C₁₋₄ haloalkyl, or a 5-7-membered heterocycle with 1 to 4 heteroatoms selected from O, N and S or combinations thereof, any of which is optionally substituted by —OH;
R³ is H, C₁₋₄ alkyl, or C₁₋₄ haloalkyl;
R⁵ is independently at each occurrence halogen, —CN, ═O, —OH, —NH₂, —(CH₂)₁₋₃—OR#, —NH—(C═O)—R*, —NH—(SO₂)—R*, —(CH₂)₁₋₃—NR#₂, —NHR#, —N(R#)₂, C₁₋₄ alkoxy, phenoxy, C₁₋₁₂ alkyl, C₁₋₁₂ alkenyl, C₁₋₁₂ alkynyl, C₁₋₄ haloalkyl, C₁₋₄ haloalkoxy, C₆₋₁₂ aryl, a 4-7-membered heterocycle with 1 to 4 heteroatoms selected from O, N and S or combinations thereof, or wherein two adjacent R⁵ groups form a 5-7 membered ring that optionally contains 1 to 3 heteroatoms selected from O, N, and S; any of which is optionally substituted with R*;
R* is halogen, —OH, C₁₋₃ alkyl, C₁₋₃ haloalkyl, phenyl, or benzyl, any of which is optionally substituted with a halogen; and
R# is C₁₋₃ alkyl, C₁₋₃ haloalkyl, phenyl, or benzyl, any of which is optionally substituted with a halogen.

In another aspect, the present disclosure provides a compound of according to formula (VIa):

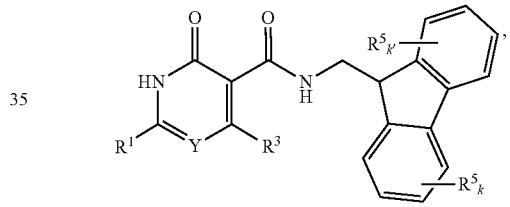

(VIa)

or a pharmaceutically acceptable salt thereof, wherein:
k and k' are independently from 0 to 4;
Y is N, —CR², —COR² or —CNHR²;
R¹ is H, C₁₋₄ alkyl, C₁₋₄ haloalkyl, or benzyl;
R² is H, halogen, C₁₋₁₂ alkyl, C₁₋₁₂ alkenyl, C₆₋₁₂ aryl, C₁₋₁₂ aralkyl, C₁₋₄ haloalkyl, or a 5-7-membered heterocycle with 1 to 4 heteroatoms selected from O, N and S or combinations thereof; any of which is optionally substituted by —OH;
R³ is H, C₁₋₄ alkyl, or C₁₋₄ haloalkyl;
R⁵ is independently at each occurrence halogen, —CN, ═O, —OH, —NH₂, —(CH₂)₁₋₃—OR#, —NH—(C═O)—R*, —NH—(SO₂)—R*, —(CH₂)₁₋₃—NR#₂, —NHR#, —N(R#)₂, C₁₋₄ alkoxy, phenoxy, C₁₋₁₂ alkyl, C₁₋₁₂ alkenyl, C₁₋₁₂ alkynyl, C₁₋₄ haloalkyl, C₁₋₄ haloalkoxy, C₆₋₁₂ aryl, a 4-7-membered heterocycle with 1 to 4 heteroatoms selected from O, N and S or combinations thereof, or wherein two adjacent R⁵ groups form a 5-7 membered ring that optionally contains 1 to 3 heteroatoms selected from O, N, and S; any of which is optionally substituted with R*;
R* is halogen, —OH, C₁₋₃ alkyl, C₁₋₃ haloalkyl, phenyl, or benzyl, any of which is optionally substituted with a halogen; and
R# is C₁₋₃ alkyl, C₁₋₃ haloalkyl, phenyl, or benzyl, any of which is optionally substituted with a halogen.

In another aspect, the present disclosure provides a compound of according to formula (VIa1):

159

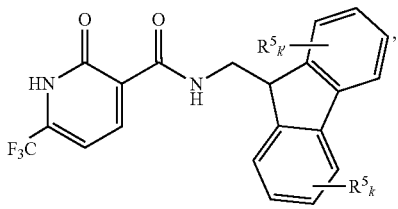
(VIa1)

or a pharmaceutically acceptable salt thereof, wherein:
k and k' are independently from 0 to 4;
$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;
R* is halogen, —OH, C$_{1-3}$ alkyl, C$_{1-3}$ haloalkyl, phenyl, or benzyl, any of which is optionally substituted with a halogen; and
R$^\#$ is C$_{1-3}$ alkyl, C$_{1-3}$ haloalkyl, phenyl, or benzyl, any of which is optionally substituted with a halogen.

In another aspect, the present disclosure provides a compound of according to formula (VII):

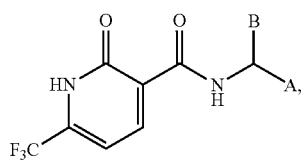
(VII)

or a pharmaceutically acceptable salt thereof, wherein:
A is A', A", CR$^4$(Ar)$_2$, or a phenyl that is optionally substituted with one or more $R^7$; wherein:
A' is

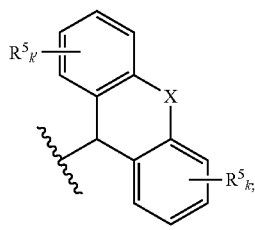

A" is

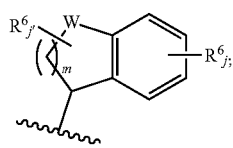

and

160

Ar is independently at each occurrence a phenyl that is optionally substituted with one or more $R^1$ or Het, where Het is a 6-membered heterocycle comprising from 1 to 3 nitrogen atoms, wherein Het is optionally substituted with one or more of halogen, —OH or =O;
B is C$_{1-12}$ alkyl or benzyl;
wherein:
when B is C$_{1-2}$ alkyl, then at least one $R^7$ is present and is not —Cl, —F, —CN, methyl, or methoxy; and
when B is C$_{3-4}$ alkyl, then $R^7$ is not C$_{2-12}$ alkyl;
k and k' are independently from 0 to 4;
j and j' are independently from 0 to 4;
$R^5$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;
$R^6$ is independently at each occurrence halogen, —OH, C$_{1-4}$ alkoxy, C$_{1-12}$ alkyl, C$_{1-12}$ alkenyl, C$_{1-4}$ haloalkyl, or C$_{6-12}$ aryl, any of which is optionally substituted with R*;
$R^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;
$R^8$ is independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, C$_{1-4}$ alkoxy, phenoxy, C$_{1-12}$ alkyl, C$_{1-12}$ alkenyl, C$_{2-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;
R* is halogen, —OH, C$_{1-3}$ alkyl, C$_{1-3}$ haloalkyl, phenyl, or benzyl, any of which is optionally substituted with a halogen; and
R$^\#$ is C$_{1-3}$ alkyl, C$_{1-3}$ haloalkyl, phenyl, or benzyl, any of which is optionally substituted with a halogen.

In another aspect, the present disclosure provides a compound of according to formula (VIIa):

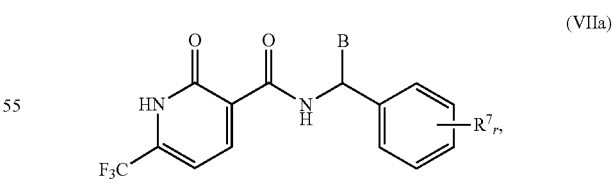
(VIIa)

or a pharmaceutically acceptable salt thereof, wherein:
r is independently from 0 to 5;
B is C$_{2-12}$ alkyl;
$R^7$ is independently at each occurrence —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, C$_{1-4}$ alkoxy, phenoxy, C$_{5-12}$ alkyl, C$_{1-12}$ alkenyl, C$_{1-4}$ haloalkyl, or C$_{6-12}$ aryl, any of which is optionally substituted with R*;

R* is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, phenyl, or benzyl, any of which is optionally substituted with a halogen.

In another aspect, the present disclosure provides a compound of according to formula (VIIa), where B is cyclohexyl.

In another aspect, the present disclosure provides a compound of according to formula (VIIb):

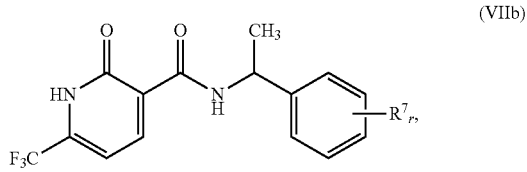

(VIIb)

or a pharmaceutically acceptable salt thereof, wherein:
r is independently from 1 to 5;
$R^7$ is independently at each occurrence =O, —OH, —$(CH_2)_{1-3}$—$OR^{\#}$, —NH—(C=O)—R*, —NH—$(SO_2)$—R*, —$(CH_2)_{1-3}$—$NR^{\#}_2$, —$NHR^{\#}$, —$N(R^{\#})_2$, phenoxy, $C_{1-12}$ alkenyl, $C_{1-4}$ haloalkyl, or $C_{6-12}$ aryl, wherein any of which is optionally substituted with R*;

R* is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, phenyl, or benzyl, any of which is optionally substituted with a halogen.

In another aspect, the present disclosure provides a compound of according to formula (VIIb), $R^7$ is a halogen substituted phenoxy.

In another aspect, the present disclosure provides a compound of according to formula (VIIc):

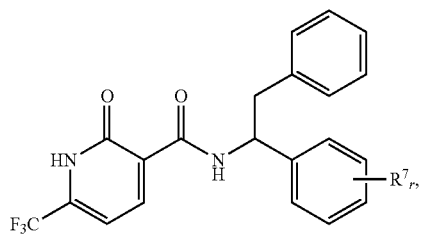

(VIIc)

or a pharmaceutically acceptable salt thereof, wherein:
r is independently from 0 to 5;
$R^7$ is independently at each occurrence halogen, —CN, =O, —OH, —$(CH_2)_{1-3}$—$OR^{\#}$, —NH—(C=O)—R*, —NH—$(SO_2)$—R*, —$(CH_2)_{1-3}$—$NR^{\#}_2$, —$NHR^{\#}$, —$N(R^{\#})_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;

R* is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, phenyl, or benzyl, any of which is optionally substituted with a halogen.

In another aspect, the present disclosure provides a compound of according to formula (VIIc), $R^7$ is independently at each occurrence a halogen selected from Cl, Br and F. In a further aspect, $R^7$ is Cl.

In another aspect, the present disclosure provides a compound of according to formula (VII), wherein B is methyl, ethyl, propyl, butyl, cyclohexyl, benzyl, or methylene substituted by oxolanyl, oxanyl, cyclopropyl, cyclobutyl, cyclopentyl, or cyclohexanyl, any of which is optionally further substituted by —$CH_3$, —OH, or —$OCH_3$.

In another aspect, the present disclosure provides a compound of according to formula (VIII):

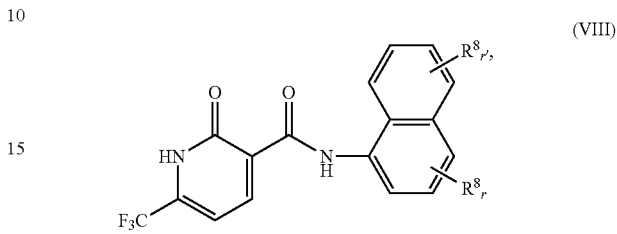

(VIII)

or a pharmaceutically acceptable salt thereof, wherein:
r and r' are independently from 0 to 4;
$R^8$ is independently at each occurrence halogen, —CN, =O, —OH, —$(CH_2)_{0-3}$—SH, —$(CH_2)_{0-3}$—SR*, —$(SO_2)$—R*, —$NH_2$, —$(CH_2)_{1-3}$—$OR^{\#}$, —NH—(C=O)—R*, —NH—$(SO_2)$—R*, —$(CH_2)_{1-3}$—$NR^{\#}_2$, —$NHR^{\#}$, or —$N(R^{\#})_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*.

In another aspect, the present disclosure provides a compound of according to formula (VIII), wherein $R^8$ is —OH or —$NH_2$.

In an additional aspect of the present disclosure, it is provided that any one of the preceding formulas I through VIII (inclusive of subgenera) do not encompass one or more the compounds of Table 1. In a further embodiment, one or more of the following compounds are specifically excluded from any one of the preceding Formulas I through VIII (inclusive of subgenera).

TABLE 1

Excluded compounds

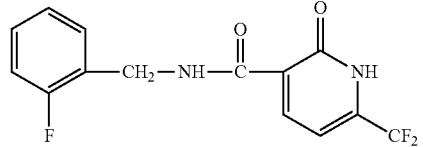

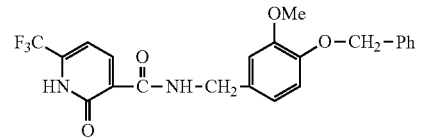 [SMILES: COc1cc(CNC(=O)c2ccc(C(F)(F)F)[nH]c2=O)ccc1OCc1ccccc1]

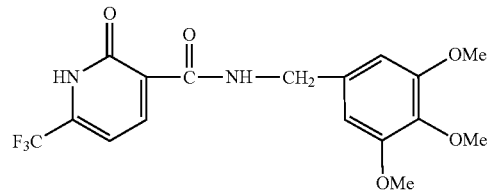 [SMILES: COc1cc(CNC(=O)c2ccc(C(F)(F)F)[nH]c2=O)cc(OC)c1OC]

TABLE 1-continued
Excluded compounds
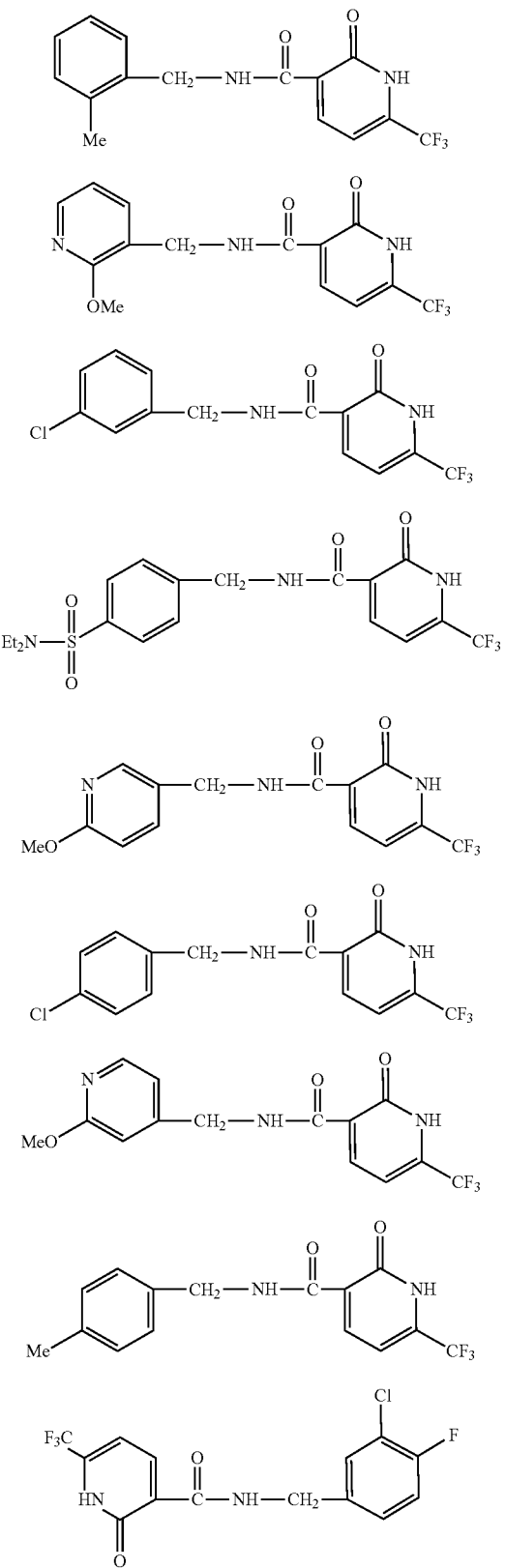
TABLE 1-continued
Excluded compounds
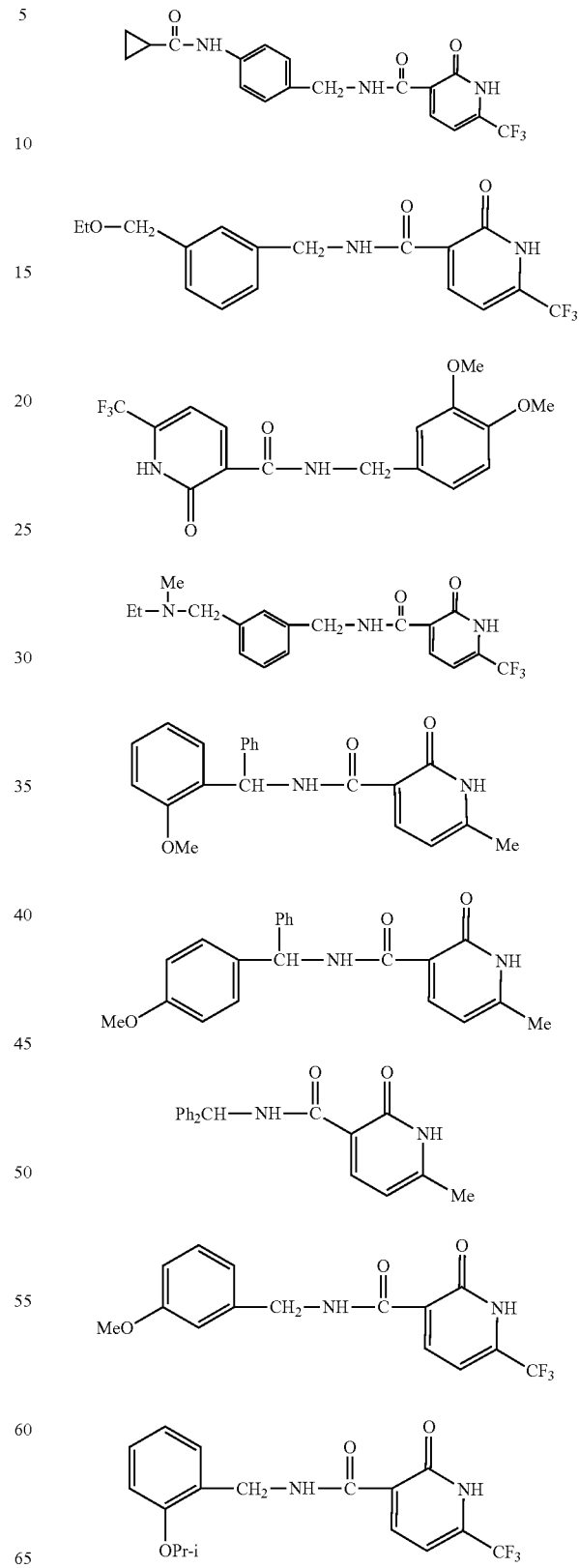

TABLE 1-continued

Excluded compounds

TABLE 1-continued
Excluded compounds
In one embodiment, the compounds of the present disclosure can be as described in Table 2.
TABLE 2
Exemplary compounds according to the disclosure
TABLE 2-continued
Exemplary compounds according to the disclosure
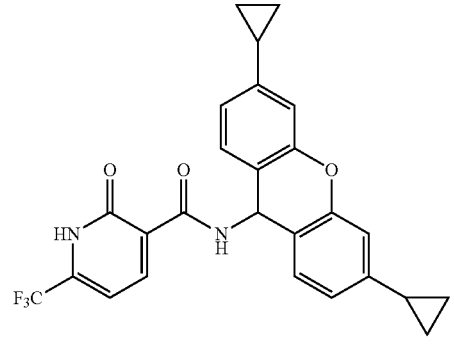

TABLE 2-continued
Exemplary compounds according to the disclosure
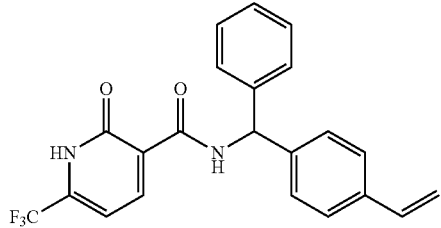
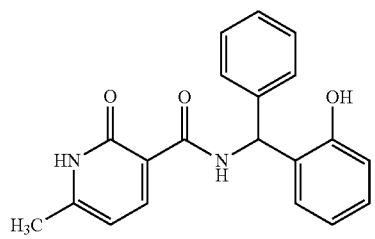
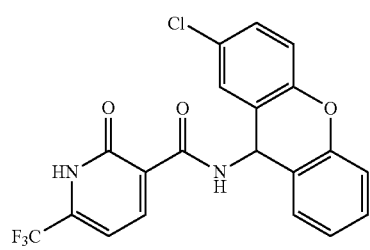
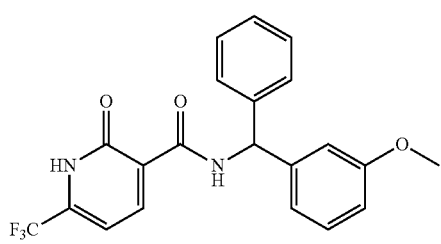
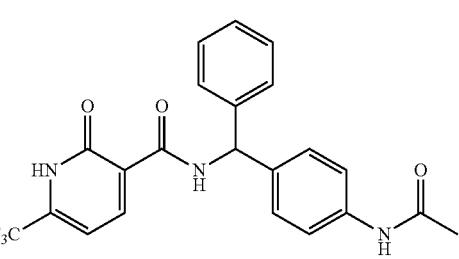
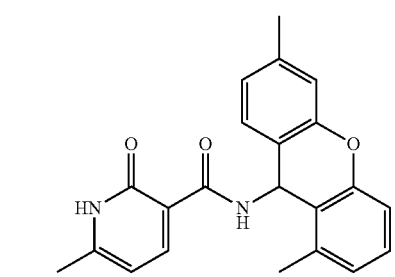 [SMILES: Cc1ccc2c(c1)Oc1cccc(C)c1C2NC(=O)c1ccc(C)[nH]c1=O]
TABLE 2-continued
Exemplary compounds according to the disclosure
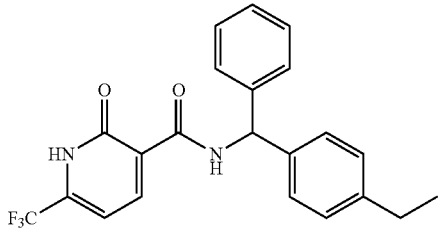
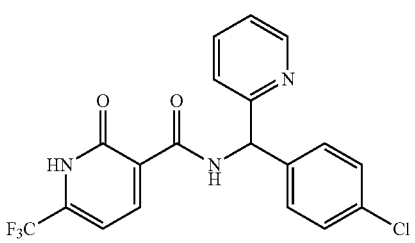
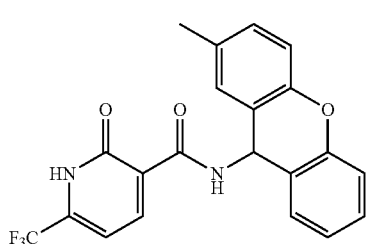
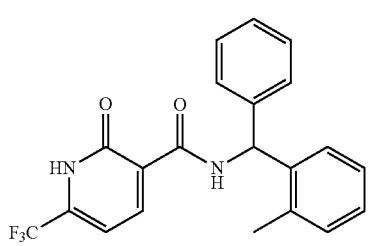 [SMILES: Cc1ccccc1C(NC(=O)c1ccc(C(F)(F)F)[nH]c1=O)c1ccccc1]
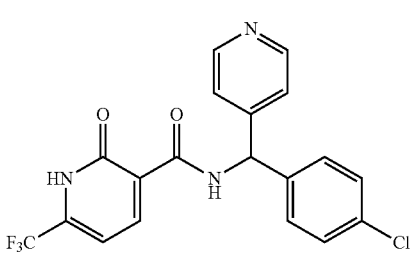
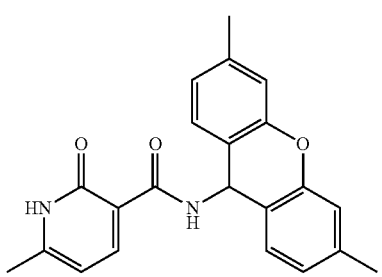

TABLE 2-continued
Exemplary compounds according to the disclosure
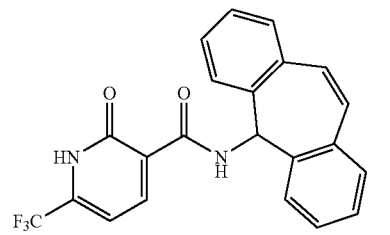 [SMILES: O=C(NC1c2ccccc2C=Cc2ccccc21)c1ccc(C(F)(F)F)[nH]c1=O]
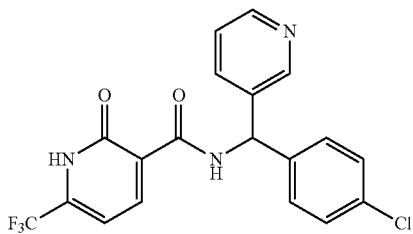
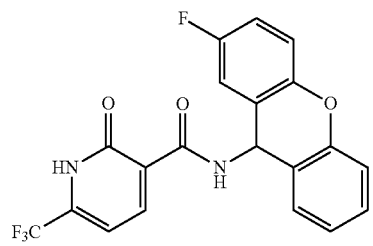
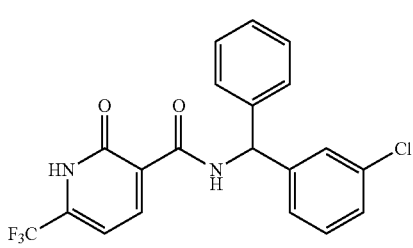 [SMILES: O=C(NC(c1ccccc1)c1cccc(Cl)c1)c1ccc(C(F)(F)F)[nH]c1=O]
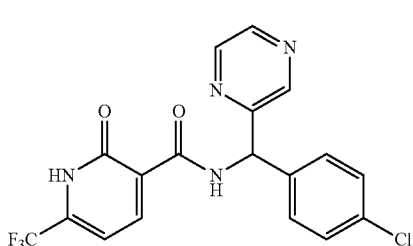
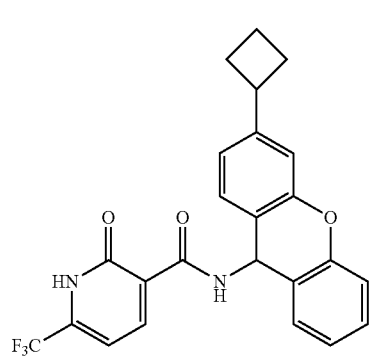 [SMILES: O=C(NC1c2ccccc2Oc2cc(C3CCC3)ccc21)c1ccc(C(F)(F)F)[nH]c1=O]
TABLE 2-continued
Exemplary compounds according to the disclosure
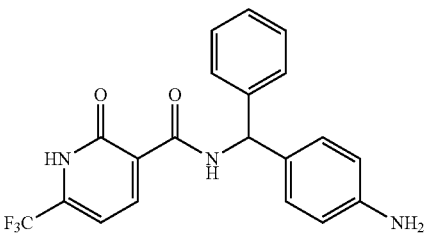 [SMILES: Nc1ccc(C(NC(=O)c2ccc(C(F)(F)F)[nH]c2=O)c2ccccc2)cc1]
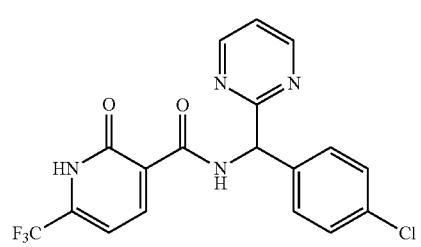 [SMILES: O=C(NC(c1ccc(Cl)cc1)c1ncccn1)c1ccc(C(F)(F)F)[nH]c1=O]
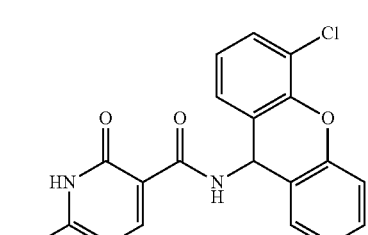
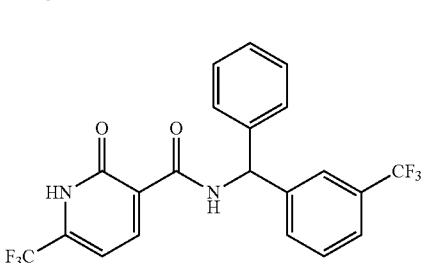
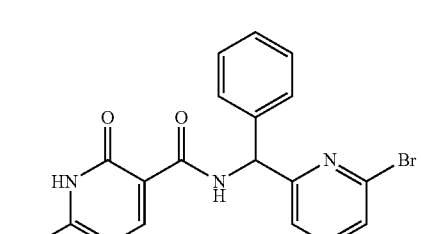
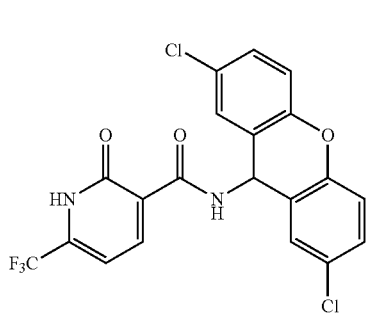 [SMILES: O=C(NC1c2cc(Cl)ccc2Oc2ccc(Cl)cc21)c1ccc(C(F)(F)F)[nH]c1=O]

TABLE 2-continued
Exemplary compounds according to the disclosure
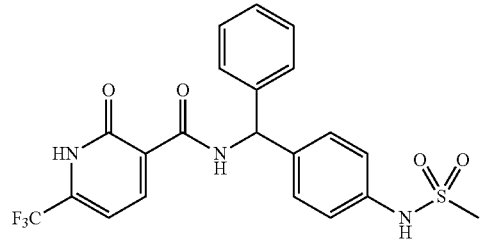 [SMILES: CS(=O)(=O)Nc1ccc(C(NC(=O)c2ccc(C(F)(F)F)[nH]c2=O)c2ccccc2)cc1]
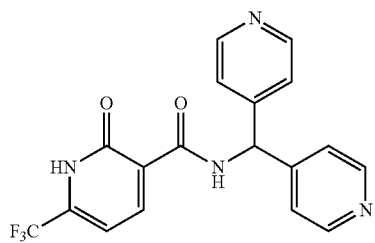 [SMILES: O=C(NC(c1ccncc1)c1ccncc1)c1ccc(C(F)(F)F)[nH]c1=O]
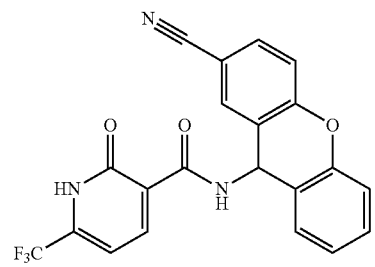 [SMILES: N#Cc1ccc2c(c1)C(NC(=O)c1ccc(C(F)(F)F)[nH]c1=O)c1ccccc1O2]
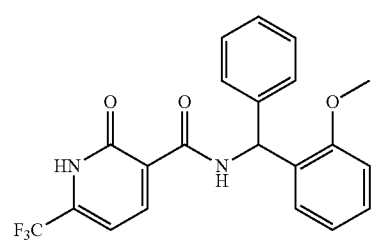
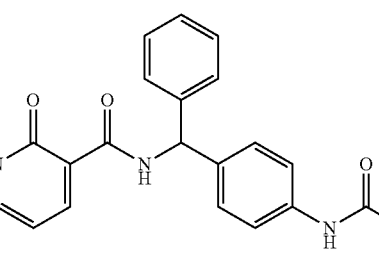
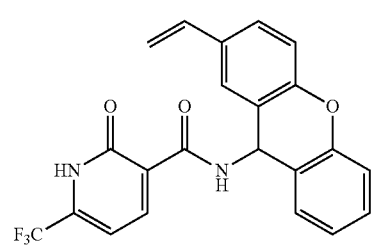
TABLE 2-continued
Exemplary compounds according to the disclosure
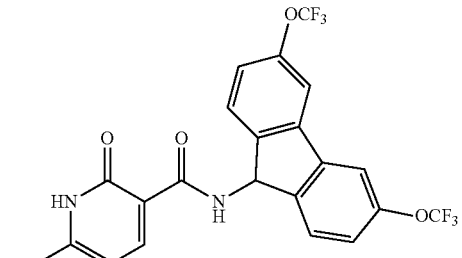
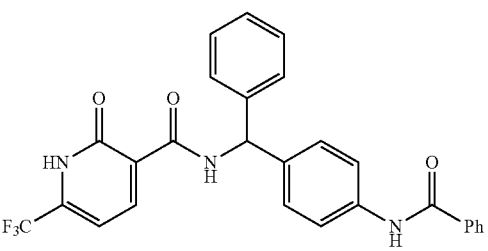 [SMILES: O=C(Nc1ccc(C(NC(=O)c2ccc(C(F)(F)F)[nH]c2=O)c2ccccc2)cc1)c1ccccc1]
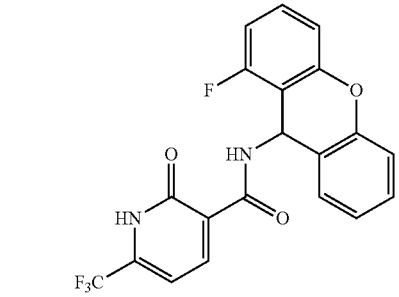 [SMILES: O=C(NC1c2ccccc2Oc2cccc(F)c21)c1ccc(C(F)(F)F)[nH]c1=O]
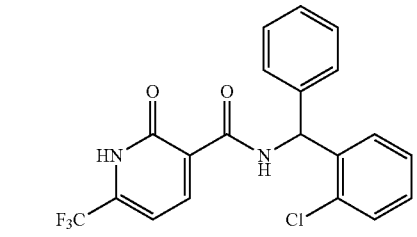
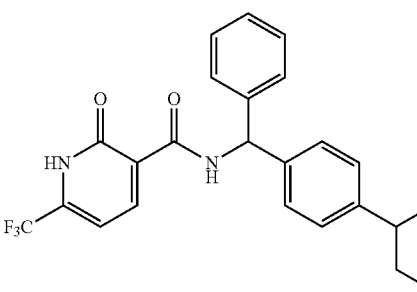

TABLE 2-continued
Exemplary compounds according to the disclosure
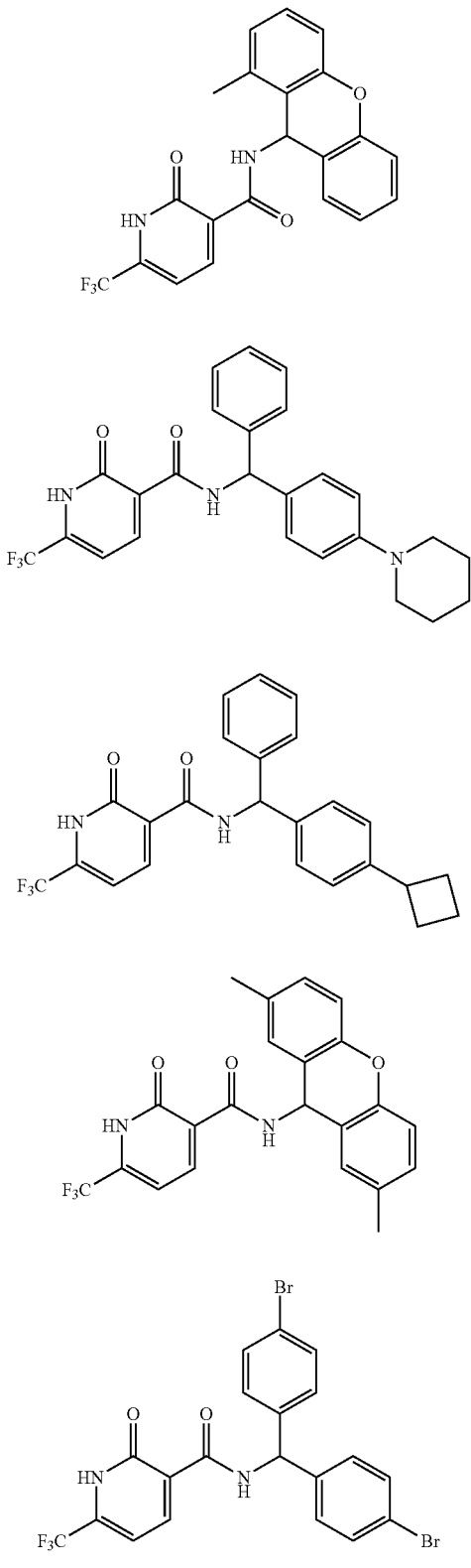
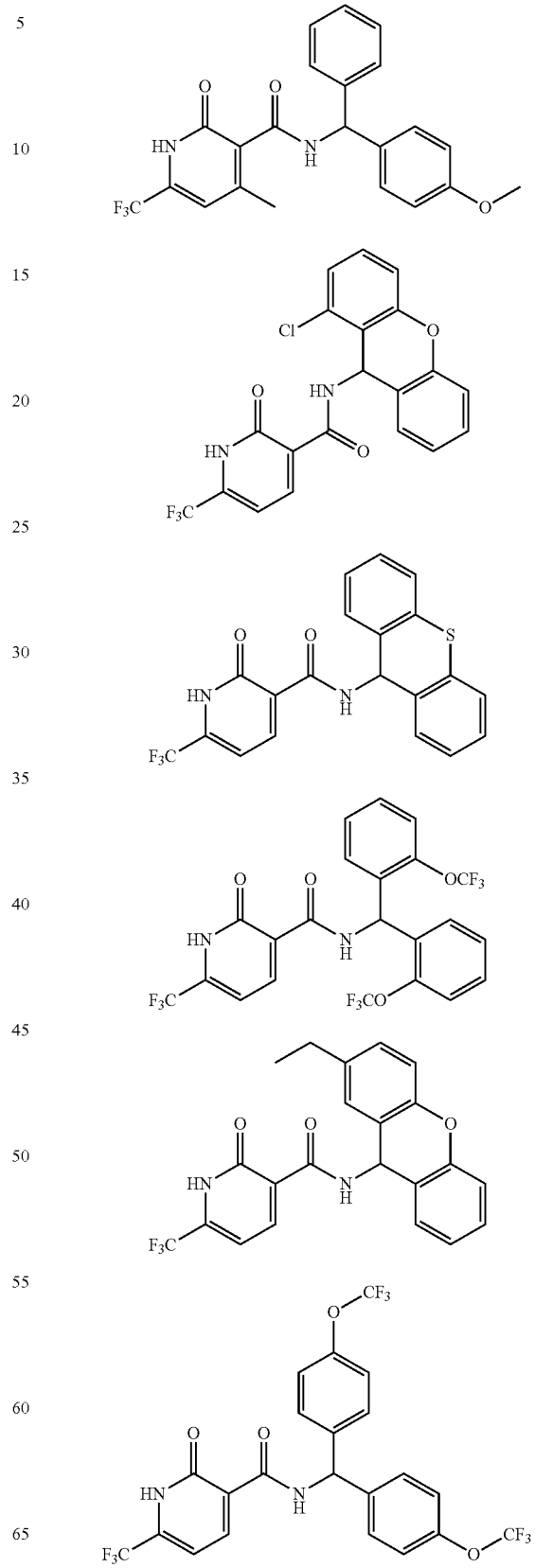

TABLE 2-continued
Exemplary compounds according to the disclosure
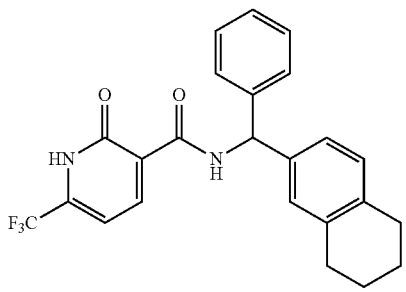 [SMILES: O=C(NC(c1ccccc1)c1ccc2c(c1)CCCC2)c1ccc(C(F)(F)F)[nH]c1=O]
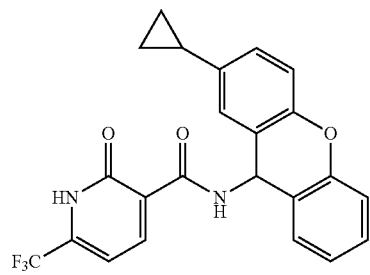
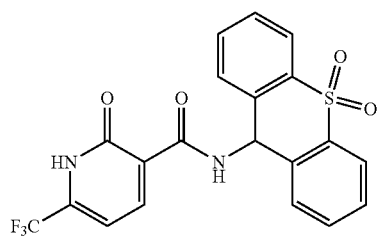 [SMILES: O=C(NC1c2ccccc2S(=O)(=O)c2ccccc21)c1ccc(C(F)(F)F)[nH]c1=O]
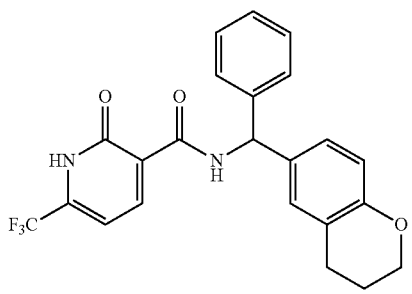 [SMILES: O=C(NC(c1ccccc1)c1ccc2c(c1)CCCO2)c1ccc(C(F)(F)F)[nH]c1=O]
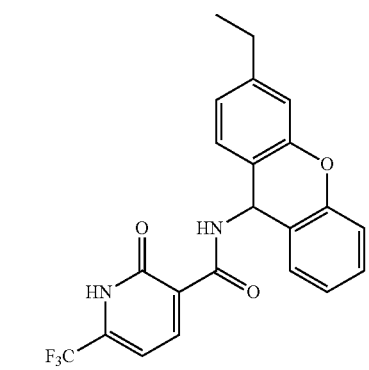 [SMILES: CCc1ccc2c(c1)Oc1ccccc1C2NC(=O)c1ccc(C(F)(F)F)[nH]c1=O]
TABLE 2-continued
Exemplary compounds according to the disclosure
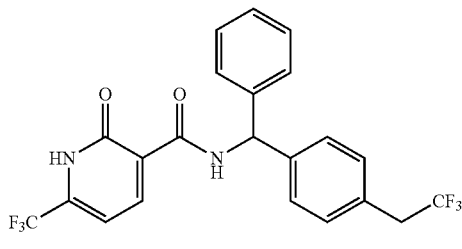 [SMILES: O=C(NC(c1ccccc1)c1ccc(CC(F)(F)F)cc1)c1ccc(C(F)(F)F)[nH]c1=O]
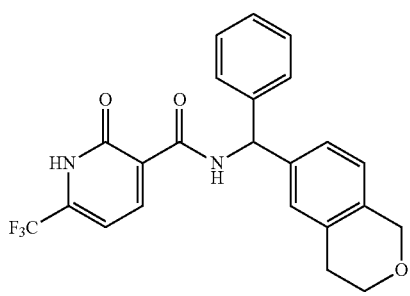 [SMILES: O=C(NC(c1ccccc1)c1ccc2c(c1)CCOC2)c1ccc(C(F)(F)F)[nH]c1=O]
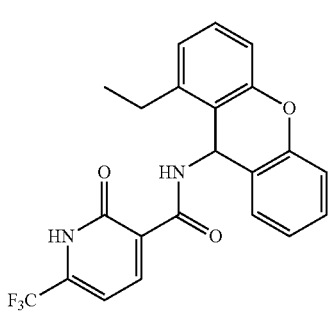
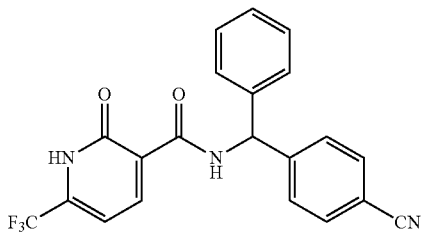 [SMILES: N#Cc1ccc(C(NC(=O)c2ccc(C(F)(F)F)[nH]c2=O)c2ccccc2)cc1]
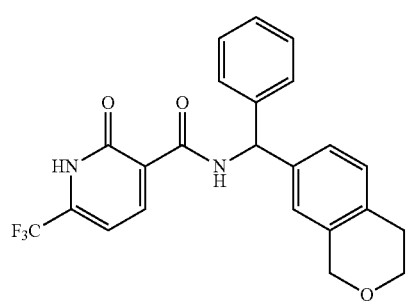 [SMILES: O=C(NC(c1ccccc1)c1ccc2c(c1)COCC2)c1ccc(C(F)(F)F)[nH]c1=O]

TABLE 2-continued
Exemplary compounds according to the disclosure
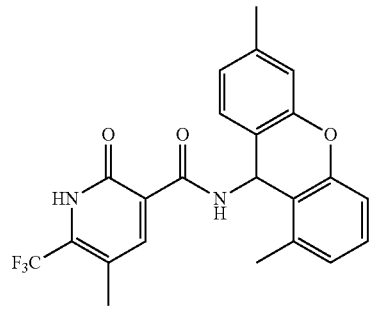
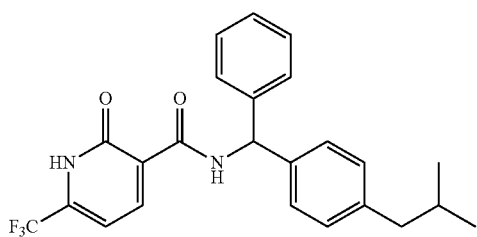 [SMILES: CC(C)Cc1ccc(C(NC(=O)c2ccc(C(F)(F)F)[nH]c2=O)c2ccccc2)cc1]
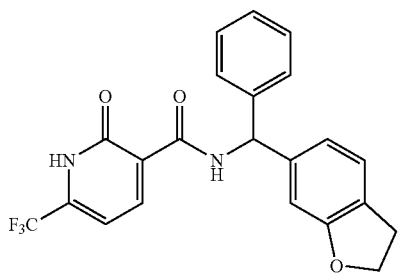
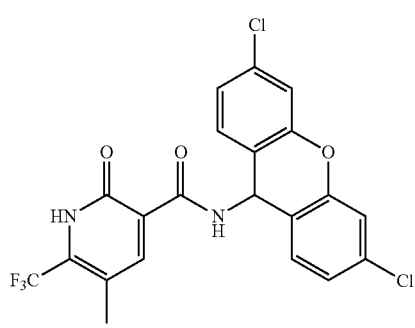
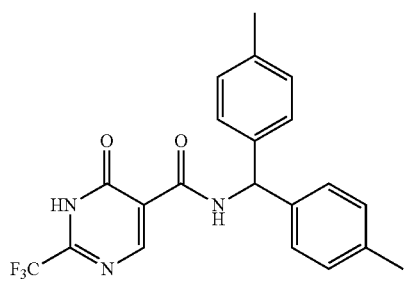
TABLE 2-continued
Exemplary compounds according to the disclosure
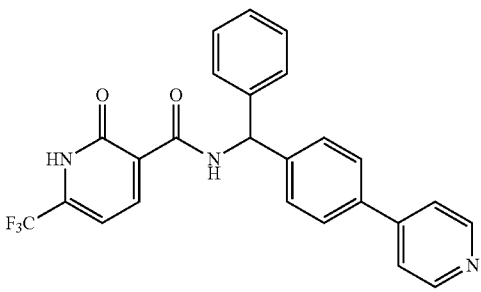 [SMILES: O=C(NC(c1ccccc1)c1ccc(-c2ccncc2)cc1)c1ccc(C(F)(F)F)[nH]c1=O]
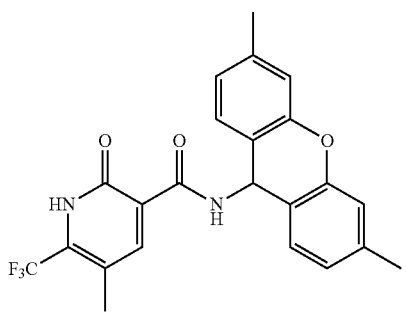 [SMILES: Cc1ccc2c(c1)Oc1cc(C)ccc1C2NC(=O)c1cc(C)c(C(F)(F)F)[nH]c1=O]
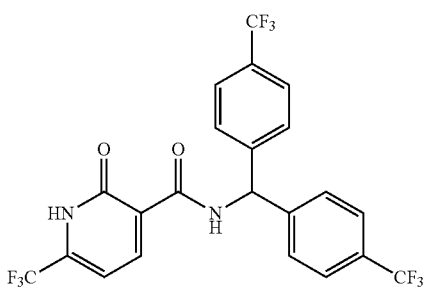
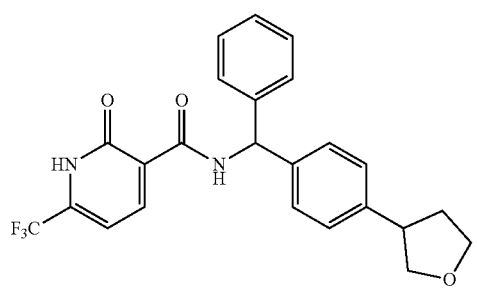 [SMILES: O=C(NC(c1ccccc1)c1ccc(C2CCOC2)cc1)c1ccc(C(F)(F)F)[nH]c1=O]
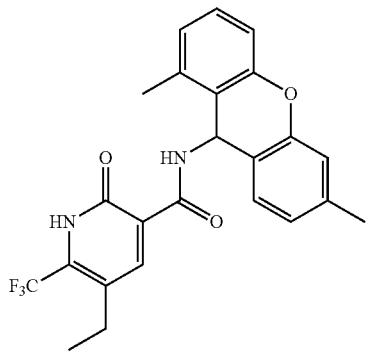 [SMILES: CCc1cc(C(=O)NC2c3ccc(C)cc3Oc3cccc(C)c32)c(=O)[nH]c1C(F)(F)F]

TABLE 2-continued
Exemplary compounds according to the disclosure
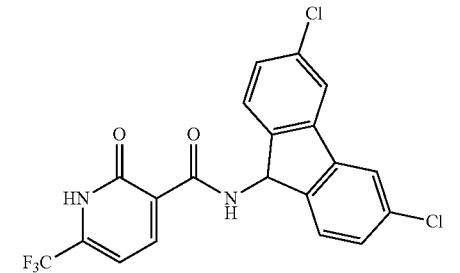 [SMILES: O=C(NC1c2ccc(Cl)cc2-c2cc(Cl)ccc21)c1ccc(C(F)(F)F)[nH]c1=O]
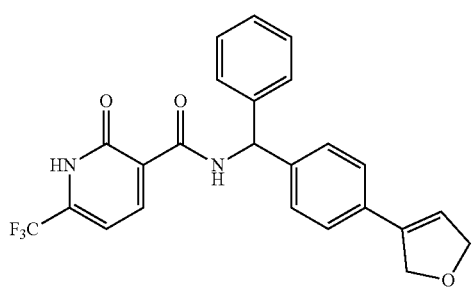 [SMILES: O=C(NC(c1ccccc1)c1ccc(C2=CCOC2)cc1)c1ccc(C(F)(F)F)[nH]c1=O]
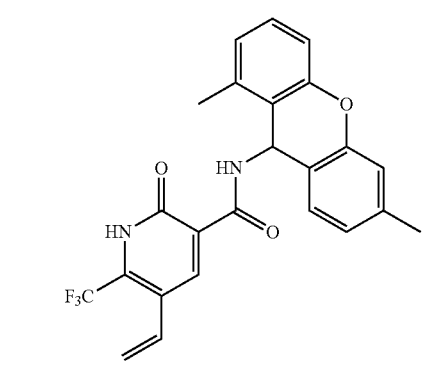 [SMILES: C=Cc1cc(C(=O)NC2c3ccc(C)cc3Oc3cccc(C)c32)c(=O)[nH]c1C(F)(F)F]
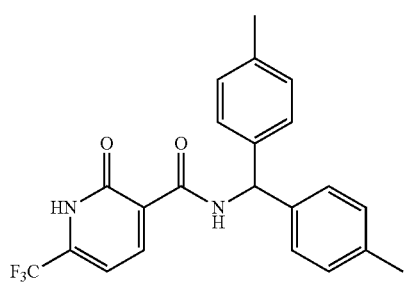 [SMILES: Cc1ccc(C(NC(=O)c2ccc(C(F)(F)F)[nH]c2=O)c2ccc(C)cc2)cc1]
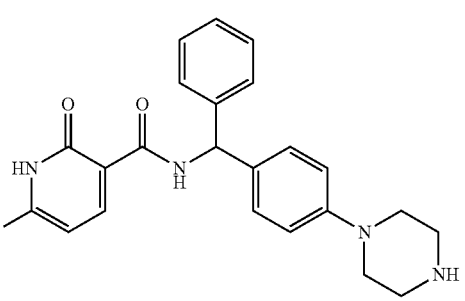
TABLE 2-continued
Exemplary compounds according to the disclosure
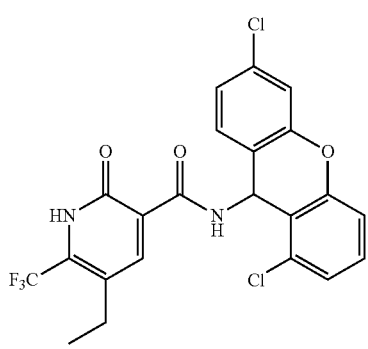 [SMILES: CCc1cc(C(=O)NC2c3ccc(Cl)cc3Oc3cccc(Cl)c32)c(=O)[nH]c1C(F)(F)F]
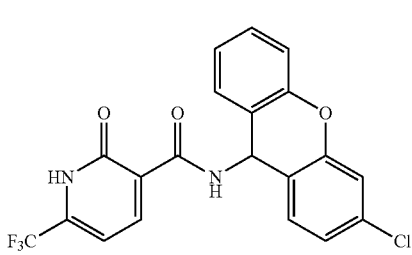
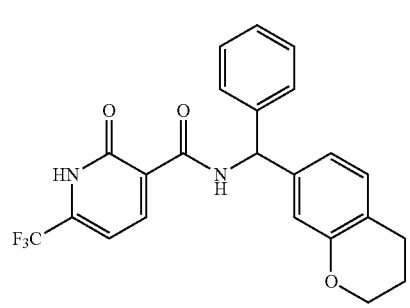 [SMILES: O=C(NC(c1ccccc1)c1ccc2c(c1)OCCC2)c1ccc(C(F)(F)F)[nH]c1=O]
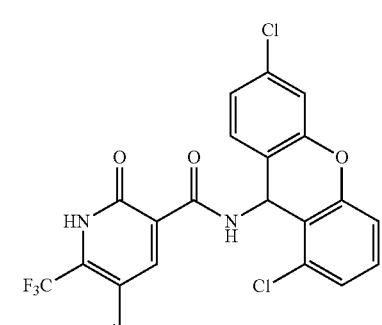
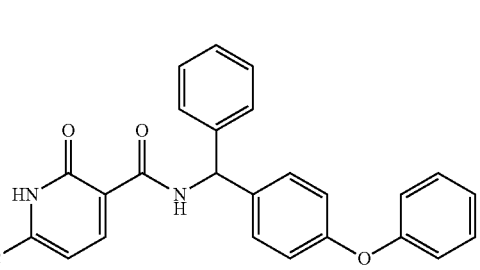

TABLE 2-continued
Exemplary compounds according to the disclosure
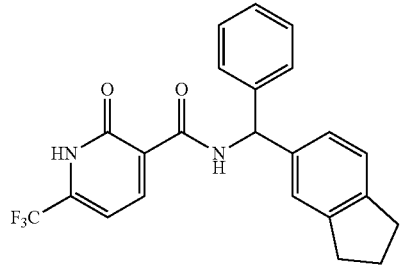
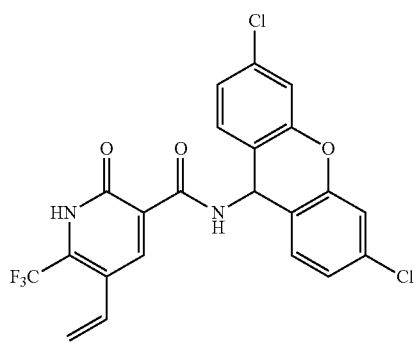 [SMILES: C=Cc1cc(C(=O)NC2c3ccc(Cl)cc3Oc3cc(Cl)ccc32)c(=O)[nH]c1C(F)(F)F]
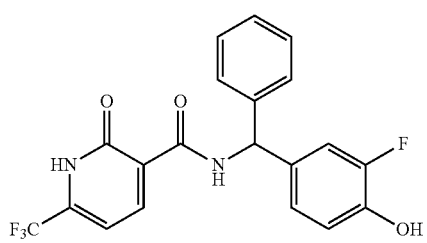
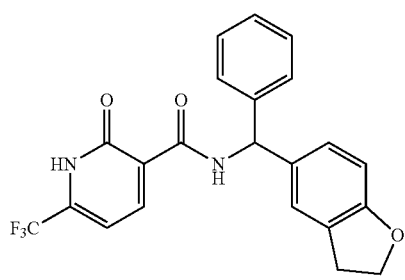
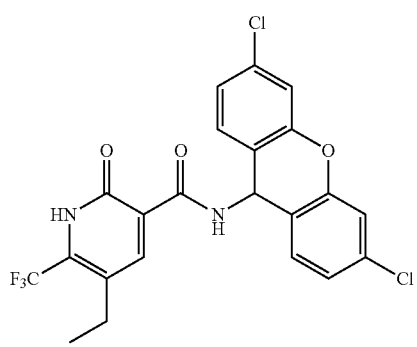 [SMILES: CCc1cc(C(=O)NC2c3ccc(Cl)cc3Oc3cc(Cl)ccc32)c(=O)[nH]c1C(F)(F)F]
TABLE 2-continued
Exemplary compounds according to the disclosure
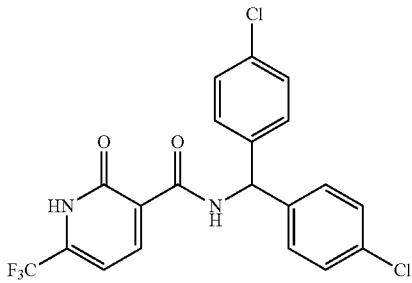
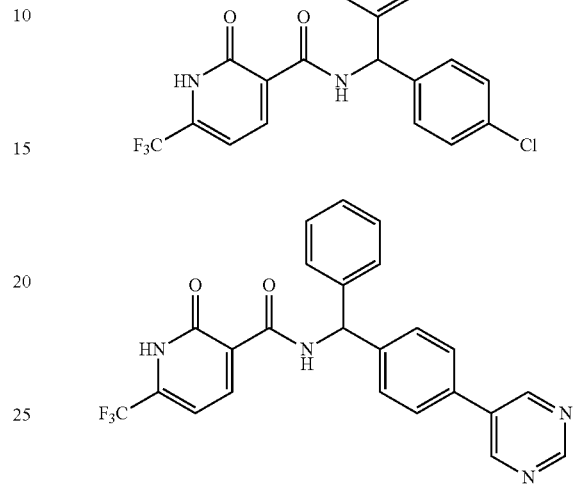
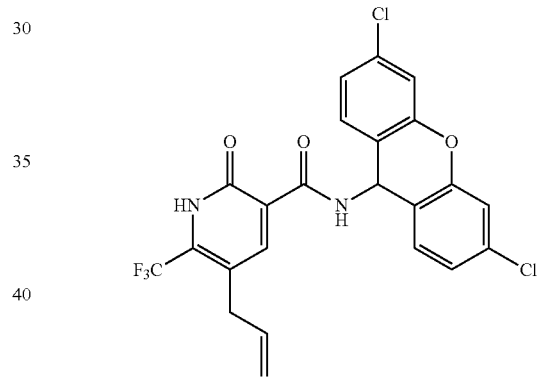
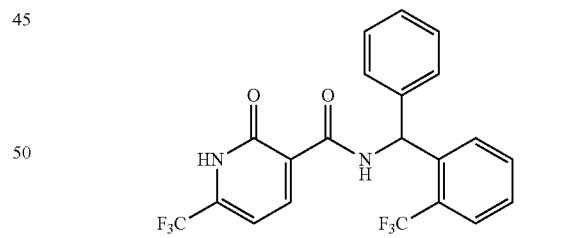
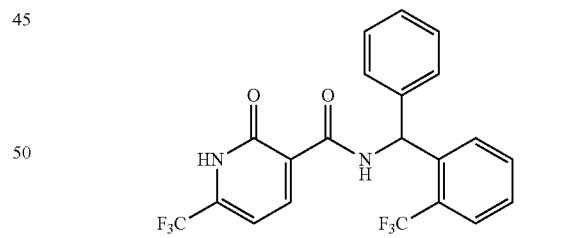

TABLE 2-continued
Exemplary compounds according to the disclosure
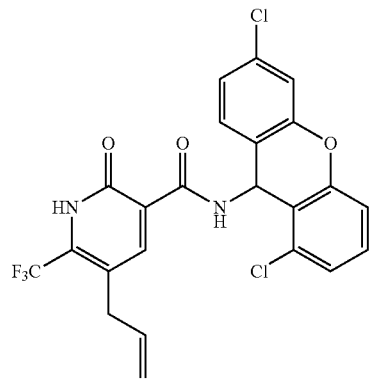 [SMILES: C=CCc1cc(C(=O)NC2c3ccc(Cl)cc3Oc3cccc(Cl)c32)c(=O)[nH]c1C(F)(F)F]
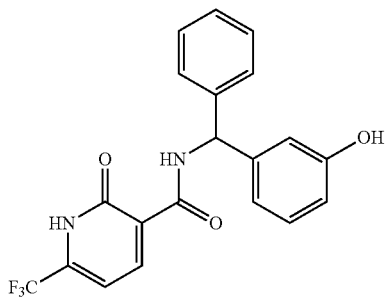
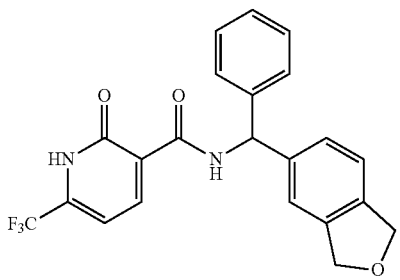 [SMILES: O=C(NC(c1ccccc1)c1ccc2c(c1)COC2)c1ccc(C(F)(F)F)[nH]c1=O]
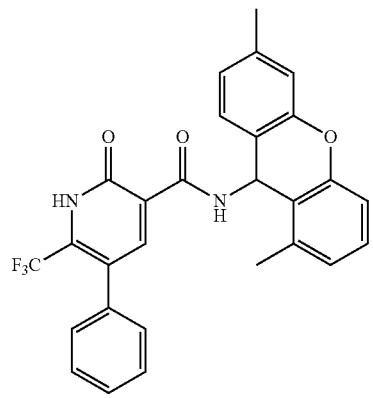
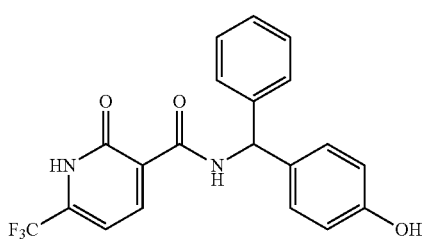
TABLE 2-continued
Exemplary compounds according to the disclosure
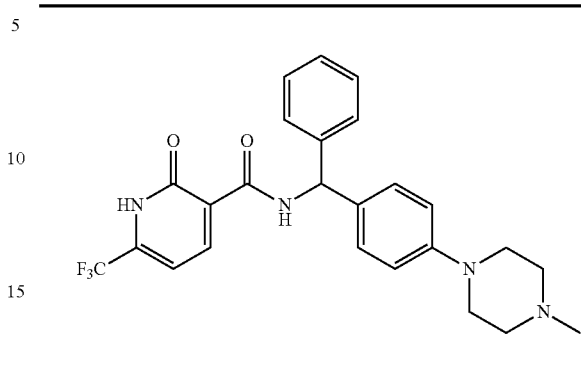
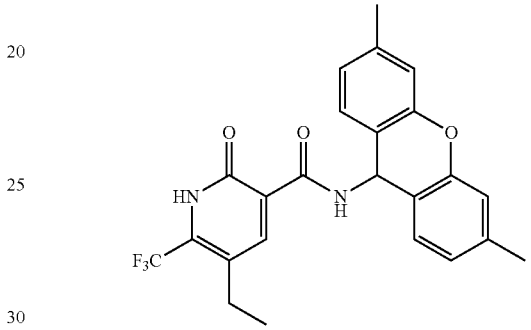
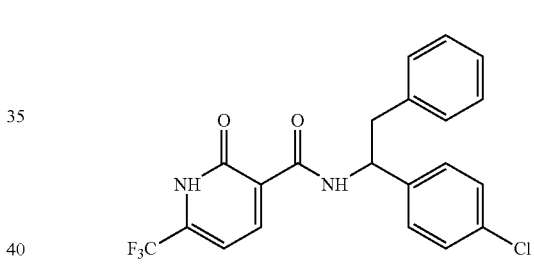
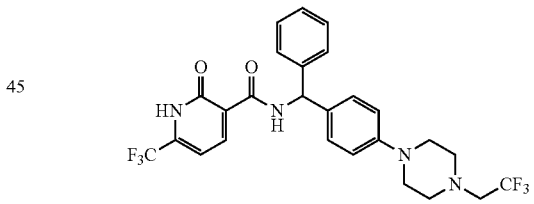
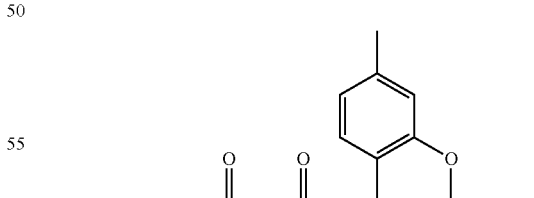
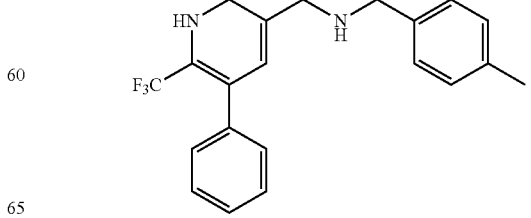

TABLE 2-continued
Exemplary compounds according to the disclosure
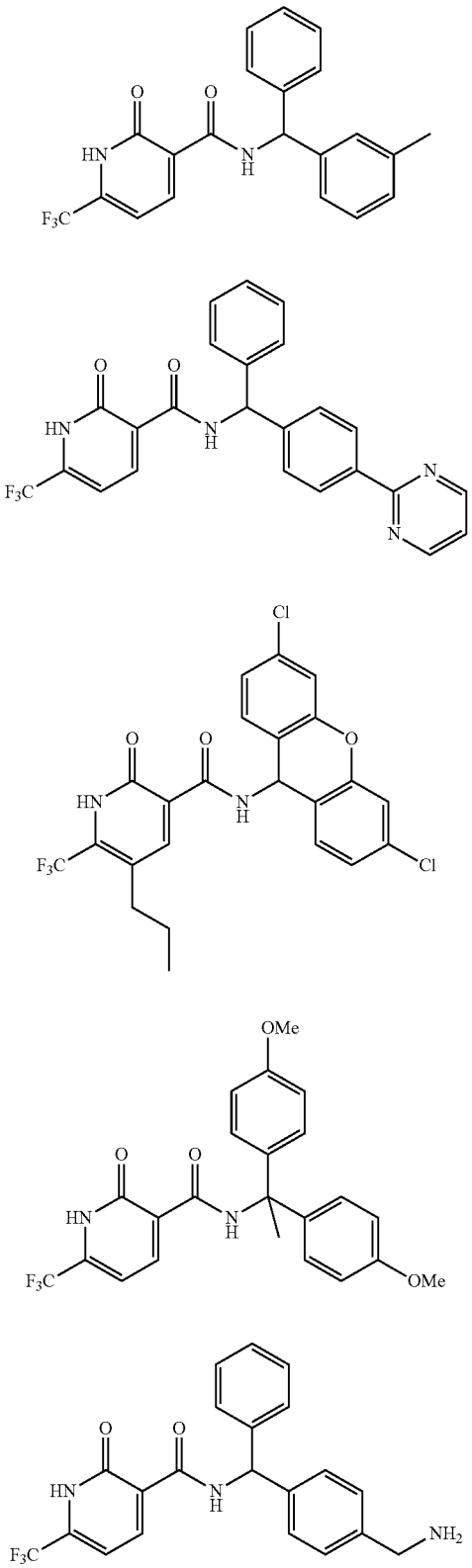
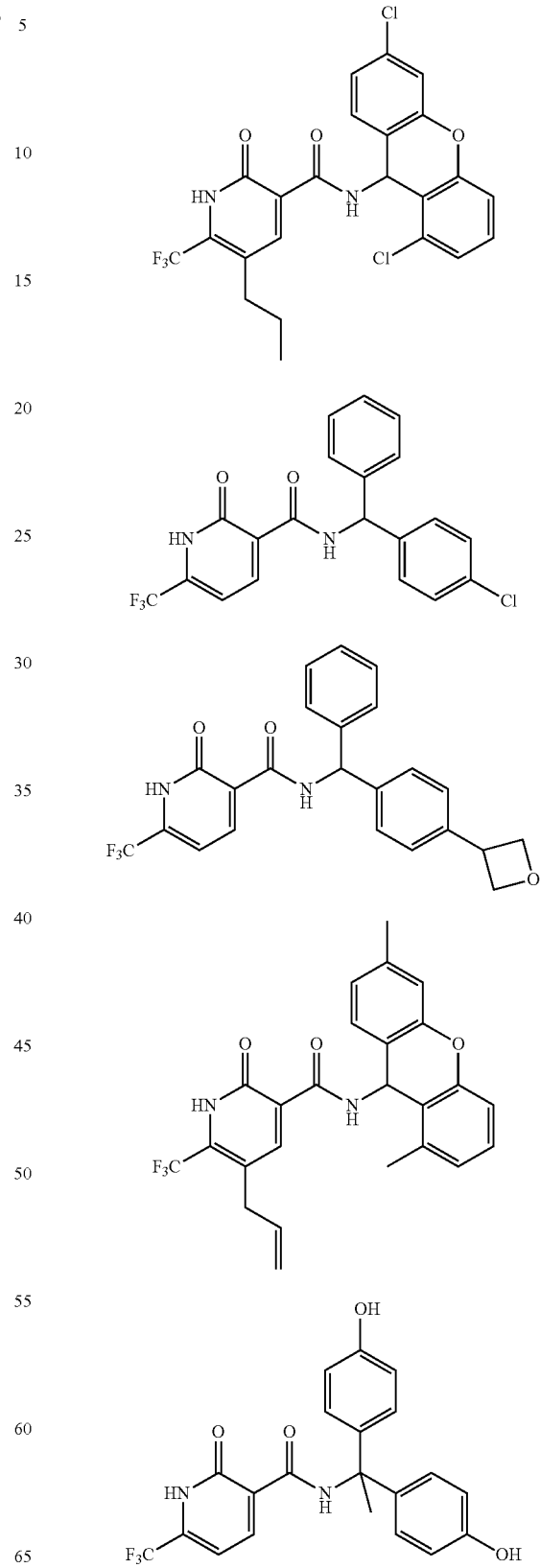

TABLE 2-continued
Exemplary compounds according to the disclosure
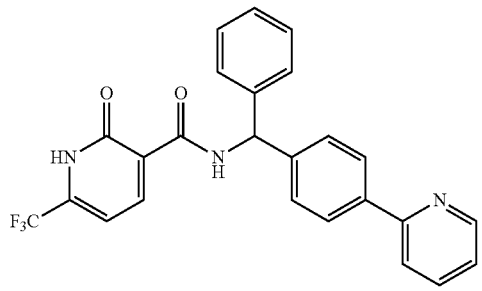 [SMILES: O=C(NC(c1ccccc1)c1ccc(-c2ccccn2)cc1)c1ccc(C(F)(F)F)[nH]c1=O]
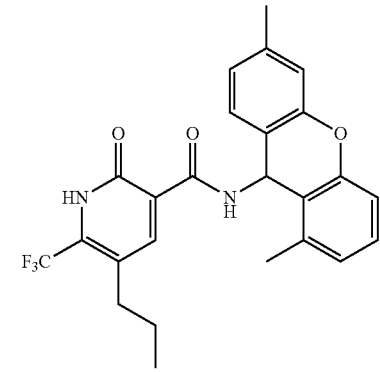
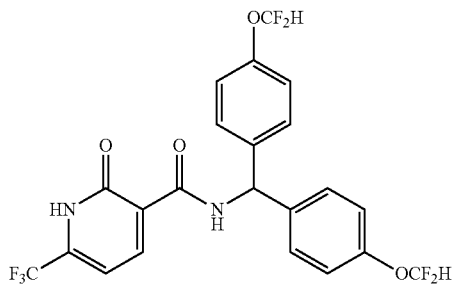
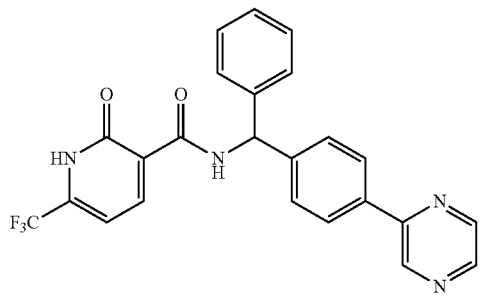 [SMILES: O=C(NC(c1ccccc1)c1ccc(-c2cnccn2)cc1)c1ccc(C(F)(F)F)[nH]c1=O]
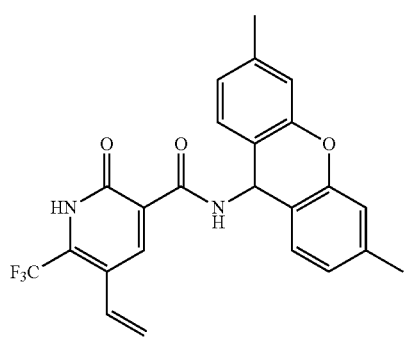
TABLE 2-continued
Exemplary compounds according to the disclosure
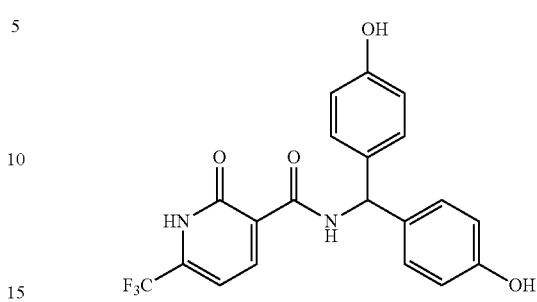
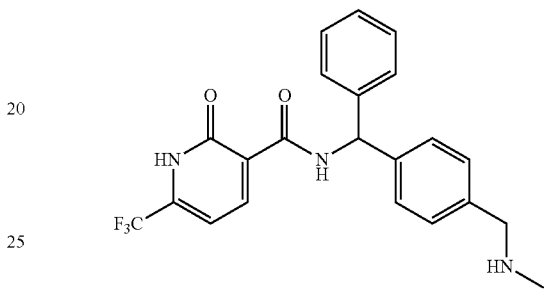
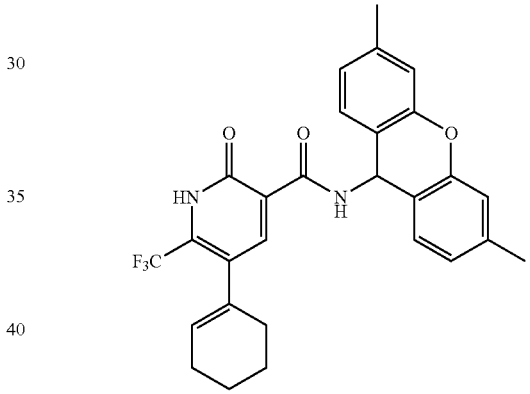
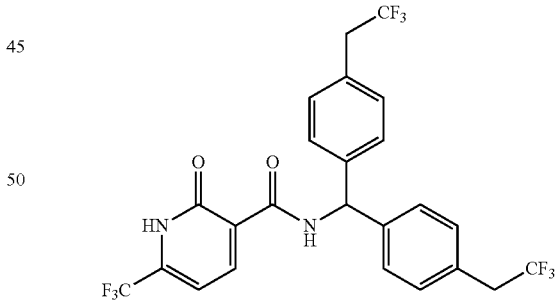
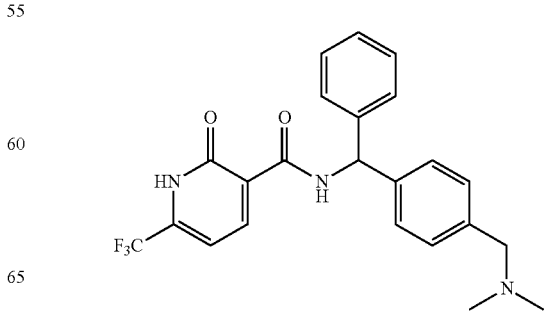

191
TABLE 2-continued
Exemplary compounds according to the disclosure
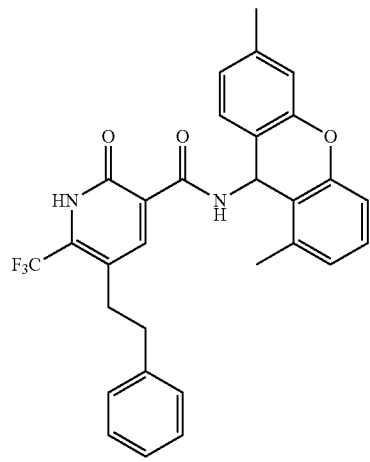
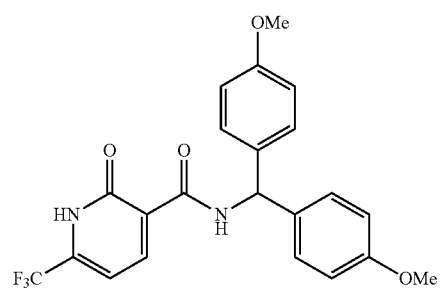
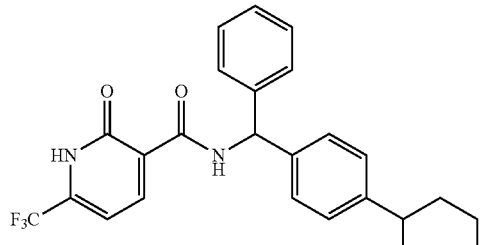
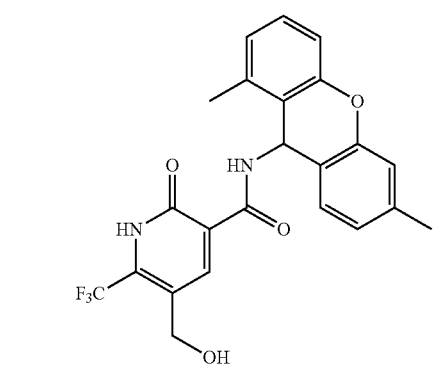 [SMILES: Cc1ccc2c(c1)Oc1cccc(C)c1C2NC(=O)c1cc(CO)c(C(F)(F)F)[nH]c1=O]
192
TABLE 2-continued
Exemplary compounds according to the disclosure

TABLE 2-continued
Exemplary compounds according to the disclosure
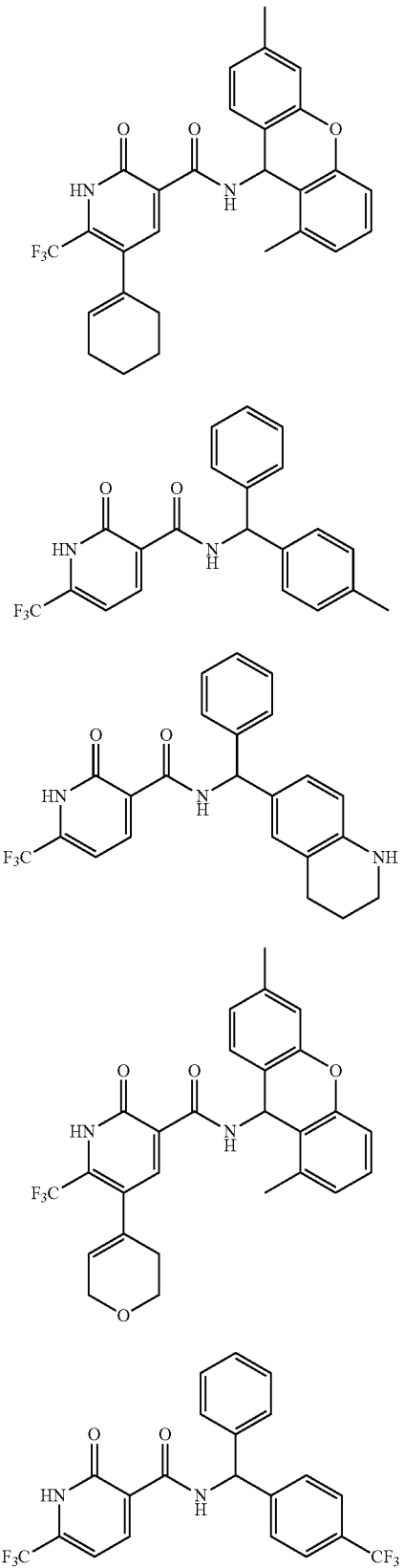
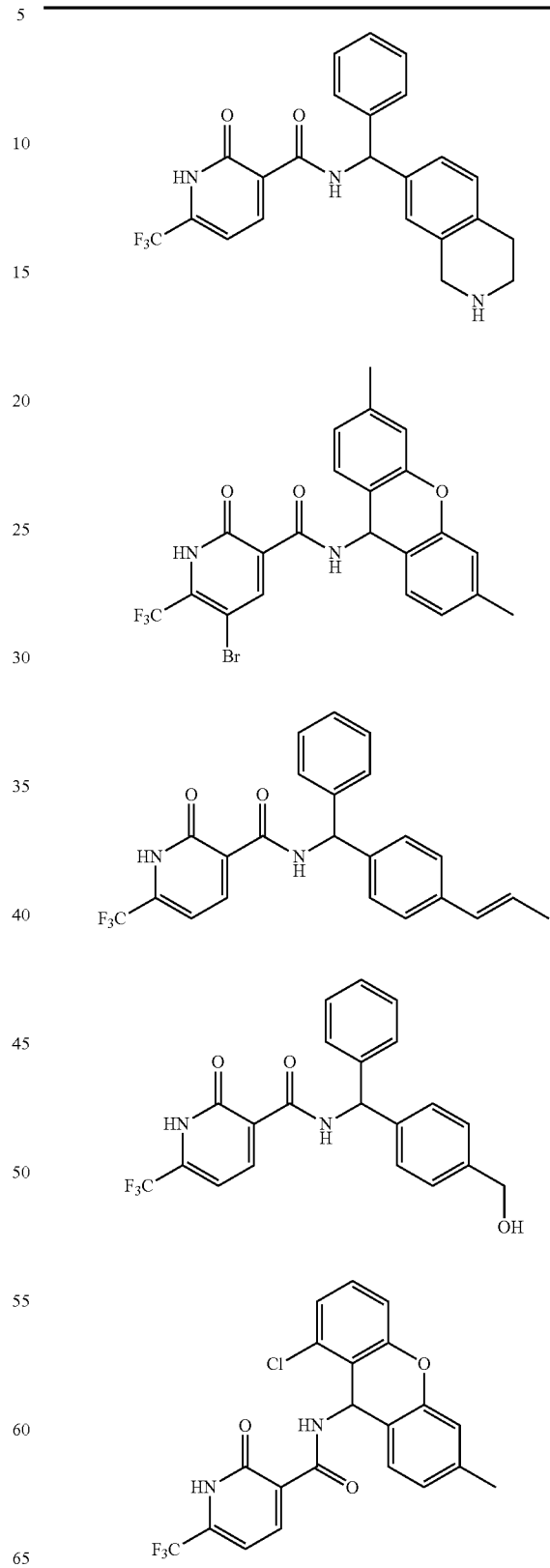

TABLE 2-continued
Exemplary compounds according to the disclosure
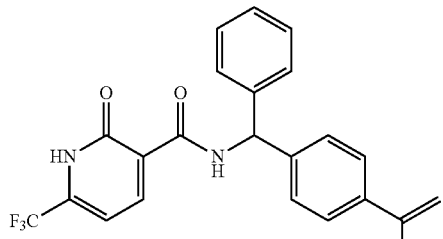
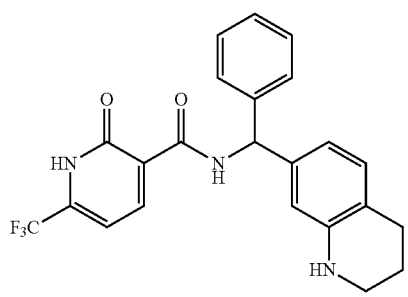 [SMILES: O=C(NC(c1ccccc1)c1ccc2c(c1)NCCC2)c1ccc(C(F)(F)F)[nH]c1=O]
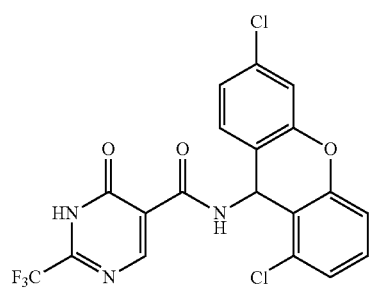
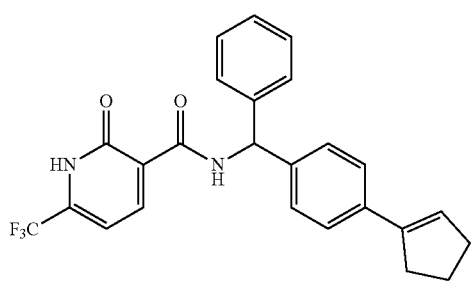 [SMILES: O=C(NC(c1ccccc1)c1ccc(C2=CCCC2)cc1)c1ccc(C(F)(F)F)[nH]c1=O]
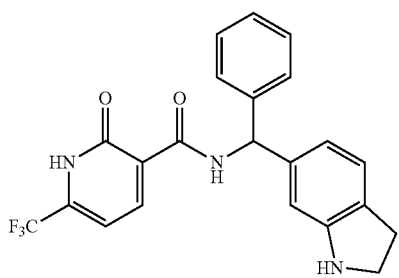 [SMILES: O=C(NC(c1ccccc1)c1ccc2c(c1)NCC2)c1ccc(C(F)(F)F)[nH]c1=O]
TABLE 2-continued
Exemplary compounds according to the disclosure
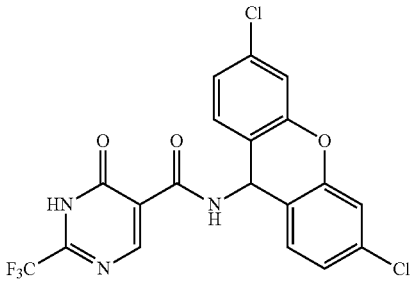
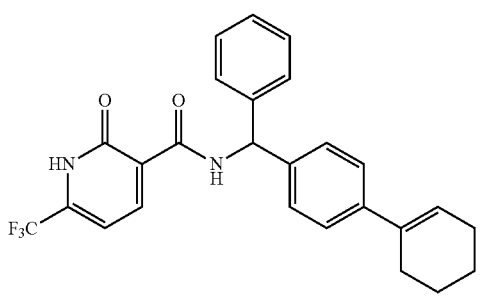 [SMILES: O=C(NC(c1ccccc1)c1ccc(C2=CCCCC2)cc1)c1ccc(C(F)(F)F)[nH]c1=O]
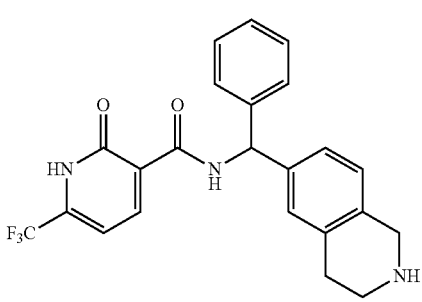 [SMILES: O=C(NC(c1ccccc1)c1ccc2c(c1)CCNC2)c1ccc(C(F)(F)F)[nH]c1=O]
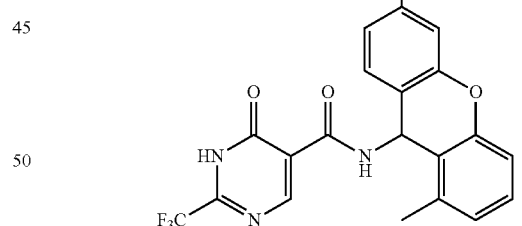
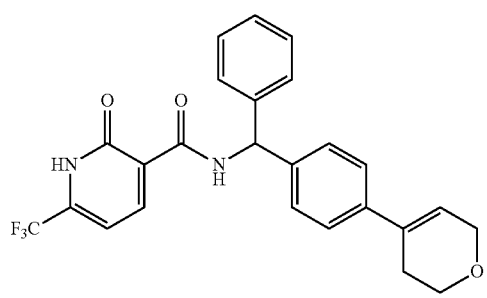 [SMILES: O=C(NC(c1ccccc1)c1ccc(C2=CCOCC2)cc1)c1ccc(C(F)(F)F)[nH]c1=O]

TABLE 2-continued
Exemplary compounds according to the disclosure
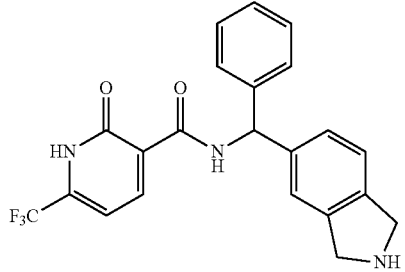 [SMILES: O=C(NC(c1ccccc1)c1ccc2c(c1)CNC2)c1ccc(C(F)(F)F)[nH]c1=O]
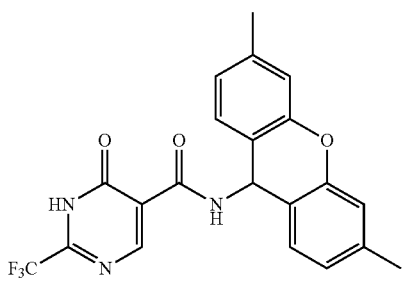
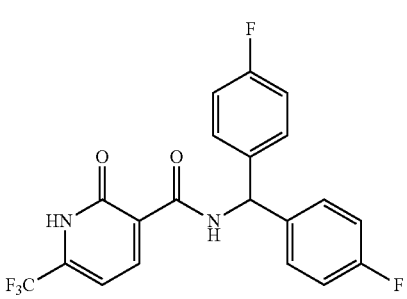 [SMILES: O=C(NC(c1ccc(F)cc1)c1ccc(F)cc1)c1ccc(C(F)(F)F)[nH]c1=O]
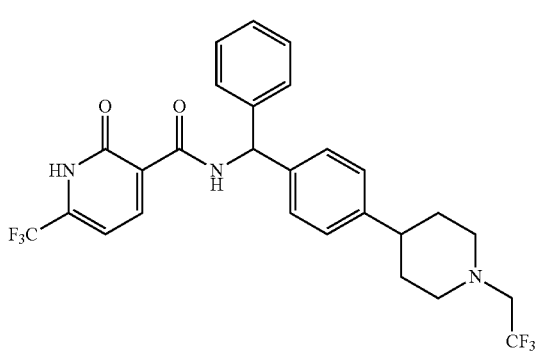 [SMILES: O=C(NC(c1ccccc1)c1ccc(C2CCN(CC(F)(F)F)CC2)cc1)c1ccc(C(F)(F)F)[nH]c1=O]
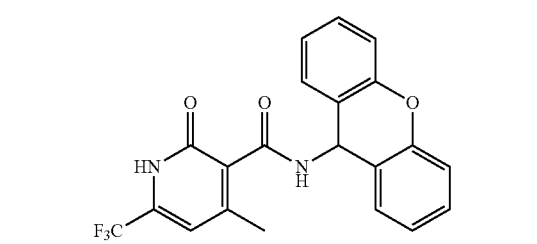
TABLE 2-continued
Exemplary compounds according to the disclosure
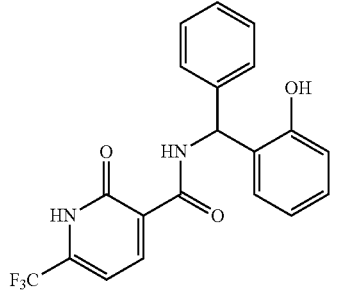
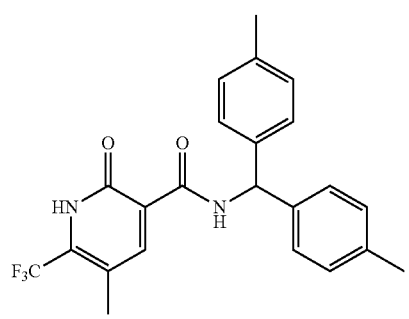 [SMILES: Cc1ccc(C(NC(=O)c2cc(C)c(C(F)(F)F)[nH]c2=O)c2ccc(C)cc2)cc1]
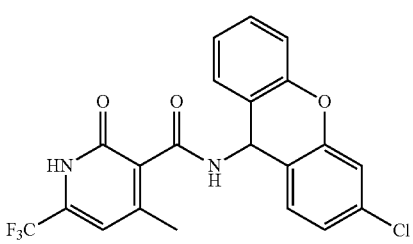 [SMILES: Cc1cc(C(F)(F)F)[nH]c(=O)c1C(=O)NC1c2ccccc2Oc2cc(Cl)ccc21]
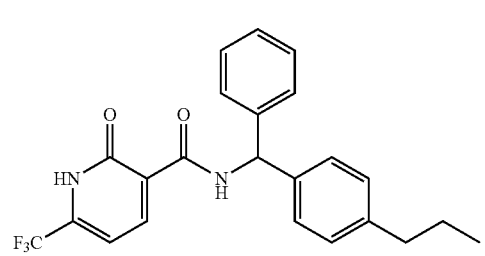
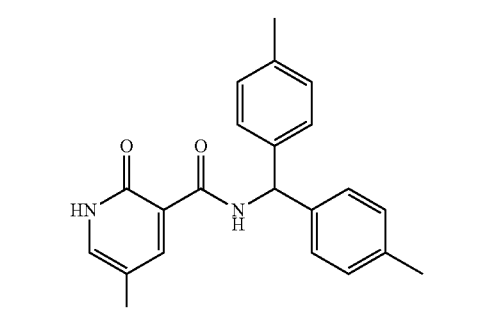

TABLE 2-continued
Exemplary compounds according to the disclosure
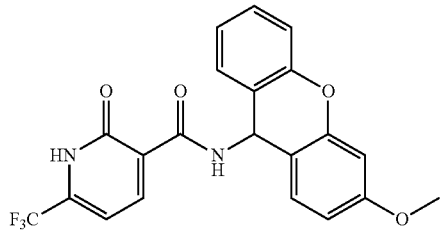
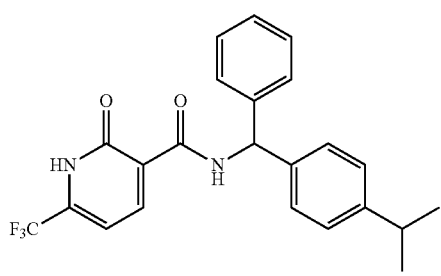
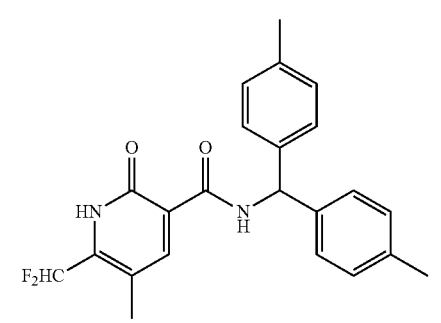 [SMILES: Cc1ccc(C(NC(=O)c2cc(C)c(C(F)F)[nH]c2=O)c2ccc(C)cc2)cc1]
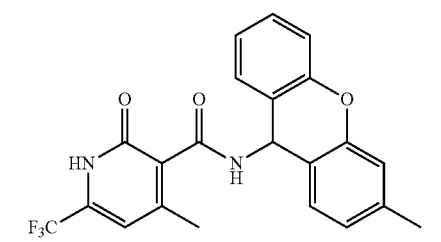
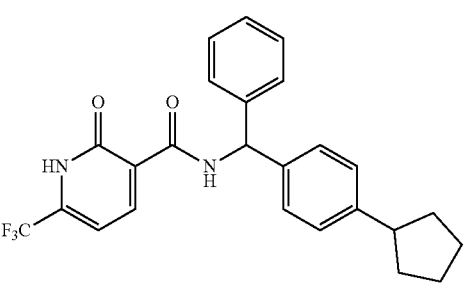 [SMILES: O=C(NC(c1ccccc1)c1ccc(C2CCCC2)cc1)c1ccc(C(F)(F)F)[nH]c1=O]
TABLE 2-continued
Exemplary compounds according to the disclosure
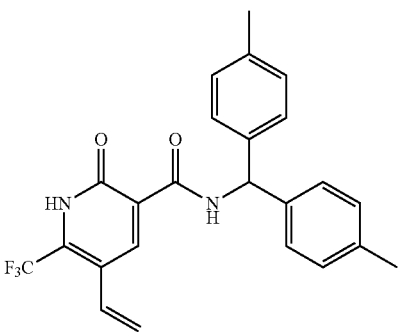 [SMILES: C=Cc1cc(C(=O)NC(c2ccc(C)cc2)c2ccc(C)cc2)c(=O)[nH]c1C(F)(F)F]
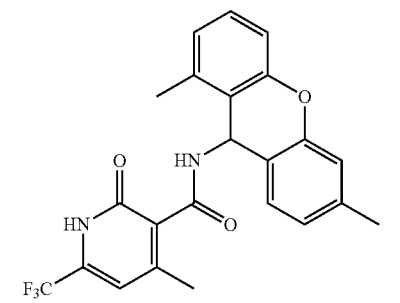 [SMILES: Cc1ccc2c(c1)Oc1cccc(C)c1C2NC(=O)c1c(C)cc(C(F)(F)F)[nH]c1=O]
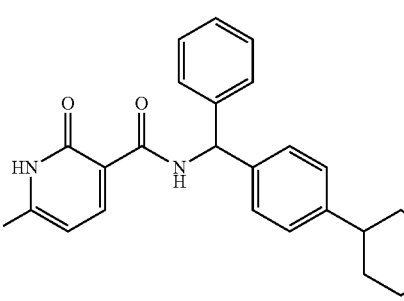
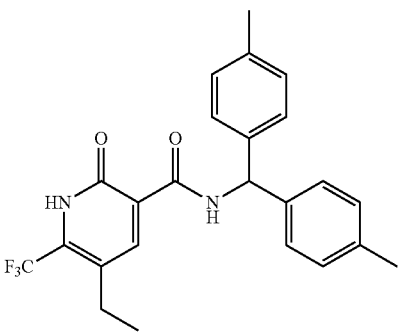 [SMILES: CCc1cc(C(=O)NC(c2ccc(C)cc2)c2ccc(C)cc2)c(=O)[nH]c1C(F)(F)F]
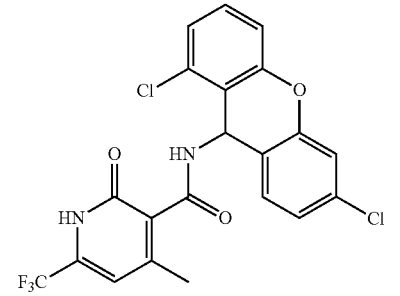 [SMILES: Cc1cc(C(F)(F)F)[nH]c(=O)c1C(=O)NC1c2ccc(Cl)cc2Oc2cccc(Cl)c21]

TABLE 2-continued
Exemplary compounds according to the disclosure
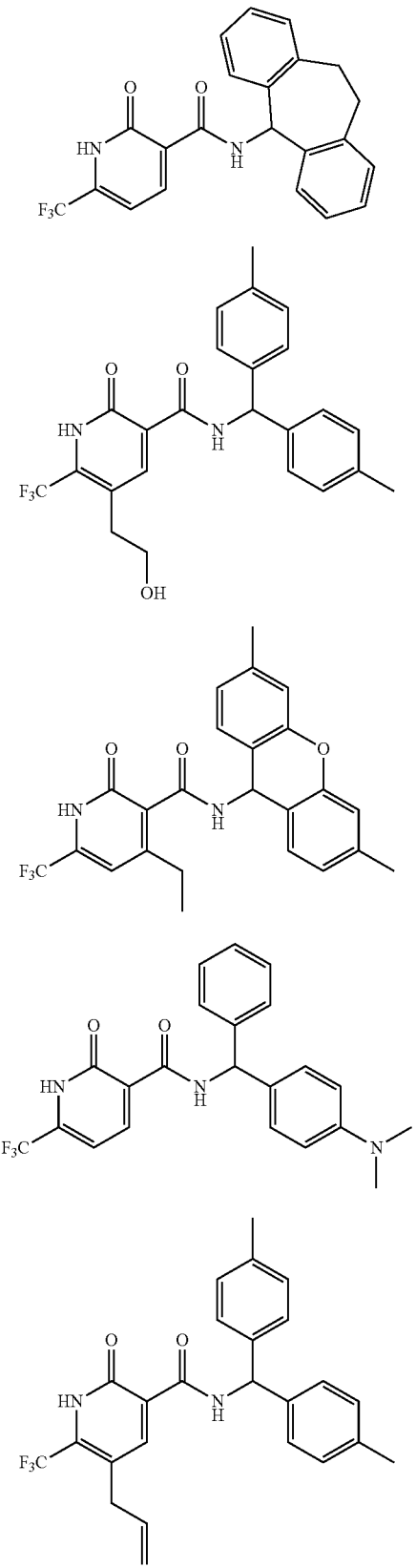
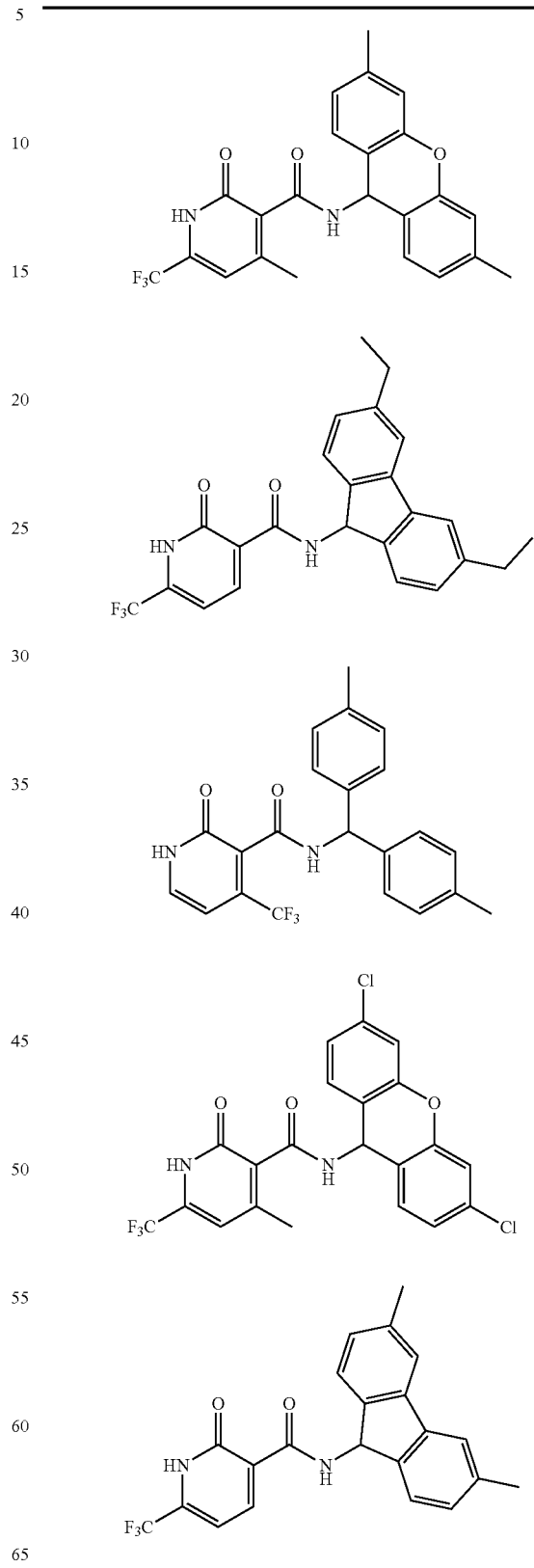

TABLE 2-continued
Exemplary compounds according to the disclosure
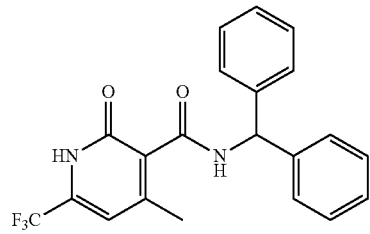 [SMILES: Cc1cc(C(F)(F)F)[nH]c(=O)c1C(=O)NC(c1ccccc1)c1ccccc1]
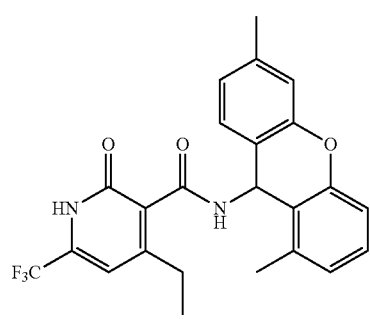 [SMILES: CCc1cc(C(F)(F)F)[nH]c(=O)c1C(=O)NC1c2ccc(C)cc2Oc2cccc(C)c21]
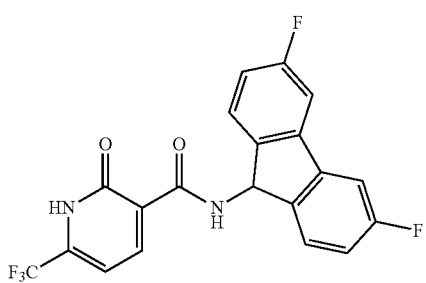 [SMILES: O=C(NC1c2ccc(F)cc2-c2cc(F)ccc21)c1ccc(C(F)(F)F)[nH]c1=O]
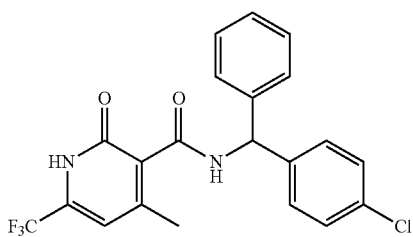 [SMILES: Cc1cc(C(F)(F)F)[nH]c(=O)c1C(=O)NC(c1ccccc1)c1ccc(Cl)cc1]
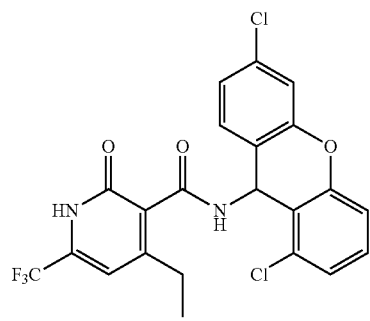 [SMILES: CCc1cc(C(F)(F)F)[nH]c(=O)c1C(=O)NC1c2ccc(Cl)cc2Oc2cccc(Cl)c21]
TABLE 2-continued
Exemplary compounds according to the disclosure
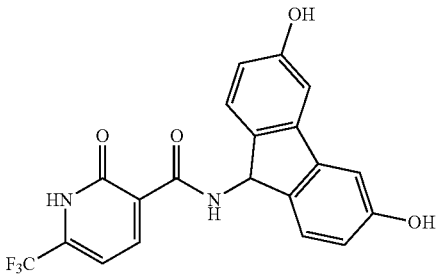 [SMILES: O=C(NC1c2ccc(O)cc2-c2cc(O)ccc21)c1ccc(C(F)(F)F)[nH]c1=O]
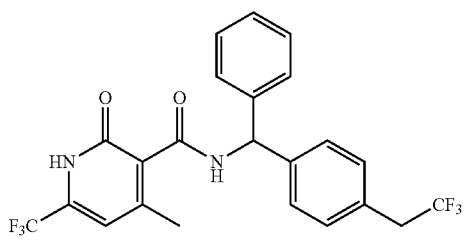
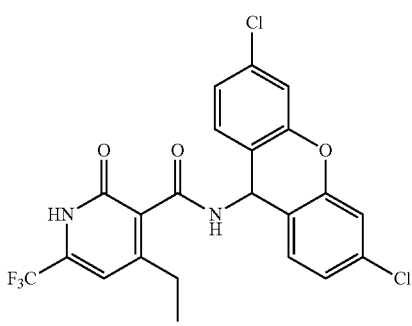 [SMILES: CCc1cc(C(F)(F)F)[nH]c(=O)c1C(=O)NC1c2ccc(Cl)cc2Oc2cc(Cl)ccc21]
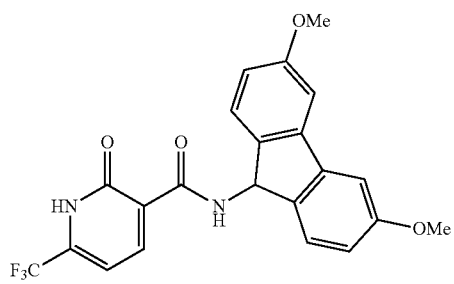 [SMILES: COc1ccc2c(c1)-c1cc(OC)ccc1C2NC(=O)c1ccc(C(F)(F)F)[nH]c1=O]
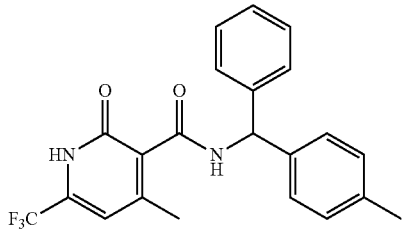

TABLE 2-continued
Exemplary compounds according to the disclosure
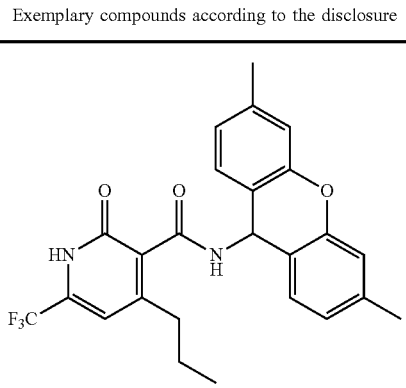
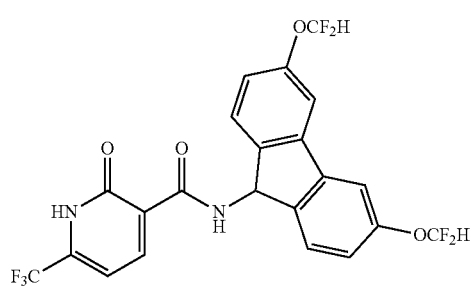
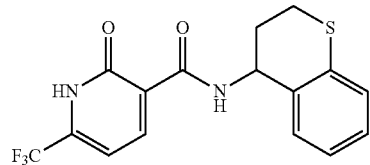
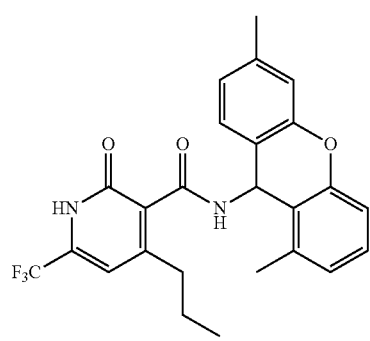 [SMILES: CCCc1cc(C(F)(F)F)[nH]c(=O)c1C(=O)NC1c2ccc(C)cc2Oc2cccc(C)c21]
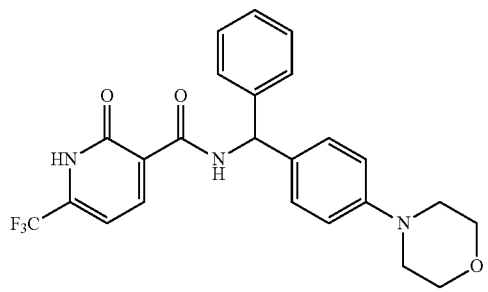 [SMILES: O=C(NC(c1ccccc1)c1ccc(N2CCOCC2)cc1)c1ccc(C(F)(F)F)[nH]c1=O]
TABLE 2-continued
Exemplary compounds according to the disclosure
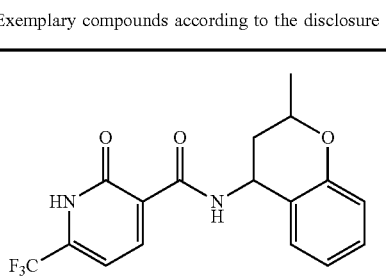
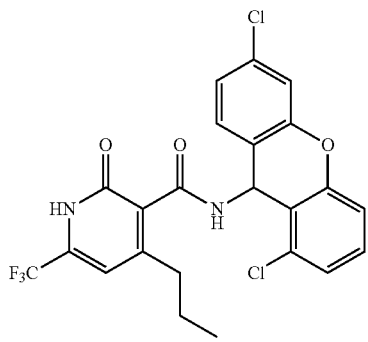 [SMILES: CCCc1cc(C(F)(F)F)[nH]c(=O)c1C(=O)NC1c2ccc(Cl)cc2Oc2cccc(Cl)c21]
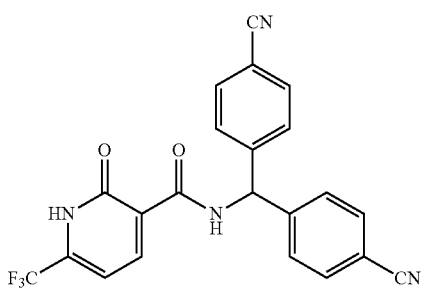 [SMILES: N#Cc1ccc(C(NC(=O)c2ccc(C(F)(F)F)[nH]c2=O)c2ccc(C#N)cc2)cc1]
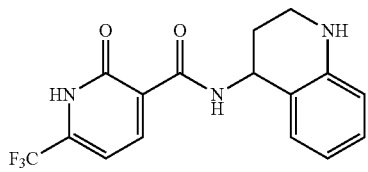
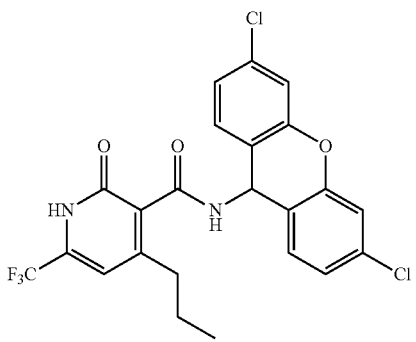 [SMILES: CCCc1cc(C(F)(F)F)[nH]c(=O)c1C(=O)NC1c2ccc(Cl)cc2Oc2cc(Cl)ccc21]

TABLE 2-continued
Exemplary compounds according to the disclosure
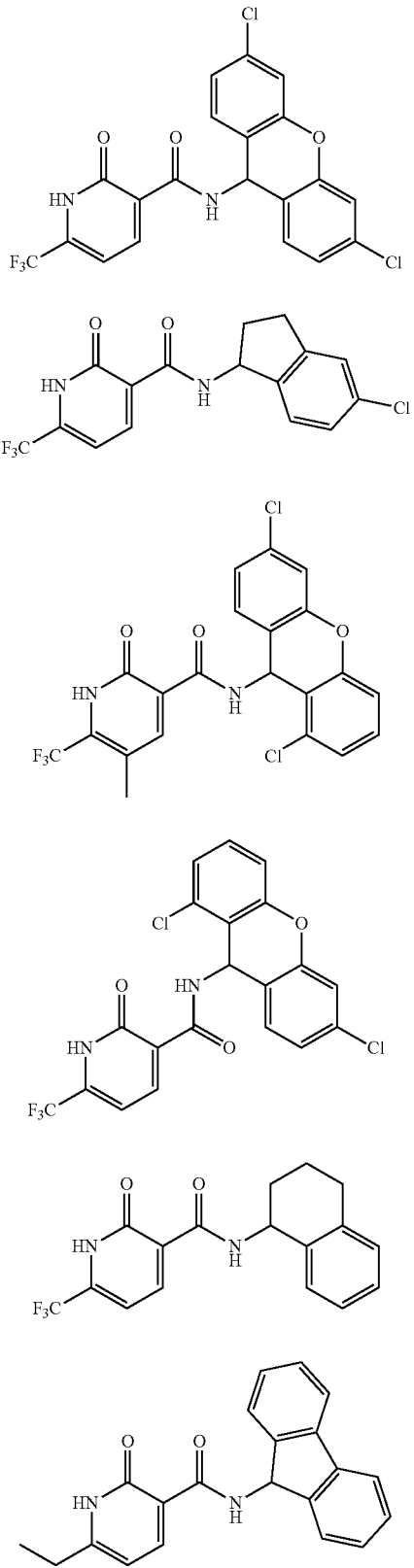
TABLE 2-continued
Exemplary compounds according to the disclosure
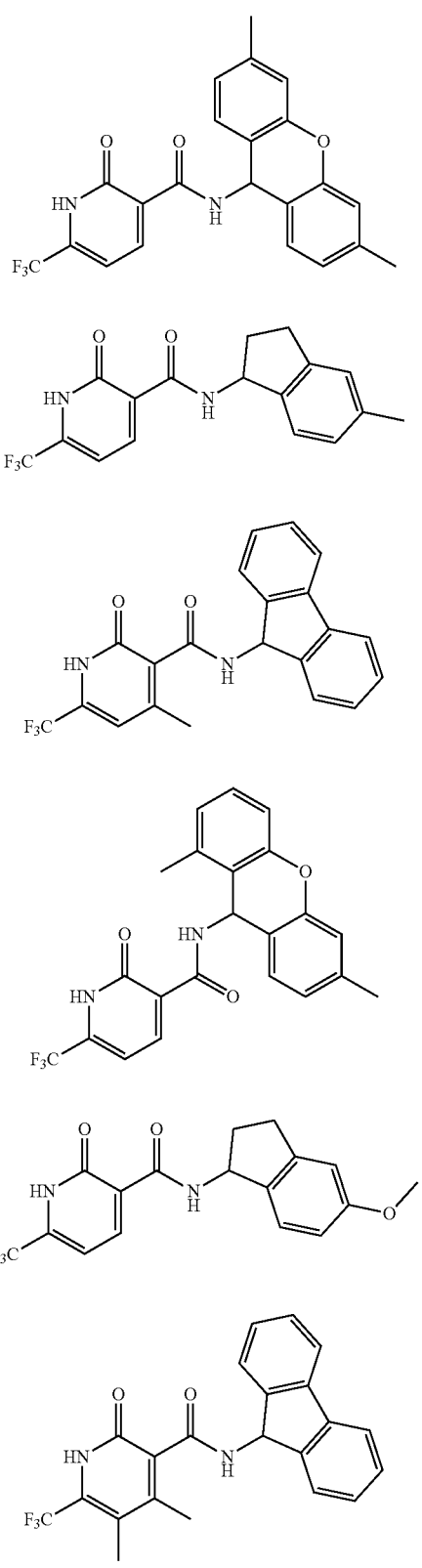

TABLE 2-continued
Exemplary compounds according to the disclosure
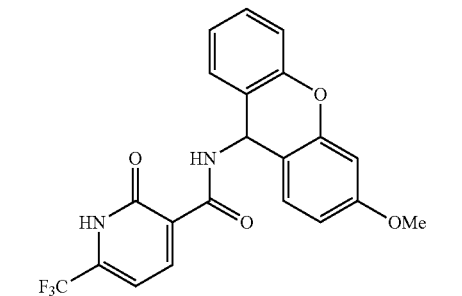 [SMILES: COc1ccc2c(c1)Oc1ccccc1C2NC(=O)c1ccc(C(F)(F)F)[nH]c1=O]
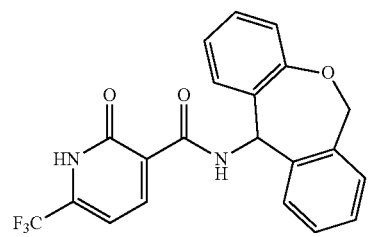
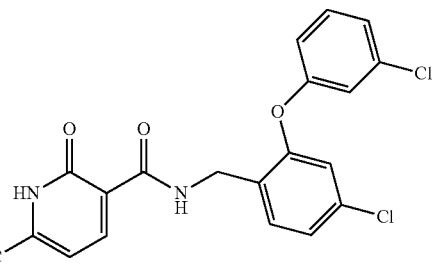
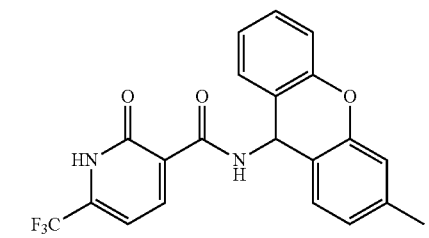
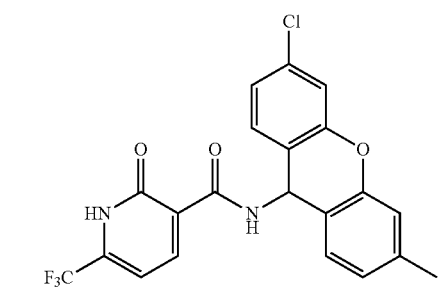 [SMILES: Cc1ccc2c(c1)Oc1cc(Cl)ccc1C2NC(=O)c1ccc(C(F)(F)F)[nH]c1=O]
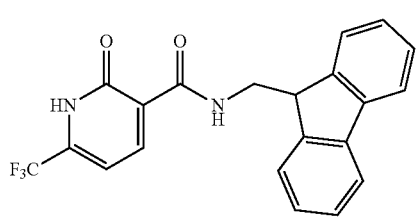 [SMILES: O=C(NCC1c2ccccc2-c2ccccc21)c1ccc(C(F)(F)F)[nH]c1=O]
TABLE 2-continued
Exemplary compounds according to the disclosure
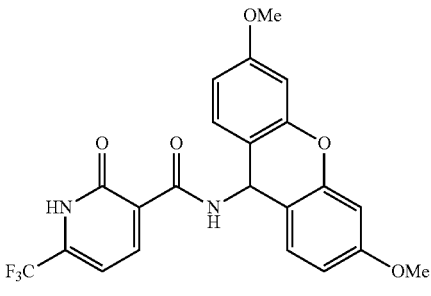
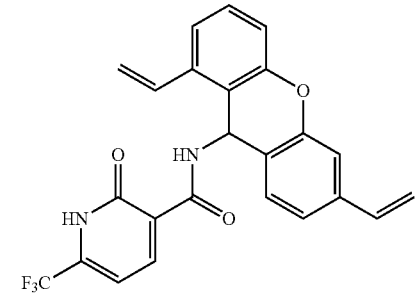 [SMILES: C=Cc1ccc2c(c1)Oc1cccc(C=C)c1C2NC(=O)c1ccc(C(F)(F)F)[nH]c1=O]
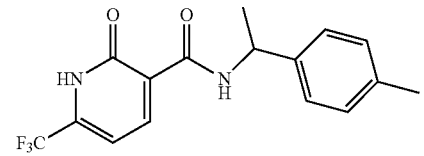
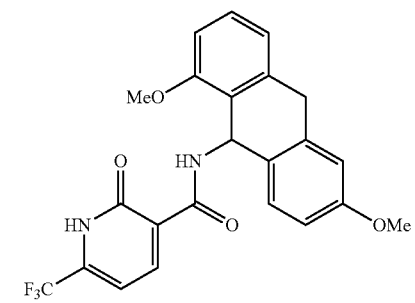
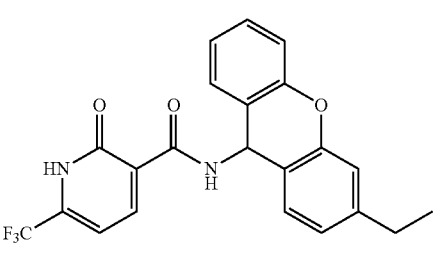 [SMILES: CCc1ccc2c(c1)Oc1ccccc1C2NC(=O)c1ccc(C(F)(F)F)[nH]c1=O]
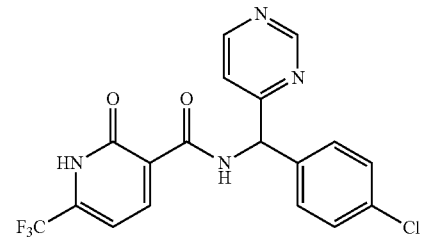

TABLE 2-continued
Exemplary compounds according to the disclosure
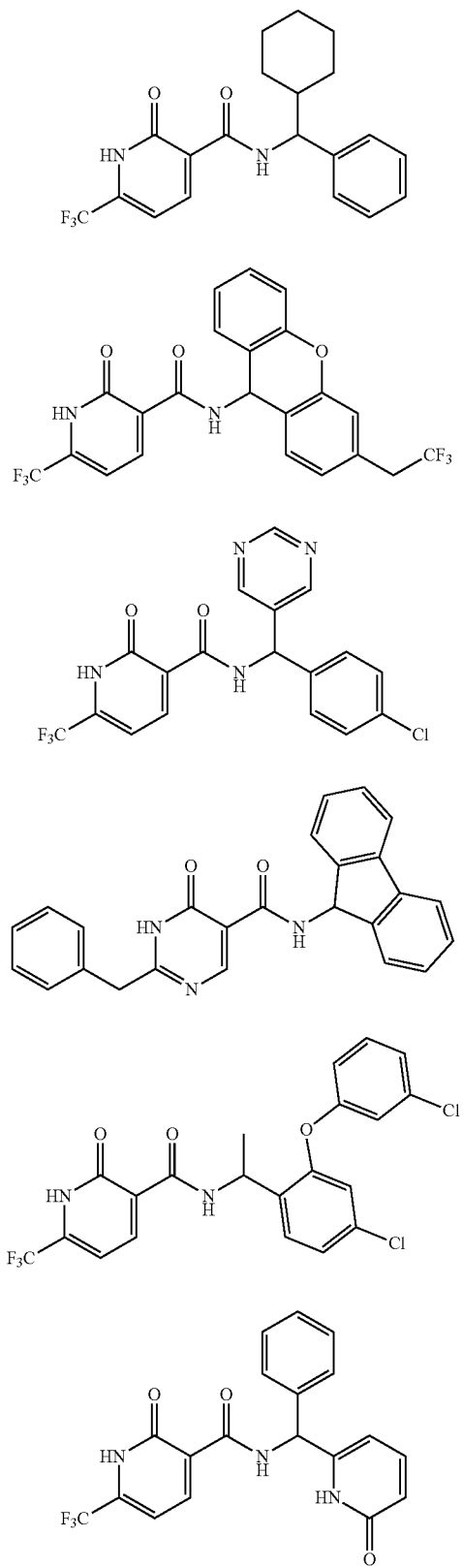
TABLE 2-continued
Exemplary compounds according to the disclosure
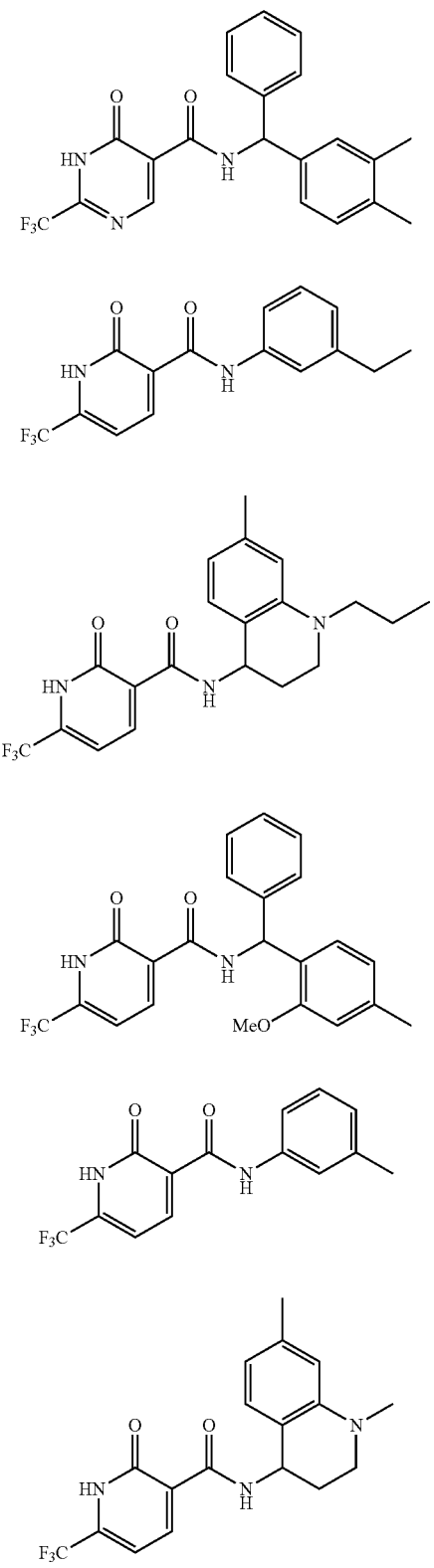

TABLE 2-continued
Exemplary compounds according to the disclosure
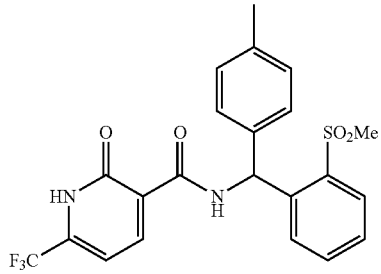
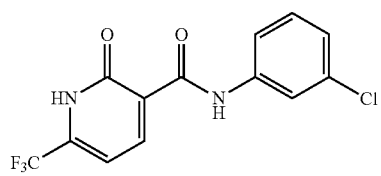 [SMILES: O=C(Nc1cccc(Cl)c1)c1ccc(C(F)(F)F)[nH]c1=O]
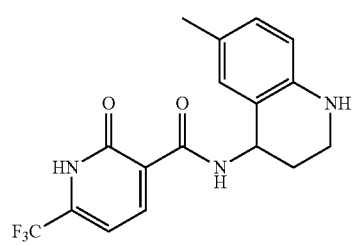
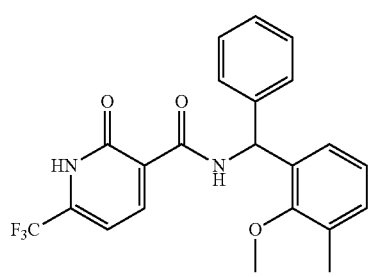 [SMILES: COc1c(C)cccc1C(NC(=O)c1ccc(C(F)(F)F)[nH]c1=O)c1ccccc1]
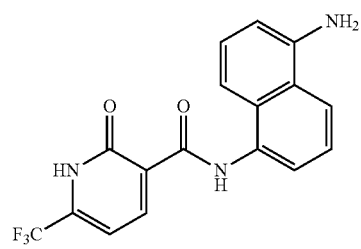
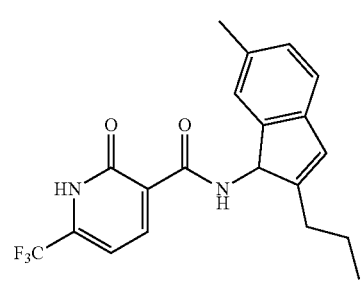 [SMILES: CCCC1=Cc2ccc(C)cc2C1NC(=O)c1ccc(C(F)(F)F)[nH]c1=O]
TABLE 2-continued
Exemplary compounds according to the disclosure
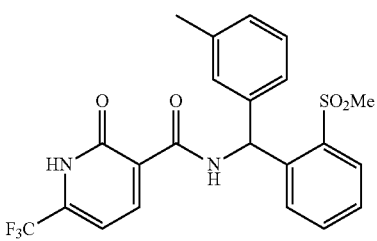
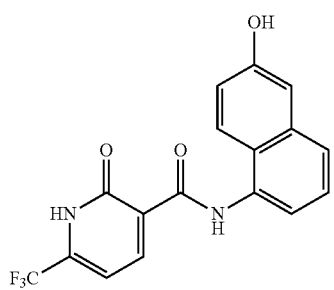
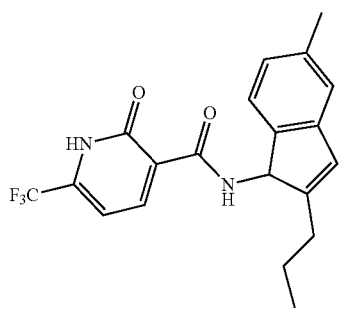 [SMILES: CCCC1=Cc2cc(C)ccc2C1NC(=O)c1ccc(C(F)(F)F)[nH]c1=O]
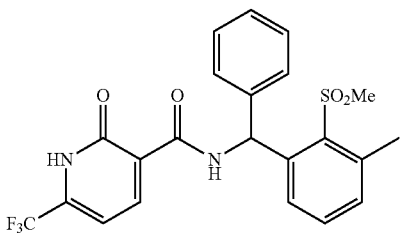
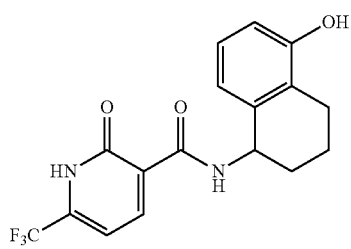

TABLE 2-continued
Exemplary compounds according to the disclosure
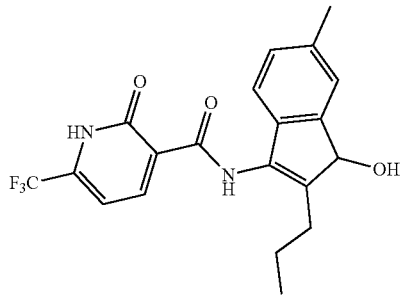 [SMILES: CCCC1=C(NC(=O)c2ccc(C(F)(F)F)[nH]c2=O)c2ccc(C)cc2C1O]
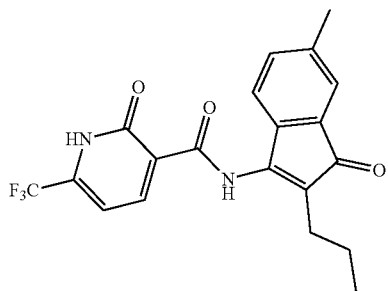
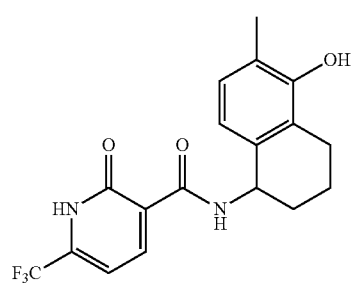 [SMILES: Cc1ccc2c(c1O)CCCC2NC(=O)c1ccc(C(F)(F)F)[nH]c1=O]
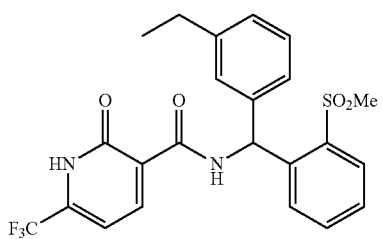
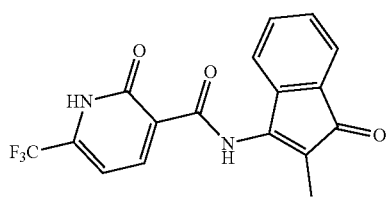 [SMILES: CC1=C(NC(=O)c2ccc(C(F)(F)F)[nH]c2=O)c2ccccc2C1=O]
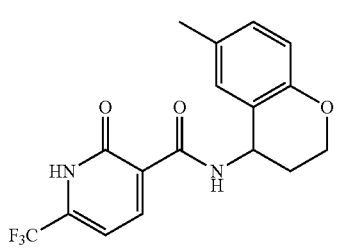
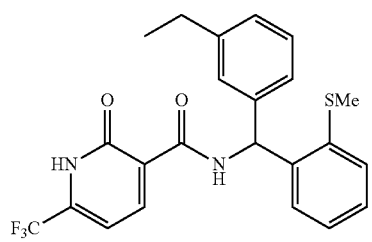
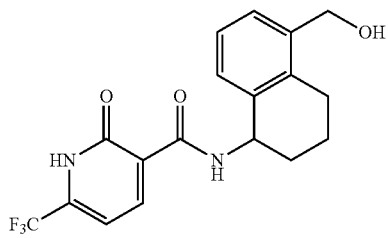
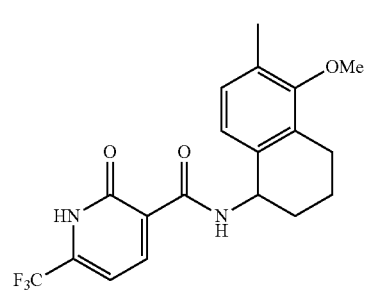 [SMILES: COc1c(C)ccc2c1CCCC2NC(=O)c1ccc(C(F)(F)F)[nH]c1=O]
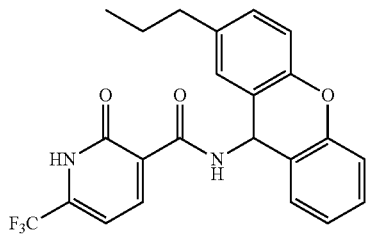
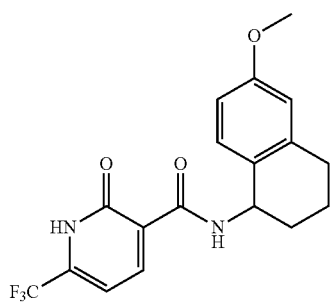

TABLE 2-continued
Exemplary compounds according to the disclosure
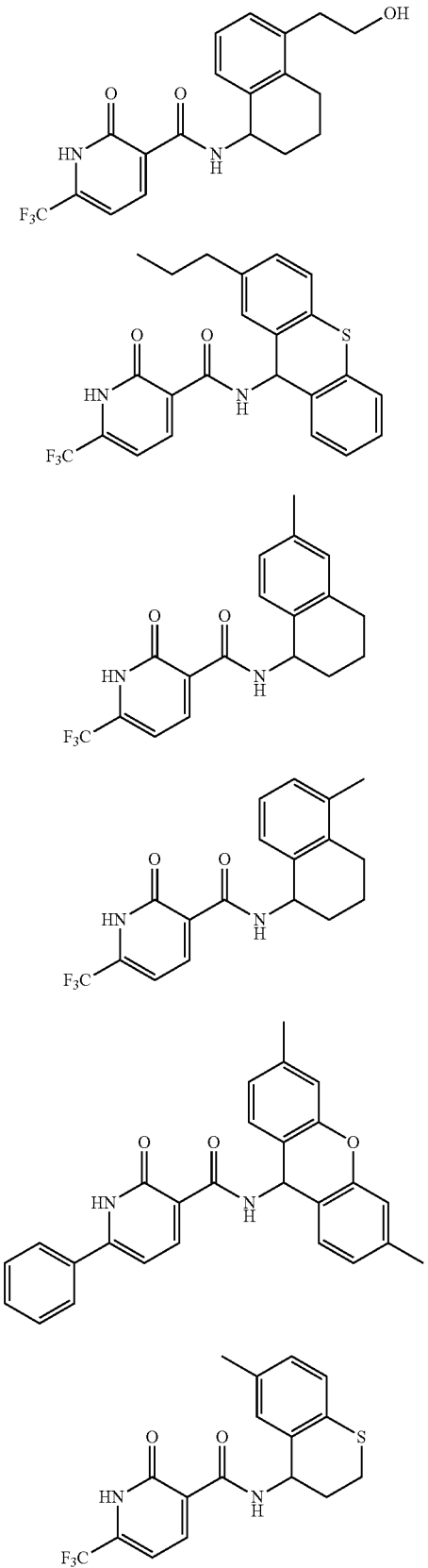
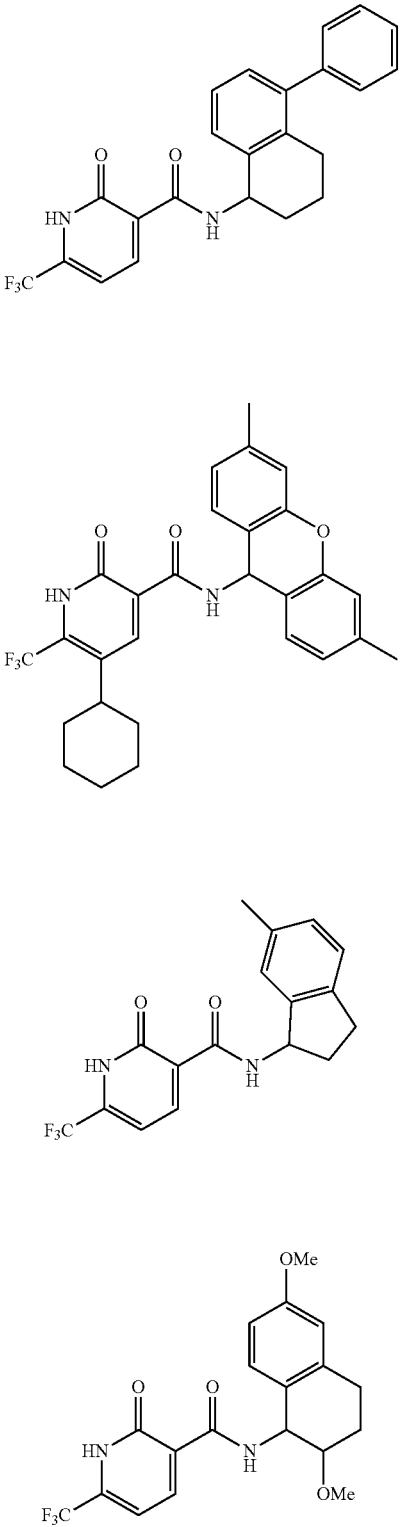

TABLE 2-continued
Exemplary compounds according to the disclosure
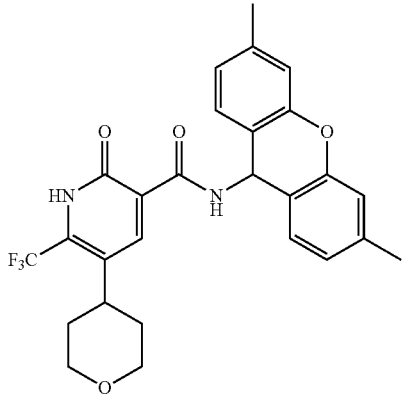
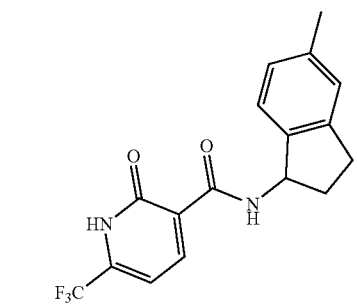 [SMILES: Cc1ccc2c(c1)CCC2NC(=O)c1ccc(C(F)(F)F)[nH]c1=O]
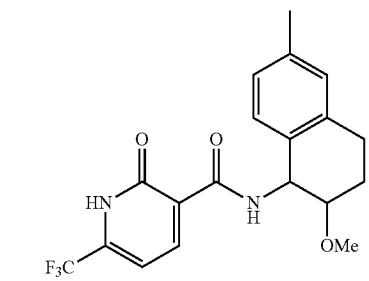
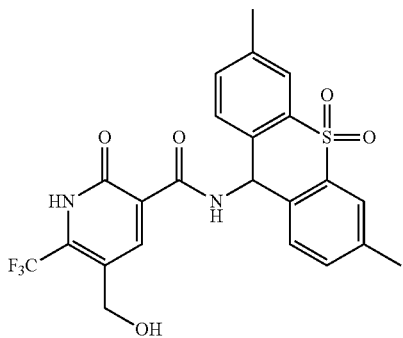 [SMILES: Cc1ccc2c(c1)S(=O)(=O)c1cc(C)ccc1C2NC(=O)c1cc(CO)c(C(F)(F)F)[nH]c1=O]
TABLE 2-continued
Exemplary compounds according to the disclosure
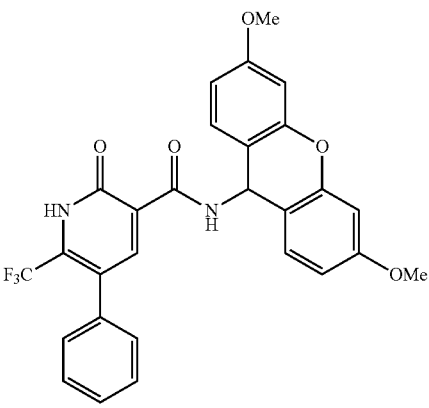 [SMILES: COc1ccc2c(c1)Oc1cc(OC)ccc1C2NC(=O)c1cc(-c2ccccc2)c(C(F)(F)F)[nH]c1=O]
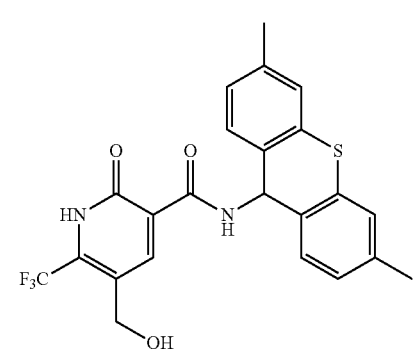
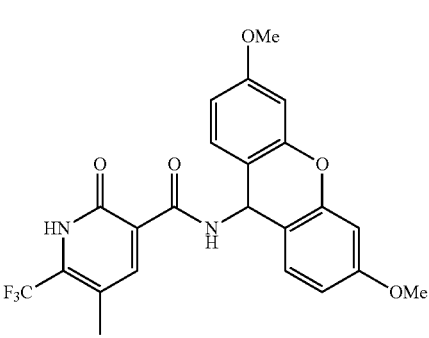 [SMILES: COc1ccc2c(c1)Oc1cc(OC)ccc1C2NC(=O)c1cc(C)c(C(F)(F)F)[nH]c1=O]

TABLE 2-continued
Exemplary compounds according to the disclosure
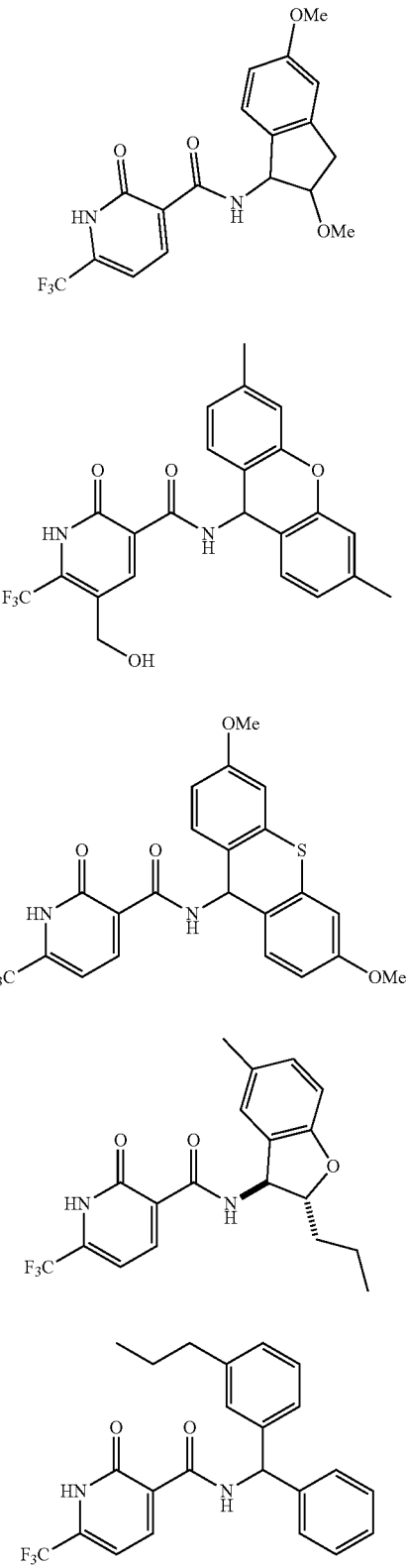
TABLE 2-continued
Exemplary compounds according to the disclosure
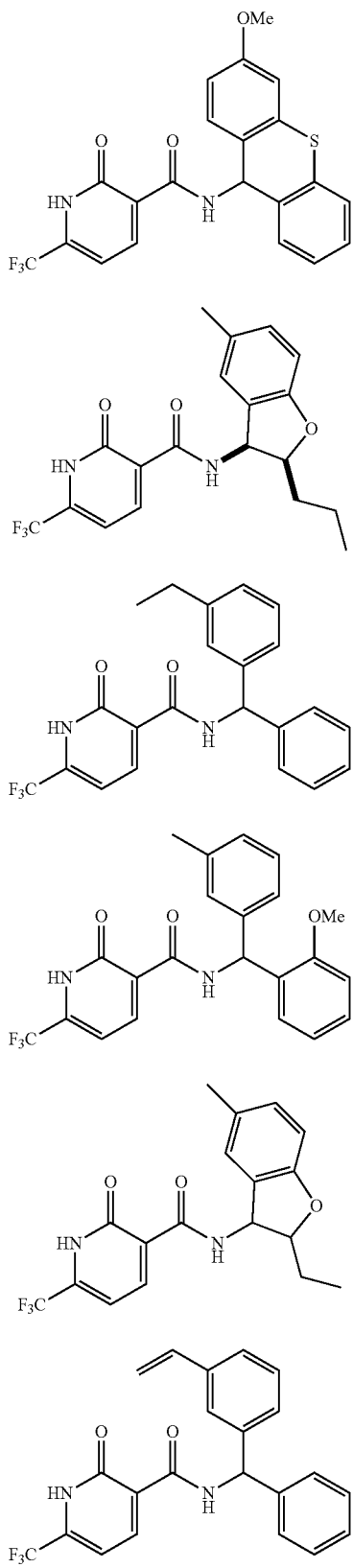

TABLE 2-continued
Exemplary compounds according to the disclosure
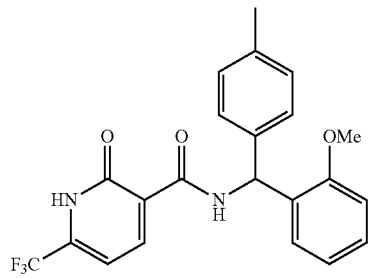
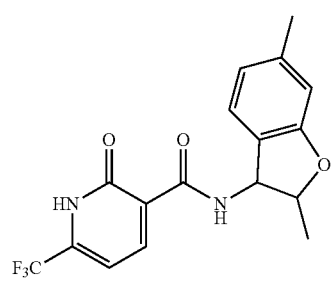 [SMILES: Cc1ccc2c(c1)OC(C)C2NC(=O)c1ccc(C(F)(F)F)[nH]c1=O]
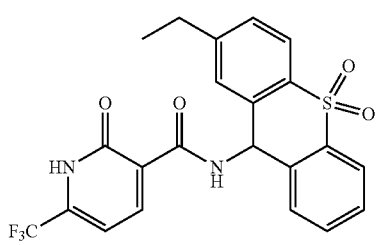
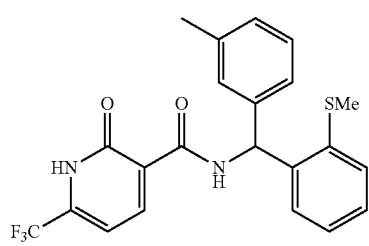
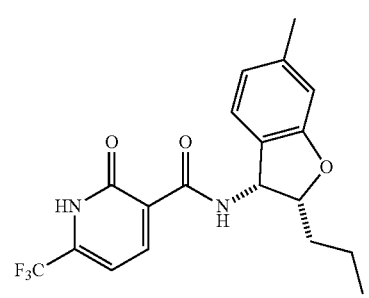
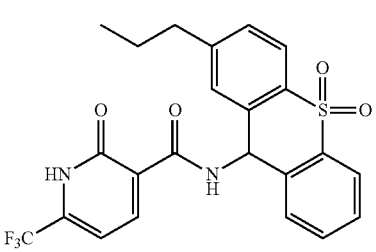
TABLE 2-continued
Exemplary compounds according to the disclosure
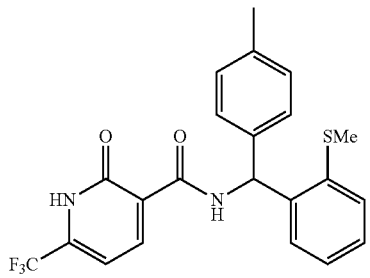
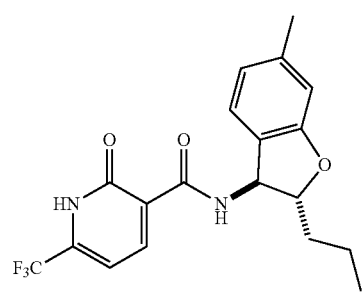
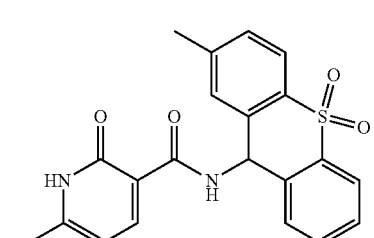
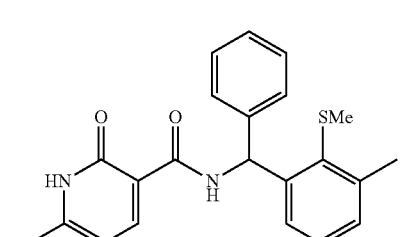
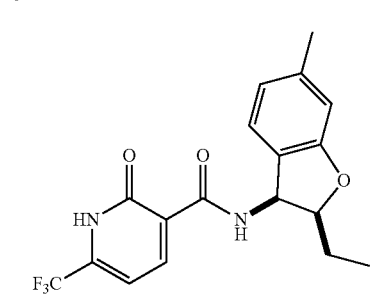
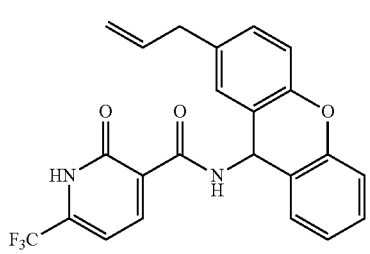 [SMILES: C=CCc1ccc2c(c1)C(NC(=O)c1ccc(C(F)(F)F)[nH]c1=O)c1ccccc1O2]

TABLE 2-continued
Exemplary compounds according to the disclosure
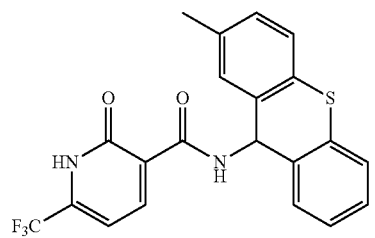
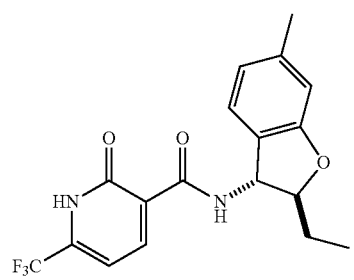
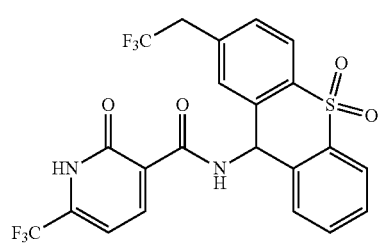
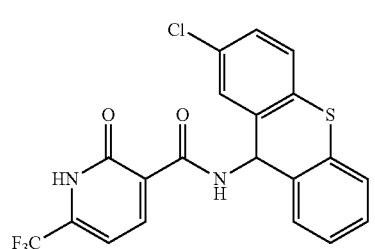
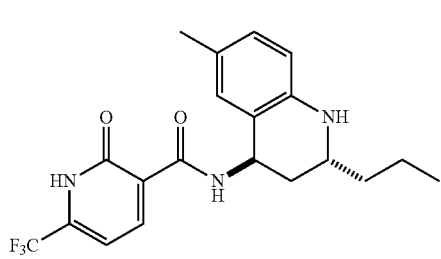
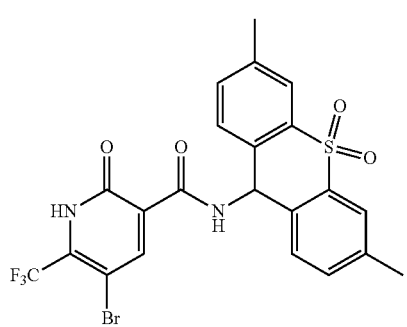 [SMILES: Cc1ccc2c(c1)S(=O)(=O)c1cc(C)ccc1C2NC(=O)c1cc(Br)c(C(F)(F)F)[nH]c1=O]
TABLE 2-continued
Exemplary compounds according to the disclosure
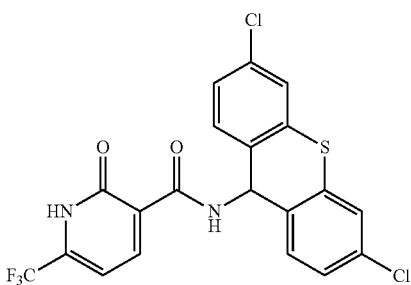
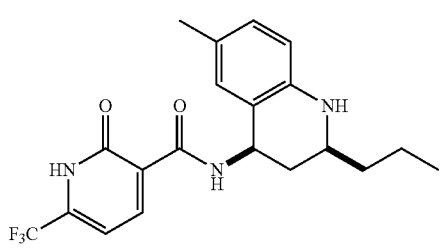
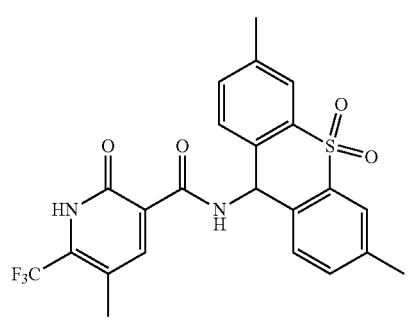 [SMILES: Cc1ccc2c(c1)S(=O)(=O)c1cc(C)ccc1C2NC(=O)c1cc(C)c(C(F)(F)F)[nH]c1=O]
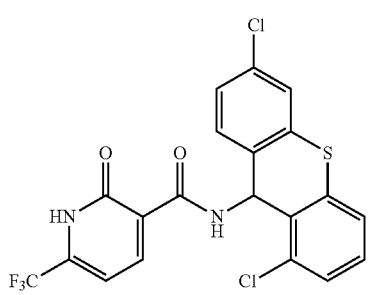 [SMILES: O=C(NC1c2ccc(Cl)cc2Sc2cccc(Cl)c21)c1ccc(C(F)(F)F)[nH]c1=O]
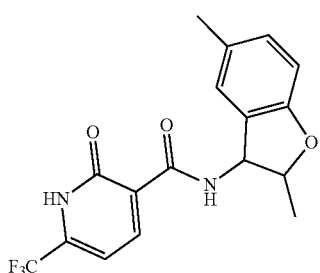

TABLE 2-continued
Exemplary compounds according to the disclosure
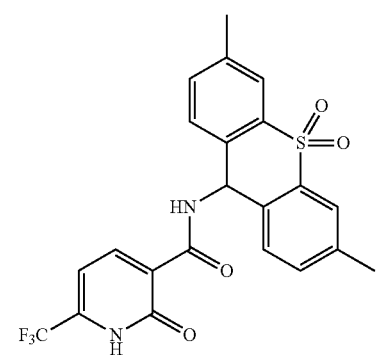 [SMILES: Cc1ccc2c(c1)S(=O)(=O)c1cc(C)ccc1C2NC(=O)c1ccc(C(F)(F)F)[nH]c1=O]
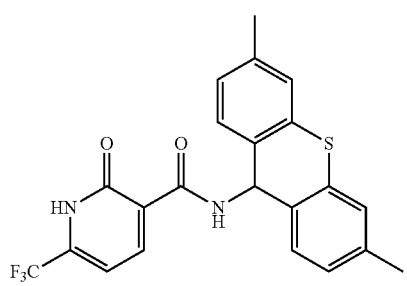
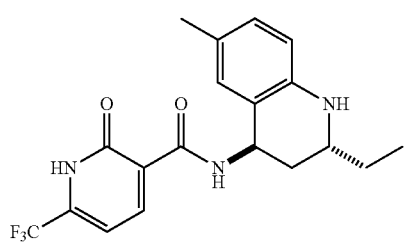
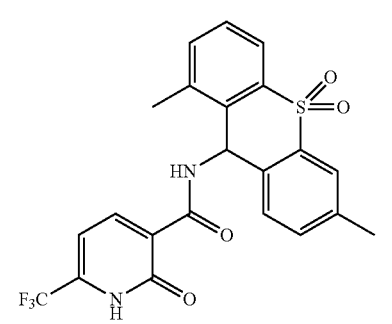 [SMILES: Cc1ccc2c(c1)S(=O)(=O)c1cccc(C)c1C2NC(=O)c1ccc(C(F)(F)F)[nH]c1=O]
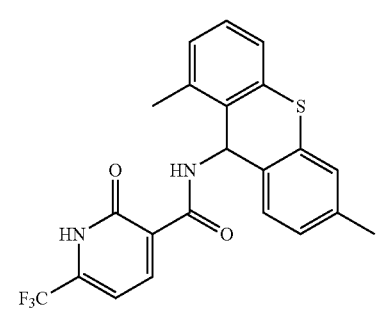 [SMILES: Cc1ccc2c(c1)Sc1cccc(C)c1C2NC(=O)c1ccc(C(F)(F)F)[nH]c1=O]
TABLE 2-continued
Exemplary compounds according to the disclosure
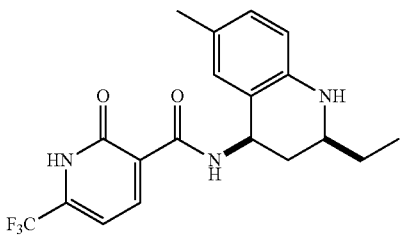
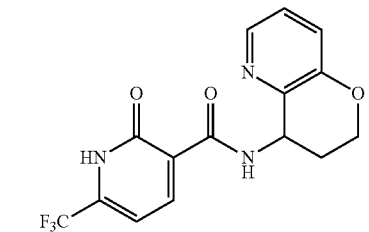 [SMILES: O=C(NC1CCOc2cccnc21)c1ccc(C(F)(F)F)[nH]c1=O]
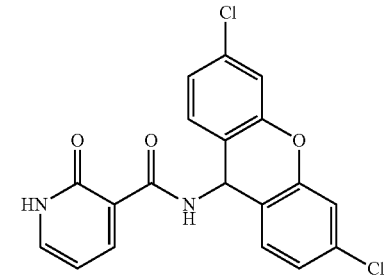
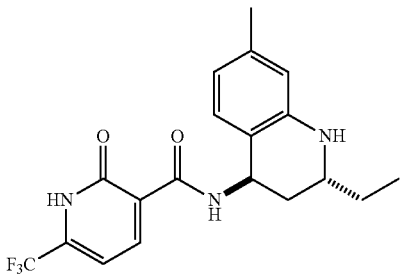
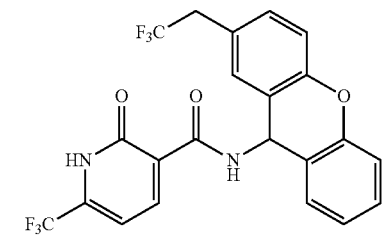
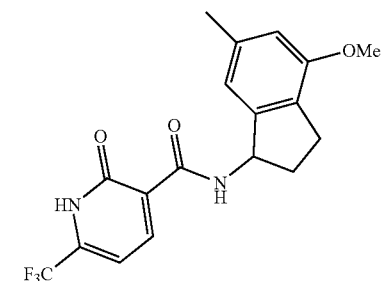

TABLE 2-continued
Exemplary compounds according to the disclosure
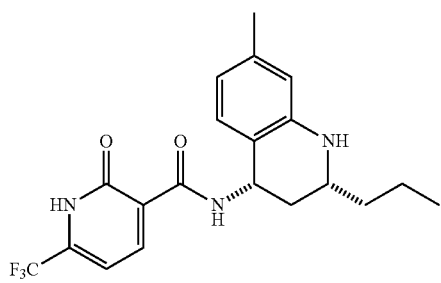
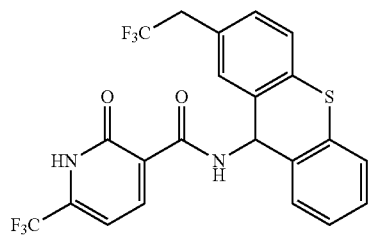
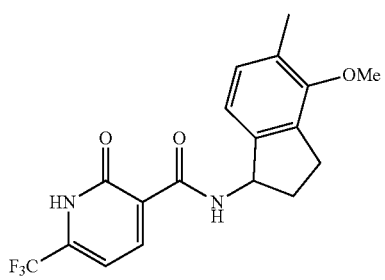 [SMILES: COc1c(C)ccc2c1CCC2NC(=O)c1ccc(C(F)(F)F)[nH]c1=O]
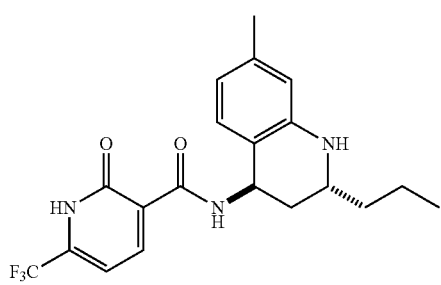
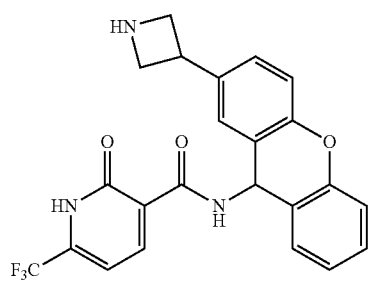
TABLE 2-continued
Exemplary compounds according to the disclosure
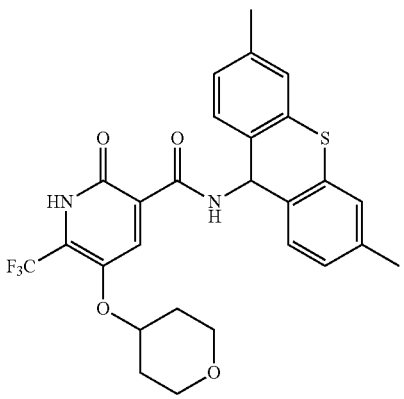 [SMILES: Cc1ccc2c(c1)Sc1cc(C)ccc1C2NC(=O)c1cc(OC2CCOCC2)c(C(F)(F)F)[nH]c1=O]
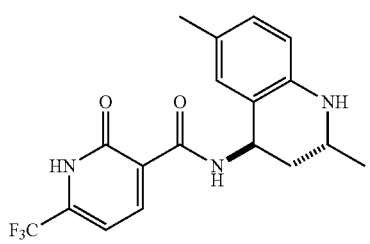
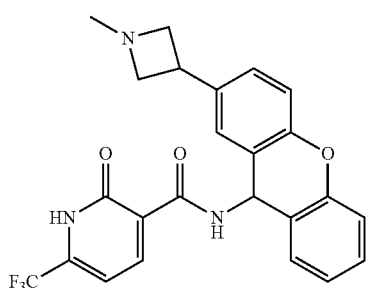
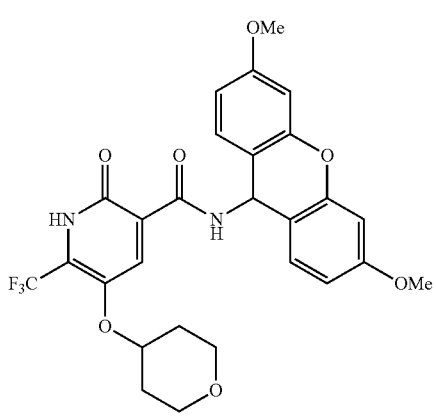 [SMILES: COc1ccc2c(c1)Oc1cc(OC)ccc1C2NC(=O)c1cc(OC2CCOCC2)c(C(F)(F)F)[nH]c1=O]
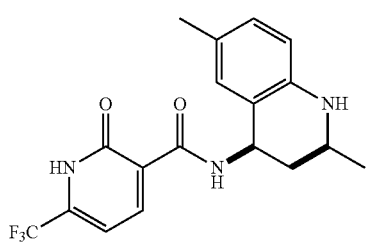

TABLE 2-continued
Exemplary compounds according to the disclosure
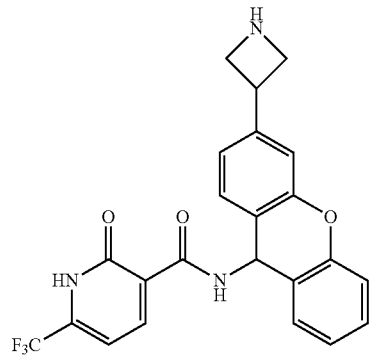
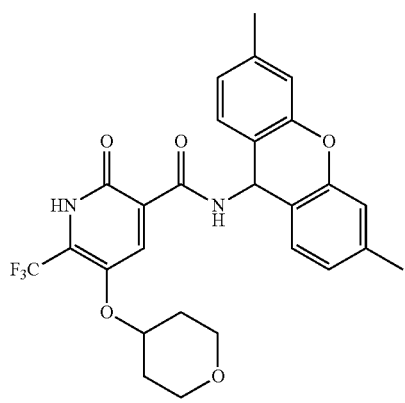
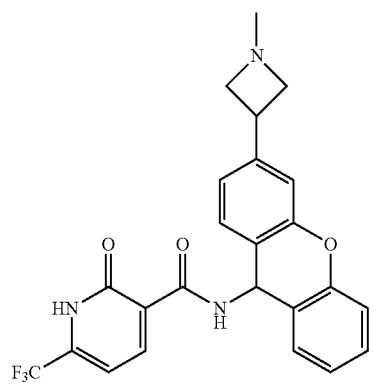 [SMILES: CN1CC(c2ccc3c(c2)Oc2ccccc2C3NC(=O)c2ccc(C(F)(F)F)[nH]c2=O)C1]
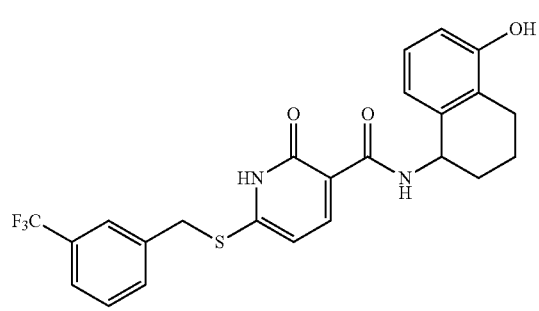 [SMILES: O=C(NC1CCCc2c(O)cccc21)c1ccc(SCc2cccc(C(F)(F)F)c2)[nH]c1=O]
TABLE 2-continued
Exemplary compounds according to the disclosure
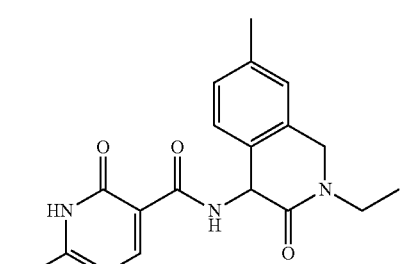
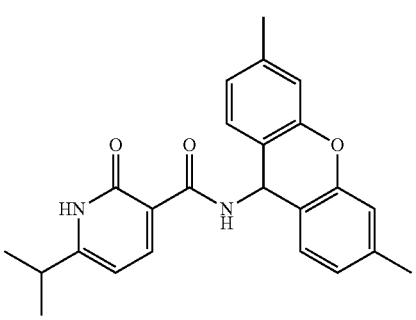 [SMILES: Cc1ccc2c(c1)Oc1cc(C)ccc1C2NC(=O)c1ccc(C(C)C)[nH]c1=O]
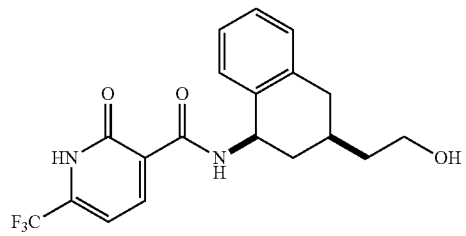
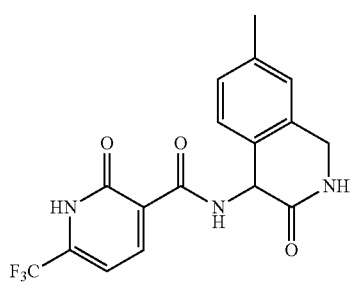 [SMILES: Cc1ccc2c(c1)CNC(=O)C2NC(=O)c1ccc(C(F)(F)F)[nH]c1=O]
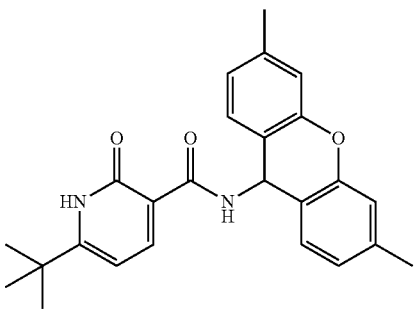 [SMILES: Cc1ccc2c(c1)Oc1cc(C)ccc1C2NC(=O)c1ccc(C(C)(C)C)[nH]c1=O]

TABLE 2-continued
Exemplary compounds according to the disclosure
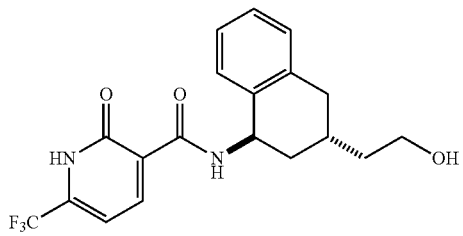
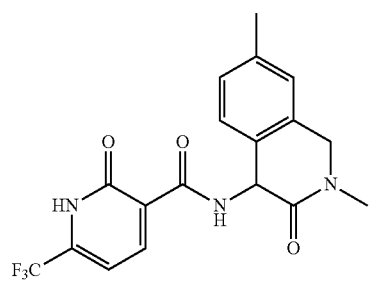 [SMILES: Cc1ccc2c(c1)CN(C)C(=O)C2NC(=O)c1ccc(C(F)(F)F)[nH]c1=O]
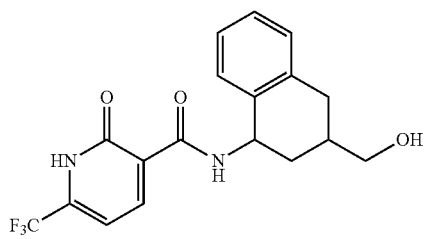 [SMILES: O=C(NC1CC(CO)Cc2ccccc21)c1ccc(C(F)(F)F)[nH]c1=O]
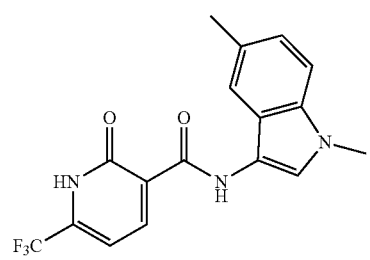 [SMILES: Cc1ccc2c(c1)c(NC(=O)c1ccc(C(F)(F)F)[nH]c1=O)cn2C]
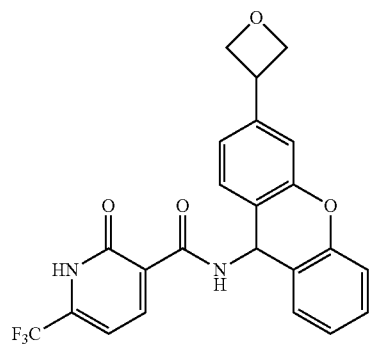 [SMILES: O=C(NC1c2ccccc2Oc2cc(C3COC3)ccc21)c1ccc(C(F)(F)F)[nH]c1=O]
TABLE 2-continued
Exemplary compounds according to the disclosure
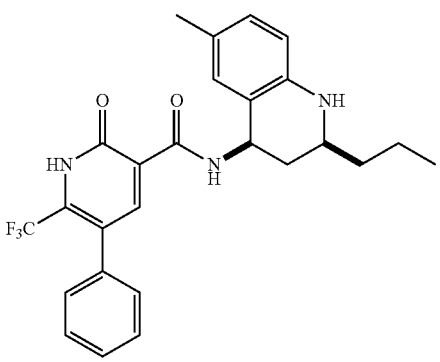
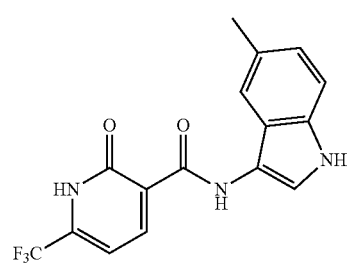 [SMILES: Cc1ccc2[nH]cc(NC(=O)c3ccc(C(F)(F)F)[nH]c3=O)c2c1]
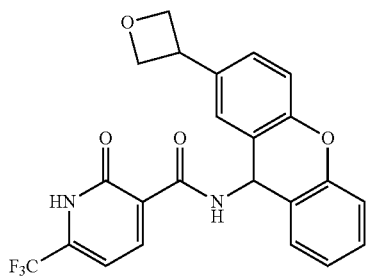 [SMILES: O=C(NC1c2ccccc2Oc2ccc(C3COC3)cc21)c1ccc(C(F)(F)F)[nH]c1=O]
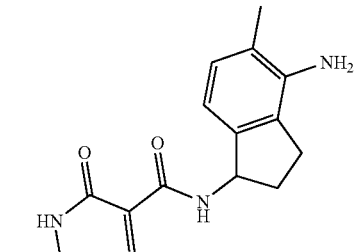
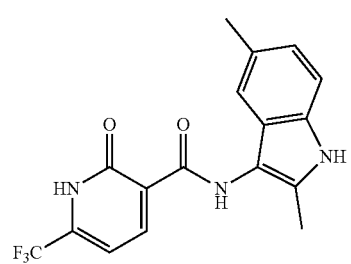 [SMILES: Cc1ccc2[nH]c(C)c(NC(=O)c3ccc(C(F)(F)F)[nH]c3=O)c2c1]

TABLE 2-continued
Exemplary compounds according to the disclosure
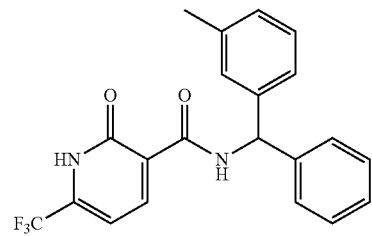 [SMILES: Cc1cccc(C(NC(=O)c2ccc(C(F)(F)F)[nH]c2=O)c2ccccc2)c1]
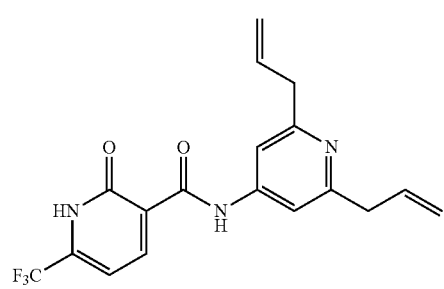
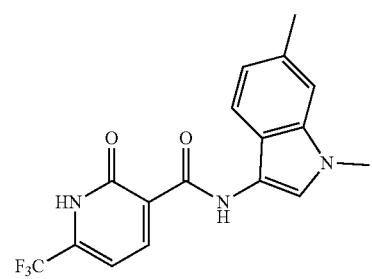 [SMILES: Cc1ccc2c(NC(=O)c3ccc(C(F)(F)F)[nH]c3=O)cn(C)c2c1]
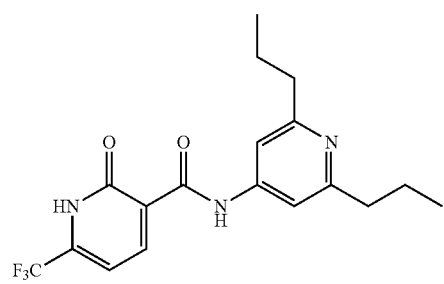 [SMILES: CCCc1cc(NC(=O)c2ccc(C(F)(F)F)[nH]c2=O)cc(CCC)n1]
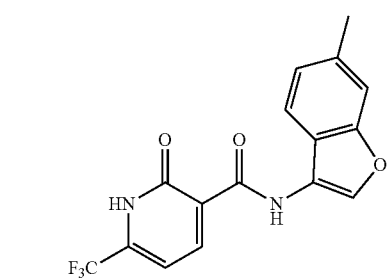
TABLE 2-continued
Exemplary compounds according to the disclosure
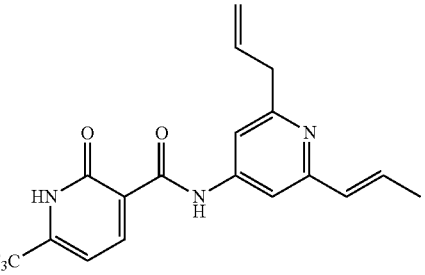
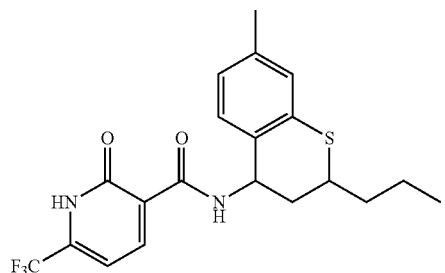
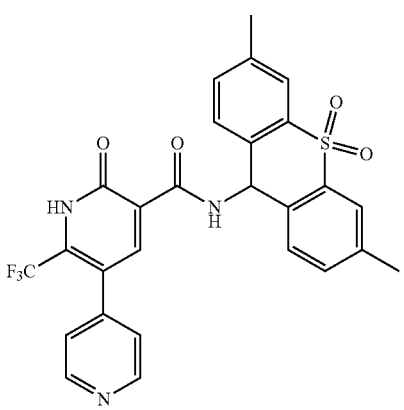 [SMILES: Cc1ccc2c(c1)S(=O)(=O)c1cc(C)ccc1C2NC(=O)c1cc(-c2ccncc2)c(C(F)(F)F)[nH]c1=O]
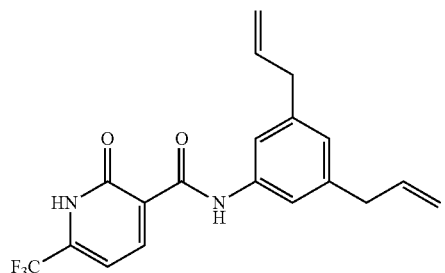
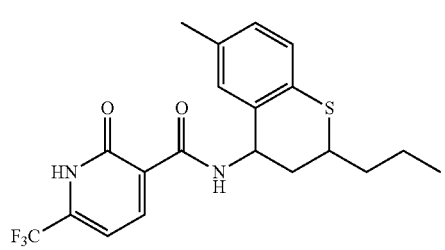

TABLE 2-continued
Exemplary compounds according to the disclosure
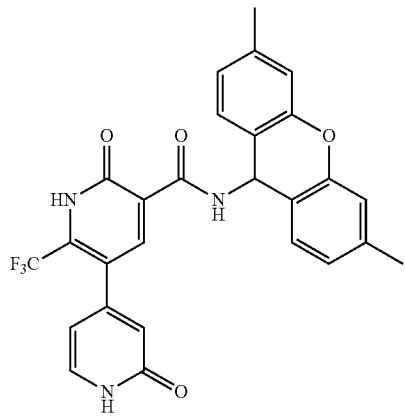 [SMILES: Cc1ccc2c(c1)Oc1cc(C)ccc1C2NC(=O)c1cc(-c2cc[nH]c(=O)c2)c(C(F)(F)F)[nH]c1=O]
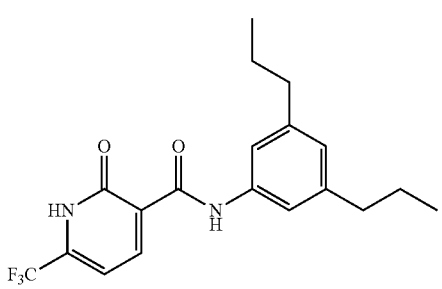
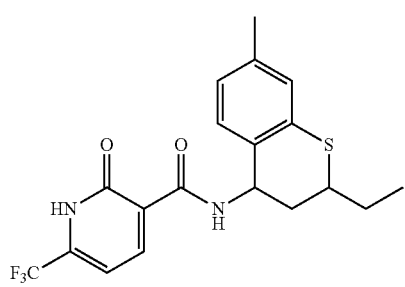
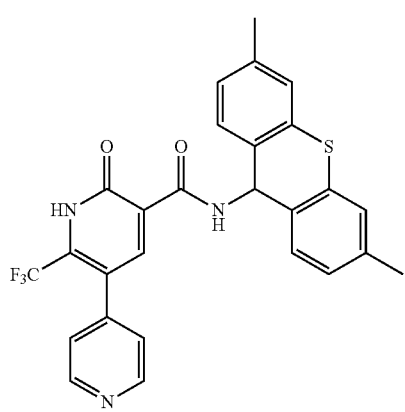
TABLE 2-continued
Exemplary compounds according to the disclosure
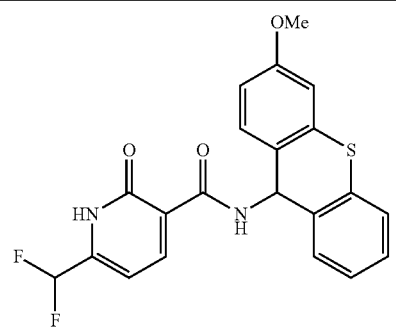
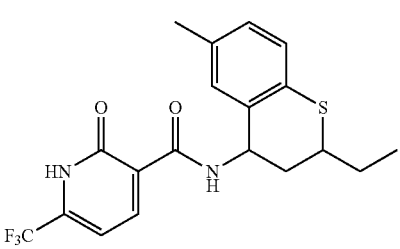 [SMILES: CCC1CC(NC(=O)c2ccc(C(F)(F)F)[nH]c2=O)c2cc(C)ccc2S1]
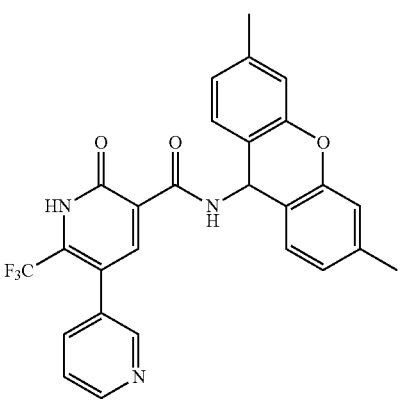
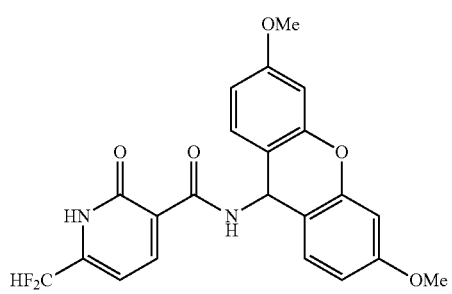
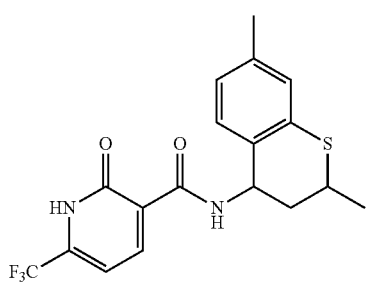

TABLE 2-continued
Exemplary compounds according to the disclosure
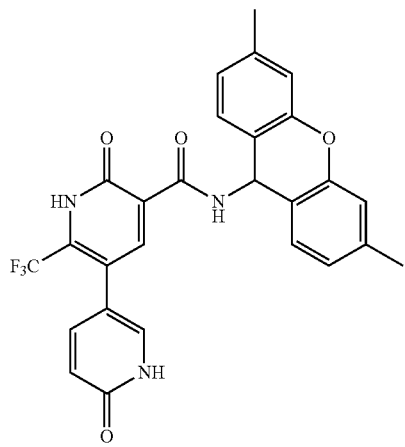 [SMILES: Cc1ccc2c(c1)Oc1cc(C)ccc1C2NC(=O)c1cc(-c2ccc(=O)[nH]c2)c(C(F)(F)F)[nH]c1=O]
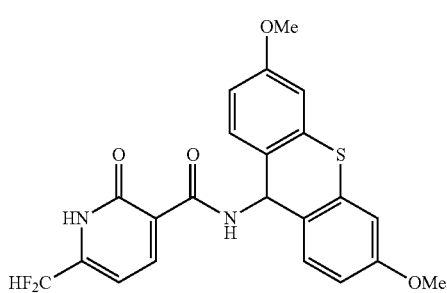
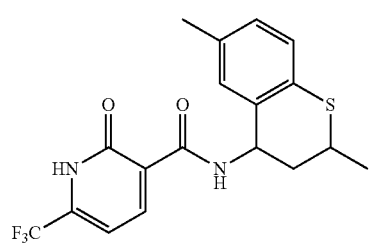
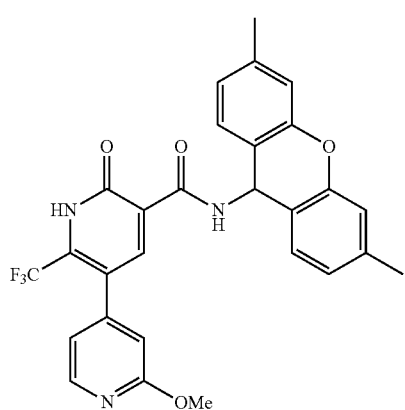
TABLE 2-continued
Exemplary compounds according to the disclosure
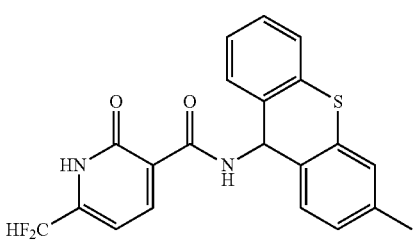
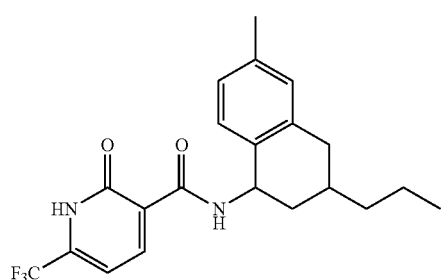
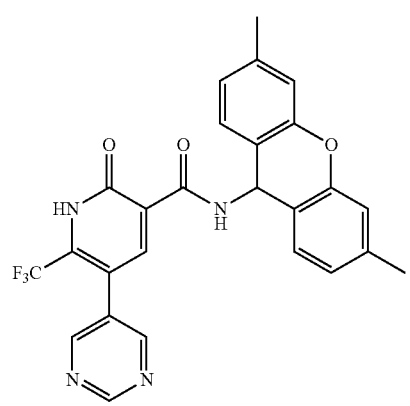
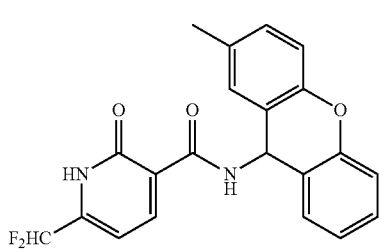
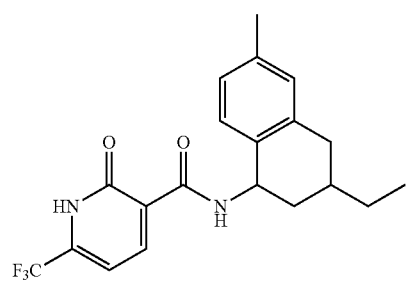

TABLE 2-continued
Exemplary compounds according to the disclosure
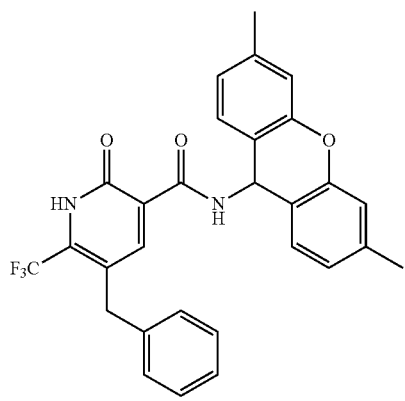
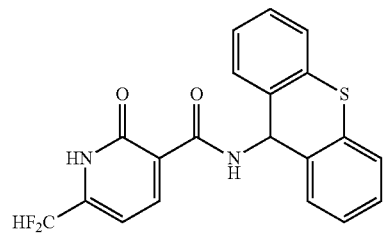
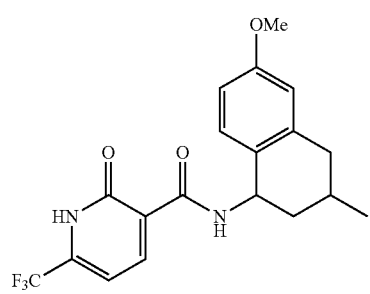 [SMILES: COc1ccc2c(c1)CC(C)CC2NC(=O)c1ccc(C(F)(F)F)[nH]c1=O]
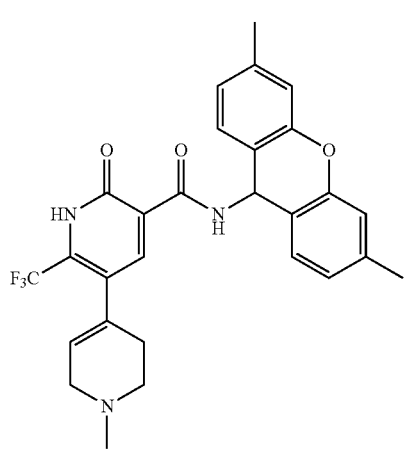
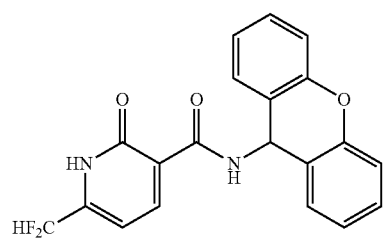
TABLE 2-continued
Exemplary compounds according to the disclosure
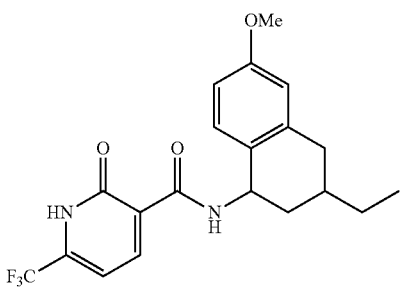 [SMILES: CCC1Cc2cc(OC)ccc2C(NC(=O)c2ccc(C(F)(F)F)[nH]c2=O)C1]
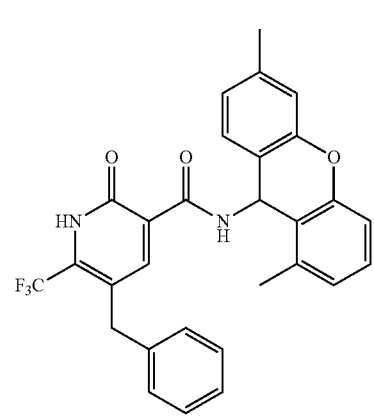
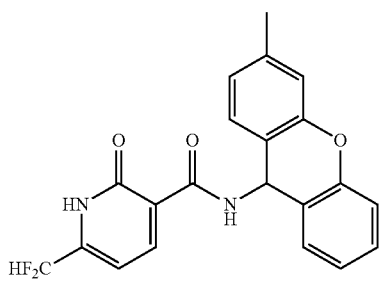
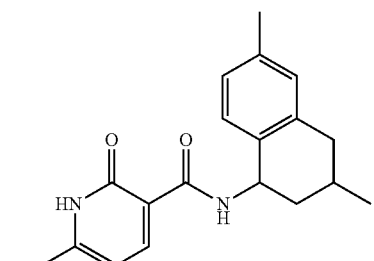

TABLE 2-continued
Exemplary compounds according to the disclosure
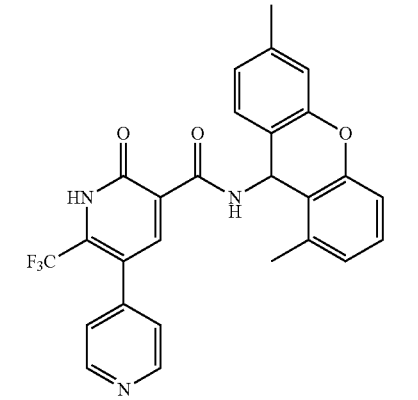 [SMILES: Cc1ccc2c(c1)Oc1cccc(C)c1C2NC(=O)c1cc(-c2ccncc2)c(C(F)(F)F)[nH]c1=O]
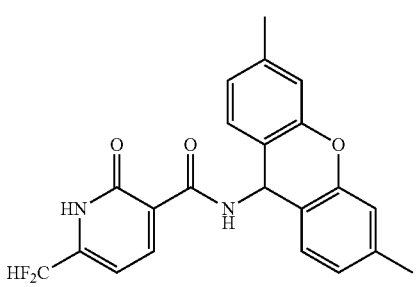
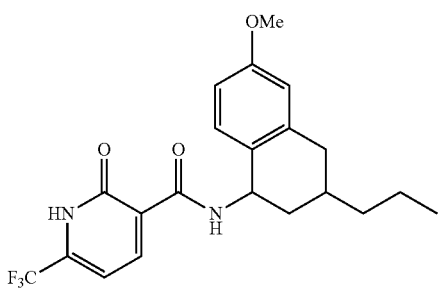 [SMILES: CCCC1Cc2cc(OC)ccc2C(NC(=O)c2ccc(C(F)(F)F)[nH]c2=O)C1]
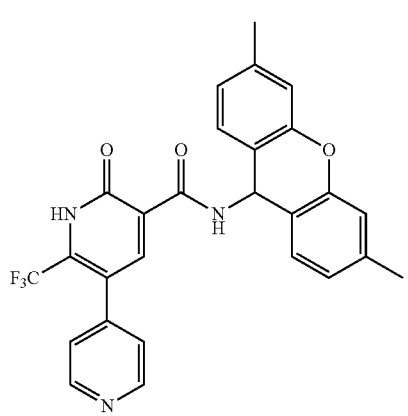
TABLE 2-continued
Exemplary compounds according to the disclosure
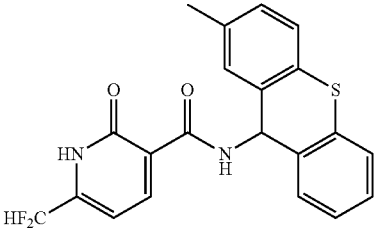
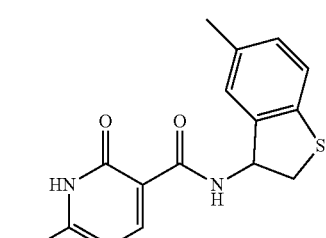
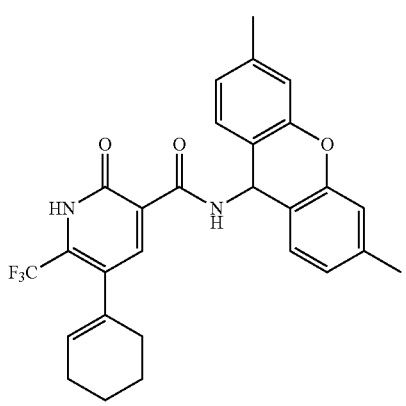
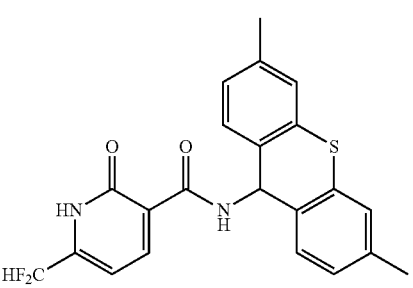
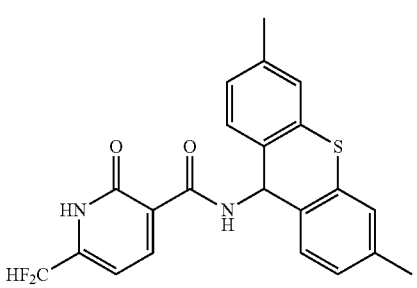

TABLE 2-continued
Exemplary compounds according to the disclosure
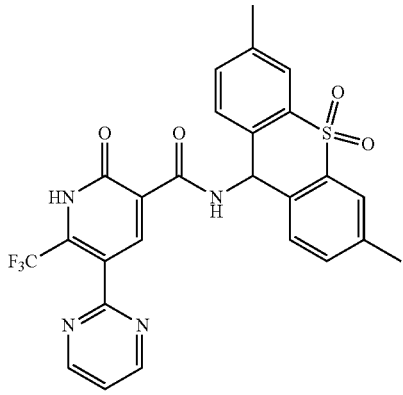
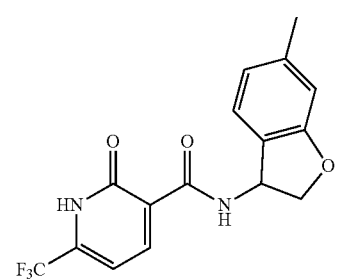
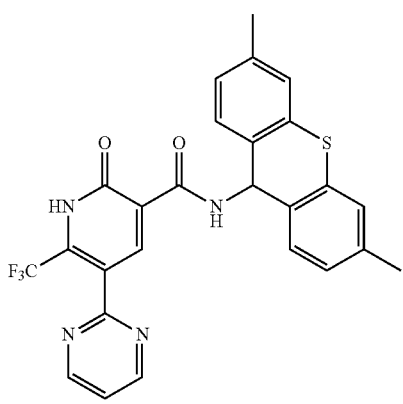
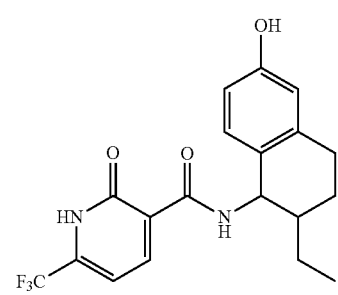 [SMILES: CCC1CCc2cc(O)ccc2C1NC(=O)c1ccc(C(F)(F)F)[nH]c1=O]
TABLE 2-continued
Exemplary compounds according to the disclosure
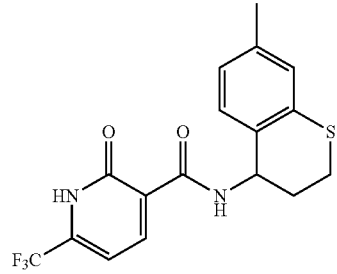
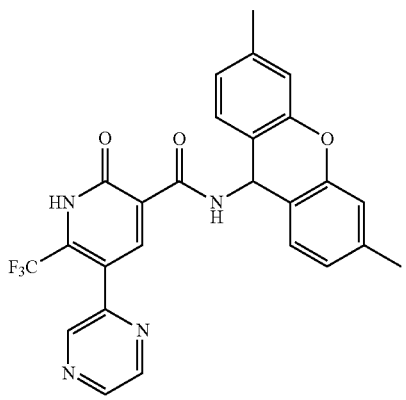
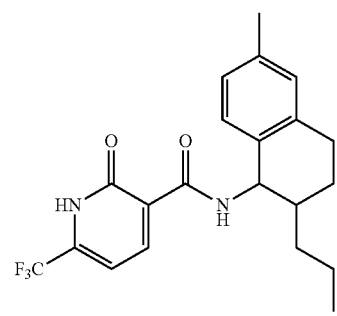 [SMILES: CCCC1CCc2cc(C)ccc2C1NC(=O)c1ccc(C(F)(F)F)[nH]c1=O]
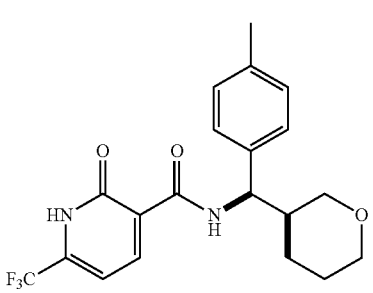

TABLE 2-continued
Exemplary compounds according to the disclosure
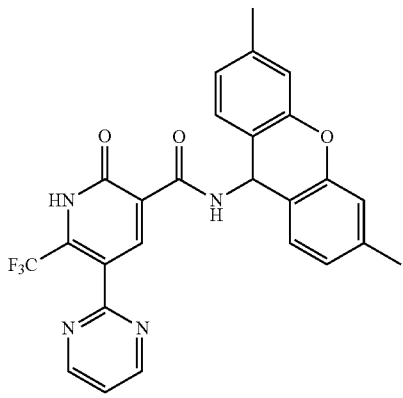
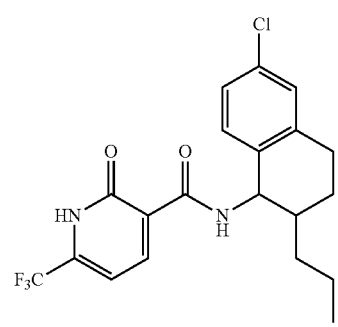 [SMILES: CCCC1CCc2cc(Cl)ccc2C1NC(=O)c1ccc(C(F)(F)F)[nH]c1=O]
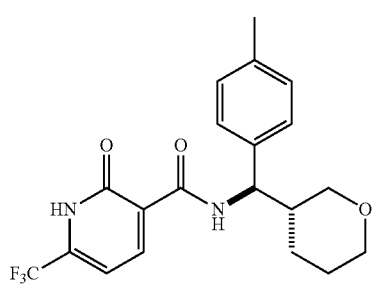
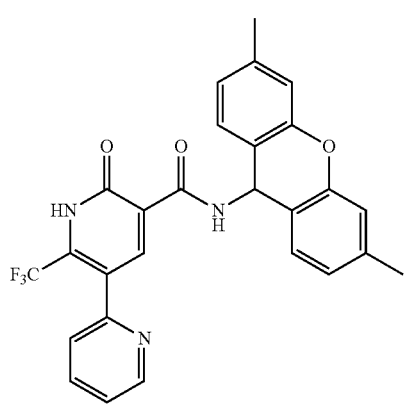
TABLE 2-continued
Exemplary compounds according to the disclosure
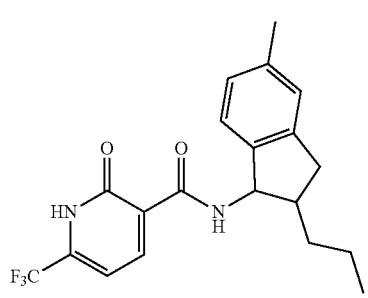 [SMILES: CCCC1Cc2cc(C)ccc2C1NC(=O)c1ccc(C(F)(F)F)[nH]c1=O]
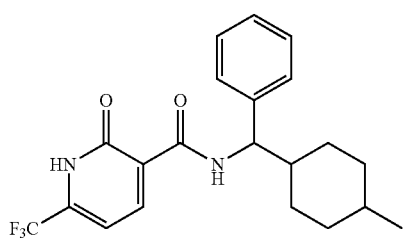 [SMILES: CC1CCC(C(NC(=O)c2ccc(C(F)(F)F)[nH]c2=O)c2ccccc2)CC1]
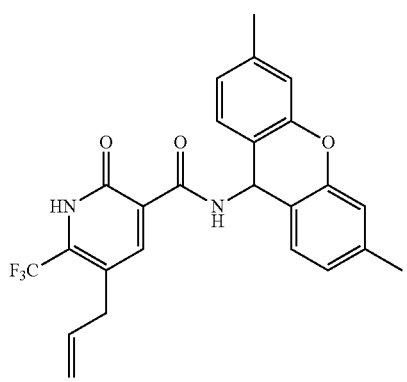 [SMILES: C=CCc1cc(C(=O)NC2c3ccc(C)cc3Oc3cc(C)ccc32)c(=O)[nH]c1C(F)(F)F]
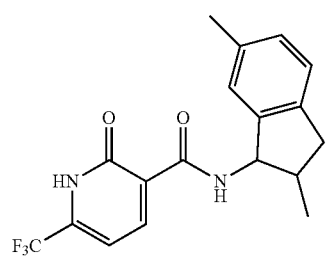 [SMILES: Cc1ccc2c(c1)C(NC(=O)c1ccc(C(F)(F)F)[nH]c1=O)C(C)C2]
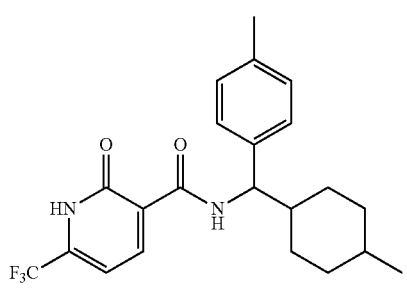 [SMILES: Cc1ccc(C(NC(=O)c2ccc(C(F)(F)F)[nH]c2=O)C2CCC(C)CC2)cc1]

TABLE 2-continued
Exemplary compounds according to the disclosure
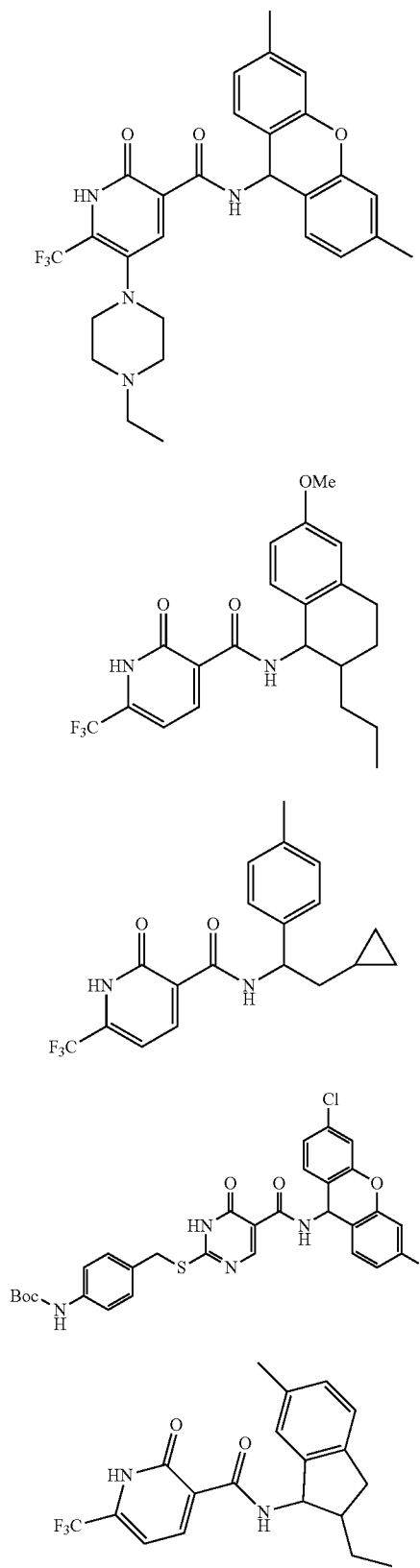
TABLE 2-continued
Exemplary compounds according to the disclosure
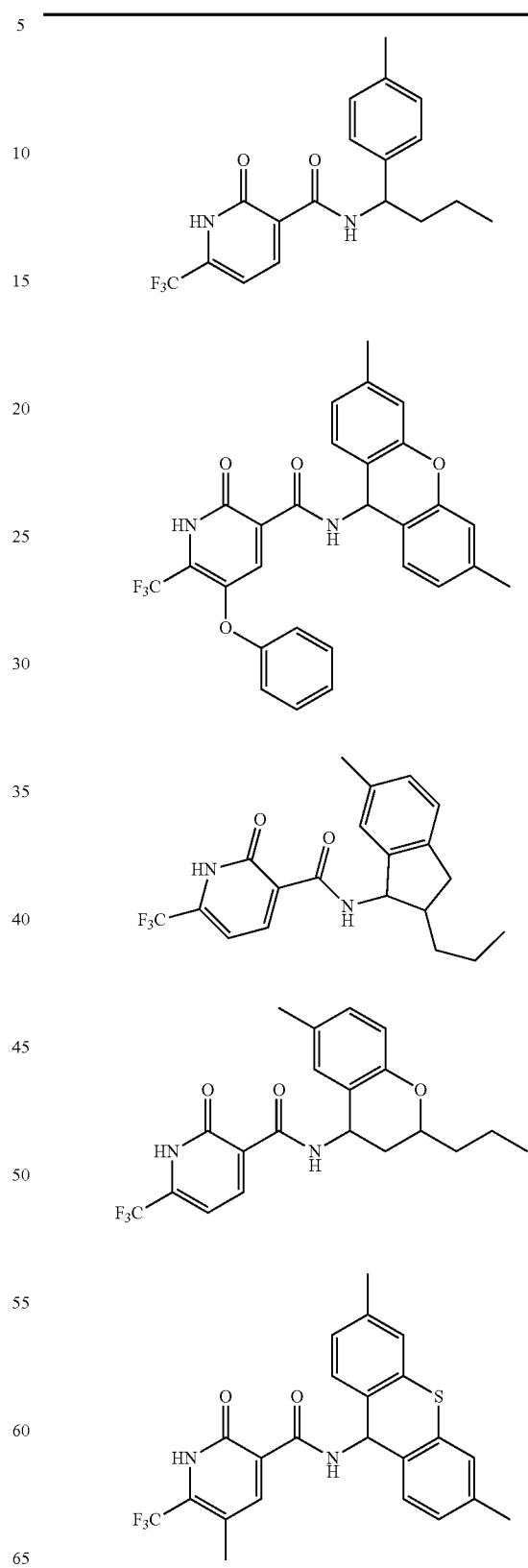

TABLE 2-continued
Exemplary compounds according to the disclosure
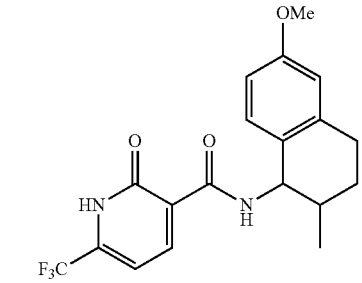
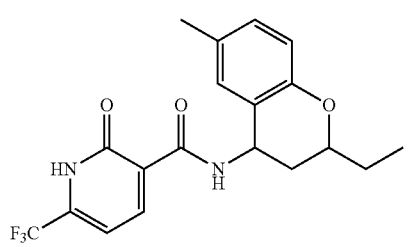
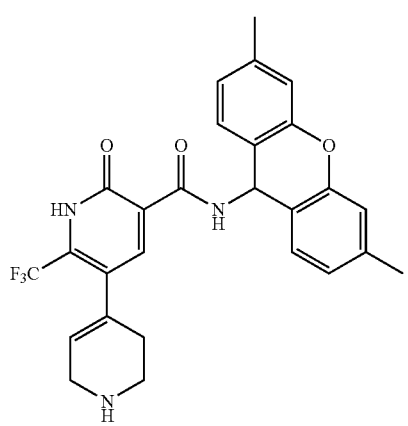 [SMILES: Cc1ccc2c(c1)Oc1cc(C)ccc1C2NC(=O)c1cc(C2=CCNCC2)c(C(F)(F)F)[nH]c1=O]
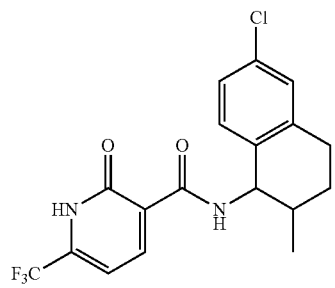 [SMILES: CC1CCc2cc(Cl)ccc2C1NC(=O)c1ccc(C(F)(F)F)[nH]c1=O]
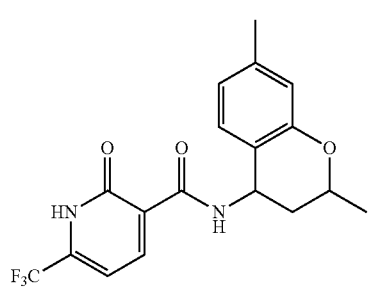
TABLE 2-continued
Exemplary compounds according to the disclosure
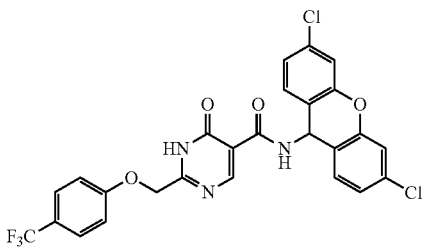 [SMILES: O=C(NC1c2ccc(Cl)cc2Oc2cc(Cl)ccc21)c1cnc(COc2ccc(C(F)(F)F)cc2)[nH]c1=O]
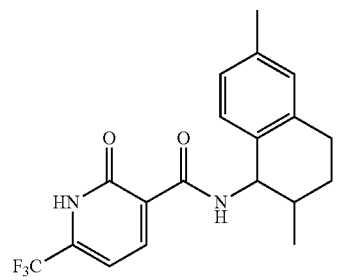
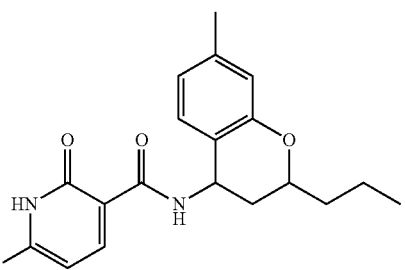
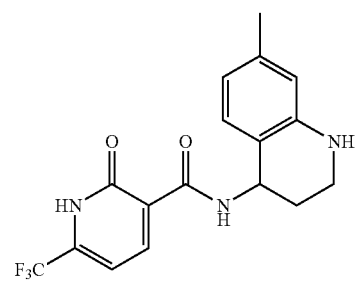 [SMILES: Cc1ccc2c(c1)NCCC2NC(=O)c1ccc(C(F)(F)F)[nH]c1=O]
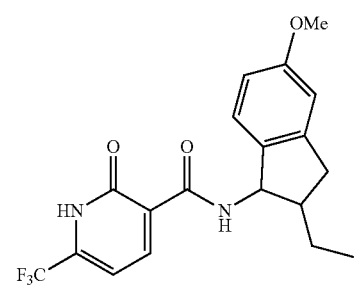 [SMILES: CCC1Cc2cc(OC)ccc2C1NC(=O)c1ccc(C(F)(F)F)[nH]c1=O]

TABLE 2-continued
Exemplary compounds according to the disclosure
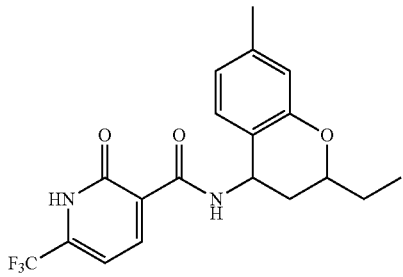
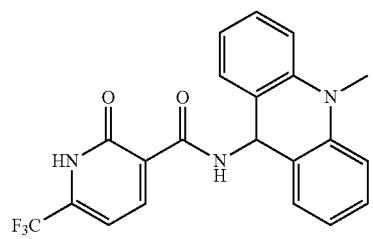 [SMILES: CN1c2ccccc2C(NC(=O)c2ccc(C(F)(F)F)[nH]c2=O)c2ccccc21]
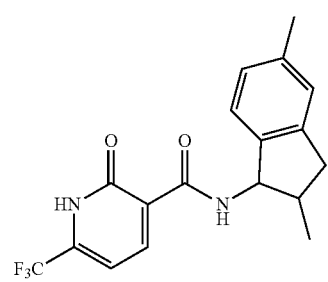 [SMILES: Cc1ccc2c(c1)CC(C)C2NC(=O)c1ccc(C(F)(F)F)[nH]c1=O]
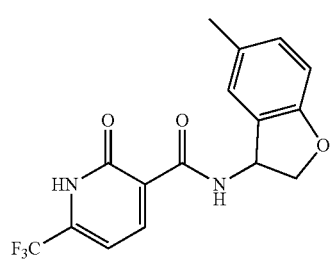 [SMILES: Cc1ccc2c(c1)C(NC(=O)c1ccc(C(F)(F)F)[nH]c1=O)CO2]
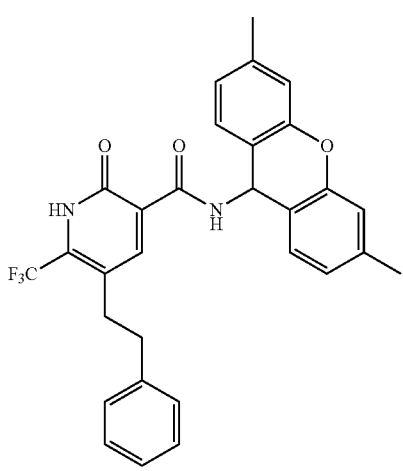
TABLE 2-continued
Exemplary compounds according to the disclosure
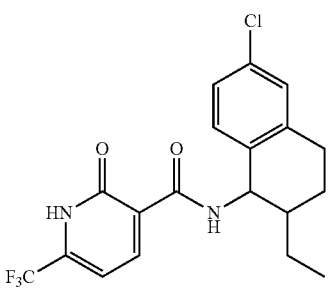
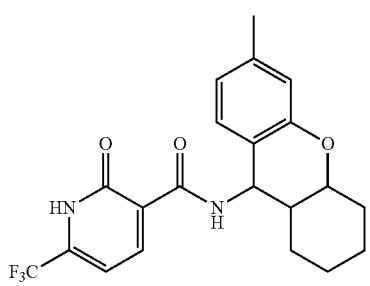 [SMILES: Cc1ccc2c(c1)OC1CCCCC1C2NC(=O)c1ccc(C(F)(F)F)[nH]c1=O]
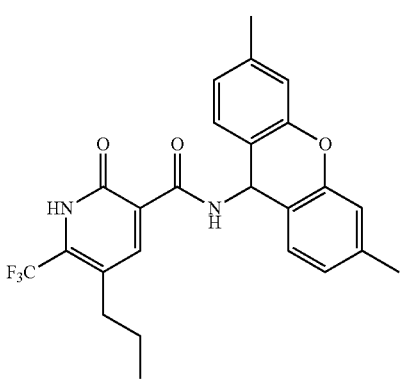 [SMILES: CCCc1cc(C(=O)NC2c3ccc(C)cc3Oc3cc(C)ccc32)c(=O)[nH]c1C(F)(F)F]
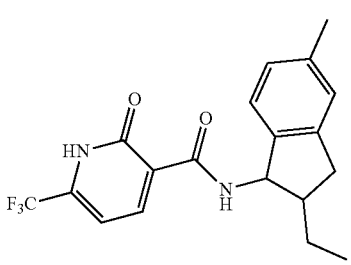 [SMILES: CCC1Cc2cc(C)ccc2C1NC(=O)c1ccc(C(F)(F)F)[nH]c1=O]
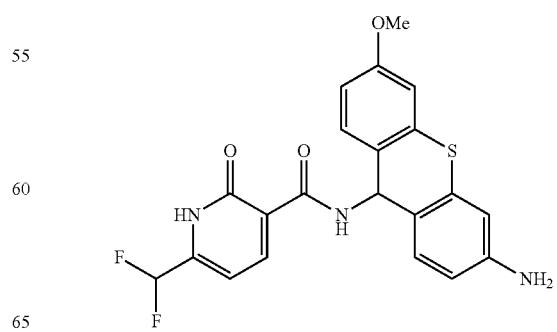

TABLE 2-continued
Exemplary compounds according to the disclosure
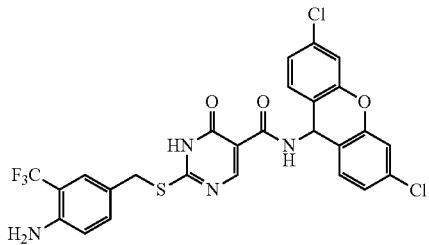 [SMILES: Nc1ccc(CSc2ncc(C(=O)NC3c4ccc(Cl)cc4Oc4cc(Cl)ccc43)c(=O)[nH]2)cc1C(F)(F)F]
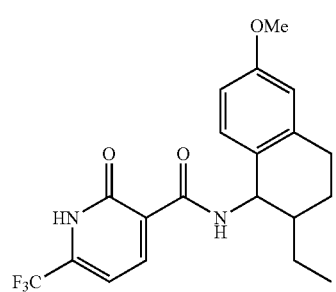
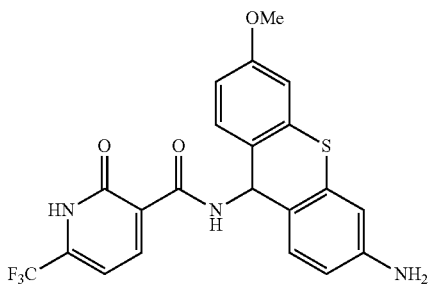 [SMILES: COc1ccc2c(c1)Sc1cc(N)ccc1C2NC(=O)c1ccc(C(F)(F)F)[nH]c1=O]
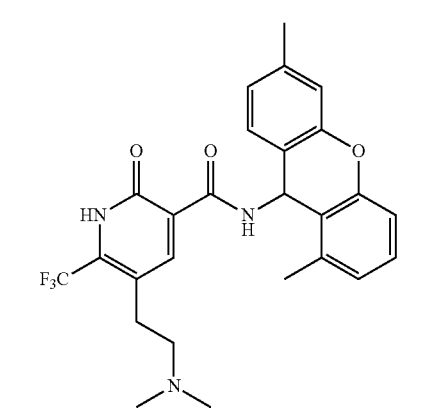
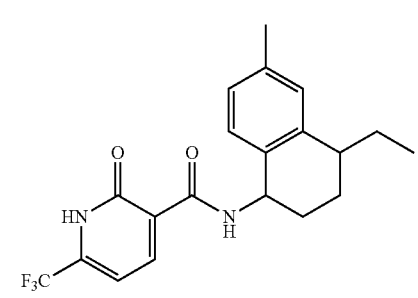
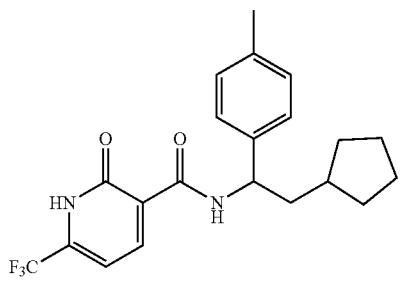 [SMILES: Cc1ccc(C(CC2CCCC2)NC(=O)c2ccc(C(F)(F)F)[nH]c2=O)cc1]
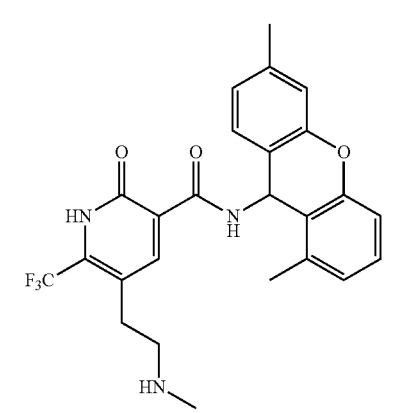
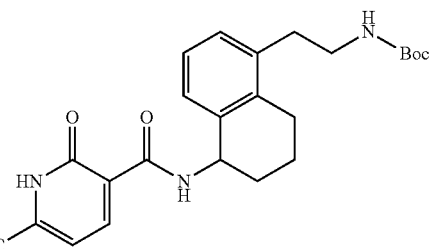
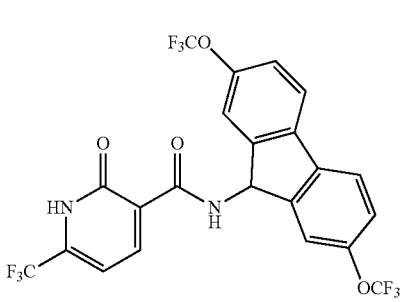 [SMILES: O=C(NC1c2cc(OC(F)(F)F)ccc2-c2ccc(OC(F)(F)F)cc21)c1ccc(C(F)(F)F)[nH]c1=O]
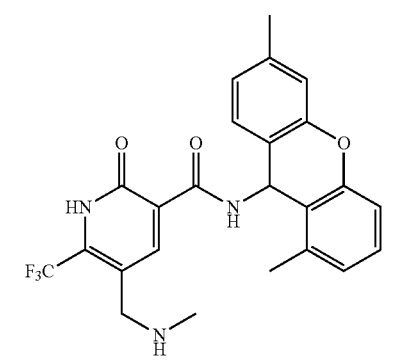

TABLE 2-continued
Exemplary compounds according to the disclosure
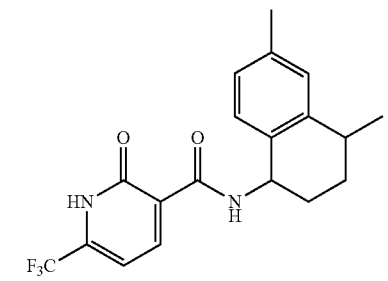 [SMILES: Cc1ccc2c(c1)C(C)CCC2NC(=O)c1ccc(C(F)(F)F)[nH]c1=O]
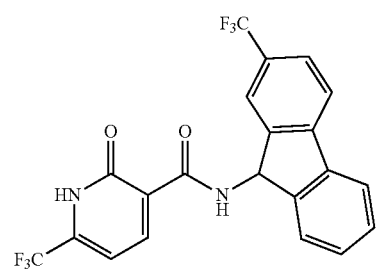 [SMILES: O=C(NC1c2ccccc2-c2ccc(C(F)(F)F)cc21)c1ccc(C(F)(F)F)[nH]c1=O]
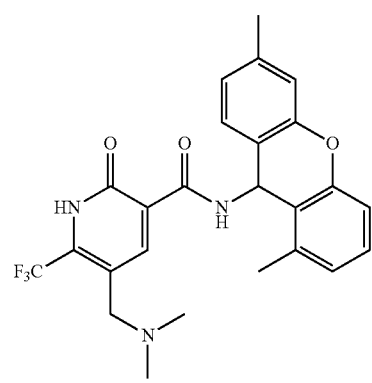 [SMILES: Cc1ccc2c(c1)Oc1cccc(C)c1C2NC(=O)c1cc(CN(C)C)c(C(F)(F)F)[nH]c1=O]
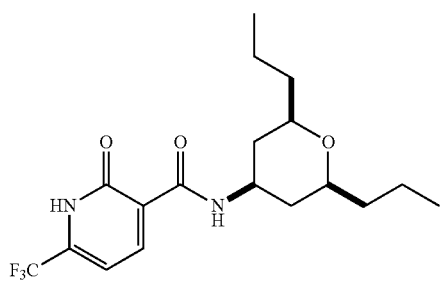
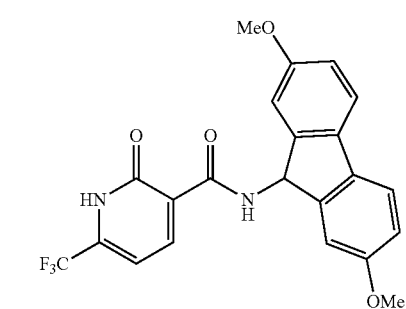 [SMILES: COc1ccc2c(c1)C(NC(=O)c1ccc(C(F)(F)F)[nH]c1=O)c1cc(OC)ccc1-2]
TABLE 2-continued
Exemplary compounds according to the disclosure
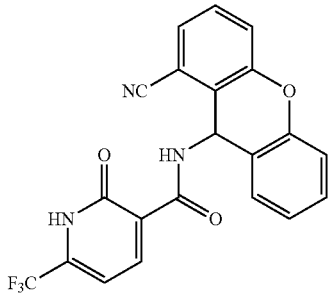 [SMILES: N#Cc1cccc2c1C(NC(=O)c1ccc(C(F)(F)F)[nH]c1=O)c1ccccc1O2]
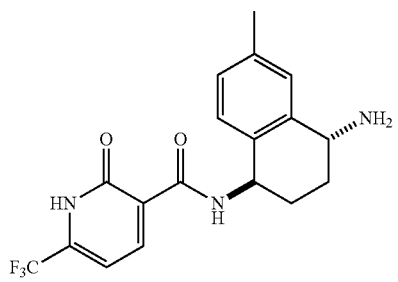
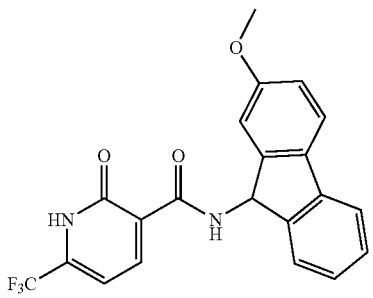 [SMILES: COc1ccc2c(c1)C(NC(=O)c1ccc(C(F)(F)F)[nH]c1=O)c1ccccc1-2]
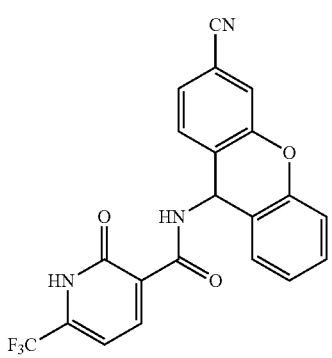 [SMILES: N#Cc1ccc2c(c1)Oc1ccccc1C2NC(=O)c1ccc(C(F)(F)F)[nH]c1=O]
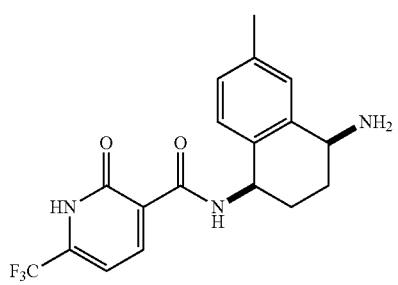

TABLE 2-continued
Exemplary compounds according to the disclosure
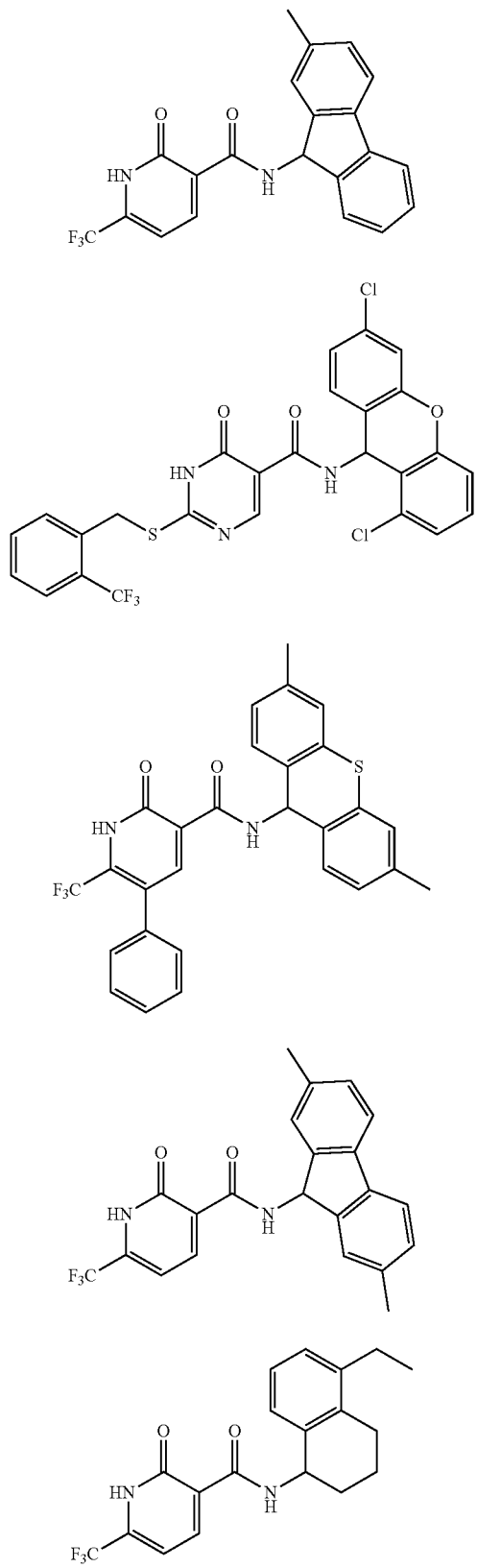
TABLE 2-continued
Exemplary compounds according to the disclosure
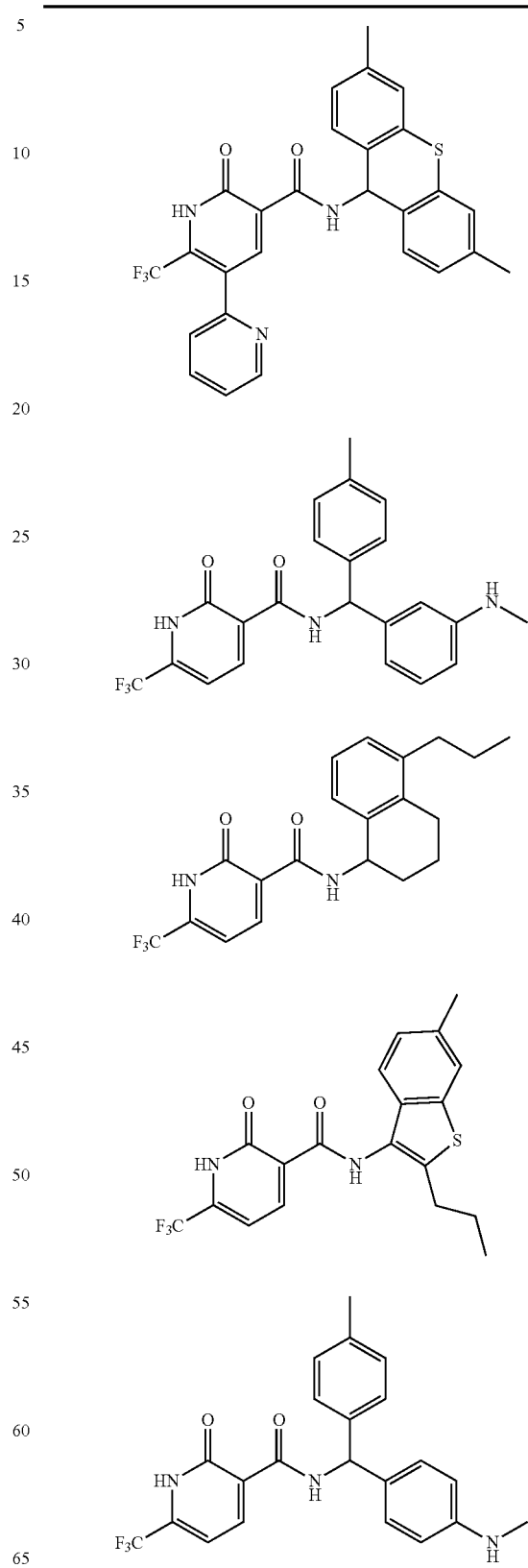

TABLE 2-continued
Exemplary compounds according to the disclosure
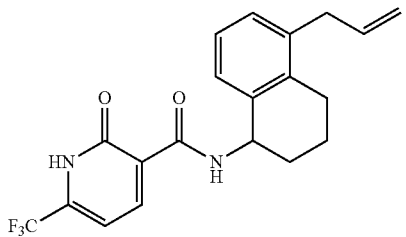
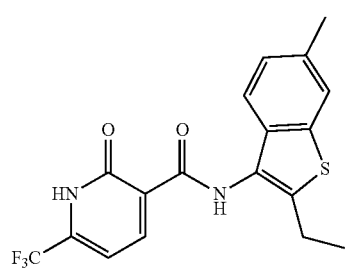 [SMILES: CCc1sc2cc(C)ccc2c1NC(=O)c1ccc(C(F)(F)F)[nH]c1=O]
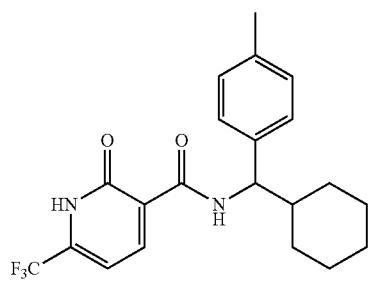 [SMILES: Cc1ccc(C(NC(=O)c2ccc(C(F)(F)F)[nH]c2=O)C2CCCCC2)cc1]
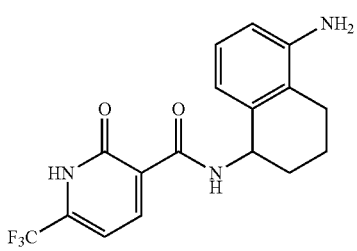 [SMILES: Nc1cccc2c1CCCC2NC(=O)c1ccc(C(F)(F)F)[nH]c1=O]
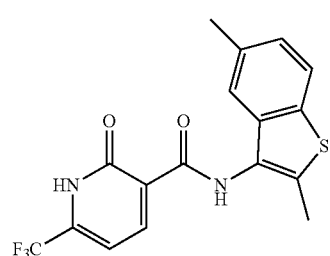
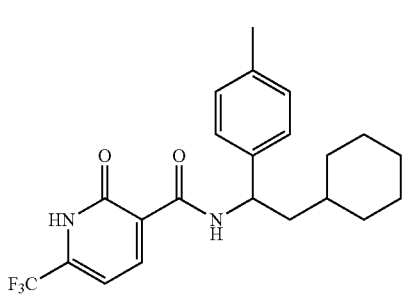
TABLE 2-continued
Exemplary compounds according to the disclosure
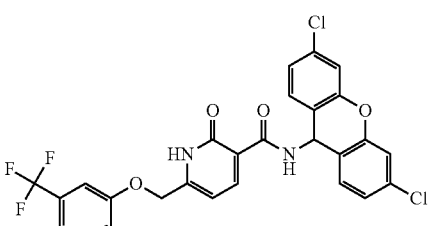
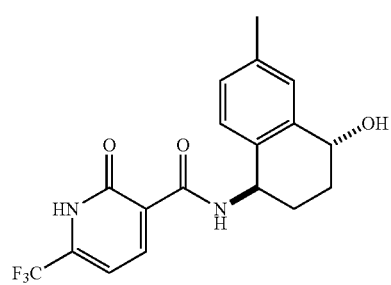
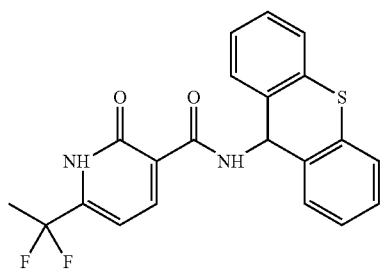 [SMILES: CC(F)(F)c1ccc(C(=O)NC2c3ccccc3Sc3ccccc32)c(=O)[nH]1]
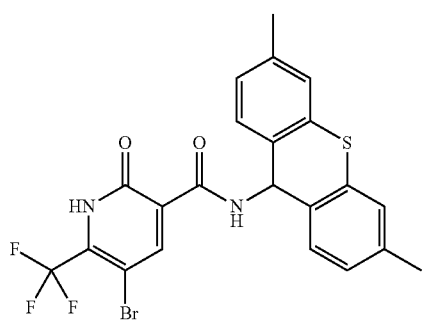 [SMILES: Cc1ccc2c(c1)Sc1cc(C)ccc1C2NC(=O)c1cc(Br)c(C(F)(F)F)[nH]c1=O]
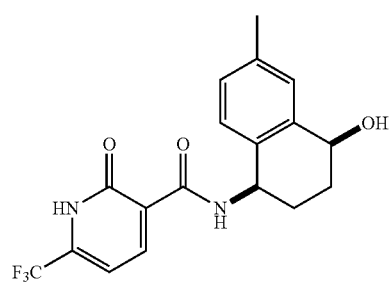

TABLE 2-continued
Exemplary compounds according to the disclosure
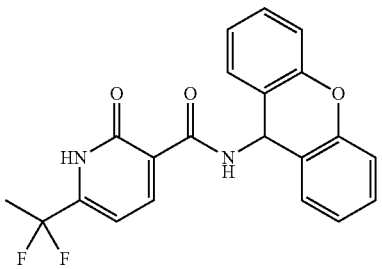 [SMILES: CC(F)(F)c1ccc(C(=O)NC2c3ccccc3Oc3ccccc32)c(=O)[nH]1]
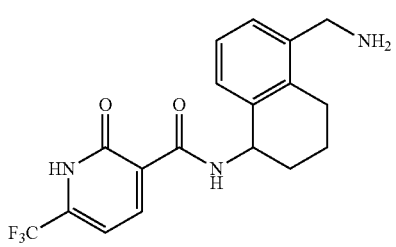 [SMILES: NCc1cccc2c1CCCC2NC(=O)c1ccc(C(F)(F)F)[nH]c1=O]
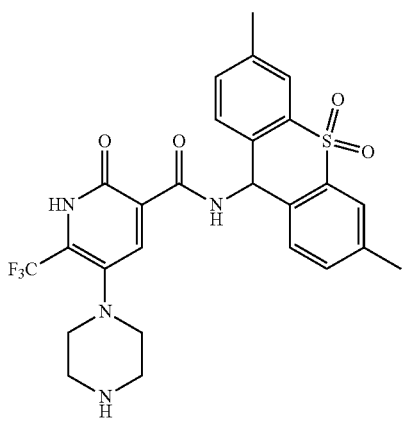 [SMILES: Cc1ccc2c(c1)S(=O)(=O)c1cc(C)ccc1C2NC(=O)c1cc(N2CCNCC2)c(C(F)(F)F)[nH]c1=O]
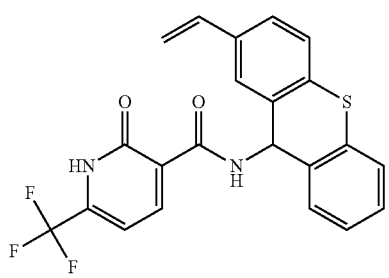 [SMILES: C=Cc1ccc2c(c1)C(NC(=O)c1ccc(C(F)(F)F)[nH]c1=O)c1ccccc1S2]
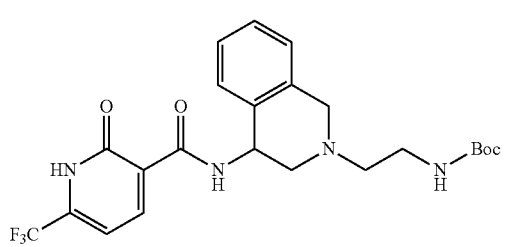 [SMILES: CC(C)(C)OC(=O)NCCN1Cc2ccccc2C(NC(=O)c2ccc(C(F)(F)F)[nH]c2=O)C1]
TABLE 2-continued
Exemplary compounds according to the disclosure
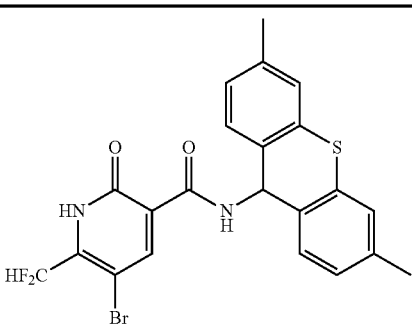
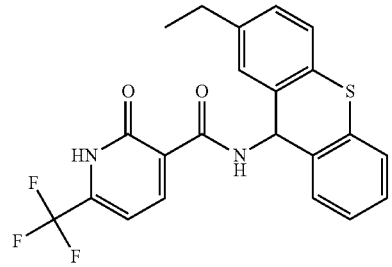 [SMILES: CCc1ccc2c(c1)C(NC(=O)c1ccc(C(F)(F)F)[nH]c1=O)c1ccccc1S2]
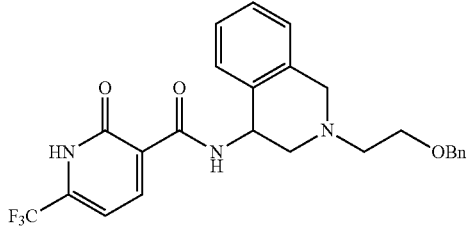
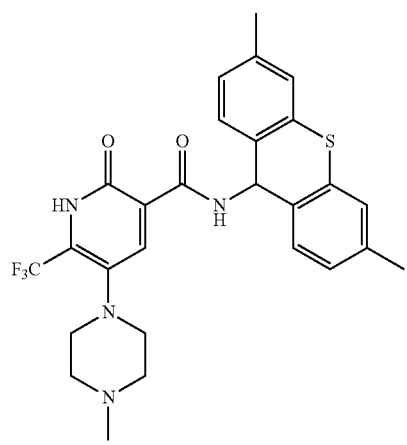
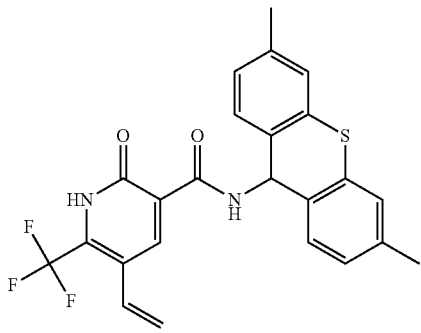 [SMILES: C=Cc1cc(C(=O)NC2c3ccc(C)cc3Sc3cc(C)ccc32)c(=O)[nH]c1C(F)(F)F]

TABLE 2-continued
Exemplary compounds according to the disclosure
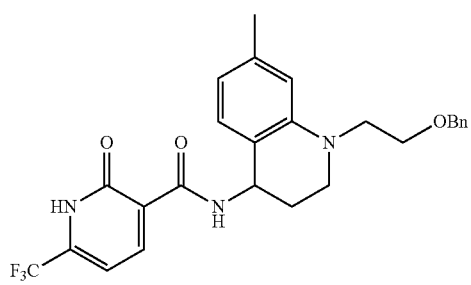 [SMILES: Cc1ccc2c(c1)N(CCOCc1ccccc1)CCC2NC(=O)c1ccc(C(F)(F)F)[nH]c1=O]
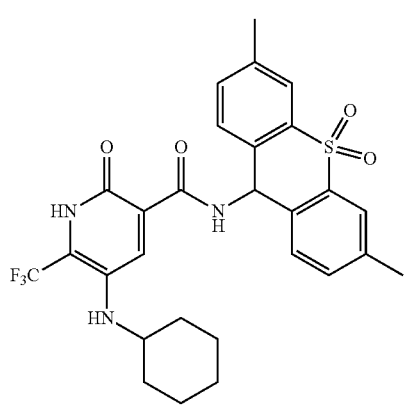 [SMILES: Cc1ccc2c(c1)S(=O)(=O)c1cc(C)ccc1C2NC(=O)c1cc(NC2CCCCC2)c(C(F)(F)F)[nH]c1=O]
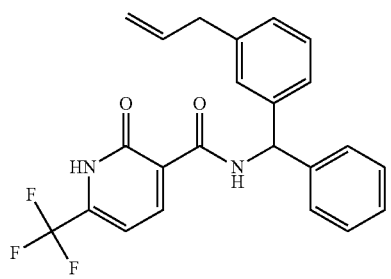 [SMILES: C=CCc1cccc(C(NC(=O)c2ccc(C(F)(F)F)[nH]c2=O)c2ccccc2)c1]
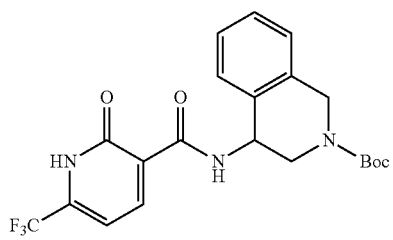 [SMILES: CC(C)(C)OC(=O)N1Cc2ccccc2C(NC(=O)c2ccc(C(F)(F)F)[nH]c2=O)C1]
TABLE 2-continued
Exemplary compounds according to the disclosure
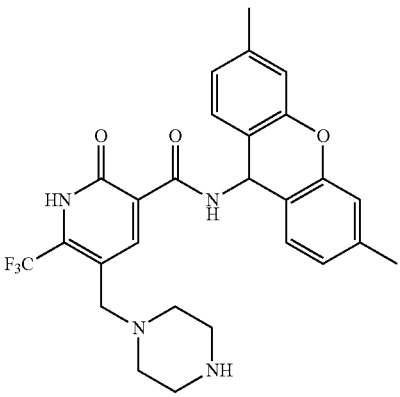 [SMILES: Cc1ccc2c(c1)Oc1cc(C)ccc1C2NC(=O)c1cc(CN2CCNCC2)c(C(F)(F)F)[nH]c1=O]
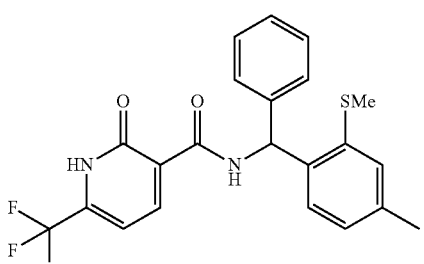
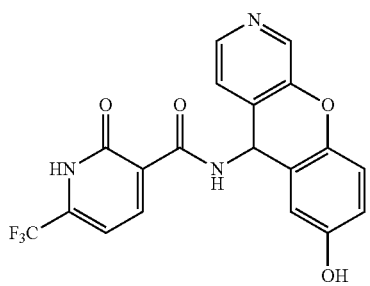
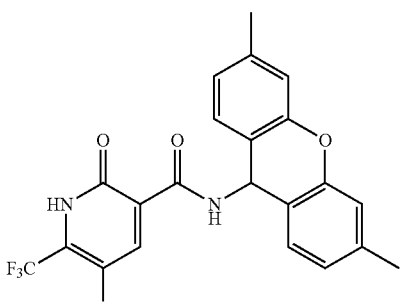
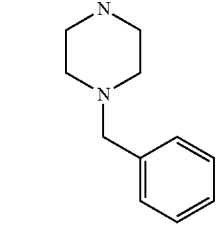

TABLE 2-continued
Exemplary compounds according to the disclosure
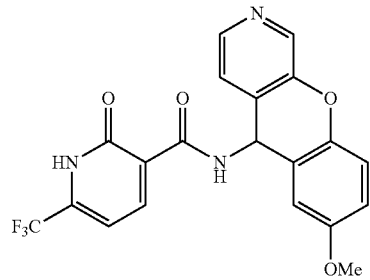
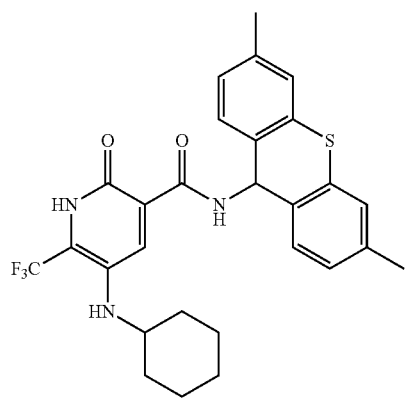 [SMILES: Cc1ccc2c(c1)Sc1cc(C)ccc1C2NC(=O)c1cc(NC2CCCCC2)c(C(F)(F)F)[nH]c1=O]
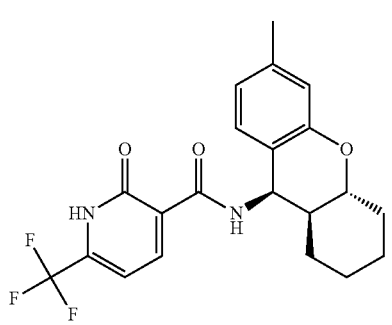 [SMILES: Cc1ccc2c(c1)O[C@@H]1CCCC[C@H]1[C@H]2NC(=O)c1ccc(C(F)(F)F)[nH]c1=O]
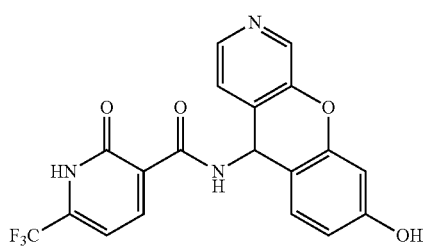 [SMILES: O=C(NC1c2ccncc2Oc2cc(O)ccc21)c1ccc(C(F)(F)F)[nH]c1=O]
TABLE 2-continued
Exemplary compounds according to the disclosure
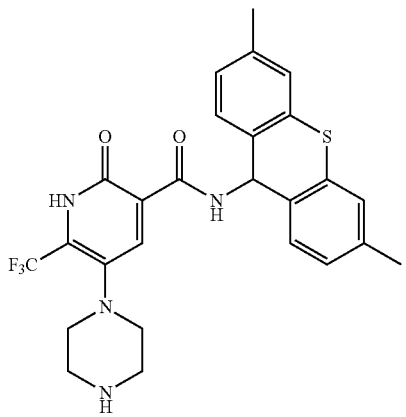 [SMILES: Cc1ccc2c(c1)Sc1cc(C)ccc1C2NC(=O)c1cc(N2CCNCC2)c(C(F)(F)F)[nH]c1=O]
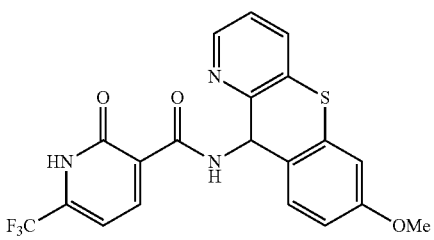 [SMILES: COc1ccc2c(c1)Sc1cccnc1C2NC(=O)c1ccc(C(F)(F)F)[nH]c1=O]
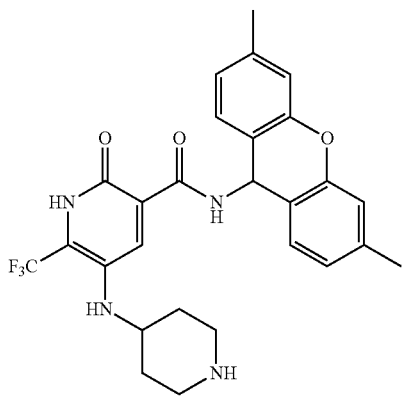 [SMILES: Cc1ccc2c(c1)Oc1cc(C)ccc1C2NC(=O)c1cc(NC2CCNCC2)c(C(F)(F)F)[nH]c1=O]
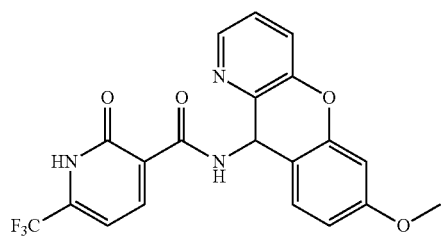 [SMILES: COc1ccc2c(c1)Oc1cccnc1C2NC(=O)c1ccc(C(F)(F)F)[nH]c1=O]

TABLE 2-continued
Exemplary compounds according to the disclosure
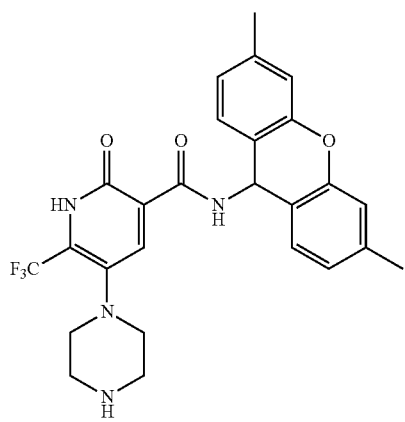 [SMILES: Cc1ccc2c(c1)Oc1cc(C)ccc1C2NC(=O)c1cc(N2CCNCC2)c(C(F)(F)F)[nH]c1=O]
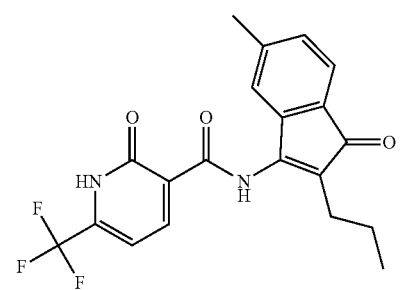 [SMILES: CCCC1=C(NC(=O)c2ccc(C(F)(F)F)[nH]c2=O)c2cc(C)ccc2C1=O]
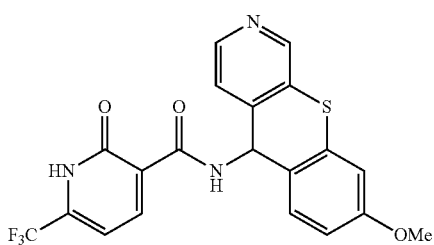
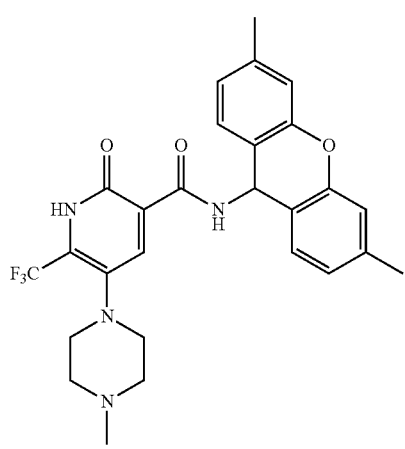 [SMILES: Cc1ccc2c(c1)Oc1cc(C)ccc1C2NC(=O)c1cc(N2CCN(C)CC2)c(C(F)(F)F)[nH]c1=O]
TABLE 2-continued
Exemplary compounds according to the disclosure
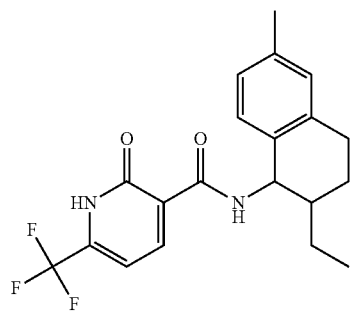 [SMILES: CCC1CCc2cc(C)ccc2C1NC(=O)c1ccc(C(F)(F)F)[nH]c1=O]
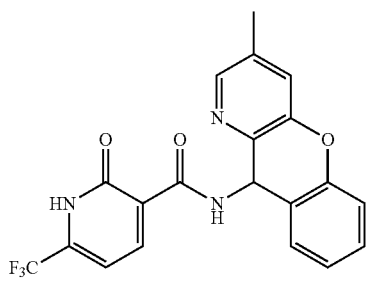
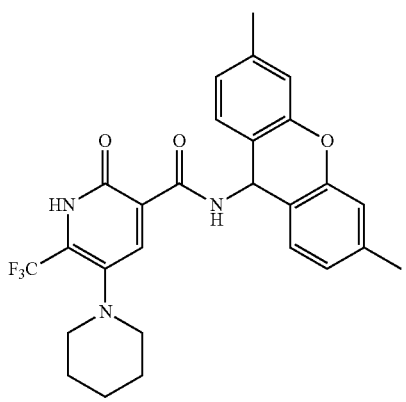
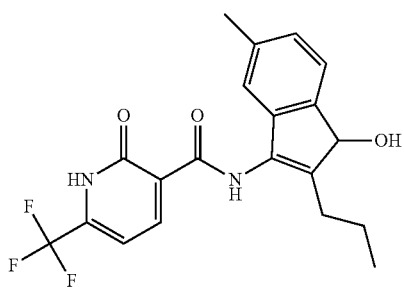 [SMILES: CCCC1=C(NC(=O)c2ccc(C(F)(F)F)[nH]c2=O)c2cc(C)ccc2C1O]
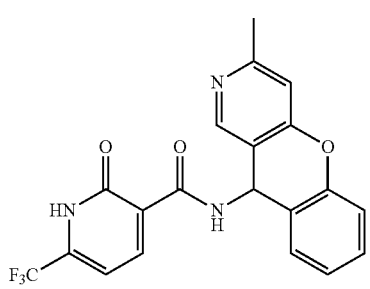

TABLE 2-continued
Exemplary compounds according to the disclosure
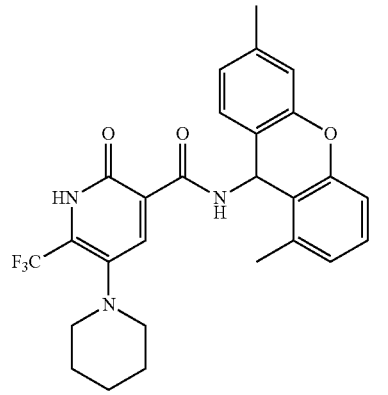
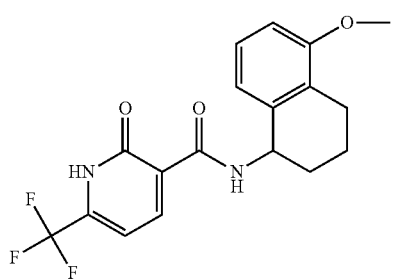 [SMILES: COc1cccc2c1CCCC2NC(=O)c1ccc(C(F)(F)F)[nH]c1=O]
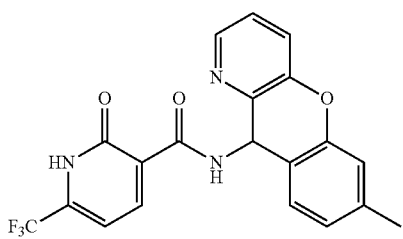
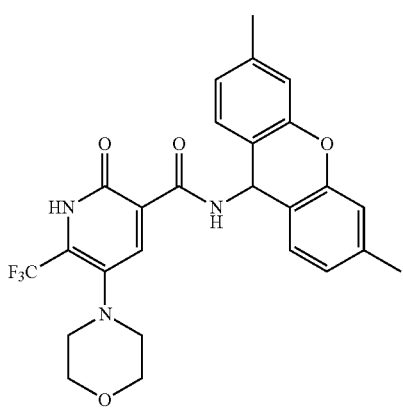 [SMILES: Cc1ccc2c(c1)Oc1cc(C)ccc1C2NC(=O)c1cc(N2CCOCC2)c(C(F)(F)F)[nH]c1=O]
TABLE 2-continued
Exemplary compounds according to the disclosure
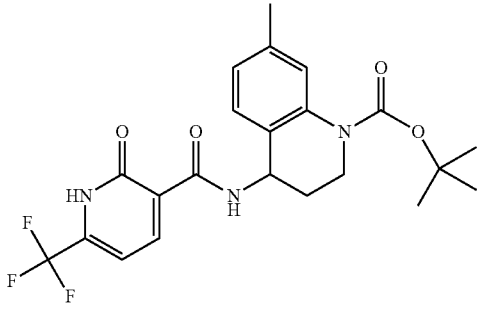 [SMILES: Cc1ccc2c(c1)N(C(=O)OC(C)(C)C)CCC2NC(=O)c1ccc(C(F)(F)F)[nH]c1=O]
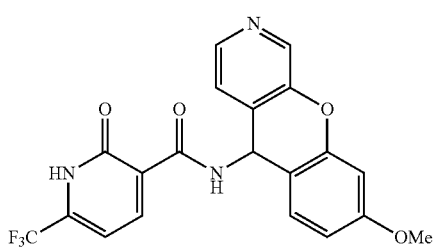
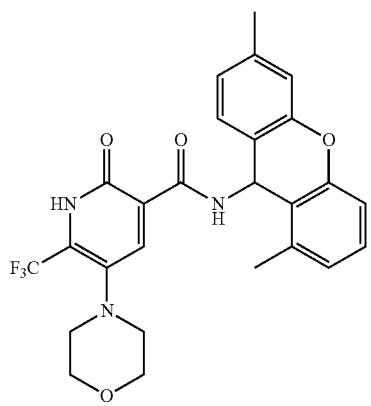 [SMILES: Cc1ccc2c(c1)Oc1cccc(C)c1C2NC(=O)c1cc(N2CCOCC2)c(C(F)(F)F)[nH]c1=O]
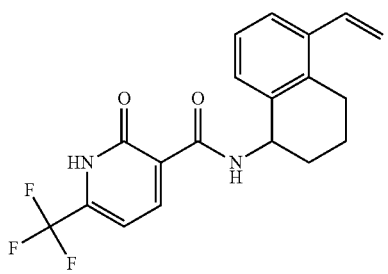 [SMILES: C=Cc1cccc2c1CCCC2NC(=O)c1ccc(C(F)(F)F)[nH]c1=O]
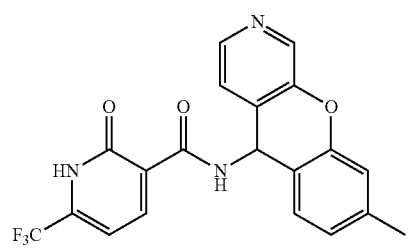 [SMILES: Cc1ccc2c(c1)Oc1cnccc1C2NC(=O)c1ccc(C(F)(F)F)[nH]c1=O]

TABLE 2-continued
Exemplary compounds according to the disclosure
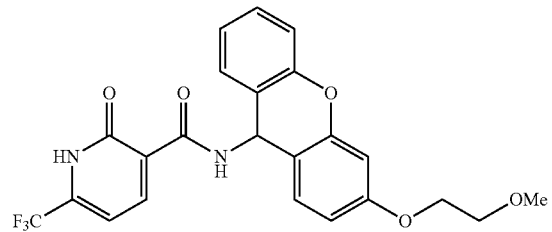 [SMILES: COCCOc1ccc2c(c1)Oc1ccccc1C2NC(=O)c1ccc(C(F)(F)F)[nH]c1=O]
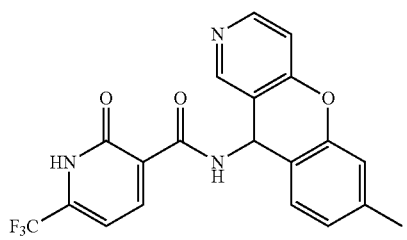
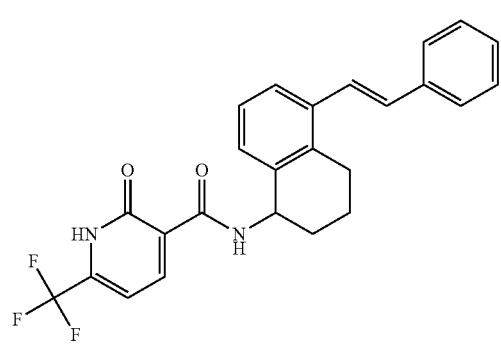 [SMILES: O=C(NC1CCCc2c(/C=C/c3ccccc3)cccc21)c1ccc(C(F)(F)F)[nH]c1=O]
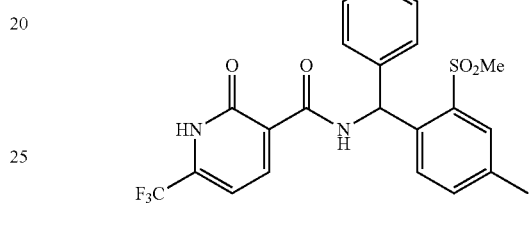
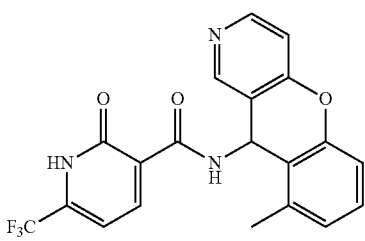
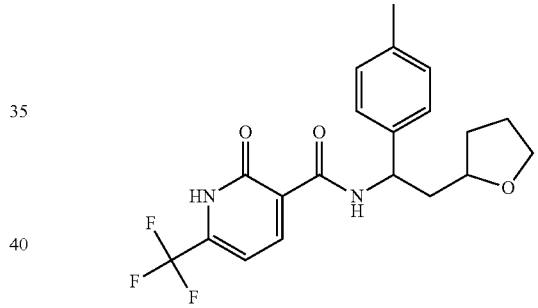
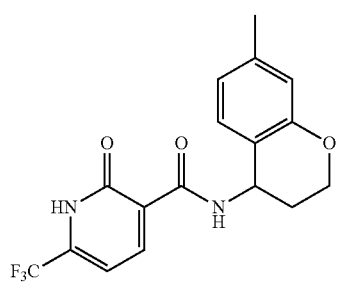
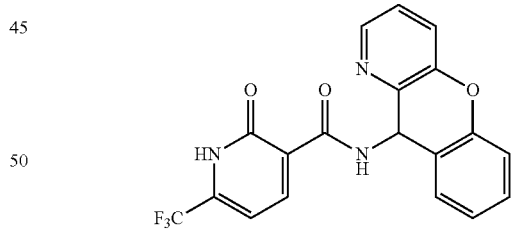
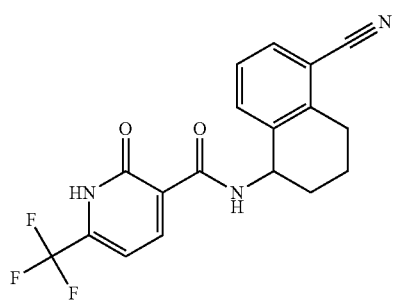 [SMILES: N#Cc1cccc2c1CCCC2NC(=O)c1ccc(C(F)(F)F)[nH]c1=O]
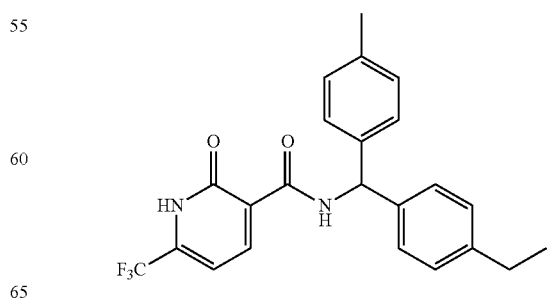

TABLE 2-continued
Exemplary compounds according to the disclosure
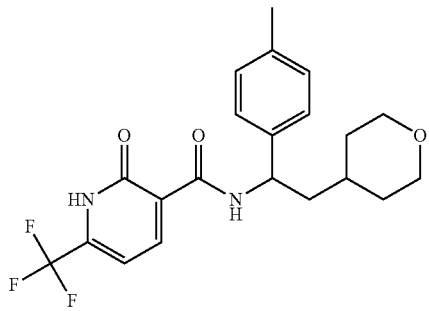 [SMILES: Cc1ccc(C(CC2CCOCC2)NC(=O)c2ccc(C(F)(F)F)[nH]c2=O)cc1]
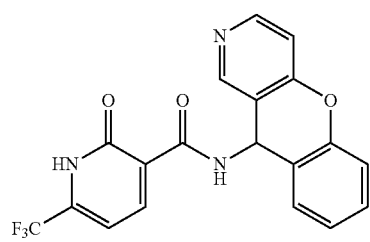
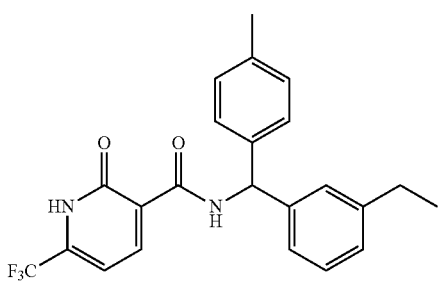
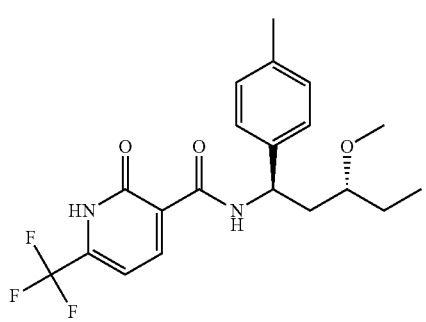 [SMILES: CC[C@H](C[C@@H](NC(=O)c1ccc(C(F)(F)F)[nH]c1=O)c1ccc(C)cc1)OC]
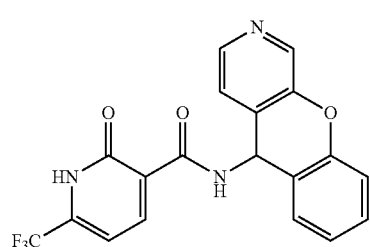
TABLE 2-continued
Exemplary compounds according to the disclosure
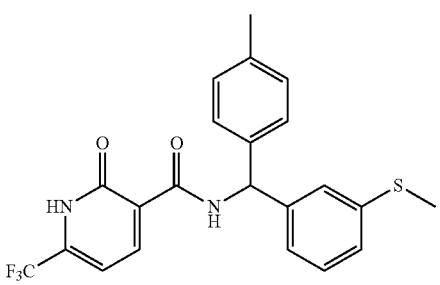
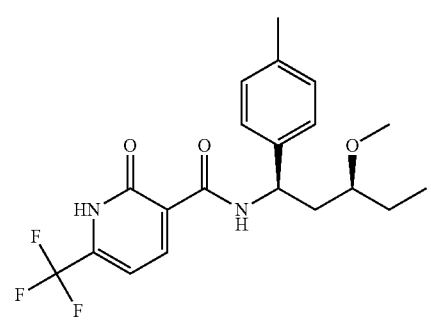 [SMILES: CC[C@@H](C[C@@H](NC(=O)c1ccc(C(F)(F)F)[nH]c1=O)c1ccc(C)cc1)OC]
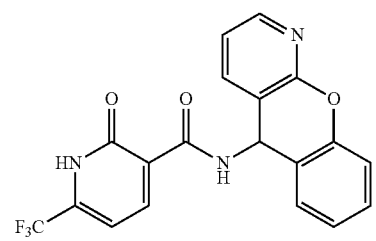
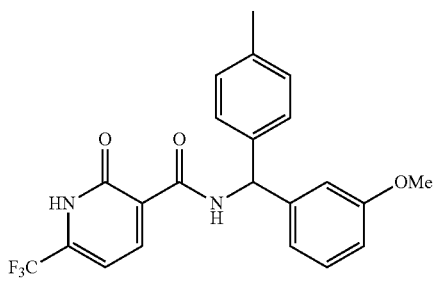
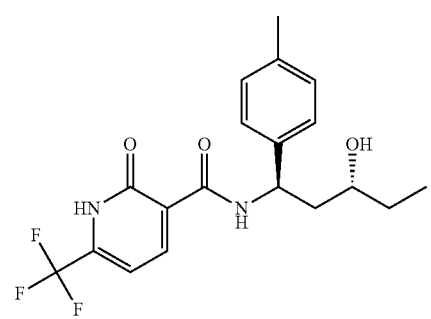 [SMILES: CC[C@@H](O)C[C@@H](NC(=O)c1ccc(C(F)(F)F)[nH]c1=O)c1ccc(C)cc1]

TABLE 2-continued
Exemplary compounds according to the disclosure
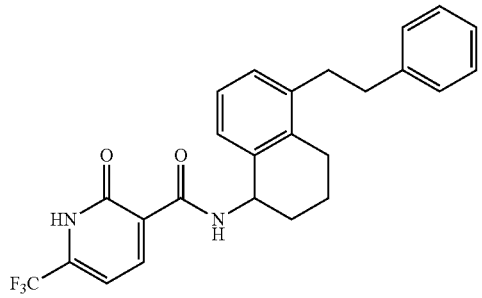 [SMILES: O=C(NC1CCCc2c(CCc3ccccc3)cccc21)c1ccc(C(F)(F)F)[nH]c1=O]
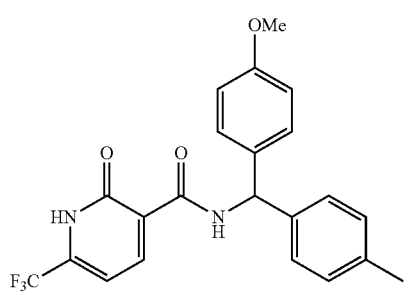
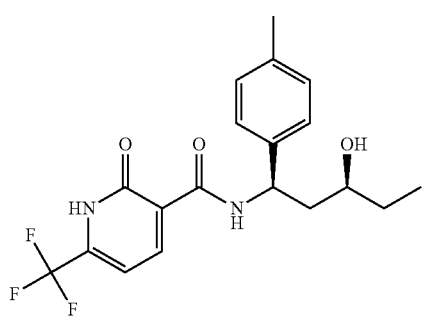
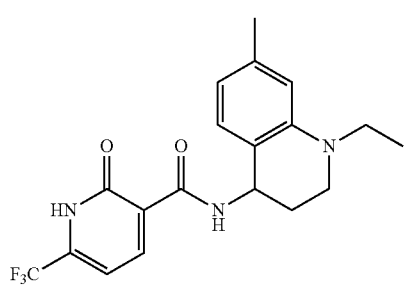
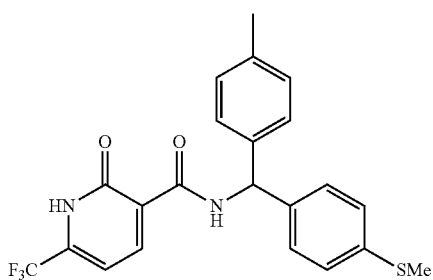 [SMILES: CSc1ccc(C(NC(=O)c2ccc(C(F)(F)F)[nH]c2=O)c2ccc(C)cc2)cc1]
TABLE 2-continued
Exemplary compounds according to the disclosure
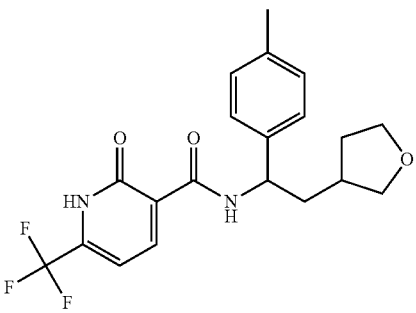 [SMILES: Cc1ccc(C(CC2CCOC2)NC(=O)c2ccc(C(F)(F)F)[nH]c2=O)cc1]
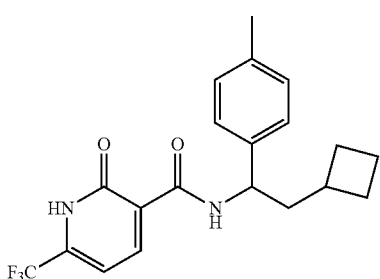
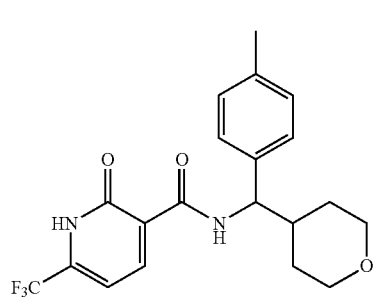
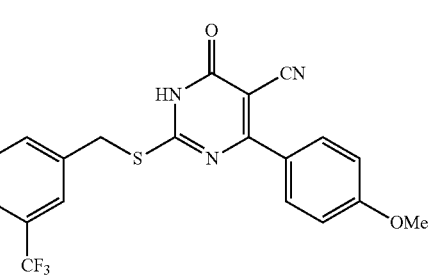
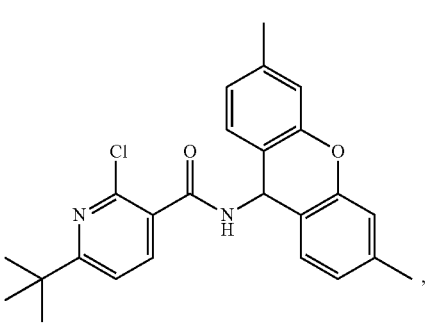 [SMILES: Cc1ccc2c(c1)Oc1cc(C)ccc1C2NC(=O)c1ccc(C(C)(C)C)nc1Cl]

TABLE 2-continued

Exemplary compounds according to the disclosure

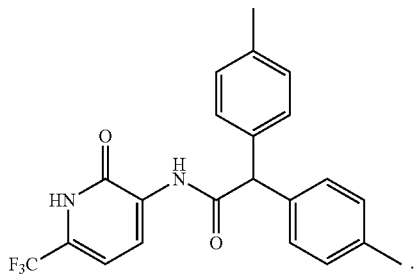 [SMILES: Cc1ccc(C(C(=O)Nc2ccc(C(F)(F)F)[nH]c2=O)c2ccc(C)cc2)cc1]

The present disclosure also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid salts of basic residues such as amines); alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety according to conventional chemical methods. Generally, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile (ACN) can be used.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Berge, S M et al, Journal of Pharmaceutical Science, 1977, 66, 1, 1-19. By way of an example, in an embodiment of the disclosure pharmaceutically acceptable salts can comprise a suitable anion selected from $F^-$, $Cl^-$, $Br^-$, $I^-$, $OR^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (where e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, arsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, oxalate, palmitate, pamoate, pantothenate, polygalacturonate, propionate, salicylate, stearate, subacetate, succinate, tartrate, teoclate, tosylate, or triethiodide. By way of another example, in an embodiment of the disclosure pharmaceutically acceptable salts can comprise a suitable cation selected from aluminum, arginine, benzathine, calcium, chloroprocaine, choline, diethanolamine, ethanolamine, ethylenediamine, lysine, magnesium, histidine, lithium, meglumine, potassium, procaine, sodium, triethylamine, or zinc. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutical Compositions and Dosage Forms

The present disclosure also provides pharmaceutical compositions comprising the compounds described herein. When employed as pharmaceuticals, the compounds of the disclosure can be administered in the form of pharmaceutical compositions which is a combination of the compounds of the disclosure and a pharmaceutically acceptable carrier. These compositions can be prepared in a manner well known in the pharmaceutical art and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. In some embodiments, the compounds are administered orally, topically, intranasally, intravenously, intramuscularly, or subcutaneously in therapeutically effective amounts to treat liver disease (e.g., liver diseases in which HSD17B13 plays a role).

Pharmaceutical compositions containing the compounds of the disclosure can be prepared in combination with one or more pharmaceutically acceptable carriers. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the disclosure can be in liquid form. Liquid forms include, by way of non-limiting example, emulsions, solutions, suspensions, syrups, slurries, dispersions, colloids and the like. In some embodiments, a pharmaceutical composition described herein can be in liquid, semi-solid or solid (e.g., powder) form. In specific embodiments, a pharmaceutical composition described herein can be in semi-solid form, e.g., a gel, a gel matrix, a cream, a paste, or the like. In some embodiments, semi-solid forms comprise a liquid vehicle. In some embodiments, the pharmaceutical composition of the disclosure can be a solid dosage form, such a tablet, a granule, a sachet, or a powder. Also provided are pharmaceutical compositions comprising a compound of the disclosure or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition can be in a unit dose formulation for oral, intranasal, intravenous, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and can be generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, a composition or unit dosage form described herein can be administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of a compound of formula (I) per day or per dose can be administered to an individual.

In some embodiments, the compound of the disclosure can be present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of compound administered daily or in a unit dose can be between about 0.5 mg and about 3 mg, between about 0.5 mg and about 4 mg, or between about 0.35 mg and about 4 mg. In other embodiments, the amount of the compound present in a unit dose or administered daily can be between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose can be administered to a patient.

In some embodiments, the compound can be present in a unit dose in an amount of between about 5 mg and about 500 mg. In some embodiments, the amount of the compound administered daily or in a unit dose can be between about 5 mg and about 300 mg. In other embodiments, the amount of the compound present in a unit dose or administered daily can be between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide rapid, sustained or delayed release of the active ingredient after administration to the patient by employing procedures known in the art.

For preparing solid compositions such as tablets, the principal active ingredient can be mixed with a pharmaceutical excipient to form a solid pre-formulation composition containing a homogeneous mixture of the compound according to the disclosure, e.g., the compound of formula (I). When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the compound according to the disclosure, e.g., the compound of formula (I), can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. In some embodiments, the compositions are administered by the oral or nasal respiratory route for local or systemic effect. Compositions in can be nebulized by use of inert gases. Nebulized solutions can be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques or can be sterile filtered. Aqueous solutions can be packaged for use as is, or lyophilized, the lyophilized preparation being combined with a sterile aqueous carrier prior to administration. The pH of the compound preparations typically will be between 3 and 11, or from 5 to 9. It will be understood that use of certain of the foregoing excipients, carriers, or stabilizers will result in the formation of pharmaceutical salts.

The therapeutic dosage of the compounds of the disclosure can vary according to, for example, the particular use for which the treatment is made, the manner of administration of the compound, the health and condition of the patient, and the judgment of the prescribing physician. The proportion or concentration of the compounds of the disclosure in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment of liver disease (e.g., liver diseases where HSD17B13 plays a role), which include one or more containers containing a pharmaceutical composition comprising a therapeutically effective amount of the compounds of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the disclosure, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Use

In another aspect, the present disclosure provides a method of modulating a HSD17B13 protein in a cell comprising administering an effective amount of a compound according to formula (I'):

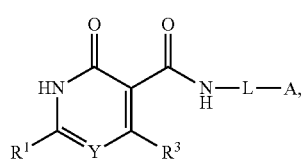

or a pharmaceutically acceptable salt thereof, wherein:
A is A', A", $CR^4(Ar)_2$, or Ar;
wherein:
A' is

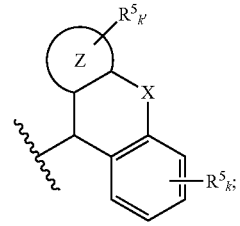

A" is

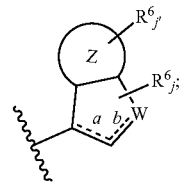

Z is phenyl, Het, or a $C_4$-$C_8$ cycloalkyl; and
Ar is independently at each occurrence a phenyl, naphthyl, or a $C_4$-$C_8$ cycloalkyl, any of which is optionally substituted with one or more $R^8$ or Het;
Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;
L is a bond, —(CH$_2$)$_n$—, —(CHB)$_n$—, —CH$_2$CHB—, or —CHBCH$_2$—;
B is benzyl or $C_{1-12}$ alkyl optionally comprising 1-4 O atoms, either of which is optionally substituted by —OH or —OCH$_3$;
n is 1 or 2;
k and k' are independently from 0 to 4;
j and j' are independently from 0 to 4;
W is =CH—, =C(R$^6$)—, —CH$_2$—, —CH(R$^6$)—, —(C=O)—, —CH$_2$CH$_2$—, —CH(R$^6$)—CH$_2$—, —O—, —O—CH$_2$—, —O—CH(R$^6$)—, —(NH)—, —N(R$^6$)—, —CH$_2$—NH—, —CH$_2$—N(R$^6$)—, or —S—;
a and b are independently a single bond or a double bond;
X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;
Y is N, —CR$^2$, or —COR$^2$;
$R^1$ is H, —(CH$_2$)$_{0-3}$—NH$_2$, —(CH$_2$)$_{0-3}$—NHR$^\#$, —(CH$_2$)$_{0-3}$—N(R$^\#$)$_2$, $C_{1-4}$ alkyl, $C_{1-4}$ haloalkyl, phenyl, benzyl, or —(CH$_2$)$_{0-3}$—X—(CH$_2$)$_{0-3}$-phenyl, wherein phenyl is optionally substituted with one or more $R^5$ groups;
$R^2$ is H, halogen, —(CH$_2$)$_{0-3}$—NH$_2$, —(CH$_2$)$_{0-3}$—NHR$^\#$, —(CH$_2$)$_{0-3}$—N(R$^\#$)$_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(C=O)O—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

$R^6$ is independently at each occurrence halogen, —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with R*;

$R^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;

$R^8$ is independently at each occurrence halogen, —CN, =O, —OH, —(CH$_2$)$_{0-3}$—SH, —(CH$_2$)$_{0-3}$—SR*, —(SO$_2$)—R*, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, $C_{3-6}$ cycloalkyl, phenyl, or benzyl, any of which is optionally substituted with a halogen.

In another aspect, the present disclosure provides a method of modulating a HSD17B13 protein in a cell comprising administering an effective amount of a compound according to formula (I):

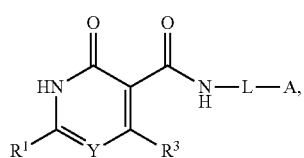

(I)

or a pharmaceutically acceptable salt thereof, wherein:

A is A', A", CR$^4$(Ar)$_2$, or a phenyl that is optionally substituted with one or more R$^7$; wherein:

A' is

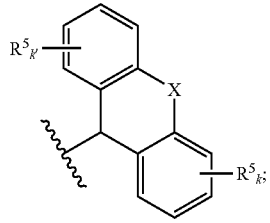

A" is

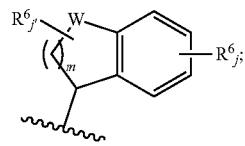

and

Ar is independently at each occurrence a phenyl that is optionally substituted with one or more R$^8$ or Het, where Het is a 6-membered heterocycle comprising from 1 to 3 nitrogen atoms, wherein Het is optionally substituted with one or more of halogen, —OH or =O;

L is a bond, —(CH$_2$)$_n$—, —(CHB)$_n$—, —CH$_2$CHB—, or —CHBCH$_2$—;

wherein:

B is $C_{1-12}$ alkyl or benzyl; and n is 1 or 2;

m is 1 or 2;

k and k' are independently from 0 to 4;

j and j' are independently from 0 to 4;

W is —CH$_2$—, —O—, —(NH)—, or —S—;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$, $R^6$, $R^7$, and $R^8$ are each optional and independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$, $R^6$, $R^7$, or $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, phenyl, or benzyl, any of which is optionally substituted with a halogen.

In other embodiments, compounds suitable for the methods of the present disclosure include those of all the formulas as described in the Compounds of the Disclosure section above, e.g., I' through VIII.

Exemplary compounds suitable for the methods of the present disclosure are described in Table 3. To the extent there is a conflict between a compound structure and a compound name, the compound structure controls.

TABLE 3

Exemplary compounds suitable for the methods of the disclosure

| Compound Ref. No: | Compound Structure | Compound name-generated by ChemBioDraw 14.0 |
|---|---|---|
| 1 | 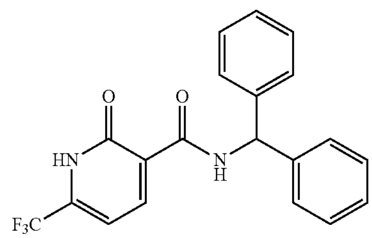 | N-benzhydryl-2-oxo-6-(trifluoromethyl)-1,2-dihydropyridine-3-carboxamide |
| 1A | 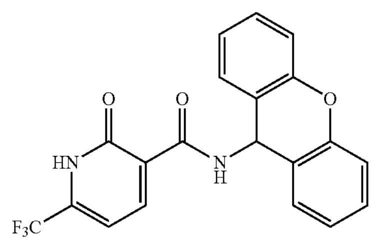 | 2-oxo-6-(trifluoromethyl)-N-(9H-xanthen-9-yl)-1,2-dihydropyridine-3-carboxamide |
| 2 | 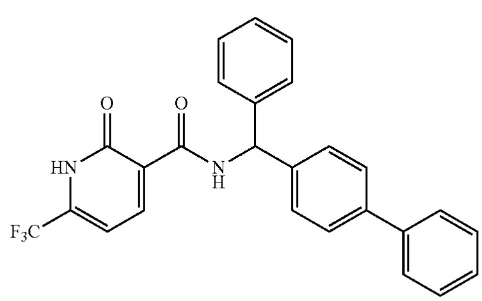 [SMILES: O=C(NC(c1ccccc1)c1ccc(-c2ccccc2)cc1)c1ccc(C(F)(F)F)[nH]c1=O] | N-([1,1'-biphenyl]-4-yl(phenyl)methyl)-2-oxo-6-(trifluoromethyl)-1,2-dihydropyridine-3-carboxamide |
| 2A | 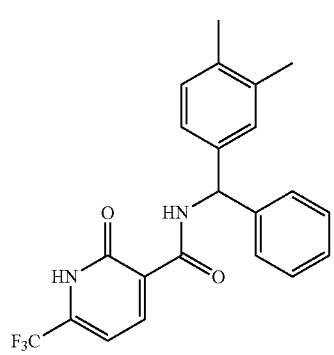 [SMILES: Cc1ccc(C(NC(=O)c2ccc(C(F)(F)F)[nH]c2=O)c2ccccc2)cc1C] | N-((3,4-dimethylphenyl)(phenyl)methyl)-2-oxo-6-(trifluoromethyl)-1,2-dihydropyridine-3-carboxamide* |

TABLE 3-continued

Exemplary compounds suitable for the methods of the disclosure

| Compound Ref. No: | Compound Structure | Compound name- generated by ChemBioDraw 14.0 |
|---|---|---|
| 3 | 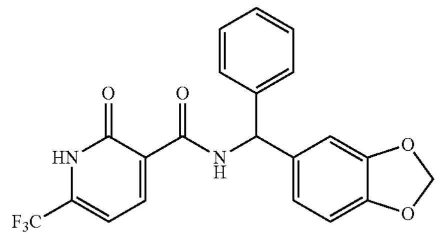 [SMILES: O=C(NC(c1ccccc1)c1ccc2c(c1)OCO2)c1ccc(C(F)(F)F)[nH]c1=O] | N-(benzo[d][1,3]dioxol-5-yl(phenyl)methyl)-2-oxo-6-(trifluoromethyl)-1,2-dihydropyridine-3-carboxamide |
| 3A | 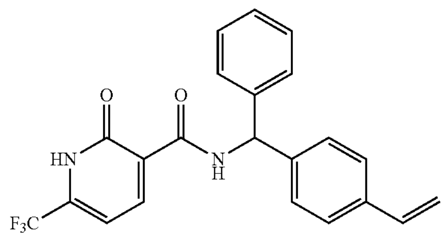 [SMILES: C=Cc1ccc(C(NC(=O)c2ccc(C(F)(F)F)[nH]c2=O)c2ccccc2)cc1] | N-(phenyl(4-vinylphenyl)methyl)-2-oxo-6-(trifluoromethyl)-1,2-dihydropyridine-3-carboxamide |
| 4 | 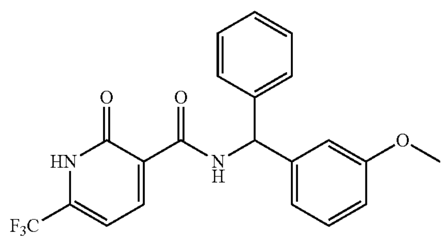 [SMILES: COc1cccc(C(NC(=O)c2ccc(C(F)(F)F)[nH]c2=O)c2ccccc2)c1] | N-((3-methoxyphenyl)(phenyl)methyl)-2-oxo-6-(trifluoromethyl)-1,2-dihydropyridine-3-carboxamide |
| 4A | 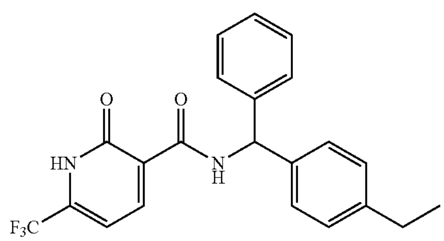 [SMILES: CCc1ccc(C(NC(=O)c2ccc(C(F)(F)F)[nH]c2=O)c2ccccc2)cc1] | N-((4-ethylphenyl)(phenyl)methyl)-2-oxo-6-(trifluoromethyl)-1,2-dihydropyridine-3-carboxamide |
| 5 | 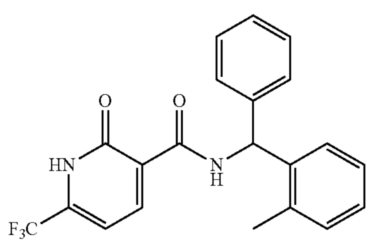 | N-(phenyl(o-tolyl)methyl)-2-oxo-6-(trifluoromethyl)-1,2-dihydropyridine-3-carboxamide |
| 5A | 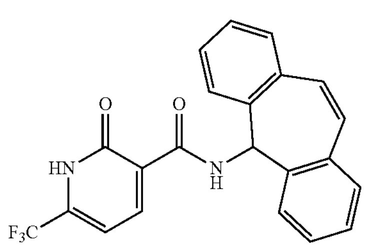 [SMILES: O=C(NC1c2ccccc2C=Cc2ccccc21)c1ccc(C(F)(F)F)[nH]c1=O] | N-(5H-dibenzo[a,d][7]annulen-5-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 6 | 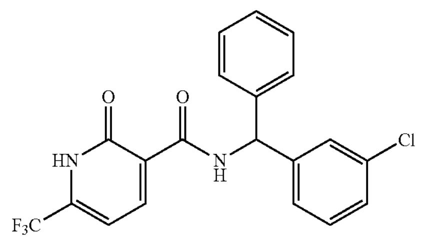 [SMILES: O=C(NC(c1ccccc1)c1cccc(Cl)c1)c1ccc(C(F)(F)F)[nH]c1=O] | N-((3-chlorophenyl)(phenyl)methyl)-2-oxo-6-(trifluoromethyl)-1,2-dihydropyridine-3-carboxamide |
| 6A | 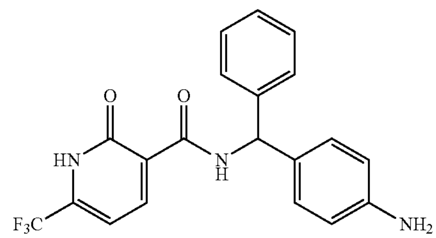 [SMILES: Nc1ccc(C(NC(=O)c2ccc(C(F)(F)F)[nH]c2=O)c2ccccc2)cc1] | N-((4-aminophenyl)(phenyl)methyl)-2-oxo-6-(trifluoromethyl)-1,2-dihydropyridine-3-carboxamide |
| 7 | 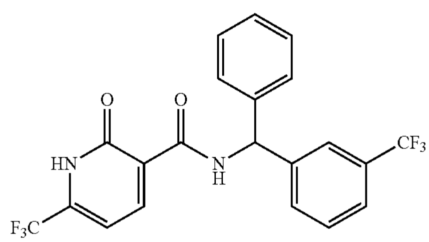 [SMILES: O=C(NC(c1ccccc1)c1cccc(C(F)(F)F)c1)c1ccc(C(F)(F)F)[nH]c1=O] | 2-oxo-N-(phenyl(3-(trifluoromethyl)phenyl)methyl)-6-(trifluoromethyl)-1,2-dihydropyridine-3-carboxamide |
| 7A | 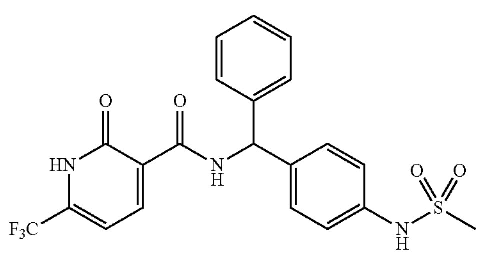 [SMILES: CS(=O)(=O)Nc1ccc(C(NC(=O)c2ccc(C(F)(F)F)[nH]c2=O)c2ccccc2)cc1] | N-((4-(methylsulfonamido)phenyl)(phenyl)methyl)-2-oxo-6-(trifluoromethyl)-1,2-dihydropyridine-3-carboxamide |
| 8 | 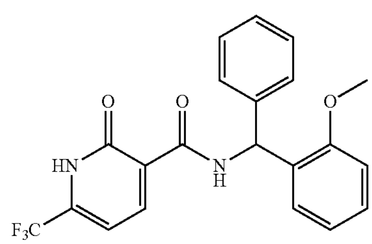 [SMILES: COc1ccccc1C(NC(=O)c1ccc(C(F)(F)F)[nH]c1=O)c1ccccc1] | N-((2-methoxyphenyl)(phenyl)methyl)-2-oxo-6-(trifluoromethyl)-1,2-dihydropyridine-3-carboxamide |
| 8A | 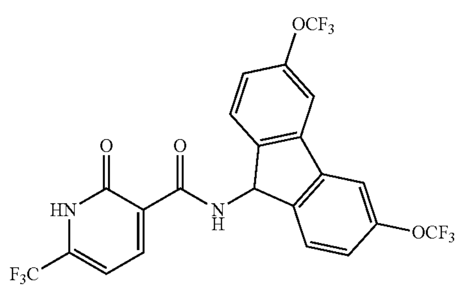 [SMILES: O=C(NC1c2ccc(OC(F)(F)F)cc2-c2cc(OC(F)(F)F)ccc21)c1ccc(C(F)(F)F)[nH]c1=O] | N-(3,6-bis(trifluoromethoxy)-9H-fluoren-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 9 | 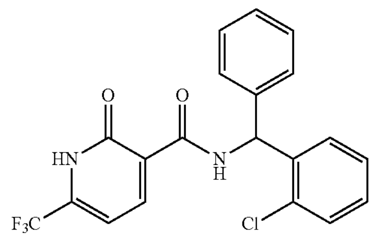 | N-((2-chlorophenyl)(phenyl)methyl)-2-oxo-6-(trifluoromethyl)-1,2-dihydropyridine-3-carboxamide |
| 9A | 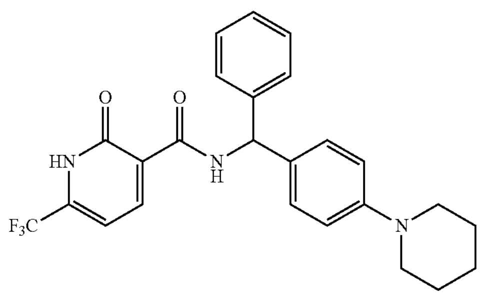 | 2-oxo-N-(phenyl(4-(piperidin-1-yl)phenyl)methyl)-6-(trifluoromethyl)-1,2-dihydropyridine-3-carboxamide |
| 10 | 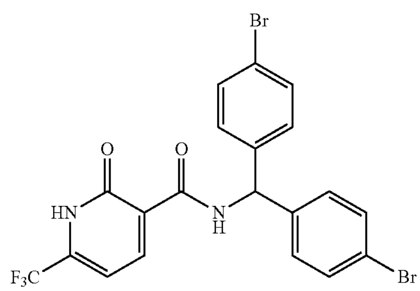 | N-(bis(4-bromophenyl)methyl)-2-oxo-6-(trifluoromethyl)-1,2-dihydropyridine-3-carboxamide |
| 10A | 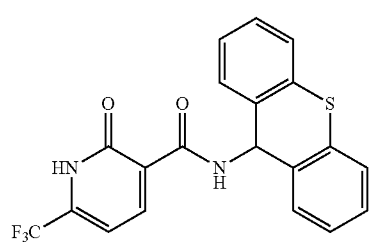 | 2-oxo-N-(9H-thioxanthen-9-yl)-6-(trifluoromethyl)-1,2-dihydropyridine-3-carboxamide |
| 11 | 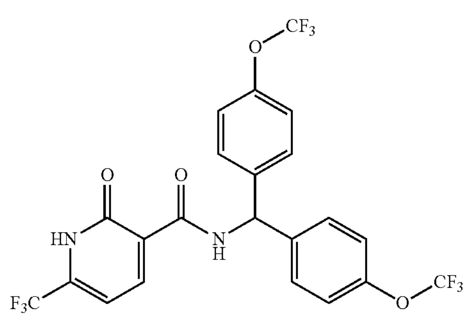 [SMILES: O=C(NC(c1ccc(OC(F)(F)F)cc1)c1ccc(OC(F)(F)F)cc1)c1ccc(C(F)(F)F)[nH]c1=O] | N-(bis(4-(trifluoromethoxy)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 11A | 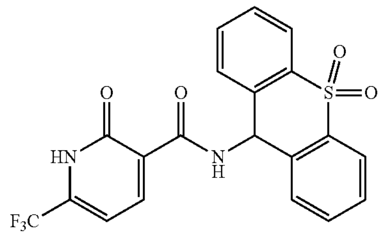 [SMILES: O=C(NC1c2ccccc2S(=O)(=O)c2ccccc21)c1ccc(C(F)(F)F)[nH]c1=O] | N-(10,10-dioxido-9H-thioxanthen-9-yl)-2-oxo-6-(trifluoromethyl)-1,2-dihydropyridine-3-carboxamide |
| 12 | 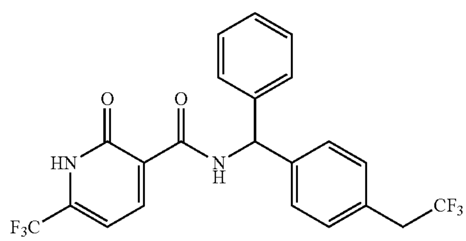 [SMILES: O=C(NC(c1ccccc1)c1ccc(CC(F)(F)F)cc1)c1ccc(C(F)(F)F)[nH]c1=O] | 2-oxo-N-(phenyl(4-(2,2,2-trifluoroethyl)phenyl)methyl)-6-(trifluoromethyl)-1,2-dihydropyridine-3-carboxamide |
| 12A | 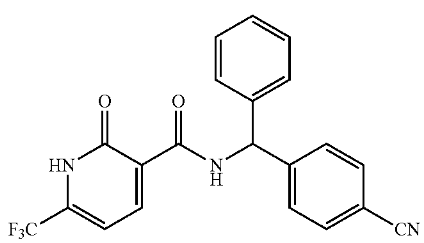 | N-((4-cyanophenyl)(phenyl)methyl)-2-oxo-6-(trifluoromethyl)-1,2-dihydropyridine-3-carboxamide |
| 13 | 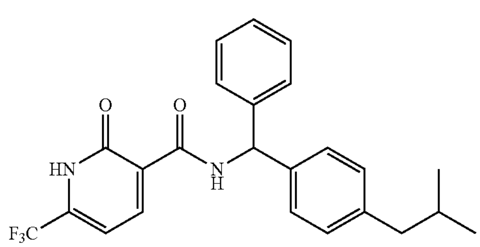 [SMILES: CC(C)Cc1ccc(C(NC(=O)c2ccc(C(F)(F)F)[nH]c2=O)c2ccccc2)cc1] | N-((4-isobutylphenyl)(phenyl)methyl)-2-oxo-6-(trifluoromethyl)-1,2-dihydropyridine-3-carboxamide |
| 13A | 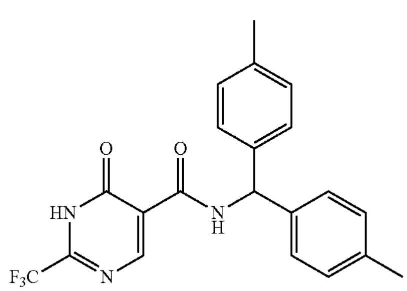 | N-(di-p-tolylmethyl)-6-oxo-2-(trifluoromethyl)-1,6-dihydropyrimidine-5-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 14 | 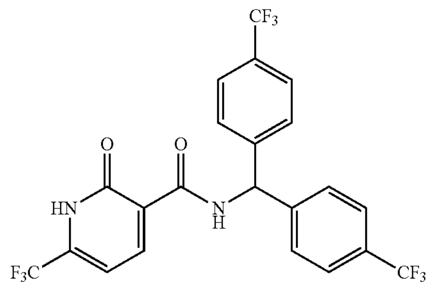 [SMILES: O=C(NC(c1ccc(C(F)(F)F)cc1)c1ccc(C(F)(F)F)cc1)c1ccc(C(F)(F)F)[nH]c1=O] | N-(bis(4-(trifluoromethyl)phenyl)methyl)-2-oxo-6-(trifluoromethyl)-1,2-dihydropyridine-3-carboxamide |
| 14A | 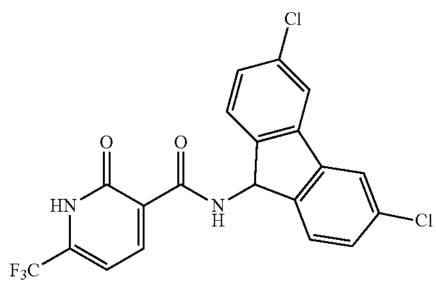 [SMILES: O=C(NC1c2ccc(Cl)cc2-c2cc(Cl)ccc21)c1ccc(C(F)(F)F)[nH]c1=O] | N-(3,6-dichloro-9H-fluoren-9-yl)-2-oxo-6-(trifluoromethyl)-1,2-dihydropyridine-3-carboxamide |
| 15 | 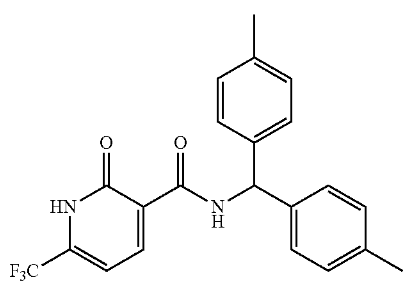 [SMILES: Cc1ccc(C(NC(=O)c2ccc(C(F)(F)F)[nH]c2=O)c2ccc(C)cc2)cc1] | N-(di-p-tolylmethyl)-2-oxo-6-(trifluoromethyl)-1,2-dihydropyridine-3-carboxamide |
| 15A | 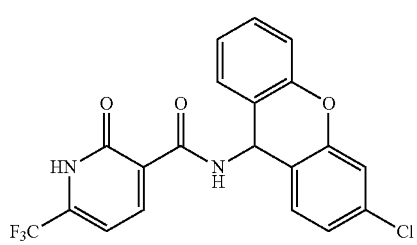 [SMILES: O=C(NC1c2ccccc2Oc2cc(Cl)ccc21)c1ccc(C(F)(F)F)[nH]c1=O] | N-(3-chloro-9H-xanthen-9-yl)-2-oxo-6-(trifluoromethyl)-1,2-dihydropyridine-3-carboxamide |
| 16 | 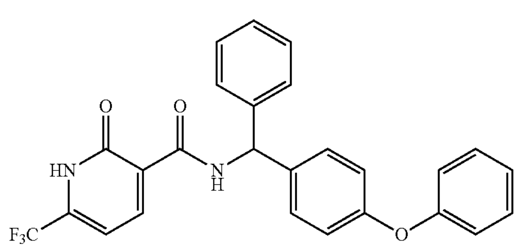 [SMILES: O=C(NC(c1ccccc1)c1ccc(Oc2ccccc2)cc1)c1ccc(C(F)(F)F)[nH]c1=O] | N-((4-phenoxyphenyl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 16A | 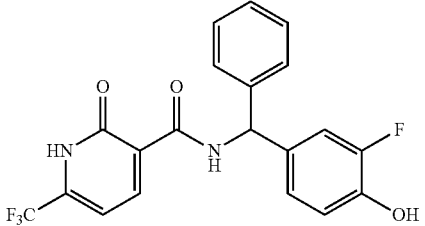 | N-((3-fluoro-4-hydroxyphenyl)(phenyl)methyl)-2-oxo-6-(trifluoromethyl)-1,2-dihydropyridine-3-carboxamide |
| 17 | 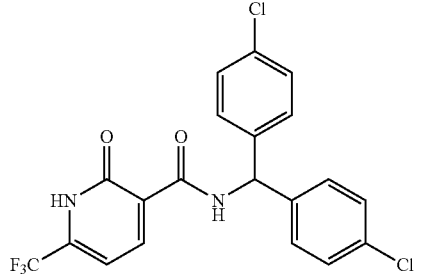 [SMILES: O=C(NC(c1ccc(Cl)cc1)c1ccc(Cl)cc1)c1ccc(C(F)(F)F)[nH]c1=O] | N-(bis(4-chlorophenyl)methyl)-2-oxo-6-(trifluoromethyl)-1,2-dihydropyridine-3-carboxamide |
| 17A | 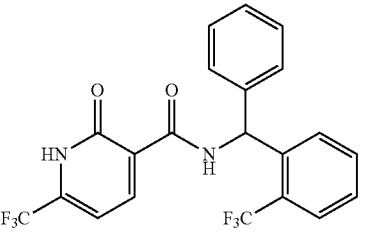 | N-(phenyl(2-(trifluoromethyl)phenyl)methyl)-2-oxo-6-(trifluoromethyl)-1,2-dihydropyridine-3-carboxamide |
| 18 | 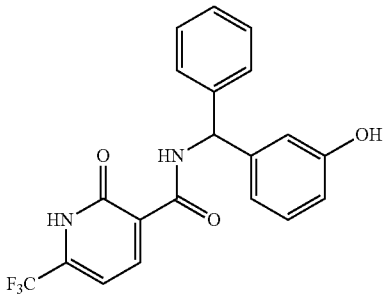 [SMILES: O=C(NC(c1ccccc1)c1cccc(O)c1)c1ccc(C(F)(F)F)[nH]c1=O] | N-((3-hydroxyphenyl)(phenyl)methyl)-2-oxo-6-(trifluoromethyl)-1,2-dihydropyridine-3-carboxamide |
| 18A | 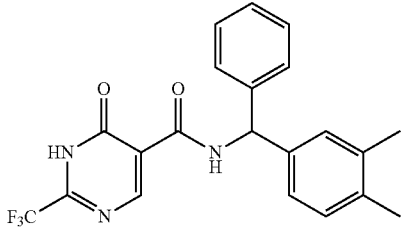 | N-((3,4-dimethylphenyl)(phenyl)methyl)-6-oxo-2-(trifluoromethyl)-1,6-dihydropyrimidine-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 19 | 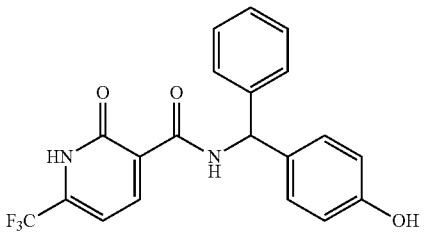 | N-((4-hydroxyphenyl)(phenyl)methyl)-2-oxo-6-(trifluoromethyl)-1,2-dihydropyridine-3-carboxamide |
| 19A | 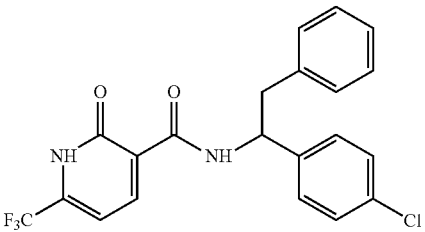 [SMILES: O=C(NC(Cc1ccccc1)c1ccc(Cl)cc1)c1ccc(C(F)(F)F)[nH]c1=O] | N-(1-(4-chlorophenyl)-2-phenylethyl)-2-oxo-6-(trifluoromethyl)-1,2-dihydropyridine-3-carboxamide |
| 20 | 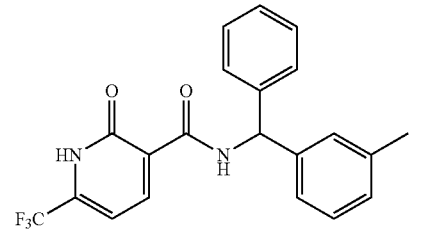 [SMILES: Cc1cccc(C(NC(=O)c2ccc(C(F)(F)F)[nH]c2=O)c2ccccc2)c1] | N-(phenyl(m-tolyl)methyl)-2-oxo-6-(trifluoromethyl)-1,2-dihydropyridine-3-carboxamide |
| 20A | 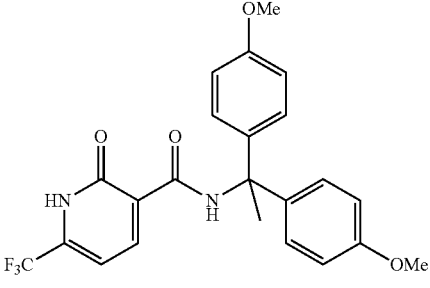 [SMILES: COc1ccc(C(C)(NC(=O)c2ccc(C(F)(F)F)[nH]c2=O)c2ccc(OC)cc2)cc1] | N-(1,1-bis(4-methoxyphenyl)ethyl)-2-oxo-6-(trifluoromethyl)-1,2-dihydropyridine-3-carboxamide |
| 21 | 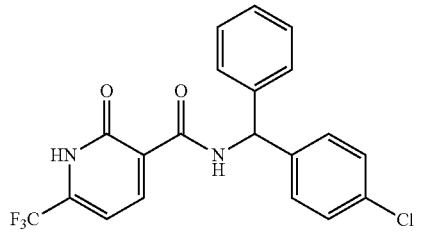 | N-((4-chlorophenyl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 21A | 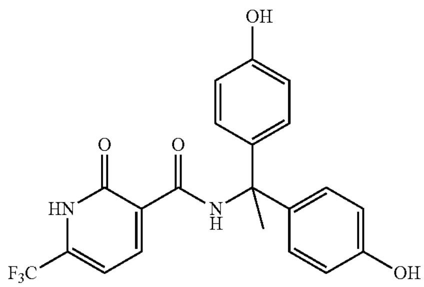 [SMILES: CC(NC(=O)c1ccc(C(F)(F)F)[nH]c1=O)(c1ccc(O)cc1)c1ccc(O)cc1] | N-(1,1-bis(4-hydroxyphenyl)ethyl)-2-oxo-6-(trifluoromethyl)-1,2-dihydropyridine-3-carboxamide |
| 22 | 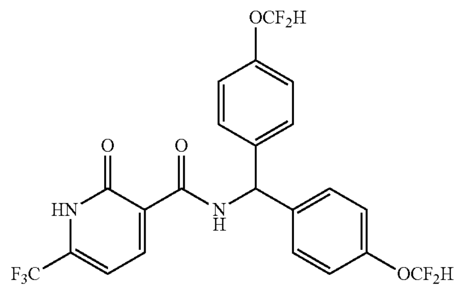 | N-(bis(4-(difluoromethoxy)phenyl)methyl)-2-oxo-6-(trifluoromethyl)-1,2-dihydropyridine-3-carboxamide |
| 22A | 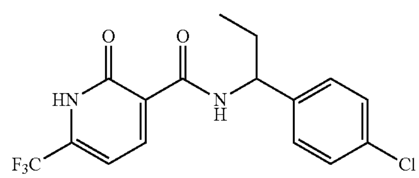 [SMILES: CCC(NC(=O)c1ccc(C(F)(F)F)[nH]c1=O)c1ccc(Cl)cc1] | N-(1-(4-chlorophenyl)propyl)-2-oxo-6-(trifluoromethyl)-1,2-dihydropyridine-3-carboxamide* |
| 23 | 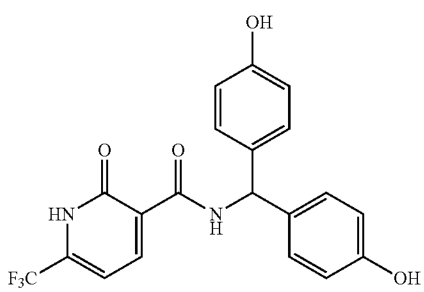 [SMILES: O=C(NC(c1ccc(O)cc1)c1ccc(O)cc1)c1ccc(C(F)(F)F)[nH]c1=O] | N-(bis(4-hydroxyphenyl)methyl)-2-oxo-6-(trifluoromethyl)-1,2-dihydropyridine-3-carboxamide |
| 23A | 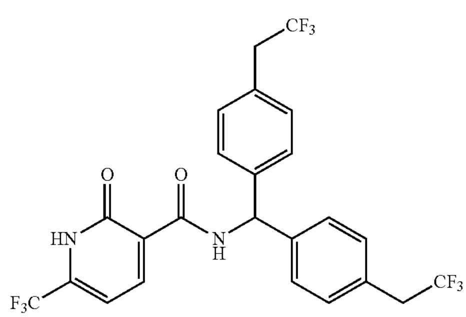 | N-(bis(4-(2,2,2-trifluoroethyl)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 24 | 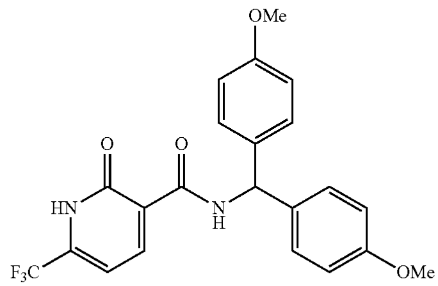 [SMILES: COc1ccc(C(NC(=O)c2ccc(C(F)(F)F)[nH]c2=O)c2ccc(OC)cc2)cc1] | N-(bis(4-methoxyphenyl)methyl)-2-oxo-6-(trifluoromethyl)-1,2-dihydropyridine-3-carboxamide |
| 25 | 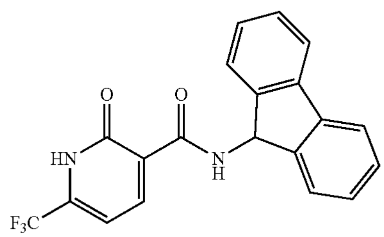 [SMILES: O=C(NC1c2ccccc2-c2ccccc21)c1ccc(C(F)(F)F)[nH]c1=O] | N-(9H-fluoren-9-yl)-2-oxo-6-(trifluoromethyl)-1,2-dihydropyridine-3-carboxamide |
| 26 | 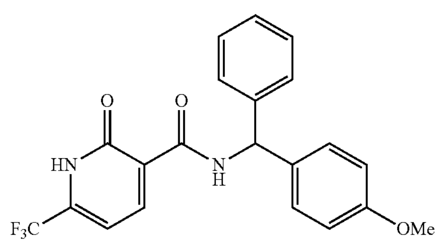 [SMILES: COc1ccc(C(NC(=O)c2ccc(C(F)(F)F)[nH]c2=O)c2ccccc2)cc1] | N-((4-methoxyphenyl)(phenyl)methyl)-2-oxo-6-(trifluoromethyl)-1,2-dihydropyridine-3-carboxamide |
| 27 | 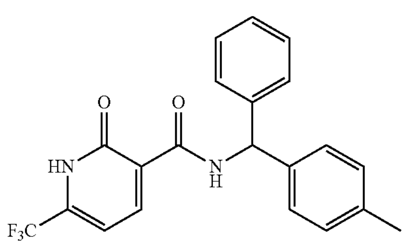 [SMILES: Cc1ccc(C(NC(=O)c2ccc(C(F)(F)F)[nH]c2=O)c2ccccc2)cc1] | N-(phenyl(p-tolyl)methyl)-2-oxo-6-(trifluoromethyl)-1,2-dihydropyridine-3-carboxamide |
| 28 | 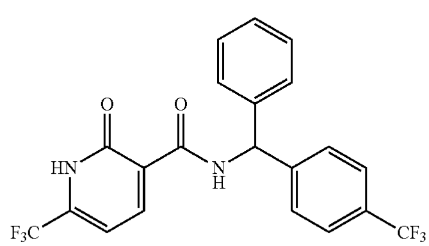 [SMILES: O=C(NC(c1ccccc1)c1ccc(C(F)(F)F)cc1)c1ccc(C(F)(F)F)[nH]c1=O] | N-(phenyl(4-(trifluoromethyl)phenyl)methyl)-2-oxo-6-(trifluoromethyl)-1,2-dihydropyridine-3-carboxamide |
| 29 | 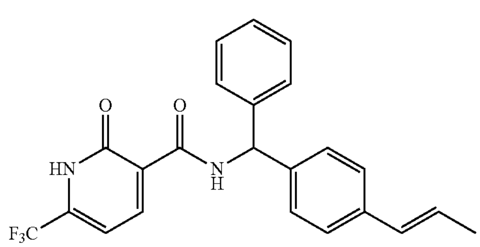 [SMILES: C/C=C/c1ccc(C(NC(=O)c2ccc(C(F)(F)F)[nH]c2=O)c2ccccc2)cc1] | (E)-2-oxo-N-(phenyl(4-(prop-1-en-1-yl)phenyl)methyl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 30 | 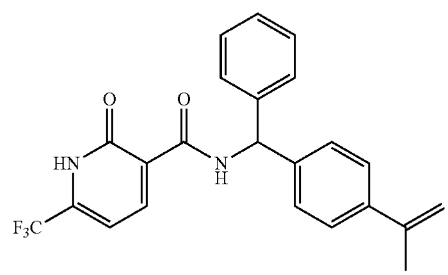 [SMILES: C=C(C)c1ccc(C(NC(=O)c2ccc(C(F)(F)F)[nH]c2=O)c2ccccc2)cc1] | 2-oxo-N-(phenyl(4-(prop-1-en-2-yl)phenyl)methyl)-6-(trifluoromethyl)-1,2-dihydropyridine-3-carboxamide |
| 31 | 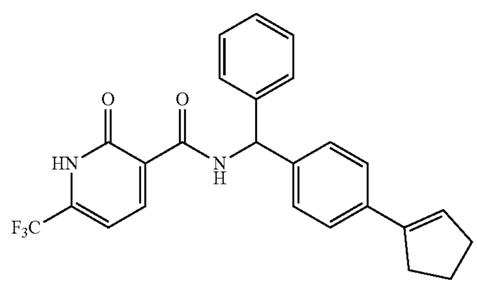 [SMILES: O=C(NC(c1ccccc1)c1ccc(C2=CCCC2)cc1)c1ccc(C(F)(F)F)[nH]c1=O] | N-((4-(cyclopent-1-en-1-yl)phenyl)(phenyl)methyl)-2-oxo-6-(trifluoromethyl)-1,2-dihydropyridine-3-carboxamide |
| 32 | 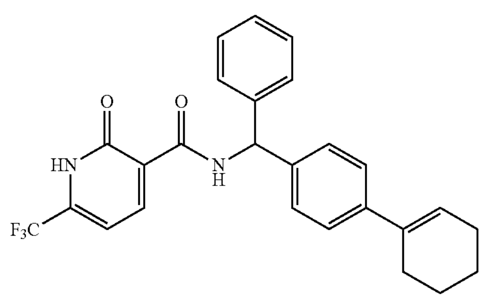 [SMILES: O=C(NC(c1ccccc1)c1ccc(C2=CCCCC2)cc1)c1ccc(C(F)(F)F)[nH]c1=O] | 2-oxo-N-(phenyl(2',3',4',5'-tetrahydro-[1,1'-biphenyl]-4-yl)methyl)-6-(trifluoromethyl)-1,2-dihydropyridine-3-carboxamide |
| 33 | 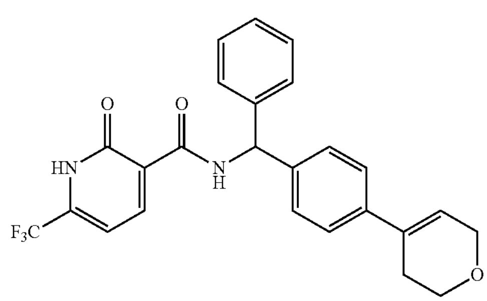 [SMILES: O=C(NC(c1ccccc1)c1ccc(C2=CCOCC2)cc1)c1ccc(C(F)(F)F)[nH]c1=O] | N-((4-(3,6-dihydro-2H-pyran-4-yl)phenyl)(phenyl)methyl)-2-oxo-6-(trifluoromethyl)-1,2-dihydropyridine-3-carboxamide |
| 34 | 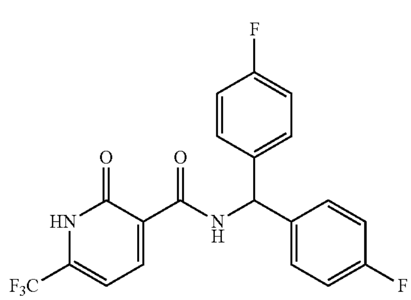 [SMILES: O=C(NC(c1ccc(F)cc1)c1ccc(F)cc1)c1ccc(C(F)(F)F)[nH]c1=O] | N-(bis(4-fluorophenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 35 | 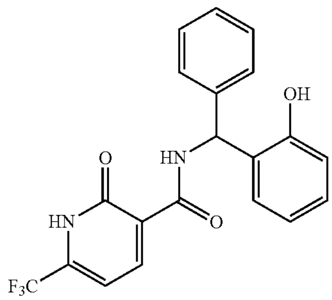 [SMILES: O=C(NC(c1ccccc1)c1ccccc1O)c1ccc(C(F)(F)F)[nH]c1=O] | N-((2-hydroxyphenyl)(phenyl)methyl)-2-oxo-6-(trifluoromethyl)-1,2-dihydropyridine-3-carboxamide |
| 36 | 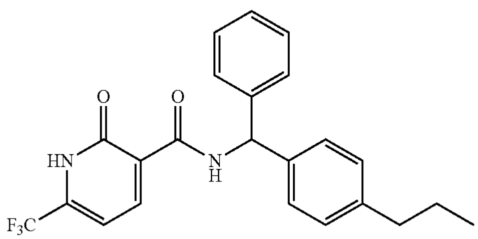 | 2-oxo-N-(phenyl(4-propylphenyl)methyl)-6-(trifluoromethyl)-1,2-dihydropyridine-3-carboxamide |
| 37 | 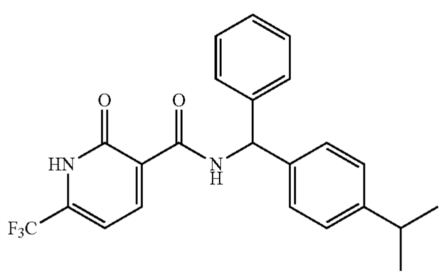 | N-((4-isopropylphenyl)(phenyl)methyl)-2-oxo-6-(trifluoromethyl)-1,2-dihydropyridine-3-carboxamide |
| 38 | 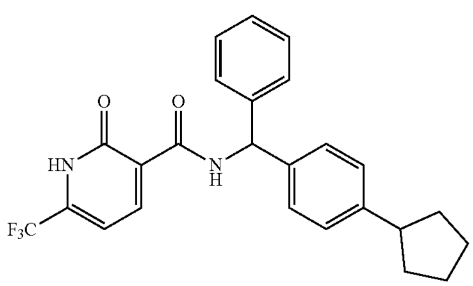 [SMILES: O=C(NC(c1ccccc1)c1ccc(C2CCCC2)cc1)c1ccc(C(F)(F)F)[nH]c1=O] | N-((4-cyclopentylphenyl)(phenyl)methyl)-2-oxo-6-(trifluoromethyl)-1,2-dihydropyridine-3-carboxamide |
| 39 | 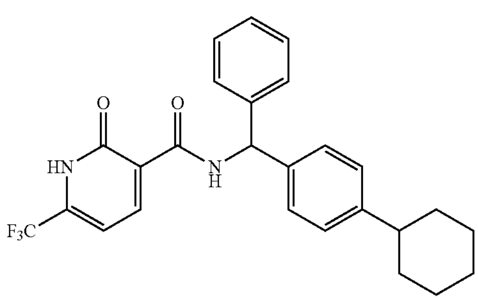 [SMILES: O=C(NC(c1ccccc1)c1ccc(C2CCCCC2)cc1)c1ccc(C(F)(F)F)[nH]c1=O] | N-((4-cyclohexylphenyl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 40 | 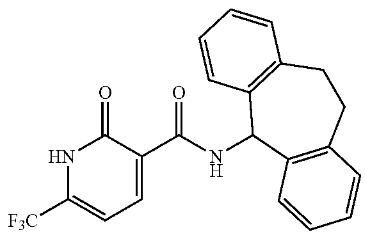 [SMILES: O=C(NC1c2ccccc2CCc2ccccc21)c1ccc(C(F)(F)F)[nH]c1=O] | N-(10,11-dihydro-5H-dibenzo[a,d][7]annulen-5-yl)-2-oxo-6-(trifluoromethyl)-1,2-dihydropyridine-3-carboxamide |
| 41 | 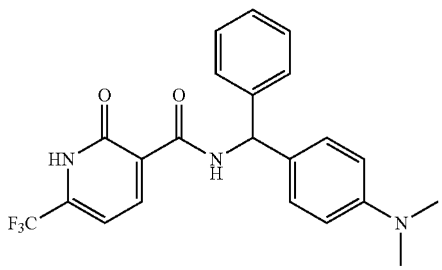 | N-((4-(dimethylamino)phenyl)(phenyl)methyl)-2-oxo-6-(trifluoromethyl)-1,2-dihydropyridine-3-carboxamide |
| 42 | 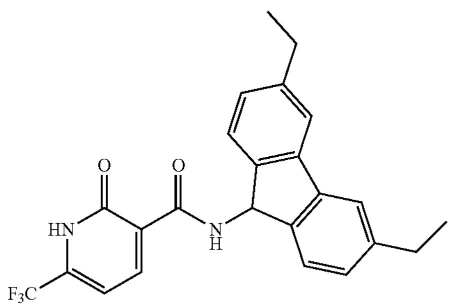 [SMILES: CCc1ccc2c(c1)-c1cc(CC)ccc1C2NC(=O)c1ccc(C(F)(F)F)[nH]c1=O] | N-(3,6-diethyl-9H-fluoren-9-yl)-2-oxo-6-(trifluoromethyl)-1,2-dihydropyridine-3-carboxamide |
| 43 | 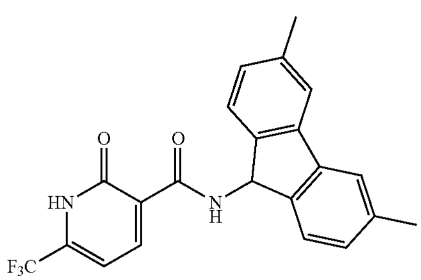 [SMILES: Cc1ccc2c(c1)-c1cc(C)ccc1C2NC(=O)c1ccc(C(F)(F)F)[nH]c1=O] | N-(3,6-dimethyl-9H-fluoren-9-yl)-2-oxo-6-(trifluoromethyl)-1,2-dihydropyridine-3-carboxamide |
| 44 | 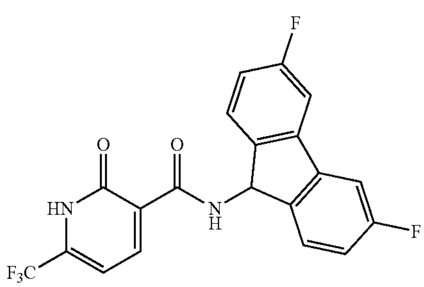 [SMILES: O=C(NC1c2ccc(F)cc2-c2cc(F)ccc21)c1ccc(C(F)(F)F)[nH]c1=O] | N-(3,6-difluoro-9H-fluoren-9-yl)-2-oxo-6-(trifluoromethyl)-1,2-dihydropyridine-3-carboxamide |

ND TABLE 3-continued

Exemplary compounds suitable for the methods of the disclosure

| Compound Ref. No: | Compound Structure | Compound name- generated by ChemBioDraw 14.0 |
|---|---|---|
| 45 | 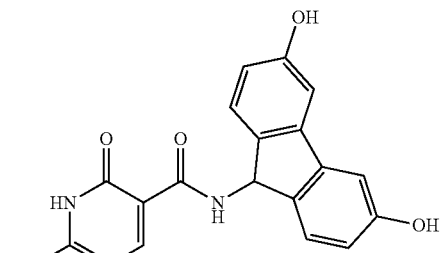 | N-(3,6-dihydroxy-9H-fluoren-9-yl)-2-oxo-6-(trifluoromethyl)-1,2-dihydropyridine-3-carboxamide |
| 46 | 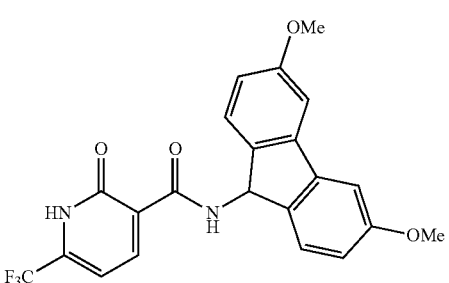 | N-(3,6-dimethoxy-9H-fluoren-9-yl)-2-oxo-6-(trifluoromethyl)-1,2-dihydropyridine-3-carboxamide |
| 47 | 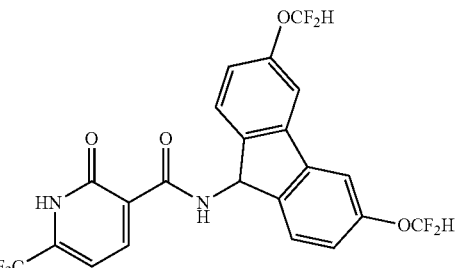 | N-(3,6-bis(difluoromethoxy)-9H-fluoren-9-yl)-2-oxo-6-(trifluoromethyl)-1,2-dihydropyridine-3-carboxamide |
| 48 | 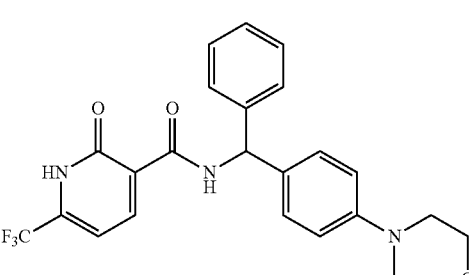 | N-((4-morpholinophenyl)(phenyl)methyl)-2-oxo-6-(trifluoromethyl)-1,2-dihydropyridine-3-carboxamide |
| 49 | 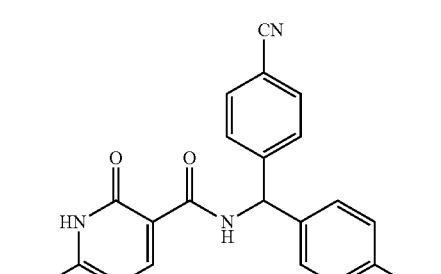 | N-(bis(4-cyanophenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 50 | 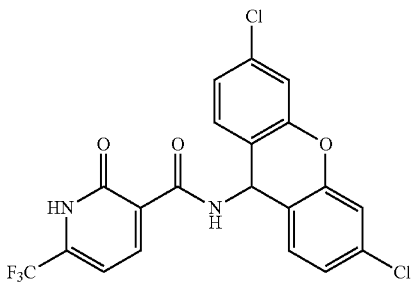 [SMILES: O=C(NC1c2ccc(Cl)cc2Oc2cc(Cl)ccc21)c1ccc(C(F)(F)F)[nH]c1=O] | N-(3,6-dichloro-9H-xanthen-9-yl)-2-oxo-6-(trifluoromethyl)-1,2-dihydropyridine-3-carboxamide |
| 51 | 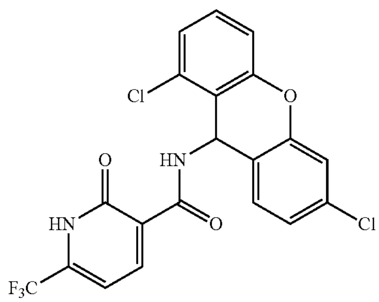 [SMILES: O=C(NC1c2ccc(Cl)cc2Oc2cccc(Cl)c21)c1ccc(C(F)(F)F)[nH]c1=O] | N-(1,6-dichloro-9H-xanthen-9-yl)-2-oxo-6-(trifluoromethyl)-1,2-dihydropyridine-3-carboxamide |
| 52 | 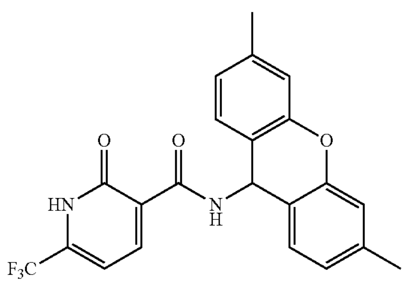 [SMILES: Cc1ccc2c(c1)Oc1cc(C)ccc1C2NC(=O)c1ccc(C(F)(F)F)[nH]c1=O] | N-(3,6-dimethyl-9H-xanthen-9-yl)-2-oxo-6-(trifluoromethyl)-1,2-dihydropyridine-3-carboxamide |
| 53 | 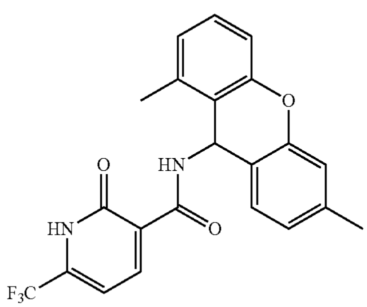 | N-(1,6-dimethyl-9H-xanthen-9-yl)-2-oxo-6-(trifluoromethyl)-1,2-dihydropyridine-3-carboxamide |
| 54 | 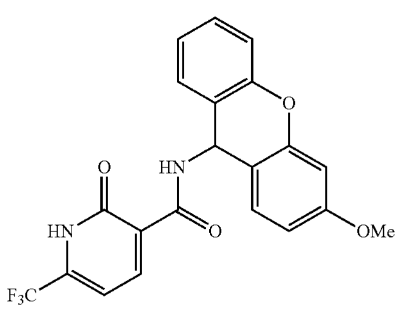 [SMILES: COc1ccc2c(c1)Oc1ccccc1C2NC(=O)c1ccc(C(F)(F)F)[nH]c1=O] | N-(3-methoxy-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 55 | 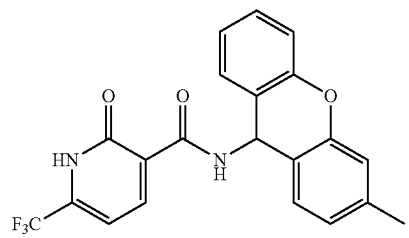 [SMILES: Cc1ccc2c(c1)Oc1ccccc1C2NC(=O)c1ccc(C(F)(F)F)[nH]c1=O] | N-(3-methyl-9H-xanthen-9-yl)-2-oxo-6-(trifluoromethyl)-1,2-dihydropyridine-3-carboxamide |
| 56 | 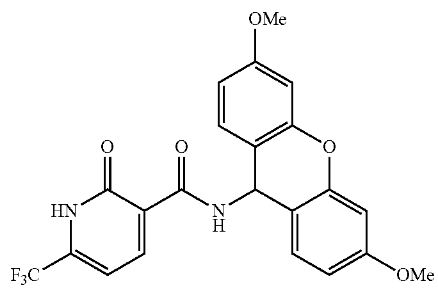 [SMILES: COc1ccc2c(c1)Oc1cc(OC)ccc1C2NC(=O)c1ccc(C(F)(F)F)[nH]c1=O] | N-(3,6-dimethoxy-9H-xanthen-9-yl)-2-oxo-6-(trifluoromethyl)-1,2-dihydropyridine-3-carboxamide |
| 57 | 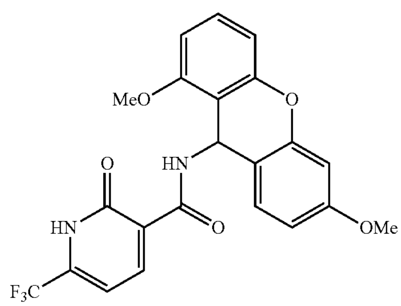 [SMILES: COc1ccc2c(c1)Oc1cccc(OC)c1C2NC(=O)c1ccc(C(F)(F)F)[nH]c1=O] | N-(1,6-dimethoxy-9H-xanthen-9-yl)-2-oxo-6-(trifluoromethyl)-1,2-dihydropyridine-3-carboxamide |
| 58 | 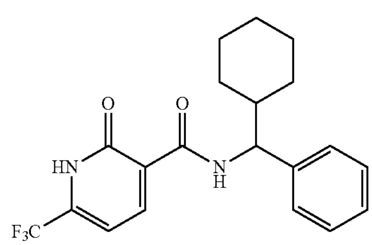 [SMILES: O=C(NC(c1ccccc1)C1CCCCC1)c1ccc(C(F)(F)F)[nH]c1=O] | N-(cyclohexyl(phenyl)methyl)-2-oxo-6-(trifluoromethyl)-1,2-dihydropyridine-3-carboxamide |
| 59 | 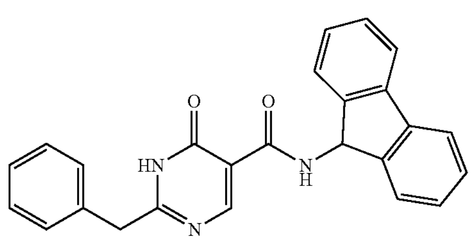 [SMILES: O=C(NC1c2ccccc2-c2ccccc21)c1cnc(Cc2ccccc2)[nH]c1=O] | 2-benzyl-N-(9H-fluoren-9-yl)-6-oxo-1,6-dihydropyrimidine-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 60 | 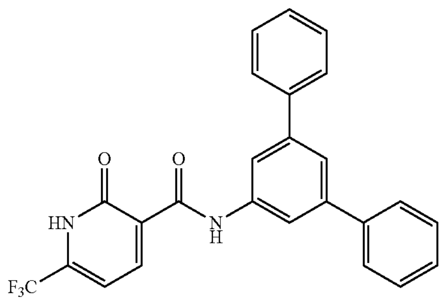 [SMILES: O=C(Nc1cc(-c2ccccc2)cc(-c2ccccc2)c1)c1ccc(C(F)(F)F)[nH]c1=O] | N-([1,1':3',1''-terphenyl]-5'-yl)-2-oxo-6-(trifluoromethyl)-1,2-dihydropyridine-3-carboxamide |
| 61 | 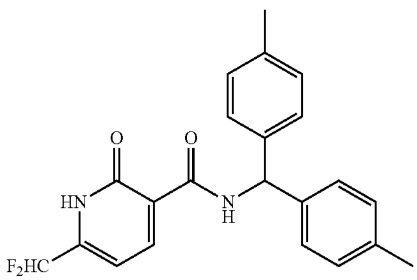 [SMILES: Cc1ccc(C(NC(=O)c2ccc(C(F)F)[nH]c2=O)c2ccc(C)cc2)cc1] | N-(di-p-tolylmethyl)-6-(difluoromethyl)-2-oxo-1,2-dihydropyridine-3-carboxamide |
| 62 | 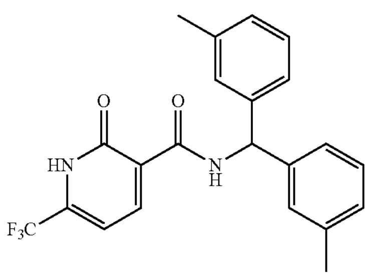 [SMILES: Cc1cccc(C(NC(=O)c2ccc(C(F)(F)F)[nH]c2=O)c2cccc(C)c2)c1] | N-(di-m-tolylmethyl)-6-(trifluoromethyl)-2-oxo-1,2-dihydropyridine-3-carboxamide |
| 63 | 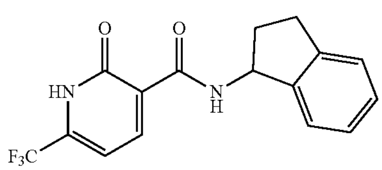 [SMILES: O=C(NC1CCc2ccccc21)c1ccc(C(F)(F)F)[nH]c1=O] | N-(2,3-dihydro-1H-inden-1-yl)-2-oxo-6-(trifluoromethyl)-1,2-dihydropyridine-3-carboxamide* |
| 64 | 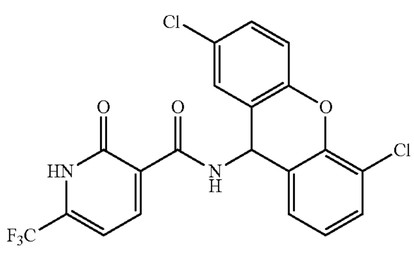 [SMILES: O=C(NC1c2cc(Cl)ccc2Oc2c(Cl)cccc21)c1ccc(C(F)(F)F)[nH]c1=O] | N-(bis(3-chlorophenyl)methyl)-2-oxo-6-(trifluoromethyl)-1,2-dihydropyridine-3-carboxamide |
| 65 | 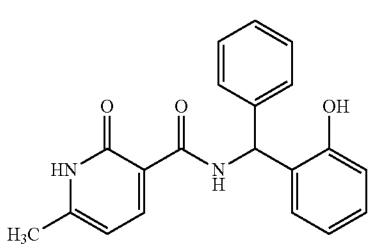 [SMILES: Cc1ccc(C(=O)NC(c2ccccc2)c2ccccc2O)c(=O)[nH]1] | N-((2-hydroxyphenyl)(phenyl)methyl)-6-methyl-2-oxo-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 66 | 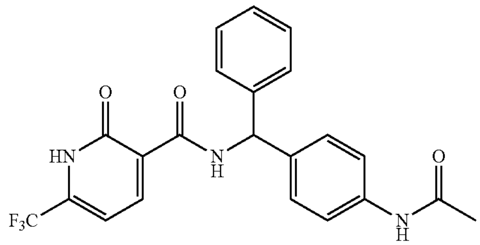 [SMILES: CC(=O)Nc1ccc(C(NC(=O)c2ccc(C(F)(F)F)[nH]c2=O)c2ccccc2)cc1] | N-((4-acetamidophenyl)(phenyl)methyl)-2-oxo-6-(trifluoromethyl)-1,2-dihydropyridine-3-carboxamide |
| 67 | 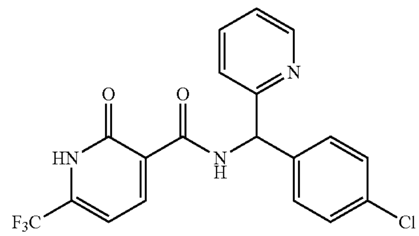 | N-((4-chlorophenyl)(pyridin-2-yl)methyl)-2-oxo-6-(trifluoromethyl)-1,2-dihydropyridine-3-carboxamide |
| 68 | 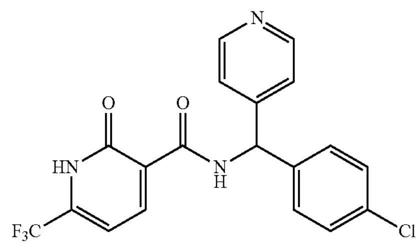 [SMILES: O=C(NC(c1ccncc1)c1ccc(Cl)cc1)c1ccc(C(F)(F)F)[nH]c1=O] | N-((4-chlorophenyl)(pyridin-4-yl)methyl)-2-oxo-6-(trifluoromethyl)-1,2-dihydropyridine-3-carboxamide |
| 69 | 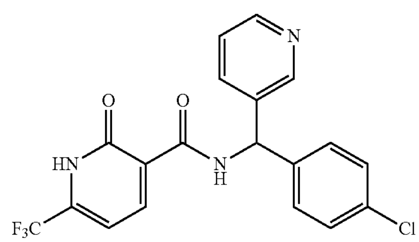 | N-((4-chlorophenyl)(pyridin-3-yl)methyl)-2-oxo-6-(trifluoromethyl)-1,2-dihydropyridine-3-carboxamide |
| 70 | 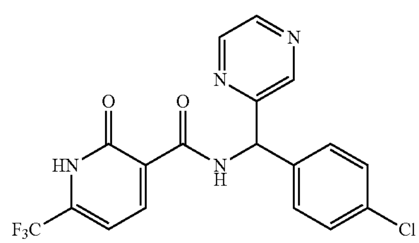 | N-((4-chlorophenyl)(pyrazin-2-yl)methyl)-2-oxo-6-(trifluoromethyl)-1,2-dihydropyridine-3-carboxamide |
| 71 | 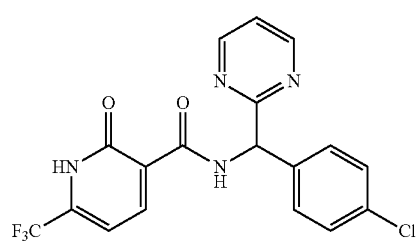 [SMILES: O=C(NC(c1ccc(Cl)cc1)c1ncccn1)c1ccc(C(F)(F)F)[nH]c1=O] | N-((4-chlorophenyl)(pyrimidin-2-yl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 72 | 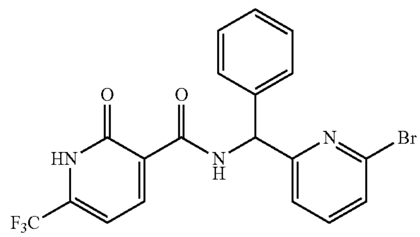 [SMILES: O=C(NC(c1ccccc1)c1cccc(Br)n1)c1ccc(C(F)(F)F)[nH]c1=O] | N-((6-bromopyridin-2-yl)(phenyl)methyl)-2-oxo-6-(trifluoromethyl)-1,2-dihydropyridine-3-carboxamide |
| 73 | 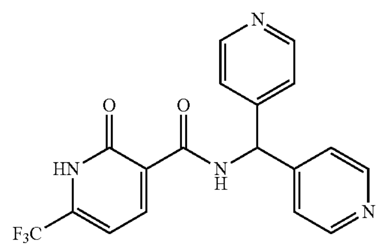 [SMILES: O=C(NC(c1ccncc1)c1ccncc1)c1ccc(C(F)(F)F)[nH]c1=O] | N-(di(pyridin-4-yl)methyl)-2-oxo-6-(trifluoromethyl)-1,2-dihydropyridine-3-carboxamide |
| 74 | 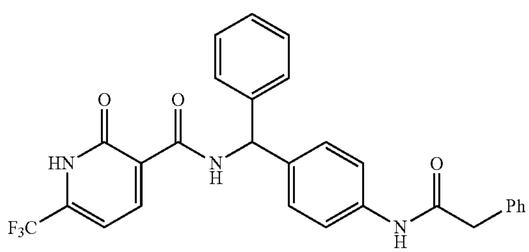 [SMILES: O=C(Cc1ccccc1)Nc1ccc(C(NC(=O)c2ccc(C(F)(F)F)[nH]c2=O)c2ccccc2)cc1] | N-(phenyl(4-(2-phenylacetamido)phenyl)methyl)-2-oxo-6-(trifluoromethyl)-1,2-dihydropyridine-3-carboxamide |
| 75 | 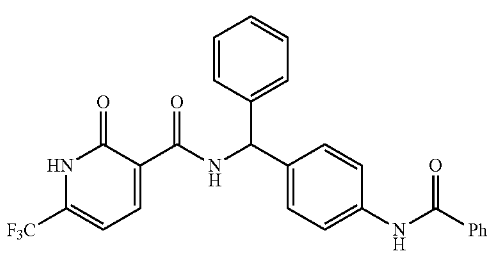 [SMILES: O=C(Nc1ccc(C(NC(=O)c2ccc(C(F)(F)F)[nH]c2=O)c2ccccc2)cc1)c1ccccc1] | N-((4-benzamidophenyl)(phenyl)methyl)-2-oxo-6-(trifluoromethyl)-1,2-dihydropyridine-3-carboxamide |
| 76 | 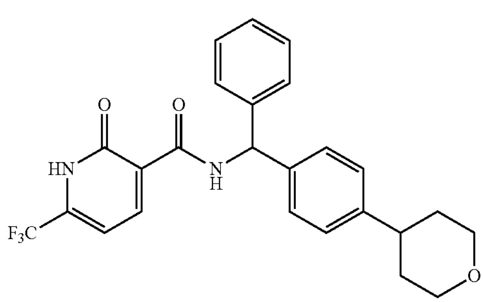 [SMILES: O=C(NC(c1ccccc1)c1ccc(C2CCOCC2)cc1)c1ccc(C(F)(F)F)[nH]c1=O] | N-(phenyl(4-(tetrahydro-2H-pyran-4-yl)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 77 | 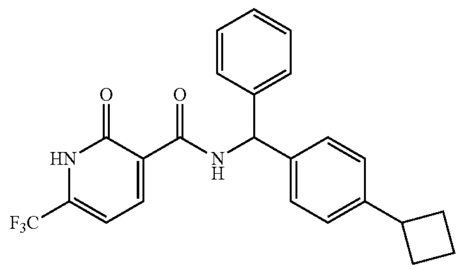 [SMILES: O=C(NC(c1ccccc1)c1ccc(C2CCC2)cc1)c1ccc(C(F)(F)F)[nH]c1=O] | N-((4-cyclobutylphenyl)(phenyl)methyl)-2-oxo-6-(trifluoromethyl)-1,2-dihydropyridine-3-carboxamide |
| 78 | 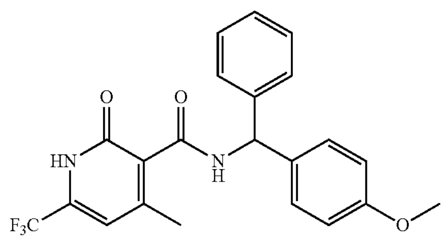 [SMILES: COc1ccc(C(NC(=O)c2c(C)cc(C(F)(F)F)[nH]c2=O)c2ccccc2)cc1] | N-((4-methoxyphenyl)(phenyl)methyl)-4-methyl-2-oxo-6-(trifluoromethyl)-1,2-dihydropyridine-3-carboxamide |
| 79 | 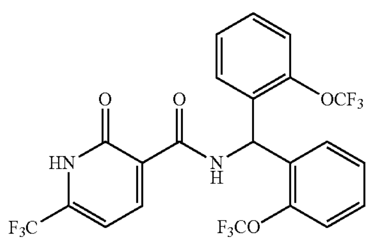 [SMILES: O=C(NC(c1ccccc1OC(F)(F)F)c1ccccc1OC(F)(F)F)c1ccc(C(F)(F)F)[nH]c1=O] | N-(bis(2-(trifluoromethoxy)phenyl)methyl)-2-oxo-6-(trifluoromethyl)-1,2-dihydropyridine-3-carboxamide |
| 80 | 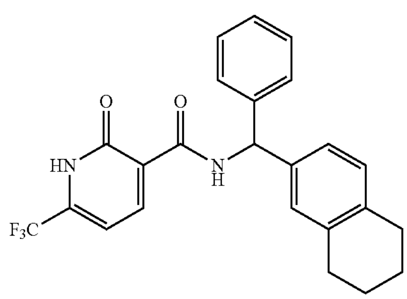 [SMILES: O=C(NC(c1ccccc1)c1ccc2c(c1)CCCC2)c1ccc(C(F)(F)F)[nH]c1=O] | N-(phenyl(5,6,7,8-tetrahydronaphthalen-2-yl)methyl)-2-oxo-6-(trifluoromethyl)-1,2-dihydropyridine-3-carboxamide |
| 81 | 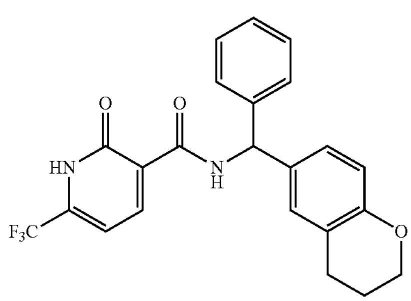 [SMILES: O=C(NC(c1ccccc1)c1ccc2c(c1)CCCO2)c1ccc(C(F)(F)F)[nH]c1=O] | N-(chroman-6-yl(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 82 | 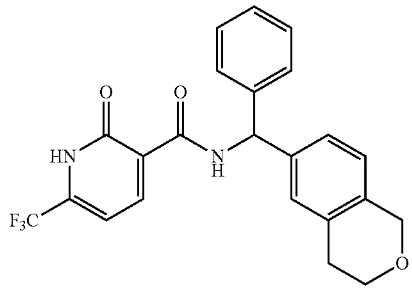 [SMILES: O=C(NC(c1ccccc1)c1ccc2c(c1)CCOC2)c1ccc(C(F)(F)F)[nH]c1=O] | N-(isochroman-6-yl(phenyl)methyl)-2-oxo-6-(trifluoromethyl)-1,2-dihydropyridine-3-carboxamide |
| 83 | 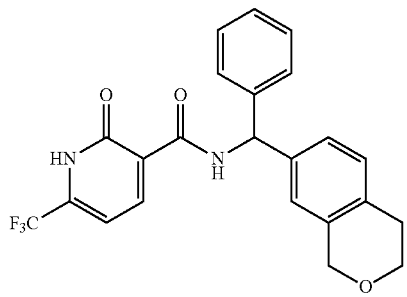 [SMILES: O=C(NC(c1ccccc1)c1ccc2c(c1)COCC2)c1ccc(C(F)(F)F)[nH]c1=O] | N-(isochroman-7-yl(phenyl)methyl)-2-oxo-6-(trifluoromethyl)-1,2-dihydropyridine-3-carboxamide |
| 84 | 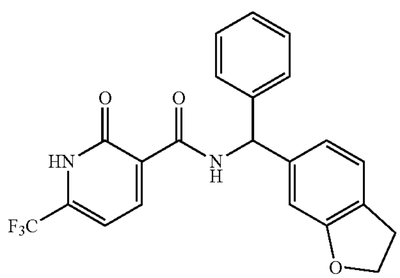 [SMILES: O=C(NC(c1ccccc1)c1ccc2c(c1)OCC2)c1ccc(C(F)(F)F)[nH]c1=O] | N-((2,3-dihydrobenzofuran-6-yl)(phenyl)methyl)-2-oxo-6-(trifluoromethyl)-1,2-dihydropyridine-3-carboxamide |
| 85 | 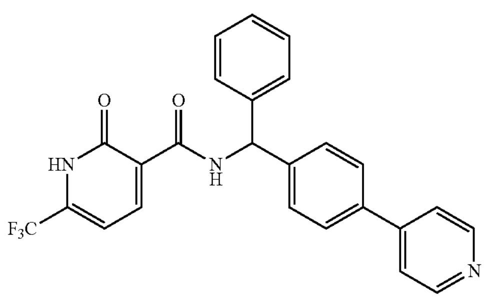 [SMILES: O=C(NC(c1ccccc1)c1ccc(-c2ccncc2)cc1)c1ccc(C(F)(F)F)[nH]c1=O] | 2-oxo-N-(phenyl(4-(pyridin-4-yl)phenyl)methyl)-6-(trifluoromethyl)-1,2-dihydropyridine-3-carboxamide |
| 86 | 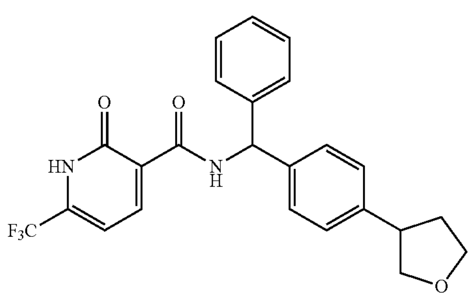 [SMILES: O=C(NC(c1ccccc1)c1ccc(C2CCOC2)cc1)c1ccc(C(F)(F)F)[nH]c1=O] | N-(phenyl(4-(tetrahydrofuran-3-yl)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 87 | 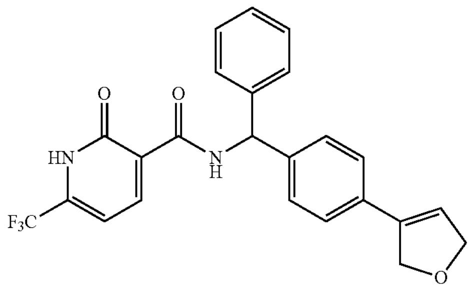 [SMILES: O=C(NC(c1ccccc1)c1ccc(C2=CCOC2)cc1)c1ccc(C(F)(F)F)[nH]c1=O] | N-((4-(2,5-dihydrofuran-3-yl)phenyl)(phenyl)methyl)-2-oxo-6-(trifluoromethyl)-1,2-dihydropyridine-3-carboxamide |
| 88 | 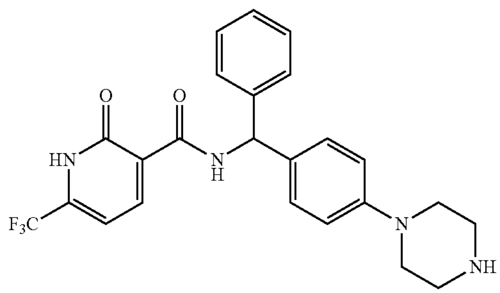 | N-(phenyl(4-(piperazin-1-yl)phenyl)methyl)-2-oxo-6-(trifluoromethyl)-1,2-dihydropyridine-3-carboxamide |
| 89 | 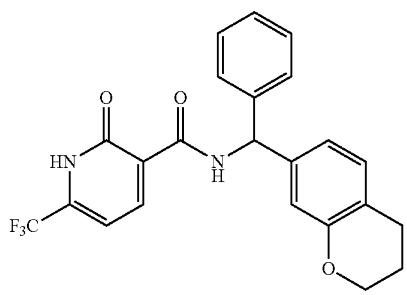 [SMILES: O=C(NC(c1ccccc1)c1ccc2c(c1)OCCC2)c1ccc(C(F)(F)F)[nH]c1=O] | N-(chroman-7-yl(phenyl)methyl)-2-oxo-6-(trifluoromethyl)-1,2-dihydropyridine-3-carboxamide |
| 90 | 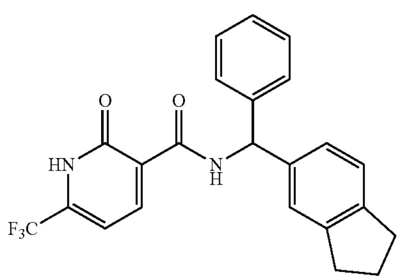 [SMILES: O=C(NC(c1ccccc1)c1ccc2c(c1)CCC2)c1ccc(C(F)(F)F)[nH]c1=O] | N-((2,3-dihydro-1H-inden-5-yl)(phenyl)methyl)-2-oxo-6-(trifluoromethyl)-1,2-dihydropyridine-3-carboxamide |
| 91 | 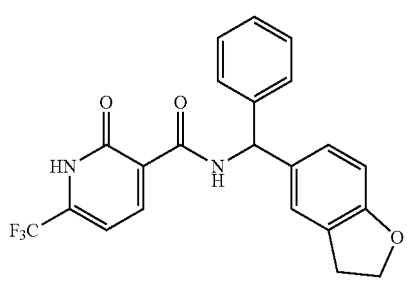 [SMILES: O=C(NC(c1ccccc1)c1ccc2c(c1)CCO2)c1ccc(C(F)(F)F)[nH]c1=O] | N-((2,3-dihydrobenzofuran-5-yl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 92 | 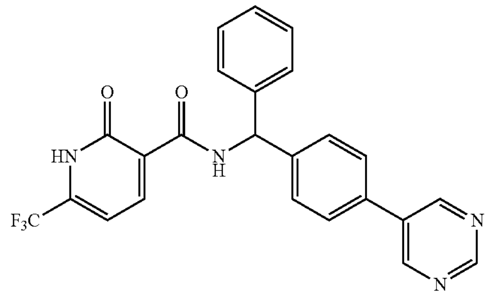 [SMILES: O=C(NC(c1ccccc1)c1ccc(-c2cncnc2)cc1)c1ccc(C(F)(F)F)[nH]c1=O] | N-(phenyl(4-(pyrimidin-5-yl)phenyl)methyl)-2-oxo-6-(trifluoromethyl)-1,2-dihydropyridine-3-carboxamide |
| 93 | 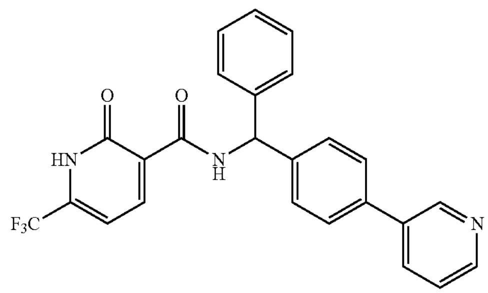 [SMILES: O=C(NC(c1ccccc1)c1ccc(-c2cccnc2)cc1)c1ccc(C(F)(F)F)[nH]c1=O] | N-(phenyl(4-(pyridin-3-yl)phenyl)methyl)-2-oxo-6-(trifluoromethyl)-1,2-dihydropyridine-3-carboxamide |
| 94 | 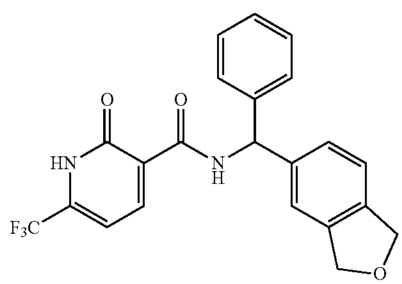 [SMILES: O=C(NC(c1ccccc1)c1ccc2c(c1)COC2)c1ccc(C(F)(F)F)[nH]c1=O] | N-((1,3-dihydroisobenzofuran-5-yl)(phenyl)methyl)-2-oxo-6-(trifluoromethyl)-1,2-dihydropyridine-3-carboxamide |
| 95 | 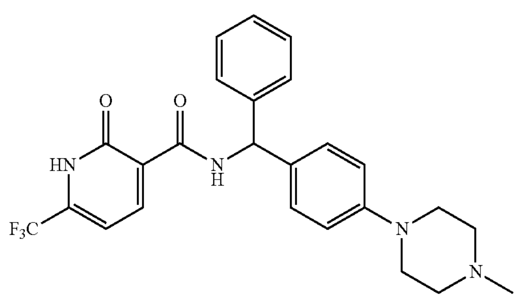 [SMILES: CN1CCN(c2ccc(C(NC(=O)c3ccc(C(F)(F)F)[nH]c3=O)c3ccccc3)cc2)CC1] | N-((4-(4-methylpiperazin-1-yl)phenyl)(phenyl)methyl)-2-oxo-6-(trifluoromethyl)-1,2-dihydropyridine-3-carboxamide |
| 96 | 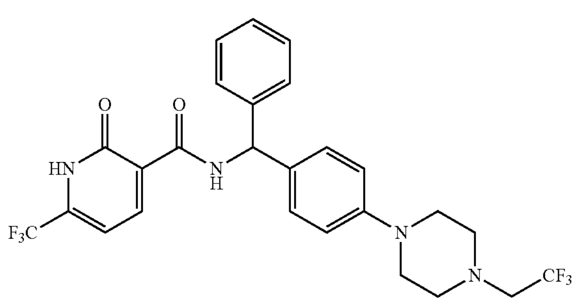 [SMILES: O=C(NC(c1ccccc1)c1ccc(N2CCN(CC(F)(F)F)CC2)cc1)c1ccc(C(F)(F)F)[nH]c1=O] | N-(phenyl(4-(4-(2,2,2-trifluoroethyl)piperazin-1-yl)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 97 | 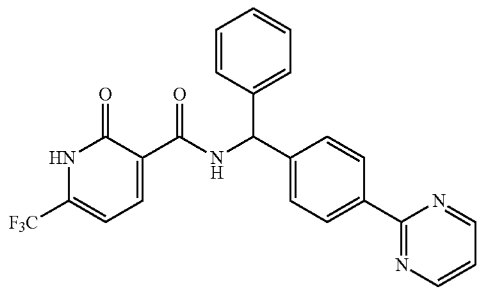 | 2-oxo-N-(phenyl(4-(pyrimidin-2-yl)phenyl)methyl)-6-(trifluoromethyl)-1,2-dihydropyridine-3-carboxamide |
| 98 | 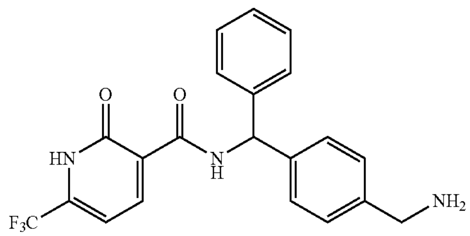 [SMILES: NCc1ccc(C(NC(=O)c2ccc(C(F)(F)F)[nH]c2=O)c2ccccc2)cc1] | N-((4-(aminomethyl)phenyl)(phenyl)methyl)-2-oxo-6-(trifluoromethyl)-1,2-dihydropyridine-3-carboxamide |
| 99 | 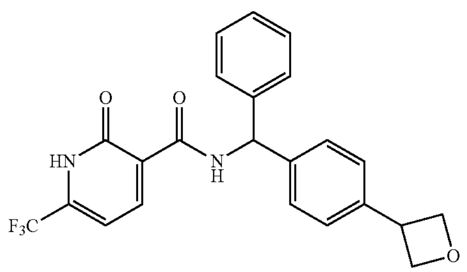 [SMILES: O=C(NC(c1ccccc1)c1ccc(C2COC2)cc1)c1ccc(C(F)(F)F)[nH]c1=O] | N-((4-(oxetan-3-yl)phenyl)(phenyl)methyl)-2-oxo-6-(trifluoromethyl)-1,2-dihydropyridine-3-carboxamide |
| 100 | 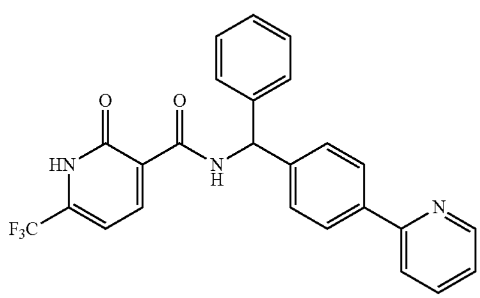 | 2-oxo-N-(phenyl(4-(pyridin-2-yl)phenyl)methyl)-6-(trifluoromethyl)-1,2-dihydropyridine-3-carboxamide |
| 101 | 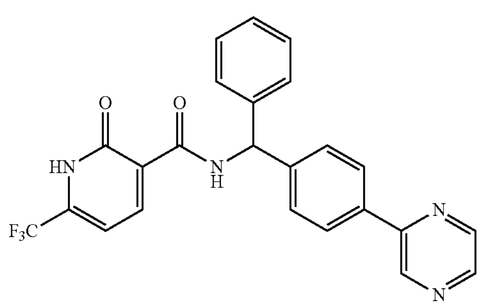 [SMILES: O=C(NC(c1ccccc1)c1ccc(-c2cnccn2)cc1)c1ccc(C(F)(F)F)[nH]c1=O] | 2-oxo-N-(phenyl(4-(pyrazin-2-yl)phenyl)methyl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 102 | 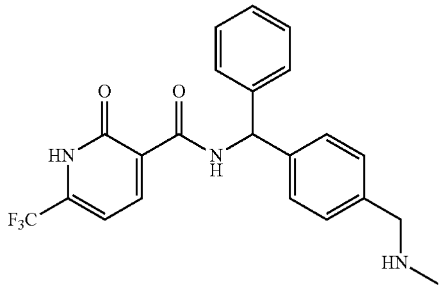 [SMILES: CNCc1ccc(C(NC(=O)c2ccc(C(F)(F)F)[nH]c2=O)c2ccccc2)cc1] | N-((4-((methylamino)methyl)phenyl)(phenyl)methyl)-2-oxo-6-(trifluoromethyl)-1,2-dihydropyridine-3-carboxamide |
| 103 | 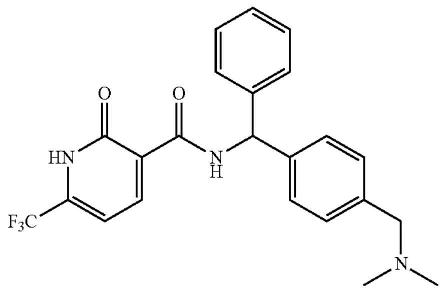 [SMILES: CN(C)Cc1ccc(C(NC(=O)c2ccc(C(F)(F)F)[nH]c2=O)c2ccccc2)cc1] | N-((4-((dimethylamino)methyl)phenyl)(phenyl)methyl)-2-oxo-6-(trifluoromethyl)-1,2-dihydropyridine-3-carboxamide |
| 104 | 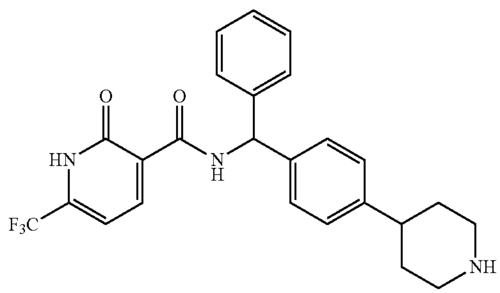 [SMILES: O=C(NC(c1ccccc1)c1ccc(C2CCNCC2)cc1)c1ccc(C(F)(F)F)[nH]c1=O] | 2-oxo-N-(phenyl(4-(piperidin-4-yl)phenyl)methyl)-6-(trifluoromethyl)-1,2-dihydropyridine-3-carboxamide |
| 105 | 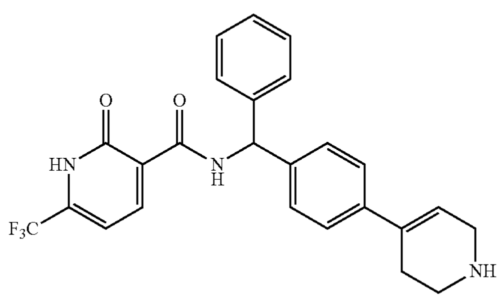 [SMILES: O=C(NC(c1ccccc1)c1ccc(C2=CCNCC2)cc1)c1ccc(C(F)(F)F)[nH]c1=O] | 2-oxo-N-(phenyl(4-(1,2,3,6-tetrahydropyridin-4-yl)phenyl)methyl)-6-(trifluoromethyl)-1,2-dihydropyridine-3-carboxamide |
| 106 | 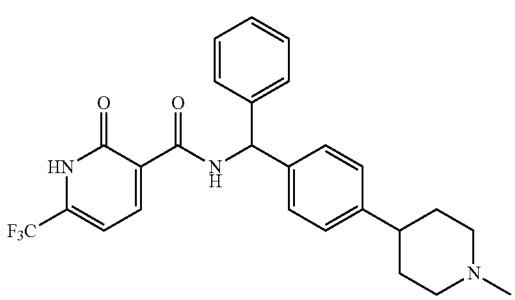 [SMILES: CN1CCC(c2ccc(C(NC(=O)c3ccc(C(F)(F)F)[nH]c3=O)c3ccccc3)cc2)CC1] | N-((4-(1-methylpiperidin-4-yl)phenyl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 107 | 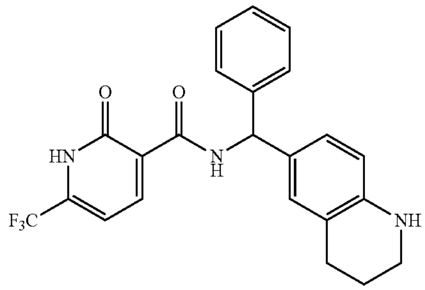 [SMILES: O=C(NC(c1ccccc1)c1ccc2c(c1)CCCN2)c1ccc(C(F)(F)F)[nH]c1=O] | 2-oxo-N-(phenyl(1,2,3,4-tetrahydroquinolin-6-yl)methyl)-6-(trifluoromethyl)-1,2-dihydropyridine-3-carboxamide |
| 108 | 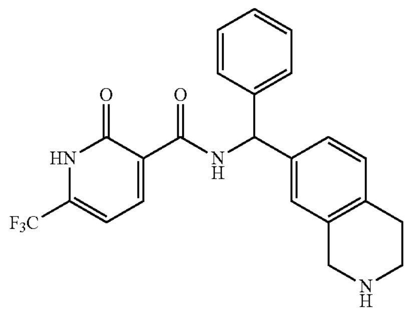 [SMILES: O=C(NC(c1ccccc1)c1ccc2c(c1)CNCC2)c1ccc(C(F)(F)F)[nH]c1=O] | 2-oxo-N-(phenyl(1,2,3,4-tetrahydroisoquinolin-7-yl)methyl)-6-(trifluoromethyl)-1,2-dihydropyridine-3-carboxamide |
| 109 | 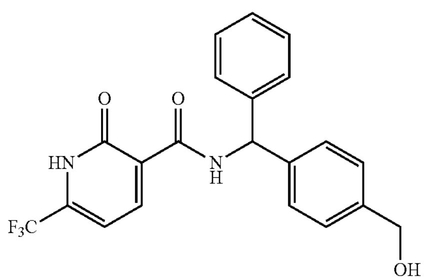 [SMILES: O=C(NC(c1ccccc1)c1ccc(CO)cc1)c1ccc(C(F)(F)F)[nH]c1=O] | N-((4-(hydroxymethyl)phenyl)(phenyl)methyl)-2-oxo-6-(trifluoromethyl)-1,2-dihydropyridine-3-carboxamide |
| 110 | 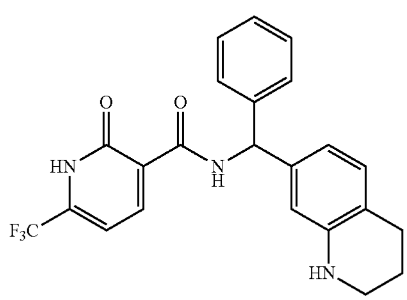 [SMILES: O=C(NC(c1ccccc1)c1ccc2c(c1)NCCC2)c1ccc(C(F)(F)F)[nH]c1=O] | 2-oxo-N-(phenyl(1,2,3,4-tetrahydroquinolin-7-yl)methyl)-6-(trifluoromethyl)-1,2-dihydropyridine-3-carboxamide |
| 111 | 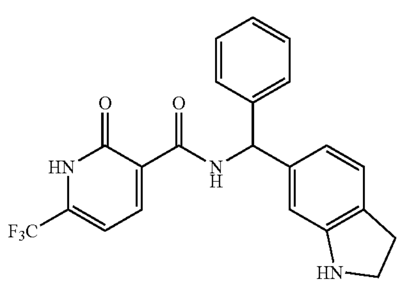 [SMILES: O=C(NC(c1ccccc1)c1ccc2c(c1)NCC2)c1ccc(C(F)(F)F)[nH]c1=O] | 2-oxo-N-(phenyl(1,2,3,4-tetrahydroisoquinolin-7-yl)methyl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 112 | 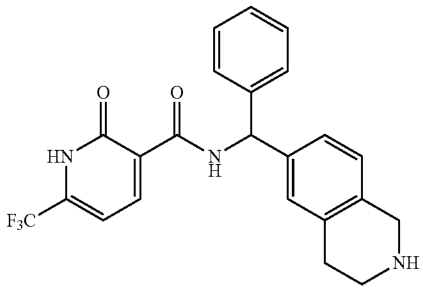 [SMILES: O=C(NC(c1ccccc1)c1ccc2c(c1)CCNC2)c1ccc(C(F)(F)F)[nH]c1=O] | 2-oxo-N-(phenyl(1,2,3,4-tetrahydroisoquinolin-6-yl)methyl)-6-(trifluoromethyl)-1,2-dihydropyridine-3-carboxamide |
| 113 | 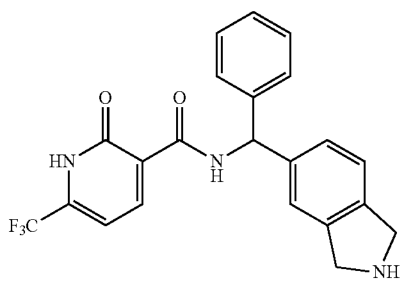 [SMILES: O=C(NC(c1ccccc1)c1ccc2c(c1)CNC2)c1ccc(C(F)(F)F)[nH]c1=O] | N-(isoindolin-5-yl(phenyl)methyl)-2-oxo-6-(trifluoromethyl)-1,2-dihydropyridine-3-carboxamide |
| 114 | 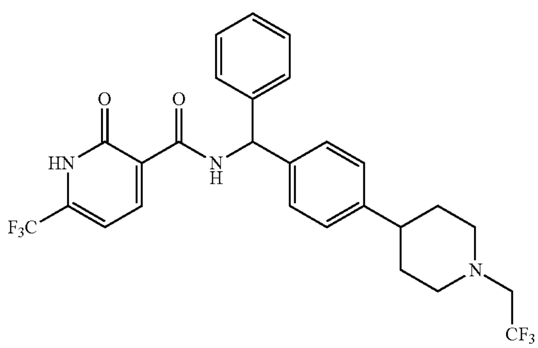 [SMILES: O=C(NC(c1ccccc1)c1ccc(C2CCN(CC(F)(F)F)CC2)cc1)c1ccc(C(F)(F)F)[nH]c1=O] | 2-oxo-N-(phenyl(4-(1-(2,2,2-trifluoroethyl)piperidin-4-yl)phenyl)methyl)-6-(trifluoromethyl)-1,2-dihydropyridine-3-carboxamide |
| 115 | 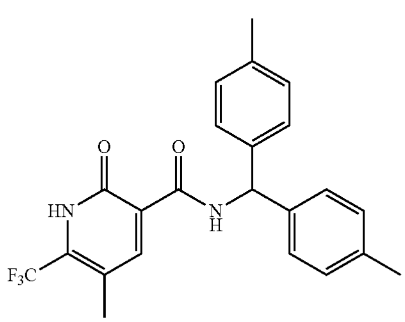 [SMILES: Cc1ccc(C(NC(=O)c2cc(C)c(C(F)(F)F)[nH]c2=O)c2ccc(C)cc2)cc1] | N-(di-p-tolylmethyl)-5-methyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 116 | 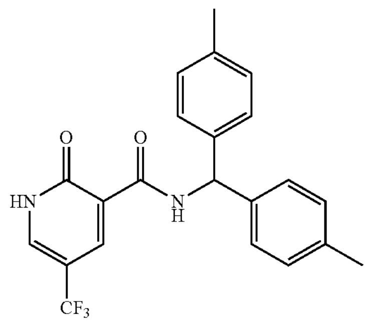 [SMILES: Cc1ccc(C(NC(=O)c2cc(C(F)(F)F)c[nH]c2=O)c2ccc(C)cc2)cc1] | N-(di-p-tolylmethyl)-2-oxo-5-(trifluoromethyl)-1,2-dihydropyridine-3-carboxamide |
| 117 | 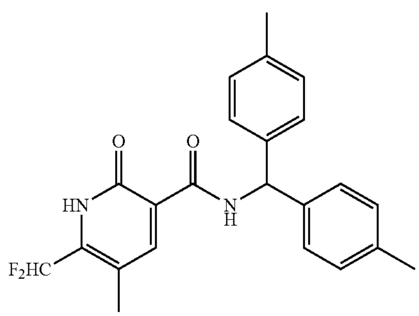 [SMILES: Cc1ccc(C(NC(=O)c2cc(C)c(C(F)F)[nH]c2=O)c2ccc(C)cc2)cc1] | N-(di-p-tolylmethyl)-6-(difluoromethyl)-5-methyl-2-oxo-1,2-dihydropyridine-3-carboxamide |
| 118 | 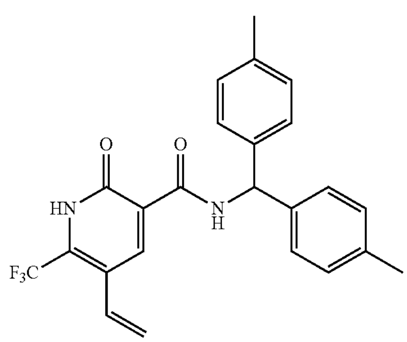 [SMILES: C=Cc1cc(C(=O)NC(c2ccc(C)cc2)c2ccc(C)cc2)c(=O)[nH]c1C(F)(F)F] | N-(di-p-tolylmethyl)-2-oxo-6-(trifluoromethyl)-5-vinyl-1,2-dihydropyridine-3-carboxamide |
| 119 | 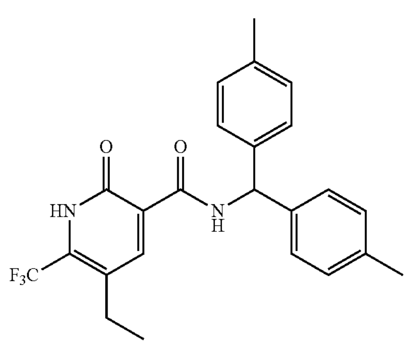 [SMILES: CCc1cc(C(=O)NC(c2ccc(C)cc2)c2ccc(C)cc2)c(=O)[nH]c1C(F)(F)F] | N-(di-p-tolylmethyl)-5-ethyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 120 | 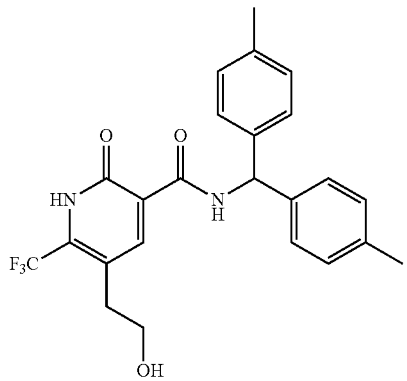 [SMILES: Cc1ccc(C(NC(=O)c2cc(CCO)c(C(F)(F)F)[nH]c2=O)c2ccc(C)cc2)cc1] | N-(di-p-tolylmethyl)-5-(2-hydroxyethyl)-2-oxo-6-(trifluoromethyl)-1,2-dihydropyridine-3-carboxamide |
| 121 | 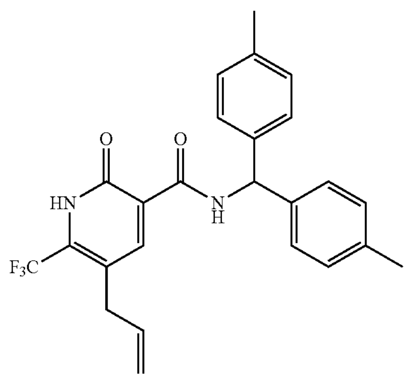 [SMILES: C=CCc1cc(C(=O)NC(c2ccc(C)cc2)c2ccc(C)cc2)c(=O)[nH]c1C(F)(F)F] | 5-allyl-N-(di-p-tolylmethyl)-2-oxo-6-(trifluoromethyl)-1,2-dihydropyridine-3-carboxamide |
| 122 | 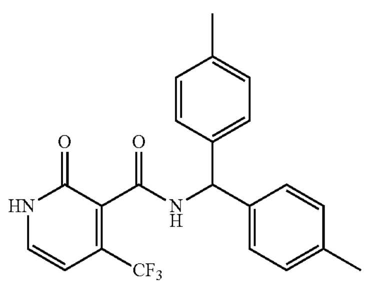 [SMILES: Cc1ccc(C(NC(=O)c2c(C(F)(F)F)cc[nH]c2=O)c2ccc(C)cc2)cc1] | N-(di-p-tolylmethyl)-2-oxo-4-(trifluoromethyl)-1,2-dihydropyridine-3-carboxamide |
| 123 | 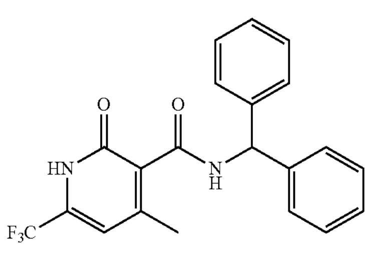 [SMILES: Cc1cc(C(F)(F)F)[nH]c(=O)c1C(=O)NC(c1ccccc1)c1ccccc1] | N-benzhydryl-4-methyl-2-oxo-6-(trifluoromethyl)-1,2-dihydropyridine-3-carboxamide |
| 124 | 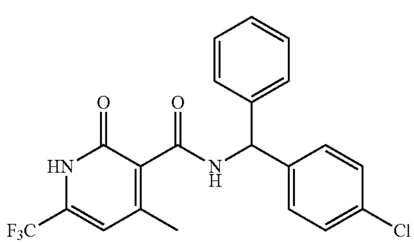 | N-((4-chlorophenyl)(phenyl)methyl)-4-methyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 125 | 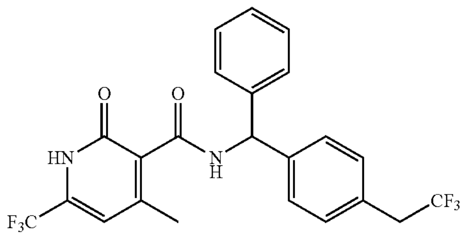 | 4-methyl-2-oxo-N-(phenyl(4-(2,2,2-trifluoroethyl)phenyl)methyl)-6-(trifluoromethyl)-1,2-dihydropyridine-3-carboxamide |
| 126 | 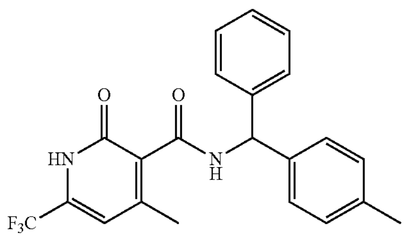 | 4-methyl-2-oxo-N-(phenyl(p-tolyl)methyl)-6-(trifluoromethyl)-1,2-dihydropyridine-3-carboxamide |
| 127 | 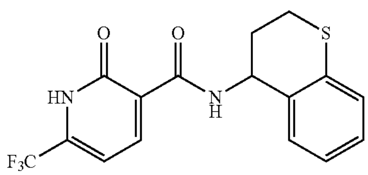 | 2-oxo-N-(thiochroman-4-yl)-6-(trifluoromethyl)-1,2-dihydropyridine-3-carboxamide |
| 128 | 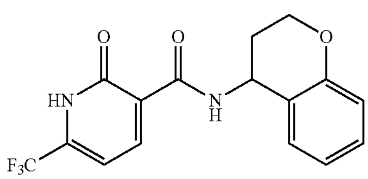 | N-(chroman-4-yl)-2-oxo-6-(trifluoromethyl)-1,2-dihydropyridine-3-carboxamide* |
| 129 | 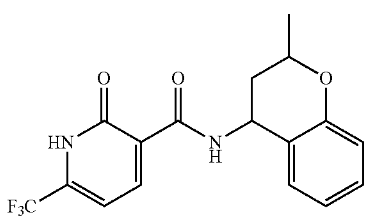 [SMILES: CC1CC(NC(=O)c2ccc(C(F)(F)F)[nH]c2=O)c2ccccc2O1] | N-(2-methylchroman-4-yl)-2-oxo-6-(trifluoromethyl)-1,2-dihydropyridine-3-carboxamide |
| 130 | 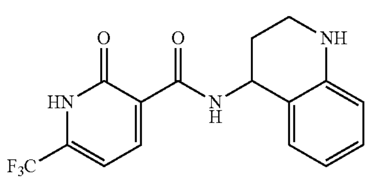 [SMILES: O=C(NC1CCNc2ccccc21)c1ccc(C(F)(F)F)[nH]c1=O] | 2-oxo-N-(1,2,3,4-tetrahydroquinolin-4-yl)-6-(trifluoromethyl)-1,2-dihydropyridine-3-carboxamide |
| 131 | 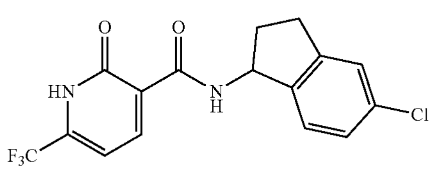 [SMILES: O=C(NC1CCc2cc(Cl)ccc21)c1ccc(C(F)(F)F)[nH]c1=O] | N-(5-chloro-2,3-dihydro-1H-inden-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 132 | 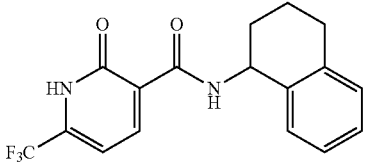 [SMILES: O=C(NC1CCCc2ccccc21)c1ccc(C(F)(F)F)[nH]c1=O] | 2-oxo-N-(1,2,3,4-tetrahydronaphthalen-1-yl)-6-(trifluoromethyl)-1,2-dihydropyridine-3-carboxamide |
| 133 | 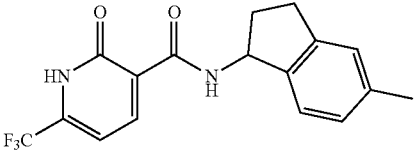 | N-(5-methyl-2,3-dihydro-1H-inden-1-yl)-2-oxo-6-(trifluoromethyl)-1,2-dihydropyridine-3-carboxamide |
| 134 | 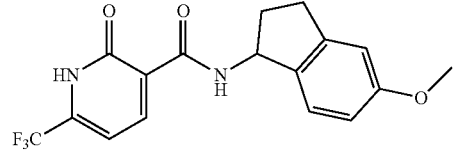 [SMILES: COc1ccc2c(c1)CCC2NC(=O)c1ccc(C(F)(F)F)[nH]c1=O] | N-(5-methoxy-2,3-dihydro-1H-inden-1-yl)-2-oxo-6-(trifluoromethyl)-1,2-dihydropyridine-3-carboxamide |
| 135 | 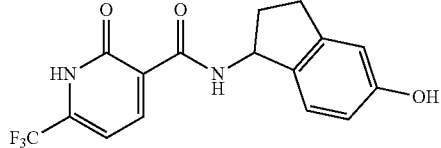 [SMILES: O=C(NC1CCc2cc(O)ccc21)c1ccc(C(F)(F)F)[nH]c1=O] | N-(5-hydroxy-2,3-dihydro-1H-inden-1-yl)-2-oxo-6-(trifluoromethyl)-1,2-dihydropyridine-3-carboxamide |
| 136 | 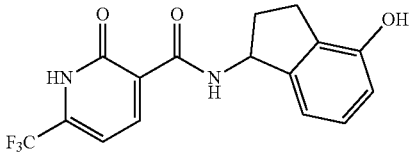 [SMILES: O=C(NC1CCc2c(O)cccc21)c1ccc(C(F)(F)F)[nH]c1=O] | N-(4-hydroxy-2,3-dihydro-1H-inden-1-yl)-2-oxo-6-(trifluoromethyl)-1,2-dihydropyridine-3-carboxamide* |
| 137 | 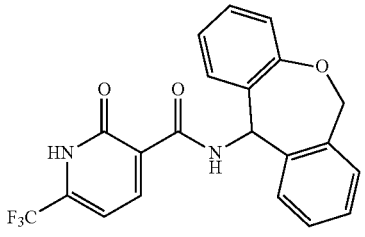 | N-(6,11-dihydrodibenzo[b,e]oxepin-11-yl)-2-oxo-6-(trifluoromethyl)-1,2-dihydropyridine-3-carboxamide |
| 138 | 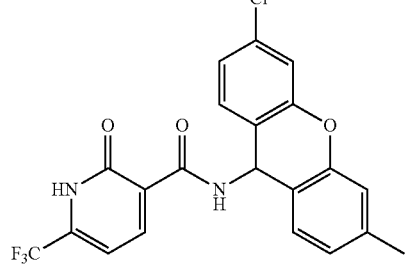 | N-(3-chloro-6-methyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 139 | 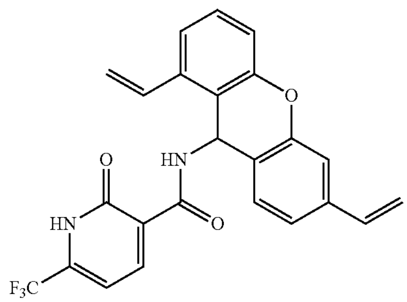 [SMILES: C=Cc1ccc2c(c1)Oc1cccc(C=C)c1C2NC(=O)c1ccc(C(F)(F)F)[nH]c1=O] | N-(1,6-divinyl-9H-xanthen-9-yl)-2-oxo-6-(trifluoromethyl)-1,2-dihydropyridine-3-carboxamide |
| 140 | 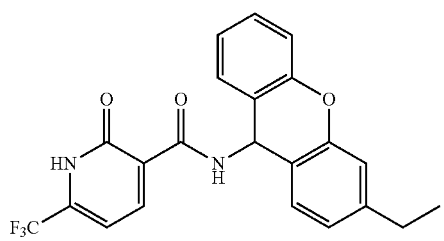 [SMILES: CCc1ccc2c(c1)Oc1ccccc1C2NC(=O)c1ccc(C(F)(F)F)[nH]c1=O] | N-(3-ethyl-9H-xanthen-9-yl)-2-oxo-6-(trifluoromethyl)-1,2-dihydropyridine-3-carboxamide |
| 141 | 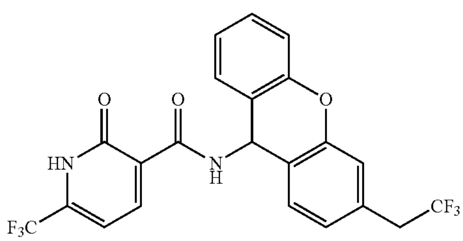 [SMILES: O=C(NC1c2ccccc2Oc2cc(CC(F)(F)F)ccc21)c1ccc(C(F)(F)F)[nH]c1=O] | 2-oxo-N-(3-(2,2,2-trifluoroethyl)-9H-xanthen-9-yl)-6-(trifluoromethyl)-1,2-dihydropyridine-3-carboxamide |
| 142 | 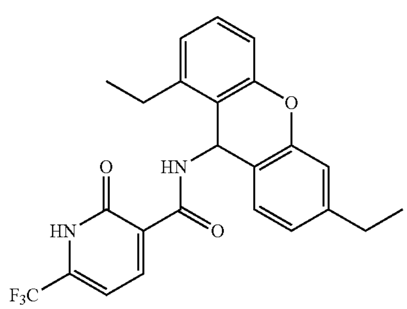 [SMILES: CCc1ccc2c(c1)Oc1cccc(CC)c1C2NC(=O)c1ccc(C(F)(F)F)[nH]c1=O] | N-(1,6-diethyl-9H-xanthen-9-yl)-2-oxo-6-(trifluoromethyl)-1,2-dihydropyridine-3-carboxamide |
| 143 | 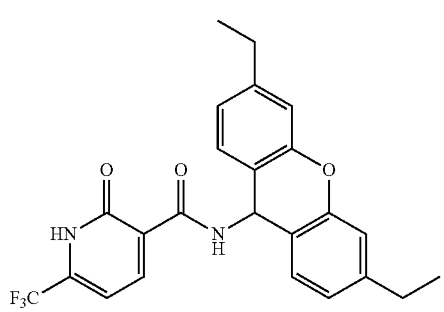 [SMILES: CCc1ccc2c(c1)Oc1cc(CC)ccc1C2NC(=O)c1ccc(C(F)(F)F)[nH]c1=O] | N-(3,6-diethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 144 | 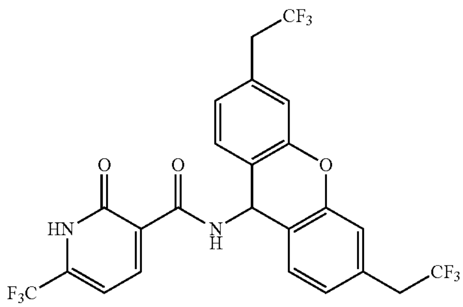 [SMILES: O=C(NC1c2ccc(CC(F)(F)F)cc2Oc2cc(CC(F)(F)F)ccc21)c1ccc(C(F)(F)F)[nH]c1=O] | N-(3,6-bis(2,2,2-trifluoroethyl)-9H-xanthen-9-yl)-2-oxo-6-(trifluoromethyl)-1,2-dihydropyridine-3-carboxamide |
| 145 | 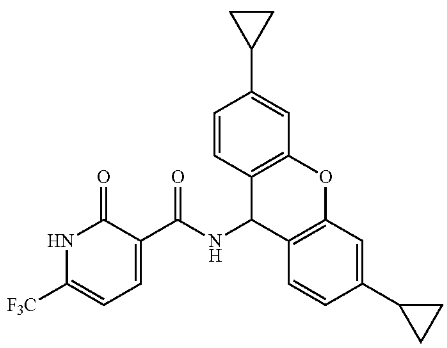 [SMILES: O=C(NC1c2ccc(C3CC3)cc2Oc2cc(C3CC3)ccc21)c1ccc(C(F)(F)F)[nH]c1=O] | N-(3,6-dicyclopropyl-9H-xanthen-9-yl)-2-oxo-6-(trifluoromethyl)-1,2-dihydropyridine-3-carboxamide |
| 146 | 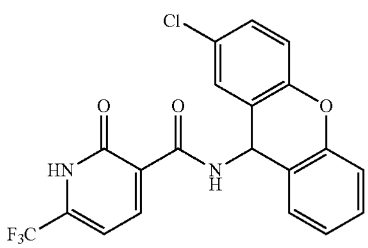 [SMILES: O=C(NC1c2ccccc2Oc2ccc(Cl)cc21)c1ccc(C(F)(F)F)[nH]c1=O] | N-(3,6-dicyclopropyl-9H-xanthen-9-yl)-2-oxo-6-(trifluoromethyl)-1,2-dihydropyridine-3-carboxamide |
| 147 | 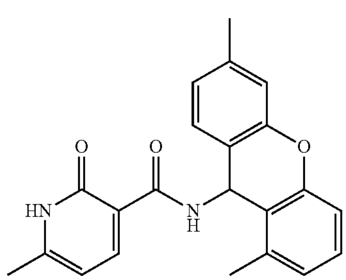 [SMILES: Cc1ccc2c(c1)Oc1cccc(C)c1C2NC(=O)c1ccc(C)[nH]c1=O] | N-(1,6-dimethyl-9H-xanthen-9-yl)-6-methyl-2-oxo-1,2-dihydropyridine-3-carboxamide |
| 148 | 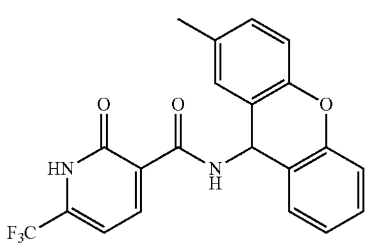 | N-(2-methyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 149 | 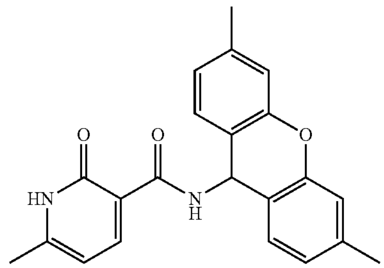 | N-(3,6-dimethyl-9H-xanthen-9-yl)-6-methyl-2-oxo-1,2-dihydropyridine-3-carboxamide |
| 150 | 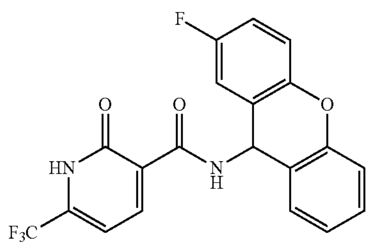 | N-(2-fluoro-9H-xanthen-9-yl)-2-oxo-6-(trifluoromethyl)-1,2-dihydropyridine-3-carboxamide |
| 151 | 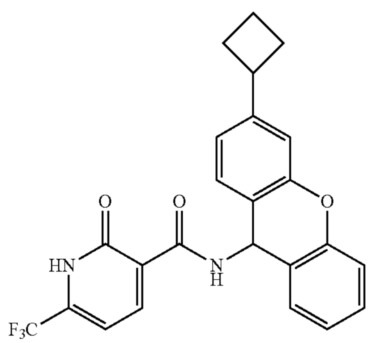 [SMILES: O=C(NC1c2ccccc2Oc2cc(C3CCC3)ccc21)c1ccc(C(F)(F)F)[nH]c1=O] | N-(3-cyclobutyl-9H-xanthen-9-yl)-2-oxo-6-(trifluoromethyl)-1,2-dihydropyridine-3-carboxamide |
| 152 | 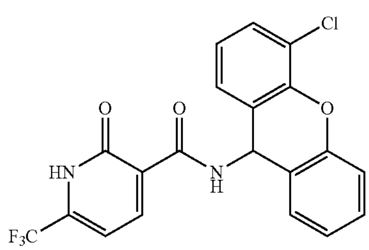 [SMILES: O=C(NC1c2ccccc2Oc2c(Cl)cccc21)c1ccc(C(F)(F)F)[nH]c1=O] | N-(4-chloro-9H-xanthen-9-yl)-2-oxo-6-(trifluoromethyl)-1,2-dihydropyridine-3-carboxamide |
| 153 | 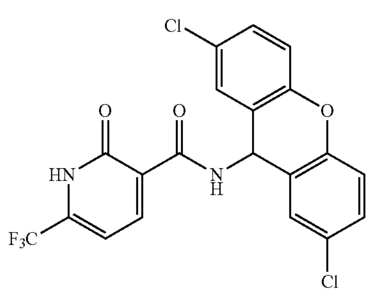 [SMILES: O=C(NC1c2cc(Cl)ccc2Oc2ccc(Cl)cc21)c1ccc(C(F)(F)F)[nH]c1=O] | N-(2,7-dichloro-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 154 | 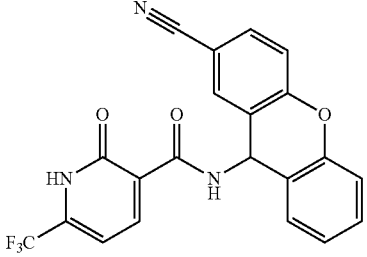 [SMILES: N#Cc1ccc2c(c1)C(NC(=O)c1ccc(C(F)(F)F)[nH]c1=O)c1ccccc1O2] | N-(2-cyano-9H-xanthen-9-yl)-2-oxo-6-(trifluoromethyl)-1,2-dihydropyridine-3-carboxamide |
| 155 | 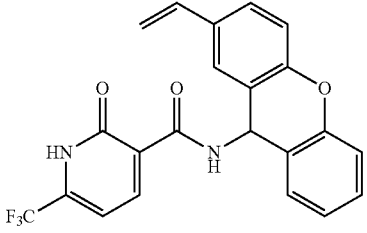 [SMILES: C=Cc1ccc2c(c1)C(NC(=O)c1ccc(C(F)(F)F)[nH]c1=O)c1ccccc1O2] | 2-oxo-6-(trifluoromethyl)-N-(2-vinyl-9H-xanthen-9-yl)-1,2-dihydropyridine-3-carboxamide |
| 156 | 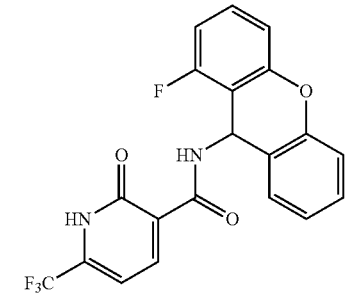 [SMILES: O=C(NC1c2ccccc2Oc2cccc(F)c21)c1ccc(C(F)(F)F)[nH]c1=O] | N-(1-fluoro-9H-xanthen-9-yl)-2-oxo-6-(trifluoromethyl)-1,2-dihydropyridine-3-carboxamide |
| 157 | 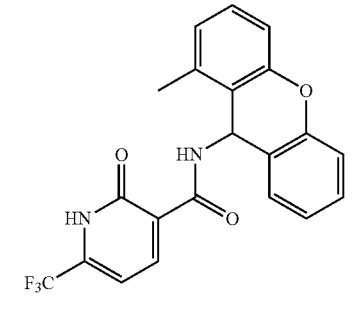 [SMILES: Cc1cccc2c1C(NC(=O)c1ccc(C(F)(F)F)[nH]c1=O)c1ccccc1O2] | N-(1-methyl-9H-xanthen-9-yl)-2-oxo-6-(trifluoromethyl)-1,2-dihydropyridine-3-carboxamide |
| 158 | 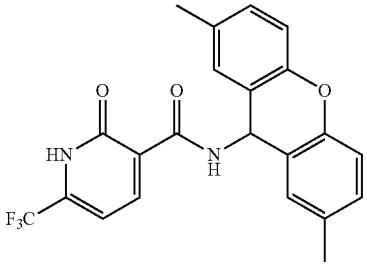 [SMILES: Cc1ccc2c(c1)C(NC(=O)c1ccc(C(F)(F)F)[nH]c1=O)c1cc(C)ccc1O2] | N-(2,7-dimethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 159 | 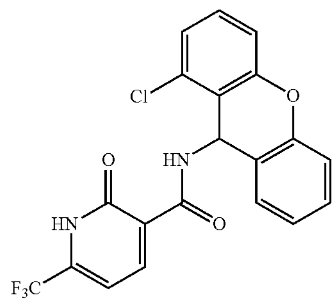 [SMILES: O=C(NC1c2ccccc2Oc2cccc(Cl)c21)c1ccc(C(F)(F)F)[nH]c1=O] | N-(1-chloro-9H-xanthen-9-yl)-2-oxo-6-(trifluoromethyl)-1,2-dihydropyridine-3-carboxamide |
| 160 | 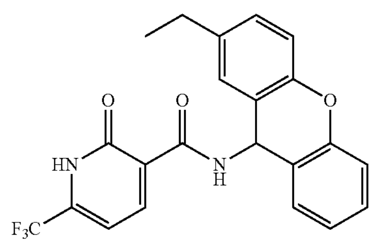 | N-(2-ethyl-9H-xanthen-9-yl)-2-oxo-6-(trifluoromethyl)-1,2-dihydropyridine-3-carboxamide |
| 161 | 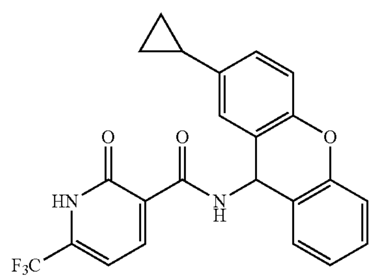 [SMILES: O=C(NC1c2ccccc2Oc2ccc(C3CC3)cc21)c1ccc(C(F)(F)F)[nH]c1=O] | N-(2-cyclopropyl-9H-xanthen-9-yl)-2-oxo-6-(trifluoromethyl)-1,2-dihydropyridine-3-carboxamide |
| 162 | 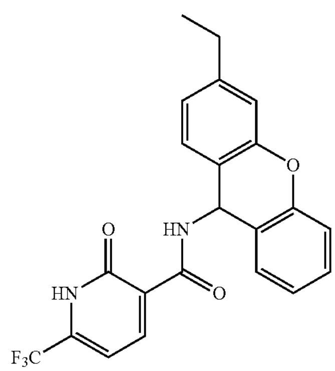 [SMILES: CCc1ccc2c(c1)Oc1ccccc1C2NC(=O)c1ccc(C(F)(F)F)[nH]c1=O] | N-(3-ethyl-9H-xanthen-9-yl)-2-oxo-6-(trifluoromethyl)-1,2-dihydropyridine-3-carboxamide |
| 163 | 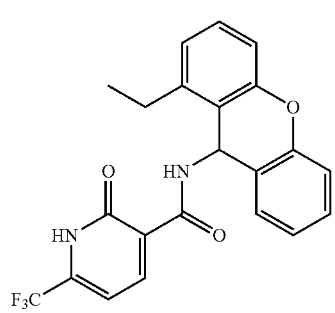 [SMILES: CCc1cccc2c1C(NC(=O)c1ccc(C(F)(F)F)[nH]c1=O)c1ccccc1O2] | N-(1-ethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 164 | 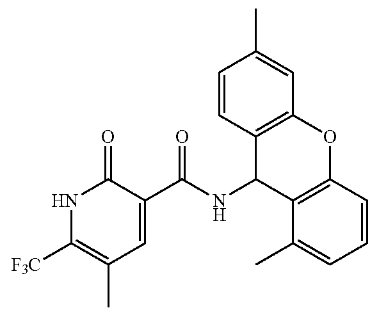 [SMILES: Cc1ccc2c(c1)Oc1cccc(C)c1C2NC(=O)c1cc(C)c(C(F)(F)F)[nH]c1=O] | N-(1,6-dimethyl-9H-xanthen-9-yl)-5-methyl-2-oxo-6-(trifluoromethyl)-1,2-dihydropyridine-3-carboxamideN-(3,6-dichloro-9H-xanthen-9-yl)-5-methyl-2-oxo-6-(trifluoromethyl)-1,2-dihydropyridine-3-carboxamide |
| 165 | 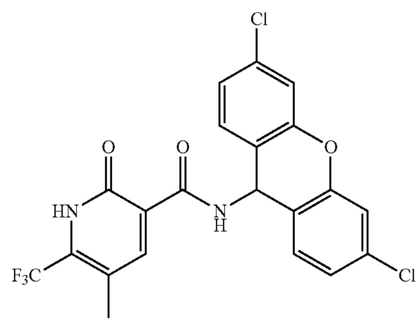 [SMILES: Cc1cc(C(=O)NC2c3ccc(Cl)cc3Oc3cc(Cl)ccc32)c(=O)[nH]c1C(F)(F)F] | N-(3,6-dichloro-9H-xanthen-9-yl)-5-methyl-2-oxo-6-(trifluoromethyl)-1,2-dihydropyridine-3-carboxamide |
| 166 | 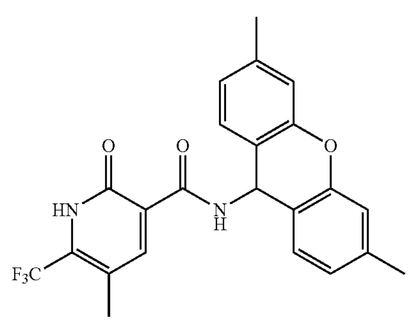 | N-(3,6-dimethyl-9H-xanthen-9-yl)-5-methyl-2-oxo-6-(trifluoromethyl)-1,2-dihydropyridine-3-carboxamide |
| 167 | 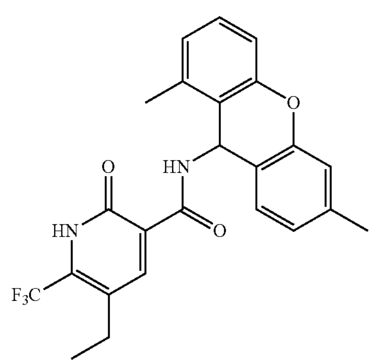 [SMILES: CCc1cc(C(=O)NC2c3ccc(C)cc3Oc3cccc(C)c32)c(=O)[nH]c1C(F)(F)F] | N-(1,6-dimethyl-9H-xanthen-9-yl)-5-ethyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 168 | 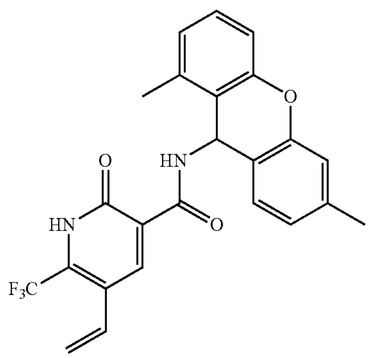 [SMILES: C=Cc1cc(C(=O)NC2c3ccc(C)cc3Oc3cccc(C)c32)c(=O)[nH]c1C(F)(F)F] | N-(1,6-dimethyl-9H-xanthen-9-yl)-2-oxo-6-(trifluoromethyl)-5-vinyl-1,2-dihydropyridine-3-carboxamide |
| 169 | 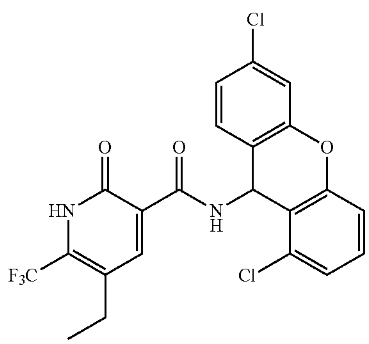 [SMILES: CCc1cc(C(=O)NC2c3ccc(Cl)cc3Oc3cccc(Cl)c32)c(=O)[nH]c1C(F)(F)F] | N-(1,6-dichloro-9H-xanthen-9-yl)-5-ethyl-2-oxo-6-(trifluoromethyl)-1,2-dihydropyridine-3-carboxamide |
| 170 | 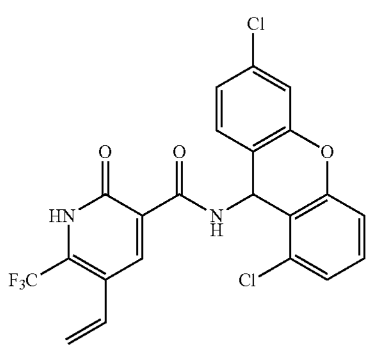 [SMILES: C=Cc1cc(C(=O)NC2c3ccc(Cl)cc3Oc3cccc(Cl)c32)c(=O)[nH]c1C(F)(F)F] | N-(1,6-dichloro-9H-xanthen-9-yl)-2-oxo-6-(trifluoromethyl)-5-vinyl-1,2-dihydropyridine-3-carboxamide |
| 171 | 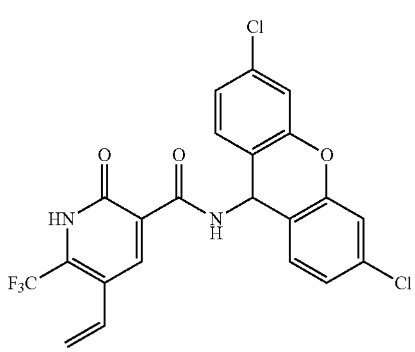 [SMILES: C=Cc1cc(C(=O)NC2c3ccc(Cl)cc3Oc3cc(Cl)ccc32)c(=O)[nH]c1C(F)(F)F] | N-(3,6-dichloro-9H-xanthen-9-yl)-2-oxo-6-(trifluoromethyl)-5-vinyl-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 172 | 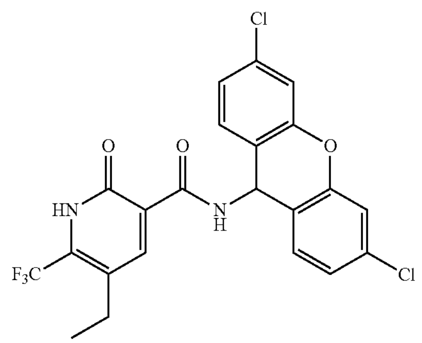 [SMILES: CCc1cc(C(=O)NC2c3ccc(Cl)cc3Oc3cc(Cl)ccc32)c(=O)[nH]c1C(F)(F)F] | N-(3,6-dichloro-9H-xanthen-9-yl)-5-ethyl-2-oxo-6-(trifluoromethyl)-1,2-dihydropyridine-3-carboxamide |
| 173 | 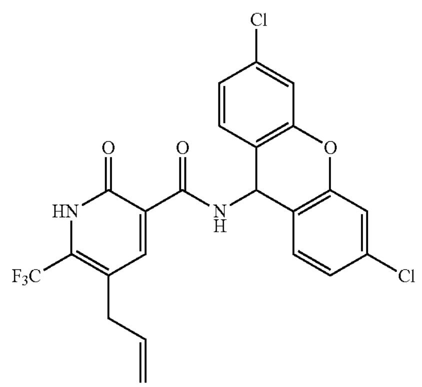 [SMILES: C=CCc1cc(C(=O)NC2c3ccc(Cl)cc3Oc3cc(Cl)ccc32)c(=O)[nH]c1C(F)(F)F] | 5-allyl-N-(3,6-dichloro-9H-xanthen-9-yl)-2-oxo-6-(trifluoromethyl)-1,2-dihydropyridine-3-carboxamide |
| 174 | 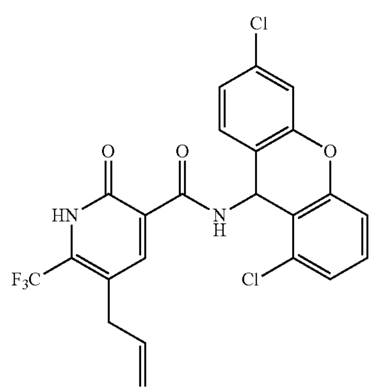 [SMILES: C=CCc1cc(C(=O)NC2c3ccc(Cl)cc3Oc3cccc(Cl)c32)c(=O)[nH]c1C(F)(F)F] | 5-allyl-N-(1,6-dichloro-9H-xanthen-9-yl)-2-oxo-6-(trifluoromethyl)-1,2-dihydropyridine-3-carboxamide |
| 175 | 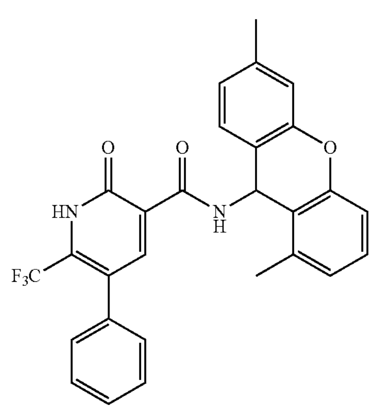 [SMILES: Cc1ccc2c(c1)Oc1cccc(C)c1C2NC(=O)c1cc(-c2ccccc2)c(C(F)(F)F)[nH]c1=O] | N-(1,6-dimethyl-9H-xanthen-9-yl)-2-oxo-5-phenyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 176 | 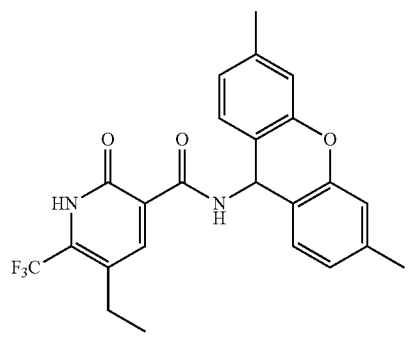 [SMILES: CCc1cc(C(=O)NC2c3ccc(C)cc3Oc3cc(C)ccc32)c(=O)[nH]c1C(F)(F)F] | N-(3,6-dimethyl-9H-xanthen-9-yl)-5-ethyl-2-oxo-6-(trifluoromethyl)-1,2-dihydropyridine-3-carboxamide |
| 177 | 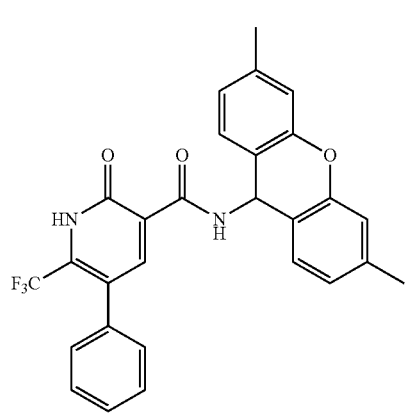 | N-(3,6-dimethyl-9H-xanthen-9-yl)-2-oxo-5-phenyl-6-(trifluoromethyl)-1,2-dihydropyridine-3-carboxamide |
| 178 | 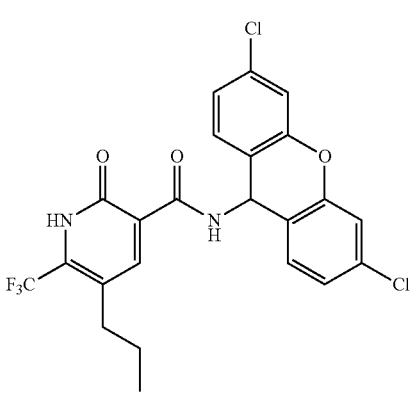 [SMILES: CCCc1cc(C(=O)NC2c3ccc(Cl)cc3Oc3cc(Cl)ccc32)c(=O)[nH]c1C(F)(F)F] | N-(3,6-dichloro-9H-xanthen-9-yl)-2-oxo-5-propyl-6-(trifluoromethyl)-1,2-dihydropyridine-3-carboxamide |
| 179 | 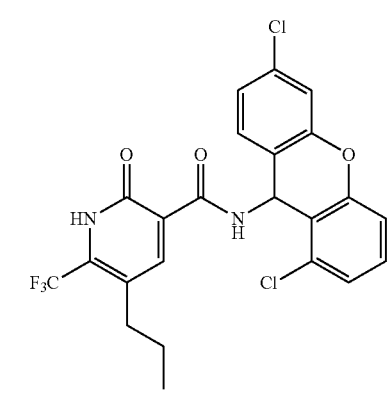 [SMILES: CCCc1cc(C(=O)NC2c3ccc(Cl)cc3Oc3cccc(Cl)c32)c(=O)[nH]c1C(F)(F)F] | N-(1,6-dichloro-9H-xanthen-9-yl)-2-oxo-5-propyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 180 | 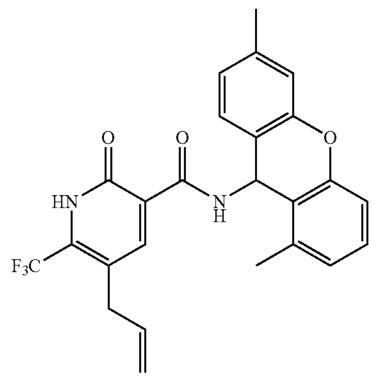 [SMILES: C=CCc1cc(C(=O)NC2c3ccc(C)cc3Oc3cccc(C)c32)c(=O)[nH]c1C(F)(F)F] | 5-allyl-N-(1,6-dimethyl-9H-xanthen-9-yl)-2-oxo-6-(trifluoromethyl)-1,2-dihydropyridine-3-carboxamide |
| 181 | 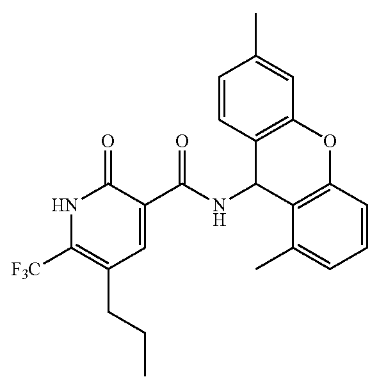 | N-(1,6-dimethyl-9H-xanthen-9-yl)-2-oxo-5-propyl-6-(trifluoromethyl)-1,2-dihydropyridine-3-carboxamide |
| 182 | 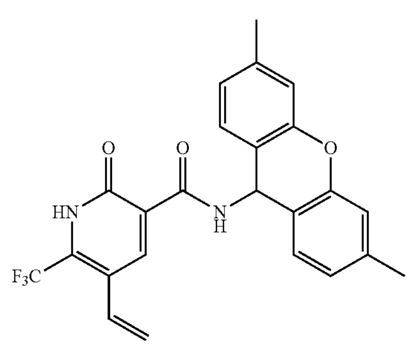 [SMILES: C=Cc1cc(C(=O)NC2c3ccc(C)cc3Oc3cc(C)ccc32)c(=O)[nH]c1C(F)(F)F] | N-(3,6-dimethyl-9H-xanthen-9-yl)-2-oxo-6-(trifluoromethyl)-5-vinyl-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 183 | 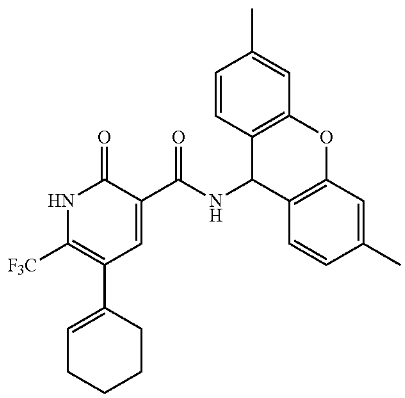 | 5-(cyclohex-1-en-1-yl)-N-(3,6-dimethyl-9H-xanthen-9-yl)-2-oxo-6-(trifluoromethyl)-1,2-dihydropyridine-3-carboxamide |
| 184 | 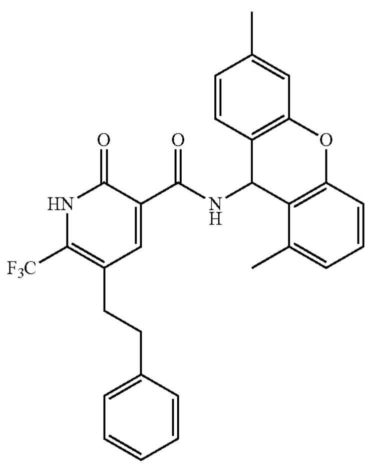 [SMILES: Cc1ccc2c(c1)Oc1cccc(C)c1C2NC(=O)c1cc(CCc2ccccc2)c(C(F)(F)F)[nH]c1=O] | N-(1,6-dimethyl-9H-xanthen-9-yl)-2-oxo-5-phenethyl-6-(trifluoromethyl)-1,2-dihydropyridine-3-carboxamide |
| 185 | 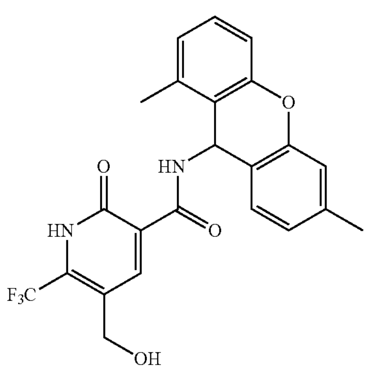 [SMILES: Cc1ccc2c(c1)Oc1cccc(C)c1C2NC(=O)c1cc(CO)c(C(F)(F)F)[nH]c1=O] | N-(1,6-dimethyl-9H-xanthen-9-yl)-5-(hydroxymethyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 186 | 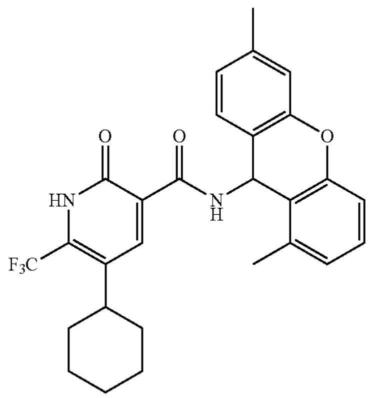 | 5-cyclohexyl-N-(1,6-dimethyl-9H-xanthen-9-yl)-2-oxo-6-(trifluoromethyl)-1,2-dihydropyridine-3-carboxamide |
| 187 | 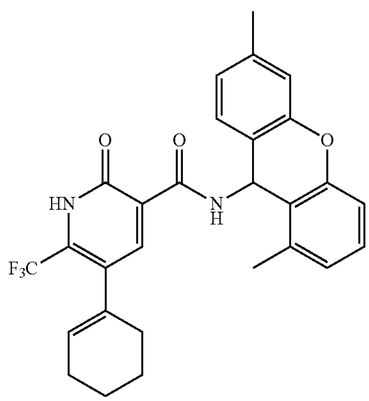 | 5-(cyclohex-1-en-1-yl)-N-(1,6-dimethyl-9H-xanthen-9-yl)-2-oxo-6-(trifluoromethyl)-1,2-dihydropyridine-3-carboxamide |
| 188 | 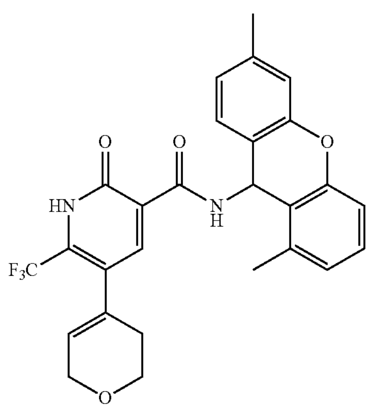 | 5-(3,6-dihydro-2H-pyran-4-yl)-N-(1,6-dimethyl-9H-xanthen-9-yl)-2-oxo-6-(trifluoromethyl)-1,2-dihydropyridine-3-carboxamide |
| 189 | 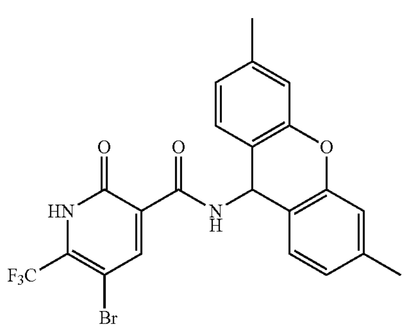 [SMILES: Cc1ccc2c(c1)Oc1cc(C)ccc1C2NC(=O)c1cc(Br)c(C(F)(F)F)[nH]c1=O] | 5-bromo-N-(3,6-dimethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 190 | 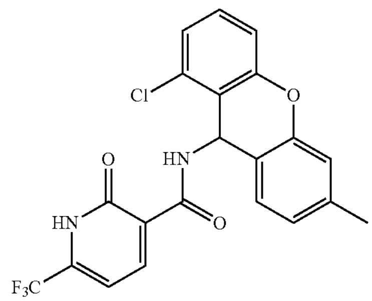 [SMILES: Cc1ccc2c(c1)Oc1cccc(Cl)c1C2NC(=O)c1ccc(C(F)(F)F)[nH]c1=O] | N-(1-chloro-6-methyl-9H-xanthen-9-yl)-2-oxo-6-(trifluoromethyl)-1,2-dihydropyridine-3-carboxamide |
| 191 | 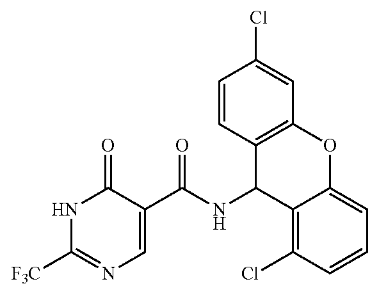 | N-(1,6-dichloro-9H-xanthen-9-yl)-6-oxo-2-(trifluoromethyl)-1,6-dihydropyrimidine-5-carboxamide |
| 192 | 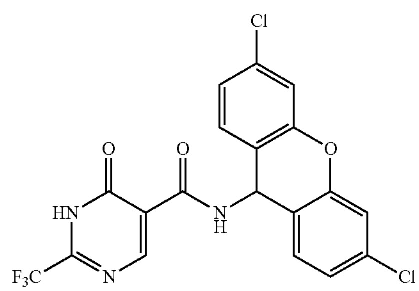 [SMILES: O=C(NC1c2ccc(Cl)cc2Oc2cc(Cl)ccc21)c1cnc(C(F)(F)F)[nH]c1=O] | N-(3,6-dichloro-9H-xanthen-9-yl)-6-oxo-2-(trifluoromethyl)-1,6-dihydropyrimidine-5-carboxamide |
| 193 | 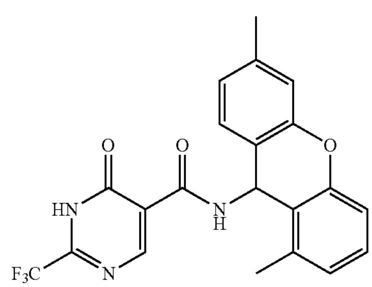 | N-(1,6-dimethyl-9H-xanthen-9-yl)-6-oxo-2-(trifluoromethyl)-1,6-dihydropyrimidine-5-carboxamide |
| 194 | 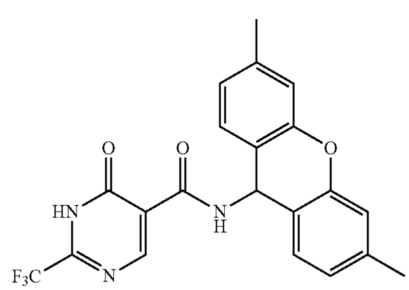 | N-(3,6-dimethyl-9H-xanthen-9-yl)-6-oxo-2-(trifluoromethyl)-1,6-dihydropyrimidine-5-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 195 | 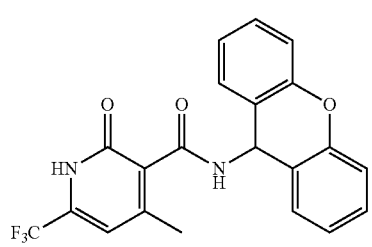 | 4-methyl-2-oxo-6-(trifluoromethyl)-N-(9H-xanthen-9-yl)-1,2-dihydropyridine-3-carboxamide |
| 196 | 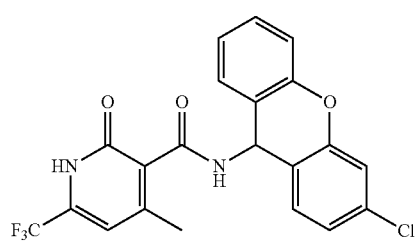 [SMILES: Cc1cc(C(F)(F)F)[nH]c(=O)c1C(=O)NC1c2ccccc2Oc2cc(Cl)ccc21] | N-(3-chloro-9H-xanthen-9-yl)-4-methyl-2-oxo-6-(trifluoromethyl)-1,2-dihydropyridine-3-carboxamide |
| 197 | 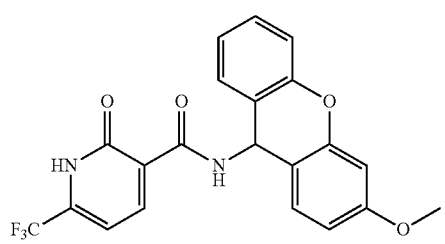 | N-(3-methoxy-9H-xanthen-9-yl)-2-oxo-6-(trifluoromethyl)-1,2-dihydropyridine-3-carboxamide |
| 198 | 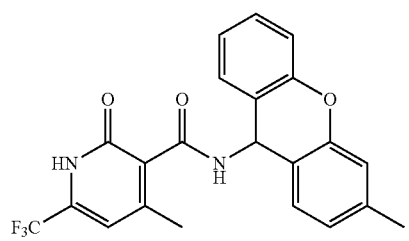 | 4-methyl-N-(3-methyl-9H-xanthen-9-yl)-2-oxo-6-(trifluoromethyl)-1,2-dihydropyridine-3-carboxamide |
| 199 | 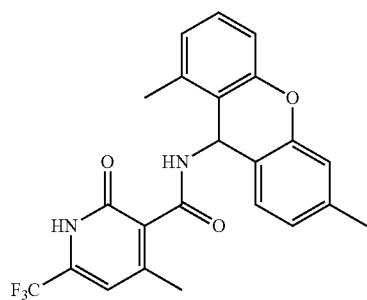 [SMILES: Cc1ccc2c(c1)Oc1cccc(C)c1C2NC(=O)c1c(C)cc(C(F)(F)F)[nH]c1=O] | N-(1,6-dimethyl-9H-xanthen-9-yl)-4-methyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 200 | 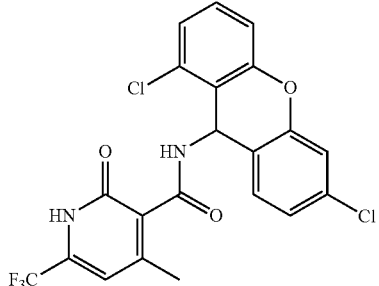 | N-(1,6-dichloro-9H-xanthen-9-yl)-4-methyl-2-oxo-6-(trifluoromethyl)-1,2-dihydropyridine-3-carboxamide |
| 201 | 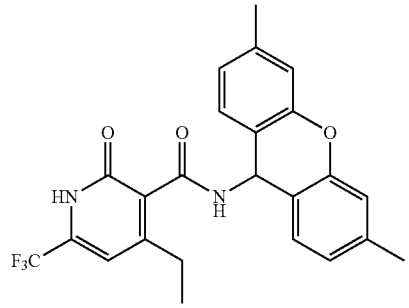 [SMILES: CCc1cc(C(F)(F)F)[nH]c(=O)c1C(=O)NC1c2ccc(C)cc2Oc2cc(C)ccc21] | N-(3,6-dimethyl-9H-xanthen-9-yl)-4-ethyl-2-oxo-6-(trifluoromethyl)-1,2-dihydropyridine-3-carboxamide |
| 202 | 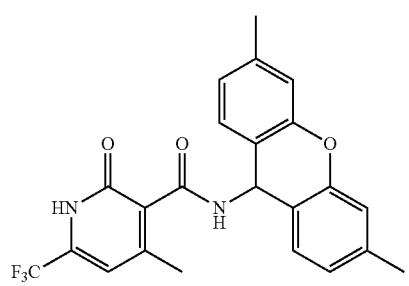 [SMILES: Cc1ccc2c(c1)Oc1cc(C)ccc1C2NC(=O)c1c(C)cc(C(F)(F)F)[nH]c1=O] | N-(3,6-dimethyl-9H-xanthen-9-yl)-4-methyl-2-oxo-6-(trifluoromethyl)-1,2-dihydropyridine-3-carboxamide |
| 203 | 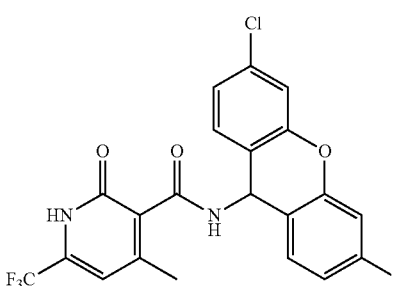 | N-(3,6-dichloro-9H-xanthen-9-yl)-4-methyl-2-oxo-6-(trifluoromethyl)-1,2-dihydropyridine-3-carboxamide |
| 204 | 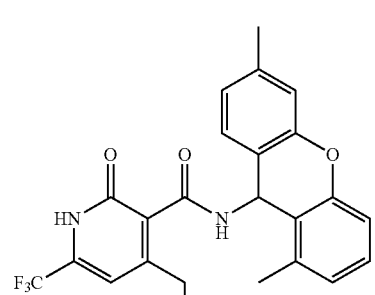 | N-(1,6-dimethyl-9H-xanthen-9-yl)-4-ethyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 205 | 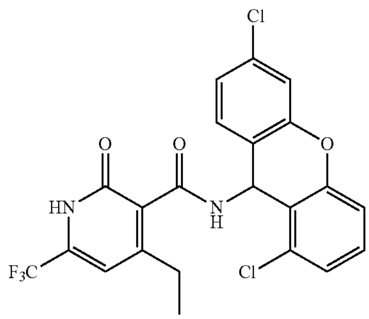 [SMILES: CCc1cc(C(F)(F)F)[nH]c(=O)c1C(=O)NC1c2ccc(Cl)cc2Oc2cccc(Cl)c21] | N-(1,6-dichloro-9H-xanthen-9-yl)-4-ethyl-2-oxo-6-(trifluoromethyl)-1,2-dihydropyridine-3-carboxamide |
| 206 | 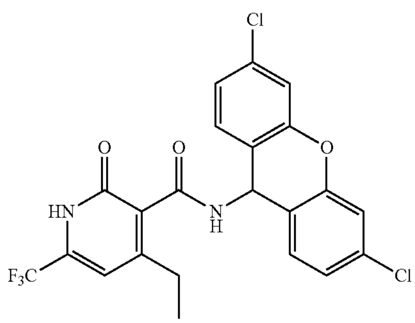 [SMILES: CCc1cc(C(F)(F)F)[nH]c(=O)c1C(=O)NC1c2ccc(Cl)cc2Oc2cc(Cl)ccc21] | N-(3,6-dichloro-9H-xanthen-9-yl)-4-ethyl-2-oxo-6-(trifluoromethyl)-1,2-dihydropyridine-3-carboxamide |
| 207 | 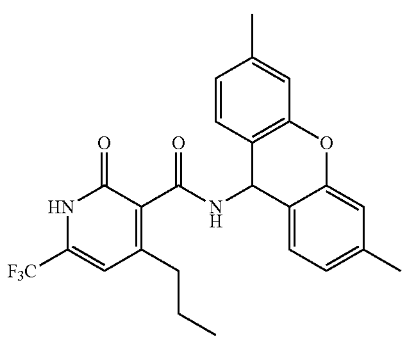 [SMILES: CCCc1cc(C(F)(F)F)[nH]c(=O)c1C(=O)NC1c2ccc(C)cc2Oc2cc(C)ccc21] | N-(3,6-dimethyl-9H-xanthen-9-yl)-2-oxo-4-propyl-6-(trifluoromethyl)-1,2-dihydropyridine-3-carboxamide |
| 208 | 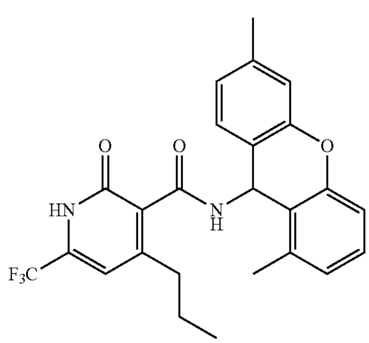 [SMILES: CCCc1cc(C(F)(F)F)[nH]c(=O)c1C(=O)NC1c2ccc(C)cc2Oc2cccc(C)c21] | N-(1,6-dimethyl-9H-xanthen-9-yl)-2-oxo-4-propyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 209 | 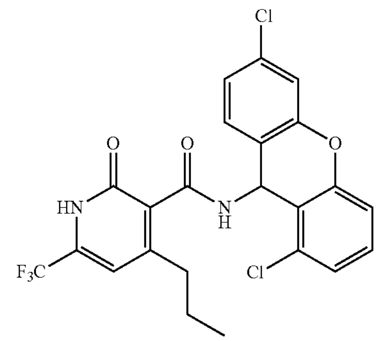 [SMILES: CCCc1cc(C(F)(F)F)[nH]c(=O)c1C(=O)NC1c2ccc(Cl)cc2Oc2cccc(Cl)c21] | N-(1,6-dichloro-9H-xanthen-9-yl)-2-oxo-4-propyl-6-(trifluoromethyl)-1,2-dihydropyridine-3-carboxamide |
| 210 | 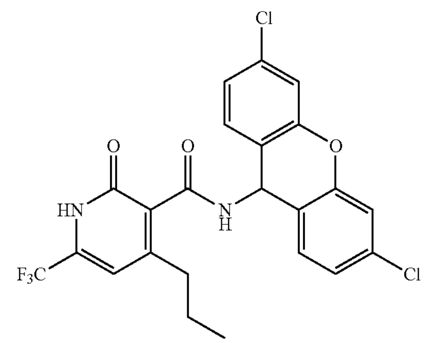 [SMILES: CCCc1cc(C(F)(F)F)[nH]c(=O)c1C(=O)NC1c2ccc(Cl)cc2Oc2cc(Cl)ccc21] | N-(3,6-dichloro-9H-xanthen-9-yl)-2-oxo-4-propyl-6-(trifluoromethyl)-1,2-dihydropyridine-3-carboxamide |
| 211 | 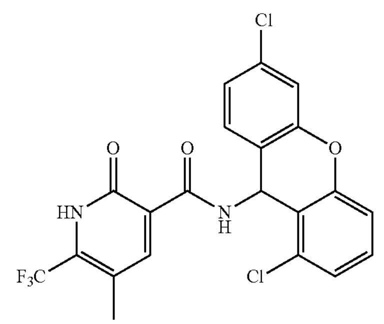 [SMILES: Cc1cc(C(=O)NC2c3ccc(Cl)cc3Oc3cccc(Cl)c32)c(=O)[nH]c1C(F)(F)F] | N-(1,6-dichloro-9H-xanthen-9-yl)-5-methyl-2-oxo-6-(trifluoromethyl)-1,2-dihydropyridine-3-carboxamide |
| 212 | 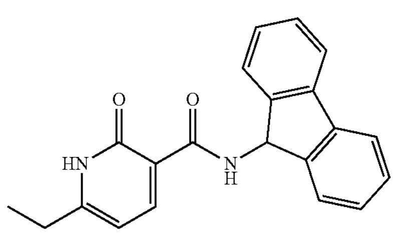 [SMILES: CCc1ccc(C(=O)NC2c3ccccc3-c3ccccc32)c(=O)[nH]1] | 6-ethyl-N-(9H-fluoren-9-yl)-2-oxo-1,2-dihydropyridine-3-carboxamide |
| 213 | 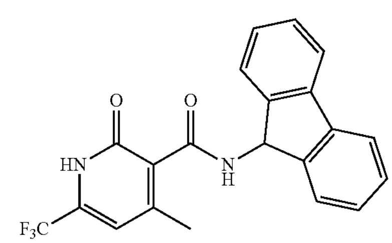 [SMILES: Cc1cc(C(F)(F)F)[nH]c(=O)c1C(=O)NC1c2ccccc2-c2ccccc21] | N-(9H-fluoren-9-yl)-4-methyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 214 | 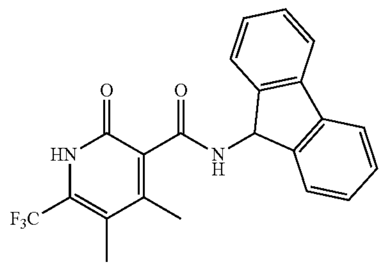 [SMILES: Cc1c(C(F)(F)F)[nH]c(=O)c(C(=O)NC2c3ccccc3-c3ccccc32)c1C] | N-(9H-fluoren-9-yl)-4,5-dimethyl-2-oxo-6-(trifluoromethyl)-1,2-dihydropyridine-3-carboxamide |
| 215 | 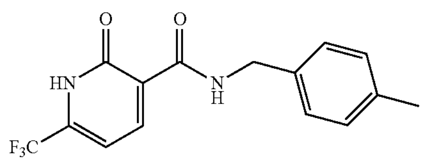 [SMILES: Cc1ccc(CNC(=O)c2ccc(C(F)(F)F)[nH]c2=O)cc1] | N-(4-methylbenzyl)-2-oxo-6-(trifluoromethyl)-1,2-dihydropyridine-3-carboxamide |
| 216 | 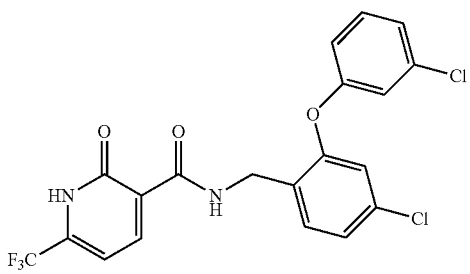 [SMILES: O=C(NCc1ccc(Cl)cc1Oc1cccc(Cl)c1)c1ccc(C(F)(F)F)[nH]c1=O] | N-(4-chloro-2-(3-chlorophenoxy)benzyl)-2-oxo-6-(trifluoromethyl)-1,2-dihydropyridine-3-carboxamide |
| 217 | 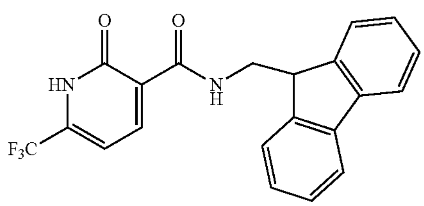 [SMILES: O=C(NCC1c2ccccc2-c2ccccc21)c1ccc(C(F)(F)F)[nH]c1=O] | N-((9H-fluoren-9-yl)methyl)-2-oxo-6-(trifluoromethyl)-1,2-dihydropyridine-3-carboxamide |
| 218 | 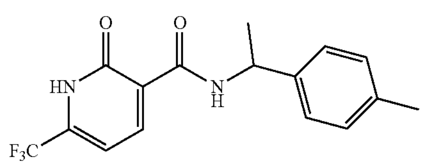 [SMILES: Cc1ccc(C(C)NC(=O)c2ccc(C(F)(F)F)[nH]c2=O)cc1] | 2-oxo-N-(1-(p-tolyl)ethyl)-6-(trifluoromethyl)-1,2-dihydropyridine-3-carboxamide |
| 219 | 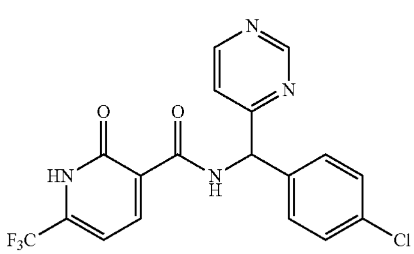 | N-((4-chlorophenyl)(pyrimidin-4-yl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 220 | 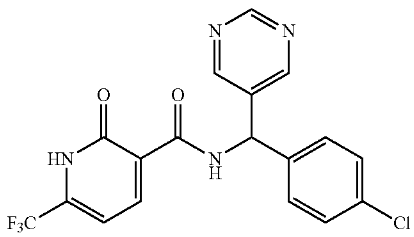 [SMILES: O=C(NC(c1ccc(Cl)cc1)c1cncnc1)c1ccc(C(F)(F)F)[nH]c1=O] | N-((4-chlorophenyl)(pyrimidin-5-yl)methyl)-2-oxo-6-(trifluoromethyl)-1,2-dihydropyridine-3-carboxamide |
| 221 | 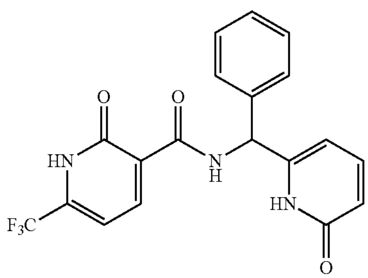 [SMILES: O=C(NC(c1ccccc1)c1cccc(=O)[nH]1)c1ccc(C(F)(F)F)[nH]c1=O] | 2-oxo-N-((6-oxo-1,6-dihydropyridin-2-yl)(phenyl)methyl)-6-(trifluoromethyl)-1,2-dihydropyridine-3-carboxamide |
| 222 | 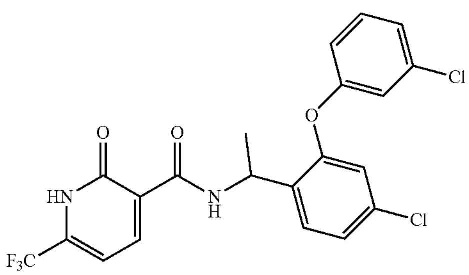 [SMILES: CC(NC(=O)c1ccc(C(F)(F)F)[nH]c1=O)c1ccc(Cl)cc1Oc1cccc(Cl)c1] | N-(1-(4-chloro-2-(3-chlorophenoxy)phenyl)ethyl)-2-oxo-6-(trifluoromethyl)-1,2-dihydropyridine-3-carboxamide |
| 223 | 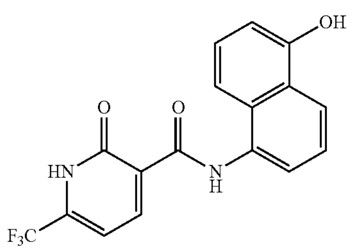 [SMILES: O=C(Nc1cccc2c(O)cccc12)c1ccc(C(F)(F)F)[nH]c1=O] | N-(5-hydroxynaphthalen-1-yl)-2-oxo-6-(trifluoromethyl)-1,2-dihydropyridine-3-carboxamide |
| 224 | 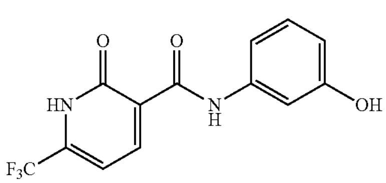 [SMILES: O=C(Nc1cccc(O)c1)c1ccc(C(F)(F)F)[nH]c1=O] | N-(3-hydroxyphenyl)-2-oxo-6-(trifluoromethyl)-1,2-dihydropyridine-3-carboxamide |
| 225 | 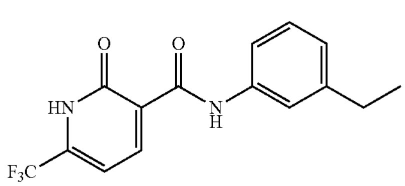 [SMILES: CCc1cccc(NC(=O)c2ccc(C(F)(F)F)[nH]c2=O)c1] | N-(3-ethylphenyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 226 | 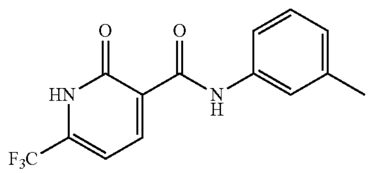 [SMILES: Cc1cccc(NC(=O)c2ccc(C(F)(F)F)[nH]c2=O)c1] | 2-oxo-N-(m-tolyl)-6-(trifluoromethyl)-1,2-dihydropyridine-3-carboxamide |
| 227 | 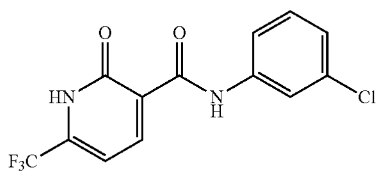 | N-(3-chlorophenyl)-2-oxo-6-(trifluoromethyl)-1,2-dihydropyridine-3-carboxamide |
| 228 | 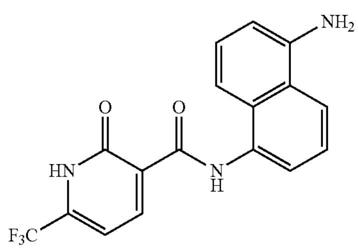 [SMILES: Nc1cccc2c(NC(=O)c3ccc(C(F)(F)F)[nH]c3=O)cccc12] | N-(5-aminonaphthalen-1-yl)-2-oxo-6-(trifluoromethyl)-1,2-dihydropyridine-3-carboxamide |
| 229 | 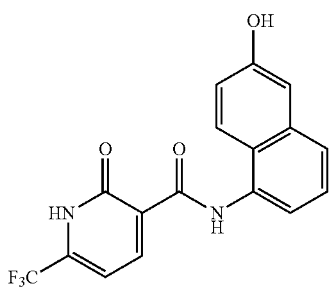 | N-(6-hydroxynaphthalen-1-yl)-2-oxo-6-(trifluoromethyl)-1,2-dihydropyridine-3-carboxamide |
| 230 | 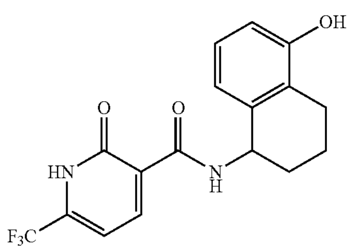 [SMILES: O=C(NC1CCCc2c(O)cccc21)c1ccc(C(F)(F)F)[nH]c1=O] | N-(5-hydroxy-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 231 | 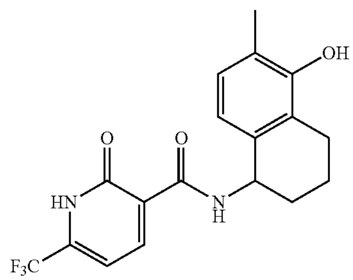 [SMILES: Cc1ccc2c(c1O)CCCC2NC(=O)c1ccc(C(F)(F)F)[nH]c1=O] | N-(5-hydroxy-6-methyl-1,2,3,4-tetrahydronaphthalen-1-yl)-2-oxo-6-(trifluoromethyl)-1,2-dihydropyridine-3-carboxamide |
| 232 | 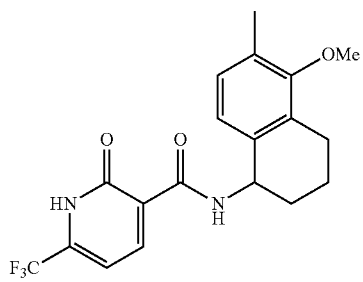 [SMILES: COc1c(C)ccc2c1CCCC2NC(=O)c1ccc(C(F)(F)F)[nH]c1=O] | N-(5-methoxy-6-methyl-1,2,3,4-tetrahydronaphthalen-1-yl)-2-oxo-6-(trifluoromethyl)-1,2-dihydropyridine-3-carboxamide |
| 233 | 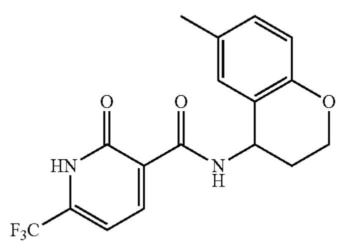 [SMILES: Cc1ccc2c(c1)C(NC(=O)c1ccc(C(F)(F)F)[nH]c1=O)CCO2] | N-(6-methylchroman-4-yl)-2-oxo-6-(trifluoromethyl)-1,2-dihydropyridine-3-carboxamide |
| 234 | 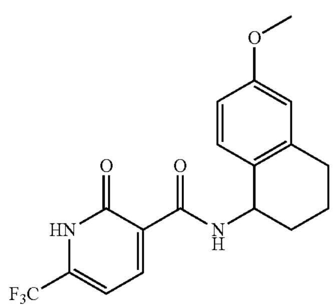 [SMILES: COc1ccc2c(c1)CCCC2NC(=O)c1ccc(C(F)(F)F)[nH]c1=O] | N-(6-methoxy-1,2,3,4-tetrahydronaphthalen-1-yl)-2-oxo-6-(trifluoromethyl)-1,2-dihydropyridine-3-carboxamide |
| 235 | 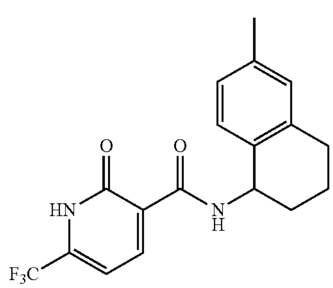 [SMILES: Cc1ccc2c(c1)CCCC2NC(=O)c1ccc(C(F)(F)F)[nH]c1=O] | N-(6-methyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 236 | 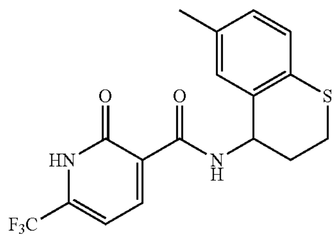 [SMILES: Cc1ccc2c(c1)C(NC(=O)c1ccc(C(F)(F)F)[nH]c1=O)CCS2] | N-(6-methylthiochroman-4-yl)-2-oxo-6-(trifluoromethyl)-1,2-dihydropyridine-3-carboxamide |
| 237 | 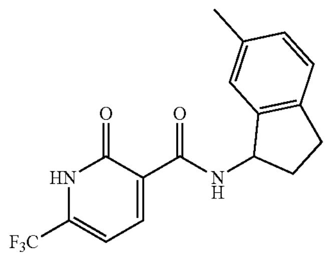 [SMILES: Cc1ccc2c(c1)C(NC(=O)c1ccc(C(F)(F)F)[nH]c1=O)CC2] | N-(6-methyl-2,3-dihydro-1H-inden-1-yl)-2-oxo-6-(trifluoromethyl)-1,2-dihydropyridine-3-carboxamide |
| 238 | 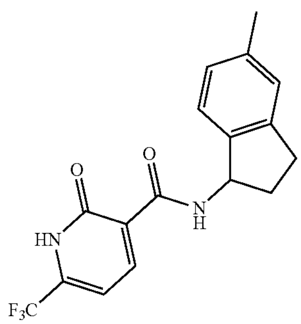 [SMILES: Cc1ccc2c(c1)CCC2NC(=O)c1ccc(C(F)(F)F)[nH]c1=O] | N-(5-methyl-2,3-dihydro-1H-inden-1-yl)-2-oxo-6-(trifluoromethyl)-1,2-dihydropyridine-3-carboxamide |
| 239 | 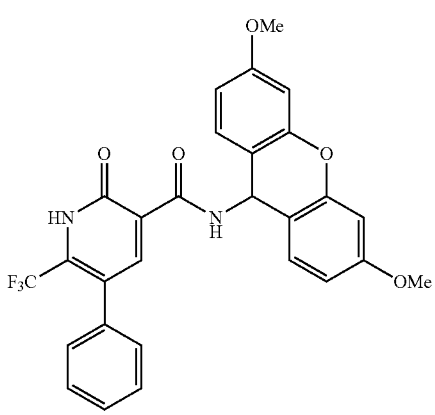 [SMILES: COc1ccc2c(c1)Oc1cc(OC)ccc1C2NC(=O)c1cc(-c2ccccc2)c(C(F)(F)F)[nH]c1=O] | N-(3,6-dimethoxy-9H-xanthen-9-yl)-2-oxo-5-phenyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 240 | 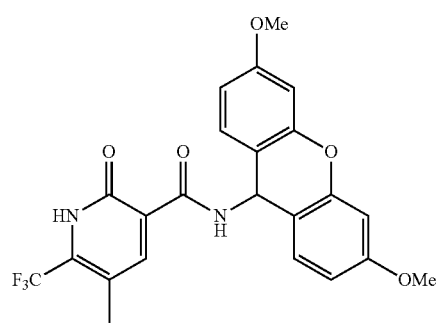 [SMILES: COc1ccc2c(c1)Oc1cc(OC)ccc1C2NC(=O)c1cc(C)c(C(F)(F)F)[nH]c1=O] | N-(3,6-dimethoxy-9H-xanthen-9-yl)-5-methyl-2-oxo-6-(trifluoromethyl)-1,2-dihydropyridine-3-carboxamide |
| 241 | 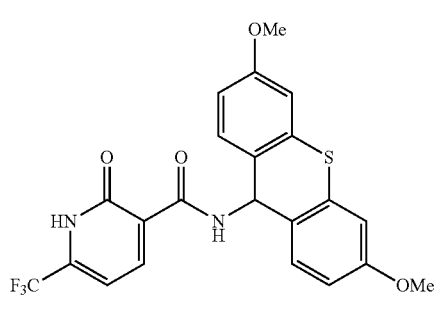 [SMILES: COc1ccc2c(c1)Sc1cc(OC)ccc1C2NC(=O)c1ccc(C(F)(F)F)[nH]c1=O] | N-(3,6-dimethoxy-9H-thioxanthen-9-yl)-2-oxo-6-(trifluoromethyl)-1,2-dihydropyridine-3-carboxamide |
| 242 | 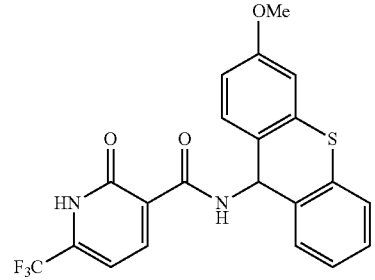 [SMILES: COc1ccc2c(c1)Sc1ccccc1C2NC(=O)c1ccc(C(F)(F)F)[nH]c1=O] | N-(3-methoxy-9H-thioxanthen-9-yl)-2-oxo-6-(trifluoromethyl)-1,2-dihydropyridine-3-carboxamide |
| 243 | 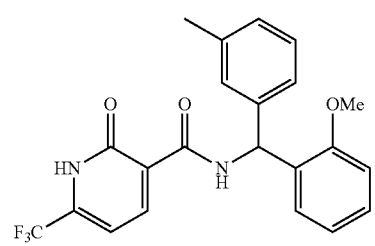 | N-((2-methoxyphenyl)(m-tolyl)methyl)-2-oxo-6-(trifluoromethyl)-1,2-dihydropyridine-3-carboxamide |
| 244 | 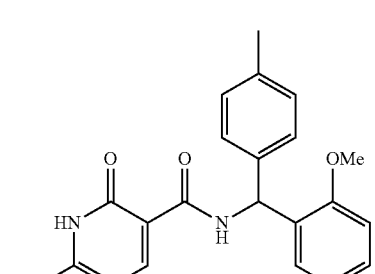 | N-((2-methoxyphenyl)(p-tolyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 245 | 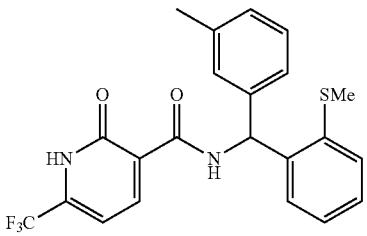 | N-((2-(methylthio)phenyl)(m-tolyl)methyl)-2-oxo-6-(trifluoromethyl)-1,2-dihydropyridine-3-carboxamide |
| 246 | 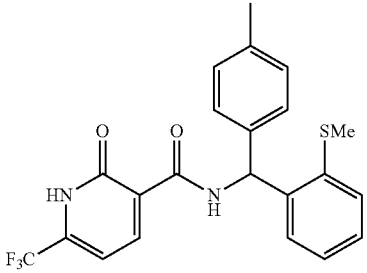 | N-((2-(methylthio)phenyl)(p-tolyl)methyl)-2-oxo-6-(trifluoromethyl)-1,2-dihydropyridine-3-carboxamide |
| 247 | 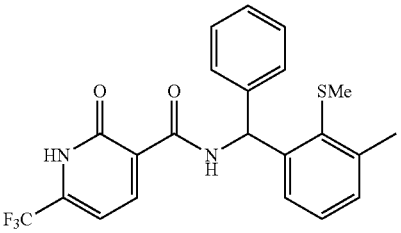 [SMILES: CSc1c(C)cccc1C(NC(=O)c1ccc(C(F)(F)F)[nH]c1=O)c1ccccc1] | N-((3-methyl-2-(methylthio)phenyl)(phenyl)methyl)-2-oxo-6-(trifluoromethyl)-1,2-dihydropyridine-3-carboxamide |
| 248 | 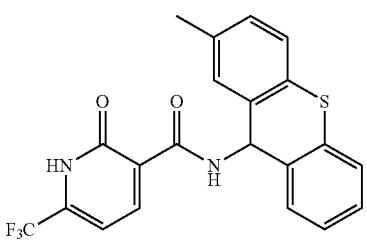 | N-(2-methyl-9H-thioxanthen-9-yl)-2-oxo-6-(trifluoromethyl)-1,2-dihydropyridine-3-carboxamide |
| 249 | 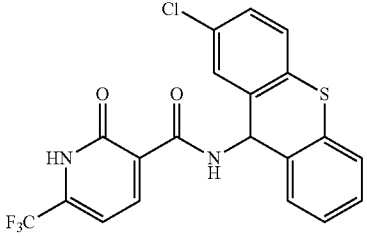 | N-(2-chloro-9H-thioxanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 250 | 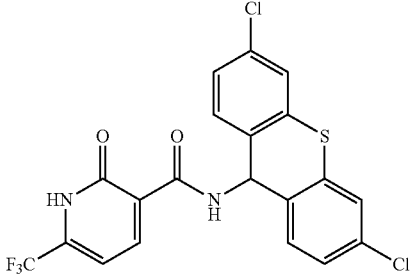 | N-(3,6-dichloro-9H-thioxanthen-9-yl)-2-oxo-6-(trifluoromethyl)-1,2-dihydropyridine-3-carboxamide |
| 251 | 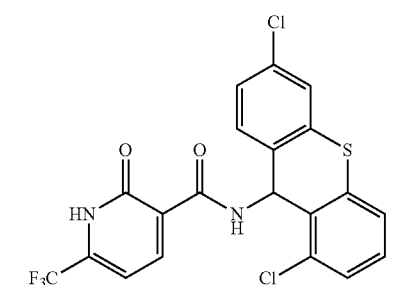 | N-(1,6-dichloro-9H-thioxanthen-9-yl)-2-oxo-6-(trifluoromethyl)-1,2-dihydropyridine-3-carboxamide |
| 252 | 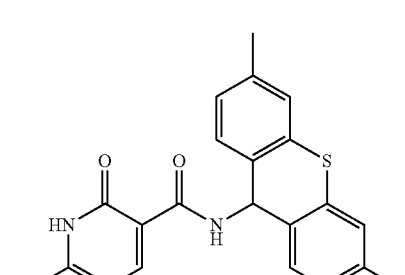 | N-(3,6-dimethyl-9H-thioxanthen-9-yl)-2-oxo-6-(trifluoromethyl)-1,2-dihydropyridine-3-carboxamide |
| 253 | 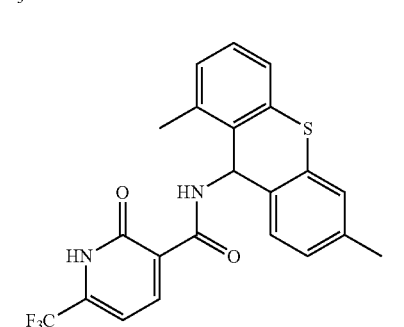 | N-(1,6-dimethyl-9H-thioxanthen-9-yl)-2-oxo-6-(trifluoromethyl)-1,2-dihydropyridine-3-carboxamide |
| 254 | 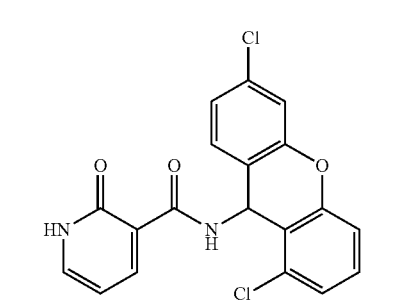 [SMILES: O=C(NC1c2ccc(Cl)cc2Oc2cccc(Cl)c21)c1ccc[nH]c1=O] | N-(1,6-dichloro-9H-xanthen-9-yl)-2-oxo-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 255 | 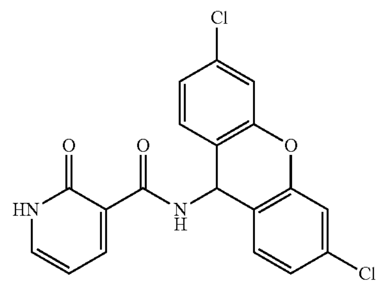 [SMILES: O=C(NC1c2ccc(Cl)cc2Oc2cc(Cl)ccc21)c1ccc[nH]c1=O] | N-(3,6-dichloro-9H-xanthen-9-yl)-2-oxo-1,2-dihydropyridine-3-carboxamide |
| 256 | 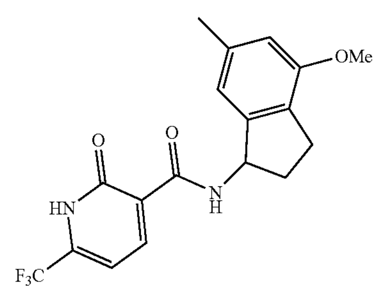 [SMILES: COc1cc(C)cc2c1CCC2NC(=O)c1ccc(C(F)(F)F)[nH]c1=O] | N-(4-methoxy-6-methyl-2,3-dihydro-1H-inden-1-yl)-2-oxo-6-(trifluoromethyl)-1,2-dihydropyridine-3-carboxamide |
| 257 | 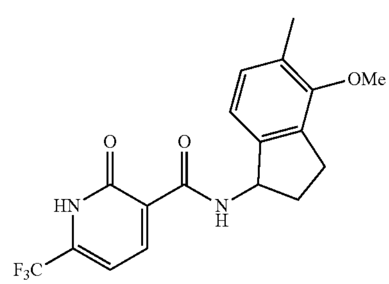 [SMILES: COc1c(C)ccc2c1CCC2NC(=O)c1ccc(C(F)(F)F)[nH]c1=O] | N-(4-methoxy-5-methyl-2,3-dihydro-1H-inden-1-yl)-2-oxo-6-(trifluoromethyl)-1,2-dihydropyridine-3-carboxamide |
| 258 | 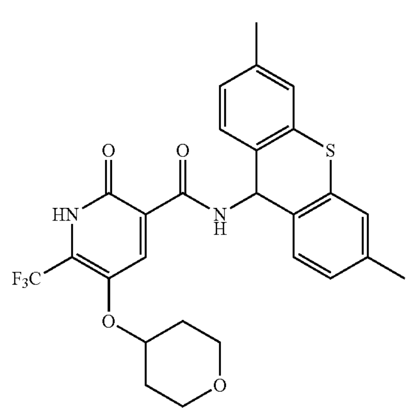 [SMILES: Cc1ccc2c(c1)Sc1cc(C)ccc1C2NC(=O)c1cc(OC2CCOCC2)c(C(F)(F)F)[nH]c1=O] | N-(3,6-dimethyl-9H-thioxanthen-9-yl)-2-oxo-5-((tetrahydro-2H-pyran-4-yl)oxy)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 259 | 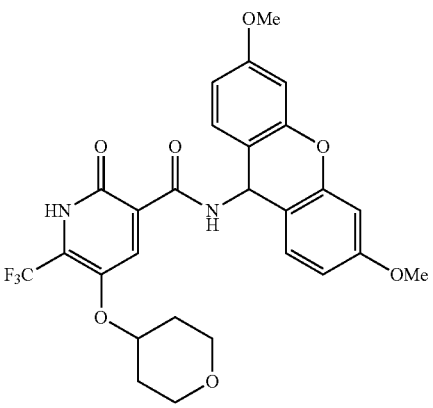 [SMILES: COc1ccc2c(c1)Oc1cc(OC)ccc1C2NC(=O)c1cc(OC2CCOCC2)c(C(F)(F)F)[nH]c1=O] | N-(3,6-dimethoxy-9H-xanthen-9-yl)-2-oxo-5-((tetrahydro-2H-pyran-4-yl)oxy)-6-(trifluoromethyl)-1,2-dihydropyridine-3-carboxamide |
| 260 | 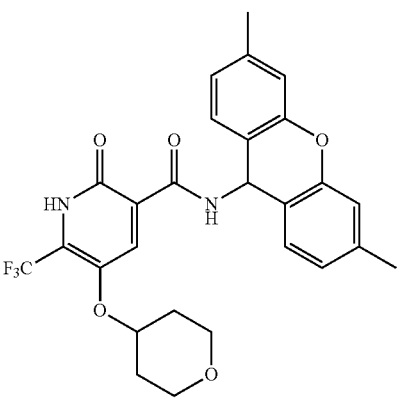 | N-(3,6-dimethyl-9H-xanthen-9-yl)-2-oxo-5-((tetrahydro-2H-pyran-4-yl)oxy)-6-(trifluoromethyl)-1,2-dihydropyridine-3-carboxamide |
| 261 | 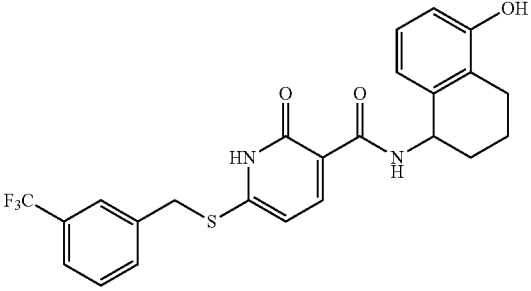 [SMILES: O=C(NC1CCCc2c(O)cccc21)c1ccc(SCc2cccc(C(F)(F)F)c2)[nH]c1=O] | N-(5-hydroxy-1,2,3,4-tetrahydronaphthalen-1-yl)-2-oxo-6-((3-(trifluoromethyl)benzyl)thio)-1,2-dihydropyridine-3-carboxamide |
| 262 | 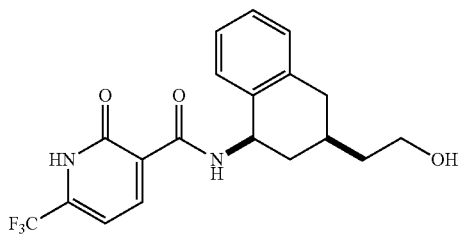 | N-((1R,3R)-3-(2-hydroxyethyl)-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 263 | 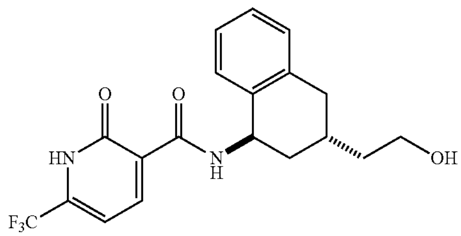 | N-((1R,3S)-3-(2-hydroxyethyl)-1,2,3,4-tetrahydronaphthalen-1-yl)-2-oxo-6-(trifluoromethyl)-1,2-dihydropyridine-3-carboxamide |
| 264 | 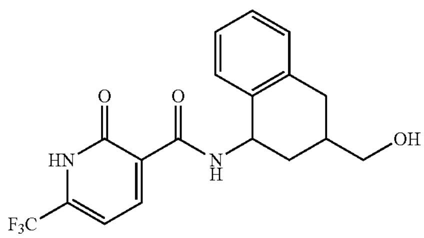 | N-(3-(hydroxymethyl)-1,2,3,4-tetrahydronaphthalen-1-yl)-2-oxo-6-(trifluoromethyl)-1,2-dihydropyridine-3-carboxamide |
| 265 | 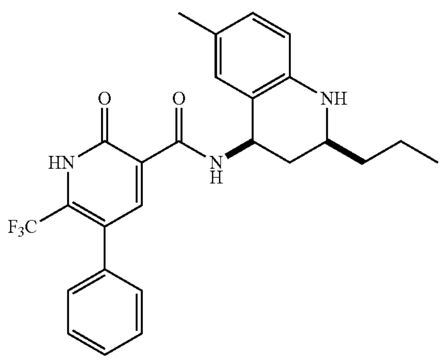 | N-((2S,4R)-6-methyl-2-propyl-1,2,3,4-tetrahydroquinolin-4-yl)-2-oxo-5-phenyl-6-(trifluoromethyl)-1,2-dihydropyridine-3-carboxamide |
| 266 | 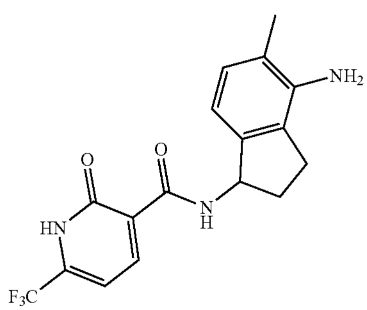 [SMILES: Cc1ccc2c(c1N)CCC2NC(=O)c1ccc(C(F)(F)F)[nH]c1=O] | N-(4-amino-5-methyl-2,3-dihydro-1H-inden-1-yl)-2-oxo-6-(trifluoromethyl)-1,2-dihydropyridine-3-carboxamide |
| 267 | 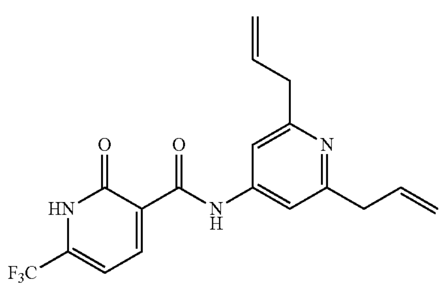 | N-(2,6-diallylpyridin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 268 | 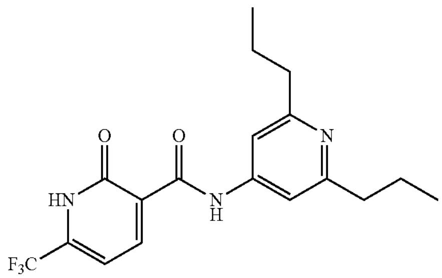 [SMILES: CCCc1cc(NC(=O)c2ccc(C(F)(F)F)[nH]c2=O)cc(CCC)n1] | N-(2,6-dipropylpyridin-4-yl)-2-oxo-6-(trifluoromethyl)-1,2-dihydropyridine-3-carboxamide |
| 269 | 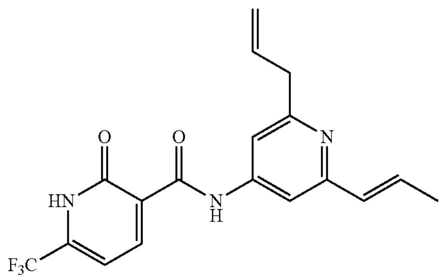 [SMILES: C=CCc1cc(NC(=O)c2ccc(C(F)(F)F)[nH]c2=O)cc(/C=C/C)n1] | (E)-N-(2-allyl-6-(prop-1-en-1-yl)pyridin-4-yl)-2-oxo-6-(trifluoromethyl)-1,2-dihydropyridine-3-carboxamide |
| 270 | 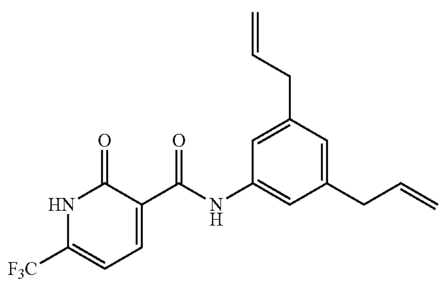 [SMILES: C=CCc1cc(CC=C)cc(NC(=O)c2ccc(C(F)(F)F)[nH]c2=O)c1] | N-(3,5-diallylphenyl)-2-oxo-6-(trifluoromethyl)-1,2-dihydropyridine-3-carboxamide |
| 271 | 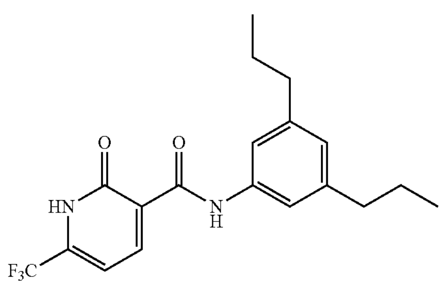 | N-(3,5-dipropylphenyl)-2-oxo-6-(trifluoromethyl)-1,2-dihydropyridine-3-carboxamide |
| 272 | 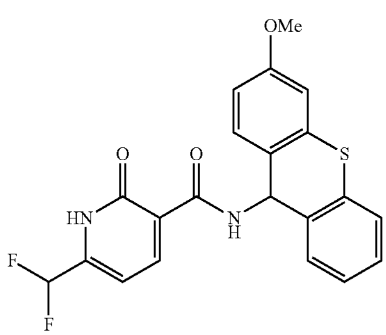 [SMILES: COc1ccc2c(c1)Sc1ccccc1C2NC(=O)c1ccc(C(F)F)[nH]c1=O] | 6-(difluoromethyl)-N-(3-methoxy-9H-thioxanthen-9-yl)-2-oxo-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 273 | 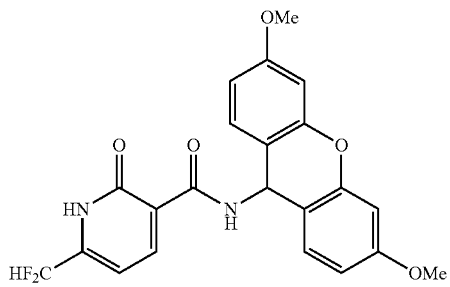 | 6-(difluoromethyl)-N-(3,6-dimethoxy-9H-xanthen-9-yl)-2-oxo-1,2-dihydropyridine-3-carboxamide |
| 274 | 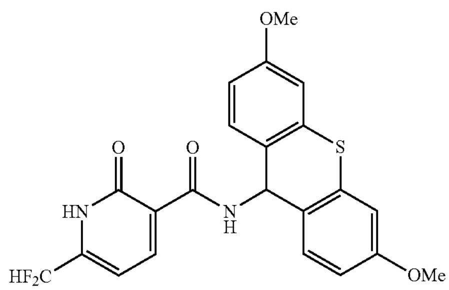 | 6-(difluoromethyl)-N-(3,6-dimethoxy-9H-thioxanthen-9-yl)-2-oxo-1,2-dihydropyridine-3-carboxamide |
| 275 | 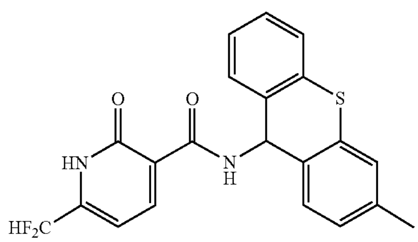 | 6-(difluoromethyl)-N-(3-methyl-9H-thioxanthen-9-yl)-2-oxo-1,2-dihydropyridine-3-carboxamide |
| 276 | 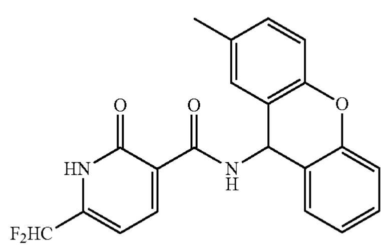 | 6-(difluoromethyl)-N-(2-methyl-9H-xanthen-9-yl)-2-oxo-1,2-dihydropyridine-3-carboxamide |
| 277 | 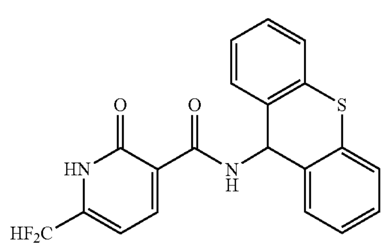 | 6-(difluoromethyl)-2-oxo-N-(9H-thioxanthen-9-yl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 278 | 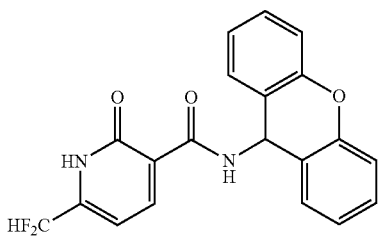 | 6-(difluoromethyl)-2-oxo-N-(9H-xanthen-9-yl)-1,2-dihydropyridine-3-carboxamide |
| 279 | 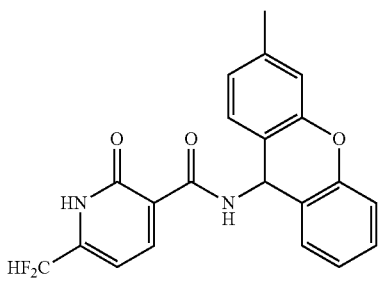 | 6-(difluoromethyl)-N-(3-methyl-9H-xanthen-9-yl)-2-oxo-1,2-dihydropyridine-3-carboxamide |
| 280 | 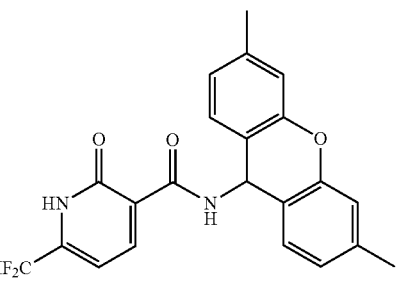 | 6-(difluoromethyl)-N-(3,6-dimethyl-9H-xanthen-9-yl)-2-oxo-1,2-dihydropyridine-3-carboxamide |
| 281 | 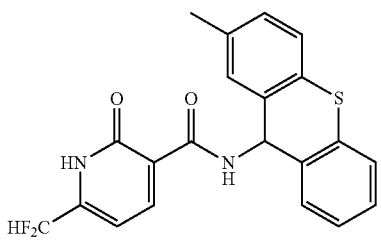 | 6-(difluoromethyl)-N-(2-methyl-9H-thioxanthen-9-yl)-2-oxo-1,2-dihydropyridine-3-carboxamide |
| 282 | 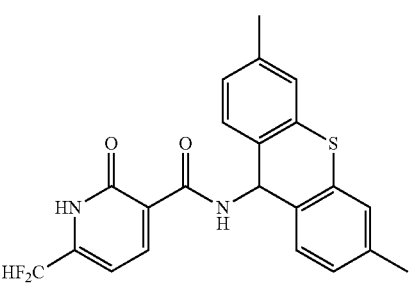 | 6-(difluoromethyl)-N-(3,6-dimethyl-9H-thioxanthen-9-yl)-2-oxo-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 283 | 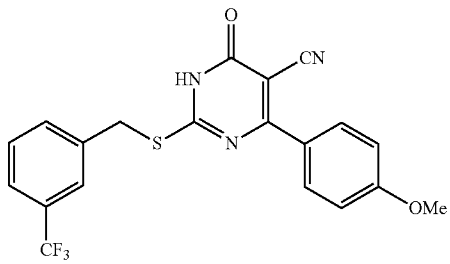 [SMILES: COc1ccc(-c2nc(SCc3cccc(C(F)(F)F)c3)[nH]c(=O)c2C#N)cc1] | 4-(4-methoxyphenyl)-6-oxo-2-((3-(trifluoromethyl)benzyl)thio)-1,6-dihydropyrimidine-5-carbonitrile |
| 284 | 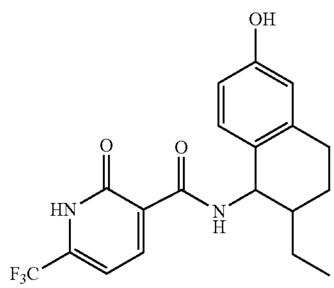 [SMILES: CCC1CCc2cc(O)ccc2C1NC(=O)c1ccc(C(F)(F)F)[nH]c1=O] | N-(2-ethyl-6-hydroxy-1,2,3,4-tetrahydronaphthalen-1-yl)-2-oxo-6-(trifluoromethyl)-1,2-dihydropyridine-3-carboxamide |
| 285 | 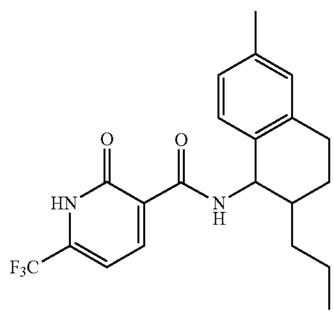 [SMILES: CCCC1CCc2cc(C)ccc2C1NC(=O)c1ccc(C(F)(F)F)[nH]c1=O] | N-(6-methyl-2-propyl-1,2,3,4-tetrahydronaphthalen-1-yl)-2-oxo-6-(trifluoromethyl)-1,2-dihydropyridine-3-carboxamide |
| 286 | 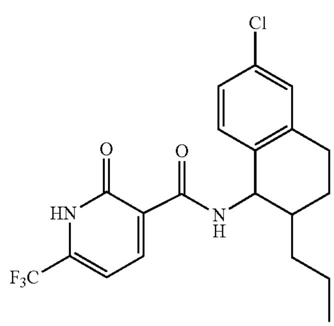 [SMILES: CCCC1CCc2cc(Cl)ccc2C1NC(=O)c1ccc(C(F)(F)F)[nH]c1=O] | N-(6-chloro-2-propyl-1,2,3,4-tetrahydronaphthalen-1-yl)-2-oxo-6-(trifluoromethyl)-1,2-dihydropyridine-3-carboxamide |
| 287 | 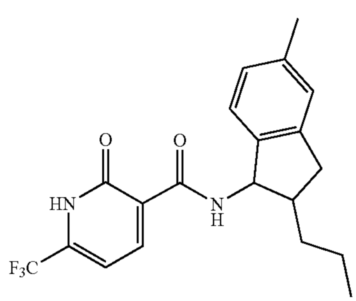 [SMILES: CCCC1Cc2cc(C)ccc2C1NC(=O)c1ccc(C(F)(F)F)[nH]c1=O] | N-(5-methyl-2-propyl-2,3-dihydro-1H-inden-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 288 | 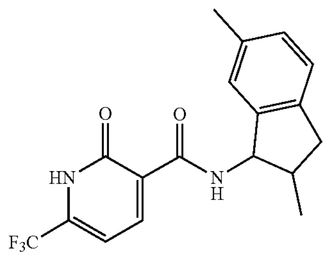 | N-(2,6-dimethyl-2,3-dihydro-1H-inden-1-yl)-2-oxo-6-(trifluoromethyl)-1,2-dihydropyridine-3-carboxamide |
| 289 | 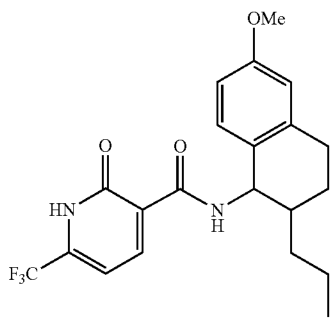 [SMILES: CCCC1CCc2cc(OC)ccc2C1NC(=O)c1ccc(C(F)(F)F)[nH]c1=O] | N-(6-methoxy-2-propyl-1,2,3,4-tetrahydronaphthalen-1-yl)-2-oxo-6-(trifluoromethyl)-1,2-dihydropyridine-3-carboxamide |
| 290 | 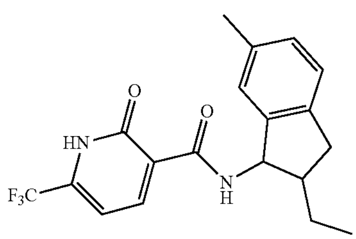 [SMILES: CCC1Cc2ccc(C)cc2C1NC(=O)c1ccc(C(F)(F)F)[nH]c1=O] | N-(2-ethyl-6-methyl-2,3-dihydro-1H-inden-1-yl)-2-oxo-6-(trifluoromethyl)-1,2-dihydropyridine-3-carboxamide |
| 291 | 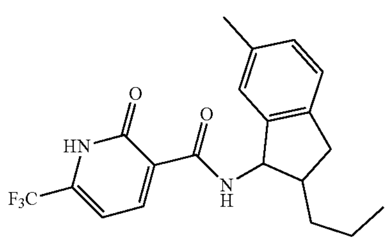 [SMILES: CCCC1Cc2ccc(C)cc2C1NC(=O)c1ccc(C(F)(F)F)[nH]c1=O] | N-(6-methyl-2-propyl-2,3-dihydro-1H-inden-1-yl)-2-oxo-6-(trifluoromethyl)-1,2-dihydropyridine-3-carboxamide |
| 292 | 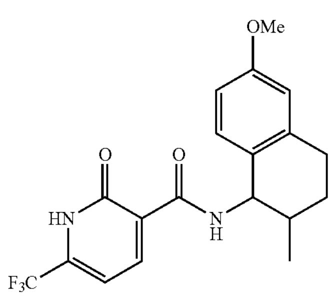 [SMILES: COc1ccc2c(c1)CCC(C)C2NC(=O)c1ccc(C(F)(F)F)[nH]c1=O] | N-(6-methoxy-2-methyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 293 | 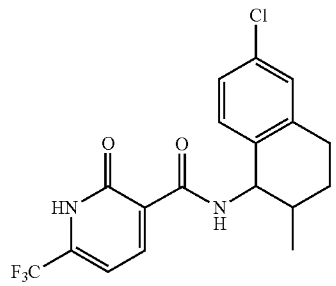 [SMILES: CC1CCc2cc(Cl)ccc2C1NC(=O)c1ccc(C(F)(F)F)[nH]c1=O] | N-(6-chloro-2-methyl-1,2,3,4-tetrahydronaphthalen-1-yl)-2-oxo-6-(trifluoromethyl)-1,2-dihydropyridine-3-carboxamide |
| 294 | 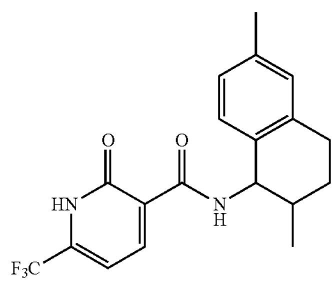 [SMILES: Cc1ccc2c(c1)CCC(C)C2NC(=O)c1ccc(C(F)(F)F)[nH]c1=O] | N-(2,6-dimethyl-1,2,3,4-tetrahydronaphthalen-1-yl)-2-oxo-6-(trifluoromethyl)-1,2-dihydropyridine-3-carboxamide |
| 295 | 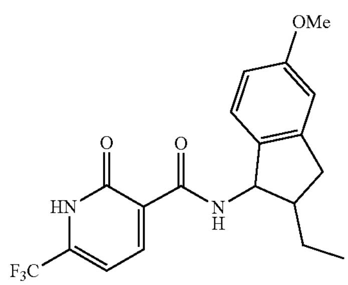 [SMILES: CCC1Cc2cc(OC)ccc2C1NC(=O)c1ccc(C(F)(F)F)[nH]c1=O] | N-(2-ethyl-5-methoxy-2,3-dihydro-1H-inden-1-yl)-2-oxo-6-(trifluoromethyl)-1,2-dihydropyridine-3-carboxamide |
| 296 | 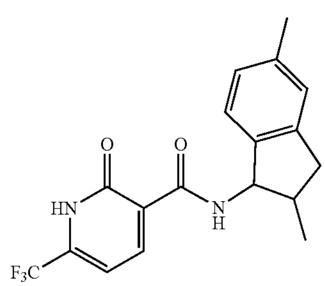 [SMILES: Cc1ccc2c(c1)CC(C)C2NC(=O)c1ccc(C(F)(F)F)[nH]c1=O] | N-(2,5-dimethyl-2,3-dihydro-1H-inden-1-yl)-2-oxo-6-(trifluoromethyl)-1,2-dihydropyridine-3-carboxamide |
| 297 | 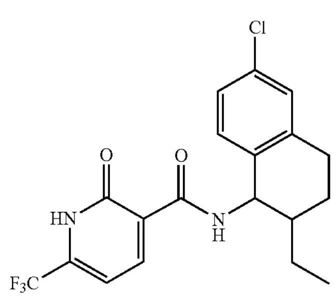 [SMILES: CCC1CCc2cc(Cl)ccc2C1NC(=O)c1ccc(C(F)(F)F)[nH]c1=O] | N-(6-chloro-2-ethyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 298 | 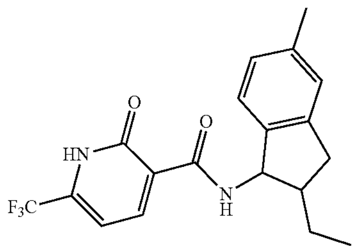 [SMILES: CCC1Cc2cc(C)ccc2C1NC(=O)c1ccc(C(F)(F)F)[nH]c1=O] | N-(2-ethyl-5-methyl-2,3-dihydro-1H-inden-1-yl)-2-oxo-6-(trifluoromethyl)-1,2-dihydropyridine-3-carboxamide |
| 299 | 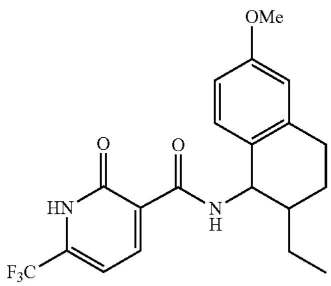 [SMILES: CCC1CCc2cc(OC)ccc2C1NC(=O)c1ccc(C(F)(F)F)[nH]c1=O] | N-(2-ethyl-6-methoxy-1,2,3,4-tetrahydronaphthalen-1-yl)-2-oxo-6-(trifluoromethyl)-1,2-dihydropyridine-3-carboxamide |
| 300 | 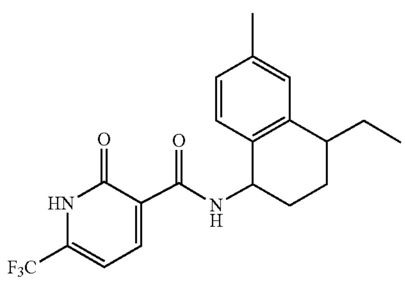 [SMILES: CCC1CCC(NC(=O)c2ccc(C(F)(F)F)[nH]c2=O)c2ccc(C)cc21] | N-(4-ethyl-6-methyl-1,2,3,4-tetrahydronaphthalen-1-yl)-2-oxo-6-(trifluoromethyl)-1,2-dihydropyridine-3-carboxamide |
| 301 | 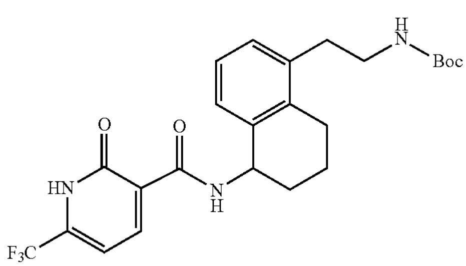 [SMILES: CC(C)(C)OC(=O)NCCc1cccc2c1CCCC2NC(=O)c1ccc(C(F)(F)F)[nH]c1=O] | tert-butyl(2-(5-(2-oxo-6-(trifluoromethyl)-1,2-dihydropyridine-3-carboxamido)-5,6,7,8-tetrahydronaphthalen-1-yl)ethyl)carbamate |
| 302 | 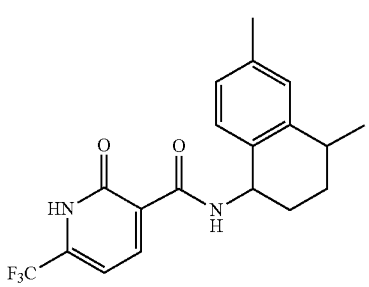 [SMILES: Cc1ccc2c(c1)C(C)CCC2NC(=O)c1ccc(C(F)(F)F)[nH]c1=O] | N-(4,6-dimethyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 303 | 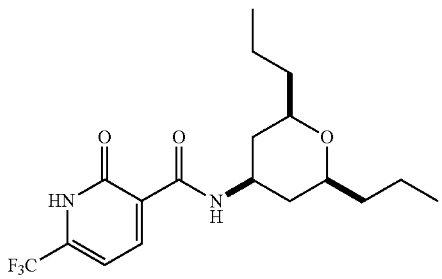 [SMILES: CCC[C@@H]1C[C@H](NC(=O)c2ccc(C(F)(F)F)[nH]c2=O)C[C@H](CCC)O1] | N-((2R,4r,6S)-2,6-dipropyltetrahydro-2H-pyran-4-yl)-2-oxo-6-(trifluoromethyl)-1,2-dihydropyridine-3-carboxamide |
| 304 | 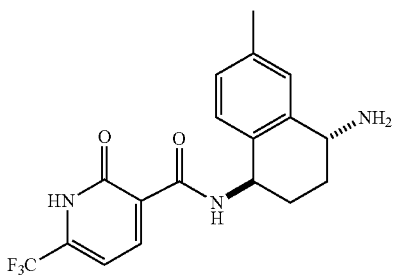 [SMILES: Cc1ccc2c(c1)[C@H](N)CC[C@H]2NC(=O)c1ccc(C(F)(F)F)[nH]c1=O] | N-((1R,4R)-4-amino-6-methyl-1,2,3,4-tetrahydronaphthalen-1-yl)-2-oxo-6-(trifluoromethyl)-1,2-dihydropyridine-3-carboxamide |
| 305 | 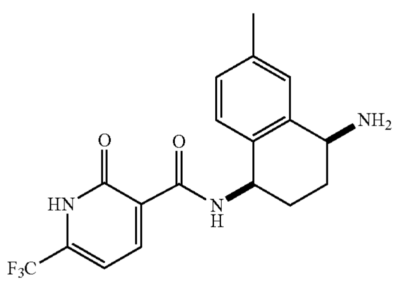 [SMILES: Cc1ccc2c(c1)[C@@H](N)CC[C@H]2NC(=O)c1ccc(C(F)(F)F)[nH]c1=O] | N-((1R,4S)-4-amino-6-methyl-1,2,3,4-tetrahydronaphthalen-1-yl)-2-oxo-6-(trifluoromethyl)-1,2-dihydropyridine-3-carboxamide |
| 306 | 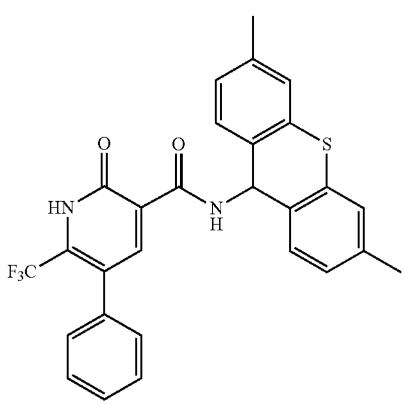 [SMILES: Cc1ccc2c(c1)Sc1cc(C)ccc1C2NC(=O)c1cc(-c2ccccc2)c(C(F)(F)F)[nH]c1=O] | N-(3,6-dimethyl-9H-thioxanthen-9-yl)-2-oxo-5-phenyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 307 | 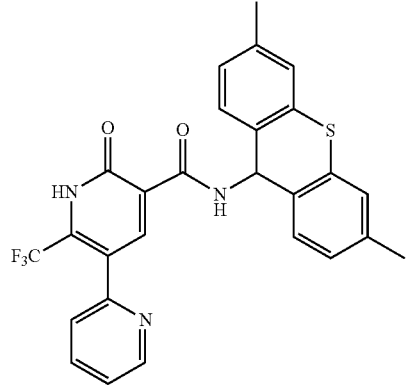 [SMILES: Cc1ccc2c(c1)Sc1cc(C)ccc1C2NC(=O)c1cc(-c2ccccn2)c(C(F)(F)F)[nH]c1=O] | N-(3,6-dimethyl-9H-thioxanthen-9-yl)-6'-oxo-2'-(trifluoromethyl)-1',6'-dihydro-[2,3'-bipyridine]-5'-carboxamide |
| 308 | 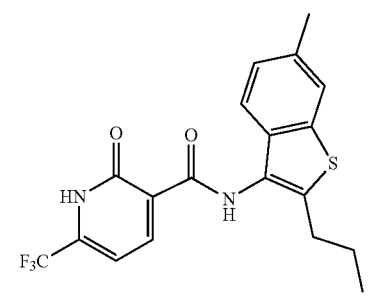 [SMILES: CCCc1sc2cc(C)ccc2c1NC(=O)c1ccc(C(F)(F)F)[nH]c1=O] | N-(6-methyl-2-propylbenzo[b]thiophen-3-yl)-2-oxo-6-(trifluoromethyl)-1,2-dihydropyridine-3-carboxamide |
| 309 | 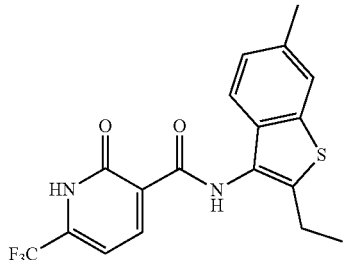 | N-(2-ethyl-6-methylbenzo[b]thiophen-3-yl)-2-oxo-6-(trifluoromethyl)-1,2-dihydropyridine-3-carboxamide |
| 310 | 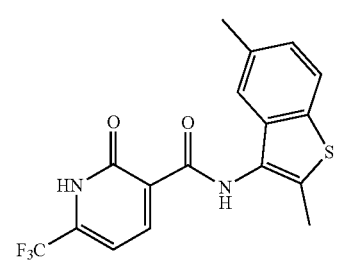 [SMILES: Cc1ccc2sc(C)c(NC(=O)c3ccc(C(F)(F)F)[nH]c3=O)c2c1] | N-(2,5-dimethylbenzo[b]thiophen-3-yl)-2-oxo-6-(trifluoromethyl)-1,2-dihydropyridine-3-carboxamide |
| 311 | 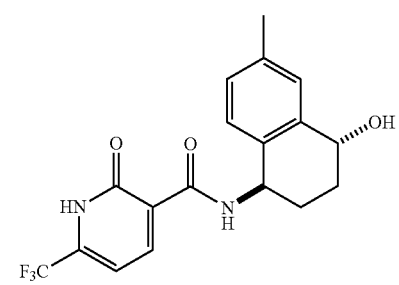 [SMILES: Cc1ccc2c(c1)[C@H](O)CC[C@H]2NC(=O)c1ccc(C(F)(F)F)[nH]c1=O] | N-((1R,4R)-4-hydroxy-6-methyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 312 | 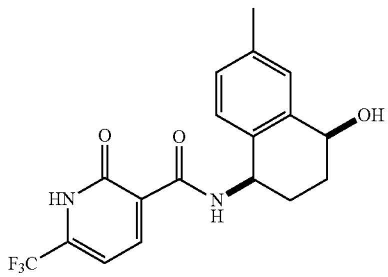 [SMILES: Cc1ccc2c(c1)[C@@H](O)CC[C@H]2NC(=O)c1ccc(C(F)(F)F)[nH]c1=O] | N-((1R,4S)-4-hydroxy-6-methyl-1,2,3,4-tetrahydronaphthalen-1-yl)-2-oxo-6-(trifluoromethyl)-1,2-dihydropyridine-3-carboxamide |
| 313 | 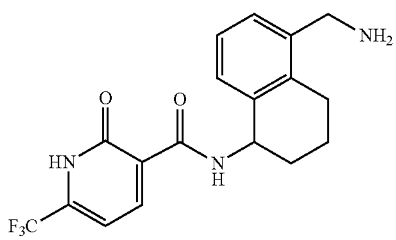 [SMILES: NCc1cccc2c1CCCC2NC(=O)c1ccc(C(F)(F)F)[nH]c1=O] | N-(5-(aminomethyl)-1,2,3,4-tetrahydronaphthalen-1-yl)-2-oxo-6-(trifluoromethyl)-1,2-dihydropyridine-3-carboxamide |
| 314 | 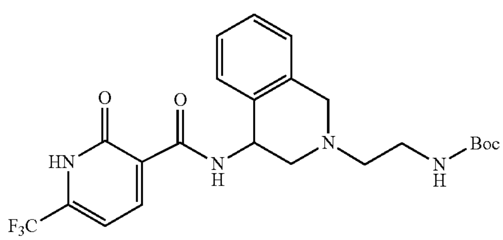 [SMILES: CC(C)(C)OC(=O)NCCN1Cc2ccccc2C(NC(=O)c2ccc(C(F)(F)F)[nH]c2=O)C1] | tert-butyl(2-(4-(2-oxo-6-(trifluoromethyl)-1,2-dihydropyridine-3-carboxamido)-3,4-dihydroisoquinolin-2(1H)-yl)ethyl)carbamate |
| 315 | 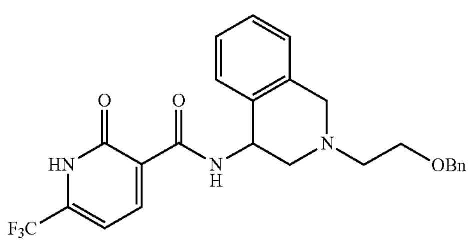 [SMILES: O=C(NC1CN(CCOCc2ccccc2)Cc2ccccc21)c1ccc(C(F)(F)F)[nH]c1=O] | N-(2-(2-(benzyloxy)ethyl)-1,2,3,4-tetrahydroisoquinolin-4-yl)-2-oxo-6-(trifluoromethyl)-1,2-dihydropyridine-3-carboxamide |
| 316 | 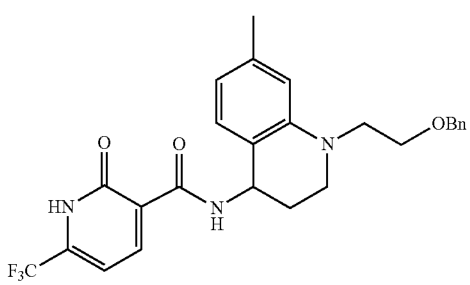 [SMILES: Cc1ccc2c(c1)N(CCOCc1ccccc1)CCC2NC(=O)c1ccc(C(F)(F)F)[nH]c1=O] | N-(1-(2-(benzyloxy)ethyl)-7-methyl-1,2,3,4-tetrahydroquinolin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 317 | 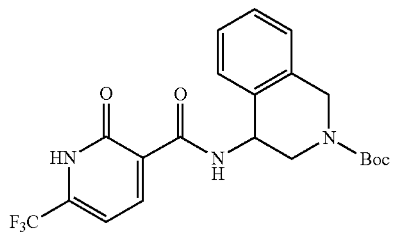 [SMILES: CC(C)(C)OC(=O)N1Cc2ccccc2C(NC(=O)c2ccc(C(F)(F)F)[nH]c2=O)C1] | tert-butyl 4-(2-oxo-6-(trifluoromethyl)-1,2-dihydropyridine-3-carboxamido)-3,4-dihydroisoquinoline-2(1H)-carboxylate |
| 318 | 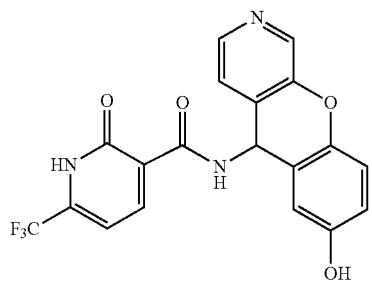 [SMILES: O=C(NC1c2ccncc2Oc2ccc(O)cc21)c1ccc(C(F)(F)F)[nH]c1=O] | N-(7-hydroxy-5H-chromeno[2,3-c]pyridin-5-yl)-2-oxo-6-(trifluoromethyl)-1,2-dihydropyridine-3-carboxamide |
| 319 | 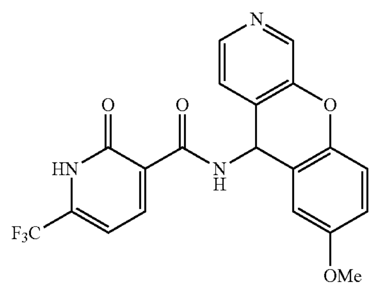 [SMILES: COc1ccc2c(c1)C(NC(=O)c1ccc(C(F)(F)F)[nH]c1=O)c1ccncc1O2] | N-(7-methoxy-5H-chromeno[2,3-c]pyridin-5-yl)-2-oxo-6-(trifluoromethyl)-1,2-dihydropyridine-3-carboxamide |
| 320 | 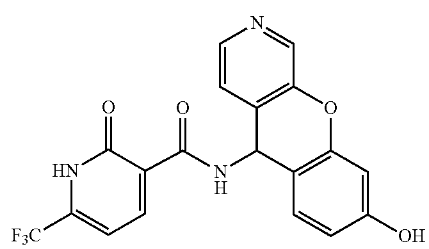 | N-(8-hydroxy-5H-chromeno[2,3-c]pyridin-5-yl)-2-oxo-6-(trifluoromethyl)-1,2-dihydropyridine-3-carboxamide |
| 321 | 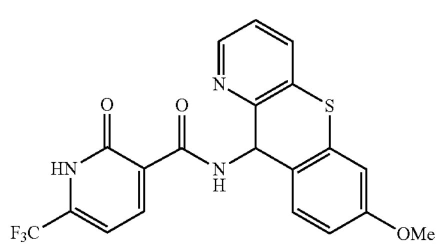 | N-(7-methoxy-10H-thiochromeno[3,2-b]pyridin-10-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 322 | 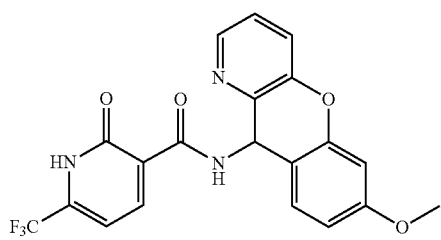 | N-(7-methoxy-10H-chromeno[3,2-b]pyridin-10-yl)-2-oxo-6-(trifluoromethyl)-1,2-dihydropyridine-3-carboxamide |
| 323 | 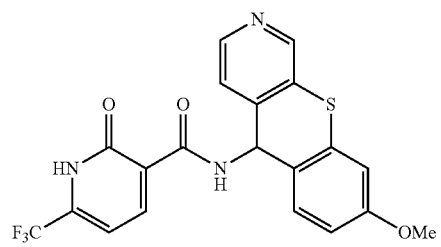 | N-(8-methoxy-5H-thiochromeno[2,3-c]pyridin-5-yl)-2-oxo-6-(trifluoromethyl)-1,2-dihydropyridine-3-carboxamide |
| 324 | 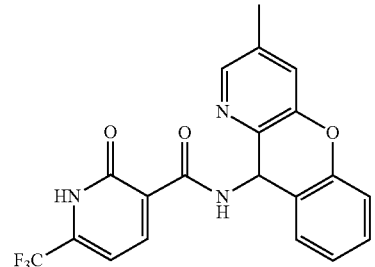 | N-(3-methyl-10H-chromeno[3,2-b]pyridin-10-yl)-2-oxo-6-(trifluoromethyl)-1,2-dihydropyridine-3-carboxamide |
| 325 | 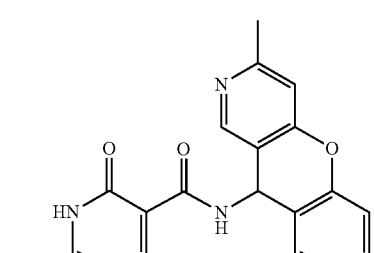 | N-(3-methyl-10H-chromeno[3,2-c]pyridin-10-yl)-2-oxo-6-(trifluoromethyl)-1,2-dihydropyridine-3-carboxamide |
| 326 | 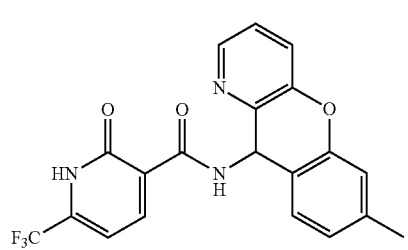 | N-(7-methyl-10H-chromeno[3,2-b]pyridin-10-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 327 | 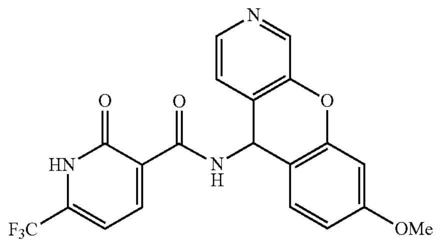 [SMILES: COc1ccc2c(c1)Sc1cnccc1C2NC(=O)c1ccc(C(F)(F)F)[nH]c1=O] | N-(8-methoxy-5H-chromeno[2,3-c]pyridin-5-yl)-2-oxo-6-(trifluoromethyl)-1,2-dihydropyridine-3-carboxamide |
| 328 | 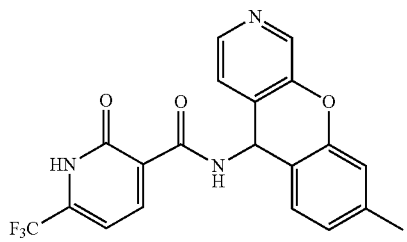 [SMILES: Cc1ccc2c(c1)Oc1cnccc1C2NC(=O)c1ccc(C(F)(F)F)[nH]c1=O] | N-(8-methyl-5H-chromeno[2,3-c]pyridin-5-yl)-2-oxo-6-(trifluoromethyl)-1,2-dihydropyridine-3-carboxamide |
| 329 | 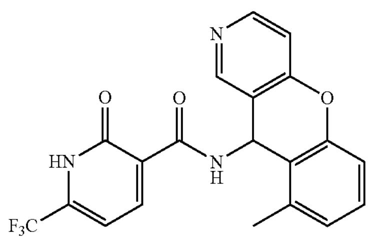 [SMILES: Cc1cccc2c1C(NC(=O)c1ccc(C(F)(F)F)[nH]c1=O)c1cnccc1O2] | N-(9-methyl-10H-chromeno[3,2-c]pyridin-10-yl)-2-oxo-6-(trifluoromethyl)-1,2-dihydropyridine-3-carboxamide |
| 330 | 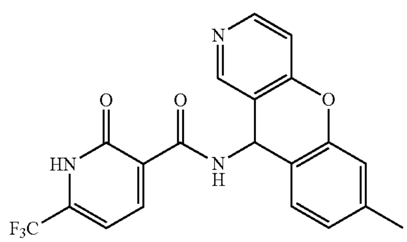 [SMILES: Cc1ccc2c(c1)Oc1ccncc1C2NC(=O)c1ccc(C(F)(F)F)[nH]c1=O] | N-(7-methyl-10H-chromeno[3,2-c]pyridin-10-yl)-2-oxo-6-(trifluoromethyl)-1,2-dihydropyridine-3-carboxamide |
| 331 | 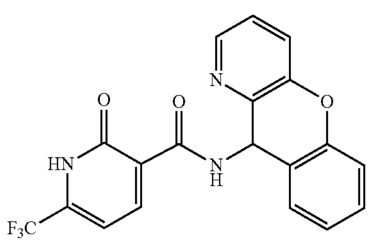 [SMILES: O=C(NC1c2ccccc2Oc2cccnc21)c1ccc(C(F)(F)F)[nH]c1=O] | N-(10H-chromeno[3,2-b]pyridin-10-yl)-2-oxo-6-(trifluoromethyl)-1,2-dihydropyridine-3-carboxamide |
| 332 | 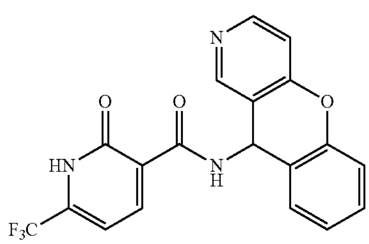 [SMILES: O=C(NC1c2ccccc2Oc2ccncc21)c1ccc(C(F)(F)F)[nH]c1=O] | N-(10H-chromeno[3,2-c]pyridin-10-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 333 | 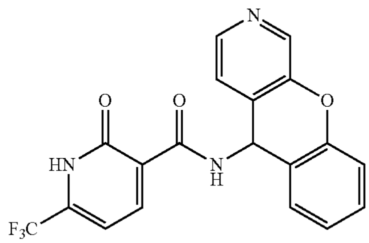 [SMILES: O=C(NC1c2ccccc2Oc2cnccc21)c1ccc(C(F)(F)F)[nH]c1=O] | N-(5H-chromeno[2,3-c]pyridin-5-yl)-2-oxo-6-(trifluoromethyl)-1,2-dihydropyridine-3-carboxamide |
| 334 | 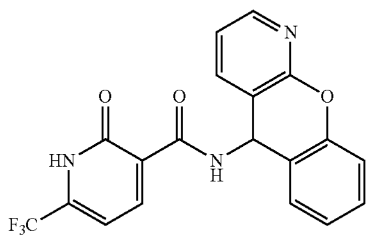 [SMILES: O=C(NC1c2ccccc2Oc2ncccc21)c1ccc(C(F)(F)F)[nH]c1=O] | N-(5H-chromeno[2,3-b]pyridin-5-yl)-2-oxo-6-(trifluoromethyl)-1,2-dihydropyridine-3-carboxamide |
| 335 | 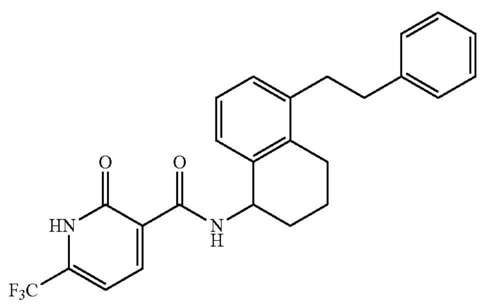 [SMILES: O=C(NC1CCCc2c(CCc3ccccc3)cccc21)c1ccc(C(F)(F)F)[nH]c1=O] | 2-oxo-N-(5-phenethyl-1,2,3,4-tetrahydronaphthalen-1-yl)-6-(trifluoromethyl)-1,2-dihydropyridine-3-carboxamide |
| 336 | 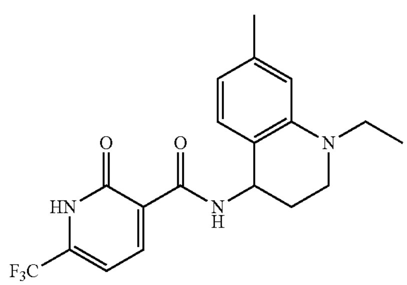 | N-(1-ethyl-7-methyl-1,2,3,4-tetrahydroquinolin-4-yl)-2-oxo-6-(trifluoromethyl)-1,2-dihydropyridine-3-carboxamide |
| 337 | 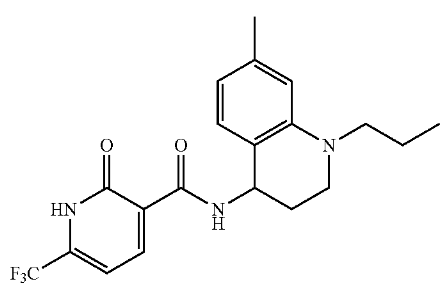 [SMILES: CCCN1CCC(NC(=O)c2ccc(C(F)(F)F)[nH]c2=O)c2ccc(C)cc21] | N-(7-methyl-1-propyl-1,2,3,4-tetrahydroquinolin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 338 | 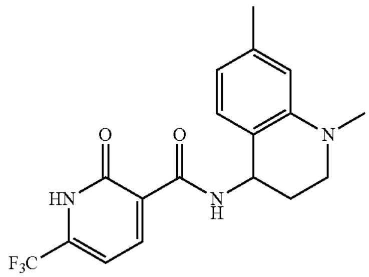 | N-(1,7-dimethyl-1,2,3,4-tetrahydroquinolin-4-yl)-2-oxo-6-(trifluoromethyl)-1,2-dihydropyridine-3-carboxamide |
| 339 | 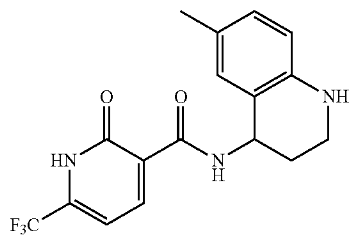 | N-(6-methyl-1,2,3,4-tetrahydroquinolin-4-yl)-2-oxo-6-(trifluoromethyl)-1,2-dihydropyridine-3-carboxamide |
| 340 | 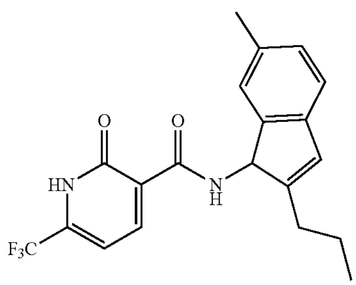 [SMILES: CCCC1=Cc2ccc(C)cc2C1NC(=O)c1ccc(C(F)(F)F)[nH]c1=O] | N-(6-methyl-2-propyl-1H-inden-1-yl)-2-oxo-6-(trifluoromethyl)-1,2-dihydropyridine-3-carboxamide |
| 341 | 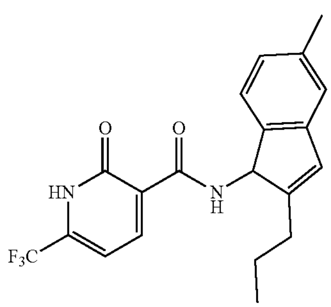 [SMILES: CCCC1=Cc2cc(C)ccc2C1NC(=O)c1ccc(C(F)(F)F)[nH]c1=O] | N-(5-methyl-2-propyl-1H-inden-1-yl)-2-oxo-6-(trifluoromethyl)-1,2-dihydropyridine-3-carboxamide |
| 342 | 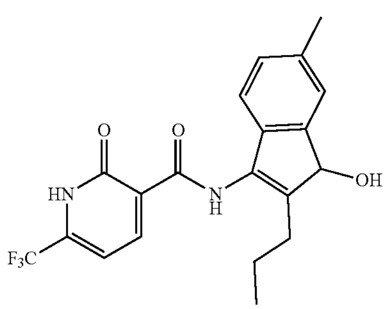 [SMILES: CCCC1=C(NC(=O)c2ccc(C(F)(F)F)[nH]c2=O)c2ccc(C)cc2C1O] | N-(1-hydroxy-6-methyl-2-propyl-1H-inden-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 343 | 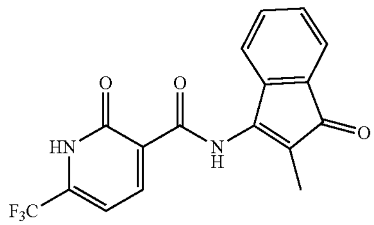 [SMILES: CC1=C(NC(=O)c2ccc(C(F)(F)F)[nH]c2=O)c2ccccc2C1=O] | N-(2-methyl-1-oxo-1H-inden-3-yl)-2-oxo-6-(trifluoromethyl)-1,2-dihydropyridine-3-carboxamide |
| 344 | 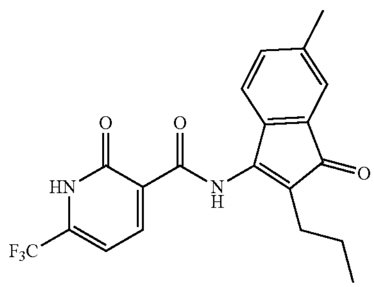 [SMILES: CCCC1=C(NC(=O)c2ccc(C(F)(F)F)[nH]c2=O)c2ccc(C)cc2C1=O] | N-(6-methyl-1-oxo-2-propyl-1H-inden-3-yl)-2-oxo-6-(trifluoromethyl)-1,2-dihydropyridine-3-carboxamide |
| 345 | 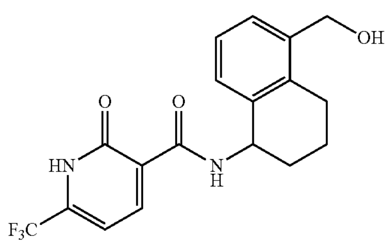 [SMILES: O=C(NC1CCCc2c(CO)cccc21)c1ccc(C(F)(F)F)[nH]c1=O] | N-(5-(hydroxymethyl)-1,2,3,4-tetrahydronaphthalen-1-yl)-2-oxo-6-(trifluoromethyl)-1,2-dihydropyridine-3-carboxamide |
| 346 | 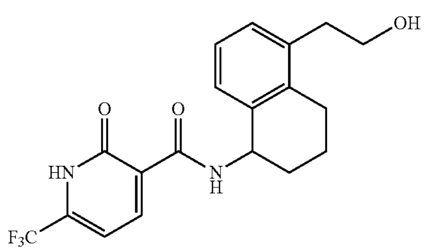 [SMILES: O=C(NC1CCCc2c(CCO)cccc21)c1ccc(C(F)(F)F)[nH]c1=O] | N-(5-(2-hydroxyethyl)-1,2,3,4-tetrahydronaphthalen-1-yl)-2-oxo-6-(trifluoromethyl)-1,2-dihydropyridine-3-carboxamide |
| 347 | 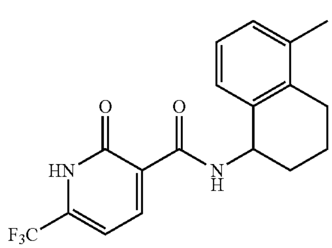 [SMILES: Cc1cccc2c1CCCC2NC(=O)c1ccc(C(F)(F)F)[nH]c1=O] | 2-oxo-N-(5-phenyl-1,2,3,4-tetrahydronaphthalen-1-yl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 348 | 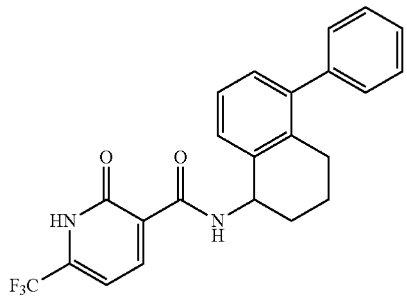 [SMILES: O=C(NC1CCCc2c(-c3ccccc3)cccc21)c1ccc(C(F)(F)F)[nH]c1=O] | 2-oxo-N-(5-phenyl-1,2,3,4-tetrahydronaphthalen-1-yl)-6-(trifluoromethyl)-1,2-dihydropyridine-3-carboxamide |
| 349 | 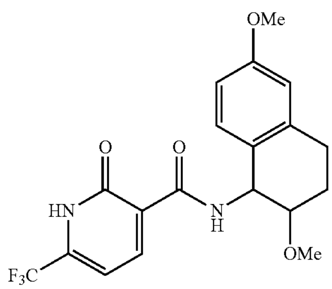 [SMILES: COc1ccc2c(c1)CCC(OC)C2NC(=O)c1ccc(C(F)(F)F)[nH]c1=O] | N-(2,6-dimethoxy-1,2,3,4-tetrahydronaphthalen-1-yl)-2-oxo-6-(trifluoromethyl)-1,2-dihydropyridine-3-carboxamide |
| 350 | 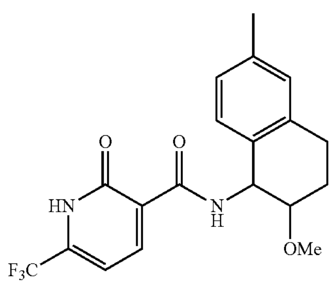 [SMILES: COC1CCc2cc(C)ccc2C1NC(=O)c1ccc(C(F)(F)F)[nH]c1=O] | N-(2-methoxy-6-methyl-1,2,3,4-tetrahydronaphthalen-1-yl)-2-oxo-6-(trifluoromethyl)-1,2-dihydropyridine-3-carboxamide |
| 351 | 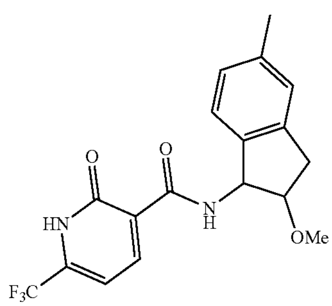 [SMILES: COC1Cc2cc(C)ccc2C1NC(=O)c1ccc(C(F)(F)F)[nH]c1=O] | N-(2-methoxy-5-methyl-2,3-dihydro-1H-inden-1-yl)-2-oxo-6-(trifluoromethyl)-1,2-dihydropyridine-3-carboxamide |
| 352 | 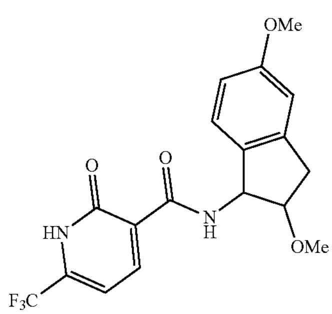 [SMILES: COc1ccc2c(c1)CC(OC)C2NC(=O)c1ccc(C(F)(F)F)[nH]c1=O] | N-(2,5-dimethoxy-2,3-dihydro-1H-inden-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 353 | 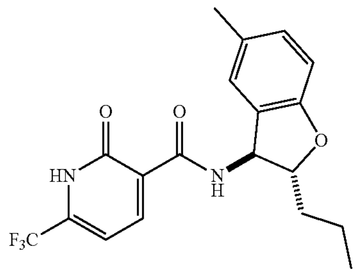 | N-((2R,3S)-5-methyl-2-propyl-2,3-dihydrobenzofuran-3-yl)-2-oxo-6-(trifluoromethyl)-1,2-dihydropyridine-3-carboxamide |
| 354 | 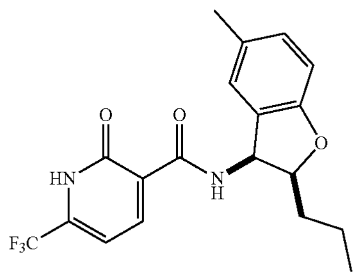 | N-((2S,3S)-5-methyl-2-propyl-2,3-dihydrobenzofuran-3-yl)-2-oxo-6-(trifluoromethyl)-1,2-dihydropyridine-3-carboxamide |
| 355 | 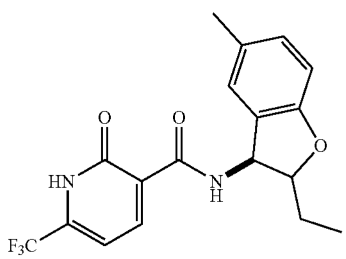 | N-(2-ethyl-5-methyl-2,3-dihydrobenzofuran-3-yl)-2-oxo-6-(trifluoromethyl)-1,2-dihydropyridine-3-carboxamide |
| 356 | 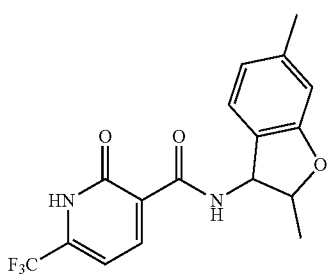 [SMILES: Cc1ccc2c(c1)OC(C)C2NC(=O)c1ccc(C(F)(F)F)[nH]c1=O] | N-(2,6-dimethyl-2,3-dihydrobenzofuran-3-yl)-2-oxo-6-(trifluoromethyl)-1,2-dihydropyridine-3-carboxamide |
| 357 | 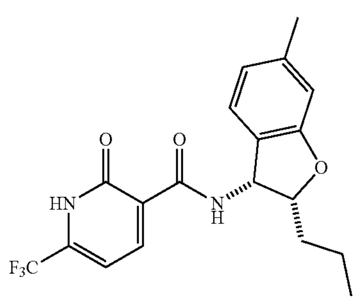 | N-((2R,3R)-6-methyl-2-propyl-2,3-dihydrobenzofuran-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 358 | 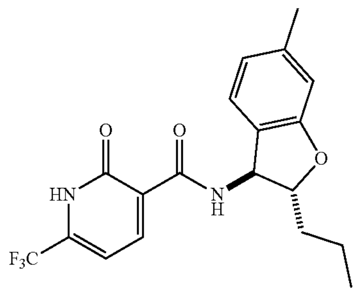 | N-((2R,3S)-6-methyl-2-propyl-2,3-dihydrobenzofuran-3-yl)-2-oxo-6-(trifluoromethyl)-1,2-dihydropyridine-3-carboxamide |
| 359 | 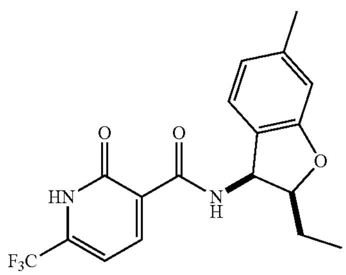 | N-((2S,3S)-2-ethyl-6-methyl-2,3-dihydrobenzofuran-3-yl)-2-oxo-6-(trifluoromethyl)-1,2-dihydropyridine-3-carboxamide |
| 360 | 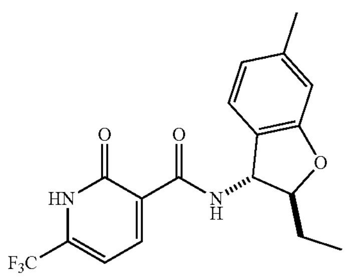 | N-((2S,3R)-2-ethyl-6-methyl-2,3-dihydrobenzofuran-3-yl)-2-oxo-6-(trifluoromethyl)-1,2-dihydropyridine-3-carboxamide |
| 361 | 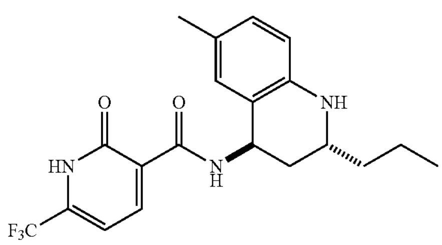 | N-((2R,4R)-6-methyl-2-propyl-1,2,3,4-tetrahydroquinolin-4-yl)-2-oxo-6-(trifluoromethyl)-1,2-dihydropyridine-3-carboxamide |
| 362 | 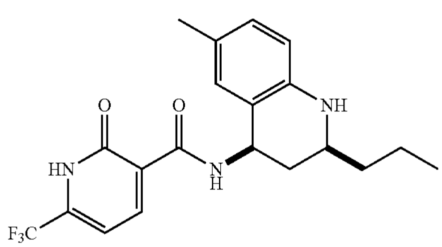 | N-((2S,4R)-6-methyl-2-propyl-1,2,3,4-tetrahydroquinolin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 363 | 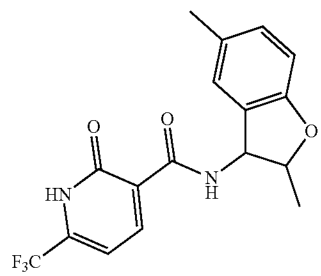 [SMILES: Cc1ccc2c(c1)C(NC(=O)c1ccc(C(F)(F)F)[nH]c1=O)C(C)O2] | N-(2,5-dimethyl-2,3-dihydrobenzofuran-3-yl)-2-oxo-6-(trifluoromethyl)-1,2-dihydropyridine-3-carboxamide |
| 364 | 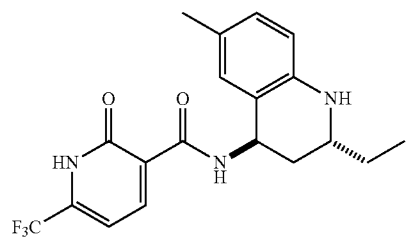 | N-((2R,4R)-2-ethyl-6-methyl-1,2,3,4-tetrahydroquinolin-4-yl)-2-oxo-6-(trifluoromethyl)-1,2-dihydropyridine-3-carboxamide |
| 365 | 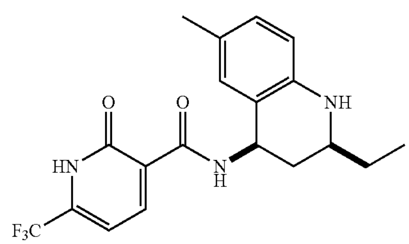 | N-((2S,4R)-2-ethyl-6-methyl-1,2,3,4-tetrahydroquinolin-4-yl)-2-oxo-6-(trifluoromethyl)-1,2-dihydropyridine-3-carboxamide |
| 366 | 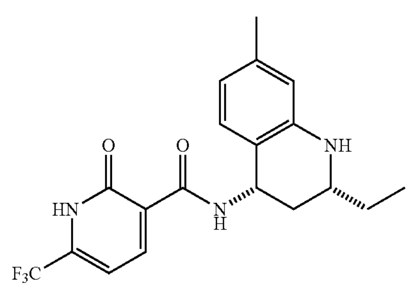 | N-((2R,4S)-2-ethyl-7-methyl-1,2,3,4-tetrahydroquinolin-4-yl)-2-oxo-6-(trifluoromethyl)-1,2-dihydropyridine-3-carboxamide |
| 367 | 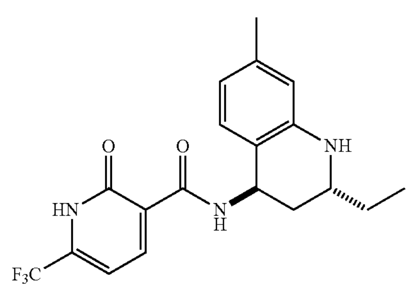 | N-((2R,4R)-2-ethyl-7-methyl-1,2,3,4-tetrahydroquinolin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 368 | 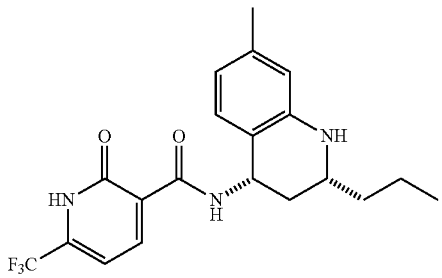 | N-((2R,4S)-7-methyl-2-propyl-1,2,3,4-tetrahydroquinolin-4-yl)-2-oxo-6-(trifluoromethyl)-1,2-dihydropyridine-3-carboxamide |
| 369 | 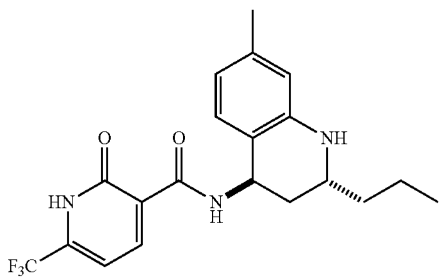 | N-((2R,4R)-7-methyl-2-propyl-1,2,3,4-tetrahydroquinolin-4-yl)-2-oxo-6-(trifluoromethyl)-1,2-dihydropyridine-3-carboxamide |
| 370 | 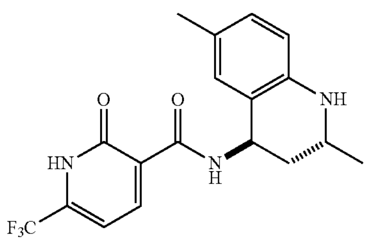 | N-((2R,4R)-2,6-dimethyl-1,2,3,4-tetrahydroquinolin-4-yl)-2-oxo-6-(trifluoromethyl)-1,2-dihydropyridine-3-carboxamide |
| 371 | 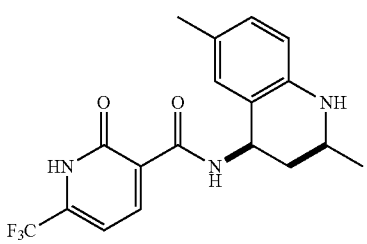 | N-((2S,4R)-2,6-dimethyl-1,2,3,4-tetrahydroquinolin-4-yl)-2-oxo-6-(trifluoromethyl)-1,2-dihydropyridine-3-carboxamide |
| 373 | 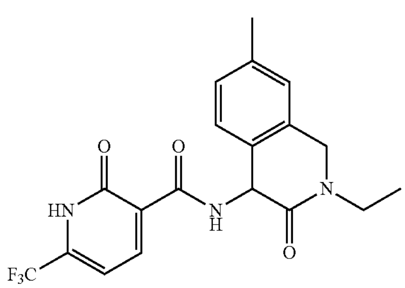 [SMILES: CCN1Cc2cc(C)ccc2C(NC(=O)c2ccc(C(F)(F)F)[nH]c2=O)C1=O] | N-(2-ethyl-7-methyl-3-oxo-1,2,3,4-tetrahydroisoquinolin-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 374 | 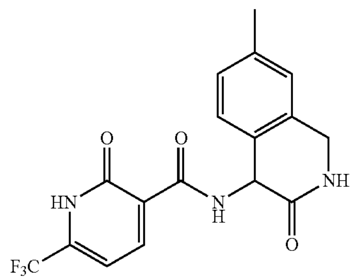 [SMILES: Cc1ccc2c(c1)CNC(=O)C2NC(=O)c1ccc(C(F)(F)F)[nH]c1=O] | N-(7-methyl-3-oxo-1,2,3,4-tetrahydroisoquinolin-4-yl)-2-oxo-6-(trifluoromethyl)-1,2-dihydropyridine-3-carboxamide |
| 375 | 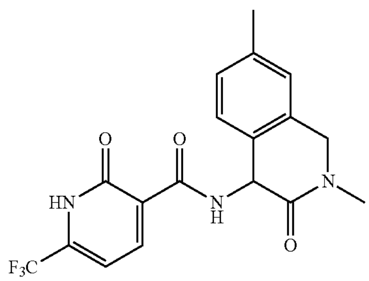 [SMILES: Cc1ccc2c(c1)CN(C)C(=O)C2NC(=O)c1ccc(C(F)(F)F)[nH]c1=O] | N-(2,7-dimethyl-3-oxo-1,2,3,4-tetrahydroisoquinolin-4-yl)-2-oxo-6-(trifluoromethyl)-1,2-dihydropyridine-3-carboxamide |
| 376 | 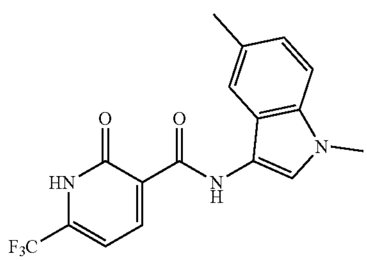 [SMILES: Cc1ccc2c(c1)c(NC(=O)c1ccc(C(F)(F)F)[nH]c1=O)cn2C] | N-(1,5-dimethyl-1H-indol-3-yl)-2-oxo-6-(trifluoromethyl)-1,2-dihydropyridine-3-carboxamide |
| 377 | 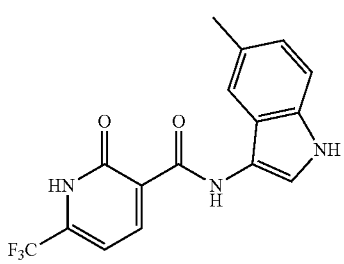 [SMILES: Cc1ccc2[nH]cc(NC(=O)c3ccc(C(F)(F)F)[nH]c3=O)c2c1] | N-(5-methyl-1H-indol-3-yl)-2-oxo-6-(trifluoromethyl)-1,2-dihydropyridine-3-carboxamide |
| 378 | 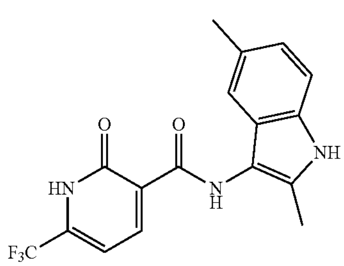 [SMILES: Cc1ccc2[nH]c(C)c(NC(=O)c3ccc(C(F)(F)F)[nH]c3=O)c2c1] | N-(2,5-dimethyl-1H-indol-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 379 | 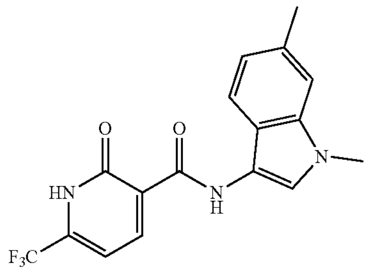 [SMILES: Cc1ccc2c(NC(=O)c3ccc(C(F)(F)F)[nH]c3=O)cn(C)c2c1] | N-(1,6-dimethyl-1H-indol-3-yl)-2-oxo-6-(trifluoromethyl)-1,2-dihydropyridine-3-carboxamide |
| 380 | 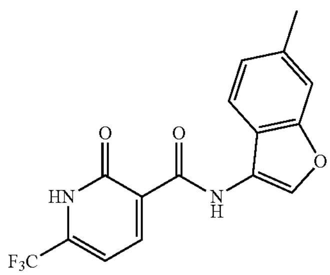 [SMILES: Cc1ccc2c(NC(=O)c3ccc(C(F)(F)F)[nH]c3=O)coc2c1] | N-(6-methylbenzofuran-3-yl)-2-oxo-6-(trifluoromethyl)-1,2-dihydropyridine-3-carboxamide |
| 381 | 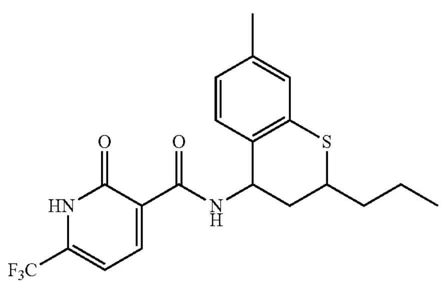 | N-(7-methyl-2-propylthiochroman-4-yl)-2-oxo-6-(trifluoromethyl)-1,2-dihydropyridine-3-carboxamide |
| 382 | 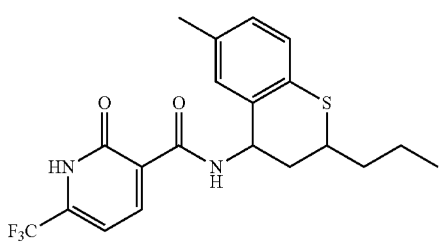 | N-(6-methyl-2-propylthiochroman-4-yl)-2-oxo-6-(trifluoromethyl)-1,2-dihydropyridine-3-carboxamide |
| 383 | 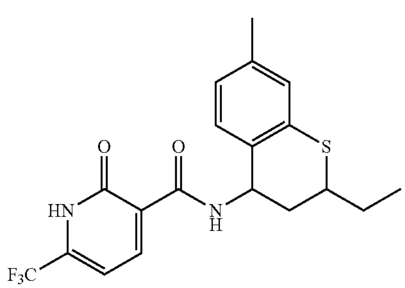 | N-(2-ethyl-6-methylthiochroman-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 384 | 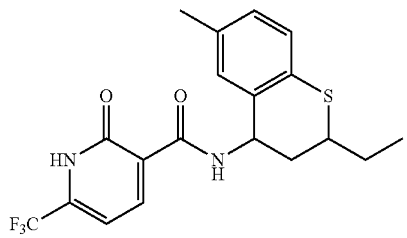 [SMILES: CCC1CC(NC(=O)c2ccc(C(F)(F)F)[nH]c2=O)c2cc(C)ccc2S1] | N-(2-ethyl-7-methylthiochroman-4-yl)-2-oxo-6-(trifluoromethyl)-1,2-dihydropyridine-3-carboxamide |
| 385 | 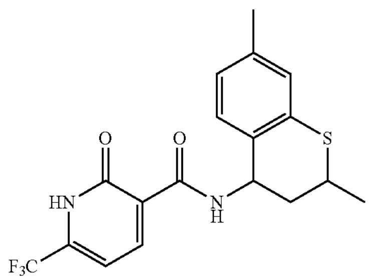 | N-(2,7-dimethylthiochroman-4-yl)-2-oxo-6-(trifluoromethyl)-1,2-dihydropyridine-3-carboxamide |
| 386 | 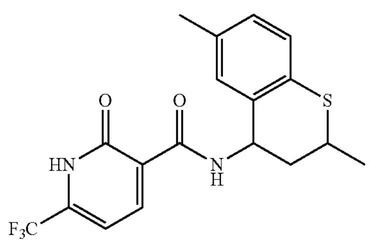 [SMILES: Cc1ccc2c(c1)C(NC(=O)c1ccc(C(F)(F)F)[nH]c1=O)CC(C)S2] | N-(2,6-dimethylthiochroman-4-yl)-2-oxo-6-(trifluoromethyl)-1,2-dihydropyridine-3-carboxamide |
| 387 | 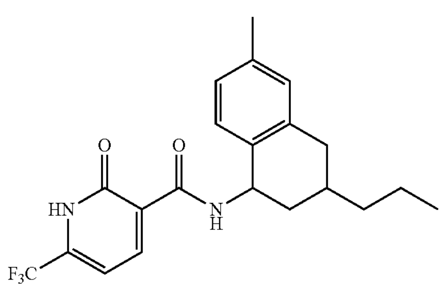 | N-(6-methyl-3-propyl-1,2,3,4-tetrahydronaphthalen-1-yl)-2-oxo-6-(trifluoromethyl)-1,2-dihydropyridine-3-carboxamide |
| 388 | 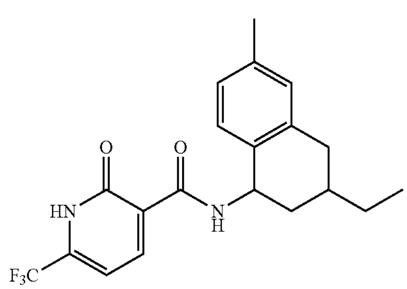 | N-(3-ethyl-6-methyl-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 389 | 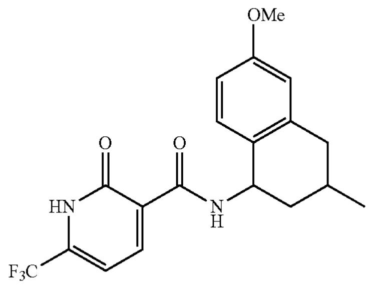 [SMILES: COc1ccc2c(c1)CC(C)CC2NC(=O)c1ccc(C(F)(F)F)[nH]c1=O] | N-(6-methoxy-3-methyl-1,2,3,4-tetrahydronaphthalen-1-yl)-2-oxo-6-(trifluoromethyl)-1,2-dihydropyridine-3-carboxamide |
| 390 | 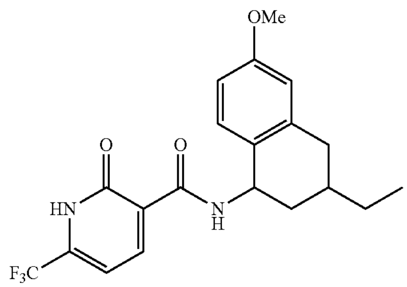 [SMILES: CCC1Cc2cc(OC)ccc2C(NC(=O)c2ccc(C(F)(F)F)[nH]c2=O)C1] | N-(3-ethyl-6-methoxy-1,2,3,4-tetrahydronaphthalen-1-yl)-2-oxo-6-(trifluoromethyl)-1,2-dihydropyridine-3-carboxamide |
| 391 | 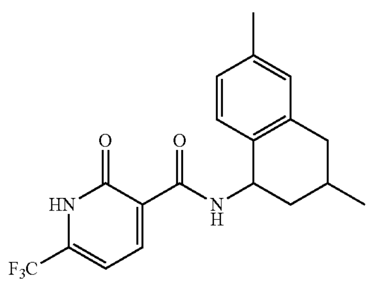 | N-(3,6-dimethyl-1,2,3,4-tetrahydronaphthalen-1-yl)-2-oxo-6-(trifluoromethyl)-1,2-dihydropyridine-3-carboxamide |
| 392 | 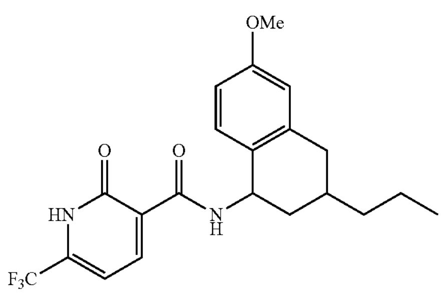 [SMILES: CCCC1Cc2cc(OC)ccc2C(NC(=O)c2ccc(C(F)(F)F)[nH]c2=O)C1] | N-(6-methoxy-3-propyl-1,2,3,4-tetrahydronaphthalen-1-yl)-2-oxo-6-(trifluoromethyl)-1,2-dihydropyridine-3-carboxamide |
| 393 | 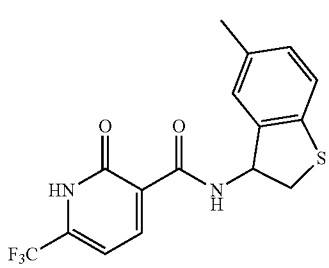 [SMILES: Cc1ccc2c(c1)C(NC(=O)c1ccc(C(F)(F)F)[nH]c1=O)CS2] | N-(5-methyl-2,3-dihydrobenzo(b)thiophen-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 394 | 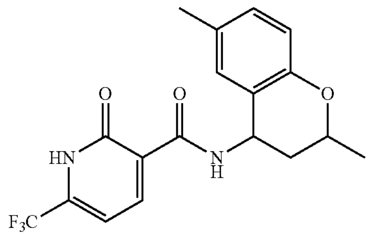 [SMILES: Cc1ccc2c(c1)C(NC(=O)c1ccc(C(F)(F)F)[nH]c1=O)CC(C)O2] | N-(2,6-dimethylchroman-4-yl)-2-oxo-6-(trifluoromethyl)-1,2-dihydropyridine-3-carboxamide |
| 395 | 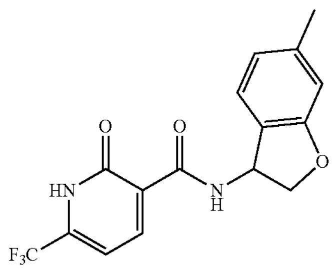 [SMILES: Cc1ccc2c(c1)OCC2NC(=O)c1ccc(C(F)(F)F)[nH]c1=O] | N-(6-methyl-2,3-dihydrobenzofuran-3-yl)-2-oxo-6-(trifluoromethyl)-1,2-dihydropyridine-3-carboxamide |
| 396 | 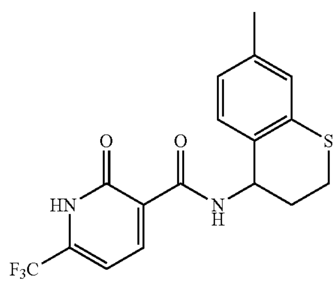 | N-(7-methylthiochroman-4-yl)-2-oxo-6-(trifluoromethyl)-1,2-dihydropyridine-3-carboxamide |
| 397 | 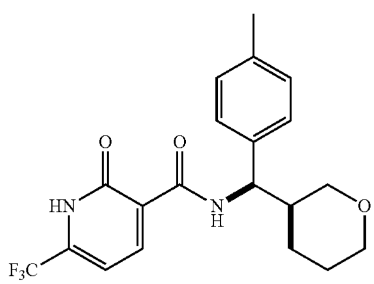 | 2-oxo-N-((R)-((S)-tetrahydro-2H-pyran-3-yl)(p-tolyl)methyl)-6-(trifluoromethyl)-1,2-dihydropyridine-3-carboxamide |
| 398 | 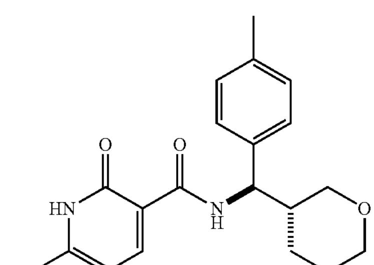 | 2-oxo-N-((R)-((R)-tetrahydro-2H-pyran-3-yl)(p-tolyl)methyl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 399 | 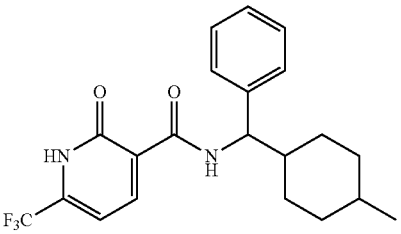 | N-((4-methylcyclohexyl)(phenyl)methyl)-2-oxo-6-(trifluoromethyl)-1,2-dihydropyridine-3-carboxamide |
| 400 | 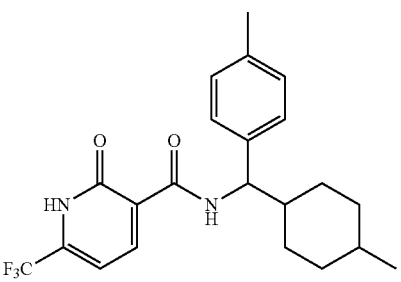 | N-((4-methylcyclohexyl)(p-tolyl)methyl)-2-oxo-6-(trifluoromethyl)-1,2-dihydropyridine-3-carboxamide |
| 401 | 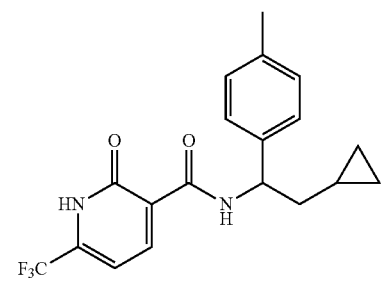 [SMILES: Cc1ccc(C(CC2CC2)NC(=O)c2ccc(C(F)(F)F)[nH]c2=O)cc1] | N-(2-cyclopropyl-1-(p-tolyl)ethyl)-2-oxo-6-(trifluoromethyl)-1,2-dihydropyridine-3-carboxamide |
| 402 | 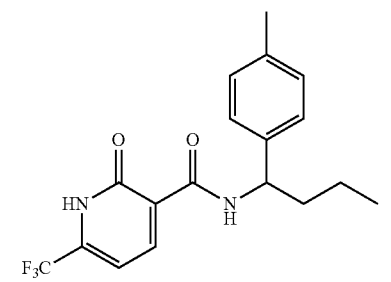 [SMILES: CCCC(NC(=O)c1ccc(C(F)(F)F)[nH]c1=O)c1ccc(C)cc1] | 2-oxo-N-(1-(p-tolyl)butyl)-6-(trifluoromethyl)-1,2-dihydropyridine-3-carboxamide |
| 403 | 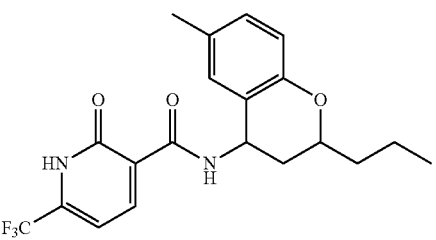 | N-(6-methyl-2-propylchroman-4-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 404 | 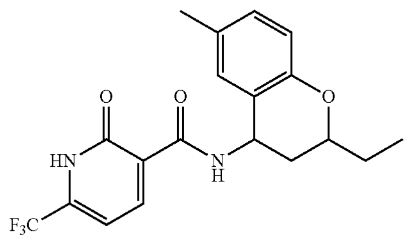 | N-(2-ethyl-6-methylchroman-4-yl)-2-oxo-6-(trifluoromethyl)-1,2-dihydropyridine-3-carboxamide |
| 405 | 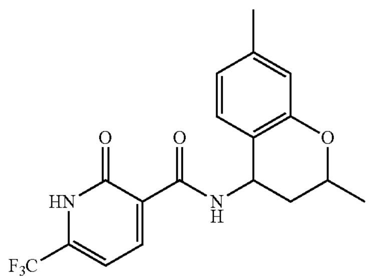 | N-(2,7-dimethylchroman-4-yl)-2-oxo-6-(trifluoromethyl)-1,2-dihydropyridine-3-carboxamide |
| 406 | 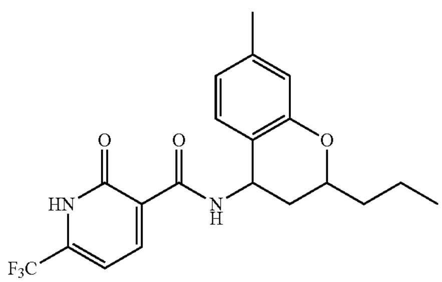 | N-(7-methyl-2-propylchroman-4-yl)-2-oxo-6-(trifluoromethyl)-1,2-dihydropyridine-3-carboxamide |
| 407 | 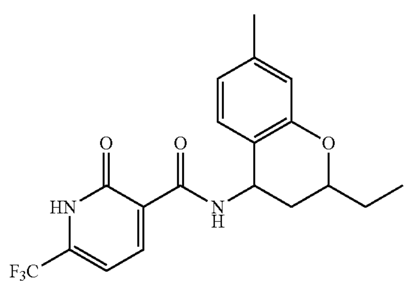 | N-(2-ethyl-7-methylchroman-4-yl)-2-oxo-6-(trifluoromethyl)-1,2-dihydropyridine-3-carboxamide |
| 408 | 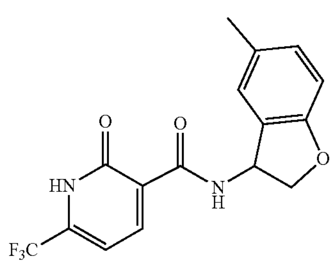 [SMILES: Cc1ccc2c(c1)C(NC(=O)c1ccc(C(F)(F)F)[nH]c1=O)CO2] | N-(5-methyl-2,3-dihydrobenzofuran-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 409 | 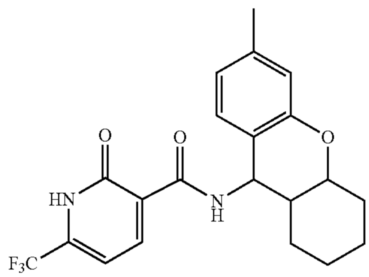 [SMILES: Cc1ccc2c(c1)OC1CCCCC1C2NC(=O)c1ccc(C(F)(F)F)[nH]c1=O] | N-(6-methyl-2,3,4,4a,9,9a-hexahydro-1H-xanthen-9-yl)-2-oxo-6-(trifluoromethyl)-1,2-dihydropyridine-3-carboxamide |
| 410 | 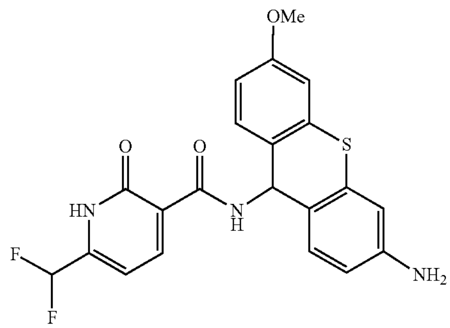 [SMILES: COc1ccc2c(c1)Sc1cc(N)ccc1C2NC(=O)c1ccc(C(F)F)[nH]c1=O] | N-(3-amino-6-methoxy-9H-thioxanthen-9-yl)-6-(difluoromethyl)-2-oxo-1,2-dihydropyridine-3-carboxamide |
| 411 | 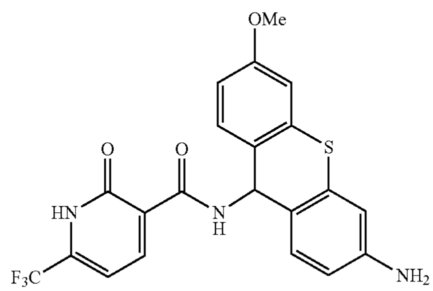 [SMILES: COc1ccc2c(c1)Sc1cc(N)ccc1C2NC(=O)c1ccc(C(F)(F)F)[nH]c1=O] | N-(3-amino-6-methoxy-9H-thioxanthen-9-yl)-2-oxo-6-(trifluoromethyl)-1,2-dihydropyridine-3-carboxamide |
| 412 | 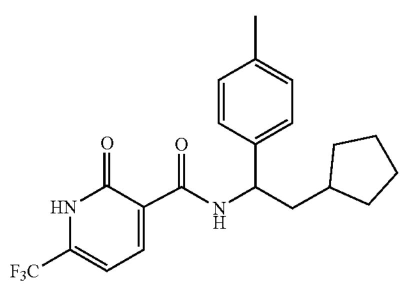 [SMILES: Cc1ccc(C(CC2CCCC2)NC(=O)c2ccc(C(F)(F)F)[nH]c2=O)cc1] | N-(2-cyclopentyl-1-(p-tolyl)ethyl)-2-oxo-6-(trifluoromethyl)-1,2-dihydropyridine-3-carboxamide |
| 413 | 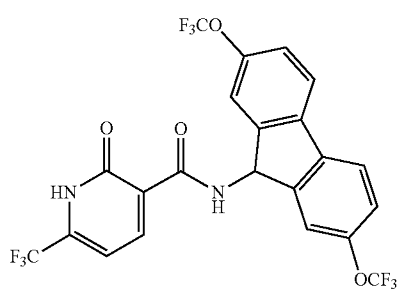 [SMILES: O=C(NC1c2cc(OC(F)(F)F)ccc2-c2ccc(OC(F)(F)F)cc21)c1ccc(C(F)(F)F)[nH]c1=O] | N-(2,7-bis(trifluoromethoxy)-9H-fluoren-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 414 | 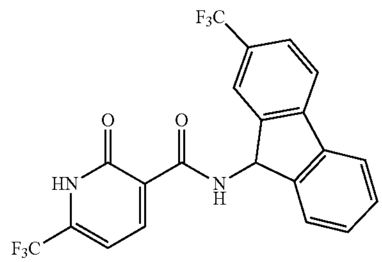 [SMILES: O=C(NC1c2ccccc2-c2ccc(C(F)(F)F)cc21)c1ccc(C(F)(F)F)[nH]c1=O] | 2-oxo-6-(trifluoromethyl)-N-(2-(trifluoromethyl)-9H-fluoren-9-yl)-1,2-dihydropyridine-3-carboxamide |
| 415 | 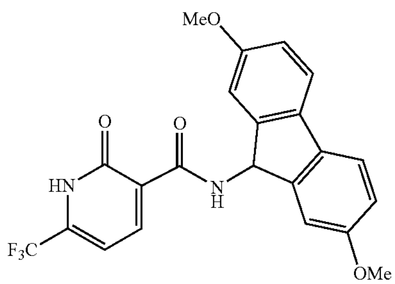 [SMILES: COc1ccc2c(c1)C(NC(=O)c1ccc(C(F)(F)F)[nH]c1=O)c1cc(OC)ccc1-2] | N-(2,7-dimethoxy-9H-fluoren-9-yl)-2-oxo-6-(trifluoromethyl)-1,2-dihydropyridine-3-carboxamide |
| 416 | 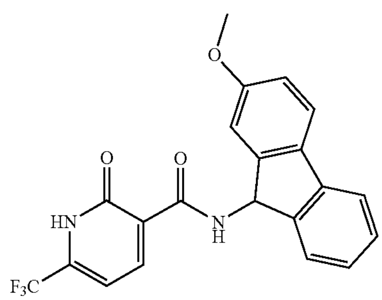 [SMILES: COc1ccc2c(c1)C(NC(=O)c1ccc(C(F)(F)F)[nH]c1=O)c1ccccc1-2] | N-(2-methoxy-9H-fluoren-9-yl)-2-oxo-6-(trifluoromethyl)-1,2-dihydropyridine-3-carboxamide |
| 417 | 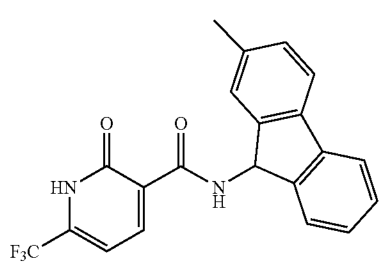 [SMILES: Cc1ccc2c(c1)C(NC(=O)c1ccc(C(F)(F)F)[nH]c1=O)c1ccccc1-2] | N-(2-methyl-9H-fluoren-9-yl)-2-oxo-6-(trifluoromethyl)-1,2-dihydropyridine-3-carboxamide |
| 418 | 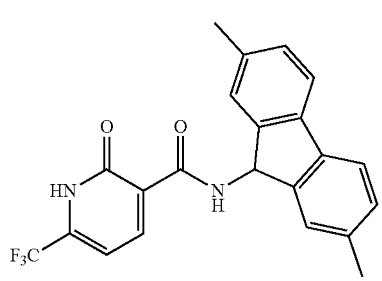 [SMILES: Cc1ccc2c(c1)C(NC(=O)c1ccc(C(F)(F)F)[nH]c1=O)c1cc(C)ccc1-2] | N-(2,7-dimethyl-9H-fluoren-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 419 | 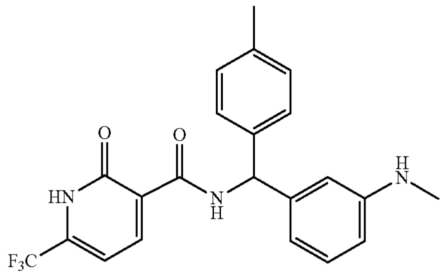 [SMILES: CNc1cccc(C(NC(=O)c2ccc(C(F)(F)F)[nH]c2=O)c2ccc(C)cc2)c1] | N-((3-(methylamino)phenyl)(phenyl)methyl)-2-oxo-6-(trifluoromethyl)-1,2-dihydropyridine-3-carboxamide |
| 420 | 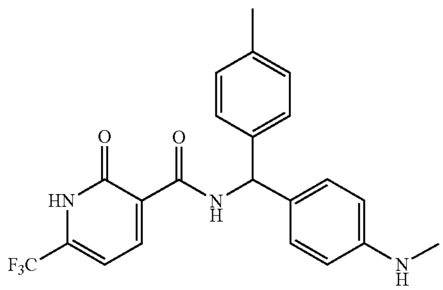 [SMILES: CNc1ccc(C(NC(=O)c2ccc(C(F)(F)F)[nH]c2=O)c2ccc(C)cc2)cc1] | N-((4-(methylamino)phenyl)(p-tolyl)methyl)-2-oxo-6-(trifluoromethyl)-1,2-dihydropyridine-3-carboxamide |
| 421 | 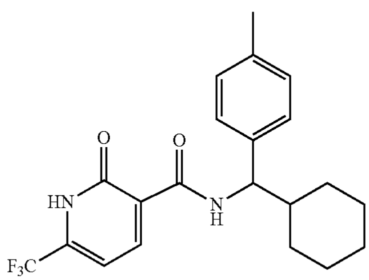 [SMILES: Cc1ccc(C(NC(=O)c2ccc(C(F)(F)F)[nH]c2=O)C2CCCCC2)cc1] | N-(cyclohexyl(p-tolyl)methyl)-2-oxo-6-(trifluoromethyl)-1,2-dihydropyridine-3-carboxamide |
| 422 | 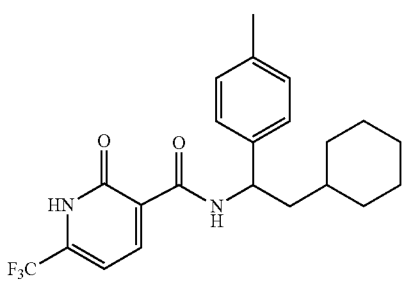 [SMILES: Cc1ccc(C(CC2CCCCC2)NC(=O)c2ccc(C(F)(F)F)[nH]c2=O)cc1] | N-(2-cyclohexyl-1-(p-tolyl)ethyl)-2-oxo-6-(trifluoromethyl)-1,2-dihydropyridine-3-carboxamide |
| 423 | 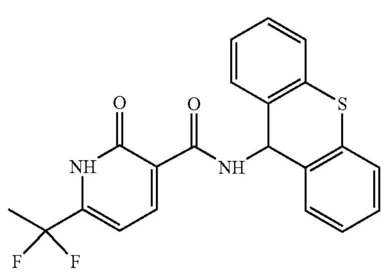 [SMILES: CC(F)(F)c1ccc(C(=O)NC2c3ccccc3Sc3ccccc32)c(=O)[nH]1] | 6-(1,1-difluoroethyl)-2-oxo-N-(9H-thioxanthen-9-yl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 424 | 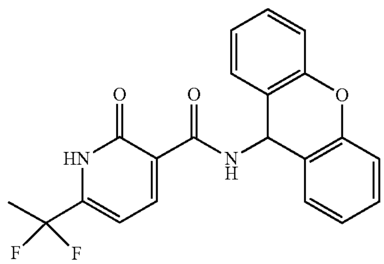 [SMILES: CC(F)(F)c1ccc(C(=O)NC2c3ccccc3Oc3ccccc32)c(=O)[nH]1] | 6-(1,1-difluoroethyl)-2-oxo-N-(9H-xanthen-9-yl)-1,2-dihydropyridine-3-carboxamide |
| 425 | 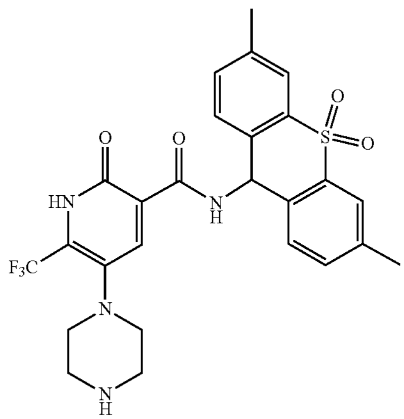 [SMILES: Cc1ccc2c(c1)S(=O)(=O)c1cc(C)ccc1C2NC(=O)c1cc(N2CCNCC2)c(C(F)(F)F)[nH]c1=O] | N-(3,6-dimethyl-10,10-dioxido-9H-thioxanthen-9-yl)-2-oxo-5-(piperazin-1-yl)-6-(trifluoromethyl)-1,2-dihydropyridine-3-carboxamide |
| 426 | 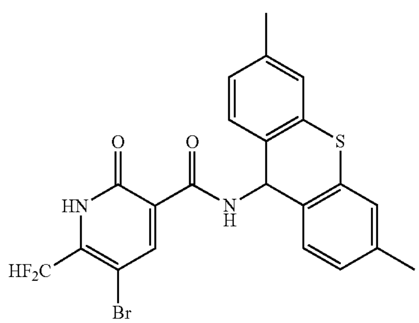 | 5-bromo-6-(difluoromethyl)-N-(3,6-dimethyl-9H-thioxanthen-9-yl)-2-oxo-1,2-dihydropyridine-3-carboxamide |
| 427 | 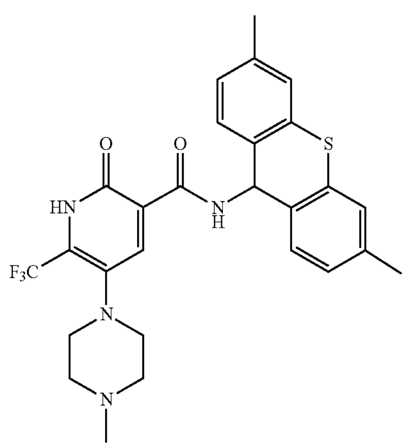 | N-(3,6-dimethyl-9H-thioxanthen-9-yl)-5-(4-methylpiperazin-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 428 | 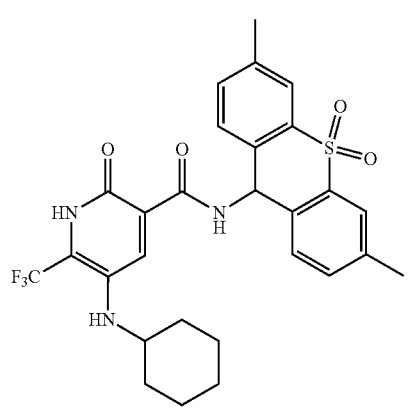 [SMILES: Cc1ccc2c(c1)S(=O)(=O)c1cc(C)ccc1C2NC(=O)c1cc(NC2CCCCC2)c(C(F)(F)F)[nH]c1=O] | 5-(cyclohexylamino)-N-(3,6-dimethyl-10,10-dioxido-9H-thioxanthen-9-yl)-2-oxo-6-(trifluoromethyl)-1,2-dihydropyridine-3-carboxamide |
| 429 | 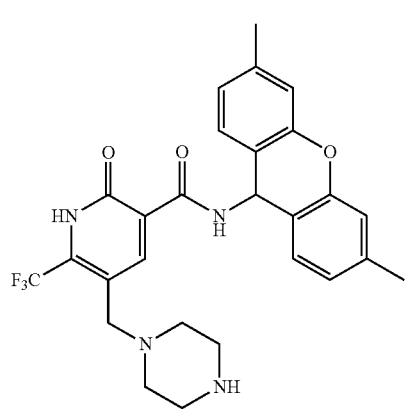 [SMILES: Cc1ccc2c(c1)Oc1cc(C)ccc1C2NC(=O)c1cc(CN2CCNCC2)c(C(F)(F)F)[nH]c1=O] | N-(3,6-dimethyl-9H-xanthen-9-yl)-2-oxo-5-(piperazin-1-ylmethyl)-6-(trifluoromethyl)-1,2-dihydropyridine-3-carboxamide |
| 430 | 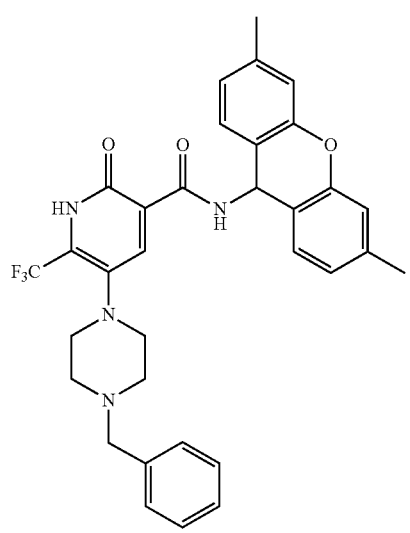 [SMILES: Cc1ccc2c(c1)Oc1cc(C)ccc1C2NC(=O)c1cc(N2CCN(Cc3ccccc3)CC2)c(C(F)(F)F)[nH]c1=O] | 5-(4-benzylpiperazin-1-yl)-N-(3,6-dimethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 431 | 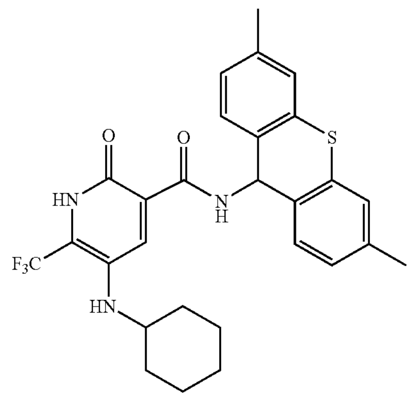 [SMILES: Cc1ccc2c(c1)Sc1cc(C)ccc1C2NC(=O)c1cc(NC2CCCCC2)c(C(F)(F)F)[nH]c1=O] | 5-(cyclohexylamino)-N-(3,6-dimethyl-9H-thioxanthen-9-yl)-2-oxo-6-(trifluoromethyl)-1,2-dihydropyridine-3-carboxamide |
| 432 | 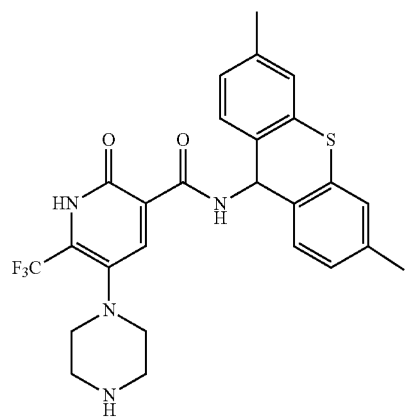 | N-(3,6-dimethyl-9H-thioxanthen-9-yl)-2-oxo-5-(piperazin-1-yl)-6-(trifluoromethyl)-1,2-dihydropyridine-3-carboxamide |
| 433 | 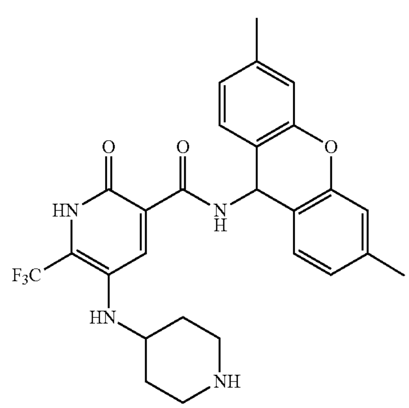 [SMILES: Cc1ccc2c(c1)Oc1cc(C)ccc1C2NC(=O)c1cc(NC2CCNCC2)c(C(F)(F)F)[nH]c1=O] | N-(3,6-dimethyl-9H-xanthen-9-yl)-2-oxo-5-(piperidin-4-ylamino)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 434 | 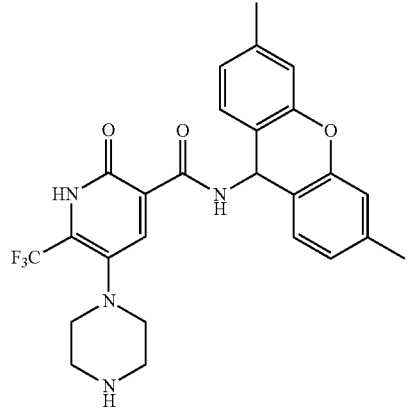 | N-(3,6-dimethyl-9H-xanthen-9-yl)-2-oxo-5-(piperazin-1-yl)-6-(trifluoromethyl)-1,2-dihydropyridine-3-carboxamide |
| 435 | 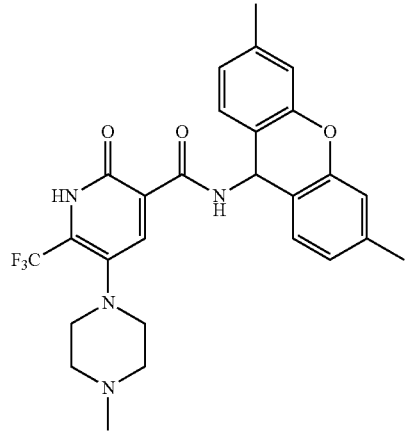 [SMILES: Cc1ccc2c(c1)Oc1cc(C)ccc1C2NC(=O)c1cc(N2CCN(C)CC2)c(C(F)(F)F)[nH]c1=O] | N-(3,6-dimethyl-9H-xanthen-9-yl)-5-(4-methylpiperazin-1-yl)-2-oxo-6-(trifluoromethyl)-1,2-dihydropyridine-3-carboxamide |
| 436 | 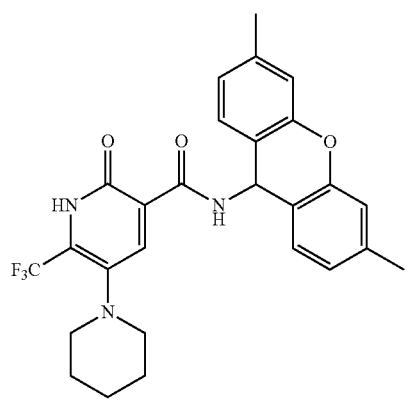 | N-(3,6-dimethyl-9H-xanthen-9-yl)-2-oxo-5-(piperidin-1-yl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 437 | 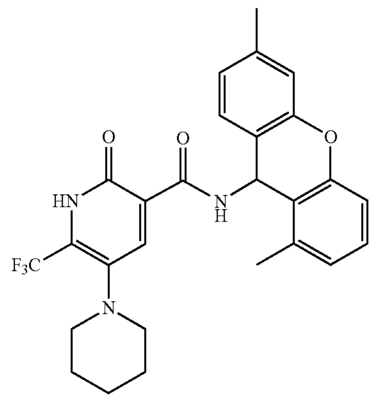 [SMILES: Cc1ccc2c(c1)Oc1cccc(C)c1C2NC(=O)c1cc(N2CCCCC2)c(C(F)(F)F)[nH]c1=O] | N-(1,6-dimethyl-9H-xanthen-9-yl)-2-oxo-5-(piperidin-1-yl)-6-(trifluoromethyl)-1,2-dihydropyridine-3-carboxamide |
| 438 | 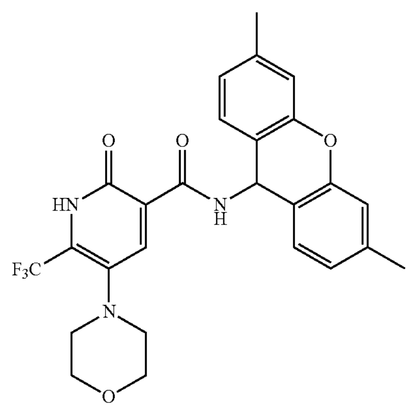 | N-(3,6-dimethyl-9H-xanthen-9-yl)-5-morpholino-2-oxo-6-(trifluoromethyl)-1,2-dihydropyridine-3-carboxamide |
| 439 | 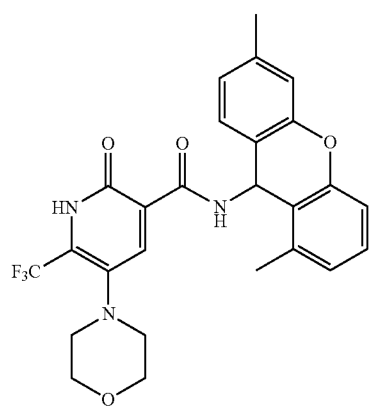 [SMILES: Cc1ccc2c(c1)Oc1cccc(C)c1C2NC(=O)c1cc(N2CCOCC2)c(C(F)(F)F)[nH]c1=O] | N-(1,6-dimethyl-9H-xanthen-9-yl)-5-morpholino-2-oxo-6-(trifluoromethyl)-1,2-dihydropyridine-3-carboxamide |
| 440 | 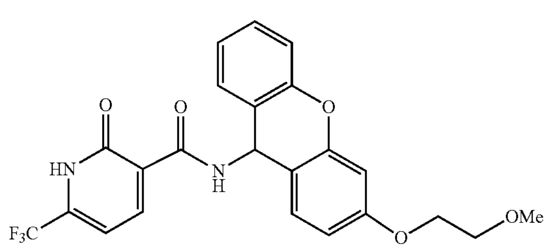 [SMILES: COCCOc1ccc2c(c1)Oc1ccccc1C2NC(=O)c1ccc(C(F)(F)F)[nH]c1=O] | N-(3-(2-methoxyethoxy)-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 441 | 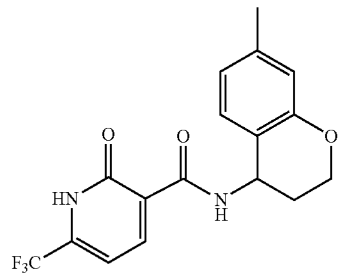 [SMILES: Cc1ccc2c(c1)OCCC2NC(=O)c1ccc(C(F)(F)F)[nH]c1=O] | N-(7-methylchroman-4-yl)-2-oxo-6-(trifluoromethyl)-1,2-dihydropyridine-3-carboxamide |
| 442 | 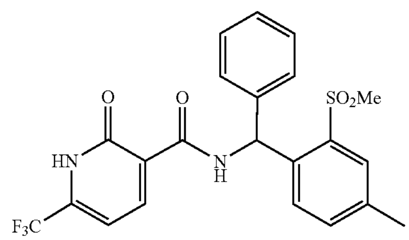 | N-((4-methyl-2-(methylsulfonyl)phenyl)(phenyl)methyl)-2-oxo-6-(trifluoromethyl)-1,2-dihydropyridine-3-carboxamide |
| 443 | 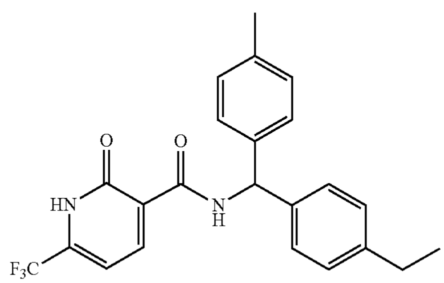 [SMILES: CCc1ccc(C(NC(=O)c2ccc(C(F)(F)F)[nH]c2=O)c2ccc(C)cc2)cc1] | N-((4-ethylphenyl)(p-tolyl)methyl)-2-oxo-6-(trifluoromethyl)-1,2-dihydropyridine-3-carboxamide |
| 444 | 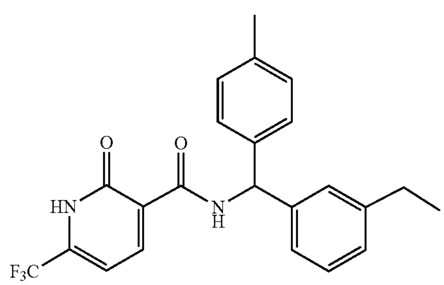 [SMILES: CCc1cccc(C(NC(=O)c2ccc(C(F)(F)F)[nH]c2=O)c2ccc(C)cc2)c1] | N-((3-ethylphenyl)(p-tolyl)methyl)-2-oxo-6-(trifluoromethyl)-1,2-dihydropyridine-3-carboxamide |
| 445 | 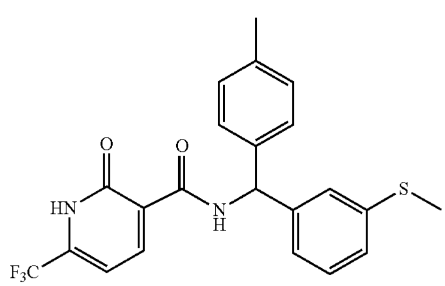 [SMILES: CSc1cccc(C(NC(=O)c2ccc(C(F)(F)F)[nH]c2=O)c2ccc(C)cc2)c1] | N-((3-(methylthio)phenyl)(p-tolyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 446 | 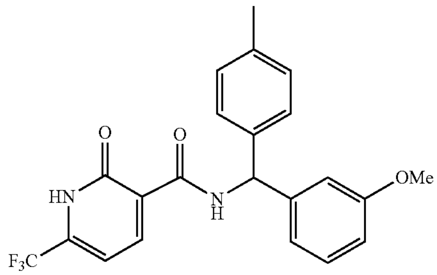 [SMILES: COc1cccc(C(NC(=O)c2ccc(C(F)(F)F)[nH]c2=O)c2ccc(C)cc2)c1] | N-((3-methoxyphenyl)(p-tolyl)methyl)-2-oxo-6-(trifluoromethyl)-1,2-dihydropyridine-3-carboxamide |
| 447 | 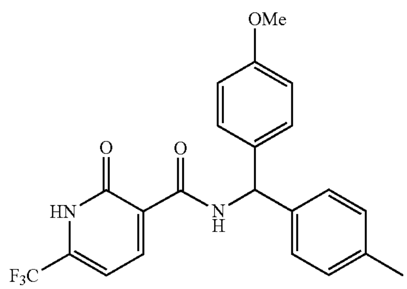 [SMILES: COc1ccc(C(NC(=O)c2ccc(C(F)(F)F)[nH]c2=O)c2ccc(C)cc2)cc1] | N-((4-methoxyphenyl)(p-tolyl)methyl)-2-oxo-6-(trifluoromethyl)-1,2-dihydropyridine-3-carboxamide |
| 448 | 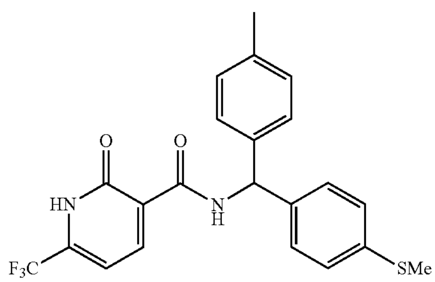 | N-((4-(methylthio)phenyl)(p-tolyl)methyl)-2-oxo-6-(trifluoromethyl)-1,2-dihydropyridine-3-carboxamide |
| 449 | 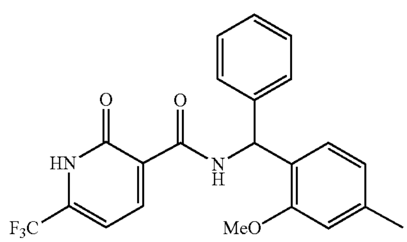 [SMILES: COc1cc(C)ccc1C(NC(=O)c1ccc(C(F)(F)F)[nH]c1=O)c1ccccc1] | N-((2-methoxy-4-methylphenyl)(phenyl)methyl)-2-oxo-6-(trifluoromethyl)-1,2-dihydropyridine-3-carboxamide |
| 450 | 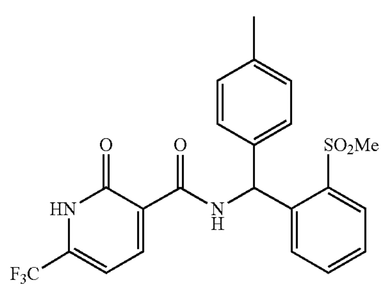 [SMILES: Cc1ccc(C(NC(=O)c2ccc(C(F)(F)F)[nH]c2=O)c2ccccc2S(C)(=O)=O)cc1] | N-((2-(methylsulfonyl)phenyl)(p-tolyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 451 | 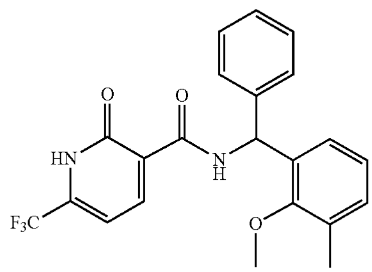 [SMILES: COc1c(C)cccc1C(NC(=O)c1ccc(C(F)(F)F)[nH]c1=O)c1ccccc1] | N-((2-methoxy-3-methylphenyl)(phenyl)methyl)-2-oxo-6-(trifluoromethyl)-1,2-dihydropyridine-3-carboxamide |
| 452 | 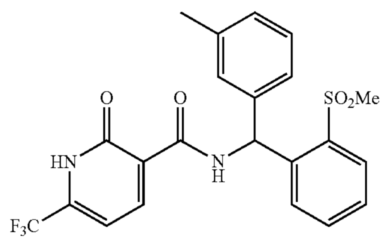 [SMILES: Cc1cccc(C(NC(=O)c2ccc(C(F)(F)F)[nH]c2=O)c2ccccc2S(C)(=O)=O)c1] | N-((2-(methylsulfonyl)phenyl)(m-tolyl)methyl)-2-oxo-6-(trifluoromethyl)-1,2-dihydropyridine-3-carboxamide |
| 453 | 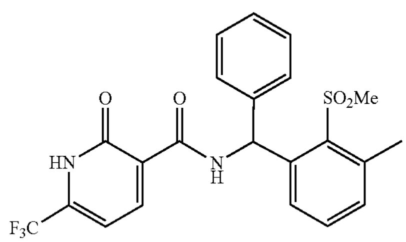 [SMILES: Cc1cccc(C(NC(=O)c2ccc(C(F)(F)F)[nH]c2=O)c2ccccc2)c1S(C)(=O)=O] | N-((3-methyl-2-(methylsulfonyl)phenyl)(phenyl)methyl)-2-oxo-6-(trifluoromethyl)-1,2-dihydropyridine-3-carboxamide |
| 454 | 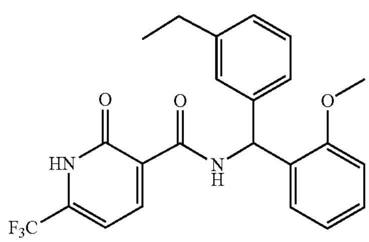 [SMILES: CCc1cccc(C(NC(=O)c2ccc(C(F)(F)F)[nH]c2=O)c2ccccc2OC)c1] | N-((3-ethylphenyl)(2-methoxyphenyl)methyl)-2-oxo-6-(trifluoromethyl)-1,2-dihydropyridine-3-carboxamide |
| 455 | 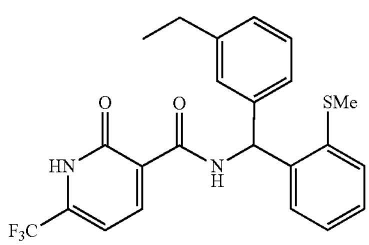 [SMILES: CCc1cccc(C(NC(=O)c2ccc(C(F)(F)F)[nH]c2=O)c2ccccc2SC)c1] | N-((3-ethylphenyl)(2-(methylthio)phenyl)methyl)-2-oxo-6-(trifluoromethyl)-1,2-dihydropyridine-3-carboxamide |
| 456 | 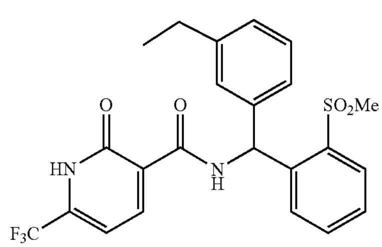 | N-((3-ethylphenyl)(2-(methylsulfonyl)phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 457 | 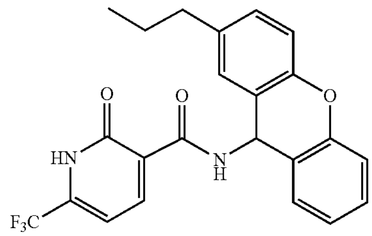 | 2-oxo-N-(2-propyl-9H-xanthen-9-yl)-6-(trifluoromethyl)-1,2-dihydropyridine-3-carboxamide |
| 458 | 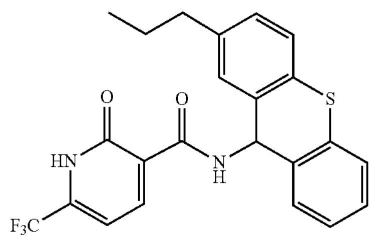 [SMILES: CCCc1ccc2c(c1)C(NC(=O)c1ccc(C(F)(F)F)[nH]c1=O)c1ccccc1O2] | 2-oxo-N-(2-propyl-9H-thioxanthen-9-yl)-6-(trifluoromethyl)-1,2-dihydropyridine-3-carboxamide |
| 459 | 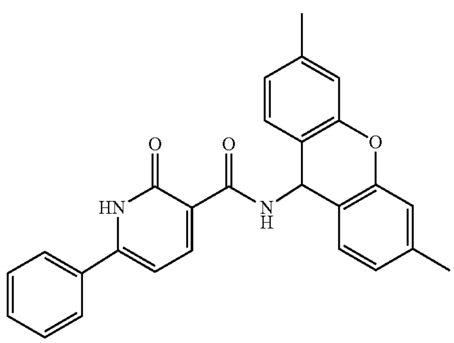 [SMILES: Cc1ccc2c(c1)Oc1cc(C)ccc1C2NC(=O)c1ccc(-c2ccccc2)[nH]c1=O] | N-(3,6-dimethyl-9H-xanthen-9-yl)-2-oxo-6-phenyl-1,2-dihydropyridine-3-carboxamide |
| 460 | 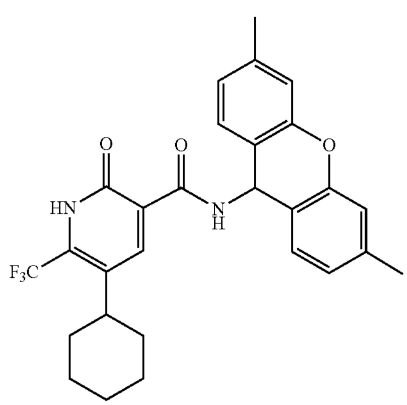 | 5-cyclohexyl-N-(3,6-dimethyl-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 461 | 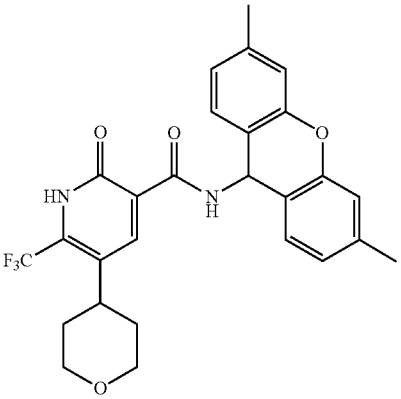 | N-(3,6-dimethyl-9H-xanthen-9-yl)-2-oxo-5-(tetrahydro-2H-pyran-4-yl)-6-(trifluoromethyl)-1,2-dihydropyridine-3-carboxamide |
| 462 | 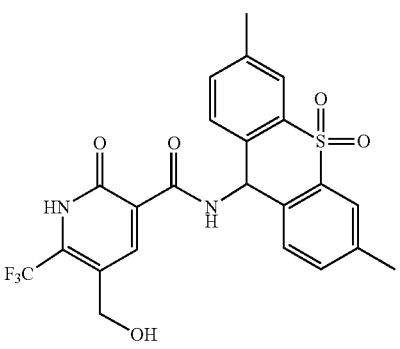 [SMILES: Cc1ccc2c(c1)S(=O)(=O)c1cc(C)ccc1C2NC(=O)c1cc(CO)c(C(F)(F)F)[nH]c1=O] | N-(3,6-dimethyl-10,10-dioxido-9H-thioxanthen-9-yl)-5-(hydroxymethyl)-2-oxo-6-(trifluoromethyl)-1,2-dihydropyridine-3-carboxamide |
| 463 | 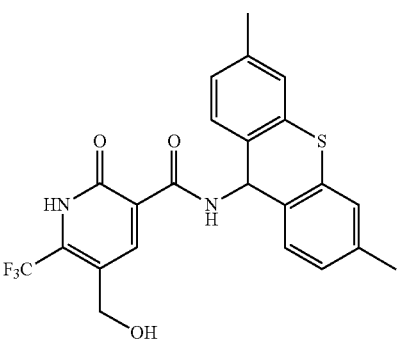 | N-(3,6-dimethyl-9H-thioxanthen-9-yl)-5-(hydroxymethyl)-2-oxo-6-(trifluoromethyl)-1,2-dihydropyridine-3-carboxamide |
| 464 | 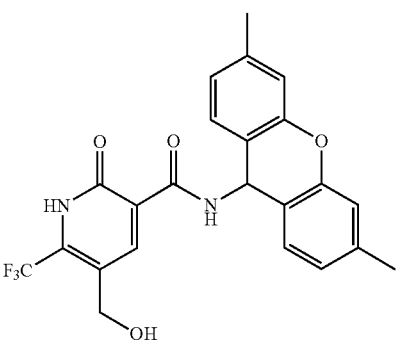 [SMILES: Cc1ccc2c(c1)Oc1cc(C)ccc1C2NC(=O)c1cc(CO)c(C(F)(F)F)[nH]c1=O] | N-(3,6-dimethyl-9H-xanthen-9-yl)-5-(hydroxymethyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 465 | 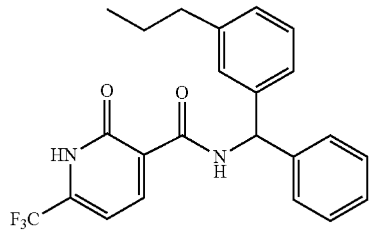 [SMILES: CCCc1cccc(C(NC(=O)c2ccc(C(F)(F)F)[nH]c2=O)c2ccccc2)c1] | 2-oxo-N-(phenyl(3-propylphenyl)methyl)-6-(trifluoromethyl)-1,2-dihydropyridine-3-carboxamide |
| 466 | 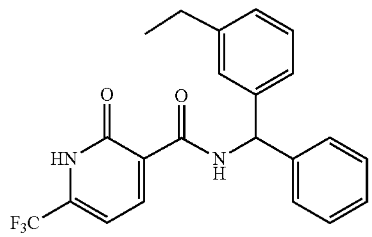 [SMILES: CCc1cccc(C(NC(=O)c2ccc(C(F)(F)F)[nH]c2=O)c2ccccc2)c1] | N-((3-ethylphenyl)(phenyl)methyl)-2-oxo-6-(trifluoromethyl)-1,2-dihydropyridine-3-carboxamide |
| 467 | 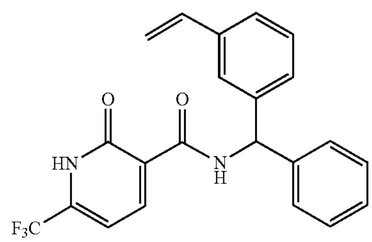 [SMILES: C=Cc1cccc(C(NC(=O)c2ccc(C(F)(F)F)[nH]c2=O)c2ccccc2)c1] | 2-oxo-N-(phenyl(3-vinylphenyl)methyl)-6-(trifluoromethyl)-1,2-dihydropyridine-3-carboxamide |
| 468 | 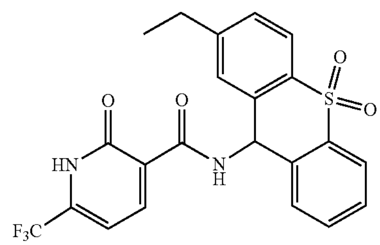 [SMILES: CCc1ccc2c(c1)C(NC(=O)c1ccc(C(F)(F)F)[nH]c1=O)c1ccccc1S2(=O)=O] | N-(2-ethyl-10,10-dioxido-9H-thioxanthen-9-yl)-2-oxo-6-(trifluoromethyl)-1,2-dihydropyridine-3-carboxamide |
| 469 | 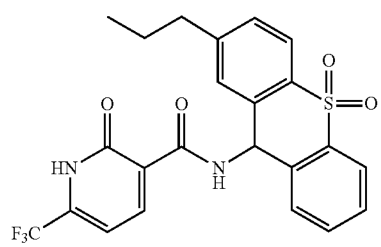 [SMILES: CCCc1ccc2c(c1)C(NC(=O)c1ccc(C(F)(F)F)[nH]c1=O)c1ccccc1S2(=O)=O] | N-(10,10-dioxido-2-propyl-9H-thioxanthen-9-yl)-2-oxo-6-(trifluoromethyl)-1,2-dihydropyridine-3-carboxamide |
| 470 | 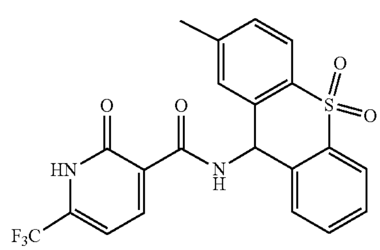 [SMILES: Cc1ccc2c(c1)C(NC(=O)c1ccc(C(F)(F)F)[nH]c1=O)c1ccccc1S2(=O)=O] | N-(2-methyl-10,10-dioxido-9H-thioxanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 471 | 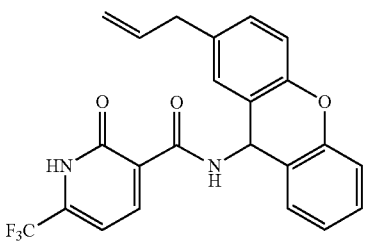 [SMILES: C=CCc1ccc2c(c1)C(NC(=O)c1ccc(C(F)(F)F)[nH]c1=O)c1ccccc1O2] | N-(2-allyl-9H-xanthen-9-yl)-2-oxo-6-(trifluoromethyl)-1,2-dihydropyridine-3-carboxamide |
| 472 | 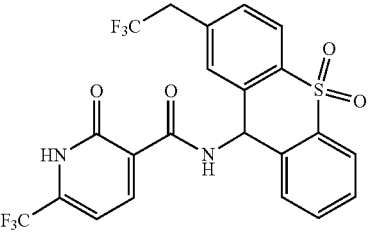 | N-(10,10-dioxido-2-(2,2,2-trifluoroethyl)-9H-thioxanthen-9-yl)-2-oxo-6-(trifluoromethyl)-1,2-dihydropyridine-3-carboxamide |
| 473 | 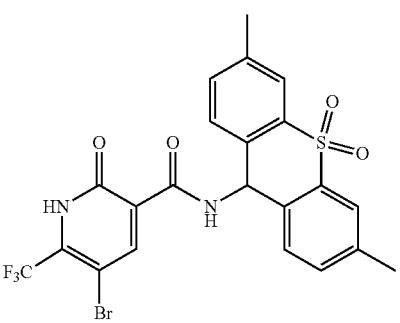 [SMILES: Cc1ccc2c(c1)S(=O)(=O)c1cc(C)ccc1C2NC(=O)c1cc(Br)c(C(F)(F)F)[nH]c1=O] | 5-bromo-N-(3,6-dimethyl-10,10-dioxido-9H-thioxanthen-9-yl)-2-oxo-6-(trifluoromethyl)-1,2-dihydropyridine-3-carboxamide |
| 474 | 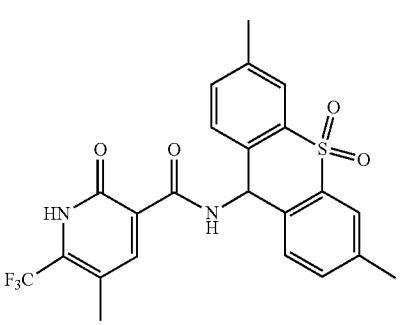 [SMILES: Cc1ccc2c(c1)S(=O)(=O)c1cc(C)ccc1C2NC(=O)c1cc(C)c(C(F)(F)F)[nH]c1=O] | N-(3,6-dimethyl-10,10-dioxido-9H-thioxanthen-9-yl)-5-methyl-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 475 | 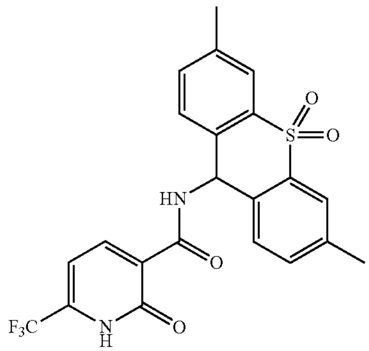 [SMILES: Cc1ccc2c(c1)S(=O)(=O)c1cc(C)ccc1C2NC(=O)c1ccc(C(F)(F)F)[nH]c1=O] | N-(3,6-dimethyl-10,10-dioxido-9H-thioxanthen-9-yl)-2-oxo-6-(trifluoromethyl)-1,2-dihydropyridine-3-carboxamide |
| 476 | 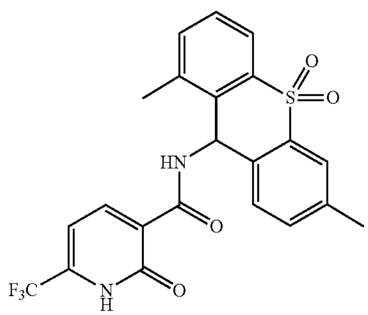 [SMILES: Cc1ccc2c(c1)S(=O)(=O)c1cccc(C)c1C2NC(=O)c1ccc(C(F)(F)F)[nH]c1=O] | N-(1,6-dimethyl-10,10-dioxido-9H-thioxanthen-9-yl)-2-oxo-6-(trifluoromethyl)-1,2-dihydropyridine-3-carboxamide |
| 477 | 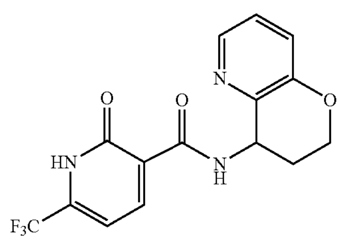 | N-(3,4-dihydro-2H-pyrano(3,2-b)pyridin-4-yl)-2-oxo-6-(trifluoromethyl)-1,2-dihydropyridine-3-carboxamide |
| 478 | 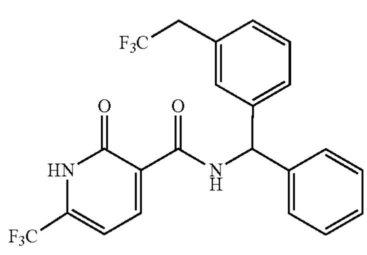 | 2-oxo-N-(phenyl(3-(2,2,2-trifluoroethyl)phenyl)methyl)-6-(trifluoromethyl)-1,2-dihydropyridine-3-carboxamide |
| 479 | 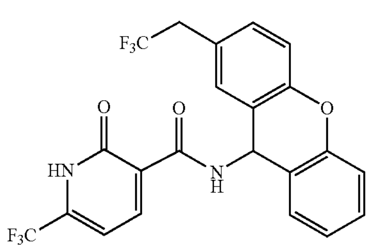 | 2-oxo-N-(2-(2,2,2-trifluoroethyl)-9H-xanthen-9-yl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 480 | 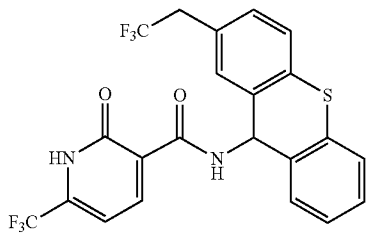 [SMILES: O=C(NC1c2ccccc2Sc2ccc(CC(F)(F)F)cc21)c1ccc(C(F)(F)F)[nH]c1=O] | 2-oxo-N-(2-(2,2,2-trifluoroethyl)-9H-thioxanthen-9-yl)-6-(trifluoromethyl)-1,2-dihydropyridine-3-carboxamide |
| 481 | 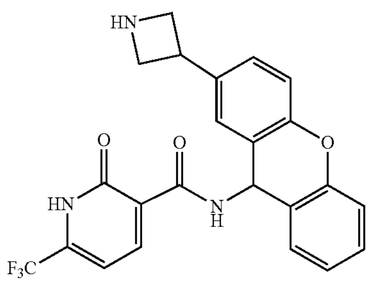 [SMILES: O=C(NC1c2ccccc2Oc2ccc(C3CNC3)cc21)c1ccc(C(F)(F)F)[nH]c1=O] | N-(2-(azetidin-3-yl)-9H-xanthen-9-yl)-2-oxo-6-(trifluoromethyl)-1,2-dihydropyridine-3-carboxamide |
| 482 | 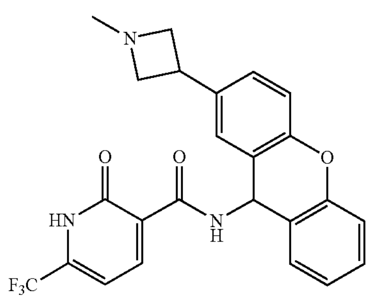 [SMILES: CN1CC(c2ccc3c(c2)C(NC(=O)c2ccc(C(F)(F)F)[nH]c2=O)c2ccccc2O3)C1] | N-(2-(1-methylazetidin-3-yl)-9H-xanthen-9-yl)-2-oxo-6-(trifluoromethyl)-1,2-dihydropyridine-3-carboxamide |
| 483 | 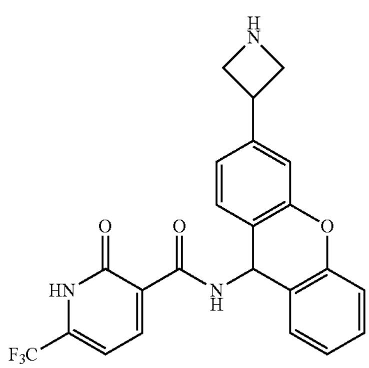 [SMILES: O=C(NC1c2ccccc2Oc2cc(C3CNC3)ccc21)c1ccc(C(F)(F)F)[nH]c1=O] | N-(3-(azetidin-3-yl)-9H-xanthen-9-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 484 | 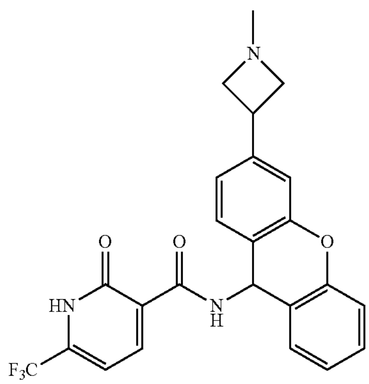 [SMILES: CN1CC(c2ccc3c(c2)Oc2ccccc2C3NC(=O)c2ccc(C(F)(F)F)[nH]c2=O)C1] | N-(3-(1-methylazetidin-3-yl)-9H-xanthen-9-yl)-2-oxo-6-(trifluoromethyl)-1,2-dihydropyridine-3-carboxamide |
| 485 | 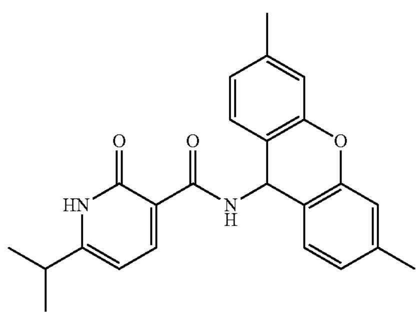 [SMILES: Cc1ccc2c(c1)Oc1cc(C)ccc1C2NC(=O)c1ccc(C(C)C)[nH]c1=O] | N-(3,6-dimethyl-9H-xanthen-9-yl)-6-isopropyl-2-oxo-1,2-dihydropyridine-3-carboxamide |
| 486 | 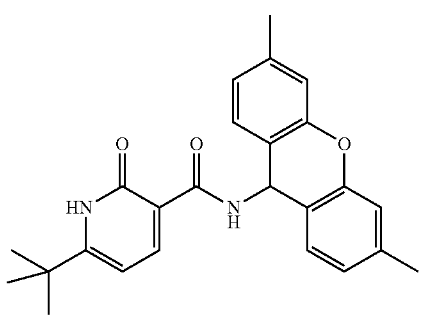 [SMILES: Cc1ccc2c(c1)Oc1cc(C)ccc1C2NC(=O)c1ccc(C(C)(C)C)[nH]c1=O] | 6-(tert-butyl)-N-(3,6-dimethyl-9H-xanthen-9-yl)-2-oxo-1,2-dihydropyridine-3-carboxamide |
| 487 | 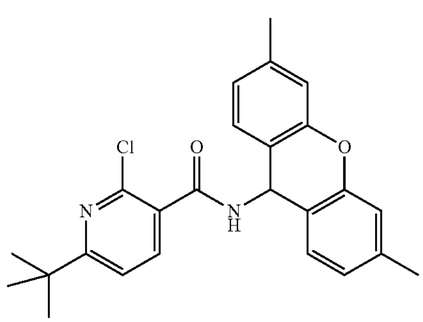 [SMILES: Cc1ccc2c(c1)Oc1cc(C)ccc1C2NC(=O)c1ccc(C(C)(C)C)nc1Cl] | 6-(tert-butyl)-2-chloro-N-(3,6-dimethyl-9H-xanthen-9-yl)nicotinamide |

TABLE 3-continued

Exemplary compounds suitable for the methods of the disclosure

| Compound Ref. No: | Compound Structure | Compound name- generated by ChemBioDraw 14.0 |
|---|---|---|
| 488 | 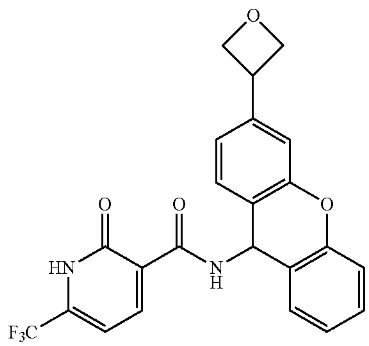 [SMILES: O=C(NC1c2ccccc2Oc2cc(C3COC3)ccc21)c1ccc(C(F)(F)F)[nH]c1=O] | N-(3-(oxetan-3-yl)-9H-xanthen-9-yl)-2-oxo-6-(trifluoromethyl)-1,2-dihydropyridine-3-carboxamide |
| 489 | 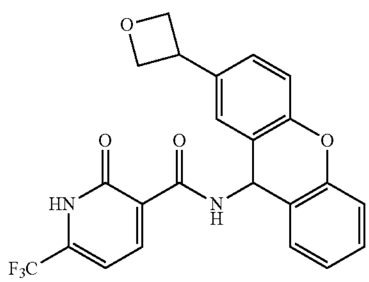 [SMILES: O=C(NC1c2ccccc2Oc2ccc(C3COC3)cc21)c1ccc(C(F)(F)F)[nH]c1=O] | N-(2-(oxetan-3-yl)-9H-xanthen-9-yl)-2-oxo-6-(trifluoromethyl)-1,2-dihydropyridine-3-carboxamide |
| 490 | 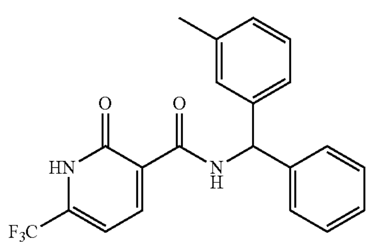 | 2-oxo-N-(phenyl(m-tolyl)methyl)-6-(trifluoromethyl)-1,2-dihydropyridine-3-carboxamide |
| 492 | 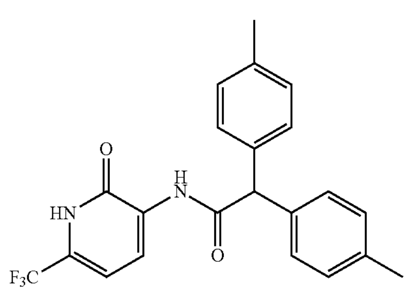 [SMILES: Cc1ccc(C(C(=O)Nc2ccc(C(F)(F)F)[nH]c2=O)c2ccc(C)cc2)cc1] | N-(2-oxo-6-(trifluoromethyl)-1,2-dihydropyridin-3-yl)-2,2-di-p-tolylacetamide |

TABLE 3-continued

Exemplary compounds suitable for the methods of the disclosure

| Compound Ref. No: | Compound Structure | Compound name-generated by ChemBioDraw 14.0 |
|---|---|---|
| 493 | 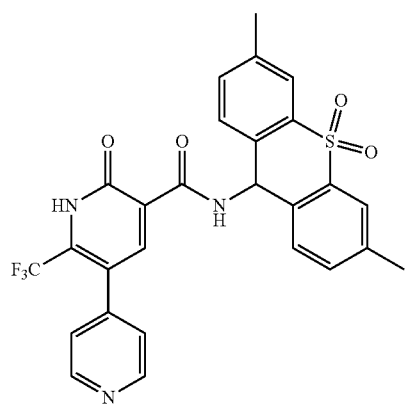 [SMILES: Cc1ccc2c(c1)S(=O)(=O)c1cc(C)ccc1C2NC(=O)c1cc(-c2ccncc2)c(C(F)(F)F)[nH]c1=O] | N-(3,6-dimethyl-10,10-dioxido-9H-thioxanthen-9-yl)-6-oxo-2-(trifluoromethyl)-1,6-dihydro-[3,4'-bipyridine]-5-carboxamide |
| 494 | 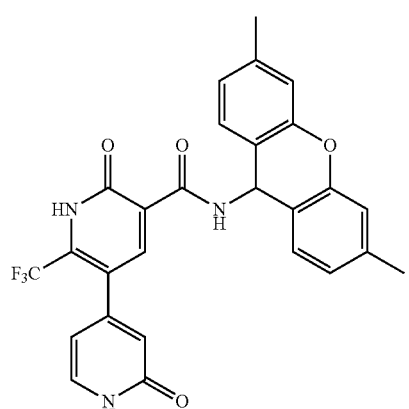 | N-(3,6-dimethyl-9H-xanthen-9-yl)-2',6-dioxo-2-(trifluoromethyl)-1,1',2',6-tetrahydro-[3,4'-bipyridine]-5-carboxamide |
| 495 | 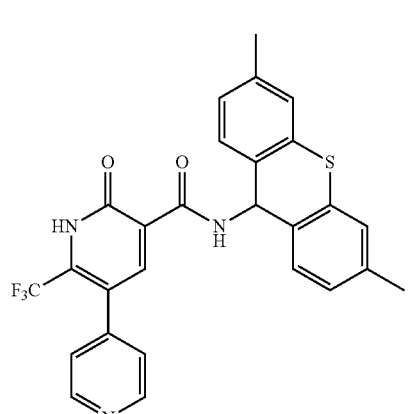 | N-(3,6-dimethyl-9H-thioxanthen-9-yl)-6-oxo-2-(trifluoromethyl)-1,6-dihydro-[3,4'-bipyridine]-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 496 | 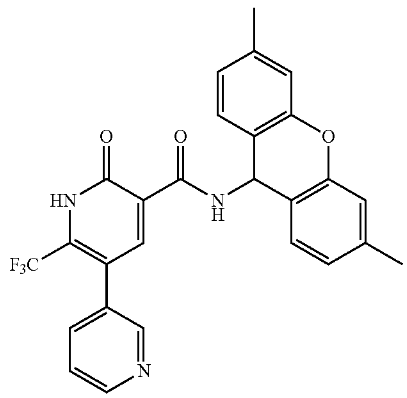 [SMILES: Cc1ccc2c(c1)Oc1cc(C)ccc1C2NC(=O)c1cc(-c2cccnc2)c(C(F)(F)F)[nH]c1=O] | N-(3,6-dimethyl-9H-xanthen-9-yl)-6-oxo-2-(trifluoromethyl)-1,6-dihydro-[3,3'-bipyridine]-5-carboxamide |
| 497 | 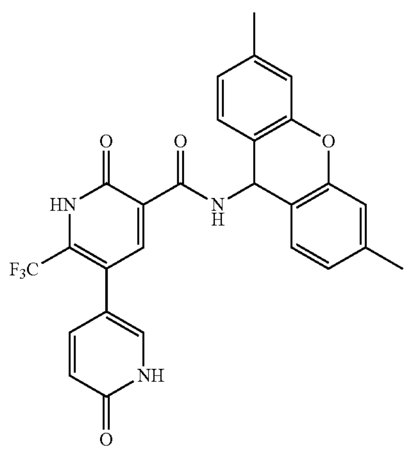 [SMILES: Cc1ccc2c(c1)Oc1cc(C)ccc1C2NC(=O)c1cc(-c2ccc(=O)[nH]c2)c(C(F)(F)F)[nH]c1=O] | N-(3,6-dimethyl-9H-xanthen-9-yl)-6,6'-dioxo-2-(trifluoromethyl)-1,1',6,6'-tetrahydro-[3,3'-bipyridine]-5-carboxamide |
| 498 | 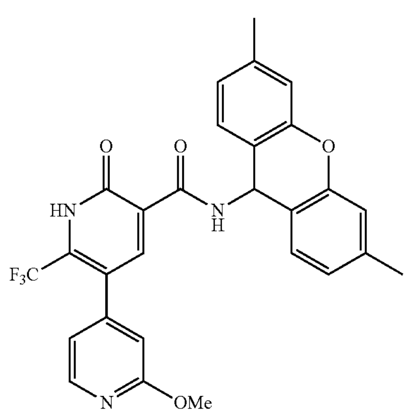 [SMILES: COc1cc(-c2cc(C(=O)NC3c4ccc(C)cc4Oc4cc(C)ccc43)c(=O)[nH]c2C(F)(F)F)ccn1] | N-(3,6-dimethyl-9H-xanthen-9-yl)-2'-methoxy-6-oxo-2-(trifluoromethyl)-1,6-dihydro-[3,4'-bipyridine]-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 499 | 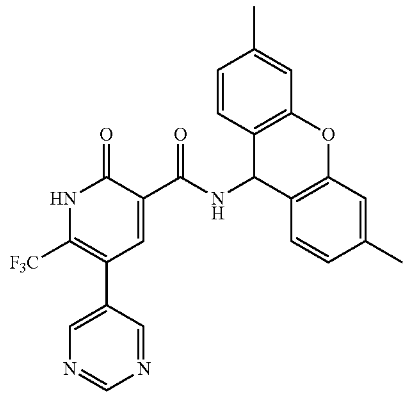 [SMILES: Cc1ccc2c(c1)Oc1cc(C)ccc1C2NC(=O)c1cc(-c2cncnc2)c(C(F)(F)F)[nH]c1=O] | N-(3,6-dimethyl-9H-xanthen-9-yl)-2-oxo-5-(pyrimidin-5-yl)-6-(trifluoromethyl)-1,2-dihydropyridine-3-carboxamide |
| 500 | 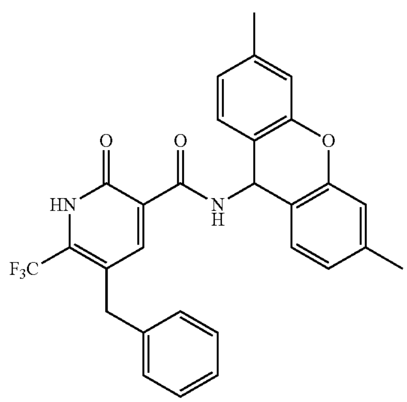 [SMILES: Cc1ccc2c(c1)Oc1cc(C)ccc1C2NC(=O)c1cc(Cc2ccccc2)c(C(F)(F)F)[nH]c1=O] | 5-benzyl-N-(3,6-dimethyl-9H-xanthen-9-yl)-2-oxo-6-(trifluoromethyl)-1,2-dihydropyridine-3-carboxamide |
| 501 | 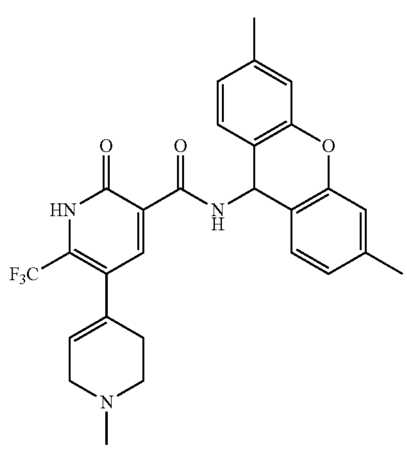 [SMILES: Cc1ccc2c(c1)Oc1cc(C)ccc1C2NC(=O)c1cc(C2=CCN(C)CC2)c(C(F)(F)F)[nH]c1=O] | N-(3,6-dimethyl-9H-xanthen-9-yl)-1'-methyl-6-oxo-2-(trifluoromethyl)-1,1',2',3',6,6'-hexahydro-[3,4'-bipyridine]-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 502 | 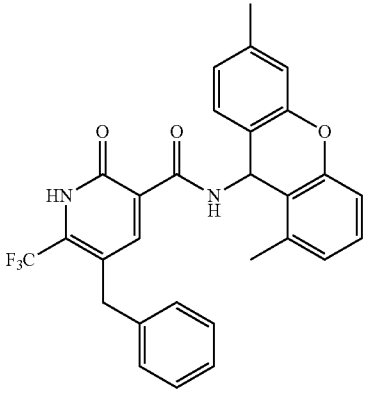 [SMILES: Cc1ccc2c(c1)Oc1cccc(C)c1C2NC(=O)c1cc(Cc2ccccc2)c(C(F)(F)F)[nH]c1=O] | 5-benzyl-N-(1,6-dimethyl-9H-xanthen-9-yl)-2-oxo-6-(trifluoromethyl)-1,2-dihydropyridine-3-carboxamide |
| 503 | 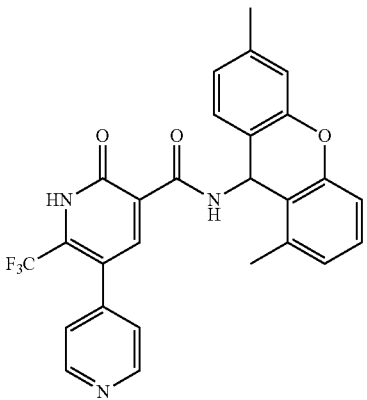 [SMILES: Cc1ccc2c(c1)Oc1cccc(C)c1C2NC(=O)c1cc(-c2ccncc2)c(C(F)(F)F)[nH]c1=O] | N-(1,6-dimethyl-9H-xanthen-9-yl)-6-oxo-2-(trifluoromethyl)-1,6-dihydro-[3,4'-bipyridine]-5-carboxamide |
| 504 | 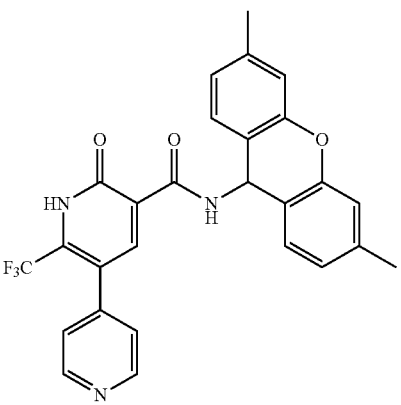 [SMILES: Cc1ccc2c(c1)Oc1cc(C)ccc1C2NC(=O)c1cc(-c2ccncc2)c(C(F)(F)F)[nH]c1=O] | N-(3,6-dimethyl-9H-xanthen-9-yl)-6-oxo-2-(trifluoromethyl)-1,6-dihydro-[3,4'-bipyridine]-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 505 | 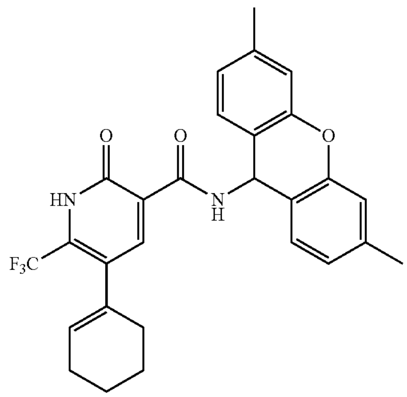 [SMILES: Cc1ccc2c(c1)Oc1cc(C)ccc1C2NC(=O)c1cc(C2=CCCCC2)c(C(F)(F)F)[nH]c1=O] | 5-(cyclohex-1-en-1-yl)-N-(3,6-dimethyl-9H-xanthen-9-yl)-2-oxo-6-(trifluoromethyl)-1,2-dihydropyridine-3-carboxamide |
| 506 | 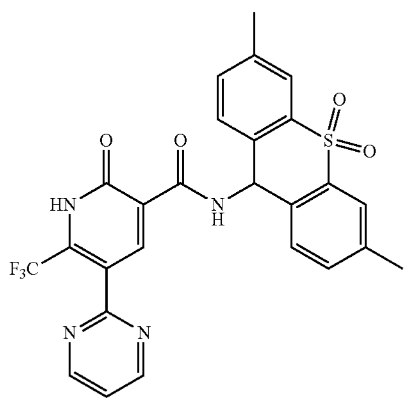 [SMILES: Cc1ccc2c(c1)S(=O)(=O)c1cc(C)ccc1C2NC(=O)c1cc(-c2ncccn2)c(C(F)(F)F)[nH]c1=O] | N-(3,6-dimethyl-10,10-dioxido-9H-thioxanthen-9-yl)-2-oxo-5-(pyrimidin-2-yl)-6-(trifluoromethyl)-1,2-dihydropyridine-3-carboxamide |
| 507 | 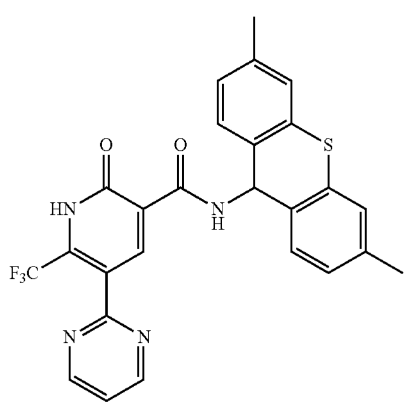 [SMILES: Cc1ccc2c(c1)Sc1cc(C)ccc1C2NC(=O)c1cc(-c2ncccn2)c(C(F)(F)F)[nH]c1=O] | N-(3,6-dimethyl-9H-thioxanthen-9-yl)-2-oxo-5-(pyrimidin-2-yl)-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 508 | 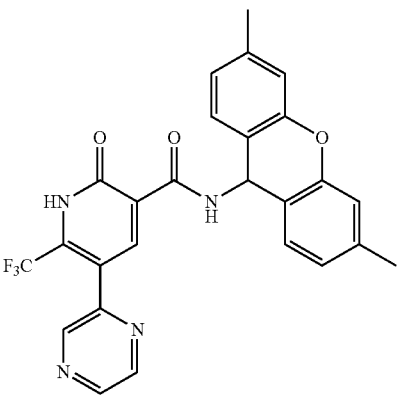 [SMILES: Cc1ccc2c(c1)Oc1cc(C)ccc1C2NC(=O)c1cc(-c2cnccn2)c(C(F)(F)F)[nH]c1=O] | N-(3,6-dimethyl-9H-xanthen-9-yl)-2-oxo-5-(pyrazin-2-yl)-6-(trifluoromethyl)-1,2-dihydropyridine-3-carboxamide |
| 509 | 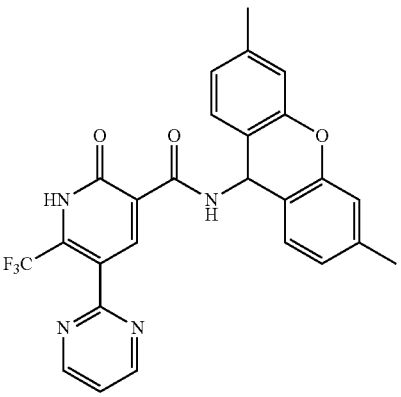 [SMILES: Cc1ccc2c(c1)Oc1cc(C)ccc1C2NC(=O)c1cc(-c2ncccn2)c(C(F)(F)F)[nH]c1=O] | N-(3,6-dimethyl-9H-xanthen-9-yl)-2-oxo-5-(pyrimidin-2-yl)-6-(trifluoromethyl)-1,2-dihydropyridine-3-carboxamide |
| 510 | 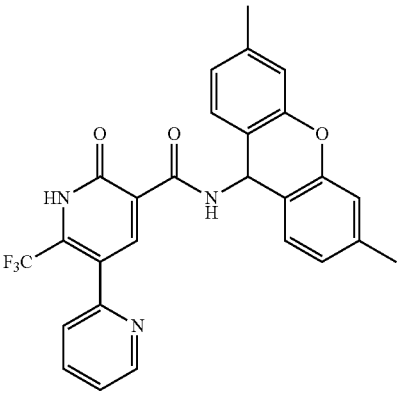 | N-(3,6-dimethyl-9H-xanthen-9-yl)-6'-oxo-2'-(trifluoromethyl)-1',6' dihydro-[2,3'-bipyridine]-5'-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 511 | 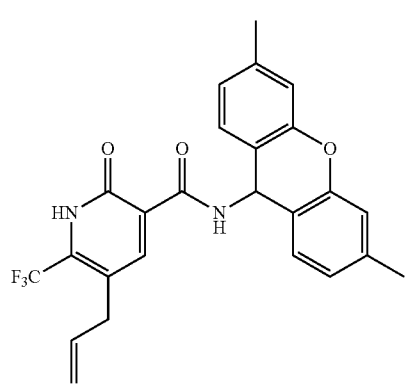 [SMILES: C=CCc1cc(C(=O)NC2c3ccc(C)cc3Oc3cc(C)ccc32)c(=O)[nH]c1C(F)(F)F] | 5-allyl-N-(3,6-dimethyl-9H-xanthen-9-yl)-2-oxo-6-(trifluoromethyl)-1,2-dihydropyridine-3-carboxamide |
| 512 | 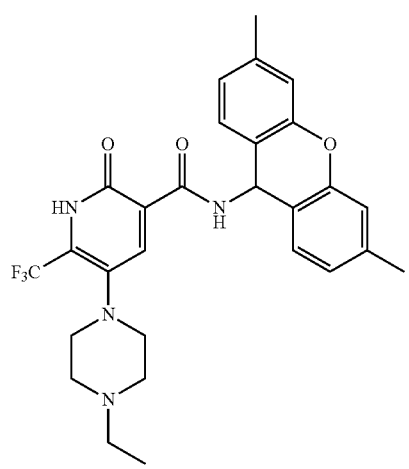 [SMILES: CCN1CCN(c2cc(C(=O)NC3c4ccc(C)cc4Oc4cc(C)ccc43)c(=O)[nH]c2C(F)(F)F)CC1] | N-(3,6-dimethyl-9H-xanthen-9-yl)-5-(4-ethylpiperazin-1-yl)-2-oxo-6-(trifluoromethyl)-1,2-dihydropyridine-3-carboxamide |
| 513 | 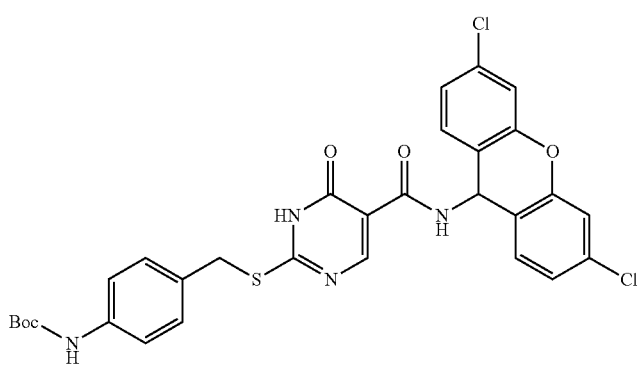 [SMILES: CC(C)(C)OC(=O)Nc1ccc(CSc2ncc(C(=O)NC3c4ccc(Cl)cc4Oc4cc(Cl)ccc43)c(=O)[nH]2)cc1] | tert-butyl(4-(((5-((3,6-dichloro-9H-xanthen-9-yl)carbamoyl)-6-oxo-1,6-dihydropyrimidin-2-yl)thio)methyl)phenyl)carbamate |

TABLE 3-continued

Exemplary compounds suitable for the methods of the disclosure

| Compound Ref. No: | Compound Structure | Compound name-generated by ChemBioDraw 14.0 |
|---|---|---|
| 514 | 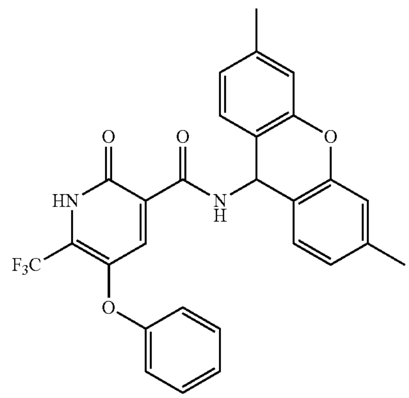 [SMILES: Cc1ccc2c(c1)Oc1cc(C)ccc1C2NC(=O)c1cc(Oc2ccccc2)c(C(F)(F)F)[nH]c1=O] | N-(3,6-dimethyl-9H-xanthen-9-yl)-2-oxo-5-phenoxy-6-(trifluoromethyl)-1,2-dihydropyridine-3-carboxamide |
| 515 | 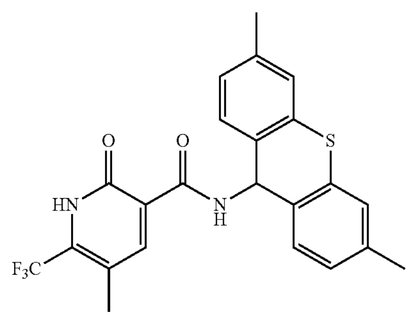 [SMILES: Cc1ccc2c(c1)Sc1cc(C)ccc1C2NC(=O)c1cc(C)c(C(F)(F)F)[nH]c1=O] | N-(3,6-dimethyl-9H-thioxanthen-9-yl)-5-methyl-2-oxo-6-(trifluoromethyl)-1,2-dihydropyridine-3-carboxamide |
| 516 | 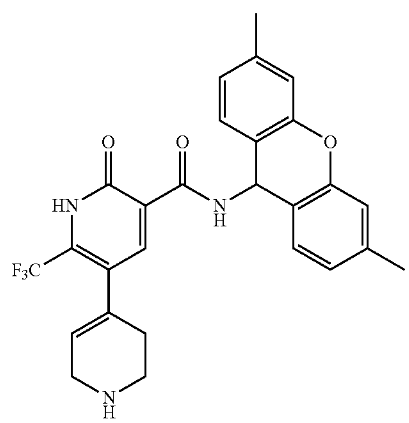 [SMILES: Cc1ccc2c(c1)Oc1cc(C)ccc1C2NC(=O)c1cc(C2=CCNCC2)c(C(F)(F)F)[nH]c1=O] | N-(3,6-dimethyl-9H-xanthen-9-yl)-6-oxo-2-(trifluoromethyl)-1,1',2',3,6,6'-hexahydro-[3,4'-bipyridine]-5-carboxamide |
| 517 | 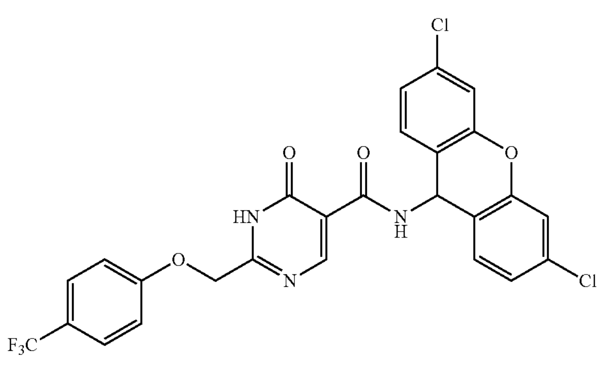 [SMILES: O=C(NC1c2ccc(Cl)cc2Oc2cc(Cl)ccc21)c1cnc(COc2ccc(C(F)(F)F)cc2)[nH]c1=O] | N-(3,6-dichloro-9H-xanthen-9-yl)-6-oxo-2-((4-(trifluoromethyl)phenoxy)methyl)-1,6-dihydropyrimidine-5-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 518 | 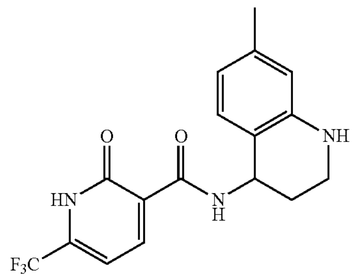 [SMILES: Cc1ccc2c(c1)NCCC2NC(=O)c1ccc(C(F)(F)F)[nH]c1=O] | N-(7-methyl-1,2,3,4-tetrahydroquinolin-4-yl)-2-oxo-6-(trifluoromethyl)-1,2-dihydropyridine-3-carboxamide |
| 519 | 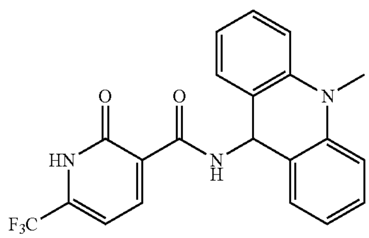 [SMILES: CN1c2ccccc2C(NC(=O)c2ccc(C(F)(F)F)[nH]c2=O)c2ccccc21] | N-(10-methyl-9,10-dihydroacridin-9-yl)-2-oxo-6-(trifluoromethyl)-1,2-dihydropyridine-3-carboxamide |
| 520 | 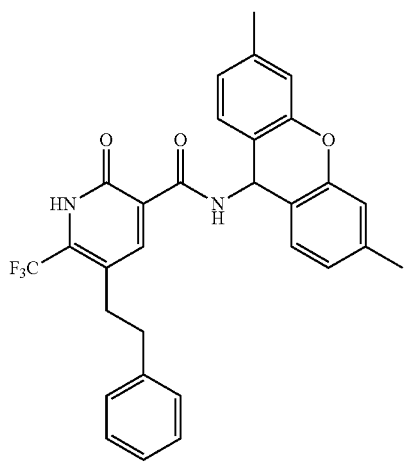 [SMILES: Cc1ccc2c(c1)Oc1cc(C)ccc1C2NC(=O)c1cc(CCc2ccccc2)c(C(F)(F)F)[nH]c1=O] | N-(3,6-dimethyl-9H-xanthen-9-yl)-2-oxo-5-phenethyl-6-(trifluoromethyl)-1,2-dihydropyridine-3-carboxamide |
| 521 | 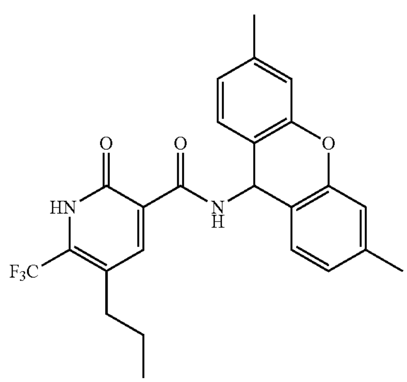 [SMILES: CCCc1cc(C(=O)NC2c3ccc(C)cc3Oc3cc(C)ccc32)c(=O)[nH]c1C(F)(F)F] | N-(3,6-dimethyl-9H-xanthen-9-yl)-2-oxo-5-propyl-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 522 | 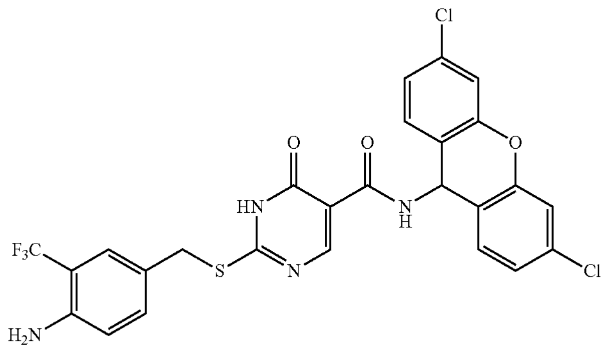 [SMILES: Nc1ccc(CSc2ncc(C(=O)NC3c4ccc(Cl)cc4Oc4cc(Cl)ccc43)c(=O)[nH]2)cc1C(F)(F)F] | 2-((4-amino-3-(trifluoromethyl)benzyl)thio)-N-(3,6-dichloro-9H-xanthen-9-yl)-6-oxo-1,6-dihydropyrimidine-5-carboxamide |
| 523 | 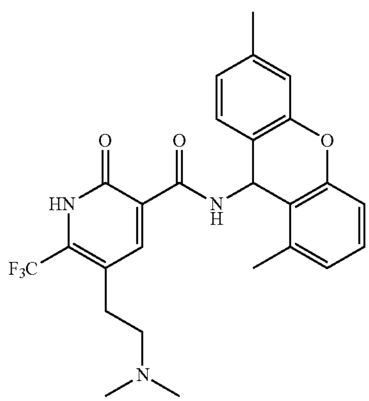 [SMILES: Cc1ccc2c(c1)Oc1cccc(C)c1C2NC(=O)c1cc(CCN(C)C)c(C(F)(F)F)[nH]c1=O] | N-(1,6-dimethyl-9H-xanthen-9-yl)-5-(2-(dimethylamino)ethyl)-2-oxo-6-(trifluoromethyl)-1,2-dihydropyridine-3-carboxamide |
| 524 | 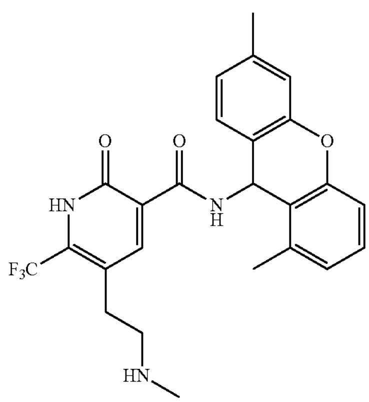 [SMILES: CNCCc1cc(C(=O)NC2c3ccc(C)cc3Oc3cccc(C)c32)c(=O)[nH]c1C(F)(F)F] | N-(1,6-dimethyl-9H-xanthen-9-yl)-5-(2-(methylamino)ethyl)-2-oxo-6-(trifluoromethyl)-1,2-dihydropyridine-3-carboxamide |
| 525 | 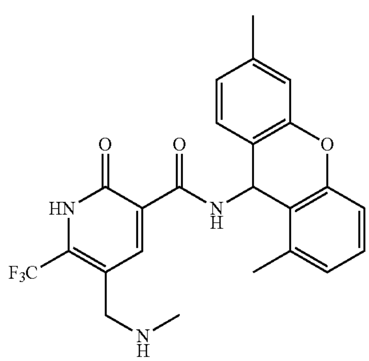 [SMILES: CNCc1cc(C(=O)NC2c3ccc(C)cc3Oc3cccc(C)c32)c(=O)[nH]c1C(F)(F)F] | N-(1,6-dimethyl-9H-xanthen-9-yl)-5-((methylamino)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 526 | 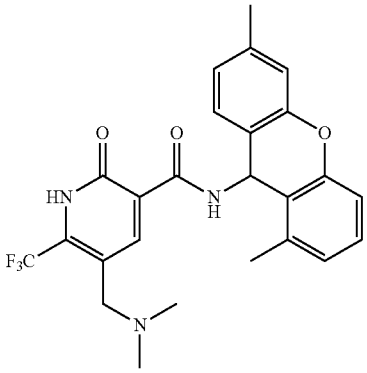 [SMILES: Cc1ccc2c(c1)Oc1cccc(C)c1C2NC(=O)c1cc(CN(C)C)c(C(F)(F)F)[nH]c1=O] | N-(1,6-dimethyl-9H-xanthen-9-yl)-5-((dimethylamino)methyl)-2-oxo-6-(trifluoromethyl)-1,2-dihydropyridine-3-carboxamide |
| 527 | 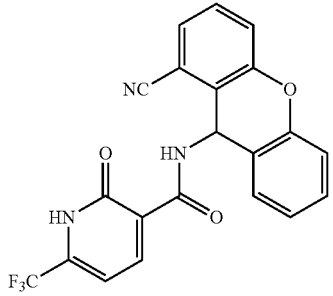 [SMILES: N#Cc1cccc2c1C(NC(=O)c1ccc(C(F)(F)F)[nH]c1=O)c1ccccc1O2] | N-(1-cyano-9H-xanthen-9-yl)-2-oxo-6-(trifluoromethyl)-1,2-dihydropyridine-3-carboxamide |
| 528 | 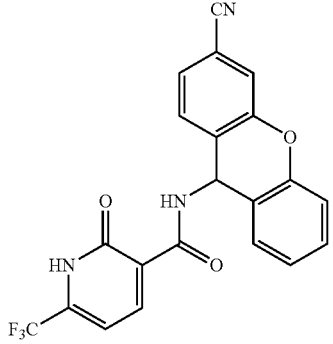 [SMILES: N#Cc1ccc2c(c1)Oc1ccccc1C2NC(=O)c1ccc(C(F)(F)F)[nH]c1=O] | N-(3-cyano-9H-xanthen-9-yl)-2-oxo-6-(trifluoromethyl)-1,2-dihydropyridine-3-carboxamide |
| 529 | 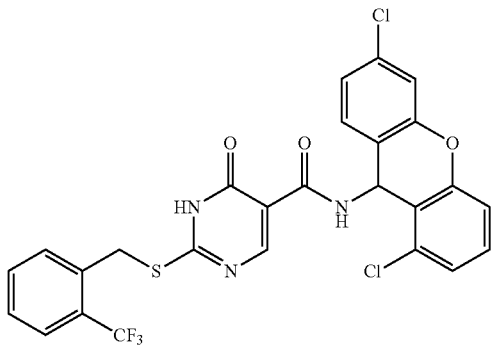 [SMILES: O=C(NC1c2ccc(Cl)cc2Oc2cccc(Cl)c21)c1cnc(SCc2ccccc2C(F)(F)F)[nH]c1=O] | N-(1,6-dichloro-9H-xanthen-9-yl)-6-oxo-2-((2-(trifluoromethyl)benzyl)thio)-1,6-dihydropyrimidine-5-carboxamide |

521
522

TABLE 3-continued

Exemplary compounds suitable for the methods of the disclosure

| Compound Ref. No: | Compound Structure | Compound name- generated by ChemBioDraw 14.0 |
|---|---|---|
| 530 | 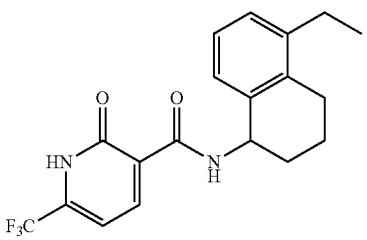 [SMILES: CCc1cccc2c1CCCC2NC(=O)c1ccc(C(F)(F)F)[nH]c1=O] | N-(5-ethyl-1,2,3,4-tetrahydronaphthalen-1-yl)-2-oxo-6-(trifluoromethyl)-1,2-dihydropyridine-3-carboxamide |
| 531 | 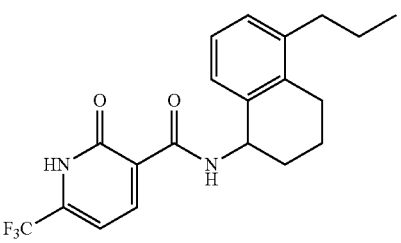 [SMILES: CCCc1cccc2c1CCCC2NC(=O)c1ccc(C(F)(F)F)[nH]c1=O] | 2-oxo-N-(5-propyl-1,2,3,4-tetrahydronaphthalen-1-yl)-6-(trifluoromethyl)-1,2-dihydropyridine-3-carboxamide |
| 532 | 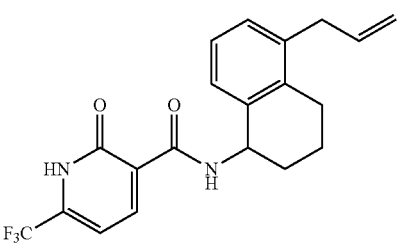 | N-(5-allyl-1,2,3,4-tetrahydronaphthalen-1-yl)-2-oxo-6-(trifluoromethyl)-1,2-dihydropyridine-3-carboxamide |
| 533 | 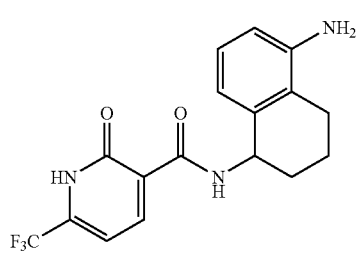 [SMILES: Nc1cccc2c1CCCC2NC(=O)c1ccc(C(F)(F)F)[nH]c1=O] | N-(5-amino-1,2,3,4-tetrahydronaphthalen-l-yl)-2-oxo-6-(trifluoromethyl)-1,2-dihydropyridine-3-carboxamide |
| 534 | 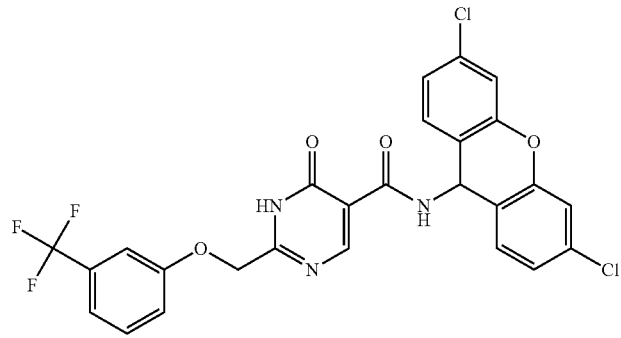 [SMILES: O=C(NC1c2ccc(Cl)cc2Oc2cc(Cl)ccc21)c1cnc(COc2cccc(C(F)(F)F)c2)[nH]c1=O] | N-(3,6-dichloro-9H-xanthen-9-yl)-6-oxo-2-((3-(trifluoromethyl)phenoxy)methyl)-1,6-dihydropyrimidine-5-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 535 | 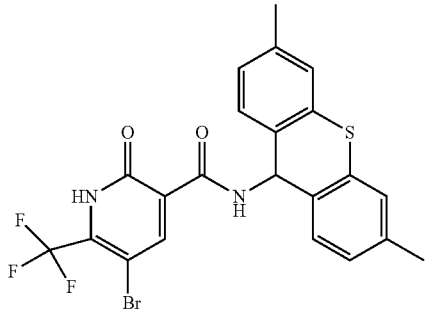 [SMILES: Cc1ccc2c(c1)Sc1cc(C)ccc1C2NC(=O)c1cc(Br)c(C(F)(F)F)[nH]c1=O] | 5-bromo-N-(3,6-dimethyl-9H-thioxanthen-9-yl)-2-oxo-6-(trifluoromethyl)-1,2-dihydropyridine-3-carboxamide |
| 536 | 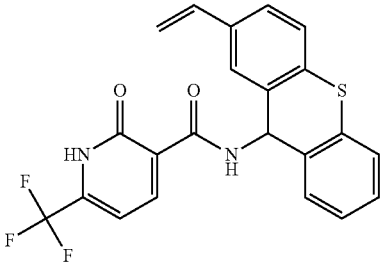 [SMILES: C=Cc1ccc2c(c1)C(NC(=O)c1ccc(C(F)(F)F)[nH]c1=O)c1ccccc1S2] | 2-oxo-6-(trifluoromethyl)-N-(2-vinyl-9H-thioxanthen-9-yl)-1,2-dihydropyridine-3-carboxamide |
| 537 | 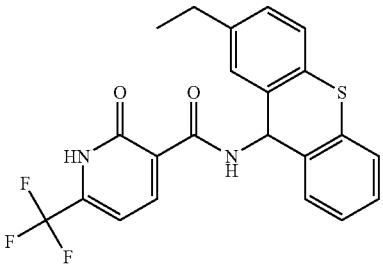 [SMILES: CCc1ccc2c(c1)C(NC(=O)c1ccc(C(F)(F)F)[nH]c1=O)c1ccccc1S2] | N-(2-ethyl-9H-thioxanthen-9-yl)-2-oxo-6-(trifluoromethyl)-1,2-dihydropyridine-3-carboxamide |
| 538 | 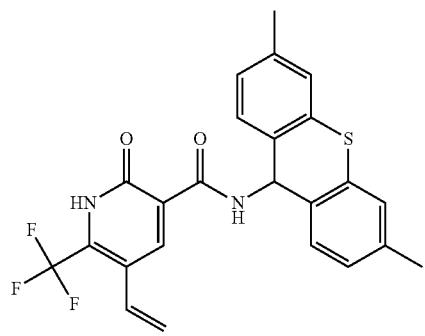 | N-(3,6-dimethyl-9H-thioxanthen-9-yl)-2-oxo-6-(trifluoromethyl)-5-vinyl-1,2-dihydropyridine-3-carboxamide |
| 539 | 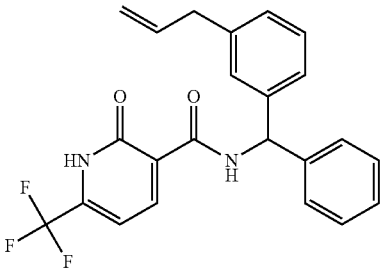 [SMILES: C=CCc1cccc(C(NC(=O)c2ccc(C(F)(F)F)[nH]c2=O)c2ccccc2)c1] | N-((3-allylphenyl)(phenyl)methyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 540 | 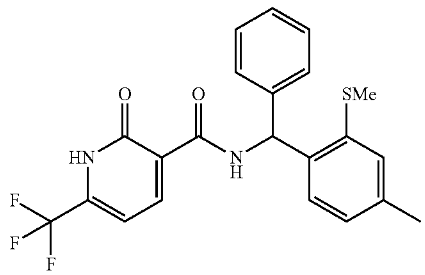 [SMILES: CSc1cc(C)ccc1C(NC(=O)c1ccc(C(F)(F)F)[nH]c1=O)c1ccccc1] | N-((4-methyl-2-(methylthio)phenyl)(phenyl)methyl)-2-oxo-6-(trifluoromethyl)-1,2-dihydropyridine-3-carboxamide |
| 541 | 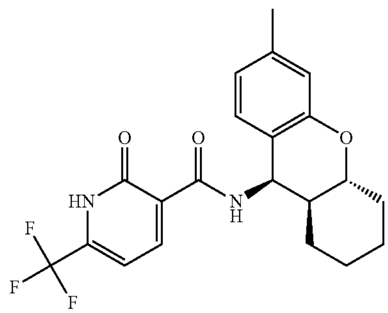 [SMILES: Cc1ccc2c(c1)O[C@@H]1CCCC[C@H]1[C@H]2NC(=O)c1ccc(C(F)(F)F)[nH]c1=O] | N-((4aR,9R,9aS)-6-methyl-2,3,4,4a,9,9a-hexahydro-1H-xanthen-9-yl)-2-oxo-6-(trifluoromethyl)-1,2-dihydropyridine-3-carboxamide |
| 542 | 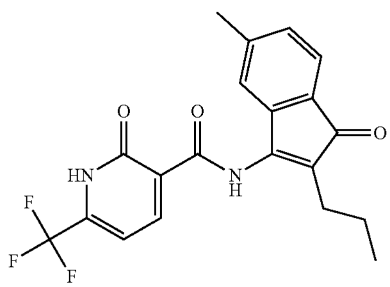 [SMILES: CCCC1=C(NC(=O)c2ccc(C(F)(F)F)[nH]c2=O)c2cc(C)ccc2C1=O] | N-(5-methyl-1-oxo-2-propyl-1H-inden-3-yl)-2-oxo-6-(trifluoromethyl)-1,2-dihydropyridine-3-carboxamide |
| 543 | 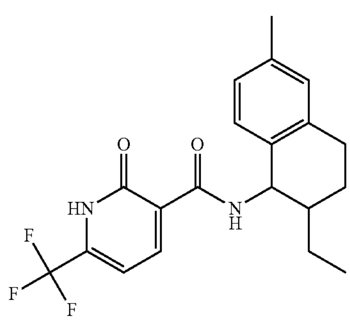 [SMILES: CCC1CCc2cc(C)ccc2C1NC(=O)c1ccc(C(F)(F)F)[nH]c1=O] | N-(2-ethyl-6-methyl-1,2,3,4-tetrahydronaphthalen-1-yl)-2-oxo-6-(trifluoromethyl)-1,2-dihydropyridine-3-carboxamide |
| 544 | 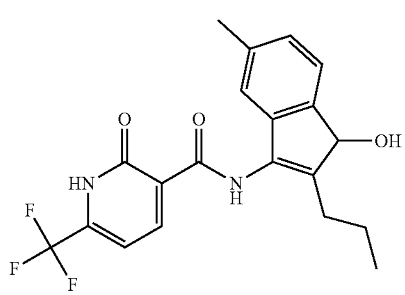 [SMILES: CCCC1=C(NC(=O)c2ccc(C(F)(F)F)[nH]c2=O)c2cc(C)ccc2C1O] | N-(1-hydroxy-5-methyl-2-propyl-1H-inden-3-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name- generated by ChemBioDraw 14.0 |
|---|---|---|
| 545 | 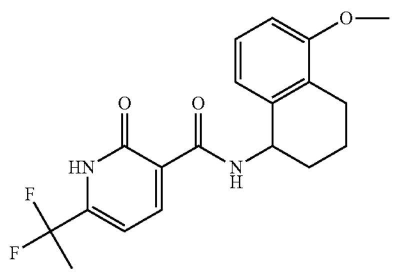 [SMILES: COc1cccc2c1CCCC2NC(=O)c1ccc(C(C)(F)F)[nH]c1=O] | N-(5-methoxy-1,2,3,4-tetrahydronaphthalen-1-yl)-2-oxo-6-(trifluoromethyl)-1,2-dihydropyridine-3-carboxamide |
| 546 | 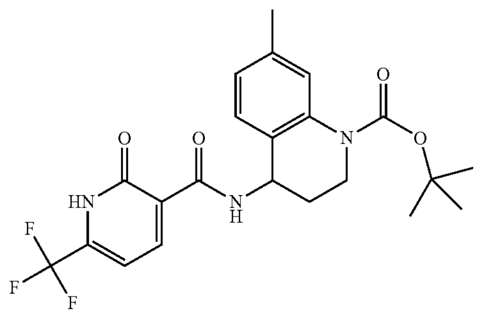 [SMILES: Cc1ccc2c(c1)N(C(=O)OC(C)(C)C)CCC2NC(=O)c1ccc(C(F)(F)F)[nH]c1=O] | tert-butyl 7-methyl-4-(2-oxo-6-(trifluoromethyl)-1,2-dihydropyridine-3-carboxamido)-3,4-dihydroquinoline-1(2H)-carboxylate |
| 547 | 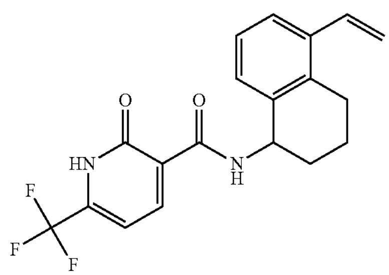 [SMILES: C=Cc1cccc2c1CCCC2NC(=O)c1ccc(C(F)(F)F)[nH]c1=O] | 2-oxo-6-(trifluoromethyl)-N-(5-vinyl-1,2,3,4-tetrahydronaphthalen-1-yl)-1,2-dihydropyridine-3-carboxamide |
| 548 | 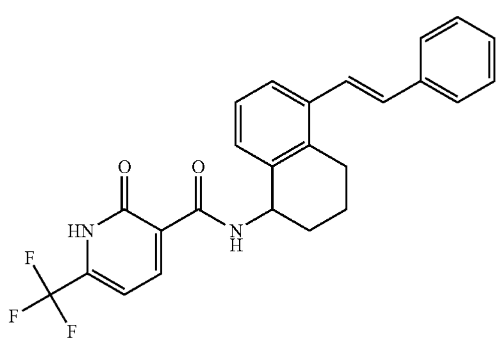 [SMILES: O=C(NC1CCCc2c(/C=C/c3ccccc3)cccc21)c1ccc(C(F)(F)F)[nH]c1=O] | (E)-2-oxo-N-(5-styryl-1,2,3,4-tetrahydronaphthalen-1-yl)-6-(trifluoromethyl)-1,2-dihydropyridine-3-carboxamide |
| 549 | 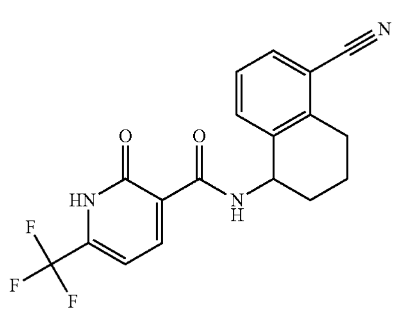 [SMILES: N#Cc1cccc2c1CCCC2NC(=O)c1ccc(C(F)(F)F)[nH]c1=O] | N-(5-cyano-1,2,3,4-tetrahydronaphthalen-1-yl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 550 | 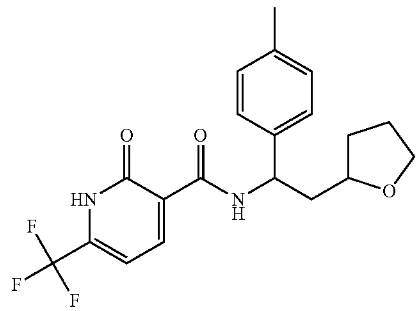 [SMILES: Cc1ccc(C(CC2CCCO2)NC(=O)c2ccc(C(F)(F)F)[nH]c2=O)cc1] | 2-oxo-N-(2-(tetrahydrofuran-2-yl)-1-(p-tolyl)ethyl)-6-(trifluoromethyl)-1,2-dihydropyridine-3-carboxamide |
| 551 | 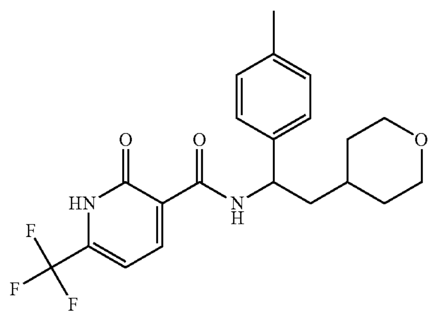 [SMILES: Cc1ccc(C(CC2CCOCC2)NC(=O)c2ccc(C(F)(F)F)[nH]c2=O)cc1] | 2-oxo-N-(2-(tetrahydro-2H-pyran-4-yl)-1-(p-tolyl)ethyl)-6-(trifluoromethyl)-1,2-dihydropyridine-3-carboxamide |
| 552 | 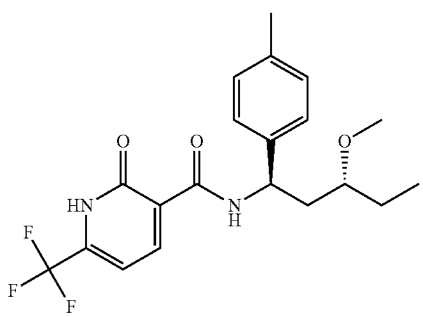 [SMILES: CC[C@H](C[C@@H](NC(=O)c1ccc(C(F)(F)F)[nH]c1=O)c1ccc(C)cc1)OC] | N-((1R,3R)-3-methoxy-1-(p-tolyl)pentyl)-2-oxo-6-(trifluoromethyl)-1,2-dihydropyridine-3-carboxamide |
| 553 | 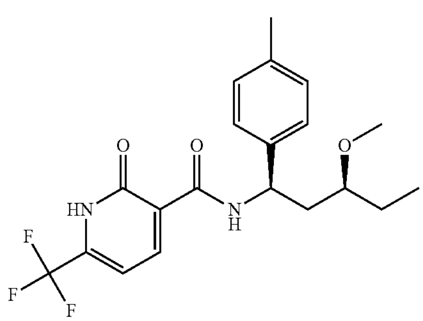 [SMILES: CC[C@@H](C[C@@H](NC(=O)c1ccc(C(F)(F)F)[nH]c1=O)c1ccc(C)cc1)OC] | N-((1R,3S)-3-methoxy-1-(p-tolyl)pentyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 554 | 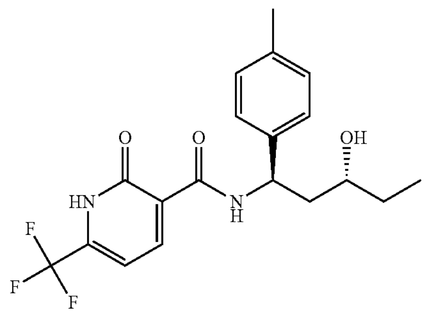 | N-((1R,3R)-3-hydroxy-1-(p-tolyl)pentyl)-2-oxo-6-(trifluoromethyl)-1,2-dihydropyridine-3-carboxamide |
| 555 | 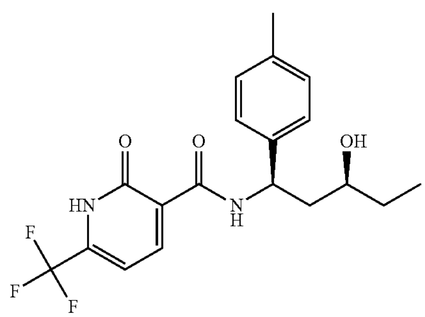 | N-((1R,3S)-3-hydroxy-1-(p-tolyl)pentyl)-2-oxo-6-(trifluoromethyl)-1,2-dihydropyridine-3-carboxamide |
| 556 | 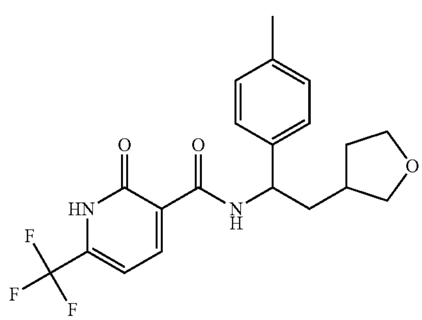 [SMILES: Cc1ccc(C(CC2CCOC2)NC(=O)c2ccc(C(F)(F)F)[nH]c2=O)cc1] | 2-oxo-N-(2-(tetrahydrofuran-3-yl)-1-(p-tolyl)ethyl)-6-(trifluoromethyl)-1,2-dihydropyridine-3-carboxamide |
| 557 | 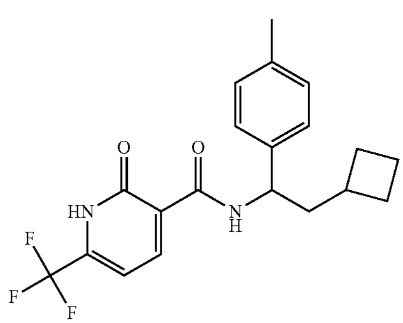 [SMILES: Cc1ccc(C(CC2CCC2)NC(=O)c2ccc(C(F)(F)F)[nH]c2=O)cc1] | N-(2-cyclobutyl-1-(p-tolyl)ethyl)-2-oxo-6-(trifluoromethyl)-1,2-dihydropyridine-3-carboxamide |

TABLE 3-continued

Exemplary compounds suitable for the methods of the disclosure

| Compound Ref. No: | Compound Structure | Compound name-generated by ChemBioDraw 14.0 |
|---|---|---|
| 558 | 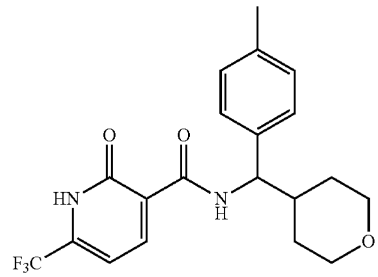 [SMILES: Cc1ccc(C(NC(=O)c2ccc(C(F)(F)F)[nH]c2=O)C2CCOCC2)cc1] | 2-oxo-N-((tetrahydro-2H-pyran-4-yl)(p-tolyl)methyl)-6-(trifluoromethyl)-1,2-dihydropyridine-3-carboxamide |

In one embodiment, modulating the HSD17B13 protein comprises inhibiting the HSD17B13 protein.

In one embodiment, the compounds of the present disclosure are selective for modulating (e.g., inhibiting) the HSD17B13 protein and are less effective at modulating (e.g., inhibiting) other HSD217B family proteins. In one embodiment, the compounds of the present disclosure are selective for modulating (e.g., inhibiting) the HSD17B13 protein with an $IC_{50}$ of less than 10 μmol, and are less effective at modulating (e.g., inhibiting) one or more of HSD17B1, HSD17B2, HSD17B3, HSD17B4, HSD17B5, HSD17B6, HSD17B7, HSD17B8, HSD17B9, HSD17B10, HSD17B11, HSD17B12, or HSD17B14. In one embodiment, the compounds of the present disclosure do not modulate one or more of HSD17B1, HSD17B2, HSD17B3, HSD17B4, HSD17B5, HSD17B6, HSD17B7, HSD17B8, HSD17B9, HSD17B10, HSD17B11, HSD17B12, or HSD17B14, i.e., the compounds of the present disclosure modulate one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14 with an $IC_{50}$ of greater than 50 μmol, or greater than 40 μmol, or greater than 30 μmol, or greater than 20 μmol, or greater than 10 μmol, or greater than 8 μmol, or greater than 5 μmol.

In one embodiment, the HSD17B13 comprises the amino acid sequence of SEQ ID NO: 6. In one embodiment, the amino acid sequence of HSD17B13 comprises one or more tags, e.g. as in SEQ ID NO: 1.

In one embodiment, the HSD17B1 comprises the amino acid sequence of SEQ ID NO: 7. In one embodiment, the HSD17B2 comprises the amino acid sequence of SEQ ID NO: 8. In one embodiment, the HSD17B4 comprises the amino acid sequence of SEQ ID NO: 9. In one embodiment, the HSD17B10 comprises the amino acid sequence of SEQ ID NO: 10.

In one embodiment, the amino acid sequences of HSD17B1, HSD17B2, HSD17B4, and/or HSD17B10 comprise one or more tags. In one embodiment, the HSD17B1 comprises the amino acid sequence of SEQ ID NO: 2. In one embodiment, the HSD17B2 comprises the amino acid sequence of SEQ ID NO: 3. In one embodiment, the HSD17B4 comprises the amino acid sequence of SEQ ID NO: 4. In one embodiment, the HSD17B10 comprises the amino acid sequence of SEQ ID NO: 5.

In one embodiment, the compounds of the present disclosure which do not modulate one or more of HSD17B1, HSD17B2, HSD17B3, HSD17B4, HSD17B5, HSD17B6, HSD17B7, HSD17B8, HSD17B9, HSD17B10, HSD17B11, HSD17B12, or HSD17B14 have an $IC_{50}$ of greater than 30 μmol.

In one embodiment, the compounds of the present disclosure which do not modulate one or more of HSD17B1, HSD17B2, HSD17B3, HSD17B4, HSD17B5, HSD17B6, HSD17B7, HSD17B8, HSD17B9, HSD17B10, HSD17B11, HSD17B12, or HSD17B14 have an $IC_{50}$ of greater than 10 μmol.

In one embodiment, the compounds of the present disclosure are selective for modulating (e.g., inhibiting) the HSD17B13 protein and are less effective at modulating (e.g., inhibiting) one or more of HSD17B1, HSD17B2, HSD17B4, HSD17B10. In one embodiment, the compounds of the present disclosure do not modulate one or more of HSD17B1, HSD17B2, HSD17B4, HSD17B10.

In one embodiment, the compounds of the present disclosure modulate HSD17B13, but do not modulate HSD17B1. In one embodiment, the compounds of the present disclosure inhibit HSD17B13, but do not inhibit HSD17B1. In one embodiment, the compounds of the present disclosure inhibit HSD17B13 with an $IC_{50}$ of less than 10 μmol, and do not inhibit HSD17B1, i.e. inhibit HSD17B1 with an $IC_{50}$ of greater than 10 μmol.

In one embodiment, the compounds of the present disclosure modulate HSD17B13, but do not modulate HSD17B2. In one embodiment, the compounds of the present disclosure inhibit HSD17B13, but do not inhibit HSD17B2. In one embodiment, the compounds of the present disclosure inhibit HSD17B13 with an $IC_{50}$ of less than 10 μmol, and do not inhibit HSD17B2, i.e. inhibit HSD17B2 with an $IC_{50}$ of greater than 10 μmol.

In one embodiment, the compounds of the present disclosure modulate HSD17B13, but do not modulate HSD17B4. In one embodiment, the compounds of the present disclosure inhibit HSD17B13, but do not inhibit HSD17B4. In one embodiment, the compounds of the present disclosure inhibit HSD17B13 with an $IC_{50}$ of less than 10 μmol, and do not inhibit HSD17B4, i.e. inhibit HSD17B4 with an $IC_{50}$ of greater than 10 μmol.

In one embodiment, the compounds of the present disclosure modulate HSD17B13, but do not modulate HSD17B10. In one embodiment, the compounds of the present disclosure inhibit HSD17B13, but do not inhibit HSD17B10. In one embodiment, the compounds of the present disclosure inhibit HSD17B13, i.e. inhibit HSD17B13 with an $IC_{50}$ of less than 10 µmol, and do not inhibit HSD17B4, i.e. inhibit HSD17B4 with an $IC_{50}$ of greater than 10 µmol.

In one embodiment, the cell can be a mammalian cell.

In one embodiment, the cell can be a human cell.

In one embodiment, the cell can be a liver cell.

In one embodiment, the cell can be ex vivo or in vivo.

In one embodiment, the cell can be ex vivo.

In one embodiment, the cell can be in vivo.

In one embodiment, the compounds according to the disclosure inhibit the HSD17B13 protein with an $IC_{50}$ of less than 10 µmol, or less than 9 µmol, or less than 8 µmol, or less than 7 µmol, or less than 6 µmol, or less than 5 µmol, or less than 4 µmol, or less than 3 µmol, or less than 2 µmol, or less than 1 µmol.

In one embodiment, the compounds according to the disclosure inhibit the HSD17B13 protein with an IC50 of less than 1 µmol, or less than 0.9 µmol, or less than 0.8 µmol, or less than 0.7 µmol, or less than 0.6 µmol, or less than 0.5 µmol, or less than 0.4 µmol, or less than 0.3 µmol, or less than 0.2 µmol, or less than 0.1 µmol.

In one embodiment, the compounds according to the disclosure inhibit the HSD17B13 protein with an IC50 of less than 1 µmol.

In one embodiment, the compounds according to the disclosure inhibit the HSD17B13 protein with an IC50 of less than 0.5 µmol.

In one embodiment, the compounds according to the disclosure inhibit the HSD17B13 protein with an IC50 of less than 0.1 µmol.

In one embodiment, modulating the HSD17B13 protein comprises inhibiting 150 nM of the HSD17B13 protein with an IC50 of less than 10 µmol, less than 8 µmol, less than 7 µmol, less than 6 µmol, less than 5 µmol, less than 4 µmol, less than 3 µmol, less than 2 µmol, less than 1 µmol, less than 0.8 µmol, less than 0.6 µmol, less than 0.4 µmol, less than 0.2 µmol.

In one embodiment, modulating the HSD17B13 protein comprises inhibiting 50 nM of the HSD17B13 protein with an $IC_{50}$ of less than 10 µmol, less than 8 µmol, less than 7 µmol, less than 6 µmol, less than 5 µmol, less than 4 µmol, less than 3 µmol, or less than 2 µmol, less than 1 µmol, less than 0.8 µmol, less than 0.6 µmol, less than 0.4 µmol, less than 0.2 µmol.

Methods of Treatment

In another aspect, the present disclosure provides a method of treating a liver disease in a subject having liver disease comprising administering to the subject an effective amount of a compound according to formula (I'):

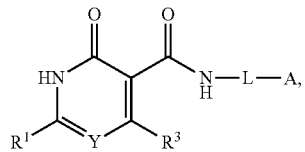

(I')

or a pharmaceutically acceptable salt thereof, wherein:

A is A', A", $CR^4(Ar)_2$, or Ar;

wherein:

A' is

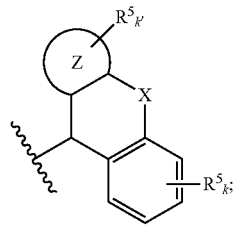

A" is

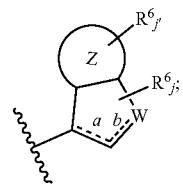

Z is phenyl, Het, or a $C_4$-$C_8$ cycloalkyl; and

Ar is independently at each occurrence a phenyl, naphthyl, or a $C_4$-$C_8$ cycloalkyl, any of which is optionally substituted with one or more $R^8$ or Het;

Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;

L is a bond, —$(CH_2)_n$—, —$(CHB)_n$—, —$CH_2CHB$—, or —$CHBCH_2$—;

wherein:

B is benzyl or $C_{1-12}$ alkyl optionally comprising 1-4 O atoms, either of which is optionally substituted by —OH or —$OCH_3$;

n is 1 or 2; and k and k' are independently from 0 to 4;

j and j' are independently from 0 to 4;

W is =CH—, =$C(R^6)$—, —$CH_2$—, —$CH(R^6)$—, —(C=O)—, —$CH_2CH_2$—, —$CH(R^6)$—$CH_2$—, —O—, —O—$CH_2$—, —O—$CH(R^6)$—, —(NH)—, —$N(R^6)$—, —$CH_2$—NH—, —$CH_2$—$N(R^6)$—, or —S—;

wherein: a and b are independently a single bond or a double bond;

X is a bond, —$CH_2$—, —$CH_2$—$CH_2$—, —$CH_2$—O—, —CH=CH—, —(C=O)—, —O—, —$NR^\#$—, —S—, —(S=O)—, or —$(SO_2)$—;

Y is N, —$CR^2$, or —$COR^2$;

$R^1$ is H, —$(CH_2)_{0-3}$—$NH_2$, —$(CH_2)_{0-3}$—$NHR^\#$, —$(CH_2)_{0-3}$—$N(R^\#)_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;

$R^2$ is H, halogen, —$(CH_2)_{0-3}$—$NH_2$, —$(CH_2)_{0-3}$—$NHR^\#$, —$(CH_2)_{0-3}$—$N(R^\#)_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$ is independently at each occurrence halogen, —CN, =O, —OH, —NH$_2$, —(CH$_2$)$_{1-3}$—OR$^\#$, —NH—(C=O)—R*, —NH—(C=O)O—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

$R^6$ is independently at each occurrence halogen, —OH, =O, —CN, —(CH$_2$)$_{0-3}$—NH$_2$, —(CH$_2$)$_{0-3}$—NHR$^\#$, —(CH$_2$)$_{0-3}$—N(R$^\#$)$_2$, —(CH$_2$)$_{0-3}$—NHCOOR$^\#$, —(CH$_2$)$_{0-3}$—COOR$^\#$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with R*;

$R^7$ is independently at each occurrence halogen, —CN, =O, —OH, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-4}$ haloalkyl, or $C_{6-12}$ aryl, any of which is optionally substituted with R*;

$R^8$ is independently at each occurrence halogen, —CN, =O, —OH, —(CH$_2$)$_{0-3}$—SH, —(CH$_2$)$_{0-3}$—SR*, —(SO$_2$)—R*, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, or —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, $C_{3-6}$ cycloalkyl, phenyl, or benzyl, any of which is optionally substituted with a halogen.

In another aspect, the present disclosure provides a method of treating a liver disease in a subject having liver disease comprising administering to the subject an effective amount of a compound according to formula (I):

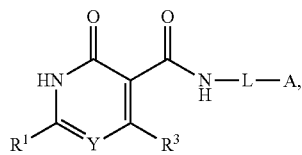

(I)

or a pharmaceutically acceptable salt thereof, wherein:

A is A', A", CR$^4$(Ar)$_2$, or a phenyl that is optionally substituted with one or more R$^7$; wherein:

A' is

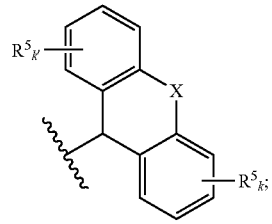

A" is

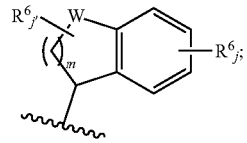

and

Ar is independently at each occurrence a phenyl that is optionally substituted with one or more R$^8$ or Het, where Het is a 6-membered heterocycle comprising from 1 to 3 nitrogen atoms, wherein Het is optionally substituted with one or more of halogen, —OH or =O;

L is a bond, —(CH$_2$)$_n$—, —(CHB)$_n$—, —CH$_2$CHB—, or —CHBCH$_2$—;

wherein:

B is $C_{1-12}$ alkyl or benzyl; and n is 1 or 2;

m is 1 or 2;

k and k' are independently from 0 to 4;

j and j' are independently from 0 to 4;

W is —CH$_2$—, —O—, —(NH)—, or —S—;

X is a bond, —CH$_2$—, —CH$_2$—CH$_2$—, —CH$_2$—O—, —CH=CH—, —(C=O)—, —O—, —NR$^\#$—, —S—, —(S=O)—, or —(SO$_2$)—;

Y is N, —CR$^2$, —COR$^2$ or —CNHR$^2$;

$R^1$ is H, $C_{1-4}$ alkyl, $C_{1-4}$ haloalkyl, or benzyl;

$R^2$ is H, halogen, $C_{1-12}$ alkyl, $C_{1-12}$ alkenyl, $C_{6-12}$ aryl, $C_{1-12}$ aralkyl, $C_{1-4}$ haloalkyl, or a 5-7-membered heterocycle with 1 to 4 heteroatoms selected from O, N and S or combinations thereof, any of which is optionally substituted by —OH;

$R^3$ is H, $C_{1-4}$ alkyl, or $C_{1-4}$ haloalkyl;

$R^4$ is H, $C_{1-4}$ alkyl, or $C_{1-4}$ haloalkyl;

$R^5$, $R^6$, $R^7$, and $R^8$ are each optional and independently at each occurrence halogen, —CN, =O, —OH, —NH$_2$, —(CH$_2$)$_{1-3}$—OR$^\#$, —NH—(C=O)—R*, —NH—(SO$_2$)—R*, —(CH$_2$)$_{1-3}$—NR$^\#_2$, —NHR$^\#$, —N(R$^\#$)$_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7-membered heterocycle with 1 to 4 heteroatoms selected from O, N and S or combinations thereof, or wherein two adjacent $R^5$, $R^6$, $R^7$, or $R^8$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and R$^\#$ is $C_{1-3}$ alkyl, $C_{1-3}$ haloalkyl, phenyl, or benzyl, any of which is optionally substituted with a halogen.

In other embodiments, compounds suitable for the methods of the present disclosure include those of any of the preceeding formulas, e.g., formulas I'-VIII as described above.

Exemplary compounds suitable for the methods of the present disclosure are described in Table 3, above.

In some embodiments, the liver disease can be a chronic liver disease.

Chronic liver diseases include diseases of the liver which last over a period of six months and can include, for example, diseases of the liver involving progressive destruction and regeneration of the liver parenchyma that can lead to fibrosis and cirrhosis. Chronic liver diseases can be alcoholic liver diseases or nonalcoholic liver diseases. Liver pathologies encompassed by chronic liver diseases can include, for example, inflammation (e.g., chronic hepatitis), liver cirrhosis, and hepatocellular carcinoma. Types of chronic liver disease are disclosed elsewhere herein and include, for example, fatty liver disease, nonalcoholic fatty liver disease, alcoholic fatty liver disease, cirrhosis, and hepatocellular carcinoma. Symptoms and signs of chronic liver diseases are known and can include, for example, enlarged liver, fatigue, pain in the upper right abdomen, abdominal swelling (ascites), enlarged blood vessels just beneath the skin's surface, enlarged breasts in men, enlarged spleen, red palms, and yellowing of the skin and eyes (jaundice). Testing for chronic liver diseases can involve blood tests, imaging of the liver, and biopsy of the liver. An individual is at increased risk of a chronic liver disease if the subject has at least one known risk-factor (e.g., genetic factor such as a disease-causing mutation) placing individuals with that risk factor at a statistically significant greater risk of developing the disease than individuals without the risk factor. Risk factors for chronic liver diseases are also well known and can include, for example, excessive alcohol use, obesity, high cholesterol, high levels of triglycerides in the blood, polycystic ovary syndrome, sleep apnea, type 2 diabetes, underactive thyroid (hypothyroidism), underactive pituitary gland (hypopituitarism), and metabolic syndromes including raised blood lipids.

In some embodiments, the chronic liver disease can be nonalcoholic fatty liver disease (NAFLD), alcoholic liver disease (ALD), non-alcoholic steatohepatitis (NASH), cirrhosis, steatosis, or hepatocellular carcinoma. In some embodiments, the chronic liver disease can be nonalcoholic fatty liver disease (NAFLD), alcoholic liver disease (ALD), non-alcoholic steatohepatitis (NASH), cirrhosis, or steatosis.

In some embodiments, the liver disease can be an alcoholic liver disease. In some embodiments, the alcoholic liver disease comprises one or more of cirrhosis, steatosis, or hepatocellular carcinoma resulting from alcohol consumption.

In some embodiments, the liver disease can be a non-alcoholic liver disease. In some embodiments, the non-alcoholic liver disease comprises nonalcoholic fatty liver disease (NAFLD) or non-alcoholic steatohepatitis (NASH).

In some embodiments, the liver disease can be non-alcoholic steatohepatitis (NASH).

In some embodiments, the liver disease can be nonalcoholic fatty liver disease (NAFLD). In some embodiments, the liver disease can be alcoholic liver disease (ALD).

In some embodiments, the liver disease can be cirrhosis.

In some embodiments, the liver disease can be steatosis.

In some embodiments, the liver disease can be hepatocellular carcinoma.

In some embodiments, the non-alcoholic liver disease comprises one or more of cirrhosis, steatosis, or hepatocellular carcinoma not caused by alcohol consumption.

In any of the methods described herein, administration of a compound of the disclosure capable of inhibiting HSD17B13 can result in the reduction or elimination of particular characteristics of liver disease. In some embodiments, the characteristics of liver disease include, but are not limited to inflammation and fibrosis.

HSD17B13 Variants

It has been observed that a splice variant (rs72613567:TA) in HSD17B13, which encodes 17-beta hydroxysteroid dehydrogenase 13, a hepatic lipid droplet protein, was reproducibly associated with reduced ALT and AST levels. It was also observed that this variant was associated with reduced risk of alcoholic and nonalcoholic liver disease and alcoholic and nonalcoholic cirrhosis for each rs72613567:TA allele in an allele dosage-dependent manner. The associations were confirmed in two independent cohorts. rs72613567:TA was associated with decreased severity of histological features of nonalcoholic steatohepatitis (NASH) for each rs72613567:TA allele among individuals with fatty liver disease, and mitigated liver injury associated with PNPLA3 p.I148M. rs72613567:TA results in a truncated isoform deficient in enzymatic activity against steroid substrates. Thus, a loss-of-function variant in HSD17B13 was associated with reduced risk of alcoholic and nonalcoholic liver disease, and progression from steatosis to NASH. U.S. Patent Application Publication No. US2018/0216084 (corresponding to PCT Publication No. WO 2018/136702) and WO 2019/075181 are incorporated herein by reference in their entirety.

The present disclosure also provides methods of treating liver disease, comprising administering a compound according to the disclosure to a subject expressing a patatin like phospholipase domain containing 3 (PNPLA3) protein comprising an I148M variation such that liver disease is treated in the subject.

In some embodiments, the HSD17B13 protein can be a wild-type HSD17B13 protein. In some embodiments, the HSD17B13 protein can be a variant of the wild-type HSD17B13 protein. In some embodiments, the HSD17B13 protein variant can be a HSD17B13 rs72613567 variant. PCT Publication No. WO 2018/136758 is incorporated herein by reference in its entirety.

In some embodiments, the subject is not a carrier of the HSD17B13 rs72613567 variant and has or is susceptible to developing a chronic liver disease.

In some embodiments, the subject can be homozygous or heterozygous for functional HSD17B13.

In some embodiments, the subject comprises: i) a first nucleic acid encoding a patatin like phospholipase domain containing 3 (PNPLA3) protein comprising an I148M variation and a second nucleic acid encoding a functional HSD17B13 protein; and/or ii) a PNPLA3 protein comprising an I148M variation and a functional HSD17B13 protein. U.S. Patent Application Publication No. US2019/0106749 is incorporated herein by reference in its entirety.

In some embodiments, the subject expresses a patatin like phospholipase domain containing 3 (PNPLA3) protein comprising an I148M variation.

Compounds of the disclosure can be used as described herein for treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the method as defined herein. In some embodiments, the variant PNPLA3 protein comprises a methionine at position 148. In some embodiments, the variant PNPLA3 protein comprises the I148M variation. In some embodiments, the variant PNPLA3 protein comprises a methionine at the position corresponding to position 144. In some embodiments, the variant PNPLA3 protein comprises the I144M variation. In some embodiments, the nucleic acid molecule encoding the variant PNPLA3 protein is genomic DNA. In some embodiments, the genomic DNA comprises an ATG codon at the positions corresponding to positions 5107 to 5109. In some embodiments, the genomic DNA comprises the nucleotide sequence encoding a PNPLA3 protein which comprises the I148M variation. In some embodiments, the nucleic acid molecule encoding the variant PNPLA3 protein is mRNA. In some embodiments, the mRNA comprises an AUG codon at the positions corresponding to positions 442 to 444. In some embodiments, the mRNA comprises the nucleotide sequence encoding a PNPLA3 protein which comprises the I148M variation. In some embodiments, the mRNA comprises an AUG codon at the positions corresponding to positions 430 to 432. In some embodiments, the mRNA comprises the nucleotide sequence encoding a PNPLA3 protein which comprises the I144M variation. In some embodiments, the nucleic acid molecule encoding the variant PNPLA3 protein is cDNA. In some embodiments, the cDNA comprises an ATG codon at the positions corresponding to positions 442 to 444. In some embodiments, the cDNA comprises the nucleotide sequence encoding a PNPLA3 protein which comprises the I148M variation. In some embodiments, the cDNA comprises an ATG codon at the positions corresponding to positions 430 to 432. In some embodiments, the cDNA comprises the nucleotide sequence encoding a PNPLA3 protein which comprises the I144M variation. In some embodiments, the liver disease is a chronic liver disease. In some embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the human subject is homozygous or heterozygous for functional HSD17B13.

The present disclosure also provides methods of detecting a variant HSD17B13 rs72613567 gene, variant HSD17B13 transcripts (such as Transcript D), and variant HSD17B13 Isoforms (such as Isoform D).

HSD17B13 Isoforms

In some embodiments, the methods comprise detecting the presence or levels of any one of variant HSD17B13 Transcripts C, D, E, F, G, and H, and particularly D, in a biological sample, and/or detecting the presence or levels of any one of HSD17B13 Isoforms C, D, F, G, or H, and particularly D, in a biological sample comprising protein prior to treatment. Such epitopes can be readily identified by comparing the sequences of Isoforms A-H and are described in more detail in WO 2018/136702, the contents of which are incorporated herein by reference in their entirety. Alternatively, the subject can be classified as being at increased risk for developing the liver disease if Isoform C, D, F, G, or H is not present in the biological sample.

In some embodiments, the detecting step determines the expression level of Isoform C, D, F, G, or H in the biological sample, wherein an increased expression level of Isoform C, D, F, G, or H compared to a control sample from a control subject homozygous for a wild type HSD17B13 allele indicates a decreased risk for developing the liver disease. Alternatively, a decreased expression level or no change in expression level of Isoform C, D, F, G, or H compared to a control sample from a control subject homozygous for a wild type HSD17B13 allele indicates an increased risk for developing the liver disease.

In some embodiments, the detecting step determines the expression level of Isoform A, B, or E or Isoform A, B, E, or F in the biological sample, wherein an increased expression level of Isoform A, B, or E or Isoform A, B, E, or F' compared to a control sample from a control subject homozygous for the HSD17B13 rs72613567 variant allele indicates an increased risk for developing the liver disease. Alternatively, a decreased expression level or no change in expression level of Isoform A, B, or E or Isoform A, B, E, or F' compared to a control sample from a control subject homozygous for the HSD17B13 rs72613567 variant allele indicates a decreased risk for developing the liver disease.

In some embodiments, methods of the present disclosure comprise the step of determining a human subject's risk for progression to more clinically advanced stages of fatty liver disease.

The present disclosure also provides methods comprising the step of detecting the presence of HSD17B13 Isoform D in a human subject, comprising performing an assay on a biological sample obtained from the human subject, wherein the assay determines the presence of HSD17B13 Isoform D in the biological sample.

The present disclosure also provides methods comprising the step of determining a human subject's susceptibility or risk for developing a liver disease, comprising or consisting of: a) detecting whether HSD17B13 Isoform D is present in a biological sample obtained from the human subject; and b) classifying the human subject as being at decreased risk for developing the liver disease if HSD17B13 Isoform D is detected in the biological sample, or classifying the human subject as being at decreased risk for developing the liver disease if HSD17B13 Isoform D is not detected in the biological sample. In some embodiments, the liver disease is a chronic liver disease. In some embodiments, the liver disease is selected from the group consisting of fatty liver disease, nonalcoholic fatty liver disease (NAFLD), alcoholic liver fatty liver disease, cirrhosis, viral hepatitis, hepatocellular carcinoma, simple steatosis, steatohepatitis, fibrosis, and non-alcoholic steatohepatitis (NASH). In some embodiments, the detecting comprises sequencing.

The present disclosure also provides methods of determining a human subject's risk for progression to more clinically advanced stages of fatty liver disease, comprising: a) detecting whether HSD17B13 Isoform D is present in a biological sample obtained from the human subject; and b) classifying the human subject as being at decreased risk for progression to more clinically advanced stages of liver disease if HSD17B13 Isoform D is detected in the biological sample.

The present disclosure also provides methods comprising the step of diagnosing a subject with a liver disease by determining whether the variant HSD17B13 rs72613567 gene, variant HSD17B13 transcripts (such as Transcript D), and variant HSD17B13 Isoforms (such as Isoform D) is present in a biological sample from the subject.

PNPLA3 Ile148Met+ Subjects

The present disclosure also provides methods of treating a subject who is PNPLA3 Ile148Met positive (i.e., "PNPLA3 Ile148Met+") or PNPLA3 Ile144Met positive (i.e., "PNPLA3 Ile144Met+"), comprising administering an inhibitor of HSD17B13 to the subject. The present disclosure also provides methods of treating or inhibiting liver disease comprising administering a compound according to the disclosure to a human liver disease patient expressing a PNPLA3 protein comprising an I148M variation such that liver disease is treated or inhibited in the patient.

The variant PNPLA3 Ile148Met positive or PNPLA3 Ile144Met positive subject can have any of the variant PNPLA3 proteins described herein. In some embodiments, the subject is also homozygous or heterozygous for functional HSD17B13. In some embodiments, the subject is homozygous for functional HSD17B13. In some embodiments, the subject is heterozygous for functional HSD17B13. In some embodiments, the subject is homozygous for the HSD17B13 loss-of-function variant. The subject can have any of the functional HSD17B13 proteins described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a PNPLA3 protein in a sample from the subject, wherein the variant PNPLA3 protein comprises a methionine at a position corresponding to position 148, or comprises a methionine at a position corresponding to position 144. The variant PNPLA3 Ile148Met positive or PNPLA3 Ile144Met positive subject can have any of the variant PNPLA3 proteins described herein.

In some embodiments, the subject who is PNPLA3 Ile148Met+ has been determined to be PNPLA3 Ile148Met+ by detection of a PNPLA3 protein in a sample from the subject, wherein the variant PNPLA3 protein comprises a methionine at a position corresponding to position 148.

In some embodiments, the subject who is PNPLA3 Ile144Met+ has been determined to be PNPLA3 Ile144Met+ by detection of a PNPLA3 protein in a sample from the subject, wherein the variant PNPLA3 protein comprises a methionine at a position corresponding to position 144.

In some embodiments, the variant PNPLA3 protein that comprises the methionine at the position corresponding to position 148, or that comprises the methionine at the position corresponding to position 144 is identified by amino acid sequencing or immunoassay as described herein.

In some embodiments, the subject who is PNPLA3 Ile148Met+ or PNPLA3 Ile144Met+ has been determined to be PNPLA3 Ile148Met+ or PNPLA3 Ile144Met+ by detection of a nucleic acid molecule encoding a PNPLA3 protein in a sample from the subject, wherein the variant PNPLA3 protein comprises a methionine at a position corresponding to position 148, or comprises a methionine at a position corresponding to position 144. The variant PNPLA3 Ile148Met positive or PNPLA3 Ile144Met positive subject can have any of the variant PNPLA3 nucleic acid molecules described herein.

In some embodiments, the nucleic acid molecule encoding the variant PNPLA3 protein is genomic DNA, mRNA, or cDNA derived from mRNA.

In some embodiments, the methods further comprise obtaining the sample from the subject. In some embodiments, the subject who is a candidate for HSD17B13 inhibition has a liver disease or is susceptible to developing a liver disease. In some embodiments, the liver disease is a chronic liver disease. In some preferred embodiments, the chronic liver disease is nonalcoholic fatty liver disease (NAFLD), alcoholic liver disease (ALD), non-alcoholic steatohepatitis (NASH), cirrhosis, steatosis, or hepatocellular carcinoma. In some preferred embodiments, the chronic liver disease is nonalcoholic fatty liver disease (NAFLD), alcoholic liver disease (ALD), non-alcoholic steatohepatitis (NASH), cirrhosis, or steatosis. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption.

The present disclosure also provides methods for treating a patient comprising administering a compound according to the disclosure, wherein the patient is suffering from a liver disease. The methods comprise determining whether a sample from the subject comprises: i) a first nucleic acid encoding a PNPLA3 protein comprising an I148M variation and a second nucleic acid encoding a functional HSD17B13 protein, and/or ii) a PNPLA3 protein comprising an I148M variation and a functional HSD17B13 protein. In some embodiments, the methods comprise determining whether a sample from the subject comprises a first nucleic acid encoding a PNPLA3 protein comprising an I148M variation and a second nucleic acid encoding a functional HSD17B13 protein. In some embodiments, the methods comprise determining whether a sample from the subject comprises a PNPLA3 protein comprising an I148M variation and a functional HSD17B13 protein.

In some embodiments, this determination is carried out by obtaining or having obtained a biological sample from the patient. In some embodiments, the methods further comprise performing or having performed a genotyping assay on the biological sample to determine if the patient has a first nucleic acid encoding a PNPLA3 protein comprising an I148M variation and a second nucleic acid encoding a functional HSD17B13 protein. In some embodiments, the methods further comprise performing or having performed an assay on the biological sample to determine if the patient has a PNPLA3 protein comprising an I148M variation and a functional HSD17B13 protein.

The present disclosure also provides an inhibitor of HSD17B13 for use in the treatment of a liver disease in a human subject having a PNPLA3 protein comprising an I148M variation and having a functional HSD17B13 protein. In some embodiments, the human subject has been tested positive for a PNPLA3 protein comprising an I148M variation and for a functional HSD17B13 protein. In some embodiments, the treatment comprises determining whether the human subject has a PNPLA3 protein comprising an I148M variation and a functional HSD17B13 protein. In some embodiments, the human subject has been identified as being a candidate for treating or inhibiting a liver disease by inhibiting HSD17B13 by using any of the methods as defined herein.

Combination Treatment

In one embodiment of any of the above methods, the method further comprises administering a second therapeutic agent.

In one embodiment, the second therapeutic agent is a second agent effective for the treatment of liver disease.

In one embodiment, the second therapeutic agent is a second agent capable of modulating HSD17B13.

Embodiments include compositions and therapeutic formulations comprising any of compounds according to the disclosure described herein in combination with one or more additional liver disease therapeutic agents, and methods of treatment comprising administering such combinations to subjects for the treatment of liver disease.

Examples of additional liver disease therapeutic agents suitable for combination treatment with the compounds according to the disclosure include, but are not limited to, Disulfiram, Naltrexone, Acamprosate, Prednisone, Prednisone, Azathioprine, Penicillamine, Trientine, Deferoxamine, Ciprofloxacin, Norofloxacin, Ceftriaxone, Ofloxacin, Amoxicillin-clavulanate, Phytonadione, Bumetanide, Furosemide, Hydrochlorothiazide, Chlorothiazide, Amiloride, Triamterene, Spironolactone, Octreotide, Atenolol, Metoprolol, Nadolol, Propranolol, Timolol, and Carvedilol.

Additional examples of liver disease therapeutic agents suitable for combination treatment with the compounds according to the disclosure (e.g., for use in chronic hepatitis C treatment) include, but are not limited to, ribavirin, paritaprevir, simeprevir (Olysio), grazoprevir, ledipasvir, ombitasvir, elbasvir, daclatasvir (Daklinza), dasabuvir, ritonavir, sofosbuvir, velpatasvir, voxilaprevir, glecaprevir, pibrentasvir, peginterferon alfa-2a, peginterferon alfa-2b, and interferon alfa-2b.

Additional examples of liver disease therapeutic agents suitable for combination treatment with the compounds according to the disclosure (e.g., for use in nonalcoholic fatty liver disease) include, but are not limited to, weight loss inducing agents such as orlistat or sibutramine; insulin sensitizing agents such as thiazolidinediones (TZDs), metformin, and meglitinides; lipid lowering agents such as statins, fibrates, and omega-3 fatty acids; atioxidants such as, vitamin E, betaine, N-Acetyl-cysteine, lecithin, silymarin, and beta-carotene; anti TNF agents such as pentoxifylline; probiotics, such as VSL #3; and cytoprotective agents such as ursodeoxycholic acid (UDCA). Other suitable treatments include ACE inhibitors/ARBs, oligofructose, and Incretin analogs.

Additional examples of liver disease therapeutic agents suitable for combination treatment with the compounds according to the disclosure (e.g., for use in NASH) include, but are not limited to, obeticholic acid (Ocaliva®), Selonsertib, Elafibranor, Cenicriviroc, GR_MD_02, MGL_3196, IMM124E, arachidyl amido cholanoic acid (Aramchol™), GS0976, Emricasan, Volixibat, NGM282, GS9674, Tropifexor, MN_001, LMB763, BI_1467335, MSDC_0602, PF_05221304, DF102, Saroglitazar, BMS986036, Lanifibranor, Semaglutide, Nitazoxanide, GRI_0621, EYP001, VK2809, Nalmefene, LIK066, MT_3995, Elobixibat, Namodenoson, Foralumab, SAR425899, Sotagliflozin, EDP_305, Isosabutate, Gemcabene, TERN_101, KBP_042, PF_06865571, DUR928, PF_06835919, NGM313, BMS_986171, Namacizumab, CER_209, ND_L02_s0201, RTU_1096, DRX_065, IONIS_DGAT2Rx, INT_767, NC_001, Seladepar, PXL770, TERN_201, NV556, AZD2693, SP_1373, VK0214, Hepastem, TGFTX4, RLBN1127, GKT_137831, RYI_018, CB4209-CB4211, and JH_0920.

In some embodiments, the methods described above further comprise administration of a second agent selected from ursodiol, norursodiol, UDCA, ursodeoxycholic acid, chenodeoxycholic acid, cholic acid, taurocholic acid, ursocholic acid, glycocholic acid, glycodeoxycholic acid, taurodeoxycholic acid, taurocholate, glycochenodeoxycholic acid, tauroursodeoxycholic acid, cholestyramine/resins, antihistamine agents (e.g., hydroxyzine, diphenhydamine), rifampin, nalaxone, Phenobarbital, dronabinol (CB1 agonist), methotrexate, corticosteroids, cyclosporine, colchicines, TPGS—vitamin A, D, E, or K optionally with polyethylene glycol, zinc, a resin or sequestrant for absorbing bile acids.

In one embodiment of any of the above methods, the method can further comprise administering a therapeutic tailored to prevent or alleviate one or more symptoms associated with progression to more clinically advanced stages of chronic liver disease (e.g., progression from simple steatosis to more clinically advanced stages of chronic liver disease, or progression from simple steatosis to one or more of steatohepatitis, fibrosis, cirrhosis, and hepatocellular carcinoma). For example, such treatments could be focused on preventing or reducing inflammation or preventing or reducing fibrosis. Examples of such therapeutics in development include OCA (obeticholic acid) (Intercept), GS-9674 (Gilead), Simtuzumab (Gilead), GS-4997 (Gilead), NDI-010976 (Gilead), GFT505/Elafibraor (Genfit), Aramchol (Galmed), Cenicriviroc (Tobira), GR-MD-02 (Galectin Therapeutics), TD139 (Galecto Biotech), SHP626 (Shire), PXS4728A (Boehringer Ingelheim), and RP103 (Cysteamine bitartrate) (Raptor).

The present disclosure also provides any of the methods described herein further comprising administering to the subject a second therapeutic agent which is an inhibitor of HSD17B13. Inhibitors of HSD17B13 include, but are not limited to, naturally occurring and synthetic ligands, antagonists, agonists, antibodies, peptides, cyclic peptides, nucleic acids, functional polynucleotides, small organic molecules, and the like. Functional polynucleotides are nucleic acid molecules that have a specific function, such as binding a target molecule or catalyzing a specific reaction. Examples of functional polynucleotides include, but are not limited to, antisense molecules, aptamers, ribozymes, and triplex forming molecules. The functional polynucleotides can act as inhibitors of a specific activity possessed by a target molecule. Antisense molecules are designed to interact with a target nucleic acid molecule through either canonical or non-canonical base pairing. The interaction of the antisense molecule and the target molecule is designed to promote the destruction of the target molecule through, for example, RNase-H-mediated RNA-DNA hybrid degradation. Alternately, the antisense molecule is designed to interrupt a processing function that normally would take place on the target molecule, such as transcription or replication. Antisense molecules can be designed based on the sequence of the target molecule. Numerous methods for optimization of antisense efficiency by identifying the most accessible regions of the target molecule exist. Exemplary methods include, but are not limited to, in vitro selection experiments and DNA modification studies using DMS and DEPC. Antisense molecules generally bind the target molecule with a dissociation constant ($K_d$) less than or equal to about 10-6, less than or equal to about 10-8, less than or equal to about 10-10, or less than or equal to about 10-12. A representative sample of methods and techniques which aid in the design and use of antisense molecules, and antisense molecules, can be found in the following non-limiting list of U.S. patents and applications: U.S. Pat. Nos. 5,135,917; 5,294,533; 5,627,158; 5,641,754; 5,691,317; 5,780,607; 5,786,138; 5,849,903; 5,856,103; 5,919,772; 5,955,590; 5,990,088; 5,994,320; 5,998,602; 6,005,095; 6,007,995; 6,013,522; 6,017,898; 6,018,042; 6,025,198; 6,033,910; 6,040,296; 6,046,004; 6,046,319; 6,057,437; and U.S. Ser. No. 62/645,941 filed Mar. 21, 2018, each of which is incorporated herein by reference in its entirety. Examples of antisense molecules include, but are not limited to, antisense RNAs, small interfering RNAs (siRNAs), and short hairpin RNAs (shRNAs). For example, the antisense RNAs, siRNAs, or shRNAs can be designed to target a region unique of the HSD17B13 genomic DNA or mRNA. In some embodiments, the inhibitor of HSD17B13 is an antisense molecule. In some embodiments, the inhibitor of HSD17B13 is an shRNA molecule. In some embodiments, the inhibitor of HSD17B13 is an siRNA molecule.

In some embodiments, the second inhibitor of HSD17B13 comprises a functional polypeptide, an antisense DNA, RNA, an siRNA, or an shRNA that hybridizes to the endogenous HSD17B13 genomic DNA or mRNA and decreases expression of HSD17B13 polypeptide in a cell in the subject. In some embodiments, the HSD17B13 inhibitor can also inhibit one or more additional members of the short-chain dehydrogenases/reductases (SDR) family, of which HSD17B13 is a member. Such other members include, but are not limited to, HSD17B1, HSD17B2, HSD17B3, HSD17B4, HSD17B6, HSD17B7, HSD17B8, HSD17B10, HSD17B11, HSD17B12, HSD17B14, HSD11B1, HSD11B2, HSD3B1, HSD3B2, and HSD3B7, as well as close homologs dehydrogenase/reductase 3 (DHRS3) and retinol dehydrogenase 10 (RDH10). In some embodiments, the inhibitor of HSD17B13 is administered to inhibit liver disease in the subject. In some embodiments, the inhibitor of HSD17B13 is administered to treat liver disease in the subject. In some embodiments, the liver disease is a chronic liver disease. In some embodiments, the chronic liver disease is one or more of nonalcoholic fatty liver disease (NAFLD), alcoholic liver disease (ALD), non-alcoholic steatohepatitis (NASH), cirrhosis, steatosis, or hepatocellular carcinoma. In some embodiments, the liver disease is an alcoholic liver disease. In some embodiments, the alcoholic liver disease comprises one or more of cirrhosis, steatosis, or hepatocellular carcinoma resulting from alcohol consumption. In some embodiments, the liver disease is a non-alcoholic liver disease. In some embodiments, the non-alcoholic liver disease comprises nonalcoholic fatty liver disease (NAFLD) or non-alcoholic steatohepatitis (NASH). In some embodiments, the non-alcoholic liver disease comprises one or more of cirrhosis, steatosis, or hepatocellular carcinoma not caused by alcohol consumption. In some embodiments, the subject is homozygous for the gene encoding the I148M variation. In some embodiments, the subject is heterozygous for the gene encoding the I148M variation. In some embodiments, the subject further is homozygous for the gene encoding the functional HSD17B13 protein. In some embodiments, the subject further is heterozygous for the gene encoding the functional HSD17B13 protein and a gene encoding a loss of function variant of HSD17B13.

The additional therapeutically active component(s), e.g., any of the agents listed above or derivatives thereof, may be administered just prior to, concurrent with, or shortly after the administration of a compound according to the disclosure; for purposes of the present disclosure, such administration regimens are considered the administration of a compound described herein "in combination with" an additional therapeutically active component. Embodiments include pharmaceutical compositions in which a compound disclosed herein is co-formulated with one or more of the additional therapeutically active component(s) as described elsewhere herein.

EXAMPLES

The following examples illustrate specific aspects of the instant description. The examples should not be construed as limiting, as the examples merely provide specific understanding and practice of the embodiments and their various aspects.

All the solvents used were purchased either from Sigma Aldrich or Fisher Scientific and were used as is.

Example 1: Synthesis of 2-oxo-6-(trifluoromethyl)-N-(9H-xanthen-9-yl)-1,2-dihydropyridine-3-carboxamide (1A)

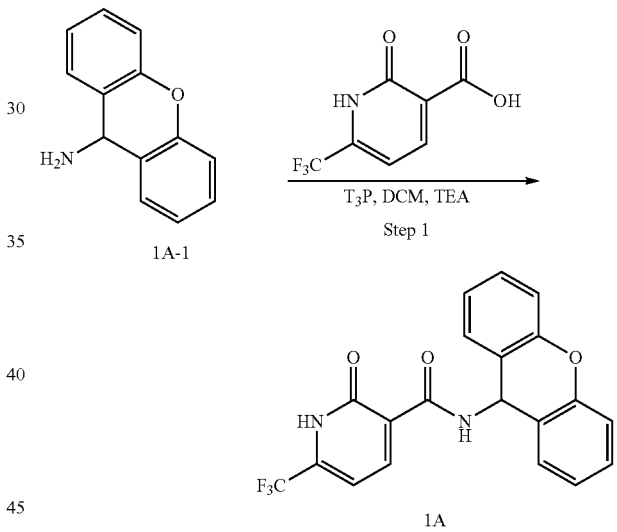

Step 1: 2-oxo-6-(trifluoromethyl)-N-(9H-xanthen-9-yl)-1,2-dihydropyridine-3-carboxamide (1A)

To a solution of Compound 1A-1 (80 mg, 406 μmol) in DCM (5.0 mL) was added 2-oxo-6-(trifluoromethyl)-1H-pyridine-3-carboxylic acid (84 mg, 406 μmol), $T_3P$ (387 mg, 608 μmol, 362 uL, 50% purity) and TEA (123 mg, 1.2 mmol, 169 uL). The mixture was stirred at 25° C. for 12 h. The reaction mixture was diluted with $H_2O$ (5.0 mL), and the water phase was extracted with EtOAc (5.0 mL×3). The combined organic layers were dried over $Na_2SO_4$, filtered and concentrated under reduced pressure to give a residue, which was purified by prep-HPLC (column: Xbridge150×30 mm×10 um; mobile phase:[water (0.1% TFA)-ACN]; B %:25%-85%, 10 min) to give Compound 1A (12 mg, 30 μmol, 7% yield, 98.4% purity) as a light yellow solid. M−H−=385.0 (LCMS). $^1$H NMR (400 MHz, METHANOL-$d_4$) δ=8.58 (d, J=7.6 Hz, 1H), 7.51 (d, J=8.4 Hz, 2H), 7.49 (t, J=15.2 Hz, 2H), 7.17-7.10 (m, 5H), 6.61 (s, 1H).

Other compounds made in a similar fashion are found in Table 4.

TABLE 4

| Compound No | Structure | HNMR and MS |
|---|---|---|
| 1 | 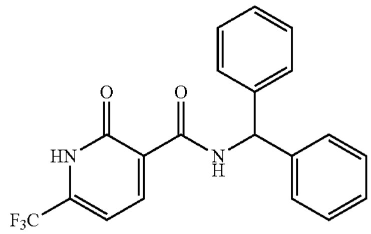 [SMILES: O=C(NC(c1ccccc1)c1ccccc1)c1ccc(C(F)(F)F)[nH]c1=O] | $^1$H NMR (400 MHz, DMSO-$d_6$) δ = 13.50 (br s, 1H), 9.84 (br s, 1H), 8.37 (d, J = 7.7 Hz, 1H), 7.38-7.32 (m, 8H), 7.31-7.23 (m, 3H), 6.30 (d, J = 8.2 Hz, 1H); ESI [M − H] = 371.0 |
| 2 | 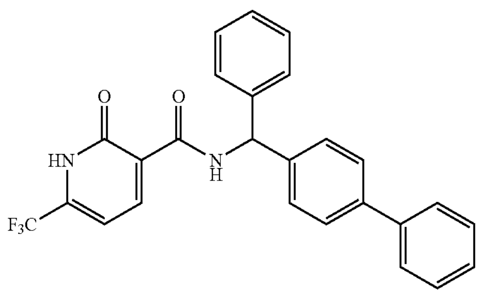 [SMILES: O=C(NC(c1ccccc1)c1ccc(-c2ccccc2)cc1)c1ccc(C(F)(F)F)[nH]c1=O] | $^1$H NMR (400 MHz, DMSO-$d_6$) δ = 13.51 (br s, 1H), 9.87 (br s, 1H), 8.39 (d, J = 7.5 Hz, 1H), 7.65 (br d, J = 7.9 Hz, 4H), 7.48-7.42 (m, 4H), 7.41-7.34 (m, 5H), 7.33-7.24 (m, 2H), 6.35 (d, J = 7.9 Hz, 1H); ESI [M − H] = 447.1 |

Example 2: Synthesis of N-((3,4-dimethylphenyl)(phenyl)methyl)-2-oxo-6-(trifluoromethyl)-1,2-dihydropyridine-3-carboxamide (2A)

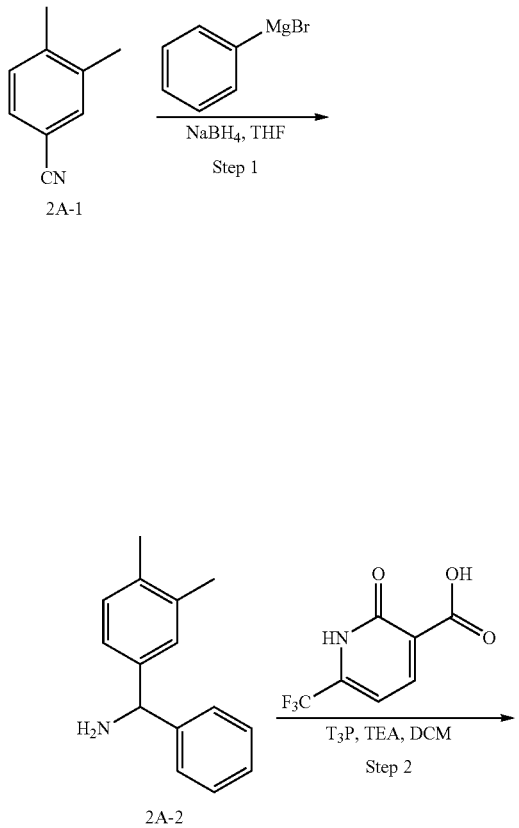

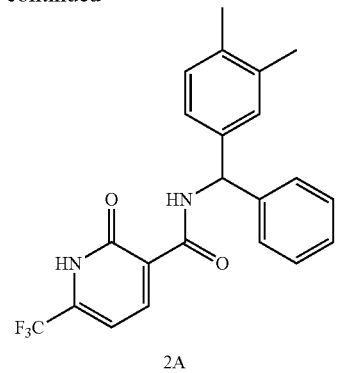

Step 1: (3,4-dimethylphenyl)(phenyl)methanamine (2A-2)

To a stirred solution of Compound 2A-1 (1.0 g, 7.6 mmol) in dry THF (20 mL) was added phenylmagnesium bromide (3 M, 3.81 mL) drop wise at 15° C. Then the mixture was stirred at 15° C. for 18 h. The mixture was cooled to 0° C. and NaBH$_4$ (374.94 mg, 9.91 mmol) was added to the mixture. The mixture was stirred at 15° C. for 30 min. TLC (Petroleum ether:Ethyl acetate=1/1) showed the reaction was complete. The mixture was quenched with Sat. aq. NH$_4$Cl (50 mL) and extracted with EtOAC (30 mL×3). The combined organic layers were dried over Na$_2$SO$_4$ and concentrated in vacuum to give Compound 2A-2 (1.0 g, crude) as an off-white solid, which was used next step directly.

Step 2: N-((3,4-dimethylphenyl)(phenyl)methyl)-2-oxo-6-(trifluoromethyl)-1,2-dihydropyridine-3-carboxamide (2A)

To a stirred solution of Compound 2A-2 (100 mg, 473.3 μmol) in DCM (2.0 mL) was added 2-oxo-6-(trifluoromethyl)-1,2-dihydropyridine-3-carboxylic acid (98 mg, 473.3 µmol) in one portion, followed by adding T₃P (602 mg, 946.5 µmol, 50% purity) and TEA (96 mg, 946.5 µmol) drop-wise at 15° C. Then the mixture was stirred at 15° C. for 18 h. TLC (Petroleum ether/Ethyl acetate=1/1) showed the reaction was completed. The mixture was washed with sat.NH₄Cl (1.0 mL×3), dried over Na₂SO₄ and concentrated in vacuum to a residue, which was purified by prep-HPLC (column: Waters Xbridge 150×25 5 u; mobile phase: [water (0.04% NH₃H₂O+10 mM NH4HCO₃)-ACN]; B %: 20%- 50%, 10 min) to give Compound 2A (61 mg, 148.2 µmol, 31.32% yield) as a white solid. M+H⁺=401.1 (LCMS); ¹H NMR (400 MHz, CDCl3-d₃) δ 10.10-10.08 (d, J=8 Hz, 1H), 8.72-8.70 (d, J=7.2 Hz, 1H), 7.34-7.33 (m, 5H), 7.10-7.00 (m, 3H), 6.90-6.88 (d, J=7.2 Hz, 1H), 6.41-6.39 (d, J=7.2 Hz, 1H), 2.22 (s, 6H).

Other compounds made in a similar fashion are shown in Table 5.

TABLE 5

| Compound No | Structure | HNMR and Ms |
|---|---|---|
| 3 | 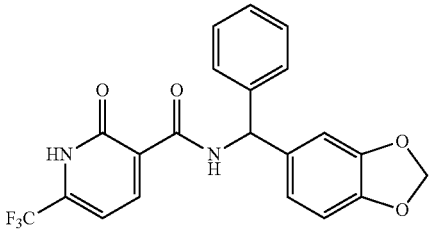 [SMILES: O=C(NC(c1ccccc1)c1ccc2c(c1)OCO2)c1ccc(C(F)(F)F)[nH]c1=O] | ¹H NMR (400 MHz, METHANOL-d₄) δ = 8.51 (d, J = 7.3 Hz, 1H), 7.37-7.23 (m, 5H), 7.04 (d, J = 7.5 Hz, 1H), 6.83-6.73 (m, 3H), 6.27-6.21 (m, 1H), 5.91 (s, 2H); ESI [M + Na] = 439.1 |
| 4 | 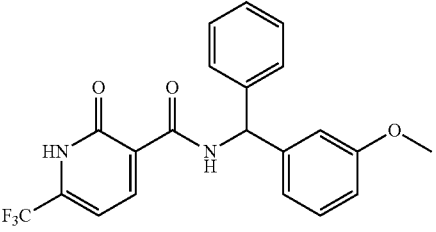 [SMILES: COc1cccc(C(NC(=O)c2ccc(C(F)(F)F)[nH]c2=O)c2ccccc2)c1] | ¹H NMR (400 MHz, DMSO-d₆) δ = 13.42 (br s, 1H), 9.84 (br s, 1H), 8.35 (d, J = 7.5 Hz, 1H), 7.35 (d, J = 4.4 Hz, 4H), 7.31-7.23 (m, 3H), 6.96-6.88 (m, 2H), 6.84 (dd, J = 2.2, 7.9 Hz, 1H), 6.26 (d, J = 7.9Hz, 1H), 3.72 (s, 3H) ESI [M − H] = 401.0 |
| 5 | 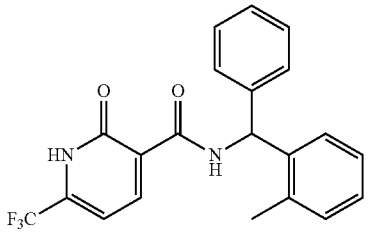 | ¹H NMR (400 MHz, CHLOROFORM-d) δ = 10.07 (br d, J = 7.9 Hz, 1H), 8.71 (br d, J = 7.3 Hz, 1H), 7.27 (br s, 6H), 7.19 (br s, 3H), 6.88 (br d, J = 7.5 Hz, 1H), 6.63 (br d, J = 8.2 Hz, 1H), 2.35 (s, 3H) ESI [M − H] = 385.1 |
| 6 | 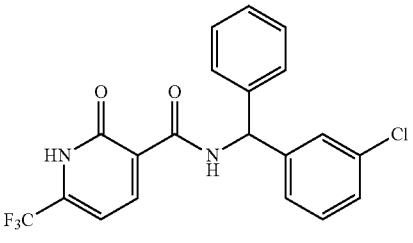 [SMILES: O=C(NC(c1ccccc1)c1cccc(Cl)c1)c1ccc(C(F)(F)F)[nH]c1=O] | ¹H NMR (400 MHz, METHANOL-d4) δ = 8.51 (d, J = 1.5 Hz, 1H), 7.54-7.23 (m, 9H), 7.05 (br d, J = 1.6 Hz, 1H), 6.32 (s, 1H) ESI [M − H] = 405.0 |
| 7 | 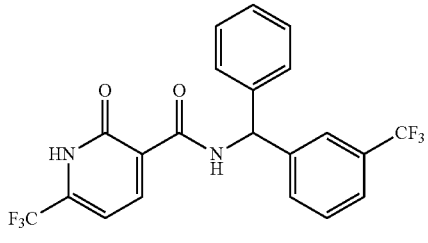 [SMILES: O=C(NC(c1ccccc1)c1cccc(C(F)(F)F)c1)c1ccc(C(F)(F)F)[nH]c1=O] | ¹H NMR (400 MHz, CHLOROFORM-d) δ ppm 10.13-10.04 (m, 1 H) 8.64-8.58 (m, 1 H) 7.52-7.34 (m, 4 H) 7.31-7.20 (m, 5 H) 6.84-6.77 (m, 1 H) 6.48-6.38 (m, 1 H) ESI [M − H] = 439.0 |

TABLE 5-continued

| Compound No | Structure | HNMR and Ms |
|---|---|---|
| 8 | 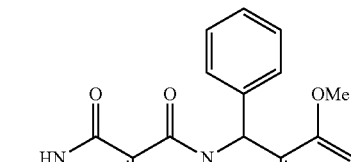 | ¹H NMR (400 MHz, DMSO-d₆) δ = 13.64 (br s, 1H), 10.10 (br s, 1H), 8.35 (d, J = 7.2 Hz, 1H), 7.38-7.24 (m, 8H), 7.05-6.97 (m, 2H), 6.51-6.48 (m, 1H), 3.78 (s, 3H)<br>ESI [M − H] = 401.1 |
| 9 | 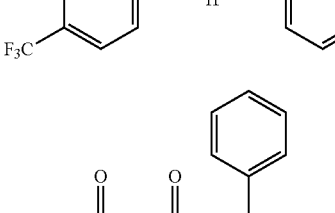 | ¹H NMR (400 MHz, DMSO-d₆) δ = 13.87-13.04 (m, 1H), 10.04-9.53 (m, 1H), 8.40-8.33 (m, 1H), 7.52-7.45 (m, 2H), 7.42-7.33 (m, 4H), 7.33-7.23 (m, 4H), 6.64-6.53 (m, 1H)<br>[M − H] = 405.0 |

Example 3: Synthesis of N-((4-ethylphenyl)(phenyl)methyl)-2-oxo-6-(tri-fluoromethyl)-1,2-dihydropyridine-3-carboxamide (3A)

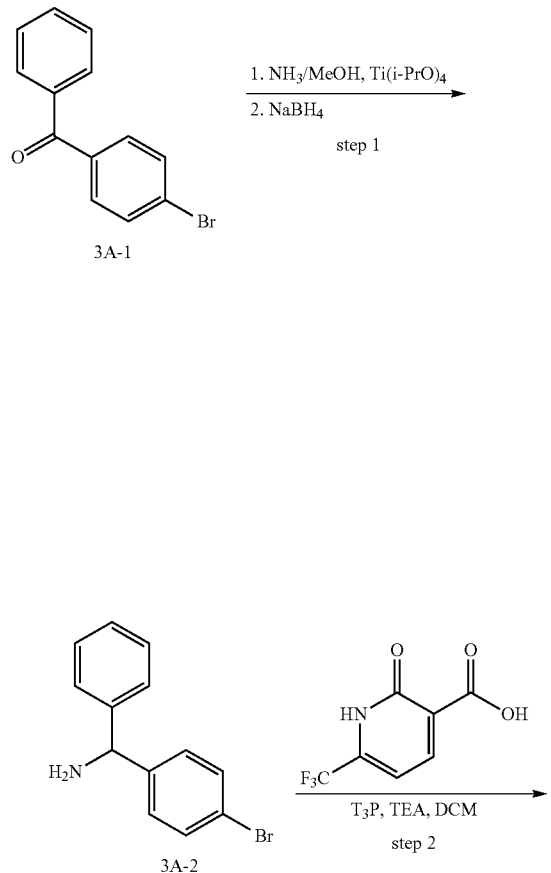

Step 1: (4-bromophenyl)(phenyl)methanamine (3A-2)

To a mixture of Compound 3A-1 (500 mg, 1.9 mmol) in NH₃/MeOH (30 mL) (10 M) was added Ti(i-PrO)₄ (1.5 g, 5.3 mmol) dropwise. The mixture was stirred at 25° C. for 12 h, then the mixture was cooled to 0° C., and NaBH₄ (120 mg, 3.17 mmol) was added. The mixture was stirred at 25° C. for another 2 h. To the mixture was added H₂O (5 mL) (lots of precipitate formed) and stirred for 1 h, then filtered. The filtrate was concentrated and extracted with DCM (5 mL×3). The combined organic layers were dried over Na₂SO₄, filtered and concentrated to give Compound 3A-2 (500 mg, crude) as brown oil, which was used directly.

Step 2: N-((4-bromophenyl)(phenyl)methyl)-2-oxo-6-(trifluoromethyl)-1,2-di-hydropyridine-3-carboxamide (3A-3)

To a solution of Compound 3A-2 (500 mg, 1.91 mmol) in DCM (20 mL) was added 2-oxo-6-(trifluoromethyl)-1,2- dihydropyridine-3-carboxylic acid (395 mg, 1.9 mmol) and TEA (579 mg, 5.7 mmol) followed by $T_3P$ (2.4 g, 3.8 mmol, 50% purity in EtOAc). The mixture was stirred at 10° C. for 12 h. The reaction mixture was quenched with $H_2O$ (10 mL), the aqueous layer was separated and then extracted with DCM (5 mL×3). The combined organic layers were dried over $Na_2SO_4$, filtered and concentrated. The residue was purified by column chromatography ($SiO_2$, Petroleum ether:Ethyl acetate=100/0 to 100/15) to give Compound 3A-3 (660 mg, 73.4% yield, 95.7% purity) was obtained as a white solid. $M+H^+$=450.8/452.8 (LCMS); $^1H$ NMR (400 MHz, DMSO-$d_6$) δ=13.45 (br s, 1H), 9.80 (br s, 1H), 8.36-8.34 (m, 1H), 7.56-7.54 (m, 2H), 7.37-7.30 (m, 8H), 6.30-6.28 (m, 1H).

Step 3: 2-oxo-N-(phenyl(4-vinylphenyl)methyl)-6-(trifluoromethyl)-1,2-dihydropyridine-3-carboxamide (3A)

To a mixture of 4,4,5,5-tetramethyl-2-vinyl-1,3,2-dioxaborolane (20 mg, 129.9 μmol), Compound 3A-3 (25 mg, 55.4 μmol) and $Na_2CO_3$ (15 mg, 141.5 μmol) in dioxane (2.5 mL) and $H_2O$ (0.5 mL) was added Pd(dppf)$Cl_2$ (5 mg, 6.83 μmol) under $N_2$. The mixture was stirred at 80° C. for 12 h. The mixture was diluted with EtOAc (5 mL), washed with $H_2O$ (3 mL×2), dried over $Na_2SO_4$, filtered and concentrated. The residue was purified by prep-HPLC (column: Nano-Micro UniSil 5-100 C18 ULTRA 100×250 mm 5 um; mobile phase: [water (0.225% FA)-ACN]; B %: 40%-80%, 10 min) to give Compound 3A (2.8 mg, 7.10 μmol, 12.82% yield, 100% purity) as a white solid. $M-H^-$=397.1 (LCMS); $^1H$ NMR (400 MHz, DMSO-$d_6$) δ=9.93 (s, 1H), 8.34 (d, J=7.5 Hz, 1H), 7.45 (d, J=8.3 Hz, 2H), 7.40-7.19 (m, 8H), 6.71 (dd, J=11.0, 17.5 Hz, 1H), 6.28 (d, J=7.9 Hz, 1H), 5.81 (d, J=18.4 Hz, 1H), 5.24 (d, J=11.4 Hz, 1H).

Other compounds made in a similar manner are shown in Table 6.

TABLE 6

| Compound No | Structure | HNMR and Ms |
|---|---|---|
| 10 | [Structure with Br substituents] | $^1H$ NMR (400 MHz, CHLOROFORM-d) δ ppm 12.86-12.52 (m, 1 H) 10.13-10.06 (m, 1 H) 8.73-8.67 (m, 1 H) 7.50-7.44 (m, 4 H) 7.20-7.14 (m, 4 H) 6.94-6.88 (m, 1 H) 6.39-6.33 (m, 1 H) ESI [M − H] = 528.9 |
| 11 | [Structure with OCF$_3$ substituents] | $^1H$ NMR (400 MHz, CHLOROFORM-d) δ = 10.15 (br d, J = 7.7 Hz, 1H), 8.71 (d, J = 7.3 Hz, 1H), 7.33 (d, J = 8.6 Hz, 4H), 7.21 (br d, J = 8.2 Hz, 4H), 6.91 (d, J = 7.5 Hz, 1H), 6.47 (d, J = 8.2 Hz, 1H) ESI [M − H] = 539.0 |
| 12 | [Structure with CF$_3$ substituent] | $^1H$ NMR (400 MHz, DMSO-$d_6$) δ = 13.47 (br s, 1H), 9.91 (br s, 1H), 8.35 (d, J = 7.7 Hz, 1H), 7.41-7.31 (m, 8H), 7.30-7.19 (m, 2H), 6.30 (d, J = 7.9 Hz, 1H), 3.62 (q, J = 11.7 Hz, 2H) ESI [M − H] = 453.1 |
| 13 | [Structure with isobutyl substituent] | $^1H$ NMR (400 MHz, DMSO-$d_6$) δ = 13.48 (br s, 1H), 9.92 (br s, 1H), 8.36 (d, J = 7.5 Hz, 1H), 7.39-7.30 (m, 4H), 7.30-7.18 (m, 4H), 7.13 (d, J = 8.2 Hz, 2H), 6.26 (d, J = 8.2 Hz, 1H), 2.41 (d, J = 7.1 Hz, 2H), 1.80 (quind, J = 6.8, 13.5 Hz, 1H), 0.84 (d, J = 6.6 Hz, 6H) ESI [M − H] = 427.1 |

TABLE 6-continued

| Compound No | Structure | HNMR and Ms |
|---|---|---|
| 14 | 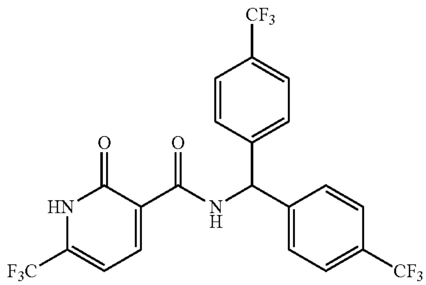 [SMILES: O=C(NC(c1ccc(C(F)(F)F)cc1)c1ccc(C(F)(F)F)cc1)c1ccc(C(F)(F)F)[nH]c1=O] | $^1$H NMR (400 MHz, CHLOROFORM-d) δ = 13.43 (br s, 1H), 10.23-10.21 (m, 1H), 8.74-8.72 (d, J = 7.2 Hz, 1H), 7.64-7.42 (m, 8H), 6.94-6.92 (d, J = 1.6 Hz, 1H), 6.55-6.53 (m, 1H)<br>ESI [M − H] = 507.0 |
| 15 | 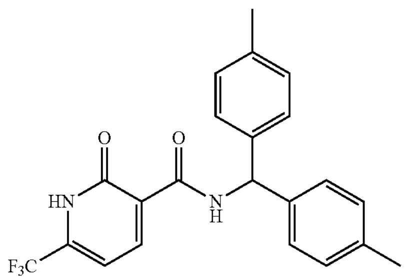 [SMILES: Cc1ccc(C(NC(=O)c2ccc(C(F)(F)F)[nH]c2=O)c2ccc(C)cc2)cc1] | $^1$H NMR (400 MHz, CHLOROFORM-d) δ = 13.72 (br s, 1H), 10.10-10.08 (m, 1H), 8.73-8.71 (d, J = 7.8 Hz, 1H), 7.27-7.12 (m, 8H), 6.90-6.88 (d, J = 1.6 Hz, 1H), 6.41-6.39 (m, 1H), 2.33 (s, 6H)<br>ESI [M − H] = 399.1 |
| 16 | 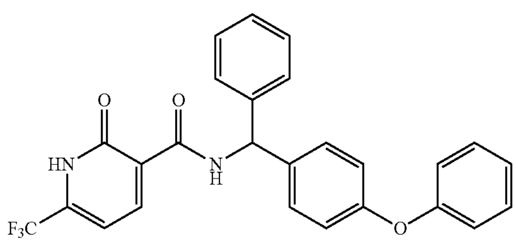 [SMILES: O=C(NC(c1ccccc1)c1ccc(Oc2ccccc2)cc1)c1ccc(C(F)(F)F)[nH]c1=O] | $^1$H NMR (400 MHz, DMSO-d$_6$) δ = 10.04 (br s, 1H), 8.36 (d, J = 7.50 Hz, 1H), 7.43-7.31 (m, 9H), 7.30-7.20 (m, 2H), 7.16-7.10 (m, 1H), 7.03-6.96 (m, 4H), 6.30 (d, J = 8.16 Hz, 1 H)<br>ESI [M − H] = 463.0 |
| 17 | 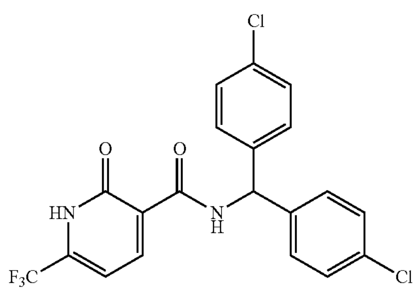 [SMILES: O=C(NC(c1ccc(Cl)cc1)c1ccc(Cl)cc1)c1ccc(C(F)(F)F)[nH]c1=O] | $^1$H NMR (400 MHz, DMSO-d$_6$) δ = 13.40 (br s, 1H), 10.14-9.53 (m, 1H), 8.33 (d, J = 7.50 Hz, 1H), 7.47-7.33 (m, 8H), 7.29 (br d, J = 7.06 Hz, 1H), 6.32 (d, J = 7.94 Hz, 1H)<br>ESI [M − H] = 439.0 |
| 18 | 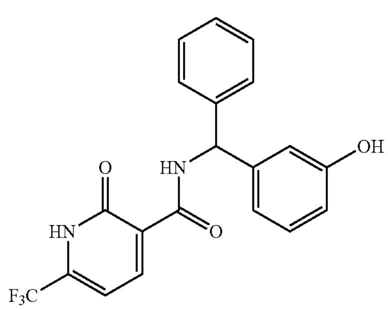 [SMILES: O=C(NC(c1ccccc1)c1cccc(O)c1)c1ccc(C(F)(F)F)[nH]c1=O] | $^1$H NMR (400 MHz, DMSO-d$_6$) δ = 13.54 (br s, 1H), 9.45 (s, 1H), 8.38 (d, J = 7.50 Hz, 1H), 7.39-7.30 (m, 5H), 7.30-7.23 (m, 2H), 7.14 (t, J = 7.83 Hz, 1H), 6.76 (d, J = 7.72 Hz, 1H), 6.69 (s, 1H), 6.65 (dd, J = 7.94, 1.98 Hz, 1H), 6.19 (d, J = 8.16 Hz, 1H)<br>ESI [M − H] = 387.0 |

TABLE 6-continued

| Compound No | Structure | HNMR and Ms |
| --- | --- | --- |
| 19 | 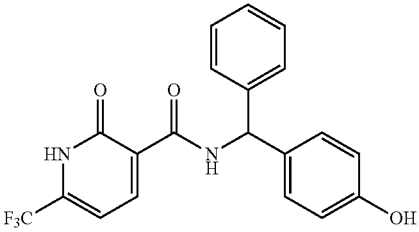 | ¹H NMR (400 MHz, CHLOROFORM-d) δ = 10.12 (br d, J = 8.60 Hz, 1 H) 8.71 (d, J = 7.50 Hz, 1 H) 7.37-7.29 (m, 4 H) 7.15 (d, J = 8 16 Hz, 2 H) 6.88 (d, J = 1.50 Hz, 1 H) 6.73 (d, J = 8.38 Hz, 2 H) 6.39 (d, J = 8.16 Hz, 1 H)<br>ESI [M − H] = 387.0 |
| 20 | 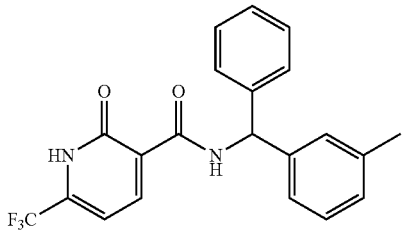 [SMILES: Cc1cccc(C(NC(=O)c2ccc(C(F)(F)F)[nH]c2=O)c2ccccc2)c1] | ¹H NMR (400 MHz, DMSO-d₆) δ = 9.84 (br s, 1H), 8.37 (d, J = 7.50 Hz, 1H), 7.38-7.32 (m, 4H), 7.30-7.20 (m, 3H), 7.19-7.05 (m, 3H), 6.25 (d, J = 7.94 Hz, 1H), 2.28 (s, 3H)<br>ESI [M − H] = 385.0 |
| 21 | 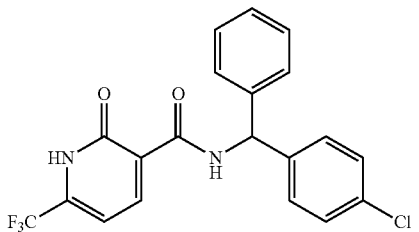 [SMILES: O=C(NC(c1ccccc1)c1ccc(Cl)cc1)c1ccc(C(F)(F)F)[nH]c1=O] | ¹H NMR (400 MHz, CHLOROFORM-d) δ ppm 13.54-13.71 (m, 1 H), 10.08-10.19 (m, 1 H), 8.69-8.77 (m, 1 H), 7.28-7.40 (m, 7 H), 7.22-7.26 (m, 1 H), 6.87-6.94 (m, 1 H), 6.40-6.48 (m, 1 H)<br>ESI [M − H] = 405.0 |
| 22 | 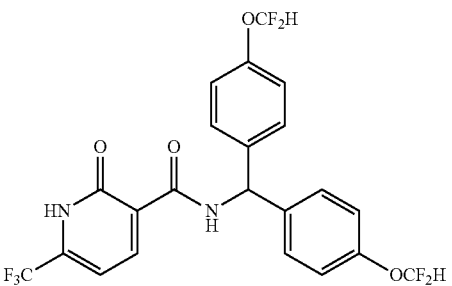 | 1H NMR (400 MHz, METHANOL-d4) δ = 8.50 (d, J = 7.6 Hz, 1H), 7.36 (d, J = 8.6 Hz, 4H), 7.13 (d, J = 8.6 Hz, 4H), 7.04 (d, J = 7.5 Hz, 1H), 6.99-6.59 (m, 2H), 6.33 (s, 1H)<br>ESI [M − H] = 503.0 |
| 23 | 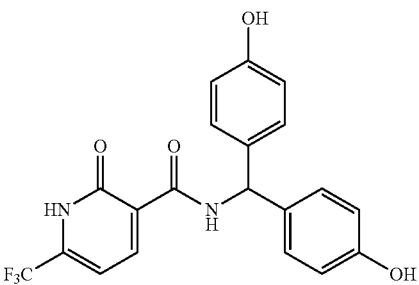 | ¹H NMR (400 MHz, DMSO-d₆) δ = 9.34 (br s, 2H), 8.32 (br d, J = 6.6 Hz, 1H), 7.06 (d, J = 8.6 Hz, 5H), 6.74-6.66 (m, 4H), 6.07 (d, J = 8.1 Hz, 1H)<br>ESI [M − H] = 403.0 |
| 24 | 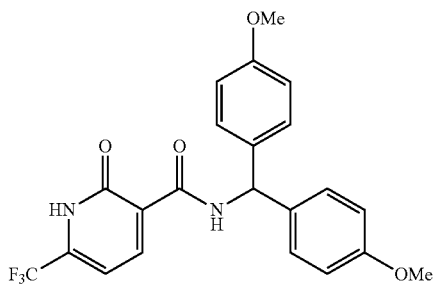 [SMILES: COc1ccc(C(NC(=O)c2ccc(C(F)(F)F)[nH]c2=O)c2ccc(OC)cc2)cc1] | ¹H NMR (400 MHz, CHLOROFORM-d) δ = 10.02 (br d, J = 7.2 Hz 1H), 8.70 (d, J = 7.2 Hz, 1H), 7.25-7.22 (m, 4H), 6.89-6.85 (m, 5H), 6.37 (d, J = 8.4 Hz, 1H), 3.79 (s, 6H)<br>ESI [M − H] = 431.1 |

TABLE 6-continued

| Compound No | Structure | HNMR and Ms |
|---|---|---|
| 25 | 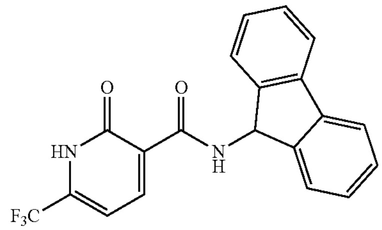 [SMILES: O=C(NC1c2ccccc2-c2ccccc21)c1ccc(C(F)(F)F)[nH]c1=O] | ¹H NMR (400 MHz, DMSO-d₆) δ = 13.49 (br s, 1H), 9.42 (br s, 1H), 8.49 (d, J = 7.7 Hz, 1H), 7.89 (d, J = 7.5 Hz, 2H), 7.59 (d, J = 7.3 Hz, 2H), 7.45 (t, J = 7.4 Hz, 2H), 7.35 (t, J = 7.3 Hz, 3H), 6.24 (d, J = 8.2 Hz, 1H) [M − H] = 369.0 |
| 26 | 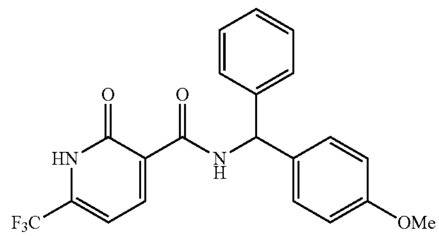 [SMILES: COc1ccc(C(NC(=O)c2ccc(C(F)(F)F)[nH]c2=O)c2ccccc2)cc1] | ¹H NMR (400 MHz, DMSO-d₆) δ = 13.49 (br s, 1H), 9.84 (br s, 1H), 8.37 (d, J = 7.5 Hz, 1H), 7.38-7.21 (m, 8H), 6.91 (d, J = 1 8.6 Hz, 2H), 6.25 (d, J = 7.9 Hz, 1H), 3.73 (s, 3H) [M − H] = 401.1 |
| 27 | 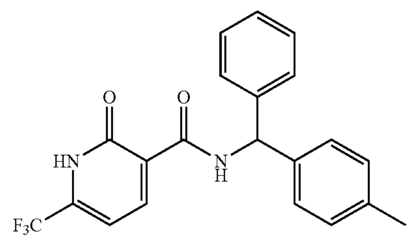 | ¹H NMR (400 MHz, DMSO-d₆) δ = 13.88-13.18 (m, 1H), 10.08-9.56 (m, 1H), 8.40-8.36 (m, 1H), 7.39-7.30 (m, 5H), 7.29-7.25 (m, 1H), 7.24-7.19 (m, 2H), 7.18-7.14 (m, 2H), 6.28-6.22 (m, 1H), 2.30-2.25 (m, 3H) [M − H] = 385.1 |
| 28 | 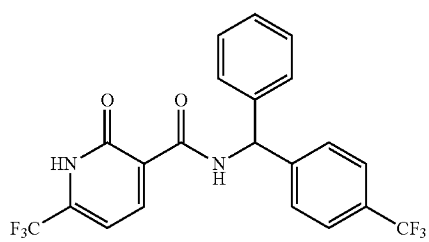 | ¹H NMR (400 MHz, DMSO-d₆) δ = 13.85-13.09 (m, 1H), 10.11-9.71 (m, 1H), 8.38-8.33 (m, 1H),7.76-7.68 (m, 2H), 7.61-7.56 (m, 2H), 7.41-7.35 (m, 4H), 7.33-7.25 (m, 2H), 6.42-6.37 (m, 1H) [M − H] = 439.1 |
| 29 | 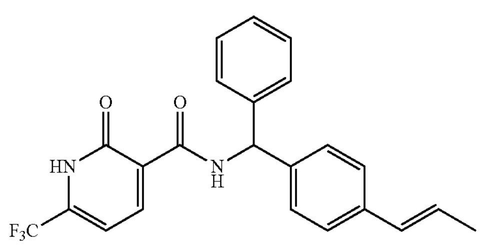 [SMILES: C/C=C/c1ccc(C(NC(=O)c2ccc(C(F)(F)F)[nH]c2=O)c2ccccc2)cc1] | ¹H NMR (400 MHz, DMSO-d₆) δ = 13.76-13.22 (m, 1H), 10.10-9.61 (m, 1H), 8.40-8.34 (m, 1H), 7.51-7.47 (m, 2H), 7.38-7.34 (m, 4H), 7.33-7.30 (m, 2H), 7.29-7.25 (m, 2H), 6.33-6.25 (m, 1H), 5.43-5.37 (m, 1H), 5.12-5.06 (m, 1H), 2.10-2.07 (m, 3H) ESI [M − H] = 411.1 |
| 30 | 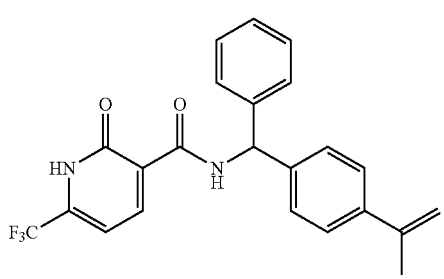 [SMILES: C=C(C)c1ccc(C(NC(=O)c2ccc(C(F)(F)F)[nH]c2=O)c2ccccc2)cc1] | ¹H NMR (400 MHz, DMSO-d₆) δ = 10.07-9.71 (m, 1H), 8.39-8.32 (m, 1H), 7.39-7.29 (m, 7H), 7.29-7.22 (m, 4H), 6.42-6.34 (m, 1H), 6.32-6.21 (m, 2H), 1.85-1.79 (m, 3H) ESI [M − H] = 411.1 |

TABLE 6-continued

| Compound No | Structure | HNMR and Ms |
|---|---|---|
| 31 | 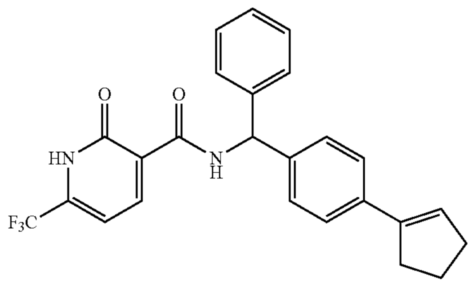 [SMILES: O=C(NC(c1ccccc1)c1ccc(C2=CCCC2)cc1)c1ccc(C(F)(F)F)[nH]c1=O] | ¹H NMR (400 MHz, CHLOROFORM-d) δ = 10.06 (br d, J = 7.9 Hz, 1H), 8.65 (d, J = 7.3 Hz, 1H), 7.34 (d, J = 8.3 Hz, 2H), 7.29-7.16 (m, 8H), 6.82 (d, J = 7.3 Hz, 1H), 6.39 (d, J = 8.2 Hz, 1H), 6.09 (br s, 1H), 2.66-2.57 (m, 2H), 2.52-2.30 (m, 2H), 1.94 (quin, J = 7.5 Hz, 2H)<br>ESI [M − H] = 437.1 |
| 32 | 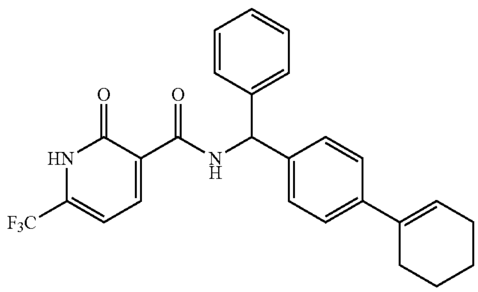 | ¹H NMR (400 MHz, CHLOROFORM-d) δ = 13.49-12.56 (m, 1H), 10.07 (br d, J = 8.2 Hz, 1H), 8.66 (d, J = 7.3 Hz, 1H), 7.31-7.27 (m, 5H), 7.24-7.18 (m, 4H), 6.83 (d, J = 7.5 Hz, 1H), 6.40 (d, J = 8.3 Hz, 1H), 6.04 (t, J = 3.9 Hz, 1H), 2.35-2.29 (m, 2H), 2.14 (br dd, J = 2.4, 6.1 Hz, 2H), 1.77-1.65 (m, 2H), 1.65-1.51 (m, 2H)<br>ESI [M − H] = 451.2 |
| 33 | 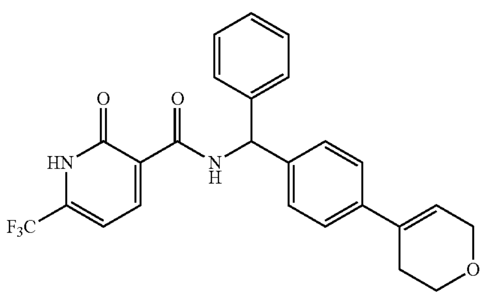 | ¹H NMR (400 MHz, CHLOROFORM-d) δ = 8.33 (br d, J = 1.5 Hz, 1H), 7.43 (d, J = 8.2 Hz, 2H), 7.39-6.93 (m, 9H), 6.28 (d, J = 7.9 Hz, 1H), 6.23 (br s, 1H), 4.20 (br d, J = 2.6 Hz, 2H), 3.80 (t, J = 5.4 Hz, 2H), 2.42 (br s, 2H)<br>ESI [M − H] = 453.1 |
| 34 | 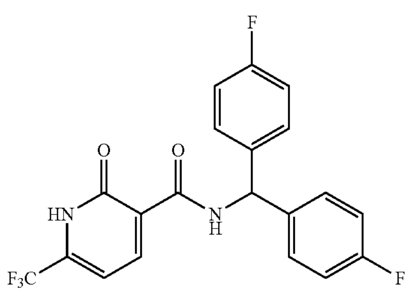 [SMILES: O=C(NC(c1ccc(F)cc1)c1ccc(F)cc1)c1ccc(C(F)(F)F)[nH]c1=O] | ¹H NMR (400 MHz, DMSO-d₆) δ = 13.37 (br s, 1H), 9.78 (br s, 1H), 8.34 (d, J = 7.5 Hz, 1H), 7.38 (dd, J = 5.4, 8.5 Hz, 4H), 7.28 (br d, J = 6.8 Hz, 1H), 7.19 (t, J = 8.8 Hz, 4H), 6.35-6.31 (m, 1H).)<br>ESI [M − H] = 407.0 |
| 35 | 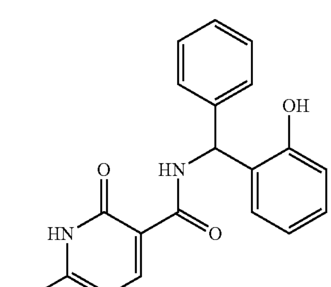 | ¹H NMR (400 MHz, DMSO-d₆) δ = 13.49 (br s, 1H), 9.96 (br s, 1H), 9.74 (br s, 1H), 8.46-8.44 (d, J = 7.6 Hz, 1H), 7.30-7.25 (m, 8H), 6.84-6.80 (m, 2H), 6.50-6.48 (m, 1H).)<br>ESI [M + 23] = 411.0 |

Example 4: Synthesis of N-((4-ethylphenyl)(phenyl)methyl)-2-oxo-6-(trifluoromethyl)-1,2-dihydropyridine-3-carboxamide (4A)

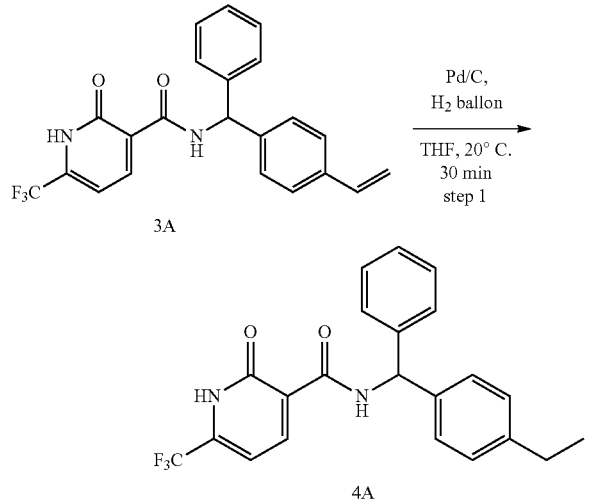

Step 1: N-((4-ethylphenyl)(phenyl)methyl)-2-oxo-6-(trifluoromethyl)-1,2-dihydropyridine-3-carboxamide (4A)

To a solution of Compound 3A (30 mg, 75.3 µmol) in THF (5 mL) was added Pd/C (5 mg, 10% purity) under $N_2$ atmosphere. The suspension was degassed and purged with $H_2$ for 3 times. The mixture was stirred under $H_2$ (15 psi) at 20° C. for 30 min, then filtered and the filtrate was concentrated. The residue was purified by prep-HPLC (column: Luna C18 100×30 5 u; mobile phase: [water (0.225% FA)-ACN]; B %: 40%-80%, 15 min) to give Compound 4A (9.2 mg, 22.98 µmol, 30.51% yield, 100% purity) as a white solid. M−H−=399.1 (LCMS); $^1$H NMR (400 MHz, DMSO-$d_6$) δ=13.49 (s, 1H), 10.08 (s, 1H), 8.35 (d, J=7.9 Hz, 1H), 7.38-7.31 (m, 4H), 7.29-7.15 (m, 6H), 6.25 (d, J=7.9 Hz, 1H), 2.57 (q, J=7.7 Hz, 2H), 1.15 (t, J=7.5 Hz, 3H)

Other compounds made in a similar manner are shown in Table 7.

TABLE 7

| Compound No | Structure | HNMR and Ms |
|---|---|---|
| 36 | 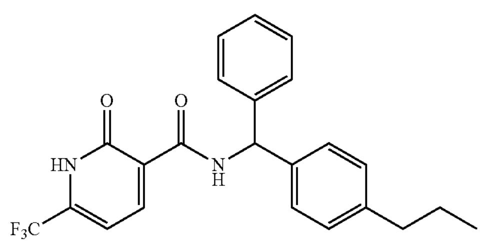 | $^1$H NMR (400 MHz, DMSO-$d_6$) δ 13.49 (br s, 1H), 9.82 (br s, 1H), 8.37 (d, J = 7.5 Hz, 1H), 7.38-7.30 (m, 4H), 7.30-7.20 (m, 4H), 7.19-7.13 (m, 2H), 6.26 (d, J = 8.2 Hz, 1H), 2.53 (br d, J = 4.2 Hz, 2H), 1.56 (sxt, J = 7.5 Hz, 2H), 0.88 (t, J = 7.4 Hz, 3H) ESI [M − H] = 413.1 |
| 37 | 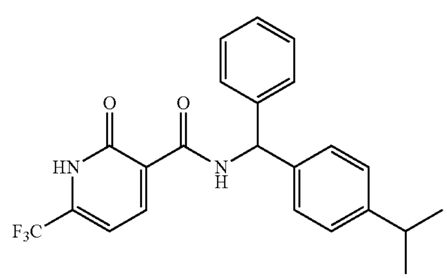 | $^1$H NMR (400 MHz, DMSO-$d_6$) δ 13.45 (br s, 1H), 10.42-9.78 (m, 1H), 8.34 (d, J = 7.5 Hz, 1H), 7.38-7.30 (m, 4H), 7.29-7.14 (m, 6H), 6.25 (d, J = 8.2 Hz, 1H), 2.85 (spt, J = 6.8 Hz, 1H), 1.17 (d, J = 7.1 Hz, 6H) ESI [M − H] = 413.1 |
| 38 | 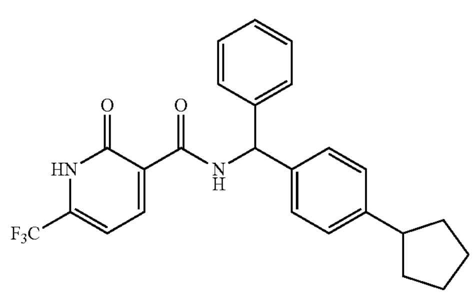 [SMILES: O=C(NC(c1ccccc1)c1ccc(C2CCCC2)cc1)c1ccc(C(F)(F)F)[nH]c1=O] | $^1$H NMR (400 MHz, CHLOROFORM-d) δ 10.11 (brd, J = 7.9 Hz, 1H), 8.70 (d, J = 7.3 Hz, 1H), 7.36-7.28 (m, 4H), 7.26-7.18 (m, 5H), 6.88 (d, J = 7.5 Hz, 1H), 6.43 (d, J = 8.4 Hz, 1H), 3.01-2.92 (m, 1H), 2.08-1.98 (m, 2H), 1.83-1.74 (m, 2H), 1.72-1.63 (m, 2H), 1.62-1.50 (m, 2H) ESI [M − H] = 439.1 |

TABLE 7-continued

| Compound No | Structure | HNMR and Ms |
|---|---|---|
| 39 | 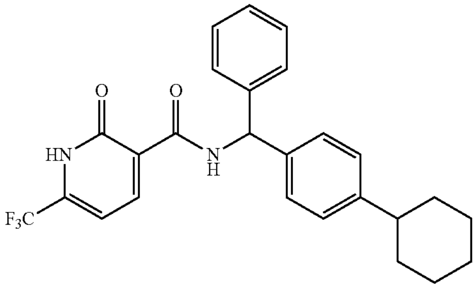 | $^1$H NMR (400 MHz, CHLOROFORM-d) δ 13.13-11.80 (m, 1H), 10.10 (br d, J = 8.1 Hz, 1H), 8.70 (d, J = 7.3 Hz, 1H), 7.35-7.29 (m, 4H), 7.25 (br s, 3H), 7.18-7.12 (m, 2H), 6.88 (d, J = 7.5 Hz, 1H), 6.42 (d, J = 8.3 Hz, 1H), 2.46 (br s, 1H), 1.87-1.69 (m, 5H), 1.43-1.21 (m, 5H) ESI [M − H] = 453.2 |

Example 5: Synthesis of N-(5H-dibenzo[a,d][7]annulen-5-yl)-2-oxo-6-(trifluoro methyl)-1,2-dihydropyridine-3-carboxamide (5A)

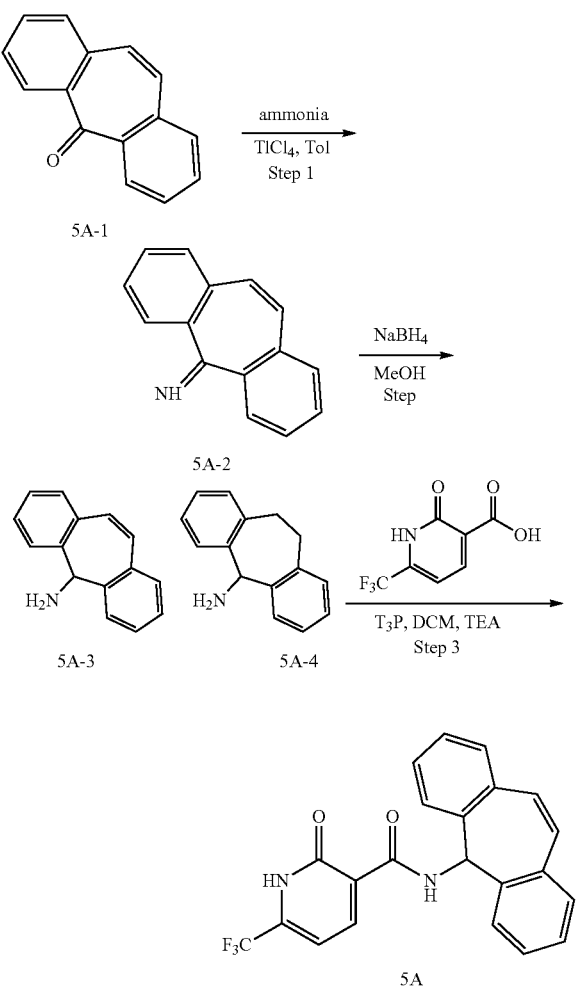

Step 1: 5H-dibenzo[a,d][7]annulen-5-imine (5A-2)

To a stirred solution of Compound 5A-1 (1 g, 4.9 mmol) in toluene (20.0 mL) was added TiCl$_4$ (1.5 g, 7.8 mmol) at 25° C. The mixture was bubbled with NH$_3$ (g) at 0° C. for 15 mins. The resulting mixture was stirred at 25° C. for 12 h. LCMS showed the desired mass was detected. The reaction mixture was quenched by addition Sat.NaHCO$_3$ 25 mL at 15° C., extracted with EtOAc (5 mL×5). The combined organic layers were concentrated under reduced pressure to give Compound 5A-2 (800 mg, 3.9 mmol, 80.4% yield) as a white gum. M+H$^+$=206.1

Step 2: 5H-dibenzo[a,d][7]annulen-5-amine (5A-3)

To a solution of Compound 5A-2 (400 mg, 2.0 mmol) in MeOH (10.0 mL) was added NaBH$_4$ (442 mg, 11.7 mmol) at 0° C. The mixture was stirred 10° C. for 20 h. The reaction mixture was quenched by adding H$_2$O 25 mL at 20° C., and then extracted with EtOAc (6 mL×5) and concentrated under reduced pressure to give a mixture of Compound 5A-3 and Compound 5A-4 (200 mg, 965 μmol, 49.5% yield) as a white gum. The mixture (5A-3:5A-4=2.3:1) was used next step directly.

Step 3: N-(5H-dibenzo[a,d][7]annulen-5-yl)-2-oxo-6-(trifluoromethyl)-1,2-dihydropyridine-3-carboxamide (5A)

To a solution of Compound 5A-3 (100 mg, 482 μmol), and 2-oxo-6-(trifluoromethyl)-1,2-dihydropyridine-3-carboxylic acid (100 mg, 482 μmol) in DMF (10.0 mL) was added TEA (73 mg, 724 μmol, 100 uL) and T$_3$P (921 mg, 1.5 mmol, 50% purity). The mixture was stirred at 25° C. for 2 h, but the compound 5A-3 remained. The mixture was stirred at 30° C. for another 12 h. LCMS showed the reaction was completed. The reaction mixture was quenched by adding H$_2$O 25 mL at 20° C., and then extracted with EtOAc 50 mL (10 mL×5) and concentrated under reduced pressure to give a residue, which was purified by prep-HPLC (column: Welch Ultimate AQ-C18 150×30 mm×5 um; mobile phase: [water (0.1% TFA)-ACN]; B %: 40%-70%, 12 min) to give Compound 5A (26 mg, 63 μmol, 13.02% yield, 96% purity) as a white solid and Compound 40 (15.5 mg, 38. μmol, 5.26% yield, 97.9% purity) as a white solid. M−H$^-$=395.0 (LCMS); $^1$H NMR (400 MHz, METHANOL-d4) δ=8.46-8.41 (m, 1H), 7.59-7.55 (m, 2H), 7.48-7.37 (m, 5H), 7.36-7.30 (m, 2H), 7.20-7.17 (m, 2H), 7.02-6.95 (m, 1H).

Compounds made in a similar manner are shown in Table 8.

TABLE 8

| Compound No | Structure | HNMR and Ms |
|---|---|---|
| 40 | 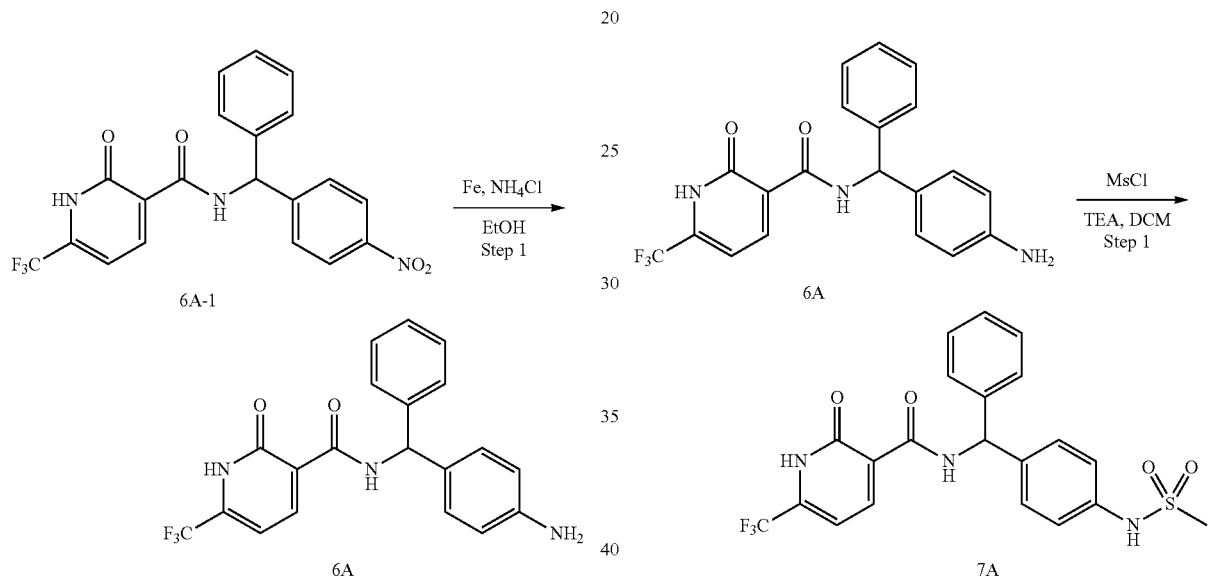 | $^1$H NMR (400 MHz, DMSO-d$_6$) δ = 8.42-8.36 (m, 1H), 7.43-7.38 (m, 2 H), 7.27-7.12 (m, 7H), 6.53-6.47 (m, 1 H), 3.32-3.23 (m, 2H), 3.23-3.13 (m, 2 H) ESI [M − H] = 397.1 |

Example 6: Synthesis of N-((4-aminophenyl)(phenyl)methyl)-2-oxo-6-(trifluoromethyl)-1,2-dihydropyridine-3-carboxamide (6A)

Example 7: Synthesis of N-((4-(methylsulfonamido)phenyl)(phenyl)methyl)-2-oxo-6-(trifluoro methyl)-1,2-dihydropyridine-3-carboxamide (7A)

Step 1: N-((4-aminophenyl)(phenyl)methyl)-2-oxo-6-(trifluoromethyl)-1,2-dihydropyridine-3-carboxamide (6A)

To a solution of Compound 6A-1 (400 mg, 958 μmol) in EtOH (5.0 mL) and H2O (1.0 mL) was added Fe (268 mg, 4.8 mmol) and NH$_4$Cl (256 mg, 4.8 mmol). The resulting mixture was stirred at 80° C. for 1 hr. TLC (Petroleum ether:Ethyl acetate=0/1) showed the reaction was completed. The mixture was filtered and the filtrate was concentrated under reduced pressure to give a residue (500 mg). 450 mg of the residue was purified by flash silica gel chromatography to give Compound 6A (320 mg, crude) as a yellow gum, which was used for next step. 50 mg of the residue was purified by Prep-HPLC (Column: HUAPU C8 Extreme BDS 150×30 5 u; mobile phase: [water (10 mM NH4HCO3)-ACN]; B %: 10%-60%, 10 min) to give another batch of Compound 7A (16 mg, 99.4% purity) as a yellow solid for delivery. M−H$^−$=386.1 (LCMS); $^1$H NMR (400 MHz, CHLOROFORM-d) δ=10.05-9.99 (m, 1H), 8.72-8.68 (m, 1H), 7.38-7.32 (m, 5H), 7.14-7.08 (m, 2H), 6.92-6.87 (m, 1H), 6.69-6.64 (m, 2H), 6.40-6.35 (m, 1H).

Step 1: N-((4-(methylsulfonamido)phenyl)(phenyl)methyl)-2-oxo-6-(trifluoromethyl)-1,2-dihydropyridine-3-carboxamide (7A)

To a solution of Compound 6A (50 mg, 129 μmol) in DCM (2.0 mL) was added TEA (39 mg, 387 μmol, 54 uL) and methanesulfonyl chloride (13 mg, 116 μmol, 9 uL) at 0° C. Then the mixture was stirred at 25° C. for 12 h. LCMS showed the desired product was detected. The reaction mixture was quenched by addition H$_2$O 10 mL at 25° C., and extracted with EtOAc (5 mL×5). The combined organic layers were dried over Na$_2$SO$_4$. Then filtered and the filtrate was concentrated under reduced pressure to give a residue. The residue was purified by prep-HPLC (column: Xtimate C18 150×25 mm×5 um; mobile phase: [water (10 mM NH4HCO3)-ACN]; B %: 15%-32%, 10 min) to give Compound 7A (4.5 mg, 9.42 μmol, 7.3% yield, 96.8% purity) as a light yellow solid. M−H$^−$=464.1 (LCMS); $^1$H NMR (400 MHz, CHLOROFORM-d) δ=10.24-10.12 (m, 1H), 8.75-8.71 (m, 1H), 8.02-7.87 (m, 1H), 7.37-7.28 (m, 7H), 7.24-7.19 (m, 2H), 6.93-6.88 (m, 1H), 6.48-6.43 (m, 1H), 3.06-3.01 (m, 3H).

Compounds made in a similar manner are shown in Table 9.

TABLE 9

| Compound No | Structure | HNMR and Ms |
|---|---|---|
| 41 | 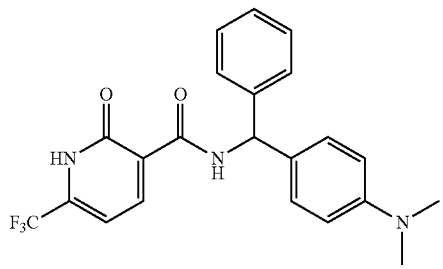 [SMILES: CN(C)c1ccc(C(NC(=O)c2ccc(C(F)(F)F)[nH]c2=O)c2ccccc2)cc1] | ¹H NMR (400 MHz, CHLOROFORM-d) δ = 10.03-9.96 (m, 1 H), 8.72-8.66 (m, 1 H), 7.37-7.29 (m, 4 H), 7.26-7.22 (m, 1 H), 7.21-7.15 (m, 2 H), 6.89-6.85 (m, 1 H), 6.72-6.66 (m, 2 H), 6.40-6.36 (m, 1 H), 2.96-2.90 (m, 6 H); ESI [M − H] = 414.1 |

Example 8: Synthesis of N-(3,6-bis(trifluoromethoxy)-9H-fluoren-9-yl)-2-oxo-6-(trifluoromethyl)-1,2-dihydropyridine-3-carboxamide (8A)

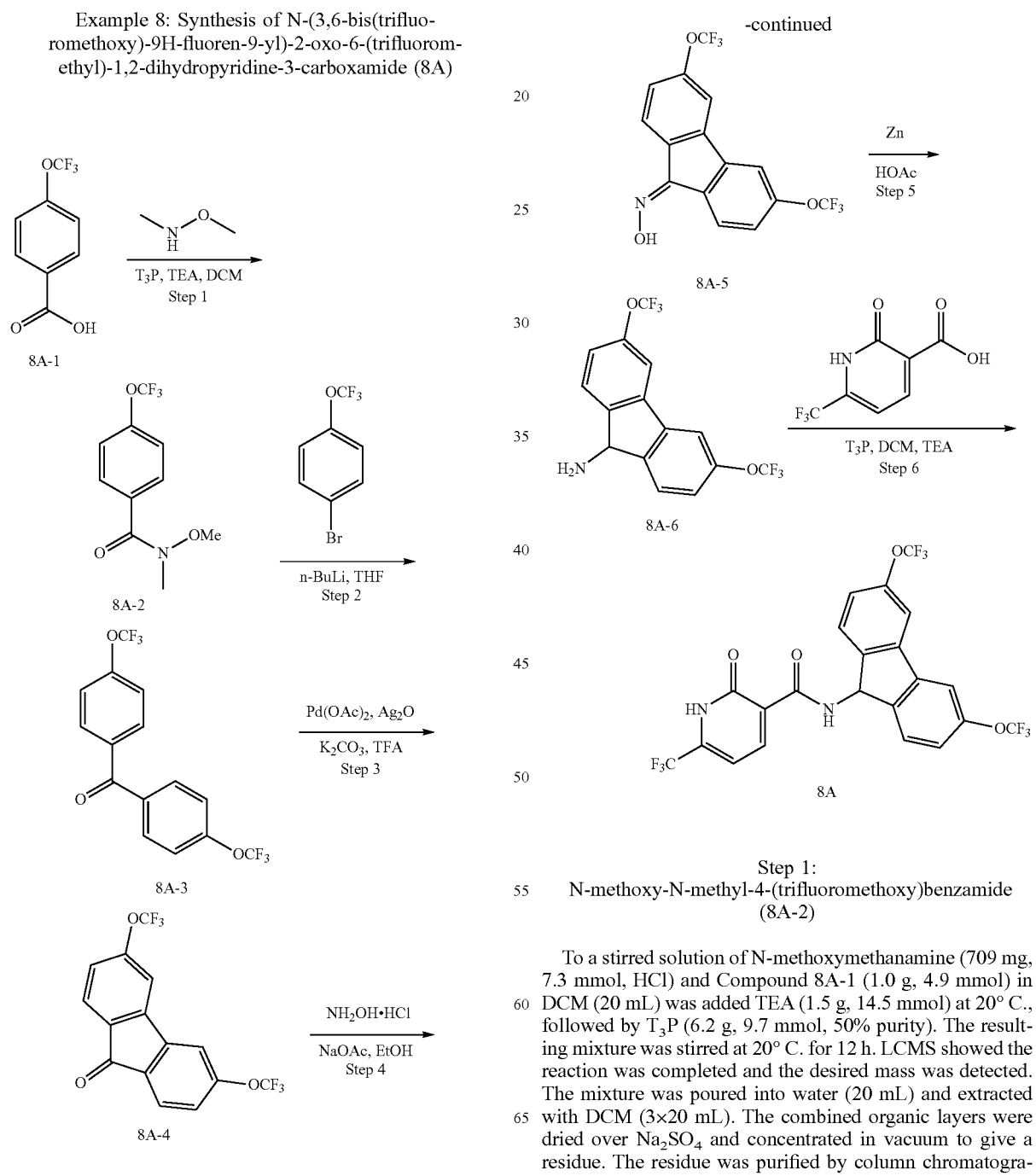

Step 1:
N-methoxy-N-methyl-4-(trifluoromethoxy)benzamide (8A-2)

To a stirred solution of N-methoxymethanamine (709 mg, 7.3 mmol, HCl) and Compound 8A-1 (1.0 g, 4.9 mmol) in DCM (20 mL) was added TEA (1.5 g, 14.5 mmol) at 20° C., followed by T₃P (6.2 g, 9.7 mmol, 50% purity). The resulting mixture was stirred at 20° C. for 12 h. LCMS showed the reaction was completed and the desired mass was detected. The mixture was poured into water (20 mL) and extracted with DCM (3×20 mL). The combined organic layers were dried over Na₂SO₄ and concentrated in vacuum to give a residue. The residue was purified by column chromatography (Petroleum ether/Ethyl acetate) to afford Compound 8A-2 (1.2 g, 4.8 mmol, 99.3% yield) as a yellow oil. M+H$^+$=250.0 (LCMS). $^1$H NMR (400 MHz, CHLOROFORM-d) δ=7.77 (d, J=8.6 Hz, 2H), 7.25 (br d, J=8.2 Hz, 2H), 3.56 (s, 3H), 3.38 (s, 3H).

Step 2: bis(4-(trifluoromethoxy)phenyl)methanone (8A-3)

To a solution of 1-bromo-4-(trifluoromethoxy)benzene (1.9 g, 8.0 mmol) in THF (25 mL) at −78° C. under nitrogen was added n-BuLi (2.5 M, 2.4 mL) over 10 min, and the solution was stirred for 60 min at −78° C. Then a solution of Compound 8A-2 (1 g, 4.0 mmol) in THF (10 mL) was added at −78° C., and the combined mixture was stirred for 15 min at −78° C. then warmed to 20° C. and stirred 1 h. LCMS showed the reaction was completed and the desired mass was detected. The reaction mixture was quenched by addition 1N HCl (20 mL) and extracted with EtOAc (20 mL×4). The combined organic layers were dried over Na$_2$SO$_4$, filtered and concentrated under reduced pressure to give a residue, which was purified by column chromatography (Petroleum ether/Ethyl acetate) to afford Compound 8A-3 (1.3 g, 3.6 mmol, 88.9% yield) as a yellow solid. M+H$^+$=351.0 (LCMS).

Step 3: 3,6-bis(trifluoromethoxy)-9H-fluoren-9-one (8A-4)

A solution of Compound 8A-3 (300 mg, 856 μmol) Pd(OAc)$_2$ (19 mg, 85 μmol) K$_2$CO$_3$ (296 mg, 2.1 mmol) and Ag$_2$O (298 mg, 1.3 mmol) in TFA (3 mL) under N$_2$ was stirred at 140° C. for 24 h. The mixture was poured into water (20 mL) and extracted with EtOAc (3×10 mL). The combined organic layers were dried over Na$_2$SO$_4$ and concentrated in vacuum to give a residue, which was purified by column chromatography (Petroleum ether/Ethyl acetate) to afford Compound 8A-4 (0.2 g, 574 μmol, 67.1% yield) as a white solid.

Step 4: 3,6-bis(trifluoromethoxy)-9H-fluoren-9-one oxime (8A-5)

To a solution of Compound 8A-4 (100 mg, 287 μmol) in EtOH (5 mL) was added NH$_2$OH.HCl (24 mg, 344 μmol) and AcONa (47 mg, 574 μmol) and the mixture was stirred at 80° C. for 12 h. TLC showed the reaction was completed and one main spot was detected. The reaction mixture was quenched by addition H$_2$O (10 mL) and extracted with EtOAc (3 mL×5). The combined organic layers were dried over Na$_2$SO$_4$, filtered and concentrated under reduced pressure to afford Compound 8A-5 (100 mg, crude) as a white solid.

Step 5
3,6-bis(trifluoromethoxy)-9H-fluoren-9-amine (8A-6)

To a solution of Compound 8A-5 (100 mg, 275 μmol) in HOAc (5 mL) was added Zn (54 mg, 825 μmol) and the mixture was stirred at 100° C. for 1 h. The reaction mixture was concentrated under N$_2$ to remove solvent. Then was poured into Sat.NaHCO$_3$ (10 mL) then extracted with DCM (3×10 mL). The combined organic layers were dried over Na$_2$SO$_4$ and concentrated in vacuum to give a residue. The residue was purified by prep-TLC (Ethyl acetate:Methanol=10:1, R$_f$=0.24) to afford Compound 8A-6 (50 mg, 143 μmol, 52.0% yield) as a yellow gum.

Step 6 N-(3,6-bis(trifluoromethoxy)-9H-fluoren-9-yl)-2-oxo-6-(trifluoromethyl)-1,2-dihydropyridine-3-carboxamide (8A)

To a stirred solution of 2-oxo-6-(trifluoromethyl)-1H-pyridine-3-carboxylic acid (29 mg, 141 μmol) and Compound 8A-6 (45 mg, 129 μmol) in DCM (3 mL) was added TEA (39 mg, 386 μmol) at 20° C., followed by T$_3$P (123 mg, 193 μmol, 50% purity). The resulting mixture was stirred at 20° C. for 0.5 h. The mixture was poured into water (10 mL) and extracted with DCM (3×5 mL). The combined organic layers were dried over Na$_2$SO$_4$ and concentrated in vacuum to give a residue. The residue was purified by prep-TLC (Petroleum ether:Ethyl acetate=1:1, R$_f$=0.35) to afford Compound 8A (14 mg, 26 μmol, 20.0% yield, 97.0% purity) as a white solid. M−H$^-$=537.0 (LCMS). $^1$H NMR (400 MHz, DMSO-d6) δ=8.26 (br d, J=7.3 Hz, 1H), 8.12 (s, 2H), 7.67 (d, J=8.2 Hz, 2H), 7.36 (br d, J=8.4 Hz, 2H), 6.86 (br s, 1H), 6.23 (d, J=7.9 Hz, 1H).

Other compounds made in a similar manner are shown in Table 10.

TABLE 10

| Compound No | Structure | HNMR and Ms |
| --- | --- | --- |
| 42 | 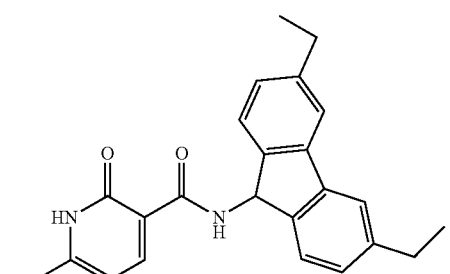 | $^1$H NMR (400 MHz, DMSO-d6) δ = 13.49 (br s, 1H), 10.04-9.16 (m, 1H), 8.45 (br d, J = 7.3 Hz, 1H), 7.73 (s, 2H), 7.46 (d, J = 7.7 Hz, 2H), 7.17 (dd, J = 1.2, 7.8 Hz, 3H), 6.14 (d, J = 8.2 Hz, 1H), 2.70 (q, J = 7.4 Hz, 4H), 1.25 (t, J = 7.5 Hz, 6H) ESI [M − H] = 425.1 |

TABLE 10-continued

| Compound No | Structure | HNMR and Ms |
|---|---|---|
| 43 | 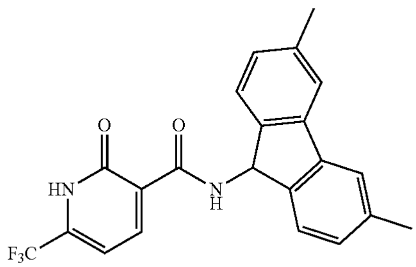 [SMILES: Cc1ccc2c(c1)-c1cc(C)ccc1C2NC(=O)c1ccc(C(F)(F)F)[nH]c1=O] | ¹H NMR (400 MHz, CHLOROFORM-d) δ 9.48 (br s, 1 H) 8.72 (br d, J = 7.50 Hz, 1 H) 7.55-7.43 (m, 4 H) 7.27 (s, 1 H) 7.10 (br d, J = 7.50 Hz, 2 H) 6.84 (br d, J = 7.72 Hz, 1 H) 6.25 (br d, J = 7.94 Hz, 1 H) 2.44 (s, 6 H) ESI [M − H] = 397.0 |
| 44 | 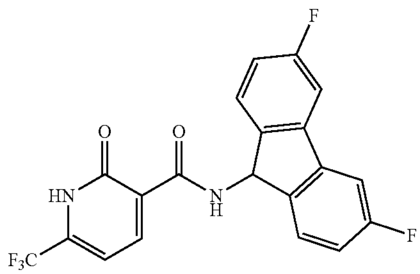 [SMILES: O=C(NC1c2ccc(F)cc2-c2cc(F)ccc21)c1ccc(C(F)(F)F)[nH]c1=O] | ¹H NMR (400 MHz, DMSO-d₆) δ = 13.48 (s, 1H), 9.49 (br.s, 1H), 8.49 (d, J = 7.6 Hz, 1H), 7.89 (dd, J = 2.4, 9.2 Hz, 2H), 7.58 (dd, J = 4.9, 8.3 Hz, 2H), 7.30 (br s, 1H), 7.24-7.13 (m, 2H), 6.15 (d, J = 8.3 Hz, 1H) ESI [M − H] = 405.0 |
| 45 | 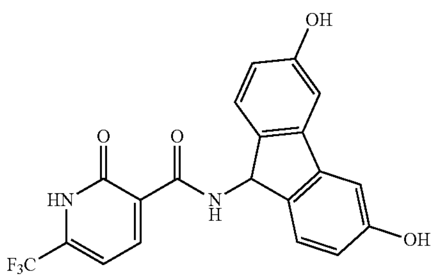 [SMILES: O=C(NC1c2ccc(O)cc2-c2cc(O)ccc21)c1ccc(C(F)(F)F)[nH]c1=O] | ¹H NMR (400 MHz, DMSO-d₆) δ = 9.58 (s, 2H), 8.50 (d, J = 7.6 Hz, 1H), 7.32 (d, J = 8.1 Hz, 3H), 7.10 (d, J = 2.2 Hz, 2H), 6.71 (dd, J = 2.3, 8.1 Hz, 2H), 6.01 (d, J = 8.1 Hz, 1H) ESI [M − H] = 401.0 |
| 46 | 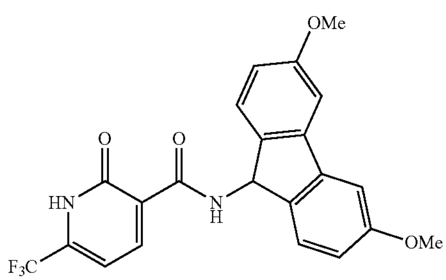 [SMILES: COc1ccc2c(c1)-c1cc(OC)ccc1C2NC(=O)c1ccc(C(F)(F)F)[nH]c1=O] | ¹H NMR (400 MHz, DMSO-d₆) δ = 8.46 (br d, J = 6.2 Hz, 1H), 7.53 (d, J = 2.4 Hz, 2H), 7.45 (d, J = 8.3 Hz, 2H), 7.24 (br s, 1H), 6.89 (dd, J = 2.4, 8.3 Hz, 2H), 6.09 (d, J = 8.1 Hz, 1H), 3.85 (s, 6H) ESI [M − H] = 429.1 |
| 47 | 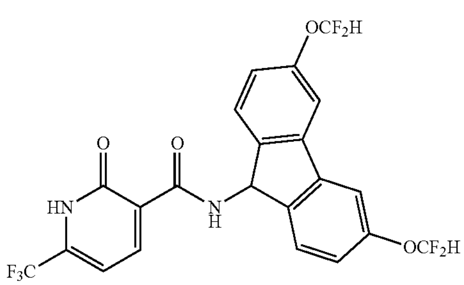 | ¹H NMR (400 MHz, DMSO-d₆) δ = 13.44 (br s, 1H), 9.50 (br s, 1H), 8.44 (d, J = 1.1 Hz, 1H), 7.83 (d, J = 2.0 Hz, 2H), 7.61 (d, J = 8.2 Hz, 2H), 7.53-7.09 (m, 5H), 6.19 (d, J = 1.9 Hz, 1H) ESI [M − H] = 501.0 |

Example 9: Synthesis of 2-oxo-N-(phenyl(4-(piperidin-1-yl)phenyl)methyl)-6-(trifluoromethyl)-1,2-dihydropyridine-3-carboxamide (9A)

Step 1: 2-oxo-N-(phenyl(4-(piperidin-1-yl)phenyl)methyl)-6-(trifluoromethyl)-1,2-dihydropyridine-3-carboxamide (9A)

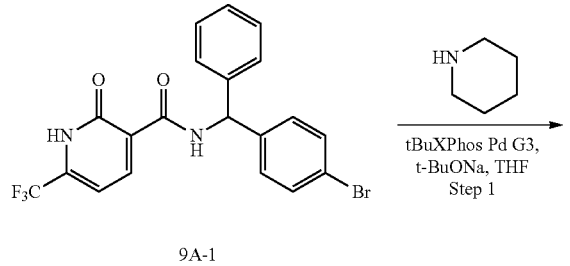

To a stirred mixture of Compound 9A-1 (30 mg, 66 μmol), piperidine (9 mg, 99 μmol) and t-BuONa (19 mg, 199 μmol) in THF (3 mL) was added tBuXPhos Pd G3 (5 mg, 7 μmol) under $N_2$ atmosphere. The resulting mixture was stirred at 80° C. for 12 h. The reaction mixture was quenched by addition $H_2O$ (10 mL) and extracted with EtOAc (5 mL×4). The combined organic layers were dried over $Na_2SO_4$, filtered and concentrated under reduced pressure to give a residue, which was purified by prep-HPLC (column: Kromasil® 150×25 mm×10 um; mobile phase: [water (0.04% $NH_3H_2O$+10 mM $NH_4HCO_3$)-ACN]; B %: 15%-45%, 20 min) to afford Compound 9A (7 mg, 15 μmol, 22.0% yield, 97.0% purity) as a yellow solid. M−H⁻=454.1 (LCMS); ¹H NMR (400 MHz, CHLOROFORM-d) δ=10.04 (br d, J=7.9 Hz, 1H), 8.68 (d, J=7.3 Hz, 1H), 7.35-7.27 (m, 4H), 7.26-7.19 (m, 2H), 7.15 (d, J=8.6 Hz, 2H), 6.86 (d, J=8.2 Hz, 3H), 6.37 (d, J=8.2 Hz, 1H), 3.19-2.98 (m, 4H), 1.66 (q, J=5.6 Hz, 4H), 1.58-1.49 (m, 2H).

Other compounds made in a similar manner are shown in Table 11.

TABLE 11

| Compound No | Structure | HNMR and Ms |
| --- | --- | --- |
| 48 | 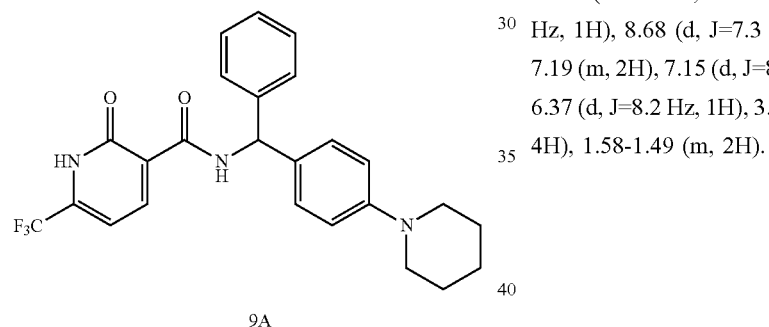 | ¹H NMR (400 MHz, CHLOROFORM-d) δ = 10.05 (br d, J = 7.9 Hz, 1H), 8.70 (d, J = 7.3 Hz, 1H), 7.33 (d, J = 4.4 Hz, 4H), 7.27-7.25 (m, 2H), 7.22 (d, J = 8.8 Hz, 2H), 6.94-6.79 (m, 3H), 6.40 (d, J = 8.4 Hz, 1H), 3.88-3.82 (m, 4H), 3.18-3.10 (m, 4H) ESI [M − H] = 456.1 |

Example 10: Synthesis of 2-oxo-N-(9H-thioxanthen-9-yl)-6-(trifluoromethyl)-1,2-dihydropyridine-3-carboxamide (10A)

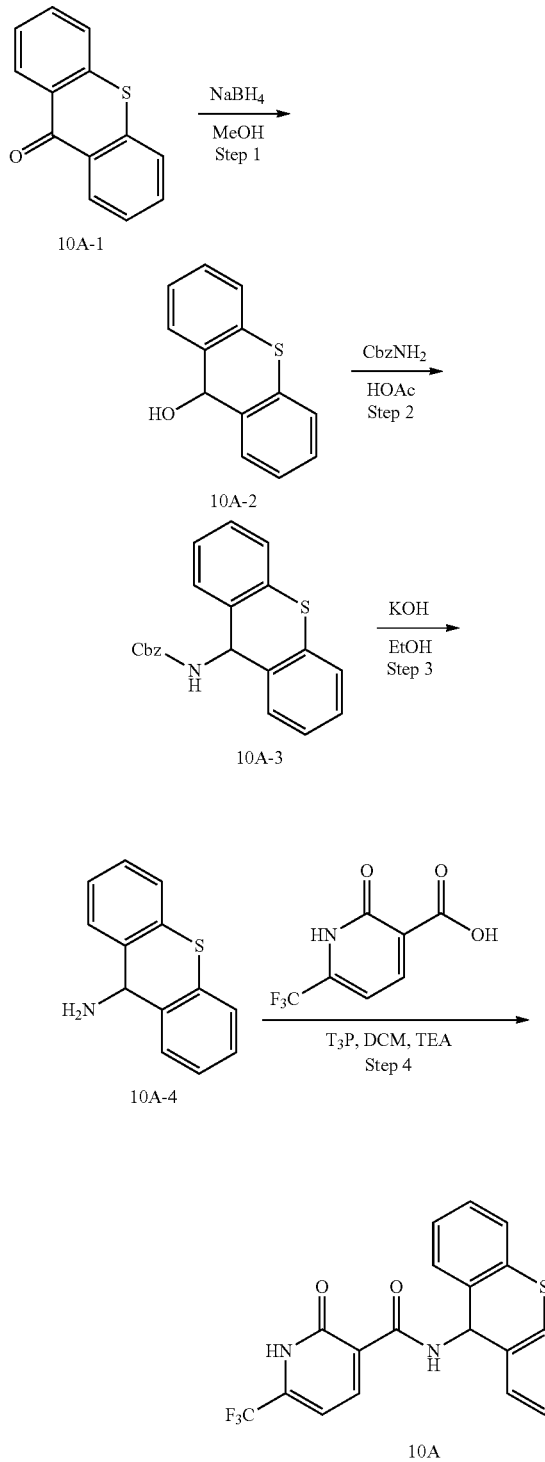

Step 1: 9H-thioxanthen-9-ol (10A-2)

To a solution of Compound 10A-1 (0.5 g, 2.4 mmol) in MeOH (10 mL) was added NaBH₄ (356 mg, 9.4 mmol) at 0° C. under N₂, then the mixture was stirred at 70° C. for 3 h. LCMS showed the reaction was completed and one main peak with desired mass was detected. The reaction mixture was quenched by addition ice water (50 mL), and then extracted with EtOAc (20 mL×5). The combined organic layers were dried over Na₂SO₄, filtered and concentrated under reduced pressure to afford Compound 10A-2 (0.45 g, crude) as a yellow solid. M−H⁻=212.9 (LCMS).

Step 2: benzyl 9H-thioxanthen-9-ylcarbamate (10A-3)

A solution of Compound 10A-2 (0.5 g, 2.1 mmol) in HOAc (3 mL) was added benzyl carbamate (380 mg, 2.5 mmol), the mixture was stirred at 25° C. for 12 h. LC-MS showed the reaction was completed and the desired mass was detected. The mixture was poured into ice-water (10 mL) and filtered, the precipitate was dried under reduced pressure to give a residue, which was purified by prep-TLC (Petroleum ether:Ethyl acetate=5:1, $R_f$=0.48) to afford Compound 10A-3 (0.6 g, 1.6 mmol, 76.8% yield) as a white solid. M−H⁻=346.0 (LCMS); ¹H NMR (400 MHz, DMSO-d6) δ=8.61 (br d, J=9.5 Hz, 1H), 7.60-7.23 (m, 13H), 5.45 (d, J=9.4 Hz, 1H), 5.15 (s, 2H).

Step 3: 9H-thioxanthen-9-amine (10A-4)

The solution of KOH (872 mg, 16 mmol) in EtOH (10 mL) and Compound 10A-3 (0.3 g, 863 μmol) was stirred at 80° C. for 12 h. The reaction mixture was quenched by addition H₂O (10 mL) and extracted with EtOAc (10 mL×4). The combined organic layers were dried over Na₂SO₄, filtered and concentrated under reduced pressure to give a residue, which was purified by column chromatography (Petroleum ether/Ethyl acetate) to afford Compound 10A-4 (85 mg, 398 μmol, 46.2% yield) as a yellow gum. ¹H NMR (400 MHz, DMSO-d6) δ=7.67 (d, J=7.7 Hz, 2H), 7.49 (d, J=7.5 Hz, 2H), 7.34 (dt, J=1.1, 7.5 Hz, 2H), 7.28-7.22 (m, 2H), 4.53 (s, 1H).

Step 4: 2-oxo-N-(9H-thioxanthen-9-yl)-6-(trifluoromethyl)-1,2-dihydropyridine-3-carboxamide (10A)

To a stirred solution of Compound 10A-4 (30 mg, 140 μmol) and 2-oxo-6-(trifluoromethyl)-1H-pyridine-3-carboxylic acid (32 mg, 154 μmol) in DCM (5 mL) was added TEA (43 mg, 422 μmol) at 25° C., followed by T₃P (179 mg, 281 μmol, 50% purity). The resulting mixture was stirred at 25° C. for 2 h. The reaction mixture was quenched by addition H₂O (5 mL) and extracted with EtOAc (5 mL×4). The combined organic layers were dried over Na₂SO₄, filtered and concentrated under reduced pressure to give a residue, which was purified by prep-HPLC (column: Welch Ultimate AQ-C18 150×30 mm×5 um; mobile phase: [water (10 mM NH₄HCO₃)-ACN]; B %: 45%-75%, 12 min) to afford Compound 10A (13 mg, 32 μmol, 22.5% yield, 97.3% purity) as a white solid. M−H⁻=401.1 (LCMS); ¹H NMR (400 MHz, DMSO-d6) δ=13.53 (br s, 1H), 9.87 (br s, 1H), 8.44 (d, J=7.5 Hz, 1H), 7.61 (dt, J=2.6, 8.8 Hz, 4H), 7.43-7.23 (m, 5H), 6.16 (d, J=8.8 Hz, 1H).

Example 11: Synthesis of N-(10,10-dioxido-9H-thioxanthen-9-yl)-2-oxo-6-(trifluoromethyl)-1,2-dihydropyridine-3-carboxamide (11A)

Example 12: Synthesis of N-((4-cyanophenyl)(phenyl)methyl)-2-oxo-6-(trifluoromethyl)-1,2-dihydropyridine-3-carboxamide (12A)

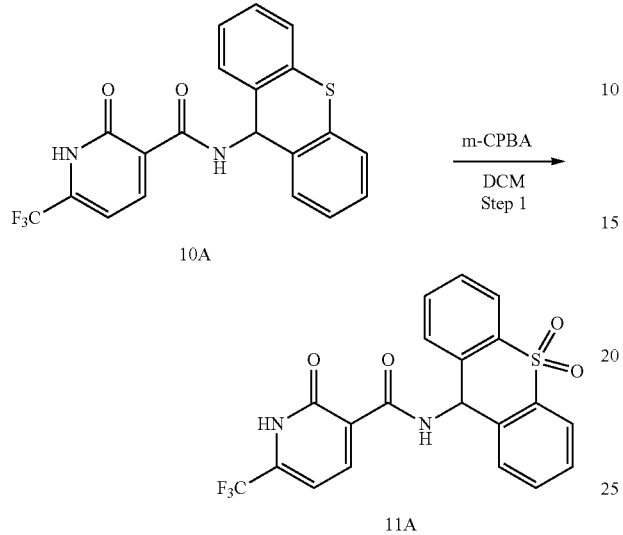
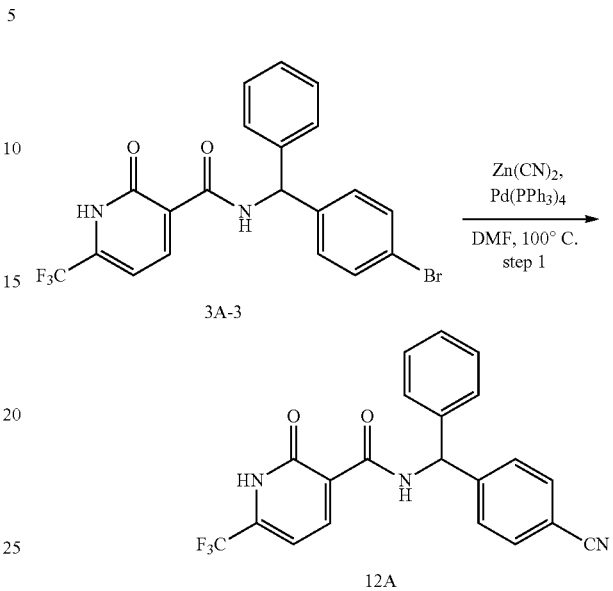

Step 1: N-(10,10-dioxido-9H-thioxanthen-9-yl)-2-oxo-6-(trifluoromethyl)-1,2-dihydropyridine-3-carboxamide (11A)

To a stirred solution of Compound 10A (35 mg, 87 μmol) in DCM (4 mL) was added m-CPBA (56 mg, 261 μmol, 80% purity) at 0° C., the resulting mixture was stirred at 20° C. for 4 h. The reaction mixture was quenched by addition Sat.NaHCO$_3$ (10 mL), and extracted with DCM (3×5 mL). The combined organic layers were dried over Na$_2$SO$_4$, filtered and concentrated under reduced pressure to give a residue, which was purified by prep-HPLC (column: Nano-micro Kromasil® C18 100×30 mm 5 um; mobile phase: [water (0.1% TFA)-ACN]; B %: 35%-65%, 10 min) to afford Compound 11A (3 mg, 8 μmol, 8.8 yield, 97.2% purity) as a white solid. M+H$^+$=435.0 (LCMS); $^1$H NMR (400 MHz, DMSO-d6) δ=8.40 (br d, J=7.3 Hz, 1H), 8.09 (d, J=7.7 Hz, 2H), 7.86-7.56 (m, 6H), 7.17 (br s, 1H), 6.74 (d, J=9.3 Hz, 1H).

Step 1: N-((4-cyanophenyl)(phenyl)methyl)-2-oxo-6-(trifluoromethyl)-1,2-di-hydro-pyridine-3-carboxamide (12A)

To a mixture of Compound 3A-3 (25 mg, 55.4 μmol), Zn(CN)$_2$ (16 mg, 136.3 μmol) in DMF (2 mL) was added Pd(PPh$_3$)$_4$ (8 mg, 6.9 μmol) under N$_2$. The mixture was stirred at 100° C. for 12 h, and then filtered. The filtrate was purified by prep-HPLC (column: Nano-Micro UniSil 5-100 C18 ULTRA 100×250 mm 5 um; mobile phase: [water (0.225% FA)-ACN]; B %: 30%-70%, 10 min) to give Compound 12A (7.4 mg, 24.65% yield, 96.18% purity) as a white solid. M−H$^−$=396.0 (LCMS); $^1$H NMR (400 MHz, DMSO-d$_6$) δ=13.44 (br s, 1H), 9.91 (br s, 1H), 8.33 (d, J=7.7 Hz, 1H), 7.83 (d, J=8.4 Hz, 2H), 7.57 (d, J=8.4 Hz, 2H), 7.43-7.34 (m, 4H), 7.34-7.20 (m, 2H), 6.38 (d, J=7.7 Hz, 1H).

Compound 49 in Table 12 was made with a similar procedure.

TABLE 12

| Compound No | Structure | HNMR and Ms |
| --- | --- | --- |
| 49 | [structure of compound with two CN groups, CF$_3$, and pyridinone-carboxamide core] | $^1$H NMR (400 MHz, CHLOROFORM-d) δ ppm 10.30-10.23 (m, 1 H) 8.76-8.70 (m, 1 H) 7.72-7.66 (m, 4 H) 7.46-7.39 (m, 4 H) 6.98-6.94 (m, 1 H) 6.57-6.52 (m, 1 H) ESI [M − H] = 421.1 |

Example 13: Synthesis of N-(di-p-tolylmethyl)-6-oxo-2-(trifluoromethyl)-1,6-dihydropyrimidine-5-carboxamide (13A)

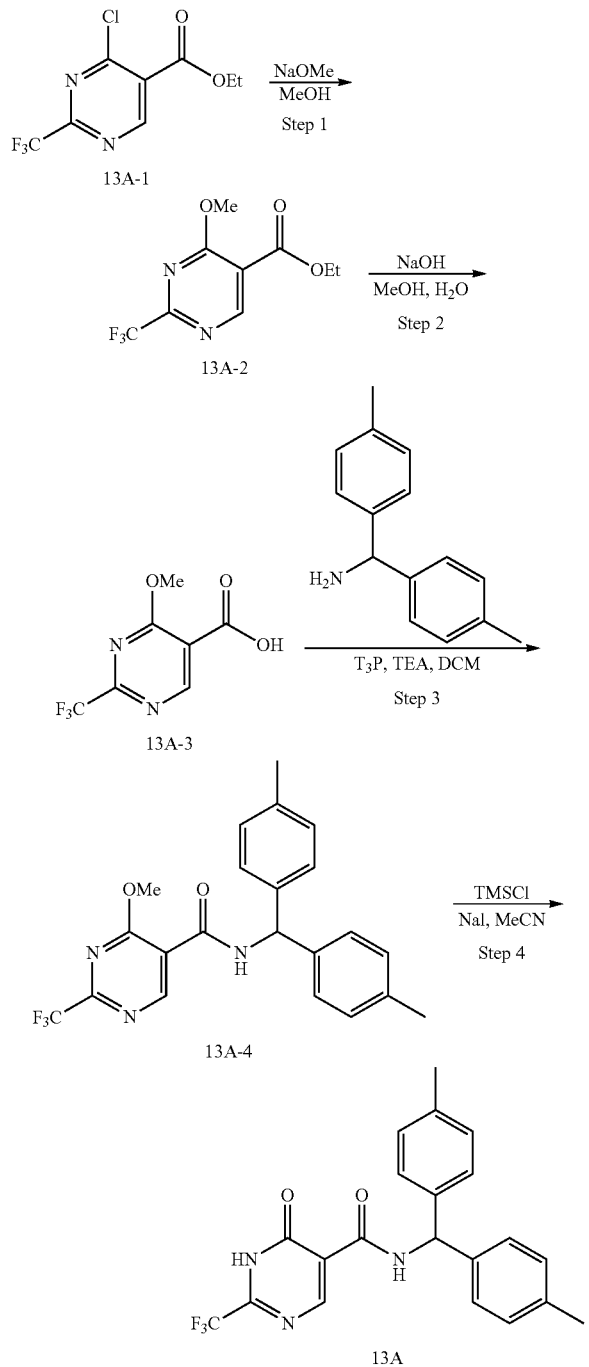

Step 1: Methyl 4-methoxy-2-(trifluoromethyl) pyrimidine-5-carboxylate (13A-2)

To a solution of Compound 13A-1 (100 mg, 392.8 μmol) in MeOH (1 mL) was added MeONa (32 mg, 471.3 μmol). Then the reaction mixture was stirred at 15° C. for 2 hr. The reaction mixture was added water (3 mL), and then extracted with dichloromethane (3 mL×3). The combined organic phase was washed with water (3 mL×3) and saturated brine (3 mL×2), dried over anhydrous $Na_2SO_4$, filtered and concentrated in vacuo to give Compound 13A-2 (100 mg, crude) as a white solid. M+H$^+$=251.0 (LCMS).

Note: during the reaction, most of hydrolyzed product was detected; the mixture was used directly for the hydrolyzed step.

Step 2: 4-methoxy-2-(trifluoromethyl) pyrimidine-5-carboxylic acid (13A-3)

To a solution of Compound 13A-2 (100 mg, 423.5 μmol) in MeOH (1.5 mL) and $H_2O$ (0.5 mL) was added NaOH (51 mg, 1.3 mmol). Then the reaction mixture was stirred at 15° C. for 2 h. The reaction mixture was added water (5 mL), and then extracted with TBME (3 mL×3), then was adjusted to pH=5-6 with HCl(1M). The product was extracted with dichloromethane (3 mL×3). The combined organic layers were washed with water (5 mL×3) and saturated brine (5 mL×2), dried over anhydrous $Na_2SO_4$, filtered and concentrated in vacuo to give Compound 13A-3 (100 mg, crude) as white solid. M−H$^-$=220.8 (LCMS).

Step 3: N-(di-p-tolylmethyl)-4-methoxy-2-(trifluoromethyl) pyrimidine-5-carboxamide (13A-4)

To a solution of Compound 13A-3 (80 mg, 360.2 μmol) and di-p-tolylmethanamine (91 mg, 432.2 μmol) in DCM (2 mL) was added TEA (109 mg, 1.1 mmol) and $T_3P$ (343 mg, 540.3 μmol). Then the reaction mixture was stirred at 15° C. for 2 h. The reaction mixture was added water (5 mL), and then extracted with dichloromethane (3 mL×3). The combined organic phase was washed with water (5 mL×3) and saturated brine (5 mL×2), dried over anhydrous $Na_2SO_4$, filtered and concentrated in vacuo to give a residue. The residue was purified by prep-TLC (Petroleum ether:Ethyl acetate) to give Compound 13A-4 (70 mg, 167.4 μmol, 47% yield, 99.3% purity) as white solid. M+H$^+$=416.0 (LCMS).

Step 4: N-(di-p-tolylmethyl)-6-oxo-2-(trifluoromethyl)-1, 6-dihydropyrimidine-5-carboxamide (13A)

To a solution of Compound 13A-4 (70 mg, 168.5 μmol) in ACN (1 mL) was added TMSCl (92 mg, 842.6 μmol) and NaI (126 mg, 842.6 μmol). Then the reaction mixture was stirred at 15° C. for 2 h. The reaction mixture was added water (3 mL), and then extracted with dichloromethane (3 mL×3). The combined organic phase was washed with water (5 mL×3) and saturated brine (5 mL×2), dried over anhydrous $Na_2SO_4$, filtered and concentrated in vacuo to give a residue. The residue was purified by prep-HPLC (neutral condition) to give Compound 13A (22.5 mg, 56.1 μmol, 33.3% yield, 99.9% purity) as white solid. M−H$^-$=400.1 (LCMS); $^1$H NMR (400 MHz, DMSO-$d_6$) δ ppm 11.59 (br d, J=8.16 Hz, 1H), 8.53 (s, 1H), 7.19-7.09 (m, 8H), 6.95 (br s, 1H), 6.16 (br d, J=8.16 Hz, 1H), 2.26 (s, 6H).

Example 14: Synthesis of N-(3, 6-dichloro-9H-fluoren-9-yl)-2-oxo-6-(trifluoromethyl)-1,2-dihydropyridine-3-carboxamide (14A)

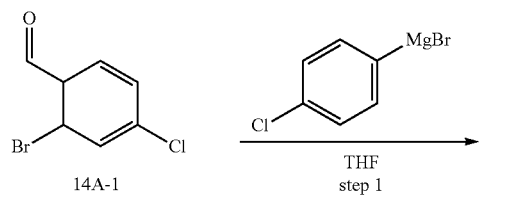

14A-1

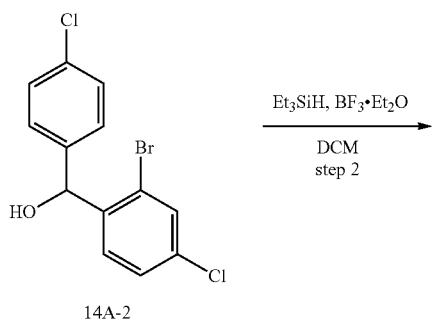

14A-2

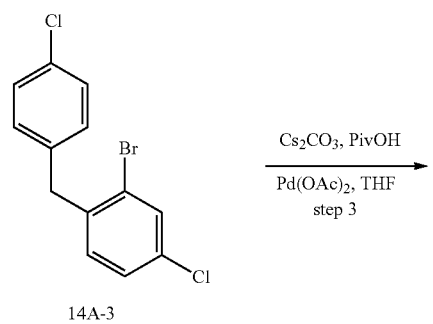

14A-3

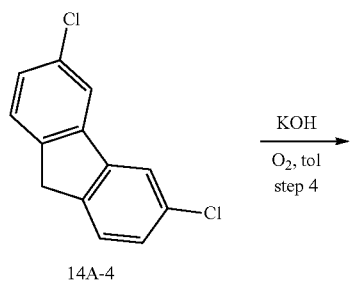

14A-4

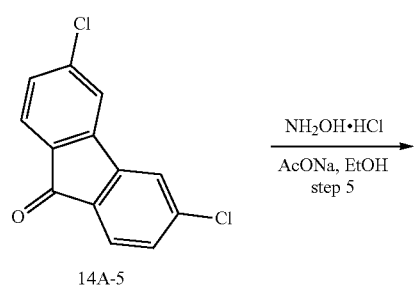

14A-5

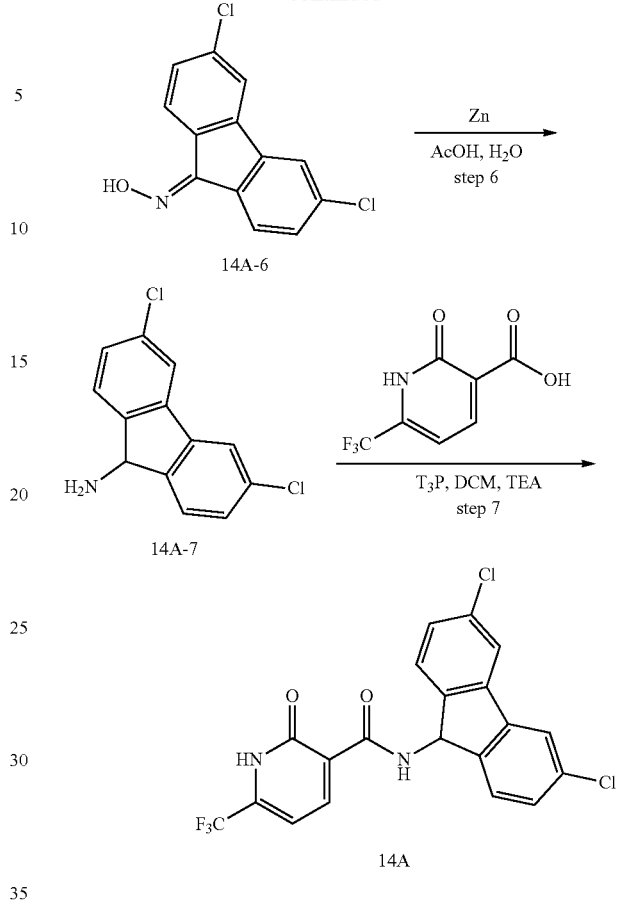

14A-6

14A-7

14A

Step 1: Synthesis of (2-bromo-4-chlorophenyl)(4-chlorophenyl) methanol (14A-2)

To a solution of Compound 14A-1 (1.0 g, 4.6 mmol) in THF (20 mL) was added (4-chlorophenyl) magnesium bromide (1 M, 5.5 mL) at 0° C. Then the reaction mixture was stirred at 15° C. for 12 h. The reaction mixture was poured into saturated ammonium chloride (10 mL), and then extracted with ethyl acetate (10 mL×3). The combined organic phase was washed with water (15 mL×3) and saturated brine (30 mL×2), dried over anhydrous $Na_2SO_4$, filtered and concentrated in vacuo to give a residue, which was purified by column chromatography (Petroleum ether/Ethyl acetate) to give Compound 14A-2 (1.4 g, 4.2 mmol, 92.5% yield) as white oil. $^1$H NMR (400 MHz, DMSO-$d_6$) δ=7.71 (d, J=2.21 Hz, 1H), 7.64 (d, J=8.38 Hz, 1H), 7.52 (dd, J=8.49, 2.09 Hz, 1H), 7.40-7.34 (m, 2H), 7.34-7.29 (m, 2H), 6.28 (d, J=4.41 Hz, 1H), 5.90 (d, J=4.41 Hz, 1H).

Step 2: Synthesis of 2-bromo-4-chloro-1-(4-chlorobenzyl) benzene (14A-3)

To a solution of Compound 14A-2 (600 mg, 1.8 mmol) in DCM (10 mL) was added $Et_3SiH$ (462 mg, 4.0 mmol) and $BF_3·Et_2O$ (564 mg, 4.0 mmol) in portions at 0° C. The resulting mixture was stirred at 15° C. for 2 h. The reaction mixture was poured into saturated ammonium chloride (10 mL), and then extracted with dichloromethane (15 mL×3). The combined organic phase was washed with water (10 mL×3) and saturated brine (10 mL×2), dried over anhydrous Na$_2$SO$_4$, filtered and concentrated in vacuo to give a Compound 14A-3 (300 mg, crude) as white oil. $^1$H NMR (400 MHz, CHLOROFORM-d) δ=7.60 (d, J=2.21 Hz, 1H), 7.30-7.26 (m, 2H), 7.24 (dd, J=8.27, 2.09 Hz, 1H), 7.11 (d, J=8.38 Hz, 2H), 7.06 (d, J=8.38 Hz, 1H), 4.05 (s, 2H).

Step 3: Synthesis of 3, 6-dichloro-9H-fluorene (14A-4)

To a solution of Compound 14A-3 (150 mg, 474.7 µmol) in THF (3 mL) was added PIVALIC ACID (145 mg, 1.4 mmol), Cs$_2$CO$_3$ (232 mg, 712 µmol), Pd(OAc)$_2$ (21 mg, 94.9 µmol) and PCy$_3$ (53 mg, 189.9 µmol). Then the reaction mixture was stirred at 120° C. for 12 h. The reaction mixture was poured into saturated ammonium chloride (4 mL), and then extracted with ethyl acetate (3 mL×3). The combined organic phase was washed with water (5 mL×3) and saturated brine (3 mL×2), dried over anhydrous Na$_2$SO$_4$, filtered and concentrated in vacuo to give a residue. The residue was purified by prep-HPLC (neutral condition) to give Compound 14A-4 (100 mg, 425.3 µmol, 44.80% yield) as white solid. $^1$H NMR (400 MHz, CHLOROFORM-d) δ ppm 7.71 (br s, 2H), 7.46 (br d, J=7.95 Hz, 2H), 7.30 (br d, J=7.95 Hz, 2H), 3.84 (s, 2H).

Step 4: Synthesis of 3, 6-dichloro-9H-fluoren-9-one (14A-5)

To a stirred solution of Compound 14A-4 (50 mg, 212.7 µmol) in toluene (1 mL) was added KOH (30 mg, 531.7 µmol) and 1, 4, 7, 10, 13, 16-hexaoxacyclooctadecane (7 mg, 25.5 µmol). Then the reaction mixture was stirred at 15° C. for 12 hr under O$_2$ (15 PSI). To the reaction mixture was added dichloromethane (2 mL), and then was filtered. The filtrate cake was concentrated in vacuo to give Compound 14A-5 (30 mg, crude) as yellow solid. $^1$H NMR (400 MHz, CHLOROFORM-d) δ ppm 7.62 (d, J=7.94 Hz, 2H), 7.51 (s, 2H), 7.33 (br d, J=7.94 Hz, 2H).

Step 5: Synthesis of 3, 6-dichloro-9H-fluoren-9-one oxime (14A-6)

To a solution of Compound 14A-5 (30 mg, 120.4 µmol) in EtOH (1 mL) was added NH$_2$OH.HCl (13 mg, 192.7 µmol) and AcONa (20 mg, 240.8 µmol). Then the reaction mixture was stirred at 60° C. for 12 hr. To the reaction mixture was added water (2 mL), and then extracted with ethyl acetate (3 mL×3). The combined organic phase was washed with water (2 mL×3) and saturated brine (3 mL×2), dried over anhydrous Na$_2$SO$_4$, filtered and concentrated in vacuo to give Compound 14A-6 (30 mg, crude) as white solid. $^1$H NMR (400 MHz, DMSO-d$_6$) δ ppm 12.87 (br s, 1H), 8.32 (d, J=8.16 Hz, 1H), 8.13 (dd, J=15.44, 1.98 Hz, 2H), 7.72 (d, J=8.16 Hz, 1H), 7.49 (dd, J=8.38, 1.98 Hz, 1H), 7.42 (dd, J=8.16, 1.76 Hz, 1H).

Step 6: Synthesis of 3, 6-dichloro-9H-fluoren-9-amine (14A-7)

To a solution of Compound 14A-6 (30 mg, 113.6 µmol) in AcOH (1 mL) and H$_2$O (0.1 mL) was added Zn (22 mg, 340.8 µmol). Then the reaction mixture was stirred at 120° C. for 1 hr. The reaction mixture was concentrated in vacuo to give a residue. Then the residue was diluted with water (2 mL), and then adjusted to pH=7-8 by saturated sodium bicarbonate, filtered and the filtrate was concentrated in vacuo to give compound 14A-7 (25 mg, crude) as a white solid.

Step 7: Synthesis of N-(3, 6-dichloro-9H-fluoren-9-yl)-2-oxo-6-(trifluoromethyl)-1,2-dihydro pyridine-3-carboxamide (14A)

To a solution of Compound 14A-7 (10 mg, 40.0 µmol) and 2-oxo-6-(trifluoro methyl)-1H-pyridine-3-carboxylic acid (10 mg, 48.0 µmol) in DCM (1 mL) was added TEA (12 mg, 120.0 µmol) and T$_3$P (38 mg, 60 µmol, 50% purity). Then the reaction mixture was stirred at 15° C. for 2 hr. To the reaction mixture was added water (2 mL), and then extracted with dichloromethane (3 mL×3). The combined organic phase was washed with water (2 mL×3) and saturated brine (2 mL×2), dried over anhydrous Na$_2$SO$_4$, filtered and concentrated in vacuo to give a residue, which was purified by prep-HPLC (neutral condition) to give Compound 14A (1.1 mg, 2.28 µmol, 5.7% yield, 95.2% purity) as yellow solid. M−H$^-$=437.0 (LCMS); $^1$H NMR (400 MHz, DMSO-d6) δ ppm 8.32 (br s, 1H) 8.12 (s, 2H) 7.57 (d, J=8.16 Hz, 2H) 7.45-7.39 (m, 2H) 6.18 (d, J=7.94 Hz, 1H) 5.76 (s, 1H).

Example 15: Synthesis of N-(3-chloro-9H-xanthen-9-yl)-2-oxo-6-(trifluoromethyl)-1,2-dihydropyridine-3-carboxamide (15A)

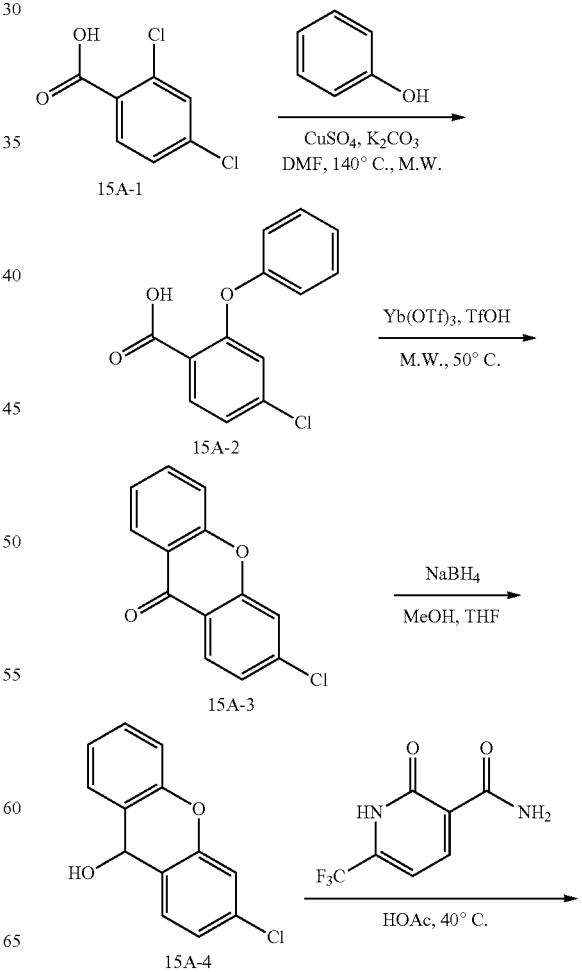

-continued

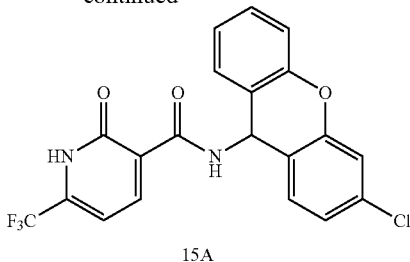

15A

Step 1: 4-chloro-2-phenoxybenzoic acid (15A-2)

Compound 15A-1 (250 mg, 1.3 mmol), phenol (307 mg, 3.3 mmol), CuSO$_4$ (167 mg, 1.0 mmol) and K$_2$CO$_3$ (271 mg, 2.0 mmol) were taken up into a microwave tube in DMF (6.0 mL) under N$_2$. The sealed tube was heated at 140° C. for 60 min under microwave. The reaction mixture was added to water (50 mL) and adjusted pH to 2-3 by adding 1N HCl, and then extracted with dichloromethane (15 mL×3). The combined organic phase was washed with saturated brine (10 mL×1), dried over anhydrous Na$_2$SO$_4$, filtered and concentrated in vacuo to give Compound 15A-2 (160 mg, crude) as yellow oil.

Step 2: 3-chloro-9H-xanthen-9-one (15A-3)

Compound 15A-2 (160 mg, 643.4 µmol), Yb(OTf)$_3$ (39 mg, 64.3 µmol) were taken up into a microwave tube in TfOH (1.0 mL). The sealed tube was heated at 50° C. for 20 min under microwave. The reaction mixture was adjusted pH to 6-7 by using 1N NaOH at 0° C. The mixture was filtered and the cake was dried in vacuum to give Compound 15A-3 (145 mg, crude) as a white solid. M+H$^+$=231.0 (LCMS).

Step 3: 3-chloro-9H-xanthen-9-ol (15A-4)

To a solution of Compound 15A-3 (80 mg, 346.8 µmol) in MeOH (2 mL) and THF (2 mL) was added NaBH$_4$ (39 mg, 1.0 mmol). The mixture was stirred at 25° C. for 0.5 h. The reaction was poured into water (10 mL) and the product was extracted with DCM (8 mL×2). The combined organic layers were dried and concentrated in vacuum to give Compound 15A-4 (75 mg, crude) as a yellow solid.

Step 4: Synthesis of N-(3-chloro-9H-xanthen-9-yl)-2-oxo-6-(trifluoromethyl)-1,2-dihydropyridine-3-carboxamide (15A)

A solution of Compound 15A-4 (70 mg, 300.8 µmol) and 2-oxo-6-(trifluoromethyl)-1H-pyridine-3-carboxamide (74 mg, 361.0 µmol) in AcOH (5.0 mL) was stirred at 40° C. for 12 hrs. The reaction mixture was concentrated under reduced pressure to give a residue, which was purified by prep-HPLC (column: Kromasil® 150*25 mm*10 um; mobile phase: [water (0.04% NH$_3$H$_2$O+10 mM NH$_4$HCO$_3$)-ACN]; B %: 15%-45%, 20 min) to give Compound 15A (9.8 mg, 23.3 µmol, 7.7% yield, 99.6% purity) as a white solid. M−H$^−$=419.0 (LCMS); $^1$H NMR (400 MHz, CHLOROFORM-d) δ=9.85 (br d, J=8.3 Hz, 1H), 8.71 (d, J=7.3 Hz, 1H), 7.50 (dd, J=7.8, 13.2 Hz, 2H), 7.38-7.29 (m, 1H), 7.21-7.15 (m, 2H), 7.11 (t, J=7.6 Hz, 1H), 7.07 (dd, J=2.0, 8.3 Hz, 1H), 6.84 (d, J=7.8 Hz, 1H), 6.57 (d, J=8.3 Hz, 1H).

Compounds made in a similar manner are shown in Table 13.

TABLE 13

| Compound No | Structure | HNMR and Ms |
| --- | --- | --- |
| 50 | 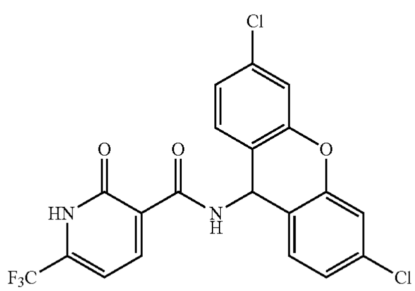 [SMILES: O=C(NC1c2ccc(Cl)cc2Oc2cc(Cl)ccc21)c1ccc(C(F)(F)F)[nH]c1=O] | $^1$HNMR (400 MHz, DMSO-d$_6$) δ = 13.91-12.99 (m, 1H), 9.99 (br s, 1H), 8.34 (d, J = 7.6 Hz, 1H), 7.48 (d, J = 8.3 Hz, 2H), 7.30 (d, J = 2.1 Hz, 2H), 7.23 (dd, J = 2.1, 8.3 Hz, 3H), 6.42 (d, J = 8.2 Hz, 1H) [M − H] = 453.0 |
| 51 | 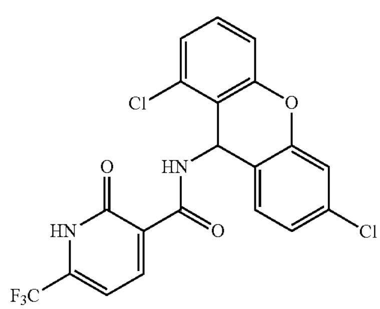 [SMILES: O=C(NC1c2ccc(Cl)cc2Oc2cccc(Cl)c21)c1ccc(C(F)(F)F)[nH]c1=O] | $^1$H NMR (400 MHz, CHLOROFORM-d) δ = 13.62-12.43 (m, 1H), 9.79 (br d, J = 8.2 Hz, 1H), 8.67 (d, J = 7.5 Hz, 1H), 7.70 (d, J = 8.3 Hz, 1H), 7.33-7.28 (m, 1H), 7.20 (s, 2H), 7.16-7.12 (m, 1H), 7.09 (dd, J = 2.0, 8.3 Hz, 1H), 6.82 (d, J = 7.5 Hz, 1H), 6.63 (d, J = 8.1 Hz, 1H) ESI [M − H] = 453.0 |

TABLE 13-continued

| Compound No | Structure | HNMR and Ms |
| --- | --- | --- |
| 52 | 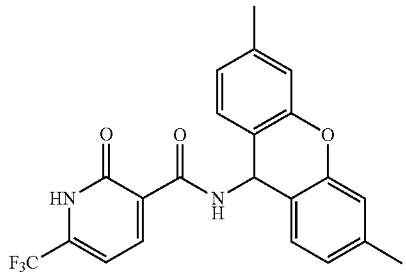 | $^1$H NMR (400 MHz, DMSO-d$_6$) δ = 8.39-8.37 (m, 1H), 7.34-7.32 (m, 2H), 7.22 (s, 1H), 6.99-6.95 (m, 4H), 6.43-6.41 (m, 1H), 2.32 (s, 6H)<br>ESI [M + H$^-$] = 413.1 |
| 53 | 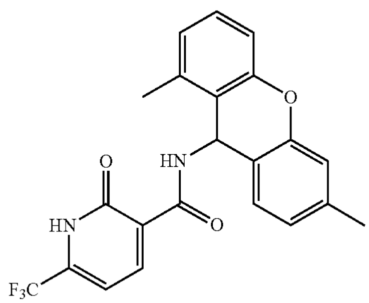 | $^1$H NMR (400 MHz, DMSO-d$_6$) δ = 13.26 (s, 1H), 9.42 (s, 1H), 8.30 (d, J = 7.6 Hz, 1 H), 7.47 (d, J = 8.0 Hz, 1 H), 7.30-7.26 (m, 2H), 7.05-6.95 (m, 4H), 6.50 (d, J = 8.4 Hz, 1 H), 2.32 (d, J = 7.2 Hz, 6 H)<br>ESI [M + H$^-$] = 413.1 |
| 54 | 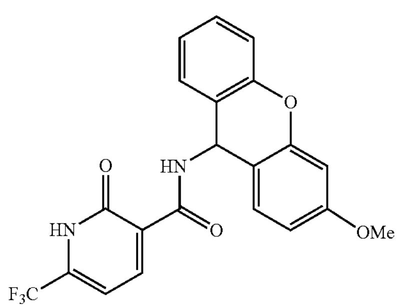 [SMILES: COc1ccc2c(c1)Oc1ccccc1C2NC(=O)c1ccc(C(F)(F)F)[nH]c1=O] | $^1$H NMR (400 MHz, CHLOROFORM-d) δ = 12.95- 11.91 (m, 1H), 9.71 (br d, J = 6.6 Hz, 1H), 8.68 (d, J = 7.7 Hz, 1H), 7.53 (d, J = 7.7 Hz, 1H), 7.41 (d, J = 8.2 Hz, 1H), 7.32-7.27 (m, 1H), 7.13 (d, J = 8.4 Hz, 1H), 7.11-7.04 (m, 1H), 6.81 (d, J = 7.5 Hz, 1H), 6.71-6.64 (m, 2H), 6.56 (d, J = 8.6 Hz, 1H), 3.82 (s, 3H)<br>ESI [M − H$^-$] = 415.0 |
| 55 | 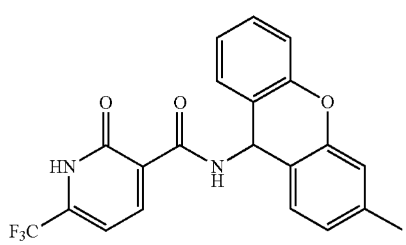 [SMILES: Cc1ccc2c(c1)Oc1ccccc1C2NC(=O)c1ccc(C(F)(F)F)[nH]c1=O] | $^1$H NMR (400 MHz, CHLOROFORM-d) δ = 9.72 (br d, J = 1.8 Hz, 1H), 8.69 (d, J = 1.3 Hz, 1H), 7.54 (d, J = 7.8 Hz, 1H), 7.40 (d, J = 7.8 Hz, 1H), 7.35-7.28 (m, 1H), 7.15 (d, J = 8.3 Hz, 1H), 7.11-7.05 (m, 1H), 6.98 (s, 1H), 6.91 (d, J=7.8 Hz, 1H), 6.82 (d, J=1.8 Hz, 1H), 6.59 (d, J=8.3 Hz, 1H), 2.64 - 2.17 (m, 3H)<br>ESI [M − H] = 399.0 |
| 56 | 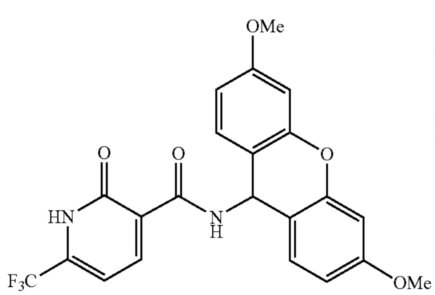 [SMILES: COc1ccc2c(c1)Oc1cc(OC)ccc1C2NC(=O)c1ccc(C(F)(F)F)[nH]c1=O] | $^1$H NMR (400 MHz, DMSO-d$_6$) δ = 12.30 (d, J = 8.8 Hz, 1H), 8.14 (d, J = 7.5 Hz, 1H), 7.32 (d, J = 8.4 Hz, 2H), 6.74-6.63 (m, 5H), 6.49 (d, J = 7.5 Hz, 1H), 6.34 (d, J = 8.6 Hz, 1H), 3.78 (s, 6H)<br>ESI [M − H] = 445.0 |

TABLE 13-continued
| Compound No | Structure | HNMR and Ms |
| --- | --- | --- |
| 57 | 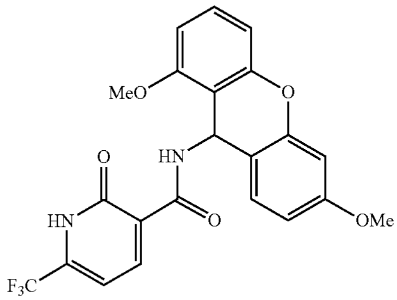 [SMILES: COc1ccc2c(c1)Oc1cccc(OC)c1C2NC(=O)c1ccc(C(F)(F)F)[nH]c1=O] | $^1$H NMR (400 MHz, CHLOROFORM-d) δ = 9.40 (br s, 1H), 8.55 (d, J = 7.5 Hz, 1H), 7.57-7.53 (m, 1H), 7.20 (t, J = 8.2 Hz, 2H), 6.75-6.70 (m, 2H), 6.59 (qd, J = 2.4, 4.6 Hz, 2H), 6.55-6.50 (m, 2H), 3.72 (s, 6H) ESI [M − H] = 445.0 |
Example 16: Synthesis of N-((3-fluoro-4-hydroxy-phenyl)(phenyl)methyl)-2-oxo-6-(trifluoromethyl)-1,2-dihydropyridine-3-carboxamide (16A)
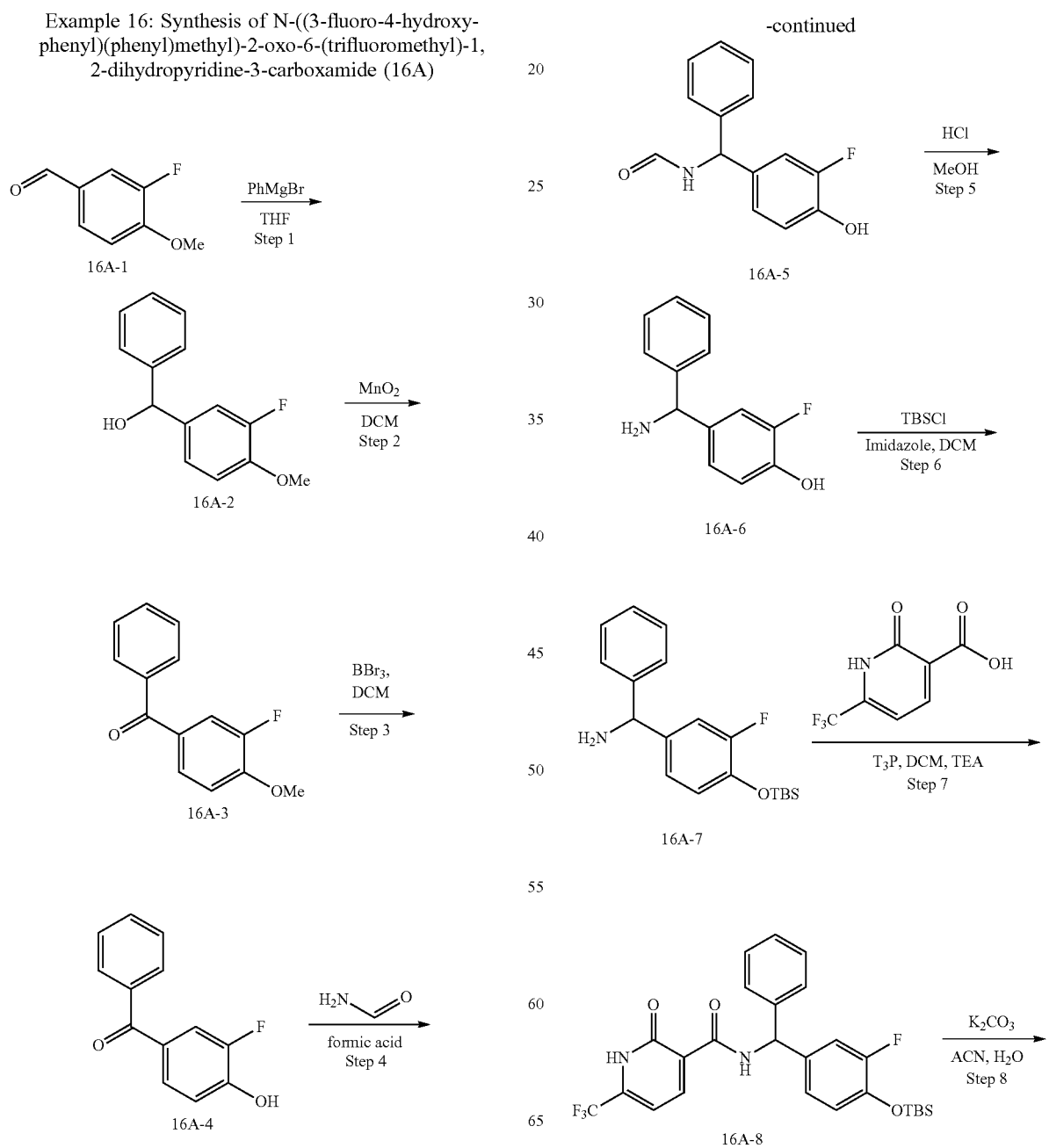

-continued

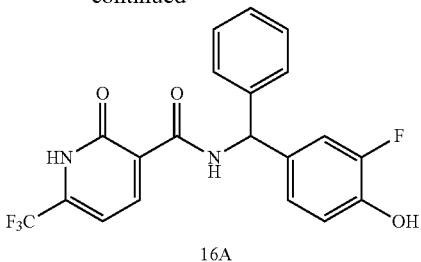

16A

Step 1:
(3-fluoro-4-methoxyphenyl)(phenyl)methanol
(16A-2)

To a stirred solution of Compound 16A-1 (1.0 g, 6.4 mmol) in THF (20 mL) was added bromo(phenyl)magnesium (3 M, 5.1 mL) dropwise at 0° C. The mixture was stirred at 25° C. for 1 h. The reaction mixture was quenched by addition saturated NH$_4$Cl solution (10 mL) at 0° C., and then diluted with water (10 mL) and extracted with EtOAc (10 mL×3). The combined organic layers were washed with brine (15 mL×1), dried over Na$_2$SO$_4$, filtered and concentrated under reduced pressure to give a residue, which was purified by column chromatography (SiO$_2$, Petroleum ether: Ethyl acetate=100:1 to 30:1) to give Compound 16A-2 (670 mg, crude) as yellow oil.

Step 2:
(3-fluoro-4-methoxyphenyl)(phenyl)methanone
(16A-3)

To a stirred solution of Compound 16A-2 in DCM (50 mL) was added MnO$_2$ (1.8 g, 21.5 mmol) in one portion at 0° C. The mixture was stirred at 25° C. for 6 h. The reaction mixture was filtered and concentrated under reduced pressure to give Compound 16A-3 (480 mg, crude) as yellow oil. M+H$^+$=231.0 (LCMS).

Step 3:
(3-fluoro-4-hydroxyphenyl)(phenyl)methanone
(16A-4)

To a stirred solution of Compound 16A-3 (300 mg, 1.30 mmol) in DCM (25.0 mL) was added BBr$_3$ (3.2 g, 13.01 mmol) dropwise at −78° C. under N$_2$. The mixture was stirred at 25° C. for 12 h. The reaction mixture was quenched by addition 10% NaHCO$_3$ solution 50 mL at 0° C., and then extracted with EtOAc (25 mL×5). The combined organic layers were washed with brine (25 mL), dried over Na$_2$SO$_4$, filtered and concentrated under reduced pressure to give Compound 16A-4 (280 mg, crude) as a yellow solid. M+H$^+$=217.2 (LCMS).

Step 4: N-((3-fluoro-4-hydroxyphenyl)(phenyl)methyl)formamide (16A-5)

A solution of Compound 16A-4 (280 mg, 1.3 mmol) in Formic acid (1.0 mL) and formamide (3.0 mL) was stirred at 160° C. for 2 h. The reaction mixture was diluted with water 15 mL and extracted with EtOAc (10 mL×5). The combined organic layers were washed with brine (15 mL×1), dried over Na$_2$SO$_4$, filtered and concentrated under reduced pressure to give Compound 16A-5 (300 mg, crude) as yellow oil.

Step 5: 4-(amino(phenyl)methyl)-2-fluorophenol (16A-6)

A solution of Compound 16A-5 (300 mg, 1.2 mmol) in MeOH (2.5 mL) and Conc.HCl (5.0 mL) was stirred at 90° C. for 2 h. The pH of the reaction mixture was adjusted to 7-8 by adding saturated Na$_2$CO$_3$ solution and extracted with EtOAc (15 mL×3). The combined organic layers were washed with brine (15 mL×1), dried over Na$_2$SO$_4$, filtered and concentrated under reduced pressure to give Compound 16A-6 (260 mg, crude) as a yellow solid.

Step 6: (4-((tert-butyldimethylsilyl)oxy)-3-fluorophenyl)(phenyl)methanamine (16A-7)

To a 0° C. solution of Compound 16A-6 (100 mg, 460.3 µmol) and imidazole (62 mg, 920.6 µmol) in DCM (10 mL) was added TBSCl (104 mg, 690.4 µmol). The mixture was stirred at 20° C. for 2 h. The reaction mixture was concentrated under reduced pressure to give a residue, which was purified by prep-TLC (SiO$_2$) to afford Compound 16A-7 (150 mg, crude) as a yellow solid.

Step 7: N-((4-((tert-butyldimethylsilyl)oxy)-3-fluorophenyl)(phenyl)methyl)-2-oxo-6-(trifluoromethyl)-1,2-dihydropyridine-3-carboxamide (16A-8)

To a stirred solution of Compound 16A-7 (150 mg, 452.5 µmol) and 2-oxo-6-(trifluoromethyl)-1H-pyridine-3-carboxylic acid (93 mg, 452.4 µmol) in DCM (10.0 mL) was added T$_3$P (432 mg, 678.7 µmol, 50% purity) and ET$_3$N (137 mg, 1.3 mmol) at 0° C. The mixture was stirred at 25° C. for 0.5 hr. The reaction mixture was quenched by addition water 10 mL at 0° C., and then extracted with DCM (5 mL×3). The combined organic layers were washed with brine (10 mL×1), dried over Na$_2$SO$_4$, filtered and concentrated under reduced pressure to give Compound 16A-8 (230 mg, crude) was obtained as yellow oil. M−H$^-$=518.9 (LCMS).

Step 8: Synthesis of N-((3-fluoro-4-hydroxyphenyl)(phenyl)methyl)-2-oxo-6-(trifluoromethyl)-1,2-dihydropyridine-3-carboxamide (16A)

To a stirred solution of Compound 16A-8 (200 mg, 384.1 µmol) in ACN (3.0 mL) and H$_2$O (3.0 mL) was added K$_2$CO$_3$ (132 mg, 960.4 µmol). The mixture was stirred at 60° C. for 5 h. The reaction mixture was diluted with H$_2$O (5 mL) and extracted with EtOAc (10 mL×3). The combined organic layers were washed with brine (10 mL), dried over Na$_2$SO$_4$, filtered and concentrated under reduced pressure to give a residue, which was purified by prep-HPLC (column: Kromasil® 150*25 mm*10 um; mobile phase: [water (0.04% NH$_3$H$_2$O+10 mM NH$_4$HCO$_3$)-ACN]; B %: 10%-30%, 10 min) to give Compound 16A (27.4 mg, 67.1 µmol, 17.4% yield, 99.2% purity) as a yellow solid. M−H$^-$=405.0 (LCMS); $^1$H NMR (400 MHz, METHANOL-d$_4$) δ 8.49 (d, J=7.2 Hz, 1H), 7.36-7.31 (m, 5H), 7.03 (d, J=7.6 Hz, 1H), 6.95-6.93 (m, 2H), 6.90 (t, J=10.4 Hz, 1H), 6.24 (s, 1H).

Example 17: Synthesis of Synthesis of 2-oxo-N-(phenyl(2-(trifluoromethyl)phenyl)methyl)-6-(trifluoromethyl)-1,2-dihydropyridine-3-carboxamide (17A)

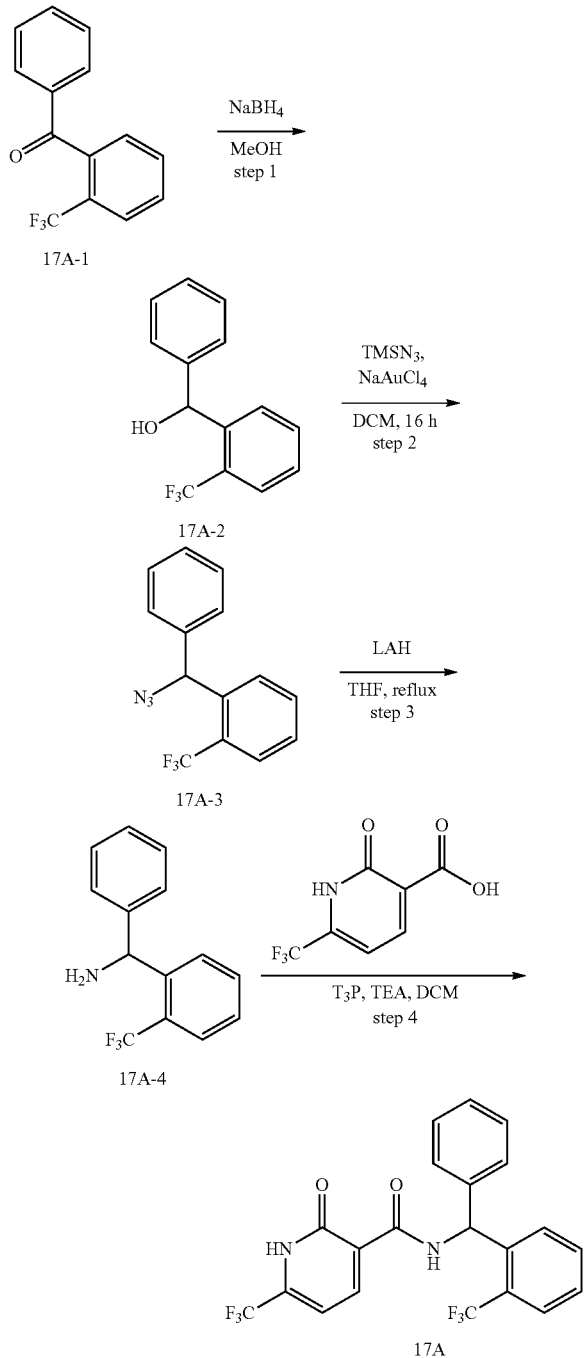

Step 1: phenyl(2-(trifluoromethyl)phenyl)methanol (17A-2)

To a stirred solution of Compound 17A-1 (50 mg, 199.8 µmol) in MeOH (5.0 mL) was added NaBH₄ (11 mg, 299.7 µmol) in portions at 0° C. The mixture was stirred at 25° C. for 2 h. The reaction mixture was diluted with water (5 mL) and extracted with EtOAc (5 mL×3). The combined organic layers were washed with brine (5 mL×1), dried over Na₂SO₄, filtered and concentrated under reduced pressure to give Compound 17A-2 (45 mg, crude) as a yellow oil.

Step 2: 1-(azido(phenyl)methyl)-2-(trifluoromethyl)benzene (17A-3)

To a solution of Compound 17A-2 (40 mg, 158.58 µmol) in DCM (5.0 mL) was added TMSN₃ (54.0 mg, 475.7 µmol) and sodium; tetrachlorogold(1-); dihydrate (6.0 mg, 15.8 µmol). The mixture was stirred at 25° C. for 12 h. The reaction mixture was diluted with H₂O (5 mL) and extracted with DCM (5 mL×3). The combined organic layers were washed with brine (5 mL×1), dried over Na₂SO₄, filtered and concentrated under reduced pressure to give Compound 17A-3 (40 mg, crude) as yellow oil.

Step 3: phenyl(2-(trifluoromethyl)phenyl)methanamine (17A-4)

To a stirred solution of Compound 17A-3 (35 mg, 126.2 µmol) in THF (5.0 mL) was added LAH (17.6 mg, 441.8 µmol,) in portions at 0° C. The mixture was stirred at 70° C. for 2 h. The mixture was quenched by addition 0.1 mL water and 0.1 mL of 20% NaOH aq. at 0° C., and then the reaction mixture was filtered and concentrated under reduced pressure to give Compound 17A-4 (25 mg, crude) as yellow oil.

Step 4: Synthesis of 2-oxo-N-(phenyl(2-(trifluoromethyl)phenyl)methyl)-6-(trifluoromethyl)-1,2-dihydropyridine-3-carboxamide (17A)

To a stirred solution of 2-oxo-6-(trifluoromethyl)-1H-pyridine-3-carboxylic acid (16 mg, 79.6 µmol) and Compound 17A-4 (20 mg, 79.6 µmol) in DCM (0.5 mL) was added T₃P (75.9 mg, 119.4 µmol) and Et₃N (24.0 mg, 238.8 µmol, 33.2 uL) at 0° C. The mixture was stirred at 25° C. for 0.5 h. The reaction mixture was diluted with water (10 mL) and extracted with EtOAc (5 mL×3). The combined organic layers were washed with brine (5 mL×1), dried over Na₂SO₄, filtered and concentrated under reduced pressure to give a residue, which was purified by prep-HPLC (column: Nano-micro Kromasil® C18 100*30 mm 5 um; mobile phase: [water (10 mM NH₄HCO₃)-ACN]; B %: 48%-72%, 10 min) to give Compound 17A (2.1 mg, 4.7 µmol, 5.9% yield, 99.4% purity) as a white solid. M−H⁻=439.1 (LCMS); ¹H NMR (400 MHz, CHLOROFORM-d) δ 10.00 (br d, J=8.0 Hz, 1H), 8.69 (d, J=7.6 Hz, 1H), 7.72 (d, J=7.2 Hz, 1H), 7.58-7.55 (m, 2H), 7.52-7.49 (m, 1H), 7.43-7.41 (m, 2H), 7.35-7.30 (m, 1H), 7.28-7.25 (m, 1H), 6.87 (t, J=7.2 Hz, 2H).

Example 18: Synthesis of N-((3,4-dimethylphenyl)(phenyl)methyl)-6-oxo-2-(trifluoromethyl)-1,6-dihydropyrimidine-5-carboxamide (18A)

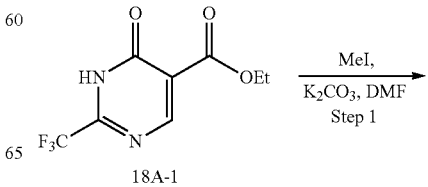

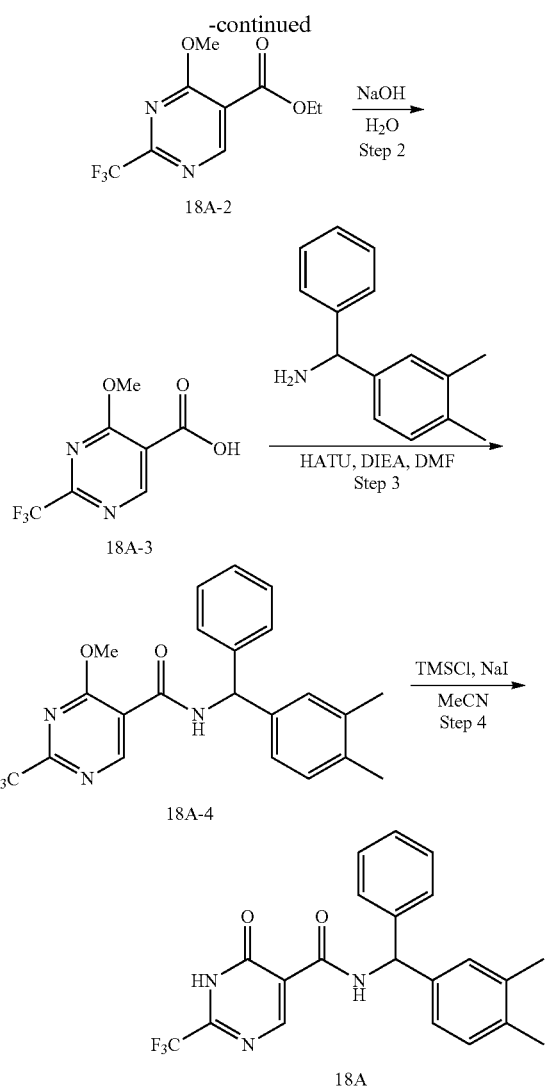

with EtOAc (15 mL×3). The combined organic layers were filtered and concentrated under reduced pressure to give Compound 18A-3 (60 mg, 270.1 μmol, 84.5% yield) as a brown solid. M+H$^+$=223.0 (LCMS).

Step 3: N-((3, 4-dimethylphenyl) (phenyl)methyl)-4-methoxy-2-(trifluoromethyl) pyrimidine-5-carboxamide (18A-4)

To a solution of Compound 18A-3 (60 mg, 270.1 μmol) in DMF (3 mL) was added HATU (154 mg, 405.2 μmol), followed by DIPEA (105 mg, 810.4 μmol, 141.2 uL), (3,4-dimethylphenyl)(phenyl)methanamine (68 mg, 324.2 μmol). The mixture was stirred at 25° C. for 2 hr. LC-MS showed one new peak with desired mass was detected. The reaction mixture was quenched by water (10 mL) and extracted with EtOAc (10 mL×3). The combined organic layers were filtered and concentrated under reduced pressure to give a residue, which was purified by prep-TLC (SiO2, Petroleum ether:Ethyl acetate=3:1, Rf=0.85). Compound 18A-4 (45 mg, 108.3 μmol, 40.10% yield) was obtained as a white solid. M+H$^+$=416.2 (LCMS).

Step 4: N-((3,4-dimethylphenyl)(phenyl)methyl)-6-oxo-2-(trifluoromethyl)-1, 6-dihydropyrimidine-5-carboxamide (18A)

To a solution of Compound 18A-4 (40 mg, 96.3 μmol) in CH$_3$CN (2 mL) was added slowly TMSCl (52 mg, 481.5 μmol, 61.11 uL) and NaI (72 mg, 481.5 μmol). The mixture was stirred at 80° C. for 2 h. LCMS showed desired mass was detected. The reaction mixture was filtered off, added water (5 mL), and then extracted with EtOAc (5 mL×2). The combined organic layers were filtered and concentrated under reduced pressure to give a residue, which was purified by prep-HPLC (column: Nano-Micro UniSil® 5-100 C18 ULTRA100×250 mm 5 um; mobile phase: [water (0.1% TFA)-ACN]; B %: 50%-80%, 10 min) to give Compound 18A (1.6 mg, 3.8 μmol, 99.34% purity) as a white solid. M−H$^−$(NEG)=400.1 (LCMS); $^1$H NMR (400 MHz, MeOD-d$_3$) δ 8.84 (s, 1H), 7.33-7.25 (m, 5H), 7.11-7.02 (m, 3H), 6.25 (s, 1H), 2.23 (s, 6H).

Example 19: Synthesis of N-(1-(4-chlorophenyl)-2-phenylethyl)-2-oxo-6-(trifluoromethyl)-1, 2-dihydropyridine-3-carboxamide (19A)

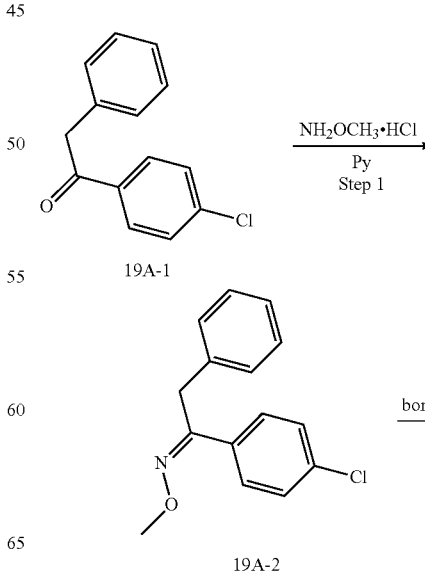

Step 1: ethyl 4-methoxy-2-(trifluoromethyl)pyrimidine-5-carboxylate (18A-2)

To a stirred solution of Compound 18A-1 (200 mg, 846.9 μmol) in DMF (4 mL) was added K$_2$CO$_3$ (176 mg, 1.3 mmol), followed by CH$_3$I (120 mg, 846.9 μmol, 52.7 uL) at 0° C., then the mixture was stirred at 25° C. for 12 hr. The reaction mixture was quenched by water (5 mL), and extracted with EtOAc (5 mL×3). The combined organic layers were filtered and concentrated under reduced pressure to give a residue, which was purified by column chromatography (SiO$_2$, Petroleum ether/Ethyl acetate) to give Compound 18A-2 (80 mg, 319.78 μmol, 37.76% yield) as a white oil.

Step 2: 4-methoxy-2-(trifluoromethyl)pyrimidine-5-carboxylic acid (18A-3)

To a solution of Compound 18A-2 (80 mg, 319.8 μmol) in H$_2$O (2 mL) was added NaOH (13 mg, 319.8 μmol). The mixture was stirred at 60° C. for 2 hr. LC-MS showed one main peak with desired mass was detected. The reaction mixture was adjusted PH+=3~4 with 6N HCl, and extracted

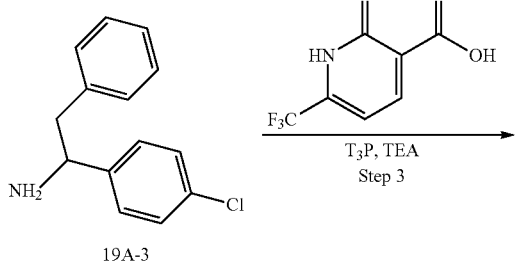

Step 1: (Z)-1-(4-chlorophenyl)-2-phenylethanone O-methyl oxime (19A-2)

To a solution of Compound 19A-1 (100 mg, 433.5 μmol) in Py (3 mL) was added O-methylhydroxylamine; hydrochloride (58 mg, 693.6 μmol, 52.7 uL). The mixture was stirred at 20° C. for 12 h. The reaction mixture was quenched by addition H₂O (10 mL) and then extracted with EtOAc (5 mL×3). The combined organic layers were dried over Na₂SO₄, filtered and concentrated under reduced pressure to give Compound 19A-2 (260 mg, crude) as colorless oil, which was used next step directly. M+H⁺=260.1 (LCMS).

Step 2: 1-(4-chlorophenyl)-2-phenylethanamine (19A-3)

To a solution of Compound 19A-2 (200 mg, 770.0 μmol) in THF (10 mL) was added BH₃-THF (1 M, 7.7 mL). The mixture was stirred at 70° C. under N₂ for 3 h. The mixture was cooled to room temperature. Water (7 mL) was carefully added, followed by 20% NaOH (7 mL). The resulting mixture was refluxed over-night with vigorous magnetic stirring. The mixture was cooled to room temperature, and then extracted with EtOAc (20 mL×3). The combined organic layers were dried over Na₂SO₄, filtered and concentrated under reduced pressure to give a residue, which was purified by prep-TLC (SiO2, Petroleum ether:Ethyl acetate=1:1.5) to give Compound 19A-3 (110 mg, crude) as yellow oil. ¹H NMR (400 MHz, DMSO-d6) δ=7.36-7.27 (m, 4H), 7.26-7.19 (m, 2H), 7.18-7.14 (m, 1H), 7.12-7.06 (m, 2H), 4.10-4.01 (m, 1H), 2.83-2.76 (m, 2H).

Step 3: N-(1-(4-chlorophenyl)-2-phenylethyl)-2-oxo-6-(trifluoromethyl)-1,2-dihydropyridine-3-carboxamide (19A)

To a solution of Compound 19A-3 (40 mg, 172.6 μmol) in DCM (1 mL) was added 2-oxo-6-(trifluoromethyl)-1H-pyridine-3-carboxylic acid (39 mg, 189.9 μmol) and TEA (52 mg, 517.9 μmol, 72.1 uL) followed by T₃P (220 mg, 345.2 μmol, 205.3 uL, 50% purity). The mixture was stirred at 20° C. for 12 h. The reaction mixture was quenched by addition H₂O (8 mL), and then extracted with EtOAc (5 mL×3). The combined organic layers were dried over Na₂SO₄, filtered and concentrated under reduced pressure to give a residue, which was purified by prep-HPLC (column: Luna C18 100×30 5 u; mobile phase: [water (0.225% FA)-ACN]; B %: 40%-80%, 12 min) to give Compound 19A (27 mg, 64.4 μmol, 37.32% yield, 100% purity) as a white solid. M−H⁻=419.0 (LCMS); ¹H NMR (400 MHz, CHLOROFORM-d) δ=13.56 (br s, 1H), 9.99 (br d, J=8.1 Hz, 1H), 8.70 (d, J=7.3 Hz, 1H), 7.35-7.23 (m, 7H), 7.20-7.16 (m, 2H), 6.98 (d, J=7.5 Hz, 1H), 5.44 (q, J=7.7 Hz, 1H), 3.27-3.13 (m, 2H).

Example 20: Synthesis of N-(1,1-bis(4-methoxyphenyl)ethyl)-2-oxo-6-(trifluoro methyl)-1,2-dihydropyridine-3-carboxamide (20A)

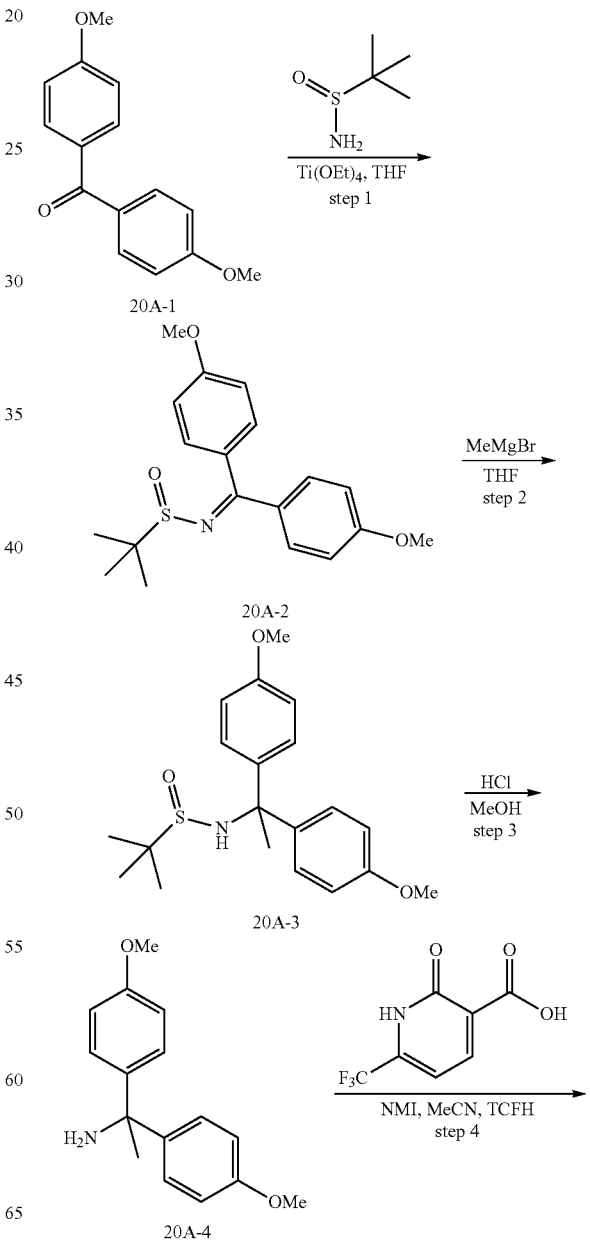

-continued

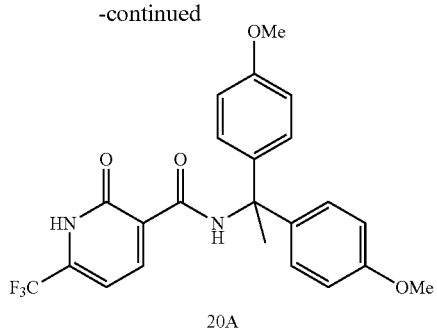

20A

Step 1: N-(bis(4-methoxyphenyl)methylene)-2-methylpropane-2-sulfinamide (20 A-2)

To a solution of 2-methylpropane-2-sulfinamide (1.0 g, 8.2 mmol) in THF (20.0 mL) was added Ti(OEt)$_4$ (3.8 g, 16.5 mmol, 3.4 mL) and Compound 20A-1 (2.2 g, 9.1 mmol). The mixture was stirred at 70° C. for 72 h. The residue was diluted with H$_2$O (10.0 mL) and extracted with EtOAc (5 mL×2). The combined organic layers were washed with H$_2$O (5 mL), dried over Na$_2$SO$_4$, filtered and concentrated under reduced pressure to give a residue, which was purified by column chromatography (Petroleum ether/Ethyl acetate) to give Compound 20A-2 (500 mg, 1.5 mmol, 17.5% yield) as yellow oil.

Step 2: N-(1,1-bis(4-methoxyphenyl)ethyl)-2-methylpropane-2-sulfinamide (20A-3)

A mixture of Compound 20A-2 (120 mg, 347 μmol) in THF (5.0 mL) was degassed with N$_2$ for 3 times at 0° C., and then the MeMgBr (3 M, 347 uL) was added at 0° C. The mixture was stirred at 20° C. for 2 h under N$_2$. The reaction mixture was quenched by addition aq.NH$_4$Cl (4.0 mL) at 20° C. and extracted with EtOAc (5.0 mL). The combined organic layers were washed with H$_2$O (2.0 mL), dried over Na$_2$SO$_4$, filtered and concentrated under reduced pressure to give Compound 20A-3 (70 mg, 40.0% yield) as a white solid.

Step 3: 1,1-bis(4-methoxyphenyl)ethanamine (20A-4)

To a solution of Compound 20A-3 (40 mg, 111 μmol) in MeOH (2 mL) was added HCl/MeOH (3 M, 2.0 mL). The mixture was stirred at 20° C. for 1 h. The reaction mixture was concentrated under reduced pressure to get crude residue. The residue was dissolved in EtOAc (2.0 mL) and washed with Sat NaHCO$_3$ (2 mL). The organic layer was concentrated to give Compound 20A-4 (80 mg, 80% yield) as a yellow solid.

Step 4: N-(1,1-bis(4-methoxyphenyl)ethyl)-2-oxo-6-(trifluoromethyl)-1,2-dihydro pyridine-3-carboxamide (20A)

To a stirred solution of Compound 20A-4 (50 mg, 194 μmol) and 2-oxo-6-(trifluoromethyl)-1,2-dihydropyridine-3-carboxylic acid (40 mg, 194 μmol,) in ACN (3.0 mL) was added N-(chloro(dimethylamino)methylene)-N-methylmethanaminium (60 mg, 214 μmol) and 1-methyl-1H-imidazole (51 mg, 621 μmol, 50 uL). The mixture was stirred at 25° C. for 12 h. The reaction mixture was concentrated under reduced pressure to give a residue, which was diluted with EtOAc (5.0 mL) and extracted with EtOAc (5.0 mL×2). The combined organic layers were washed with H$_2$O (5 mL×2), dried over Na$_2$SO$_4$, filtered and concentrated under reduced pressure to give a residue, which was purified by prep-HPLC (basic condition) to give Compound 20A (30 mg, 73% yield) was as a yellow solid. M-H$^-$=445.1 (LCMS). $^1$H NMR (400 MHz, CHLOROFORM-d$_4$) δ10.07 (s, 1H), 8.60 (d, J=7.2 Hz, 1H), 7.26-7.24 (m, 4H), 6.87-6.82 (m, 5H), 3.80 (s, 6H), 2.23 (s, 3H).

Example 21: Synthesis of N-(1,1-bis(4-hydroxyphenyl)ethyl)-2-oxo-6-(trifluoro methyl)-1,2-dihydropyridine-3-carboxamide (21A)

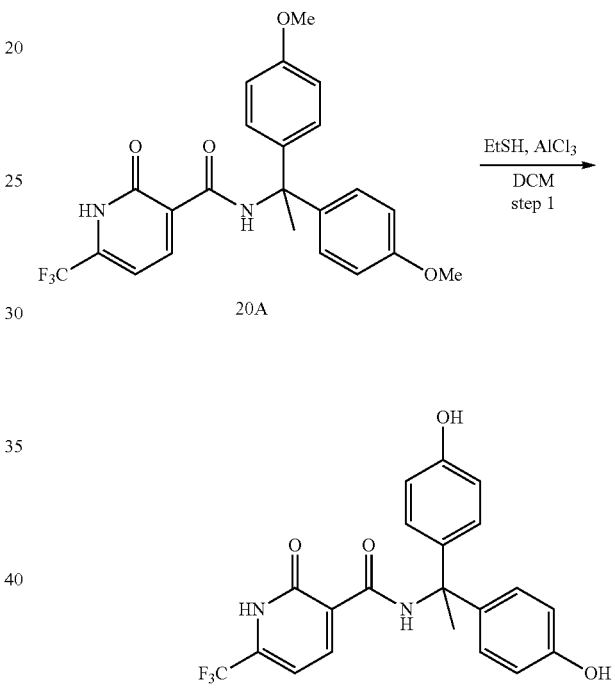

Step 1: N-(1,1-bis(4-hydroxyphenyl)ethyl)-2-oxo-6-(trifluoromethyl)-1,2-dihy dropyridine-3-carboxamide (21A)

To a solution of DCM (1.0 mL) in EtSH (0.1 mL) was added AlCl$_3$ (5 mg, 34 μmol, 2 uL) and Compound 20A (5 mg, 11 μmol) at 0° C. The mixture was stirred at 20° C. for 12 h. The reaction mixture was quenched by addition H$_2$O (5.0 mL), and then diluted with DCM (5.0 mL). The mixture was extracted with DCM (5 mL). The combined organic layers were washed with H$_2$O (5.0 mL), dried over Na$_2$SO$_4$, filtered and concentrated under reduced pressure to give a residue, which was purified by prep-HPLC (basic condition) to give Compound 21A (5 mg, 13 μmol, 23.2% yield, 98.8% purity) as a gray solid. M-H$^-$=417.0 (LCMS). $^1$H NMR (400 MHz, METHANOL-d$_4$) δ8.40 (d, J=7.2 Hz, 1H), 7.15-7.12 (m, 4H), 7.00 (d, J=7.6 Hz, 1H), 6.73-6.71 (m, 4H), 2.16 (s, 3H).

Example 22: Synthesis of N-(1-(4-chlorophenyl)propyl)-2-oxo-6-(trifluoromethyl)-1,2-dihydropyridine-3-carboxamide (22A)

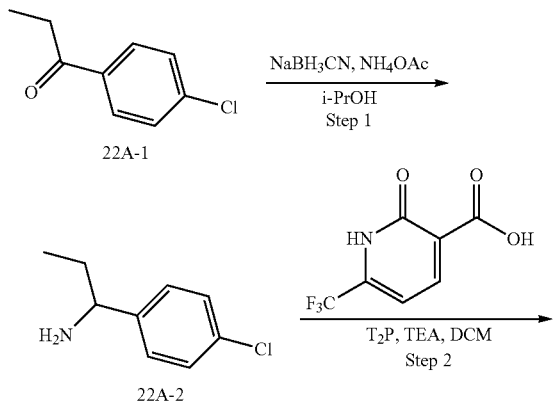

Step 1: (1-(4-chlorophenyl)propan-1-amine (22A-2)

To a stirred solution of Compound 22A-1 (100 mg, 593.1 µmol) in i-PrOH (4 mL) was added NaBH₃CN (261 mg, 4.2 mmol) and NH₄OAc (1.4 g, 17.8 mmol). The mixture was stirred at 120° C. for 1 h. The reaction mixture was quenched by adding H₂O (8 mL), and then extracted with EtOAc (5 mL×3). The combined organic layers were dried over Na₂SO₄, filtered and concentrated under reduced pressure to give a residue, which was purified by prep-TLC (Dichloromethane:Methanol=20:1,) to give Compound 22A-2 (60 mg, crude) as yellow oil. ¹H NMR (400 MHz, DMSO-d6) δ=7.43-7.30 (m, 4H), 3.71-3.65 (m, 1H), 1.60-1.42 (m, 2H), 1.21-1.13 (m, 3H).

Step 2: N-(1-(4-chlorophenyl)propyl)-2-oxo-6-(trifluoromethyl)-1,2-dihydropyridine-3-carboxamide (22A)

Two batches: To a solution of Compound 22A-2 (30 mg, 176.8 µmol) in DCM (1 mL) was added 2-oxo-6-(trifluoromethyl)-1H-pyridine-3-carboxylic acid (40.3 mg, 194.5 µmol) and TEA (53.7 mg, 530.5 µmol, 73.8 uL), followed by T₃P (225.1 mg, 353.7 µmol, 210.3 uL, 50% purity). The mixture was stirred at 20° C. for 12 h. The reaction mixture was quenched by H₂O (10 mL) and extracted with EtOAc (5 mL×3). The combined organic layers were dried over Na₂SO₄, filtered and concentrated under reduced pressure to give a residue. The two batches were combined and purified by prep-HPLC (column: Luna C18 100×30 5 u; mobile phase:[water (0.225% FA)-ACN]; B %: 40%-80%, 12 min) to give Compound 22A (51 mg, 142.6 µmol, 40.3% yield, 99.7% purity) as a white solid. M−H⁻=357.0 (LCMS); ¹H NMR (400 MHz, CHLOROFORM-d) δ=13.88 (br s, 1H), 9.92-9.77 (m, 1H), 8.74-8.67 (m, 1H), 7.27 (br s, 4H), 6.99-6.89 (m, 1H), 5.09-4.95 (m, 1H), 1.97-1.80 (m, 2H), 1.04-0.89 (m, 3H).

Other compounds made in a similar manner are shown in Table 14.

TABLE 14

| Compound No | Structure | HNMR and Ms |
|---|---|---|
| 58 | 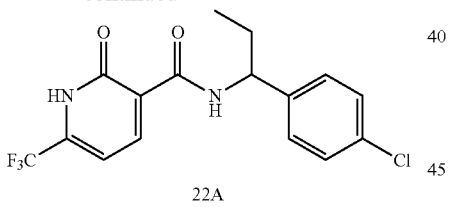 | ¹H NMR (400 MHz, DMSO-d₆) δ ppm 8.37-8.31 (m, 1H) 7.38-7.20 (m, 6 H) 4.87-4.80 (m, 1 H) 1.84-1.54 (m, 5 H) 1.45-1.34 (m, 1 H) 1.23-0.91 (m, 5 H) ESI [M − H] = 377.1 |

Example 23: Synthesis of N-(bis(4-(2,2,2-trifluoroethyl)phenyl)methyl)-2-oxo-6-(trifluoromethyl)-1,2-dihydropyridine-3-carboxamide (23A)

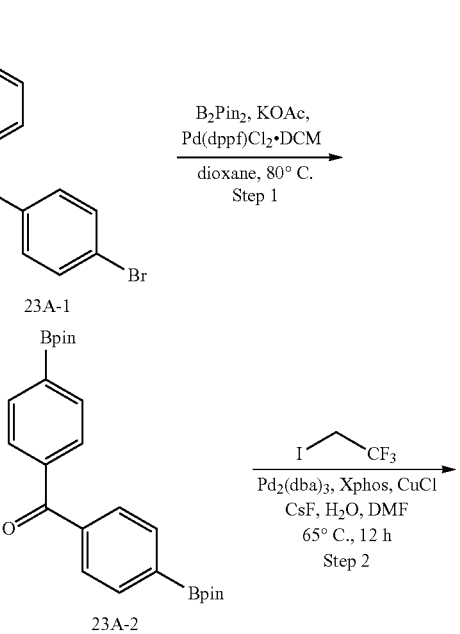

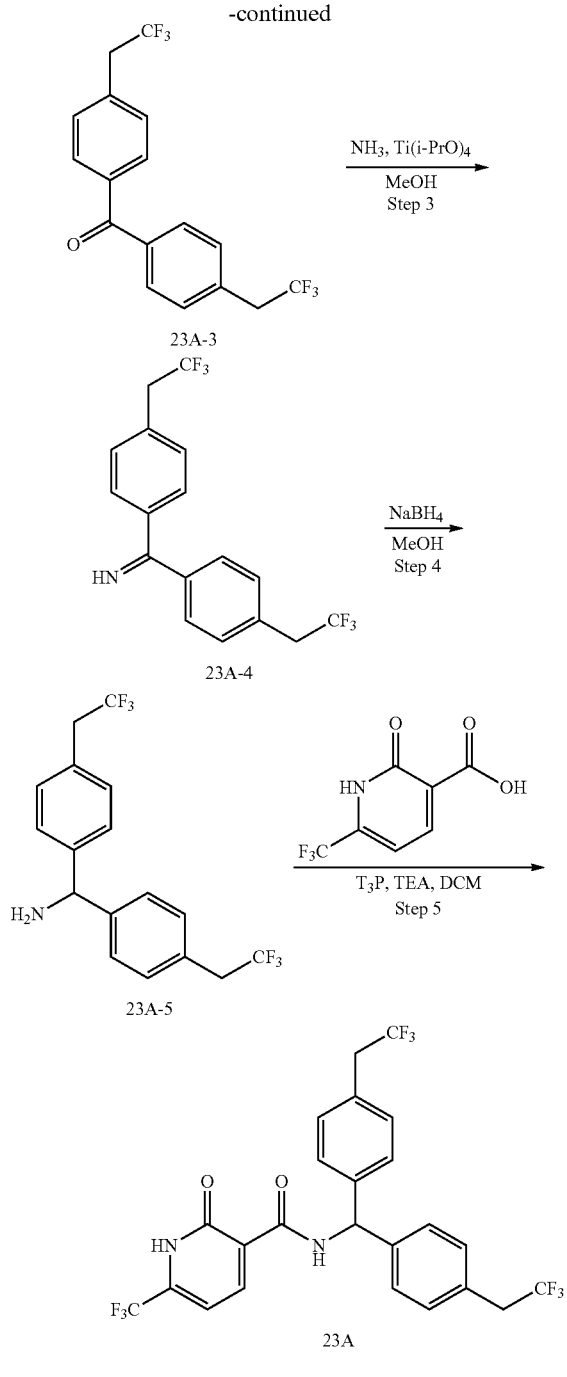

Step 1: bis(4-(4,4,5,5-tetramethyl-1,3,2-dioxaborolan-2-yl)phenyl)methanone (23A-2)

To a mixture of Compound 21-1 (1 g, 2.9 mmol), 4,4,5,5-tetramethyl-2-(4,4,5,5-tetramethyl-1,3,2-dioxaborolan-2-yl)-1,3,2-dioxaborolane (2.2 g, 8.8 mmol) and KOAc (1.4 g, 14.7 mmol) in dioxane (20 mL) was added Pd(dppf)Cl$_2$·CH$_2$Cl$_2$ (400 mg, 489.8 μmol). The mixture was stirred at 80° C. under N$_2$ for 12 h. The reaction mixture was filtered, and the cake was washed with EtOAc (30 mL). The filtrate was concentrated under reduced pressure to give a residue, which was purified by column chromatography (SiO$_2$, Plate 1,Petroleum ether:Ethyl acetate) to give Compound 23A-2 (1.5 g, crude) as a light-yellow solid. $^1$H NMR (400 MHz, DMSO-d$_6$) δ=7.89-7.81 (m, 4H), 7.76-7.67 (m, 4H), 1.36-1.30 (m, 24H).

Step 2: bis(4-(2,2,2-trifluoroethyl)phenyl)methanone (23A-3)

To a mixture of 1,1,1-trifluoro-2-iodo-ethane (794.9 mg, 3.8 mmol, 371.4 uL), Compound 23A-2 (470 mg, 1.08 mmol), CsF (986 mg, 6.5 mmol, 239.3 uL), H$_2$O (331.3 mg, 18.4 mmol, 331.3 uL), CuCl (320 mg, 3.2 mmol, 77.3 uL) and XPhos (103.1 mg, 216.4 μmol) in DMF (20 mL), was added Pd$_2$(dba)$_3$ (80 mg, 87.4 μmol) under N$_2$. The mixture was stirred at 65° C. for 12 hr. The mixture was diluted with Petroleum ether/Ethyl acetate (1/1, 20 mL), then filtered. The filtrate was washed with H$_2$O (20 mL×3), dried over Na$_2$SO$_4$, filtered and concentrated. The residue was purified by column chromatography (SiO$_2$, Petroleum ether:Ethyl acetate) to give Compound 23A-3 (120 mg, crude) as a yellow solid. 1H NMR (400 MHz, DMSO-d6) δ=7.78-7.74 (m, 4H), 7.59-7.54 (m, 4H), 3.88-3.75 (m, 4H).

Step 3: bis(4-(2,2,2-trifluoroethyl)phenyl)methanimine (23A-4)

To a solution of Compound 23A-3 (120 mg, 346.6 μmol) in MeOH (15 mL) was added Ti(i-PrO)$_4$ (492.5 mg, 1.7 mmol) and NH$_3$/MeOH (4M, 10 mL). The mixture was stirred at 15° C. for 12 h. The reaction mixture was used next step directly without any working-up as Compound 23A-4.

Step 4: bis(4-(2,2,2-trifluoroethyl)phenyl)methanamine (23A-5)

To the reaction mixture of Compound 23A-4 in step 3 was added NaBH$_4$ (74 mg, 1.9 mmol) at 0° C. The mixture was stirred at 15° C. for 1 h. The reaction mixture was quenched by addition ice H$_2$O (15 mL), the reaction mixture was filtered, and the filter cake was washed with EtOAc (30 mL) and the filtrate was extracted with EtOAc (15 mL×3). The combined organic layers were dried over Na$_2$SO$_4$, filtered and concentrated under reduced pressure to give a residue, which was purified by column chromatography by prep-TLC (SiO2, Petroleum ether:Ethyl acetate=1:1,Rf=0.24) to give Compound 23A-5 (55 mg crude) as a yellow solid. 1H NMR (400 MHz, DMSO-d6) δ=7.44-7.35 (m, 4H), 7.26 (d, J=7.9 Hz, 4H), 5.11-5.07 (m, 1H), 3.62-3.50 (m, 4H).

Step 5: N-(bis(4-(2,2,2-trifluoroethyl)phenyl)methyl)-2-oxo-6-(trifluoromethyl)-1,2-dihydropyridine-3-carboxamide (23A)

To a solution of Compound 23A-5 (50 mg, 144.0 μmol) in DCM (3 mL) was added 2-oxo-6-(trifluoromethyl)-1H-pyridine-3-carboxylic acid (30 mg, 144.0 μmol) and TEA (43.7 mg, 431.9 μmol, 60.1 uL), followed by T$_3$P (183 mg, 288.0 μmol, 171.3 uL, 50% purity). The mixture was stirred at 10° C. for 1 h. The reaction mixture was quenched by addition H$_2$O (8 mL), and then extracted with EtOAc (5 mL×3). The combined organic layers were dried over Na$_2$SO$_4$, filtered and concentrated under reduced pressure to give a residue, which was purified by prep-HPLC (column: Luna C18 100×30 5 u; mobile phase: [water (0.225% FA)-ACN]; B %: 40%-80%, 12 min) to give Compound 23A (13 mg, 23.3 μmol, 16.2% yield, 98.0% purity) as a white solid. M−H⁻=535.1 (LCMS); ¹H NMR (400 MHz, DMSO-d6) δ=13.63-13.27 (m, 1H), 10.19-9.56 (m, 1H), 8.39-8.32 (m, 1H), 7.39-7.31 (m, 8H), 7.31-7.24 (m, 1H), 6.33-6.28 (m, 1H), 3.68-3.55 (m, 4H).

Example 24: Synthesis of 2-oxo-N-(phenyl(1,2,3,4-tetrahydroquinolin-6-yl)methyl)-6-(trifluoromethyl)-1,2-dihydropyridine-3-carboxamide (107)

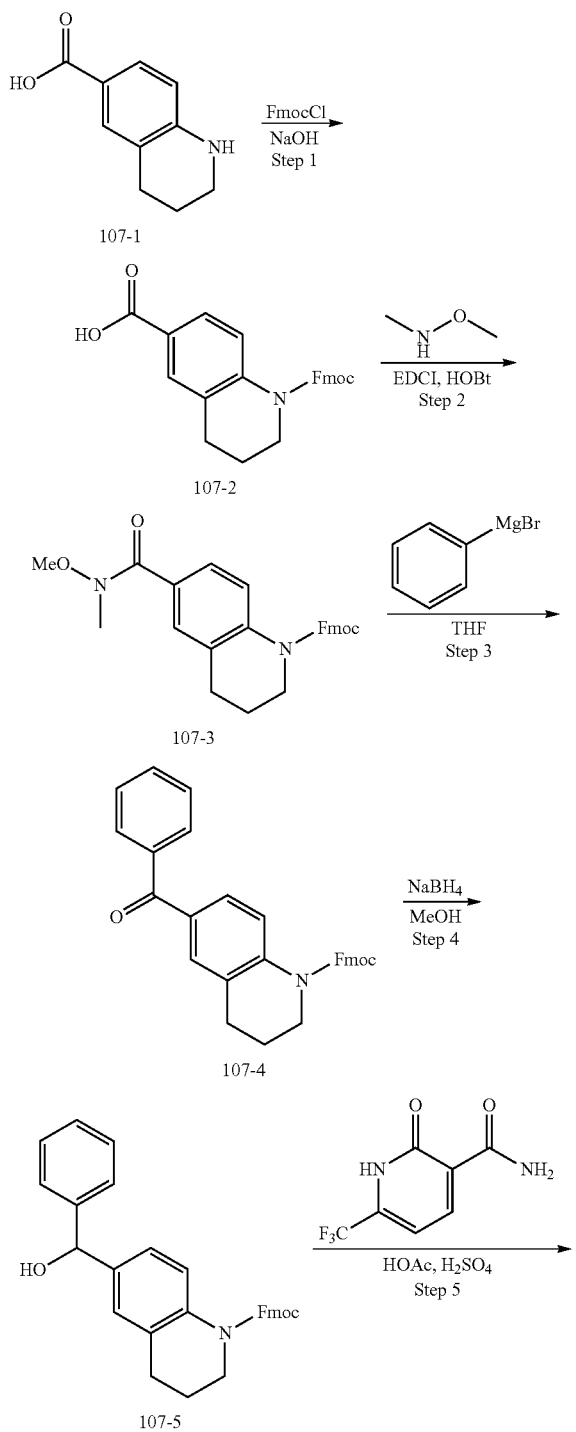

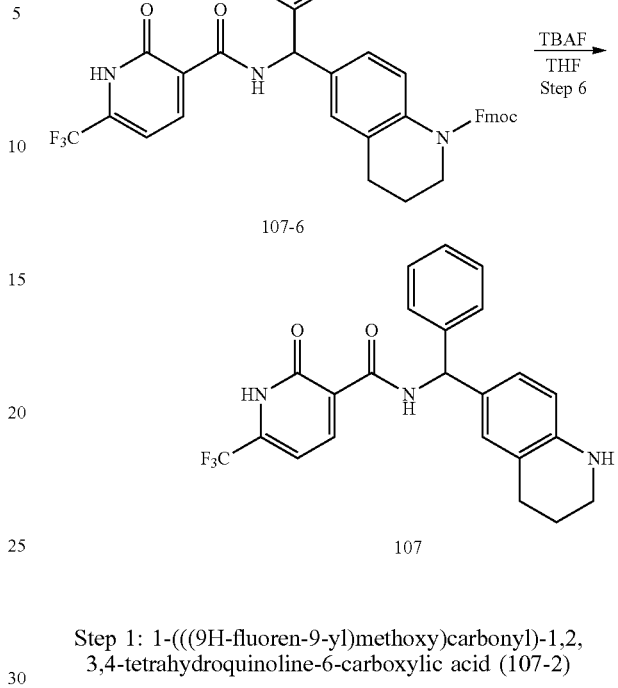

Step 1: 1-(((9H-fluoren-9-yl)methoxy)carbonyl)-1,2,3,4-tetrahydroquinoline-6-carboxylic acid (107-2)

To a solution of Compound 107-1 (1 g, 5.6 mmol) in dioxane (10 mL) was added NaOH (0.5 M, 10 mL) and FmocCl (1.6 g, 6.2 mmol). The mixture was stirred at 25° C. for 12 hrs. LCMS showed the reaction was complete and the desired mass was detected. The reaction mixture was quenched by addition H₂O 50 (mL) at 25° C., and then filtered. The cake was triturated with (Petroleum ether:Ethyl acetate=5:1, 40 mL) at 20° C. for 30 mins to give Compound 107-2 (2.2 g, crude) as a white solid. M+H⁺=398.0 (LCMS); ¹H NMR (400 MHz, DMSO-d6) δ=7.90 (d, J=7.7 Hz, 2H), 7.67-7.60 (m, 3H), 7.47-7.36 (m, 3H), 7.35-7.29 (m, 2H), 7.20 (br d, J=8.2 Hz, 1H), 4.68 (d, J=5.1 Hz, 2H), 4.35 (t, J=5.2 Hz, 1H), 3.55-3.51 (m, 2H), 2.69 (t, J=6.4 Hz, 2H), 1.72 (quin, J=6.2 Hz, 2H).

Step 2: (9H-fluoren-9-yl)methyl 6-(methoxy(methyl)carbamoyl)-3,4-dihydroquinoline-1(2H)-carboxylate (107-3)

To a solution of Compound 107-2 (2.2 g, 5.5 mmol,) in DMF (40 mL) was added HATU (2.7 g, 7.2 mmol) and DIEA (2.1 g, 16.5 mmol) and N,O-dimethylhydroxylamine (645 mg, 6.6 mmol). The mixture was stirred at 20° C. for 12 hrs. LCMS showed the reaction was complete and the desired mass was detected. The reaction mixture was poured into H₂O (80 mL) and extracted with EtOAc (30 mL×3). The combined organic layers were dried over Na₂SO₄, filtered and concentrated under reduced pressure to give a residue. The residue was purified by flash silica gel chromatography to give crude Compound 107-3 (1.8 g) as brown oil. M+H⁺=443.1 (LCMS).

Step 3: (9H-fluoren-9-yl)methyl 6-benzoyl-3,4-dihydroquinoline-1(2H)-carboxylate (107-4)

To a solution of Compound 107-3 (1.8 g, 4.1 mmol) in THF (40 mL) was added phenylmagnesium bromide (3 M, 2.0 mL) at 0° C. and stirred for 10 mins, and then the mixture was stirred at 15° C. for 3 hrs. LCMS showed the reaction was completed and desired mass was detected. The reaction mixture was poured into Sat.NH$_4$Cl (50 mL) at 15° C. and extracted with EtOAc (30 ml×3). The combined organic layers were dried over Na$_2$SO$_4$ and filtered, concentrated under reduced pressure to give a residue. The residue was purified by flash silica gel chromatography to give Compound 107-4 (870 mg, crude) as a white solid. M+H$^+$=460.1 (LCMS).

Step 4: (9H-fluoren-9-yl)methyl 6-(hydroxy(phenyl)methyl)-3,4-dihydroquinoline-1(2H)-carboxylate (107-5)

To a solution of Compound 107-4 (600 mg, 1.3 mmol,) in MeOH (20 mL) was added NaBH$_4$ (148 mg, 3.9 mmol) at 0° C. The mixture was stirred at 15° C. for 1.5 hrs. TLC indicated the reaction was completed. The reaction mixture was poured into ice-water (40 mL) and extracted with DCM (20 mL×3). The combined organic layers were dried over Na$_2$SO$_4$ filtered and concentrated under reduced pressure to give Compound 107-5 (600 mg, crude) as colorless oil, which was used into the next step without further purification.

Step 5: (9H-fluoren-9-yl)methyl 6-((2-oxo-6-(trifluoromethyl)-1,2-dihydropyridine-3-carboxamido)(phenyl)methyl)-3,4-dihydroquinoline-1(2H)-carboxylate (107-6)

To a solution of Compound 107-5 (600 mg, 1.3 mmol) in AcOH (20 mL) was added 2-oxo-6-(trifluoromethyl)-1,2-dihydropyridine-3-carboxamide and H$_2$SO$_4$ (13 mg, 130 µmol). The mixture was stirred at 100° C. for 4 hrs. TLC indicated the reaction completed. The reaction mixture was concentrated under reduced pressure to give a residue, which was purified by flash silica gel chromatography to give compound 107-6 (600 mg, crude) a light yellow solid. M−H$^-$=648.1 (LCMS); $^1$H NMR (400 MHz, DMSO-d6) δ=13.73-13.34 (m, 1H), 10.01-9.43 (m, 1H), 8.40 (d, J=7.5 Hz, 1H), 7.82 (dd, J=5.0, 7.4 Hz, 2H), 7.60 (d, J=7.5 Hz, 2H), 7.43-7.19 (m, 10H), 7.01 (s, 1H), 6.95-6.73 (m, 2H), 6.18 (d, J=7.9 Hz, 1H), 4.64 (d, J=5.3 Hz, 1H), 4.31 (t, J=5.0 Hz, 1H), 3.54-3.44 (m, 2H), 2.60 (t, J=6.6 Hz, 2H), 1.69 (quin, J=6.3 Hz, 2H).

Step 6: 2-oxo-N-(phenyl(1,2,3,4-tetrahydroquinolin-6-yl)methyl)-6-(trifluoromethyl)-1,2-dihydropyridine-3-carboxamide (107)

To a solution of Compound 107-6 (600 mg, 923.6 µmol) in THF (50 mL) was added TBAF (1 M, 1.9 mL). The mixture was stirred at 30° C. for 12 hrs. TLC indicated Reactant was remained. Another batch of TBAF (1 M, 1.9 mL) was added and stirred at 30° C. for 4 hrs. LCMS showed the reaction was completed and desired mass was detected. The reaction mixture was poured into H$_2$O (80 mL) and extracted with EtOAc (30 mL×3). The combined organic layers were dried over Na$_2$SO$_4$, filtered and concentrated under reduced pressure to give a residue. The residue was purified by flash silica gel chromatography to give Compound 107 (82 mg, 179.0 µmol, 19% yield) as a light yellow solid. M−H$^-$=426.2 (LCMS); $^1$H NMR (400 MHz, DMSO-d6) δ=9.76-9.51 (m, 1H), 8.39 (d, J=7.6 Hz, 1H), 7.37-7.14 (m, 6H), 6.82-6.69 (m, 2H), 6.41-6.30 (m, 1H), 6.06 (d, J=7.9 Hz, 1H), 3.16-3.10 (m, 2H), 2.60 (t, J=6.2 Hz, 2H), 1.75 (quin, J=5.8 Hz, 2H).

Example 25: Synthesis of N-(5-hydroxynaphthalen-1-yl)-2-oxo-6-(trifluoromethyl)-1,2-dihydropyridine-3-carboxamide (223)

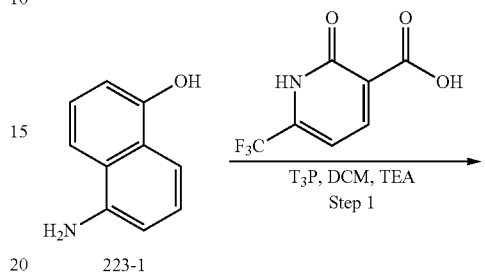

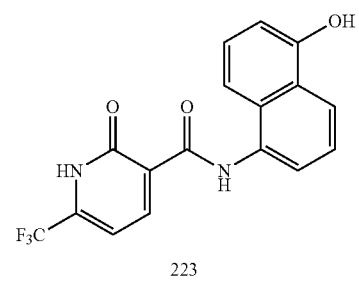

Step 1: N-(5-hydroxynaphthalen-1-yl)-2-oxo-6-(trifluoromethyl)-1,2-dihydropyridine-3-carboxamide (223)

To a solution of Compound 223-1 (50 mg, 314 µmol) in DCM (6.0 mL) was added 2-oxo-6-(trifluoromethyl)-1H-pyridine-3-carboxylic acid (71.6 mg, 346 µmol), HATU (119.4 mg, 314 µmol), DIEA (40.6 mg, 314 µmol). The mixture was stirred at 25° C. for 12 hrs. The reaction mixture was diluted with H$_2$O (5.0 mL) and extracted with EtOAc (5.0 mL×3). The combined organic layers were dried over Na$_2$SO$_4$, filtered and concentrated under reduced pressure to give a residue, which was purified by prep-HPLC to give Compound 223 (3 mg, 8 µmol, 3% yield) as a yellow solid. M−H$^-$=347.1 (LCMS). $^1$H NMR (400 MHz, DMSO-d6) δ=8.58 (d, J=7.5 Hz, 1H), 8.30 (br d, J=7.5 Hz, 1H), 8.00 (d, J=8.4 Hz, 1H), 7.58 (d, J=8.4 Hz, 1H), 7.44 (td, J=8.0, 19.6 Hz, 2H), 7.28 (br d, J=7.5 Hz, 1H), 6.94 (d, J=7.5 Hz, 1H).

Other compounds made in a similar manner are shown in Table 15.

TABLE 15

| Compound No | Structure | HNMR and Ms |
|---|---|---|
| 224 | 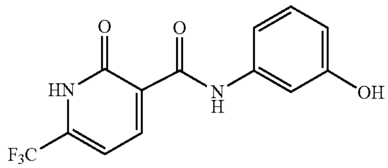 [SMILES: O=C(Nc1cccc(O)c1)c1ccc(C(F)(F)F)[nH]c1=O] | $^1$H NMR (400 MHz, DMSO-d$_6$) δ = 9.46 (s, 1H), 8.35 (br d, J = 7.7 Hz, 1H), 7.29 (s, 1H), 7.23 (br s, 1H), 7.16-7.10 (m, 1H), 7.02 (d, J = 8.6 Hz, 1H), 6.51 (br d, J = 7.9 Hz, 1H)<br>ESI [M − H] = 297.0 |
| 225 | 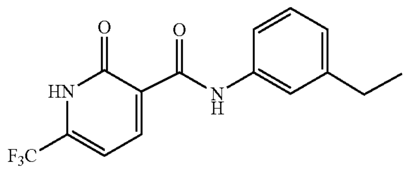 [SMILES: CCc1cccc(NC(=O)c2ccc(C(F)(F)F)[nH]c2=O)c1] | 1H NMR (400 MHz, DMSO-d6) δ = 8.39 (d, J = 7.5 Hz, 1H), 7.56-7.50 (m, 2H), 7.33-7.23 (m, 2H), 6.98 (d, J = 7.3 Hz, 1H), 2.61 (d, J = 7.6 Hz, 2H), 1.19 (t, J = 7.5 Hz, 3H)<br>ESI [M − H] = 309.0 |
| 226 | 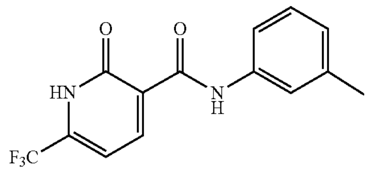 [SMILES: Cc1cccc(NC(=O)c2ccc(C(F)(F)F)[nH]c2=O)c1] | $^1$H NMR (400 MHz, DMSO-d$_6$) δ = 8.38 (d, J = 7.5 Hz, 1H), 7.52 (br s, 2H), 7.28-7.22 (m, 2H), 6.95 (d, J = 7.7 Hz, 1H), 2.31 (s, 3H)<br>ESI [M − H] = 295.1 |
| 227 | 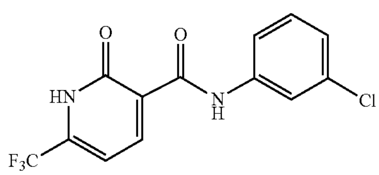 [SMILES: O=C(Nc1cccc(Cl)c1)c1ccc(C(F)(F)F)[nH]c1=O] | $^1$H NMR (400 MHz, DMSO-d) δ = 8.20 (d, J = 7.3 Hz, 1H), 8.01 (t, J = 2.0 Hz, 1H), 7.44 (dd, J = 0.9, 8.2 Hz, 1H), 7.38-7.31 (m, 1H), 7.10 (td, J = 1.0, 6.8 Hz, 1H), 6.77 (br d, J = 7.5 Hz, 1H)<br>ESI [M − H] = 315.0 |
| 228 | 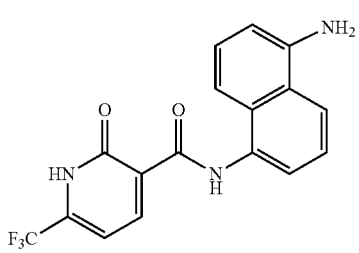 [SMILES: Nc1cccc2c(NC(=O)c3ccc(C(F)(F)F)[nH]c3=O)cccc12] | $^1$H NMR (400 MHz, DMSO-d) δ = 11.81 (br s, 1H), 8.59 (d, J = 7.3 Hz, 1H), 8.26 (d, J = 7.3 Hz, 1H), 7.93 (d, J = 8.4 Hz, 1H), 7.43-7.24 (m, 4H), 6.75 (dd, J = 1.2, 7.0 Hz, 1H)<br>ESI [M − H] = 346.1 |
| 229 | 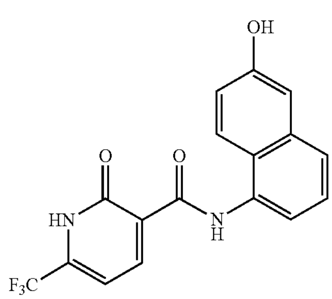 [SMILES: O=C(Nc1cccc2cc(O)ccc12)c1ccc(C(F)(F)F)[nH]c1=O] | $^1$H NMR (400 MHz, DMSO-d$_6$) δ = 11.78 (br s, 1H), 9.86 (br s, 1H), 8.57 (d, J = 7.5 Hz, 1H), 8.00 (dd, J = 8.3, 13.4 Hz, 2H), 7.55 (d, J = 8.2 Hz, 1H), 7.45-7.39 (m, 1H), 7.29 (d, J = 7.5 Hz, 1H), 7.20-7.14 (m, 2H)<br>ESI [M − H] = 347.1 |

Example 26: Synthesis of N-(5-hydroxy-1,2,3,4-tetrahydronaphthalen-1-yl)-2-oxo-6-(trifluoromethyl)-1,2-dihydropyridine-3-carboxamide (230)

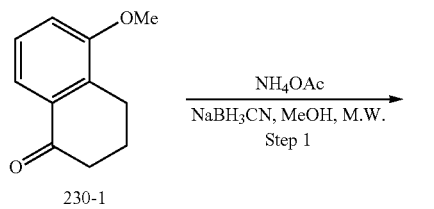

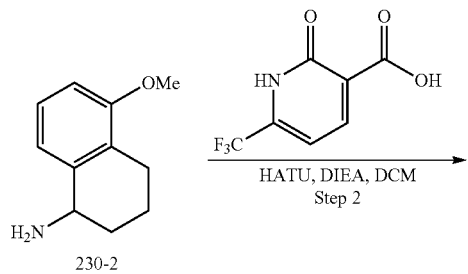

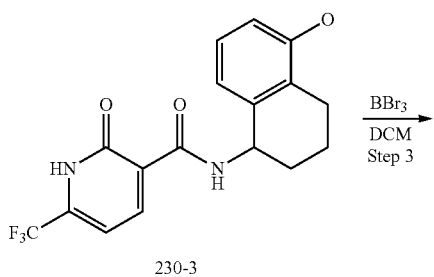

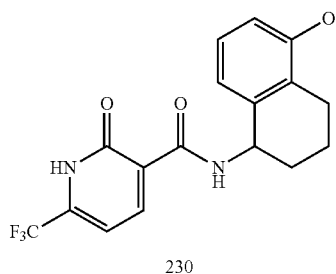

Step 1: 5-methoxy-1,2,3,4-tetrahydronaphthalen-1-amine (230-2)

To a solution of Compound 230-1 (200 mg, 1.1 mmol) in MeOH (3 mL) was added NH$_4$OAc (1.31 g, 17.0 mmol) and stirred at 20° C. for 10 min. NaBH$_3$CN (285 mg, 4.5 mmol) was added. The mixture was stirred at 90° C. for 7 hrs under microwave. LCMS showed the reaction was completed. The reaction mixture was poured into H$_2$O (15 mL), and then extracted with EtOAc (5 mL×3). The combined organic layers were dried over Na$_2$SO$_4$, filtered and concentrated under reduced pressure to give Compound 230-2 (130 mg, crude) as a white solid. Fragment Ms=161.1 (LCMS).

Step 2: N-(5-methoxy-1,2,3,4-tetrahydronaphthalen-1-yl)-2-oxo-6-(trifluoromethyl)-1,2-dihydropyridine-3-carboxamide (230-3)

To a stirred solution of 2-oxo-6-(trifluoromethyl)-1,2-dihydropyridine-3-carboxylic acid (117 mg, 564 μmol) in DCM (3 mL) was added HATU (257 mg, 677 μmol) and DIEA (219 mg, 1.7 mmol), then Compound 230-2 (100 mg, 564 μmol) was added. The mixture was stirred at 20° C. for 3 hrs. LCMS showed the reaction was completed and desired mass was detected. The reaction mixture was poured into H$_2$O (15 mL), and then extracted with DCM (5 mL×3). The combined organic layers were dried over Na$_2$SO$_4$, filtered and concentrated under reduced pressure to give a residue, which was purified by prep-TLC (Petroleum ether/Ethyl acetate=3/1) to give Compound 230-3 (30 mg, 82 μmol, 15% yield) as a white solid. M−H−=365.1 (LCMS); $^1$H NMR (400 MHz, CHLOROFORM-d) δ=9.59 (br d, J=7.1 Hz, 1H), 8.70 (d, J=7.3 Hz, 1H), 7.13 (t, J=7.9 Hz, 1H), 6.93 (d, J=7.7 Hz, 1H), 6.85 (d, J=7.3 Hz, 1H), 6.75 (d, J=8.1 Hz, 1H), 5.37-5.31 (m, 1H), 3.85 (s, 3H), 2.82 (td, J=5.5, 17.7 Hz, 1H), 2.66-2.55 (m, 1H), 2.08-1.95 (m, 2H), 1.93-1.81 (m, 2H).

Step 3: N-(5-hydroxy-1,2,3,4-tetrahydronaphthalen-1-yl)-2-oxo-6-(trifluoromethyl)-1,2-dihydropyridine-3-carboxamide (230)

To a solution of Compound 230-3 (30 mg, 82 μmol) in DCM (2 mL) was added BBr$_3$ (103 mg, 409 μmol) in DCM (1 mL) at −78° C. The mixture was stirred at −78° C. for 1 hr then at 20° C. for 12 hrs. LCMS showed the reaction was completed and the desired mass was detected. The reaction mixture was poured into ice-water (12 mL), and then extracted with DCM (4 mL×3). The combined organic layers were dried over Na$_2$SO$_4$, filtered and concentrated under reduced pressure to give a residue, which was purified by prep-HPLC to give Compound 230 (2 mg, 5 μmol, 7% yield) as a white solid. M−H−=351.1 (LCMS); 1H NMR (400 MHz, DMSO-d6) δ=13.49 (br s, 1H), 9.33 (s, 1H), 8.45 (d, J=7.5 Hz, 1H), 7.28 (br s, 1H), 7.00-6.92 (m, 1H), 6.70 (t, J=8.4 Hz, 2H), 5.18-5.11 (m, 1H), 2.64-2.54 (m, 2H), 2.00-1.90 (m, 1H), 1.87-1.72 (m, 3H).

Other compounds made in a similar manner are shown in Table 16.

TABLE 16

| Compound No | Structure | HNMR and Ms |
|---|---|---|
| 231 | 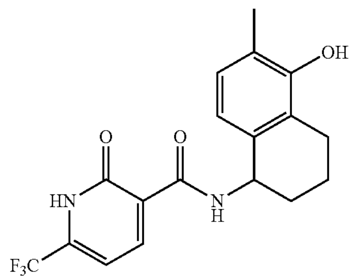 [SMILES: Cc1ccc2c(c1O)CCCC2NC(=O)c1ccc(C(F)(F)F)[nH]c1=O] | ¹H NMR (400 MHz, CHLOROFORM-d) δ = 9.57 (br d, J = 7.9 Hz, 1H), 8.70 (d, J = 7.3 Hz, 1H), 6.95 (d, J = 7.7 Hz, 1H), 6.85 (dd, J = 4.7, 7.5 Hz, 2H), 5.36-5.23 (m, 1H), 2.77 (td, J = 5.2, 16.5 Hz, 1H), 2.69-2.54 (m, 1H), 2.24 (s, 3H), 2.07-1.87 (m, 4H)<br>ESI [M − H] = 365.1 |
| 232 | 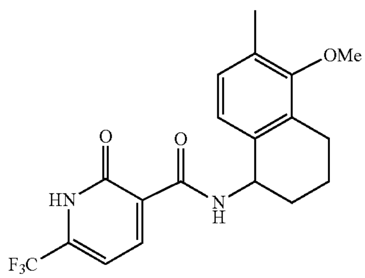 [SMILES: COc1c(C)ccc2c1CCCC2NC(=O)c1ccc(C(F)(F)F)[nH]c1=O] | ¹H NMR (400 MHz, CHLOROFORM-d) δ = 13.74-12.84 (m, 1H), 9.61 (br d, J = 7.5 Hz, 1H), 8.71 (d, J = 7.4 Hz, 1H), 7.07-6.93 (m, 2H), 6.85 (d, J = 7.4 Hz, 1H), 5.38-5.24 (m, 1H), 3.74 (s, 3H), 2.92 (td, J = 5.3, 17.3 Hz, 1H), 2.76-2.61 (m, 1H), 2.28 (s, 3H), 2.08-1.94 (m, 2H), 1.91-1.78 (m, 2H)<br>ESI [M − H] = 379.1 |
| 233 | 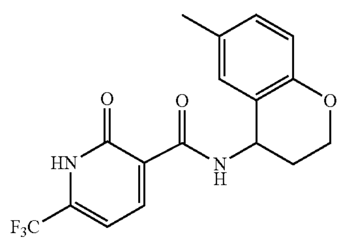 [SMILES: Cc1ccc2c(c1)C(NC(=O)c1ccc(C(F)(F)F)[nH]c1=O)CCO2] | ¹H NMR (400 MHz, CHLOROFORM-d) δ = 9.59 (br s, 1H), 8.63 (br d, J = 7.3 Hz, 1H), 6.96 (s, 1H), 6.92 (br d, J = 8.4 Hz, 1H), 6.78 (d, J = 7.5 Hz, 1H), 6.69 (d, J = 8.3 Hz, 1H), 5.29-5.09 (m, 1H), 4.26-4.15 (m, 1H), 4.14-4.01 (m, 1H), 2.27-2.16 (m, 1H), 2.15 (s, 3H), 2.11-1.97 (m, 1H)<br>ESI[M − H] = 351.1 |
| 234 | 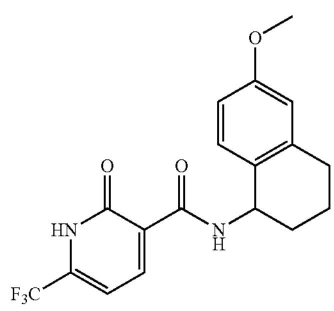 [SMILES: COc1ccc2c(c1)CCCC2NC(=O)c1ccc(C(F)(F)F)[nH]c1=O] | 1H NMR (400 MHz, CHLOROFORM-d) δ = 9.53 (br d, J = 7.9 Hz, 1H), 8.68 (d, J = 7.3 Hz, 1H), 7.22 (d, J = 8.4 Hz, 1H), 6.86 (d, J = 7.5 Hz, 1H), 6.72 (dd, J = 2.5, 8.5 Hz, 1H), 6.67-6.59 (m, 1H), 5.35-5.24 (m, 1H), 3.81-3.74 (m, 3H), 2.94-2.65 (m, 2H), 2.21-1.71 (m, 4H)<br>ESI[M − H] = 365.1 |
| 235 | 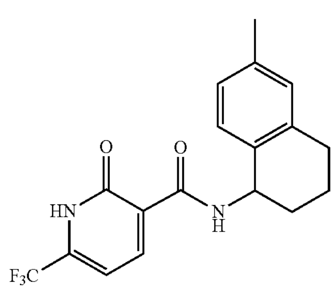 | 1H NMR (400 MHz, CHLOROFORM-d) δ = 9.53 (br d, J = 6.4 Hz, 1H), 8.70 (d, J = 7.3 Hz, 1H), 7.19 (d, J = 8.2 Hz, 1H), 7.00-6.92 (m, 2H), 6.85 (d, J = 7.3 Hz, 1H), 5.38-5.23 (m, 1H), 2.90-2.69 (m, 2H), 2.30 (s, 3H), 2.12-1.78 (m, 4H)<br>ESI [M − H] = 349.1 |

TABLE 16-continued

| Compound No | Structure | HNMR and Ms |
|---|---|---|
| 236 | 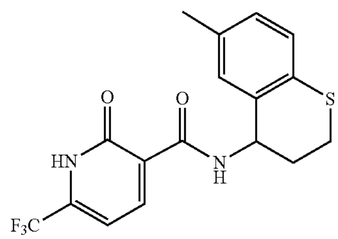 | 1H NMR (400 MHz, CHLOROFORM-d) δ = 9.60 (br s, 1H), 8.70 (br d, J = 7.3 Hz, 1H), 7.11-7.03 (m, 2H), 7.01-6.95 (m, 1H), 6.87 (d, J = 7.3 Hz, 1H), 5.44-5.25 (m, 1H), 3.21-3.05 (m, 1H), 3.01-2.92 (m, 1H), 2.59-2.36 (m, 1H), 2.30-2.19 (m, 4H) ESI [M − H] = 367.1 |
| 237 | 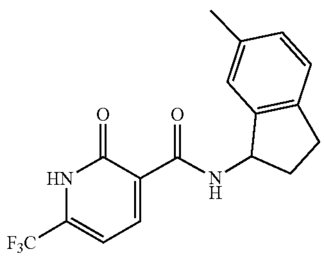 [SMILES: Cc1ccc2c(c1)C(NC(=O)c1ccc(C(F)(F)F)[nH]c1=O)CC2] | 1H NMR (400 MHz, DMSO-d6) δ = 13.45 (br s, 1H), 9.41 (br s, 1H), 8.44 (d, J = 7.5 Hz, 1H), 7.27 (br d, J = 4.0Hz, 1H),7.17 (d, J = 7.6 Hz, 1H), 7.11-7.01 (m, 2H), 5.48 (q, J = 7.8 Hz, 1H), 2.99-2.87 (m, 1H), 2.87-2.75 (m, 1H), 2.57-2.53 (m, 1H), 2.28 (s, 3H), 1.94-1.82 (m, 1H) ESI [M − H] = 335.1 |
| 238 | 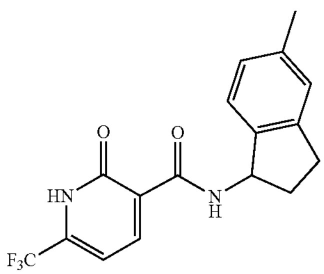 [SMILES: Cc1ccc2c(c1)CCC2NC(=O)c1ccc(C(F)(F)F)[nH]c1=O] | 1H NMR (400 MHz, DMSO-d6) δ = 8.44 (d, J = 7.5 Hz, 1H), 7.37-7.29 (m, 1H), 7.16 (d, J = 7.7 Hz, 1H), 7.09 (s, 1H), 7.02 (d, J = 7.7 Hz, 1H), 5.50-5.40 (m, 1H), 2.98-2.89 (m, 1H), 2.88-2.76 (m, 1H), 2.29 (s, 3H), 1.94-1.81 (m, 1H) ESI [M − H]= 335.1 |

Example 27: Synthesis of N-(3,6-dimethoxy-9H-xanthen-9-yl)-2-oxo-5-phenyl-6-(trifluoromethyl)-1,2-dihydropyridine-3-carboxamide (239)

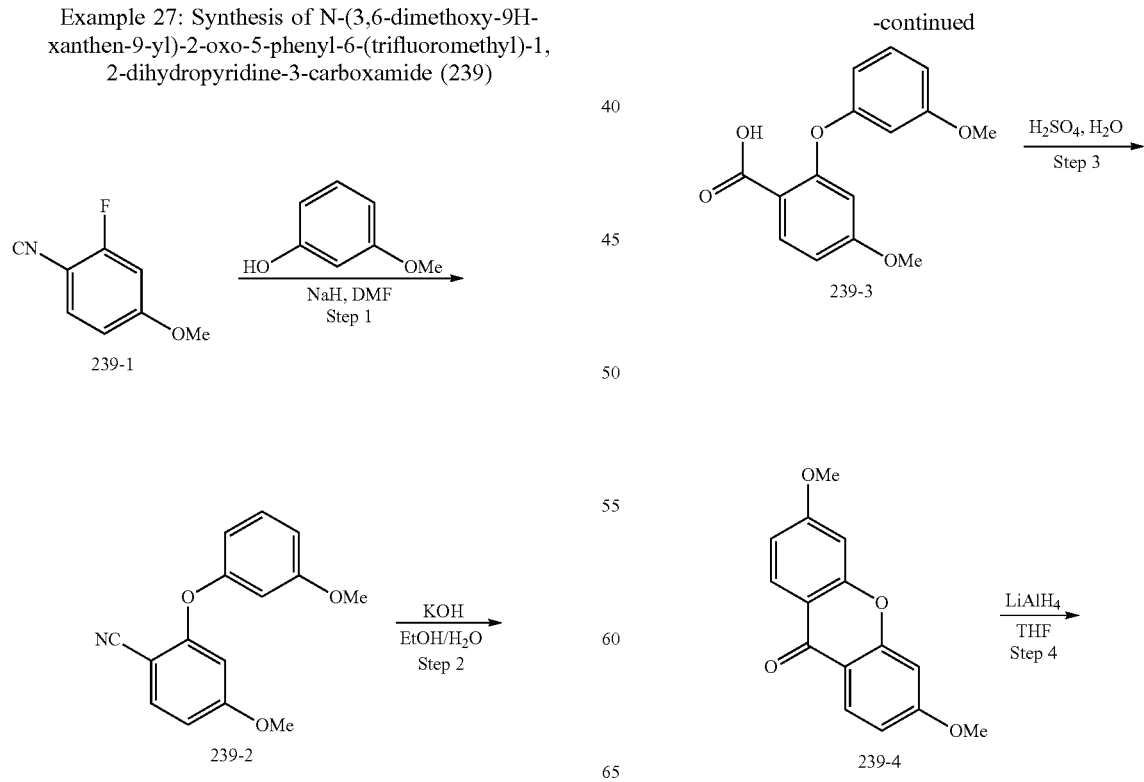

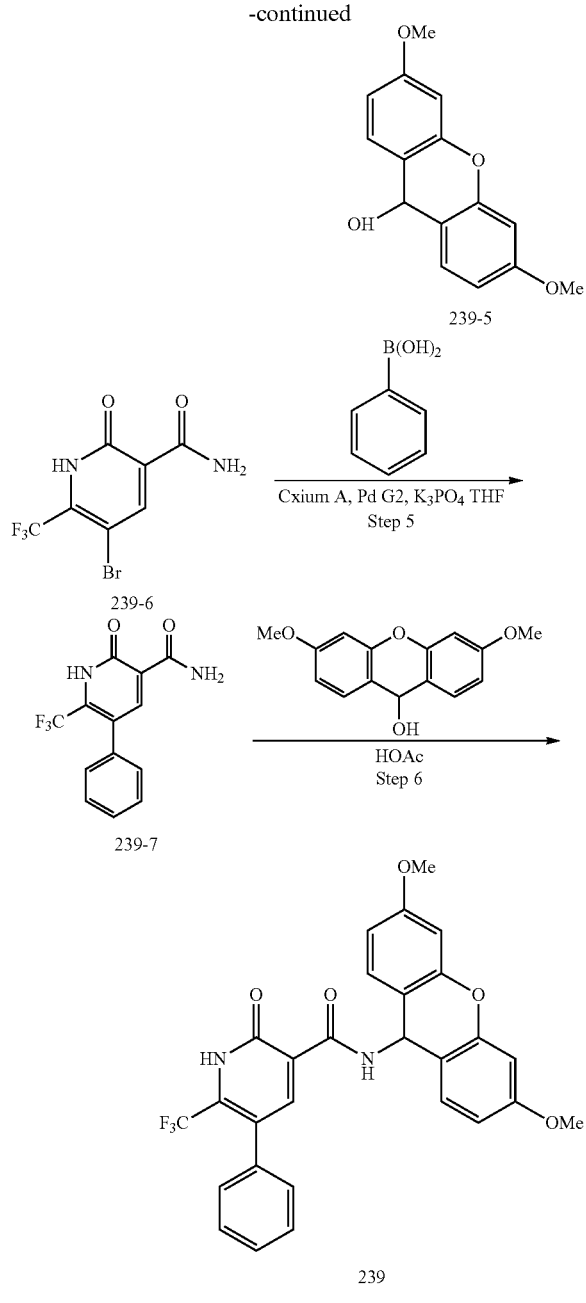

Step 1: 4-methoxy-2-(3-methoxyphenoxy)benzonitrile (239-2)

To a solution of 3-methoxyphenol (9 g, 72.8 mmol) in DMF (100 mL) was added NaH (3.2 g, 79.4 mmol, 60% purity) at 0° C. After stirring for 30 mins, Compound 239-1 (10 g, 66.2 mmol) in DMF (50 mL) was added. The mixture was stirred at 50° C. for 3 hrs. LCMS showed the reaction completed and desired mass was detected. The reaction mixture was quenched by addition water (200 mL) and extracted with ethyl acetate 200 mL (50 mL×4). The combined organic layers were washed with brine 2 (50 mL×4), dried over $Na_2SO_4$, filtered and concentrated in vacuum to give residue, which was purified by column chromatography to give Compound 239-2 (15.2 g, 59.6 mmol, 90% yield) as a white oil. $M+H^+$=256.1 (LCMS); $^1H$ NMR (400 MHz, DMSO-d6) δ=7.82 (d, J=8.7 Hz, 1H), 7.35 (t, J=8.2 Hz, 1H), 6.88 (dd, J=2.4, 8.7 Hz, 1H), 6.83 (ddd, J=0.6, 2.4, 8.3 Hz, 1H), 6.74 (t, J=2.4 Hz, 1H), 6.67 (ddd, J=0.6, 2.3, 8.1 Hz, 1H), 6.46 (d, J=2.3 Hz, 1H), 3.76 (d, J=1.3 Hz, 6H).

Step 2: 4-methoxy-2-(3-methoxyphenoxy)benzoic acid (239-3)

To a solution of KOH (33 g, 587.6 mmol) in EtOH (80 mL) and $H_2O$ (80 mL) was added Compound 239-2 (10 g, 39.2 mmol). The mixture was stirred at 80° C. for 48 hrs. LCMS showed the reaction completed and desired mass was detected. The reaction mixture was adjusted to pH=6 by using conc. HCl, and then some solid appeared. The mixture was filtered and the cake was dried in vacuum to give Compound 239-3 (10 g, 36.5 mmol, 93% yield) as a white solid.

Step 3: 3,6-dimethoxy-9H-xanthen-9-one (239-4)

A mixture of Compound 239-3 (10 g, 36.5 mmol) in $H_2SO_4$ (120 mL) and $H_2O$ (40 mL) was stirred at 90° C. for 30 mins. TLC indicated the reaction completed. The reaction mixture was cooled to 25° C. then poured into ice and and solid appeared, and then filtered. The filter cake was dried under reduced pressure to give a residue, which was triturated with THF (30 mL) to give Compound 239-4 (4 g, 15.6 mmol) as a white solid. $^1H$ NMR (400 MHz, DMSO-d6) δ=8.06 (d, J=8.9 Hz, 2H), 7.08 (d, J=2.3 Hz, 2H), 7.03 (dd, J=2.4, 8.8 Hz, 2H), 3.95-3.88 (m, 6H).

Step 4: 3,6-dimethoxy-9H-xanthen-9-ol (239-5)

To a solution of Compound 239-4 (50 mg, 195 μmol) in THF (5 mL) was added $LiAlH_4$ (14.8 mg, 390 μmol) at 0° C. The mixture was stirred at 0° C. for 1 hr. TLC indicated the reaction completed. The reaction mixture was poured into Sat. $NH_4Cl$ (25 mL) and extracted with DCM (10 mL×4). The combined organic layers were dried over $Na_2SO_4$ and concentrated in vacuum to give Compound 239-5 (40 mg, crude) as a white solid, which was unstable and should be used next step directly.

Step 5: 2-oxo-5-phenyl-6-(trifluoromethyl)-1,2-dihydropyridine-3-carboxamide (239-7)

A mixture of Compound 239-6 (300 mg, 1.05 mmol), phenylboronic acid (128 mg, 1 mmol) and $K_3PO_4$ (0.5 M, 6.3 mL), Cxium A, Pd G2 (70 mg, 105.0 μmol) in THF (24 mL) was degassed and purged with $N_2$ for 3 times, and then the mixture was stirred at 80° C. for 12 hrs. LCMS showed the reaction was completed and desired mass was detected. The reaction mixture was poured into brine (24 mL) and extracted with EtOAc (12 mL×2). The combined organic layers were dried over $Na_2SO_4$, filtered and concentrated in vacuum to give residue, which was purified by column chromatography to give Compound 239-7 (170 mg, 602 μmol) as a pure white solid. $M-H^-$=280.9 (LCMS).

Step 6: N-(3,6-dimethoxy-9H-xanthen-9-yl)-2-oxo-5-phenyl-6-(trifluoromethyl)-1,2-dihydropyridine-3-carboxamide (239)

A mixture of Compound 239-7 (100 mg, 354 μmol) and Compound 239-5 (92 mg, 354.0 μmol) in HOAc (10 mL) was stirred at 25° C. for 12 hrs. LCMS showed the reaction was completed and desired mass was detected. The reaction mixture was poured into brine (10 mL) and extracted with DCM (5 mL×2). The combined organic layers were dried over Na₂SO₄, filtered and concentrated under reduced pressure to give a residue, which was purified by Prep-HPLC to give Compound 239 (34 mg, 7.0 μmol) as a yellow solid.

M−H⁻=521.1 (LCMS); ¹H NMR (400 MHz, DMSO-d6) δ=8.18 (s, 1H), 7.48-7.40 (m, 3H), 7.38 (d, J=8.6 Hz, 2H), 7.32 (br d, J=7.6 Hz, 2H), 6.81-6.65 (m, 4H), 6.41 (d, J=8.3 Hz, 1H), 3.78 (s, 6H).

Other compounds made in a similar manner are shown in Table 17.

TABLE 17

| Compound No | Structure | HNMR and Ms |
|---|---|---|
| 240 | 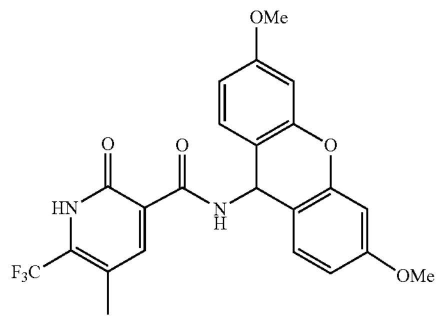 [SMILES: COc1ccc2c(c1)Oc1cc(OC)ccc1C2NC(=O)c1cc(C)c(C(F)(F)F)[nH]c1=O] | ¹H NMR (400 MHz, DMSO-d) δ = 12.95 (br s, 1H), 9.63-9.15 (m, 1H), 8.28 (s, 1H), 7.38 (d, J = 8.6 Hz, 2H), 6.78-6.70 (m, 4H), 6.40 (d, J = 8.3 Hz, 1H), 3.78 (s, 6H), 2.33 (br d, J = 2.1 Hz, 3H) ESI [M − H⁻] = 459.1 |
| 241 | 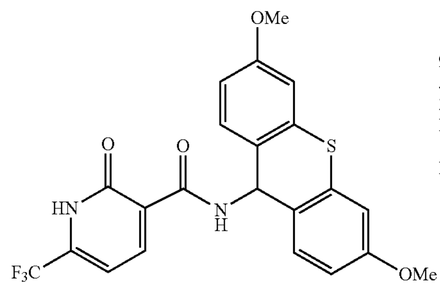 | ¹H NMR (400 MHz, DMSO-d6) δ = 13.51 (br s, 1H), 9.87-9.39 (m, 1H), 8.43 (d, J = 7.6 Hz, 1H), 7.51 (d, J = 8.6 Hz, 2H), 7.26 (br s, 1H), 7.13 (d, J = 2.3 Hz, 2H), 6.89 (dd, J = 2.4, 8.4 Hz, 2H), 6.19 (d, J=8.4 Hz, 1H), 3.77 (s, 6H) ESI [M −H⁻] = 461.1 |
| 242 | 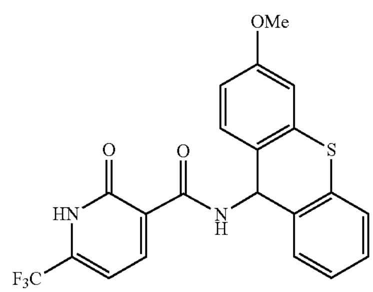 [SMILES: COc1ccc2c(c1)Sc1ccccc1C2NC(=O)c1ccc(C(F)(F)F)[nH]c1=O] | ¹H NMR (400 MHz, DMSO-d6) δ = 13.40 (s, 1H), 9.86 (s, 1H), 8.42 (d , J = 7.6 Hz, 1H), 7.54 (m, 3H), 7.34 (d, J = 3.6 Hz, 2H), 7.32 (brs, 1H), 7.16 (d, J = 2.4 Hz, 1H), 6.92 (d, J = 2.8 Hz, 1H), 6.17 (d, J = 8.4 Hz, 1H), 3.78 (s, 3H) ESI [M − H⁻] = 431.1 |
| 243 | 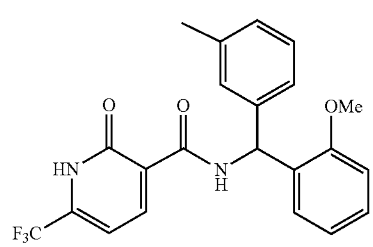 [SMILES: COc1ccccc1C(NC(=O)c1ccc(C(F)(F)F)[nH]c1=O)c1cccc(C)c1] | ¹H NMR (400 MHz, CHLOROFORM-d) δ = 13.25 (brs, 1H), 10.09 (d, J = 7.2 Hz, 1H), 8.71 (d, J = 7.2 Hz, 1H), 7.32 (d, J = 7.2 Hz, 1H), 7.18-7.14 (m, 1H), 7.05 (s, 3H), 6.95-6.90 (m, 4H), 6.88 (d, J = 4.4 Hz, 1H), 3.79 (s, 3H), 2.30 (s, 3H) ESI [M − H⁻] = 415.2 |
| 244 | 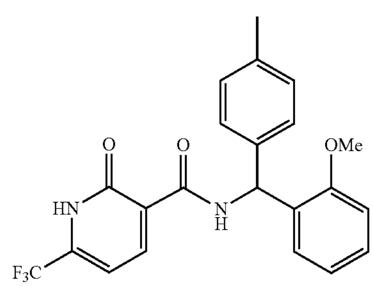 [SMILES: COc1ccccc1C(NC(=O)c1ccc(C(F)(F)F)[nH]c1=O)c1ccc(C)cc1] | ¹H NMR (400 MHz, CHLOROFORM-d) δ = 10.07 (d, J = 8.4 Hz, 1H), 8.66 (d, J = 7.2 Hz, 1H), 7.28 (d, J = 7.2 Hz, 1H), 7.22-7.09 (m, 4H), 6.97-6.90 (m, 2H), 6.88 (t, J = 7.2 Hz, 1H), 6.87-6.78 (m, 2H), 6.7 (d, J = 7.2 Hz, 1H), 3.79 (s, 3H), 2.31 (s, 3H) ESI [M − H⁻] = 415.2 |

TABLE 17-continued

| Compound No | Structure | HNMR and Ms |
|---|---|---|
| 245 | 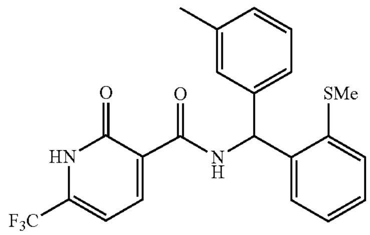 | ¹H NMR (400 MHz, CHLOROFORM-d) δ = 10.04 (d, J = 6.4 Hz, 1H), 8.67 (d, J = 7.2 Hz, 1H), 7.32-7.30 (m, 3H), 7.28-7.27 (m, 6H), 6.84 (dd, J = 5.6, 18.4 Hz, 2H), 2.44 (s, 3H), 2.31 (s, 3H)<br>ESI [M − H⁻] = 431.1 |
| 246 | 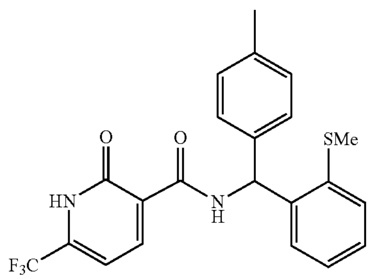 [SMILES: CSc1ccccc1C(NC(=O)c1ccc(C(F)(F)F)[nH]c1=O)c1ccc(C)cc1] | ¹H NMR (400 MHz, CHLOROFORM-d) δ = 9.99 (d, J = 7.6 Hz, 1H), 8.69 (d, J = 7.2 Hz, 1H), 7.31-7.30 (m, 3H), 7.28-7.27 (m, 6H), 6.87 (d, J = 7.2 Hz, 1H), 6.80 (d, J = 7.6 Hz, 1H), 2.44 (s, 3H), 2.32 (s, 3H)<br>ESI [M − H⁻] = 431.1 |
| 247 | 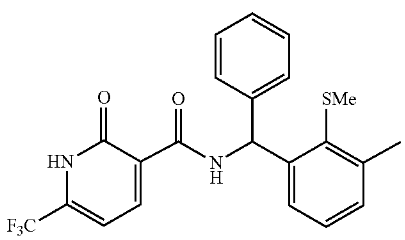 [SMILES: CSc1c(C)cccc1C(NC(=O)c1ccc(C(F)(F)F)[nH]c1=O)c1ccccc1] | ¹H NMR (400 MHz, DMSO-d6) δ = 8.36 (d, J = 8.4 Hz, 1H), 7.35-7.22 (m, 10H), 7.08 (d, J = 7.2 Hz, 1H), 2.53 (s, 3H), 2.10 (s, 3H)<br>ESI [M −H⁻] = 431.1 |
| 248 | 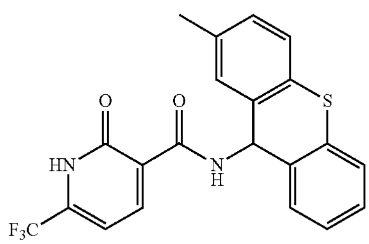 [SMILES: Cc1ccc2c(c1)C(NC(=O)c1ccc(C(F)(F)F)[nH]c1=O)c1ccccc1S2] | ¹H NMR (400 MHz, CHLOROFORM-d) δ = 9.84 (s, 1H), 8.63 (d, J = 7.2Hz, 1H), 7.60-7.59 (m, 1H), 7.48-7.41 (m, 1H), 7.40-7.38 (m, 2H), 7.27-7.26 (m, 2H), 7.25 (d, J = 2.4 Hz, 1H), 6.83 (d, J = 7.6 Hz, 1H), 6.35 (d, J = 8.0 Hz, 1H), 2.35 (s, 3H)<br>ESI [M − H⁻] = 415.1 |
| 249 | 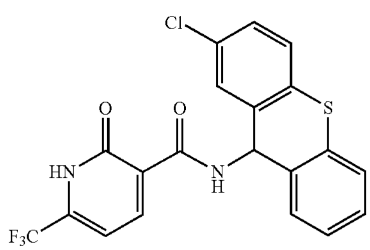 [SMILES: O=C(NC1c2ccccc2Sc2ccc(Cl)cc21)c1ccc(C(F)(F)F)[nH]c1=O] | ¹H NMR (400 MHz, DMSO-d6) δ = 9.90-9.8 (m, 1H), 8.41 (d, J = 7.6 Hz, 1H), 7.69 (s, 1H), 7.64-7.60 (m, 3H), 7.38-7.27 (m, 4H), 6.14 (d, J = 8.8 Hz, 1H)<br>ESI [M − H⁻] = 435.0 |
| 250 | 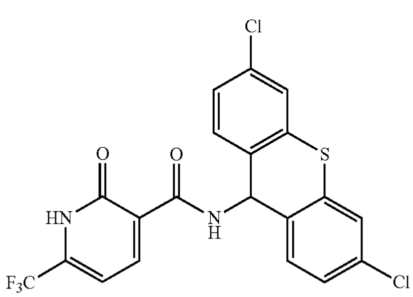 [SMILES: O=C(NC1c2ccc(Cl)cc2Sc2cc(Cl)ccc21)c1ccc(C(F)(F)F)[nH]c1=O] | ¹H NMR (400 MHz, CHLOROFORM-d) δ = 9.87 (d, J = 7.2 Hz, 1H), 8.66 (d, J = 7.6 Hz, 1H), 7.54 (d, J = 8.4 Hz, 2H), 7.49 (s, 2H), 7.25(s, 1H), 6.85 (d, J = 7.6 Hz, 1H), 6.30 (d, J = 8.0 Hz, 1H)<br>ESI [M − H⁻] = 469.0 |

TABLE 17-continued

| Compound No | Structure | HNMR and Ms |
|---|---|---|
| 251 | 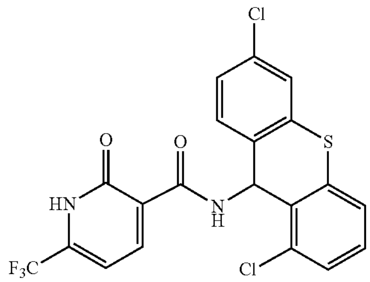 [SMILES: O=C(NC1c2ccc(Cl)cc2Sc2cccc(Cl)c21)c1ccc(C(F)(F)F)[nH]c1=O] | ¹H NMR (400 MHz, CHLOROFORM-d) δ = 9.68 (d,<br>J = 7.2 Hz, 1H), 8.63 (d, J = 7.2 Hz, 1H), 7.79 (d,<br>J = 8.4 Hz, 2H), 7.44-7.36 (m, 3H), 7.27-7.24 (m,<br>1H), 7.00 (d, J = 7.2 Hz, 1H), 6.89 (d, J = 7.6 Hz,<br>1H), 1.57(m, 1H)<br>ESI [M − H⁻] = 469.0 |
| 252 | 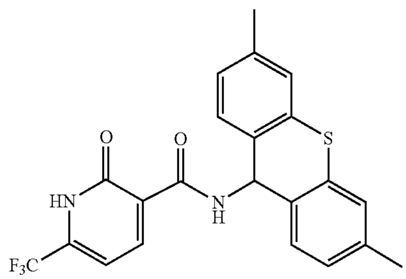 [SMILES: Cc1ccc2c(c1)Sc1cc(C)ccc1C2NC(=O)c1ccc(C(F)(F)F)[nH]c1=O] | ¹H NMR (400 MHz, CHLOROFORM-d) δ = 9.74 (d,<br>J = 7.2 Hz, 1H), 8.62 (d, J = 6.8 Hz, 1H), 7.49 (d,<br>J = 7.6 Hz, 2H), 7.30 (s, 2H), 7.07 (d, J = 7.6 Hz,<br>1H),<br>6.80 (d, J = 7.6 Hz, 1H), 6.30 (d, J = 8.0 Hz, 1H),<br>2.34<br>(m, 6H)<br>ESI [M − H⁻] = 429.1 |
| 253 | 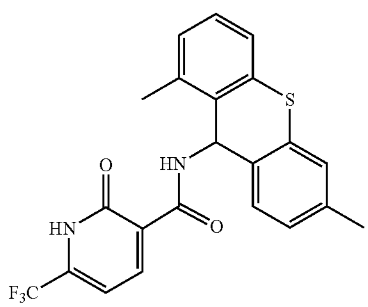 | ¹H NMR (400 MHz, DMSO-d6) δ = 13.51 (s, 1H),<br>9.58 (s, 1H), 8.41 (d, J = 7.6 Hz, 1H), 7.58 (d, J =<br>7.6 Hz, 1H), 7.42-7.40 (m, 1H), 7.37 (s, 1H),<br>7.23-7.21 (m, 3H), 7.13 (d, J = 7.6 Hz, 1H), 6.70<br>(d, J = 8.4 Hz, 1H), 2.55 (s, 3H), 2.30 (s, 3H)<br>ESI [M − H] = 429.1 |
| 254 | 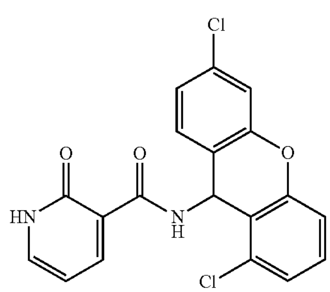 | ¹H NMR (400 MHz, DMSO-d6) δ = 12.50 (br s,<br>1H),<br>10.43 (d, J = 7.9 Hz, 1H), 8.31 (dd, J = 2.2, 7.2 Hz,<br>1H), 7.69 (dd, J = 2.2, 6.2 Hz, 1H), 7.65 (d, J = 8.4<br>Hz, 1H), 7.48-7.42 (m, 1H), 7.35-7.29 (m, 2H),<br>7.27-7.20 (m, 2H), 6.50-6.45 (m, 1H), 6.41 (d,<br>J = 7.9 Hz, 1H)<br>ESI [M − H⁻] = 385.0 |
| 255 | 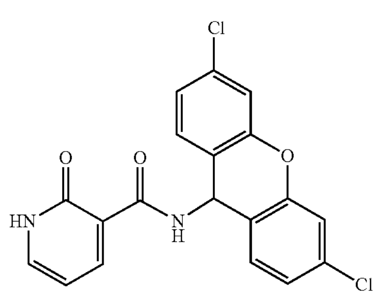 [SMILES: O=C(NC1c2ccc(Cl)cc2Oc2cc(Cl)ccc21)c1ccc[nH]c1=O] | ¹H NMR (400 MHz, DMSO-d6) δ = 12.6 (s, 1H),<br>10.54 (d, J = 8.4 Hz, 1H), 8.39 (dd, J = 2.2, 7.3 Hz,<br>1H), 7.73 (dd, J = 2.3, 6.3 Hz, 1H), 7.46 (d, J = 8.4<br>Hz, 2H), 7.31 (d, J = 2.0 Hz, 2H), 7.23 (dd, J = 2.1,<br>8.3 Hz, 2H), 6.51 (t, J = 6.7 Hz, 1H), 6.41 (d, J =<br>8.4<br>Hz, 1H)<br>ESI [M − H⁻] = 384.9 |

TABLE 17-continued
| Compound No | Structure | HNMR and Ms |
|---|---|---|
| 56 | 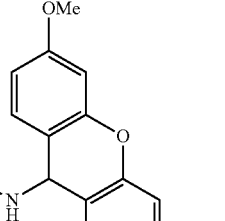 | 1H NMR (400MHz, DMSO-d) δ = 12.30 (d, J = 8.8 Hz, 1H), 8.14 (d, J = 7.5 Hz, 1H), 7.32 (d, J = 8.4 Hz, 2H), 6.78-6.68 (m, 5H), 6.49 (d, J = 7.5 Hz, 1H), 6.34 (d, J = 8.6 Hz, 1H), 3.78 (s, 6H) ESI [M − H⁻] = 445.0 |
| 55 | 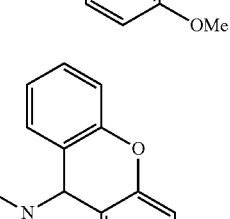 | $^1$H NMR (400 MHz, CHLOROFORM-d) δ = 9.68 (br s, 1H), 8.68 (d, J = 7.3 Hz, 1H), 7.53 (d, J = 1.1 Hz, 1H), 7.40 (d, J = 7.9 Hz, 1H), 7.35-7.28 (m, 1H), 7.15 (d, J = 7.9 Hz, 1H), 7.08 (t, J = 7.5 Hz, 1H), 6.98 (s, 1H), 6.92 (d, J = 1.1 Hz, 1H), 6.83 (d, J = 1.5 Hz, 1H), 6.61 (d, J = 8.6 Hz, 1H), 2.37 (s, 3H) ESI [M − H⁻] = 399.1 |
Example 28: Synthesis of N-(4-methoxy-6-methyl-2,3-dihydro-1H-inden-1-yl)-2-oxo-6-(trifluoromethyl)-1,2-dihydropyridine-3-carboxamide (256)
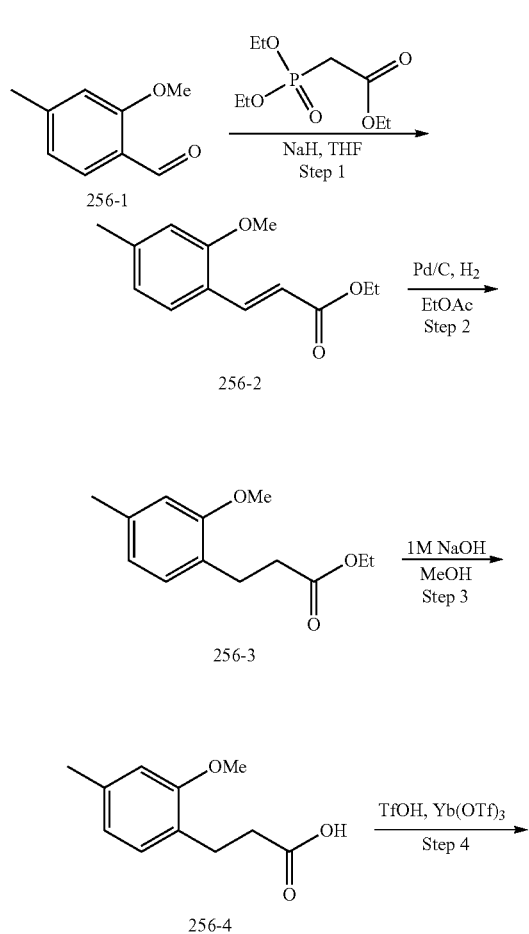
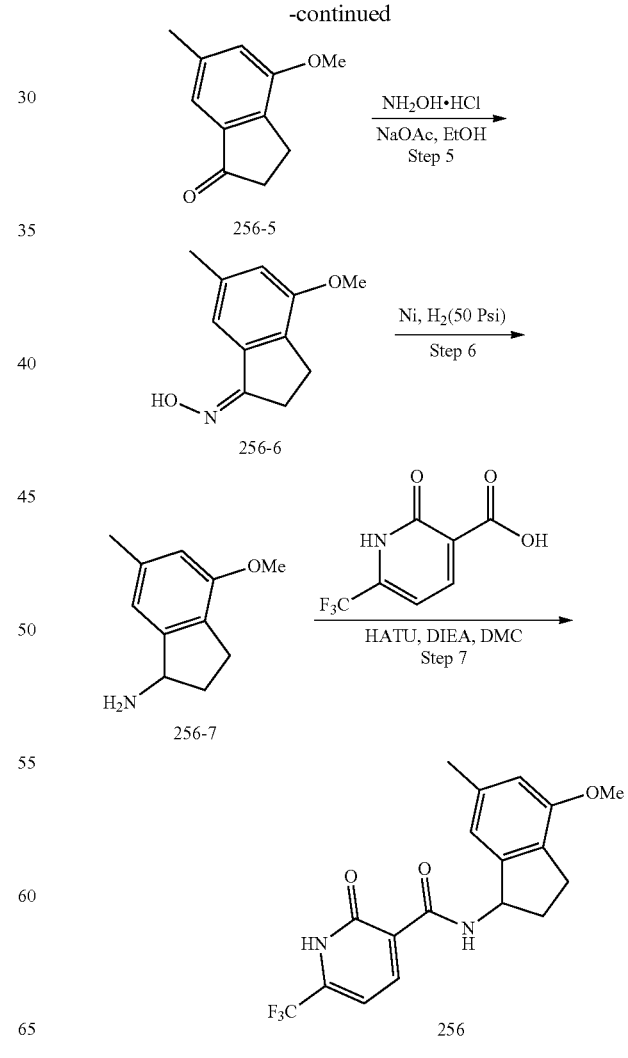

Step 1: (E)-ethyl 3-(2-methoxy-4-methylphenyl) acrylate (256-2)

To a solution of ethyl 2-(diethoxyphosphoryl)acetate (7.1 g, 32.0 mmol) in THF (30 mL) was added NaH (639 mg, 16.0 mmol, 60% purity) at 0° C., the mixture was stirred at 0° C. for 15 min, then 256-1 (2 g, 13.3 mmol) in THF (5 mL) was added to the mixture. The mixture was stirred at 20° C. for 12 hrs. LCMS showed the reaction completed. The reaction mixture was added to $H_2O$ (40 mL) at 25° C. and extracted with EtOAc (15 ml×3). The combined organic layers were dried over $Na_2SO_4$, filtered and concentrated under reduced pressure to give a residue, which was purified by column chromatography to give Compound 256-2 (2 g, crude) as white oil. $M+H^+$=221.0 (LCMS). $^1$H NMR (400 MHz, $CHCl_3$-d) δ=7.96 (d, J=16.1 Hz, 1H), 7.40 (d, J=7.7 Hz, 1H), 6.78 (d, J=7.7 Hz, 1H), 6.73 (s, 1H), 6.50 (d, J=16.1 Hz, 1H), 4.26 (q, J=7.2 Hz, 2H), 3.88 (s, 3H), 2.38 (s, 3H), 1.34 (t, J=7.2 Hz, 3H).

Step 2: ethyl 3-(2-methoxy-4-methylphenyl)propanoate (256-3)

To a solution 256-2 (2 g, 9.1 mmol) in EtOAc (15 mL) was added Pd/C (300 mg, 10% purity). The mixture was degassed and purged with $H_2$ for 3 times, and then stirred at 25° C. for 1 hr under $H_2$ (15 Psi). TLC indicated the reaction was completed. The reaction mixture was filtered and the filtrate was concentrated in vacuum to give Compound 256-3 (2 g, crude) as white oil.

Step 3: 3-(2-methoxy-4-methylphenyl)propanoic acid (256-4)

To a solution of 256-3 (1 g, 4.5 mmol) in MeOH (9 mL) was added NaOH (1M, 9.0 mL) at 0° C., then the mixture was stirred at 15° C. for 12 hrs. TLC indicated the reaction completed. The reaction mixture was added to $H_2O$ (3 mL) and extracted with HCl (1M) to adjust the pH to 6-7. The mixture was filtered and concentrated in vacuum to give Compound 256-4 (700 mg, crude) as a white solid. $^1$H NMR (400 MHz, CHLOROFORM-d) δ=7.04 (d, J=7.5 Hz, 1H), 6.77-6.63 (m, 2H), 3.82 (s, 3H), 2.95-2.84 (m, 2H), 2.71-2.60 (m, 2H), 2.34 (s, 3H).

Step 4: 4-methoxy-6-methyl-2,3-dihydro-1H-inden-1-one (256-5)

A mixture of 256-4 (500 mg, 2.6 mmol), Yb(OTf)3 (160 mg, 257.4 μmol) in TfOH (5 mL) was stirred at 50° C. for 30 mins under microwave. LCMS showed the reaction completed. The reaction mixture was poured into Sat. $NaHCO_3$ aq. (10 mL) and extracted with DCM (10 mL×3). The combined organic layers were concentrated under reduced pressure to give a residue, which was purified by column chromatography to give Compound 256-5 (120 mg, crude) as a white solid. $M+H^+$=177.1 (LCMS)

Step 5: (Z)-4-methoxy-6-methyl-2,3-dihydro-1H-inden-1-one oxime (256-6)

To a solution of 256-5 (10 mg, 56.7 μmol) in EtOH (1 mL) was added $NH_2OH.HCl$ (6 mg, 85 μmol) and NaOAc (11 mg, 142 μmol). The mixture was stirred at 70° C. for 12 hrs. LCMS showed the reaction completed. The reaction mixture was added to $H_2O$ (2 mL) and extracted with EtOAc (2 ml×3), then dried over $Na_2SO_4$, filtered and the cake was dried in vacuum to give Compound 256-6 (11 mg, crude) as a white solid. $M+H^+$=192.0 (LCMS)

Step 6: 4-methoxy-6-methyl-2,3-dihydro-1H-inden-1-amine (256-7)

To a solution of Compound 256-6 (10 mg, 57 μmol) in MeOH (5 mL) and $NH_3 \cdot H_2O$ (1 mL) was added Raney-Ni (20 mg). The mixture was stirred at 50° C. for 12 hrs under $H_2$ (50 Psi). LCMS showed the reaction was completed. The reaction mixture was filtered and the cake was dried in vacuum to give Compound 256-7 (11 mg, crude) as a white solid. Fragment MS=161.0 (LCMS).

Step 7: N-(4-methoxy-6-methyl-2,3-dihydro-1H-inden-1-yl)-2-oxo-6-(trifluoro methyl)-1,2-dihydro-pyridine-3-carboxamide (256)

To a solution of 256-7 (10 mg, 57 μmol) 2-oxo-6-(trifluoromethyl)-1,2-dihydro pyridine-3-carboxylic acid (12 mg, 57 μmol) in DCM (1.5 mL) was added DIEA (22 mg, 170 μmol) and HATU (26 mg, 68 μmol). The mixture was stirred at 20° C. for 1 hr. LCMS showed the reaction completed. The reaction mixture was added to $H_2O$ (3 mL) and extracted with EtOAc (5 ml×3), then dried over $Na_2SO_4$, filtered and concentrated under reduced pressure to give a residue, which was purified by prep-HPLC to give Compound 256 (2 mg, 4.1 μmol, 8% yield) as a white solid. $M-H^-$=365.1 (LCMS); $^1$H NMR (400 MHz, $CHCl_3$-d) δ=9.49 (br d, J=6.6 Hz, 1H), 8.71 (d, J=7.4 Hz, 1H), 6.88 (d, J=7.4 Hz, 1H), 6.79 (s, 1H), 6.60 (s, 1H), 5.59 (q, J=7.5 Hz, 1H), 3.85 (s, 3H), 3.06-2.93 (m, 1H), 2.79 (td, J=7.8, 15.6 Hz, 1H), 2.70-2.59 (m, 1H), 2.34 (s, 3H), 2.04-1.87 (m, 1H).

Another compound made in a similar manner is shown in Table 18.

TABLE 18

| Compound No | Structure | HNMR and Ms |
| --- | --- | --- |
| 257 | 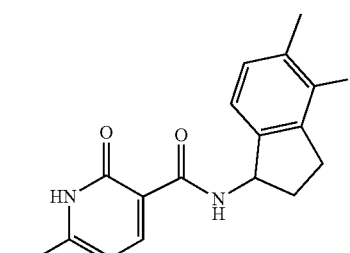 | $^1$H NMR (400 MHz, CHLOROFORM-d) δ = 12.37 (br s, 1H), 9.50 (br d, J = 7.1 Hz, 1H), 8.70 (d, J = 7.5 Hz, 1H), 7.11-6.98 (m, 2H), 6.87 (d, J = 7.3 Hz, 1H), 5.58 (q, J = 7.4 Hz, 1H), 3.82 (s, 3H), 3.20-3.07 (m, 1H), 2.96 (td, J = 7.7, 15.9 Hz, 1H), 2.76-2.57 (m, 1H), 2.29 (s, 3H), 2.06-1.91 (m, 1H) ESI [M− H] = 365.1 |

Example 29: Synthesis of N-(3,6-dimethyl-9H-thio-xanthen-9-yl)-2-oxo-5-((tetrahydro-2H-pyran-4-yl)oxy)6-(trifluoromethyl)-1,2-dihydropyridine-3-carboxamide (258)

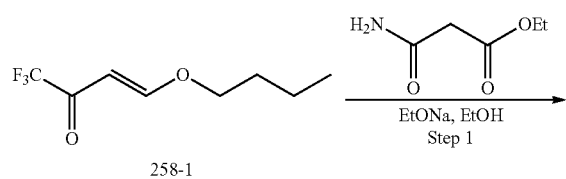

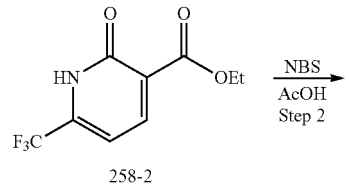

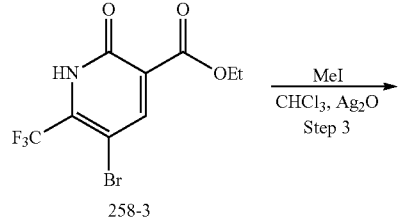

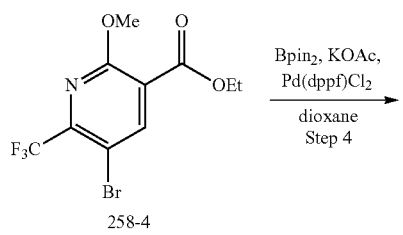

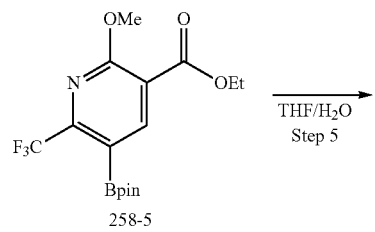

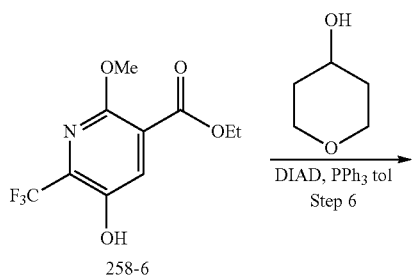

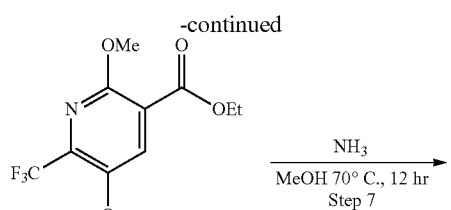

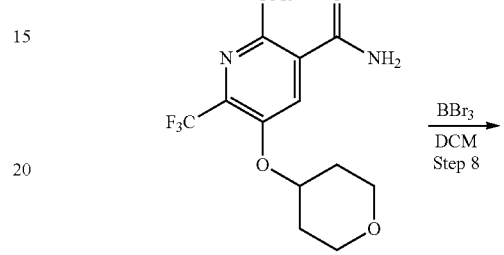

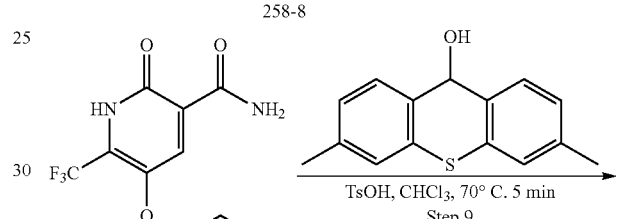

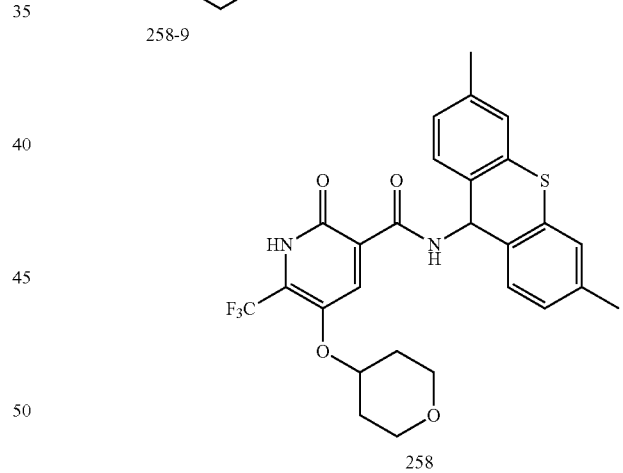

Step 1: ethyl 2-oxo-6-(trifluoromethyl)-1,2-dihydropyridine-3-carboxylate (258-2)

To a solution of Compound 258-1 (10 g, 51 mmol) in EtOH (150 mL) was added ethyl 3-amino-3-oxopropanoate (6.7 g, 51 mmol) and EtONa/EtOH (17.3 g, 51 mmol) at 0° C. The mixture was stirred at 80° C. for 12 hrs. LCMS showed the reaction was completed and desired mass was detected. The reaction mixture was poured into H$_2$O (200 mL), neutralized with HCl solution (1 M) to pH=7 and then extracted with EtOAc (200 mL×3). The combined organic layers were dried over Na$_2$SO$_4$, filtered and concentrated under reduced pressure to give a residue, which was purified by flash silica gel chromatography to give a Compound 258-2 (7.1 g, crude) as a light brown solid. M+H$^+$=236.0 (LCMS); $^1$H NMR (400 MHz, CDCl$_3$) δ=11.56 (s, 1H), 8.46-8.35 (m, 1H), 7.32 (d, J=7.8 Hz, 1H), 4.51 (q, J=7.1 Hz, 2H), 1.46 (t, J=7.2 Hz, 3H).

Step 2: ethyl 5-bromo-2-oxo-6-(trifluoromethyl)-1,2-dihydropyridine-3-carboxylate (258-3)

To a solution of Compound 258-2 (7 g, 29.8 mmol) in AcOH (120 mL) was added NBS (8 g, 44.6 mmol). The mixture was stirred at 120° C. for 12 hrs. LCMS showed 20% of the starting material still remained. Another batch of NBS (2 g, 11.2 mmol) was added and stirred at 120° C. for another 12 hrs. LCMS showed the reaction completed and desired mass was detected. The reaction mixture was concentrated under reduced pressure to give a residue, which was purified by flash silica gel chromatography to give a Compound 258-3 (7.4 g, crude) as light yellow oil. M+H$^+$=316.0 (LCMS); $^1$H NMR (400 MHz, DMSO-d$_6$) δ=12.74 (br s, 1H), 8.45 (s, 1H), 4.30 (q, J=7.1 Hz, 2H), 1.30 (t, J=7.2 Hz, 3H).

Step 3: ethyl 5-bromo-2-methoxy-6-(trifluoromethyl)nicotinate (258-4)

To a solution of 258-3 (7.4 g, 23.6 mmol) in CHCl$_3$ (80 mL) was added MeI (33.5 g, 235.6 mmol) and Ag$_2$O (10.9 g, 47.3 mmol). The mixture was stirred at 80° C. for 12 hrs. LCMS showed the reaction was completed and desired mass was detected. The reaction mixture was filtered and concentrated to give a residue, which was purified by flash silica gel chromatography to give a product 258-4 (4.5 g, crude) as a white solid. M+H$^+$=330.0 (LCMS); $^1$H NMR (400 MHz, DMSO-d$_6$) δ=8.50 (s, 1H), 4.31 (q, J=7.2 Hz, 2H), 3.96 (s, 3H), 1.31 (t, J=7.1 Hz, 3H).

Step 4: ethyl 2-methoxy-5-(4,4,5,5-tetramethyl-1,3,2-dioxaborolan-2-yl)-6-(trifluoromethyl)nicotinate (258-5)

To a mixture of Compound 258-4 (4 g, 12.2 mmol), 4,4,4',4',5,5,5',5'-octamethyl-2,2'-bi(1,3,2-dioxaborolane) (3.4 g, 13.4 mmol), KOAc (3.6 g, 36.6 mmol) in dioxane (80 mL) was added Pd(dppf)Cl$_2$·DCM (996 mg, 1.2 mmol). The mixture was stirred at 80° C. under N$_2$ for 12 hrs. LCMS showed the reaction completed and desired mass was detected. The reaction mixture was filtered and concentrated under reduced pressure to give a residue. The residue was purified by flash silica gel chromatography to give a Compound 258-5 (4 g, crude) as brown oil. M+H$^+$=376.1 (LCMS).

Step 5: ethyl 5-hydroxy-2-methoxy-6-(trifluoromethyl)nicotinate (258-6)

To a solution of Compound 258-5 (4 g, 10.7 mmol) in THF (60 mL) and H$_2$O (4 mL) was added sodium perborate tetrahydrate (2.5 g, 16 mmol). The mixture was stirred at 20° C. for 12 hrs. LCMS showed the reaction was completed and desired mass was detected. The reaction mixture was poured into water 100 mL and extracted with EtOAc (40 mL×3). The combined organic layers were dried over Na$_2$SO$_4$, filtered and concentrated under reduced pressure to give a residue. The residue was purified by flash silica gel chromatography to give a Compound 258-6 (1.2 g, crude) as a white solid. M+H$^+$=266.1 (LCMS); $^1$H NMR (400 MHz, CDCl$_3$) δ=7.90 (s, 1H), 5.93 (br s, 1H), 4.40 (q, J=7.1 Hz, 2H), 4.01 (s, 3H), 1.39 (t, J=7.1 Hz, 3H).

Step 6: ethyl 2-methoxy-5-((tetrahydro-2H-pyran-4-yl)oxy)-6-(trifluoromethyl)nicotinate (258-7)

To a solution of Compound 258-6 (1.2 g, 4.5 mmol), tetrahydro-2H-pyran-4-ol (693 mg, 6.8 mmol) and PPh$_3$ (1.8 g, 6.8 mmol) in Tol (20 mL) was added DIAD (1.4 g, 6.8 mmol, 1.3 mL) at 0° C. The mixture was stirred at 15° C. under N$_2$ for 12 hrs. LCMS showed Reactant was consumed completely and desired mass was detected. The reaction mixture was poured into H$_2$O (50 mL) and extracted with EtOAc (30 mL×2). The combined organic layers were dried over Na$_2$SO$_4$, filtered and concentrated under reduced pressure to give a residue, which was purified by column chromatography to give a product Compound 258-7 (1.4 g, crude) as a colorless solid. M+H$^+$=350.1 (LCMS); $^1$H NMR (400 MHz, CDCl$_3$) δ=7.88 (s, 1H), 4.56 (td, J=3.6, 7.2 Hz, 1H), 4.41 (q, J=7.2 Hz, 2H), 4.03 (s, 3H), 3.97 (ddd, J=3.6, 7.3, 11.4 Hz, 2H), 3.61 (ddd, J=3.5, 7.5, 11.5 Hz, 2H), 2.08-1.96 (m, 2H), 1.84 (ttd, J=3.7, 7.1, 10.2 Hz, 2H), 1.41 (t, J=7.2 Hz, 3H).

Step 7: 2-methoxy-5-((tetrahydro-2H-pyran-4-yl)oxy)-6-(trifluoromethyl)nicotin amide (258-8)

A mixture of Compound 258-7 (800 mg, 2.3 mmol) and NH$_3$/MeOH (7 M, 12 mL) was stirred at 70° C. for 3 hrs in a sealed tube. LCMS showed the reaction was completed and desired mass was detected. The reaction mixture was concentrated under reduced pressure to give a Compound 258-8 (730 mg, crude) as a white solid. M+H$^+$=321.1 (LCMS); $^1$H NMR (400 MHz, DMSO-d$_6$) δ=8.12 (s, 1H), 7.96-7.68 (m, 2H), 4.89-4.75 (m, 1H), 3.93 (s, 3H), 3.86-3.71 (m, 2H), 3.49 (ddd, J=3.0, 8.7, 11.5 Hz, 2H), 1.98-1.88 (m, 2H), 1.59 (dtd, J=4.0, 8.5, 12.8 Hz, 2H).

Step 8: 2-oxo-5-((tetrahydro-2H-pyran-4-yl)oxy)-6-(trifluoromethyl)-1,2-dihydro pyridine-3-carboxamide (258-9)

To a solution of Compound 258-8 (600 mg, 1.9 mmol) in DCM (30 mL) was added BBr$_3$ (2.8 g, 11.2 mmol) in DCM (2 mL) at −78° C. under N$_2$. Then the mixture was stirred at 20° C. for 3 hrs. TLC showed the reaction completed. The reaction mixture was added to ice-H$_2$O (50 mL) slowly, and then extracted with DCM:MeOH=10:1 (30 mL×3). The combined organic layers were dried over Na$_2$SO$_4$, filtered and concentrated under reduced pressure to give a residue. The crude product was triturated with Petroleum ether (6 mL) at 20° C. for 2 hrs and filtered to give Compound 258-9 (500 mg, crude) as brown solid. $^1$H NMR (400 MHz, DMSO-d$_6$) δ=13.63-12.44 (m, 1H), 8.41 (br s, 1H), 8.26 (s, 1H), 8.20 (br s, 1H), 4.71 (td, J=4.1, 8.0 Hz, 1H), 3.87-3.72 (m, 2H), 3.48 (ddd, J=2.9, 8.6, 11.5 Hz, 2H), 2.02-1.89 (m, 2H), 1.59 (dtd, J=4.0, 8.5, 12.8 Hz, 2H).

Step 9: N-(3,6-dimethyl-9H-thioxanthen-9-yl)-2-oxo-5-((tetrahydro-2H-pyran-4-yl)oxy)-6-(trifluoromethyl)-1,2-dihydropyridine-3-carboxamide (258)

A mixture of 3,6-dimethyl-9H-thioxanthen-9-ol (150 mg, 619 μmol) in DCM (8 mL) was added to a mixture of Compound 258-9 (120 mg, 391.9 μmol) and TsOH.H$_2$O (177 mg, 928.5 μmol) in CHCl$_3$ (8 mL) at 70° C., the mixture was stirred at 70° C. for 5 mins. LCMS showed reactant was consumed completely and desired mass was detected. The reaction mixture was poured into H$_2$O (20 mL) and extracted with DCM (10 mL×2). The combined organic layers were dried over Na$_2$SO$_4$, filtered and concentrated under reduced pressure to give a residue. The residue was purified by prep-HPLC to give Compound 258 (10 mg, 18.3 μmol, 3% yield) as yellow solid. M−H$^-$=529.1 (LCMS); $^1$H NMR (400 MHz, DMSO-d$_6$) δ=13.27-12.43 (m, 1H), 9.92-9.21 (m, 1H), 8.21 (s, 1H), 7.49 (d, J=7.8 Hz, 2H), 7.38 (s, 2H), 7.13 (d, J=7.7 Hz, 2H), 6.12 (br d, J=8.6 Hz, 1H), 4.71 (br d, J=3.3 Hz, 1H), 3.89-3.71 (m, 2H), 3.47 (ddd, J=2.9, 8.7, 11.5 Hz, 2H), 2.30 (s, 6H), 1.99-1.83 (m, 2H), 1.66-1.49 (m, 2H).

Other compounds made in a similar manner are shown in Table 19.

Example 30: Synthesis of N-(5-hydroxy-1,2,3,4-tetrahydronaphthalen-1-yl)-2-oxo-6-((3-(trifluoromethyl)benzyl)thio)-1,2-dihydropyridine-3-carboxamide (261)

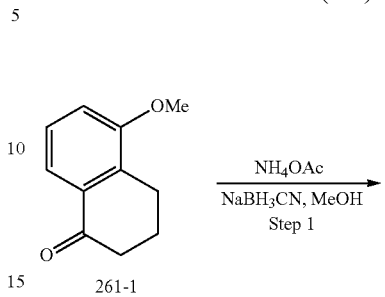

TABLE 19

| Compound No | Structure | HNMR and Ms |
|---|---|---|
| 259 | [Structure: pyridinone carboxamide with F$_3$C, tetrahydropyran-O, linked via NH to xanthene bearing two OMe groups] | $^1$H NMR (400 MHz, DMSO-d$_6$) δ = 12.77 (br s, 1H), 9.52-9.02 (m, 1H), 8.21 (s, 1H), 7.39 (d, J = 8.6 Hz, 2H), 6.81-6.65 (m, 4H), 6.39 (d, J = 8.2 Hz, 1H), 4.78-4.66 (m, 1H), 3.78 (s, 8H), 3.52-3.40 (m, 2H), 1.99-1.86 (m, 2H), 1.58 (dtd, J = 3.9, 8.3, 12.6 Hz, 2H). ESI [M − H] = 545.1 |
| 260 | [Structure: pyridinone carboxamide with F$_3$C, tetrahydropyran-O, linked via NH to xanthene bearing two methyl groups] | $^1$H NMR (400 MHz, DMSO-d$_6$) δ = 12.75 (br s, 1H), 9.49 (s, 1H), 8.38-8.08 (m, 1H), 7.36 (d, J = 7.8 Hz, 2H), 7.07-6.89 (m, 4H), 6.43 (d, J = 8.3 Hz, 1H), 4.69 (br s, 1H), 3.88-3.75 (m, 2H), 3.48 (ddd, J = 3.1, 8.5, 11.5 Hz, 2H), 2.33 (s, 6H), 1.99-1.87 (m, 2H), 1.59 (dtd, J = 4.0, 8.4, 12.7 Hz, 2H) ESI [M − H] = 513.2 |

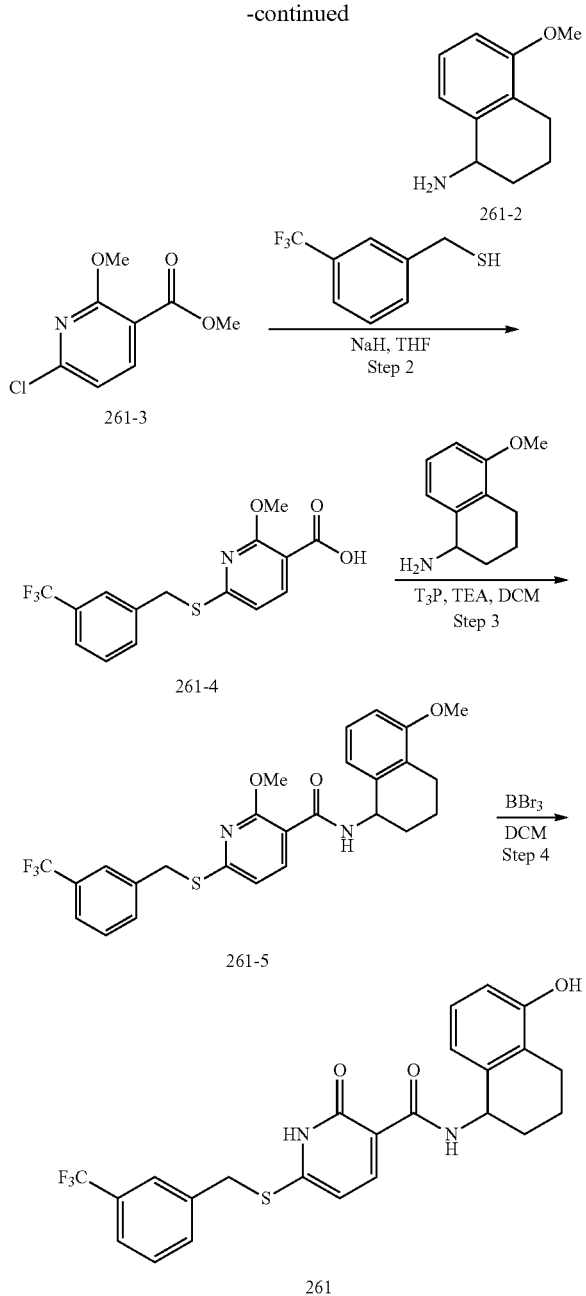

Step 1: 5-methoxy-1,2,3,4-tetrahydronaphthalen-1-amine (261-2)

To a stirred solution of Compound 261-1 (300 mg, 1.7 mmol) in MeOH (6 mL) was added then NH₄OAc (1.9 g, 25.5 mmol), the reaction was stirred for 10 min at 20° C., NaBH₃CN (428 mg, 6.8 mmol) was added and the reaction was stirred at 90° C. for 6 hrs under microwave. LCMS showed the reaction completed and the fragment of desired mass was detected. The reaction mixture was poured into H₂O (10 mL), then was extracted with EtOAc (10 mL×3). The combined organic layers were washed with Sat.NaCl (10 mL), dried over Na₂SO₄, filtered and concentrated under reduced pressure to give crude Compound 261-2 (300 mg, crude) as a yellow gum. Fragment Ms=161.0 (LCMS)

Step 2: 2-methoxy-6-((3-(trifluoromethyl)benzyl) thio)nicotinic acid (261-4)

To a 0° C. solution of (3-(trifluoromethyl)phenyl)methanethiol (420 mg, 2.2 mmol) in THF (16 mL) was added NaH (157 mg, 3.9 mmol, 60% purity) in portions. After addition, the mixture was stirred at 20° C. for 15 min, and then Compound 261-3 (440 mg, 2.2 mmol) was added dropwise at 0° C. The resulting mixture was stirred at 20° C. for 2 hrs. LCMS showed the reaction completed and the desired mass was detected. The reaction mixture was poured into H₂O (15 mL) at 0° C., and then extracted with EtOAc (10 mL×5). The combined organic layers were washed with brine (10 mL×1), dried over Na₂SO₄, filtered and concentrated under reduced pressure to give a residue, which was purified by column chromatography (Ethyl acetate/Petroleum) to give Compound 261-4 (150 mg, 437 μmol, 20% yield) as a white gum. M+H⁺=344.0 (LCMS); ¹H NMR (400 MHz, DMSO-d₆) δ=7.80 (s, 1H), 7.73 (br d, J=7.7 Hz, 2H), 7.63-7.50 (m, 2H), 6.89-6.83 (m, 1H), 4.55 (s, 2H), 3.86-3.81 (m, 3H).

Step 3: 2-methoxy-N-(5-methoxy-1,2,3,4-tetrahydronaphthalen-1-yl)-6-((3-(trifluoromethyl)benzyl) thio)nicotinamide (261-5)

To a stirred solution of Compound 261-4 (170 mg, 495 μmol) and Compound 6A-2 (105 mg, 594 μmol) in DCM (8 mL) was added TEA (150 mg, 1.5 mmol), followed by T₃P (473 mg, 742 μmol, 50% purity). The resulting mixture was stirred at 25° C. for 1 hr. TLC showed the reaction was completed. Then the mixture was diluted with H₂O (10 mL) and extracted with EtOAc (10 mL×3). The combined organic layers dried over Na₂SO₄ and concentrated under reduced pressure to give a residue, which was purified by prep-TLC (Petroleum ether/Ethyl acetate=3/1) to give Compound 261-5 (160 mg, 318 μmol, 64% yield) as a white solid.

Step 4: N-(5-hydroxy-1,2,3,4-tetrahydronaphthalen-1-yl)-2-oxo-6-((3-(trifluoromethyl) benzyl)thio)-1,2-dihydropyridine-3-carboxamide (261)

To a solution of Compound 261-5 (50 mg, 99 μmol) in DCM (5 mL) was added BBr₃ (249 mg, 995 μmol) in DCM (0.5 mL) at −78° C. The mixture was stirred at −78° C. for 1 hr then at 20° C. for 2 hrs. LCMS showed the reaction completed and one main peak with desired mass was detected. Then the mixture was diluted with H₂O (15 mL) and extracted with DCM (10 mL×6). The combined organic layers dried over Na₂SO₄ and concentrated under reduced pressure to give a residue, which was purified by prep-HPLC to give Compound 261 (15.90 mg, 32 μmol, 32% yield) as a white solid. M+H⁺=473.1 (LCMS), ¹H NMR (400 MHz, DMSO-d₆) δ=12.82 (br s, 1H), 9.81 (br s, 1H), 9.32 (s, 1H), 8.20 (d, J=7.8 Hz, 1H), 7.80 (s, 1H), 7.73 (br d, J=7.5 Hz, 1H), 7.69-7.62 (m, 1H), 7.61-7.54 (m, 1H), 6.99-6.88 (m, 1H), 6.67 (dd, J=2.9, 7.7 Hz, 2H), 6.53 (br s, 1H), 5.10 (br d, J=6.8 Hz, 1H), 4.51 (s, 2H), 2.67-2.53 (m, 2H), 1.97-1.85 (m, 1H), 1.82-1.60 (m, 3H).

Example 31: Synthesis of N-((1R,3R)-3-(2-hydroxyethyl)-1,2,3,4-tetrahydronaphthalen-1-yl)-2-oxo-6-(trifluoromethyl)-1,2-dihydropyridine-3-carboxamide (262) and N-((1R,3S)-3-(2-hydroxyethyl)-1,2,3,4-tetrahydronaphthalen-1-yl)-2-oxo-6-(trifluoromethyl)-1,2-dihydropyridine-3-carboxamide (263)

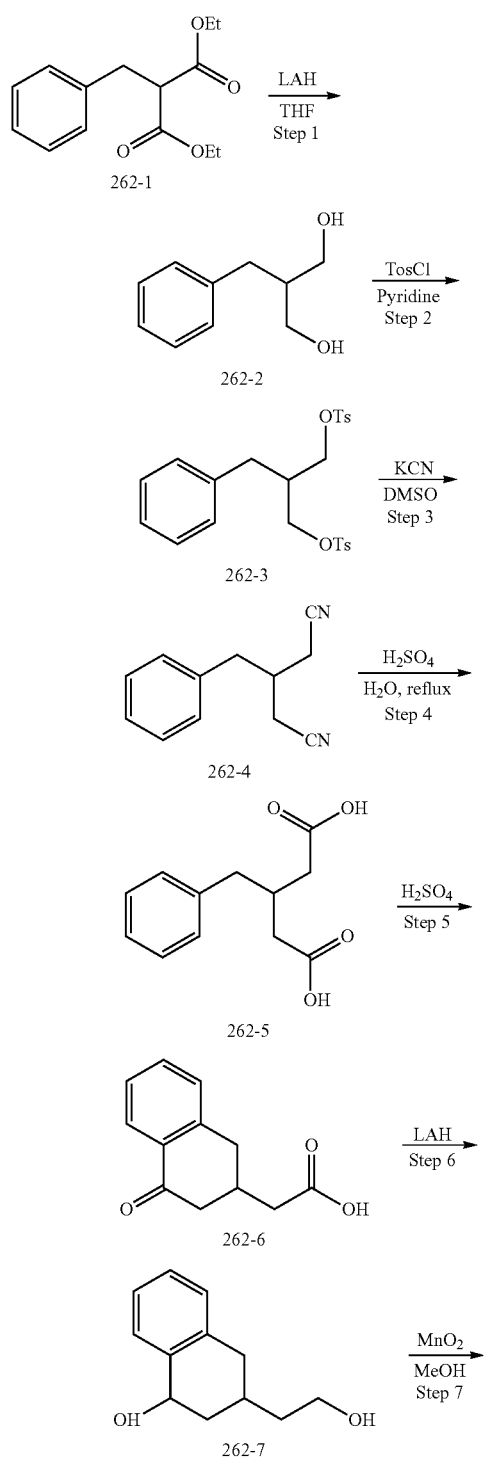

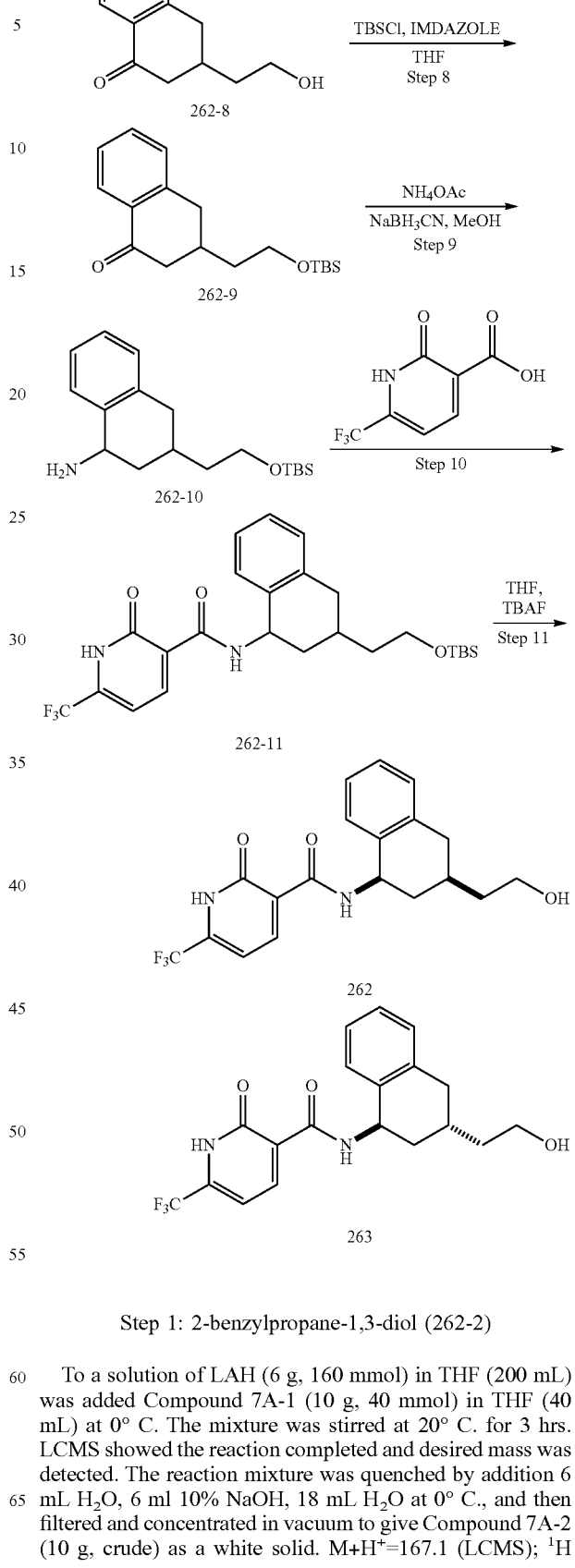

Step 1: 2-benzylpropane-1,3-diol (262-2)

To a solution of LAH (6 g, 160 mmol) in THF (200 mL) was added Compound 7A-1 (10 g, 40 mmol) in THF (40 mL) at 0° C. The mixture was stirred at 20° C. for 3 hrs. LCMS showed the reaction completed and desired mass was detected. The reaction mixture was quenched by addition 6 mL H$_2$O, 6 ml 10% NaOH, 18 mL H$_2$O at 0° C., and then filtered and concentrated in vacuum to give Compound 7A-2 (10 g, crude) as a white solid. M+H$^+$=167.1 (LCMS); $^1$H NMR (400 MHz, CHCl$_3$-d) δ=7.38-7.29 (m, 2H), 7.26-7.20 (m, 3H), 3.86 (dd, J=3.8, 10.6 Hz, 2H), 3.77-3.68 (m, 2H), 2.68 (d, J=7.6 Hz, 2H), 2.18-2.04 (m, 1H).

Step 2: 2-benzylpropane-1,3-diyl bis(4-methylbenzenesulfonate) (262-3)

To a solution of TosCl (10 g, 53 mmol) in Py (24 mL) was a solution of Compound 7A-2 (4 g, 24 mmol) in Py (16 mL) drop wise at 0° C. The mixture was stirred at 15° C. for 4 hrs. LCMS showed the reaction completed and desired mass was detected. The reaction mixture was added to HCl (3 M aq., 40 mL) at 0° C. and extracted with EtOAc (5 ml×3), and then dried over Na$_2$SO$_4$, filtered and concentrated under reduced pressure to give a residue. The crude product was triturated with EtOH 50° C. for 10 mins and filtered to give Compound 7A-3 (10 g, crude) as a white solid. M+H$^+$=475.1 (LCMS); $^1$H NMR (400 MHz, CHCl$_3$-d) δ=7.74 (d, J=8.3 Hz, 4H), 7.35 (d, J=7.9 Hz, 4H), 7.23-7.15 (m, 3H), 7.01-6.92 (m, 2H), 4.01-3.96 (m, 2H), 3.93-3.86 (m, 2H), 2.59 (d, J=7.6 Hz, 2H), 2.48 (s, 6H), 2.32-2.19 (m, 1H).

Step 3: 3-benzylpentanedinitrile (262-4)

To a solution of Compound 7A-3 (10 g, 21 mmol) in DMSO (200 mL) was added KCN (6 g, 92 mmol). The mixture was stirred at 80° C. for 4 hrs. TLC indicated the reaction completed. The reaction mixture was added to Sat. aq. NaCl (200 mL) and extracted with EtOAc (50 ml×5). The combined organic layers were dried over Na$_2$SO$_4$, filtered and concentrated under reduced pressure to give a residue, which was purified by column chromatography to give Compound 7A-4 (3 g, crude) as a white solid. $^1$H NMR (400 MHz, CHCl$_3$-d) δ=7.40-7.34 (m, 2H), 7.33-7.28 (m, 1H), 7.20 (d, J=7.1 Hz, 2H), 2.86 (d, J=7.1 Hz, 2H), 2.60-2.38 (m, 5H).

Step 4: 3-benzylpentanedioic acid (262-5)

Compound 7A-4 (3 g, 16 mmol) was added to a solution of H$_2$O (60 mL) and H$_2$SO$_4$ (60 mL). The mixture was stirred at 100° C. for 12 hrs. TLC indicated the reaction completed. The reaction mixture was added to H$_2$O (3 mL) and extracted with EtOAc (5 ml×3), then dried over Na$_2$SO$_4$, filtered and concentrate to give Compound 7A-5 (2.5 g, crude) as yellow oil. M+H$^+$=223.1 (LCMS).

Step 5: 2-(4-oxo-1,2,3,4-tetrahydronaphthalen-2-yl)acetic acid (262-6)

To a solution of H$_2$SO$_4$ (8 mL) was added 7A-5 (2.5 g, 11 mmol), then the mixture was stirred at 25° C. for 1 hr. TLC indicated the reaction completed. The reaction mixture was added to H$_2$O (3 mL) and extracted with EtOAc (5 ml×3), and then dried over Na$_2$SO$_4$, filtered and concentrated to give Compound 7A-6 (1.5 g, crude) as a white oil. $^1$H NMR (400 MHz, CHCl$_3$-d) δ=10.68 (br s, 1H), 8.04 (d, J=7.8 Hz, 1H), 7.51 (dt, J=1.3, 7.5 Hz, 1H), 7.34 (t, J=7.5 Hz, 1H), 7.29 (s, 1H), 3.13 (br d, J=15.2 Hz, 1H), 2.92-2.72 (m, 3H), 2.59-2.39 (m, 3H)

Step 6: 3-(2-hydroxyethyl)-1,2,3,4-tetrahydronaphthalen-1-ol (262-7)

To a solution of 7A-6 (950 mg, 4.6 mmol) in THF (40 mL) was added LAH (1.7 g, 45.8 mmol) at 0° C. The mixture was stirred at 15° C. for 12 hrs. LCMS showed the reaction completed. The reaction mixture was added to H$_2$O (50 mL) and extracted with EtOAc (15 ml×5), then dried over Na$_2$SO$_4$, filtered and concentrated to give Compound 7A-7 (750 mg, crude) as a black solid. Fragment MS=175.1 (LCMS)

Step 7: 3-(2-hydroxyethyl)-3,4-dihydronaphthalen-1(2H)-one-one (262-8)

To a solution of 7A-7 (700 mg, 3.6 mmol) in CHCl$_3$ (60 mL) was added MnO$_2$ (7.9 g, 91 mmol). The mixture was stirred at 15° C. for 12 hrs. LCMS showed the reaction completed and desired mass was detected. The reaction mixture was filtered and concentrated to give Compound 7A-8 (700 mg, crude) as a white solid. M+H$^+$=191.1 (LCMS).

Step 8: 3-(2-((tert-butyldimethylsilyl)oxy)ethyl)-3,4-dihydronaphthalen-1(2H)-one (262-9)

To a solution Compound 7A-8 (500 mg, 2.6 mmol) in THF (20 mL) was added IMIDAZOLE (268 mg, 4 mmol) and TBSCl (475 mg, 3 mmol) at 0° C. The mixture was stirred at 15° C. for 12 hrs. LCMS showed the reaction completed and desired mass was detected. The reaction mixture was added to H$_2$O (30 mL) and extracted with EtOAc (15 ml×3). The combined organic layers were dried over Na$_2$SO$_4$, filtered and concentrated under reduced pressure to give a residue, which purified by column chromatography to give Compound 7A-9 (600 mg, crude) as a white solid. M+H$^+$=305.1 (LCMS)

Step 9: 3-(2-((tert-butyldimethylsilyl)oxy)ethyl)-1,2,3,4-tetrahydronaphthalen-1-amine (262-10)

To a solution of Compound 7A-9 (300 mg, 985 μmol) in MeOH (10 mL) was added NH$_4$OAc (1.2 g, 15 mmol), after stirred for 10 mins at 15° C., NaBH$_3$CN (248 mg, 4 mmol) was added. The mixture was stirred at 80° C. for 3 hrs under Microwave. LCMS showed the reaction was completed and desired mass was detected. The reaction mixture was added to H$_2$O (10 mL) and extracted with EtOAc (15 ml×3). The organic phases were combined, dried over Na$_2$SO$_4$ and concentrated to give crude Compound 7A-10 (220 mg, 720 μmol, 73% yield) as white oil. M+H$^+$=306.1 (LCMS)

Step 10: N-(3-(2-((tert-butyldimethylsilyl)oxy)ethyl)-1,2,3,4-tetrahydronaphthalen-1-yl)-2-oxo-6-(trifluoromethyl)-1,2-dihydropyridine-3-carboxamide (262-11)

To a solution of Compound 7A-10 (150 mg, 490 μmol) and 2-oxo-6-(trifluoromethyl)-1,2-dihydropyridine-3-carboxylic acid (102 mg, 490 μmol) in DCM (7 mL) was added HATU (205 mg, 540 μmol) and DIEA (127 mg, 982 μmol). The mixture was stirred at 15° C. for 1 hr. LCMS showed the reaction completed and desired mass was detected. The reaction mixture was added to H$_2$O (10 mL) and extracted with EtOAc (5 ml×3). The combined organic layers were dried over Na$_2$SO$_4$, filtered and concentrated under reduced pressure to give a residue, which was purified by column chromatography to give Compound 7A-11 (120 mg, crude) as a white solid. M−H⁻=493.1 (LCMS)

Step 11: N-((1R,3R)-3-(2-hydroxyethyl)-1,2,3,4-tetrahydronaphthalen-1-yl)-2-oxo-6-(trifluoromethyl)-1,2-dihydropyridine-3-carboxamide (262) and N-((1R,3S)-3-(2-hydroxyethyl)-1,2,3,4-tetrahydronaphthalen-1-yl)-2-oxo-6-(trifluoromethyl)-1,2-dihydropyridine-3-carboxamide (263)

To a solution of 7A-11 (120 mg, 242 μmol) in THF (2 mL) was added TBAF (1 M, 485 uL). The mixture was stirred at 15° C. for 12 hrs. LCMS showed the reaction was completed and one main peak with desired mass was detected. The reaction mixture was added to H₂O (3 mL) and extracted with EtOAc (5 ml×3). The combined organic layers were dried over Na₂SO₄, filtered and concentrated under reduced pressure to give a residue, which was purified by prep-HPLC to give Compound 7A (6 mg, 16 μmol, 7% yield) as a white solid. M−H⁻=379.1 (LCMS); ¹H NMR (400 MHz, CHCl₃-d) δ=9.52 (br s, 1H), 8.71 (br d, J=7.4 Hz, 1H), 7.32 (br d, J=7.9 Hz, 1H), 7.21-7.12 (m, 3H), 6.89 (br d, J=7.4 Hz, 1H), 5.45 (br s, 1H), 3.82 (t, J=6.8 Hz, 2H), 2.94 (br d, J=19.8 Hz, 1H), 2.64-2.53 (m, 1H), 2.41 (br d, J=7.3 Hz, 1H), 2.12 (br s, 1H), 1.71 (q, J=6.8 Hz, 3H). Compound 7B (7 mg, 19 μmol, 8% yield) was obtained as a white solid. M−H⁻=379.1 (LCMS); ¹H NMR (400 MHz, CHCl₃-d) δ=9.65 (br d, J=7.6 Hz, 1H), 8.78-8.63 (m, 1H), 7.30 (br s, 1H), 7.26-7.09 (m, 3H), 6.92-6.80 (m, 1H), 5.53-5.25 (m, 1H), 3.80 (br t, J=6.6 Hz, 2H), 2.99 (br dd, J=4.2, 16.2 Hz, 1H), 2.51 (br dd, J=10.7, 16.5 Hz, 1H), 2.24-2.01 (m, 2H), 1.82-1.64 (m, 3H).

Note: The configurations of these two diastereoisomers were assigned randomly, and they could be separated by Prep-HPLC successfully.

Another compound made in a similar manner is shown in Table 20.

TABLE 20

| Compound No | Structure | HNMR and Ms |
| --- | --- | --- |
| 264 | ![structure] | ¹H NMR (400 MHz, CHCl₃-d) δ = 9.62 (br d, J = 7.8 Hz, 1H), 8.69 (d, J = 7.3 Hz, 1H), 7.30 (d, J = 7.6 Hz, 1H), 7.25-7.13 (m, 3H), 6.83 (d, J = 7.5 Hz, 1H), 5.42 (td, J = 3.8, 7.5 Hz, 1H), 3.75-3.62 (m, 2H), 3.00 (dd, J = 4.7, 16.2 Hz, 1H), 2.57 (dd, J = 11.2, 16.5 Hz, 1H), 2.27-2.06 (m, 2H), 1.73 (dt, J = 4.6, 12.6 Hz, 1H) ESI [M − H] = 365.1 |

Example 32: Synthesis of N-((2S,4R)-6-methyl-2-propyl-1,2,3,4-tetrahydroquinolin-4-yl)-2-oxo-5-phenyl-6-(trifluoromethyl)-1,2-dihydropyridine-3-carboxamide (265)

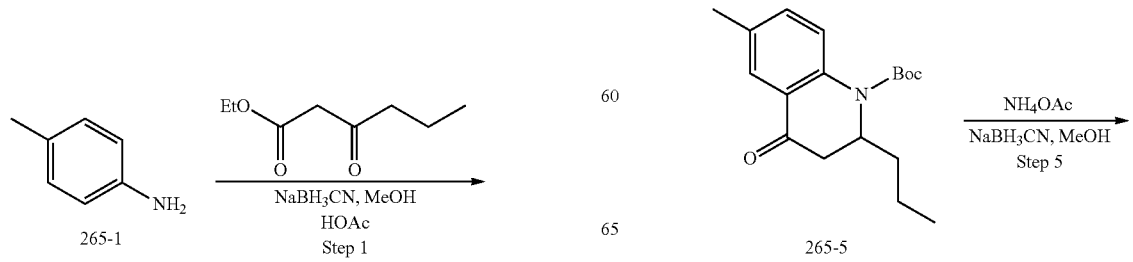

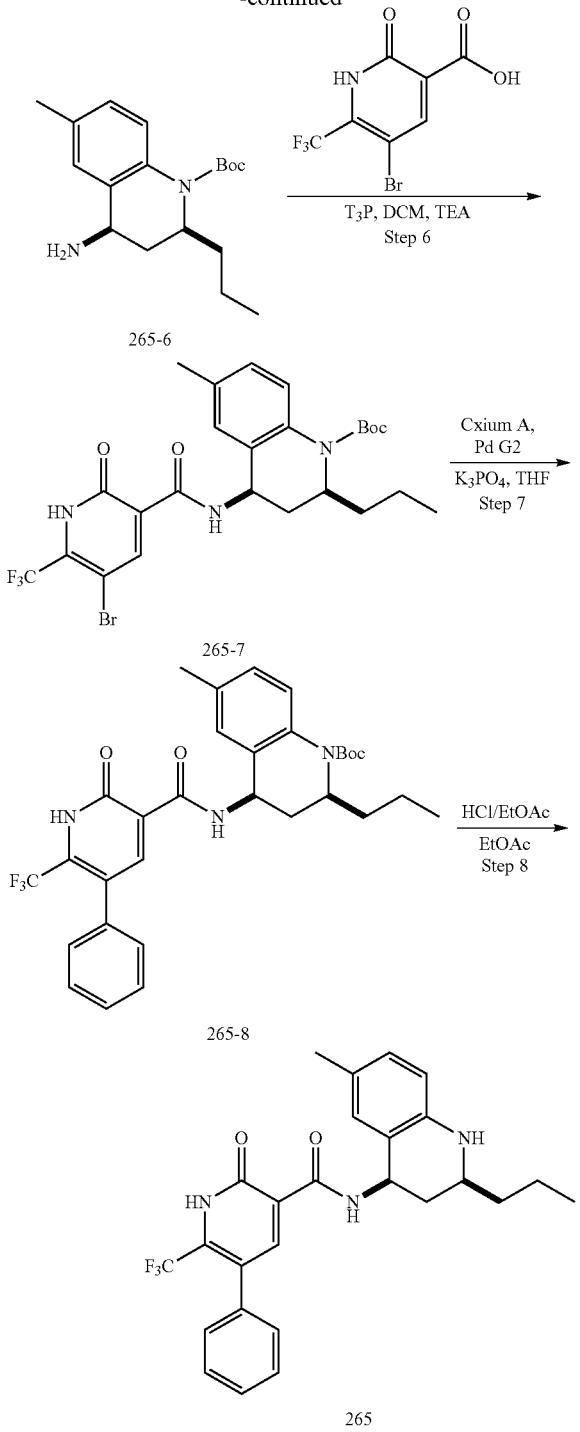

Step 1: ethyl 3-(p-tolylamino) hexanoate (265-2)

To a stirred solution of Compound 265-1 (5.0 g, 47 mmol) in MeOH (100 mL) was added ethyl 3-oxohexanoate (22.0 g, 140 mmol), then was added HOAc (2.8 g, 47 mmol) to the pH=5-6, The resulting mixture was stirred at 20° C. for 3 hrs. NaBH₃CN (5.9 g, 93 mmol) was added and the mixture was stirred at 20° C. for 12 hrs. LCMS showed the reaction completed and desired mass was detected. The reaction mixture was poured into H₂O (20 mL) and extracted with EtOAc (50 mL×3). The combined organic layers were dried over Na₂SO₄, filtered and concentrated in vacuum to give residue, which was purified by column chromatography to give Compound 265-2 (8.5 g, crude) as a yellow solid. M+H⁺=250.1 (LCMS).

Step 2: 3-(p-tolylamino)hexanoic acid (265-3)

A solution of Compound 265-2 (6.5 g, 26.1 mmol) in MeOH (52 mL) was added NaOH (1 M, 52 mL). The mixture was stirred at 20° C. for 12 hrs. TLC indicated the reaction completed. The reaction mixture was poured into H₂O (50 mL), and then adjusted pH=5-6 extracted with EtOAc (50 mL×3). The combined organic layers were dried over Na₂SO₄, filtered and concentrated under reduced pressure to give a residue. The Compound 265-3 (5.5 g, 24.9 mmol, 95% yield) was obtained as yellow oil. ¹H NMR (400 MHz, CHLOROFORM-d) δ=8.09 (br s, 2H), 7.03 (d, J=8.2 Hz, 2H), 6.68 (br d, J=6.8 Hz, 2H), 3.76 (m, J=6.3 Hz, 1H), 2.57 (dd, J=2.9, 6.0 Hz, 2H), 2.27 (s, 3H), 1.66-1.53 (m, 2H), 1.49-1.36 (m, 2H), 0.93 (t, J=7.3 Hz, 3H).

Step 3: 6-methyl-2-propyl-2,3-dihydroquinolin-4(1H)-one (265-4)

A solution of Compound 265-3 (4.2 g, 11.3 mmol) in PPA (20 mL) was stirred at 120° C. for 20 mins. TLC indicated the reaction completed. The reaction mixture was poured into H₂O (50 mL) and neutralized to pH=8-9 using NaOH. Then the mixture was extracted with EtOAc (30 mL×3). The combined organic layers were dried over Na₂SO₄, filtered and concentrated in vacuum to give residue, which was purified by column chromatography to give Compound 265-4 (2.0 g, 10.8 mmol, 52% yield) as a yellow solid. ¹H NMR (400 MHz, CHLOROFORM-d) δ=7.63 (s, 1H), 7.13 (dd, J=2.1, 8.3 Hz, 1H), 6.65-6.54 (m, 1H), 3.61 (dtd, J=3.7, 6.4, 12.7 Hz, 1H), 2.66 (dd, J=3.6, 16.1 Hz, 1H), 2.50-2.41 (m, 1H), 2.27-2.19 (m, 3H), 1.70-1.52 (m, 2H), 1.49-1.36 (m, 2H), 1.01-0.92 (m, 3H).

Step 4: tert-butyl 6-methyl-4-oxo-2-propyl-3,4-dihydroquinoline-1(2H)-carboxylate (265-5)

To a solution of Compound 265-4 (1.4 g, 6.6 mmol) in THF (12 mL) was added Boc₂O (2.2 g, 10.0 mmol), TEA (1.0 g, 10.0 mmol) and DMAP (811.0 mg, 6.6 mmol). The mixture was stirred at 60° C. for 72 hrs. TLC showed most of the starting material was consumed. The reaction mixture was poured into H₂O (10 mL) and then extracted with EtOAc (15 mL×3). The combined organic layers were dried over Na₂SO₄, filtered and concentrated under reduced pressure to give a residue. The residue was purified by flash silica gel chromatography to give Compound 265-5 (0.6 g, 2.0 mmol, 33% yield) as a yellow solid. ¹H NMR (400 MHz, CHLOROFORM-d) δ=7.77 (d, J=1.7 Hz, 1H), 7.63 (br d, J=8.3 Hz, 1H), 7.32 (dd, J=2.0, 8.5 Hz, 1H), 4.97-4.86 (m, 1H), 3.02 (dd, J=5.7, 17.5 Hz, 1H), 2.58 (dd, J=1.7, 17.5 Hz, 1H), 2.40-2.29 (m, 3H), 1.55 (s, 9H), 1.44-1.24 (m, 4H), 0.87 (t, J=7.2 Hz, 3H).

Step 5: (2S,4R)-tert-butyl 4-amino-6-methyl-2-propyl-3,4-dihydroquinoline-1(2H)-carboxylate (265-6)

To a solution of Compound 265-5 (0.6 g, 2.0 mmol) in MeOH (20 mL) was added NH₄OAc (2.3 g, 30.0 mmol), after stirred for 10 mins, NaBH₃CN (497 mg, 7.9 mmol) was added. The mixture was stirred at 90° C. for 2 hrs under microwave. TLC indicated the reaction completed. The reaction mixture was poured into H₂O (20 mL) and then extracted with EtOAc (50 mL×3). The organic phases were combined and washed with NaHCO₃·aq (100 mL), dried over Na₂SO₄ and concentrated to give crude Compound 265-6 (0.6 g, crude) as yellow oil, which was mainly the Cis isomer.

Step 6: (2S,4R)-tert-butyl 4-(5-bromo-2-oxo-6-(trifluoromethyl)-1,2-dihydropyridine-3-carboxamido)-6-methyl-2-propyl-3,4-dihydroquinoline-1(2H)-carboxylate (265-7)

To a solution of Compound 265-6 (0.5 g, 1.6 mmol), 5-bromo-2-oxo-6-(trifluoro methyl)-1,2-dihydropyridine-3-carboxylic acid (470 mg, 1.6 mmol) in DCM (30 mL) was added TEA (499 mg, 4.9 mmol) and T₃P (2.1 g, 3.3 mmol, 50% purity). The mixture was stirred at 25° C. for 1 hr. LCMS showed the reaction was completed. The reaction mixture was poured into H₂O (20 mL) and extracted with DCM (10 mL×3). The combined organic layers dried over Na₂SO₄ and concentrated under reduced pressure to give a residue, which was treated with MeOH (2 mL) and 3M NaOH (2 mL) and stirred at 20° C. for 2 hrs. LCMS showed the desired mass was detected. Then the mixture was diluted with H₂O (5 mL) and adjust to pH=5-6, then extracted with DCM (5 mL×3). The combined organic layers dried over Na₂SO₄ and concentrated under reduced pressure to give a residue, which was purified by column chromatography to give a residue. The residue was purified by Prep-TLC (Petroleum ether:Ethyl acetate=1:1) to give Compound 265-7 (0.1 g, crude) as a yellow solid. M−H⁻=571.0 (LCMS).

Step 7: (2S,4R)-tert-butyl 6-methyl-4-(2-oxo-5-phenyl-6-(trifluoromethyl)-1,2-dihydropyridine-3-carboxamido)-2-propyl-3,4-dihydroquinoline-1(2H)-carboxylate (265-8)

To a solution of Compound 265-7 (100 mg, 174.70 μmol), phenylboronic acid (64 mg, 524.1 μmol) in THF (6 mL) was added Cxium A-Pd G2 (11.7 mg, 17.5 μmol) and K₃PO₄ (0.5 M, 1.1 mL). The mixture was stirred at 70° C. for 12 hrs. LCMS showed the reaction completed and desired mass was detected. The reaction mixture was poured into H₂O (10 mL) and then extracted with DCM (10 mL×3). The combined organic layers were dried over Na₂SO₄, filtered and concentrated under reduced pressure to give a residue. The residue was purified by prep-TLC (Petroleum ether:Ethyl acetate=1:1) to give Compound 265-8 (60 mg, crude) as a yellow solid. M−H⁻=568.1 (LCMS).

Step 8: N-((2S,4R)-6-methyl-2-propyl-1,2,3,4-tetrahydroquinolin-4-yl)-2-oxo-5-phenyl-6-(trifluoromethyl)-1,2-dihydropyridine-3-carboxamide (265)

To a solution of Compound 265-8 (60 mg, 105.3 μmol) in EtOAc (5 mL) was added HCl/EtOAc (4 M, 5 mL). The mixture was stirred at 15° C. for 30 mins. LCMS showed the reaction completed and desired mass was detected. The reaction mixture was concentrated in vacuum to give a residue, which was purified by prep-HPLC to give Compound 265 (10 mg, 18.98 μmol, 18% yield) as a yellow solid. M+H⁺=470.2 (LCMS); ¹H NMR (400 MHz, MeOH-d₄) δ=8.37 (s, 1H), 7.50-7.43 (m, 3H), 7.39-7.34 (m, 2H), 6.86 (br d, J=8.3 Hz, 1H), 6.60 (d, J=8.2 Hz, 1H), 5.38 (br dd, J=5.7, 10.8 Hz, 1H), 3.40 (br d, J=9.8 Hz, 1H), 2.36 (br dd, J=5.9, 10.9 Hz, 1H), 2.18 (s, 3H), 1.72-1.38 (m, 5H), 1.04-0.93 (m, 3H).

Example 33: Synthesis of N-(4-amino-5-methyl-2,3-dihydro-1H-inden-1-yl)-2-oxo-6-(trifluoromethyl)-1,2-dihydropyridine-3-carboxamide (266)

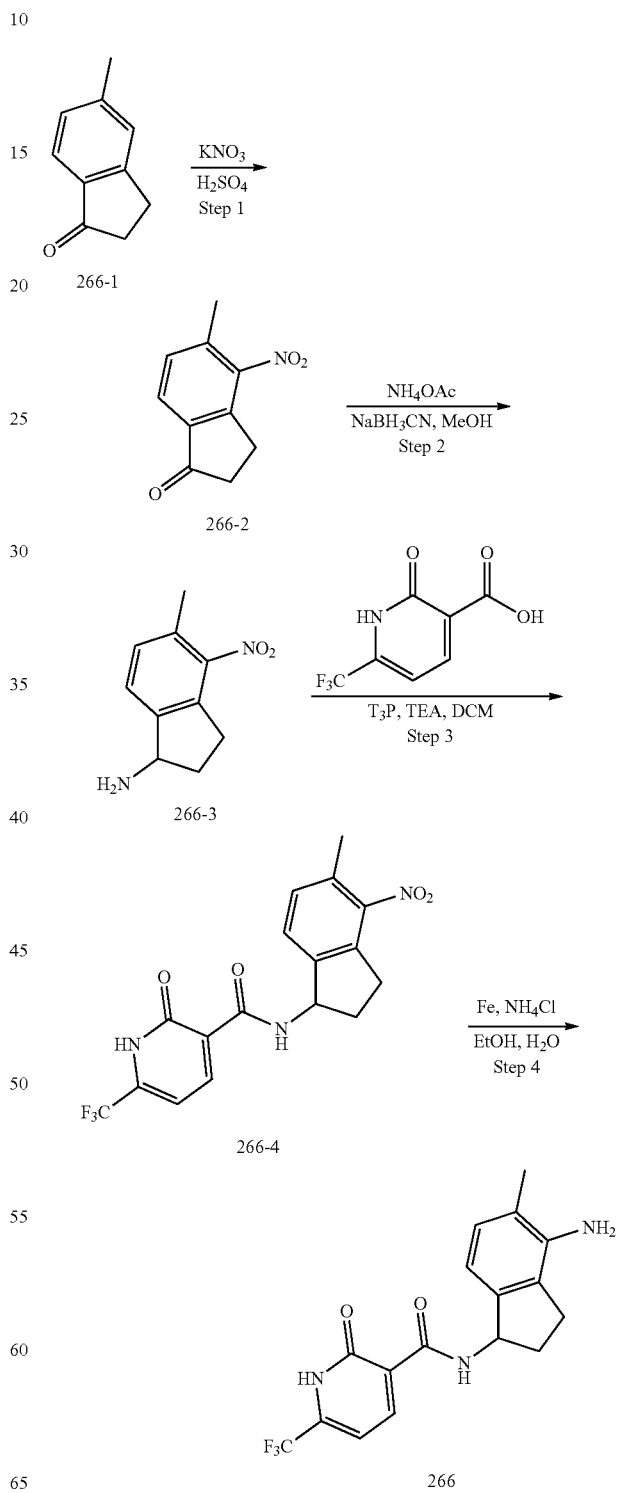

Step 1: 5-methyl-4-nitro-2,3-dihydro-1H-inden-1-one (266-2)

A mixture of Compound 266-1 (1 g, 6.8 mmol) in concentrated H$_2$SO$_4$ (8.7 mL) cooled at −5° C., a solution of KNO$_3$ (622 mg, 6.2 mmol) in concentrated H$_2$SO$_4$ (2.3 mL) was dropwise added in 1 hr. The mixture was stirred for 2 hrs at −5° C. TLC showed trace of starting material was remained. The mixture was poured into ice (30 g). The resulting mixture was stirred for 2 hrs at 20° C., then the precipitate was filtered and the filter cake was concentrated under reduced pressure to give a residue, which was purified by silica gel chromatography (Ethyl acetate/Petroleum) to give Compound 266-2 (0.38 g, 2.0 mmol, 29% yield) as a white solid. $^1$H NMR (400 MHz, CHLOROFORM-d) δ=7.84 (d, J=7.8 Hz, 1H), 7.40 (d, J=7.3 Hz, 1H), 3.39-3.26 (m, 2H), 2.84-2.72 (m, 2H), 2.60 (s, 3H).

Step 2: 5-methyl-4-nitro-2,3-dihydro-1H-inden-1-amine (266-3)

To a stirred solution of Compound 266-2 (280 mg, 1.5 mmol) in MeOH (10 mL) was added NH$_4$OAc (1.7 g, 21.9 mmol), the reaction was stirred for 10 min at 20° C., then NaBH$_3$CN (368 mg, 5.8 mmol) was added and the reaction was stirred at 90° C. for 1.5 hrs under microwave. LCMS showed the reaction was completed. The reaction mixture was poured into H$_2$O (10 mL), then extracted with EtOAc (10 mL×3). The combined organic layers were washed with Sat.NaCl (10 mL), dried over Na$_2$SO$_4$, filtered and concentrated under reduced pressure to give Compound 266-3 (280 mg, crude) as a yellow gum. Fragment Ms=176.0 (LCMS).

Step 3: N-(5-methyl-4-nitro-2,3-dihydro-1H-inden-1-yl)-2-oxo-6-(trifluoromethyl)-1,2-dihydropyridine-3-carboxamide (266-4)

To a stirred solution of 2-oxo-6-(trifluoromethyl)-1,2-dihydropyridine-3-carboxylic acid (302 mg, 1.5 mmol) and Compound 266-3 (280 mg, 1.5 mmol) in DCM (15 mL) was added TEA (442 mg, 4.4 mmol) at 20° C., followed by T$_3$P (1.8 g, 2.9 mmol, 50% purity). The resulting mixture was stirred at 20° C. for 5 hrs. Then the mixture was diluted with H$_2$O (5 mL) and extracted with DCM (3 mL×3). The combined organic layers dried over Na$_2$SO$_4$ and concentrated under reduced pressure to give a residue. The residue was diluted with MeOH (5 mL) and 3M NaOH (0.5 mL) and stirred at 20° C. for 12 hrs. LCMS showed the reaction was completed. Then the mixture was diluted with H$_2$O (10 mL) and extracted with DCM (5 mL×3). The combined organic layers dried over Na$_2$SO$_4$ and concentrated under reduced pressure to give a residue, which was purified by silica gel chromatography (Ethyl acetate/Petroleum) to give Compound 266-4 (120 mg, 315 μmol, 21% yield) as a white solid. M−H$^-$=380.0 (LCMS).

Step 4: N-(4-amino-5-methyl-2,3-dihydro-1H-inden-1-yl)-2-oxo-6-(trifluoromethyl)-1,2-dihydropyridine-3-carboxamide (266)

To a solution of Compound 266-4 (60 mg, 157 μmol) and NH$_4$Cl (42 mg, 787 μmol) in EtOH (6 mL) and H$_2$O (1.2 mL) was added Fe (44 mg, 787 μmol). The resulting mixture was stirred at 80° C. for 1 hr. LCMS showed the reaction was completed and the desired mass was detected. The mixture was filtered and the filtrate was concentrated in vacuum to give a residue, which was purified by prep-HPLC to give Compound 266 (34 mg, 96 μmol, 61% yield) as a yellow solid. M−H$^-$=350.1 (LCMS), $^1$H NMR (400 MHz, DMSO-d6) δ=9.17 (br s, 1H), 8.45 (d, J=7.6 Hz, 1H), 7.31 (br d, J=7.5 Hz, 1H), 6.81 (d, J=7.5 Hz, 1H), 6.43 (d, J=7.5 Hz, 1H), 5.39 (q, J=7.5 Hz, 1H), 2.86-2.74 (m, 1H), 2.64-2.53 (m, 1H), 2.46-2.39 (m, 1H), 2.06 (s, 3H), 1.89-1.76 (m, 1H).

Example 34: Synthesis of N-(2,6-diallylpyridin-4-yl)-2-oxo-6-(trifluoromethyl)-1,2-dihydropyridine-3-carboxamide (267)

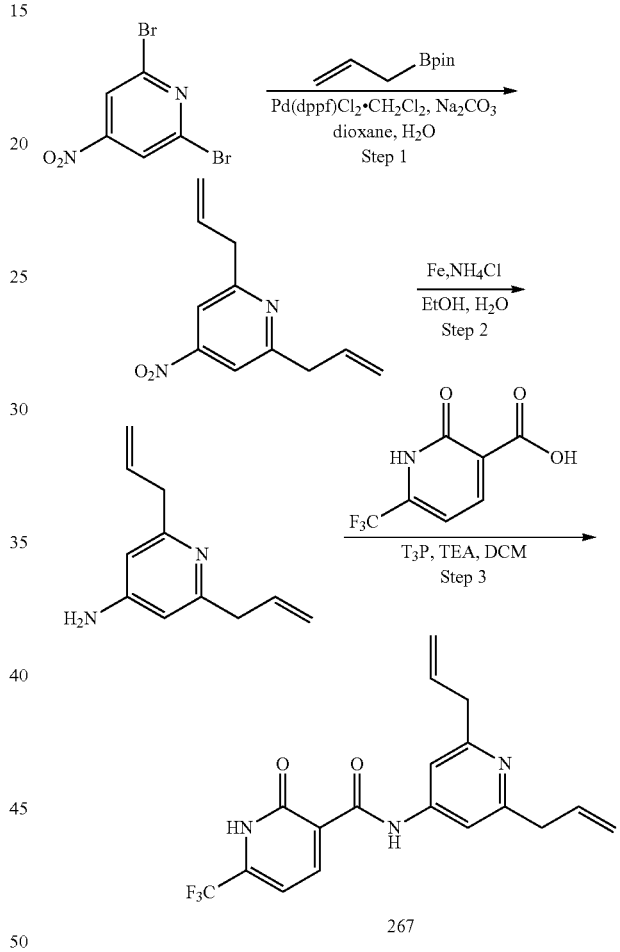

Step 1: 2,6-diallyl-4-nitropyridine (267-2)

A mixture of Compound 267-1 (1 g, 3.6 mmol), 2-allyl-4,4,5,5-tetramethyl-1,3,2-dioxaborolane (2.7 g, 16 mmol), Pd(dppf)Cl$_2$·CH$_2$Cl$_2$ (290 mg, 354.8 μmol) and Na$_2$CO$_3$ (1.9 g, 17.7 mmol) in dioxane (20 mL)/H$_2$O (4 mL) was degassed and purged with N$_2$ for 3 times, and then the mixture was stirred at 80° C. for 12 hrs. LCMS showed the reaction was completed and desired mass was detected. The reaction mixture was poured into H$_2$O (20 mL) and extracted with EtOAc (10 mL×3). The combined organic layers were dried over Na$_2$SO$_4$, filtered and concentrated under reduced pressure to give a crude product. The residue was purified by flash silica gel chromatography to give Compound 267-2 (400 mg, crude) as a brown solid. M+H$^+$=205.1 (LCMS); $^1$H NMR (400 MHz, CDCl$_3$) δ=7.74 (s, 2H), 6.24-5.88 (m, 2H), 5.32-5.07 (m, 4H), 3.72 (d, J=6.8 Hz, 4H).

Step 2: 2,6-diallylpyridin-4-amine (267-3)

To a mixture of Compound 267-2 (80 mg, 391.7 μmol) and NH$_4$Cl (105 mg, 2 mmol) in EtOH (5 mL) and H$_2$O (1 mL) was added Fe (110 mg, 2 mmol). The resulting mixture was stirred at 80° C. for 1 hr. LCMS showed the reaction was completed and desired mass was detected. The reaction mixture was filtered and concentrated under reduced pressure to give a residue. The residue was diluted with (DCM: MeOH=10:1.6 mL) and washed with H$_2$O (6 mL). The organic layer was dried over Na$_2$SO$_4$, filtered and concentrated under reduced pressure to give Compound 267-3 (45 mg, crude) as brown oil. M+H$^+$=175.1 (LCMS); $^1$H NMR (400 MHz, DMSO-d$_6$) δ=6.17 (s, 2H), 6.04-5.82 (m, 4H), 5.15-4.92 (m, 4H), 3.25 (br d, J=6.6 Hz, 4H).

Step 3: N-(2,6-diallylpyridin-4-yl)-2-oxo-6-(trifluoromethyl)-1,2-dihydropyridine-3-carboxamide (267)

To a solution of Compound 267-3 (45 mg, 258.26 μmol), 2-oxo-6-(trifluoro methyl)-1,2-dihydropyridine-3-carboxylic acid (54 mg, 258.3 μmol) in DCM (3 mL) was added TEA (78 mg, 774.8 μmol) and T$_3$P (329 mg, 516.5 μmol). The mixture was stirred at 20° C. for 1 hr. LCMS showed the reaction was completed. The reaction mixture was poured into H$_2$O (5 mL) and extracted with EtOAc (3 mL×3). The combined organic layers dried over Na$_2$SO$_4$ and concentrated under reduced pressure to give a residue, which was treated with MeOH (1.5 mL) and 3M NaOH (1.5 mL) and stirred at 20° C. for 2 hrs. LCMS showed the desired mass was detected. The reaction mixture was poured into H$_2$O (5 mL) and extracted with EtOAc (3 mL×3). The combined organic layers were dried over Na$_2$SO$_4$ and concentrated under reduced pressure to give a residue, which was purified by Prep-HPLC to give Compound 267 (7 mg, 18.2 μmol, 7% yield) as a white solid. M-H$^-$=362.1 (LCMS); $^1$H NMR (400 MHz, DMSO-d$_6$) δ=12.78-12.12 (m, 1H), 8.30 (br d, J=7.5 Hz, 1H), 7.48 (s, 2H), 7.20-7.06 (m, 1H), 6.02 (tdd, J=6.8, 10.1, 17.0 Hz, 2H), 5.21-5.09 (m, 4H), 3.51 (br d, J=6.7 Hz, 4H).

Other compounds made in a similar manner are shown in Table 21.

TABLE 21

| Compound No | Structure | HNMR and Ms |
|---|---|---|
| 268 | 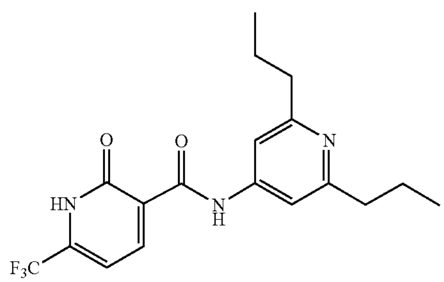 [SMILES: CCCc1cc(NC(=O)c2ccc(C(F)(F)F)[nH]c2=O)cc(CCC)n1] | $^1$H NMR (400 MHz, DMSO-d6) δ = 8.26 (d, J= 7.6 Hz, 1H), 7.68 (brs, 2H), 6.94 (brd, J = 7.3 Hz, 1H), 2.76 (br t, J = 7.6 Hz, 4H), 1.70 (sxt, J = 7.4 Hz, 4H), 0.93 (t, J = 7.3 Hz, 6H) ESI [M − H] = 366.1 |
| 369 | 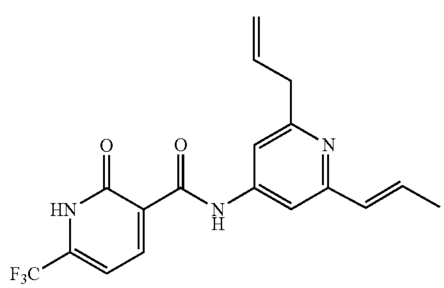 [SMILES: C=CCc1cc(NC(=O)c2ccc(C(F)(F)F)[nH]c2=O)cc(/C=C/C)n1] | $^1$H NMR (400 MHz, DMSO-d$_6$) δ = 14.08-12.88 (m, 1H), 12.45-11.70 (m, 1H), 8.39-8.25 (m, 1H), 7.60-7.36 (m, 2H), 7.18 (br d, J = 6.7 Hz, 1H), 6.81-6.67 (m, 1H), 6.54-6.36 (m, 1H), 6.13-5.95 (m, 1H), 5.23-4.98 (m, 2H), 3.53-3.47 (m, 2H), 1.99-1.76 (m, 3H) ESI [M − H] = 362.1 |
| 270 | 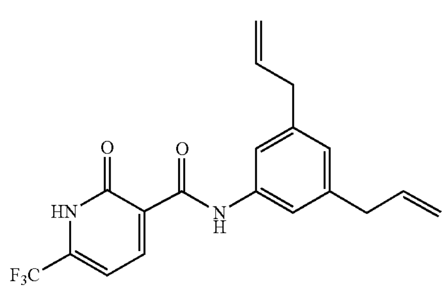 [SMILES: C=CCc1cc(CC=C)cc(NC(=O)c2ccc(C(F)(F)F)[nH]c2=O)c1] | $^1$H NMR (400 MHz, DMSO-d$_6$) δ = 13.52 (br s, 1H), 11.12 (brs, 1H), 8.37 (d, J = 7.5 Hz, 1H), 7.39 (s, 2H), 7.28 (br d, J = 7.3 Hz, 1H), 6.79 (s, 1H), 5.94 (tdd, J = 6.8, 10.0, 17.0 Hz, 2H), 5.16-5.00 (m, 4H), 3.33 (br s, 4H) ESI [M − H] = 361.1 |

TABLE 21-continued
| Compound No | Structure | HNMR and Ms |
|---|---|---|
| 271 | 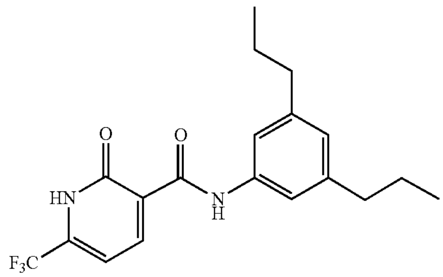 | $^1$H NMR (400 MHz, DMSO-d$_6$) δ = 13.48 (br s, 1H), 10.93 (br s, 1H), 8.40 (d, J = 7.5 Hz, 1H), 7.36 (s, 2H), 7.31 (brd, J = 7.1 Hz, 1H), 6.79 (s, 1H), 2.56-2.51 (m, 4H), 1.59 (sxt, J = 7.4 Hz, 4H), 0.90 (t, J = 7.3 Hz, 6H) ESI [M − H] = 365.1 |
Example 35: Synthesis of 6-(difluoromethyl)-N-(3-methoxy-9H-thioxanthen-9-yl)-2-oxo-1,2-dihydropyridine-3-carboxamide (272)
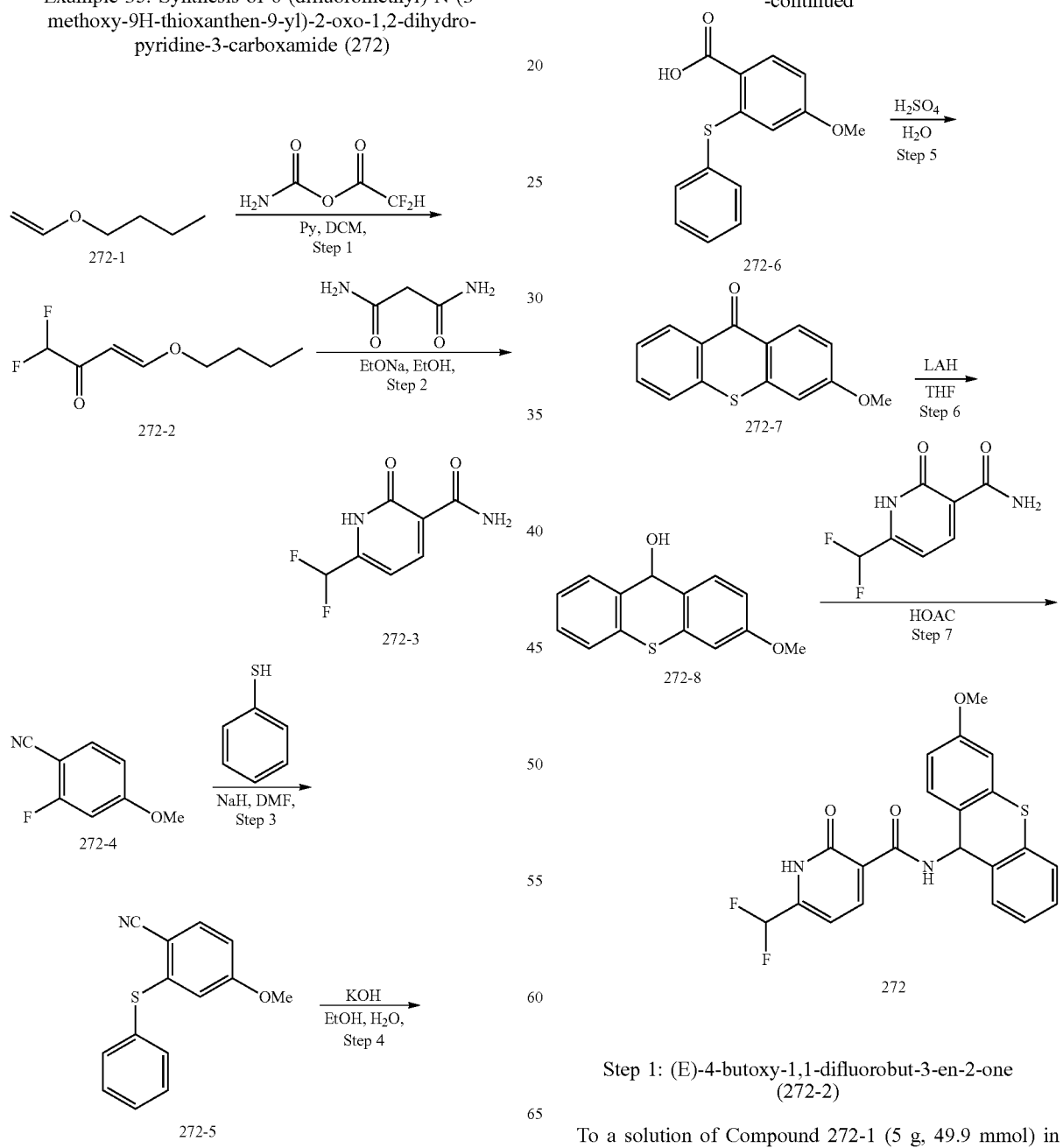
Step 1: (E)-4-butoxy-1,1-difluorobut-3-en-2-one (272-2)
To a solution of Compound 272-1 (5 g, 49.9 mmol) in DCM (50 mL) was added Pyridine (4.3 g, 54.9 mmol,) and 2,2-difluoroacetic anhydride (8.7 g, 49.9 mmol) in DCM (10 mL) at 0° C. The mixture was stirred at 25° C. for 12 hrs. LC-MS showed the reaction completed and desired mass was detected. The resulting solution was washed with 1M HCl aq. (100 mL), and then with sat. aq NaHCO$_3$ (100 mL), and sat. aq NaCl (100 mL). Each aqueous phase was sequentially re-extracted with further DCM (30 mL×2). The organic phases were combined, dried over Na$_2$SO$_4$ and concentrated to give crude Compound 272-2 (8.4 g, crude) as brown oil. M+H$^+$=179.0 (LCMS)

Step 2: 6-(difluoromethyl)-2-oxo-1,2-dihydropyridine-3-carboxamide (272-3)

To a stirred solution of Compound 272-2 (5 g, 28.1 mmol) in EtOH (60 mL) was added malonamide (2.9 g, 28.1 mmol) and EtONa in EtOH solution (9.6 g, 28.1 mmol, 20% purity) at 0° C. The mixture was stirred at 80° C. for 4 hrs. LCMS showed the reaction was completed and desired mass was detected. The reaction mixture was quenched by water (80 mL), extracted with EtOAc (50 mL) to remove some impurity. The aqueous was neutralized with 1M HCl to pH=4, and most solid appeared. The mixture was filtered and the cake was dried in vacuum to give Compound 272-3 (2.5 g) as a brown solid. M+H$^+$=189.0 (LCMS); $^1$H NMR (400 MHz, DMSO-d$_6$) δ=13.12 (br, 1H), 8.89 (br, 1H), 8.40-8.38 (d, J=7.2 Hz, 1H), 7.76 (s, 1H), 7.03-6.76 (t, J=53.6 Hz, 1H), 6.78 (s, 1H).

Step 3: 4-methoxy-2-(phenylthio) benzonitrile (272-5)

To a solution of benzenethiol (1.6 g, 14.6 mmol) in DMF (10 mL) was added NaH (635 mg, 15.9 mmol, 60% purity) at 0° C., after stirred at 25° C. for 30 mins, Compound 272-4 (2 g, 13.2 mmol) in DMF (10 mL) was added drop wise. The mixture was stirred at 25° C. for 2 hrs. LCMS showed the reaction complete and the desired mass was detected. The reaction mixture was poured into H$_2$O (10 mL) and extracted with EtOAc 30 ml (10 ml×3). The combined organic layers were dried over Na$_2$SO$_4$, filtered and concentrated in vacuum to give residue, which was purified by column chromatography to give Compound 272-5 (2.8 g, 11.6 mmol, 88% yield) as yellow oil. M+H$^+$=242.0 (LCMS); $^1$H NMR (400 MHz, CDCl$_3$) δ=7.51-7.40 (m, 6H), 6.77-6.74 (m, 1H), 6.57 (s, 1H), 3.72 (s, 3H).

Step 4: 4-methoxy-2-(phenylthio)benzoic acid (272-6)

To a solution of Compound 272-5 (1 g, 4.1 mmol) in EtOH (10 mL) and H$_2$O (10 mL) was added KOH (3.5 g, 62.2 mmol). The mixture was stirred at 80° C. for 12 hr. LCMS indicated some intermediate amide was remained. Another KOH (1 g) was added and stirred at 80° C. for another 12 hrs. LCMS showed the reaction went on completely and desired mass was detected. The reaction mixture was adjusted to pH=7-8 by using conc. HCl, and then some solid appeared. The mixture was filtered and the cake was dried in vacuum to give Compound 272-6 (900 mg, 3.5 mmol, 83% yield) as a white solid. M+H$^+$=261.0 (LCMS); $^1$H NMR (400 MHz, DMSO-d6) δ=8.14-8.11 (d, J=8.8 Hz, 1H), 7.63-7.60 (m, 1H), 7.47-7.45 (m, 1H), 6.67-6.64 (m, 1H), 6.25 (s, 1H), 3.61 (s, 3H).

Step 5: 3-methoxy-9H-thioxanthen-9-one (272-7)

A stirred mixture of Compound 272-6 (500 mg, 1.9 mmol) in H$_2$SO$_4$ (15 mL) and H$_2$O (5 mL) was stirred at 90° C. for 40 mins. LCMS showed the reaction completed and desired mass was detected. The reaction mixture was quenched by H$_2$O (5 mL) and adjusted pH=5-6 with NaOH (3M aq.). The mixture was filtered and the cake was dried in vacuum to give Compound 272-7 (400 mg, 1.7 mmol, 86% yield) as a white solid. M+H$^+$=243.0 (LCMS); $^1$H NMR (400 MHz, DMSO-d$_6$) δ=8.43-8.81 (m, 2H), 7.79-7.73 (m, 2H), 7.57-7.55 (m, 1H), 7.31 (s, 1H), 7.15-7.12 (m, 1H), 3.90 (s, 3H).

Step 6: 3-methoxy-9H-thioxanthen-9-ol (272-8)

To a stirred solution of Compound 272-7 (100 mg, 412.7 µmol) in THF (5 mL) was added LAH (31 mg, 825.5 µmol) in portions at 0° C. The resulting mixture was stirred at 25° C. for 30 mins. TLC indicated the reaction completed. The reaction mixture was poured into Sat.NH$_4$Cl (25 mL) extracted with DCM (10 mL×4). The combined organic layers were dried over Na$_2$SO$_4$ and concentrated in vacuum to give Compound 272-8 (100 mg, 409.3 µmol, 99% yield) as a white solid, which was unstable and should be used next step directly.

Step 7: 6-(difluoromethyl)-N-(3-methoxy-9H-thioxanthen-9-yl)-2-oxo-1,2-dihydropyridine-3-carboxamide (272)

A mixture of Compound 272-8 (100 mg, 409.3 µmol) and Compound 1A-3 (77 mg, 409.3 µmol) in AcOH (8 mL) was stirred at 50° C. for 12 hrs. LCMS showed the reaction was complete and the desired mass was detected. The reaction mixture was concentrated in vacuum to give a residue, which was purified by prep-HPLC to give Compound 272 (19 mg, 45.1 µmol, 11.03% yield) as a pink solid. M−H$^-$=413.1 (LCMS); $^1$H NMR (400 MHz, DMSO-d$_6$) δ=13.10 (br, 1H), 10.44 (br, 1H), 8.43-8.41 (d, J=7.6 Hz, 1H), 7.58-7.57 (m, 8H), 7.51-7.48 (m, 1H), 7.35-7.32 (m, 2H), 7.16 (s, 1H), 6.90-6.88 (m, 1H), 6.72-6.73 (m, 1H), 6.20-6.18 (d, J=8.4 Hz, 1H), 3.78 (s, 3H).

Other compounds made in a similar manner are shown in Table 22.

TABLE 22

| Compound No | Structure | HNMR and Ms |
|---|---|---|
| 273 | 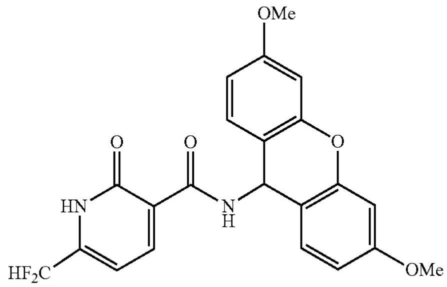 | ¹H NMR (400 MHz, DMSO-d₆) δ = 11.74 (br s, 1H), 8.21 (br d, J = 7.3 Hz, 1H), 7.34 (br d, J = 8.3 Hz, 2H), 6.78-6.38 (m, 6H), 6.34 (br d, J = 8.3 Hz, 1H), 3.98-3.65 (m, 6H) ESI [M − H] = 427.1 |
| 274 | 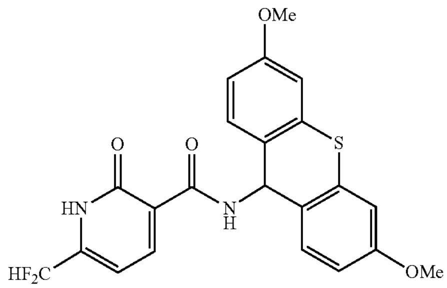 | ¹H NMR (400 MHz, DMSO-d₆) δ = 10.52 - 10.28 (m, 1H), 8.40 (d, J = 7.3 Hz, 1H), 7.48 (d, J = 8.4 Hz, 2H), 7.12 (d, J = 2.4 Hz, 2H), 7.05-6.71 (m, 4H), 6.18 (d, J = 8.4 Hz, 1H), 3.77 (s, 6H) ESI [M − H] = 443.0 |
| 275 | 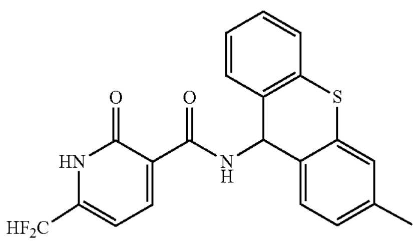 | ¹H NMR (400 MHz, DMSO-d₆) δ = 13.13 (br s, 1H), 10.71 (br s, 1H), 8.40 (d, J = 7.3 Hz, 1H), 7.57-7.56 (m, 2H), 7.44-6.88 (m, 7H), 6.14 (d, J = 8.6 Hz, 1H), 2.31(s, 3H). ESI [M − H] = 397.1 |
| 276 | 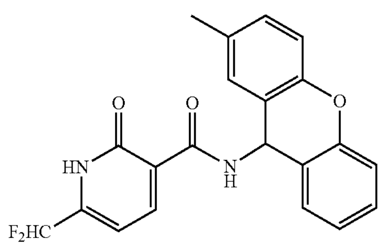 [SMILES: Cc1ccc2c(c1)C(NC(=O)c1ccc(C(F)F)[nH]c1=O)c1ccccc1O2] | 1H NMR (400 MHz, DMSO-d6) δ = 13.18 (br s, 1H), 10.28 (br s, 1H), 8.52 (d, J = 7.2 Hz, 1H), 7.46 (d, J = 7.7 Hz, 1H), 7.36 (t, J = 7.3 Hz, 1H), 7.25 (s, 1H), 7.22-7.04 (m, 4H), 6.91 (s, 1H), 6.85 (br s, 1H), 6.48 (d, J = 8.7 Hz, 1H), 2.88-2.60 (m, 3H), 2.60-2.52 (m, 4H), 2.38-2.30 (m, 1H), 2.28 (s, 3H) ESI [M − H] = 381.1 |
| 277 | 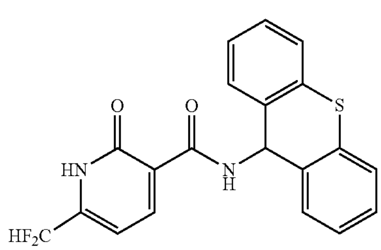 | ¹H NMR (400 MHz, DMSO-d₆) δ 13.06 (br s, 1H), 10.56 (br s, 1H), 8.44 (d, J = 7.3 Hz, 1H), 7.59 (td, J = 2.1, 4.6 Hz, 4H), 7.40-7.29 (m, 4H), 7.09-6.76 (m, 2H), 6.18 (d, J = 8.6 Hz, 1H) ESI [M − H] = 383.0 |
| 278 | 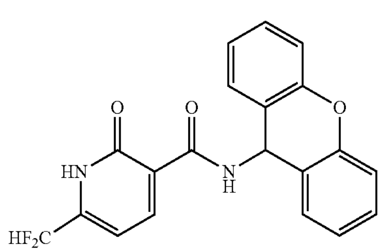 | ¹H NMR (400 MHz, DMSO-d₆) δ = 13.18 (br s, 1H), 10.30 (br s, 1H), 8.50 (d, J = 7.3 Hz, 1H), 7.47 (d, J = 7.5 Hz, 2H), 7.40-7.33 (m, 2H), 7.23-7.10 (m, 4H), 7.06-6.73 (m, 2H), 6.51 (d, J = 8.6 Hz, 1H) ESI [M − H] = 367.1 |

TABLE 22-continued

| Compound No | Structure | HNMR and Ms |
|---|---|---|
| 279 | 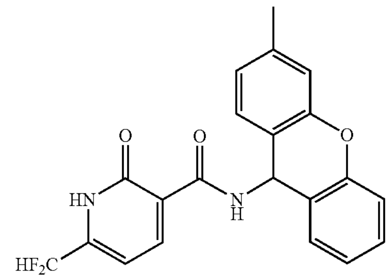 | $^1$H NMR (400 MHz, DMSO-d$_6$) δ = 10.22 (br s, 1H), 8.49 (d, J = 7.6 Hz, 1H), 7.45 (d, J = 7.6 Hz, 1H), 7.34-7.32 (m, 2H),7.19-7.14 (m, 2H), 7.02-6.98 (m, 2H), 6.89-6.76 (m, 2H), 6.45 (d, J = 8.8 Hz, 1H), 2.32 (s, 3H)<br>ESI [M − H] = 381.1 |
| 280 | 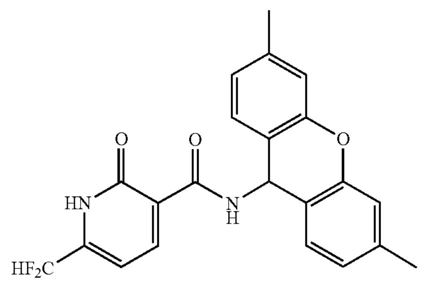 | $^1$H NMR (400 MHz, DMSO-d$_6$) δ = 13.28-13.00 (m, 1H), 10.34-10.09 (m, 1H), 8.49 (d, J = 7.3 Hz, 1H), 7.33 (d, J = 7.9 Hz, 2H), 7.06-6.93 (m, 4H), 6.90-6.74 (m, 2H), 6.41 (d, J = 8.6 Hz, 1H), 2.32 (s, 6H)<br>ESI [M − H] = 395.0 |
| 281 | 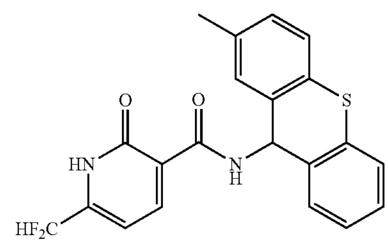 | $^1$H NMR (400 MHz, DMSO-d$_6$) δ = 13.13 (s, 1H), 10.52 (s, 1H), 8.42 (d, J = 7.5 Hz, 1H), 7.56-7.29 (m, 6H), 7.14 (d, 7.7 Hz, 1H), 7.07 - 6.89 (m, 2H), 6.13 (d, J = 8.6 Hz, 1H), 2.30 (s, 6H)<br>ESI [M − H] = 397.1 |
| 282 | 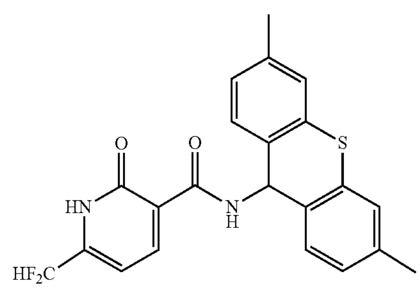 | $^1$H NMR (400 MHz, DMSO-d$_6$) δ = 13.35-12.98 (m, 1H), 10.63-10.19 (m, 1H), 8.42 (d, J = 7.5 Hz, 1H), 7.50-7.29 (m, 4H), 7.13 (dd, J = 0.9, 7.7 Hz, 2H), 7.07-6.71 (m, 2H), 6.13 (d, J = 8.6 Hz, 1H), 2.30 (s, 6H)<br>ESI [M − H] = 411.1 |

Example 36: Synthesis of 4-(4-methoxyphenyl)-6-oxo-2-((3-(trifluoromethyl)benzyl)thio)-1,6-dihydro-pyrimidine-5-carbonitrile (283)

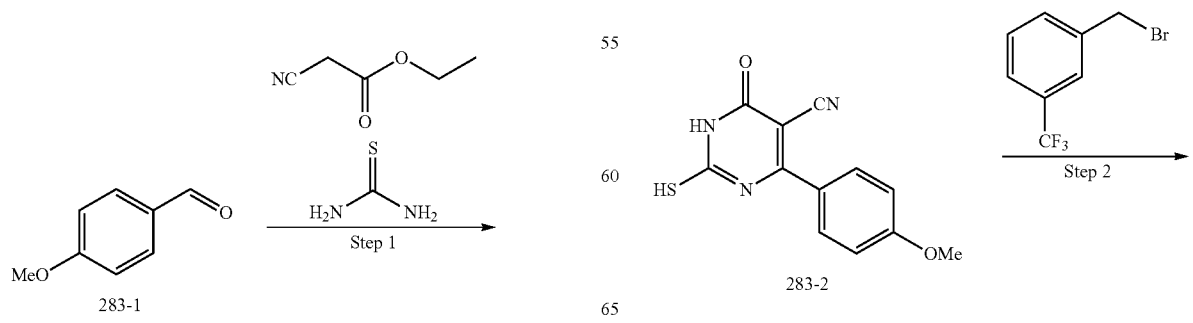

-continued

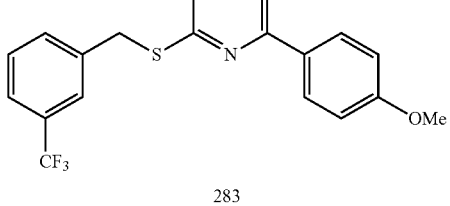

283

Step 1: 2-mercapto-4-(4-methoxyphenyl)-6-oxo-1,6-dihydropyrimidine-5-carbonitrile (283-2)

A mixture of Compound 283-1 (2 g, 14.7 mmol), thiourea (1.2 g, 15.8 mmol) and ethyl 2-cyanoacetate (1.7 g, 15.0 mmol) and $K_2CO_3$ (2.1 g, 15.2 mmol) in EtOH (100 mL) was stirred at 80° C. for 12 hrs. One main peak with desired mass was detected on LCMS. The mixture was poured into $H_2O$ (200 mL) and used Conc. HCl to adjust pH=4, then extracted with EtOAc/THF (4:1, 100 mL×3). The combined organic layers were washed with brine (50 mL), dried over $Na_2SO_4$, filtered and concentrated. The crude product was triturated with Petroleum ether:Ethyl acetate (1:1, 50 mL). The solid was collected by filtration, and dried in vacuum to give Compound 283-2 (3 g, 11.6 mmol, 79% yield) as a yellow solid. M+H$^+$=260.1 (LCMS)

Step 2: 4-(4-methoxyphenyl)-6-oxo-2-((3-(trifluoromethyl)benzyl)thio)-1,6-dihydropyrimidine-5-carbonitrile (283)

A mixture of Compound 283-2 and $K_2CO_3$ (250 mg, 1.8 mmol,) in DMF (3 mL) was stirred at 20° C. for 15 mins. Then 1-(bromomethyl)-3-(trifluoromethyl)benzene (300 mg, 1.3 mmol) was added. The mixture was stirred at 20° C. for 2 hrs. LC-MS showed the reaction was completed and one main peak with desired mass was detected. The mixture was poured into $H_2O$ (10 mL), the pH was adjusted to around 5 using Conc. acid, and extracted with EtOAc/THF (4:1, 5 mL×3). The combined organic layers were dried over $Na_2SO_4$, filtered and concentrated to give a residue, which was purified by prep-HPLC (TFA). Compound 283 (200 mg, 479 μmol, 41% yield) was obtained as a white solid. M+H$^+$=418.1 (LCMS); $^1$H NMR (400 MHz, DMSO-d6) δ=13.71 (br s, 1H), 7.97 (br d, J=8.8 Hz, 2H), 7.80 (s, 1H), 7.74 (br d, J=7.5 Hz, 1H), 7.63-7.48 (m, 2H), 7.10 (d, J=8.8 Hz, 2H), 4.62 (s, 2H), 3.85 (s, 3H).

Example 37: Synthesis of N-(2-ethyl-6-hydroxy-1,2,3,4-tetrahydronaphthalen-1-yl)-2-oxo-6-(trifluoromethyl)-1,2-dihydropyridine-3-carboxamide (284)

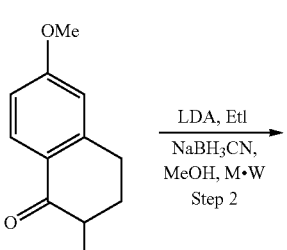

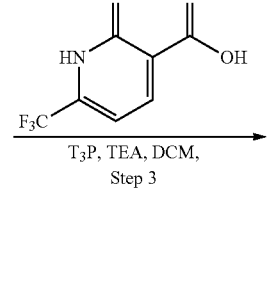

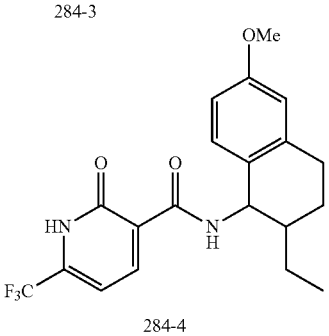

Step 1: 2-ethyl-6-methoxy-3,4-dihydronaphthalen-1(2H)-one (284-2)

Compound 284-1 (1.1 g, 5.7 mmol) was slowly added dropwise to a stirred solution of LDA (2 M, 2.8 mL) in THF (25 mL) at −78° C. and stirred for 20 minutes, then EtI (885 mg, 6 mmol) was added and this solution was stirred for 12 hrs at 20° C. LCMS showed the desired mass was detected. The reaction mixture was poured into Sat.NH$_4$Cl (20 mL) and extracted with EtOAc (10 mL×4). The combined organic layers were dried over $Na_2SO_4$, filtered and concentrated under reduced pressure to give a residue, which was purified by column chromatography to give Compound 284-2 (170 mg, 832.0 µmol, 15% yield) as an orange solid. M+H⁺=205.1 (LCMS)

Step 2: 2-ethyl-6-methoxy-1,2,3,4-tetrahydronaphthalen-1-amine (284-3)

To a solution of Compound 284-2 (120 mg, 587 µmol) in MeOH (3 mL) was added NH₄OAc (679 mg, 9 mmol), the mixture was stirred at 25° C. for 10 mins, then NaBH₃CN (148 mg, 2 mmol) was added to the mixture, the reaction was stirred at 90° C. for 8 hrs under microwave. LCMS showed the reaction was completed and desired mass was detected. The reaction mixture was added to H₂O (3 mL) and extracted with EtOAc (5 ml×3). The combined organic layers were dried over Na₂SO₄, filtered and concentrated to give Compound 284-3 (190 mg, crude) as a white solid. M−H⁻=206.1 (LCMS).

Step 3: N-(2-ethyl-6-methoxy-1,2,3,4-tetrahydronaphthalen-1-yl)-2-oxo-6-(trifluoromethyl)-1,2-dihydropyridine-3-carboxamide (284-4)

To a stirred solution of compound 284-3 (85 mg, 414.0 µmol), 2-oxo-6-(trifluoro methyl)-1,2-dihydropyridine-3-carboxylic acid (86 mg, 414.0 µmol) in DCM (2 mL) was added TEA (125 mg, 1 mmol), T3P (395 mg, 621 µmol, 50% purity). The reaction was stirred at 25° C. for 1 hr. LCMS showed the reaction was completed. Then the mixture was diluted with H₂O (5 mL) and extracted with DCM (5 mL×3). The combined organic layers dried over NaSO₄ and concentrated under reduced pressure to give a residue, which was treated with MeOH (3 mL) and 3M NaOH aq. (2 mL) and stirred at 20° C. for 12 hrs. LCMS showed the desired mass was detected. The reaction mixture was added to H₂O (3 mL) and extracted with EtOAc (5 m×3). The combined organic layers were dried over Na₂SO₄, filtered and concentrated under reduced pressure to give a residue, which was purified by column chromatography to give Compound 284-4 (50 mg, crude) as yellow oil. It was a mixture of two diastereisomers. M−H⁻=393.2 (LCMS); ¹HNMR (400 MHz, CHCl₃-d) δ=11.56-11.89 (m, 1H), 9.38 (br s, 1H), 8.69 (d, J=7.3 Hz, 1H), 7.37-7.17 (m, 1H), 6.90-6.89-6.87 (m, 1H), 6.71 (dd, J=2.6, 8.6 Hz, 1H), 6.64 (s, 1H), 5.49-5.06 (m, 1H), 3.78 (s, 3H), 2.83-2.79 (m, 1H), 2.05-1.34 (m, 6H), 1.05-0.96 (m, 3H).

Step 4: N-(2-ethyl-6-hydroxy-1,2,3,4-tetrahydronaphthalen-1-yl)-2-oxo-6-(trifluoromethyl)-1,2-dihydropyridine-3-carboxamide (284)

To a solution of Compound 284-4 (40 mg, 101 µmol) in DCM (2 mL) was added BBr₃ (127 mg, 507 µmol) in DCM (0.5 mL) at −78° C. The mixture was stirred at −78° C. for 1 hr, then at 15° C. for 12 hrs. LCMS showed the reaction was completed and desired mass was detected. The reaction mixture was added to H₂O (5 mL) and extracted with DCM (5 ml×2). The combined organic layers were dried over Na₂SO₄, filtered and concentrated under reduced pressure to give a residue, which was purified by Prep-HPLC to give Compound 284 (4 mg, 10 µmol, 11% yield, a mixture of two diastereoisomers) as a white solid. M−H⁻=379.1 (LCMS); ¹HNMR (400 MHz, CHCl₃-d) δ=9.45 (br d, J=9.5 Hz, 1H), 8.70 (d, J=7.4 Hz, 1H), 7.27-7.12 (m, 1H), 7.13 (d, J=8.1 Hz, 1H), 6.89-6.86 (m, 1H), 6.61-6.58 (m, 2H), 5.47-5.05 (m, 1H), 2.83-2.75 (m, 2H), 2.07-1.32 (m, 5H), 1.01-0.96 (dt, J=4.9, 7.4 Hz, 3H).

Other compounds made in a similar manner are shown in Table 23.

TABLE 23

| Compound No | Structure | HNMR and Ms |
| --- | --- | --- |
| 285 | 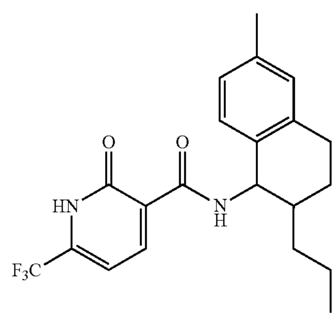 [SMILES: CCCC1CCc2cc(C)ccc2C1NC(=O)c1ccc(C(F)(F)F)[nH]c1=O] | ¹H NMR (400 MHz, CHLOROFORM-d) δ = 13.12 (br s, 1H), 9.45 (br d, J = 9.4 Hz, 1H), 8.72 (d, J = 7.3 Hz, 1H), 7.29-7.12 (m, 1H), 6.94 (br s, 2H), 6.87 (dd, J = 7.5, 12.3 Hz, 1H), 5.47-4.95 (m, 1H), 2.93-2.73 (m, 2H), 2.29 (d, J = 2.8 Hz, 3H), 2.10-1.84 (m, 2H), 1.72-1.58 (m, 1H), 1.54-1.17 (m, 4H), 0.90 (dt, J = 3.4, 6.9 Hz, 3H) ESI [M − H] = 391.2 |
| 286 | 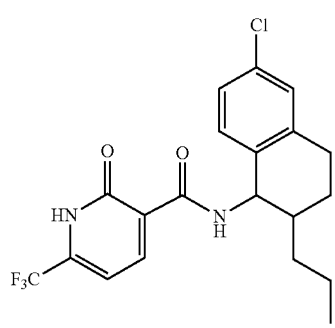 [SMILES: CCCC1CCc2cc(Cl)ccc2C1NC(=O)c1ccc(C(F)(F)F)[nH]c1=O] | ¹H NMR (400 MHz, CHLOROFORM-d) δ = 9.74-9.48 (m, 1H), 8.73 (d, J = 7.5 Hz, 1H), 7.34-7.20 (m, 1H), 7.14-7.06 (m, 2H), 6.89 (dd, J = 7.6, 10.5 Hz, 1H), 5.47-5.06 (m, 1H), 2.97-2.73 (m, 2H), 2.09-1.81 (m, 2H), 1.68-1.25 (m, 5H), 0.90 (qd, J = 3.5, 7.1 Hz, 3H) ESI (M − H) = 411.2 |

TABLE 23-continued

| Compound No | Structure | HNMR and Ms |
|---|---|---|
| 287 | 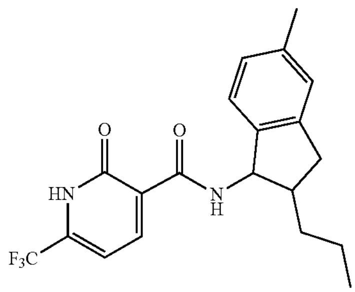 [SMILES: CCCC1Cc2cc(C)ccc2C1NC(=O)c1ccc(C(F)(F)F)[nH]c1=O] | ¹H NMR (400 MHz, CHLOROFORM-d) δ = 12.60-12.00 (m, 1H), 9.47 (br s, 1H), 8.78-8.57 (m, 1H), 7.26-7.11 (m, 1H), 7.09-7.03 (m, 1H), 6.99 (d, J = 7.5 Hz, 1H), 6.91-6.84 (m, 1H), 5.77-5.19 (m, 1H), 3.18-2.96 (m, 1H), 2.78-2.52 (m, 1H), 2.40-2.25 (m, 4H), 1.82-1.70 (m, 1H), 1.61-1.46 (m, 3H), 0.99-0.88 (m, 3H)<br>ESI (M − H) = 377.2 |
| 54 | 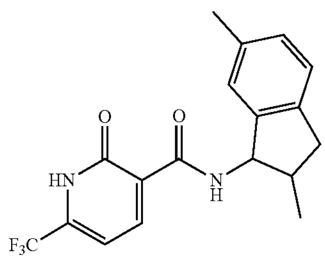 | ¹H NMR (400 MHz, CHLOROFORM-d) δ 9.50 (br s, 1H), 8.74 (br d, J = 6.2 Hz, 1H), 7.20-6.98 (m, 3H), 6.89 (br d, J = 6.7 Hz, 1H), 5.83-5.00 (m, 1H), 3.18-2.99 (m, 1H), 2.96-2.34 (m, 2H), 2.30 (br s, 3H), 1.01-.29 (m, 3H).<br>ESI (M − H) = 349.1 |
| 289 | 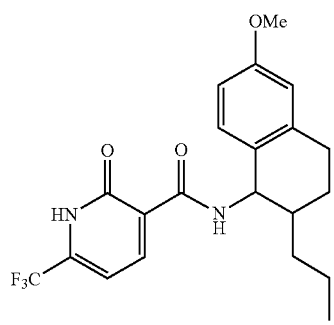 [SMILES: CCCC1CCc2cc(OC)ccc2C1NC(=O)c1ccc(C(F)(F)F)[nH]c1=O] | 1H NMR (400 MHz, CHLOROFORM-d) δ = 9.37 (br s, 1H), 8.68 (br d, J = 7.3 Hz, 1H), 7.33-7.18 (m, 1H), 6.87 (dd, J = 7.6, 12.3 Hz, 1H), 6.70 (br d, J = 8.7 Hz, 1H), 6.64 (s, 1H), 5.53 -5.02 (m, 1H), 3.78 (d, J = 3.3 Hz, 3H), 2.92-2.72 (m, 2H), 2.14-1.79 (m, 2H), 1.70-1.58 (m, 2H), 1.52-1.42 (m, 3H), 1.35-1.26 (m, 1H), 0.90 (td, J = 3.6, 7.0 Hz, 3H)<br>ESI [M − H] = 407.2 |
| 290 | 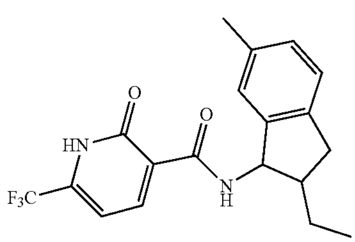 [SMILES: CCC1Cc2ccc(C)cc2C1NC(=O)c1ccc(C(F)(F)F)[nH]c1=O] | ¹H NMR (400 MHz, CHLOROFORM-d) δ = 9.64-9.29 (m, 1H), 8.73 (br s, 1H), 7.20-7.00 (m, 3H), 6.93-6.84 (m, 1H), 5.65-5.34 (m, 1H), 3.12-3.02 (m, 1H), 2.79-2.57 (m, 1H), 2.37-2.27 (m, 3H), 2.26-2.17 (m, 1H), 1.93-1.74 (m, 1H), 1.70-1.50 (m, 1H), 1.47-1.22 (m, 1H), 1.13-0.91 (m, 3H)<br>ESI [M − H] = 363.1 |
| 291 | 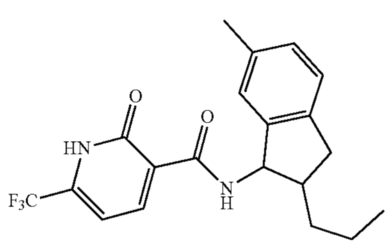 | ¹H NMR (400 MHz, CHLOROFORM-d) δ = 13.22 (br s, 1H), 9.55 (br d, J = 8.2 Hz, 1H), 8.77 (d, J = 7.3 Hz, 1H), 7.14-7.09 (m, 1H), 7.07-7.01 (m, 2H), 6.90 (d, J = 7.5 Hz, 1H), 5.67-5.34 (m, 1H), 3.13 (dd, J = 7.8, 15.5 Hz, 1H), 2.57 (dd, J = 8.7, 15.5 Hz, 1H), 2.30 (s, 3H), 1.82-1.69 (m, 1H), 1.61 - 1.25 (m, 4H), 0.94 (t, J=7.3 Hz, 3H)<br>ESI [M-H]=375.1 |

TABLE 23-continued

| Compound No | Structure | HNMR and Ms |
|---|---|---|
| 292 | 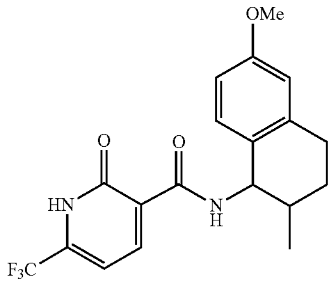 | $^1$H NMR (400 MHz, CHLOROFORM-d) δ = 9.44 (br t, J = 8.5 Hz, 1H), 8.72 (d, J = 7.3 Hz, 1H), 7.24 (s, 1H), 7.18 (d, J = 8.6 Hz, 1H), 6.87 (dd, J = 7.5, 10.6 Hz, 1H), 6.70 (dd, J = 2.1, 8.5 Hz, 1H), 6.65 (t, J = 3.2 Hz, 1H), 5.38 (dd, J = 4.3, 9.4 Hz, 1H), 4.99 (1, J = 8.0 Hz, 1H), 3.78 (d, J = 1.1 Hz, 3H), 2.90-2.80 (m, 2H), 2.20-1.92 (m, 1H), 1.84-1.59 (m, 1H), 1.08 (dd, J = 6.7, 19.7 Hz, 3H) ESI [M − H] = 379.1 |
| 293 | 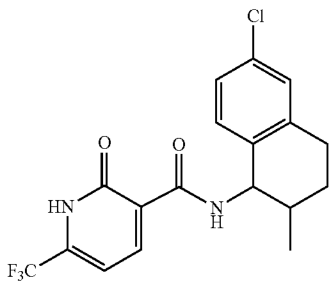 | $^1$H NMR (400 MHz, CDCl$_3$) δ = 9.62 - 9.47 (m, 1H), 8.74 (dd, J = 3.3, 7.1 Hz, 1H), 7.28-7.19 (m, 1H), 7.15-7.04 (m, 2H), 6.89 (dd, J = 7.9, 9.5 Hz, 1H), 5.41-5.00 (m, 1H), 2.95-2.76 (m, 2H), 2.25-1.75 (m, 2H), 1.73-1.54 (m, 1H), 1.15-1.01 (m, 3H) ESI [M − H] = 383.1 |
| 294 | 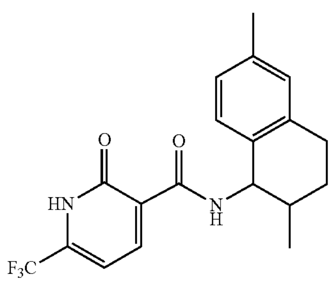 [SMILES: Cc1ccc2c(c1)CCC(C)C2NC(=O)c1ccc(C(F)(F)F)[nH]c1=O] | $^1$H NMR (400 MHz, CHLOROFORM-d) δ = 9.44 (br s, 1H), 8.77-8.65 (m, 1H), 7.24-7.13 (m, 1H), 6.94 (br d, J = 6.8 Hz, 2H), 6.87 (dd, J = 7.4, 11.7 Hz, 1H), 5.50-4.96 (m, 1H), 2.83 (br dd, J = 4.6, 9.6 Hz, 1H), 2.29 (s, 3H), 2.21-1.95 (m, 1H), 1.85-1.63 (m, 2H), 1.17-1.01 (m, 3H) ESI [M − H] = 363.1 |
| 295 | 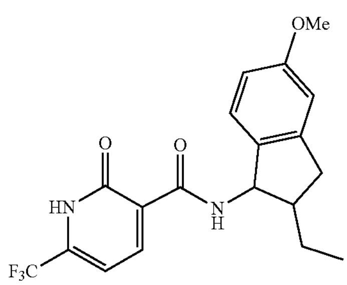 | $^1$H NMR (400 MHz, CHLOROFORM-d) δ = 9.61-9.24 (m, 1H), 8.70 (br d, J = 6.8 Hz, 1H), 7.25-7.11 (m, 1H), 6.90-6.83 (m, 1H), 6.81-6.75 (m, 1H), 6.72 (brd, J = 8.2 Hz, 1H), 5.66-5.22 (m, 1H), 3.79 (s, 3H), 3.22-2.94 (m, 1H), 2.78-2.51 (m, 1H), 2.32-2.10 (m, 1H), 1.90-1.30 (m, 2H), 1.06 - 0.90 (m, 3H) M+H$^+$ = 379.1 |
| 296 | 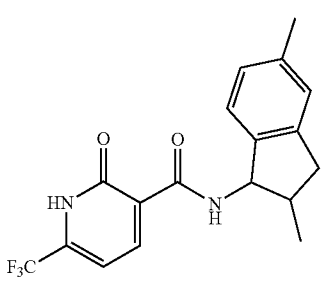 [SMILES: Cc1ccc2c(c1)CC(C)C2NC(=O)c1ccc(C(F)(F)F)[nH]c1=O] | $^1$H NMR (400 MHz, CHLOROFORM-d) δ = 9.43 (br s, 1H), 8.73 (d, J = 7.5 Hz, 1H), 7.24-7.14 (m, 1H), 7.11-6.98 (m, 2H), 6.92-6.85 (m, 1H), 5.75-4.98 (m, 1H), 3.19-3.03 (m, 1H), 2.71-2.53 (m, 1H), 2.45-2.37 (m, 1H), 2.37-2.33 (m, 3H), 1.33-1.04 (m, 3H) M + H$^+$ = 349.1 |

TABLE 23-continued

| Compound No | Structure | HNMR and Ms |
|---|---|---|
| 297 | 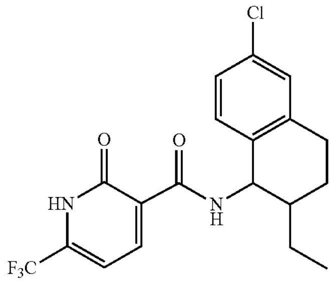 [SMILES: CCC1CCc2cc(Cl)ccc2C1NC(=O)c1ccc(C(F)(F)F)[nH]c1=O] | 1H NMR (400 MHz, CHLOROFORM-d) δ = 9.54 (br dd, J = 9.3, 17.6 Hz, 1H), 8.73 (dd, J = 2.4, 7.4 Hz, 1H), 7.34 (d, J = 8.3 Hz, 1H), 7.20 (d, J = 8.2 Hz, 1H), 7.13-7.04 (m, 2H), 6.89 (dd, J = 7.6, 11.6 Hz, 1H), 5.49-5.09 (m, 1H), 2.92-2.77 (m, 2H), 2.09-1.75 (m, 2H), 1.70-1.52 (m, 2H), 1.39-1.27 (m, 1H), 1.06-0.95 (m, 3H) ESI [M − H] = 397.1 |
| 298 | 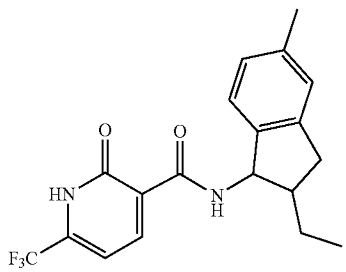 [SMILES: CCC1Cc2cc(C)ccc2C1NC(=O)c1ccc(C(F)(F)F)[nH]c1=O] | 1H NMR (400 MHz, CHLOROFORM-d) δ = 9.48-9.37 (m, 1H), 8.73-8.70 (m, 1H), 7.25 (s, 1H), 7.25-7.14 (d, J = 8 Hz, 1H), 7.05-6.88 (m, 2H), 5.69-5.30 (m, 1H), 3.16-3.10 (m, 1H), 2.61-2.55 (m, 1H), 2.34 (s, 3H), 2.24-2.22 (m, 1H), 1.80-1.81 (m, 1H), 1.60-1.57 (m, 1H), 1.00-0.96 (m, 3H) ESI [M − H] = 363.1 |
| 299 | 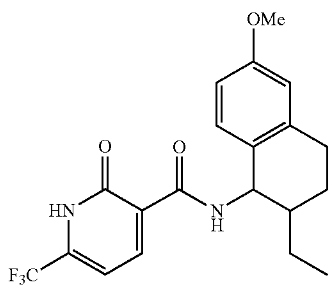 [SMILES: CCC1CCc2cc(OC)ccc2C1NC(=O)c1ccc(C(F)(F)F)[nH]c1=O] | $^1$H NMR (400 MHz, CHLOROFORM-d) δ = 9.46 (br t, J = 10.6 Hz, 1H), 8.72 (d, J = 7.5 Hz, 1H), 7.30-7.15 (m, 1H), 6.94 (br s, 2H), 6.87 (dd, J = 7.4, 13.6 Hz, 1H), 5.49-5.10 (m, 1H), 2.93-2.75 (m, 2H), 2.29 (s, 3H), 2.08-1.77 (m, 2H), 1.71-1.49 (m, 2H), 1.39-1.25 (m, 1H), 1.05-0.95 (m, 3H) ESI [M −H] = 393.1 |

Example 38: Synthesis of N-(4-ethyl-6-methyl-1,2,3,4-tetrahydronaphthalen-1-yl)-2-oxo-6-(trifluoromethyl)-1,2-dihydropyridine-3-carboxamide (300)

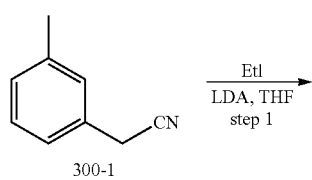

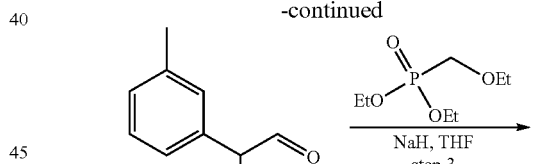

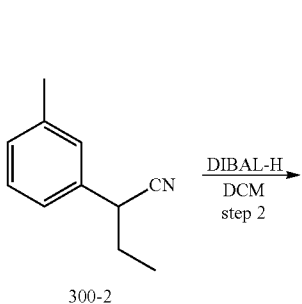

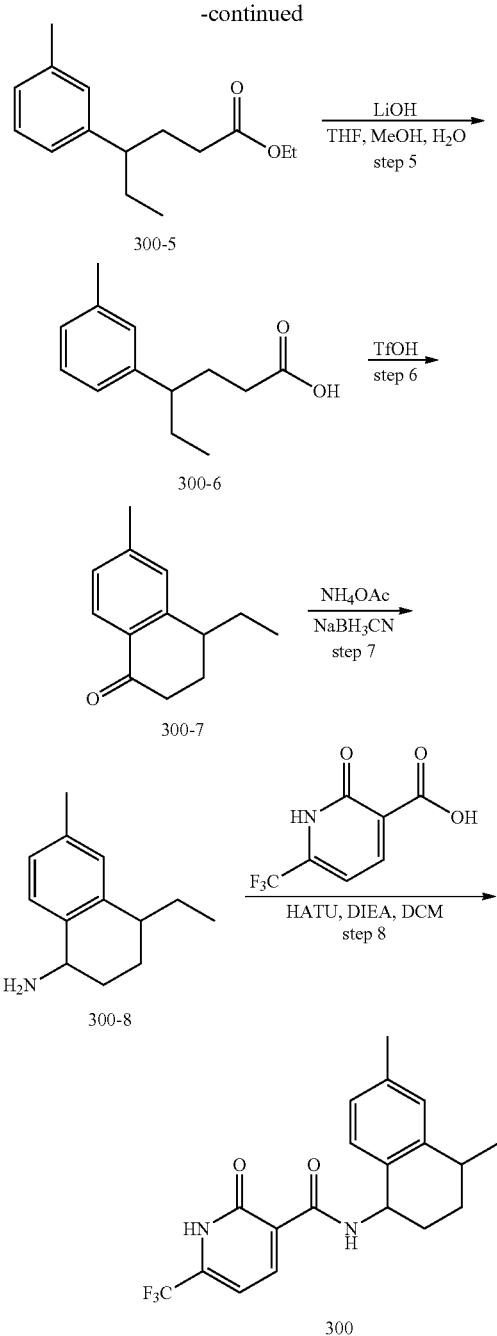

mmol) as a white solid. $^1$H NMR (400 MHz, CHLOROFORM-d) δ=7.30-7.27 (m, 1H), 7.17-7.08 (m, 3H), 3.70 (t, J=7.2 Hz, 1H), 2.38 (s, 3H), 2.01-1.86 (m, 2H), 1.08 (t, J=7.4 Hz, 3H).

Step 2: 2-(m-tolyl)butanal (300-3)

To a solution of Compound 300-2 (3.1 g, 19.4 mmol) in THF (140 mL) was added DIBAL-H (1 M, 48.7 mL) dropwise at −78° C. under N$_2$ atmosphere. The mixture was stirred at −78° C. for 1 hr and stirred at 25° C. for additional 3 hrs. TLC indicated the reaction was completed. LCMS showed the reaction was completed and desired mass was detected. The reaction mixture was added to sat.NH$_4$Cl (20 mL) at 25° C. and extracted with EtOAc (20 ml×4). The combined organic layers were dried over Na$_2$SO$_4$, filtered and concentrated under reduced pressure to give a residue, which was purified by flash silica gel chromatography to give Compound 300-3 (790 mg, 4.8 mmol) as pale yellow oil. M+H$^+$=163.1 (LCMS).

Step 3: (E)-ethyl 4-(m-tolyl) hex-2-enoate (300-4)

To a solution of diethyl (ethoxymethyl)phosphonate (2.5 g, 10.1 mmol) in THF (30 mL) was added NaH (222 mg, 5.6 mmol, 60% purity) at 0° C. and then the mixture was stirred at 0° C. for 15 mins. Compound 300-3 (350 mg, 2.1 mmol) in THF (2 mL) was added at 0° C. The mixture was stirred at 25° C. for 12 hrs. LCMS showed the reaction was completed and desired mass was detected. The reaction mixture was added to sat.NH$_4$Cl (10 mL) at 25° C. and extracted with EtOAc (10 mL×3). The combined organic layers were dried over Na$_2$SO$_4$, filtered and concentrated under reduced pressure to give a residue, which was purified by flash silica gel chromatography to give Compound 300-4 (820 mg, 3.6 mmol) as colorless oil. M+H$^+$=233.1 (LCMS).

Step 4: ethyl 4-(m-tolyl) hexanoate (300-5)

A mixture of compound 300-4 (810 mg, 3.5 mmol), Pd/C (200 mg, 3.5 mmol, 10% purity) in EtOAc (10 mL) was degassed and purged with H$_2$ for 3 times, and then the mixture was stirred at 20° C. for 2 hrs under H$_2$ (15 Psi). LCMS showed the reaction was completed and desired mass was detected. The reaction mixture was filtered and the filtrate was concentrated under reduced pressure to give compound 300-5 (830 mg, crude) as yellow oil. M+H$^+$=235.1 (LCMS).

Step 5: 4-(m-tolyl)hexanoic acid (300-6)

To a solution of compound 300-5 (830 mg, 3.5 mmol) in THF (16 mL) and MeOH (16 mL) was added LiOH (2 M, 7 mL). The mixture was stirred at 50° C. for 2.5 hrs. TLC showed the reaction was completed. The reaction mixture was added to H$_2$O (10 ml), adjusted pH=7 with HCl (1M), and extracted with EtOAc (10 mL×4). The combined organic layers were washed with brine (5 mL×2), dried over Na$_2$SO$_4$, filtered and concentrated under reduced pressure to give compound 300-6 (590 mg, crude) as a colorless gum.

Step 6: 4-ethyl-6-methyl-3, 4-dihydronaphthalen-1 (2H)-one (300-7)

To a solution of compound 300-6 (200 mg, 969.6 µmol) in DCM (2 mL) was added slowly TfOH (2.3 g, 15.5 mmol) at 0° C. under N$_2$. Then the mixture was stirred at 0° C. for Step 1: 2-(m-tolyl)butanenitrile (300-2)

To a solution of Compound 300-1 (6 g, 45.7 mmol) in THF (110 mL) was added LDA (2 M, 27 mL) at −78° C. under N$_2$ atmosphere; After stirring 30 mins, iodoethane (8.9 g, 57.2 mmol) was added at −78° C., then the mixture was stirred at −78° C. for 1 hr and stirred at 0° C. for additional 1 hr. TLC indicated the reaction was completed. The reaction mixture was poured into Sat.NH$_4$Cl (20 mL) and extracted with EtOAc (10 mL×5). The combined organic layers were washed with brine (5 mL×2), dried over Na$_2$SO$_4$, filtered and concentrated under reduced pressure to give a residue, which was purified by flash silica gel chromatography to give Compound 300-2 (3.1 g, 19.4

0.5 hr. LCMS showed the reaction was completed and desired mass was detected. The reaction mixture was quenched by addition sat.NaHCO₃ (20 mL) at 0° C., and extracted with DCM (10 mL×3). The combined organic layers were washed with sat.NaHCO₃ (10 mL×3), dried over Na₂SO₄, filtered and concentrated under reduced pressure to give compound 300-7 (180 mg, crude) as yellow oil. M+H⁺= 189.1 (LCMS).

Step 7: 4-ethyl-6-methyl-1, 2, 3, 4-tetrahydronaphthalen-1-amine (300-8)

To a stirred solution of compound 300-7 (100 mg, 531.1 μmol) in MeOH (6 mL) was was added NH₄OAc (614 mg, 7.9 mmol). The mixture was stirred for 10 mins at 25° C., and then NaBH₃CN (133 mg, 2.1 mmol) was added. The mixture was stirred at 90° C. for 1 hr under microwave. TLC indicated the reaction was completed. The reaction mixture was poured into H₂O (10 mL) at 20° C., and extracted with EtOAc (10 mL×3). The combined organic layers were washed with sat.NaHCO₃ (5 mL×3), dried over Na₂SO₄, filtered and concentrated under reduced pressure to give compound 300-8 (100 mg, crude) as brown solid.

Step 8: N-(4-ethyl-6-methyl-1,2,3,4-tetrahydronaphthalen-1-yl)-2-oxo-6-(trifluoromethyl)-1,2-dihydropyridine-3-carboxamide (300)

To a mixture of Compound 300-8 (100 mg, 528.2 μmol), 2-oxo-6-(trifluoromethyl)-1, 2-dihydropyridine-3-carboxylic acid (131 mg, 633.2 μmol) in DCM (4 mL) was added DIEA (82 mg, 634.3 μmol) and HATU (200 mg, 528.6 μmol). The mixture was stirred at 25° C. for 1 hr. LCMS showed the reaction was completed and desired mass was detected. The reaction mixture was added into H₂O (10 mL) and extracted with DCM (10 ml×3). The combined organic layers were dried over Na₂SO₄, filtered and concentrated under reduced pressure to give a residue, which was purified by prep-HPLC to give Compound 300 (41 mg, 104 μmol, 19% yield) as a white solid. M-H⁻=377.1. (LCMS); $^1$H NMR (400 MHz, CHLOROFORM-d) δ=9.53 (br s, 1H), 8.71 (dd, J=4.6, 7.2 Hz, 1H), 7.18 (dd, J=7.9, 13.5 Hz, 1H), 7.05 (br d, J=14.1 Hz, 1H), 6.96 (br d, J=8.0 Hz, 1H), 6.85 (dd, J=3.3, 7.5 Hz, 1H), 5.36-5.17 (m, 1H), 2.76-2.59 (m, 1H), 2.32 (s, 3H), 2.25-1.75 (m, 6H), 1.01 (dt, J=2.2, 7.4 Hz, 3H).

Example 39: Synthesis of tert-butyl (2-(5-(2-oxo-6-(trifluoromethyl)-1,2-dihydropyridine-3-carboxamido)-5,6,7,8-tetrahydronaphthalen-1-yl)ethyl)carbamate (301)

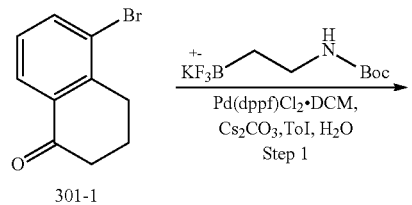

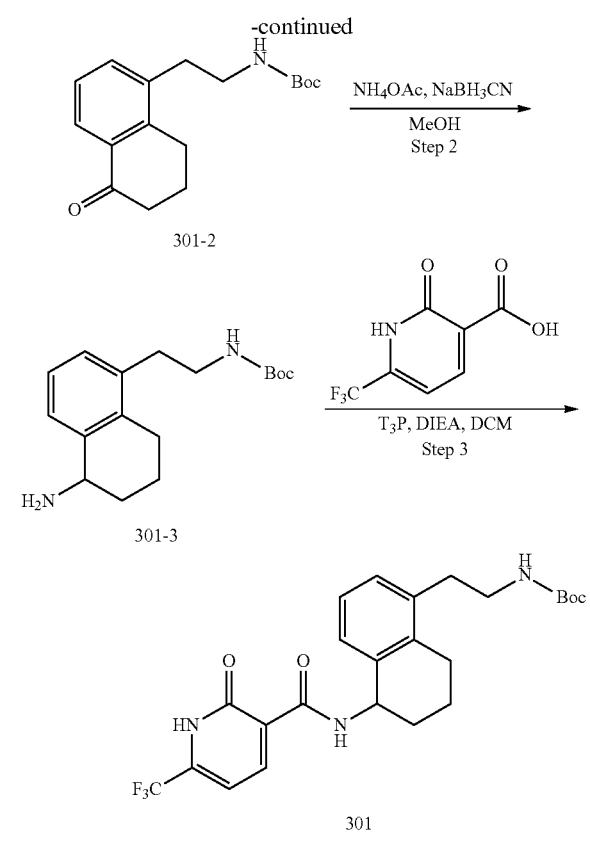

Step 1: tert-butyl (2-(5-oxo-5,6,7,8-tetrahydronaphthalen-1-yl)ethyl)carbamate (301-2)

A mixture of Compound 301-1 (200 mg, 888 μmol) Cs₂CO₃ (579 mg, 1.8 mmol) Pd(dppf)Cl₂·CH₂Cl₂ (73 mg, 89 μmol) and potassium; 2-(tert-butoxycarbonylamino) ethyl-trifluoro-boranuide (245 mg, 977 μmol) in Tol. (6 mL) and H₂O (2 mL) was stirred at 80° C. for 12 hrs. TLC showed the reaction was completed. Then the mixture was diluted with H₂O (10 mL) and extracted with EtOAc (10 mL×3). The combined organic layers dried over Na₂SO₄ and concentrated under reduced pressure to give a residue, which was purified by silica gel chromatography (Ethyl acetate/Petroleum) to give Compound 301-2 (0.2 g, 691 μmol, 78% yield) as a yellow gum.

Step 2: tert-butyl (2-(5-amino-5,6,7,8-tetrahydronaphthalen-1-yl)ethyl)carbamate (301-3)

To a stirred solution of Compound 301-2 (50 mg, 173 μmol) in MeOH (2 mL) was added NH₄OAc (200 mg, 26 mmol), the reaction was stirred for 10 min at 20° C., then NaBH₃CN (43 mg, 691 μmol) was added and the reaction was stirred at 90° C. for 1 hrs under microwave. LCMS showed the reaction was completed and the desired mass was detected. The reaction mixture was poured into H₂O (10 mL) then was extracted with EtOAc (5 mL×3), The combined organic layers were washed with Sat.NaCl (10 mL), dried over Na₂SO₄, filtered and concentrated under reduced pressure to give Compound 301-3 (50 mg, crude) as a yellow gum. M+H⁺=291.2 (LCMS).

Step 3: tert-butyl (2-(5-(2-oxo-6-(trifluoromethyl)-1,2-dihydropyridine-3-carboxamido)-5,6,7,8-tetrahydronaphthalen-1-yl)ethyl)carbamate (301)

To a stirred solution of 2-oxo-6-(trifluoromethyl)-1,2-dihydropyridine-3-carboxylic acid (36 mg, 172 μmol) and Compound 301-3 (50 mg, 172 μmol) in DCM (5 mL) was added TEA (52 mg, 517 μmol) at 20° C., followed by T$_3$P (219 mg, 344 μmol, 50% purity). The resulting mixture was stirred at 20° C. for 12 hrs. Then the mixture was diluted with H$_2$O (5 mL) and extracted with EtOAc (5 mL×3). The combined organic layers dried over Na$_2$SO$_4$ and concentrated under reduced pressure to give a residue. The residue was added MeOH (2 mL) and 3M NaOH (0.2 mL) and stirred at 30° C. for 12 hrs. LCMS showed the reaction was completed. Then the mixture was diluted with H$_2$O (5 mL) and extracted with DCM (5 mL×5). The combined organic layers dried over Na$_2$SO$_4$ and concentrated under reduced pressure to give a residue, which was purified by prep-HPLC to give Compound 301 (17 mg, 37 μmol, 21% yield) as a white solid. M−H⁻=478.2 (LCMS), $^1$H NMR (400 MHz, CHLOROFORM-d) δ=9.57 (br s, 1H), 8.70 (d, J=7.3 Hz, 1H), 7.22 (d, J=7.6 Hz, 1H), 7.16-7.01 (m, 2H), 6.85 (d, J=7.5 Hz, 1H), 5.46-5.26 (m, 1H), 4.61 (br s, 1H), 3.35 (br s, 2H), 2.96-2.52 (m, 4H), 2.13-1.77 (m, 4H), 1.53-1.34 (m, 9H).

Example 40: Synthesis of N-(4,6-dimethyl-1,2,3,4-tetrahydronaphthalen-1-yl)-2-oxo-6-(trifluoromethyl)-1,2-dihydropyridine-3-carboxamide (302)

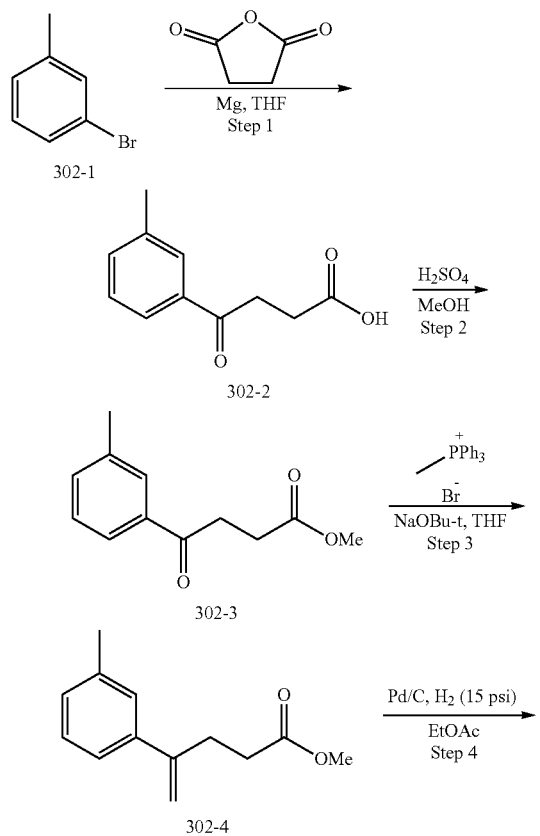

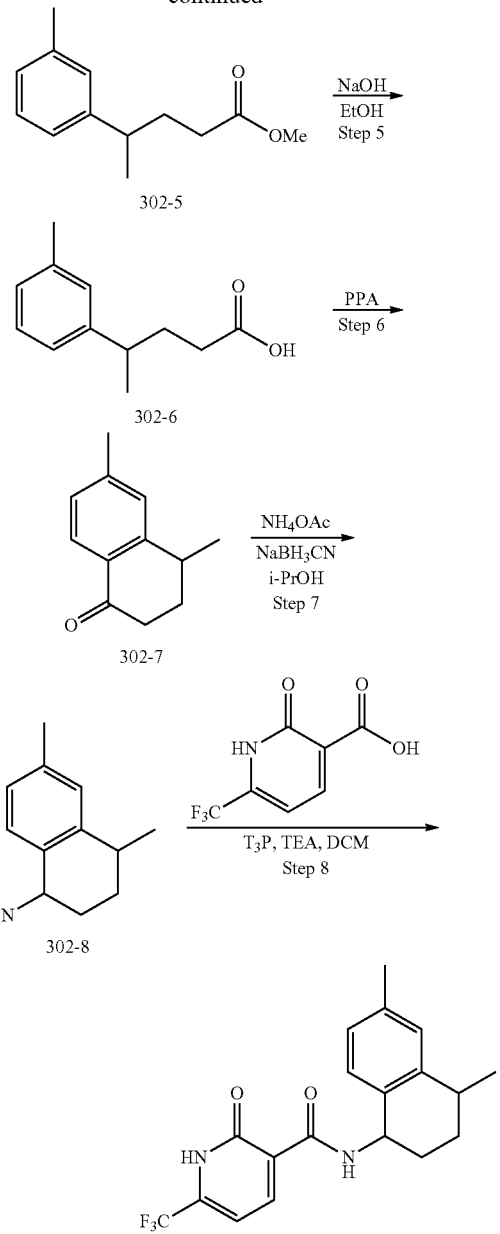

Step 1: 4-oxo-4-(m-tolyl)butanoic acid (302-2)

To a solution of Mg (2 g, 82.3 mmol) in THF (10 mL) was added I$_2$ (1 g, 3.9 mmol). 10% of Compound 302-1 (1 M, 58.5 mL) was added in portions to the mixture. The resulting mixture was stirred at refluxing for 10 mins, the color of the mixture turned from brown to colorless. The resulting Compound 302-1 was added in portions. The resulting mixture was heated at 70° C. for 1 hr. Then the mixture was cooled to room temperature and added to a solution of dihydrofuran-2,5-dione (5.9 g, 58.5 mmol) in THF (80 mL) at −78° C. under N$_2$. The resulting mixture was warmed to room temperature and stirred at 15° C. for 12 hrs. LCMS showed the reaction was completed and desired mass was detected. The resulting mixture was diluted with DCM (200 mL) and washed with 1 M HCl (150 mL) solution, 10% NaHCO$_3$ (50 mL), and brine (150 mL), the organic layers were dried over anhydrous $Na_2SO_4$, filtered and concentrated in vacuum to give Compound 302-2 (10 g, crude) as light yellow solid. $M+H^+$=193.1 (LCMS).

Step 2: methyl 4-oxo-4-(m-tolyl)butanoate (302-3)

To a solution of Compound 302-2 (10 g, 52 mmol) in MeOH (100 mL) was added $H_2SO_4$ (383 mg, 3.9 mmol). The mixture was stirred at 60° C. for 2 hrs. LCMS showed the reaction was completed and desired mass was detected. The reaction mixture was poured into $H_2O$ (150 mL) and extracted with EtOAc (100 mL×3). The combined organic layers dried over $Na_2SO_4$ and concentrated under reduced pressure to give a residue. The residue was purified by flash silica gel chromatography to give Compound 302-3 (4.5 g, crude) as light yellow oil. $M+H^+$=207.1 (LCMS); $^1H$ NMR (400 MHz, $CDCl_3$) δ=7.83-7.74 (m, 2H), 7.42-7.33 (m, 2H), 3.72 (s, 3H), 3.32 (t, J=6.7 Hz, 2H), 2.77 (t, J=6.7 Hz, 2H), 2.42 (s, 3H).

Step 3: methyl 4-(m-tolyl)pent-4-enoate (302-4)

To a stirred solution of t-BuONa (2.8 g, 29.1 mmol) in THF (40 mL) was added methyl triphenylphosphonium bromide (10.4 g, 29.1 mmol) at 0° C. After stirring for 30 mins at 0° C., a solution of Compound 302-3 (2 g, 9.7 mmol) in THF (10 mL) was added at 0° C. Then the mixture was warmed to 25° C. and stirred at 25° C. for 12 hrs. TLC indicated the reaction was completed. The reaction mixture was poured into Sat.$NH_4Cl$ (40 mL) and extracted with EtOAc (20 mL×3). The combined organic layers were dried over $Na_2SO_4$, filtered and concentrated under reduced pressure to give a residue. The residue was purified by flash silica gel chromatography to give Compound 302-4 (900 mg, crude) as light yellow oil. $^1H$ NMR (400 MHz, $CDCl_3$) δ=7.26-7.18 (m, 3H), 7.13-7.07 (m, 1H), 5.29 (s, 1H), 5.08 (d, J=1.2 Hz, 1H), 3.67 (s, 3H), 2.88-2.80 (m, 2H), 2.55-2.46 (m, 2H), 2.37 (s, 3H).

Step 4: methyl 4-(m-tolyl)pentanoate (302-5)

To a solution of Compound 302-4 (900 mg, 4.4 mmol) in EtOAc (100 mL) was added Pd/C (1 g, 10% purity) under $N_2$ atmosphere. The suspension was degassed and purged with $H_2$ for 5 times. The mixture was stirred under $H_2$ (15 Psi) at 15° C. for 1.5 hrs. LCMS showed the reaction was completed and desired mass was detected. The reaction mixture was filtered and concentrated under reduced pressure to give Compound 302-5 (850 mg, crude) as light yellow oil. $M+H^+$=207.1 (LCMS).

Step 5: 4-(m-tolyl)pentanoic acid (302-6)

To a solution of Compound 302-5 (850 mg, 4.1 mmol) in EtOH (20 mL) was added NaOH (494 mg, 12.4 mmol). The mixture was stirred at 15° C. for 2 hrs. LCMS showed the reaction was completed and desired mass was detected. The reaction mixture was quenched by addition $H_2O$ 50 mL, and then washed with Petroleum ether (20 mL×3). The water phase was neutralized with HCl solution (1 M) to pH=4 and extracted with EtOAc (20 mL×3). The combined organic layers were dried over $Na_2SO_4$, filtered and concentrated under reduced pressure to give Compound 302-6 (600 mg, crude) as brown oil. $M-H^-$=191.0 (LCMS); $^1H$ NMR (400 MHz, $CDCl_3$) δ=11.64-10.28 (m, 1H), 7.24-7.17 (m, 1H), 7.06-6.91 (m, 3H), 2.82-2.63 (m, 1H), 2.39-2.33 (m, 3H), 2.29-2.22 (m, 2H), 2.01-1.82 (m, 2H), 1.33-1.26 (m, 3H).

Step 6: 4,6-dimethyl-3,4-dihydronaphthalen-1(2H)-one (302-7)

A solution of Compound 302-6 (600 mg, 3.1 mmol) in PPA (6 mL) was stirred at 120° C. for 1 hr. LCMS showed the reaction was completed and desired mass was detected. The mixture was diluted with $H_2O$ (10 mL) and extracted with EtOAc (10 mL×3). The combined organic layers dried over $Na_2SO_4$ and concentrated under reduced pressure to give a residue. The residue was purified by flash silica gel chromatography to give Compound 302-7 (400 mg, 2.30 mmol) as brown oil. $M+H^+$=175.1 (LCMS); $^1H$ NMR (400 MHz, $CDCl_3$) δ=7.97-7.91 (m, 1H), 7.18-7.09 (m, 2H), 3.06 (dt, J=4.7, 6.9 Hz, 1H), 2.85-2.70 (m, 1H), 2.58 (ddd, J=4.8, 8.4, 17.4 Hz, 1H), 2.40 (s, 3H), 2.24 (dt, J=4.5, 8.9 Hz, 1H), 1.90 (dddd, J=4.6, 7.2, 8.5, 13.3 Hz, 1H), 1.40 (d, J=7.1 Hz, 3H).

Step 7: 4,6-dimethyl-1,2,3,4-tetrahydronaphthalen-1-amine (302-8)

To a solution of Compound 302-7 (200 mg, 1.2 mmol) in i-PrOH (6 mL) was added $NH_4OAc$ (1.8 g, 23 mmol), then $NaBH_3CN$ (361 mg, 5.7 mmol) was added to the mixture, the mixture was stirred at 80° C. for 2 hrs. LCMS showed the reaction was completed and desired mass was detected. The reaction mixture was poured into $H_2O$ (15 mL), and then extracted with EtOAc (5 mL×3). The combined organic layers were dried over $Na_2SO_4$, filtered and concentrated under reduced pressure to give a Compound 302-8 (200 mg, crude) as brown oil. Fragment Ms=159.1 (LCMS).

Step 8: N-(4,6-dimethyl-1,2,3,4-tetrahydronaphthalen-1-yl)-2-oxo-6-(trifluoromethyl)-1,2-dihydropyridine-3-carboxamide (302)

To a solution of Compound 302-8 (200 mg, 1.1 mmol) in DCM (5 mL) was added 2-oxo-6-(trifluoromethyl)-1,2-dihydropyridine-3-carboxylic acid (200 mg, 965.7 μmol), TEA (346.4 mg, 3.4 mmol) and $T_3P$ (1.5 g, 2.3 mmol, 50% purity). The mixture was stirred at 15° C. for 12 hrs. LCMS showed the reaction was completed. The reaction mixture was poured into $H_2O$ (10 mL) and extracted with EtOAc (5 mL×3). The combined organic layers dried over $Na_2SO_4$ and concentrated under reduced pressure to give a residue. The residue was treated with MeOH (3 mL) and 3M NaOH (3 mL) and stirred at 15° C. for 2 hrs. LCMS showed the desired mass was detected. The reaction mixture was poured into $H_2O$ (10 mL) and extracted with EtOAc (5 mL×3). The combined organic layers were dried over $Na_2SO_4$ and concentrated under reduced pressure to give a residue. The residue was purified by prep-HPLC to give Compound 302 (77 mg, 211.2 μmol, 19% yield) as a white solid. $M-H^-$= 363.1 (LCMS); $^1H$ NMR (400 MHz, DMSO-d6) δ=8.10 (d, J=7.5 Hz, 1H), 7.08 (dd, J=2.4, 7.8 Hz, 1H), 7.04 (s, 1H), 6.92 (br d, J=7.8 Hz, 1H), 6.49 (d, J=7.5 Hz, 1H), 5.13-5.01 (m, 1H), 2.96-2.75 (m, 1H), 2.24 (s, 3H), 2.12-1.82 (m, 2H), 1.80-1.40 (m, 2H), 1.32-1.21 (m, 3H).

Example 41: Synthesis of N-((2R,4R,6S)-2,6-dipropyltetrahydro-2H-pyran-4-yl)-2-oxo-6-(trifluoromethyl)-1,2-dihydropyridine-3-carboxamide (303)

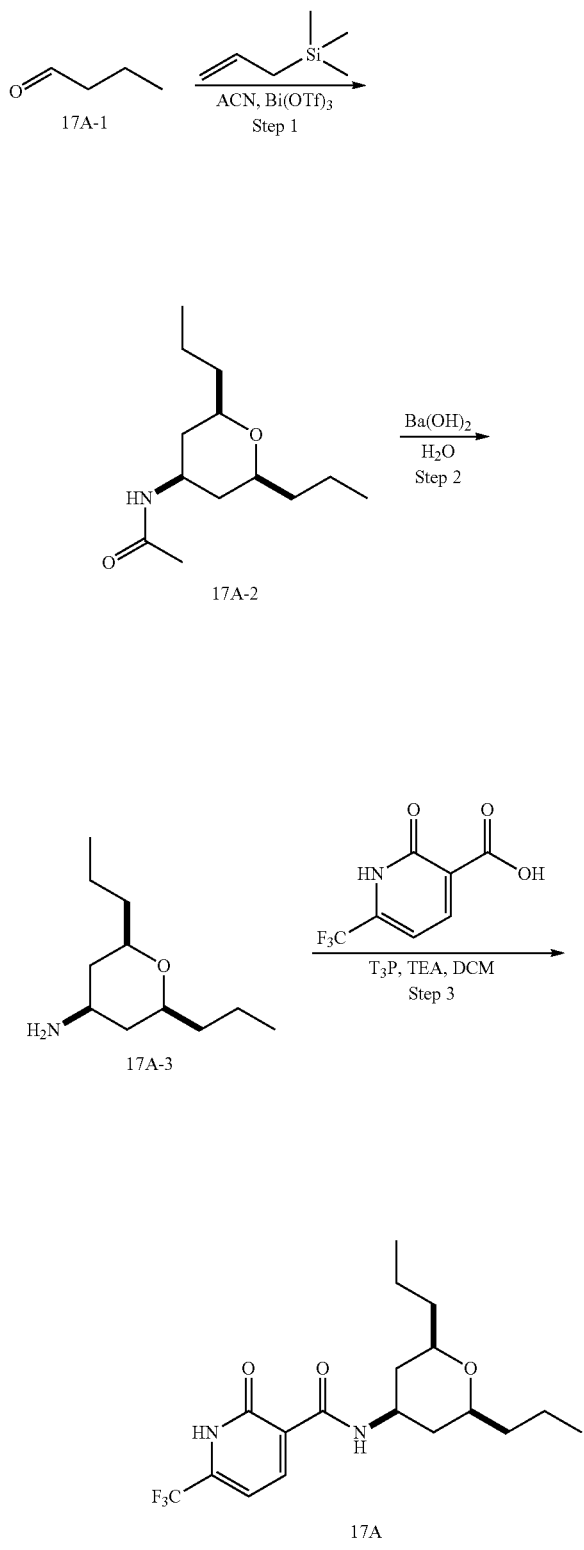

Step 1: N-((2R,4R,6S)-2,6-dipropyltetrahydro-2H-pyran-4-yl)acetamide (303-2)

Allyltrimethylsilane (950 mg, 8.3 mmol) was added to a mixture of Compound 303-1 (1 g, 13.9 mmol) and Bi(OTf)$_3$ (910 mg, 1.4 mmol) in ACN (70 mL), and the mixture was stirred at 20° C. for 20 min. TLC showed the reaction completed. The reaction mixture was poured into H$_2$O (20 mL), then was extracted with EtOAc (20 mL×5). The combined organic layers were dried over Na$_2$SO$_4$, filtered and concentrated under reduced pressure to give a residue, which was purified by silica gel chromatography (Ethyl acetate/Petroleum ether) to give Compound 303-2 (0.6 g, 2.6 mmol, 18% yield) as a yellow solid. $^1$H NMR (400 MHz, CHLOROFORM-d) δ=5.30 (br s, 1H), 4.18-3.86 (m, 1H), 3.46-3.22 (m, 2H), 1.97 (s, 3H), 1.93 (br dd, J=4.3, 12.1 Hz, 2H), 1.59-1.43 (m, 4H), 1.42-1.27 (m, 4H), 1.06-0.95 (m, 2H), 0.94-0.85 (m, 6H).

Step 2: (2R,4R,6S)-2,6-dipropyltetrahydro-2H-pyran-4-amine (303-3)

Compound 303-2 (200 mg, 879 μmol) was dissolved in H$_2$O (70 mL) at 20° C. and Ba(OH)$_2$ (15 g, 87.9 mmol) octahydrate was added. The solution was stirred magnetically while it vigorously boiled under reflux (130° C.) for 12 hrs. TLC showed the reaction was completed. The reaction mixture was filtered and the filtrate was extracted with EtOAc (20 mL×4). The combined organic layers were dried over Na$_2$SO$_4$, filtered and concentrated under reduced pressure to give Compound 303-3 (160 mg, crude) as a yellow gum. $^1$H NMR (400 MHz, CHLOROFORM-d) δ=3.33-3.18 (m, 2H), 2.85 (tt, J=4.3, 11.3 Hz, 1H), 1.80 (br dd, J=4.2, 12.3 Hz, 2H), 1.60-1.46 (m, 4H), 1.40-1.31 (m, 4H), 1.01-0.87 (m, 8H).

Step 3: N-((2R,4R,6S)-2,6-dipropyltetrahydro-2H-pyran-4-yl)-2-oxo-6-(trifluoromethyl)-1,2-dihydropyridine-3-carboxamide (303)

To a stirred solution of 2-oxo-6-(trifluoromethyl)-1,2-dihydropyridine-3-carboxylic acid (89 mg, 431 μmol) and Compound 303-3 (80 mg, 431 μmol) in DCM (8 mL) was added TEA (13 1mg, 1.3 mmol) at 20° C., followed by T$_3$P (549 mg, 863 μmol, 50% purity). The resulting mixture was stirred at 20° C. for 2 hrs. Then the mixture was diluted with H$_2$O (5 mL) and extracted with DCM (3 mL×3). The combined organic layers dried over Na$_2$SO$_4$ and concentrated under reduced pressure to give a residue. The residue was diluted with MeOH (2 mL) and 3M NaOH (0.2 mL) and stirred at 20° C. for 12 hrs. LCMS showed the reaction was completed and the desired mass was detected. Then the mixture was diluted with H$_2$O (5 mL) and extracted with DCM (5 mL×5). The combined organic layers dried over Na$_2$SO$_4$ and concentrated under reduced pressure to give a residue, which was purified by prep-HPLC to give Compound 303 (42 mg, 108 μmol, 25% yield) as a white solid. M−H$^−$=373.1 (LCMS) $^1$H NMR (400 MHz, CHLOROFORM-d) δ=9.38 (br d, J=7.7 Hz, 1H), 8.70 (d, J=7.3 Hz, 1H), 6.93 (d, J=7.5 Hz, 1H), 4.30-4.08 (m, 1H), 3.48-3.32 (m, 2H), 2.04 (dd, J=4.2, 12.2 Hz, 2H), 1.67-1.29 (m, 8H), 1.24-1.02 (m, 2H), 0.97-0.83 (m, 6H).

Example 42: Synthesis of N-((1R,4R)-4-amino-6-methyl-1,2,3,4-tetrahydronaphthalen-1-yl)-2-oxo-6-(trifluoromethyl)-1,2-dihydropyridine-3-carboxamide (304) and N-((1R,4S)-4-amino-6-methyl-1,2,3,4-tetrahydronaphthalen-1-yl)-2-oxo-6-(trifluoromethyl)-1,2-dihydropyridine-3-carboxamide (305)

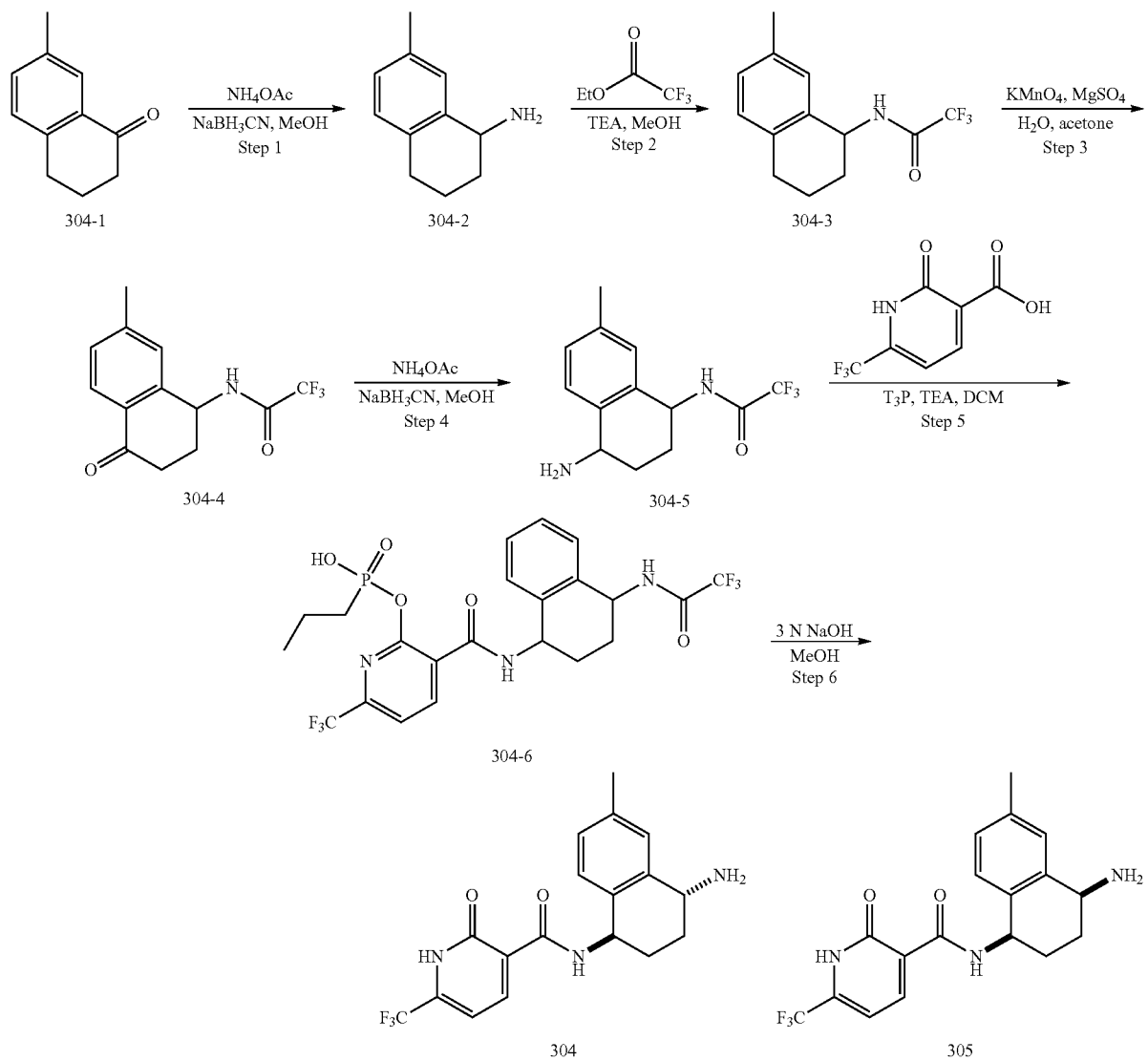

Step 1: 7-methyl-1,2,3,4-tetrahydronaphthalen-1-amine (304-2)

To a solution of Compound 304-1 (1 g, 6.2 mmol) in i-PrOH (40 mL) was added NH₄OAc (9.6 g, 124.8 mmol), then NaBH₃CN (1.9 g, 31.2 mmol) was added to the mixture, the mixture was stirred at 80° C. for 8 hrs. LCMS showed the reaction was completed and the desired mass was detected. The reaction mixture was poured into H₂O (40 mL) and extracted with CHCl₃ (20 mL×4). The combined organic layers were washed with Sat.NaCl (10 mL×3), dried over Na₂SO₄, filtered and concentrated under reduced pressure to give a residue, which was triturated with DCM/EtOAc/Petroleum ether=1/1/1 (5 ml/5 ml/5 ml) at 20° C. to give Compound 304-2 (0.8 g, 4.9 mmol, 80% yield) as a white solid. Fragment Ms=145.1 (LCMS), $^1$HNMR (400 MHz, DMSO-d$_6$) δ=8.41 (br s, 2H), 7.40 (br s, 1H), 7.12-6.97 (m, 2H), 4.34 (t, J=5.4 Hz, 1H), 2.79-2.57 (m, 2H), 2.27 (s, 3H), 2.15-1.82 (m, 3H), 1.79-1.61 (m, 1H).

Step 2: 2,2,2-trifluoro-N-(7-methyl-1,2,3,4-tetrahydronaphthalen-1-yl)acetamide (304-3)

To a solution of ethyl 2,2,2-trifluoroacetate (560 mg, 3.9 mmol) in MeOH (10 mL) was added TEA (499 mg, 4.9 mmol) and Compound 304-2 (0.5 g, 3.3 mmol). The mixture was stirred at 20° C. for 4 hrs. LCMS showed the reaction was completed and one main peak with desired mass was detected. The reaction mixture concentrated to remove half of the solvent then was poured into H$_2$O (20 mL), the precipitate was filtered and the filter cake was washed with H$_2$O, dried in vacuum to give Compound 304-3 (0.6 g, 2.5 mmol, 75% yield) as a white solid. M−H$^−$=256.0 (LCMS), $^1$H NMR (400 MHz, DMSO-d$_6$) δ=9.79 (br d, J=8.3 Hz, 1H), 7.02 (br s, 2H), 6.90 (s, 1H), 5.09-4.94 (m, 1H), 2.79-2.60 (m, 2H), 2.24 (s, 3H), 2.00-1.81 (m, 2H), 1.80-1.65 (m, 2H).

Step 3: 2,2,2-trifluoro-N-(7-methyl-4-oxo-1,2,3,4-tetrahydronaphthalen-1-yl)acetamide (304-4)

To a solution of Compound 304-3 (330 mg, 1.3 mmol) in acetone (20 mL) was added MgSO$_4$ (370 mg, 3.1 mmol), H$_2$O (10 mL) at 0° C., followed by KMnO$_4$ (1.1 g, 6.7 mmol). The mixture was stirred at 20° C. for 8 hrs. LCMS showed the reaction was completed and the desired mass was detected. The reaction mixture was poured into Sat. Na$_2$SO$_3$ (30 mL), filtered and the filtrate was extracted with EtOAc (15 mL×5). The combined organic layers were dried over Na$_2$SO$_4$, filtered and concentrated under reduced pressure to give Compound 304-4 (340 mg, 1.3 mmol, 98% yield) as a white solid. M−H$^−$=269.9 (LCMS), $^1$H NMR (400 MHz, CHLOROFORM-d) δ=7.99 (d, J=8.1 Hz, 1H), 7.30 (s, 1H), 7.14 (s, 1H), 6.54 (br s, 1H), 5.39 (dt, J=4.3, 8.4 Hz, 1H), 2.86-2.65 (m, 2H), 2.51-2.42 (m, 4H), 2.30-2.18 (m, 1H).

Step 4: N-(4-amino-7-methyl-1,2,3,4-tetrahydronaphthalen-1-yl)-2,2,2-trifluoroacetamide (304-5)

To a stirred solution of Compound 304-4 (200 mg, 737 μmol) in MeOH (8 mL) was added NH$_4$OAc (853 mg, 11.0 mmol) the reaction was stirred for 10 min at 20° C. NaBH$_3$CN (185 mg, 2.9 mmol) was added and the reaction was stirred at 90° C. for 1 hrs under Microwave. LCMS showed the reaction was completed and the desired mass was detected. The reaction mixture was poured into H$_2$O (10 mL) and extracted with DCM (10 mL×4). The combined organic layers were washed with brine (10 mL×2), dried over Na$_2$SO$_4$, filtered and concentrated under reduced pressure to give Compound 304-5 (150 mg, crude) as a yellow gum. Fragment Ms=271.0 (LCMS).

Step 5: 3-((6-methyl-4-(2,2,2-trifluoroacetamido)-1,2,3,4-tetrahydronaphthalen-1-yl)carbamoyl)-6-(trifluoromethyl)pyridin-2-yl hydrogen propylphosphonate (304-6)

To a stirred solution of 2-oxo-6-(trifluoromethyl)-1,2-dihydropyridine-3-carboxylic acid (114.10 mg, 551 μmol) and Compound 304-5 (150 mg, 551 μmol) in DCM (10 mL) was added TEA (167 mg, 1.6 mmol) at 20° C., followed by T$_3$P (701 mg, 1.1 mmol, 50% purity). The resulting mixture was stirred at 20° C. for 12 hrs. LCMS showed the reaction was completed and the desired mass was detected. Then the mixture was diluted with H$_2$O (10 mL) and extracted with DCM (5 mL×3). The combined organic layers dried over Na$_2$SO$_4$ and concentrated under reduced pressure to give Compound 304-6 (0.3 g, 528 μmol, 96% yield) as a yellow gum.

Step 6: N-((1R,4R)-4-amino-6-methyl-1,2,3,4-tetrahydronaphthalen-1-yl)-2-oxo-6-(trifluoromethyl)-1,2-dihydropyridine-3-carboxamide (304) and N-((1R,4S)-4-amino-6-methyl-1,2,3,4-tetrahydronaphthalen-1-yl)-2-oxo-6-(trifluoromethyl)-1,2-dihydropyridine-3-carboxamide (305)

To a solution of Compound 304-6 (0.3 g, 529 μmol) in MeOH (10 mL) was added NaOH (3 M, 1 mL), the resulting mixture was stirred at 20° C. for 4 hrs and at 50° C. for 24 hrs. LCMS showed a little of the starting material was remained and most of desired compound was detected. The reaction mixture was poured into H$_2$O (10 mL), and then extracted with CHCl$_3$/i-PrOH=3/1 (10 mL×10). The combined organic layers were dried over Na$_2$SO$_4$, filtered and concentrated under reduced pressure to give a residue, which was purified by prep-HPLC to give Compound 304 (23 mg, 58 μmol, 10% yield) as a white solid and Compound 304 (29 mg, 78.6 μmol, 15% yield) as a white solid. 304: M−H$^−$=364.1 (LCMS); $^1$H NMR (400 MHz, DMSO-d6) δ=8.13 (br d, J=7.3 Hz, 1H), 7.25 (br s, 1H), 7.21-7.10 (m, 2H), 6.61 (br d, J=7.3 Hz, 1H), 5.07 (br s, 1H), 4.49-4.20 (m, 1H), 2.26 (s, 3H), 2.12-1.85 (m, 4H). 305: M−H$^−$=364.1 (LCMS); 1H NMR (400 MHz, DMSO-d6) δ=8.13 (br s, 1H), 7.27 (br s, 1H), 7.22-7.11 (m, 2H), 6.59 (br d, J=6.1 Hz, 1H), 5.15 (br s, 1H), 4.41 (br s, 1H), 2.26 (s, 3H), 2.18 (br s, 2H), 1.92-1.63 (m, 2H).

Example 43: Synthesis of N-(3,6-dimethyl-9H-thioxanthen-9-yl)-2-oxo-5-phenyl-6-(trifluoromethyl)-1,2-dihydropyridine-3-carboxamide (306)

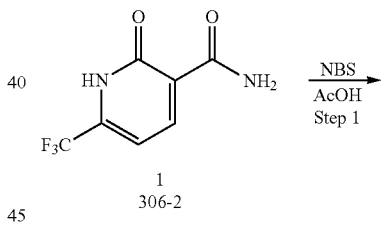

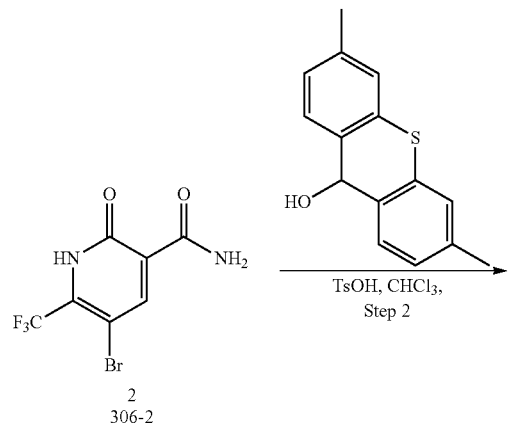

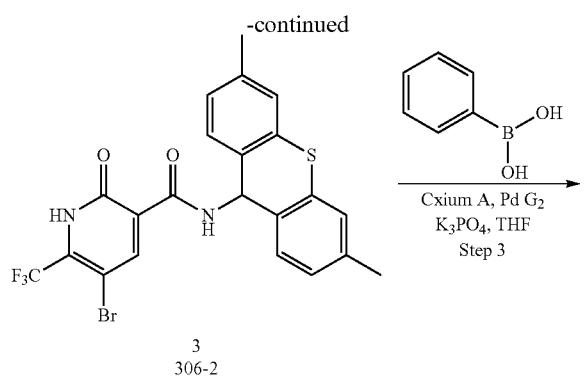

Step 1: 5-bromo-2-oxo-6-(trifluoromethyl)-1,2-dihydropyridine-3-carboxamide (306-2)

To a solution of Compound 306-1 (2 g, 9.7 mmol) in AcOH (30 mL) was added NBS (2.6 g, 14.6 mmol). The mixture was stirred at 100° C. for 2 hrs. TLC indicated the reaction was completed. The reaction mixture was concentrated under reduced pressure to give a residue. The residue was treated with THF:Petroleum ether (v/v=1:1, 30 mL) and stirred at 15° C. for 10 mins. The mixture was filtered and the cake was dried in vacuum to give Compound 306-2 (2.5 g, crude) as a light yellow solid. $^1$H NMR (400 MHz, DMSO-$d_6$) δ=13.78 (br d, J=4.9 Hz, 1H), 8.61 (s, 1H), 8.36 (br s, 1H), 8.24 (br s, 1H).

Step 2: 5-bromo-N-(3,6-dimethyl-9H-thioxanthen-9-yl)-2-oxo-6-(trifluoromethyl)-1,2-dihydropyridine-3-carboxamide (306-3)

A solution of 3,6-dimethyl-9H-thioxanthen-9-ol (400 mg, 1.7 mmol) in DCM (20 mL) was added to a mixture of Compound 306-2 (400 mg, 1.4 mmol) and TsOH.H$_2$O (500 mg, 2.6 mmol) in CHCl$_3$ (20 mL) at 70° C. The mixture was stirred at 70° C. for 5 mins. TLC indicated the reaction was completed. The reaction mixture was poured into H$_2$O (10 mL) and extracted with DCM (10 mL×2). The combined organic layers were dried over Na$_2$SO$_4$, filtered and concentrated under reduced pressure to give a residue. The crude product was confirmed by prep-TLC to give Compound 306-3 (100 mg, crude) as yellow solid. M−H$^-$=508.9 (LCMS).

Step 3: N-(3,6-dimethyl-9H-thioxanthen-9-yl)-2-oxo-5-phenyl-6-(trifluoromethyl)-1,2-dihydropyridine-3-carboxamide (306)

To a mixture of Compound 306-3 (90 mg, 176.7 μmol), phenylboronic acid (65 mg, 530.1 μmol) and K$_3$PO$_4$ (0.5 M, 1.1 mL) in THF (5 mL) was added Cxium A, Pd G2 (12 mg, 17.7 μmol) under N$_2$. The mixture was stirred at 80° C. for 12 hrs under N$_2$. LCMS showed the reaction was complete and the desired mass was detected. The reaction mixture was added to H$_2$O (10 mL), and then extracted with EtOAc (5 mL×4). The combined organic layers were dried over Na$_2$SO$_4$, filtered and concentrated under reduced pressure to give a residue. The residue was purified by prep-HPLC to give Compound 306 (8.5 mg, 16.57 μmol, 10% yield) as a white solid. M−H$^-$=505.1 (LCMS); $^1$H NMR (400 MHz, DMSO-$d_6$) δ=13.95-12.92 (m, 1H), 10.64-9.13 (m, 1H), 8.17 (s, 1H), 7.52-7.41 (m, 5H), 7.38 (s, 2H), 7.35-7.28 (m, 2H), 7.17-7.10 (m, 2H), 6.12 (br d, J=8.6 Hz, 1H), 2.31 (s, 6H).

Other compounds made in a similar manner are shown in Table 24.

TABLE 24

| Compound No | Structure | HNMR and Ms |
|---|---|---|
| 307 | 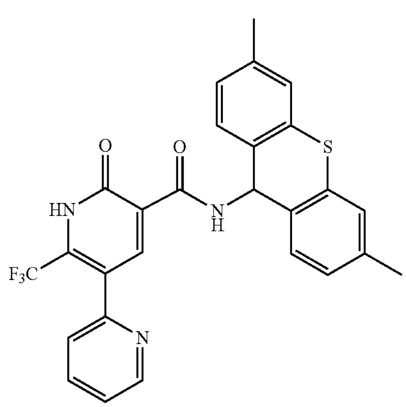 [SMILES: Cc1ccc2c(c1)Sc1cc(C)ccc1C2NC(=O)c1cc(-c2ccccn2)c(C(F)(F)F)[nH]c1=O] | 1H NMR (400 MHz, DMSO-d6) δ = 8.65 (d, J = 4.2 Hz, 1H), 8.31 (s, 1H), 7.90 (dt, J = 1.7, 7.7 Hz, 1H), 7.52 (d, J = 7.8 Hz, 1H), 7.48 (d, J = 7.9 Hz, 2H), 7.42 (dd, J = 5.1, 7.1 Hz, 1H), 7.38 (s, 2H), 7.14 (d, J = 7.7 Hz, 2H), 6.10 (br d, J = 8.6 Hz, 1H), 2.30 (s, 6H) ESI [M − H] = 506.1 |

689

Example 44: Synthesis of N-(6-methyl-2-propyl-benzo[b]thiophen-3-yl)-2-oxo-6-(trifluoromethyl)-1,2-dihydropyridine-3-carboxamide (308)

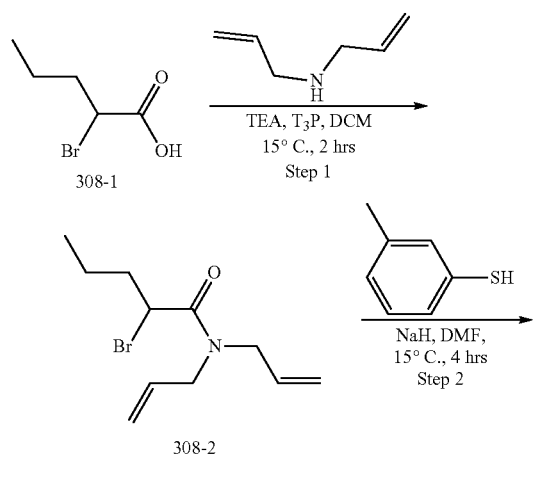

690

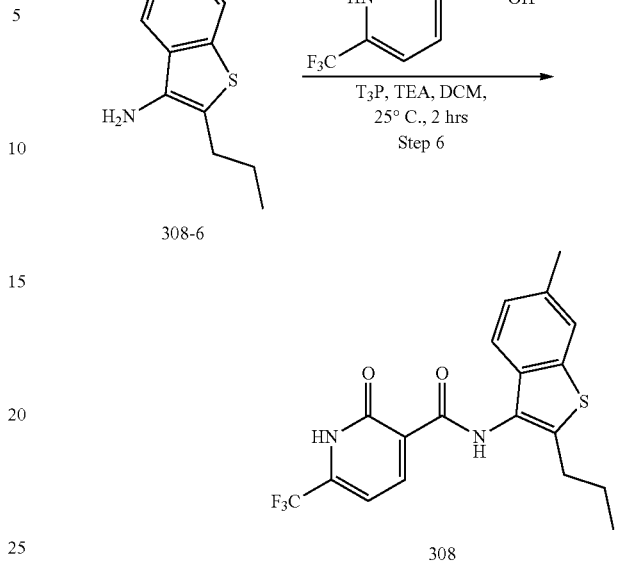

Step 1: N,N-diallyl-2-bromopentanamide (308-2)

To a solution of Compound 308-1 (1 g, 5.5 mmol) in DCM (20 mL) was added diallylamine (537 mg, 5.5 mmol), TEA (1.7 g, 16.6 mmol), T$_3$P (7 g, 11.1 mmol, 50% purity). The mixture was stirred at 15° C. for 2 hrs. LCMS showed the reaction was completed and desired mass was detected. The reaction mixture was poured into H$_2$O (50 mL) and extracted with DCM (20 mL×3). The combined organic layers were dried over Na$_2$SO$_4$, filtered and concentrated under reduced pressure to give a residue. The residue was purified by flash silica gel chromatography to give Compound 308-2 (1.3 g, 90% yield) as colourless oil. M+H$^+$=262.0 (LCMS); $^1$H NMR (400 MHz, CDCl$_3$) δ=5.92-5.70 (m, 2H), 5.30-5.09 (m, 4H), 4.44-4.27 (m, 2H), 4.16 (tdd, J=1.4, 3.2, 18.0 Hz, 1H), 3.81 (tdd, J=1.9, 4.2, 18.1 Hz, 1H), 3.66 (dd, J=6.3, 15.3 Hz, 1H), 2.20-1.92 (m, 2H), 1.49-1.29 (m, 2H), 0.93 (t, J=7.3 Hz, 3H).

Step 2: N,N-diallyl-2-(m-tolylthio)pentanamide (308-3)

To a solution of Compound 308-2 (838 mg, 3.2 mmol) in DMF (30 mL) was added NaH (142 mg, 60% purity, 3.5 mmol) at 0° C., and the mixture was stirred at 0° C. for 20 mins. A solution of 3-methylbenzenethiol (400 mg, 3.2 mmol) in DMF (2 mL) was added, the resulting mixture was stirred at 15° C. for 4 hrs. LCMS showed the reaction was completed and desired mass was detected. The reaction mixture was poured into H$_2$O (30 mL) and then extracted with EtOAc (20 mL×4). The combined organic layers were dried over Na$_2$SO$_4$, filtered and concentrated under reduced pressure to give a residue. The residue was purified by flash silica gel chromatography to give Compound 308-3 (800 mg, 81% yield) as colorless oil. M+H$^+$=304.1 (LCMS); $^1$H NMR (400 MHz, CDCl$_3$) δ=7.28-7.24 (m, 2H), 7.20 (t, J=7.6 Hz, 1H), 7.13-7.07 (m, 1H), 5.81-5.63 (m, 2H), 5.27-5.00 (m, 4H), 4.36-4.21 (m, 1H), 4.07-3.94 (m, 1H), 3.81-3.52 (m, 3H), 2.33 (s, 3H), 2.05-1.92 (m, 1H), 1.78-1.65 (m, 1H), 1.45-1.30 (m, 2H), 0.90 (t, J=7.3 Hz, 3H).

Step 3: N,N-diallyl-6-methyl-2-propylbenzo[b]thiophen-3-amine (308-4)

Compound 308-3 (350 mg, 1.15 mmol) and 2-fluoropyridine (134 mg, 1.4 mmol) were dissolved in CHCl$_3$ (10 mL) at 15° C. under N$_2$ atmosphere. Tf$_2$O (358 mg, 1.3 mmol) was then slowly added and the reaction mixture was stirred at 15° C. for 25 hrs. LCMS showed the reaction was completed and desired mass was detected. The reaction mixture was poured into ice-H$_2$O (20 mL) and extracted with DCM (10 mL×3). The combined organic layers were dried over Na$_2$SO$_4$, filtered and concentrated under reduced pressure to give a residue. The residue was purified by flash silica gel chromatography to give Compound 308-4 (200 mg, crude) as light yellow oil. M+H$^+$=286.1 (LCMS); $^1$H NMR (400 MHz, CDCl$_3$) δ=7.62 (d, J=8.2 Hz, 1H), 7.51 (s, 1H), 7.16-7.10 (m, 1H), 5.84 (tdd, J=6.4, 10.3, 16.9 Hz, 2H), 5.12 (dd, J=1.5, 17.2 Hz, 2H), 5.03 (dd, J=0.8, 10.0 Hz, 2H), 3.77 (d, J=6.4 Hz, 4H), 2.95-2.84 (m, 2H), 2.45 (s, 3H), 1.77-1.64 (m, 2H), 1.02 (t, J=7.3 Hz, 3H).

Step 4: tert-butyl (6-methyl-2-propylbenzo[b]thiophen-3-yl)carbamate (308-5)

To a solution of Compound 308-4 (200 mg, 700.7 μmol), 1,3-dimethylpyrimidine-2,4,6(1H,3H,5H)-trione (164 mg, 1.1 mmol), Boc$_2$O (459 mg, 2.1 mmol), TEA (284 mg, 2.8 mmol) in DCM (5 mL) was added Pd(PPh$_3$)$_4$ (81 mg, 70.1 μmol) under N$_2$. The resulting mixture was stirred at 35° C. for 20 hrs. TLC indicated the reaction was completed. The reaction mixture was quenched by addition H$_2$O (10 mL), and then extracted with DCM (10 mL×3). The combined organic layers were dried over Na$_2$SO$_4$, filtered and concentrated under reduced pressure to give a residue. The residue was purified by prep-TLC to give Compound 308-5 (220 mg, crude) as a light yellow solid.

Step 5: 6-methyl-2-propylbenzo[b]thiophen-3-amine (308-6)

To a solution of Compound 308-5 (200 mg, 654.8 umol) in EtOAc (1 mL) was added HCl/EtOAc (4 M, 8 mL) at 0° C. for 5 mins. Then the mixture was stirred at 15° C. for 0.5 hr. LCMS showed the reaction was completed and one main peak with desired mass was detected. The reaction mixture was concentrated to give Compound 308-6 (200 mg, crude, HCl) as white solid. M+H$^+$=206.1 (LCMS).

Step 6: N-(6-methyl-2-propylbenzo[b]thiophen-3-yl)-2-oxo-6-(trifluoromethyl)-1,2-dihydropyridine-3-carboxamide (308)

To a solution of Compound 308-6 (100 mg, 413.6 μmol, HCl) in DCM (3 mL) was added 2-oxo-6-(trifluoromethyl)-1,2-dihydropyridine-3-carboxylic acid (86 mg, 413.6 μmol), TEA (209 mg, 2.1 mmol) and T$_3$P (526 mg, 827.2 μmol). The mixture was stirred at 15° C. for 12 hrs. LCMS showed the starting material was consumed completely. Then the mixture was diluted with H$_2$O (5 mL) and extracted with DCM (3 mL×3). The combined organic layers dried over Na$_2$SO$_4$ and concentrated under reduced pressure to give a residue. The residue was treated with MeOH (2 mL) and 3M NaOH (2 mL) and stirred at 15° C. for 12 hrs. LCMS the desired mass was detected. The mixture was diluted with H$_2$O (5 mL) and extracted with EtOAc (3 mL×3). The combined organic layers dried over Na$_2$SO$_4$ and concentrated under reduced pressure to give a residue. The residue was purified by prep-HPLC to give Compound 308 (21 mg, 53.3 μmol, 13% yield) as a light yellow solid. M−H$^−$=393.1 (LCMS); $^1$H NMR (400 MHz, CHLOROFORM-d) δ=10.88 (s, 1H), 8.83 (d, J=7.3 Hz, 1H), 7.56 (s, 1H), 7.45 (d, J=8.2 Hz, 1H), 7.17 (d, J=8.1 Hz, 1H), 6.96 (d, J=7.3 Hz, 1H), 2.86 (t, J=7.6 Hz, 2H), 2.47 (s, 3H), 1.87-1.68 (m, 2H), 1.01 (t, J=7.3 Hz, 3H).

Other compounds made in a similar manner are shown in Table 25.

TABLE 25

| Compound No | Structure | HNMR and Ms |
| --- | --- | --- |
| 309 | (structure) | $^1$H NMR (400 MHz, CDCl$_3$) δ = 10.97 (br s, 1H), 8.81 (d, J = 7.3 Hz, 1H), 7.56 (s, 1H), 7.46 (d, J = 8.2 Hz, 1H), 7.16 (d, J = 8.1 Hz, 1H), 6.96 (d, J = 7.5 Hz, 1H), 2.91 (q, J = 7.6 Hz, 2H), 2.46 (s, 3H), 1.35 (t, J = 7.6 Hz, 3H) ESI [M − H] = 379.1 |
| 301 | (structure) | $^1$H NMR (400 MHz, CDCl$_3$) δ = 10.95 (s, 1H), 8.86 (d, J = 7.5 Hz, 1H), 7.63 (d, J = 8.2 Hz, 1H), 7.38 (s, 1H), 7.15 (d, J = 8.2 Hz, 1H), 6.99 (d, J = 7.5 Hz, 1H), 2.51 (s, 3H), 2.45 (s, 3H) ESI [M − H] = 365.1 |

Example 45: Synthesis of N-((1R,4R)-4-hydroxy-6-methyl-1,2,3,4-tetrahydronaphthalen-1-yl)-2-oxo-6-(trifluoromethyl)-1,2-dihydropyridine-3-carboxamide (311) and N-((1R,4S)-4-hydroxy-6-methyl-1,2,3,4-tetrahydronaphthalen-1-yl)-2-oxo-6-(trifluoromethyl)-1,2-dihydropyridine-3-carboxamide (312)

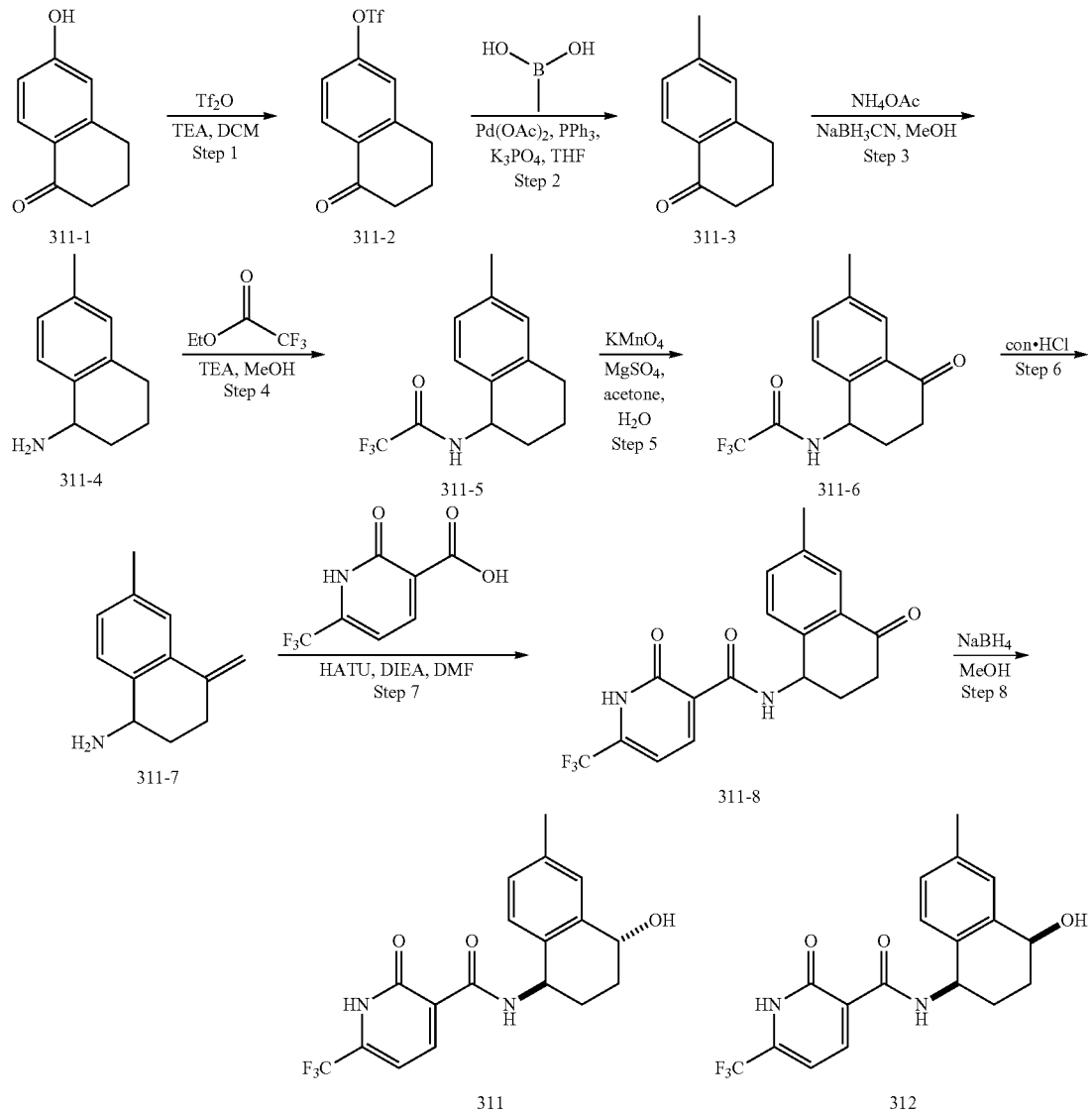

Step 1: 5-oxo-5,6,7,8-tetrahydronaphthalen-2-yl-trifluoromethanesulfonate (311-2)

To a solution of Compound 311-1 (2 g, 12 mmol) in DCM (30 mL) was added TEA (1.3 g, 12 mmol) and Tf$_2$O (3.5 g, 12 mmol) at 0° C., the resulting mixture was stirred at 20° C. for 12 hrs. LCMS showed the reaction was completed. Then the reaction mixture was poured into H$_2$O (20 mL) and extracted with DCM (20 mL×3). The combined organic layers were dried over Na$_2$SO$_4$, filtered and concentrated under reduced pressure to give a residue, which was purified by silica gel chromatography (Ethyl acetate/Petroleum) to give Compound 311-2 (1.3 g, 4.4 mmol, 36% yield) as a yellow gum. M+H$^+$=294.9 (LCMS), $^1$H NMR (400 MHz, CHLOROFORM-d) δ=8.14 (d, J=8.3 Hz, 1H), 7.24-7.17 (m, 2H), 3.03 (t, J=6.1 Hz, 2H), 2.75-2.63 (m, 2H), 2.23-2.12 (m, 2H).

Step 2: 6-methyl-3,4-dihydronaphthalen-1(2H)-one (311-3)

A solution of Compound 311-2 (1.2 g, 4.1 mmol), methylboronic acid (366 mg, 6.1 mmol), Pd(OAc)$_2$ (46 mg, 204 µmol), PPh$_3$ (107 mg, 408 µmol) and K$_3$PO$_4$ (3.5 g, 16.3 mmol) in THF (30 mL) was stirred at 70° C. for 12 hrs under N$_2$ atmosphere. TLC showed the reaction was completed.

The reaction mixture was poured into H₂O (30 mL) and then extracted with EtOAc (20 mL×4). The combined organic layers were dried over Na₂SO₄, filtered and concentrated under reduced pressure to give a residue, which was purified by silica gel chromatography (Ethyl acetate/Petroleum) to give Compound 311-3 (0.5 g, 3.1 mmol, 77% yield) as a yellow oil.

Step 3:
6-methyl-1,2,3,4-tetrahydronaphthalen-1-amine
(311-4)

To a solution of Compound 311-3 (700 mg, 4.4 mmol) in MeOH (4 mL) was added NH₄OAc (5.1 g, 65.5 mmol), the reaction was stirred for 10 min at 20° C., then NaBH₃CN (1.1 g, 17.5 mmol) was added and the reaction was stirred at 90° C. for 7 hrs under microwave. LCMS showed the reaction was completed. The reaction mixture was poured into H₂O (30 mL) and extracted with DCM (10 mL×4). The combined organic layers were dried over Na₂SO₄, filtered and concentrated under reduced pressure to give Compound 311-4 (0.7 g, crude) as a yellow gum. Fragment Ms=145.1 (LCMS).

Step 4: 2,2,2-trifluoro-N-(6-methyl-1,2,3,4-tetrahydronaphthalen-1-yl)acetamide (311-5)

To a solution of Compound 311-4 (0.7 g, 4.3 mmol) in MeOH (10 mL) was added TEA (659 mg, 6.5 mmol) and ethyl 2,2,2-trifluoroacetate (740 mg, 5.2 mmol). The mixture was stirred at 20° C. for 2 hrs. LCMS showed the reaction was completed and one main peak with desired mass was detected. The reaction mixture was poured into H₂O (20 mL), the precipitate was filtered and the cake was washed with H₂O, dried in vacuum to give Compound 311-5 (0.9 g, 3.4 mmol, 78% yield) as a white solid. M−H⁻=256.0 (LCMS), ¹H NMR (400 MHz, CHLOROFORM-d) δ=7.15-7.10 (m, 1H), 7.03 (d, J=7.9 Hz, 1H), 6.97 (s, 1H), 6.37 (br s, 1H), 5.18 (t, J=5.3 Hz, 1H), 2.86-2.74 (m, 2H), 2.32 (s, 2H), 2.31-2.31 (m, 1H), 2.14-2.04 (m, 1H), 1.92-1.79 (m, 3H).

Step 5: 2,2,2-trifluoro-N-(6-methyl-4-oxo-1,2,3,4-tetrahydronaphthalen-1-yl)acetamide (311-6)

To a solution of Compound 311-5 (400 mg, 1.6 mmol) in acetone (25 mL) was added MgSO₄ (449 mg, 3.7 mmol) H₂O (12.5 mL) at 0° C., followed by KMnO₄ (1.3 g, 8.1 mmol). The mixture was stirred at 20° C. for 8 hrs. TLC showed the reaction was completed. The reaction mixture was poured into Sat.Na₂SO₃ (30 mL), filtered and the filtrate was extracted with EtOAc (15 mL×5). The combined organic layers were dried over Na₂SO₄, filtered and concentrated under reduced pressure to give a residue, which was purified by silica gel chromatography (Ethyl acetate/ Petroleum) to give Compound 311-6 (320 mg, 1.2 mmol, 76% yield) as a white solid. ¹H NMR (400 MHz, CHLOROFORM-d) δ=7.90 (s, 1H), 7.44 (dd, J=1.5, 7.9 Hz, 1H), 7.25 (d, J=7.9 Hz, 1H), 6.48 (br s, 1H), 5.40 (dt, J=4.3, 8.4 Hz, 1H), 2.90-2.66 (m, 2H), 2.53-2.44 (m, 1H), 2.42 (s, 3H), 2.28-2.17 (m, 1H).

Step 6: 4-amino-7-methyl-3,4-dihydronaphthalen-1 (2H)-one (311-7)

A solution of Compound 311-6 (150 mg, 553 μmol) in HCl (10 mL) was stirred at 110° C. for 3 hrs. LCMS showed the reaction was completed and the desired mass was detected. The reaction mixture was concentrated under reduced pressure to give Compound 311-7 (110 mg, crude, HCl) as an orange solid. Fragment Ms=159.1 (LCMS).

Step 7: N-(6-methyl-4-oxo-1,2,3,4-tetrahydronaphthalen-1-yl)-2-oxo-6-(trifluoromethyl)-1,2-dihydropyridine-3-carboxamide (311-8)

To a stirred solution of Compound 311-7 (110 mg, 519 μmol, HCl) in DMF (10 mL) was added 2-oxo-6-(trifluoromethyl)-1,2-dihydropyridine-3-carboxylic acid (108 mg, 520 μmol), HATU (296 mg, 779 μmol) and DIEA (201 mg, 1.6 mmol) at 20° C. The resulting mixture was stirred at 20° C. for 2 hrs. LCMS showed the reaction was completed and the desired mass was detected. The reaction mixture was poured into H₂O (10 mL), and then extracted with DCM (5 mL×5). The combined organic layers were dried over Na₂SO₄, filtered and concentrated under reduced pressure to give a residue, which was purified by prep-TLC (Ethyl acetate/Petroleum ether=2/1, R_f=0.24) to give Compound 311-8 (40 mg, 110 μmol, 21% yield) as a yellow solid. M−H⁻=363.0 (LCMS).

Step 8: N-((1R,4R)-4-hydroxy-6-methyl-1,2,3,4-tetrahydronaphthalen-1-yl)-2-oxo-6-(trifluoromethyl)-1,2-dihydropyridine-3-carboxamide (311) and N-((1R,4S)-4-hydroxy-6-methyl-1,2,3,4-tetrahydronaphthalen-1-yl)-2-oxo-6-(trifluoromethyl)-1,2-dihydropyridine-3-carboxamide (312)

To a solution of Compound 311-8 (40 mg, 110 μmol) in MeOH (5 mL) was added NaBH₄ (10 mg, 274 μmol) at 0° C., the resulting mixture was stirred at 0° C. for 30 min. LCMS showed the reaction was completed and the desired mass was detected. The residue was quenched by H₂O (3 mL) then was concentrated under reduced pressure to give a residue, which was purified by prep-HPLC to give Compound 311 (5.00 mg, 14 μmol, 12% yield) as a white solid, M−H⁻=365.1 (LCMS), ¹H NMR (400 MHz, CHLOROFORM-d) δ=9.67 (br d, J=7.3 Hz, 1H), 8.66 (d, J=7.5 Hz, 1H), 7.31 (s, 1H), 7.24 (d, J=7.8 Hz, 1H), 7.08 (d, J=7.5 Hz, 1H), 6.87 (d, J=7.5 Hz, 1H), 5.35-5.17 (m, 1H), 4.77 (br d, J=4.5 Hz, 1H), 2.34 (s, 3H), 2.13-1.96 (m, 4H) and Compound 312 (5.40 mg, 15 μmol, 13% yield) as a white solid. M−H⁻=365.1 (LCMS), ¹H NMR (400 MHz, CHLOROFORM-d) δ=9.57 (br d, J=7.7 Hz, 1H), 8.69 (d, J=7.3 Hz, 1H), 7.30 (s, 1H), 7.23 (d, J=7.9 Hz, 1H), 7.08 (d, J=7.9 Hz, 1H), 6.86 (d, J=7.5 Hz, 1H), 5.41-5.30 (m, 1H), 4.83 (t, J=4.7 Hz, 1H), 2.45-2.27 (m, 4H), 2.26-2.07 (m, 1H), 1.99-1.83 (m, 2H).

Example 46: Synthesis of N-(5-(aminomethyl)-1,2, 3,4-tetrahydronaphthalen-1-yl)-2-oxo-6-(trifluoromethyl)-1,2-dihydropyridine-3-carboxamide (313)

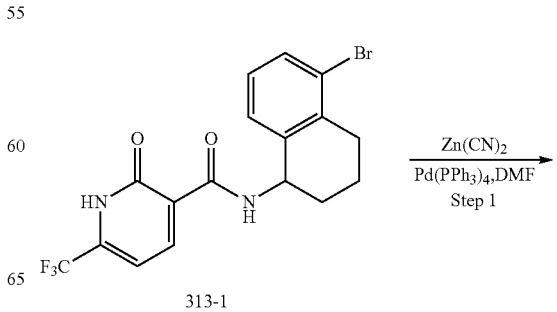

313-1

697

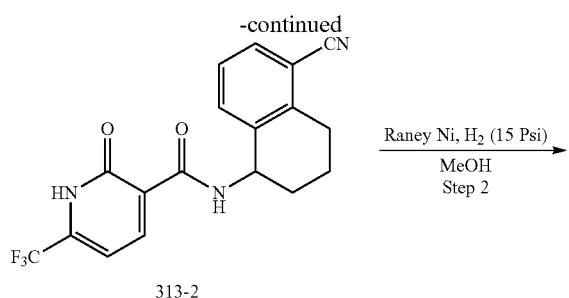

313-2

Raney Ni, H₂ (15 Psi)
MeOH
Step 2

313

Step 1: N-(5-cyano-1, 2, 3, 4-tetrahydronaphthalen-1-yl)-2-oxo-6-(trifluoromethyl)-1, 2-dihydropyridine-3-carboxamide (313-2)

A mixture of Compound 313-1 (50 mg, 120.4 µmol), Zn(CN)₂ (28 mg, 240.9 µmol), Pd(PPh₃)₄ (14 mg, 12.0 µmol) in DMF (2 mL) was degassed and purged with N₂ for three times, and then the mixture was stirred at 100° C. for 12 hrs. LCMS showed the reaction was complete and desired mass was detected. The reaction mixture was quenched by pouring into water 15 mL and extracted with EtOAc (5 mL×2). The combined organic layers were washed with brine (5 mL×3), dried over Na₂SO₄, filtered and concentrated under reduced pressure to give a residue. The residue was purified by prep-HPLC to give Compound 313-2 (5.4 mg, 14.9 µmol, 12% yield) as a white solid. M−H⁻=360.1 (LCMS); 1H NMR (400 MHz, CHLOROFORM-d) δ=9.71 (br d, J=8.2 Hz, 1H), 8.73 (d, J=7.2 Hz, 1H), 7.57 (dd, J=2.8, 7.7 Hz, 2H), 7.27-7.22 (m, 1H), 6.89 (d, J=7.5 Hz, 1H), 5.44-5.34 (m, 1H), 3.16-3.06 (m, 1H), 3.02-2.92 (m, 1H), 2.15-1.93 (m, 4H)

Step 2: N-(5-(aminomethyl)-1,2,3,4-tetrahydronaphthalen-1-yl)-2-oxo-6-(trifluoromethyl)-1,2-dihydropyridine-3-carboxamide (313)

To a solution of Compound 313-2 (50 mg, 138.4 µmol) in MeOH (5 mL) was added NH₃·H₂O (2.0 mg, 13.8 µmol, 25% purity) and Raney-Ni (50 mg, 583.6 µmol). The mixture was stirred at 15° C. under H₂ (15 Psi) for 2 hrs. LCMS showed the reaction was completed and desired mass was detected. The suspension was filtered through a pad of Celite and the pad was washed with MeOH (10 mL×2). The combined filtrates were concentrated to dryness to give a residue. The residue was purified by prep-HPLC to give Compound 313 (20 mg, 53.7 µmol, 39% yield) as a white solid. M−H⁻=364.1 (LCMS); 1H NMR (400 MHz, DMSO-d₆) δ=8.14 (d, J=7.5 Hz, 1H), 7.31-7.14 (m, 3H), 6.56 (d, J=7.6 Hz, 1H), 5.25-5.13 (m, 1H), 4.07-3.91 (m, 2H), 2.87-2.64 (m, 2H), 2.00-1.66 (m, 4H).

698

Example 47: Synthesis of tert-butyl (2-(4-(2-oxo-6-(trifluoromethyl)-1,2-dihydropyridine-3-carboxamido)-3,4-dihydroisoquinolin-2(1H)-yl)ethyl)carbamate (314)

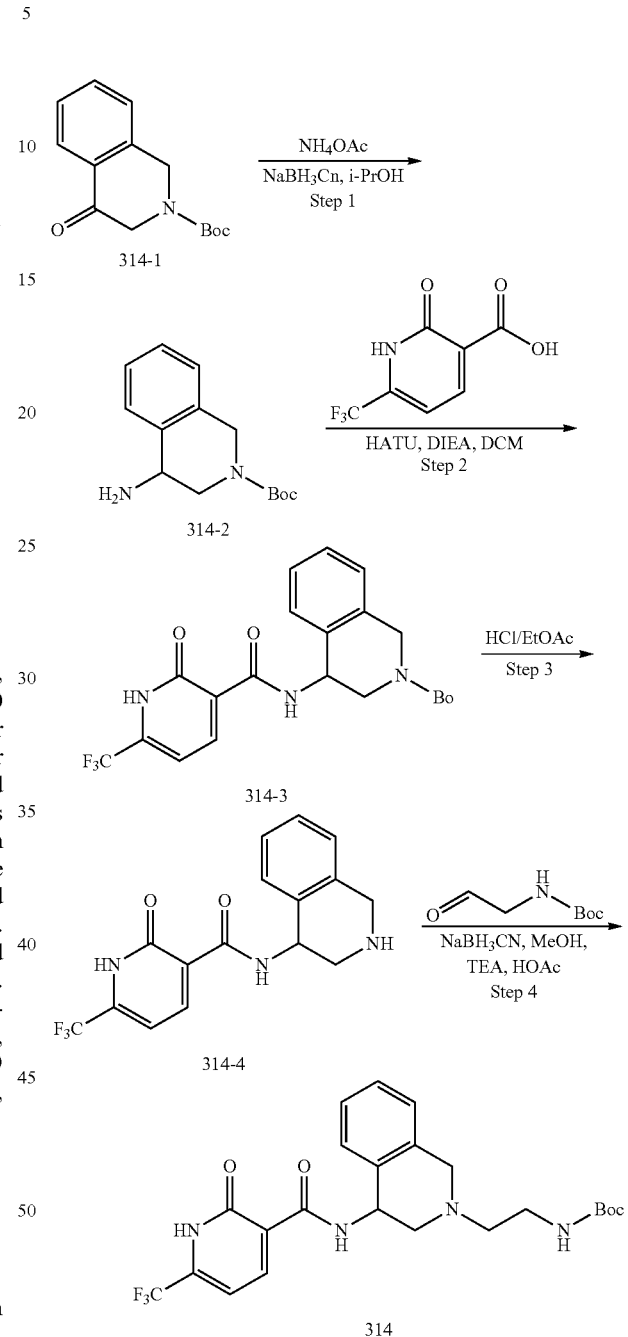

Step 1: tert-butyl 4-amino-3,4-dihydroisoquinoline-2(1H)-carboxylate (314-2)

To a solution of Compound 314-1 (400 mg, 1.6 mmol) in i-PrOH (20 mL) was added NaBH₃CN (508 mg, 8.1 mmol), then NH₄OAc (2.5 g, 32.4 mmol) was added to the mixture, the mixture was stirred at 15° C. for 3 hrs, then the mixture was stirred at 80° C. for 12 hrs. TLC showed the reaction was completed. The reaction mixture was poured into H₂O (10 mL) and extracted with EtOAc (15 mL×3), then dried over Na₂SO₄, filtered and concentrated under reduced pressure to give a residue, which was purified by column chromatography (Petroleum ether/Ethyl acetate) to give Compound 314-2 (350 mg, crude) as a white solid.

Step 2: tert-butyl 4-(2-oxo-6-(trifluoromethyl)-1,2-dihydropyridine-3-carboxamido)-3,4-dihydroisoquinoline-2(1H)-carboxylate (314-3)

To a solution of Compound 314-2 (300 mg, 1.2 mmol) in DCM (6 mL) was added 2-oxo-6-(trifluoromethyl)-1,2-dihydropyridine-3-carboxylic acid (250 mg, 1.2 mmol), DIEA (187 mg, 1.4 mmol) and HATU (459 mg, 1.2 mmol), then the mixture was stirred at 25° C. for 2 hrs. TLC showed the reaction was completed. The reaction mixture was poured into H₂O (10 mL) and extracted with EtOAc (15 mL×3). The combined organic layers were dried over Na₂SO₄, filtered and concentrated under reduced pressure to give a residue, which was purified by column chromatography (Petroleum ether/Ethyl acetate) to give Compound 314-3 (180 mg, crude) as a white solid.

Step 3: 2-oxo-N-(1,2,3,4-tetrahydroisoquinolin-4-yl)-6-(trifluoromethyl)-1,2-dihydropyridine-3-carboxamide (314-4)

To a stirred solution of Compound 314-3 (160 mg, 366 μmol) in EtOAc (5 mL) was added EtOAc/HCl (4 M, 10 mL) slowly at 15° C. The mixture was stirred at 15° C. for 12 hrs. LCMS showed the reaction was completed. The mixture was concentrated in vacuum to give a Compound 314-4 (120 mg, 303 μmol, 83% yield, HCl) as a white solid. M–H⁻=335.9 (LCMS), ¹H NMR (400 MHz, DMSO-d6) δ=13.40 (br s, 1H), 10.04-9.59 (m, 2H), 9.38 (br s, 1H), 8.49 (d, J=7.5 Hz, 1H), 7.50-7.17 (m, 5H), 5.56 (q, J=6.5 Hz, 1H), 4.40-4.24 (m, 2H), 3.64-3.53 (m, 1H), 3.45 (br dd, J=6.8, 12.5 Hz, 1H).

Step 4: tert-butyl (2-(4-(2-oxo-6-(trifluoromethyl)-1,2-dihydropyridine-3-carboxamido)-3,4-dihydroisoquinolin-2(1H)-yl)ethyl)carbamated (314)

To a stirred solution of Compound 314-4 (50 mg, 134 μmol, HCl) in MeOH (5 mL) was added TEA (14 mg, 134 μmol) and tert-butyl (2-oxoethyl)carbamate (64 mg, 401 μmol), then was added HOAc (8 mg, 134 μmol) to pH=5-6. The resulting mixture was stirred at 20° C. for 0.5 hr, then added NaBH₃CN (17 mg, 268 μmol) and stirred at 20° C. for 14 hrs. LCMS showed the reaction was completed and one main peak with desired mass was detected. The reaction mixture was poured into H₂O (3 mL). The reaction mixture was filtered and the cake was washed with H₂O (2 mL×3), dried in vacuum to give a residue, which was purified by prep-HPLC to give Compound 314 (6 mg, 12 μmol, 9% yield) as a light yellow solid. M–H⁻=479.2 (LCMS), ¹H NMR (400 MHz, CHLOROFORM-d) δ=9.67 (br s, 1H), 8.63 (br s, 1H), 7.44 (br s, 1H), 7.26-7.16 (m, 2H), 7.07 (br d, J=7.2 Hz, 1H), 6.90 (br d, J=7.3 Hz, 1H), 5.44-5.17 (m, 2H), 3.91 (br d, J=13.8 Hz, 1H), 3.66-3.46 (m, 1H), 3.32 (br d, J=5.0 Hz, 2H), 3.00 (br d, J=11.6 Hz, 1H), 2.88-2.60 (m, 3H), 1.48-1.29 (m, 9H).

Other compounds made in a similar manner are shown in Table 26.

TABLE 26

| Compound No | Structure | HNMR and Ms |
|---|---|---|
| 315 | 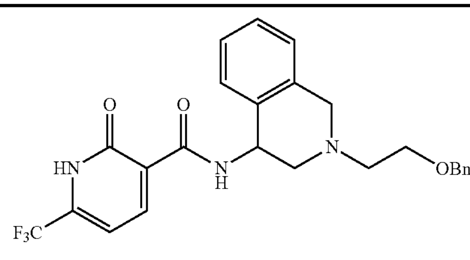 | ¹H NMR (400 MHz, CHLOROFORM-d) δ = 9.28 (br s, 1H), 8.20 (br d, J = 7.0 Hz, 1H), 7.37 (br d, J = 7.8 Hz, 1H), 7.33 – 7.28 (m, 4H), 7.26 – 7.15 (m, 2H), 7.00 (d, J = 7.6 Hz, 1H), 6.72 (d, J = 7.6 Hz, 1H), 5.35 – 5.25 (m, 1H), 4.50 (s, 2H), 4.03 (br d, J = 15.3 Hz, 1H), 3.80 – 3.64 (m, 3H), 3.43 (br d, J = 8.8 Hz, 1H), 3.18 – 3.05 (m, 1H), 3.03 – 2.92 (m, 1H), 2.88 (dd, J = 3.4, 12.0 Hz, 1H) ESI [M − H] = 470.2 |
| 316 | 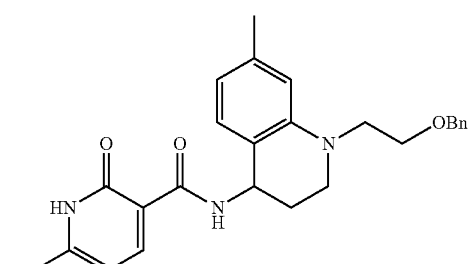 | ¹H NMR (400 MHz, DMSO-d₆) δ = 13.49 (br s, 1H), 8.43 (br d, J = 7.6 Hz, 1H), 7.39 – 7.18 (m, 6H), 6.96 (d, J = 7.7 Hz, 1H), 6.51 (s, 1H), 6.36 (d, J = 7.5 Hz, 1H), 5.15 – 4.95 (m, 1H), 4.61 – 4.44 (in, 2H), 3.73 – 3.59 (m, 2H), 3.58 – 3.45 (m, 2H), 3.36 (br d, J = 6.5 Hz, 2H), 2.19 (s, 3H), 2.02 – 1.89 (m, 2H) ESI [M − H] = 484.2 |
| 317 | 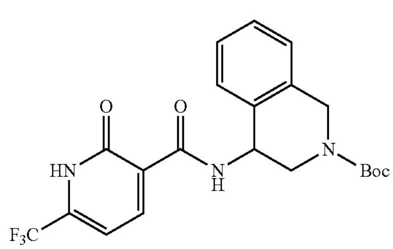 [SMILES: CC(C)(C)OC(=O)N1Cc2ccccc2C(NC(=O)c2ccc(C(F)(F)F)[nH]c2=O)C1] | ¹H NMR (400 MHz, CHLOROFORM-d) δ = 8.10 (br d, J = 6.6 Hz, 1H), 7.33 – 7.23 (m, 4H), 6.49 (d, J = 7.3 Hz, 1H), 5.12 – 5.04 (m, 1H), 4.72 – 4.40 (m, 2H), 3.82 – 3.58 (m, 2H), 1.42 – 1.28 (m, 9H) ESI [M − H] = 436.2 |

Example 48: Synthesis of N-(7-hydroxy-5H-chromeno[2,3-c]pyridin-5-yl)-2-oxo-6-(trifluoromethyl)-1,2-dihydropyridine-3-carboxamide (318)

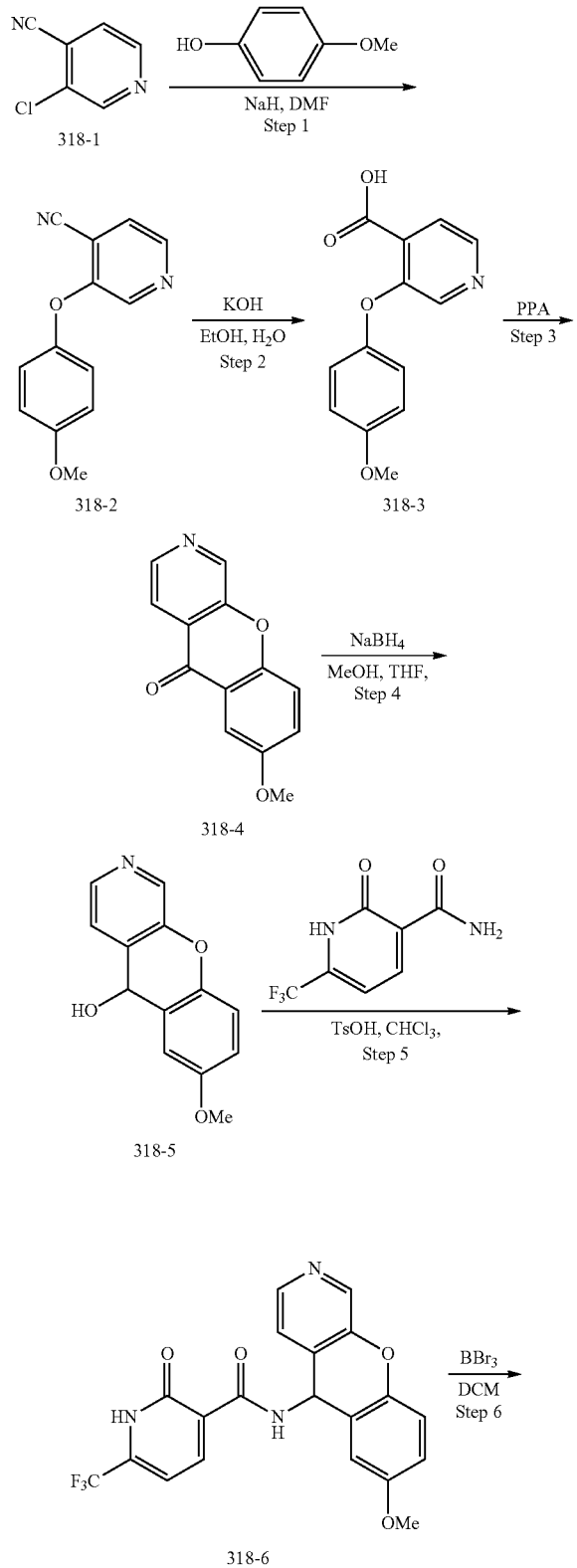

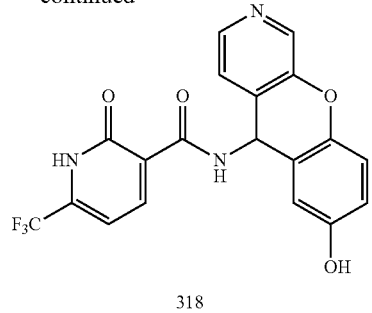

318

Step 1: 3-(4-methoxyphenoxy)isonicotinonitrile (318-2)

To a solution of 4-methoxyphenol (896 mg, 7.2 mmol) in DMF (10 mL) was added NaH (346.4 mg, 8.66 mmol, 60% purity) at 0° C. The mixture was stirred at 15° C. for 30 mins. A solution of Compound 318-1 (1 g, 7.2 mmol) in DMF (5 mL) was added drop wise. After the addition, the mixture was stirred at 15° C. for 4 hrs. TLC indicated the reaction completed. The reaction mixture was poured into $H_2O$ (50 mL) and lots of white solid appeared. The solid was filtered and the cake was washed with water. Compound 318-2 (1.2 g, crude) was obtained as a white solid, which was used into the next step without further purification.

Step 2: 3-(4-methoxyphenoxy)isonicotinic acid (318-3)

To a solution of KOH (4.5 g, 79.6 mmol) in EtOH (10 mL) and $H_2O$ (10 mL) was added Compound 318-2 (1.2 g, 5.3 mmol). The resulting mixture was stirred at 80° C. for 4 hrs. LCMS showed the reaction completed and desired mass was detected. The aqueous phase was neutralized to pH=5-6 using 1M HCl and then the precipitate was filtered. The reaction mixture was filtered and the cake was washed with 20 mL of $H_2O$, dried in vacuum to give Compound 318-3 (680 mg, 2.8 mmol, 52% yield) as a white solid. $^1$H NMR (400 MHz, DMSO-$d_6$) δ=13.58 (s, 1H), 8.45 (d, J=4.9 Hz, 1H), 8.25 (s, 1H), 7.68 (d, J=4.9 Hz, 1H), 7.08-6.89 (m, 4H), 3.74 (s, 3H).

Step 3: 7-methoxy-5H-chromeno[2,3-c]pyridin-5-one (318-4)

A mixture of Compound 318-3 (350 mg, 1.4 mmol) in PPA (10 mL) was stirred at 120° C. for 2 hrs. TLC indicated the reaction was completed. The reaction mixture was poured into $H_2O$ (50 mL) and then extracted with EtOAc (50 mL×3). The combined organic layers were washed with $NaHCO_3$·aq (100 mL), dried over $Na_2SO_4$, filtered and concentrated under reduced pressure to give Compound 318-4 (200 mg, 880 μmol, 62% yield) as a yellow solid. $^1$H NMR (400 MHz, CHLOROFORM-d) δ=9.06 (s, 1H), 8.65 (d, J=5.3 Hz, 1H), 8.15-8.06 (m, 1H), 7.69 (d, J=3.1 Hz, 1H), 7.55-7.49 (m, 1H), 7.42 (dd, J=3.1, 9.0 Hz, 1H), 3.95 (s, 3H).

Step 4: 7-methoxy-5H-chromeno[2,3-c]pyridin-5-ol (318-5)

To a solution of Compound 318-4 (200 mg, 880.2 μmol) in MeOH (8 mL) and THF (8 mL) was added $NaBH_4$ (99.9 mg, 2.6 mmol) at 0° C. The mixture was stirred at 15° C. for 3 hrs. TLC indicated the reaction completed. The reaction mixture was poured into H$_2$O (15 mL) and extracted with DCM (5 mL×3). The combined organic layers were dried over Na$_2$SO$_4$, filtered and concentrated to give Compound 318-5 (200 mg, crude) as white oil, which was used into the next step directly. This kind of benzyl alcohol was more stable in solution (DCM).

Step 5: N-(7-methoxy-5H-chromeno[2,3-c]pyridin-5-yl)-2-oxo-6-(trifluoromethyl)-1,2-dihydropyridine-3-carboxamide (318-6)

A mixture of Compound 318-5 (190 mg, crude) in DCM (6 mL) was added to a mixture of 2-oxo-6-(trifluoromethyl)-1,2-dihydropyridine-3-carboxamide (170.9 mg, 828.9 μmol) and TsOH·H$_2$O (203.4 mg, 1.1 mmol) in CHCl$_3$ (15 mL) at 70° C., the mixture was stirred at 70° C. for 6 hrs. LCMS showed the reaction was completed and desired mass was detected. The reaction mixture was poured into H$_2$O (10 mL) and extracted with DCM (6 mL×3). The combined organic layers were dried over Na$_2$SO$_4$, filtered and concentrated under reduced pressure to give a residue. The residue was purified by prep-TLC (DCM:MeOH=10:1) to give Compound 318-6 (100 mg, crude) as a yellow solid.

Step 6: N-(7-hydroxy-5H-chromeno[2,3-c]pyridin-5-yl)-2-oxo-6-(trifluoromethyl)-1,2-dihydropyridine-3-carboxamide (318)

To a solution of Compound 318-6 (100 mg, 240 μmol) in DCM (5 mL) was added BBr$_3$ (300 mg, 1.2 mmol) in DCM (0.5 mL) at −78° C. The mixture was stirred at −78° C. for 1 hr then at 25° C. for 12 hrs. LCMS showed the reaction was completed and desired mass was detected. The reaction mixture was poured into H$_2$O (5 mL). The aqueous phase was neutralized to pH=5-6 using NH$_3$·H$_2$O and then the precipitate was filtered. The crude cake was triturated with mixture solvent of Petroleum ether (1.5 mL) and EtOAc (0.5 mL) at 15° C. for 10 mins. Then the mixture was concentrated under reduced pressure to give Compound 318 (16.2 mg, 38.1 μmol, 16% yield) as a yellow solid. M−H$^-$=402.1 (LCMS); $^1$H NMR (400 MHz, DMSO-d$_6$) δ=13.39 (br s, 1H), 9.77 (br d, J=6.6 Hz, 1H), 9.38 (s, 1H), 8.47 (s, 1H), 8.40 (d, J=7.6 Hz, 1H), 8.28 (d, J=5.0 Hz, 1H), 7.42 (d, J=5.0 Hz, 1H), 7.35 (br d, J=7.5 Hz, 1H), 7.07 (d, J=8.8 Hz, 1H), 6.82 (d, J=2.7 Hz, 1H), 6.77 (dd, J=2.8, 8.7 Hz, 1H), 6.43 (d, J=8.3 Hz, 1H).

Other compounds made in a similar manner are shown in Table 27.

TABLE 27

| Compound No | Structure | HNMR and Ms |
|---|---|---|
| 319 | (structure) | $^1$H NMR (400 MHz, CHLOROFORM-d) δ = 9.94 (br d, J = 8.8 Hz, 1H), 8.73 (d, J = 7.3 Hz, 1H), 8.54 (s, 1H), 8.31 (d, J = 5.0 Hz, 1H), 7.45 (d, J = 5.1 Hz, 1H), 7.15 (d, J = 8.9 Hz, 1H), 6.97 (d, J = 2.9 Hz, 1H), 6.95 – 6.91 (m, 1H), 6.87 (d, J = 7.5 Hz, 1H), 6.62 (d, J = 8.7 Hz, 1H), 3.77 (s, 3H). ESI [M − H] = 416.1 |
| 320 | (structure) | 1H NMR (400 MHz, DMSO-d6) δ = 9.84 (s, 1H), 8.49 (s, 1H), 8.38 (d, J = 7.5 Hz, 1H), 8.30 (d, J = 5.0 Hz, 1H), 7.45 (d, J = 5.1 Hz, 1H), 7.35 – 7.22 (m, 2H), 6.67 – 6.54 (m, 2H), 6.38 (d, J = 8.2 Hz, 1H) ESI [M − H] = 402.1 |
| 321 | (structure) | $^1$H NMR (400 MHz, CHLOROFORM-d) δ = 10.31 (br d, J = 6.7 Hz, 1H), 8.70 (d, J = 7.3 Hz, 1H), 8.51 (dd, J = 1.5, 4.8 Hz, 1H), 7.83 (dd, J = 1.5, 7.8 Hz, 1H), 7.40 (d, J = 8.7 Hz, 1H), 7.22 (dd, J = 4.8, 7.8 Hz, 1H), 7.07 (d, J = 2.6 Hz, 1H), 6.93 (d, J = 7.5 Hz, 1H), 6.85 (dd, J = 2.5, 8.6 Hz, 1H), 6.11 (d, J = 7.2 Hz, 1H), 3.81 (s, 3H) ESI [M − H] = 432.1 |

TABLE 27-continued

| Compound No | Structure | HNMR and Ms |
|---|---|---|
| 322 | 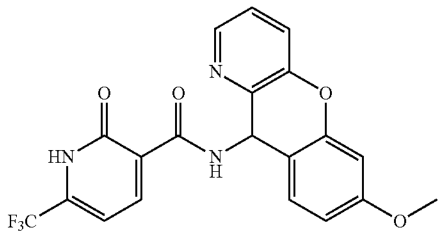 | ¹H NMR (400 MHz, CHCL₃-d) δ = 9.91 (br d, J = 7.5 Hz, 1H), 8.64 (d, J = 7.3 Hz, 1H), 8.45 (d, J = 3.5 Hz, 1H), 7.55 – 7.45 (m, 2H), 7.33 – 7.28 (m, 1H), 6.82 (d, J = 7.5 Hz, 1H), 6.75 – 6.67 (m, 2H), 6.59 (d, J = 8.4 Hz, 1H), 3.83 (s, 3H)<br>ESI [M − H] = 416.01 |
| 323 | 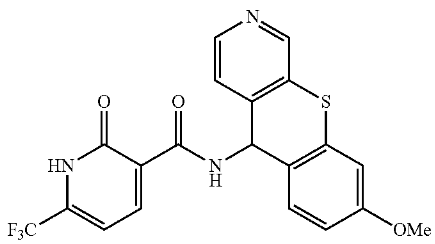 | 1H NMR (400 MHz, DMSO-d₆) δ = 8.72 (s, 1H), 8.50 (d, J = 5.1 Hz, 1H), 8.11 (d, J = 7.5 Hz, 1H), 7.51 – 7.41 (m, 2H), 7.21 (d, J = 2.6 Hz, 1H), 6.95 (dd, J = 2.6, 8.7 Hz, 1H), 6.56 – 6.51 (m, 1H), 5.91 (s, 1H), 3.78 (s, 3H)<br>ESI [M − H] = 432.1 |
| 324 | 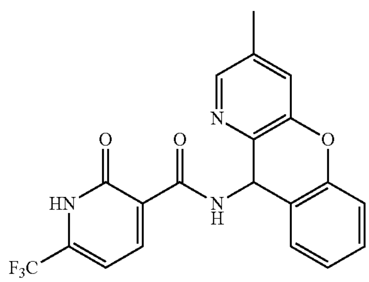 [SMILES: Cc1cnc2c(c1)Oc1ccccc1C2NC(=O)c1ccc(C(F)(F)F)[nH]c1=O] | ¹H NMR (400 MHz, CHLOROFORM-d) δ = 10.00 (br s, 1H), 8.60 (d, J = 7.5 Hz, 1H), 8.31 (s, 1H), 7.62 (d, J = 7.3 Hz, 1H), 7.35 – 7.28 (m, 2H), 7.17 – 7.08 (m, 2H), 6.81 (d, J = 7.5 Hz, 1H), 6.61 (d, J = 8.8 Hz, 1H), 2.38 (s, 3H)<br>ESI [M − H] = 400.1 |
| 325 | 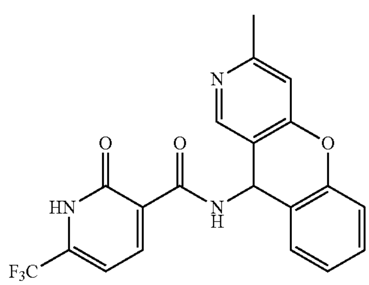 | ¹H NMR (400 MHz, CDCl₃-d) δ = 9.95 – 9.93 (d, J = 7.2 Hz, 1H), 8.71 – 8.69 (d, J = 7.6 Hz, 1H), 8.60 (s, 1H), 7.58 – 7.56 (d, J = 7.2 Hz, 1H), 7.34 – 7.32 (m, 1H), 7.17 – 7.15 (m, 2H), 6.93 (s, 1H), 6.86 – 6.84 (d, J = 7.6 Hz, 1H), 6.65 – 6.63 (d, J = 8.4 Hz, 1H), 2.55 (s, 3H).<br>ESI [M − H] = 400.1 |
| 326 | 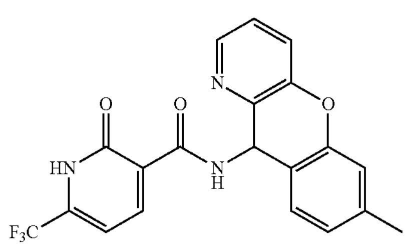 | ¹H NMR (400 MHz, DMSO-d₆) δ = 13.80 – 13.10 (m, 1H), 10.45 – 9.52 (m, 1H), 8.39 – 8.30 (m, 2H), 7.61 (dd, J = 1.2, 8.3 Hz, 1H), 7.44 – 7.35 (m, 2H), 7.28 – 7.16 (m, 1H), 7.03 – 6.96 (m, 2H), 6.40 (d, J = 8.2 Hz, 1H), 2.33 (s, 3H)<br>ESI [M − H] = 400.0 |
| 327 | 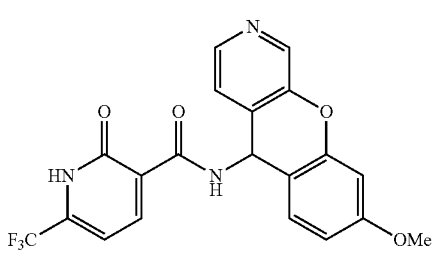 | ¹H NMR (400 MHz, DMS0-d₆) δ = 13.76 – 12.94 (m, 1H), 10.36 (br s, 1H), 8.50 (s, 1H), 8.37 – 8.25 (m, 2H), 7.45 (d, J = 5.0 Hz, 1H), 7.35 (d, J = 8.4 Hz, 1H), 7.16 (br s, 1H), 6.86 – 6.72 (m, 2H), 6.41 (d, J = 8.2 Hz, 1H), 3.79 (s. 3H)<br>ESI [M − H] = 416.1 |

TABLE 27-continued

| Compound No | Structure | HNMR and Ms |
|---|---|---|
| 328 | 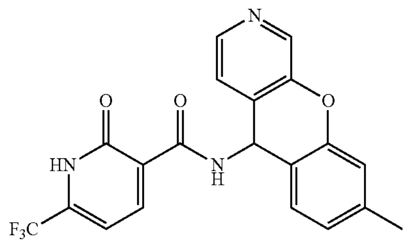 [SMILES: Cc1ccc2c(c1)Oc1cnccc1C2NC(=O)c1ccc(C(F)(F)F)[nH]c1=O] | $^1$H NMR (400 MHz, DMSO-d$_6$) δ = 10.12 (s, 1H), 8.49 (s, 1H), 8.38 – 8.26 (m, 2H), 7.44 (d, J = 4.9 Hz, 1H), 7.33 (d, J = 8.2 Hz, 1H), 7.21 (br s, 1H), 7.05 (s, 1H), 7.00 (d, J = 7.9 Hz, 1H), 6.43 (d, J = 8.4 Hz, 1H), 2.33 (s, 3H)<br>[M − H] = 400.01 |
| 329 | 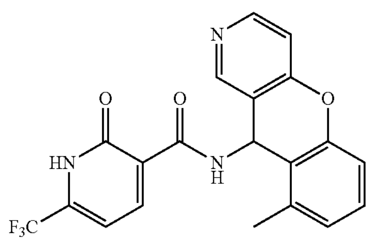 [SMILES: Cc1cccc2c1C(NC(=O)c1ccc(C(F)(F)F)[nH]c1=O)c1cnccc1O2] | $^1$H NMR (400 MHz. DMSO-d$_6$) δ = 13.16 (br s, 1H), 8.74 (s, 1H), 8.42 (s, 1H), 8.22-8.21 (d, J = 6.8 Hz, 1H), 7.34 – 7.07 (m, 6H), 6.52-6.50 (d, J = 8 Hz, 1H), 2.35 (s, 3H).<br>ESI [M − H] = 400.0 |
| 330 | 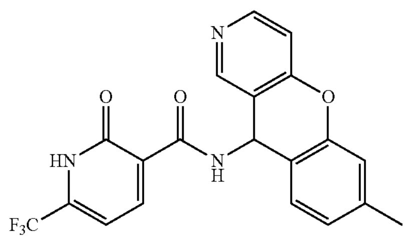 | $^1$H MR (400 MHz, CDCl$_3$-d$_6$) δ = 9.93 − 9.90 (d, J = 8.4 Hz, 1H), 8.75 (s, 1H), 8.71-8.69 (d, J = 7.2 Hz, 1H), 8.47 (s, 1H), 7.42-7.40 (d, J = 7.6 Hz, 1H), 7.27 (s, 1H), 7.05-6.97 (m, 2H), 6.86 – 6.84 (d, J = 7.2 Hz, 1H), 6.64-6.62 (d, J = 8.8 Hz, 1H), 2.37 (s, 3H).<br>ESI [M − H] = 400.1 |
| 331 | 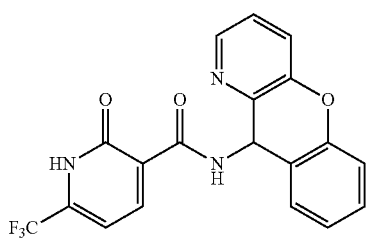 [SMILES: O=C(NC1c2ccccc2Oc2cccnc21)c1ccc(C(F)(F)F)[nH]c1=O] | $^1$H NMR (400 MHz, CDCl$_3$-d$_6$) δ = 10.00 − 9.98 (br s, 1H), 8.66 − 8.64 (d, J = 7.2 Hz, 1H), 8.45 − 8.44 (d, J = 3.6 Hz, 1H), 7.62 − 7.60 (d, J = 8.0 Hz, 1H), 7.50 (s, 1H), 7.33 − 7.31(m, 2H), 7.18-7.14 (m. 2H), 6.83 − 6.81 (d, J = 7.2 Hz. 1H). 6.67 − 6.65(d, J = 8.4 Hz, 1H).<br>ESI [M − H] = 386.0 |
| 332 | 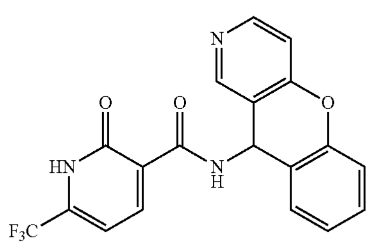 | $^1$H NMR (400 MHz, DMSO-d$_6$) δ = 9.97 (br s, 1H), 8.63 (s, 1H), 8.45 − 8.44 (d, J = 5.6 Hz, 1H), 8.35 − 8.34 (d, J = 7.6 Hz, 1H), 7.53 − 7.51 (d, J = 8.0 Hz, 1H), 7.39 (m. 1H), 7.26 − 7.19 (m, 4H), 6.53 − 6.51 (d. J = 8.4 Hz, 1H).<br>ESI [M − H] = 386.0 |
| 333 | 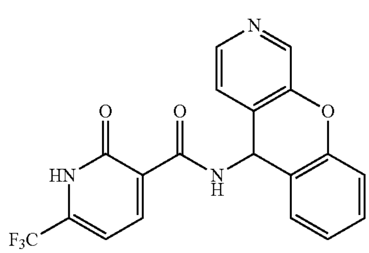 | $^1$H NMR (400 MHz, DMSO-d$_6$) δ = 13.31 (br s, 1H), 9.87 (br d, J = 1.9 Hz, 1H), 8.51 (s, 1H), 8.38 (d, J = 7.6 Hz, 1H), 8.32 (br d, J = 4.8 Hz, 1H), 7.51 − 7.43 (m, 2H), 7.41 − 7.36 (m, 1H), 7.32 (d, J = 7.6 Hz, 1H), 7.26 − 7.16 (m, 2H), 6.49 (d, J = 8.3 Hz, 1H)<br>ESI [M − H] = 386.1 |

TABLE 27-continued

| Compound No | Structure | HNMR and Ms |
|---|---|---|
| 334 | 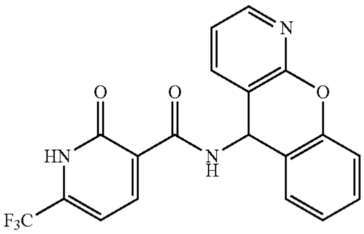 [SMILES: O=C(NC1c2ccccc2Oc2ncccc21)c1ccc(C(F)(F)F)[nH]c1=O] | $^1$H NMR (400 MHz, DMSO-$d_6$) δ = 9.78 (br s, 1H), 8.36 – 8.34 (d, J = 7.6 Hz, 1H), 8.26 – 8.25 (d, J = 4.8 Hz, 1H), 7.93 – 7.91 (d, J = 8.4 Hz. 1H), 7.47 – 7.45 (d, J = 7.6 Hz. 1H), 7.37 – 7.24 (m. 1H), 7.23 – 7.22 (d, J = 4.8 Hz. 1H), 7.21 – 7.17 (m. 3H), 6.53 – 6.51 (d, J = 8.4 Hz. 1H). ESI [M + H] = 388.0 |

Example 49: Synthesis of 2-oxo-N-(5-phenethyl-1,2,3,4-tetrahydronaphthalen-1-yl)-6-(trifluoromethyl)-1,2-dihydropyridine-3-carboxamide (335)

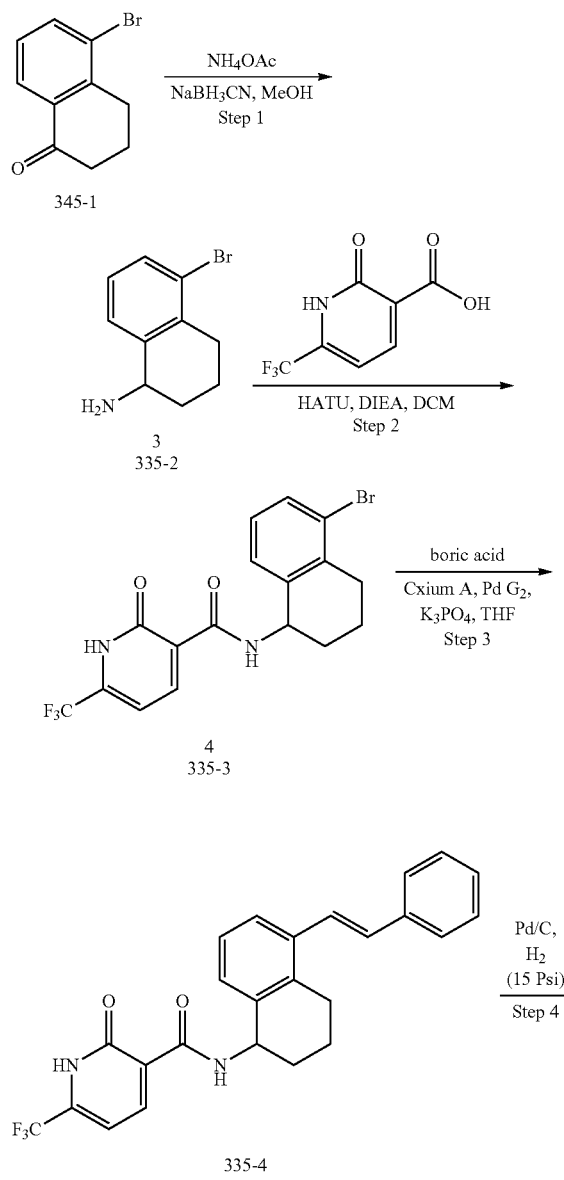

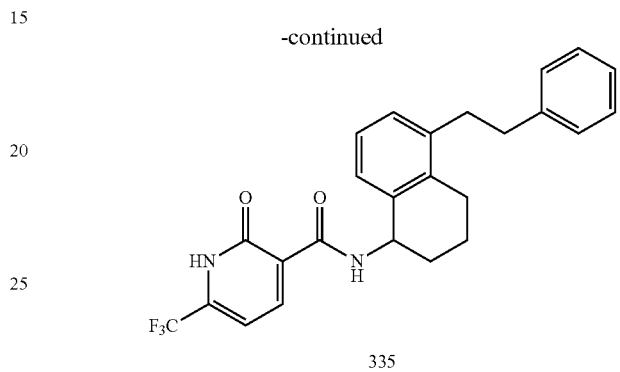

Step 1: 5-bromo-1,2,3,4-tetrahydronaphthalen-1-amine (335-2)

To a solution of Compound 335-1 in MeOH (10 mL) was added NH$_4$OAc (2.6 g, 33.3 mmol), NaBH$_3$CN (558.4 mg, 8.9 mmol). The mixture was stirred at 90° C. for 1 hr under microwave. LCMS showed the starting material was consumed. The reaction mixture was poured into water (15 mL) and extracted with DCM (5 mL×2). The combined organic layers were washed with brine (5 mL×2), dried over Na$_2$SO$_4$, filtered and concentrated under reduced pressure to give Compound 335-2 (430 mg, crude) as a yellow solid. Fragment MS=209.0 (LCMS).

Step 2: N-(5-bromo-1,2,3,4-tetrahydronaphthalen-1-yl)-2-oxo-6-(trifluoromethyl)-1,2-dihydropyridine-3-carboxamide (335-3)

To a solution of Compound 335-2 (0.4 g, 1.8 mmol), 2-oxo-6-(trifluoromethyl)-1,2-dihydropyridine-3-carboxylic acid (403.0 mg, 1.9 mmol) in DCM (10 mL) was added HATU (672.6 mg, 1.8 mmol), DIEA (274.36 mg, 2.1 mmol). The mixture was stirred at 15° C. for 2 hrs. LCMS showed the starting material was consumed. The reaction mixture was poured into water (15 mL) and extracted with DCM (5 mL×2). The combined organic layers were dried over Na$_2$SO$_4$, filtered and concentrated under reduced pressure to give residue, which was purified by prep-HPLC to give Compound 335-3 (250 mg, 602.1 μmol, 34% yield) as a white solid. M–H$^-$=414.9 (LCMS).

Step 3: (E)-2-oxo-N-(5-styryl-1,2,3,4-tetrahydronaphthalen-1-yl)-6-(trifluoromethyl)-1,2-dihydropyridine-3-carboxamide (335-4)

A mixture of (E)-styrylboronic acid (235.2 mg, 1.6 mmol), Compound 335-3 (220 mg, 529.8 μmol) and K$_3$PO$_4$ (337.4 mg, 1.6 mmol), Pd(t-Bu₃P)₂ (35.4 mg, 53 μmol) in THF (20 mL) was degassed and purged with N₂ for 3 times, and then the mixture was stirred at 80° C. for 12 hrs. LCMS showed the starting material was consumed. The reaction mixture was poured into brine (10 mL) and extracted with EtOAc (3 mL×2). The combined organic layers were dried over Na₂SO₄, filtered and concentrated under reduced pressure to give residue, which was purified by prep-HPLC to give Compound 335-4 (94 mg, 76.4 μmol, 32% yield) as a white solid. M−H⁻=437.1 (LCMS); ¹H NMR (400 MHz, DMSO-d₆) δ=13.50 (br s, 1H), 9.32 (br s, 1H), 8.47-8.45 (d, J=7.6 Hz, 1H), 7.64-7.62 (d, J=7.2 Hz, 2H), 7.38-7.37 (d, J=7.6 Hz, 1H), 7.43 (s, 1H), 7.38-7.37 (d, J=7.6 Hz, 2H), 7.28-7.20 (m, 4H), 7.11-7.06 (d, J=16.4 Hz, 1H), 5.24-5.17 (m, 1H), 2.95-2.83 (m, 2H), 2.0-1.84 (m, 4H).

Step 4: 2-oxo-N-(5-phenethyl-1,2,3,4-tetrahydronaphthalen-1-yl)-6-(trifluoromethyl)-1,2-dihydropyridine-3-carboxamide (335)

A mixture of Compound 335-4 (60 mg, 136.9 μmol), Pd/C (30 mg, 136.8 μmol, 10% purity) in EtOAc (6 mL) was degassed and purged with H₂ for 3 times, and then the mixture was stirred at 15° C. for 30 mins under H₂ (15 Psi). LCMS showed the starting material was consumed. The suspension was filtered through a pad of celite and the filter cake was washed with EtOAc (5 mL×2). The combined filtrates were concentrated to dryness to give a residue, which was purified by prep-HPLC to give Compound 335 (28 mg, 62.4 μmol, 45% yield) as a white solid. M−H⁻=439.2 (LCMS); ¹H NMR (400 MHz, DMSO-d₆) δ=8.13-8.11 (br s, 1H), 7.29-7.23 (m, 4H), 7.15-7.05 (m, 3H), 6.58-6.56 (d, J=7.6 Hz, 1H), 5.12 (s, 1H), 2.78 (s, 4H), 2.71-2.64 (m, 2H), 1.91-1.66 (m, 4H).

Example 50: Synthesis of N-(1-ethyl-7-methyl-1,2,3,4-tetrahydroquinolin-4-yl)-2-oxo-6-(trifluoromethyl)-1,2-dihydropyridine-3-carboxamide (336)

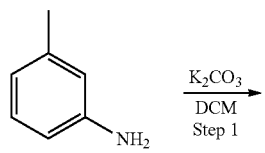

336-1

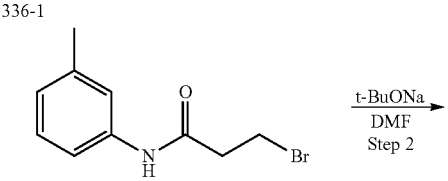

336-2

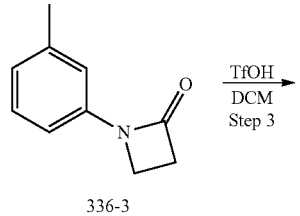

336-3

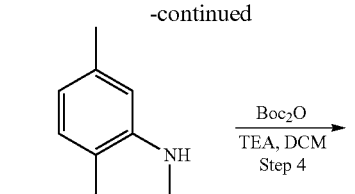

336-4

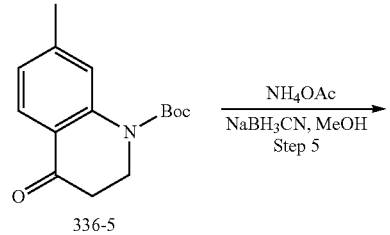

336-5

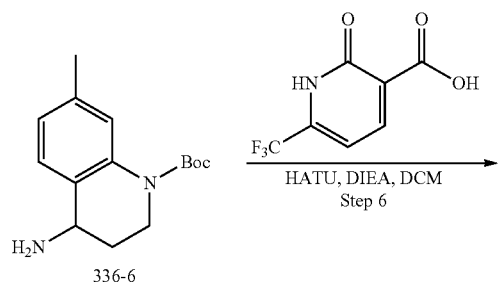

336-6

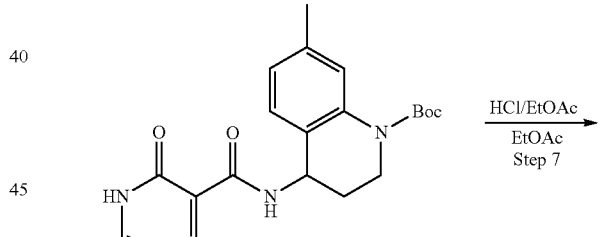

336-7

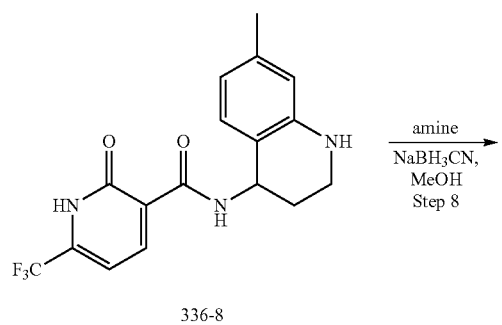

336-8

-continued

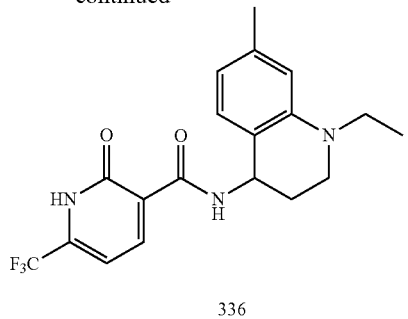

336

Step 1: 3-bromo-N-(m-tolyl)propanamide (336-2)

To a solution of Compound 336-1 (5 g, 46.7 mmol) in DCM (50 mL) was added K$_2$CO$_3$ (7.7 g, 56.0 mmol), then 3-bromopropanoyl chloride (9.6 g, 56.0 mmol) was added at 0° C. in drop wise. The mixture was stirred at 15° C. for 12 hrs. TLC indicated the reaction completed. The reaction mixture was quenched by poured into water (200 mL) and then extracted with EtOAc (20 mL×2). The combined organic layers were dried over Na$_2$SO$_4$, filtered and concentrated under reduced pressure to give Compound 336-2 (10 g, 41.3 mmol, 88% yield) as a gray solid.

Step 2: 1-(m-tolyl)azetidin-2-one (336-3)

To a solution of Compound 336-2 (10 g, 41.3 mmol) in DMF (100 mL) was added t-BuONa (4.4 g, 45.4 mmol) at 0° C. The mixture was stirred at 15° C. for 12 hrs. TLC indicated the reaction completed. The reaction mixture was poured into water (200 mL) and extracted with EtOAc (30 mL×3). The combined organic layers were washed with brine (20 mL×3), dried over Na$_2$SO$_4$, filtered and concentrated under reduced pressure to give a residue. The crude product was triturated with Petroleum ether/Ethyl acetate=3/1 (10 mL) at 20° C. for 5 mins to give Compound 336-3 (5 g, 31.0 mmol, 75 yield) as a white solid.

Step 3: 7-methyl-2,3-dihydroquinolin-4(1H)-one (336-4)

To a solution of Compound 336-3 (5 g, 31.0 mmol) in DCM (100 mL) was added TfOH (9.3 g, 62.0 mmol) at 0° C. under N$_2$. The mixture was stirred at 20° C. for 1 hr. TLC indicated the reaction completed. The reaction mixture was quenched by poured into ice water (60 mL) and extracted with EtOAc (10 mL×2). The combined organic layers were dried over Na$_2$SO$_4$, filtered and concentrated under reduced pressure to give a residue, which was purified by prep-HPLC to give Compound 336-7 (2.3 g, 14.3 mmol, 46% yield) as a yellow solid. $^1$H NMR (400 MHz, CHLOROFORM-d) δ=7.76-7.74 (d, J=8 Hz, 1H), 6.58-6.56 (d, J=8.4 Hz, 1H), 6.47 (s, 1H), 4.32 (s, 1H), 3.58-3.54 (m, 2H), 2.69-2.66 (m, 2H), 2.26 (s, 3H).

Step 4: tert-butyl 7-methyl-4-oxo-3,4-dihydroquinoline-1(2H)-carboxylate (336-5)

To a solution of Compound 336-4 (2.3 g, 14.3 mmol) in DCM (50 mL) was added Boc$_2$O (3.4 g, 15.7 mmol), TEA (1.4 g, 14.3 mmol) and DMAP (174.3 mg, 1.4 mmol). The mixture was stirred at 25° C. for 12 hrs. LCMS showed most of the starting material was consumed. The reaction mixture was poured into H$_2$O (15 mL) and extracted with EtOAc (5 mL×2). The combined organic layers were dried over Na$_2$SO$_4$, filtered and concentrated under reduced pressure to give a residue, which was purified by prep-HPLC to give Compound 336-5 (2.8 g, 10.7 mmol, 75% yield) as a white solid. M+H$^+$=262.4 (LCMS); $^1$H NMR (400 MHz, CHLOROFORM-d) δ=7.90-7.88 (d, J=8 Hz, 1H), 7.61 (s, 1H), 7.01-6.96 (m, 1H), 4.15-4.12 (m, 2H), 2.75-2.72 (m, 2H), 2.39 (s, 3H), 1.56 (s, 9H).

Step 5: tert-butyl 4-amino-7-methyl-3,4-dihydroquinoline-1(2H)-carboxylate (336-6)

To a solution of Compound 336-5 (500 mg, 1.9 mmol) in MeOH (10 mL) was added NH$_4$OAc (2.2 g, 28.7 mmol), after stirred for 10 mins, NaBH$_3$CN (481 mg, 7.6 mmol) was added. The mixture was stirred at 80° C. for 1 hr under microwave. TLC showed the reaction completed. The reaction mixture was poured into H$_2$O (5 mL) and extracted with DCM (5 mL×3). The combined organic layers were dried over Na$_2$SO$_4$, filtered and concentrated under reduced pressure to give Compound 336-6 (500 mg, crude) as colorless oil.

Step 6: tert-butyl 7-methyl-4-(2-oxo-6-(trifluoromethyl)-1,2-dihydropyridine-3-carboxamido)-3,4-dihydroquinoline-1(2H)-carboxylate (336-7)

To a solution of 2-oxo-6-(trifluoromethyl)-1,2-dihydropyridine-3-carboxylic acid (340 mg, 1.6 mmol), Compound 336-6 (430 mg, 1.6 mmol) in DCM (15 mL) was added DIEA (635.5 mg, 4.9 mmol) and HATU (747.9 mg, 2.0 mmol). The mixture was stirred at 15° C. for 1 hr. LCMS showed the reaction was completed and desired mass was detected. The reaction mixture was poured into H$_2$O (5 mL) and extracted with DCM (10 mL×3). The combined organic layers were dried over Na$_2$SO$_4$, filtered and concentrated under reduced pressure to give a residue, which was purified by prep-HPLC to give Compound 336-7 (160 mg, 351.4 μmol, 21% yield) as a white solid. M−H$^-$=450.2 (LCMS); $^1$H NMR (400 MHz, DMSO-d$_6$) δ=13.42 (br s, 1H), 9.25 (br s, 1H), 8.41 (d, J=7.6 Hz, 1H), 7.50 (s, 1H), 7.32 (br s, 1H), 7.15 (d, J=7.8 Hz, 1H), 6.87 (d, J=7.8 Hz, 1H), 5.16 (q, J=6.8 Hz, 1H), 3.84-3.75 (m, 1H), 3.73-3.63 (m, 1H), 2.27 (s, 3H), 2.16-2.05 (m, 1H), 1.97-1.87 (m, 1H), 1.48 (s, 9H).

Step 7: N-(7-methyl-1,2,3,4-tetrahydroquinolin-4-yl)-2-oxo-6-(trifluoromethyl)-1,2-dihydropyridine-3-carboxamide (336-8)

To a solution of Compound 336-7 (150 mg, 332.3 μmol) in EtOAc (5 mL) was added HCl/EtOAc (4 M, 13.00 mL). The mixture was stirred at 15° C. for 30 mins. LC-MS showed the reaction completed and desired mass was detected. The mixture was concentrated under reduced pressure to give Compound 336-8 (0.1 g, crude) as a white solid. M−H$^-$=350.1 (LCMS); $^1$H NMR (400 MHz, DMSO-d$_6$) δ=9.24 (br s, 1H), 8.43 (d, J=7.6 Hz, 1H), 7.33 (br d, J=5.9 Hz, 1H), 7.17 (br d, J=7.8 Hz, 1H), 6.92-6.74 (m, 2H), 5.21 (q, J=6.6 Hz, 1H), 3.44-3.29 (m, 2H), 2.26 (s, 3H), 2.17-1.99 (m, 2H).

Step 8: N-(1-ethyl-7-methyl-1,2,3,4-tetrahydroquinolin-4-yl)-2-oxo-6-(trifluorom-ethyl)-1,2-dihydropyridine-3-carboxamide (336)

To a stirred solution of Compound 336-8 (50 mg, 129 μmol) in MeOH (4 mL) was added TEA (13.1 mg, 128.9

μmol) and acetaldehyde (5 M, 77 uL), then was added HOAc (7.7 mg, 128.9 μmol) to the pH=5-6. The resulting mixture was stirred at 20° C. for 0.5 hr, then added NaBH$_3$CN (16.2 mg, 257.9 μmol) and stirred at 20° C. for 2 hrs. LCMS showed the reaction completed and desired mass was detected. The reaction mixture was poured into H$_2$O (5 mL) and extracted with EtOAc (10 mL×3). The combined organic layers were dried over Na$_2$SO$_4$, filtered and concentrated under reduced pressure to give a residue, which was purified by prep-HPLC to give Compound 336 (10.7 mg, 27.2 μmol, 21% yield) as a yellow solid. M−H⁻=378.2 (LCMS); $^1$H NMR (400 MHz, CHLOROFORM-d) δ=9.41 (br d, J=6.6 Hz, 1H), 8.67 (d, J=7.5 Hz, 1H), 7.06 (d, J=7.7 Hz, 1H), 6.85 (d, J=7.5 Hz, 1H), 6.50 (s, 1H), 6.43 (d, J=7.5 Hz, 1H), 5.28-5.15 (m, 1H), 3.48-3.20 (m, 4H), 2.29 (s, 3H), 2.18-2.09 (m, 2H), 1.16 (t, J=7.1 Hz, 3H).

Other compounds made in a similar manner are shown in Table 28.

TABLE 28

| Compound No | Structure | HNMR and Ms |
|---|---|---|
| 337 | 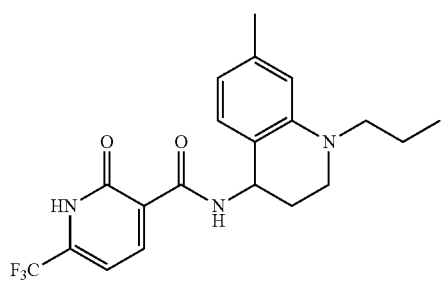 [SMILES: CCCN1CCC(NC(=O)c2ccc(C(F)(F)F)[nH]c2=O)c2ccc(C)cc21] | $^1$H NMR (400 MHz, CHLOROFORM-d) δ = 12.46 – 11.94 (m, 1H), 9.31 (brs, 1H), 8.65 (d, J = 7.5 Hz, 1H), 7.06 (d, J = 7.7 Hz, 1H), 6.85 (d, J = 7.5 Hz, 1H), 6.51 – 6.39 (m, 2H), 5.28 – 5.18 (m, 1H), 3.42 – 3.16 (m, 4H), 2.29 (s, 3H), 2.16 – 2.08 (m, 2H), 1.71 – 1.59 (m, 2H), 0.97 (t, J = 7.4 Hz, 3H) ESI [M + H] = 394.2 |
| 338 | 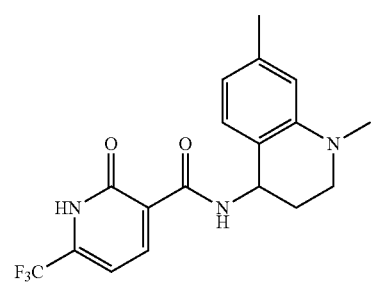 | $^1$H NMR (400 MHz, CHLOROFORM-d) δ = 12.75 (brs, 1H), 9.41 (brs, 1H), 8.67 (d, J = 7.3 Hz, 1H), 7.07 (d, J = 8.1 Hz, 1H), 6.85 (d, J = 7.5 Hz, 1H), 6.55 – 6.43 (m, 2H), 5.30 – 5.19 (m, 1H), 3.32 – 3.19 (m, 2H), 2.93 (s, 3H), 2.30 (s, 3H), 2.23 – 2.09 (m, 2H). ESI [M + H] = 366.1 |
| 339 | 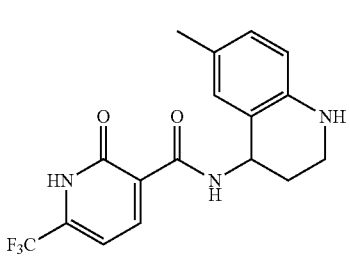 | $^1$H NMR (400 MHz, MeOH-d) δ = 8.57- 8.55 (m, J = 7.5 Hz 1H), 7.25 (s, 1H), 7.18 – 7.16 (d, J = 9.2 Hz, 1H), 7.10 – 7.08 (d, J = 7.6 Hz, 1H), 7.02 – 7.0 (d, J = 8 Hz, 1H), 5.34 – 5.32 (m, 1H), 3.52 (m, 2H), 2.34 – 2.30 (m, 4H), 2.23 – 2.20 (m, 1H). ESI [M + H] = 352.1 |

Example 51: Synthesis of N-(6-methyl-2-propyl-1H-inden-1-yl)-2-oxo-6-(trifluoromethyl)-1,2-dihydropyridine-3-carboxamide (340)

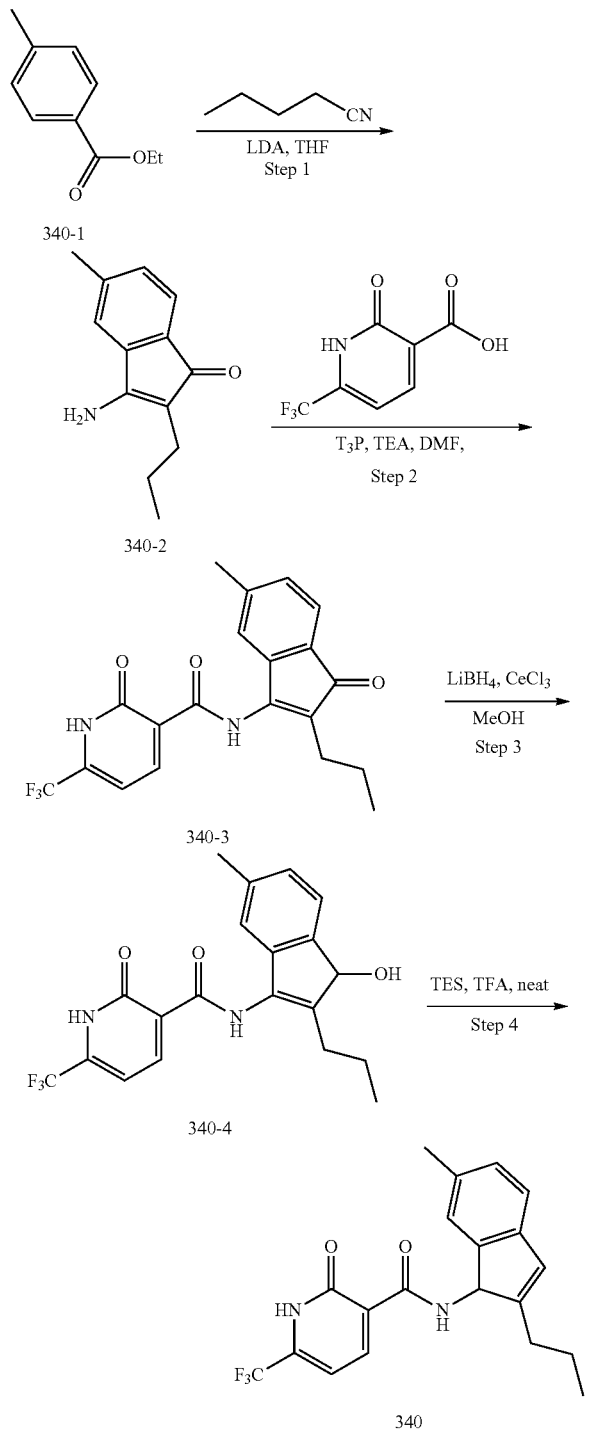

Step 1: 3-amino-5-methyl-2-propyl-1H-inden-1-one (340-2)

To a solution of Compound 340-1 (1 g, 6.1 mmol) and pentanenitrile (507 mg, 6.1 mmol) in THF (20 mL) was added LDA (2 M, 18.3 mL) at −10° C., then the mixture was stirred at 20° C. for 12 hrs. LCMS showed the reaction was completed and desired mass was detected. The reaction mixture was quenched by addition H₂O (15 mL) at 0° C., and then extracted with EtOAc (25 mL×2). The combined organic layers were dried over Na₂SO₄, filtered and concentrated under reduced pressure to give a residue, which was purified by flash silica gel chromatography (Ethyl acetate/Petroleum ether gradient) to give Compound 340-2 (1 g, 82% yield) as a red solid. M+H⁺=202.4 (LCMS); ¹H NMR (400 MHz, DMSO-d6) δ=7.45 (br s, 2H), 7.28 (s, 1H), 7.06-6.99 (m, 2H), 2.30 (s, 3H), 2.12 (t, J=7.4 Hz, 2H), 1.37 (sxt, J=7.4 Hz, 2H), 0.84 (t, J=7.3 Hz, 3H).

Step 2: N-(5-methyl-1-oxo-2-propyl-1H-inden-3-yl)-2-oxo-6-(trifluoromethyl)-1,2-dihydropyridine-3-carboxamide (340-3)

To a solution of Compound 340-2 (100 mg, 496.9 μmol) and 2-oxo-6-(trifluoro methyl)-1,2-dihydropyridine-3-carboxylic acid (103 mg, 496.9 μmol) in DMF (5 mL) was added TEA (151 mg, 1.5 mmol) and T₃P (474 mg, 745.3 μmol, 50% purity). The mixture was stirred at 100° C. for 12 hrs. LCMS showed the reaction was completed and desired mass was detected. The reaction mixture was quenched by addition H₂O (5 mL) at 20° C. and then extracted with EtOAc (5 mL×3). The combined organic layers were dried over Na₂SO₄, filtered and concentrated under reduced pressure to give a residue, which was purified by prep-HPLC to give Compound 340-3 (20 mg, 10.5% yield) as an orange solid. M+H⁺=391.1 (LCMS); 1H NMR (400 MHz, DMSO-d6) δ=11.70-11.58 (m, 1H), 8.48 (d, J=7.5 Hz, 1H), 7.28-7.23 (m, 3H), 7.11-7.09 (m, 1H), 2.38-2.33 (m, 5H), 2.33 (s, 3H), 1.48-1.39 (m, 2H), 0.87-0.84 (m, 3H).

Step 3: N-(1-hydroxy-5-methyl-2-propyl-1H-inden-3-yl)-2-oxo-6-(trifluoromethyl)-1,2-dihydropyridine-3-carboxamide (340-4)

To a solution of Compound 340-3 (40 mg, 102.5 μmol) in MeOH (3 mL) was added LiBH₄ (7 mg, 307.5 μmol) at 0° C. CeCl₃.7H₂O (19 mg, 51.2 μmol) was added to the mixture. The mixture was stirred at 0° C. for 0.5 hr. TLC indicated the reaction was completed and desired spot was detected. The reaction mixture was quenched by addition H₂O (5 mL) at 20° C., and then extracted with EtOAc (5 mL×5). The combined organic layers were dried over Na₂SO₄, filtered and concentrated under reduced pressure to give a residue which was purified by prep-TLC (Petroleum ether:Ethyl acetate=1:1) to give Compound 340-4 (30 mg) as a yellow gum. M+H⁺=391.2 (LCMS); 1H NMR (400 MHz, DMSO-d6) δ=13.66-13.58 (m, 1H), 10.66-10.55 (m, 1H), 8.46-8.44 (d, J=7.2 Hz, 1H), 7.34-7.28 (m, 2H), 6.97-6.94 (m, 2H), 5.44 (s, 1H), 4.90 (s, 1H), 2.38-2.28 (m, 5H), 1.62-1.50 (m, 2H), 0.91-0.87 (m, 3H).

Step 4: N-(6-methyl-2-propyl-1H-inden-1-yl)-2-oxo-6-(trifluoromethyl)-1,2-dihydropyridine-3-carboxamide (340)

To a stirred solution of Compound 340-4 (25 mg, 63.7 μmol) was added TFA (434 mg, 382.3 μmol) followed by TES (73 mg, 318.6 μmol) and heated to 60° C. under N₂ for 12 hrs. LCMS showed the reaction was completed and the desired mass was detected. The reaction mixture was quenched by addition H₂O (5 mL) at 15° C. and then extracted with EtOAc (5 mL×5). The combined organic layers were dried over Na$_2$SO$_4$, filtered and concentrated under reduced pressure to give a residue. The residue was purified by prep-HPLC to give Compound 340 (9.1 mg, 37.4% yield) as an off white solid. M+H$^+$=377.2 (LCMS); 1H NMR (400 MHz, DMSO-d6) δ=13.59-13.37 (m, 1H), 9.16-8.98 (m, 1H), 8.46 (d, J=7.5 Hz, 1H), 7.32 (br s, 1H), 7.19-7.12 (m, 2H), 7.06 (d, J=7.5 Hz, 1H), 6.54 (s, 1H), 5.60 (d, J=8.7 Hz, 1H), 2.31-2.24 (m, 5H), 1.68-1.49 (m, 2H), 0.91 (t, J=7.3 Hz, 3H).

Other compounds made in a similar manner are shown in Table 29.

TABLE 29

| Compound No | Structure | HNMR and Ms |
|---|---|---|
| 341 | 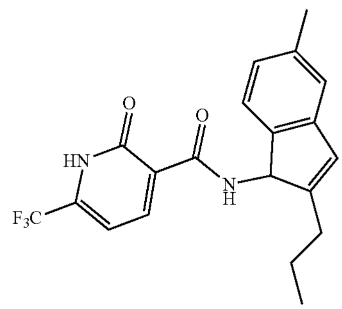 [SMILES: CCCC1=Cc2cc(C)ccc2C1NC(=O)c1ccc(C(F)(F)F)[nH]c1=O] | $^1$H NMR (400 MHz, CHLOROFORM-d) δ = 9.20 (br d, J = 9.0 Hz, 1H), 8.71 (d, J = 7.3 Hz, 1H), 7.29 (s, 1H), 7.06-7.03 (m, 1H), 6.90 (dd, J = 7.6, 13.8 Hz, 2H), 6.47 (s, 1H), 5.74 (d, J = 8.8 Hz, 1H), 2.36 (s, 3H), 2.34-2.31 (m, 2H), 1.76-1.50 (m, 2H), 0.96 (t, J = 7.4 Hz, 3H) ESI [M − H] = 375.2 |
| 342 | 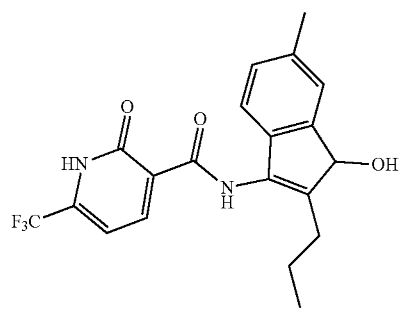 [SMILES: CCCC1=C(NC(=O)c2ccc(C(F)(F)F)[nH]c2=O)c2ccc(C)cc2C1O] | $^1$H NMR (400 MHz, DMSO-d$_6$) δ = 13.83-13.29 (m, 1H), 11.00-10.28 (m, 1H), 8.43 (d, J = 7.3 Hz, 1H), 7.31-7.21 (m, 2H), 7.03 (s, 2H), 5.45 (brd, J = 7.7 Hz, 1H), 4.90 (d, J =7.3 Hz, 1H), 2.40-2.33 (m, 2H), 2.32 (s, 3H), 1.70-1.41 (m, 2H), 0.90 (t, J = 7.4 Hz, 3H) ESI [M − H] = 391.1 |
| 343 | 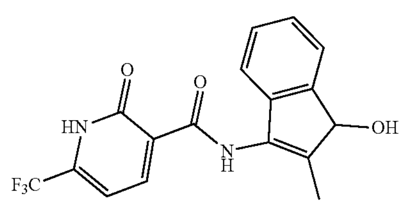 | $^1$H NMR (400 MHz, DMSO-d$_6$) δ = 14.11-13.15 (m, 1H), 11.61 (brs, 1H), 8.44 (br d, J = 7.5 Hz, 1H), 7.49-7.41 (m, 1H),7.35 (brdd, J = 7.1, 14.8 Hz, 2H), 7.31-7.23 (m, 2H), 1.83 (s, 3H) ESI [M − H] = 347.1 |
| 344 | 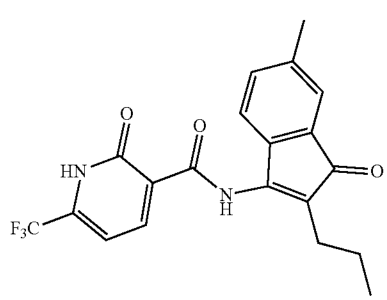 [SMILES: CCCC1=C(NC(=O)c2ccc(C(F)(F)F)[nH]c2=O)c2ccc(C)cc2C1=O] | $^1$H NMR (400 MHz, DMSO-d$_6$) δ = 8.18 (d, J = 1.5 Hz, 1H), 7.46 (d, J = 7.4 Hz, 1H), 7.23 (d, J = 7.5 Hz, 1H), 7.14 (s, 1H), 6.64 (d, J = 7.6 Hz, 1H), 2.47-2.41 (m, 2H), 2.30 (s, 3H), 1.38 (sxt, J = 7.3 Hz, 2H), 0.82 (t, J = 7.3 Hz, 3H) ESI [M − H] = 389.1 |

Example 52: Synthesis of N-(5-(hydroxymethyl)-1,2,3,4-tetrahydronaphthalen1-yl)-2-oxo-6-(trifluoromethyl)-1,2-dihydropyridine-3-carboxamide (345)

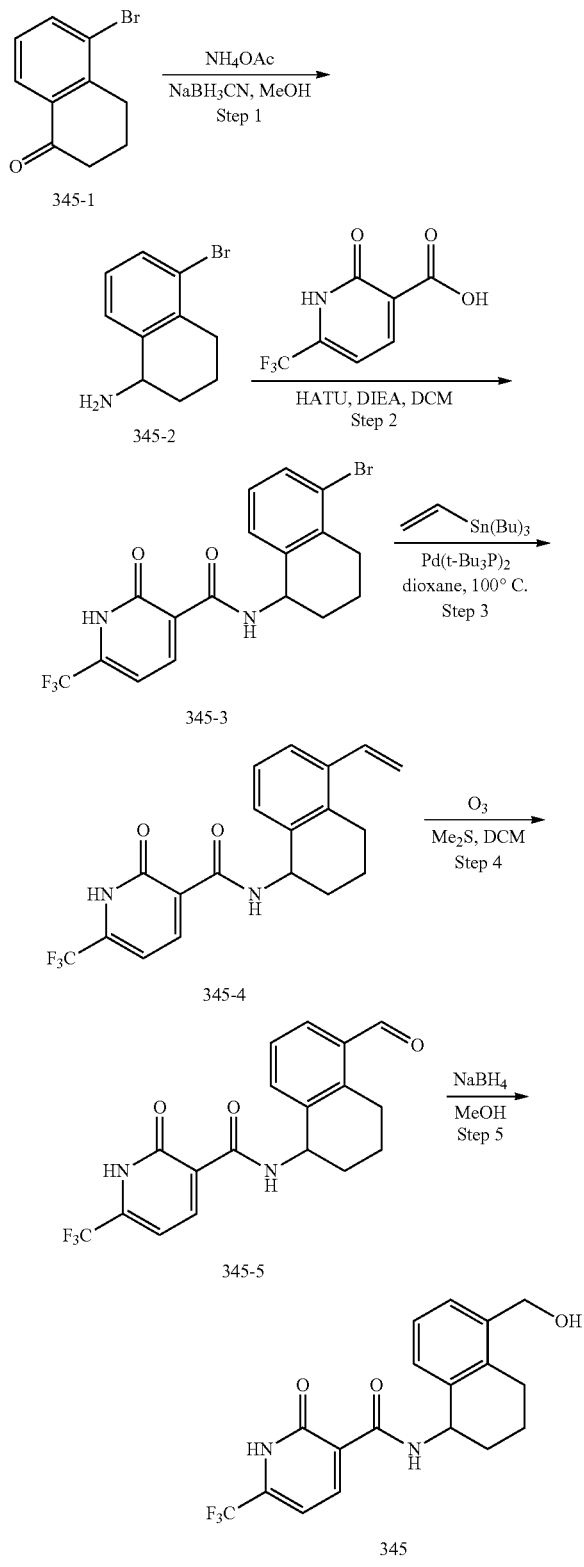

Step 1: 5-bromo-1,2,3,4-tetrahydronaphthalen-1-amine (345-2)

To a solution of Compound 345-1 (0.5 g, 2.2 mmol) in MeOH (10 mL) was added NH$_4$OAc (2.6 g, 33.3 mmol). After stirring for 10 min at 15° C., NaBH$_3$CN (558 mg, 8.9 mmol) was added. The mixture was stirred at 90° C. for 1 hr under microwave. LCMS showed the reaction was completed and desired mass was detected. The reaction mixture was quenched by pouring into water (20 mL) and extracted with EtOAc (10 mL×3). The combined organic layers were washed with brine (10 mL×2), dried over Na$_2$SO$_4$, filtered and concentrated under reduced pressure to give Compound 345-2 (0.4 g, crude) as yellow oil used directly.

Step 2: N-(5-bromo-1,2,3,4-tetrahydronaphthalen-1-yl)-2-oxo-6-(trifluoromethyl)-1,2-dihydropyridine-3-carboxamide (345-3)

To a solution of Compound 345-2 (0.35 g, 1.6 mmol) and 2-oxo-6-(trifluoromethyl)-1,2-dihydropyridine-3-carboxylic acid (321 mg, 1.6 mmol) in DCM (20 mL) was added DIEA (600 mg, 4.6 mmol) and HATU (706 mg, 1.9 mmol). The mixture was stirred at 15° C. for 2 hrs. TLC showed the reaction was completed. The reaction mixture was quenched by pouring into water (15 mL) and extracted with DCM (5 mL×2). The combined organic layers were washed with brine (5 mL×2), dried over Na$_2$SO$_4$, filtered and concentrated under reduced pressure to give a residue, which was purified by column chromatography to give Compound 345-3 (0.3 g, 722 µmol, 47% yield) as white solid. $^1$H NMR (400 MHz, CHLOROFORM-d) δ=12.95 (br s, 1H), 9.66 (br d, J=7.9 Hz, 1H), 8.72 (d, J=7.1 Hz, 1H), 7.49 (dd, J=0.8, 7.8 Hz, 1H), 7.29 (d, J=7.7 Hz, 1H), 7.02 (t, J=7.8 Hz, 1H), 6.87 (d, J=7.7 Hz, 1H), 5.42-5.30 (m, 1H), 2.92 (td, J=5.4, 17.6 Hz, 1H), 2.72 (td, J=7.2, 17.8 Hz, 1H), 2.04-1.85 (m, 4H)

Step 3: 2-oxo-6-(trifluoromethyl)-N-(5-vinyl-1,2,3,4-tetrahydronaphthalen-1-yl)-1,2-dihydropyridine-3-carboxamide (345-4)

A mixture of Compound 345-3 (0.3 g, 722 µmol), tributyl(vinyl)stannane (275 mg, 867 µmol), Pd(t-Bu$_3$P)$_2$ (37 mg, 72 µmol) in toluene (8 mL) was degassed and purged with N$_2$ for three times, then the mixture was stirred at 80° C. for 12 hrs. LCMS showed the reaction was completed and desired mass was detected. The reaction mixture was quenched by pouring into water (15 mL) and extracted with EtOAc (5 mL×3). The combined organic layers were washed with brine (5 mL×2), dried over Na$_2$SO$_4$, filtered and concentrated under reduced pressure to give a residue, which was purified by column chromatography to give Compound 345-4 (0.15 g, 414 µmol, 57% yield) as a white solid.

Step 4: N-(5-formyl-1,2,3,4-tetrahydronaphthalen-1-yl)-2-oxo-6-(trifluoromethyl)-1,2-dihydropyridine-3-carboxamide (345-5)

To a solution of Compound 345-4 (50 mg, 138 µmol) in DCM (10 mL) was bubbled with O$_3$ (138 µmol) at −78° C. When the color of the reaction turned blue, the reaction was bubbled with O$_2$ for 20 min, Me$_2$S (43 mg, 690 µmol) was added. The mixture was stirred at 15° C. for 12 hrs. LCMS showed the reaction was complete and desired mass was detected. The reaction mixture was quenched by pouring into water (10 mL) and extracted with DCM (5 mL×2). The combined organic layers were dried over Na$_2$SO$_4$, filtered and concentrated under reduced pressure to give Compound 345-5 (50 mg, crude) as yellow oil used directly.

Step 5: N-(5-(hydroxymethyl)-1,2,3,4-tetrahydronaphthalen-1-yl)-2-oxo-6-(trifluoromethyl)-1,2-dihydropyridine-3-carboxamide (345)

To a solution of Compound 345-5 (50 mg, 137 μmol) in MeOH (2 mL) was added NaBH$_4$ (16 mg, 412 μmol) at 0° C. The mixture was stirred at 15° C. for 1.5 hrs. LCMS showed the reaction was complete and desired mass was detected. The reaction mixture was quenched by pouring into water (15 mL) and extracted with EtOAc (5 mL×3). The aqueous layer was concentrated under reduced pressure to give a residue, which was purified by Prep-HPLC to give Compound 345 (12 mg, 30.54 μmol, 22% yield) as a white solid. M−H$^−$=365.1 (LCMS); $^1$H NMR (400 MHz, DMSO-d$_6$) δ=13.49 (br s, 1H), 9.36 (br s, 1H), 8.44 (d, J=7.5 Hz, 1H), 7.32-7.25 (m, 2H), 7.19-7.12 (m, 2H), 5.21 (br d, J=6.8 Hz, 1H), 5.08 (br s, 1H), 4.48 (br s, 2H), 2.77-2.56 (m, 2H), 2.04-1.74 (m, 4H).

Other compounds made in a similar manner are shown in Table 30.

TABLE 30

| Compound No | Structure | HNMR and Ms |
|---|---|---|
| 346 | 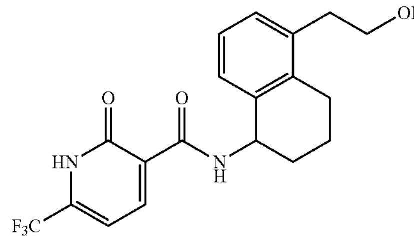 | $^1$H NMR (400 MHz, CHLOROFORM-d) δ = 9.60 (br d, J = 8.1 Hz, 1H), 8.71 (d, J = 7.3 Hz, 1H), 7.25 – 7.19 (m, 1H), 7.12 (d, J = 4.0 Hz, 2H), 6.85 (d, J = 7.5 Hz, 1H), 5.44 – 5.23 (m, 1H), 3.87 (t, J = 6.8 Hz, 2H), 2.92 (t, J = 6.8 Hz, 2H), 2.86 (br t, J = 5.1 Hz, 1H), 2.79 – 2.67 (m, 1H), 2.10 – 1.86 (m, 4H) ESI [M − H] = 379.1 |
| 347 | 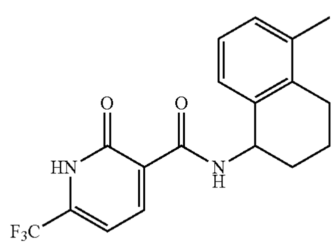 [SMILES: Cc1cccc2c1CCCC2NC(=O)c1ccc(C(F)(F)F)[nH]c1=O] | $^1$H NMR (400 MHz, CHLOROFORM-d) δ = 9.57 (br d, J = 7.7 Hz, 1H), 8.70 (d, J = 7.3 Hz, 1H), 7.19 – 7.14 (m, 1H), 7.11 – 7.03 (m, 2H), 6.85 (d, J = 7.5 Hz, 1H), 5.41 – 5.28 (m, 1H), 2.82 – 2.54 (m, 2H), 2.26 (s, 3H), 2.12 – 1.86 (m, 4H) ESI [M − H] = 349.1 |
| 348 | 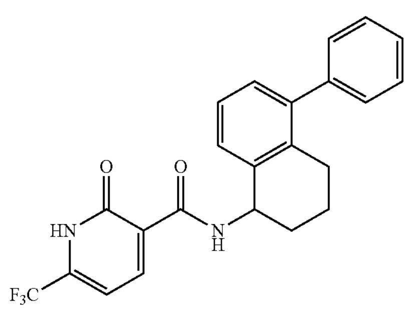 [SMILES: O=C(NC1CCCc2c(-c3ccccc3)cccc21)c1ccc(C(F)(F)F)[nH]c1=O] | $^1$H NMR (400 MHz, CHLOROFORM-d) δ = 9.64 (br d, J = 8.4 Hz, 1H), 8.73 (d, J = 7.5 Hz, 1H), 7.46 – 7.39 (m, 2H), 7.38 – 7.33 (m, 2H), 7.31 (d, J = 7.1 Hz, 2H), 7.22 (t, J = 7.5 Hz, 1H), 7.16 – 7.11 (m, 1H), 6.88 (d, J = 7.3 Hz, 1H), 5.51 – 5.39 (m, 1H), 2.76 – 2.54 (m, 2H), 2.16 – 2.06 (m, 1H), 2.04 – 1.94 (m, 1H), 1.89 – 1.69 (m, 2H) ESI [M − H] = 411.2 |

Example 53: Synthesis of N-(2,6-dimethoxy-1,2,3,4-tetrahydronaphthalen-1-yl)-2-oxo-6-(trifluoromethyl)-1,2-dihydropyridine-3-carboxamide (349)

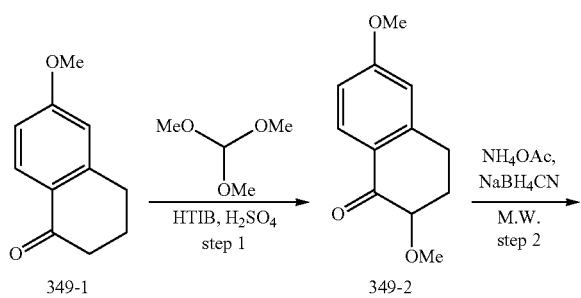

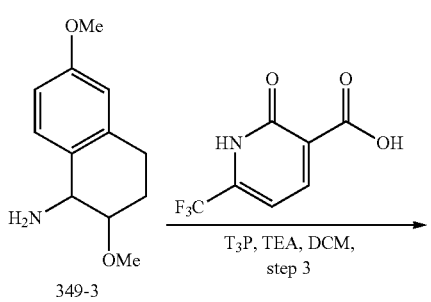

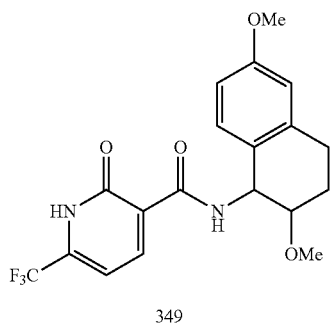

Step 1: 2,6-dimethoxy-3,4-dihydronaphthalen-1(2H)-one (349-2)

A solution of MeOH (10 mL) was cooled to −20° C. and then H₂SO₄ (2.2 g, 22.4 mmol) was added dropwise and the temperature was maintained between −25° C. to −18° C. for 5 mins. Trimethoxymethane (2.8 g, 26.4 mmol) was added slowly, followed by Compound 349-1 (2 g, 11.4 mmol). A solution of HTIB (4.90 g, 12.5 mmol) in MeOH (10 mL) was added to the reaction mixture over 10 mins. The resulting mixture was stirred at −20° C. for 1 hr. LCMS showed the reaction completed and desired mass was detected. The reaction mixture was added to H₂O (20 mL) and extracted with EtOAc (15 ml×3), then dried over Na₂SO₄, filtered and concentrated under reduced pressure to give a residue, which was purified by column chromatography to give Compound 349-2 (750 mg, crude) as a white solid. M+H⁺=207.0 (LCMS).

Step 2: 2,6-dimethoxy-1,2,3,4-tetrahydronaphthalen-1-amine (349-3)

To a solution of Compound 349-2 (200 mg, 970 µmol) in MeOH (2 mL) was added NH₄OAc (1.1 g, 15 mmol). The mixture was stirred for 10 mins, NaBH₃CN (245 mg, 4 mmol) was added and the reaction was stirred 90° C. for 2.5 hrs under microwave. LCMS showed the reaction completed and desired mass was detected. The reaction mixture was added to H₂O (3 mL) and extracted with EtOAc (5 ml×3). The combined organic layers were dried over Na₂SO₄, filtered and concentrated in vacuum to give Compound 349-3 (200 mg, crude) as a white solid. M+H⁺=208.0 (LCMS)

Step 3: N-(2,6-dimethoxy-1,2,3,4-tetrahydronaphthalen-1-yl)-2-oxo-6-(trifluoro methyl)-1,2-dihydropyridine-3-carboxamide (349)

To a solution of Compound 349-3 (150 mg, 724 µmol) in DCM (5 mL) was added 2-oxo-6-(trifluoromethyl)-1,2-dihydropyridine-3-carboxylic acid (150 mg, 724 µmol), TEA (220 mg, 2.2 mmol) and T₃P (691 mg, 1.1 mmol, 50% purity). The mixture was stirred at 25° C. for 12 hrs. Then the mixture was diluted with H₂O (5 mL) and extracted with DCM (5 mL×3). The combined organic layers were dried over NaSO₄ and concentrated under reduced pressure to give a residue, which was treated with MeOH (3 mL) and 3M NaOH (2 mL) and stirred at 20° C. for 12 hrs. Then the mixture was diluted with H₂O (5 mL) and adjusted pH to 5-6, then extracted with DCM (5 mL×3). The combined organic layers dried over NaSO₄ and concentrated under reduced pressure to give a residue, which was purified by prep-HPLC to give Compound 349 (25 mg, 60 µmol, 8% yield, a mixture of diastereoisomers) as a white solid. M−H⁻=395.2 (LCMS); ¹H NMR (400 MHz, DMSO-d₆) δ=8.67-8.24 (m, 1H), 7.27 (br s, 1H), 7.13-7.06 (m, 1H), 6.77-6.65 (m, 2H), 5.33-5.05 (m, 1H), 3.73-3.66 (m, 3H), 3.63-3.43 (m, 1H), 3.34-3.29 (m, 3H), 2.91-2.78 (m, 1H), 2.76-2.61 (m, 1H), 2.11 (br dd, J=6.6, 13.3 Hz, 1H), 1.88 (br dd, J=6.9, 13.3 Hz, 1H).

Other compounds made in a similar manner are shown in Table 31.

TABLE 31

| Compound No | Structure | HNMR and Ms |
|---|---|---|
| 350 | (structure shown) | ¹H NMR (400 MHz, CHCl₃-d) δ = 9.54 – 9.32 (m, 1H), 8.67 (dd, J = 7.4, 19.2 Hz, 1H), 7.24 – 7.11 (m, 1H), 7.02 – 6.92 (m, 2H), 6.87 (dd, J = 4.9, 7.4 Hz, 1H), 5.75 – 5.10 (m, 1H), 3.81 – 3.69 (m, 1H), 3.47 (d, J = 13.6 Hz, 3H), 3.05 – 2.89 (m, 1H), 2.84 – 2.65 (m, 1H), 2.29 (d, J = 2.3 Hz, 3H), 2.21 – 1.91 (m, 2H) ESI [M − H] = 379.1 |
| 351 | (structure shown) | ¹H NMR (400 MHz, DMSO-d6) δ = 8.54 (d, J = 7.5 Hz, 1H), 8.42 – 7.28 (m, 1H), 7.13 – 6.97 (m, 5H), 5.50 – 5.35 (m,1H), 4.20 – 4.15 (m, 1H), 4.11 (q, J = 6.2 Hz, 1H), 2.99 (br d, J = 2.9 Hz, 2H), 2.31 – 2.25 (m, 5H) ESI [M − H] = 365.1 |
| 352 | (structure shown) | ¹H NMR (400 MHz, DMSO-d₆) δ = 13.43 (br s, 1H), 9.26 (br s, 1H), 8.53-8.42 (m, 1H), 7.30 (br s, 1H), 7.16 – 7.09 (m, 1H), 6.83 (br s, 1H), 6.80 – 6.73 (m, 1H), 5.48 – 5.32 (m, 1H), 4.22 – 4.15 (m, 1H), 4.10 (q, J = 5.9 Hz, 1H), 3.73 – 3.37 (m, 3H), 3.30 (br s, 2H), 3.04 – 2.97 (m, 1H), 2.77 (dd, J = 5.7, 16.1 Hz, 1H) ESI [M − H] = 381.1 |

Example 54: Synthesis of N-((2R,3S)-5-methyl-2-propyl-2,3-dihydrobenzofuran-3-yl)-2-oxo-6-(trifluoromethyl)-1,2-dihydropyridine-3-carboxamide (353) & N-((2S,3S)-5-methyl-2-propyl-2,3-dihydrobenzofuran-3-yl)-2-oxo-6-(trifluoromethyl)-1,2-dihydropyridine-3-carboxamide (354)

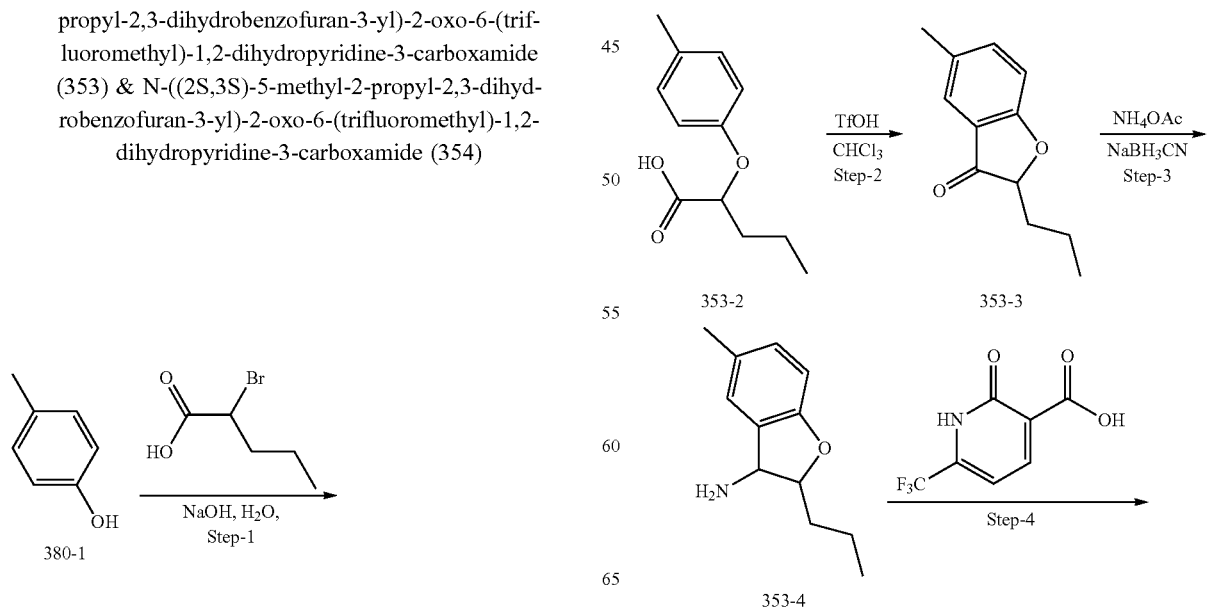

-continued

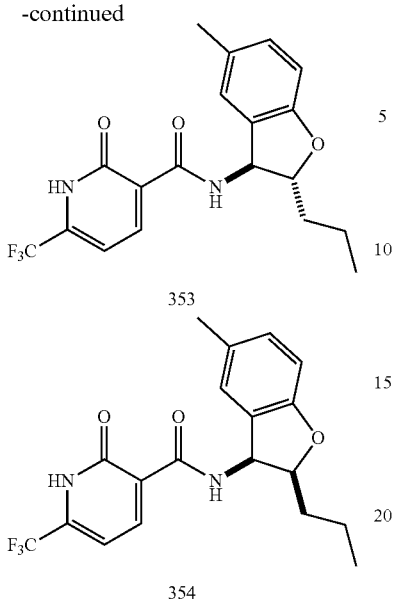

353

354

Step 1: 2-(p-tolyloxy)pentanoic acid (353-2)

A solution of NaOH (5 M, 2.11 mL) was added to 2-bromopentanoic acid (1.8 g, 10.1 mmol) at 0° C. To the resulting solution was added a solution of Compound 353-1 (1 g, 9.2 mmol) in NaOH (5 M, 2.00 mL). Then the mixture was stirred at 100° C. for 20 hrs. LCMS showed the reaction was completed and the desired mass was detected. The reaction mixture was quenched by addition H$_2$O (5 mL) at 0° C., and then adjusted pH to 5-6 The combined organic layers were extracted with EtOAc (5×5 ml) filtered and concentrated under reduced pressure to give a Compound 353-2 (1 g, 51.9% yield) as a white solid. M+H$^+$=209.0 (LCMS).

Step 2: 5-methyl-2-propylbenzofuran-3(2H)-one (353-3)

To a solution of Compound 353-2 (0.9 g, 4.3 mmol) in CHCl$_3$ (15 mL) was added TfOH (19.4 g, 129.6 mmol) at 0° C. The mixture was stirred at 20° C. for 1.5 hrs. TLC indicated the reaction was completed. The reaction mixture was quenched by addition H$_2$O (5 mL) at 20° C., and then extracted with EtOAc (5 mL×5). The combined organic layers were dried over Na$_2$SO$_4$, filtered and concentrated under reduced pressure to give a residue, which was purified by prep-TLC (Petroleum ether:Ethyl acetate=5:1) to give Compound 353-3 (60 mg, 8% yield) as a colorless gum.

Step 3: 5-methyl-2-propyl-2,3-dihydrobenzofuran-3-amine (353-4)

To a solution of Compound 353-3 (30 mg, 157.7 µmol) in MeOH (2 mL) was added NH$_4$OAc (182 mg, 2.3 mmol) and NaBH$_3$CN (39 mg, 630.7 µmol). The mixture was stirred at 90° C. for 3 hrs under M.W. LCMS showed the desired mass was detected. The reaction mixture was quenched by addition H$_2$O (5 mL) at 0° C., and then extracted with EtOAc (5 mL×5). The combined organic layers were dried over Na$_2$SO$_4$, filtered and concentrated under reduced pressure to give a Compound 353-4 (30 mg, 99% yield) as a yellow gum. Fragment MS=175.0 (LCMS).

Step 4: N-((2R,3S)-5-methyl-2-propyl-2,3-dihydrobenzofuran-3-yl)-2-oxo-6-(trifluoromethyl)-1,2-dihydropyridine-3-carboxamide (353) & N-((2S,3S)-5-methyl-2-propyl-2,3-dihydrobenzofuran-3-yl)-2-oxo-6-(trifluoromethyl)-1,2-dihydropyridine-3-carboxamide (354)

To a solution of Compound 353-4 (30 mg, 156.8 µmol), 2-oxo-6-(trifluoromethyl)-1,2-dihydropyridine-3-carboxylic acid (32 mg, 156 µmol) in DCM (2 mL) was added TEA (47 mg, 470.5 µmol) and T$_3$P (199 mg, 313.6 µmol, 50% purity). The mixture was stirred at 20° C. for 0.5 hr. LCMS showed the reaction was completed and the desired mass was detected. The reaction mixture was quenched by addition H$_2$O (5 mL) at 20° C., and then extracted with EtOAc (5 mL×5). The combined organic layers were dried over Na$_2$SO$_4$, filtered and concentrated under reduced pressure to give a residue which was purified by prep-HPLC to give Compound 353 (5.97 mg, 9.6% yield,) as a white solid. M−H$^-$=379.2 (LCMS); 1H NMR (400 MHz, CHLOROFORM-d) δ=9.62 (br d, J=6.6 Hz, 1H), 8.70 (d, J=7.3 Hz, 1H), 7.12 (s, 1H), 7.05 (br d, J=8.2 Hz, 1H), 6.87 (d, J=7.5 Hz, 1H), 6.75 (d, J=8.1 Hz, 1H), 5.40 (dd, J=4.4, 7.0 Hz, 1H), 4.54 (td, J=5.0, 7.4 Hz, 1H), 2.29 (s, 3H), 1.87-1.77 (m, 2H), 1.65-1.48 (m, 2H), 0.98 (t, J=7.4 Hz, 3H) and Compound 354 (2 mg, 3.3% yield) as a white solid. M−H$^-$=379.2 (LCMS); 1H NMR (400 MHz, CHLOROFORM-d) δ=9.53 (br d, J=8.8 Hz, 1H), 8.70 (d, J=7.4 Hz, 1H), 7.10 (s, 1H), 7.04 (br d, J=8.3 Hz, 1H), 6.87 (d, J=7.4 Hz, 1H), 6.76 (d, J=8.1 Hz, 1H), 5.73 (t, J=8.0 Hz, 1H), 4.75-4.64 (m, 1H), 2.27 (s, 3H), 1.79-1.51 (m, 4H), 0.95 (t, J=7.0 Hz, 3H).

Other compounds made in a similar manner are shown in Table 32.

TABLE 32

| Compound No | Structure | HNMR and Ms |
|---|---|---|
| 355 | (structure shown) | $^1$H NMR (400 MHz, CHLOROFORM-d) δ = 9.65 – 9.43 (m, 1H), 8.69 (dd, J = 2.5, 7.4 Hz, 1H), 7.12 (s, 1H), 7.09 – 6.99 (m, 1H), 6.87 (dd, J = 2.5, 7.4 Hz, 1H), 6.79 – 6.69 (m, 1H), 5.75 (t, J = 8.0 Hz, 1H), 4.66 – 4.43 (m, 1H), 2.31 – 2.24 (m, 3H), 1.97 – 1.71 (m, 2H), 1.09 (t, J = 7.4 Hz, 3H) ESI [M − H] = 365.2 |

TABLE 32-continued

| Compound No | Structure | HNMR and Ms |
|---|---|---|
| 356 | 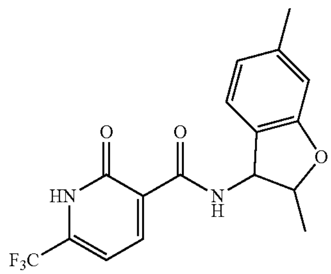 [SMILES: Cc1ccc2c(c1)OC(C)C2NC(=O)c1ccc(C(F)(F)F)[nH]c1=O] | $^1$H NMR (400 MHz, CHLOROFORM-d) δ = 9.66 – 9.43 (m, 1H), 8.74 – 8.63 (m, 1H), 7.23 – 7.15 (m, 1H), 6.86 (d, J = 7.5 Hz, 1H), 6.77 – 6.71 (m, 1H), 6.68 (s, 1H), 5.73 – 5.22 (m, 1H), 4.97 – 4.61 (m, 1H), 2.35 (s, 3H), 1.53 (d, J = 6.6 Hz, 2H), 1.41 (d, J = 6.4 Hz, 1H)<br>ESI [M – H] = 351.1 |
| 357 | 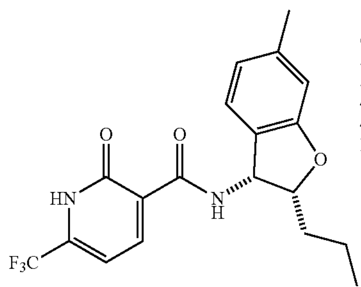 | $^1$H NMR (400 MHz, CHLOROFORM-d) δ = 9.44 (br d, J = 8.6 Hz, 1H), 8.66 (d, J = 7.5 Hz, 1H), 7.16 (d, J = 7.5 Hz, 1H), 6.85 (d, J = 7.5 Hz, 1H), 6.71 (d, J = 7.5 Hz, 1H), 6.68 (s, 1H), 5.72 (t, J = 7.9 Hz, 1H), 4.73 – 4.63 (m, 1H), 2.32 (s, 3H), 1.81 – 1.39 (m, 4H), 1.00 – 0.88 (m, 3H)<br>ESI [M – H] = 379.1 |
| 358 | 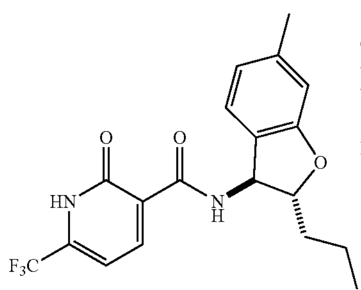 | $^1$H NMR (400 MHz, CHLOROFORM-d) δ = 9.61 (br d, J = 6.8 Hz, 1H), 8.68 (d, J = 7.3 Hz, 1H), 7.19 (d, J = 7.5 Hz, 1H), 6.86 (d, J = 7.5 Hz, 1H), 6.73 (d, J = 7.7 Hz, 1H), 6.68 (s, 1H), 5.37 (dd, J = 3.9, 6.9 Hz, 1H), 4.60 – 4.48 (m, 1H), 2.34 (s, 3H), 1.92 – 1.70 (m, 2H), 1.69 – 1.43 (m, 2H), 0.97 (t, J = 7.4 Hz, 3H)<br>ESI [M – H] = 379.1 |
| 359 | 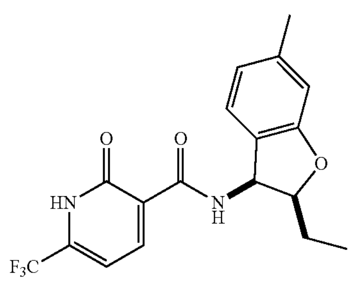 | $^1$H NMR (400 MHz, CHLOROFORM-d) δ = 9.47 (br d, J = 8.3 Hz, 1H), 8.68 (d, J = 7.4 Hz, 1H), 7.17 (d, J = 7.5 Hz, 1H), 6.85 (d, J = 7.4 Hz, 1H), 6.78 – 6.58 (m, 2H), 5.74 (t, J = 8.0 Hz, 1H), 4.76 – 4.47 (m, 1H), 2.50 – 2.23 (m, 3H), 1.87 – 1.67 (m, 2H), 1.09 (t, J = 7.4 Hz, 3H)<br>ESI [M – H] = 365.1 |
| 360 | 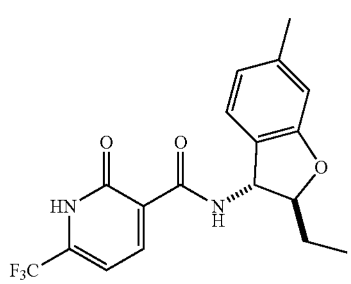 | $^1$H NMR (400 MHz, CHLOROFORM-d) δ = 13.00 – 12.40 (m, 1H), 9.58 (br s, 1H), 8.67 (d, J = 7.4 Hz, 1H), 7.19 (d, J = 7.5 Hz, 1H), 6.86 (d, J = 7.4 Hz, 1H), 6.73 (d, J = 7.6 Hz, 1H), 6.69 (s, 1H), 5.40 (dd, J = 4.1, 7.2 Hz, 1H), 4.58 – 4.38 (m, 1H), 2.34 (s, 3H), 1.86 (tq, J = 7.0, 14.2 Hz, 2H), 1.09 (t, J = 7.4 Hz, 3H)<br>ESI [M – H] = 365.1 |

TABLE 32-continued
| Compound No | Structure | HNMR and Ms |
|---|---|---|
| 363 | 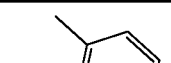 | 1H NMR (400 MHz, CHLOROFORM-d) δ = 9.90 – 9.46 (m, 1H), 8.71 – 8.67 (m, 1H), 7.17 – 7.01 (m, 2H), 6.88 (d, J = 7.5 Hz, 1H), 6.75 (d, J = 8.1 Hz, 1H), 5.72 – 5.30 (m, 1H), 4.92 – 4.65 (m, 1H), 2.29 (s, 3H), 1.55 – 1.39 (m, 3H).<br>ESI [M − H] = 351.1 |
Example 55: Synthesis of N-((2R,4R)-6-methyl-2-propyl-1,2,3,4-tetrahydroquinolin-4-yl)-2-oxo-6-(trifluoromethyl)-1,2-dihydropyridine-3-carboxamide (361) & N-((2S,4R)-6-methyl-2-propyl-1,2,3,4-tetrahydroquinolin-4-yl)-2-oxo-6-(trifluoromethyl)-1,2-dihydropyridine-3-carboxamide (362)
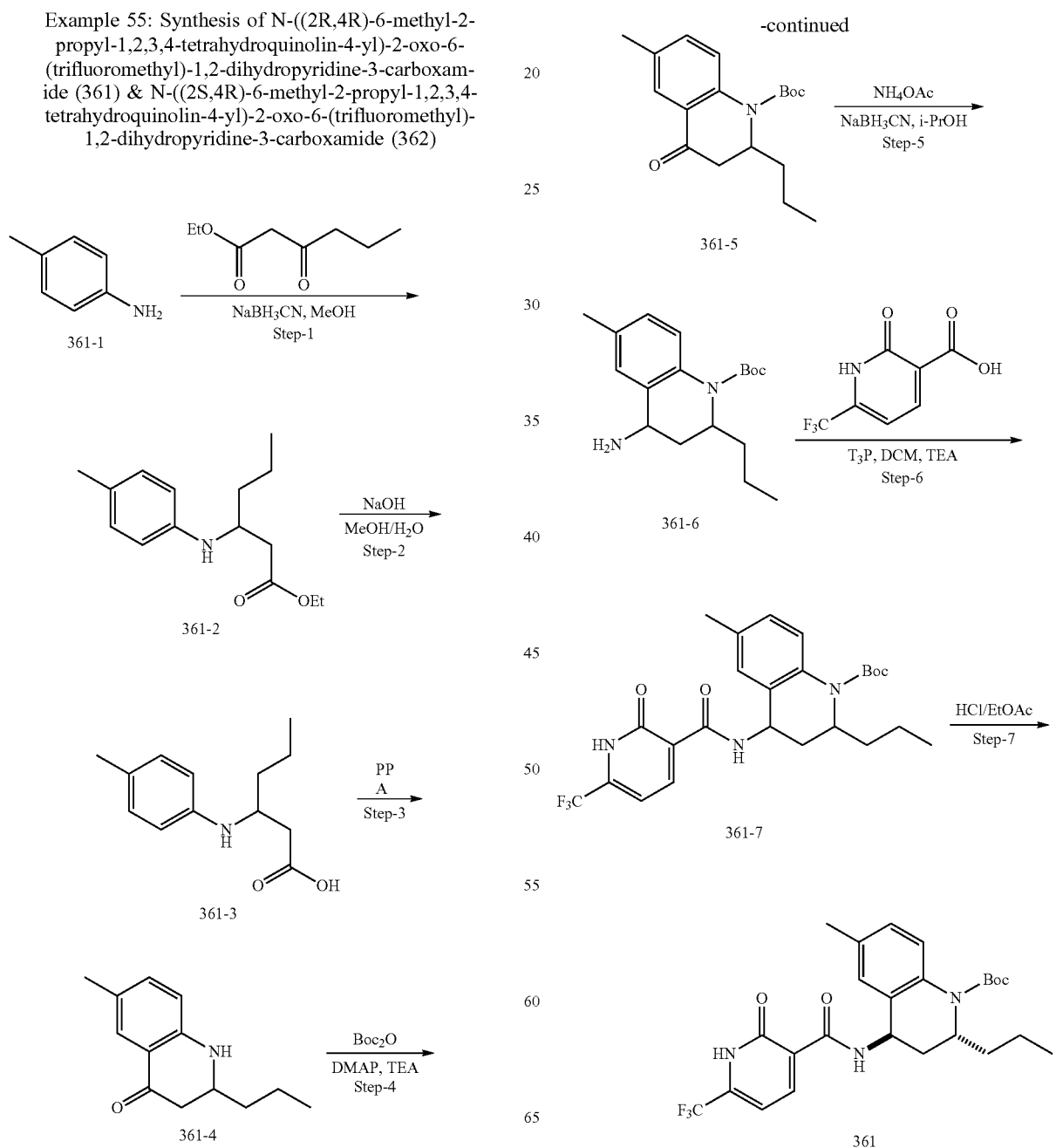

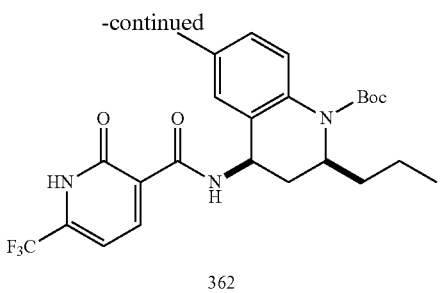

362

Step 1: ethyl 3-(p-tolylamino)hexanoate (361-2)

To a solution of Compound 361-1 (2 g, 18.6 mmol) and ethyl 3-oxohexanoate (5.91 g, 37.33 mmol, 5.91 mL, 2 eq) in MeOH (10 mL) was added HOAc (515 mg, 8.5 mmol) adjusted pH to 5-6 and stirred at 20° C. for 10 mins then NaBH$_3$CN (2.35 g, 37.3 mmol) was added. The mixture was stirred at 20° C. for 3 hrs. LCMS showed the reaction was completed and the desired mass was detected. The reaction mixture was quenched by addition H$_2$O (15 mL) at 20° C., and then extracted with EtOAc (10 mL×3). The combined organic layers were dried over Na$_2$SO$_4$, filtered and concentrated under reduced pressure to give a residue, which was purified by flash silica gel chromatography (Ethyl acetate/Petroleum ether gradient) to give Compound 361-2 (2.5 g, 53.7% yield) as a colorless gum. M+H$^+$=250.0 (LCMS)

Step 2: 3-(p-tolylamino)hexanoic acid (361-3)

To a solution of Compound 361-2 (1 g, 4.0 mmol) in MeOH (20 mL) was added NaOH (0.32 M, 25.1 mL). The mixture was stirred at 20° C. for 12 hrs. TLC showed the reaction was completed. The reaction mixture was poured into H$_2$O (5 mL) at 20° C., and then adjusted pH=7, extracted with EtOAc (10 mL×3). The combined organic layers were dried over Na$_2$SO$_4$, filtered and concentrated under reduced pressure to give a Compound 361-3 (0.7 g, crude) as a yellow gum.

Step 3: 6-methyl-2-propyl-2,3-dihydroquinolin-4 (1H)-one (361-4)

To a solution of Compound 361-3 (0.7 g, 3.1 mmol) in PPA (4 mL). The mixture was stirred at 120° C. for 20 min. TLC showed the reaction was completed. The reaction mixture was poured into H$_2$O (10 mL) at 0° C., and then adjusted pH to 7-8 and extracted with EtOAc (5 mL×5). The combined organic layers were dried over Na$_2$SO$_4$, filtered and concentrated under reduced pressure to give a residue, which was purified by flash silica gel chromatography (Ethyl acetate/Petroleum ether gradient) to give Compound 361-4 (300 mg, 46.6% yield) as a yellow solid.

Step 4: tert-butyl 6-methyl-4-oxo-2-propyl-3,4-dihydroquinoline-1(2H)-carboxylate (361-5)

To a solution of Compound 361-4 (150 mg, 737.90 µmol, 1 eq) in THF (5 mL) was added Boc$_2$O (177 mg, 811.6 µmol) and DMAP (90 mg, 737.9 µmol), followed by TEA (74 mg, 737.9 µmol,). The mixture was stirred at 60° C. for 12 hrs. TLC showed the reaction was completed. The reaction mixture was concentrated under reduced pressure to give a residue, which was purified by prep-TLC (Petroleum ether: Ethyl acetate=3:1) to give Compound 361-5 (120 mg, 54% yield) as a yellow solid.

Step 5: tert-butyl 4-amino-6-methyl-2-propyl-3,4-dihydroquinoline-1(2H)-carboxylate (361-6)

To a solution of Compound 361-5 (120 mg, 395.5 µmol) in MeOH (4 mL) was added NH$_4$OAc (457 mg, 5.9 mmol). The mixture was stirred at 20° C. for 10 min. NaBH$_3$CN (99 mg, 1.6 mmol) was added. The mixture was stirred at 90° C. for 1.5 hrs. TLC showed the reaction was completed. The reaction mixture was quenched by addition H$_2$O (5 mL) at 20° C., and then extracted with EtOAc (5 mL×5). The combined organic layers were dried over Na$_2$SO$_4$, filtered and concentrated under reduced pressure to give a Compound 361-6 (120 mg, crude) as a yellow gum.

Step 6: tert-butyl 6-methyl-4-(2-oxo-6-(trifluoromethyl)-1,2-dihydropyridine-3-carboxamido)-2-propyl-3,4-dihydroquinoline-1(2H)-carboxylate (361-7)

To a solution of 2-oxo-6-(trifluoromethyl)-1,2-dihydropyridine-3-carboxylic acid (82 mg, 394.2 µmol) in DCM (5 mL) was added HATU (149 mg, 394.1 µmol) and Compound 361-6 (120 mg, 394.1 µmol), followed by DIEA (50 mg, 394.1 µmol). The mixture was stirred at 20° C. for 2 hrs. LCMS the desired mass was detected. The reaction mixture was quenched by addition H$_2$O (5 mL) at 20° C., and then extracted with EtOAc (5 mL×3). The combined organic layers were dried over Na$_2$SO$_4$, filtered and concentrated under reduced pressure to give a residue, which was purified by Prep-TLC (Petroleum ether:Ethyl acetate=3:1) to give Compound 361-7 (90 mg, 47% yield) was obtained as a white solid. M−H$^-$=492.1 (LCMS).

Step 7: N-((2R,4R)-6-methyl-2-propyl-1,2,3,4-tetrahydroquinolin-4-yl)-2-oxo-6-(trifluoromethyl)-1,2-dihydropyridine-3-carboxamide (361) & N-((2S,4R)-6-methyl-2-propyl-1,2,3,4-tetrahydroquinolin-4-yl)-2-oxo-6-(trifluoromethyl)-1,2-dihydropyridine-3-carboxamide (362)

To a solution of Compound 361-7 (80 mg, 162.1 µmol) in EtOAc (2 mL) was added EtOAc/HCl (4 M, 4 mL) at 0° C. The mixture was stirred at 15° C. for 30 min. LCMS indicated the desired compounds were detected. The reaction mixture was concentrated under reduced pressure to give a residue, which was purified by prep-HPLC to give Compound 361 (25 mg, 38% yield) as a white solid. M−H$^-$=392.5 (LCMS); 1H NMR (400 MHz, METHANOL-d4) δ=8.57 (d, J=7.4 Hz, 1H), 7.37 (s, 1H), 7.35-7.23 (m, 1H), 7.33-7.21 (m, 1H), 7.29-7.26 (m, 2H), 7.12 (br d, J=7.4 Hz, 1H), 5.48 (br dd, J=6.1, 11.1 Hz, 1H), 3.81-3.62 (m, 1H), 2.70-2.56 (m, 1H), 2.36 (s, 3H), 2.01-1.71 (m, 3H), 1.68-1.48 (m, 2H), 1.06 (t, J=7.3 Hz, 3H) and Compound 362 (2.08 mg, 3.3% yield) as a white solid, M−H$^-$=392.5 (LCMS); 1H NMR (400 MHz, METHANOL-d4) δ=8.55 (d, J=7.4 Hz, 1H), 7.36 (s, 1H), 7.29 (br d, J=8.3 Hz, 1H), 7.23-7.16 (m, 1H), 7.09 (br d, J=7.5 Hz, 1H), 5.36 (br t, J=3.8 Hz, 1H), 3.70-3.58 (m, 1H), 2.46-2.32 (m, 4H), 2.17-2.00 (m, 1H), 1.91-1.67 (m, 2H), 1.62-1.40 (m, 2H), 1.02 (t, J=7.3 Hz, 3H).

Other compounds made in a similar manner are shown in Table 33.

TABLE 33

| Compound No | Structure | HNMR and Ms |
|---|---|---|
| 364 | 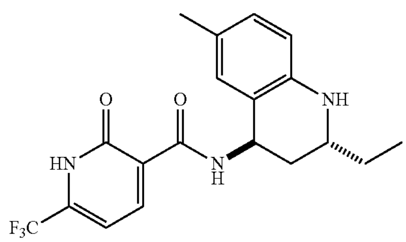 [SMILES: CC[C@@H]1C[C@@H](NC(=O)c2ccc(C(F)(F)F)[nH]c2=O)c2cc(C)ccc2N1] | ¹H NMR (400 MHz, CHLOROFORM-d) δ = 8.54 (d, J = 7.2 Hz, 1H), 7.34 (s, 1H), 7.27 (d, J = 8.4 Hz, 1H) 7.18 (d, J = 8.0 Hz, 1H), 7.08 (d, J = 7.2 Hz, 1H), 5.36 (m, 1 H), 3.55 (m, 1H), 2.43 – 2.40 (d, J = 14.4 Hz, 1H), 2.34 (s, 3H), 2.09-2.08 (m, 1H), 1.90-1.73 (m, 2H), 1.10 (t, J = 7.6 Hz, 3H)<br>ESI [M + H] = 380.1 |
| 365 | 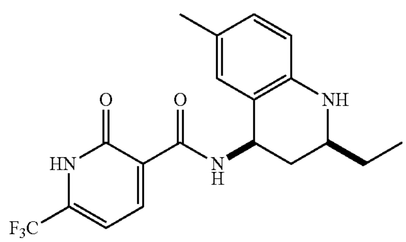 [SMILES: CC[C@H]1C[C@@H](NC(=O)c2ccc(C(F)(F)F)[nH]c2=O)c2cc(C)ccc2N1] | ¹H NMR (400 MHz, CHLOROFORM-d) δ = 8.57 (d, J = 7.6 Hz, 1H), 7.37 (s, 1H), 7.31-7.25 (m, 2H), 7.11 (d, J = 6.4 Hz, 1H), 5.49-5.45 (m, 1H), 3.69-3.66 (m, 1H), 2.68-2.63 (m, 1H), 2.36 (s, 3H), 1.97-1.81 (m, 3H), 1.15(t, J = 7.6 Hz, 3H)<br>ESI [M + H] = 380.1 |
| 366 | 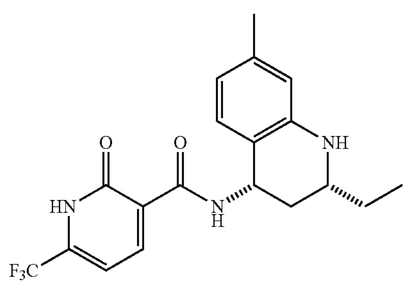 | ¹H NMR (400 MHz, METHANOL-d₄) δ = 8.57 (d, J = 7.5 Hz, 1H), 7.30 (d, J = 7.9 Hz, 1H), 7.09 (br dd, J = 7.8, 18.0 Hz, 2H), 6.96 (s, 1H), 5.43 (dd, J = 6.2, 11.2 Hz, 1H), 3.66 – 3.49 (m, 1H), 2.57 (ddd, J = 2.0, 6.0, 13.4 Hz, 1H), 2.35 (s, 3H), 1.97 – 1.63 (m, 3H), 1.12 (t, J = 7.5 Hz, 3H)<br>ESI [M + H]⁺ = 380.1 |
| 367 | 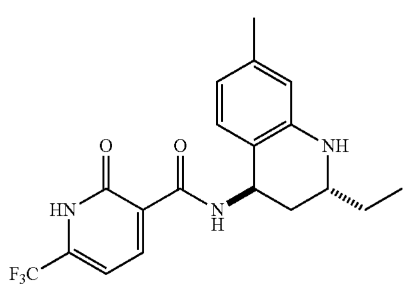 [SMILES: CC[C@@H]1C[C@@H](NC(=O)c2ccc(C(F)(F)F)[nH]c2=O)c2ccc(C)cc2N1] | ¹H NMR (400 MHz, METHANOL-d₄) δ = 8.54 (d, J = 7.3 Hz, 1H), 7.44 (d, J = 7.9 Hz, 1H), 7.26 (d, J = 7.9 Hz, 1H), 7.14 (s, 1H), 7.08 (br d, J = 7.3 Hz, 1H), 5.37 (t, J = 4.0 Hz, 1H), 3.64 – 3.52 (m, 1H), 2.44 (td, J = 2.9, 14.8 Hz, 1H), 2.40 (s, 3H), 2.11 (ddd, J = 4.9, 11.5, 14.8 Hz, 1H), 1.99 – 1.86 (m, 1H), 1.85 – 1.70 (m, 1H), 1.11 (t, J = 7.5 Hz, 3H)<br>ESI [M + H]⁺ = 380.1 |
| 368 | 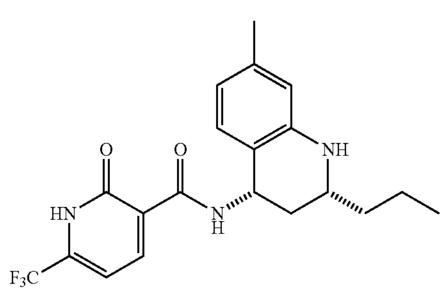 | ¹H NMR (400 MHz, METHANOL-d₄) δ = 8.53 (d, J = 7.5 Hz, 1H), 7.45 (d, J = 7.9 Hz, 1H), 7.28 (d, J = 7.9 Hz, 1H), 7.15 (s, 1H), 7.08 (br d, J = 7.5 Hz, 1H), 5.36 (t, J = 3.7 Hz, 1H), 3.73 – 3.58 (m, 1H), 2.44 (td, J = 2.7, 14.8 Hz, 1H), 2.40 (s, 3H), 2.19 – 2.03 (m, 1H), 1.92 – 1.67 (m, 2H), 1.66 – 1.40 (m, 2H), 1.02 (t, J = 7.3 Hz, 3H)<br>ESI [M + H]⁺ = 394.2 |

| Compound No | Structure | HNMR and Ms |
|---|---|---|
| 369 | 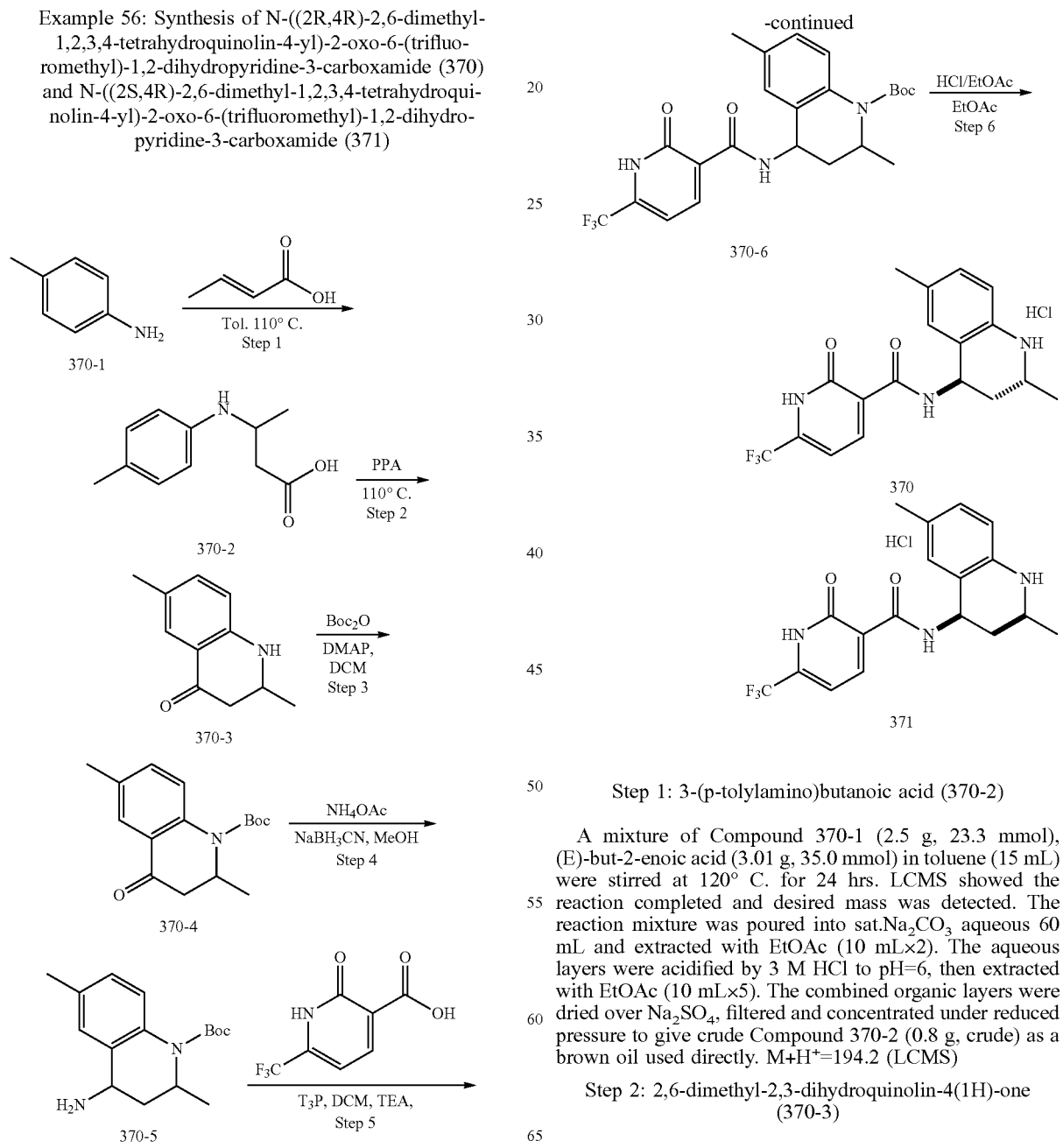 | $^1$H NMR (400 MHz, METHANOL-d$_4$) δ = 8.56 (d, J = 7.5 Hz, 1H), 7.24 (d, J = 7.9 Hz. 1H), 7.11 (br d, J = 7.1 Hz, 1H), 6.97 (br d, J = 7.7 Hz, 1H), 6.88 (s, 1H), 5.41 (dd, J = 5.8, 11.1 Hz, 1H), 3.61 (td, J = 5.8, 11.4 Hz, 1H), 2.57 – 2.45 (m, 1H), 2.32 (s, 3H), 1.83 – 1.61 (m, 3H), 1.61 – 1.44 (m, 2H), 1.03 (1, J = 7.3 Hz, 3H).<br>ESI [M + H]$^+$ = 394.2 |

Example 56: Synthesis of N-((2R,4R)-2,6-dimethyl-1,2,3,4-tetrahydroquinolin-4-yl)-2-oxo-6-(trifluoromethyl)-1,2-dihydropyridine-3-carboxamide (370) and N-((2S,4R)-2,6-dimethyl-1,2,3,4-tetrahydroquinolin-4-yl)-2-oxo-6-(trifluoromethyl)-1,2-dihydropyridine-3-carboxamide (371)

Step 1: 3-(p-tolylamino)butanoic acid (370-2)

A mixture of Compound 370-1 (2.5 g, 23.3 mmol), (E)-but-2-enoic acid (3.01 g, 35.0 mmol) in toluene (15 mL) were stirred at 120° C. for 24 hrs. LCMS showed the reaction completed and desired mass was detected. The reaction mixture was poured into sat.Na$_2$CO$_3$ aqueous 60 mL and extracted with EtOAc (10 mL×2). The aqueous layers were acidified by 3 M HCl to pH=6, then extracted with EtOAc (10 mL×5). The combined organic layers were dried over Na$_2$SO$_4$, filtered and concentrated under reduced pressure to give crude Compound 370-2 (0.8 g, crude) as a brown oil used directly. M+H$^+$=194.2 (LCMS)

Step 2: 2,6-dimethyl-2,3-dihydroquinolin-4(1H)-one (370-3)

A mixture of Compound 370-2 (0.8 g, 4.1 mmol) in PPA (8 mL) was stirred at 110° C. for 1 hr. LCMS showed the reaction was complete and desired mass was detected. The reaction mixture was quenched by pouring into ice water (30 mL) and then basified to pH=7 by using sat.Na$_2$CO$_3$ aqueous, then extracted with EtOAc (10 mL×3). The combined organic layers were dried over Na$_2$SO$_4$, filtered and concentrated under reduced pressure to give Compound 370-3 (0.6 g, crude) as a brown gum. M+H$^+$=176.1 (LCMS)

Step 3: tert-butyl 2,6-dimethyl-4-oxo-3,4-dihydroquinoline-1(2H)-carboxylate (370-4)

To a solution of 2 Compound 370-3 (0.6 g, 3.4 mmol) in DCM (10 mL) was added Boc$_2$O (747 mg, 3.4 mmol) and DMAP (418 mg, 3.4 mmol). The mixture was stirred at 20° C. for 12 hrs. LCMS showed the starting material was remained and desired mass was detected. The mixture was stirred at 20° C. for 12 hrs. LCMS showed desired mass was detected. The reaction mixture was quenched by pouring into water (15 mL) and extracted with EtOAc (5 mL×2). The combined organic layers were dried over Na$_2$SO$_4$, filtered and concentrated under reduced pressure to give a residue, which was purified by column chromatography to give Compound 370-4 (0.2 g, 726.4 μmol) as yellow oil.

Step 4: tert-butyl 4-amino-2,6-dimethyl-3,4-dihydroquinoline-1(2H)-carboxylate (370-5)

To a solution of Compound 370-4 (120 mg, 436 μmol) in MeOH (2 mL) was added NH$_4$OAc (504 mg, 6.5 mmol), the mixture was stirred at 15° C. for 10 min, then NaBH$_3$CN (110 mg, 1.7 mmol) was added. The mixture was stirred at 80° C. for 1 hr under microwave. TLC showed the reaction was completed. The reaction mixture was quenched by pouring into water (15 mL) and extracted with DCM (5 mL×2). The combined organic layers were washed with brine (5 mL×2), dried over Na$_2$SO$_4$, filtered and concentrated under reduced pressure to give Compound 370-5 (0.11 g, crude) as a white solid, which was used directly.

Step 5: tert-butyl 2,6-dimethyl-4-(2-oxo-6-(trifluoromethyl)-1,2-dihydropyridine-3-carboxamido)-3,4-dihydroquinoline-1(2H)-carboxylate (370-6)

To a solution of Compound 370-5 (110 mg, 398 μmol) and 2-oxo-6-(trifluoromethyl)-1, 2-dihydropyridine-3-carboxylic acid (83 mg, 398 μmol) in DCM (10 mL) was added TEA (121 mg, 1.2 mmol) and T$_3$P (380 mg, 597 μmol, 50% purity). The mixture was stirred at 15° C. for 1 hr. TLC showed the reaction was completed. The reaction mixture was quenched by pouring into water (15 mL) and extracted with DCM (5 mL×2). The combined organic layers were washed with brine (5 mL×2), dried over Na$_2$SO$_4$, filtered and concentrated under reduced pressure to give a residue. The residue was treated with MeOH (3 mL) and 3M NaOH (1 mL), and stirred at 15° C. for 2 hrs. Then the mixture was diluted with H$_2$O (5 mL) and extracted with DCM (5 mL×3). The combined organic layers dried over Na$_2$SO$_4$ and concentrated under reduced pressure to give a residue, which was purified by prep-TLC (DCM:MeOH=10:1) to give Compound 370-6 (70 mg, 150 μmol) as a yellow solid.

Step 6: N-((2R,4R)-2,6-dimethyl-1,2,3,4-tetrahydroquinolin-4-yl)-2-oxo-6-(trifluoromethyl)-1,2-dihydropyridine-3-carboxamide (370) and N-((2S,4R)-2,6-dimethyl-1,2,3,4-tetrahydroquinolin-4-yl)-2-oxo-6-(trifluoromethyl)-1,2-dihydropyridine-3-carboxamide (371)

To a solution of Compound 370-6 (70 mg, 150) in EtOAc (1 mL) was added HCl/EtOAc (4 M, 35.00 mL). The mixture was stirred at 15° C. for 1 hr. LCMS showed the reaction was completed and desired mass was detected. The reaction mixture was concentrated under reduced pressure to give a residue, which was purified by Prep-HPLC to give Compound 370 (50 mg, 121 μmol, 80% yield, HCl salt) as a yellow gum. M−H$^-$=364.2 (LCMS); $^1$H NMR (400 MHz, METHANOL-d4) δ=8.57 (d, J=7.5 Hz, 1H), 7.39 (s, 1H), 7.33-7.29 (m, 1H), 7.27-7.23 (m, 1H), 7.12 (br d, J=7.3 Hz, 1H), 5.50 (dd, J=6.2, 11.1 Hz, 1H), 3.94-3.77 (m, 1H), 2.57 (ddd, J=2.0, 6.2, 13.9 Hz, 1H), 2.37 (s, 3H), 2.10-1.95 (m, 1H), 1.56 (d, J=6.5 Hz, 3H); Compound 371 (9 mg, 21 μmol, 14% yield) as a yellow solid. M−H$^-$=364.2 (LCMS); $^1$H NMR (400 MHz, METHANOL-d$_4$) δ=8.55 (d, J=7.5 Hz, 1H), 7.38 (s, 1H), 7.31 (br d, J=8.2 Hz, 1H), 7.20 (d, J=8.3 Hz, 1H), 7.09 (br d, J=7.3 Hz, 1H), 5.43-5.32 (m, 1H), 3.79 (ddd, J=2.2, 6.5, 11.4 Hz, 1H), 2.43-2.32 (m, 4H), 2.24-2.09 (m, 1H), 1.50 (d, J=6.5 Hz, 3H).

Example 57: Synthesis of N-(2-ethyl-7-methyl-3-oxo-1,2,3,4-tetrahydroisoquinolin-4-yl)-2-oxo-6-(trifluoromethyl)-1,2-dihydropyridine-3-carboxamide (373)

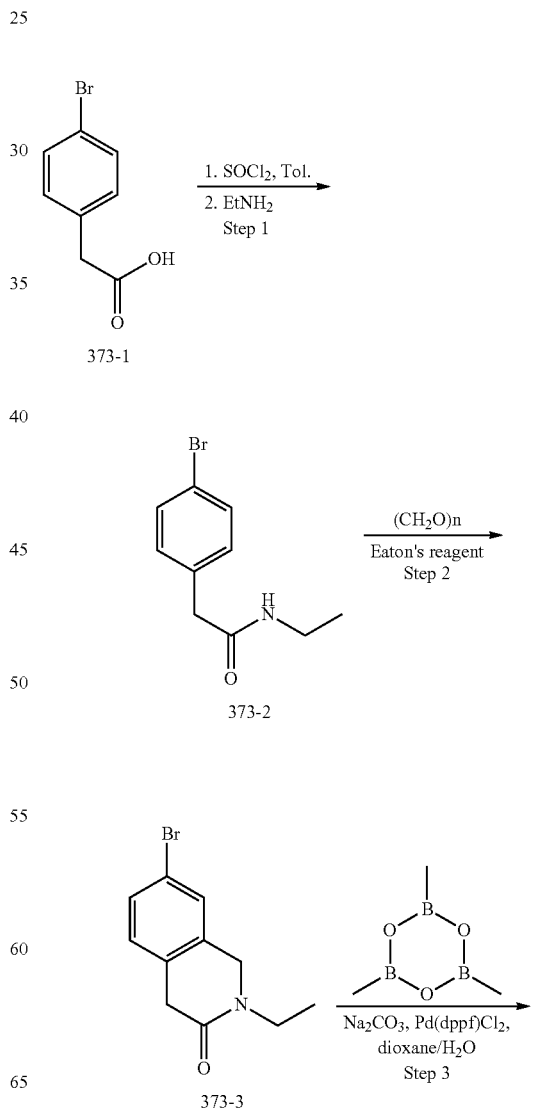

-continued

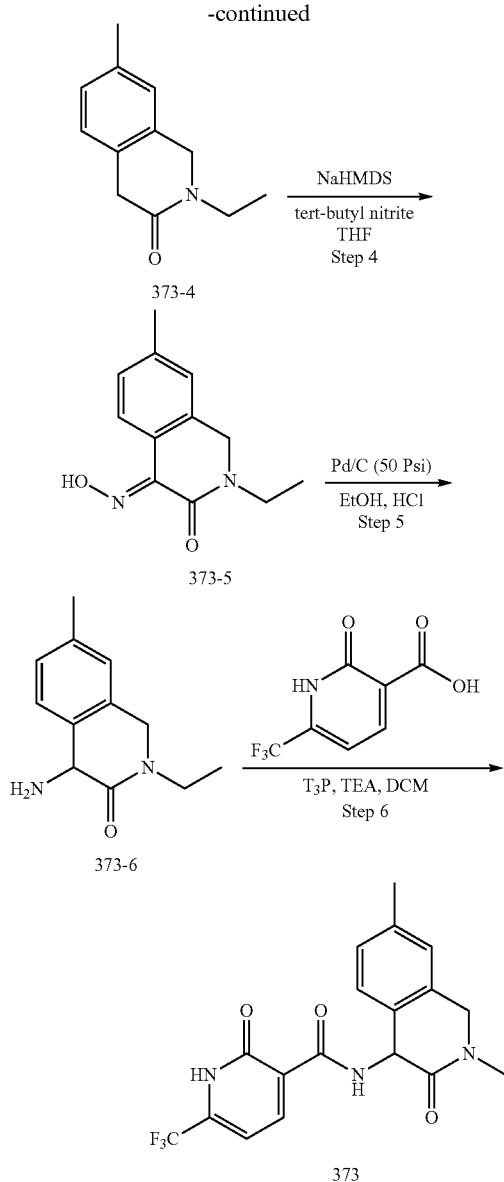

Step 1: 2-(4-bromophenyl)-N-ethylacetamide (373-2)

To a solution of Compound 373-1 (3 g, 14 mmol) in toluene (10 mL) was added DMF (1.2 g, 16 mmol) and SOCl$_2$ (2 g, 16.7 mmol). The mixture was stirred at 40° C. for 30 mins. The resulting acid chloride solution was concentrated in vacuum to give a residue, which was treated with toluene (10 mL). The resulting mixture was added to a vigorously stirred ethanamine (10.5 g, 69.8 mmol, THF solution) at 0° C. The mixture was stirred at 25° C. for 1 hr. LCMS showed the reaction was completed and desired mass was detected. The reaction was quenched with water (50 mL) and extracted with ethyl acetate (3×30 mL). The combined organic layers were washed with saturated NaHCO$_3$ (20 mL×2), brine (20 mL×2), and dried over sodium sulfate filtered and concentrated in vacuum to give Compound 373-2 (2 g, crude) as white solid. M+H$^+$=243.9 (LCMS).

Step 2: 7-bromo-2-ethyl-1,2-dihydroisoquinolin-3 (4H)-one (373-3)

To a solution of Compound 373-2 (1 g, 4.1 mmol) in Eaton's reagent (4 mL) was added paraformaldehyde (132 mg, 5 mmol). The mixture was stirred at 80° C. for 3 hrs. LCMS showed the reaction was completed and desired mass was detected. The reaction mixture was poured into water (10 mL) and basified with 50% NaOH aqueous to pH=8. The resulting solution was extracted with EtOAc (3×10 mL) and the organic layers were dried over Na$_2$SO$_4$, filtered, and concentrated to give a Compound 373-3 (1 g, crude) as yellow oil. M+H$^+$=254.9 (LCMS).

Step 3: 2-ethyl-7-methyl-1,2-dihydroisoquinolin-3 (4H)-one (373-4)

A solution of Compound 373-3 (1 g, 3.9 mmol), 2,4,6-trimethyl-1,3,5,2,4,6-trioxatriborinane (2 g, 7.9 mmol), Na$_2$CO$_3$ (1 g, 9.8 mmol), Pd(dppf)Cl$_2$ (167 mg, 204.1 μmol) in dioxane (15 mL) and H$_2$O (3 mL) was degassed and purged with N$_2$ for 3 times, and then the mixture was stirred at 80° C. for 24 hrs. LCMS showed the reaction was completed and desired mass was detected. The reaction mixture was added to H$_2$O (30 mL), and then extracted with EtOAc (10 mL×4). The combined organic layers were dried over Na$_2$SO$_4$, filtered and concentrated under reduced pressure to give a residue. The residue was purified by flash silica gel chromatography to give Compound 373-4 (400 mg, crude) as brown oil. M+H$^+$=190.1 (LCMS).

Step 4: (E)-2-ethyl-4-(hydroxyimino)-7-methyl-1,2-dihydroisoquinolin-3(4H)-one (373-5)

To a solution of Compound 373-4 (300 mg, 1.6 mmol) in THF (4 mL) was added NaHMDS (1 M, 1.9 mL) at −78° C. drop wise. The mixture was stirred at same temperature for 20 mins, tert-butyl nitrite (654 mg, 6.3 mmol) was added at −78° C. The mixture was stirred at −78° C. for 1 hr. TLC indicated the reaction was completed. The reaction mixture was added to H$_2$O (10 mL) and extracted with EtOAc (5 mL×3). The combined organic layers were washed with brine (5 mL×2), dried over Na$_2$SO$_4$, filtered and concentrated under reduced pressure to give a residue. The residue was purified by flash silica gel chromatography to give Compound 373-5 (180 mg, 60% yield) as white solid. $^1$H NMR (400 MHz, CDCl$_3$) δ=15.85 (s, 1H), 7.98-7.90 (m, 1H), 7.16 (dd, J=0.9, 8.3 Hz, 1H), 6.97 (s, 1H), 4.61 (s, 2H), 3.62 (q, J=7.2 Hz, 2H), 2.37 (s, 2H), 1.36-1.23 (m, 3H)

Step 5: 4-amino-2-ethyl-7-methyl-1,2-dihydroisoquinolin-3(4H)-one (373-6)

To a stirred solution of Compound 373-5 (150 mg, 687.3 μmol) in EtOH (10 mL) was added Pd/C (100 mg, 10% purity) and HCl (3 M, 687.3 uL). The suspension was degassed under vacuum and purged with H$_2$ for 5 times. The mixture was stirred under H$_2$ (50 Psi) at 25° C. for 1 hr. LCMS showed the reaction was completed and desired mass was detected. The reaction mixture was filtered and concentrated under reduced pressure to give Compound 373-6 (150 mg, crude, HCl) as white solid. M+H$^+$=205.1 (LCMS).

Step 6: 4-amino-2-ethyl-7-methyl-1,2-dihydroisoquinolin-3(4H)-one (373)

To a solution of Compound 373-6 (150 mg, 623.1 μmol, HCl) and 2-oxo-6-(trifluoro methyl)-1,2-dihydropyridine-3- carboxylic acid (129 mg, 623.1 μmol) in DCM (3 mL) was added TEA (315.3 mg, 3.1 mmol) and T₃P (595 mg, 934.7 μmol, 50% purity). The mixture was stirred at 15° C. for 12 hrs. LCMS showed the reaction was completed. Then the mixture was diluted with H₂O (5 mL) and extracted with DCM (3 mL×3). The combined organic layers dried over Na₂SO₄ and concentrated under reduced pressure to give a residue. The residue was treated with MeOH (2 mL) and 3M NaOH aq. (2 mL) and stirred at 15° C. for 3 hrs. LCMS showed the desired mass was detected. The mixture was diluted with H₂O (5 mL) and extracted with EtOAc (3 mL×3). The combined organic layers dried over Na₂SO₄ and concentrated under reduced pressure to give a residue. The residue was purified by prep-HPLC to give Compound 373 (38 mg, 95.2 μmol, 15% yield) as a white solid. M−H⁻ =392.1 (LCMS); ¹H NMR (400 MHz, DMSO-d₆) δ=13.88-13.43 (m, 1H), 10.43-9.54 (m, 1H), 8.48 (br d, J=7.3 Hz, 1H), 7.34-7.20 (m, 1H), 7.17 (s, 1H), 7.13-7.08 (m, 1H), 7.05-6.99 (m, 1H), 5.55 (br d, J=7.2 Hz, 1H), 4.82-4.62 (m, 1H), 4.38 (d, J=15.6 Hz, 1H), 3.55-3.39 (m, 2H), 2.31 (s, 3H), 1.08 (t, J=7.1 Hz, 3H).

Other compounds made in a similar manner are shown in Table 34.

TABLE 34

| Compound No | Structure | HNMR and Ms |
|---|---|---|
| 374 | 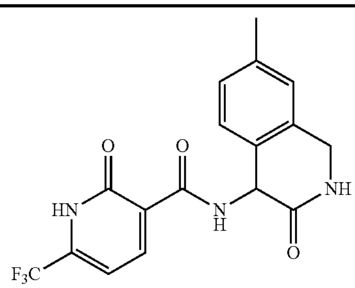 | ¹H NMR (400 MHz, DMSO-d6) δ = 8.41 (br s, 2H), 7.18 – 6.99 (m, 4H), 5.54 (brd, J = 7.7 Hz, 1H), 4.48 (brd, J = 15.9 Hz, 1H), 4.20 (dd, J = 5.2, 15.7 Hz, 1H), 2.29 (s, 3H) ESI [M − H] = 364.1 |
| 375 | 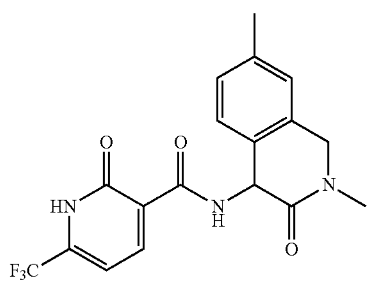 | ¹H NMR (400 MHz, DMSO-d₆) δ = 12.57 − 12.31 (m, 1H), 8.07 (br d, J = 7.3 Hz, 1H), 7.18 − 6.99 (m, 3H), 6.46 (d, J = 7.5 Hz, 1H), 5.56 (br d, J = 7.8 Hz, 1H), 4.68 (br d, J = 15.4 Hz, 1H), 4.36 (br d, J = 15.8 Hz, 1H), 3.00 (s, 3H), 2.30 (s, 3H) ESI [M − H] = 378.1 |

Example 58: Synthesis of N-(1,5-dimethyl-1H-indol-3-yl)-2-oxo-6-(trifluoromethyl)-1,2-dihydropyridine-3-carboxamide (376)

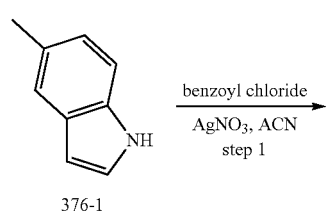

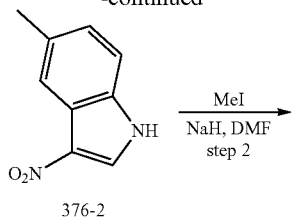

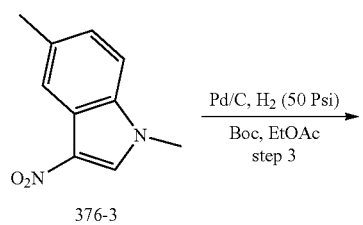

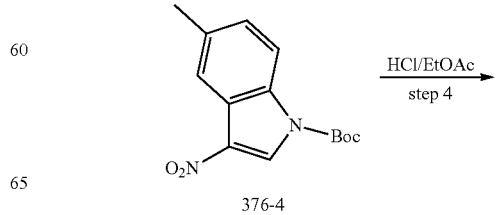

-continued

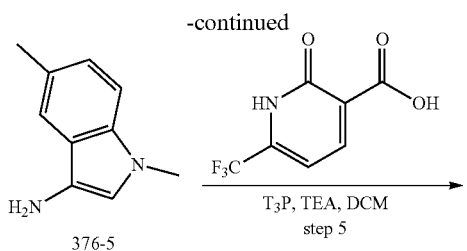

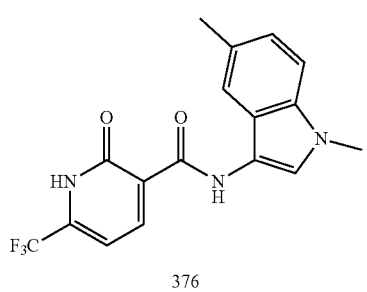

376

Step 1: 5-methyl-3-nitro-1H-indole (376-2)

To a solution of Compound 376-1 (1 g, 7.6 mmol) in ACN (20 mL) was added AgNO₃ (1.4 g, 8 mmol), the mixture was stirred at 0° C. under N₂, then benzoyl chloride (1.1 g, 8 mmol) was added to the solution. The mixture was stirred at 0° C. for 5 hrs. TLC indicated the reaction completed. The reaction mixture was filtered and the filtrate was added to H₂O (20 mL) and extracted with EtOAc (15 ml×3). The combined organic layers were dried over Na₂SO₄, filtered and concentrated in vacuum to give Compound 376-2 (300 mg, crude) as a red solid. ¹H NMR (400 MHz, DMSO-d₆) δ=12.54 (br s, 1H), 8.58 (d, J=3.5 Hz, 1H), 7.89 (s, 1H), 7.45 (d, J=8.3 Hz, 1H), 7.16 (dd, J=1.3, 8.3 Hz, 1H), 2.45 (s, 3H).

Step 2: 1,5-dimethyl-3-nitro-1H-indole (376-3)

To a solution of Compound 376-2 (300 mg, 1.7 mmol) in DMF (15 mL) was added NaH (88 mg, 2.2 mmol, 60% purity). The mixture was stirred at 0° C. for 30 mins, and then MeI (362 mg, 3 mmol) was added to the solution, the mixture was stirred at 25° C. for 2 hrs. TLC indicated the reaction was completed. The reaction mixture was added to H₂O (10 mL) and stirred. Most solid appeared and the mixture was filtered. The cake was dried in vacuum to give Compound 376-3 (300 mg, crude) as a red solid. ¹H NMR (400 MHz, DMSO-d₆) δ=8.65 (s, 1H), 7.90 (s, 1H), 7.56 (d, J=8.6 Hz, 1H), 7.23 (d, J=8.4 Hz, 1H), 3.89 (s, 3H), 2.46 (s, 3H).

Step 3: tert-butyl 5-methyl-3-nitro-1H-indole-1-carboxylate (376-4)

To a solution of Compound 376-3 (150 mg, 788 μmol) in MeOH (5 mL) was added Pd/C (200 mg, 10% purity) and Boc₂O (516 mg, 2.4 mmol). The suspension was degassed and purged with H₂ for 3 times. The mixture was stirred under H₂ (15 Psi) at 50° C. for 5 hrs. TLC indicated the reaction was completed. The reaction mixture was filtered and concentrated in vacuum to give Compound 376-4 (300 mg, crude) as a white solid. M+H⁺=261.2 (LCMS)

Step 4: 1,5-dimethyl-1H-indol-3-amine (376-5)

To a solution of Compound 376-4 (300 mg, 1.2 mmol) in EtOAc (1 mL) was added HCl/EtOAc (4 M, 2 mL), then the mixture was stirred at 15° C. for 1 hr. TLC indicated the reaction was completed. The reaction mixture was concentrated in vacuum to give Compound 376-5 (300 mg, HCl salt) as a white solid.

Step 5: N-(1,5-dimethyl-1H-indol-3-yl)-2-oxo-6-(trifluoromethyl)-1,2-dihydropyridine-3-carboxamide (376)

To a solution of Compound 376-5 (110 mg, 559 μmol, HCl) in DCM (10 mL) was added 2-oxo-6-(trifluoromethyl)-1,2-dihydropyridine-3-carboxylic acid (116 mg, 559 μmol), EDCI (160 mg, 839 μmol), HOBt (113 mg, 839 μmol) and DIEA (217 mg, 1.7 mmol), then the mixture was stirred at 15° C. for 2 hrs. LCMS showed the reaction was completed and desired mass was detected. The reaction mixture was added to H₂O (10 mL) and extracted with DCM (15 ml×3). The combined organic layers were dried over Na₂SO₄, filtered and concentrated under reduced pressure to give a residue, which was Purified by prep-HPLC to give Compound 376 (2 mg, 6 μmol, 1% yield) as a yellow solid. M−H⁻=348.1 (LCMS); ¹H NMR (400 MHz, DMSO-d6) δ=12.48-11.42 (m, 1H), 8.43 (d, J=7.5 Hz, 1H), 7.86 (s, 1H), 7.37-7.31 (m, 2H), 7.16 (br s, 1H), 7.05 (d, J=8.6 Hz, 1H), 3.76 (s, 3H), 2.42 (s, 3H).

Other compounds made in a similar manner are shown in Table 35.

TABLE 35

| Compound No | Structure | HNMR and Ms |
|---|---|---|
| 377 | ![structure] | ¹H NMR (400 MHz, DMSO-d₆) δ = 14.56 (s, 1H), 10.59 (brs, 1H), 8.13 (d, J = 7.3 Hz, 1H), 7.81 (d, J = 2.2 Hz, 1H), 7.36 (s, 1H), 7.24 (d, J = 8.2 Hz, 1H), 6.94 (d, J = 8.4 Hz, 1H), 6.54 (d, J = 7.3 Hz, 1H), 6.07 (brs, 1H), 2.43 (s, 3H) ESI [M − H] = 334.1 |

TABLE 35-continued

| Compound No | Structure | HNMR and Ms |
|---|---|---|
| 378 | 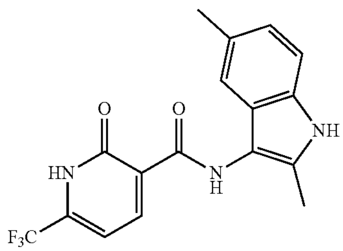 [SMILES: Cc1ccc2[nH]c(C)c(NC(=O)c3ccc(C(F)(F)F)[nH]c3=O)c2c1] | $^1$H NMR (400 MHz, DMSO-d$_6$) δ = 13.56 (br s, 1H), 10.84 (s, 1H), 8.45 (d, J = 2.5 Hz, 1H), 7.22 (br s, 1H), 7.16 (d, J = 8.2 Hz, 1H), 7.11 (s, 1H), 6.85 (d, J = 8.4 Hz, 1H), 2.34 (s, 3H), 2.28 (s, 3H) ESI [M − H] = 348.1 |
| 379 | 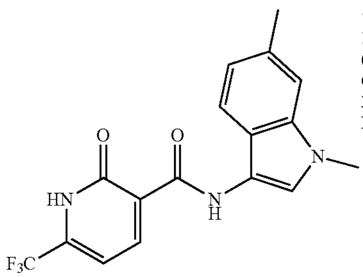 | $^1$H NMR (400 MHz, DMSO-d$_6$) δ = 13.73 (br s, 1H), 11.52 (brs, 1H), 8.48-8.46 (d, J = 7.2Hz, 1H), 7.83 (s, 1H), 7.48-7.45 (d, J = 8.1 Hz, 1H), 7.25(s, 2H), 6.96-6.94 (d, J = 8.2 Hz, 1H), 3.76 (s, 3H), 2.44(s, 3H) ESI [M − H] = 348.1 |

Example 59: Synthesis of N-(6-methylbenzofuran-3-yl)-2-oxo-6-(trifluoromethyl)-1,2-dihydropyridine-3-carboxamide (380)

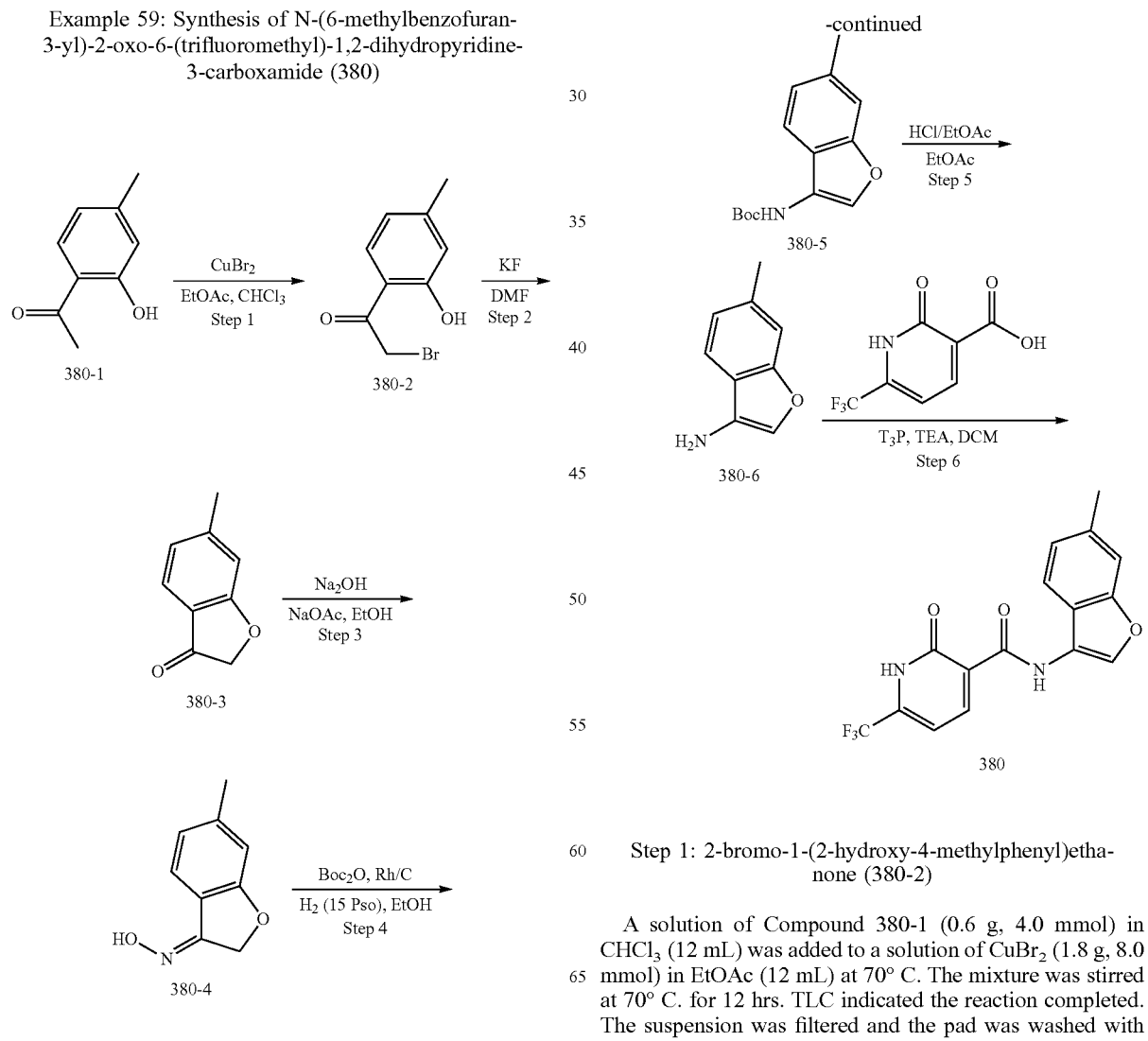

Step 1: 2-bromo-1-(2-hydroxy-4-methylphenyl)ethanone (380-2)

A solution of Compound 380-1 (0.6 g, 4.0 mmol) in CHCl$_3$ (12 mL) was added to a solution of CuBr$_2$ (1.8 g, 8.0 mmol) in EtOAc (12 mL) at 70° C. The mixture was stirred at 70° C. for 12 hrs. TLC indicated the reaction completed. The suspension was filtered and the pad was washed with EtOAc (5 mL×2). The combined filtrates were concentrated to dryness to give Compound 380-2 (0.7 g, crude) as a yellow solid.

Step 2: 6-methylbenzofuran-3(2H)-one (380-3)

To a solution of Compound 380-2 (700 mg, 3.1 mmol) in DMF (10 mL) was added KF (302 mg, 5.2 mmol). The mixture was stirred at 20° C. for 30 min. TLC indicated the reaction completed. The reaction mixture was quenched by pouring into water (30 mL) and extracted with EtOAc (10 mL×3). The combined organic layers were washed with brine (10 mL×3), dried over $Na_2SO_4$, filtered and concentrated under reduced pressure to give a residue. The residue was purified by column chromatography to give Compound 380-3 (0.4 g, 2.7 mmol, 88% yield) as a white solid. $^1$H NMR (400 MHz, CHLOROFORM-d) δ=7.56 (d, J=7.9 Hz, 1H), 6.97-6.89 (m, 2H), 4.62 (s, 2H), 2.45 (s, 3H).

Step 3: (E)-6-methylbenzofuran-3(2H)-one oxime (380-4)

To a solution of Compound 380-3 (0.2 g, 1.4 mmol) in EtOH (5 mL) was added $NH_2OH.HCl$ (375 mg, 5.4 mmol) and NaOAc (664 mg, 8.1 mmol). The mixture was stirred at 80° C. for 3 hrs. TLC indicated the reaction completed. The reaction mixture was quenched by pouring into water (15 mL) and extracted with EtOAc (5 mL×3). The combined organic layers were washed with brine (5 mL×3), dried over $Na_2SO_4$, filtered and concentrated under reduced pressure to give Compound 380-4 (0.2 g, crude) as a white solid.

Step 4: tert-butyl (6-methylbenzofuran-3-yl)carbamate (380-5)

To a solution of Compound 380-4 (200 mg, 1.2 mmol) and $Boc_2O$ (803 mg, 3.7 mmol) in EtOH (15 mL) was added Rh/C (7.2 g, 3.1 mmol, 5% purity). The mixture was stirred at 15° C. for 3 hrs under $H_2$ (15 Psi). TLC showed 18% Compound 380-4 was remained and 30% desired product was detected. The suspension was filtered through a pad of Celite and the pad was washed with EtOH (5 mL×3). The combined filtrates were concentrated to dryness to give a residue, which was purified by column chromatography to give Compound 380-5 (0.15 g, 50% yield) as a white solid.

Step 5: 6-methylbenzofuran-3-amine (380-6)

To a solution of Compound 380-5 (0.15 g, 606.6 μmol) in EtOAc (1 mL) was added HCl/EtOAc (4 M, 6 mL). The mixture was stirred at 15° C. for 1 hr. TLC indicated the reaction completed. The reaction mixture was concentrated under reduced pressure to give Compound 380-6 (0.1 g, crude, HCl salt) as a yellow solid.

Step 6: N-(6-methylbenzofuran-3-yl)-2-oxo-6-(trifluoromethyl)-1,2-dihydropyridine-3-carboxamide (380)

To a stirred solution of Compound 380-6 (50 mg, 272.3 μmol, HCl) and 2-oxo-6-(trifluoromethyl)-1,2-dihydropyridine-3-carboxylic acid (56 mg, 272.3 μmol) in DCM (5 mL) was added TEA (138 mg, 1.4 mmol) and $T_3P$ (260 mg, 408.4 μmol, 50% purity). The mixture was stirred at 15° C. for 1 hr. LCMS showed the reaction was complete and desired mass was detected. The reaction mixture was quenched by pouring into water (10 mL) and extracted with DCM (3 mL×2). The combined organic layers were dried over $Na_2SO_4$, filtered and concentrated under reduced pressure to give a residue. The residue was treated with MeOH (3 mL) and 3M NaOH aq. (1 mL) and stirred at 15° C. for 2 hrs. Then the mixture was diluted with $H_2O$ (5 mL) and extracted with DCM (5 mL×3). The combined organic layers were dried over $Na_2SO_4$ and concentrated under reduced pressure to give a residue, which was purified by prep-HPLC to give Compound 380 (2 mg, 6.9 μmol, 3% yield) as a yellow solid. M−H$^-$=335.1 (LCMS); $^1$H NMR (400 MHz, DMSO-d$_6$) δ=8.40 (s, 1H), 8.30 (d, J=7.5 Hz, 1H), 7.56 (d, J=7.9 Hz, 1H), 7.41 (s, 1H), 7.20-6.96 (m, 3H), 2.45 (s, 3H).

Example 60: Synthesis of N-(7-methyl-2-propylthiochroman-4-yl)-2-oxo-6-(trifluoromethyl)-1,2-dihydropyridine-3-carboxamide (381)

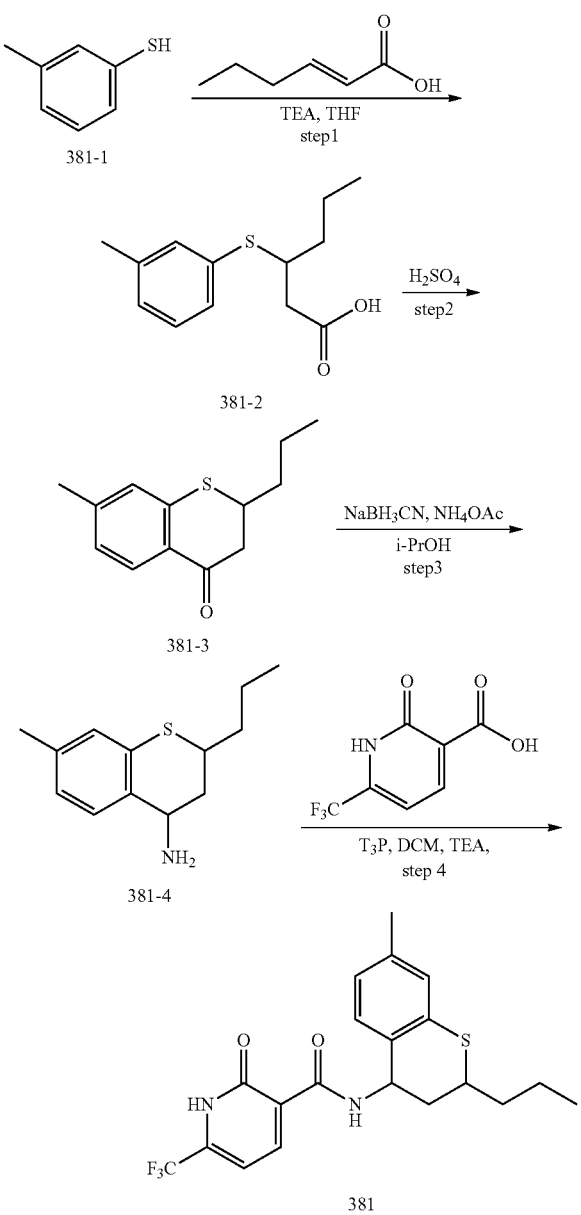

Step 1: 3-(m-tolylthio)hexanoic acid (381-2)

To a solution of Compound 381-1 (1.0 g, 8.0 mmol), TEA (896 mg, 8.8 mmol) in THF (10 mL) was added 3-(m-tolylthio)hexanoic acid (919 mg, 8.0 mmol) at 0° C. The mixture was stirred at 25° C. for 12 hrs. LCMS showed the reaction was completed and desired mass was detected. The reaction mixture was poured into H$_2$O (20 mL) and washed with EtOAc (10 mL×2). The aqueous layers were acidified by 1M HCl to pH=5 and extracted with EtOAc (10 mL×3). The combined organic layers were dried over Na$_2$SO$_4$, filtered and concentrated under reduced pressure to give Compound 381-2 (300 mg, 1.3 mmol) as yellow oil. M−H$^-$=237.0 (LCMS).

Step 2: 7-methyl-2-propylthiochroman-4-one (381-3)

Compound 381-2 (260 mg, 1.1 mmol) was added to H$_2$SO$_4$ (1 mL) at 0° C. The mixture was stirred at 25° C. for 40 mins. TLC indicated the reaction was completed. The reaction mixture was poured into H$_2$O (10 mL) and extracted with EtOAc (10 mL×4). The combined organic layers were washed with brine (5 mL×3), dried over Na$_2$SO$_4$, filtered and concentrated under reduced pressure to give a residue, which was purified by prep-TLC to give Compound 381-3 (50 mg, 226.9 μmol) as a pale yellow solid.

Step 3: 7-methyl-2-propylthiochroman-4-amine (381-4)

To a stirred solution of Compound 381-3 (45 mg, 204.1 μmol) in MeOH (2 mL) was added NH$_4$OAc (236 mg, 3.1 mmol) was added and stirred for 10 mins at 25° C. NaBH$_3$CN (51 mg, 817.2 μmol) was added and the reaction was stirred at 90° C. for 1 hr under microwave. LCMS showed the reaction was completed and desired mass was detected. The reaction mixture was poured into H$_2$O (10 mL) and extracted with EtOAc (10 mL×4). The combined organic layers were washed with brine (5 mL×3), dried over Na$_2$SO$_4$, filtered and concentrated under reduced pressure to give Compound 381-4 (40 mg, crude) as a yellow solid. Fragment Ms=205.1 (LCMS).

Step 4: N-(7-methyl-2-propylthiochroman-4-yl)-2-oxo-6-(trifluoromethyl)-1,2-dihydropyridine-3-carboxamide (381)

To a solution of 2-oxo-6-(trifluoromethyl)-1, 2-dihydropyridine-3-carboxylic acid (45 mg, 216.2 μmol), Compound 381-4 (40 mg, 180.7 μmol) in DCM (6 mL) was added TEA (55 mg, 542.1 μmol) and T$_3$P (230 mg, 361.4 μmol, 50% purity). The mixture was stirred at 25° C. for 1 hr. The mixture was poured into H$_2$O (5 mL) and extracted with DCM (5 mL×3). The combined organic layers dried over Na$_2$SO$_4$ and concentrated under reduced pressure to give a residue. The residue was treated with MeOH (3 mL) and NaOH (2 mL, 3M) and stirred at 20° C. for 5 hrs. LCMS showed the reaction was completed and desired mass was detected. Then the mixture was poured into H$_2$O (5 mL) and adjusted pH to 5~6, extracted with DCM (5 mL×3). The combined organic layers dried over Na$_2$SO$_4$ and concentrated under reduced pressure to give a residue, which was purified by Prep-TLC to give Compound 381 (6 mg, 14.9 μmol, 8% yield, a mixture of diastereoisomers) as a gray solid. M−H$^-$=409.2 (LCMS); $^1$H NMR (400 MHz, CHLOROFORM-d) δ=9.73-9.44 (m, 1H), 8.78-8.59 (m, 1H), 7.22-7.11 (m, 1H), 7.02-6.94 (m, 1H), 6.92-6.80 (m, 2H), 5.57-5.19 (m, 1H), 3.51-3.33 (m, 1H), 2.63-2.47 (m, 1H), 2.36-2.21 (m, 3H), 2.00-1.77 (m, 1H), 1.76-1.59 (m, 2H), 1.58-1.39 (m, 2H), 1.01-0.88 (m, 3H).

Other compounds made in a similar manner are shown in Table 36.

TABLE 36

| Compound No | Structure | HNMR and Ms |
|---|---|---|
| 382 | 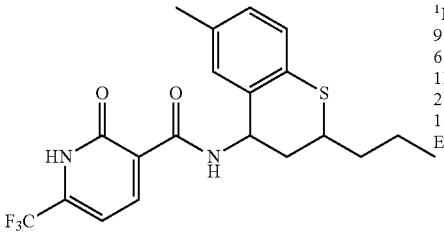 | $^1$H NMR (400 MHz, CHLOROFORM-d) δ = 9.80 – 9.42 (m, 1H), 8.69 (br s, 1H), 7.10 – 7.01 (m, 2H), 7.00 – 6.92 (m, 1H), 6.90 – 6.83 (m, 1H), 5.51 – 5.25 (m, 1H), 3.60 – 3.22 (m, 1H), 2.58 – 2.44 (m, 1H), 2.27 – 2.18 (m, 3H), 1.97 – 1.78 (m, 1H), 1.72 – 1.59 (m, 2H), 1.56 – 1.40 (m, 2H), 0.93 (q, J = 7.5 Hz, 3H) ESI [M − H] = 409.1 |
| 383 | 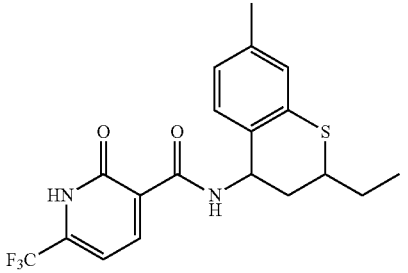 [SMILES: CCC1CC(NC(=O)c2ccc(C(F)(F)F)[nH]c2=O)c2ccc(C)cc2S1] | $^1$H NMR (400 MHz, CHLOROFORM-d) δ = 13.06 (br s, 1H), 9.76 – 9.50 (m, 1H), 8.83 – 8.63 (m, 1H), 7.21 – 7.12 (m, 1H), 7.01 – 6.94 (m, 1H), 6.93 – 6.80 (m, 2H), 5.51 – 5.29 (m, 1H), 3.54 – 3.22 (m, 1H), 2.62 – 2.47 (m, 1H), 2.27 (s, 3H), 1.97-1.61 (m, 3H), 1.09 – 1.01 (m, 3H). ESI [M − H] = 395.1 |

TABLE 36-continued

| Compound No | Structure | HNMR and Ms |
|---|---|---|
| 384 | 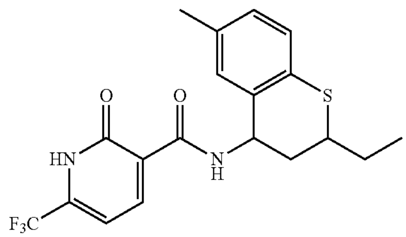 [SMILES: CCC1CC(NC(=O)c2ccc(C(F)(F)F)[nH]c2=O)c2cc(C)ccc2S1] | $^1$H NMR (400 MHz, CHLOROFORM-d) δ = 9.73 – 9.53 (m, 1H), 8.72 (dd, J = 7.4, 13.8 Hz, 1H), 7.09 – 7.02 (m, 2H), 7.00 – 6.92 (m, 1H), 6.87 (dd, J = 7.3, 12.1 Hz, 1H), 5.46 – 5.34 (m, 1H), 3.48 – 3.21 (m, 1H), 2.57 – 2.45 (m, 1H), 2.22 (d, J = 5.1 Hz, 3H), 1.95 – 1.61 (m, 3H), 1.03 (1, J = 7.4 Hz, 3H). ESI [M − H] = 395.1 |
| 385 | 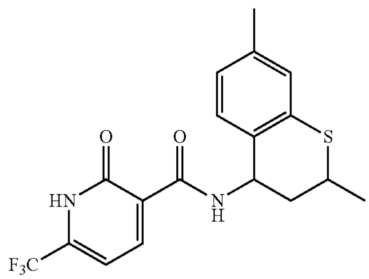 [SMILES: Cc1ccc2c(c1)SC(C)CC2NC(=O)c1ccc(C(F)(F)F)[nH]c1=O] | $^1$H NMR (400 MHz, CHLOROFORM-d) δ = 12.19 (br s, 1H), 9.68 – 9.42 (m, 1H), 8.69 (dd, J = 7.5, 12.2 Hz, 1H), 7.21 – 7.15 (m, 1H), 6.96 (d, J = 7.7 Hz, 1H), 6.91 – 6.81 (m, 2H), 5.50 – 5.35 (m, 1H), 3.66 – 3.38 (m, 1H), 2.61 – 2.47 (m, 1H), 2.27 (d, J = 3.8 Hz, 3H), 1.99 – 1.78 (m, 1H), 1.38 (1, J = 6.1 Hz, 3H). ESI [M − H] = 381.1 |
| 386 | 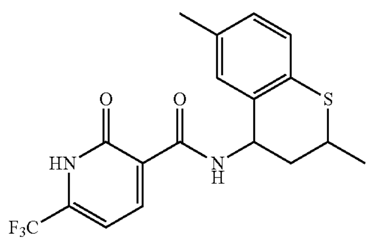 [SMILES: Cc1ccc2c(c1)C(NC(=O)c1ccc(C(F)(F)F)[nH]c1=O)CC(C)S2] | $^1$H NMR (400 MHz, CHLOROFORM-d) δ = 13.42 (br s, 1H), 9.85 – 9.49 (m, 1H), 8.91 – 8.60 (m, 1H), 7.14 – 6.80 (m, 4H), 5.66 – 5.26 (m, 1H), 3.65 – 3.43 (m, 1H), 2.60 – 2.42 (m, 1H), 2.23 (br d, J = 7.5 Hz, 3H), 1.98 – 1.73 (m, 1H), 1.37 (br t, J = 5.7 Hz, 3H). ESI [M − H] = 381.0 |

Example 61: Synthesis of N-(6-methyl-3-propyl-1,2,3,4-tetrahydronaphthalen-1-yl)-2-oxo-6-(trifluoromethyl)-1,2-dihydropyridine-3-carboxamide (387)

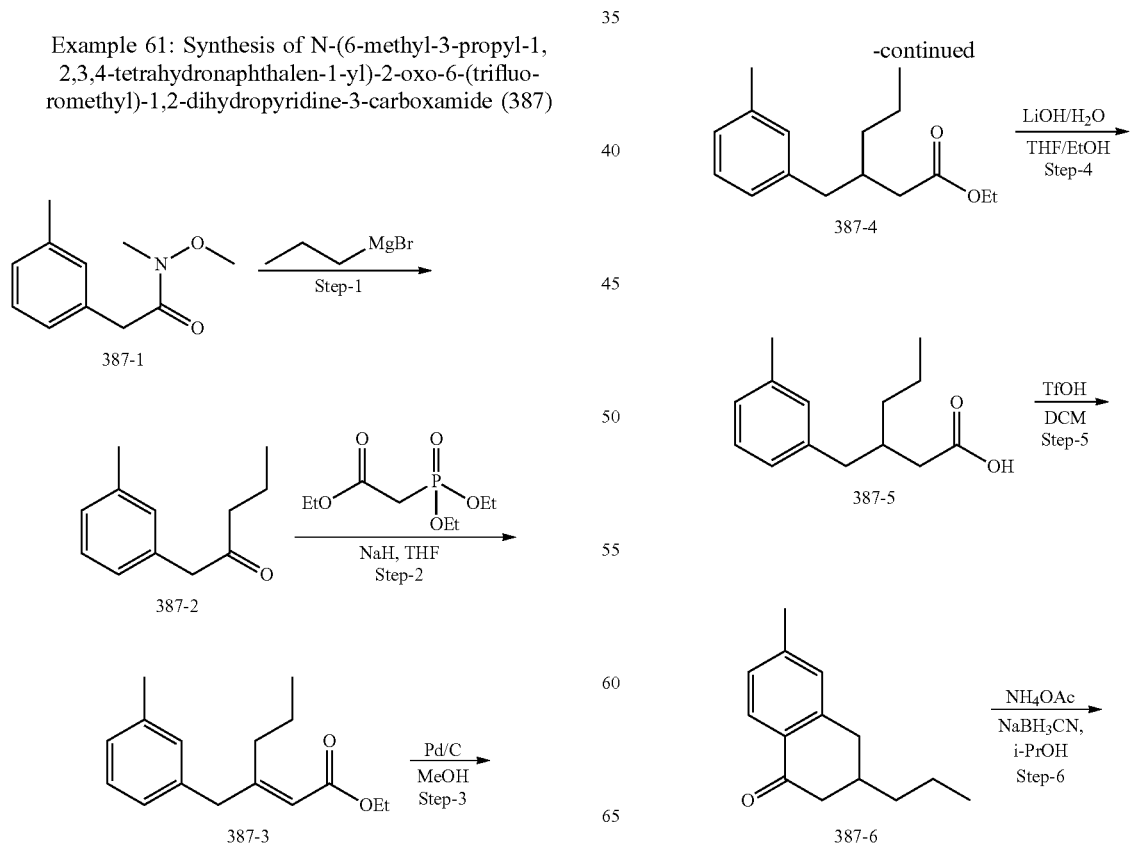

-continued

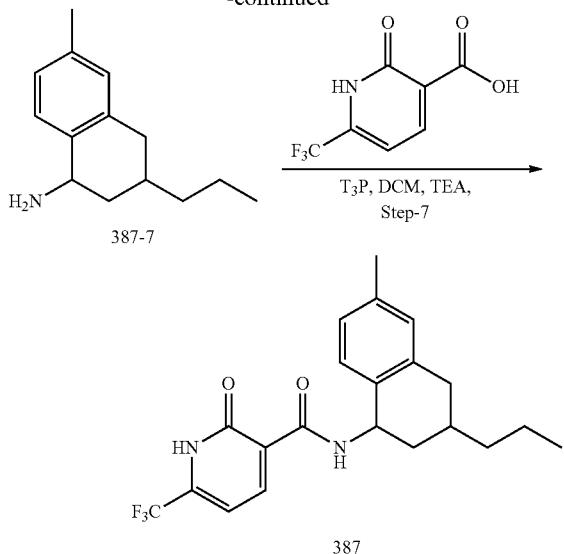

Step 1: 1-(m-tolyl)pentan-2-one (387-2)

To a solution of Compound 387-1 (2 g, 10.4 mmol) in THF (16 mL) was added propylmagnesium bromide (2 M, 12.9 mL) at −78° C. The mixture was stirred at −78° C. for 3 hrs. LCMS showed the reaction was completed and the desired mass was detected. The reaction mixture was poured into ice-water (25 mL) at 20° C., then extracted with EtOAc (50 mL×5). The combined organic layers were dried over Na2SO4, filtered and concentrated under reduced pressure to give a residue, which was purified by flash silica gel chromatography (Ethyl acetate/Petroleum ether gradient) to give Compound 387-2 (1.3 g, 71% yield) as a colorless gum. M+H$^+$=177.3 (LCMS).

Step 2: (E)-ethyl 3-(3-methylbenzyl)hex-2-enoate (387-3)

To a mixture of NaH (170 mg, 4.3 mmol, 60% purity) in THF (5 mL) was added ethyl 2-(diethoxyphosphoryl)acetate (763 mg, 3.4 mmol) and stirred at 0° C. for 15 mins, then a solution of Compound 387-2 (0.5 g, 2.84 mmol) in THF (2 mL) was added to the mixture slowly. The resulting mixture was stirred at 20° C. for 12 hrs. LCMS showed the reaction was completed and the desired mass was detected. The reaction mixture was poured into ice-water (5 mL) and extracted with EtOAc (5 mL×5). The combined organic layers were dried over Na$_2$SO$_4$, filtered and concentrated under reduced pressure to give a residue, which was purified by flash silica gel chromatography (Ethyl acetate/Petroleum ether gradient) to give Compound 387-3 (400 mg, 57% yield) as a colorless gum. M+H$^+$=247.3 (LCMS).

Step 3: ethyl 3-(3-methylbenzyl)hexanoate (387-4)

To a solution of Compound 387-3 (400 mg, 1.6 mmol) in MeOH (5 mL) was added Pd/C (20 mg, 10% purity). The mixture was stirred at 25° C. for 0.5 hr under H$_2$ (15 Psi). LCMS showed the reaction was completed and the desired mass was detected. The reaction mixture was filtered and concentrated under reduced pressure to give a residue, which was triturated by MeOH (5 mL) to give Compound 387-4 (320 mg, 79% yield) as a colorless gum. M+H$^+$=249.1 (LCMS).

Step 4: 3-(3-methylbenzyl)hexanoic acid (387-5)

To a solution of Compound 387-4 (150 mg, 604.0 µmol) in THF (2 mL) and EtOH (2 mL) was added LiOH (2 M, 1.51 mL, aq). The resulting mixture was stirred at 50° C. for 2.5 hrs. LCMS showed the reaction was completed and the desired mass was detected. The reaction mixture was poured into H$_2$O (5 mL), then adjusted pH 5-6 and extracted with EtOAc (5 mL×5). The combined organic layers were dried over Na$_2$SO$_4$, filtered and concentrated under reduced pressure to give Compound 387-5 (130 mg, 98% yield) as a colorless gum. M−H$^+$=219.0 (LCMS).

Step 5: 6-methyl-3-propyl-3,4-dihydronaphthalen-1(2H)-one (387-6)

To a solution of Compound 387-5 (130 mg, 590.1 µmol) in DCM (4 mL) was added slowly TfOH (1.4 g, 9.4 mmol) at 0° C. under N$_2$. Then the mixture was stirred at 0° C. for 0.5 hr. LCMS showed the reaction was completed and the desired mass was detected. The reaction mixture was poured into H$_2$O (5 mL) and extracted with EtOAc (5 mL×5). The combined organic layers were dried over Na$_2$SO$_4$, filtered and concentrated under reduced pressure to give Compound 387-6 (70 mg, 59% yield) as a yellow gum. M+H$^+$=203.2 (LCMS).

Step 6: 6-methyl-3-propyl-1,2,3,4-tetrahydronaphthalen-1-amine (387-7)

To a solution of Compound 387-6 (35 mg, 173.0 µmol) in i-PrOH (2 mL) was added NH$_4$OAc (400 mg, 5.2 mmol) and NaBH$_3$CN (76 mg, 1.2 mmol). The mixture was stirred at 120° C. for 1 hr. LCMS showed the reaction was completed and the desired mass was detected. The reaction mixture was poured into H$_2$O (3 mL), then extracted with EtOAc (5 mL×3). The combined organic layers were dried over Na$_2$SO$_4$, filtered and concentrated under reduced pressure to give Compound 387-7 (30 mg, 85% yield) as a colorless gum. Fragment Ms=187.1 (LCMS).

Step 7: N-(6-methyl-3-propyl-1,2,3,4-tetrahydronaphthalen-1-yl)-2-oxo-6-(trifluoromethyl)-1,2-dihydropyridine-3-carboxamide (387)

A mixture of Compound 387-7 (30 mg, 147.5 µmol), 2-oxo-6-(trifluoromethyl)-1,2-dihydropyridine-3-carboxylic acid (31 mg, 147.5 µmol), TEA (45 mg, 442.6 µmol), T$_3$P (188 mg, 295.1 µmol, 50% purity) in DCM (3 mL) was stirred at 20° C. for 2 hrs. LCMS showed the reaction was completed and desired mass was detected. The reaction mixture was poured into H$_2$O (5 mL) and extracted with EtOAc (5 mL×3). The combined organic layers were dried over Na$_2$SO$_4$, filtered and concentrated under reduced pressure to give a residue, which was purified by prep-TLC (Petroleum ether:Ethyl acetate=3:1) to give Compound 387 (6 mg, 10% yield) as a white solid. It was a mixture of diastereoisomers. M−H$^-$=391.2 (LCMS); 1H NMR (400 MHz, CHLOROFORM-d) δ=12.47-12.29 (br, 1H), 9.54-9.37 (m, 1H), 8.77-8.60 (m, 1H), 7.21-7.14 (m, 1H), 6.98-6.92 (m, 2H), 6.86-6.83 (m, 1H), 5.42-5.33 (m, 1H), 2.93-2.86 (m, 1H), 2.41-2.13 (m, 5H), 1.95-1.84 (m, 1H), 1.61-1.37 (m, 6H), 0.95-0.89 (m, 3H).

Other compounds made in a similar manner are shown in Table 37.

TABLE 37

| Compound No | Structure | HNMR and Ms |
| --- | --- | --- |
| 388 | 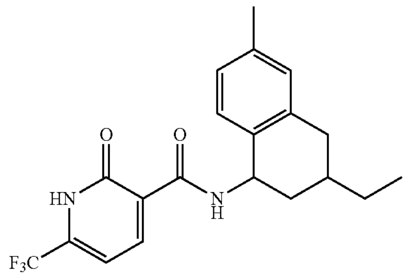 [SMILES: CCC1Cc2cc(C)ccc2C(NC(=O)c2ccc(C(F)(F)F)[nH]c2=O)C1] | 1H NMR (400 MHz, CHLOROFORM-d) δ = 9.63 – 9.44 (m, 1H), 8.77 – 8.64 (m, 1H), 7.19 (t, J = 7.3 Hz, 1H), 6.95 (brd, J = 10.3 Hz, 2H), 6.86 (dd, J = 7.8, 9.7 Hz, 1H), 5.49 – 5.27 (m, 1H), 2.89 – 2.79 (m, 1H), 2.41 – 2.09 (m, 5H), 1.88 – 1.72 (m, 1H), 1.69 – 1.30 (m, 4H), 0.99 – 0.94 (m, 3H)<br>ESI [M – H] = 377.2 |
| 389 | 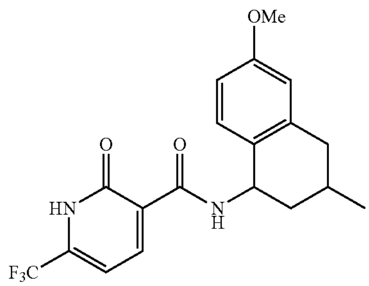 [SMILES: COc1ccc2c(c1)CC(C)CC2NC(=O)c1ccc(C(F)(F)F)[nH]c1=O] | 1H NMR (400 MHz, CHLOROFORM-d) δ = 9.50 – 9.44 (m, 1H), 8.71 – 8.67 (m, 1H), 7.24 – 7.22 (m, 1H), 6.89 – 6.84 (m, 1H), 6.72 – 6.71 (m, 1H), 6.65 – 6.63 (m, 1H), 5.42 – 5.34 (m, 1H), 3.78 (s, 1H), 2.89 – 2.84 (m, 1H), 2.43 – 1.80 (m, 3H), 1.65 – 1.32 (m, 1H), 1.10 – 1.08 (m, 3H)<br>ESI [M – H] = 379.1 |
| 390 | 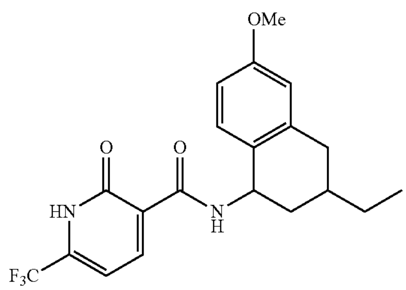 [SMILES: CCC1Cc2cc(OC)ccc2C(NC(=O)c2ccc(C(F)(F)F)[nH]c2=O)C1] | $^1$H NMR (400 MHz, CHLOROFORM-d) δ = 9.48 (br d, J = 8.6 Hz, 1H), 8.86 – 8.48 (m, 1H), 7.25 – 7.19 (m, 1H), 6.91 – 6.82 (m, 1H), 6.75 – 6.69 (m, 1H), 6.68 – 6.62 (m, 1H), 5.44 – 5.28 (m, 1H), 3.82 – 3.76 (m, 3H), 2.98 – 2.77 (m, 1H), 2.56 – 2.33 (m, 2H), 1.82 (br dd, J = 4.6, 11.5 Hz, 1H), 1.50 – 1.38 (m, 2H), 1.37 – 1.20 (m, 1H), 1.03 – 0.94 (m, 3H)<br>ESI [M – H] = 393.2 |
| 391 | 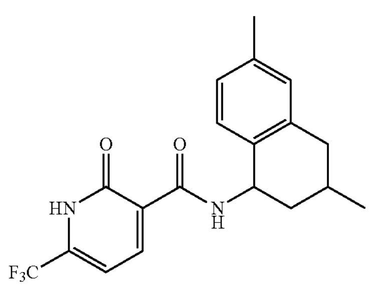 [SMILES: Cc1ccc2c(c1)CC(C)CC2NC(=O)c1ccc(C(F)(F)F)[nH]c1=O] | $^1$H NMR (400 MHz, CHLOROFORM-d) δ = 9.48 (br s, 1H), 8.69 (br t, J = 6.0 Hz, 1H), 7.20 (d, J = 7.7 Hz, 1H), 6.99 – 6.91 (m, 2H), 6.86 (dd, J = 7.5, 10.5 Hz, 1H), 5.47 – 5.28 (m, 1H), 2.93 – 2.70 (m, 1H), 2.53 – 2.32 (m, 1H), 2.30 (d, J = 1.7 Hz, 3H), 2.17 – 1.93 (m, 2H), 1.66 – 1.24 (m, 2H), 1.09 (dd, J = 2.3, 6.5 Hz, 3H).<br>ESI [M – H] = 363.1 |
| 392 | 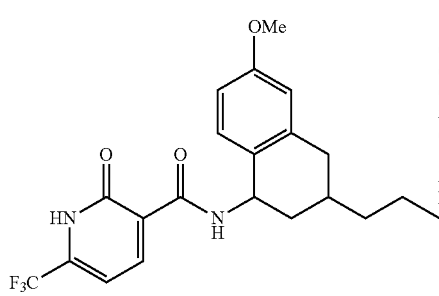 [SMILES: CCCC1Cc2cc(OC)ccc2C(NC(=O)c2ccc(C(F)(F)F)[nH]c2=O)C1] | $^1$H NMR (400 MHz, CHLOROFORM-d) δ = 12.74 (br s, 1H), 9.50 (br s, 1H), 8.92 – 8.55 (m, 1H), 7.21 (t, J = 8.2 Hz, 1H), 6.87 (dd, J = 7.5, 10.4 Hz, 1H), 6.76 – 6.69 (m, 1H), 6.65 (dd, J = 2.2, 6.0 Hz, 1H), 5.48 – 5.20 (m, 1H), 3.88 – 3.69 (m, 3H), 2.96 – 2.81 (m, 1H), 2.55 – 2.04 (m, 2H), 1.90 (br s, 1H), 1.70 – 1.52 (m, 1H), 1.48 – 1.24 (m, 4H), 1.03 – 0.78 (m, 3H)<br>ESI [M – H] = 407.2 |

Example 62: Synthesis of N-(5-methyl-2,3-dihydrobenzo[b]thiophen-3-yl)-2-oxo-6-(trifluoromethyl)-1,2-dihydropyridine-3-carboxamide (393)

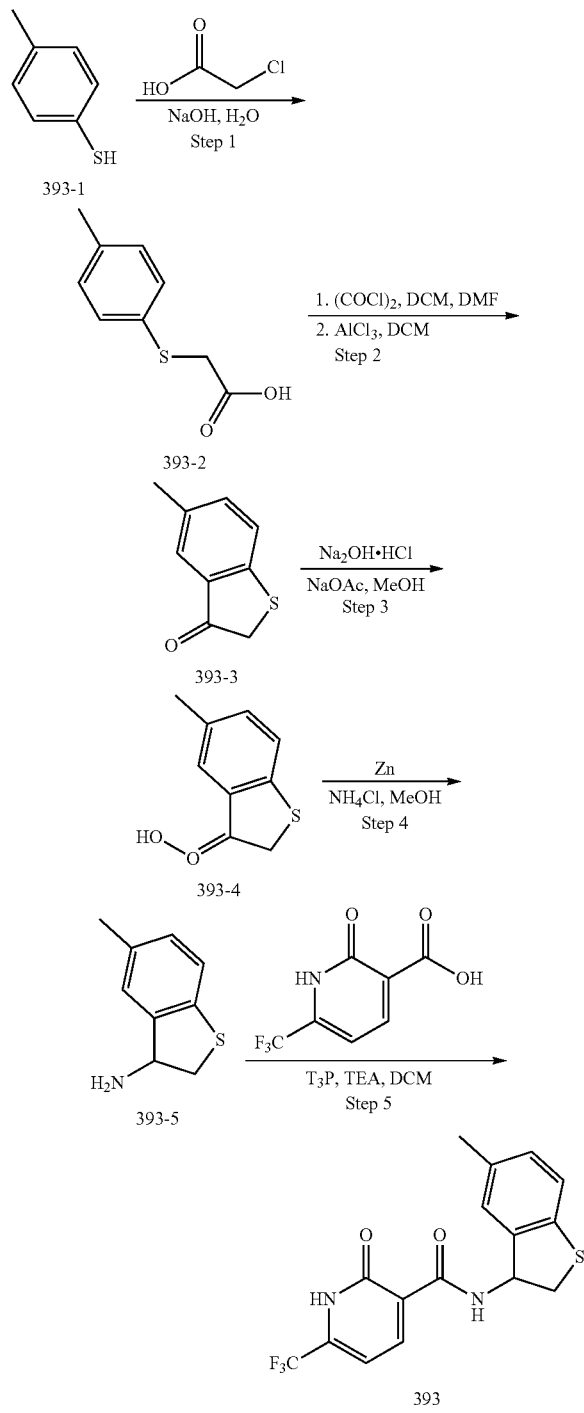

Step 1: 2-(p-tolylthio)acetic acid (393-2)

To a solution of NaOH (3.2 g, 80.5 mmol) in H$_2$O (16 mL) was added Compound 393-1 (1 g, 8.1 mmol). A solution of 2-chloroacetic acid (913 mg, 9.7 mmol) in H$_2$O (2 mL) was added dropwise to the reaction mixture. After stirring for 30 min at 25° C., the reaction mixture was stirred at 100° C. for 1.5 hrs. LCMS showed the reaction was completed and one main peak with desired mass was detected. The reaction mixture was poured into H$_2$O (10 mL) then was acidified to pH=1 using 1 M HCl, the precipitate was filtered and to give Compound 393-2 (1.4 g, 7.5 mmol, 93% yield) as a white solid. M+H$^+$=183.0 (LCMS), $^1$H NMR (400 MHz, CHLOROFORM-d) δ=7.35 (d, J=7.9 Hz, 2H), 7.13 (d, J=7.9 Hz, 2H), 3.63 (s, 2H), 2.34 (s, 3H).

Step 2: 5-methylbenzo[b]thiophen-3(2H)-one (393-3)

To a stirred solution of Compound 393-2 (600 mg, 3.3 mmol) in DCM (15 mL) was added (COCl)$_2$ (627 mg, 4.9 mmol) at 0° C., followed by a drop of DMF (24 mg, 329 μmol). The mixture was stirred at 25° C. for 1 hr. The mixture was concentrated in vacuum to give a residue, which was diluted with DCM (15 mL) and was added AlCl$_3$ (702 mg, 5.3 mmol) at 0° C. The resulting mixture was stirred at 25° C. for 2 hrs. LCMS showed the reaction was completed and one main peak with desired mass was detected. The reaction mixture was poured into H$_2$O (20 mL) at 0° C., and then extracted with DCM (10 mL×5). The combined organic layers were dried over Na$_2$SO$_4$, filtered and concentrated under reduced pressure to give a residue, which was purified by silica gel chromatography (Ethyl acetate/Petroleum) to give Compound 393-3 (380 mg, 2.3 mmol, 70% yield) as a pink solid. M+H$^+$=165.0 (LCMS), $^1$H NMR (400 MHz, CHLOROFORM-d) δ=7.60 (s, 1H), 7.42-7.36 (m, 1H), 7.35-7.30 (m, 1H), 3.80 (s, 2H), 2.38 (s, 3H).

Step 3: 5-methylbenzo[b]thiophen-3(2H)-one (393-4)

To a stirred solution of Compound 393-3 (270 mg, 1.6 mmol) in MeOH (10 mL) was added NH$_2$OH.HCl (606 mg, 8.7 mmol) and NaOAc (836 mg, 10.2 mmol) at 25° C. The reaction mixture was stirred at 70° C. for 3 hrs. TLC showed the reaction was completed. The reaction mixture was cooled to room temperature and diluted with water (10 mL) and solid was appeared and filtered, the solid was washed with water and dried in vacuum to give Compound 393-4 (250 mg, 1.4 mmol, 85% yield) as a yellow solid. $^1$H NMR (400 MHz, CHLOROFORM-d) δ=7.56 (br s, 1H), 7.49 (s, 1H), 7.20-7.13 (m, 2H), 4.20 (s, 2H), 2.34 (s, 3H).

Step 4: 5-methyl-2,3-dihydrobenzo[b]thiophen-3-amine (393-5)

To a stirred solution of Compound 393-4 (50 mg, 279 μmol) in dry MeOH (5 mL) was added Zn (182 mg, 2.8 mmol) and NH$_4$Cl (149 mg, 2.8 mmol). The reaction mixture was heated at 70° C. for 0.5 hr. TLC showed the reaction was completed. The reaction mixture was filtered and the filtrate was concentrated under reduced pressure to give Compound 393-5 (20 mg, crude) as a yellow solid.

Step 5: N-(5-methyl-2,3-dihydrobenzo[b]thiophen-3-yl)-2-oxo-6-(trifluoromethyl)-1,2-dihydropyridine-3-carboxamide (393)

To a stirred solution of 2-oxo-6-(trifluoromethyl)-1,2-dihydropyridine-3-carboxylic acid (25 mg, 123 μmol) and Compound 393-5 (20 mg, 123 μmol) in DCM (5 mL) was added TEA (37 mg, 367 μmol) at 25° C., followed by T$_3$P (156 mg, 245 μmol, 50% purity). The resulting mixture was stirred at 25° C. for 1 hr. LCMS showed the reaction was completed. The reaction mixture was poured into H$_2$O (5 mL) and extracted with DCM (3 mL×5). The combined organic layers were dried over Na$_2$SO$_4$, filtered and concentrated under reduced pressure to give a residue, which was purified by prep-HPLC to give Compound 393 (1.45 mg, 4 μmol, 3% yield) as a white solid. M–H$^-$=353.1 (LCMS), $^1$H NMR (400 MHz, CHLOROFORM-d) δ=9.71 (br d, J=7.9 Hz, 1H), 8.69 (d, J=7.3 Hz, 1H), 7.18-7.11 (m, 2H), 7.07 (d, J=8.1 Hz, 1H), 6.87 (d, J=7.5 Hz, 1H), 5.85-5.74 (m, 1H), 3.75 (dd, J=7.0, 11.6 Hz, 1H), 3.29 (dd, J=5.4, 11.6 Hz, 1H), 2.30 (s, 3H).

Example 63: Synthesis of N-(2,6-dimethylchroman-4-yl)-2-oxo-6-(trifluoromethyl)-1,2-dihydropyridine-3-carboxamide (394)

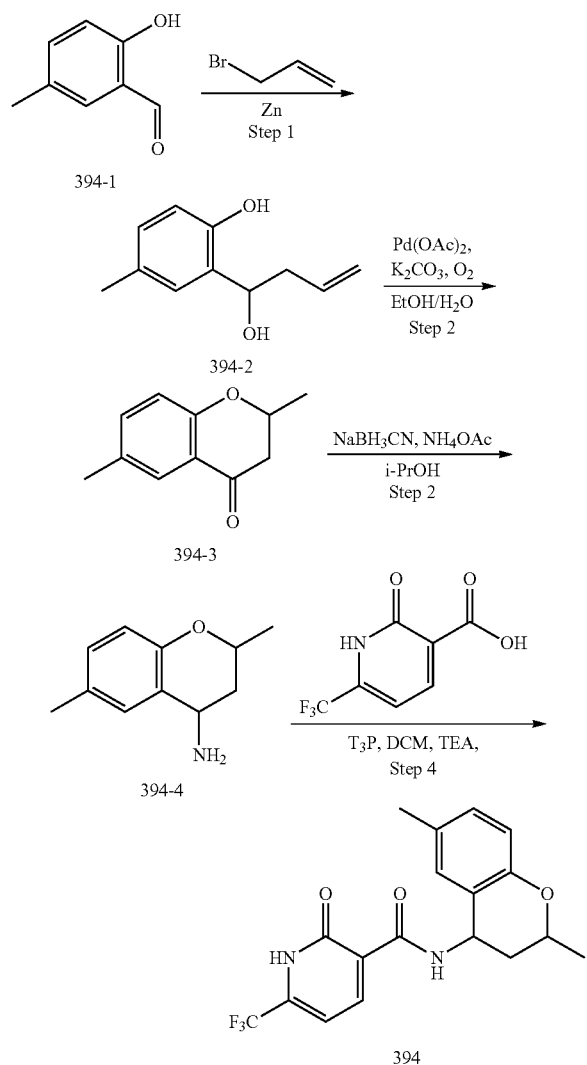

Step 1: 2-(1-hydroxybut-3-en-1-yl)-4-methylphenol (394-2)

To a mixture of Compound 394-1 (1 g, 7.3 mmol) in THF (16 mL) and Sat.NH$_4$Cl aq. (32 mL) was added Zn (961 mg, 14.7 mmol 7) and 3-bromoprop-1-ene (1.8 g, 14.7 mmol) at 20° C. The mixture was stirred at same temperature for 4 hrs. LCMS showed the reaction was completed and a main peak with desired mass was detected. The reaction mixture was poured into H$_2$O (20 mL), and then extracted with EtOAc (15×2 mL). The combined organic layers were dried over Na$_2$SO$_4$, filtered and concentrated under reduced pressure to give Compound 394-2 (0.8 g, crude) as a white solid. Fragment MS=161.0 (LCMS).

Step 2: 2,6-dimethylchroman-4-one (394-3)

To a solution of Compound 394-2 (500 mg, 2.8 mmol) in EtOH (16 mL) and H$_2$O (8 mL) was added K$_2$CO$_3$ (465 mg, 3.4 mmol) and Pd(OAc)$_2$ (63 mg, 280.5 μmol). The mixture was heated at 35° C. under O$_2$ (15 Psi) for 24 hrs. LCMS showed the reaction was completed and a main peak with desired mass was detected. The solvent was removed under reduced pressure and diluted with H$_2$O (10 mL), extracted with EtOAc (10 mL×2). The combined organic layers were dried over Na$_2$SO$_4$, filtered and concentrated under reduced pressure to give a residue, which was purified by flash silica gel chromatography (Ethyl acetate/Petroleum ether) to give Compound 394-3 (150 mg, 851.3 μmol, 30% yield) as a gray solid. M+H$^+$=177.1 (LCMS).

Step 3: 2,6-dimethylchroman-4-amine (394-4)

To a solution of Compound 394-3 (60 mg, 340.5 μmol, 1 eq) in i-PrOH (3 mL) was added NH$_4$OAc (787 mg, 10.2 mmol) and NaBH$_3$CN (150 mg, 2.4 mmol). The resulting mixture was warmed to 120° C. slowly and stirred for 1 hr. LCMS showed the reaction was completed and a main peak with desired mass was detected. The mixture was poured into H$_2$O (5 mL) and extracted with CHCl$_3$:i-PrOH=3:1 (4 mL×3). The combined organic layers were dried over Na$_2$SO$_4$, filtered and concentrated under reduced pressure to give Compound 394-4 (60 mg, crude) as a white solid. Fragment Ms=161.0 (LCMS).

Step 4: N-(2,6-dimethylchroman-4-yl)-2-oxo-6-(trifluoromethyl)-1,2-dihydropyridine-3-carboxamide (394)

To a solution of Compound 394-4 (50 mg, 282.1 μmol) in DCM (10 mL) was added 2-oxo-6-(trifluoromethyl)-1,2-dihydropyridine-3-carboxylic acid (58 mg, 282.1 μmol), T$_3$P (269 mg, 423.1 μmol, 50% purity) and TEA (86 mg, 846.3 μmol). The mixture was stirred at 25° C. for 1 hr. LCMS showed the reaction was completed and a main peak with desired mass was detected. The reaction mixture was poured into H$_2$O (2 ml) and then extracted with DCM (2 mL×2). The combined organic layers were dried over Na$_2$SO$_4$, filtered and concentrated under reduced pressure to give a residue, which was purified by Prep-TLC (etroleum ether: Ethyl acetate=2:1, R$_f$=0.55) to give Compound 394 (7 mg, 19 μmol, 6.67% yield) as a white solid, which was a mixture of diasteroisomers (the ratio was 1:1). M–H$^-$=365.1 (LCMS); $^1$H NMR (400 MHz, CDCl$_3$) δ=9.57-9.44 (m, 1H), 8.66-8.61 (m, 1H), 6.98-6.92 (m, 2H), 6.82-6.78 (m, 1H), 6.72-6.65 (m, 1H), 6.46-6.39 (m, 1H), 4.23-4.08 (m, 1H), 2.36-2.09 (m, 4H), 1.85-1.62 (m, 4H), 1.36-1.34 (m, 3H).

Example 64: Synthesis of N-(6-methyl-2,3-dihydrobenzofuran-3-yl)-2-oxo-6-(trifluoromethyl)-1,2-dihydropyridine-3-carboxamide (395)

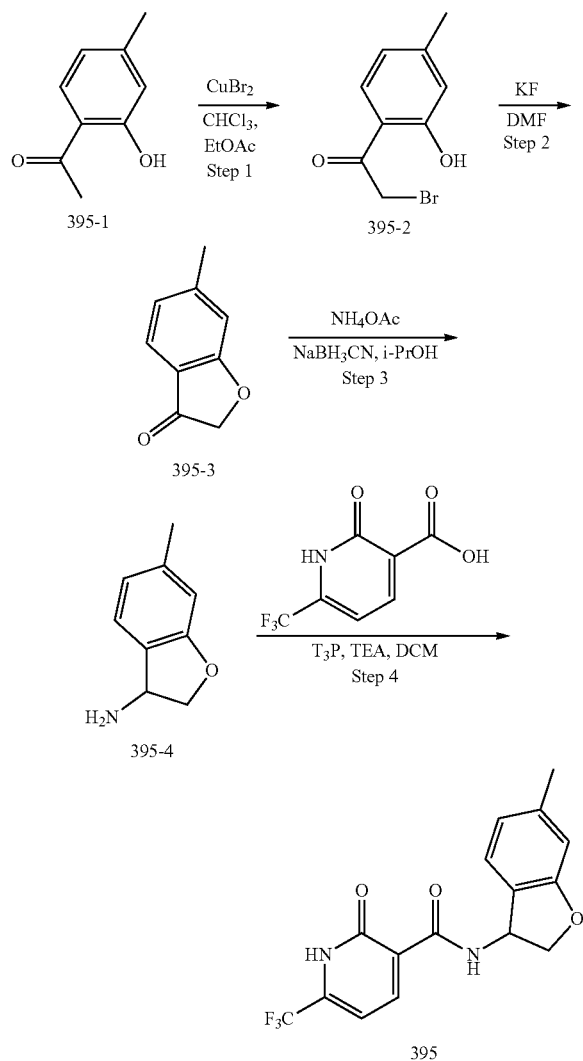

Step 1: 2-bromo-1-(2-hydroxy-4-methylphenyl)ethanone (395-2)

A solution of Compound 395-1 (0.6 g, 4.0 mmol) in CHCl₃ (12 mL) was added to a solution of CuBr₂ (1.8 g, 8.0 mmol) EtOAc (12 mL) at 70° C. The mixture was stirred at 70° C. for 12 hrs. TLC showed the reaction complete. The suspension was filtered and the pad was washed with EtOAc (5 mL×2). The combined filtrates were concentrated to dryness to give Compound 395-2 (0.6 g, crude) as a yellow solid used directly.

Step 2: 6-methylbenzofuran-3(2H)-one (395-3)

To a solution of Compound 395-2 (0.5 g, 2.2 mmol) in DMF (10 mL) was added KF (216 mg, 3.7 mmol). The mixture was stirred at 20° C. for 1 hr. TLC showed the reaction was complete. The reaction mixture was quenched by pouring into water (60 mL) and extracted with EtOAc (20 mL×3). The combined organic layers were dried over Na₂SO₄, filtered and concentrated under reduced pressure to give a residue, which was purified by column chromatography to give Compound 395-3 (0.25 g, 1.7 mmol, 77% yield) as a white solid.

Step 3: 6-methyl-2,3-dihydrobenzofuran-3-amine (395-4)

To a solution of Compound 395-3 (100 mg, 674.9 μmol) in i-PrOH (2 mL) was added NH₄OAc (1.6 g, 20.3 mmol) and NaBH₃CN (297 mg, 4.7 mmol), then the mixture was stirred at 100° C. for 1.5 hrs. LCMS showed the reaction was complete and fragments of desired mass were detected. The reaction mixture was quenched by pouring into water 15 mL and extracted with DCM (5 mL×3). The combined organic layers were dried over Na₂SO₄, filtered and concentrated under reduced pressure to give Compound 395-4 a residue. Fragments Ms=133.5[LCMS].

Step 4: N-(6-methyl-2,3-dihydrobenzofuran-3-yl)-2-oxo-6-(trifluoromethyl)-1,2-dihydropyridine-3-carboxamide (395)

To a solution of Compound 395-4 (90 mg, 603.3 μmol) and 2-oxo-6-(trifluoro methyl)-1, 2-dihydropyridine-3-carboxylic acid (125 mg, 603.3 μmol) in DCM (5 mL) was added TEA (183 mg, 1.8 mmol) and T₃P (576 mg, 905 μmol, 50% purity). The mixture was stirred at 20° C. for 1 hr. LCMS showed the reaction was completed and desired mass was detected. The reaction mixture was pouring into water (15 mL) and extracted with DCM (5 mL×3). The combined organic layers were dried over Na₂SO₄, filtered and concentrated under reduced pressure to give a residue. The residue was treated with MeOH/3M NaOH aq.=3 mL: 3 mL (v/v), then stirred at 20° C. for 12 hrs. The reaction mixture was pouring into water (15 mL) and extracted with DCM (5 mL×3). The combined organic layers were dried over Na₂SO₄, filtered and concentrated under reduced pressure to give a residue, which was purified by Prep-HPLC to give Compound 395 (4 mg, 11.41 μmol, 2% yield) as a white solid. M−H⁻=337.1 (LCMS); 1H NMR (400 MHz, CHLOROFORM-d) δ=9.59 (br d, J=6.2 Hz, 1H), 8.67 (d, J=7.5 Hz, 1H), 7.25 (d, J=7.5 Hz, 1H), 6.86 (d, J=7.3 Hz, 1H), 6.77 (d, J=7.7 Hz, 1H), 6.72 (s, 1H), 5.67 (dt, J=3.7, 7.1 Hz, 1H), 4.77 (dd, J=7.8, 10.0 Hz, 1H), 4.44 (dd, J=3.7, 10.1 Hz, 1H), 2.35 (s, 3H).

Example 65: Synthesis of N-(7-methylthiochroman-4-yl)-2-oxo-6-(trifluoromethyl)-1, 2-dihydropyridine-3-carboxamide (396)

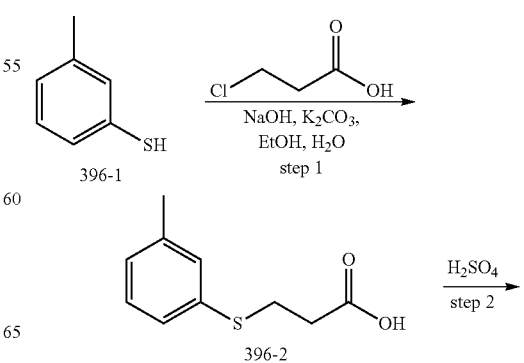

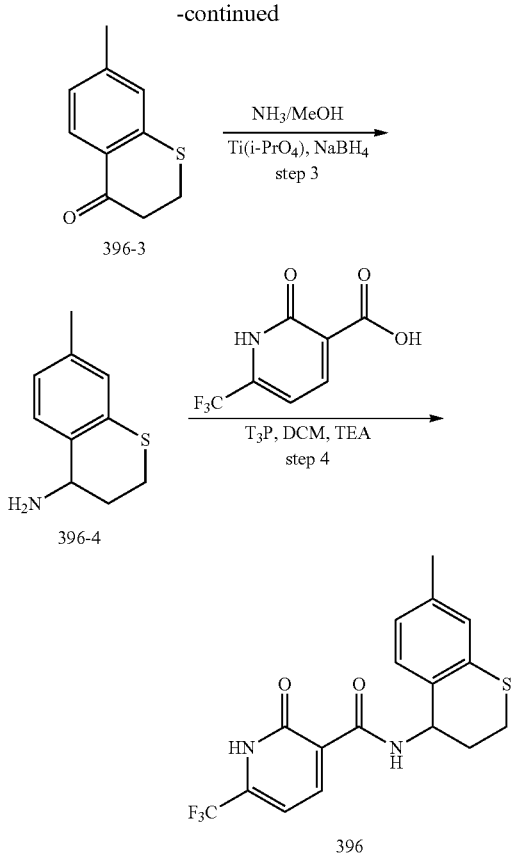

Step 1: 3-(m-tolylthio)propanoic acid (396-2)

To a mixture of Compound 396-1 (1 g, 8.0 mmol), 3-chloropropanoic acid (873 mg, 8.0 mmol) in EtOH (5 mL) was added a solution of $K_2CO_3$ (1.1 g, 8.0 mmol) and KOH (451 mg, 8.0 mmol) in $H_2O$ (5 mL) at 25° C. The reaction mixture was stirred at 90° C. for 5 hrs. LCMS showed the reaction was completed and desired mass was detected. The reaction mixture was poured into $H_2O$ (10 mL), acidified by 1 M HCl to pH=7, and extracted with EtOAc (30 mL×3). The combined organic layers were washed with brine (5 mL×3), dried over $Na_2SO_4$, filtered and concentrated under reduced pressure to give Compound 396-2 (1.4 g, crude) as a pale yellow solid. $M+H^+=197.2$ (LCMS).

Step 2: 7-methylthiochroman-4-one (396-3)

Compound 396-2 (1.1 g, 5.6 mmol) was added to $H_2SO_4$ (3 mL) at 0° C. The mixture was stirred at 25° C. for 40 mins. LCMS showed the reaction was completed and desired mass was detected. The reaction mixture was poured into $H_2O$ (20 mL) and extracted with EtOAc (10 mL×4). The combined organic layers were washed with brine (5 mL×3), dried over $Na_2SO_4$, filtered and concentrated under reduced pressure to give a residue, which was purified by flash silica gel chromatography to give Compound 396-3 (345 mg, 1.9 mmol) as colorless oil. $M+H^+=179.0$ (LCMS). $^1$H NMR (400 MHz, CHLOROFORM-d) δ=8.02 (d, J=8.1 Hz, 1H), 7.10 (s, 1H), 6.99 (d, J=8.1 Hz, 1H), 3.28-3.19 (m, 2H), 3.03-2.91 (m, 2H), 2.34 (s, 3H).

Step 3: 7-methylthiochroman-4-amine (396-4)

To a stirred mixture of Compound 396-3 (190 mg, 1.1 mmol) in MeOH (1 mL) was added $NH_3$/MeOH (7 M, 11.6 mL), followed by Ti(i-PrO)$_4$ (1.8 g, 6.4 mmol). The mixture was stirred at 15° C. for 12 hrs. Then NaBH$_4$ (241 mg, 6.4 mmol) was added at 0° C. The reaction mixture was stirred at 15° C. for 2 hrs. LCMS showed the reaction was completed and desired mass was detected. The reaction mixture was poured into ice water (5 mL), and extracted with DCM (10 mL×3). The combined organic layers were dried over $Na_2SO_4$, filtered and concentrated under reduced pressure to give a residue, which was purified by column chromatography to give Compound 396-4 (30 mg, 167 μmol) as a yellow solid. Fragment MS=163.0 (LCMS).

Step 4: N-(7-methylthiochroman-4-yl)-2-oxo-6-(trifluoromethyl)-1H-pyridine-3-carboxamide (396)

To a mixture of Compound 396-4 (30 mg, 167 μmol), 2-oxo-6-(trifluoromethyl)-1,2-dihydropyridine-3-carboxylic acid (34 mg, 167 μmol) in DCM (1.5 mL) was added TEA (50 mg, 502 μmol) and T$_3$P (213 mg, 334 μmol). The mixture was stirred at 25° C. for 1 hr. LCMS showed the reaction was completed and desired mass was detected. The reaction mixture was poured $H_2O$ (10 mL) and extracted with EtOAc (10 mL×4). The combined organic layers were washed with brine (5 mL×3), dried over $Na_2SO_4$, filtered and concentrated under reduced pressure to give a residue, which was purified by prep-HPLC to give Compound 396 (48 mg, 131 μmol, 78% yield) as a white solid. $M-H^-=367.1$ (LCMS). $^1$H NMR (400 MHz, CHLOROFORM-d) δ=9.61 (br d, J=7.3 Hz, 1H), 8.70 (d, J=7.5 Hz, 1H), 7.15 (d, J=7.7 Hz, 1H), 6.98 (s, 1H), 6.89-6.81 (m, 2H), 5.38-5.27 (m, 1H), 3.13 (dt, J=2.9, 12.1 Hz, 1H), 3.00-2.90 (m, 1H), 2.49 (dtd, J=3.1, 5.5, 13.9 Hz, 1H), 2.27 (s, 3H), 2.20 (tdd, J=3.5, 11.1, 14.1 Hz, 1H).

Example 66: Synthesis of 2-oxo-N—((R)—((S)-tetrahydro-2H-pyran-3-yl)(p-tolyl)methyl)-6-(trifluoromethyl)-1,2-dihydropyridine-3-carboxamide (397) and 2-oxo-N—((R)—((R)-tetrahydro-2H-pyran-3-yl)(p-tolyl)methyl)-6-(trifluoromethyl)-1,2-dihydropyridine-3-carboxamide (398)

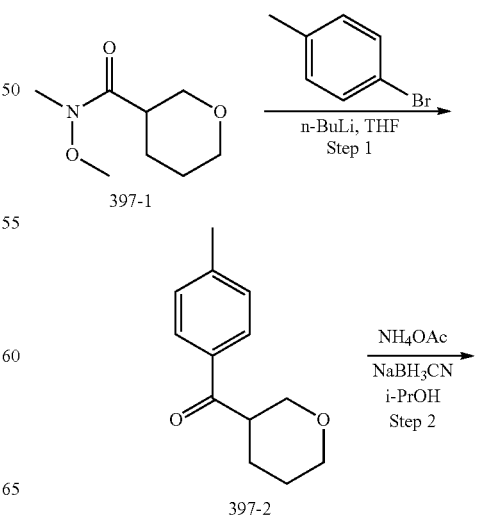

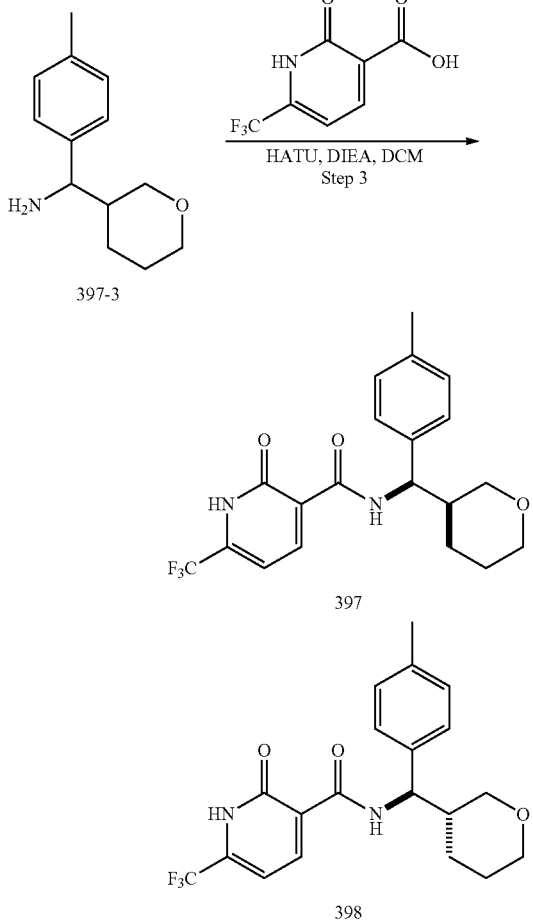

under reduced pressure to give a residue. The residue was purified by column chromatography to give Compound 397-2 (180 mg, crude) as colorless oil.

Step 2: (tetrahydro-2H-pyran-3-yl)(p-tolyl)methanamine (397-3)

To a mixture of Compound 397-2 (90 mg, 440.6 μmol) in MeOH (1 mL) was added $NH_3$/MeOH (7 M, 7 mL), followed by Ti(i-PrO)$_4$ (751 mg, 2.6 mmol). The mixture was stirred at 15° C. for 12 hrs. To the mixture was added NaBH$_4$ (100 mg, 2.6 mmol) at 0° C. and stirred at 15° C. for 2 hrs. TLC indicated the reaction was completed. The reaction mixture was added to ice-$H_2O$ (20 mL) and extracted with EtOAc (10 mL×4). The combined organic layers were dried over $Na_2SO_4$, filtered and concentrated under reduced pressure to give Compound 397-3 (120 mg, crude) as light yellow oil.

Step 3: 2-oxo-N—((R)—((S)-tetrahydro-2H-pyran-3-yl)(p-tolyl)methyl)-6-(trifluoromethyl)-1,2-dihydropyridine-3-carboxamide (397)

To a solution of Compound 43A-3 (120 mg, 579.4 μmol) in DCM (3 mL) was added HATU (264 mg, 695.3 μmol) 2-oxo-6-(trifluoromethyl)-1,2-dihydro pyridine-3-carboxylic acid (119 mg, 579 μmol) and DIEA (225 mg, 1.7 mmol). The mixture was stirred at 15° C. for 1 hr. LCMS showed the reaction was complete and the desired mass was detected. The mixture was quenched by addition $H_2O$ (10 mL) and extracted with EtOAc (4 mL×4). The combined organic layers were dried over $Na_2SO_4$, filtered and concentrated under reduced pressure to give a residue, which was purified by prep-HPLC to give Compound 397 (17 mg, 44 μmol, 7.6% yield) as a white solid and Compound 398 (11 mg, 27.2 μmol, 4.7% yield) as a white solid. 397: M-H$^-$=393.2 (LCMS); $^1$H NMR (400 MHz, CDCl$_3$) δ=9.88 (br d, J=8.8 Hz, 1H), 8.69 (d, J=7.5 Hz, 1H), 7.24-7.18 (m, 2H), 7.16-7.11 (m, 2H), 6.94 (d, J=7.5 Hz, 1H), 5.01 (t, J=9.0 Hz, 1H), 3.86 (br d, J=11.1 Hz, 1H), 3.65 (br d, J=10.6 Hz, 1H), 3.38 (dt, J=2.5, 10.9 Hz, 1H), 3.16 (t, J=10.5 Hz, 1H), 2.32 (s, 3H), 2.15-2.00 (m, 2H), 1.75-1.60 (m, 2H), 1.52-1.24 (m, 2H). 397: M-H$^-$=393.2 (LCMS); $^1$H NMR (400 MHz, CDCl$_3$) δ=9.89 (br d, J=8.8 Hz, 1H), 8.67 (d, J=7.3 Hz, 1H), 7.25-7.20 (m, 2H), 7.18-7.12 (m, 2H), 6.91 (d, J=7.3 Hz, 1H), 4.97 (t, J=9.4 Hz, 1H), 4.10 (br dd, J=2.6, 11.4 Hz, 1H), 3.87 (br d, J=10.8 Hz, 1H), 3.47-3.20 (m, 2H), 2.33 (s, 3H), 2.19-2.03 (m, 1H), 1.72-1.46 (m, 3H), 1.28-1.11 (m, 1H).

Other compounds made in a similar manner are shown in Table 38.

Step 1: (tetrahydro-2H-pyran-3-yl)(p-tolyl)methanone (397-2)

To a solution of 1-bromo-4-methylbenzene (199 mg, 1.2 mmol) in THF (4 mL) was added n-BuLi (2.5 M, 692.80 uL) under $N_2$, the mixture was stirred at −78° C. for 0.5 hr under $N_2$, then Compound 397-1 (200.00 mg, 1.2 mmol) in THF (1 mL) was added to the mixture. The mixture was stirred at −78° C. for 2 hrs. TLC indicated the reaction completed. The reaction mixture was added to Sat.NH$_4$Cl (10 mL) and extracted with DCM (5 mL×3). The combined organic layers were dried over $Na_2SO_4$, filtered and concentrated

TABLE 38

| Compound No | Structure | HNMR and Ms |
|---|---|---|
| 399 | 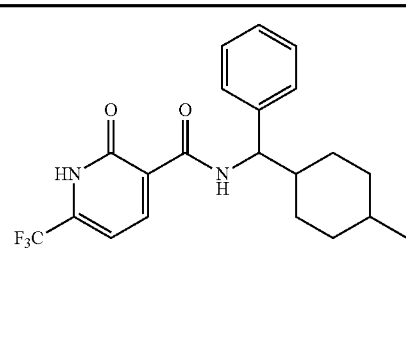 | $^1$H NMR (400 MHz, CDCl$_3$) δ = 9.84-9.78 (m, 1H), 8.63-8.61 (d, J = 7.2 Hz, 1H), 7.26-7.15 (m, 5H), 6.86-6.84 (d, J = 7.6 Hz, 1H), 5.08-4.86 (m, 1H), 1.87-1.83 (m, 1H), 0.63-0.90 (m, 8H), 0.87-0.77 (m, 4H). ESI [M − H] = 391.2. |

TABLE 38-continued

| Compound No | Structure | HNMR and Ms |
|---|---|---|
| 400 | 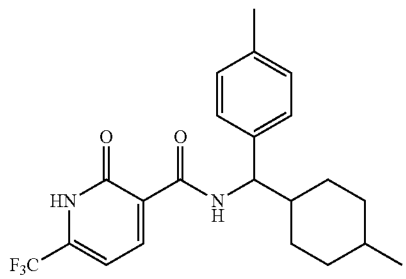 [SMILES: Cc1ccc(C(NC(=O)c2ccc(C(F)(F)F)[nH]c2=O)C2CCC(C)CC2)cc1] | ¹H NMR (400 MHz, CDCl₃) δ = 9.91-9.77 (m, 1H), 8.69 (dd, J = 2.7, 7.3 Hz, 1H), 7.25-7.17 (m, 2H), 7.13 (br d, J = 7.9 Hz, 2H), 6.92 (d, J = 7.3 Hz, 1H), 5.23-4.80 (m, 1H), 2.32 (s, 3H), 2.00-1.81 (m, 1H), 1.76-1.59 (m, 3H), 1.56-1.21 (m, 5H), 1.18-0.98 (m, 1H), 0.96-0.84 (m, 3H) ESI [M − H] = 405.2 |
| 401 | 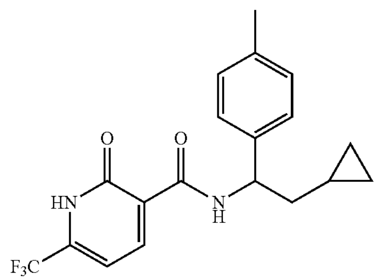 [SMILES: Cc1ccc(C(CC2CC2)NC(=O)c2ccc(C(F)(F)F)[nH]c2=O)cc1] | 1H NMR (400 MHz, CHLOROFORM-d) δ = 9.78-9.70 (m, 1H), 8.65 (d, J = 7.3 Hz, 1H), 7.26 (s, 2H), 7.15 (d, J = 7.9 Hz, 2H), 6.89 (d, J = 7.5 Hz, 1H), 5.22 (q, J = 7.6 Hz, 1H), 2.33 (s, 3H), 1.85-1.71 (m, 2H), 0.76-0.65 (m, 1H), 0.51-0.39 (m, 2H), 0.21--0.02 (m, 2H) ESI [M − H] = 363.1 |
| 402 | 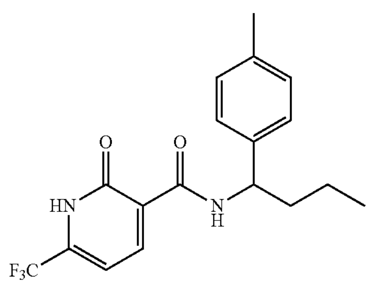 [SMILES: CCCC(NC(=O)c1ccc(C(F)(F)F)[nH]c1=O)c1ccc(C)cc1] | ¹H NMR (400 MHz, CDCl₃) δ = 9.76-9.74 (m, 1H), 8.69-8.67 (dd, J = 2.7, 7.3 Hz, 1H), 7.25-7.17 (m, 2H), 7.13 (br d, J = 7.9 Hz, 2H), 6.92 (d, J = 7.3 Hz, 1H), 5.14-5.08 (m, 1H), 2.34 (s, 3H), 1.89-1.82 (m, 2H), 1.43-1.36 (m, 2H), 0.97-0.94 (m, 3H) ESI [M − H] = 351.1 |

Example 67: Synthesis of N-(6-methyl-2-propyl-chroman-4-yl)-2-oxo-6-(trifluoromethyl)-1,2-dihydropyridine-3-carboxamide (403)

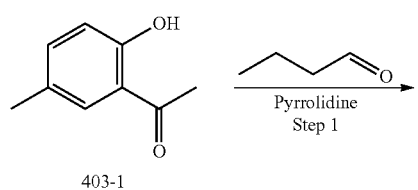

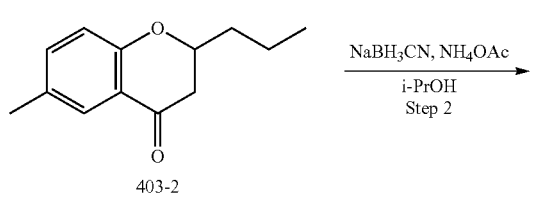

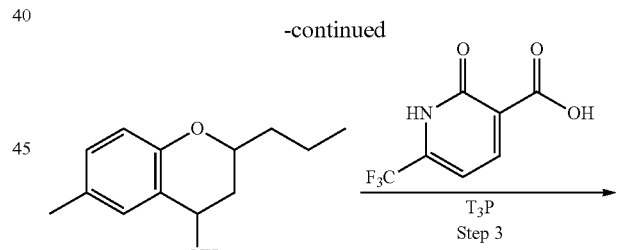

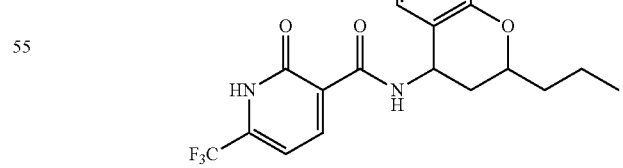

Step 1: 6-methyl-2-propylchroman-4-one (403-2)

To a solution of Compound 403-1 (1 g, 6.7 mmol) and butanal (960 mg, 13.3 mmol) in MeOH (20 mL) was added Pyrrolidine (94 mg, 1.3 mmol) at 20° C. Then the mixture was stirred at 50° C. for 24 hrs. LCMS showed most of the starting material have been consumed. The solvent was removed under vacuum and the residue was diluted with water (10 mL) and extracted with ethyl acetate (10 mL×2). The combined organic layer was washed with 1 N HCl (10 mL), water (10 mL) and brine (10 mL), dried over $Na_2SO_4$, and then concentrated under vacuum to give a crude residue, which was purified by flash silica gel chromatography (Ethyl acetate/Petroleum ether) to give Compound 403-2 (300 mg, 881 μmol, 13% yield) as yellow oil. M+H$^+$=205.2 (LCMS)

Step 2: 6-methyl-2-propylchroman-4-amine (403-3)

To a solution of Compound 403-2 (100 mg, 489.6 μmol) in i-PrOH (5 mL) was added $NH_4OAc$ (1.1 g, 14.7 mmol) and $NaBH_3CN$ (215 mg, 3.4 mmol). The resulting mixture was warmed to 120° C. slowly and stirred for 1 h. LCMS showed the reaction was completed and a main peak with desired mass was detected. The residue was poured into $H_2O$ (5 mL) and extracted with CHCl3:i-PrOH=3:1 (4 mL×3). The combined organic layers were dried over $Na_2SO_4$, filtered and concentrated under reduced pressure to give a residue, which was purified by Prep-TLC (Petroleum ether: Ethyl acetate=5:1, $R_f$=0.24) to give Compound 403-3 (30 mg, 146.1 μmol, 29.85% yield) as a white solid. Ms[fragment Mass]=189.2 (LCMS).

Step 3: N-(6-methyl-2-propylchroman-4-yl)-2-oxo-6-(trifluoromethyl)-1,2-dihydropyridine-3-carboxamide (403)

To a stirred solution of Compound 403-3 (30 mg, 146.1 μmol) 2-oxo-6-(trifluoro methyl)-1,2-dihydropyridine-3-carboxylic acid (30 mg, 146.1 μmol) in DCM (3 mL) was added $T_3P$ (139 mg, 219.2 μmol, 50% purity) and TEA (44 mg, 438.4 μmol). The mixture was stirred at 25° C. for1 hr. LCMS showed that the reaction was completed and a main peak with desired mass was detected. The reaction mixture was poured into $H_2O$ (2 ml) and extracted with DCM (2 mL×2). The combined organic layers were dried over $Na_2SO_4$, filtered and concentrated under reduced pressure to give a residue, which was purified by Prep-HPLC to give Compound 403 (6 mg, 14.1 μmol, 9.62% yield) as a white solid (it was a mixture of diasteroisomers). M–H$^-$=393.2 (LCMS); $^1$H NMR (400 MHz, CDCl$_3$) δ=9.65-9.51 (m, 1H), 8.74-8.69 (m, 1H), 7.27-7.02 (m, 2H), 6.96-6.86 (m, 1H), 6.80-6.73 (m, 1H), 5.53-5.23 (m, 1H), 4.17-4.02 (m, 1H), 2.43-2.22 (m, 4H), 1.78-1.48 (m, 5H), 3.72 (s, 3H), 1.00-0.94 (m, 3H).

Other compounds made in a similar manner are shown in Table 39.

TABLE 39

| Compound No | Structure | HNMR and Ms |
|---|---|---|
| 404 | 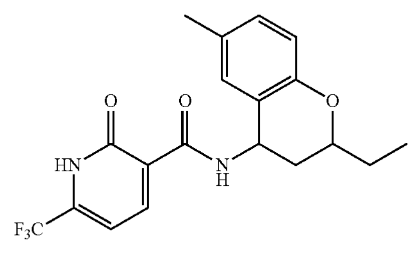 | $^1$H NMR $^1$H NMR (400 MHz, CDCl3) δ = 9.62-9.46 (m, 1H), 8.72-8.68 (m, 1H), 7.04-6.94 (m, 2H), 6.90-6.86 (m, 1H), 6.81-6.74 (m, 1H), 5.53-5.23 (m, 1H), 4.11-3.92 (m, 1H), 2.40-1.67 (m, 7H), 1.07-1.03 (m, 3H). ESI [M – H] = 379.1 |
| 405 | 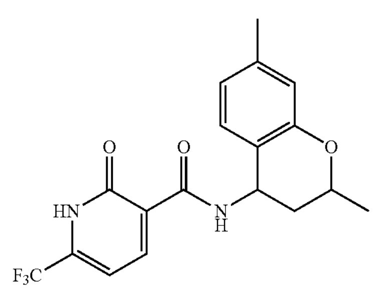 | $^1$H NMR (400 MHz, DMSO-d$_6$) δ = 9.23 (m, 1H), 8.42-8.41 (m, 1H), 7.33-7.31 (m, 1H), 7.15-7.06 (m, 1H), 6.73-6.59 (m, 2H), 5.38-5.08 (m, 1H), 4.33-4.17 (m, 1H), 2.27-2.06 (m, 4H), 1.84-1.67 (m, 1H), 1.36-1.33 (m, 3H). ESI [M – H] = 365.1 |
| 406 | 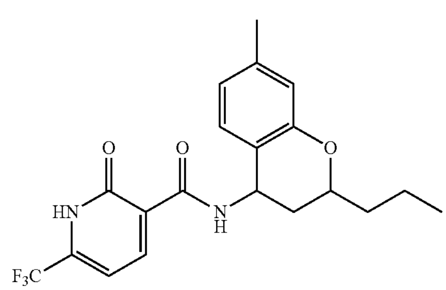 [SMILES: CCCC1CC(NC(=O)c2ccc(C(F)(F)F)[nH]c2=O)c2ccc(C)cc2O1] | $^1$H NMR (400 MHz, DMSO-d$_6$) δ = 9.31-9.35 (m, 1H), 8.42-8.38 (m, 1H), 7.26-7.12 (m, 1H), 7.08-7.06 (m, 1H), 6.72-6.59 (m, 2H), 5.38-5.08 (m, 1H), 4.20-4.06 (m, 1H), 2.27-2.21 (m, 3H), 2.07-2.04 (m, 1H), 1.67-1.55 (m, 6H), 0.95-0.90 (m, 3H). ESI [M – H] = 393.1 |

TABLE 39-continued

| Compound No | Structure | HNMR and Ms |
|---|---|---|
| 407 | 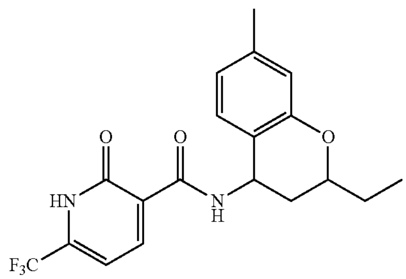 | ¹H NMR (400 MHz, DMSO-d₆) δ = 8.37-8.32 (m, 1H), 7.14-7.05 (m, 2H), 6.72-6.60 (m, 2H), 5.36-5.08 (m, 1H), 4.13-3.94 (m, 1H), 2.23-2.21 (m, 3H), 2.07-1.65 (m, 4H), 1.00-0.96 (m, 3H). ESI [M − H] = 379.1 |

Example 68: Synthesis of N-(5-methyl-2,3-dihydrobenzofuran-3-yl)-2-oxo-6-(trifluoromethyl)-1,2-dihydropyridine-3-carboxamide (408)

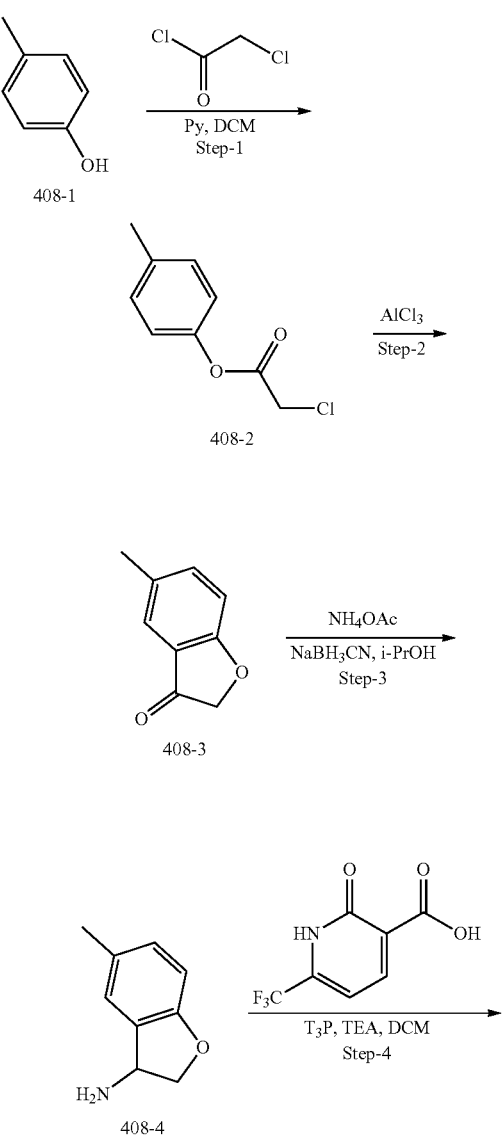

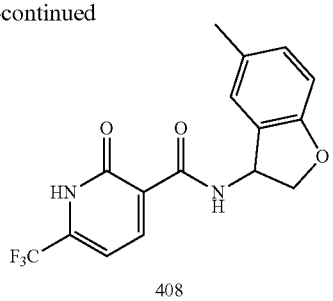

Step 1: p-tolyl 2-chloroacetate (408-2)

To a solution of Compound 408-1 (1 g, 9.3 mmol) in DCM (20 mL) was added 2-chloroacetyl chloride (1.6 g, 13.9 mmol) and Pyridine (1.1 g, 13.9 mmol) at 0° C. The mixture was stirred at 20° C. for 1 hr. TLC showed the reaction was completed. The reaction mixture was poured into ice-water (5 mL) and extracted with EtOAc (5 mL×5). The combined organic layers were dried over Na₂SO₄, filtered and concentrated under reduced pressure to give a residue, which was purified by flash silica gel chromatography (Ethyl acetate/Petroleum ether gradient) to give Compound 408-2 (1.5 g, 88% yield) as a white solid.

Step 2: 5-methylbenzofuran-3(2H)-one (408-3)

A mixture of Compound 408-2 (0.1 g, 541.7 μmol) and AlCl₃ (108 mg, 812.5 μmol,) was stirred at 140° C. for 2 hrs. LCMS showed the reaction was completed and desired mass was detected. The reaction mixture was poured into 1M HCl (5 mL) at 0° C., then extracted with EtOAc (5 mL×5). The combined organic layers were dried over Na₂SO₄, filtered and concentrated under reduced pressure to give a residue, which was purified by prep-TLC (Petroleum ether:Ethyl acetate=8:1) to give Compound 408-3 (20 mg, 30% yield) as a white solid. M+H⁺=149.0 (LCMS); ¹H NMR (400 MHz, CHLOROFORM-d) δ=7.50-7.40 (m, 2H), 7.05 (d, J=8.4 Hz, 1H), 4.62 (s, 2H), 2.37 (s, 3H).

Step 3: 5-methyl-2,3-dihydrobenzofuran-3-amine (408-4)

To a solution of Compound 408-3 (20 mg, 135.0 μmol) in i-PrOH (1 mL) was added NH₄OAc (312 mg, 4.1 mmol) and NaBH₃CN (59 mg, 945 μmol). The mixture was stirred at 120° C. for 1 hr. LCMS showed the reaction was completed and desired mass was detected. The reaction mixture was poured into H₂O (5 mL) at 20° C., then extracted with EtOAc (5 mL×5). The combined organic layers were dried over Na₂SO₄, filtered and concentrated under reduced pressure to give a Compound 408-4 (20 mg, crude) as a colorless gum. Fragment Ms=133.0 (LCMS).

Step 4: N-(5-methyl-2,3-dihydrobenzofuran-3-yl)-2-oxo-6-(trifluoromethyl)-1,2-dihydropyridine-3-carboxamide (408)

To a mixture of Compound 408-4 (20 mg, 134.1 μmol), 2-oxo-6-(trifluoromethyl)-1,2-dihydropyridine-3-carboxylic acid (28 mg, 134.1 μmol) in DCM (2 mL) was added TEA (41 mg, 402.2 μmol), T₃P (171 mg, 268.1 μmol, 50% purity). The mixture was stirred at 25° C. for 4 hrs. LCMS showed the reaction was completed and desired mass was detected. The reaction mixture was quenched by addition H₂O (5 mL) and extracted with EtOAc (5 mL×5). The combined organic layers were dried over Na₂SO₄, filtered and concentrated under reduced pressure to give a residue, which was purified by prep-TLC (Petroleum ether:Ethyl acetate=3:1) to give Compound 408 (9 mg, 17% yield) as a yellow solid. M−H⁻=377.1 (LCMS); ¹H NMR (400 MHz, CHLOROFORM-d) δ=9.65-9.49 (m, 1H), 8.68 (d, J=7.5 Hz, 1H), 7.18 (s, 1H), 7.07 (br d, J=7.9 Hz, 1H), 6.87 (d, J=7.5 Hz, 1H), 6.79 (d, J=8.2 Hz, 1H), 5.69 (dt, J=4.2, 7.1 Hz, 1H), 4.78 (dd, J=7.9, 9.9 Hz, 1H), 4.42 (dd, J=4.1, 10.0 Hz, 1H), 2.31 (s, 3H).

Example 69: Synthesis of N-(6-methyl-2,3,4,4a,9,9a-hexahydro-1H-xanthen-9-yl)-2-oxo-6-(trifluoromethyl)-1,2-dihydropyridine-3-carboxamide (409)

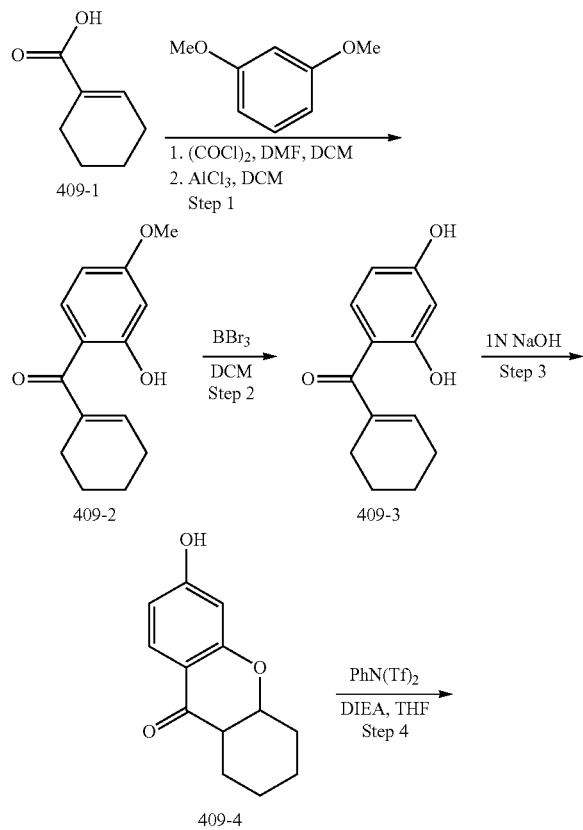

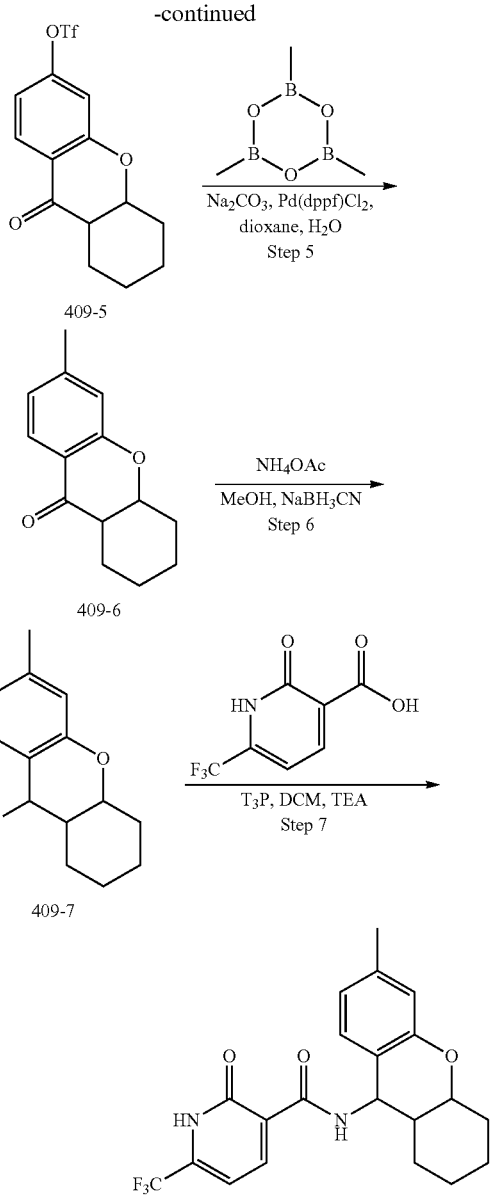

Step 1: cyclohex-1-en-1-yl(2-hydroxy-4-methoxyphenyl)methanone (409-2)

To a stirred solution of Compound 409-1 (1.3 g, 10.3 mmol) in DCM (78 mL) was added (COCl)₂ (1.9 g, 15.5 mmol) at 0° C., followed by a drop of DMF (75 mg, 1.0 mmol). The mixture was stirred at 25° C. for 1 hr. The mixture was concentrated in vacuum to give a residue, which was diluted with DCM (97 mL). Then the solution was added 1,3-dimethoxybenzene (1.4 g, 10.3 mmol) and AlCl₃ (2.2 g, 16.5 mmol) at 25° C. The resulting mixture was stirred at 25° C. for 12 hrs. LCMS showed the reaction was completed. The reaction mixture was poured into H₂O (50 mL) at 0° C., and then extracted with DCM (20 mL×5). The combined organic layers were dried over Na₂SO₄, filtered and concentrated under reduced pressure to give a residue, which was purified by column chromatography (Petroleum ether/Ethyl acetate) to give Compound 409-2 (1.7 g, 7.2 mmol, 69% yield) as a yellow oil. M+H⁺=233.0 (LCMS), ¹HNMR (400 MHz, CHLOROFORM-d) δ=12.64 (s, 1H), 7.64 (d, J=8.9 Hz, 1H), 6.47 (d, J=2.4 Hz, 1H), 6.41 (dd, J=2.4, 8.9 Hz, 1H), 6.26 (br s, 1H), 3.85 (s, 3H), 2.46-2.22 (m, 4H), 1.83-1.65 (m, 4H).

Step 2: cyclohex-1-en-1-yl(2,4-dihydroxyphenyl)methanone (409-3)

To a solution of Compound 409-2 (1 g, 4.3 mmol) in DCM (40 mL) was added BBr₃ (5.4 g, 21.5 mmol) in DCM (4 mL) at −78° C. The mixture was stirred at −78° C. for 1 hr then at 25° C. for 12 hrs. TLC showed the reaction was completed. The mixture was poured into H₂O (30 mL) and then extracted with DCM (10 mL×5). The combined organic layers were dried over Na₂SO₄, filtered and concentrated under reduced pressure to give a residue, which was purified by column chromatography (Petroleum ether/Ethyl acetate) to give Compound 409-3 (650 mg, 3.0 mmol, 69% yield) as a yellow oil. ¹H NMR (400 MHz, CHLOROFORM-d) δ=12.55 (s, 1H), 7.63 (d, J=8.7 Hz, 1H), 6.57-6.09 (m, 3H), 5.36 (s, 1H), 2.43-2.21 (m, 4H), 1.82-1.66 (m, 4H).

Step 3: 6-hydroxy-2,3,4,4a-tetrahydro-1H-xanthen-9 (9aH)-one (409-4)

A mixture of Compound 409-3 (650 mg, 3.0 mmol) in NaOH (1 M, 14.9 mL) was stirred at 25° C. for 3 hrs. TLC showed the reaction was completed. The reaction mixture was diluted with water (5 mL) and acidified to pH=1 with 1N HCl, the precipitate was collected by filtration to give Compound 409-4 (470 mg, 2.2 mmol, 72% yield) as a yellow solid. ¹H NMR (400 MHz, CHLOROFORM-d) δ=7.82 (dd, J=5.1, 8.6 Hz, 1H), 6.55-6.46 (m, 1H), 6.39 (dd, J=2.2, 9.9 Hz, 1H), 5.56 (br d, J=9.0 Hz, 1H), 4.58-4.08 (m, 1H), 2.56-2.37 (m, 2H), 2.31-2.08 (m, 1H), 1.99-1.82 (m, 1H), 1.80-1.67 (m, 2H), 1.45-1.18 (m, 3H).

Step 4: 9-oxo-2,3,4,4a,9,9a-hexahydro-1H-xanthen-6-yl trifluoromethanesulfonate (409-5)

To a mixture of PhN(Tf)₂ (982 mg, 2.7 mmol) and Compound 409-4 (500 mg, 2.3 mmol) in THF (30 mL) was added DIEA (370 mg, 2.7 mmol), the resulting mixture was stirred at 25° C. for 12 hrs. TLC showed the reaction was completed. The reaction mixture was concentrated under reduced pressure to give a residue, which was purified by column chromatography (Petroleum ether/Ethyl acetate) to give Compound 409-5 (670 mg, 1.9 mmol, 83% yield) as a white gum.

Step 5: 6-methyl-2,3,4,4a-tetrahydro-1H-xanthen-9 (9aH)-one (409-6)

A mixture of Compound 409-5 (400 mg, 1.1 mmol), Na₂CO₃ (242 mg, 2.3 mmol) in dioxane (24 mL) and H₂O (4 mL) was degassed and purged with N₂ for 3 times. To the mixture was added 2,4,6-trimethyl-1,3,5,2,4,6-trioxatriborinane (573 mg, 2.3 mmol), Pd(dppf)Cl₂ (84 mg, 114 μmol), then the mixture was stirred at 80° C. for 12 hrs under N₂ atmosphere. TLC showed the reaction was completed. The reaction mixture was poured into H₂O (20 mL) and extracted with EtOAc (10 mL×5). The combined organic layers were dried over Na₂SO₄, filtered and concentrated under reduced pressure to give a residue, which was purified by column chromatography (Petroleum ether/Ethyl acetate) to give Compound 409-6 (0.2 g, 925 μmol, 81% yield) as a colorless gum.

Step 6: 6-methyl-2,3,4,4a,9,9a-hexahydro-1H-xanthen-9-amine (409-7)

To a stirred solution of Compound 409-6 (50 mg, 231 μmol) in MeOH (2 mL) was added NH₄OAc (214 mg, 2.7 mmol), the reaction was stirred for 10 min at 25° C., then NaBH₃CN (58 mg, 925 μmol) was added and the reaction was stirred at 100° C. for 3 hrs under microwave. LCMS showed the reaction was completed. The reaction mixture was poured into H₂O (5 mL) and extracted with DCM (5 mL×4). The combined organic layers were dried over Na₂SO₄, filtered and concentrated under reduced pressure to give Compound 409-7 (100 mg, crude) as a yellow gum. Fragment Ms=201.1 (LCMS).

Step 7: N-(6-methyl-2,3,4,4a,9,9a-hexahydro-1H-xanthen-9-yl)-2-oxo-6-(trifluoromethyl)-1,2-dihydropyridine-3-carboxamide (409)

To a stirred solution of 2-oxo-6-(trifluoromethyl)-1,2-dihydropyridine-3-carboxylic acid (95 mg, 460 μmol) and Compound 409-7 (100 mg, 460 μmol) in DCM (8 mL) was added TEA (139 mg, 1.4 mmol) at 25° C., followed by T₃P (586 mg, 920 μmol, 50% purity). The resulting mixture was stirred at 25° C. for 2 hrs. LCMS showed the reaction was completed. The reaction mixture was poured into H₂O (5 mL) and extracted with DCM (3 mL×5). The combined organic layers were dried over Na₂SO₄, filtered and concentrated under reduced pressure to give a residue, which was purified by prep-HPLC to give Compound 409 (24.38 mg, 58 μmol, 13% yield, it was a mixture of diastereoisomers) as a white solid. M−H⁻=405.0 (LCMS), ¹H NMR (400 MHz, CHLOROFORM-d) δ=9.55-9.38 (m, 1H), 8.90-8.55 (m, 1H), 7.15-7.02 (m, 1H), 6.94-6.84 (m, 1H), 6.74-6.60 (m, 2H), 5.70-5.19 (m, 1H), 4.44-3.77 (m, 1H), 2.37-2.16 (m, 5H), 2.09 (br d, J=12.7 Hz, 1H), 1.98-1.61 (m, 2H), 1.47-1.11 (m, 4H).

Example 70: Synthesis of N-(3-amino-6-methoxy-9H-thioxanthen-9-yl)-6-(difluoromethyl)-2-oxo-1,2-dihydropyridine-3-carboxamide (410)

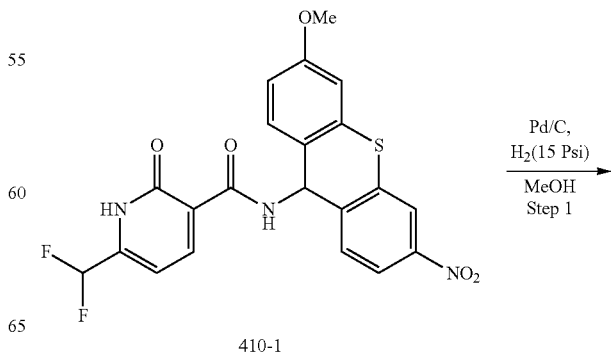

410-1

781
-continued

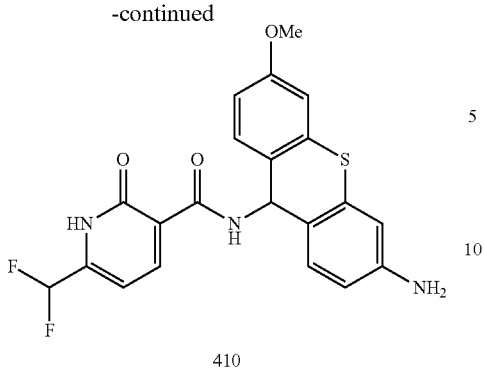

410

Step 1: N-(3-amino-6-methoxy-9H-thioxanthen-9-yl)-6-(difluoromethyl)-2-oxo-1, 2-dihydropyridine-3-carboxamide (410)

A mixture of Compound 410-1 (60 mg, 130.6 μmol) in MeOH (10 mL) was added Pd/C (0.1 g, 130.6 μmol, 10% purity) and degassed with $H_2$ for three times. The mixture was stirred at 25° C. for 0.5 hr under $H_2$. LCMS showed the reaction was completed and desired mass was detected. The suspension was filtered through a pad of Celite and the pad was washed with MeOH (5 mL×2). The combined filtrates were concentrated to dryness to give a residue, which was purified by prep-HPLC to give Compound 410 (5 mg, 11.6 μmol, 9% yield) as an orange solid. M–H⁻=428.2 (LCMS); $^1$H NMR (400 MHz, DMSO-$d_6$) δ=10.18 (br s, 1H), 8.40 (d, J=7.3 Hz, 1H), 7.44 (d, J=8.6 Hz, 1H), 7.20 (d, J=8.3 Hz, 1H), 7.06 (d, J=2.6 Hz, 1H), 7.04-6.74 (m, 3H), 6.68 (d, J=2.1 Hz, 1H), 6.49 (dd, J=2.2, 8.2 Hz, 1H), 6.08 (d, J=8.3 Hz, 1H), 5.30 (br s, 1H), 3.76 (s, 3H).

Other compounds made in a similar manner are shown in Table 40.

Example 71: Synthesis of N-(2-cyclopentyl-1-(p-tolyl)ethyl)-2-oxo-6-(trifluoromethyl)-1,2-dihydropyridine-3-carboxamide (412)

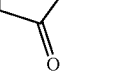

412-1

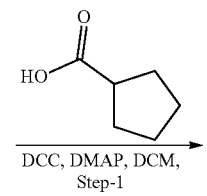

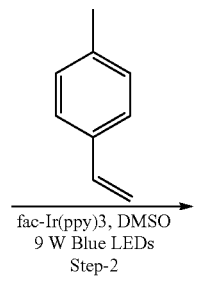

412-2

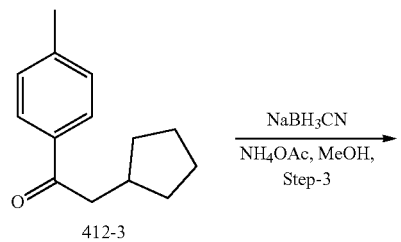

412-3

TABLE 40

| Compound No | Structure | HNMR and Ms |
|---|---|---|
| 411 | OMe (structure shown) | $^1$H NMR (400 MHz, DMSO-$d_6$) δ = 8.31 (br d, J = 7.3 Hz, 1H), 7.42 (d, J = 8.6 Hz, 1H), 7.19 (d, J = 8.2 Hz, 1H), 7.04 (d, J = 2.3 Hz, 1H), 6.97 (br s, 1H), 6.83 (dd, J = 2.4, 8.4 Hz, 1H), 6.68 (d, J = 2.0 Hz, 1H), 6.49 (dd, J = 2.1, 8.3 Hz, 1H), 6.01 (s, 1H), 3.74 (s, 3H) ESI [M – H] = 446.1 |

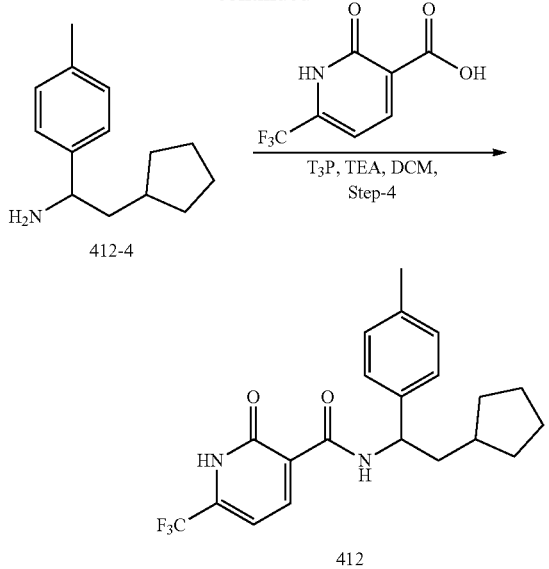

Step 1: 1,3-dioxoisoindolin-2-yl cyclopentanecarboxylate (412-2)

Cyclopentanecarboxylic acid (1 g, 8.8 mmol) and DMAP (53 mg, 438.0 μmol) in DCM (18 mL) were mixed in a flask. Compound 412-1 (1.7 g, 10.5 mmol) and DCC (2.2 g, 10.5 mmol) in DCM (6 mL) was added slowly at 25° C. Then the reaction mixture was stirred at 25° C. for 3 hrs. TLC showed the reaction was completed. The white solid was filtered off and the filtrate was concentrated under reduced pressure to give a residue, which was purified by flash silica gel chromatography (Ethyl acetate/Petroleum ether gradient) to give Compound 412-2 (1.2 g, 53% yield) as a white solid.

Step 2: 2-cyclopentyl-1-(p-tolyl)ethanone (412-3)

Compound 412-2 (617 mg, 2.4 mmol) and Ir(PPY)$_3$ (249 mg, 380.8 μmol) were added to a stirring bar and purged with N$_2$ three times. In the absence of light, DMSO (18 mL) and 1-methyl-4-vinyl-benzene (225 mg, 1.9 mmol) were added and the flask was sealed. The mixture was stirred under irradiation from 9 W Blue LEDs and stirred at 25° C. for 12 hrs. TLC the reaction was completed. The reaction mixture was poured into ice-water (15 mL) and extracted with EtOAc (10 mL×5). The combined organic layers dried over Na$_2$SO$_4$, filtered and concentrated under reduced pressure to give a residue, which was purified by flash silica gel chromatography (Ethyl acetate/Petroleum ether gradient) to give Compound 412-3 (120 mg, 31% yield) as a yellow gum. 1H NMR (400 MHz, CHLOROFORM-d) δ=7.87 (d, J=8.2 Hz, 2H), 7.28-7.23 (m, 2H), 2.96 (d, J=7.1 Hz, 2H), 2.42 (s, 3H), 1.88 (dt, J=6.7, 11.4 Hz, 2H), 1.70-1.52 (m, 5H), 1.25-1.13 (m, 2H).

Step 3: 2-cyclopentyl-1-(p-tolyl)ethanamine (412-4)

To a stirred solution of Compound 412-3 (80 mg, 395.5 μmol) in MeOH (6 mL) was added NH$_4$OAc (366 mg, 4.8 mmol). The reaction was stirred at 25° C. for 10 min. Then NaBH$_3$CN (99 mg, 1.6 mmol) was added and the reaction was heated to 60° C. and stirred at 60° C. for 12 hrs. LCMS showed the desired mass was detected. The reaction mixture was poured into H$_2$O (10 mL) and extracted with EtOAc (5 mL×5). The combined organic layers were dried over Na$_2$SO$_4$ filtered and concentrated under reduced pressure to give a Compound 412-4 (50 mg, 62.2% yield) as yellow oil. Fragment Ms=187.1 (LCMS).

Step 4: N-(2-cyclopentyl-1-(p-tolyl)ethyl)-2-oxo-6-(trifluoromethyl)-1,2-dihydropyridine-3-carboxamide (412)

To a mixture of Compound 412-4 (25 mg, 104.3 μmol, HCl), 2-oxo-6-(trifluoromethyl)-1,2-dihydropyridine-3-carboxylic acid (24 mg, 115 μmol) in DCM (3 mL) was added TEA (32 mg, 312.8 μmol), T$_3$P (133 mg, 208.5 μmol, 50% purity). The mixture was stirred at 25° C. for 2 hrs. LCMS showed the reaction was completed and the desired mass was detected. The reaction mixture was poured into H$_2$O (5 mL) and extracted with EtOAc (5 mL×3). The combined organic layers were dried over Na$_2$SO$_4$, filtered and concentrated under reduced pressure to give a residue, which was purified by Prep-TLC (Petroleum ether:Ethyl acetate=3:1) to give Compound 412 (20 mg, 46.0% yield) as a white solid. M-H$^-$=391.1 (LCMS); 1H NMR (400 MHz, METHANOL-d4) δ=8.45 (d, J=7.5 Hz, 1H), 7.27-7.20 (m, 2H), 7.16-7.11 (m, 2H), 7.02 (br d, J=6.6 Hz, 1H), 5.09-5.03 (m, 1H), 2.35-2.27 (m, 3H), 1.96-1.88 (m, 1H), 1.86-1.71 (m, 4H), 1.68-1.57 (m, 2H), 1.56-1.44 (m, 2H), 1.26-1.08 (m, 2H).

Example 72: Synthesis of N-(2,7-bis(trifluoromethoxy)-9H-fluoren-9-yl)-2-oxo-6-(trifluoromethyl)-1,2-dihydropyridine-3-carboxamide (413)

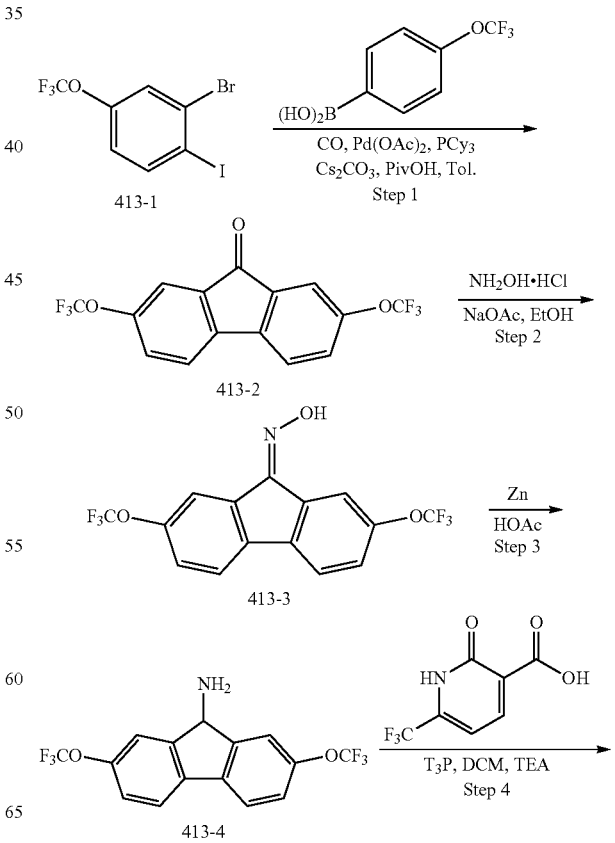

-continued

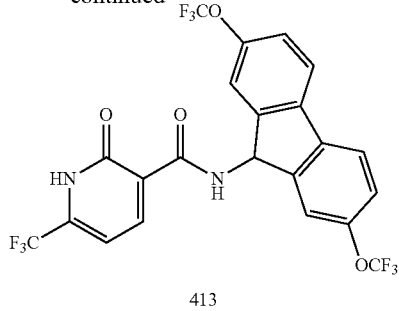

413

Step 1: 2,7-bis(trifluoromethoxy)-9H-fluoren-9-one (413-2)

(4-(trifluoromethoxy)phenyl)boronic acid (0.5 g, 2.4 mmol), $Cs_2CO_3$ (2 g, 6.1 mmol), $Pd(OAc)_2$, (55 mg, 243 μmol), $PCy_3$ (68 mg, 243 μmol) was added to a mixture of Compound 413-1 (742 mg, 2 mmol) and 2,2-dimethylpropanoic acid (248 mg, 2.4 mmol) in toluene (20 mL) under $Ar_2$. The mixture was stirred at 100° C. under CO (15 Psi) for 5 hrs. LCMS showed the reaction was completed and desired mass was detected. The reaction mixture was poured into Sat.$NH_4Cl$ (30 mL) and extracted with EtOAc (20 mL×3). The combined organic layers were dried over $Na_2SO_4$, filtered and concentrated under reduced pressure to give a residue. The residue was purified by column chromatography to give Compound 413-2 (350 mg, crude) as brown oil. M+H$^+$=351.0 (LCMS); $^1$H NMR (400 MHz, $CDCl_3$) δ=7.63-7.50 (m, 4H), 7.37 (dd, J=1.3, 8.2 Hz, 2H).

Step 2: 2,7-bis(trifluoromethoxy)-9H-fluoren-9-one oxime (413-3)

To a solution of Compound 413-2 (300 mg, 862 μmol) in EtOH (5 mL) was added $NH_2OH·HCl$ (120 mg, 1.7 mmol) and NaOAc (141 mg, 1.7 mmol). The mixture was stirred at 80° C. for 12 hrs. LCMS showed the reaction was completed and desired mass was detected. The reaction mixture was quenched by addition $H_2O$ (5 mL) and extracted with EtOAc (5 mL×3). The combined organic layers were dried over $Na_2SO_4$, filtered and concentrated under reduced pressure to give a residue. The residue was purified by prep-TLC to give Compound 413-3 (170 mg, crude) as a yellow solid. M+H$^+$=351.0 (LCMS);

Step 3: 2,7-bis(trifluoromethoxy)-9H-fluoren-9-amine (413-4)

A mixture of Compound 413-4 (100 mg, 275 μmol) and Zn (54 mg, 826 μmol) in AcOH (3 mL) was stirred at 100° C. for 1 hr. LCMS showed the reaction was completed and desired mass was detected. The reaction mixture was concentrated under $N_2$ and poured into Sat. $NaHCO_3$ aq. (5 mL) and extracted with EtOAc (5 mL×3). The combined organic layers were dried over $Na_2SO_4$, filtered and concentrated under reduced pressure to give Compound 413-4 (100 mg, crude) as a light brown solid. M+H$^+$=350.0 (LCMS).

Step 4: N-(2,7-bis(trifluoromethoxy)-9H-fluoren-9-yl)-2-oxo-6-(trifluoromethyl)-1,2-dihydropyridine-3-carboxamide (413)

To a solution of Compound 413-4 (100 mg, 286 μmol) and 2-oxo-6-(trifluoro methyl)-1,2-dihydropyridine-3-carboxylic acid (70 mg, 338 μmol) in DCM (3 mL) was added TEA (87 mg, 859 mol) and $T_3P$ (364 mg, 573 μmol, 50% purity). The mixture was stirred at 25° C. for 12 hrs. The reaction mixture was quenched by addition $H_2O$ (5 mL) and extracted with EtOAc (5 mL×3). The combined organic layers were dried over $Na_2SO_4$, filtered and concentrated under reduced pressure to give a residue. The residue was purified by prep-HPLC to give Compound 413 (32 mg, 58.9 μmol, 21% yield) as a light yellow solid. M−H$^-$=537.0 (LCMS); $^1$H NMR (400 MHz, DMSO-$d_6$) δ=14.01-12.36 (m, 1H), 9.94-9.42 (m, 1H), 8.41 (d, J=7.5 Hz, 1H), 8.06 (d, J=8.4 Hz, 2H), 7.56 (s, 2H), 7.48 (br d, J=8.2 Hz, 2H), 7.32 (br d, J=6.8 Hz, 1H), 6.26 (d, J=7.7 Hz, 1H).

Other compounds made in a similar manner are shown in Table 41.

TABLE 41

| Compound No | Structure | HNMR and Ms |
|---|---|---|
| 414 | ![structure] | $^1$H NMR (400 MHz, DMSO-$d_6$) δ = 8.25 (d, J = 7.5 Hz, 1H), 8.10 (d, J = 7.9 Hz, 1H), 8.00 (d, J = 7.6 Hz, 1H), 7.88-7.75 (m, 2H), 7.60 (d, J = 7.5 Hz, 1H), 7.53-7.48 (m, 1H), 7.47-7.40 (m, 1H), 6.73 (br d, J = 7.3 Hz, 1H), 6.27 (s, 1H). ESI [M − H] = 437.0 |

TABLE 41-continued

| Compound No | Structure | HNMR and Ms |
|---|---|---|
| 415 | 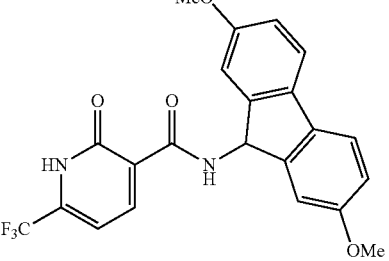 | ¹H NMR (400 MHz, DMSO-d₆) δ = 8.47 (d, J = 7.6 Hz, 1H), 7.67 (d, J = 8.4 Hz, 2 H), 7.30 (m, 1H), 7.10 (m, 2H), 6.98-6.95 (m, 2H), 6.11 (d, J = 6.11 Hz, 1H), 3.77 (s, 6H). ESI [M − H] = 429.1 |
| 416 | 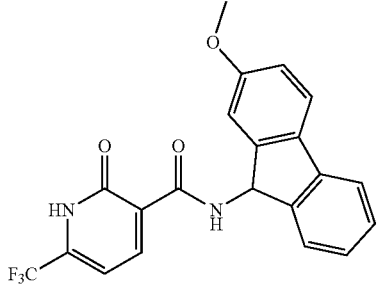 [SMILES: COc1ccc2c(c1)C(NC(=O)c1ccc(C(F)(F)F)[nH]c1=O)c1ccccc1-2] | 1H NMR (400 MHz, DMSO-d6) δ = 13.46 (br s, 1H), 9.50 (br s, 1H), 8.48 (br d, J = 7.5 Hz, 1H), 7.84-7.73 (m, 2H), 7.53 (br d, J = 7.3 Hz, 1H), 7.40 (br t, J = 7.4 Hz, 1H), 7.34-7.22 (m, 2H), 7.15 (s, 1H), 7.02 (br d, J = 8.3 Hz, 1H), 6.17 (br d, J = 8.1 Hz, 1H), 3.79 (s, 3H). ESI [M − H] = 399.1 |
| 417 | 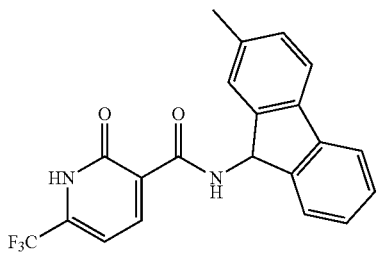 | 1H NMR (400 MHz, DMSO-d6) δ = 9.57 (d, J = 8.0 Hz, 1H), 8.75 (d, J = 7.6 Hz, 1H), 7.68 (d, J = 7.2 Hz, 1H), 7.61-7.58 (m, 2H), 7.43-7.39 (m, 2H), 7.28-7.21 (m, 2H), 6.85 (d, J = 7.2 Hz, 1H), 6.31 (d, J = 8.4 Hz, 1H), 2.38 (s, 3H). ESI [M − H] = 383.1 |
| 418 | 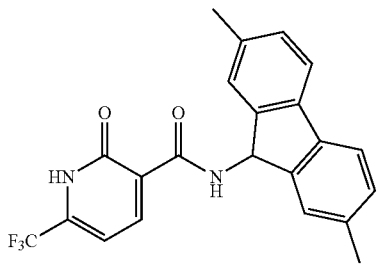 [SMILES: Cc1ccc2c(c1)C(NC(=O)c1ccc(C(F)(F)F)[nH]c1=O)c1cc(C)ccc1-2] | 1H NMR (400 MHz, DMSO-d6) δ = 9.49 (br s, 1H), 8.75 (d, J = 7.6 Hz, 1H), 7.56 (d, J = 7.6 Hz, 2H), 7.4 (s, 2H), 7.20 (d, J = 7.6 Hz, 2H), 6.86 (d, J = 7.6 Hz, 1H), 6.28 (d, J = 8.0 Hz, 1H), 2.37 (s, 6H). ESI [M − H] = 397.1 |

Example 73: Synthesis of N-((3-(methylamino)phenyl)(p-tolyl)methyl)-2-oxo-6-(trifluoromethyl)-1,2-dihydropyridine-3-carboxamide (419)

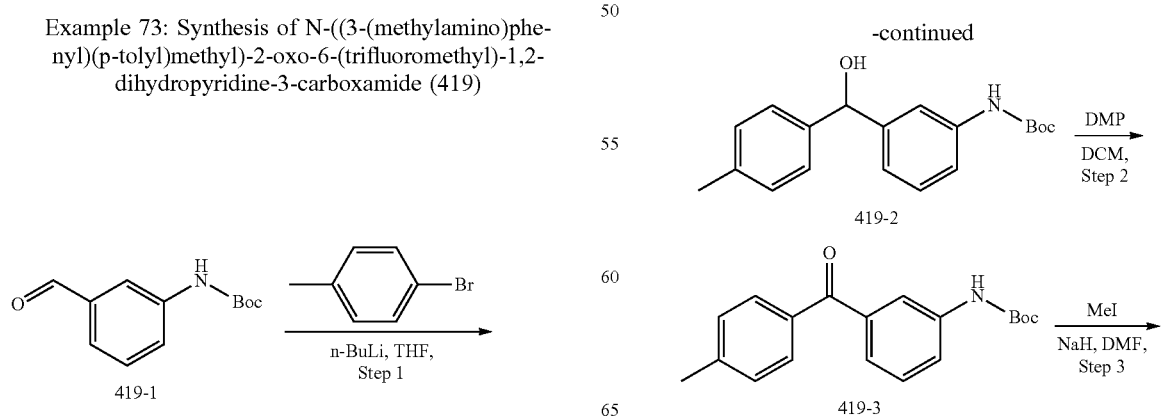

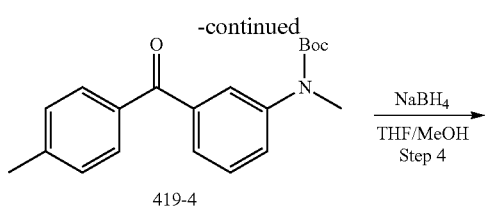

419-4

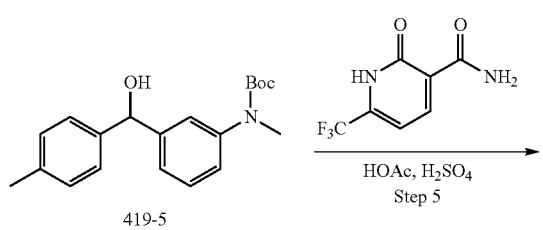

419-5

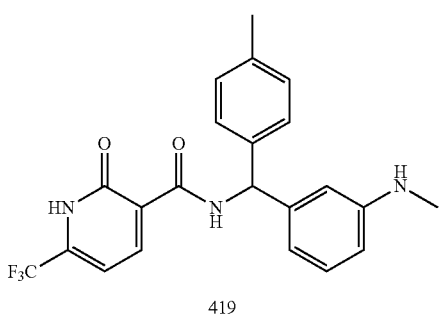

419

Step 1: tert-butyl (3-(hydroxy(p-tolyl)methyl)phenyl)carbamate (419-2)

To a stirred solution of 1-bromo-4-methylbenzene (580 mg, 3.4 mmol) in THF (10 mL) was added n-BuLi (2.5 M, 1.36 mL) at −78° C. and stirred for 0.5 hr, then Compound 419-1 (500 mg, 2.3 mmol) in THF (5 mL) was added. The resulting mixture was stirred at −78° C. for 2 hrs. TLC showed that most of the starting material had been consumed and a new spot was formed. The reaction mixture was poured into water (15 mL) and extracted with EtOAc (10 mlx5) and dried over Na$_2$SO$_4$, filtered and concentrated under reduced pressure to give a residue, which was purified by flash silica gel chromatography (Ethyl acetate/Petroleum ethergradient) to give Compound 419-2 (350 mg, crude) as yellow oil.

Step 2: tert-butyl (3-(4-methylbenzoyl)phenyl)carbamate (419-3)

To a stirred solution of Compound 419-2 (350 mg, 1.12 mmol) in DCM (10 mL) was added Dess-Martin (711 mg, 1.7 mmol) at 25° C. The mixture was stirred at 25° C. for 12 hrs. LCMS showed the reaction was completed and a main peak with desired mass was detected. The reaction mixture was poured into Sat.Na$_2$SO$_3$ (10 mL), and then extracted with DCM (5 mL×4). The combined organic layers were washed with Sat.NaHCO$_3$ (5 mL×2), dried over Na$_2$SO$_4$, filtered and concentrated under reduced pressure to give Compound 419-3 (200 mg, crude) as a yellow solid. [M+1-56]$^+$=256.0 (LCMS).

Step 3: tert-butyl methyl(3-(4-methylbenzoyl)phenyl)carbamate (419-4)

To a solution of Compound 419-3 (200 mg, 642.3 μmol) in THF (10 mL) was added NaH (39 mg, 963.5 μmol, 60% purity) at 0° C., then MeI (137 mg, 963.5 μmol,) in THF (3 mL) was added and the resulting mixture was stirred at 25° C. for 1 h. LCMS showed the reaction was completed and a main peak with desired mass was detected. The reaction mixture was poured into H$_2$O (15 mL), and then extracted with EtOAc (10 mL×4). The combined organic layers were dried over Na$_2$SO$_4$, filtered and concentrated under reduced pressure to give Compound 419-4 (200 mg) as a crude yellow solid. M+23$^+$=348.3 (LCMS).

Step 4: tert-butyl (3-(hydroxy(p-tolyl) methyl) phenyl)(methyl) carbamate (419-5)

To a stirred solution of Compound 419-4 (84 mg, 256.9 μmol) in THF (3 mL) and MeOH (3 mL) was added NaBH$_4$ (29 mg, 770.8 μmol) at 0° C. The resulting mixture was stirred at 25° C. for 30 min. TLC showed the reaction was completed. The mixture was poured into H$_2$O (3 mL) and extracted with EtOAc (2 mL×4). The combined organic layers were dried over Na$_2$SO$_4$, filtered and concentrated under reduced pressure to give Compound 419-5 (80 mg, crude) as a white solid.

Step 5: N-((3-(methylamino)phenyl) (p-tolyl)methyl)-2-oxo-6-(trifluoromethyl)-1,2-dihydropyridine-3-carboxamide (419)

A solution of Compound 419-5 (80 mg, 244.3 μmol) and 2-oxo-6-(trifluoromethyl)-1,2-dihydropyridine-3-carboxamide (50 mg, 244.3 μmol) in HOAc (3 mL) was stirred at 25° C. for 20 mins. Then to the mixture was added H$_2$SO$_4$ (24 mg, 244.3 μmol) and the mixture was stirred at 100° C. for 10 mins. LCMS showed the reaction was completed and a main peak with desired mass was detected. The reaction mixture was concentrated in vacuum to give a residue, which was dissolved with CH$_3$CN. The mixture was filtered and the filtrate was concentrated under reduced pressure to give a residue, which was purified by Prep-HPLC (NH$_3$·H$_2$O system) to give Compound 419 (3 mg, 6.91 μmol, 2.83% yield) as a yellow solid. M−H$^-$=414.1 (LCMS); $^1$H NMR (400 MHz, CDCl$_3$) δ=10.03-10.01 (d, J=8 Hz, 1H), 8.70-8.68 (d, J=7.2 Hz, 1H), 7.24-7.11 (m, 5H), 6.88-6.86 (d, J=7.2 Hz, 1H), 6.69-6.66 (d, J=7.6 Hz, 1H), 6.56-6.52 (m, 1H), 6.35-6.33 (d, J=8 Hz, 1H), 2.80 (s, 3H), 2.33 (s, 3H).

Other compounds made in a similar manner are shown in Table 42.

TABLE 42

| Compound No | Structure | HNMR and Ms |
|---|---|---|
| 420 | 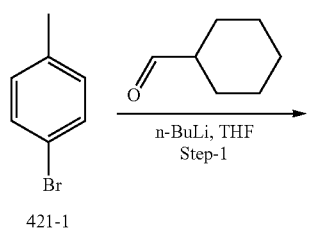 | ¹H NMR (400 MHz, CDCl3) δ = 9.97-9.95 (d, J = 8.4 Hz, 1H), 8.69-8.75 (m, 1H), 7.22-7.20 (d, J = 8 Hz, 1H), 7.13-7.11 (m, 4H), 6.88-6.86 (d, J = 7.2 Hz, 1H), 6.58-6.55 (m, 2H), 6.34-6.31 (d, J = 8 Hz, 1H), 2.81 (s, 3H), 2.32 (s, 3H). ESI [M − H] = 414.1 |

Example 74: Synthesis of N-(cyclohexyl(p-tolyl)methyl)-2-oxo-6-(trifluoromethyl)-1,2-dihydropyridine-3-carboxamide (421)

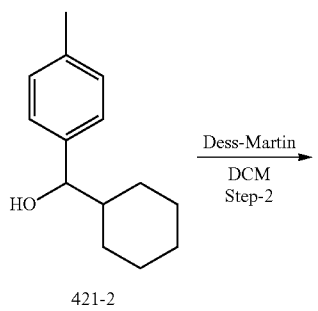

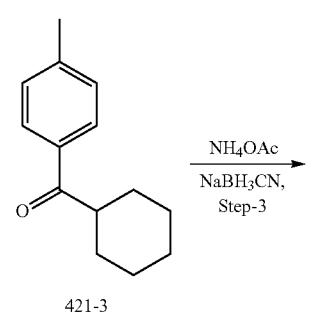

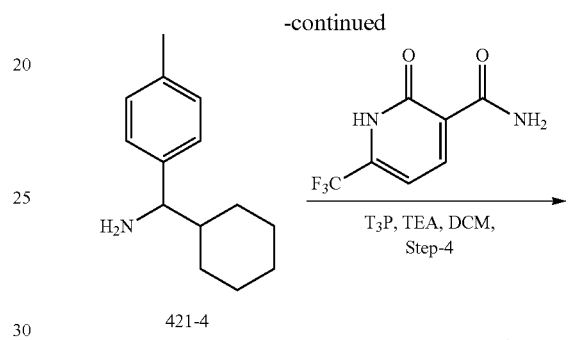

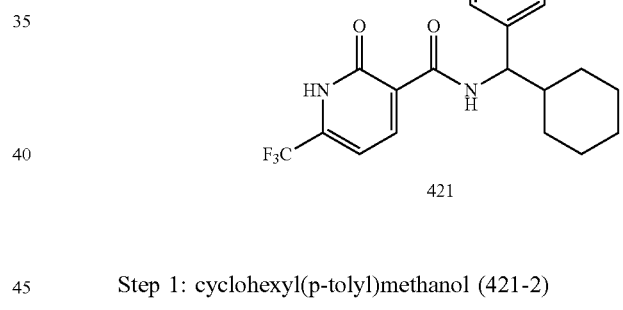

Step 1: cyclohexyl(p-tolyl)methanol (421-2)

To a solution of Compound 421-1 (1 g, 5.89 mmol) in THF (10 mL) was added n-BuLi (2.5 M, 2.34 mL) at −78° C., and stirred at −78° C. for 0.5 hr under N₂ then added cyclohexanecarbaldehyde (596 mg, 5.3 mmol) in THF (5 mL) and stirred at −78° C. for 2 hrs under N₂. LCMS showed the reaction was completed and desired mass was detected. The reaction mixture was poured into ice-water (20 mL) at 0° C. and extracted with EtOAc (25 mL×2). The combined organic layers were dried over Na₂SO₄ filtered and concentrated under reduced pressure to give a residue which was purified by flash silica gel chromatography (Ethyl acetate/Petroleum ether gradient) to give Compound 421-2 (600 mg, 55.2% yield) obtained as a colorless gum. Fragment Ms=187.1 (LCMS).

Step 2: cyclohexyl(p-tolyl)methanone (421-3)

To a solution of Compound 421-2 (300 mg, 1.5 mmol) in DCM (30 mL) was added Dess-Martin (934 mg, 2.2 mmol). The mixture was stirred at 25° C. for 0.5 hr. LCMS showed the reaction was completed and the desired mass was detected. The reaction mixture was quenched by addition Sat.Na$_2$SO$_3$ (10 mL) then extracted with DCM (5 mL×4). The combined organic layers were washed with Sat-.NaHCO$_3$ (5 mL×2), dried over Na$_2$SO$_4$, filtered and concentrated under reduced pressure to give a Compound 421-3 (300 mg, crude) as a white solid. M+H$^+$=203.1 (LCMS).

Step 3: cyclohexyl(p-tolyl)methanamine (421-4)

To a stirred solution of Compound 421-3 (150 mg, 741.5 µmol) was dissolved in MeOH (9 mL) and then NH$_4$OAc (686 mg, 8.9 mmol) was added. Then the reaction was stirred at 25° C. for 10 min. NaBH$_3$CN (187 mg, 3.0 mmol) was added and the reaction was heated to 60° C. and stirred at 60° C. for 24 hrs. LCMS showed the reaction was completed and desired mass was detected. Then the reaction mixture was quenched by addition H$_2$O (10 mL) at 15° C. and extracted with EtOAc (10 mL×5). The combined organic layers were dried over Na$_2$SO$_4$, filtered and concentrated under reduced pressure to give Compound 421-4 (150 mg, 99% yield) as a white gum, which was used for next step directly. M+H$^+$=187.1 (LCMS).

Step 4: N-(cyclohexyl(p-tolyl)methyl)-2-oxo-6-(trifluoromethyl)-1,2-dihydropyridine-3-carboxamide (421)

To a solution of Compound 421-4 (150 mg, 737.7 µmol) and 2-oxo-6-(trifluoro methyl)-1,2-dihydropyridine-3-carboxamide (153 mg, 737.7 µmol) in DCM (5 mL) was added TEA (112 mg, 1.1 mmol) and T$_3$P (1.4 g, 2.2 mmol, 50% purity). The mixture was stirred at 25° C. for 2 hrs. LCMS showed the reaction was completed and the desired mass was detected. The reaction mixture was poured into H$_2$O (5 mL) at 25° C. then extracted with EtOAc (5 mL×5). The combined organic layers were dried over Na$_2$SO$_4$, filtered and concentrated under reduced pressure to give a residue, which was purified by prep-HPLC to give Compound 421 (33 mg, 12% yield) as a white solid. M−H$^-$=391.1 (LCMS); 1H NMR (400 MHz, CHLOROFORM-d) δ=13.44-13.06 (m, 1H), 9.85 (br d, J=8.4 Hz, 1H), 8.69 (d, J=7.3 Hz, 1H), 7.22-7.17 (m, 2H), 7.15-7.10 (m, 2H), 6.92 (d, J=7.5 Hz, 1H), 4.93 (t, J=8.4 Hz, 1H), 2.32 (s, 3H), 1.92 (br d, J=12.3 Hz, 1H), 1.81-1.60 (m, 5H), 1.29-0.95 (m, 5H).

Example 75: Synthesis of N-(2-cyclohexyl-1-(p-tolyl)ethyl)-2-oxo-6-(trifluoromethyl)-1,2-dihydropyridine-3-carboxamide (422)

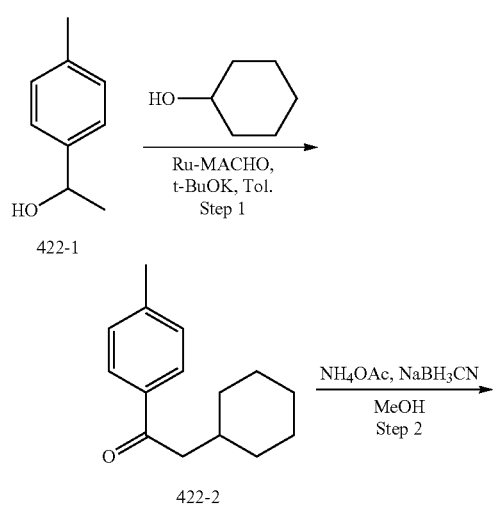

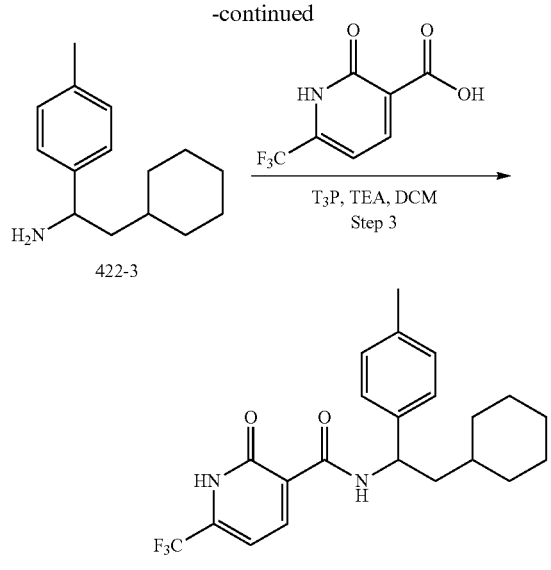

Step 1: 2-cyclohexyl-1-(p-tolyl)ethanone (422-2)

To a stirred solution of Compound 422-1 (700 mg, 5.1 mmol), cyclohexanol (515 mg, 5.1 mmol) in Toluene (15 mL) was added t-BuOK (29 mg, 257 µmol) and Ru-MACHO (35 mg, 51 µmol) under N$_2$. The mixture was stirred at 115° C. for 4 hrs. LCMS showed the reaction was completed and the desired mass was detected. The residue was poured into H$_2$O (15 mL) and extracted with EtOAc (10 mL×4). The combined organic layers were dried over Na$_2$SO$_4$, filtered and concentrated under reduced pressure to give a residue, which was purified by column chromatography (Petroleum ether/Ethyl acetate) to give Compound 422-2 (330 mg, 1.5 mmol, 30% yield) as a yellow oil. M+H$^+$=217.2 (LCMS), $^1$H NMR (400 MHz, CHLOROFORM-d) δ=7.86 (d, J=8.2 Hz, 2H), 7.25 (d, J=8.2 Hz, 2H), 2.80 (d, J=6.8 Hz, 2H), 2.42 (s, 3H), 1.97 (tqd, J=3.5, 7.2, 14.5 Hz, 1H), 1.81-1.62 (m, 5H), 1.39-1.18 (m, 3H), 1.09-0.93 (m, 2H).

Step 2: 2-cyclohexyl-1-(p-tolyl)ethanamine (422-3)

To a stirred solution of Compound 422-2 (150 mg, 693 µmol) in MeOH (10 mL) was added NH$_4$OAc (641 mg, 8.3 mmol), the reaction was stirred for 10 min at 25° C., then NaBH$_3$CN (174 mg, 2.8 mmol) was added and the reaction was heated to 60° C. and stirred at 60° C. for 12 hrs. LCMS showed lost of starting material was remained. Then the mixture was stirred another 12 hrs at 60° C. LCMS showed the reaction was completed. The reaction mixture was poured into H$_2$O (10 mL) and extracted with DCM (5 mL×3). The combined organic layers were dried over Na$_2$SO$_4$, filtered and concentrated under reduced pressure to give a Compound 422-3 (150 mg, 690 µmol, crude) as a colorless gum. M+H$^+$=218.3 (LCMS).

Step 3: N-(2-cyclohexyl-1-(p-tolyl)ethyl)-2-oxo-6-(trifluoromethyl)-1,2-dihydropyridine-3-carboxamide (422)

To a stirred solution of 2-oxo-6-(trifluoromethyl)-1,2-dihydropyridine-3-carboxylic acid (76 mg, 368 µmol) and Compound 422 (80 mg, 368 μmol) in DCM (5 mL) was added TEA (56 mg, 552 μmol) at 25° C., followed by T₃P (257 mg, 405 μmol, 50% purity). The resulting mixture was stirred at 25° C. for 2 hrs. LCMS showed the reaction was completed and the desired mass was detected. The reaction mixture was poured into H₂O (10 mL) and extracted with DCM (5 mL×5). The combined organic layers were dried over Na₂SO₄, filtered and concentrated under reduced pressure to give a residue, which was purified by prep-TLC (Petroleum ether/Ethyl acetate=3/1) to give Compound 422 (26.51 mg, 64 μmol, 18% yield) as a white solid. M−H⁻= 405.1 (LCMS), 1H NMR (400 MHz, CHLOROFORM-d) δ=13.60-13.05 (m, 1H), 9.71 (br d, J=7.2 Hz, 1H), 8.67 (d, J=7.3 Hz, 1H), 7.24 (d, J=8.1 Hz, 2H), 7.14 (d, J=7.9 Hz, 2H), 6.91 (d, J=7.5 Hz, 1H), 5.32-5.02 (m, 1H), 2.32 (s, 3H), 1.89-1.74 (m, 3H), 1.73-1.60 (m, 4H), 1.41-1.30 (m, 1H), 1.24-1.11 (m, 3H), 1.07-0.87 (m, 2H).

Example 76: Synthesis of 6-(1,1-difluoroethyl)-2-oxo-N-(9H-thioxanthen-9-yl)-1,2-dihydropyridine-3-carboxamide (423)

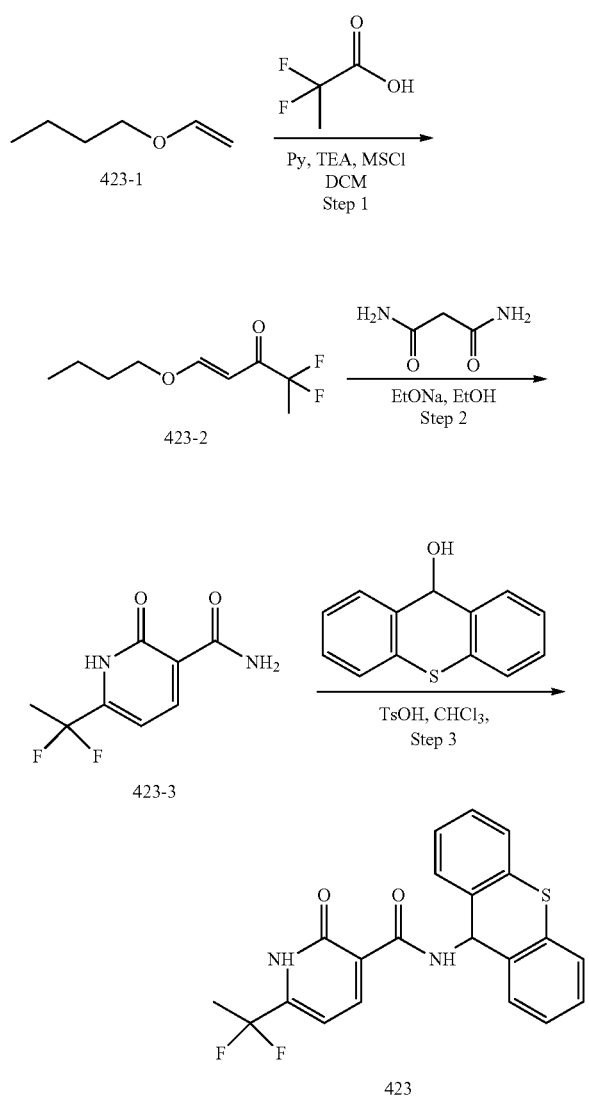

Step 1: (E)-1-butoxy-4,4-difluoropent-1-en-3-one (423-2)

To a solution of 2,2-difluoropropanoic acid (500 mg, 4.5 mmol) in DCM (10 mL) was added Py (359 mg, 4.5 mmol), TEA (552 mg, 5.5 mmol), Compound 423-1 (455 mg, 4.5 mmol) and MsCl (520 mg, 4.5 mmol) at 0° C. The mixture was stirred at 25° C. for 30 hrs. TLC indicated the reaction was completed. 10 mL of ice-water was added to the reaction mixture, and the mixture was extracted with 10 ml of chloroform. The obtained organic layer was washed with 10 mL of HCl (1 M) and 10 mL of a Sat. NaHCO₃ aq, dried over MgSO₄, concentrated under reduced pressure to give a residue, which was purified by column chromatography to give Compound 423-2 (550 mg, crude) as light brown oil.

Step 2: 6-(1,1-difluoroethyl)-2-oxo-1,2-dihydropyridine-3-carboxamide (423-3)

To a stirred solution of Compound 423-3 (550 mg, 1.8) in EtOH (7 mL) was added malonamide (292 mg, 2.9 mmol) and EtONa/EtOH (974 mg, 2.9 mmol) at 0° C. The mixture was stirred at 80° C. for 3 hrs. LCMS showed the reaction was completed and desired mass was detected. The reaction mixture was quenched by addition H₂O (15 mL), and washed with EtOAc (10 mL×3). The water phase was neutralized with HCl solution (1 M) to pH=4 and filtered. The cake was dried in vacuum to give Compound Compound 423-3 (160 mg, 43% yield) as a light brown solid. M+H⁺=203.0 (LCMS); ¹H NMR (400 MHz, DMSO-d₆) δ=13.26-12.62 (m, 1H), 9.15-8.62 (m, 1H), 8.37 (d, J=7.5 Hz, 1H), 7.91-7.41 (m, 1H), 7.14-6.20 (m, 1H), 1.99 (t, J=19.3 Hz, 3H).

Step 3: 6-(1,1-difluoroethyl)-2-oxo-N-(9H-thioxanthen-9-yl)-1,2-dihydropyridine-3-carboxamide (423)

A solution of 9H-thioxanthen-9-ol (100 mg, 466.7 μmol) in DCM (4 mL) was added to a mixture of Compound 423-3 (80 mg, 395.7 μmol) and TsOH.H₂O (113 mg, 593.6 μmol) in CHCl₃ (4 mL) at 70° C., the mixture was stirred at 70° C. for 5 mins. LCMS showed the reaction was completed and desired mass was detected. The reaction mixture was quenched by addition H₂O (10 mL) and extracted with DCM (10 mL×2). The combined organic layers were dried over Na₂SO₄, filtered and concentrated under reduced pressure to give a residue. The residue was purified by Prep-HPLC to give Compound 423 (26 mg, 64.9 μmol, 16% yield) as a white solid. M−H⁻=397.1 (LCMS); ¹H NMR (400 MHz, DMSO-d₆) δ=13.31-12.81 (m, 1H), 10.78-10.34 (m, 1H), 8.42 (d, J=7.3 Hz, 1H), 7.64-7.51 (m, 4H), 7.42-7.21 (m, 4H), 6.76 (br s, 1H), 6.16 (d, J=9.0 Hz, 1H), 2.00 (t, J=19.3 Hz, 3H).

Other compounds made in a similar manner are shown in Table 43.

TABLE 43
| Compound No | Structure | HNMR and Ms |
|---|---|---|
| 424 | 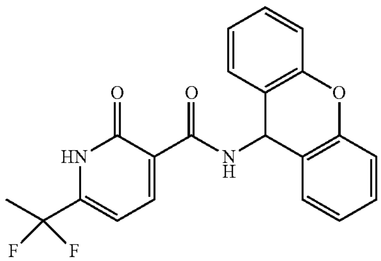 [SMILES: CC(F)(F)c1ccc(C(=O)NC2c3ccccc3Oc3ccccc32)c(=O)[nH]1] | $^1$H NMR (400 MHz, DMSO-d$_6$) δ = 12.36 (br d, J = 5.5 Hz, 1H), 8.14 (d, J = 7.5 Hz, 1H), 7.42 (d, J = 7.5 Hz, 2H), 7.38-7.26 (m, 2H), 7.23-7.07 (m, 4H), 6.48 (dd, J = 2.9, 8.2 Hz, 2H), 6.11 (br s, 1H), 1.82 (t, J = 19.0 Hz, 3H) ESI [M − H] = 381.1 |
Example 77: Synthesis of N-(3,6-dimethyl-10,10-dioxido-9H-thioxanthen-9-yl)-2-oxo-5-(piperazin-1-yl)-6-(trifluoromethyl)-1,2-dihydropyridine-3-carboxamide (425)
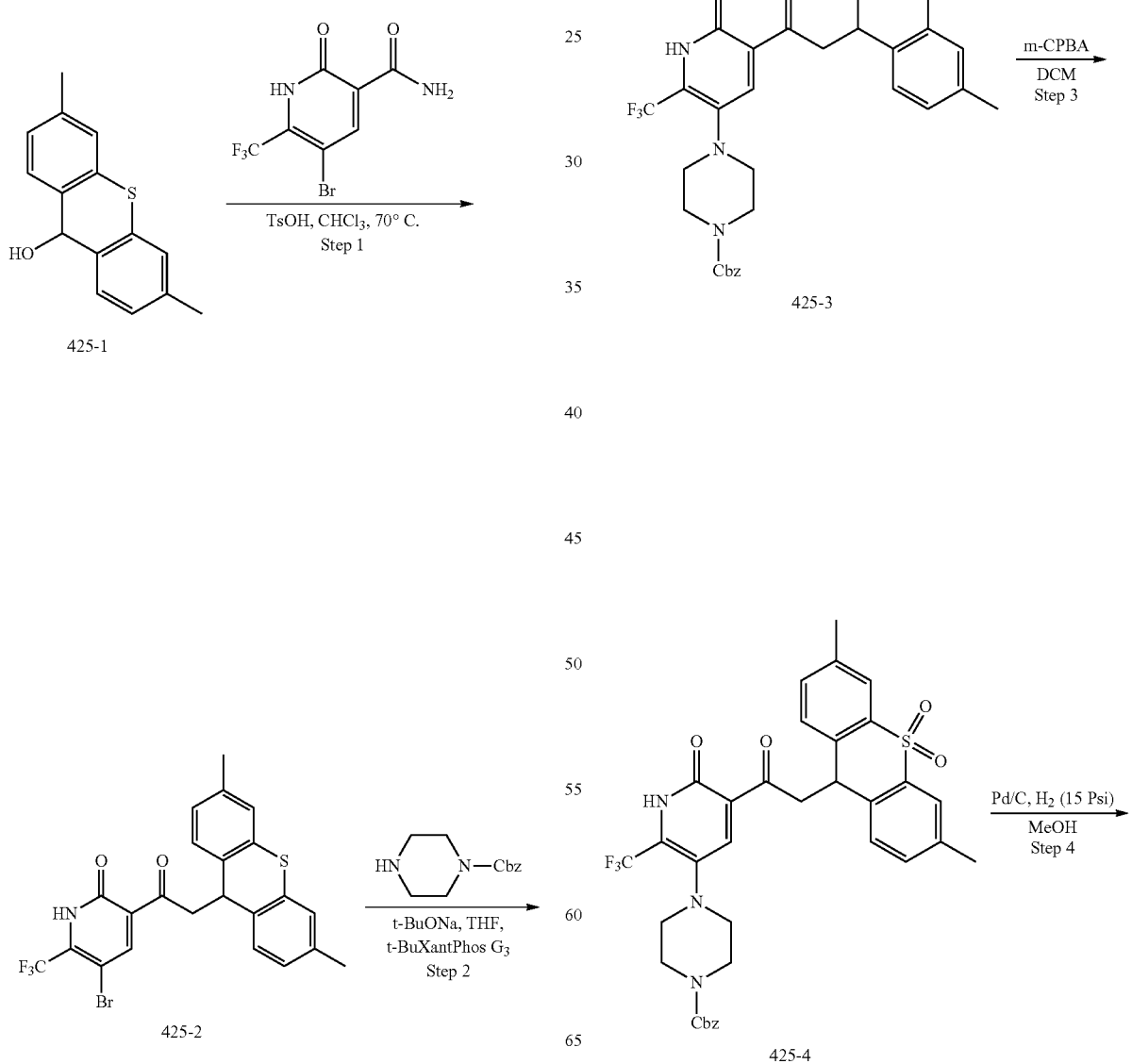

-continued

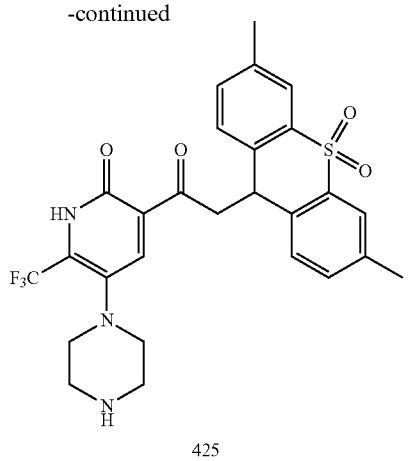

425

Step 1: 5-bromo-N-(3,6-dimethyl-9H-thioxanthen-9-yl)-2-oxo-6-(trifluoromethyl)-1, 2-dihydropyridine-3-carboxamide (425-2)

Compound 425-1 (500 mg, 2.1 mmol) in DCM (30 mL) was added to a mixture of 5-bromo-2-oxo-6-(trifluoromethyl)-1,2-dihydropyridine-3-carboxamide (500 mg, 1.8 mmol) and TsOH.H$_2$O (589 mg, 3.1 mmol) in CHCl$_3$ (15 mL) at 70° C. The mixture was stirred at 70° C. for 10 min. TLC indicated the reaction was complete. The reaction mixture was partitioned between water (10 mL) and DCM (30 mL). The organic phase was separated, dried over Na$_2$SO$_4$, filtered and concentrated under reduced pressure to give a residue, which was purified by Prep-TLC (Petroleum ether/Ethyl acetate=1/2) to give Compound 425-2 (0.1 g, 196.0 μmol) as a white solid.

Step 2: benzyl 4-(5-((3,6-dimethyl-9H-thioxanthen-9-yl)carbamoyl)-6-oxo-2-(trifluoromethyl)-1,6-dihydropyridin-3-yl)piperazine-1-carboxylate (425-3)

A mixture of Compound 425-2 (50 mg, 98 μmol), benzyl piperazine-1-carboxylate (33 mg, 147 μmol), t-BuONa (28 mg, 294 μmol), t-Buxantphos G$_3$ (8 mg, 10 μmol) in THF (4 mL) was degassed and purged with N$_2$ for three times, and then the mixture was stirred at 80° C. for 3 hrs under N$_2$ atmosphere. TLC indicated the reaction was complete. The reaction mixture was poured into water (15 mL) and extracted with EtOAc (5 mL×3). The combined organic layers were washed with brine (5 mL×3), dried over Na$_2$SO$_4$, filtered and concentrated under reduced pressure to give a residue, which was purified by prep-TLC (SiO2, Petroleum ether/Ethyl acetate=1/1) to give Compound 425-3 (10 mg, 15 μmol) as a yellow solid.

Step 3: benzyl 4-(5-((3,6-dimethyl-10,10-dioxido-9H-thioxanthen-9-yl)carbamoyl)-6-oxo-2-(trifluoromethyl)-1,6-dihydropyridin-3-yl)piperazine-1-carboxylate (425-4)

To a solution of Compound 425-3 (10 mg, 15 μmol) in DCM (2 mL) was added m-CPBA (10 mg, 46 μmol, 80% purity) at 0° C. The mixture was stirred at 25° C. for 2 hrs. LCMS showed the reaction was complete and desired mass was detected. The reaction mixture was pouring into sat-.NaHSO$_3$ aqueous 15 mL and extracted with DCM (5 mL×3). The combined organic layers were washed with sat.NaHCO$_3$ (5 mL×3), dried over Na$_2$SO$_4$, filtered and concentrated under reduced pressure to give a residue. The residue was purified by Prep-TLC (Petroleum ether/Ethyl acetate=1/1) to give Compound 425-4 (10 mg, crude) as a white solid. M−H$^-$=679.0 (LCMS).

Step 4: N-(3,6-dimethyl-10,10-dioxido-9H-thioxanthen-9-yl)-2-oxo-5-(piperazin-1-yl)-6-(trifluoromethyl)-1,2-dihydropyridine-3-carboxamide (425)

To a solution of Compound 425-4 (10 mg, 15 μmol) in MeOH (1 mL) was added Pd/C (5 mg, 15 μmol, 10% purity) and purged with H$_2$ for three times. The mixture was stirred at 25° C. for 15 min under H$_2$ (15 Psi). LCMS showed the reaction was complete and desired mass was detected. The suspension was filtered through a pad of Celite and the filter cake was washed with MeOH (3 mL×2). The combined filtrates were concentrated to dryness to give a residue, which was purified by Prep-HPLC to give Compound 425 (2 mg, 3 μmol, 20% yield) as a gray solid. M−H$^-$=545.1 (LCMS); $^1$H NMR (400 MHz, DMSO-d$_6$) δ=13.28 (br s, 1H), 8.59 (br s, 1H), 8.18 (s, 1H), 7.88 (s, 2H), 7.57-7.48 (m, 4H), 6.64 (br d, J=9.2 Hz, 1H), 3.17 (br s, 4H), 2.95 (br s, 4H), 2.42 (s, 6H).

Other compounds made in a similar manner are shown in Table 44.

TABLE 44

| Compound No | Structure | HNMR and Ms |
| --- | --- | --- |
| 426 | 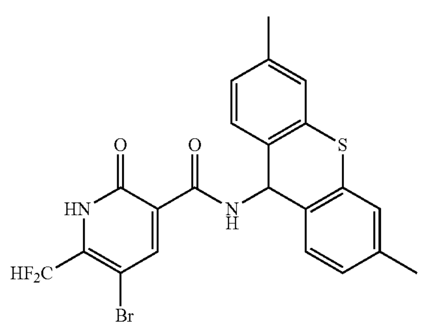 | $^1$H NMR (400 MHz, DMSO-d6) δ = 8.46 (s, 1H), 7.47 (d, J = 7.7 Hz, 2H), 7.36 (s, 2H), 7.13 (br d, J = 7.5 Hz, 2H), 6.07 (s, 1H), 2.29 (s, 6H) ESI [M − H] = 507.0 |

| Compound No | Structure | HNMR and Ms |
|---|---|---|
| 427 | 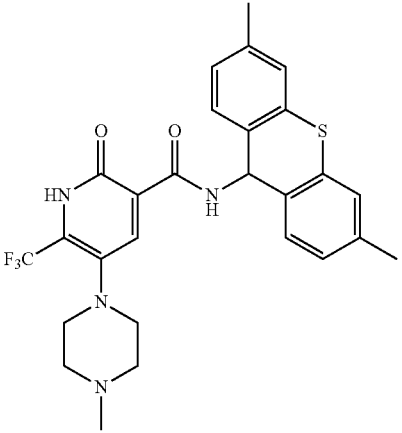 | $^1$H NMR (400 MHz, METHANOL-d$_4$) δ = 8.34 (s, 1H), 7.44 (br d, J = 7.3 Hz, 2H), 7.27 (s, 2H), 7.04 (br d, J = 6.0 Hz, 2H), 6.15 (s, 1H), 3.14 (br d, J = 1.7 Hz, 4H), 3.02 (br s, 4H), 2.76 (s, 3H), 2.27 (s, 6H) ESI [M − H] = 527.1 |
| 428 | 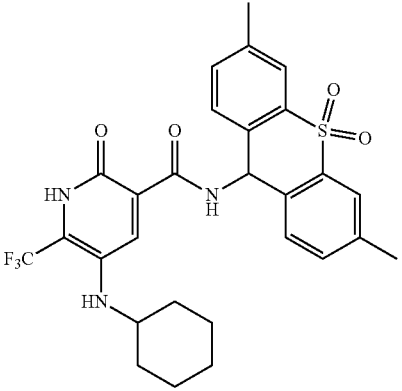 [SMILES: Cc1ccc2c(c1)S(=O)(=O)c1cc(C)ccc1C2NC(=O)c1cc(NC2CCCCC2)c(C(F)(F)F)[nH]c1=O] | $^1$H NMR (400 MHz, DMSO-d$_6$) δ = 12.37-11.69 (m, 1H), 10.21-9.36 (m, 1H), 8.02-7.87 (m, 3H), 7.67 (d, J = 7.9 Hz, 2H), 7.52 (d, J = 7.9 Hz, 2H), 6.60 (br d, J = 9.0 Hz, 1H), 4.56-4.32 (m, 1H), 2.43 (s, 6H), 1.99-1.85 (m, 2H), 1.78-1.53 (m, 3H), 1.42-1.11 (m, 5H) ESI [M − H] = 558.2 |
| 429 | 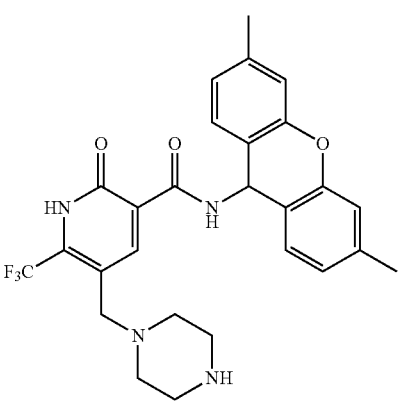 [SMILES: Cc1ccc2c(c1)Oc1cc(C)ccc1C2NC(=O)c1cc(CN2CCNCC2)c(C(F)(F)F)[nH]c1=O] | $^1$H NMR (400 MHz, DMSO-d6) δ = 12.18 (br s, 1H), 8.15 (s, 1H), 7.27 (d, J = 8.8 Hz, 2H), 6.98-6.92 (m, 4H), 6.36 (d, J = 8.8 Hz, 1H), 3.41 (s, 2H), 3.04 (m, 4H), 2.30 (s, 6H) ESI [M − H] = 511.2 |

TABLE 44-continued
| Compound No | Structure | HNMR and Ms |
|---|---|---|
| 430 | 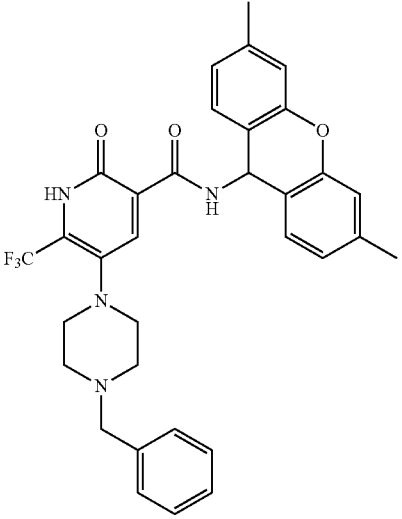 [SMILES: Cc1ccc2c(c1)Oc1cc(C)ccc1C2NC(=O)c1cc(N2CCN(Cc3ccccc3)CC2)c(C(F)(F)F)[nH]c1=O] | $^1$H NMR (400 MHz, DMSO-d6) δ = 8.46 (s, 1H), 7.40-7.22 (m, 6H), 7.04-6.92 (m, 4H), 6.46 (d, J = 8.1 Hz, 1H), 3.60 (br s, 2H), 2.83 (br s, 4H), 2.61-2.53 (m, 4H), 2.33 (s, 6H) ESI [M − H] = 587.2 |
| 431 | 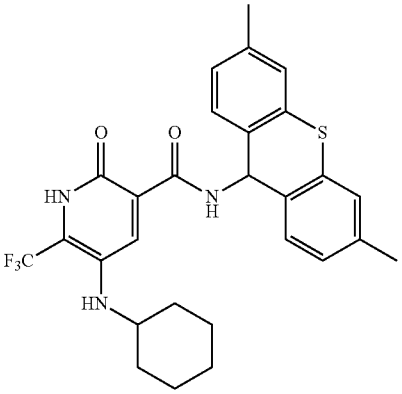 | $^1$H NMR (400 MHz, DMSO-d$_6$) δ = 12.20 (br s, 1H), 9.31-9.26 (m, 1H), 8.02-7.90 (s, 1H), 7.48 (d, J = 8.0 Hz, 2H), 7.38 (s, 2H), 7.14-7.12 (m, 2H), 6.14 (d, J = 8.4 Hz, 1H), 4.43 (d, J = 7.9 Hz , 1H), 2.50 (s, 6H), 1.88-1.85 (m, 2H), 1.70-1.67 (m, 2H), 1.60-1.57 (m, 1H), 1.35-1.24 (m, 5H) ESI [M − H] = 526.1 |
| 432 | 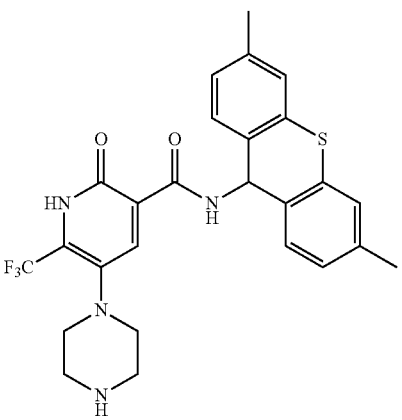 [SMILES: Cc1ccc2c(c1)Sc1cc(C)ccc1C2NC(=O)c1cc(N2CCNCC2)c(C(F)(F)F)[nH]c1=O] | $^1$H NMR (400 MHz, DMSO-d$_6$) δ = 13.31-12.51 (m, 1H), 8.73-8.31 (m, 1H), 8.11 (br s, 1H), 7.42-7.33 (m, 4H), 7.12 (d, J = 7.8 Hz, 2H), 5.91 (br d, J = 7.7 Hz, 1H), 3.14 (br s, 4H), 2.90 (br s, 4H), 2.29 (s, 6H) ESI [M − H] = 513.1 |

TABLE 44-continued

| Compound No | Structure | HNMR and Ms |
|---|---|---|
| 433 | 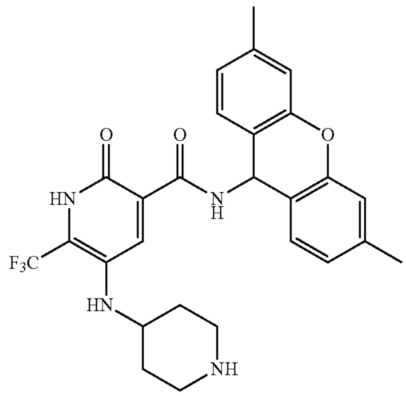 [SMILES: Cc1ccc2c(c1)Oc1cc(C)ccc1C2NC(=O)c1cc(NC2CCNCC2)c(C(F)(F)F)[nH]c1=O] | ¹H NMR (400 MHz, DMSO-d₆) δ = 7.89 (s, 1H), 7.29-7.27 (m, 2H), 6.97-6.91 (m, 2H), 6.36-6.34 (br d, J = 7.7 Hz, 1H), 3.76 (s, 1H), 3.23-3.20 (m, 2H), 2.96-2.89 (m, 2H), 2.30 (s, 6H), 1.95-1.91 (m, 2H), 1.55-1.47 (m, 2H). ESI [M − H] = 511.1 |
| 434 | 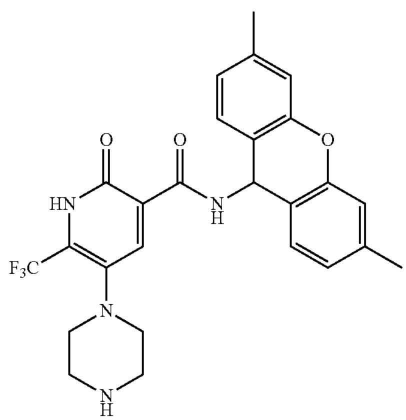 [SMILES: Cc1ccc2c(c1)Oc1cc(C)ccc1C2NC(=O)c1cc(N2CCNCC2)c(C(F)(F)F)[nH]c1=O] | ¹H NMR (400 MHz, DMSO-d6) δ = 12.01 (br s, 1H), 8.88 (br s, 1H), 8.17 (s, 1H), 7.28 (d, J = 7.8 Hz, 2H), 7.03-6.83 (m, 4H), 6.38 (br d, J = 8.6 Hz, 1H), 3.16 (br s, 4H), 2.91 (br s, 4H), 2.31 (s, 6H) ESI [M − H] = 497.1 |
| 435 | 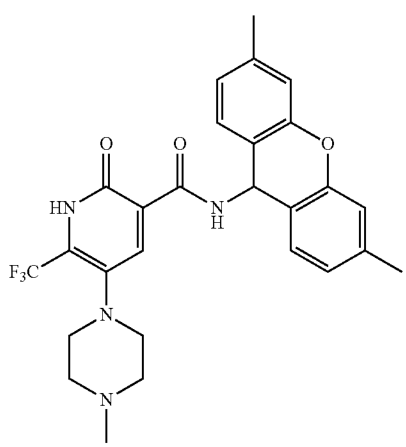 [SMILES: Cc1ccc2c(c1)Oc1cc(C)ccc1C2NC(=O)c1cc(N2CCN(C)CC2)c(C(F)(F)F)[nH]c1=O] | ¹H NMR (400 MHz, DMSO-d6) δ = 8.28 (s, 1H), 7.31 (d, J = 7.9 Hz, 2H), 7.03-6.90 (m, 4H), 6.40 (d, J = 8.4 Hz, 1H), 2.87 (br s, 8H), 2.59-2.51 (m, 3H), 2.31 (s, 6H) ESI [M − H] = 511.0 |

TABLE 44-continued

| Compound No | Structure | HNMR and Ms |
|---|---|---|
| 436 | 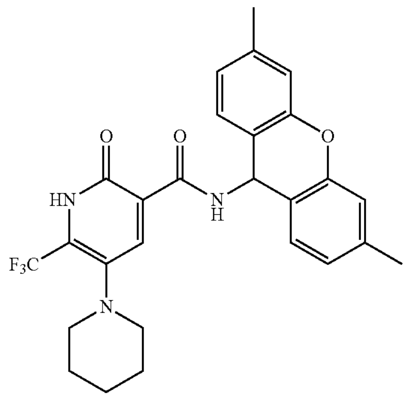 [SMILES: Cc1ccc2c(c1)Oc1cc(C)ccc1C2NC(=O)c1cc(N2CCCCC2)c(C(F)(F)F)[nH]c1=O] | ¹H NMR (400 MHz, DMSO-d6) δ = 13.06 (br s, 1H), 9.60 (br s, 1H), 8.41 (s, 1H), 7.34 (d, J = 7.7 Hz, 2H), 7.05-6.91 (m, 4H), 6.45 (br d, J = 8.3 Hz, 1H), 2.74 (br s, 4H), 2.32 (s, 6H), 1.68-1.43 (m, 6H) ESI [M − H] = 496.2 |
| 437 | 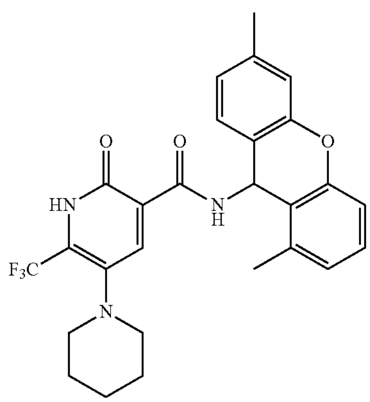 [SMILES: Cc1ccc2c(c1)Oc1cccc(C)c1C2NC(=O)c1cc(N2CCCCC2)c(C(F)(F)F)[nH]c1=O] | ¹H NMR (400 MHz, DMSO-d6) δ = 8.13 (br s, 1H), 7.48 (d, J = 7.8 Hz, 1H), 7.25 (t, J = 7.8 Hz, 1H), 7.07-6.95 (m, 3H), 6.92 (br d, J = 7.7 Hz, 1H), 6.44 (br d, J = 8.4 Hz, 1H), 2.66 (br s, 4H), 2.28 (d, J = 9.0 Hz, 6H), 1.65-1.37 (m, 6H) ESI [M − H] = 496.2 |
| 438 | 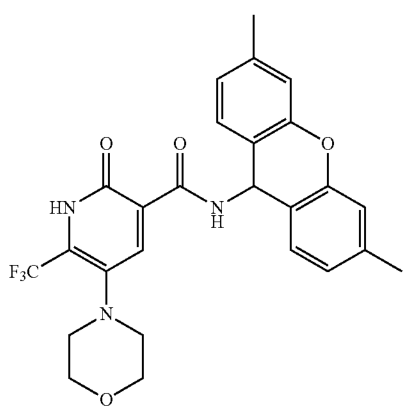 [SMILES: Cc1ccc2c(c1)Oc1cc(C)ccc1C2NC(=O)c1cc(N2CCOCC2)c(C(F)(F)F)[nH]c1=O] | ¹H NMR (400 MHz, DMSO-d₆) δ = 13.16 (br s, 1H), 9.54 (br s, 1H), 8.47 (s, 1H), 7.35 (d, J = 7.9 Hz, 2H), 7.08-6.91 (m, 4H), 6.46 (d, J = 8.2 Hz, 1H), 3.76-3.59 (m, 4H), 2.88-2.73 (m, 4H), 2.32 (s, 6H) ESI [M − H] = 498.1 |

TABLE 44-continued

| Compound No | Structure | HNMR and Ms |
|---|---|---|
| 439 | 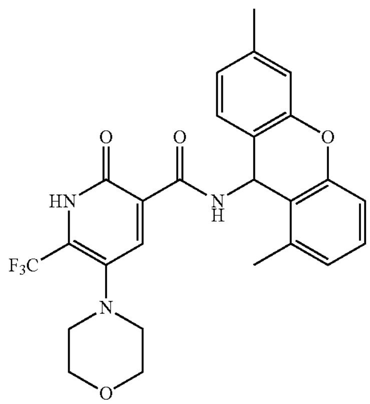 [SMILES: Cc1ccc2c(c1)Oc1cccc(C)c1C2NC(=O)c1cc(N2CCOCC2)c(C(F)(F)F)[nH]c1=O] | 1H NMR (400 MHz, DMSO-d6) δ = 13.09 (br s, 1H), 9.41 (br s, 1H), 8.44-8.28 (m, 1H), 7.47 (d, J = 7.8 Hz, 1H), 7.32-7.24 (m, 1H), 7.08-6.93 (m, 4H), 6.53 (d, J = 8.3 Hz, 1H), 3.70-3.59 (m, 4H), 2.80-2.71 (m, 4H), 2.32 (d, J = 5.1 Hz, 6H) ESI [M + Na]⁺ = 522.2 |

Example 78: Synthesis of N-(3-(2-methoxyethoxy)-9H-xanthen-9-yl)-2-oxo-6-(trifluoromethyl)-1,2-dihydropyridine-3-carboxamide (440)

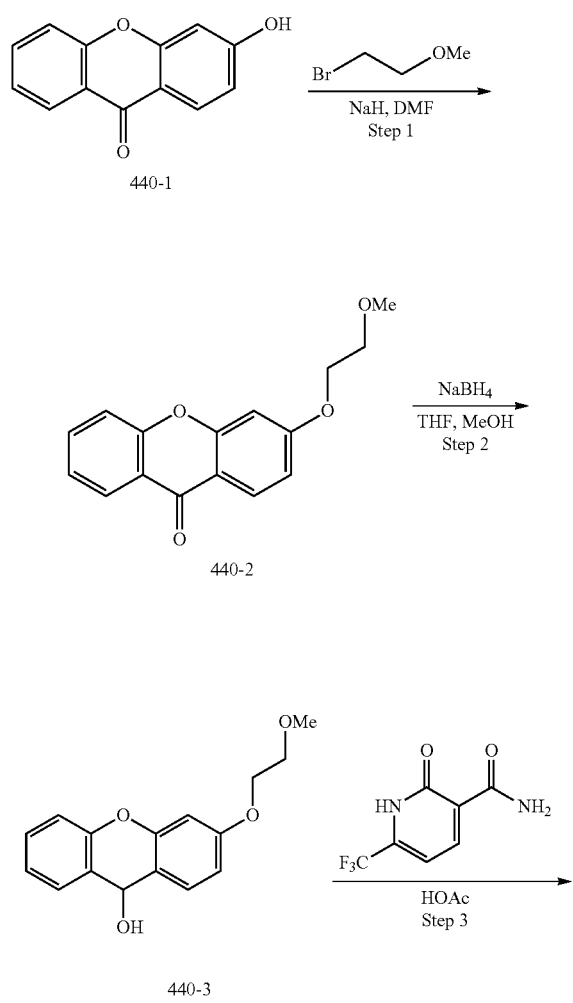

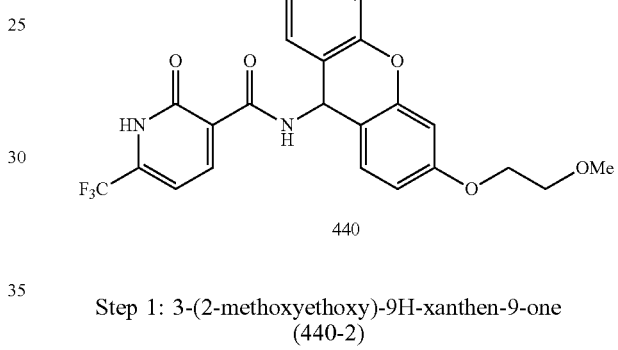

Step 1: 3-(2-methoxyethoxy)-9H-xanthen-9-one (440-2)

To a stirred solution of Compound 440-1 (300 mg, 1.4 mmol) in DMF (5 mL) was added NaH (678 mg, 1.7 mmol, 60% purity) at 0° C. The mixture was stirred at 25° C. for 30 mins, and then 1-bromo-2-methoxyethane (236 mg, 1.7 mmol) in DMF (1 mL) was added. The mixture was stirred at 50° C. for 2 hrs. TLC showed the reaction was completed and one major new spot was detected. The reaction mixture was poured into H₂O (10 mL). The resulting solid was filtered. The caked was washed with H₂O (3 mL×2) and dried in vacuum to give Compound 440-2 (230 mg, 851.0 μmol, 60.19% yield) as a white solid.

Step 2: 3-(2-methoxyethoxy)-9H-xanthen-9-ol (440-3)

To a solution of Compound 440-2 (150 mg, 555.0 μmol) in THF (7.5 mL) was added LAH (42 mg, 1.1 mmol) at 0° C. The resulting mixture was stirred at 25° C. for 30 mins. TLC showed the reaction was complete and one new spot formed. The reaction mixture was poured into Sat.NH₄Cl (25 mL) and extracted with DCM (10 mL×4). The combined organic layers were dried over Na₂SO₄, filtered and concentrated under reduced pressure to give Compound 440-3 (150 mg, 550.9 μmol, 99.26% yield) as a crude white solid.

Step 3: N-(3-(2-methoxyethoxy)-9H-xanthen-9-yl)-2-oxo-6-(trifluoromethyl)-1,2-dihydropyridine-3-carboxamide (440)

A solution of Compound 440-3 (150 mg, 550.9 μmol) and 2-oxo-6-(trifluoromethyl)-1,2-dihydropyridine-3-carboxamide (114 mg, 550.9 μmol) in HOAc (12 mL) was stirred at 50° C. for 12 hrs. LC-MS showed the reaction was completed and one main peak with desired mass was detected. The reaction mixture was concentrated under reduced pressure to give a residue, which was purified by Prep-HPLC (basic condition) to give Compound 440 (30 mg, 62.7 μmol, 11.39% yield) as a yellow solid. M–H⁻= 459.1 (LCMS); ¹H NMR (400 MHz, MeOD) δ=8.37-8.40 (d, J=7.6 Hz, 1H), 7.51-7.48 (d, J=8 Hz, 1H), 7.41-7.38 (d, J=8.4 Hz, 1H), 7.30-7.11 (m, 2H), 6.79-6.71 (m, 3H), 6.54 (s, 1H), 4.15-4.12 (t, J=4.4 Hz, 2H), 3.76-3.73 (t, J=4.4 Hz, 2H), 3.42 (s, 3H).

Example 79: Synthesis of N-(7-methylchroman-4-yl)-2-oxo-6-(trifluoromethyl)-1,2-dihydropyridine-3-carboxamide (441)

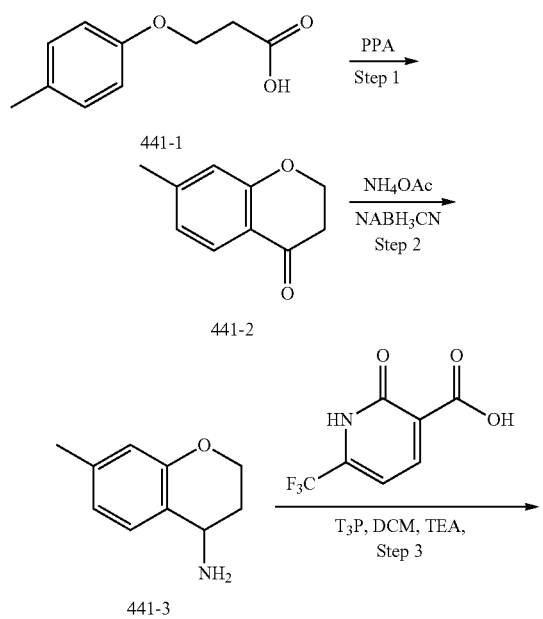

Step 1: 7-methylchroman-4-one (441-2)

A mixture of Compound 441-1 (500 mg, 2.8 mmol) and PPA (5 mL) was stirred at 100° C. for 15 min. TLC showed the reaction was completed. The reaction mixture was poured into H₂O and the mixture was extracted with EtOAc (10 mL×4). The combined organic layers were washed with aqueous sodium bicarbonate solution (20 mL), dried and evaporated to give Compound 441-2 (440 mg, 2.7 mmol, 98% yield) as yellow oil.

Step 2: 7-methylchroman-4-amine (441-3)

To a solution of Compound 441-2 (180 mg, 1.1 mmol) in i-PrOH (6 mL) was added NH₄OAc (2.6 g, 33.3 mmol) and NaBH₃CN (488 mg, 7.8 mmol). The resulting mixture was warmed to 120° C. slowly and stirred for 1 h. LCMS showed the reaction was completed and one main peak with desired mass was detected. The mixture was poured into H₂O (20 mL) and extracted with CHCl₃:i-PrOH=3:1 (10 mL×4). The combined organic layers were dried over Na₂SO₄, filtered and concentrated under reduced pressure to give a residue. The residue was purified by Prep-HPLC (neutral) to give Compound 441-3 (60 mg, 367.6 μmol, 33% yield) as a white solid. Fragment Ms=147.1; ¹H NMR (400 MHz, CDCl₃) δ=7.11 (s, 1H), 6.93-6.97 (m, 1H), 6.73-6.71 (d, J=8.4 Hz, 1H), 4.28-4.20 (m, 2H), 4.01-4.00 (m, 1H), 2.28 (s, 3H), 2.18-2.14 (m, 1H), 1.86-1.82 (m, 1H).

Step 3: N-(7-methylchroman-4-yl)-2-oxo-6-(trifluoromethyl)-1,2-dihydropyridine-3-carboxamide (441)

To a stirred solution of 2-oxo-6-(trifluoromethyl)-1,2-dihydropyridine-3-carboxylic acid (63 mg, 306.3 μmol) and Compound 441-4 (50 mg, 306.3 μmol) in DCM (5 mL) was added TEA (93 mg, 919 μmol) at 25° C., followed by T₃P (234 mg, 367.6 μmol, 50% purity). The resulting mixture was stirred at 25° C. for 15 mins. LCMS showed the reaction was completed and desired mass was detected. The mixture was diluted with H₂O (5 mL) and extracted with DCM (5 mL×3). The combined organic layers were dried over Na₂SO₄ and concentrated in vacuum to give a residue, which was purified by Prep-HPLC (FA) to give Compound 441 (22 mg, 61.8 μmol, 20.16% yield) as a yellow solid. M–H⁻= 351.1 (LCMS); ¹H NMR (400 MHz, MeOD) δ=13.40 (br, 1H), 9.28 (br, 1H), 8.44-8.42 (d, J=7.2 Hz, 1H), 7.32 (br, 1H), 7.04-6.97 (m, 2H), 6.72-6.69 (d, J=8 Hz, 1H), 5.22-5.16 (m, 1H), 4.24-4.14 (m, 2H), 2.19 (s, 3H), 2.16-2.02 (m, 2H).

Example 80: Synthesis of N-((4-methyl-2-(methylsulfonyl)phenyl)(phenyl)methyl)-2-oxo-6-(trifluoromethyl)-1,2-dihydropyridine-3-carboxamide (442)

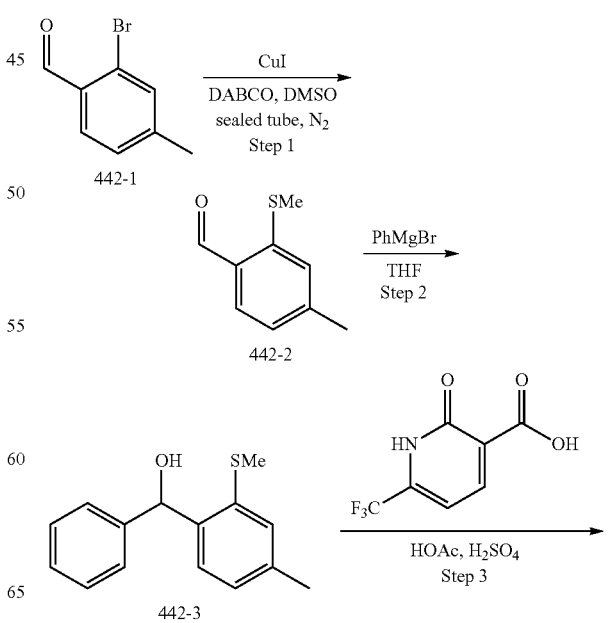

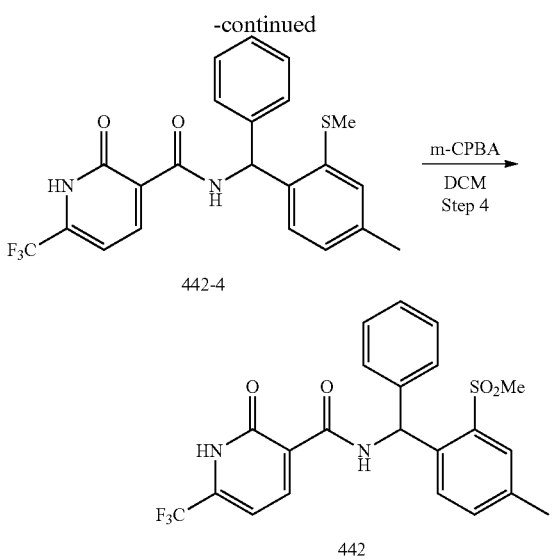

442-4

442

Step 1: 4-methyl-2-(methylthio)benzaldehyde (442-2)

An oven dried pressure tube was charged with Compound 442-1 (1.5 g, 7.5 mmol), CuI (1.4 g, 7.5 mmol), DABCO (1.7 g, 15.1 mmol) and DMSO (15 mL). Then the sealed tube was heated with stirring at 130° C. under $N_2$ for 36 hrs. LCMS showed the reaction was completed and the desired mass was detected. The reaction mixture was quenched by addition $H_2O$ (30 mL), and then extracted with EtOAc (20 mL×3). The combined organic layers were dried over $Na_2SO_4$, filtered and concentrated under reduced pressure to give a residue, which was purified by column chromatography to give Compound 442-2 (550 mg, crude) as yellow oil. M+H$^+$=167.0 (LCMS); $^1$H NMR (400 MHz, CDCl$_3$) δ=10.21 (s, 1H), 7.70 (d, J=7.7 Hz, 1H), 7.13 (s, 1H), 7.09 (d, J=7.7 Hz, 1H), 2.49 (s, 3H), 2.43 (s, 3H).

Step 2: (4-methyl-2-(methylthio)phenyl)(phenyl)methanol (442-3)

To a solution of Compound 442-2 (400 mg, 2.4 mmol) in THF (5 mL) was added phenylmagnesium bromide (3 M, 1.2 mL) at 0° C. under $N_2$. The mixture was stirred at 25° C. under $N_2$ for 2 hrs. TLC indicated the reaction was completed. The reaction mixture was poured into Sat. NH$_4$Cl (20 mL) and extracted with DCM (10 mL×3). The combined organic layers were dried over Na$_2$SO$_4$ and concentrated in vacuum to give Compound 442-3 (550 mg, crude) as brown oil.

Step 3: N-((4-methyl-2-(methylthio)phenyl)(phenyl)methyl)-2-oxo-6-(trifluoro methyl)-1,2-dihydropyridine-3-carboxamide (442-4)

To a solution of Compound 442-3 (400 mg, 1.6 mmol) and 2-oxo-6-(trifluoromethyl)-1,2-dihydropyridine-3-carboxamide (337 mg, 1.6 mmol) in AcOH (10 mL) was added H$_2$SO$_4$ (161 mg, 1.6 mmol). The mixture was stirred at 25° C. for 10 mins and then stirred at 100° C. for 10 mins. TLC indicated the reaction completed. The reaction mixture was concentrated to give a residue, which was treated with H$_2$O (5 mL) and extracted with EtOAc (5 mL×3). The combined organic layers were dried over Na$_2$SO$_4$, filtered and concentrated under reduced pressure to give a residue. The residue was purified by prep-TLC to give Compound 442-4 (70 mg, 10% yield) as brown oil. M−H$^-$=431.1 (LCMS); $^1$H NMR (400 MHz, CDCl$_3$) δ=9.99 (br d, J=7.7 Hz, 1H), 8.69 (d, J=7.3 Hz, 1H), 7.32 (d, J=4.2 Hz, 4H), 7.27-7.22 (m, 1H), 7.18-7.10 (m, 2H), 6.97 (d, J=7.9 Hz, 1H), 6.85 (dd, J=7.7, 17.2 Hz, 2H), 2.43 (s, 3H), 2.34 (s, 3H)

Step 4: N-((4-methyl-2-(methylsulfonyl)phenyl)(phenyl)methyl)-2-oxo-6-(trifluoromethyl)-1,2-dihydropyridine-3-carboxamide (442)

To a solution of Compound 442-4 (70 mg, 161.9 μmol) in DCM (4 mL) was added m-CPBA (82 mg, 404.7 μmol) at 0° C. The mixture was stirred at 25° C. for 3 hrs. LCMS showed the reaction was completed and the desired mass was detected. The reaction mixture was added to Sat. NaHSO$_3$ (8 mL) and extracted with DCM (5 mL×3). The combined organic layers were dried over Na$_2$SO$_4$, filtered and concentrated under reduced pressure to give a residue. The residue was purified by prep-HPLC to give Compound 442 (27 mg, 57.7 μmol, 36% yield) as white solid. M−H$^-$= 463.1 (LCMS); $^1$H NMR (400 MHz, CDCl$_3$) δ=10.24 (br d, J=7.5 Hz, 1H), 8.66 (d, J=7.3 Hz, 1H), 7.94 (s, 1H), 7.52-7.47 (m, 1H), 7.46-7.39 (m, 1H), 7.34-7.30 (m, 4H), 7.27 (s, 2H), 6.90 (d, J=7.3 Hz, 1H), 3.29 (s, 3H), 2.43 (s, 3H).

Other compounds made in a similar manner are shown in Table 45.

TABLE 45

| Compound No | Structure | HNMR and Ms |
|---|---|---|
| 443 | 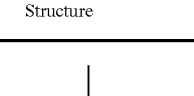 | $^1$H NMR (400 MHz, DMSO-d) δ = 8.35 (br d, J = 7.6 Hz, 1H), 7.48 – 6.99 (m, 9H), 6.20 (br d, J = 7.9 Hz, 1H), 2.60 – 2.53 (m, 2H), 2.27 (s, 3H), 1.15 (br t, J = 7.6 Hz, 3H) ESI [M − H] = 413.1 |

TABLE 45-continued

| Compound No | Structure | HNMR and Ms |
|---|---|---|
| 444 | 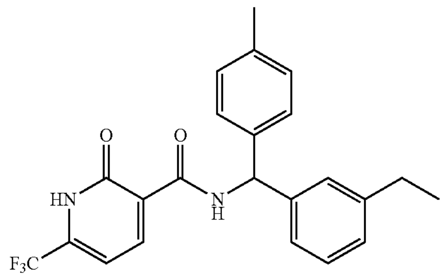 | ¹H NMR (400 MHz, CDCl₃) δ = 10.06 (d, J = 7.2 Hz, 1H), 8.69 (d, J = 7.2 Hz, 1H), 7.24-7.12 (m, 8H), 6.87 (d, J = 7.2 Hz, 1H), 6.40 (d, J = 8.4 Hz, 1H), 2.64-2.59 (m, 2H), 2.32 (s, 3H), 1.20 (t, J = 7.6 Hz, 3H)<br>ESI [M − H] = 413.1 |
| 445 | 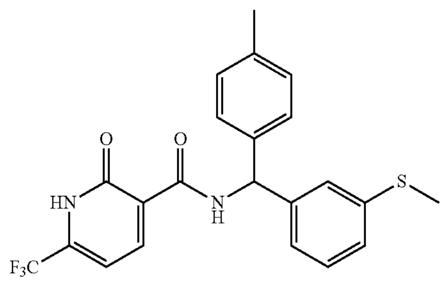 | ¹H NMR (400 MHz, DMSO-d6) δ = 8.33 (br d, J = 7.6 Hz, 1H), 7.31 − 7.25 (m, 1H), 7.22 (br d, J = 7.8 Hz, 4H), 7.18 − 7.13 (m, 3H), 7.08 (br d, J = 7.6 Hz, 1H), 6.22 (d, J = 7.9 Hz, 1H), 2.44 (s, 3H), 2.27 (s, 3H)<br>ESI [M − H] = 431.1 |
| 446 | 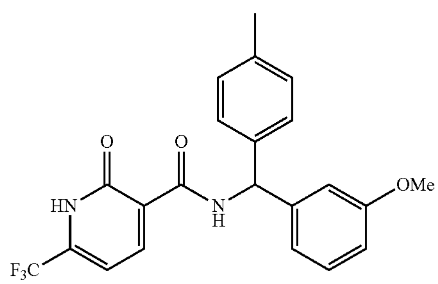 [SMILES: COc1cccc(C(NC(=O)c2ccc(C(F)(F)F)[nH]c2=O)c2ccc(C)cc2)c1] | ¹H NMR (400 MHz, CDCl3) δ = 10.06 (d, J = 8.0 Hz, 1H), 8.70 (d, J = 7.2 Hz, 1H), 7.27-7.12 (m, 5H), 6.93 − 6.86 (m, 3H), 6.81-6.79 (m, 1H), 6.39-6.37 (d, J = 8.0 Hz, 1H), 3.76 (s, 3H), 2.32 (s, 3H)<br>ESI [M − H] = 415.1 |
| 447 | 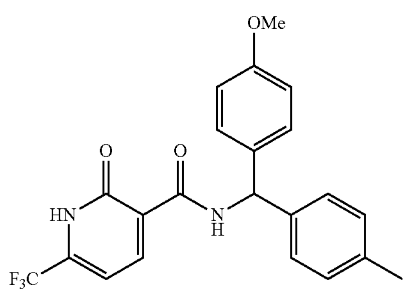 [SMILES: COc1ccc(C(NC(=O)c2ccc(C(F)(F)F)[nH]c2=O)c2ccc(C)cc2)cc1] | ¹H NMR (400 MHz, CDCl3) δ = 10.01 (d, J = 7.2 Hz, 1H), 8.68 (d, J = 7.6 Hz, 1H), 7.24-7.14 (m, 6H), 6.88-6.84 (m, 3H), 6.36 (d, J = 8 Hz, 1H), 3.78 (s, 3H), 2.32 (s, 3H)<br>ESI [M − H] = 415.1 |
| 448 | 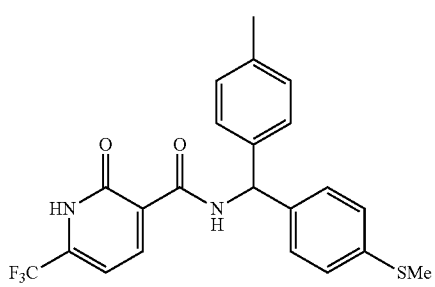 [SMILES: CSc1ccc(C(NC(=O)c2ccc(C(F)(F)F)[nH]c2=O)c2ccc(C)cc2)cc1] | ¹H NMR (400 MHz, CDCl₃) δ = 10.06 (d, J = 7.2 Hz, 1H), 8.70 (d, J = 7.2 Hz, 1H), 7.23-7.12 (m, 8H), 6.89 (d, 1H), 6.37 (d, J = 7.6 Hz, 1H), 2.46 (s, 3H), 2.33 (s, 3H)<br>ESI [M − H] = 431.1 |

TABLE 45-continued

| Compound No | Structure | HNMR and Ms |
| --- | --- | --- |
| 449 | 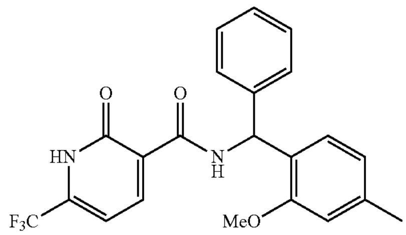 | ¹H NMR (400 MHz, CDCl₃) δ = 10.08 (d, J = 8.4 Hz, 1H), 8.63 (d, J = 7.6 Hz, 1H), 7.22-7.18 (m, 6H), 6.87 (d, J = 7.6 Hz, 1H), 6.77-6.64 (m, 3H), 3.77 (s, 3H), 2.34 (s, 3H)<br>ESI [M − H] = 415.1 |
| 450 | 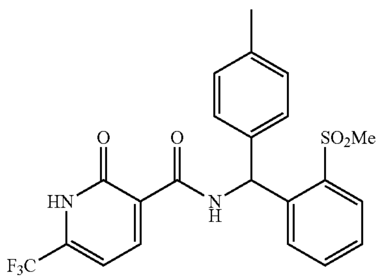 [SMILES: Cc1ccc(C(NC(=O)c2ccc(C(F)(F)F)[nH]c2=O)c2ccccc2S(C)(=O)=O)cc1] | ¹H NMR (400 MHz, CDCl₃) δ = 10.20 (br d, 1H), 8.62 (d, J = 7.2 Hz, 1H), 8.12 (d, J = 8 Hz, 1H), 7.64 (d, J = 2.4 Hz, 2H), 7.49 (br d, 1H), 7.21-7.11 (m, 4H), 6.88 (d, J = 7.2 Hz, 2H), 3.29 (s, 3H), 2.31 (s, 3H)<br>ESI [M − H] = 463.1 |
| 451 | 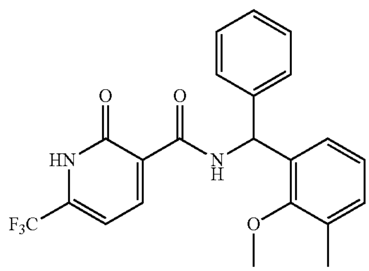 [SMILES: COc1c(C)cccc1C(NC(=O)c1ccc(C(F)(F)F)[nH]c1=O)c1ccccc1] | ¹H NMR (400 MHz, DMSO-d₆) δ = 13.99 − 13.07 (m, 1H), 10.68 − 9.94 (m, 1H), 8.33 (d, J = 7.5 Hz, 1H), 7.37 − 7.30 (m, 2H), 7.29 − 7.22 (m, 3H), 7.18 − 7.10 (m, 3H), 7.07 − 7.00 (m, 1H), 6.58 (d, J = 8.4 Hz, 1H), 3.61 (s, 3H), 2.25 (s, 3H)<br>ESI [M − H] = 415.1 |
| 452 | 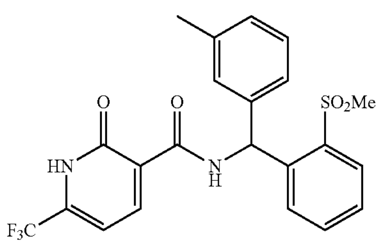 | 1H NMR (400 MHz, CDCl3) δ = 10.21 (d, J = 7.6 Hz, 1H), 8.62 (d, J = 7.2 Hz, 1H), 8.13 (d, J = 8.4 Hz, 1H), 7.65 (d, J = 3.6 Hz, 2H), 7.50 (m, 1H), 7.30-7.21 (m, 2H), 7.12-7.07 (m, 3H), 6.89 (d, J = 7.6 Hz, 1H), 3.27 (s, 3H), 2.30 (s, 3H)<br>ESI [M − H] = 463.1 |
| 453 | 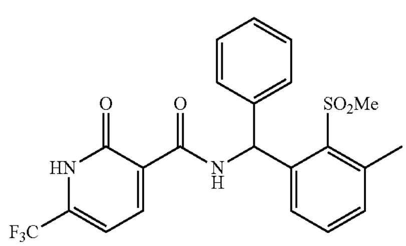 | ¹H NMR (400 MHz, CDCl₃) δ = 10.21 (d, J = 7.2 Hz, 1H), 8.62 (d, J = 7.2 Hz, 1H), 7.59 (d, J = 7.2 Hz, 1H), 7.46 − 7.43 (m, 2H), 7.32 − 7.27 (m, 4H), 6.88 (d, J = 7.2 Hz, 1H), 3.30 (s, 3H), 2.76 (s, 3H)<br>ESI [M − H] = 463.1 |
| 454 | 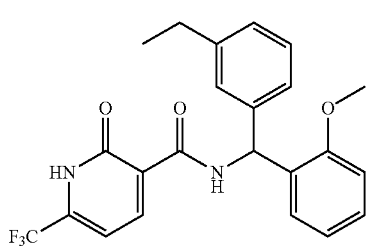 [SMILES: CCc1cccc(C(NC(=O)c2ccc(C(F)(F)F)[nH]c2=O)c2ccccc2OC)c1] | ¹H NMR (400 MHz, CDCl₃) δ = 10.08 (d, J = 8 Hz, 1H), 8.66 (d, J = 8 Hz, 1H), 7.32-7.27 (m, 3H), 7.15 − 6.95 (m, 4H), 6.90 − 6.73 (m, 3H), 6.72 (d, J = 8.4 Hz, 1H), 3.79 (s, 3H), 2.60 (q, J = 15.2 Hz, 7.6 Hz, 1H), 1.19 (t, J = 8 Hz, 3H)<br>ESI [M − H] = 429.1 |

TABLE 45-continued

| Compound No | Structure | HNMR and Ms |
|---|---|---|
| 455 | 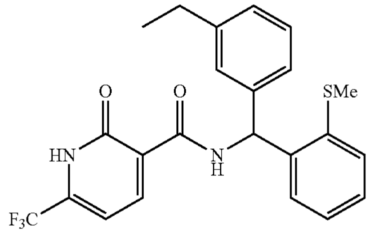 | $^1$H NMR (400 MHz, CDCl$_3$) δ = 9.99 (br d, J = 7.9 Hz, 1H), 8.70 (d, J = 7.3 Hz, 1H), 7.33 – 7.21 (m, 4H), 7.19 – 7.07 (m, 4H), 6.86 (dd, J = 7.8, 10.7 Hz, 2H), 2.61 (q, J = 7.6 Hz, 2H), 2.44 (s, 3H), 1.19 (t, J = 7.6 Hz, 3H) ESI [M – H] = 445.1 |
| 456 | 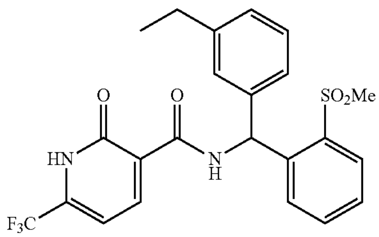 [SMILES: CCc1cccc(C(NC(=O)c2ccc(C(F)(F)F)[nH]c2=O)c2ccccc2S(C)(=O)=O)c1] | $^1$H NMR (400 MHz, CDCl$_3$) δ = 10.22 (br d, J = 7.6 Hz, 1H), 8.66 (d, J = 7.5 Hz, 1H), 8.13 (d, J = 7.9 Hz, 1H), 7.64 (d, J = 4.0 Hz, 2H), 7.55 – 7.46 (m, 1H), 7.33 (d, J = 7.6 Hz, 1H), 7.26 – 7.20 (m, 1H), 7.18 – 7.07 (m, 3H), 6.90 (d, J = 7.5 Hz, 1H), 3.26 (s, 3H), 2.60 (q, J = 7.6 Hz, 2H), 1.18 (t, J = 7.6 Hz, 3H) ESI [M – H] = 477.1 |

Example 81: Synthesis of 2-oxo-N-(2-propyl-9H-xanthen-9-yl)-6-(trifluoromethyl)-1,2-dihydropyridine-3-carboxamide (457)

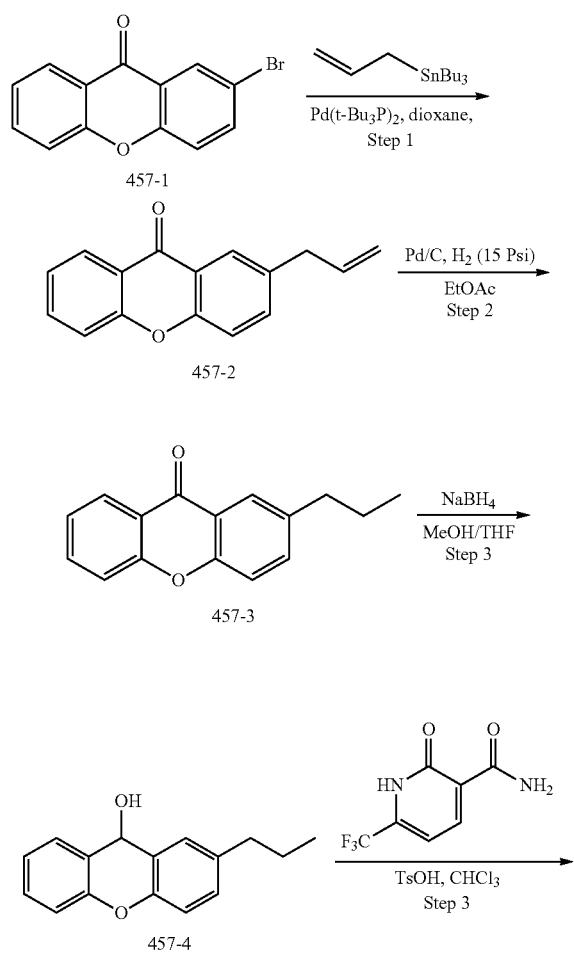

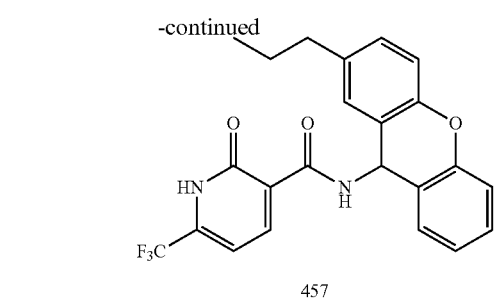

Step 1: 2-allyl-9H-xanthen-9-one (457-2)

To a solution of Compound 457-1 (1 g, 3.6 mmol) and allyltributylstannane (2.4 g, 7.3 mmol) in dioxane (15 mL) was added Pd(t-Bu$_3$P)$_2$ (50 mg, 97.8 µmol) under N$_2$. The mixture was stirred at 100° C. under N$_2$ for 12 hrs. LCMS showed the reaction was complete and the desired mass was detected. The reaction mixture was diluted by added EtOAc (30 mL) and filtered. The filtrate was concentrated in vacuum to give a residue, which was purified by column chromatography to give Compound 457-2 (700 mg, crude) as a white solid. M+H$^+$=237.0 (LCMS); $^1$H NMR (400 MHz, DMSO-d$_6$) δ=8.17 (br d, J=7.9 Hz, 1H), 7.96 (s, 1H), 7.90-7.81 (m, 1H), 7.71-7.54 (m, 3H), 7.45 (t, J=7.4 Hz, 1H), 6.08-5.90 (m, 1H), 5.22-5.06 (m, 2H), 3.50 (br d, J=6.6 Hz, 2H).

Step 2: 2-propyl-9H-xanthen-9-one (457-3)

To a solution of Compound 457-2 (300 mg, 1.3 mmol) in EtOAc (30 mL) was added Pd/C (100 mg, 10% purity) under N$_2$ atmosphere. The suspension was degassed and purged with H$_2$ for 3 times. The mixture was stirred under H$_2$ (15 Psi) at 25° C. for 2 hrs. LCMS showed the reaction was completed and the desired mass was detected. The reaction mixture was filtered and concentrated under reduced pressure to give Compound 457-3 (300 mg, crude) as a white solid. M+H$^+$=239.0 (LCMS).

Step 3: 2-propyl-9H-xanthen-9-ol (457-4)

To a solution of Compound 457-3 (150 mg, 629.5 μmol) in THF (5 mL) was added LAH (48 mg, 1.3 mmol) at 0° C. Then the mixture was stirred at 25° C. for 1 hrs. TLC indicated the reaction was completed. The reaction mixture was poured into Sat.NH₄Cl (10 mL) and extracted with DCM (8 mL×3). The combined organic layers were dried over Na₂SO₄ and concentrated in vacuum to give Compound 457-4 (150 mg, crude) as brown solid.

Step 4: 2-oxo-N-(2-propyl-9H-xanthen-9-yl)-6-(trifluoromethyl)-1,2-dihydropyridine-3-carboxamide (457)

To a solution of Compound 457-4 (150 mg, 624.2 μmol) in AcOH (5 mL) was added 2-oxo-6-(trifluoromethyl)-1,2-dihydropyridine-3-carboxamide (129 mg, 624.2 μmol). The mixture was stirred at 50° C. for 2 hrs. LCMS showed the reaction was completed and the desired mass was detected. The reaction mixture was concentrated and the residue was added to H₂O (10 mL) and extracted with EtOAc (5 mL×3). The combined organic layers were dried over Na₂SO₄, filtered and concentrated under reduced pressure to give a residue. The residue was purified by prep-HPLC to give Compound 457 (68 mg, 156.6 μmol, 25% yield) as light yellow solid. M−H⁻=427.1 (LCMS); ¹H NMR (400 MHz, CDCl₃) δ=9.80 (br d, J=8.2 Hz, 1H), 8.71 (d, J=7.3 Hz, 1H), 7.52 (d, J=6.8 Hz, 1H), 7.36-7.27 (m, 2H), 7.19-7.00 (m, 4H), 6.83 (d, J=7.5 Hz, 1H), 6.61 (d, J=8.6 Hz, 1H), 2.53 (t, J=7.6 Hz, 2H), 1.59 (qd, J=7.4, 15.1 Hz, 2H), 0.90 (t, J=7.4 Hz, 3H).

Other compounds made in a similar manner are shown in Table 46.

TABLE 46

| Compound No | Structure | HNMR and Ms |
|---|---|---|
| 458 | 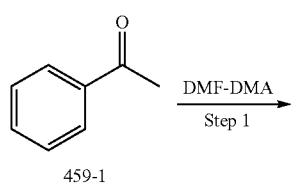 | ¹H NMR (400 MHz, CHLOROFORM-d) δ = 9.85 (br d, J = 7.7 Hz, 1H), 8.64 (d, J = 7.5 Hz, 1H), 7.66-7.57 (m, 1H), 7.52-7.45 (m, 1H), 7.42-7.37 (m, 2H), 7.27-7.21 (m, 2H), 7.10 (dd, J = 1.7, 8.0 Hz, 1H), 6.82 (d, J = 7.5 Hz, 1H), 6.36 (d, J = 8.2 Hz, 1H), 2.69-2.47 (m, 2H), 1.61 (sxt, J = 7.5 Hz, 2H), 0.91 (t, J = 7.3 Hz, 3H) ESI = 443.1 |

Example 82: Synthesis of N-(3,6-dimethyl-9H-xanthen-9-yl)-2-oxo-6-phenyl-1,2-dihydropyridine-3-carboxamide (459)

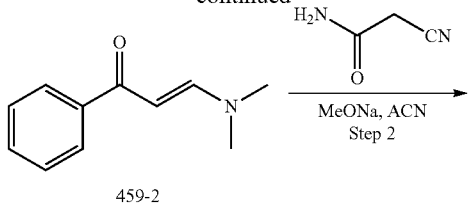

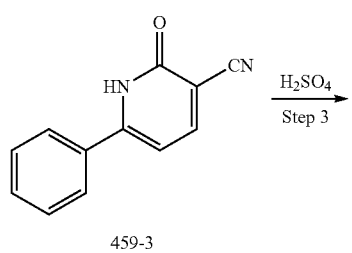

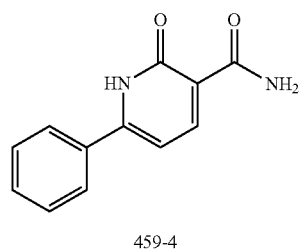

Step 1: (E)-3-(dimethylamino)-1-phenylprop-2-en-1-one (459-2)

To a stirred solution of Compound 459-1 (2 g, 16.7 mmol) in toluene (30 mL) was added DMF-DMA (3.97 g, 33.3 mmol) and the reaction was stirred at 110° C. for 12 hrs. LCMS showed the reaction was completed and the desired mass was detected. The reaction mixture was concentrated under reduced pressure to give a residue, which was purified by column chromatography (Petroleum ether/Ethyl acetate) to give Compound 459-2 (0.7 g, 4.2 mmol, 25% yield) as a yellow solid. M+H⁺=176.3 (LCMS), ¹H NMR (400 MHz, DMSO-d6) δ=7.88 (br d, J=7.1 Hz, 2H), 7.71 (br d, J=12.1 Hz, 1H), 7.53-7.34 (m, 3H), 5.82 (d, J=12.1 Hz, 1H), 3.14 (s, 3H), 2.91 (s, 3H).

Step 2: 2-oxo-6-phenyl-1,2-dihydropyridine-3-carbonitrile (459-3)

To a mixture of Compound 459-2 (300 mg, 1.7 mmol) in MeCN (15 mL) was added 2-cyanoacetamide (173 mg, 2.1 mmol) and NaOMe (277 mg, 5.1 mmol), the mixture was stirred at 80° C. for 12 hrs. TLC showed the reaction was completed. The reaction mixture was poured into $H_2O$ (20 mL) and extracted with EtOAc (10 mL×6). The combined organic layers were dried over $Na_2SO_4$, filtered and concentrated under reduced pressure to give a residue, which was triturated with EtOAc (10 mL) to give Compound 459-3 (150 mg, 764 μmol, 45% yield) as a yellow solid. $^1$H NMR (400 MHz, DMSO-d6) δ=12.71 (br s, 1H), 8.17 (d, J=7.6 Hz, 1H), 7.82 (br d, J=6.4 Hz, 2H), 7.61-7.46 (m, 3H), 6.76 (br s, 1H).

Step 3: 2-oxo-6-phenyl-1,2-dihydropyridine-3-carboxamide (459-4)

Compound 459-3 (100 mg, 509 μmol) was dissolved in $H_2SO_4$ (2 mL) and heated to 90° C. for 3 hrs. LCMS showed the reaction was completed and one main peak with desired mass was detected. The reaction mixture was poured into ice (20 g) and adjust pH=5-6 using $Na_2CO_3$, then the precipitate was filtered to give Compound 459-4 (100 mg, 467 μmol, 92% yield) as a yellow solid. M−H$^-$=212.9 (LCMS).

Step 4: N-(3,6-dimethyl-9H-xanthen-9-yl)-2-oxo-6-phenyl-1,2-dihydropyridine-3-carboxamide (459)

To a solution of Compound 459-4 (47 mg, 221 μmol) TsOH.H$_2$O (84 mg, 442 μmol) in CHCl$_3$ (5 mL) was added 3,6-dimethyl-9H-xanthen-9-ol (100 mg, 442 μmol) at 70° C. and the mixture was stirred at 70° C. for 5 min. LCMS showed the reaction was completed and the desired mass was detected. The reaction mixture was poured into H$_2$O (20 mL) and extracted with DCM (10 mL×4). The combined organic layers were dried over Na$_2$SO$_4$, filtered and concentrated under reduced pressure to give a residue, which was purified by prep-HPLC to give Compound 459 (5 mg, 12 μmol, 3% yield) as a light yellow solid. M−H$^-$=421.1 (LCMS), $^1$H NMR (400 MHz, DMSO-d6) δ=12.64 (br s, 1H), 10.37 (br d, J=8.1 Hz, 1H), 8.48 (d, J=7.7 Hz, 1H), 7.83-7.70 (m, 2H), 7.60-7.48 (m, 3H), 7.34 (d, J=7.9 Hz, 2H), 7.04-6.91 (m, 4H), 6.84 (br d, J=7.6 Hz, 1H), 6.44 (d, J=8.8 Hz, 1H), 2.32 (s, 6H).

Example 83: Synthesis of 5-cyclohexyl-N-(3,6-dimethyl-9H-xanthen-9-yl)-2-oxo-6-(trifluoromethyl)-1,2-dihydropyridine-3-carboxamide (460)

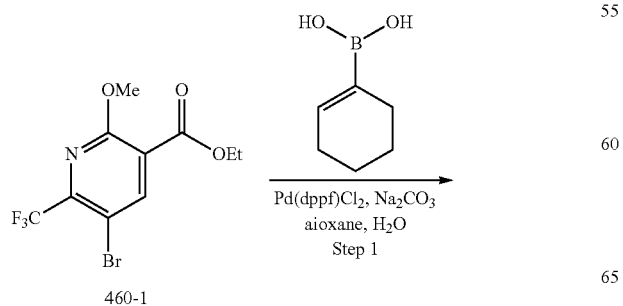

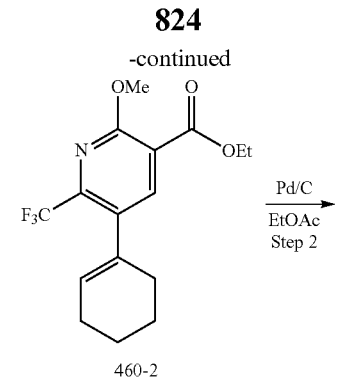

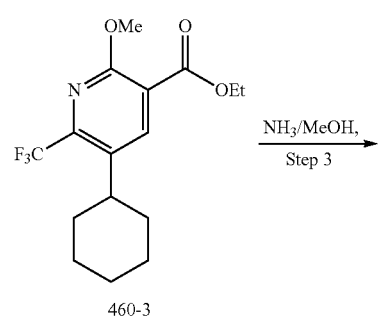

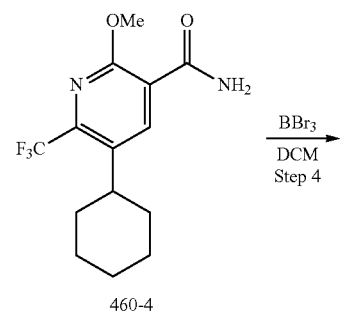

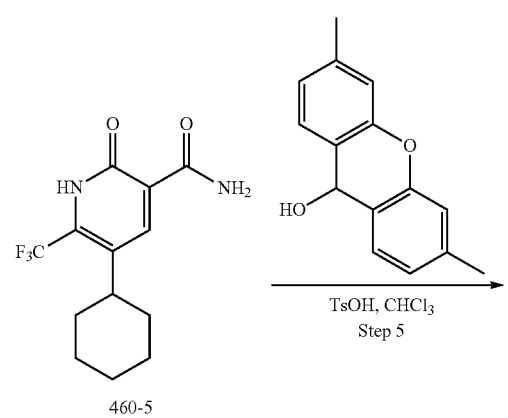

Step 3: 5-cyclohexyl-2-methoxy-6-(trifluoromethyl) nicotinamide (460-4)

A mixture of Compound 460-3 (400 mg, 1.2 mmol) and NH$_3$/MeOH (20 M, 15 mL) was stirred at 70° C. for 5 hrs in a sealed tube. LCMS showed the reaction was completed and desired mass was detected. The reaction mixture was concentrated to give Compound 460-4 (300 mg, crude) as a white solid. M+H$^+$=303.1 (LCMS).

Step 4: 5-cyclohexyl-2-oxo-6-(trifluoromethyl)-1,2-dihydropyridine-3-carboxamide (460-5)

To a solution of Compound 460-5 (200 mg, 661.6 μmol) in DCM (4 mL) was added BBr$_3$ (1.3 g, 5.2 mmol) at −78° C. under N$_2$. then stirred at same temperature for 2 hrs. TLC indicated the reaction completed. The reaction mixture was poured into H$_2$O (15 mL) and extracted with DCM (10 mL×4). The combined organic layers were dried over Na$_2$SO$_4$ and concentrated in vacuum to give Compound 460-5 (170 mg, crude) as a light yellow solid. M+H$^+$=289.1 (LCMS); $^1$H NMR (400 MHz, DMSO-d$_6$) δ=13.83-12.96 (m, 1H), 8.59-8.37 (m, 2H), 8.17 (br s, 1H), 2.76 (br t, J=10.9 Hz, 1H), 1.81 (br d, J=11.5 Hz, 2H), 1.75-1.63 (m, 3H), 1.57-1.43 (m, 2H), 1.39-1.28 (m, 3H).

Step 5: 5-cyclohexyl-N-(3,6-dimethyl-9H-xanthen-9-yl)-2-oxo-6-(trifluoromethyl)-1,2-dihydropyridine-3-carboxamide (460)

A solution of 3,6-dimethyl-9H-xanthen-9-ol (120 mg, 530 μmol) in DCM (3 mL) was added to a mixture of Compound 460-5 (130 mg, 451 μmol) and TsOH.H$_2$O (151 mg, 795.5 μmol) in CHCl$_3$ (3 mL) at 70° C., the mixture was stirred at 70° C. for 5 mins. LCMS showed the reaction was completed and desired mass was detected. The reaction mixture was quenched by addition H$_2$O (10 mL) and extracted with DCM (10 mL×2). The combined organic layers were dried over Na$_2$SO$_4$, filtered and concentrated under reduced pressure to give a residue, which was purified by Prep-HPLC to give Compound 460 (16 mg, 31.7 μmol, 6% yield) as a light yellow solid. M−H$^-$=495.2 (LCMS); $^1$H NMR (400 MHz, DMSO-d$_6$) δ=13.37-12.82 (m, 1H), 9.84-9.30 (m, 1H), 8.41 (s, 1H), 7.34 (d, J=7.7 Hz, 2H), 7.07-6.90 (m, 4H), 6.45 (d, J=8.4 Hz, 1H), 2.74 (br t, J=11.1 Hz, 1H), 2.32 (s, 6H), 1.79 (br d, J=10.4 Hz, 2H), 1.71-1.58 (m, 3H), 1.47 (q, J=11.4 Hz, 2H), 1.39-1.17 (m, 3H).

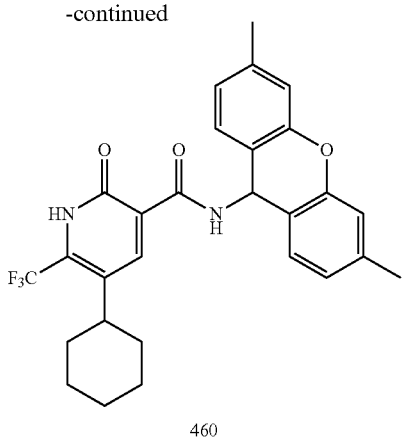

460

Step 1: ethyl 5-(cyclohex-1-en-1-yl)-2-methoxy-6-(trifluoromethyl)nicotinate (460-2)

To a mixture of Compound 460-2 (700 mg, 2.1 mmol) and cyclohex-1-en-1-ylboronic acid (806 mg, 6.4 mmol) in dioxane (9 mL) and H$_2$O (0.9 mL) was added Na$_2$CO$_3$ (678 mg, 6.4 mmol) and Pd(dppf)Cl$_2$ (156 mg, 213.4 μmol) under N$_2$. The mixture was stirred at 80° C. under N$_2$ for 12 hrs. LCMS showed the reaction was completed and desired mass was detected. The reaction mixture was diluted with EtOAc (20 mL), filtered and concentrated to give a residue, which was purified by column chromatography to give Compound 460-2 (650 mg, 99% yield) as colorless oil. M+H$^+$=330.1 (LCMS); $^1$H NMR (400 MHz, CDCl$_3$) δ=7.97 (s, 1H), 5.63 (td, J=1.9, 3.5 Hz, 1H), 4.39 (q, J=7.1 Hz, 2H), 4.07 (s, 3H), 2.23-2.12 (m, 4H), 1.82-1.73 (m, 2H), 1.72-1.64 (m, 2H), 1.40 (t, J=7.2 Hz, 3H).

Step 2: ethyl 5-cyclohexyl-2-methoxy-6-(trifluoromethyl)nicotinate (460-3)

To a solution of ethyl Compound 460-3 (580 mg, 1.8 mmol) in EtOAc (40 mL) was added Pd/C (500 mg, 10% purity) under N$_2$ atmosphere. The suspension was degassed and purged with H$_2$ for 3 times. Then the mixture was stirred under H$_2$ (15 Psi) at 25° C. for 17 hrs. The reaction mixture was filtered and concentrated to give Compound 460-3 (600 mg, crude) as colorless oil. M+H$^+$=332.1 (LCMS).

Other compounds made in a similar manner are shown in Table 47.

TABLE 47

| Compound No | Structure | HNMR and Ms |
|---|---|---|
| 461 | 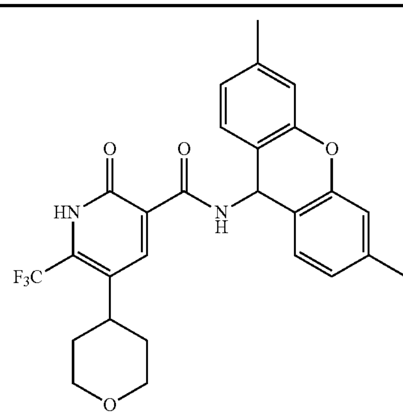 | $^1$H NMR (400 MHz, DMSO-d$_6$) δ = 13.46-13.02 (m, 1H), 10.39-9.42 (m, 1H), 8.42 (br s, 1H), 7.34 (d, J = 7.7 Hz, 2H), 7.07-6.85 (m, 4H), 6.51-6.45 (m, 1H), 3.93 (br dd, J = 3.5, 11.2 Hz, 2H), 3.47-3.37 (m, 2H), 3.05-2.93 (m, 1H), 2.32 (s, 6H), 1.82-1.66 (m, 2H), 1.54 (br d, J = 11.5 Hz, 2H) ESI [M − H] = 497.1 |

Example 84: Synthesis of N-(3,6-dimethyl-10,10-dioxido-9H-thioxanthen-9-yl)-5-(hydroxymethyl)-2-oxo-6-(trifluoromethyl)-1,2-dihydropyridine-3-carboxamide (462)

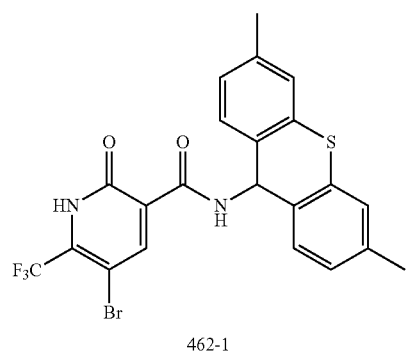
462-1

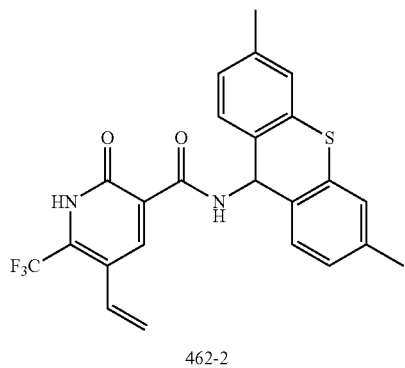
462-2

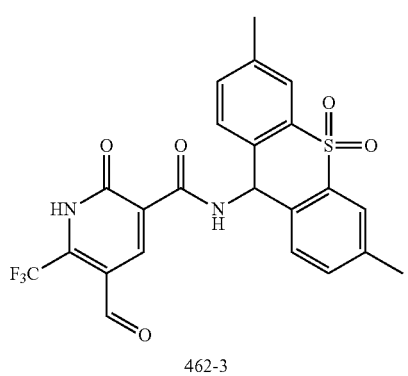
462-3

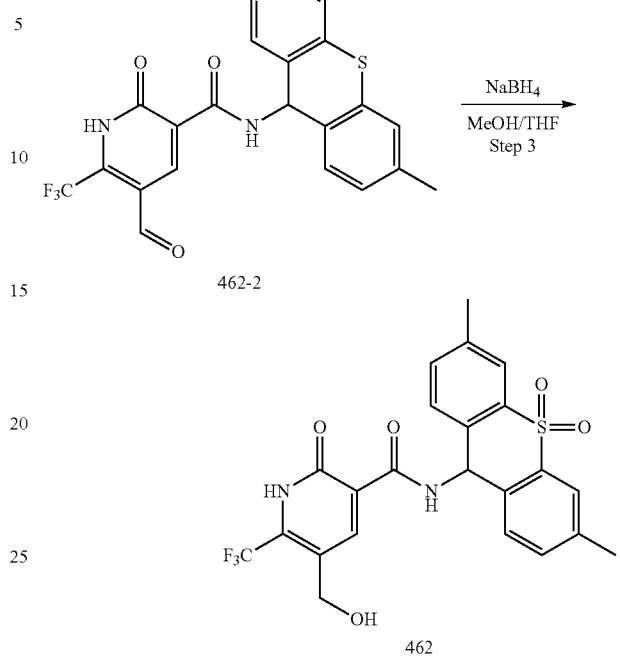
462-2

462

Step 1: N-(3,6-dimethyl-9H-thioxanthen-9-yl)-2-oxo-6-(trifluoromethyl)-5-vinyl-1,2-dihydropyridine-3-carboxamide (462-2)

To a stirred solution of Compound 462-1 (120 mg, 235.6 μmol) in dioxane (5.0 mL) was added tributyl(vinyl)stannane (112 mg, 353.4 μmol), followed by adding Pd(t-Bu$_3$P)$_2$ (12 mg, 23.6 μmol). Then the mixture was degassed in vacuum and purged into N$_2$ three times. The resulting mixture was stirred at 100° C. for 3 hrs. TLC showed the reaction was complete. The mixture was filtered via a pad of celite, and the filtrate was concentrated in vacuum to give a residue, which was purified by Prep-TLC (Petroleum ether: Ethyl acetate=5/1, R$_f$=0.54) to give Compound 462-2 (70 mg, crude) as a light yellow solid. M−H⁻=455.0 (LCMS); $^1$H NMR (400 MHz, DMSO-d$_6$) δ=13.40 (br, 1H), 9.57 (br, 1H), 8.60 (s, 1H), 7.51-7.49 (d, J=8 Hz, 2H), 7.38 (s, 2H), 7.15-7.13 (m, 2H), 6.92-9.84 (m, 1H), 6.14-6.11 (m, 1H), 5.94-5.89 (d, J=17.2 Hz, 1H), 5.52-5.49 (d, J=10.4 Hz, 1H), 2.30 (s, 6H).

Step 2: N-(3,6-dimethyl-10,10-dioxido-9H-thioxanthen-9-yl)-5-formyl-2-oxo-6-(trifluoromethyl)-1,2-dihydropyridine-3-carboxamide and N-(3,6-dimethyl-9H-thioxanthen-9-yl)-5-formyl-2-oxo-6-(trifluoromethyl)-1,2-dihydropyridine-3-carboxamide (462-3 and 462-4)

To a stirred solution of Compound 462-2 (70 mg, 153.4 μmol) in dioxane (1 mL) and H$_2$O (0.3 mL) was added NaIO$_4$ (66 mg, 306.7 μmol) and K$_2$OsO4.2H$_2$O (6 mg, 15.3 μmol) at 0° C. Then the mixture was stirred at 20° C. for 1 hr. TLC showed the reaction was completed. The mixture was diluted with H$_2$O (2.0 mL) and extracted with DCM (1.0 mL×3). The combined organic layers were dried over Na$_2$SO$_4$ and concentrated in vacuum to give a residue, which was purified by Prep-HPLC to give Compound 462-3 (10 mg, 20.4 µmol, 13% yield) as a white solid and Compound 462-4 (11 mg, 24.0 µmol, 16% yield) as an off-white solid. M–H⁻=487.1 (LCMS) and M–H⁻=457.1 (LCMS).

Step 3: N-(3,6-dimethyl-10,10-dioxido-9H-thioxanthen-9-yl)-5-(hydroxymethyl)-2-oxo-6-(trifluoromethyl)-1,2-dihydropyridine-3-carboxamide (462)

To a stirred solution of Compound 462-3 (10 mg, 19.67 µmol, 1 eq) in MeOH (1 mL) and THF (1 mL) was added NaBH₄ (4 mg, 98.4 µmol) in one portion. Then the mixture was stirred at 25° C. for 2 hrs. LCMS showed the reaction was completed. The reaction was poured into water (5 mL) and adjusted pH=7 with 1N HCl. The product was extracted with DCM (2 mL×2). The combined organic layers were concentrated in vacuum to give a residue, which was purified by Prep-HPLC to give Compound 462 (4 mg, 8.8 µmol, 44.79% yield) as a white solid. M–H⁻=491.1 (LCMS); $^1$H NMR (400 MHz, DMSO-d₆) δ=8.53 (br, 1H), 7.90 (s, 2H), 7.65-7.63 (d, J=8.0 Hz, 1H), 7.54-7.52 (d, J=8.2 Hz, 1H), 6.65 (d, 1H), 5.50 (s, 1H), 4.59 (s, 2H), 2.43 (s, 6H).

Other compounds made in a similar manner are shown in Table 48.

Example 85: Synthesis of 2-oxo-N-(phenyl(3-propylphenyl)methyl)-6-(trifluoromethyl)-1,2-dihydropyridine-3-carboxamide (465)

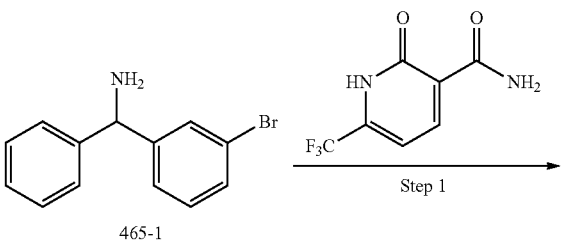

TABLE 48

| Compound No | Structure | HNMR and Ms |
|---|---|---|
| 463 | 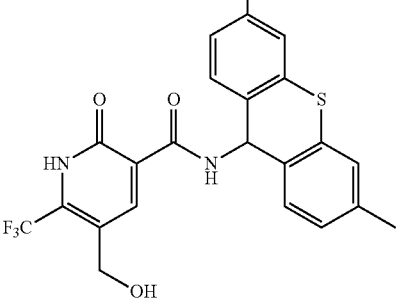 | $^1$H NMR (400 MHz, DMSO-d₆) δ = 8.50 (br, 1H), 7.48-7.45 (m, 2H), 7.38 (s, 2H), 7.15-7.12 (m, 2H), 6.10 (d, 1H), 5.19 (s, 1H), 4.59 (s, 2H), 2.43 (s, 6H) ESI [M – H] = 459.1 |
| 464 | 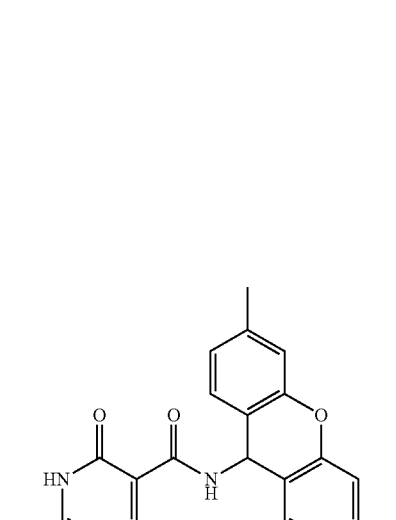 | $^1$H NMR (400 MHz, DMSO-d₆) δ = 13.31-12.92 (m, 1H), 9.83-9.18 (m, 1H), 8.54 (br s, 1H), 7.34 (d, J = 7.8 Hz, 2H), 7.03-6.94 (m, 4H), 6.44 (d, J = 8.6 Hz, 1H), 5.62-5.43 (m, 1H), 4.56 (br d, J = 3.8 Hz, 2H), 2.32 (s, 6H) ESI [M – H] = 443.1 |

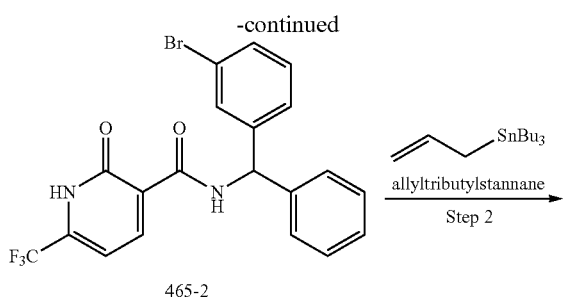

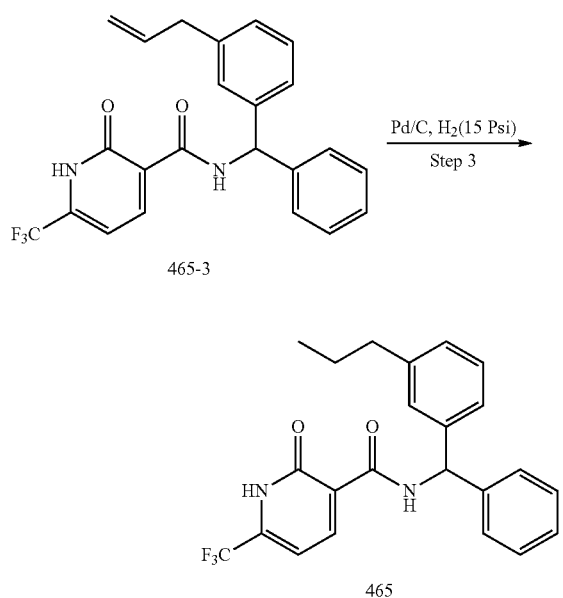

Step 1: N-((3-bromophenyl)(phenyl)methyl)-2-oxo-6-(trifluoromethyl)-1,2-dihydropyridine-3-carboxamide (465-2)

To a stirred solution of 2-oxo-6-(trifluoromethyl)-1,2-dihydropyridine-3-carboxylic acid (395 mg, 1.9 mmol) in DCM (6 mL) was added HATU (725 mg, 1.9 mmol). The mixture was stirred at 25° C. for 5 min. Then Compound 465-1 (500 mg, 1.9 mmol) and DIEA (740 mg, 5.7 mmol) was added. The mixture was stirred at 25° C. for 55 min. LCMS showed the reaction was complete and one main peak with desired mass was detected. The reaction was poured into $H_2O$ (5 mL) and extracted with EtOAc (10 mL×3). The combined organic layers were dried over $Na_2SO_4$, filtered and concentrated under reduced pressure to give a residue, which was purified by flash silica gel chromatography to give Compound 465-2 (650 mg, crude) as yellow oil. M−H⁻=448.9 (LCMS).

Step 2: N-((3-allylphenyl)(phenyl)methyl)-2-oxo-6-(trifluoromethyl)-1,2-dihydropyridine-3-carboxamide (465-3)

To a mixture of Compound 465-2 (200 mg, 443.2 μmol), allyltributylstannane (176 mg, 531.9 μmol) in dioxane (6 mL) was added palladium; tritert-butylphosphane (23 mg, 44.3 μmol) under $N_2$. The mixture was stirred at 100° C. for 3 hrs under $N_2$. LCMS showed the reaction was complete and one main peak with desired mass was detected. The reaction mixture was diluted with EtOAc (15 mL), then filtered and concentrated under reduced pressure to give a residue, which was purified by Prep-TLC (Petroleum ether: Ethyl acetate=3:1, $R_f$=0.53) to give Compound 465-3 (160 mg, crude) as colorless oil. M−H⁻=411.1 (LCMS). $^1$H NMR (400 MHz, MeOD) δ=8.29-8.27 (m, 1H), 7.36-7.20 (m, 8H), 7.07-7.03 (m, 1H), 6.76-6.74 (d, J=7.6 Hz, 1H), 6.30 (s, 1H), 5.05-4.98 (m, 2H), 3.36-3.34 (m, 2H).

Step 3: 2-oxo-N-(phenyl(3-propylphenyl)methyl)-6-(trifluoromethyl)-1,2-dihydropyridine-3-carboxamide (465)

To a mixture of Compound 465-3 (100 mg, 242.5 μmol) in EtOAC (3 mL) was added Pd/C (25 mg, 10% purity). The mixture was degassed and purged with $H_2$ for 3 times, and then was stirred at 25° C. for 30 mins under $H_2$ (15 psi). LC-MS showed the reaction was complete and one main peak with desired mass was detected. The reaction mixture was filtered and concentrated under reduced pressure to give a residue, which was purified by Prep-HPLC to give Compound 465 (16 mg, 38.0 μmol, 16% yield) as a yellow solid. M−H⁻=413.1 (LCMS); $^1$H NMR (400 MHz, MeOD) δ=8.53-8.50 (d, J=7.2 Hz, 1H), 7.33-7.22 (m, 6H), 7.14-7.03 (m, 4H), 6.30 (s, 1H), 2.57-2.54 (t, J=7.6 Hz, 2H), 1.64-1.55 (m, 2H), 0.92-0.88 (t, J=7.2 Hz, 3H).

Other compounds made in a similar manner are shown in Table 49.

TABLE 49

| Compound No | Structure | HNMR and Ms |
|---|---|---|
| 466 | 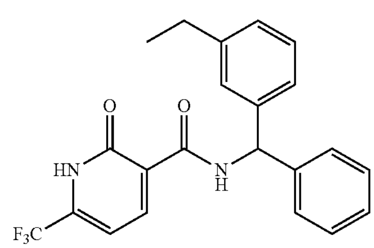 | $^1$H NMR (400 MHz, MeOD) δ = 8.44-8.42 (d, J = 7.2 Hz, 1H), 7.34-7.32 (m, 4H), 7.24-7.22 (m, 2H), 7.18-7.09 (m, 3H), 6.91 (d, 1H), 6.30 (s, 1H), 2.64-2.58 (q, J = 7.6 Hz, 2H), 1.21-1.17 (t, J = 7.2 Hz, 3H) ESI [M − H] = 399.1 |

TABLE 49-continued

| Compound No | Structure | HNMR and Ms |
|---|---|---|
| 467 | 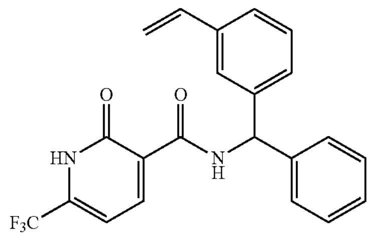 | ¹H NMR (400 MHz, MeOD) δ = 8.48-8.46 (d, J = 7.6 Hz, 1H), 7.39-7.23 (m, 9H), 7.00-6.97 (d, J = 7.6 Hz, 1H), 6.71-6.67 (m, 1H), 6.33 (s, 1H), 5.77-5.72 (d, J = 17.6 Hz, 1H), 5.23-5.20 (d, J = 11.2 Hz, 1H). ESI [M − H] = 397.1. |

Example 86: Synthesis of N-(2-ethyl-10,10-dioxido-9H-thioxanthen-9-yl)-2-oxo-6-(trifluoromethyl)-1,2-dihydropyridine-3-carboxamide (468)

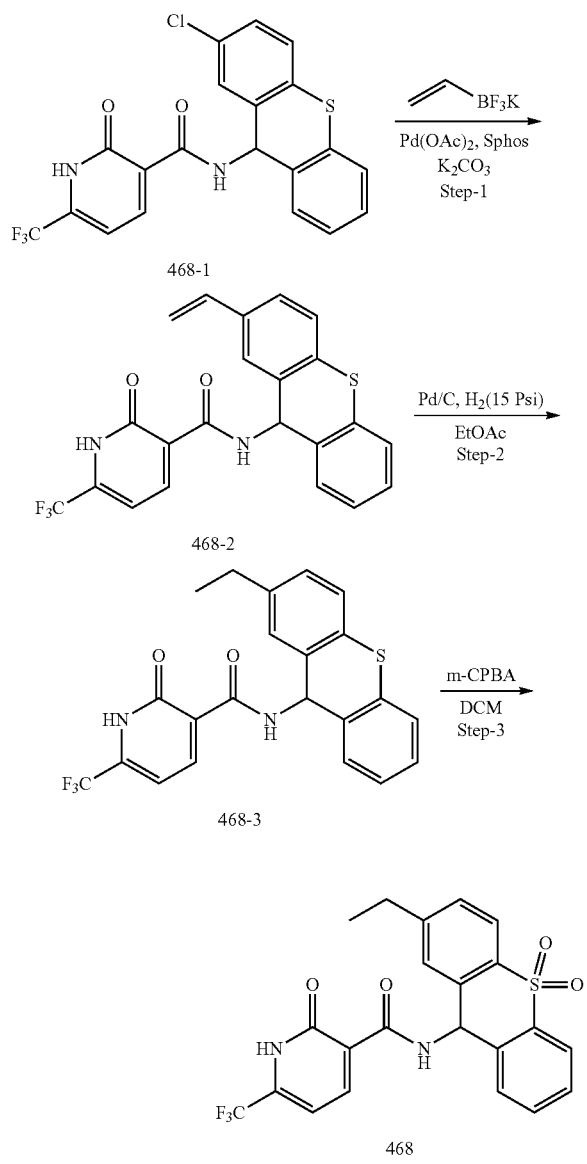

Step 1: 2-oxo-6-(trifluoromethyl)-N-(2-vinyl-9H-thioxanthen-9-yl)-1,2-dihydropyridine-3-carboxamide (468-2)

To a mixture of Compound 468-1 (20 mg, 45.8 μmol) in dioxane (2 mL) and H₂O (0.4 mL) was added potassium vinyltrifluoroborate (6 mg, 45.8 μmol), SPhos (1 mg, 2.8 μmol), K₂CO₃ (19 mg, 137.3 μmol) and Pd(OAc)₂ (308 ug, 1.4 μmol). The mixture was degassed and purged with N₂ for 3 times and stirred at 90° C. for 5 hrs. LCMS showed the reaction was completed and desired mass was detected. The reaction mixture was poured into H₂O (5 mL) and extracted with EtOAc (5 mL×3). The combined organic layers were dried over Na₂SO₄, filtered and concentrated under reduced pressure to give a residue, which was purified by prep-HPLC to give Compound 468-2 (3 mg, 15% yield) as a yellow solid. M−H⁻=427.0 (LCMS); ¹H NMR (400 MHz, DMSO-d6) δ=13.51-13.42 (br, 1H), 10.11-9.22 (m, 1H), 8.41-8.39 (d, J=7.3 Hz, 1H), 7.75-7.17 (m, 8H), 6.79-6.72 (m, 1H), 6.17-6.14 (d, J=8.6 Hz, 1H), 5.89-5.84 (d, J=17.6 Hz, 1H), 5.30-5.27 (d, J=10.8 Hz, 1H).

Step 2: N-(2-ethyl-9H-thioxanthen-9-yl)-2-oxo-6-(trifluoromethyl)-1,2-dihydropyridine-3-carboxamide (468-3)

To a solution of Compound 468-2 (80 mg, 186.7 μmol) in EtOAc (2 mL) was added Pd/C (10 mg, 186.7 μmol, 10% purity) under H₂ (15 Psi). The mixture was stirred at 25° C. for 0.5 hr. LCMS showed the reaction was completed and the desired mass was detected. The reaction mixture was filtered and concentrated under reduced pressure to give a residue, which was purified by prep-HPLC to give Compound 468-3 (8 mg, 10% yield) as a light yellow solid. M−H⁻=429.0 (LCMS); ¹H NMR (400 MHz, DMSO-d6) δ=13.67-13.36 (m, 1H), 10.27-9.58 (m, 1H), 8.42 (br d, J=7.5 Hz, 1H), 7.64-7.55 (m, 2H), 7.51-7.46 (m, 2H), 7.36-7.29 (m, 2H), 7.20 (br d, J=8.1 Hz, 2H), 6.12 (br d, J=8.8 Hz, 1H), 2.61 (br s, 2H), 1.17 (t, J=7.6 Hz, 3H).

Step 3: N-(2-ethyl-10,10-dioxido-9H-thioxanthen-9-yl)-2-oxo-6-(trifluoromethyl)-1,2-dihydropyridine-3-carboxamide (468)

To a mixture of Compound 468-3 (60 mg, 139.4 μmol) in DCM (8 mL) was added m-CPBA (105 mg, 4879 μmol) at 0° C. and the mixture was stirred at 25° C. for 1 hr. LCMS showed the reaction was completed and desired mass was detected. The reaction mixture was poured into Sat. aq. NaHCO₃ (5 mL) and extracted with EtOAc (5 mL×5). The combined organic layers were dried over Na₂SO₄, filtered and concentrated under reduced pressure to give a residue, which was purified by Prep-HPLC to give Compound 468 (9 mg, 14% yield) as a yellow solid. M−H⁻=461.1 (LCMS); ¹H NMR (400 MHz, DMSO-d6) δ=9.98-9.95 (m, 1H), 8.47 (d, J=7.5 Hz, 1H), 8.07 (dd, J=1.2, 7.5 Hz, 1H), 8.00 (d, J=7.9 Hz, 1H), 7.81-7.76 (m, 1H), 7.75-7.69 (m, 2H), 7.69-7.63 (m, 1H), 7.56-7.49 (m, 1H), 7.39 (br d, J=7.0 Hz, 1H), 6.71 (d, J=9.3 Hz, 1H), 2.76-2.68 (m, 2H), 1.19 (t, J=7.6 Hz, 3H).

Other compounds made in a similar manner are shown in Table 50.

TABLE 50

| Compound No | Structure | HNMR and Ms |
| --- | --- | --- |
| 469 | 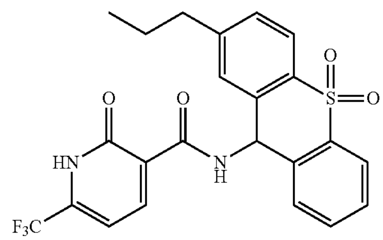 [SMILES: CCCc1ccc2c(c1)C(NC(=O)c1ccc(C(F)(F)F)[nH]c1=O)c1ccccc1S2(=O)=O] | ¹H NMR (400 MHz, METHANOL-d4) δ = 8.53 (d, J = 7.5 Hz, 1H), 8.08 (d, J = 7.3 Hz, 1H), 7.99 (d, J = 7.9 Hz, 1H), 7.77 (d, J = 7.7 Hz, 1H), 7.70 – 7.55 (m, 3H), 7.44 (d, J = 7.7 Hz, 1H), 7.02 (d, J = 7.6 Hz, 1H), 6.85 (s, 1H), 2.70 (t, J = 7.6 Hz, 2H), 1.66 (sxt, J = 7.5 Hz, 2H), 0.93 (t, J = 7.3 Hz, 3H) ESI [M − H] = 475.1 |
| 470 | 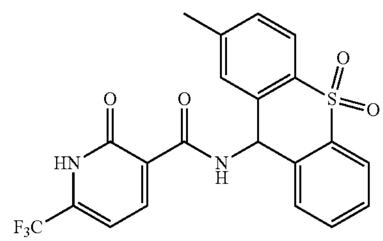 [SMILES: Cc1ccc2c(c1)C(NC(=O)c1ccc(C(F)(F)F)[nH]c1=O)c1ccccc1S2(=O)=O] | ¹H NMR (400 MHz, DMSO-d6) δ = 13.49 (m, 1H), 10.31 (m, 1H), 8.46 – 8.44 (d, J = 7.6 Hz, 1H), 8.08 – 8.06 (d, J = 7.6 Hz, 1H), 7.98 – 7.96 (d, J = 8 Hz, 1H), 7.77 – 7.65 (m, 4H), 7.49 – 7.46 (d, J = 8.4 Hz, 1H), 7.31 (s, 1H), 6.72 – 6.69 (d, J = 9.2 Hz, 1H), 2.41 (s, 3H). ESI [M − H] = 447.0 |
| 471 | 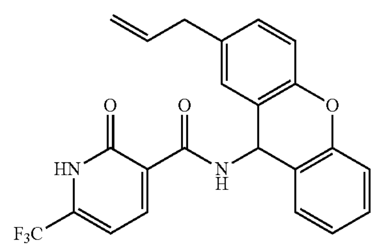 | ¹H NMR (400 MHz, DMSO-d₆) δ = 13.76 – 12.48 (m, 1H), 10.60 – 9.69 (m, 1H), 8.36 (brd, J = 7.5 Hz, 1H), 7.45 (d, J = 7.5 Hz, 1H), 7.38-7.31 (m, 1H), 7.27 (s, 1H), 7.20 – 7.08 (m, 5H), 6.49 (d, J = 8.6 Hz, 1H), 5.93 (tdd, J = 6.8, 10.1, 16.9 Hz, 1H), 5.12-4.99 (m, 2H), 3.3 (m, 2H). ESI [M − H] = 425.1 |
| 472 | 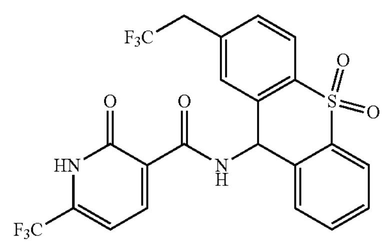 | ¹H NMR (400 MHz, METHANOL-d₄) δ = 8.60 (d, J = 7.5 Hz, 1H), 8.10 (d, J = 7.9 Hz, 2H), 7.79 (br s, 2H), 7.73 – 7.59 (m, 3H), 7.11 (d, J = 7.5 Hz, 1H), 6.85 (s, 1H), 3.67 (q, J = 11.0 Hz, 2H) ESI [M − H] = 515.0 |
| 473 | 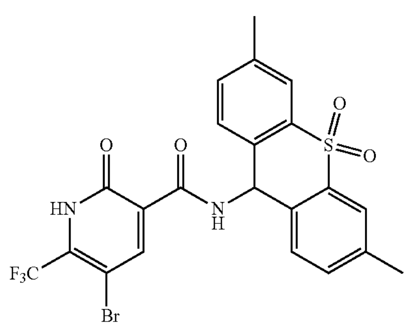 [SMILES: Cc1ccc2c(c1)S(=O)(=O)c1cc(C)ccc1C2NC(=O)c1cc(Br)c(C(F)(F)F)[nH]c1=O] | ¹H NMR (400 MHz, DMSO-d₆) δ = 8.61 (s, 1H), 7.90 (s, 2H), 7.66 – 7.64 (d, J = 7.6 Hz, 2H), 7.50 – 7.47 (d, J = 7.2 Hz, 2H), 6.72 (s, 1H), 2.46 (s, 6H). ESI [M − H] = 539.0 |

TABLE 50-continued
| Compound No | Structure | HNMR and Ms |
|---|---|---|
| 474 | 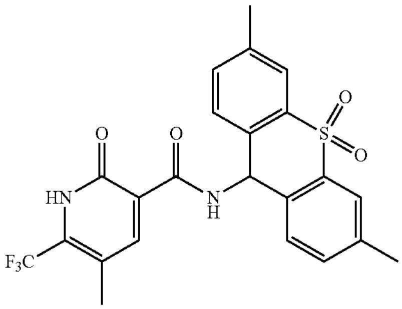 [SMILES: Cc1ccc2c(c1)S(=O)(=O)c1cc(C)ccc1C2NC(=O)c1cc(C)c(C(F)(F)F)[nH]c1=O] | ¹H NMR (400 MHz, DMSO-d₆) δ = 8.15 (s, 1H), 7.87 (s, 2H), 7.60 – 7.55 (m, 2H), 7.51 – 7.45 (m, 2H), 6.62 (s, 1H), 2.41 (s, 6H), 2.29 (brd, J = 1.7 Hz, 3H)<br>ESI [M − H] = 475.1 |
| 475 | 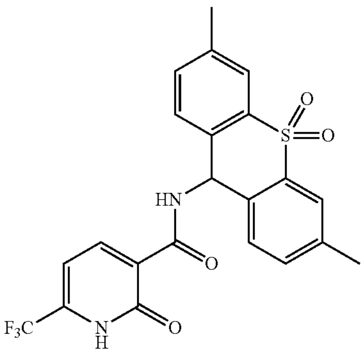 [SMILES: Cc1ccc2c(c1)S(=O)(=O)c1cc(C)ccc1C2NC(=O)c1ccc(C(F)(F)F)[nH]c1=O] | ¹H NMR (400 MHz, DMSO-d₆) δ = 11.04 (s, 1H), 8.39 – 8.37 (d, J = 7.6 Hz, 2H), 7.89 (s, 2H), 7.63 – 7.61 (d, J = 8 Hz, 2H), 7.52 – 7.50 (d, J = 7.6 Hz, 2H), 7.12 – 7.10 (m, 1H), 6.63-6.61 (d, J = 8.8 Hz, 1H), 2.50 (s, 3H), 2.43 (s, 3H).<br>ESI [M − H] = 460.9 |
| 476 | 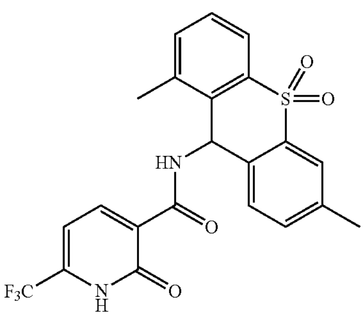 | ¹H NMR (400 MHz, DMSO-d₆) δ = 13.55 (s, 1H), 9.76 (s, 1H), 8.50 – 8.48 (d, J = 4.36 Hz, 1H), 7.92 – 7.75 (m, 3H), 7.61 – 7.54 (m, 3H), 7.21 (s, 1H), 6.84 – 6.82 (d, J = 9.2 Hz, 1H), 2.50 (s, 3H), 2.41 (s, 3H).<br>ESI [M − H] = 461.0. |
Example 87: Synthesis of N-(3,4-dihydro-2H-pyrano[3,2-b]pyridin-4-yl)-2-oxo-6-(trifluoromethyl)-1,2-dihydropyridine-3-carboxamide (477)
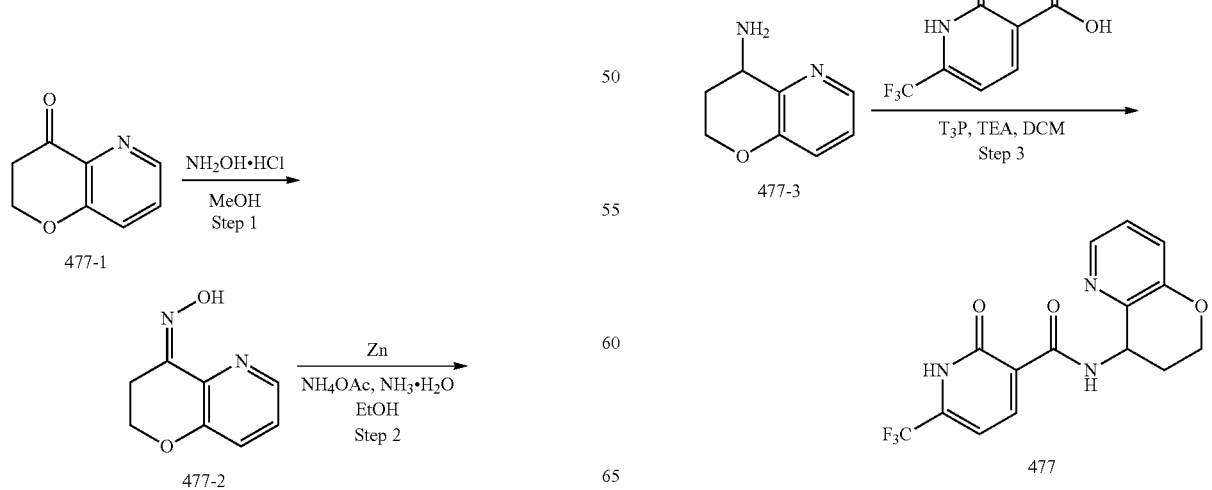

Step 1: (Z)-2H-pyrano[3,2-b]pyridin-4(3H)-one oxime (477-2)

To a solution of Compound 477-1 (0.2 g, 1.3 mmol) in MeOH (4 mL) was added NH$_2$OH·HCl (112 mg, 1.6 mmol). The mixture was stirred at 25° C. for 12 hrs. LCMS showed the reaction completed and one main peak with desired mass was detected. The reaction mixture was quenched by Sat. NaHCO$_3$ aqueous solution to pH=7 and extracted with CH$_2$Cl$_2$ (3×10 mL). The organic layers were washed with brine (2×10 mL), dried over Na$_2$SO$_4$, filtered and concentrated to give Compound 477-2 (0.15 g, crude) as a pink solid. M+H$^+$=165.2 (LCMS)

Step 2: 3,4-dihydro-2H-pyrano[3,2-b]pyridin-4-amine (477-3)

To a solution of Compound 477-2 (50 mg, 304.58 µmol) in EtOH (0.25 mL) was added NH$_3$1120 (1.28 g, 9.2 mmol, 25% purity), NH$_4$OAc (26 mg, 342.58 µmol) and Zn (60 mg, 913.74 µmol) at 0° C. The mixture was stirred at 25° C. for 12 hrs. LCMS showed the reaction completed and desired mass was detected. The mixture was filtered and washed with H$_2$O (10 mL), extracted with CH$_2$Cl$_2$ (3×5 mL), washed with brine, dried over Na$_2$SO$_4$, filtered and concentrated to give Compound 477-3 (40 mg, crude) as a pink gum. M+H$^+$=151.3 (LCMS); $^1$H NMR (400 MHz, CHLOROFORM-d) δ=8.17 (dd, J=1.8, 4.1 Hz, 1H), 7.14-7.08 (m, 2H), 4.33-4.31 (m, 1H), 4.26-4.24 (m, 1H), 4.23-4.12 (m, 1H), 2.32-2.28 (m, 1H), 1.99-1.93 (m, 1H).

Step 3: N-(3,4-dihydro-2H-pyrano[3,2-b]pyridin-4-yl)-2-oxo-6-(trifluoromethyl)-1,2-dihydropyridine-3-carboxamide (477)

To a solution of Compound 477-3 (30 mg, 199.76 µmol) and 2-oxo-6-(trifluoro methyl)-1,2-dihydropyridine-3-carboxylic acid (41 mg, 199.76 µmol) in DCM (2 mL) was added TEA (61 mg, 599.29 µmol) and T$_3$P (153 mg, 239.72 µmol, 50% purity). The mixture was stirred at 25° C. for 0.5 hr. LCMS showed the reaction completed, desired mass and by-product mass was detected. The reaction mixture was pouring into water 10 mL and extracted with DCM (3 mL×2). The combined organic layers were dried over Na$_2$SO$_4$, filtered and concentrated under reduced pressure to give a residue. The residue was treated with 3 mL MeOH/3M NaOH aq. (v/v=1:1) and stirred at 25° C. for 12 hrs. The reaction mixture was poured into water (10 mL) and extracted with DCM (3 mL×2). The combined organic layers were dried over Na$_2$SO$_4$, filtered and concentrated under reduced pressure to give a residue, which was purified by prep-HPLC to give Compound 477 (52 mg, 154.4 µmol, 77% yield,) as a light yellow solid. M−H$^−$=338.1 (LCMS); $^1$H NMR (400 MHz, METHANOL-d4) δ=8.56 (br d, J=7.3 Hz, 1H), 8.13 (br s, 1H), 7.36-7.26 (m, 2H), 7.09 (br d, J=7.5 Hz, 1H), 5.28 (br t, J=5.4 Hz, 1H), 4.42-4.24 (m, 2H), 251-2.43 (m, 1H), 2.32-2.19 (m, 1H).

Example 88: Synthesis of 2-oxo-N-(phenyl(3-(2,2,2-trifluoroethyl)phenyl)methyl)-6-(trifluoromethyl)-1,2-dihydropyridine-3-carboxamide (478)

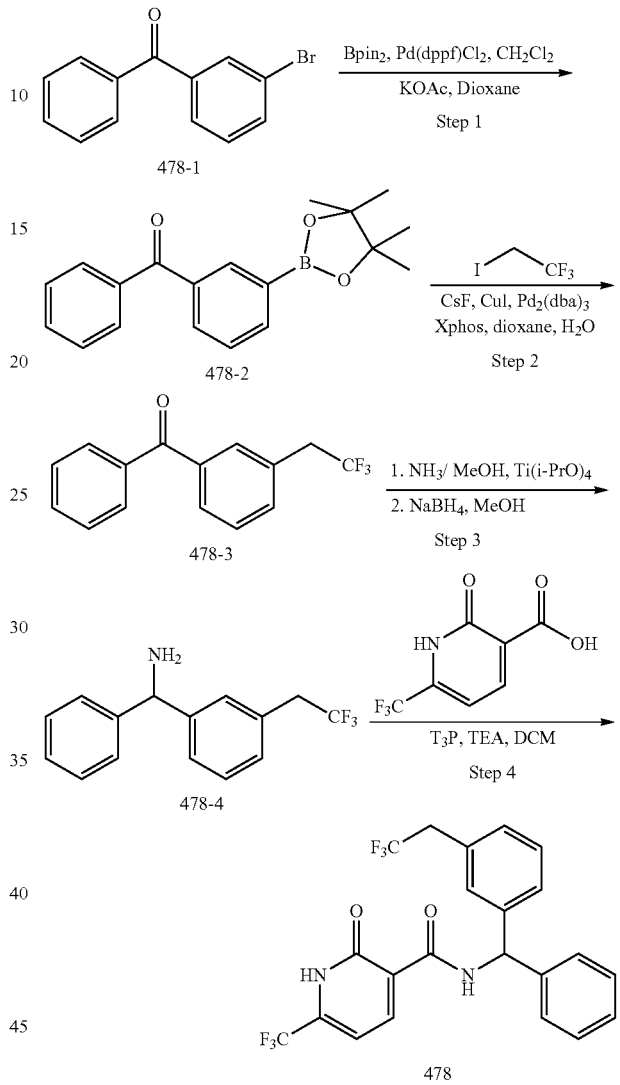

Step 1: phenyl(3-(4,4,5,5-tetramethyl-1,3,2-dioxaborolan-2-yl)phenyl)methanone (478-2)

A mixture of Compound 478-1 (1.0 g, 3.8 mmol), BPD (1.5 g, 5.9 mmol) Pd(dppf)Cl$_2$·CH$_2$Cl$_2$, (313 mg, 383 µmol), KOAc (1.1 g, 11.5 mmol) in dioxane (30 mL) was degassed and purged with N$_2$ for 3 times, and then the mixture was stirred at 80° C. for 12 hrs under N$_2$ atmosphere. LCMS showed the reaction was completed. The reaction mixture was poured into H$_2$O (30 mL), extracted with EtOAc (20 mL×5). The combined organic layers were dried over Na$_2$SO$_4$, filtered and concentrated under reduced pressure to give a residue, which was purified by column chromatography (Petroleum ether/Ethyl acetate) to give Compound 478-2 (1.1 g, 3.6 mmol, 93% yield) as a light yellow solid. $^1$H NMR (400 MHz, CHLOROFORM-d) δ=8.23 (s, 1H), 8.03 (d, J=7.3 Hz, 1H), 7.87 (d, J=7.8 Hz, 1H), 7.81 (d, J=7.2 Hz, 2H), 7.64-7.56 (m, 1H), 7.53-7.45 (m, 3H), 1.36 (s, 12H).

Step 2: phenyl(3-(2,2,2-trifluoroethyl)phenyl)methanone (478-3)

To a mixture of 1,1,1-trifluoro-2-iodoethane (668 mg, 3.2 mmol), Compound 478-2 (500 mg, 1.6 mmol), H$_2$O (233 mg, 12.9 mmol), CuCl (167 mg, 1.7 mmol), XPhos (83 mg, 175 μmol) and CsF (733 mg, 4.8 mmol) in DMF (10 mL) was added Pd$_2$(dba)$_3$ (42 mg, 46 μmol) under N$_2$, then the mixture was stirred at 65° C. for 12 hrs under N$_2$ atmosphere. LCMS showed the reaction was completed and the desired mass was detected. The reaction mixture was poured into H$_2$O (30 mL), extracted with EtOAc (10 mL×5). The combined organic layers were dried over Na$_2$SO$_4$, filtered and concentrated under reduced pressure to give a residue, which was purified by column chromatography (Petroleum ether/Ethyl acetate) to give Compound 478-3 (250 mg, 946 μmol, 58% yield) as a yellow oil. M+H$^+$=265.0 (LCMS).

Step 3: phenyl(3-(2,2,2-trifluoroethyl)phenyl)methanamine (478-4)

To a solution of Compound 478-3 (150 mg, 568 μmol) in MeOH (5 mL) was added NH$_3$/MeOH (10 M, 19.88 mL) and Ti(i-PrO)$_4$ (1.4 g, 5.0 mmol). The mixture was stirred at 20° C. for 12 hrs. Then to the mixture was added NaBH$_4$ (107 mg, 2.8 mmol) at 0° C. and the mixture was stirred for 2 hrs at 20° C. LCMS showed the reaction was completed. The mixture was poured into ice water (20 g) and extracted with EtOAc (3×20 mL). The combined organic layers were dried over Na$_2$SO$_4$ and concentrated in vacuum to give a Compound 478-4 (100 mg, crude) as a yellow gum. Fragment Ms=249.0 (LCMS).

Step 4: 2-oxo-N-(phenyl(3-(2,2,2-trifluoroethyl) phenyl)methyl)-6-(trifluoromethyl)-1,2-dihydropyridine-3-carboxamide (478)

To a stirred solution of 2-oxo-6-(trifluoromethyl)-1,2-dihydropyridine-3-carboxylic acid (39 mg, 188 μmol) and Compound 478-4 (50 mg, 188 μmol) in DCM (5 mL) was added TEA (57 mg, 565 μmol) at 25° C., followed by T$_3$P (240 mg, 377 μmol, 50% purity). The resulting mixture was stirred at 25° C. for 2 hrs. LCMS showed the reaction was completed and the desired mass was detected. The mixture was poured into water (10 mL) and extracted with EtOAc (3×10 mL). The combined organic layers were dried over Na$_2$SO$_4$ and concentrated in vacuum to give a residue, which was purified by prep-HPLC to give Compound 478 (13.50 mg, 27 μmol, 14% yield) as a white solid. M−H$^-$=453.1 (LCMS), $^1$H NMR (400 MHz, CHLOROFORM-d) δ=10.16 (br d, J=8.2 Hz, 1H), 8.72 (d, J=7.3 Hz, 1H), 7.39-7.28 (m, 6H), 7.26-7.18 (m, 2H), 6.90 (d, J=7.5 Hz, 1H), 6.48 (d, J=8.2 Hz, 1H), 3.34 (q, J=10.6 Hz, 2H).

Example 89: Synthesis of 2-oxo-N-(2-(2,2,2-trifluoroethyl)-9H-xanthen-9-yl)-6-(trifluoromethyl)-1,2-dihydropyridine-3-carboxamide (479)

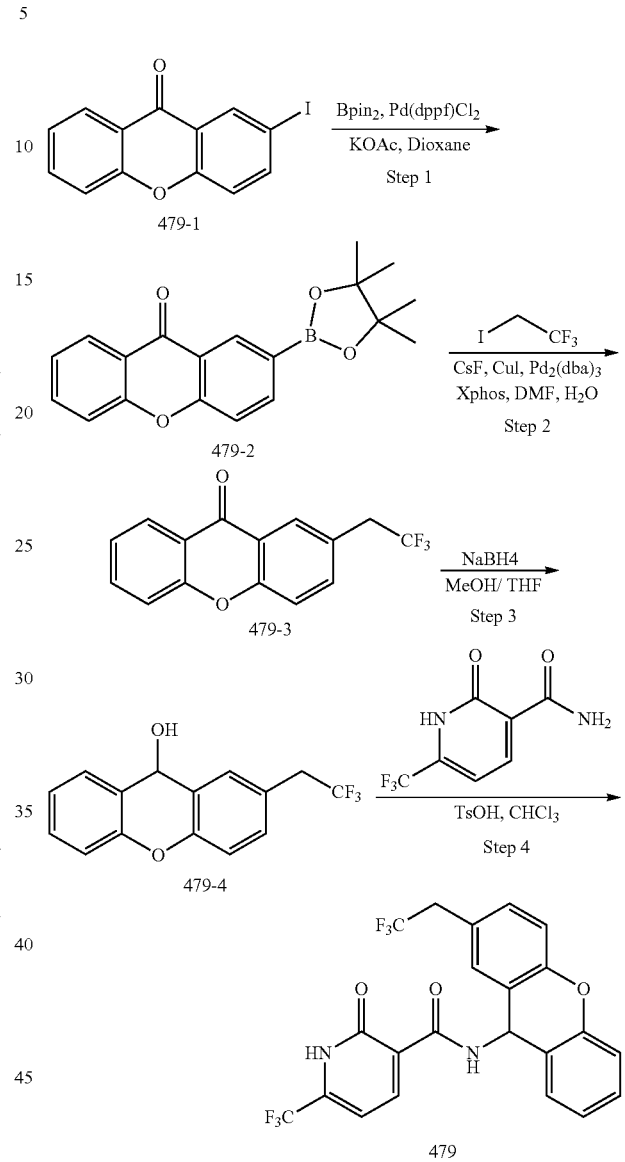

Step 1: 2-(4,4,5,5-tetramethyl-1,3,2-dioxaborolan-2-yl)-9H-xanthen-9-one (479-2)

To a mixture of Compound 479-1 (300 mg, 931 μmol), BPD (355 mg, 1.4 mmol) and KOAc (243 mg, 2.5 mmol) in dioxane (6 mL) was added Pd(dppf)Cl$_2$·CH$_2$Cl$_2$ (105 mg, 129 μmol). The mixture was stirred at 80° C. under N$_2$ for 12 hrs. LCMS showed the reaction was competed and one main peak with desired mass was detected. The reaction mixture was filtered and the filter cake was washed with EtOAc (30 mL), the filtrate was concentrated under reduced pressure to give a residue, which was purified by column chromatography (Petroleum ether/Ethyl acetate) to give Compound 479-2 (400 mg, crude) as a white solid. M+H$^+$=323.1 (LCMS).

Step 2: 2-(2,2,2-trifluoroethyl)-9H-xanthen-9-one (479-3)

To a mixture of 1,1,1-trifluoro-2-iodoethane (280 mg, 1.3 mmol), Compound 479-2 (200 mg, 621 μmol), XPhos (35 mg, 73 μmol), CsF (300 mg, 1.9 mmol), H₂O (100 mg, 5.6 mmol) and CuCl (65 mg, 657 μmol) in DMF (3 mL) was added Pd₂(dba)₃ (15 mg, 16 μmol) under N₂. The mixture was stirred at 65° C. for 12 hrs. LCMS showed the reaction was competed and one main peak with desired mass was detected. The mixture was poured into NH₄Cl (10 mL) and extracted with EtOAc (3 mL×3). The combined organic layers were dried over Na₂SO₄, filtered and concentrated, which was purified by prep-TLC (Petroleum ether/Ethyl acetate=10/1) to give Compound 479-3 (100 mg, crude) as a gray solid.

Step 3: 2-(2,2,2-trifluoroethyl)-9H-xanthen-9-ol (479-4)

To a solution of Compound 479-3 (40 mg, 144 μmol) in THF (2 mL) and MeOH (2 mL) was added NaBH₄ (16 mg, 431 μmol) at 0° C., the resulting mixture was stirred at 25° C. for 30 min. TLC showed the reaction was completed. The reaction mixture was poured into H₂O (15 mL) extracted with DCM 10 mL×3). The combined organic layers were dried over Na₂SO₄, filtered and concentrated under reduced pressure to give Compound 479-4 (40 mg, crude) as a yellow gum.

Step 4: 2-oxo-N-(2-(2,2,2-trifluoroethyl)-9H-xanthen-9-yl)-6-(trifluoromethyl)-1,2-dihydropyridine-3-carboxamide (479)

To a solution of 2-oxo-6-(trifluoromethyl)-1,2-dihydropyridine-3-carboxamide (29 mg, 143 μmol), TsOH (123 mg, 714 μmol) in CHCl₃ (3 mL) was added Compound 479-4 (40 mg, 143 μmol) at 70° C. and was stirred at 70° C. for 5 min. LCMS showed the reaction was completed. The reaction mixture was poured into H₂O (5 mL) and extracted with DCM (5 mL×4). The combined organic layers were dried over Na₂SO₄, filtered and concentrated under reduced pressure to give a residue, which was purified by prep-HPLC to give Compound 479 (15.88 mg, 34 μmol, 24% yield) as a white solid. M−H⁻=467.1 (LCMS), ¹H NMR (400 MHz, CHLOROFORM-d) δ=9.86 (br d, J=8.3 Hz, 1H), 8.73 (d, J=7.5 Hz, 1H), 7.53 (d, J=7.6 Hz, 1H), 7.47 (s, 1H), 7.36-7.30 (m, 1H), 7.25 (s, 1H), 7.21-7.15 (m, 2H), 7.12 (t, J=7.5 Hz, 1H), 6.85 (d, J=7.5 Hz, 1H), 6.65 (d, J=8.6 Hz, 1H), 3.33 (q, J=10.8 Hz, 2H).

Other compounds made in a similar manner are shown in Table 51.

Example 90: Synthesis of N-(2-(azetidin-3-yl)-9H-xanthen-9-yl)-2-oxo-6-(trifluoromethyl)-1,2-dihydropyridine-3-carboxamide (481)

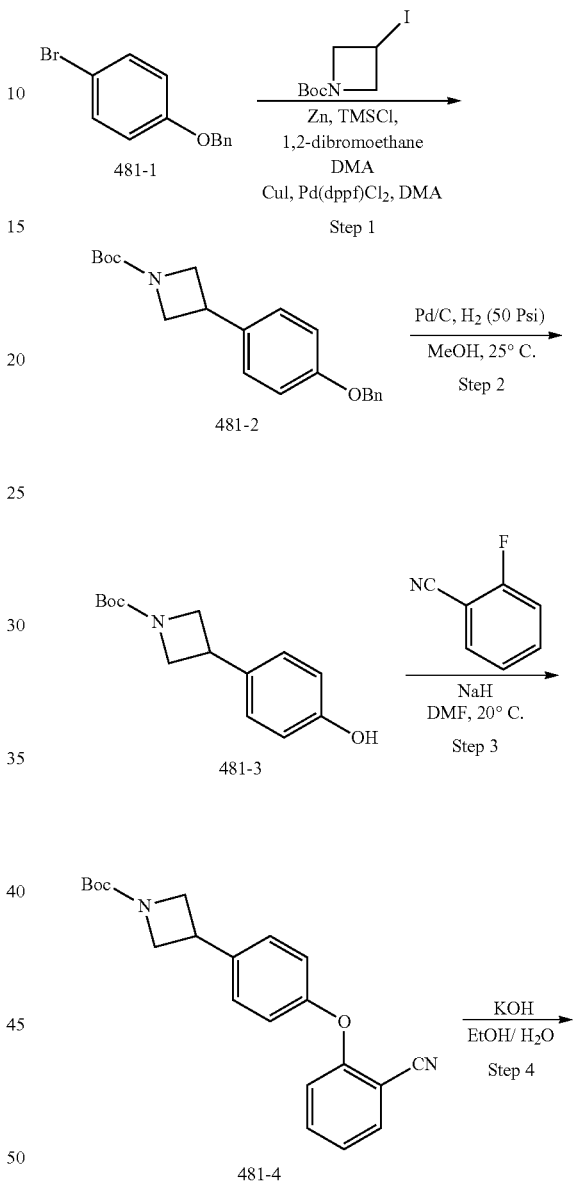

TABLE 51

| Compound No | Structure | HNMR and Ms |
|---|---|---|
| 480 | ![structure] | ¹H NMR (400 MHz, CHLOROFORM-d) δ = 9.91 (br d, J = 6.8 Hz, 1H), 8.65 (d, J = 7.3 Hz, 1H), 7.65-7.60 (m, 1H), 7.55-7.47 (m, 3H), 7.29 (br d, J = 4.3 Hz, 2H), 7.22 (br d, J = 7.6 Hz, 1H), 6.83 (d, J = 7.5 Hz, 1H), 6.38 (d, J = 8.2 Hz, 1H), 3.51-3.22 (m, 2H) ESI [M − H] = 483.0 |

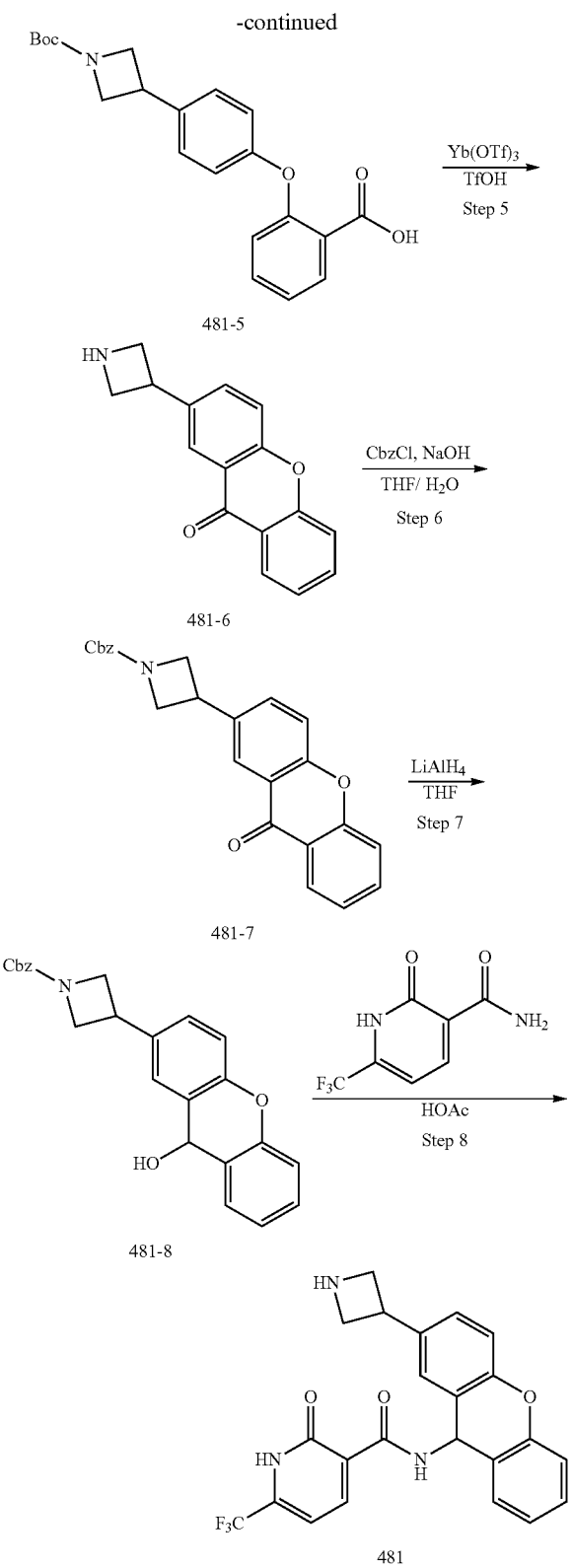

mmol) in DMA (6 mL) was added, followed by TMSCl (691 mg, 6.4 mmol) in DMA (6 mL), after stirred for 30 min, tert-butyl 3-iodoazetidine-1-carboxylate (12 g, 42.4) in DMA (18 mL) was added to the solution. The mixture was stirred at 40° C. for 1 hr. TLC indicated the reaction was completed. The resulting Zinc reagent (0.574 M, 72 mL) solution was added to a mixture of Compound 481-1 (4 g, 15.2 mmol), Pd(dppf)Cl$_2$·CH$_2$Cl$_2$ (621 mg, 760 µmol), CuI (290 mg, 1.5 mmol) in DMA (32 mL) then purged with N$_2$ for three times, and the mixture was stirred at 90° C. for 12 hrs. TLC indicated new spot with larger polarity was detected. The reaction mixture was quenched by pouring into sat.NH$_4$Cl (100 mL) and extracted with EtOAc (30 mL×2). The combined organic layers were washed with brine (20 mL×3), dried over Na$_2$SO$_4$, filtered and concentrated under reduced pressure to give a residue, which was purified by column chromatography to give Compound 481-2 (2.8 g, 8.1 mmol, 53% yield) as yellow oil.

Step 2: tert-butyl 3-(4-hydroxyphenyl)azetidine-1-carboxylate (481-3)

To a solution of Compound 481-2 (2.75 g, 8.1 mmol) in MeOH (150 mL) was added Pd/C (400 mg, 10% purity) and purged with H$_2$ for three times. The mixture was stirred at 25° C. for 12 hrs under H$_2$ (50 Psi). TLC indicated the reaction was completed. The suspension was filtered through a pad of Celite and the pad was washed with MeOH (5 mL×5). The combined filtrates were concentrated to dryness to give a residue. The residue was purified by column chromatography to give Compound 481-3 (0.9 g, 3.6 mmol, 45% yield) as a white solid.

Step 3: tert-butyl 3-(4-(2-cyanophenoxy)phenyl) azetidine-1-carboxylate (481-4)

To a solution of Compound 481-3 (0.9 g, 3.6 mmol) in DMF (10 mL) was added NaH (173 mg, 4.3 mmol, 60% purity) at 0° C., the mixture was stirred for 30 min, then 2-fluorobenzonitrile (481 mg, 4 mmol) in DMF (5 mL) was added. The mixture was stirred at 70° C. for 2 hrs. LCMS showed the reaction was complete and desired mass was detected. The reaction mixture was pouring into water (60 mL) and extracted with EtOAc (20 mL×3). The combined organic layers were washed with brine (20 mL×3), dried over Na$_2$SO$_4$, filtered and concentrated under reduced pressure to give a residue. The residue was purified by column chromatography to give Compound 481-4 (1 g, 2.8 mmol, 79% yield) as white oil. $^1$H NMR (400 MHz, CHLOROFORM-d) δ=7.67 (br d, J=7.7 Hz, 1H), 7.48 (br t, J=7.9 Hz, 1H), 7.35 (br d, J=8.4 Hz, 2H), 7.14 (t, J=7.6 Hz, 1H), 7.07 (d, J=8.2 Hz, 2H), 6.87 (d, J=8.4 Hz, 1H), 4.35 (t, J=8.6 Hz, 2H), 4.03-3.93 (m, 2H), 3.79-3.70 (m, 1H), 1.48 (s, 9H)

Step 4: 2-(4-(1-(tert-butoxycarbonyl)azetidin-3-yl) phenoxy)benzoic acid (481-5)

KOH (2.9 g, 51.8 mmol) in EtOH (12 mL) and H$_2$O (12 mL) was added Compound 481-4 (1 g, 2.8 mmol) at 25° C., and then the mixture was stirred at 80° C. for 12 hrs under N$_2$ atmosphere. LCMS showed the reaction was complete and 47% desired product and 49% de-Boc product was detected. After cooling to 25° C., 0.5 mL Boc$_2$O was added, the mixture was stirred for 30 min, LCMS showed desired product was obtained. 25 mL water was added then extracted with MTBE (10 mL×2), the aqueous layer was adjust to pH=6 then extracted with CHCl$_3$:i-PrOH=3:1 (10 mL×3).

Step 1: tert-butyl 3-(4-(benzyloxy)phenyl)azetidine-1-carboxylate (481-2)

A mixture of Zn (5.54 g, 84.8 mmol) in DMA (42 mL) was heated to 40° C., then 1,2-dibromoethane (2.55 g, 13.6

The combined organic layers were dried over Na$_2$SO$_4$, filtered and concentrated under reduced pressure to give Compound 481-5 (1 g, crude) as yellow oil used directly.

Step 5: 2-(azetidin-3-yl)-9H-xanthen-9-one (481-6)

To a solution of Compound 481-5 (0.5 g, 1.4 mmol) in TfOH (4 mL) was added Yb(OTf)$_3$ (84 mg, 135 μmol). The mixture was stirred at 50° C. for 20 min under microwave. LCMS showed the reaction was completed and desired product was detected. The reaction mixture was pouring into 3M NaOH aqueous (15 mL) and extracted with DCM (5 mL×3). The combined organic layers were dried over Na$_2$SO$_4$, filtered and concentrated under reduced pressure to give Compound 481-6 (0.3 g, 1.2 mmol, 88% yield) as white solid. M+H$^+$=252.2 (LCMS)

Step 6: benzyl 3-(9-oxo-9H-xanthen-2-yl)azetidine-1-carboxylate (481-7)

To a solution of Compound 481-6 (130 mg, 517 μmol) in THF (1.5 mL) and H$_2$O (1.5 mL) was added NaOH (23 mg, 4M) at 0° C., then CbzCl (97 mg, 569 μmol) was added. The mixture was stirred at 25° C. for 12 hrs. TLC showed the reaction was complete and new spot was detected. The reaction mixture was pouring into water (10 mL) and extracted with EtOAc (3 mL×3). The combined organic layers were dried over Na$_2$SO$_4$, filtered and concentrated under reduced pressure to give a residue, which was purified by column chromatography to give Compound 481-7 (0.1 g, 259 μmol, 50% yield) as yellow oil.

Step 7: benzyl 3-(9-hydroxy-9H-xanthen-2-yl)azetidine-1-carboxylate (481-8)

To a solution of Compound 481-7 (100 mg, 259 mol) in THF (6 mL) was added LiAlH$_4$ (20 mg, 519 mol) at 0° C. The mixture was stirred at 25° C. for 0.5 hr. TLC showed the reaction was complete and new spot was detected. The reaction mixture was pouring into sat.NH$_4$Cl (10 mL) and extracted with DCM (3 mL×2). The combined organic layers were dried over Na$_2$SO$_4$, filtered and concentrated under reduced pressure to give Compound 481-8 (100 mg, crude) as white solid.

Step 8: N-(2-(azetidin-3-yl)-9H-xanthen-9-yl)-2-oxo-6-(trifluoromethyl)-1,2-dihydropyridine-3-carboxamide (481)

A mixture of Compound 481-8 (100 mg, 258 μmol), 2-oxo-6-(trifluoromethyl)-1, 2-dihydropyridine-3-carboxamide (53 mg, 258 μmol) in HOAc (3 mL) was stirred at 50° C. for 12 hrs. LCMS showed the reaction was complete and desired product was detected. The reaction mixture was concentrated under reduced pressure to give a residue, which was purified by prep-HPLC to give Compound 481 (2.9 mg, 5.6 μmol, 2% yield) as white solid. M+H$^+$=442.0 (LCMS); $^1$H NMR (400 MHz, DMSO-d$_6$) δ=12.33 (br d, J=7.8 Hz, 1H), 8.20 (d, J=7.3 Hz, 1H), 8.16 (s, 1H), 7.49-7.40 (m, 3H), 7.38-7.32 (m, 1H), 7.25-7.11 (m, 3H), 6.62-6.57 (m, 1H), 6.49 (d, J=8.4 Hz, 1H), 4.28-4.17 (m, 2H), 4.13-3.93 (m, 3H).

Other compounds made in a similar manner are shown in Table 52.

TABLE 52

| Compound No | Structure | HNMR and Ms |
|---|---|---|
| 482 | 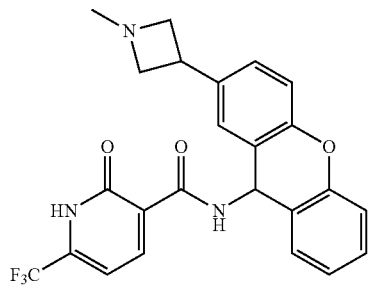 [SMILES: CN1CC(c2ccc3c(c2)C(NC(=O)c2ccc(C(F)(F)F)[nH]c2=O)c2ccccc2O3)C1] | $^1$H NMR (400 MHz, DMSO-d$_6$) δ = 12.07 (br d, J = 8.4 Hz, 1H), 8.23 (d, J = 7.5 Hz, 1H), 8.18 (s, 1H), 7.50-7.43 (m, 2H), 7.40-7.31 (m, 2H), 7.23-7.10 (m, 3H), 6.67 (d, J = 7.6 Hz, 1H), 6.47 (d, J = 8.4 Hz, 1H), 4.21 (br d, J = 13.9 Hz, 2H), 4.03-3.87 (m, 3H), 2.79-2.75 (m, 3H) <br> ESI [M − H] = 454.0 |
| 483 | 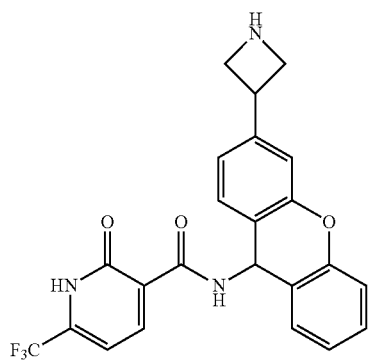 | $^1$H NMR (400 MHz, DMSO-d6) δ = 12.49 (br d, J = 8.4 Hz, 1H), 8.18 (d, J = 7.6 Hz, 1H), 7.45 (dd, J = 3.4, 7.6 Hz, 2H), 7.39-7.32 (m, 1H), 7.31-7.27 (m, 1H), 7.21-7.11 (m, 3H), 6.56-6.45 (m, 2H), 4.32-4.18 (m, 2H), 4.16-4.00 (m, 3H) <br> ESI [M − H] = 440.1 |

TABLE 52-continued

| Compound No | Structure | HNMR and Ms |
|---|---|---|
| 484 | 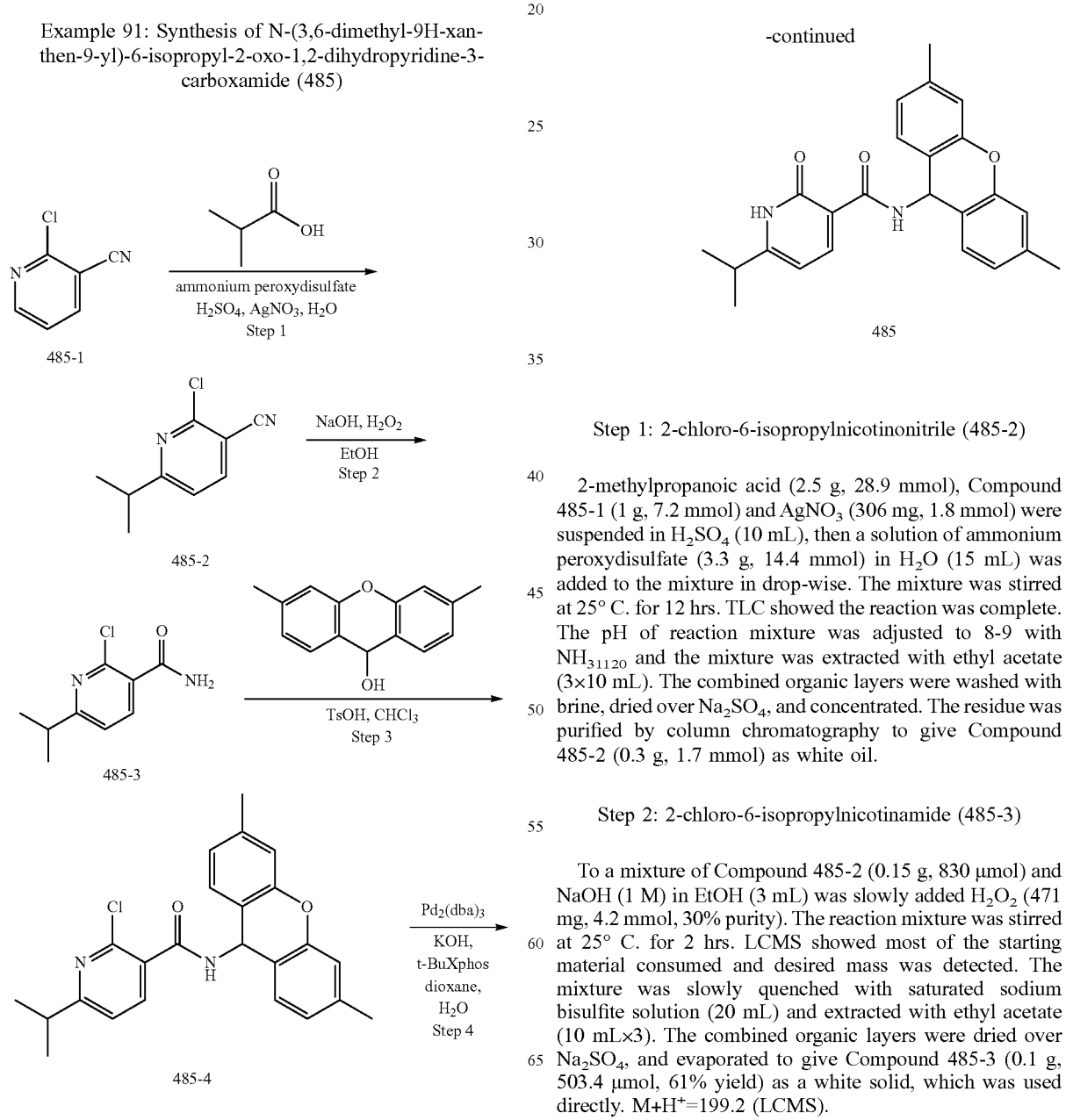 | $^1$H NMR (400 MHz, DMSO-d$_6$) δ = 12.17 (br s, 1H), 8.20 (d, J = 7.5 Hz, 1H), 7.48-7.42 (m, 2H), 7.39-7.31 (m, 1H), 7.30 (d, J = 1.2 Hz, 1H), 7.20-7.07 (m, 3H), 6.62 (d, J = 7.6 Hz, 1H), 6.46 (d, J = 8.6 Hz, 1H), 4.22 (br s, 2H), 4.08-3.93 (m, 3H), 2.80 (s, 3H) ESI [M − H] = 454.1 |

Example 91: Synthesis of N-(3,6-dimethyl-9H-xanthen-9-yl)-6-isopropyl-2-oxo-1,2-dihydropyridine-3-carboxamide (485)

Step 1: 2-chloro-6-isopropylnicotinonitrile (485-2)

2-methylpropanoic acid (2.5 g, 28.9 mmol), Compound 485-1 (1 g, 7.2 mmol) and AgNO$_3$ (306 mg, 1.8 mmol) were suspended in H$_2$SO$_4$ (10 mL), then a solution of ammonium peroxydisulfate (3.3 g, 14.4 mmol) in H$_2$O (15 mL) was added to the mixture in drop-wise. The mixture was stirred at 25° C. for 12 hrs. TLC showed the reaction was complete. The pH of reaction mixture was adjusted to 8-9 with NH$_3$H$_2$O and the mixture was extracted with ethyl acetate (3×10 mL). The combined organic layers were washed with brine, dried over Na$_2$SO$_4$, and concentrated. The residue was purified by column chromatography to give Compound 485-2 (0.3 g, 1.7 mmol) as white oil.

Step 2: 2-chloro-6-isopropylnicotinamide (485-3)

To a mixture of Compound 485-2 (0.15 g, 830 µmol) and NaOH (1 M) in EtOH (3 mL) was slowly added H$_2$O$_2$ (471 mg, 4.2 mmol, 30% purity). The reaction mixture was stirred at 25° C. for 2 hrs. LCMS showed most of the starting material consumed and desired mass was detected. The mixture was slowly quenched with saturated sodium bisulfite solution (20 mL) and extracted with ethyl acetate (10 mL×3). The combined organic layers were dried over Na$_2$SO$_4$, and evaporated to give Compound 485-3 (0.1 g, 503.4 µmol, 61% yield) as a white solid, which was used directly. M+H$^+$=199.2 (LCMS).

Step 3: 2-chloro-N-(3,6-dimethyl-9H-xanthen-9-yl)-6-isopropylnicotinamide (485-4)

3,6-dimethyl-9H-xanthen-9-ol (98 mg, 435 µmol) in 15 mL DCM was added to a solution of TsOH·H$_2$O (77 mg, 402.7 µmol) and Compound 485-3 (80 mg, 402.7 µmol) in CHCl$_3$ (5 mL) at 70° C. The mixture was stirred at 70° C. for 10 min. TLC showed the reaction was complete. The reaction mixture was pouring into water (10 mL) and extracted with DCM (5 mL×2). The combined organic layers were dried over Na$_2$SO$_4$, filtered and concentrated under reduced pressure to give a residue, which was purified by Prep-TLC (Petroleum ether/Ethyl acetate=3:1) to give Compound 485-4 (25 mg, 61.4 µmol, 15% yield) as a white solid.

Step 4: N-(3,6-dimethyl-9H-xanthen-9-yl)-6-isopropyl-2-oxo-1,2-dihydropyridine-3-carboxamide (485)

To a solution of Compound 485-4 (25 mg, 61.4 µmol) in dioxane (2.5 mL) and H$_2$O (2.5 mL) was added KOH (69 mg, 1.23 mmol) and Pd$_2$(dba)$_3$ (2 mg, 1.2 µmol), t-Bu Xphos (2 mg, 4.9 µmol). The mixture was stirred at 110° C. for 2 hrs under N$_2$. LCMS showed the reaction was complete and desired mass was detected. The reaction mixture was pouring into water 15 mL and extracted with DCM (5 mL×3). The combined organic layers were dried over Na$_2$SO$_4$, filtered and concentrated under reduced pressure to give a residue, which was purified by prep-HPLC to give Compound 485 (4 mg, 10.3 µmol, 17% yield) as gray solid. M−H$^-$=387.1 (LCMS); $^1$H NMR (400 MHz, DMSO-d$_6$) δ=12.39 (br s, 1H), 10.32 (d, J=8.8 Hz, 1H), 8.39 (d, J=7.5 Hz, 1H), 7.31 (d, J=7.9 Hz, 2H), 7.06-6.90 (m, 4H), 6.42-6.40 (m, 1H), 2.87 (td, J=6.8, 13.8 Hz, 1H), 2.32 (s, 6H), 1.21-1.17 (m, 6H).

Other compounds made in a similar manner are shown in Table 53.

TABLE 53

| Compound No | Structure | HNMR and Ms |
| --- | --- | --- |
| 486 | 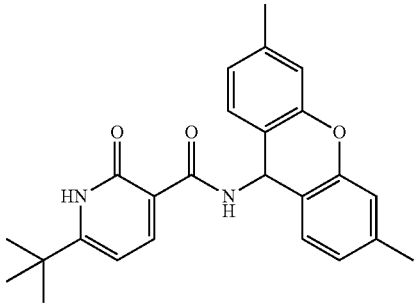 [SMILES: Cc1ccc2c(c1)Oc1cc(C)ccc1C2NC(=O)c1ccc(C(C)(C)C)[nH]c1=O] | $^1$H NMR (400 MHz, CHLOROFORM-d) δ = 11.87 (br s, 1H), 10.09 (d, J = 8.9 Hz, 1H), 8.57 (d, J = 7.7 Hz, 1H), 7.40 (d, J = 7.8 Hz, 2H), 6.94-6.90 (m, 1H), 6.92 (s, 1H), 6.87 (dd, J = 1.0, 7.9 Hz, 2H), 6.66 (d, J = 9.0 Hz, 1H), 6.34 (dd, J = 1.7, 7.8 Hz, 1H), 2.34 (s, 6H), 1.01 (s, 9H) ESI [M − H] = 401.1 |
| 487 | 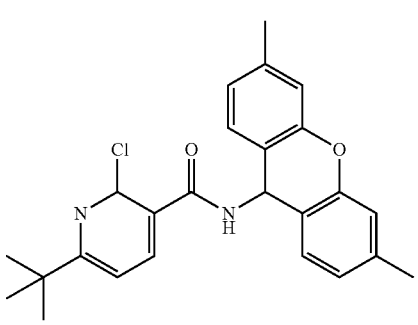 | $^1$H NMR (400 MHz, CHLOROFORM-d) δ = 8.04 (d, J = 8.2 Hz, 1H), 7.47 (d, J = 8.2 Hz, 2H), 7.33 (d, J = 7.9 Hz, 1H), 6.98-6.92 (m, 4H), 6.85 (br d, J = 8.8 Hz, 1H), 6.68 (d, J = 8.8 Hz, 1H), 2.38 (s, 6H), 1.33 (s, 9H) ESI [M − H] = 419.0 |

Example 92: Synthesis of N-(3-(oxetan-3-yl)-9H-xanthen-9-yl)-2-oxo-6-(trifluoromethyl)-1,2-dihydropyridine-3-carboxamide (488)

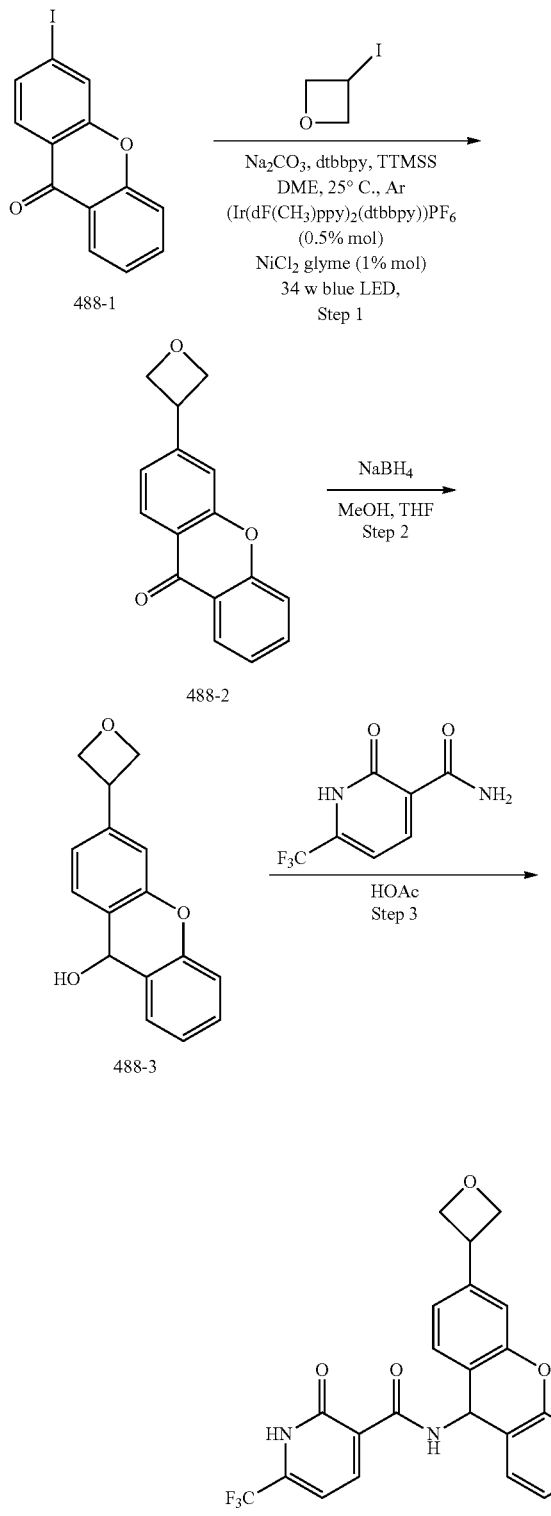

Step 1: 3-(oxetan-3-yl)-9H-xanthen-9-one (488-2)

A mixture of Compound 488-1 (28 mg, 152.2 µmol), 3-iodooxetane (7 mg, 21.7 µmol), 4-tert-butyl-2-(4-tert-butyl-2-pyridyl)pyridine (29 ug, 0.5% mmol), bis[3,5-difluoro-2-[5-(methyl)-2-pyridyl]phenyl]iridium(1+); 4-tert-butyl-2-(4-tert-butyl-2-pyridyl)pyridine hexafluorophosphate (110 ug, 0.5% mmol), bis(trimethylsilyl) silyl-tri methyl-silane (5 mg, 21.7 µmol), $Na_2CO_3$ (5 mg, 43.5 µmol) and dichloro nickel; 1,2-dimethoxyethane (48 ug, 1% mmol) in DME (1 mL) was stirred at 25° C. for 12 hrs under $N_2$ under 34w blue LED. LCMS showed the reaction was complete and one main peak with desired mass was detected. The mixture was filtered and the filtrate was concentrated to give a residue, which was purified by Prep-TLC (Petroleum ether:Ethyl acetate=2:1, Rf=0.3) to give Compound 488-2 (10 mg, crude) as yellow gum. $M+H^+$=253.2 (LCMS).

Step 2: 3-(oxetan-3-yl)-9H-xanthen-9-ol (488-3)

To a stirred mixture of Compound 488-2 (10 mg, 39.6 µmol) in THF (2 mL) and MeOH (2 mL) was added $NaBH_4$ (10 mg, 264.3 µmol) at 0° C. The mixture was stirred at 20° C. for 3 hrs. TLC showed the reaction was completed. The mixture was diluted with DCM (10 mL), and washed with $H_2O$ (3 mL). The organic layer was dried over $Na_2SO_4$, filtered and concentrated in vacuum to give Compound 488-3 (10 mg, crude) as colorless gum, which was used directly.

Step 3: N-(3-(oxetan-3-yl)-9H-xanthen-9-yl)-2-oxo-6-(trifluoromethyl)-1,2-dihydropyridine-3-carboxamide (488)

A mixture of 2-oxo-6-(trifluoromethyl)-1,2-dihydropyridine-3-carboxamide (10 mg, 48.5 µmol) and Compound 488-3 (10 mg, 39.3 µmol) in AcOH (2 mL) was stirred at 60° C. for 3 hrs. LCMS showed the reaction was complete and one main peak with desired mass was detected. The mixture was concentrated in vacuum to give a residue, which was purified via Prep-HPLC to give Compound 488 (4 mg, 9.1 µmol, 23% yield,) as a white solid. $M-H^-$=441.1 (LCMS); $^1$H NMR (400 MHz, DMSO-$d_6$) δ=13.50 (br, 1H), 9.70 (br, 1H), 8.41-8.34 (m, 1H), 7.48-7.46 (m, 2H), 7.38-7.15 (m, 6H), 6.51-6.49 (d, J=8.8 Hz, 1H), 4.96-4.92 (m, 2H), 4.65-4.61 (m, 2H), 4.31-4.25 (m, 1H).

Other compounds made in a similar manner are shown in Table 54.

TABLE 54

| Compound No | Structure | HNMR and Ms |
|---|---|---|
| 489 | 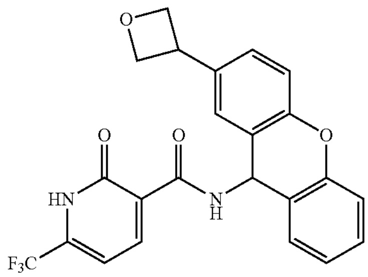 [SMILES: O=C(NC1c2ccccc2Oc2ccc(C3COC3)cc21)c1ccc(C(F)(F)F)[nH]c1=O] | $^1$H NMR (400 MHz, DMSO-d$_6$) δ = 8.35-8.33 (d, J = 7.2 Hz, 1H), 7.46-7.42 (m, 3H), 7.33-7.21 (m, 1H), 7.19-7.12 (m, 4H), 6.47 (s, 1H), 4.92-4.88 (m, 2H), 4.58-4.53 (m, 2H), 4.25-4.19 (m, 1H). ESI [M − H] = 441.1. |

Example 93: Synthesis of 2-oxo-N-(phenyl(m-tolyl)methyl)-6-(trifluoromethyl)-1,2-dihydropyridine-3-carboxamide (490)

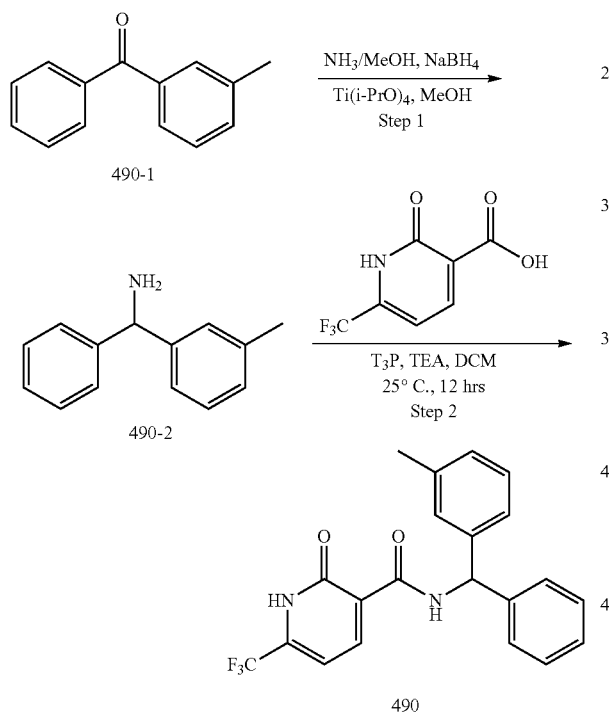

Step 1: phenyl(m-tolyl)methanamine (490-2)

To a solution of Compound 490-1 (2 g, 10.2 mmol) in MeOH (10 mL) was added NH$_3$/MeOH (20 M, 40 mL), followed by Ti(i-PrO)$_4$ (14.5 g, 51 mmol), the resulting mixture was stirred at 20° C. for 12 hrs. Then the reaction mixture was added NaBH$_4$ (2.2 g, 57.2 mmol) at 0° C. and stirred at 20° C. for 2 hrs. LCMS showed the starting material was consumed completely and one main peak with desired mass was detected. The reaction mixture was poured into ice-H$_2$O (80 mL) slowly, the mixture was filtered and the filtrate was washed with EtOAc (50 mL×3). The combined organic layers were dried over Na$_2$SO$_4$, filtered and concentrated under reduced pressure to give a Compound 490-2 (1.9 g, crude) as light yellow oil. Fragment Ms=181.0 (LCMS); $^1$H NMR (400 MHz, DMSO-d$_6$) δ=7.39 (d, J=7.5 Hz, 2H), 7.27 (t, J=7.5 Hz, 2H), 7.23-7.11 (m, 4H), 6.98 (br d, J=6.8 Hz, 1H), 5.04 (s, 1H), 2.26 (s, 3H).

Step 2: 2-oxo-N-(phenyl(m-tolyl)methyl)-6-(trifluoromethyl)-1,2-dihydropyridine-3-carboxamide (490)

To a solution of Compound 490-2 (200 mg, 1 mmol) and 2-oxo-6-(trifluoromethyl)-1,2-dihydropyridine-3-carboxylic acid (210 mg, 1 mmol) in DCM (4 mL) was added TEA (307.8 mg, 3.0 mmol) and T$_3$P (1.3 g, 2.0 mmol, 50% purity), the mixture was stirred at 15° C. for 12 hrs. LCMS showed the reaction was completed and the desired mass was detected. The reaction mixture was poured into H$_2$O (8 mL), and then extracted with EtOAc (5 mL×3). The combined organic layers were dried over Na$_2$SO$_4$, filtered and concentrated under reduced pressure to give a residue. The residue was purified by flash silica gel chromatography to give a Compound 490 (148 mg, 374.5 μmol, 37% yield) as a white solid. M−H$^-$=385.1 (LCMS); $^1$H NMR (400 MHz, DMSO-d$_6$) δ=13.51 (br s, 1H), 10.18-9.61 (m, 1H), 8.38 (d, J=7.5 Hz, 1H), 7.38-7.32 (m, 4H), 7.31-7.20 (m, 3H), 7.19-7.04 (m, 3H), 6.25 (d, J=7.9 Hz, 1H), 2.28 (s, 3H).

Example 94: Synthesis of N-(2-oxo-6-(trifluoromethyl)-1,2-dihydropyridin-3-yl)-2,2-di-p-tolylacetamide (492)

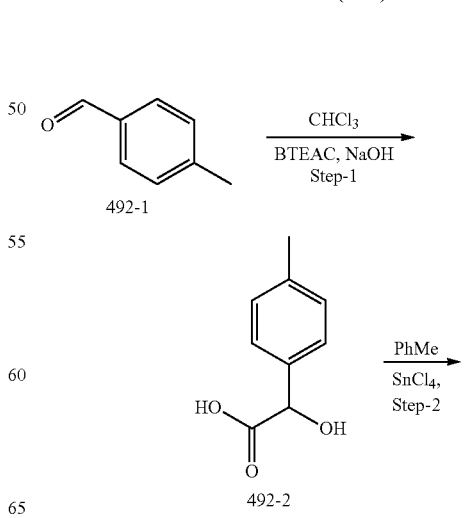

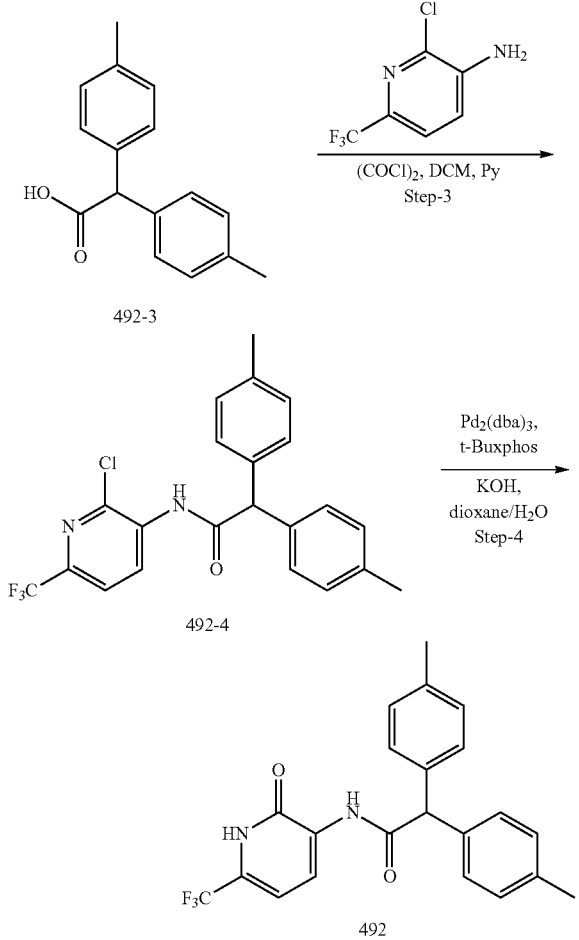

492-3

492-4

492

Step 1: 2-hydroxy-2-(p-tolyl)acetic acid (492-2)

A mixture of Compound 492-1 (1 g, 8.3 mmol) and BTEAC (1.8 g, 8.3 mmol) in CHCl$_3$ (1.5 mL) was heated to 50° C. and NaOH aq. (1.5 mL, 50% purity) was added. The mixture was stirred at 50° C. for 12 hrs. TLC showed the reaction was completed. The reaction mixture was poured into 1N NaOH aq. (10 mL) and extracted with EtOAc (10 mL×2). The combined organic layers were washed with 1N NaOH (5 mL×2) and adjusted the aqueous phase pH to 1 with Conc.HCl, and extracted with EtOAc (10 mL×2). The combined organic layers were dried over with Na$_2$SO$_4$, filtered and concentrated under reduced pressure to give a residue, which was triturated with toluene (5 mL×2) to give Compound 492-2 (0.5 g, 36% yield) as a white solid.

Step 2: 2,2-di-p-tolylacetic acid (492-3)

To a solution of Compound 492-2 (50 mg, 300.9 μmol) in toluene (194 mg, 2.11 mmol) was added SnCl$_4$ (118 mg, 451.3 μmol) at 70° C., then the mixture was stirred at 20° C. for 18 hrs. LCMS showed the reaction was completed and the desired mass was detected. The reaction mixture was poured into H$_2$O (10 mL) and extracted with MTBE (5 mL×2). The combined organic layers were washed with 8% Na$_2$CO$_3$ aq. (20 mL), adjusted pH to 5-6 with Conc.HCl and extracted with EtOAc (10 mL×3). The combined organic layers were dried over Na$_2$SO$_4$, filtered and concentrated under reduced pressure to give a residue, which was purified by Prep-HPLC to give Compound 492-3 (2 mg, 3% yield) as a colorless gum. M−H$^-$=239.0 (LCMS); 1H NMR (400 MHz, DMSO-d6) δ=7.20-7.13 (m, 4H), 7.11-7.06 (m, 4H), 4.88 (s, 1H), 2.25 (s, 6H).

Step 3: N-(2-chloro-6-(trifluoromethyl)pyridin-3-yl)-2,2-di-p-tolylacetamide (492-4)

To a solution of Compound 492-3 (250 mg, 1.0 mmol) in DCM (3 mL) was added (COCl)$_2$ (132 mg, 1.0 mmol) and DMF (0.02 mL) slowly at 0° C., the mixture was stirred at same temperature for 15 min, then concentrated under reduced pressure to give a residue, to which was added a solution of 2-chloro-6-(trifluoromethyl) pyridin-3-amine (205 mg, 1.0 mmol) in Pyridine (3 mL). The mixture was stirred at 25° C. for 2 hrs. LCMS showed the reaction was completed and desired mass was detected. The reaction mixture was poured into H$_2$O (10 mL) and extracted with EtOAc (5 mL×5). The combined organic layers were dried over Na$_2$SO$_4$, filtered and concentrated under reduced pressure to give a residue, which was washed by MeOH (5 mL). The mixture was filtered and the cake was dried in vacuum to give Compound 492-4 (110 mg, 262.6 μmol, 25% yield). M+H$^+$=419.1 (LCMS); 1H NMR (400 MHz, DMSO-d6) δ=10.24 (s, 1H), 8.54 (br d, J=8.2 Hz, 1H), 7.94 (br d, J=8.2 Hz, 1H), 7.28-7.19 (m, 4H), 7.14 (br d, J=7.8 Hz, 4H), 5.47 (s, 1H), 2.27 (s, 6H).

Step 4: N-(2-oxo-6-(trifluoromethyl)-1,2-dihydropyridin-3-yl)-2,2-di-p-tolylacetamide (492)

To a solution of Compound 492-4 (60 mg, 143.3 μmol) in dioxane (2.5 mL) and H$_2$O (2.5 mL) was added KOH (161 mg, 2.9 mmol) t-Bu Xphos (4.87 mg, 11.46 μmol, 0.08 eq) and Pd$_2$(dba)3 (3 mg, 2.9 μmol) under N$_2$. The mixture was stirred at 110° C. for 12 hrs. LCMS showed the reaction was completed and the desired mass was detected. The reaction mixture was poured into H$_2$O (25 mL) and extracted with EtOAc (10 mL×3). The combined organic layers were dried over Na$_2$SO$_4$, filtered and concentrated under reduced pressure to give a residue, which was purified by Prep-HPLC to give Compound 492 (14 mg, 21% purity) as a white solid. M+H$^+$=401.1 (LCMS); $^1$H NMR (400 MHz, DMSO-d6) δ=12.79-12.61 (s, 1H), 9.81 (s, 1H), 8.60-8.41 (m, 1H), 7.24-7.18 (m, 4H), 7.14-7.06 (m, 4H), 5.57 (s, 1H), 2.26 (s, 6H).

Example 95: Synthesis of N-(3,6-dimethyl-10,10-dioxido-9H-thioxanthen-9-yl)-6-oxo-2-(trifluoromethyl)-1,6-dihydro-[3,4'-bipyridine]-5-carboxamide (493)

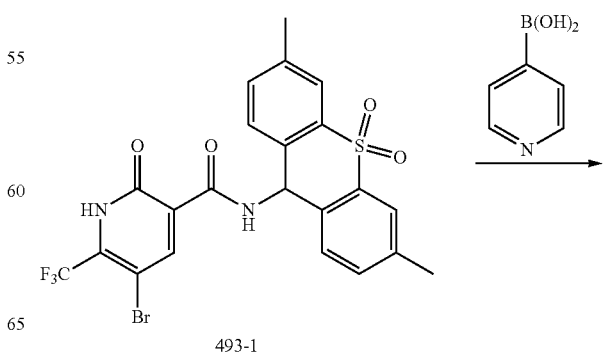

493-1

Step 1: N-(3,6-dimethyl-10,10-dioxido-9H-thioxanthen-9-yl)-6-oxo-2-(trifluoro methyl)-1,6-dihydro-[3,4'-bipyridine]-5-carboxamide (493)

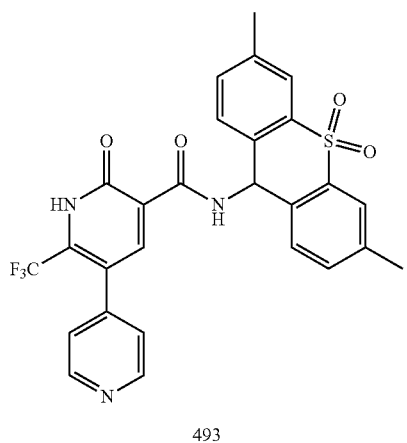

493

To a solution of Compound 493-1 (60 mg, 110.8 μmol) in dioxane (2 mL) was added pyridin-4-ylboronic acid (20. mg, 166.3 μmol), aq K₂CO₃ (1 M, 665.02 uL, 6 eq) and Pd(dppf)Cl₂·CH₂Cl₂ (9 mg, 11.1 μmol) under N₂. The mixture was stirred at 100° C. for 5 hrs. TLC showed the reaction was complete. The reaction mixture was concentrated under reduced pressure to remove solvent to give a residue, which was diluted with water (10 mL) and extracted with CH₂Cl₂ (8 mL×3). The combined organic layers were dried over Na₂SO₄, filtered and concentrated under reduced pressure to give a residue, which was purified by Prep-HPLC to give Compound 493 (2 mg, 3% yield) as a yellow solid. M−H⁻= 538.1 (LCMS); ¹H NMR (400 MHz, CDCl3) δ=9.86 (br, 1H), 8.74 (m, 2H), 8.36 (s, 1H), 7.93 (s, 2H), 7.60-7.58 (d, J=7.6 Hz, 2H), 7.38-7.36 (d, J=7.6 Hz, 2H), 7.27 (m, 2H), 6.62-6.60 (d, J=8.8 Hz, 1H), 2.44 (s, 6H).

Other compounds made in a similar manner are shown in Table 55.

TABLE 55

| Compound No | Structure | HNMR and Ms |
|---|---|---|
| 494 | 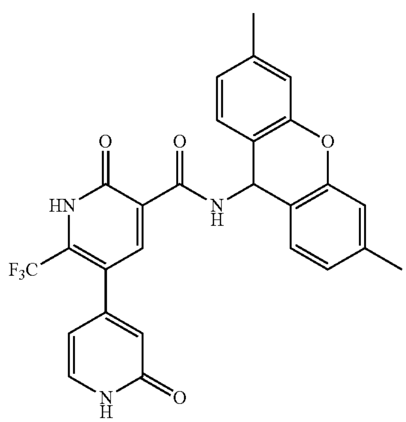 [SMILES: Cc1ccc2c(c1)Oc1cc(C)ccc1C2NC(=O)c1cc(-c2cc[nH]c(=O)c2)c(C(F)(F)F)[nH]c1=O] | ¹H NMR (400 MHz, DMSO-d₆) δ = 11.75 (br s, 1H), 8.17 (s, 1H), 7.42 (d, J = 6.6 Hz, 1H), 7.34 (d, J = 7.8 Hz, 2H), 7.01-6.92 (m, 4H), 6.44 (br d, J = 8.3 Hz, 1H), 6.25 (s, 1H), 6.13 (br d, J = 6.6 Hz, 1H), 2.31 (s, 6H)<br>ESI [M − H] = 506.1 |
| 495 | 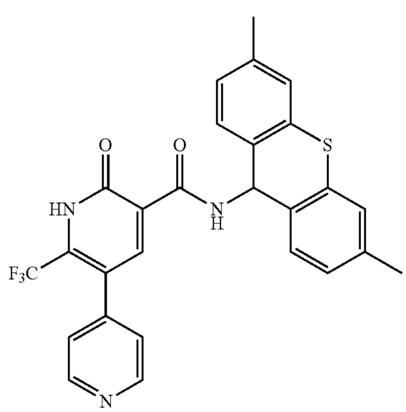 | ¹H NMR (400 MHz, DMSO-d6) δ = 8.66-8.64 (d, J = 6 Hz, 1H), 8.21 (s, 1H), 7.50-7.47 (m, 2H), 7.41-7.38 (m, 4H), 7.14-7.12 (d, J = 8 Hz, 2H), 6.13-6.11 (d, J = 7.6 Hz, 1H), 2.31 (s, 6H).<br>ESI [M − H] = 506.1 |

TABLE 55-continued
| Compound No | Structure | HNMR and Ms |
|---|---|---|
| 496 | 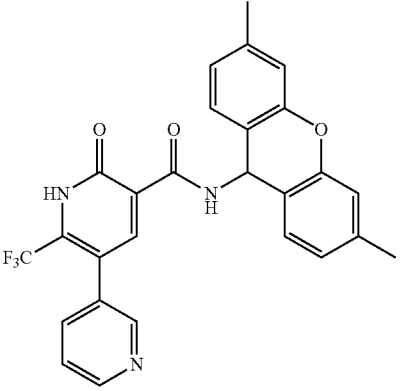 | $^1$H NMR (400 MHz, DMSO-d) δ = 9.69 (m, 1 H) 8.62-8.61 (d, J = 4 Hz, 2H), 8.53 (s, 1 H), 8.24 (s, 1H), 7.78 (d, J = 7.6 Hz, 1H), 7.50-7.47 (m, 1H), 7.34 (d, J = 7.6 Hz, 2H), 6.98-6.94 (m, 4H), 6.45 (d, J = 8.4 Hz, 1H), 2.31 (s, 6H)<br>ESI [M + H] = 492.1 |
| 497 | 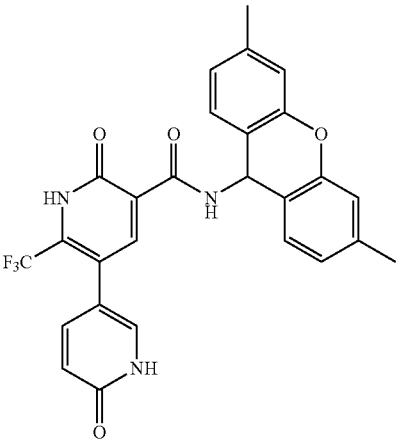 [SMILES: Cc1ccc2c(c1)Oc1cc(C)ccc1C2NC(=O)c1cc(-c2ccc(=O)[nH]c2)c(C(F)(F)F)[nH]c1=O] | $^1$H NMR (400 MHz, DMSO-d) δ = 11.81 (m, 1H), 9.70 (m, 1H), 8.20 (s, 1H), 7.40-7.32 (m, 4H), 6.98-6.95 (m, 4H), 6.44 (d, J = 8.4 Hz, 1H), 6.37 (d, J = 9.6 Hz, 1H), 2.31 (s, 6H).<br>ESI [M − H] = 506.1 |
| 498 | 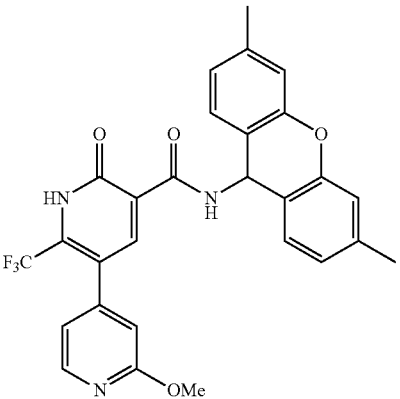 [SMILES: COc1cc(-c2cc(C(=O)NC3c4ccc(C)cc4Oc4cc(C)ccc43)c(=O)[nH]c2C(F)(F)F)ccn1] | $^1$H NMR (400 MHz, METHANOL-d) δ = 8.27 (s, 1H), 8.16 (d, J = 5.3 Hz, 1H), 7.35 (d, J = 8.2 Hz, 2H), 6.97-6.89 (m, 5H), 6.77 (s, 1H), 6.51 (s, 1H), 3.95 (s, 3H), 2.34 (s, 6H)<br>ESI [M − H] = 520.0 |

TABLE 55-continued

| Compound No | Structure | HNMR and Ms |
|---|---|---|
| 499 | 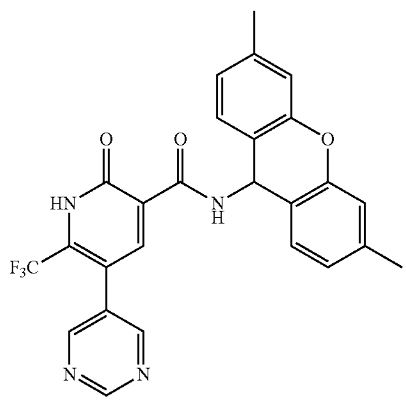 | $^1$H NMR (400 MHz, DMSO-d) δ = 9.16 (s, 1 H), 8.73 (s, 2 H), 8.07 (s, 1 H), 7.29 (, J = 8 Hz, 2H), 6.97-6.93 (m, 4 H), 6.39 (s, 1 H), 2.30 (s, 6 H) ESI [M − H] = 491.0 |
| 500 | 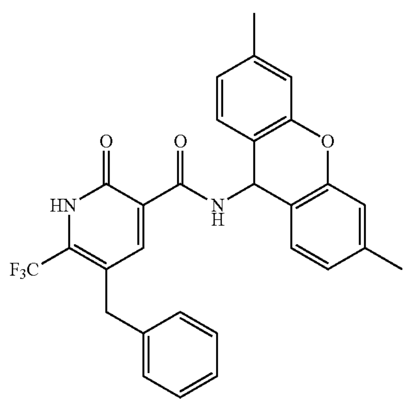 | $^1$H NMR (400 MHz, DMSO-d6) δ = 13.12 (brs, 1H), 9.70 (brs, 1H), 8.18 (s, 1H), 7.35-6.95 (m, 12H), 6.38 (s, 1H), 4.05 (s, 2H), 2.31 (s, 6H). ESI [M − H] = 503.0 |
| 501 | 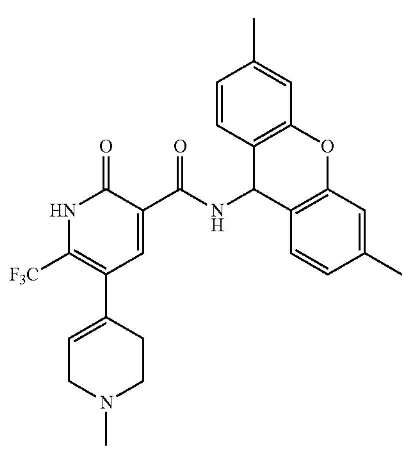 [SMILES: Cc1ccc2c(c1)Oc1cc(C)ccc1C2NC(=O)c1cc(C2=CCN(C)CC2)c(C(F)(F)F)[nH]c1=O] | $^1$H NMR (400 MHz, DMSO-d) δ = 12.24-11.01 (m, 1H), 7.97 (s, 1H), 7.74-7.39 (m, 1H), 7.28 (d, J = 7.8 Hz, 2H), 6.98 (s, 2H), 6.93 (d, J = 7.7 Hz, 2H), 6.39 (d, J = 8.6 Hz, 1H), 5.52 (br s, 1H), 3.63-3.47 (m, 2H), 3.22-3.07 (m, 2H), 2.80-2.65 (m, 3H), 2.43 (br s, 2H), 2.31 (s, 6H) ESI [M − H] = 508.0 |

TABLE 55-continued

| Compound No | Structure | HNMR and Ms |
|---|---|---|
| 502 | 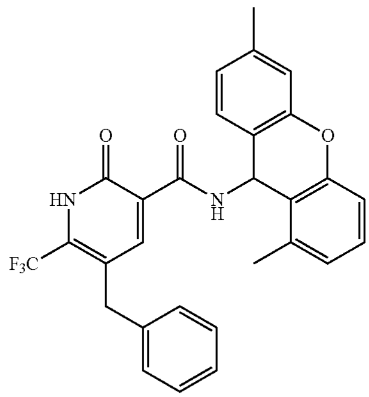 [SMILES: Cc1ccc2c(c1)Oc1cccc(C)c1C2NC(=O)c1cc(Cc2ccccc2)c(C(F)(F)F)[nH]c1=O] | $^1$H NMR (400 MHz, CDCl3) δ = 11.78 (br, 1H), 9.67 (br, 1H), 8.46 (s, 1H), 7.56-7.54 (d, J = 7.6 Hz, 1H) 7.32-6.92 (m, 10H), 6.56-6.54 (d, J = 8.4 Hz, 1H), 3.93 (s, 2H), 2.34 (s, 6H).<br>ESI [M − H] = 503.0 |
| 503 | 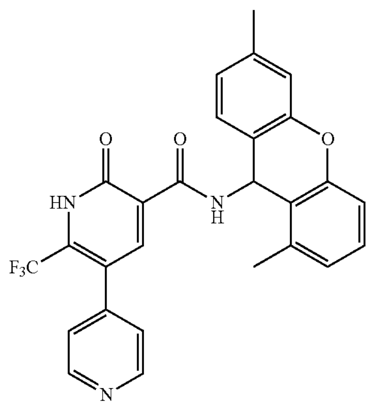 [SMILES: Cc1ccc2c(c1)Oc1cccc(C)c1C2NC(=O)c1cc(-c2ccncc2)c(C(F)(F)F)[nH]c1=O] | $^1$H NMR (400 MHz, CDCl$_3$) δ = 9.39 (d, J = 8.4 Hz, 1H), 8.72 (d, J = 4.8 Hz, 1H), 8.50 (s, 1 H), 7.57 (d, J = 7.6 Hz, 1H), 7.26-7.18 (m, 3 H), 7.01-6.90 (m, 4 H), 6.62 (d, J = 8.8 Hz, 1H), 2.37 (s, 3 H), 2.34 (s, 3 H)<br>ESI [M − H] = 490.0 |
| 504 | 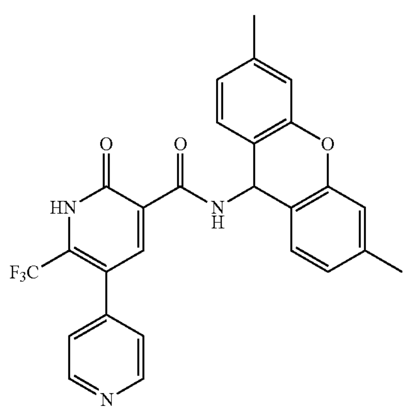 | $^1$H NMR (400 MHz, DMSO-d$_6$) δ = 9.58 (s, 1H), 8.65 (d, J = 6.0 Hz, 2H), 8.21 (s, 1H), 7.42-7.31 (m, 4H), 7.04-6.91 (m, 4H), 6.45 (d, J = 8.4 Hz, 1H), 2.31 (s, 6H)<br>ESI [M − H] = 490.0 |
| 505 | 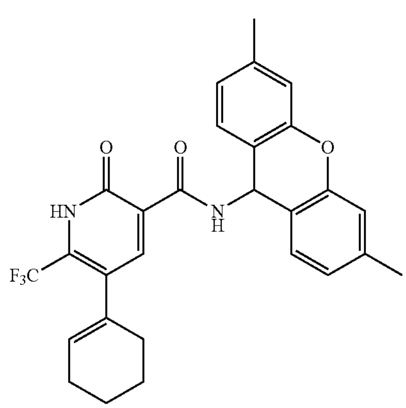 | $^1$H NMR (400 MHz, CDCl3) δ = 11.50 (br, 1H), 9.86 (br, 1H), 8.46 (s, 1H), 7.40-7.37 (m, 2H) 6.94-6.87 (m, 4H), 6.56-6.54 (d, J = 8.4 Hz, 1H), 5.62 (m, 1H), 2.35 (s, 6H), 2.14 (m, 4H), 1.75-1.66 (m, 4H).<br>ESI [M − H] = 493.0 |

TABLE 55-continued

| Compound No | Structure | HNMR and Ms |
|---|---|---|
| 188 | 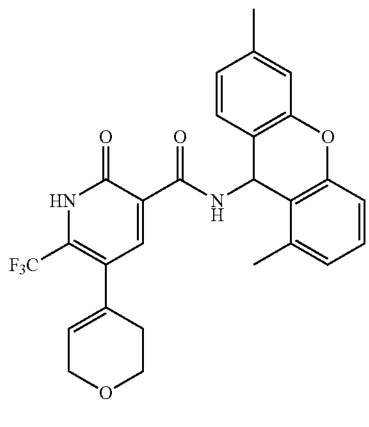 [SMILES: Cc1ccc2c(c1)Oc1cccc(C)c1C2NC(=O)c1cc(C2=CCOCC2)c(C(F)(F)F)[nH]c1=O] | ¹H NMR (400 MHz, DMSO-d₆) δ = 11.83 (brs, 1H), 9.59 (s, 1H), 8.45 (s, 1H), 7.59-7.57 (d, J = 7.6 Hz, 1H), 7.24-7.22 (m, 2H), 7.04-6.88 (m, 3H), 6.62-6.60 (d, J = 8.8 Hz, 1H), 5.71 (s, 1H), 4.26 (m, 2H), 3.90-3.88 (m, 2H), 2.37-2.28 (m, 8H)<br>ESI [M − H] = 495.2 |
| 177 | 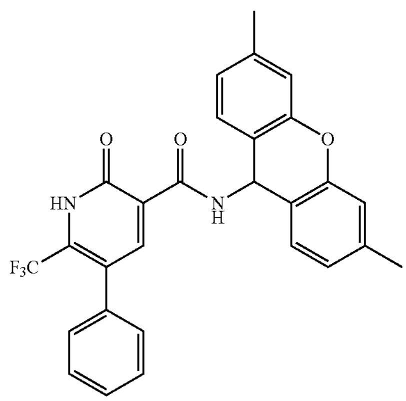 | ¹H NMR (400 MHz, MeOD) δ = 8.36 (br d, J = 5.1 Hz, 1H), 7.46-7.43 (m, 3H), 7.37-7.32 (m, 4H), 6.96-6.94 (m, 4H), 6.52 (s, 1H), 2.35 (s, 6H)<br>ESI [M − H] = 489.2 |

Example 96: Synthesis of N-(3,6-dimethyl-10,10-dioxido-9H-thioxanthen-9-yl)-2-oxo-5-(pyrimidin-2-yl)-6-(trifluoromethyl)-1,2-dihydropyridine-3-carboxamide (506)

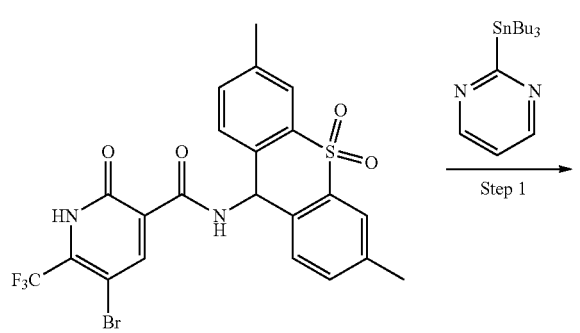

506-1

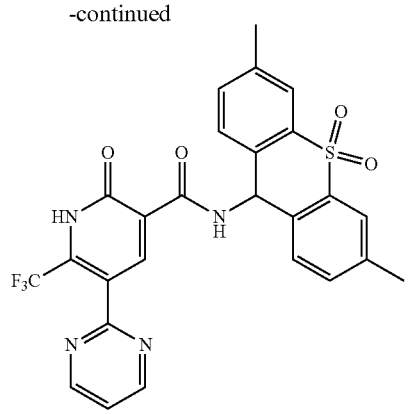

506

Step 1: N-(3,6-dimethyl-10,10-dioxido-9H-thioxanthen-9-yl)-2-oxo-5-(pyrimidin-2-yl)-6-(trifluoromethyl)-1,2-dihydropyridine-3-carboxamide (506)

To a solution of Compound 506-1 (70 mg, 129.3 μmol) in dioxane (2.5 mL) was added 2-(tributylstannyl)pyrimidine (72 mg, 194.0 μmol) and Pd(t-Bu₃P)₂ (7 mg, 12.9 μmol)

under N₂. The mixture was stirred at 100° C. for 3 hrs. LC-MS showed the reaction was completed. The reaction mixture was concentrated under reduced pressure to give a residue, which was diluted with water (10 mL) and extracted with EtOAc (8 mL×3). The combined organic layers were dried over Na₂SO₄, filtered and concentrated under reduced pressure to give a residue, which was purified by Prep-HPLC to give Compound 506 (5 mg, 9.2 µmol, 7% yield) as a yellow solid. M−H⁻=539.1 (LCMS); ¹H NMR (400 MHz, CDCl₃) δ=10.00 (br, 1H), 9.06 (s, 1H), 8.45-8.83 (d, J=4.8 Hz, 1H), 7.93 (s, 2H), 7.59-7.57 (d, J=8.0 Hz, 2H), 7.37-7.30 (m, 3H), 6.71-6.68 (d, J=9.2 Hz, 1H), 2.44 (s, 6H).

Other compounds made in a similar manner are shown in Table 56.

TABLE 56

| Compound No | Structure | HNMR and Ms |
| --- | --- | --- |
| 507 | 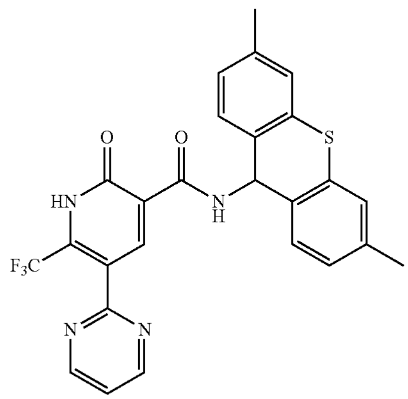 | ¹H NMR (400 MHz, DMSO-d6) δ = 8.93-8.92 (d, J = 4.8 Hz, 1H), 8.60 (s, 1H), 7.52-7.48 (m, 3 H), 7.38 (s, 2H), 7.15-7.13 (m, 2 H), 2.31 (s, 6H). ESI [M − H] = 507.1 |
| 508 | 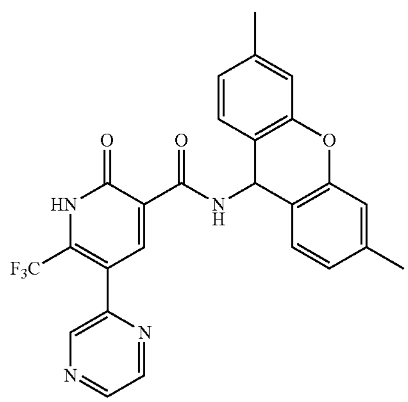 | ¹H NMR (400 MHz, CHLOROFORM-d) δ = 9.50 (br, 1H), 8.73-8.67 (m, 4H), 7.40-7.38 (d, J = 8 Hz, 2H), 6.94-6.88 (m, 4H), 6.59-6.57 (d, J = 8.8 Hz, 1H), 2.34 (s, 6H). ESI [M − H] = 491.0 |
| 509 | 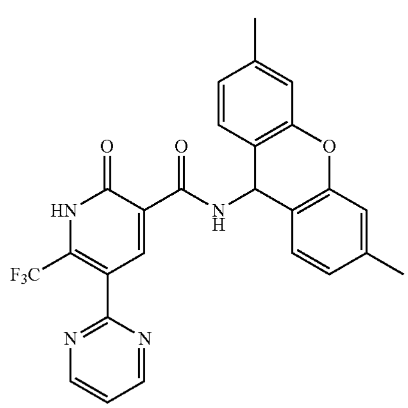 | ¹H NMR (400 MHz, DMSO-d6) δ = 13.56 (br, 1H), 9.70 (br, 1H), 8.93-8.92 (d, J = 4.8 Hz, 2H), 8.59 (s, 1H), 7.55-7.53 (m, 1H), 7.37-7.35 (d, J = 8 Hz, 2H), 6.99-6.95 (m, 4H), 6.46-6.44 (d, J = 8.8 Hz, 1H), 2.31 (s, 6H). ESI [M − H] = 491.0 |

TABLE 56-continued
| Compound No | Structure | HNMR and Ms |
|---|---|---|
| 510 | 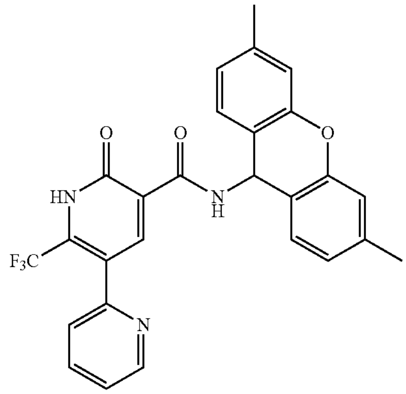 | ¹H NMR (400 MHz, DMSO-d6) δ = 13.46 (br, 1H), 8.65-8.63 (d, J = 4 Hz, 2H), 8.33 (s, 1H), 7.92-7.88 (m, 1H), 7.53-7.51 (m, 1H), 7.44-7.42 (m, 1H), 7.36-7.34 (m, 2H), 6.99-6.95 (m, 4H), 6.46-6.44 (d, J = 8.8 Hz, 1H), 2.31 (s, 6H). ESI [M − H] = 490.0 |
| 511 | 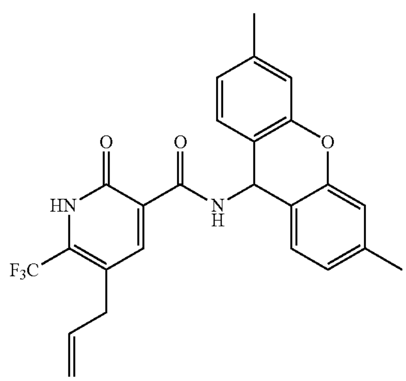 [SMILES: C=CCc1cc(C(=O)NC2c3ccc(C)cc3Oc3cc(C)ccc32)c(=O)[nH]c1C(F)(F)F] | ¹H NMR (400 MHz, DMSO-d6) δ = 8.19 (br s, 1H), 7.32 (d, J = 7.8 Hz, 2H), 6.98 (s, 2H), 6.95 (br d, J = 7.8 Hz, 2H), 6.41 (br d, J = 8.3 Hz, 1H), 5.99-5.82 (m, 1H), 5.10-4.95 (m, 2H), 3.40 (br d, J = 4.8 Hz, 2H), 2.31 (s, 6H) ESI [M − H] = 453.1 |
Example 97: Synthesis of N-(3,6-dimethyl-9H-xanthen-9-yl)-5-(4-ethylpiperazin-1-yl)-2-oxo-6-(trifluoromethyl)-1,2-dihydropyridine-3-carboxamide (512)
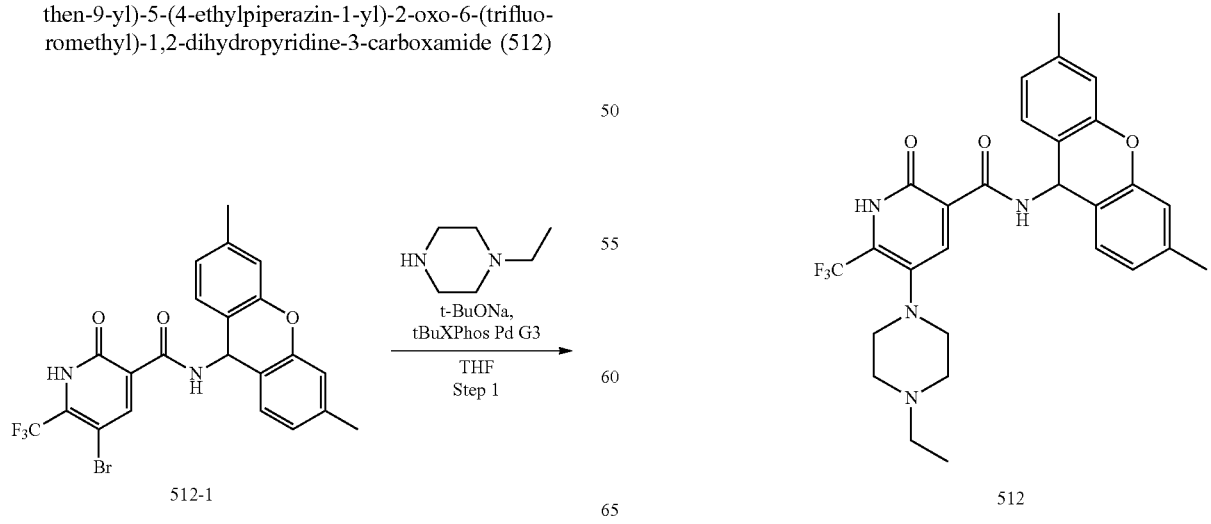

Step 1: N-(3,6-dimethyl-9H-xanthen-9-yl)-5-(4-ethylpiperazin-1-yl)-2-oxo-6-(trifluoromethyl)-1,2-dihydropyridine-3-carboxamide (512)

To a stirred mixture of Compound 512-1 (120 mg, 243 µmol), 1-ethylpiperazine (42 mg, 365 µmol) and t-BuONa (70 mg, 730 µmol) in THF (6 mL) was added tBuXPhos Pd G3 (19 mg, 24 µmol) under $N_2$ atmosphere. The resulting mixture was stirred at 80° C. for 3 hrs. LCMS showed the reaction was completed and the desired mass was detected. The reaction mixture was poured into $H_2O$ (15 mL) extracted with EtOAc (10 mL×4). The combined organic layers were dried over $Na_2SO_4$, filtered and concentrated under reduced pressure to give a residue, which was purified by prep-HPLC to give Compound 512 (14 mg, 24 µmol, 10% yield) as a yellow solid. M+H⁺=525.2 (LCMS), ¹H NMR (400 MHz, DMSO-d6) δ=8.32 (s, 1H), 7.32 (d, J=7.9 Hz, 2H), 7.02-6.89 (m, 4H), 6.41 (d, J=8.6 Hz, 1H), 3.13-2.81 (m, 8H), 2.53 (br d, J=6.8 Hz, 2H), 2.31 (s, 6H), 1.17 (br t, J=7.2 Hz, 3H).

Example 98: Synthesis of tert-butyl (4-(((5-((3,6-dichloro-9H-xanthen-9-yl)carbamoyl)-6-oxo-1,6-dihydropyrimidin-2-yl)thio)methyl)phenyl)carbamate (513)

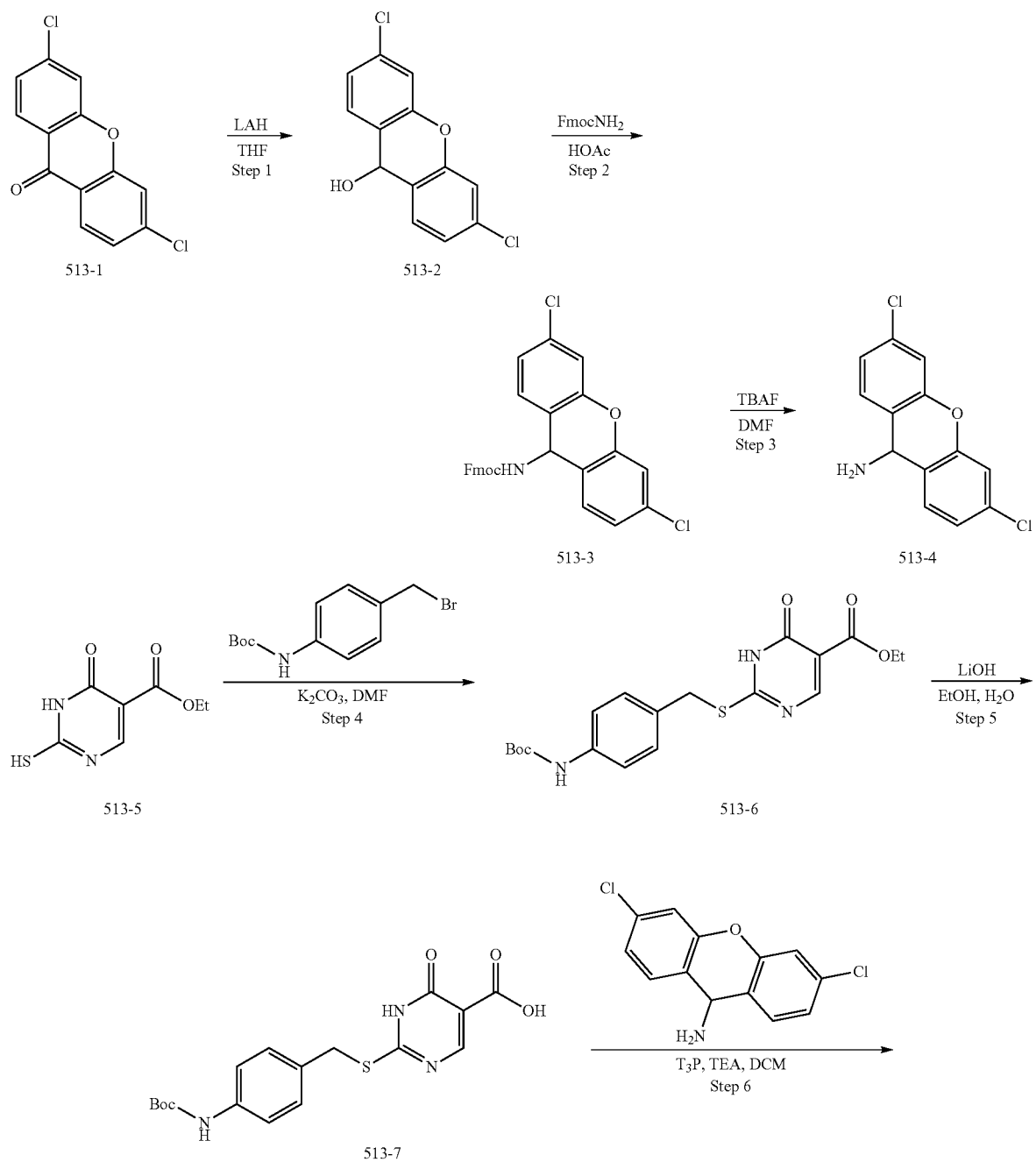

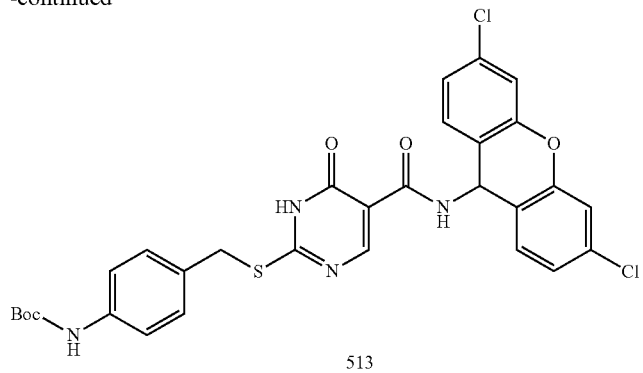

513

Step 1: 3,6-dichloro-9H-xanthen-9-ol (513-2)

To a solution of Compound 513-1 (300 mg, 1.1 mmol) in THF (4 mL) and MeOH (4 mL) was added NaBH$_4$ (128 mg, 3.4 mmol). The mixture was stirred at 25° C. for 0.5 hr. TLC showed the reaction was completed. The mixture was poured into Sat. NH$_4$Cl aq. (8 mL), and extracted with DCM (10 mL×3). The combined organic layers were dried over Na$_2$SO$_4$, filtered and concentrated under reduced pressure to give Compound 513-2 (300 mg, crude) as a white solid. This product was unstable, and should be used next step directly.

Step 2: (9H-fluoren-9-yl)methyl (3,6-dichloro-9H-xanthen-9-yl)carbamate (513-3)

To a solution of Compound 513-2 (300 mg, 1.1 mmol) in HOAc (10 mL) was added FmocNH$_2$ (296 mg, 1.2 mmol). The mixture was stirred at 25° C. for 0.5 hr. TLC showed the reaction was completed. The mixture was treated with water (30 mL) and stirred for 10 mins, most of solid appeared. The solid was filtered and dried in vacuum to give Compound 513-3 (500 mg, crude) as a white solid.

Step 3: 3,6-dichloro-9H-xanthen-9-amine (513-4)

To a solution of Compound 513-3 (500 mg, 1.0 mmol) in DMF (10 mL) was added TBAF (1 M, 1.02 mL). The mixture was stirred at 25° C. for 14 hrs. LCMS the reaction was completed and the desired mass was detected. The reaction mixture was diluted with H$_2$O (20 mL) and extracted with EtOAC (20 mL×3). The combined organic layers were dried over Na$_2$SO$_4$, filtered and concentrated under reduced pressure to give a residue, which was purified by flash silica gel chromatography (Ethyl acetate/Petroleum ether) to give Compound 513-4 (180 mg, crude) as a white solid. Fragment MS=249.0 (LCMS).

Step 4: ethyl 2-((4-((tert-butoxycarbonyl)amino)benzyl)thio)-6-oxo-1,6-dihydropyrimidine-5-carboxylate (513-6)

To a stirred solution of Compound 513-5 (150 mg, 749.2 μmol) in DMF (5 mL) was added tert-butyl (4-(bromomethyl)phenyl)carbamate (193 mg, 674.3 μmol) and K$_2$CO$_3$ (155 mg, 1.1 mmol). The mixture was stirred at 20° C. for 2 hrs. LCMS showed the reaction was completed and one main peak with desired mass was detected. The reaction mixture was diluted with H$_2$O 10 mL and extracted with EtOAC (10 mL×3). The combined organic layers were dried over Na$_2$SO$_4$, filtered and concentrated under reduced pressure to give Compound 513-6 (250 mg, crude) as a white solid. M+H$^+$=406.1 (LCMS).

Step 5: 2-((4-((tert-butoxycarbonyl)amino)benzyl)thio)-6-oxo-1,6-dihydropyrimidine-5-carboxylic acid (513-7)

To a solution of Compound 513-6 (150 mg, 369.9 μmol) in H$_2$O (4 mL) and EtOH (4 mL) was added LiOH.H$_2$O (78 mg, 1.9 mmol). The mixture was stirred at 25° C. for 12 hrs. LCMS showed the reaction was completed. The mixture was diluted with H$_2$O (2 mL) and the pH was adjusted to 5 with 1M HCl aq, most of solid appeared. The mixture was filtered and the cake was dried in vacuum to give Compound 513-7 (150 mg, crude) as a white solid. M+H$^+$=378.1 (LCMS); $^1$H NMR (400 MHz, DMSO-d$_6$) δ=9.36 (br, 1H), 8.55 (s, 1H), 7.40-7.37 (d, J=8.4 Hz, 2H), 7.31-7.29 (d, J=8.4 Hz, 2H), 4.40 (s, 2H), 1.46 (s, 9H).

Step 6: tert-butyl (4-(((5-((3,6-dichloro-9H-xanthen-9-yl)carbamoyl)-6-oxo-1,6-dihydropyrimidin-2-yl)thio)methyl)phenyl)carbamate (513)

To a solution of Compound 513-4 (80 mg, 300.6 μmol) in DCM (4 mL) was added Compound 513-7 (91 mg, 240.5 μmol), TEA (91 mg, 901.8 μmol) and T$_3$P (191 mg, 300.6 μmol, 50% purity). The mixture was stirred at 25° C. for 0.5 hr. LCMS showed the reaction was completed and one main peak desired mass was detected. The reaction mixture was then diluted with H$_2$O (5 mL) and extracted with DCM (5 mL×3). The combined organic layers were dried over Na$_2$SO$_4$, filtered and concentrated under reduced pressure to give a residue (80 mg, crude), 30 mg of which was purified by Prep-HPLC to give Compound 513 (20 mg, 31.7 μmol, 29% yield) as a light yellow solid. M−H$^-$=623.1 (LCMS); $^1$H NMR (400 MHz, DMSO-d$_6$) δ=9.94 (br, 1H), 9.35 (br, 1H), 8.56 (s, 1H), 7.46-7.44 (d, J=8.4 Hz, 2H), 7.29-7.21 (m, 6H), 6.38-6.35 (d, J=8.0 Hz, 1H), 4.37 (s, 2H), 1.46 (s, 9H).

Example 99: Synthesis of N-(3,6-dimethyl-9H-xanthen-9-yl)-2-oxo-5-phenoxy-6-(trifluoromethyl)-1,2-dihydropyridine-3-carboxamide (514)

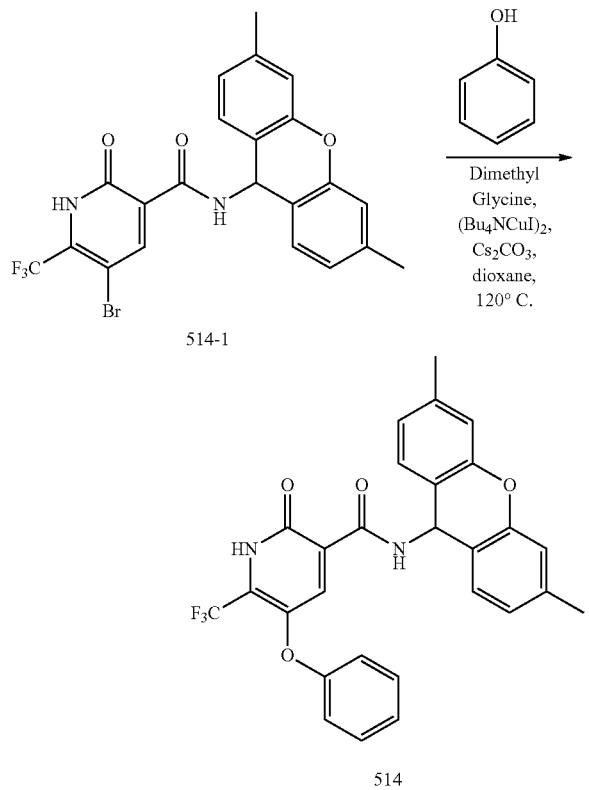

Step 1: N-(3,6-dimethyl-9H-xanthen-9-yl)-2-oxo-5-phenoxy-6-(trifluoromethyl)-1,2-dihydropyridine-3-carboxamide (514)

A mixture of Compound 514-1 (50 mg, 101.4 μmop, phenol (29 mg, 304.1 mol,), 2-(dimethylamino)acetic acid (4 mg, 40.6 mol), Bis(tetrabutylammonium)copper(I) iodide (11 mg, 10.1 μmol) and $Cs_2CO_3$ (66 mg, 202.7 mol) in dioxane (1 mL) was degassed and purged with $N_2$ for 3 times, and then was stirred at 120° C. for 12 hrs under $N_2$. LCMS showed the reaction was completed and the desired mass was detected. The reaction mixture was diluted with $H_2O$ (5 mL) and extracted with EtOAc (5 mL×3). The combined organic layers were concentrated under reduced pressure to give a residue, which was purified by Prep-HPLCT to give Compound 514 (13 mg, 25.6 μmol, 13% yield) as a light yellow solid. M–H⁻=505.1 (LCMS); $^1$H NMR (400 MHz, CDCl3) δ=13.25 (br, 1H), 9.43 (br, 1H), 8.03 (s, 1H), 7.39-7.31 (m, 4H), 7.15-7.10 (m, 1H), 7.02-6.93 (m, 6H), 6.39-6.37 (d, J=7.6 Hz, 1H), 2.31 (s, 6H).

Example 100: Synthesis of N-(3,6-dimethyl-9H-thioxanthen-9-yl)-5-methyl-2-oxo-6-(trifluoromethyl)-1,2-dihydropyridine-3-carboxamide (515)

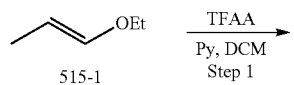

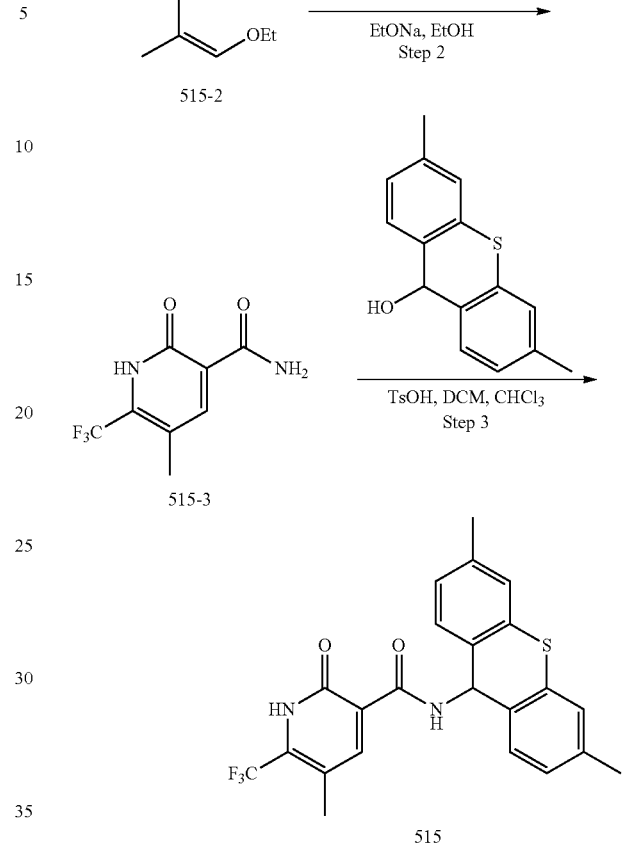

Step 1: (Z)-4-ethoxy-1,1,1-trifluoro-3-methylbut-3-en-2-one (515-2)

To a solution of Compound 515-1 (4 g, 46.4 mmol) in DCM (40 mL) was added a solution of Py (4 g, 51.1 mmol) and TFAA (9.8 g, 46.4 mmol) in DCM (10 mL) at 0° C. The mixture was stirred at 15° C. for 12 hrs. LCMS showed the reaction was completed and the desired mass was detected. The reaction mixture was poured into $H_2O$ (50 mL), and then washed by HCl (1M, 40 mL) and $NH_4Cl$.aq (40 mL). The combined organic layers were dried over $Na_2SO_4$, filtered and concentrated under reduced pressure to give a Compound 515-2 (7 g, crude) as yellow oil. M+H⁺=183.2 (LCMS).

Step 2: 5-methyl-2-oxo-6-(trifluoromethyl)-1,2-dihydropyridine-3-carboxamide (515-3)

To a solution of Compound 515-2 (1 g, 5.5 mmol) in EtOH (15 mL) was added malonamide (560.5 mg, 5.5 mmol) and EtONa/EtOH (1.8 g, 5.5 mmol) at 0° C. The mixture was stirred at 80° C. for 12 hrs. LCMS showed the reaction was complete and the desired mass was detected. The reaction mixture was poured into $H_2O$ (40 mL) and washed with EtOAc (20 mL×3). The water phase was neutralized with HCl solution (1 M) to pH=4 and most solid appeared. The mixture was filtered and the cake was dried in vacuum to give Compound 515-3 (600 mg, crude) as a brown solid. M+H⁺=221.0 (LCMS); ¹H NMR (400 MHz, DMSO-d6) δ=13.20 (br s, 1H), 8.31 (s, 2H), 8.06 (br s, 1H), 2.35 (br d, J=2.0 Hz, 3H).

Step 3: N-(3,6-dimethyl-9H-thioxanthen-9-yl)-5-methyl-2-oxo-6-(trifluoromethyl)-1,2-dihydropyridine-3-carboxamide (515)

A solution of 3,6-dimethyl-9H-thioxanthen-9-ol (50 mg, 206.3 µmol) in DCM (5 mL) was added to a mixture of Compound 515-3 (50 mg, 227.1 µmol) and TsOH·H₂O (39.3 mg, 206.3 µmol) in CHCl₃ (4 mL) at 70° C., the mixture was stirred at 70° C. for 5 mins. TLC indicated the reaction was completed. The reaction mixture was poured into H₂O (10 mL) and extracted with DCM (10 mL×2). The combined organic layers were dried over Na₂SO₄, filtered and concentrated under reduced pressure to give a residue, which was purified by Prep-HPLC to give Compound 515 (12 mg, 27.3 µmol, 13% yield,) as a gray solid. M−H⁻=443.0 (LCMS); ¹H NMR (400 MHz, DMSO-d₆) δ=13.24-12.86 (m, 1H), 9.82-9.26 (m, 1H), 8.30 (s, 1H), 7.48 (d, J=7.7 Hz, 2H), 7.38 (s, 2H), 7.14 (d, J=7.7 Hz, 2H), 6.12 (d, J=8.6 Hz, 1H), 2.40-2.21 (m, 9H).

Example 101: Synthesis of N-(3,6-dimethyl-9H-xanthen-9-yl)-6-oxo-2-(trifluoromethyl)-1,1',2',3',6,6'-hexahydro-[3,4'-bipyridine]-5-carboxamide (516)

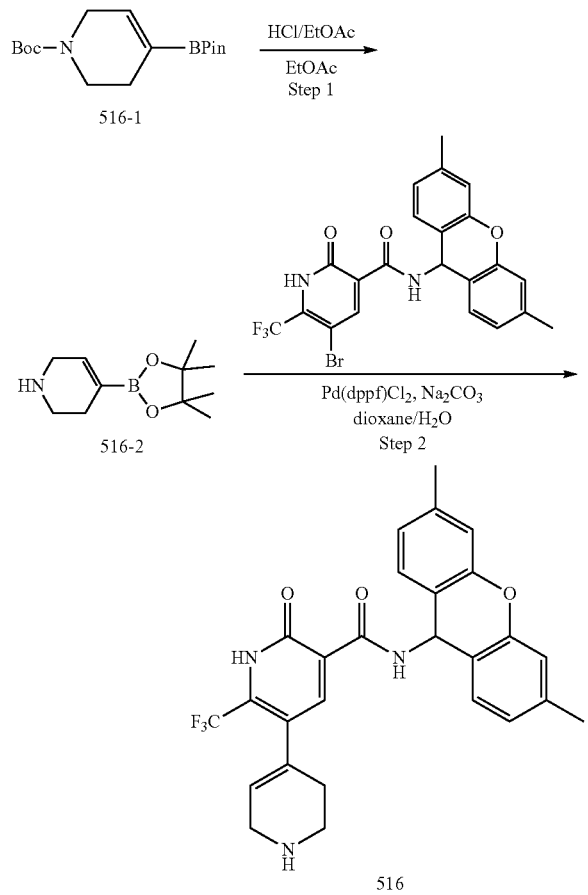

Step 1: 4-(4,4,5,5-tetramethyl-1,3,2-dioxaborolan-2-yl)-1,2,3,6-tetrahydropyridine (516-2)

To a solution of Compound 516-1 (500 mg, 1.6 mmol) in EtOAc (5 mL) was added HCl/EtOAc (4 M, 5 mL) at 0° C. The mixture was stirred at 20° C. for 3 hrs. TLC indicated the reaction completed. The reaction mixture was concentrated to give a Compound 516-2 (400 mg, crude, HCl) as a white solid. ¹HNMR (400 MHz, DMSO-d₆) δ=9.30 (br d, J=0.7 Hz, 2H), 6.35 (br s, 1H), 3.58 (br d, J=2.4 Hz, 2H), 3.14-2.93 (m, 2H), 2.33-2.21 (m, 2H), 1.21 (s, 12H).

Step 2: N-(3,6-dimethyl-9H-xanthen-9-yl)-6-oxo-2-(trifluoromethyl)-1,1',2',3',6,6'-hexahydro-[3,4'-bipyridine]-5-carboxamide (516)

To a solution of 5-bromo-N-(3,6-dimethyl-9H-xanthen-9-yl)-2-oxo-6-(trifluoromethyl)-1,2-dihydropyridine-3-carboxamide (100 mg, 202.7 µmol) in dioxane (2 mL) and H₂O (0.5 mL) was added Compound 516-2 (100 mg, 407.2 µmol, HCl), Na₂CO₃ (100 mg, 943.5 µmol) and Pd(dppf)Cl₂ (25 mg, 34.2 µmol) under N₂. The mixture was stirred at 80° C. under N₂ for 12 hrs. LCMS showed the reaction was complete and the desired mass was detected. The reaction mixture was quenched by addition H₂O (10 mL) and extracted with EtOAc (10 mL×3). The combined organic layers were dried over Na₂SO₄, filtered and concentrated under reduced pressure to give a residue, which was purified by re-crystallization from EtOAc (2 mL) and Petroleum ether (5 mL) to give a Compound 516 (3 mg, 5.2 µmol, 3% yield) as a yellow solid. M−H⁻=494.0 (LCMS); ¹H NMR (400 MHz, MeOD) δ=8.32 (br s, 1H), 7.35 (d, J=7.7 Hz, 2H), 7.02-6.91 (m, 4H), 6.51 (s, 1H), 5.80 (br s, 1H), 3.84 (br d, J=2.4 Hz, 2H), 3.47 (br d, J=7.1 Hz, 2H), 2.63-2.54 (m, 2H), 2.36 (s, 6H).

Example 102: Synthesis of N-(3,6-dichloro-9H-xanthen-9-yl)-6-oxo-2-((4-(trifluoromethyl)phenoxy)methyl)-1,6-dihydropyrimidine-5-carboxamide (517)

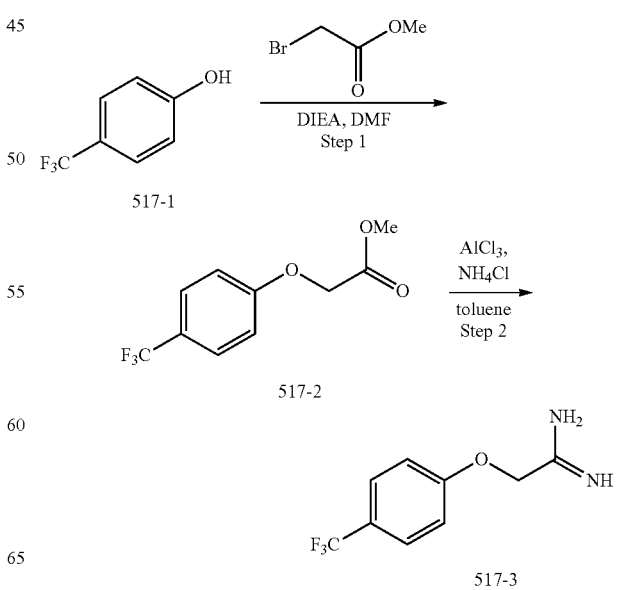

-continued

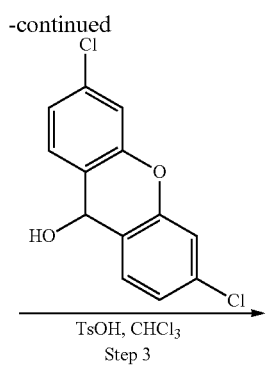

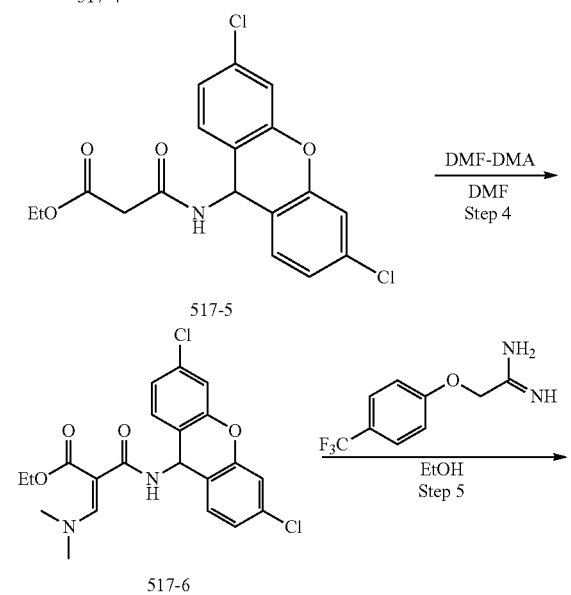

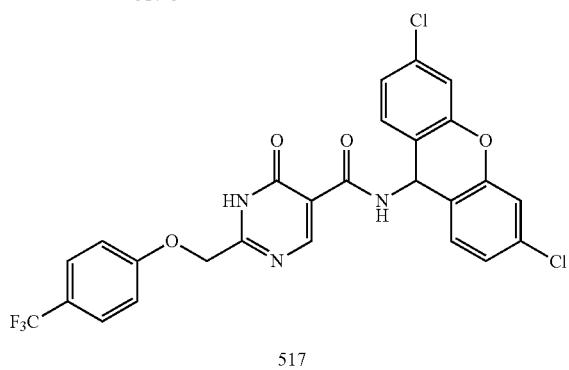

517

Step 1: methyl 2-(4-(trifluoromethyl)phenoxy)acetate (517-2)

To a solution of Compound 517-1 (3 g, 18.5 mmol) in DMF (30 mL) was added methyl 2-bromoacetate (3.5 g, 23.0 mmol) and DIPEA (5.0 g, 38.7 mmol). The mixture was stirred at 60° C. for 12 hrs. The reaction mixture was concentrated under reduced pressure to remove solvent. The residue was diluted with water (15 mL) and extracted with EtOAc (10 mL×3). The combined organic layers were dried over Na$_2$SO$_4$, filtered and concentrated under reduced pressure to give a residue, which was purified by column chromatography (Petroleum ether/Ethyl acetate) to give Compound 517-2 (3.8 g, 16.2 mmol, 88% yield) as colorless liquid. $^1$H NMR (400 MHz, CDCl3) δ=7.58-7.56 (d, J=8.8 Hz, 2H), 6.99-6.96 (d, J=8.4 Hz, 2H), 4.69 (s, 2H), 3.83 (s, 3H).

Step 2: 2-(4-(trifluoromethyl)phenoxy)acetimidamide (517-3)

To a stirred solution of NH$_4$Cl (1.4 g, 25.6 mmol) in Toluene (40 mL) was added AlCl$_3$ (2 M, 12.81 mL, 3 eq) drop wise at 0° C. and the mixture was stirred at 20° C. for 2 hrs. Compound 517-2 (2 g, 8.5 mmol) in Toluene (10 mL) was added, and the mixture was stirred at 80° C. for 12 hrs. LCMS showed the reaction was completed. The reaction mixture was poured into MeOH (30 mL) and stirred. The mixture was filtered and the cake was washed with MeOH (15 mL×4). The combined organic layers were concentrated under reduced pressure to give a residue, which was purified by Prep-HPLC to give Compound 517-3 (210 mg, 794.9 μmol, 9.31% yield, FA salt) as a white solid. M+H$^+$=219.0 (LCMS).

Step 3: ethyl 3 ((3,6-dichloro-9H-xanthen-9-yl)amino)-3-oxopropanoate (517-5)

To a solution of Compound 517-4 (49 mg, 370.6 μmol) in CHCl$_3$ (5 mL) was added TsOH·H$_2$O (128 mg, 673.9 μmol), then 3,6-dichloro-9H-xanthen-9-ol (90 mg, 336.9 μmol) (in 6 mL CH$_2$Cl$_2$ from previous step) was added at 70° C. and the mixture was stirred at 70° C. for 20 min. TLC indicated the reaction was completed. The reaction mixture was poured into water (10 mL), and then extracted with DCM (5 mL×3). The combined organic layers were concentrated under reduced pressure to give a residue, which was purified by Prep-TLC (Petroleum ether/Ethyl acetate=1:1) to give Compound 517-5 (32 mg, 84.2 μmol) as a white solid. $^1$H NMR (400 MHz, CDCl$_3$) δ=7.54-7.52 (d, J=8.8 Hz, 1H), 7.42-7.39 (d, J=8.4 Hz, 2H), 7.16-7.10 (m, 3H), 6.48-6.46 (d, J=8.8 Hz, 1H), 4.19-4.13 (q, J=7.2 Hz, 2H), 1.28-1.23 (t, J=7.2 Hz, 3H).

Step 4: (Z)-ethyl 2-((3,6-dichloro-9H-xanthen-9-yl)carbamoyl)-3-(dimethylamino)acrylate (517-6)

To a solution of Compound 517-5 (32 mg, 84.1 μmol) in DMF (1 mL) was added DMF-DMA (30 mg, 252.5 μmol). The mixture was stirred at 30° C. for 5 hrs. TLC indicated the reaction was completed. The reaction mixture was diluted with water (10 mL) and extracted with EtOAc (8 mL×3). The combined organic layers were dried over Na$_2$SO$_4$, filtered and concentrated under reduced pressure to give Compound 517-6 (30 mg, crude) as a light yellow solid, which was used into the next step without further purification.

Step 5: N-(3,6-dichloro-9H-xanthen-9-yl)-6-oxo-2-((4-(trifluoromethyl)phenoxy)methyl)-1,6-dihydropyrimidine-5-carboxamide (517)

To a solution of Compound 517-6 (30 mg, 68.9 μmol) in EtOH (1 mL) was added Compound 517-3 (18 mg, 68.9 μmol) and EtONa/EtOH (35 mg, 103.4 μmol, 20% purity). The mixture was stirred at 80° C. for 1 hr. LCMS showed the reaction was completed and desired mass was detected. The reaction mixture was concentrated under reduced pressure to give a residue, which was purified by prep-HPLC to give Compound 517 (4 mg, 7.2 μmol, 10.4% yield) as a white solid. M−H$^-$=559.9 (LCMS); $^1$H NMR (400 MHz, DMSO-d$_6$) δ=10.21 (br, 1H), 8.61 (s, 1H), 7.68-7.65 (d, J=8.8 Hz, 2H), 7.47-7.44 (d, J=8.4 Hz, 2H), 7.30 (s, 2H), 7.24-7.19 (m, 4H), 6.39-6.37 (d, J=8.4 Hz, 1H), 5.13 (s, 2H).

Other compounds made in a similar manner are shown in Table 57.

TABLE 57

| Compound No | Structure | HNMR and Ms |
|---|---|---|
| 518 | 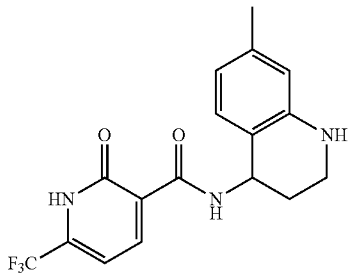 [SMILES: Cc1ccc2c(c1)NCCC2NC(=O)c1ccc(C(F)(F)F)[nH]c1=O] | $^1$H NMR (400 MHz, DMSO-d$_6$) δ = 13.31 (br s, 1H), 9.87 (brd, J = 7.9 Hz, 1H), 8.51 (s, 1H), 8.38 (d, J = 7.6 Hz, 1H), 8.32 (br d, J = 4.8 Hz, 1H), 7.51-7.43 (m, 2H), 7.41-7.36 (m, 1H), 7.32 (d, J = 7.6 Hz, 1H), 7.26-7.16 (m, 2H), 6.49 (d, J = 8.3 Hz, 1H)<br>ESI [M − H] = 350.1 |

Example 103: Synthesis of N-(10-methyl-9,10-dihydroacridin-9-yl)-2-oxo-6-(trifluoromethyl)-1,2-dihydropyridine-3-carboxamide (519)

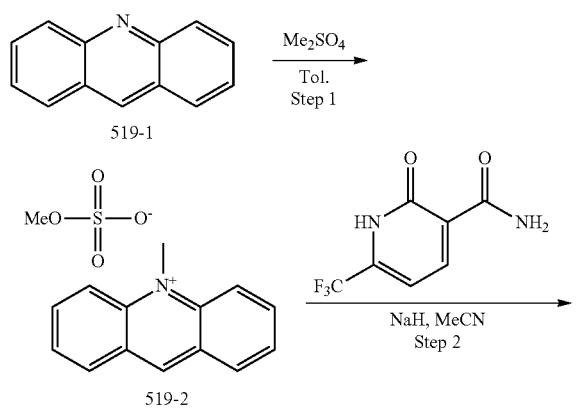

Step 1: 10-methylacridin-10-ium methyl sulfate (519-2)

A solution of Compound 519-1 (300 mg, 1.7 mmol) and Me$_2$SO$_4$ (422 mg, 3.4 mmol) in toluene (6 mL) was stirred at 110° C. for 1 hr. LCMS showed trace of the starting material was remained and lots of desired compound was detected. The precipitate was filtered and washed with toluene (5 mL), then the cake was dried under reduced pressure to give a residue, which was purified by re-crystallization from EtOH (5 mL) at 80° C. to give Compound 519-2 (450 mg, 1.5 mmol, 88% yield) as a yellow solid.

Step 2: N-(10-methyl-9,10-dihydroacridin-9-yl)-2-oxo-6-(trifluoromethyl)-1,2-dihydropyridine-3-carboxamide (519)

To a solution of 2-oxo-6-(trifluoromethyl)-1,2-dihydropyridine-3-carboxamide (100 mg, 485 μmol) in MeCN (0.1 mL) was added NaH (19 mg, 485 mol, 60% purity) at 20° C. When gas bubbling was ceased, Compound 519-2 (98 mg, 320 mol) was added. The mixture was stirred vigorously at 20° C. for 0.5 hr. LCMS showed the reaction was completed and the desired mass was detected. The reaction mixture was added MTBE (10 mL) and the precipitate was filtered, which was purified by prep-HPLC to give Compound 519 (5 mg, 12 mol, 3% yield) as a yellow solid. M−H$^-$=398.0 (LCMS), $^1$H NMR (400 MHz, CHLOROFORM-d) δ=9.41 (br s, 1H), 8.63 (d, J=7.6 Hz, 1H), 7.56 (d, J=7.5 Hz, 2H), 7.38-7.28 (m, 2H), 7.10-6.95 (m, 4H), 6.80 (d, J=7.5 Hz, 1H), 6.51 (d, J=7.9 Hz, 1H), 3.48 (s, 3H).

Example 104: Synthesis of N-(3,6-dimethyl-9H-xanthen-9-yl)-2-oxo-5-phenethyl-6-(trifluoromethyl)-1,2-dihydropyridine-3-carboxamide (520)

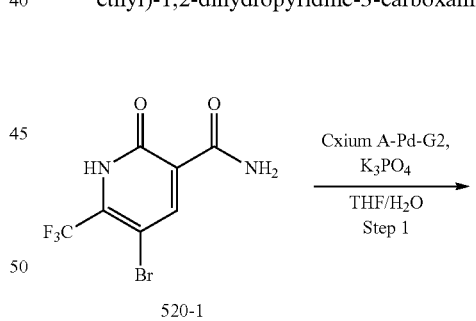

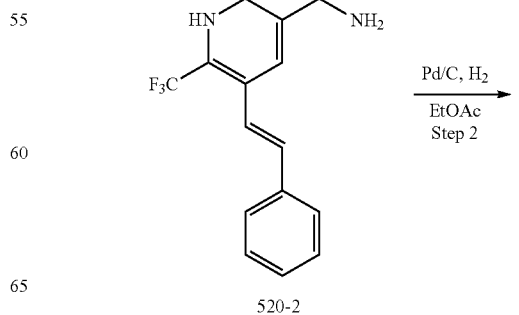

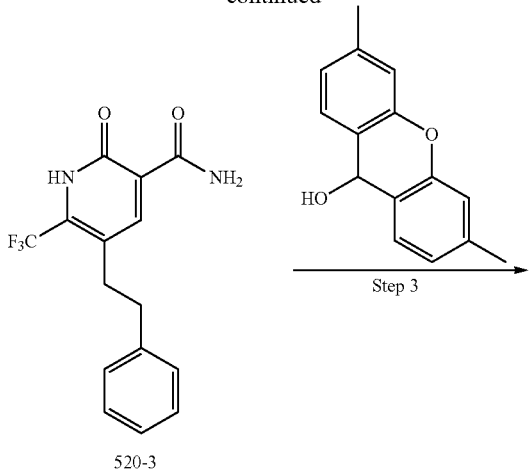

520-3

520

Step 1: (E)-2-oxo-5-styryl-6-(trifluoromethyl)-1,2-dihydropyridine-3-carboxamide (520-2)

A mixture of Compound 520-1 (50 mg, 175.4 μmol), (E)-4,4,5,5-tetramethyl-2-styryl-1,3,2-dioxaborolane (78 mg, 526.3 μmol), K₃PO₄ (0.5 M, 1.05 Ml, aq.), Cxium A-Pd-G2 (12 mg, 17.5 μmol) in THF (4 mL) was degassed and purged with N₂ for 3 times. The mixture was stirred at 80° C. for 12 hrs under N₂. LCMS showed the reaction was completed and the desired compound was detected. The reaction mixture was poured into brine (10 mL) and extracted with EtOAc (3 mL×2). The combined organic layers were dried over Na₂SO₄, filtered and concentrated under reduced pressure to give a residue, which was triturated DCM/MeOH (10/1, 3 mL) and filtered. The cake was washed with 3 mL of DCM, dried in vacuum to give Compound 520-2 (50 mg, 162.2 μmol) as a green solid. M−H⁻=306.9 (LCMS).

Step 2: 2-oxo-5-phenethyl-6-(trifluoromethyl)-1,2-dihydropyridine-3-carboxamide (520-3)

To a solution of Compound 520-2 (30 mg, 97.3 μmol) in EtOAc (6 mL) was added Pd/C (30 mg, 10% purity) and purged with H₂ for 3 times. The mixture was stirred at 20° C. for 10 min under H₂ (15 Psi). LCMS showed the reaction was completed and the desired compound was detected. The suspension was filtered through a pad of Celite and the cake was washed with EtOAc (3 mL×3). The filtrate was concentrated to give Compound 520-2 (30 mg, crude) as a white solid. M+H⁺=308.9 (LCMS).

Step 3: N-(3,6-dimethyl-9H-xanthen-9-yl)-2-oxo-5-phenethyl-6-(trifluoromethyl)-1,2-dihydropyridine-3-carboxamide (520)

To a stirred solution of Compound 520-3 (30 mg, 96.7 μmol,) in CHCl₃ (1 mL) was added TsOH.H₂O (37 mg, 193.4 μmol) and 3,6-dimethyl-9H-xanthen-9-ol (22 mg, 96.7 μmol). The mixture was stirred at 70° C. for 5 min. LCMS showed most of the starting material was consumed. The reaction mixture was diluted with H₂O (5 mL) and extracted with DCM (10 mL×3). The combined organic layers were dried over Na₂SO₄, filtered and concentrated under reduced pressure to give a residue, which was purified by Prep-HPLC to give Compound 520 (15 mg, 28.6 μmol, 30% yield) as a light yellow solid. M−H⁻=517.2 (LCMS); ¹H NMR (400 MHz, DMSO-d6) δ=12.99 (br, 1H), 9.54 (br, 1H), 8.33 (s, 1H), 7.35-7.20 (m, 7H), 7.00-6.96 (m, 4H), 6.45-6.42 (d, J=8.8 Hz, 1H), 2.92-2.79 (m, 4), 2.32 (s, 6H).

Other compounds made in a similar manner are shown in Table 58.

TABLE 58

| Compound No | Structure | HNMR and Ms |
| --- | --- | --- |
| 521 | 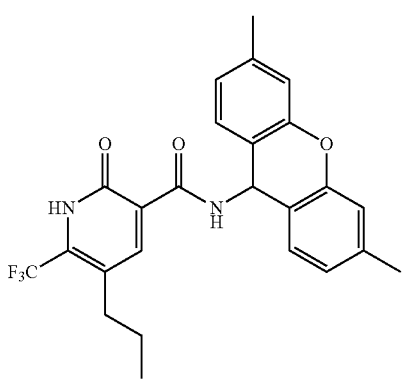 [SMILES: CCCc1cc(C(=O)NC2c3ccc(C)cc3Oc3cc(C)ccc32)c(=O)[nH]c1C(F)(F)F] | ¹H NMR (400 MHz, CHLOROFORM-d) δ ppm = 9.50 (m, 1 H), 8.30 (s, 1 H), 7.35-7.33 (d, J = 8.0 Hz, 1H), 6.99-6.95 (m, 4 H), 6.45-6.42 (d, J = 8.4 Hz, 1H), 2.64-2.60 (m, 2H), 2.32 (s, 6H), 1.58-1.51 (m, 2H), 0.93-0.89 (t, J = 7.2 Hz, 3H). ESI [M − H] = 455.1 |

Example 105: Synthesis of 2-((4-amino-3-(trifluoromethyl)benzyl)thio)-N-(3,6-dichloro-9H-xanthen-9-yl)-6-oxo-1,6-dihydropyrimidine-5-carboxamide (522)
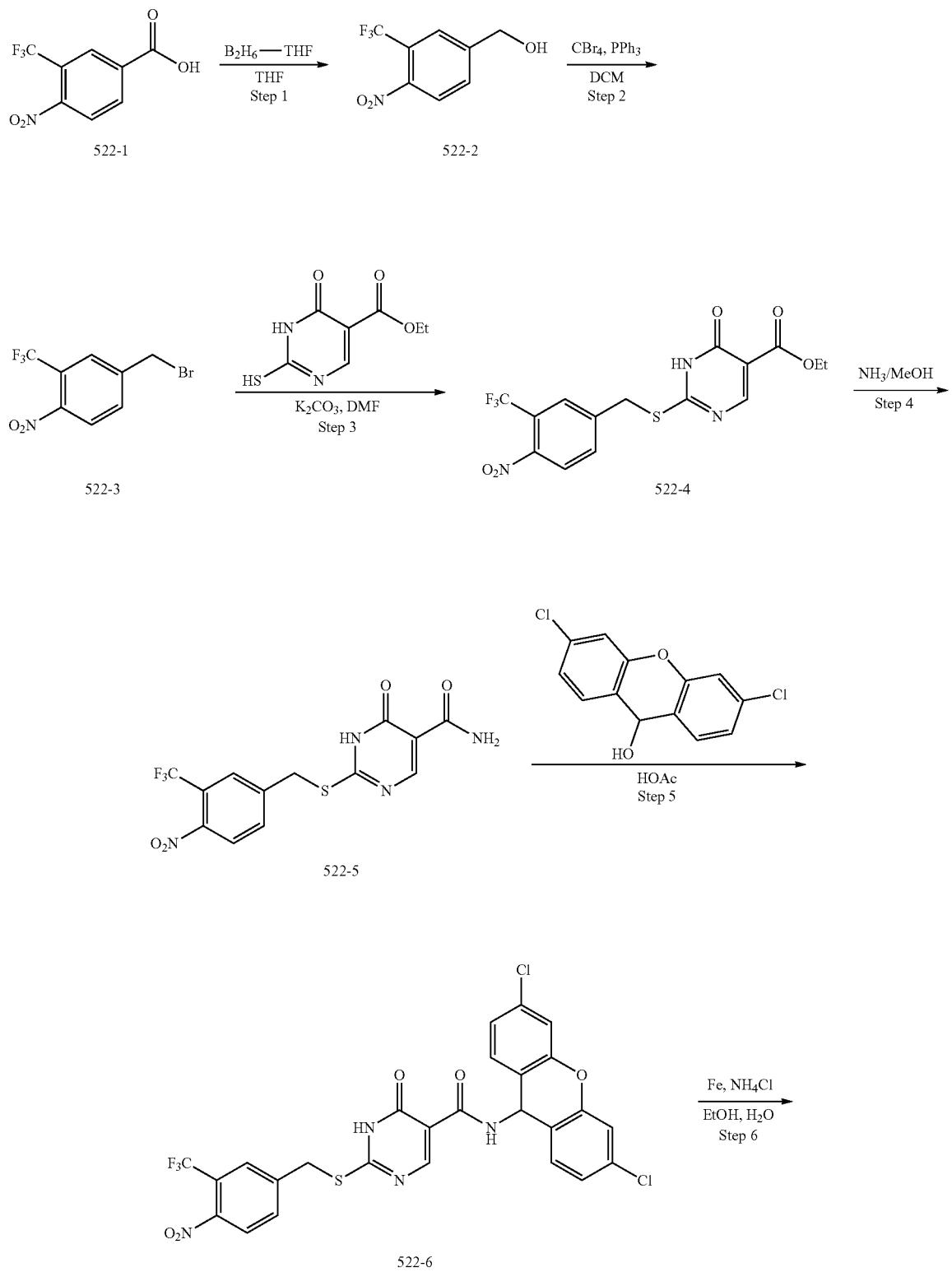

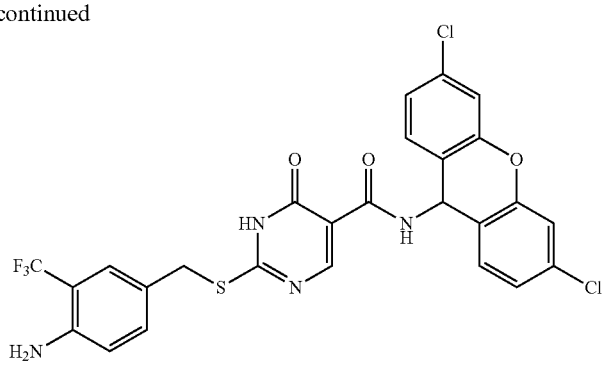

522

Step 1: (4-nitro-3-(trifluoromethyl)phenyl)methanol (522-2)

To a stirred solution of Compound 522-1 (1.5 g, 6.4 mmol) in THF (8 mL) at 0° C. was added BH$_3$·THF (1 M, 31.9 mL) dropwise under N$_2$, This reaction mixture was allowed to stir at 20° C. for 2 hrs. TLC indicated the reaction was completed. The reaction mixture was poured into Sat-.NaHCO$_3$ (30 mL), and extracted with DCM (10 mL×5). The combined organic layers were dried over Na$_2$SO$_4$, filtered and concentrated under reduced pressure to give a residue, which was purified by column chromatography (Petroleum ether/Ethyl acetate) to give Compound 522-2 (1.4 g, 6.3 mmol, 99% yield) as a colorless oil. $^1$H NMR (400 MHz, METHANOL-d4) δ=7.97 (d, J=8.3 Hz, 1H), 7.91 (s, 1H), 7.81 (d, J=8.2 Hz, 1H), 4.76 (s, 2H).

Step 2: 4-(bromomethyl)-1-nitro-2-(trifluoromethyl)benzene (522-3)

To a solution of Compound 522-2 (1.3 g, 5.9 mmol) in DCM (26 mL) was added CBr4 (3.1 g, 9.4 mmol) then PPh$_3$ (2.5 g, 9.4 mmol). The resulting mixture was stirred at 20° C. for 16 hrs. TLC indicated the reaction was completed. The reaction mixture was poured into H$_2$O (20 mL) extracted with DCM (10 mL×5). The combined organic layers were dried over Na$_2$SO$_4$, filtered and concentrated under reduced pressure to give a residue, which was purified by column chromatography (Petroleum ether/Ethyl acetate) to give Compound 522-3 (1.3 g, 4.6 mmol, 78% yield) as a yellow solid. $^1$H NMR (400 MHz, CHLOROFORM-d) δ=7.93-7.82 (m, 2H), 7.76 (br s, 1H), 4.62-4.42 (m, 2H).

Step 3: ethyl 2-((4-nitro-3-(trifluoromethyl)benzyl)thio)-6-oxo-1,6-dihydropyrimidine-5-carboxylate (522-4)

To a stirred mixture of ethyl 2-mercapto-6-oxo-1,6-dihydropyrimidine-5-carboxylate (0.5 g, 2.5 mmol) in DMF (5 mL) was K$_2$CO$_3$ (518 mg, 3.7 mmol), followed by adding Compound 522-3 (638 mg, 2.2 mmol) in portions at 20° C. Then the mixture was stirred at 20° C. for 2 hrs. TLC showed the reaction was completed. The reaction mixture was poured into H$_2$O (30 mL) extracted with DCM (10 mL×6). The combined organic layers were dried over Na$_2$SO$_4$, filtered and concentrated under reduced pressure to give a residue, which was triturated with DCM/MTBE=1/1 (20 mL) to give Compound 522-4 (0.8 g, 2.0 mmol, 79% yield) as a light yellow solid. $^1$H NMR (400 MHz, DMSO-d6) δ=8.23 (s, 1H), 8.12-8.04 (m, 2H), 7.97 (d, J=9.0 Hz, 1H), 4.40 (s, 2H), 4.14-4.07 (m, 2H), 1.22 (t, J=7.1 Hz, 3H).

Step 4: 2-((4-nitro-3-(trifluoromethyl)benzyl)thio)-6-oxo-1,6-dihydropyrimidine-5-carboxamide (522-5)

To a solution of Compound 522-4 (300 mg, 744 μmol) in MeOH (5 mL) was added NH$_3$/MeOH (4 M, 45.00 mL), then the mixture was stirred at 70° C. for 12 hrs under autoclave. LCMS showed the reaction was completed and one main peak with desired mass was detected. The reaction mixture was concentrated under reduced pressure to remove solvent. Then was diluted with EtOAc (5 mL) and H$_2$O (10 mL), neutralized to pH=5-6 using 1M HCl and the precipitate was filtered, then washed with water (5 mL×2), and concentrated under reduced pressure to give Compound 522-5 (0.2 g, 534 μmol, 72% yield) as a yellow solid. M+H$^+$=375.0 (LCMS), $^1$H NMR (400 MHz, DMSO-d6) δ=8.21 (s, 1H), 7.48 (d, J=8.3 Hz, 2H), 7.30 (d, J=1.8 Hz, 2H), 7.23 (dd, J=2.0, 8.3 Hz, 2H), 6.48-6.37 (m, 1H), 2.59 (br d, J=7.0 Hz, 2H), 1.64-1.46 (m, 2H), 0.90 (t, J=7.3 Hz, 3H).

Step 5: N-(3,6-dichloro-9H-xanthen-9-yl)-2-((4-nitro-3-(trifluoromethyl)benzyl)thio)-6-oxo-1,6-dihydropyrimidine-5-carboxamide (522-6)

A mixture of Compound 522-5 (147 mg, 393 μmol) and 3,6-dichloro-9H-xanthen-9-ol (150 mg, 562 μmol) in HOAc (6 mL) was stirred at 100° C. for 12 hrs. LCMS showed the reaction was completed. The reaction mixture was concentrated under reduced pressure to remove solvent. The residue was triturated with DCM at 20° C. for 5 min to give Compound 522-6 (150 mg, 241 μmol, 43% yield) as a light yellow solid. M−H$^-$=620.9 (LCMS).

Step 6: 2-((4-amino-3-(trifluoromethyl)benzyl)thio)-N-(3,6-dichloro-9H-xanthen-9-yl)-6-oxo-1,6-dihydropyrimidine-5-carboxamide (522)

To a mixture of Compound 522-6 (150 mg, 241 μmol) and NH₄Cl (64 mg, 1.2 mmol) in EtOH (7.5 mL) and H₂O (1.5 mL) was added Fe (67 mg, 1.2 mmol). The resulting mixture was stirred at 80° C. for 1 hr. LCMS showed the reaction was completed. The mixture was filtered and poured into water (30 mL) and extracted with EtOAc (3×10 mL). The combined organic layers were dried over Na₂SO₄ and concentrated in vacuum to give a residue, which was purified by prep-HPLC to give Compound 522 (3 mg, 4 μmol, 2% yield) as a gray solid. M−H⁻=590.9 (LCMS), ¹H NMR (400 MHz, DMSO-d6) δ=13.57 (br s, 1H), 9.96 (s, 1H), 8.55 (s, 1H), 7.46 (d, J=8.4 Hz, 2H), 7.39 (s, 1H), 7.35-7.27 (m, 3H), 7.23 (dd, J=2.1, 8.3 Hz, 2H), 6.76 (d, J=8.6 Hz, 1H), 6.37 (d, J=8.2 Hz, 1H), 5.61 (s, 2H), 4.34 (s, 2H).

Example 106: Synthesis of N-(1,6-dimethyl-9H-xanthen-9-yl)-5-(2-(dimethylamino)ethyl)-2-oxo-6-(trifluoromethyl)-1,2-dihydropyridine-3-carboxamide (523)

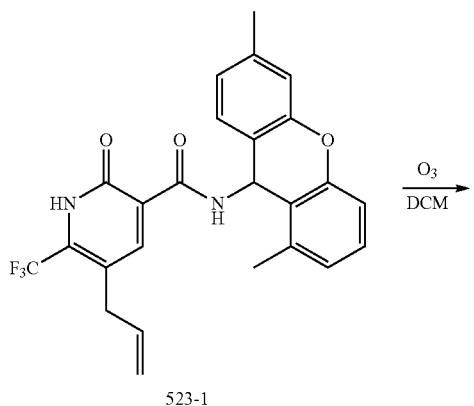

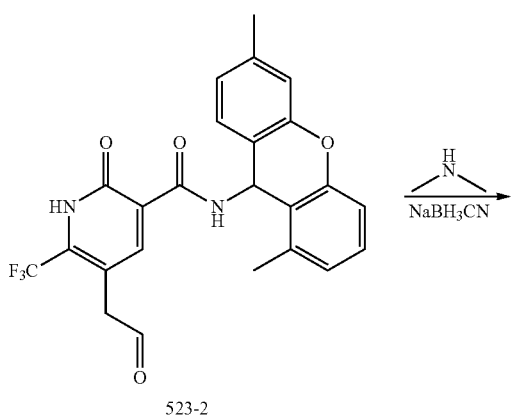

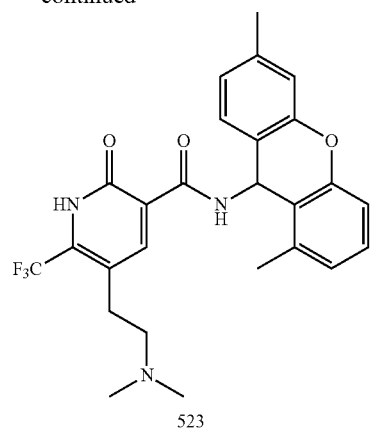

Step 1: N-(1,6-dimethyl-9H-xanthen-9-yl)-2-oxo-5-(2-oxoethyl)-6-(trifluoromethyl)-1,2-dihydropyridine-3-carboxamide (523-2)

To a solution of Compound 523-1 (250 mg, 550.1 μmol) in DCM (5 mL) and MeOH (5 mL) was bubbled with O3 (15 psi) at −60° C. for 10 min, then Me₂S (200 mg, 3.2 mmol) was added. The mixture was stirred at 15° C. for 12 hrs. LCMS showed the reaction was completed and one main peak with desired mass was detected. The mixture was concentrated to give Compound 523-2 (250 mg, crude) as a white gum, which was used directly. M−H⁻=455.1 (LCMS).

Step 2: N-(1,6-dimethyl-9H-xanthen-9-yl)-5-(2-(dimethylamino)ethyl)-2-oxo-6-(trifluoromethyl)-1,2-dihydropyridine-3-carboxamide (523)

A mixture of Me₂NH (400 mg, 2.7 mmol) (30% in MeOH), Compound 523-2 (120 mg, 262.9 μmol) and AcOH (120 mg, 2.0 mmol) in MeOH (4 mL) was stirred at 15° C. for 30 min. After that, NaBH₃CN (35 mg, 557.0 μmol) was added. The mixture was stirred at 15° C. for 1 hr. LCMS showed the reaction was completed and one main peak with desired mass was detected. The mixture was diluted with Sat.NH₄Cl (5 mL) and extracted with EtOAc (4 mL×3). The combined organic layers were dried over Na₂SO₄, filtered and concentrated in vacuum to give a residue, which was purified by Prep-HPLC to give Compound 523 (7 mg, 13.9 μmol, 5% yield) as a white solid. M−H⁻=484.0 (LCMS); ¹H NMR (400 MHz, DMSO-d₆+TFA) δ=9.79 (br, 1H), 9.22-9.19 (d, J=8.8 Hz, 1H), 8.29 (s, 1H), 7.49-7.46 (d, J=7.6 Hz, 1H), 7.29-7.25 (m, 1H), 7.05-6.94 (m, 4H), 6.50-6.48 (d, J=8.4 Hz, 1H), 3.20-3.19 (m, 2H), 3.04-3.01 (m, 2H), 2.84-2.83 (m, 6H), 2.34-2.30 (d, 6H).

Other compounds made in a similar manner are shown in Table 59.

TABLE 59
| Compound No | Structure | HNMR and Ms |
|---|---|---|
| 524 | 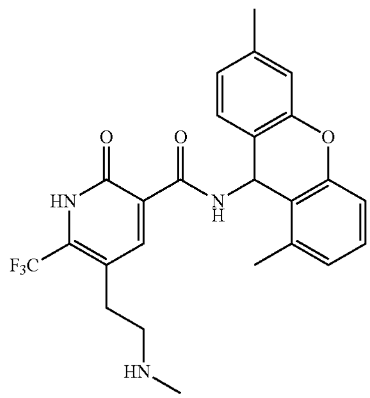 [SMILES: CNCCc1cc(C(=O)NC2c3ccc(C)cc3Oc3cccc(C)c32)c(=O)[nH]c1C(F)(F)F] | $^1$H NMR (400 MHz, CHLOROFORM-d) δ ppm = 11.97 (br, 1 H), 8.69 (br, 1H), 8.02 (s, 1 H), 7.49-7.46 (d, J = 8.0 Hz, 1H),7.24-7.21 (m, 1H), 7.02-6.89 (m, 4 H), 6.47-6.44 (d, J = 8.8 Hz, 1H), 2.99-2.94 (m, 2H), 2.78-2.75 (m, 2H), 2.56 (s, 3H), 2.29-2.26 (d, 6H). ESI [M − H] = 470.1 |
Example 107: Synthesis of N-(1,6-dimethyl-9H-xanthen-9-yl)-5-((methylamino)methyl)-2-oxo-6-(trifluoromethyl)-1,2-dihydropyridine-3-carboxamide (525)
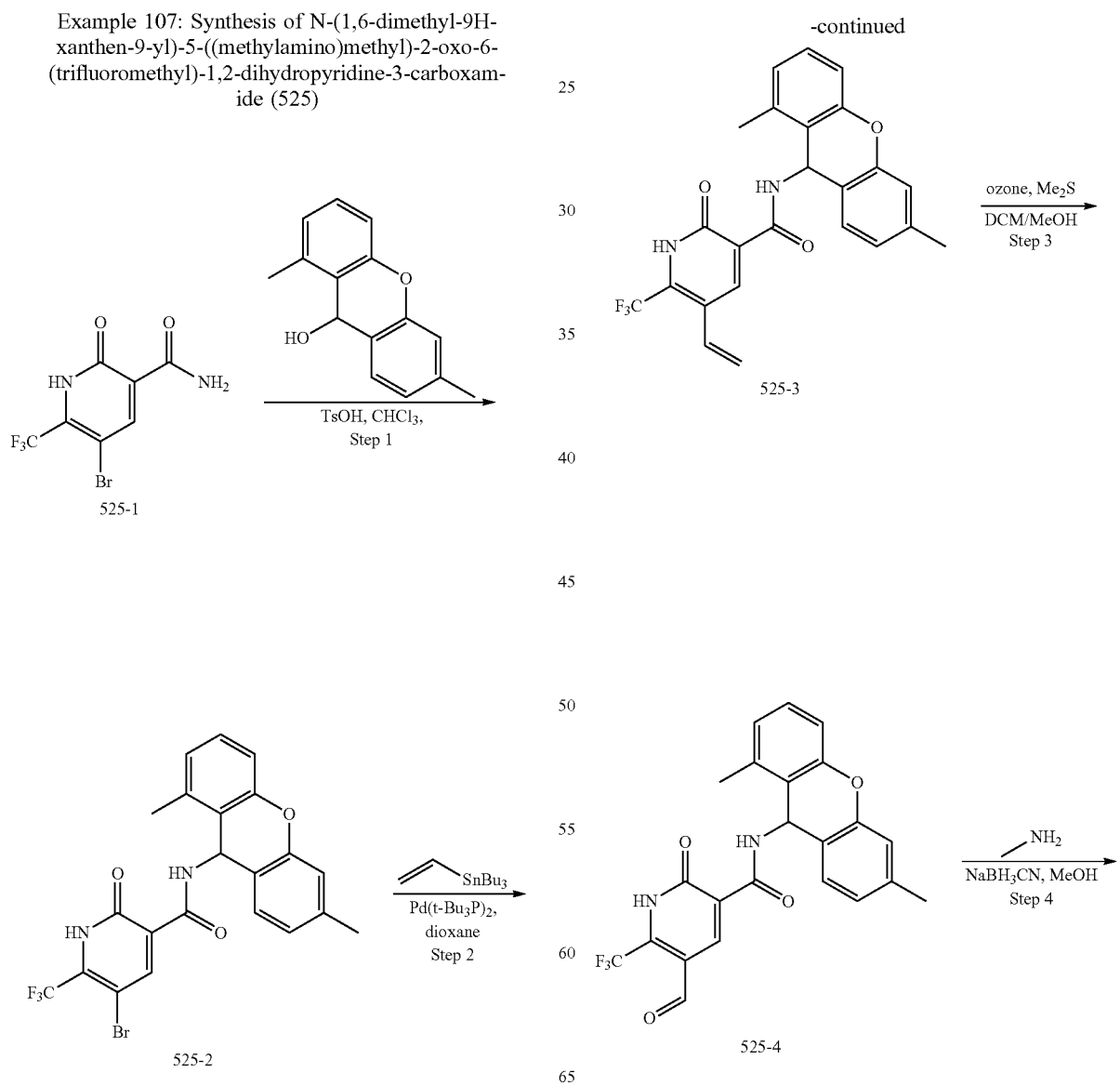

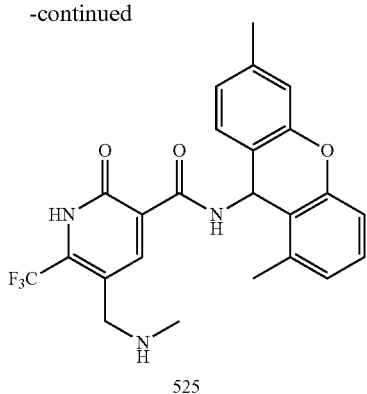

525

Step 1: 5-bromo-N-(1,6-dimethyl-9H-xanthen-9-yl)-2-oxo-6-(trifluoromethyl)-1,2-dihydropyridine-3-carboxamide (525-2)

A mixture of 1,6-dimethyl-9H-xanthen-9-ol (500 mg, 2.2 mmol) in DCM (5 mL) was added to a mixture of Compound 525-1 (630 mg, 2.2 mmol) and TsOH·H$_2$O (841 mg, 4.4 mmol) in CHCl$_3$ (10 mL) at 70° C., the mixture was stirred at 70° C. for 10 mins. LCMS showed the reaction was completed and the desired mass was detected. The reaction mixture was poured into H$_2$O (15 mL) and then extracted with DCM (10 mL×3). The combined organic layers were dried over Na$_2$SO$_4$, filtered and concentrated under reduced pressure to give a residue, which was purified by silica column chromatography to give Compound 525-2 (500 mg, crude) as a white solid. M–H$^+$=492.9 (LCMS).

Step 2: N-(1,6-dimethyl-9H-xanthen-9-yl)-2-oxo-6-(trifluoromethyl)-5-vinyl-1,2-dihydropyridine-3-carboxamide (525-3)

To a solution of Compound 525-2 (450 mg, 912.3 μmol) and tributyl(vinyl)stannane (579 mg, 1.8 mmol) in dioxane (10 mL) was added Pd(t-Bu$_3$P)$_2$ (90.0 mg, 176.1 μmol). The mixture was stirred at 100° C. under N$_2$ for 12 hrs. LCMS showed the reaction was completed and the desired mass was detected. The reaction mixture was diluted with EtOAc (20 mL), filtered and the filtrate was concentrated to give a residue, which was purified by column chromatography to give a crude Compound 525-3 (400 mg) as a white solid. M–H$^-$=439.0 (LCMS).

Step 3: N-(1,6-dimethyl-9H-xanthen-9-yl)-5-formyl-2-oxo-6-(trifluoromethyl)-1,2-dihydropyridine-3-carboxamide (525-4)

To a solution of Compound 525-3 (400 mg, 908.2 μmol) in DCM (15 mL) and MeOH (15 mL) was bubbled with O3 at −76° C. for 10 mins. To the mixture was added Me$_2$S (282 mg, 4.5 mmol) and stirred at 15° C. for 12 hrs. LCMS showed the reaction was completed and the desired mass was detected. The reaction was quenched by addition H$_2$O (20 mL), NaClO.aq (10 mL) and then extracted with DCM (15 mL×3). The combined organic layers were dried over Na$_2$SO$_4$, filtered and concentrated under reduced pressure to give a crude Compound 525-4 (400 mg, crude) as a brown solid. M–H$^-$=441.0 (LCMS).

Step 4: N-(1,6-dimethyl-9H-xanthen-9-yl)-5-((methylamino)methyl)-2-oxo-6-(trifluoromethyl)-1,2-dihydropyridine-3-carboxamide (525)

To a solution of Compound 525-4 (100 mg, 226.1 μmol) in MeOH (2 mL) was added MeNH2 (47 mg, 452.1 μmol) (30% EtOH.aq) and AcOH (50 mg, 832.8 μmol). The mixture was stirred at 15° C. for 0.5 hr. NaBH$_3$CN (28 mg, 452.1 μmol) was added and stirred at 15° C. for 12 hrs. LCMS showed the reaction was complete and the desired mass was detected. The reaction mixture was poured into NH$_4$Cl.aq (3 mL) and extracted with DCM:MeOH=10:1 (3 mL×3). The combined organic layers were dried over Na$_2$SO$_4$, filtered and concentrated under reduced pressure to give a residue, which was purified by prep-HPLC to give Compound 525 (24 mg, 47.3 μmol, 21% yield) as a light yellow solid. M–H$^-$=456.0 (LCMS); HNMR $^1$H NMR (400 MHz, DMSO-d6) δ=11.86 (br d, J=6.4 Hz, 1H), 8.74-8.35 (m, 1H), 8.27 (s, 1H), 7.48 (d, J=7.9 Hz, 1H), 7.31-7.23 (m, 1H), 7.04 (d, J=8.2 Hz, 1H), 7.01-6.95 (m, 2H), 6.91 (dd, J=0.9, 7.8 Hz, 1H), 6.48 (d, J=8.8 Hz, 1H), 4.00 (s, 2H), 2.55 (s, 3H), 2.30 (s, 3H), 2.26 (s, 3H).

Other compounds made in a similar manner are shown in Table 60.

TABLE 60

| Compound No | Structure | HNMR and Ms |
|---|---|---|
| 526 | (structure shown) | $^1$H NMR (400 MHz, DMSO-d$_6$) δ = 8.30 (s, 1H), 7.48 (d, J = 7.8 Hz, 1H), 7.35-7.22 (m, 1H), 7.09-6.87 (m, 4H), 6.48 (d, J = 8.6 Hz, 1H), 4.51-3.56 (m, 2H), 2.49-2.40 (m, 6H), 2.30 (d, J = 4.4 Hz, 6H) ESI [M − H] = 470.0 |

Example 108: Synthesis of N-(1-cyano-9H-xanthen-9-yl)-2-oxo-6-(trifluoromethyl)-1,2-dihydropyridine-3-carboxamide (527)
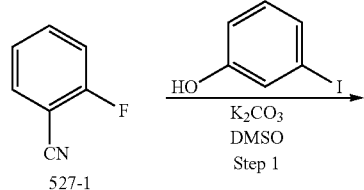
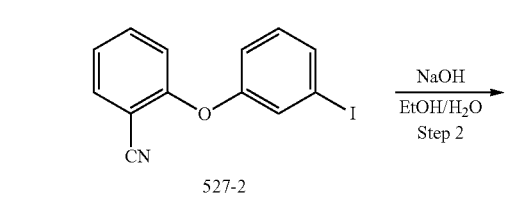
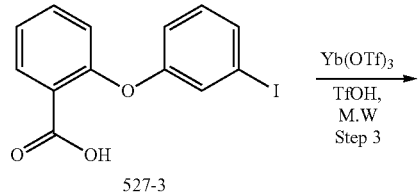
-continued
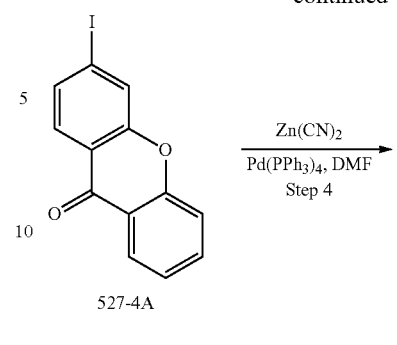
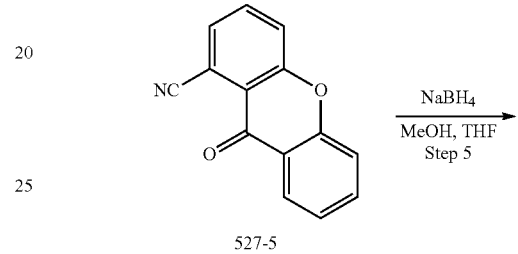
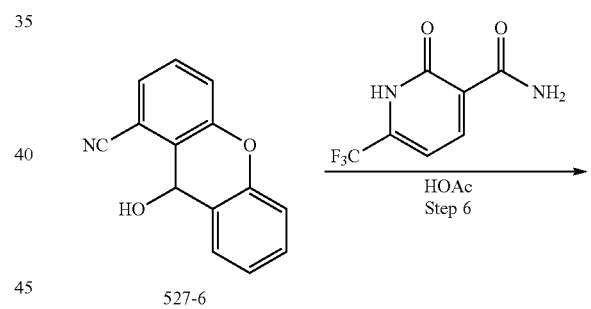
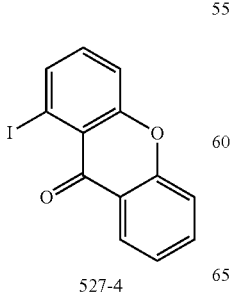
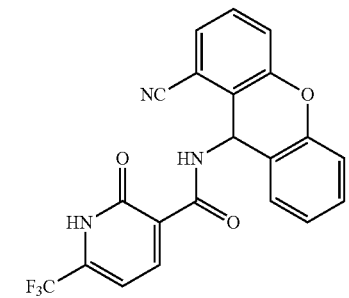

Step 1: (E)-4-butoxy-1,1-difluorobut-3-en-2-one (527-2)

A mixture of 3-iodophenol (4.5 g, 20.6 mmol and $K_2CO_3$ (4.3 g, 31 mmol) in DMSO (25 mL) was stirred at 25° C. for 0.5 hr. Then compound 527-1 (2.5 g, 20.6 mmol) was added and the resulting mixture was stirred at 80° C. for 4 hrs. LCMS showed the starting material was consumed completely. The reaction mixture was diluted with water (400 mL) and most of solid appeared. The mixture was filtered and the cake was dried in vacuum to give Compound 527-2 (6.5 g, crude) as a yellow solid. $M+H^+=321.9$ (LCMS).

Step 2: 6-(difluoromethyl)-2-oxo-1,2-dihydropyridine-3-carboxamide (527-3)

To a solution of Compound 527-2 (2.0 g, 6.2 mmol) in EtOH (15 mL) and $H_2O$ (15 mL) was added NaOH (4.5 g, 112.1 mmol). The mixture was stirred at 80° C. for 3 hrs. LCMS showed the starting material was consumed completely. The reaction mixture was concentrated under reduced pressure to give a residue, which was diluted with water (50 mL) and then adjusted pH to 3-4 by adding 1N HCl aq, extracted with EtOAc (25 mL×4). The combined organic layers were dried over $Na_2SO_4$, filtered and concentrated under reduced pressure to give Compound 527-3 (600 mg, crude) as a yellow solid. $M+H^+=340.9$ (LCMS).

Step 3: 1-iodo-9H-xanthen-9-one (527-4)

To a solution of Compound 527-3 (200 mg, 588.0 μmol) in TfOH (5 mL) was added $Yb(OTf)_3$ (36 mg, 58.8 μmol). The mixture was stirred at 50° C. for 30 min under Microwave. TLC showed the reaction was completed. The reaction mixture was poured into NaOH (10 mL, 10% aq.) and stirred. The mixture was filtered and the cake was dried in vacuo to give a residue, which was purified by Prep-HPLC to give Compound 527-4 (60 mg, 186.3 μmol) as a white solid and Compound 527-4A (40 mg, 124.2 μmol, 21% yield) as a white solid. Compound 527-4: $M+H^+=322.8$ (LCMS); $^1H$ NMR (400 MHz, MeOD) δ=8.25-8.23 (m, 1H), 8.10-8.07 (m, 1H), 7.82-7.80 (m, 1H), 7.64-7.62 (m, 1H), 7.56-7.54 (m, 1H), 7.46-7.39 (m, 2H); Compound 527-4A: $M+H^+=322.8$ (LCMS); $^1H$ NMR (400 MHz, MeOD) δ=8.26-8.23 (m, 1H), 8.04 (s, 1H), 7.97-7.94 (d, J=8.4 Hz, 1H), 7.85-7.78 (m, 2H), 7.60-7.57 (d, J=8.4 Hz, 1H), 7.50-7.40 (m, 1H).

Step 4: 9-oxo-9H-xanthene-1-carbonitrile (527-5)

To a solution of Compound 527-4 (60 mg, 186.3 μmol) in DMF (1 mL) was added $Pd(PPh_3)_4$ (43 mg, 37.3 μmol) and $Zn(CN)_2$ (109 mg, 931.4 μmol). The reaction mixture was stirred at 100° C. for 2 hrs. TLC showed the reaction was completed. The reaction mixture was poured into water (5 mL) and extracted with DCM (3 mL×3). The combined organic layers were dried over $Na_2SO_4$, filtered and concentrated in vacuum to give a residue, which was purified by Prep-TLC (Petroleum ether/Ethyl acetate=1/1) to give Compound 527-4 (30 mg, 135.6 μmol) as a white solid.

Step 5: 9-hydroxy-9H-xanthene-1-carbonitrile (527-6)

To a stirred solution of Compound 527-5 (30 mg, 135.6 μmol) in MeOH (1 mL) and THF (1 mL) was added $NaBH_4$ (26 mg, 678.1 μmol) in portions at 0° C. The resulting mixture was warmed to 35° C. slowly and stirred for 2 hrs. TLC showed the reaction was completed. The reaction mixture was poured into ice water (1 mL) and extracted with dichloromethane (1 mL×3). The combined organic layers were dried over $Na_2SO_4$, filtered and concentrated in vacuum to give Compound 527-6 (20 mg, crude) as a white solid.

Step 6: N-(1-cyano-9H-xanthen-9-yl)-2-oxo-6-(trifluoromethyl)-1,2-dihydropyridine-3-carboxamide (527)

A mixture of Compound 527-6 (20 mg, 89.6 μmol) and 2-oxo-6-(trifluoromethyl)-1,2-dihydropyridine-3-carboxamide (18 mg, 89.6 μmol) in AcOH (0.5 mL) was stirred at 80° C. for 1 hr. LC-MS showed the reaction was completed and desired mass was detected. The reaction mixture was concentrated under reduced pressure to give a residue, which was purified by Prep-HPLC to give Compound 527 (2 mg, 3.0 μmol, 4% yield) as a white solid. $M-H^-=410.0$ (LCMS); $^1H$ NMR (400 MHz, $CDCl_3$) δ=9.98 (br, 1H), 8.72-8.70 (d, J=7.6 Hz, 1H), 7.74-7.72 (d, J=6.8 Hz, 1H), 7.48-7.43 (m, 4H), 7.17-7.15 (m, 2H), 6.83-6.78 (m, 2H).

Other compounds made in a similar manner are shown in Table 61.

TABLE 61

| Compound No | Structure | HNMR and Ms |
|---|---|---|
| 528 | 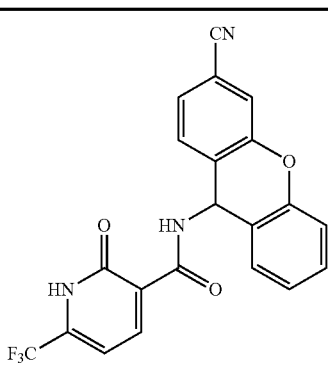 | $^1H$ NMR (400 MHz, $CDCl_3$) δ = 9.86 (br, 1H), 8.65-8.63 (d, J = 7.2 Hz, 1H), 7.61-7.58 (d, J = 7.6 Hz, 1H), 7.42-7.38 (m, 2H), 7.39-7.29 (m, 2H), 7.13-7.07 (m, 2H), 6.80-6.72 (d, J = 7.6 Hz, 1H), 6.58-6.56 (d, J = 8.4 Hz, 1H) ESI [M − H] = 410.0 |

Example 109: Synthesis of N-(1,6-dichloro-9H-xanthen-9-yl)-6-oxo-2-((2-(trifluoromethyl)benzyl)thio)-1,6-dihydropyrimidine-5-carboxamide (529)

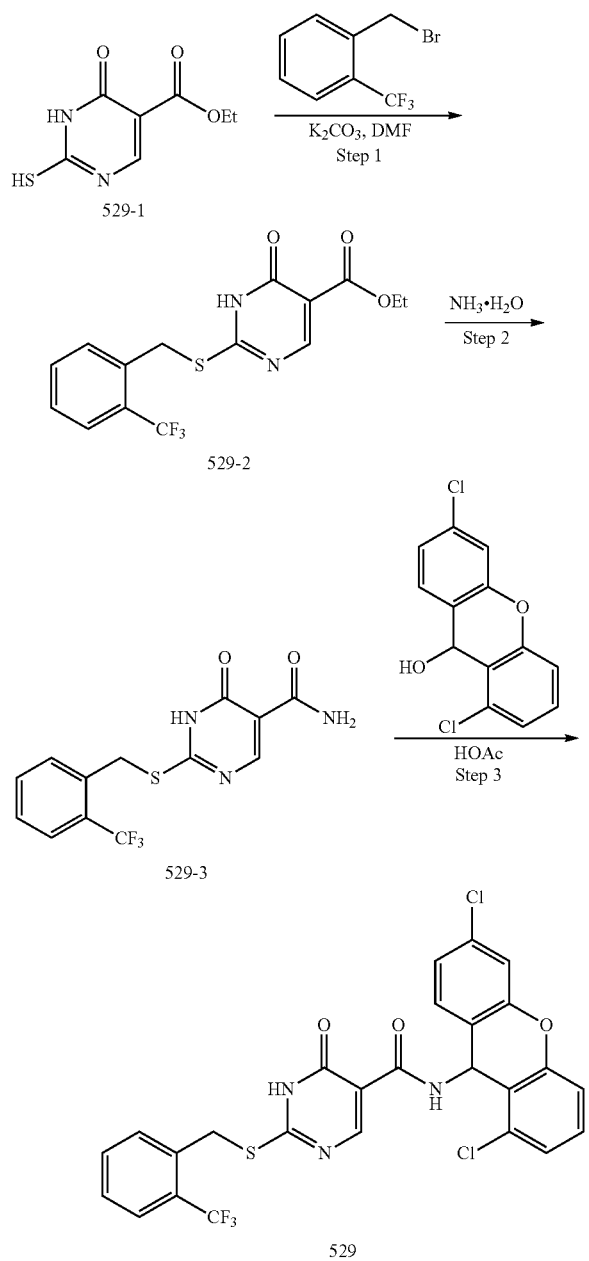

Step 1: ethyl 6-oxo-2-((2-(trifluoromethyl)benzyl)thio)-1,6-dihydropyrimidine-5-carboxylate (529-2)

To a solution of Compound 529-1 (1 g, 5.0 mmol) in DMF (15 mL) was added $K_2CO_3$ (1 g, 7.2 mmol) and 1-(bromomethyl)-2-(trifluoromethyl)benzene (1.2 g, 5.0 mmol). The mixture was stirred at 15° C. for 12 hrs. LCMS showed the reaction was completed and one main peak with desired mass was detected. The mixture was diluted with $H_2O$ (30 mL) and the pH was adjusted to about with 1M HCl, and then extracted with Ethyl acetate (10 mL×3). The combined organic layers were dried over $Na_2SO_4$, filtered and concentrated to give Compound 529-2 (1.8 g, crude) as an off-white solid. M–H⁻=356.9 (LCMS).

Step 2: 6-oxo-2-((2-(trifluoromethyl)benzyl)thio)-1,6-dihydropyrimidine-5-carboxamide (529-3)

A mixture of ethyl Compound 529-2 (100 mg, 279.0 μmol) in $NH_3 \cdot H_2O$ (1 mL) was stirred at 70° C. in a sealed tube for 15 hrs. LCMS showed the reaction was completed and one main peak with r desired mass was detected. The mixture was concentrated to give Compound 529-3 (100 mg, crude) as a pink solid. M–H⁻=327.9 (LCMS).

Step 3: N-(1,6-dichloro-9H-xanthen-9-yl)-6-oxo-2-((2-(trifluoromethyl)benzyl)thio)-1,6-dihydropyrimidine-5-carboxamide (529)

A mixture of Compound 529-3 (25 mg, 75.9) and 1,6-dichloro-9H-xanthen-9-ol (20 mg, 74.9 μmol) in AcOH (2 mL) was stirred at 100° C. for 2 hrs. LCMS showed the reaction was completed and one main peak with desired mass was detected. The mixture was concentrated to give a residue, which was purified by Prep-HPLC to give Compound 529 (12 mg, 18.5 μmol, 25% yield) as a yellow solid. M–H⁻=575.9 (LCMS); $^1$H NMR (400 MHz, DMSO-d6) δ=13.60 (s, 1H), 9.75 (br s, 1H), 8.59 (br s, 1H), 7.75 (d, J=8.2 Hz, 2H), 7.65 (t, J=7.7 Hz, 1H), 7.56-7.49 (m, 1H), 7.46 (d, J=8.4 Hz, 2H), 7.37-7.05 (m, 4H), 6.37 (d, J=8.2 Hz, 1H), 4.64 (s, 2H).

Example 110: Synthesis of N-(5-ethyl-1,2,3,4-tetrahydronaphthalen-1-yl)-2-oxo-6-(trifluoromethyl)-1,2-dihydropyridine-3-carboxamide (530)

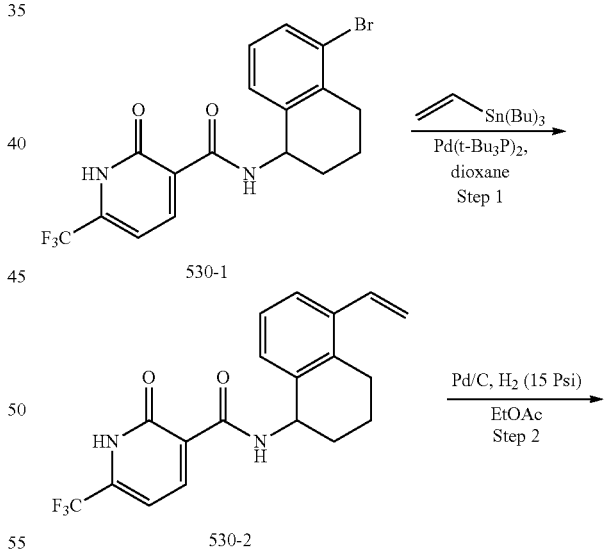

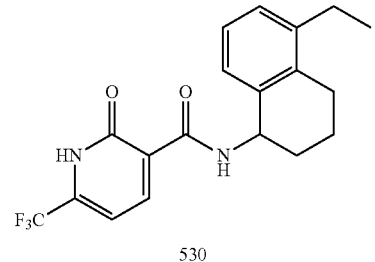

Step 1: 2-oxo-6-(trifluoromethyl)-N-(5-vinyl-1, 2, 3, 4-tetrahydronaphthalen-1-yl)-1, 2-dihydropyridine-3-carboxamide (530-2)

A mixture of Compound 530-1 (0.2 g, 482 µmol), tributyl (vinyl)stannane (183 mg, 578 µmol, Pd(t-Bu₃P)₂ (25 mg, 48 µmol) in toluene (5 mL) was degassed and purged with N₂ for three times, then the mixture was stirred at 100° C. for 12 hrs. LCMS showed the reaction was completed and desired mass was detected. The reaction mixture was quenched by pouring into water (15 mL) and extracted with EtOAc (5 mL×3). The combined organic layers were washed with brine (5 mL×2), dried over Na₂SO₄, filtered and concentrated under reduced pressure to give a residue. 50 mg crude product was purified by prep-HPLC to give Compound 530-2 (16 mg, 40.42 µmol, 9% yield) as a white solid. M–H⁻=361.1 (LCMS); ¹H NMR (400 MHz, DMSO-d₆) δ=13.12 (br, 1H), 8.89 (br, 1H), 8.40-8.38 (d, J=7.2 Hz, 1H), 7.76 (s, 1H), 7.03-6.76 (t, J=53.6 Hz, 1H), 6.78 (s, 1H).

Step 2: N-(5-ethyl-1,2,3,4-tetrahydronaphthalen-1-yl)-2-oxo-6-(trifluoromethyl)-1,2-dihydropyridine-3-carboxamide (530)

To a solution of Compound 530-2 (50 mg, 138 µmol) in EtOAc (2 mL) was added Pd/C (10 mg, 138 µmol, 10% purity) then purged with H₂ for three times. The mixture was stirred at 15° C. for 40 min under H₂ (15 Psi). LCMS showed the reaction was complete and desired mass was detected. The suspension was filtered through a pad of Celite and the pad was washed with EtOAc (5 mL×3). The combined filtrates were concentrated to dryness to give a residue, which was purified by prep-HPLC to give Compound 530 (26 mg, 69.19 µmol, 50% yield) as a white solid. M–H⁻=363.1 (LCMS); ¹H NMR (400 MHz, CHLOROFORM-d) δ=12.71 (br s, 1H), 9.55 (br s, 1H), 8.70 (d, J=7.3 Hz, 1H), 7.21-7.08 (m, 3H), 6.85 (d, J=7.5 Hz, 1H), 5.45-5.30 (m, 1H), 2.85 (td, J=5.3, 17.1 Hz, 1H), 2.75-2.58 (m, 3H), 2.10-1.86 (m, 4H), 1.24 (t, J=7.6 Hz, 3H).

Other compounds made in a similar manner are shown in Table 62.

TABLE 62

| Compound No | Structure | HNMR and Ms |
| --- | --- | --- |
| 531 | 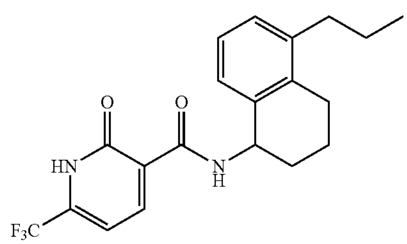 [SMILES: CCCc1cccc2c1CCCC2NC(=O)c1ccc(C(F)(F)F)[nH]c1=O] | ¹H NMR (400 MHz, CHLOROFORM-d) δ = 9.49 (br s, 1H), 8.67 (d, J = 7.5 Hz, 1H), 7.19-7.14 (m, 1H), 7.13-7.06 (m, 2H), 6.86 (d, J = 7.3 Hz, 1H), 5.42-5.33 (m, 1H), 2.89-2.79 (m, 1H), 2.75-2.65 (m, 1H), 2.61-2.54 (m, 2H), 2.13-2.03 (m, 1H), 1.97 (br t, J = 5.2 Hz, 1H), 1.94-1.86 (m, 2H), 1.68-1.60 (m, 2H), 1.01 (t, J = 7.3 Hz, 3H) ESI [M − H] = 377.1 |
| 532 | 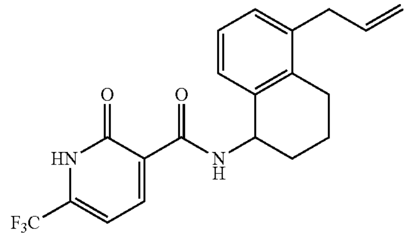 [SMILES: C=CCc1cccc2c1CCCC2NC(=O)c1ccc(C(F)(F)F)[nH]c1=O] | ¹H NMR (400 MHz, CHLOROFORM-d) δ = 13.18 (br s, 1H), 9.63 (br d, J = 7.5 Hz, 1H), 8.71 (d, J = 7.4 Hz, 1H), 7.22-7.18 (m, 1H), 7.14-7.07 (m, 2H), 6.86 (d, J = 7.5 Hz, 1H), 5.96 (tdd, J = 6.4, 10.3, 16.9 Hz, 1H), 5.40-5.33 (m, 1H), 5.12-4.99 (m, 2H), 3.37 (d, J = 6.3 Hz, 2H), 2.87-2.78 (m, 1H), 2.72-2.62 (m, 1H), 2.09-1.86 (m, 4H) ESI [M − H] = 375.2 |

Example 111: Synthesis of N-(5-amino-1,2,3,4-tetrahydronaphthalen-1-yl)-2-oxo-6-(trifluoromethyl)-1,2-dihydropyridine-3-carboxamide (533)

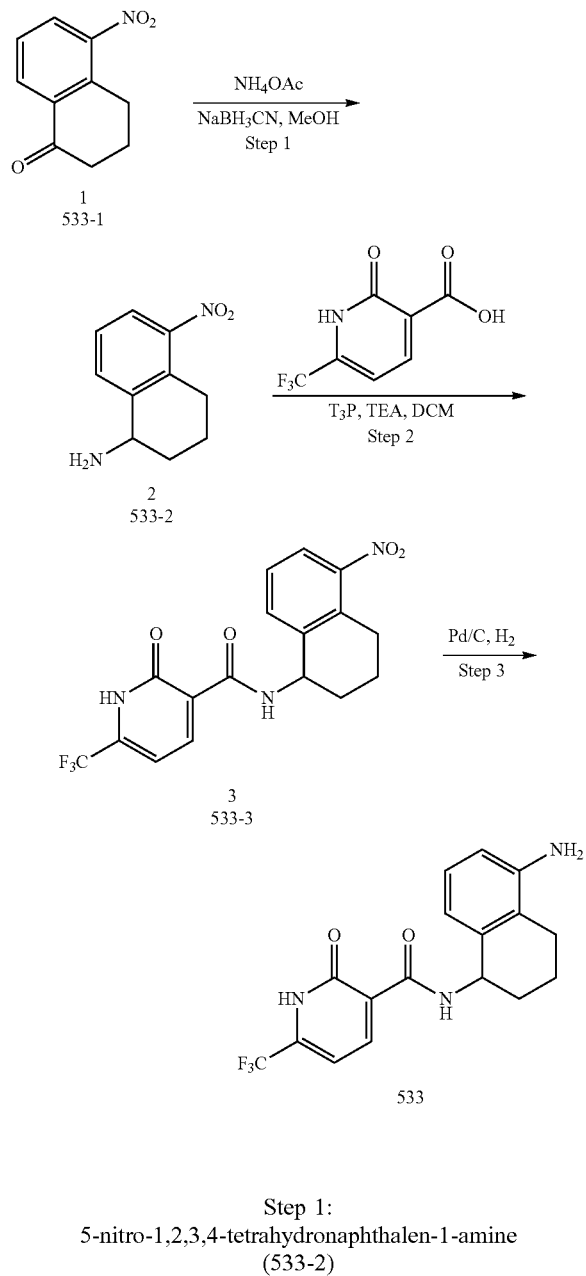

Step 1: 5-nitro-1,2,3,4-tetrahydronaphthalen-1-amine (533-2)

To a solution of Compound 533-1 (100 mg, 523.0 μmol) in MeOH (2 mL) was added NH$_4$OAc (604 mg, 7.8 mmol). The mixture was stirred at 20° C. for 10 min and NaBH$_3$CN (131 mg, 2.1 mmol) was added. The mixture was stirred at 90° C. for 1 hr under microwave. LCMS showed the reaction was completed and the desired mass was detected. The reaction mixture was poured into H$_2$O (15 mL), and then extracted with EtOAc (5 mL×3). The combined organic layers were dried over Na$_2$SO$_4$, filtered and concentrated under reduced pressure to afford Compound 533-2 (120 mg, crude) as a white solid. M+H$^+$=193.1 (LCMS).

Step 2: N-(5-nitro-1,2,3,4-tetrahydronaphthalen-1-yl)-2-oxo-6-(trifluoromethyl)-1,2-dihydropyridine-3-carboxamide (533-3)

To a solution of 2-oxo-6-(trifluoromethyl)-1,2-dihydropyridine-3-carboxylic acid (108 mg, 520.2 μmol) in DCM (3 mL) was added HATU (237 mg, 624.3 μmol) and DIEA (202 mg, 1.5 mmol, 271.8 uL), followed by Compound 533-2 (100 mg, 520.2 μmol). The mixture was stirred at 20° C. for 3 hrs. TLC indicated the reaction was completed. The reaction was poured into H$_2$O (15 mL), and then extracted with DCM (5 mL×3). The combined organic layers were dried over Na$_2$SO$_4$, filtered and concentrated under reduced pressure to give a residue, which was purified by column chromatography by Prep-TLC (Petroleum ether:Ethyl acetate=1:1) to give Compound 533-3 (40 mg, 104.9 μmol, 20% yield) as a yellow solid.

Step 3: N-(5-amino-1,2,3,4-tetrahydronaphthalen-1-yl)-2-oxo-6-(trifluoromethyl)-1,2-dihydropyridine-3-carboxamide (533)

A mixture of Compound 533-3 (30 mg, 78.6 μmol) and Pd/C (40 mg, 78.6 μmol, 10% purity) in EtOAc (1 mL) was degassed and purged with H$_2$ for 3 times. The mixture was stirred at 20° C. for 15 min under H$_2$ (15 Psi). LCMS showed the reaction was completed and desired mass was detected. The reaction mixture was filtered and the filtrate was concentrated to give a residue, which was purified by Prep-HPLC to give Compound 533 (4 mg, 9.8 μmol, 13% yield) was obtained as a white solid. M−H$^-$=350.1 (LCMS). $^1$H NMR (400 MHz, CHLOROFORM-d) δ=9.56 (br d, J=7.7 Hz, 1H), 8.70 (d, J=7.3 Hz, 1H), 7.03-6.96 (m, 1H), 6.85 (d, J=7.5 Hz, 1H), 6.78 (d, J=7.5 Hz, 1H), 6.62 (d, J=7.7 Hz, 1H), 5.35-5.29 (m, 1H), 2.62-2.52 (m, 1H), 2.51-2.41 (m, 1H), 2.09-1.92 (m, 4H).

Example 112: HSD17B13 enzymatic blocking assay

Compounds of the disclosure were screened for their ability to block HSD17B13 function using an enzymatic blocking assay. HSD17B13 activity was quantified using a NADH Glo luminescence assay (Promega, #Cat. No. G9062) to measure the formation of NADH from the oxidation of LTB4, a known HSD17B13 substrate. Compounds were over a 10-point dose curve using an Echo-555 liquid handling dispenser. HSD17B13 (SEQ ID NO: 1, expressed in *E. coli*) was added at either a final concentration of 50 nM or 150 nM, depending on the assay run, in a buffer containing 0.2M Tris-HCl pH 7.5 containing 0.01% Triton-X into a low volume white 384-well assay plate. Compounds were incubated with the enzyme for 30 minutes at room temperature. The assay reaction was then initiated by addition of 10 μM LTB4 substrate (Cayman chemicals, Cat. No. 20110) and 500 μM NAD, and the reaction mixture was incubated for 1 or 2 hours at room temperature depending on the assay run. DMSO at a concentration of 0.5% was used as a negative control, and a 'no substrate' control was used as a positive control (100% inhibition) in the assay. Detection reagent was then added as per manufacturer's instructions, and the plate was subsequently incubated in the dark for 1 hour at room temperature. Generation of NADH was detected in the luminescence mode on the Envision Perkin Elmer plate reader. The IC$_{50}$ values were determined using Dotmatics analysis software.

As shown in Table 63, 8 of the 9 inhibitors tested in the enzymatic assay with 150 nM HSD17B13 inhibited with $IC_{50}$ values ranging from 470 nM to 4.70 µM. One molecule tested did not demonstrate complete blockade and an $IC_{50}$ value could not be determined. In assays using 50 nM HSD17B13, 517 of the 564 inhibitors inhibited with $IC_{50}$ values ranging from 10 nM to 9.85 µM. 47 molecules tested did not demonstrate complete blockade and $IC_{50}$ values could not be determined.

TABLE 63

$IC_{50}$ values of inhibition of HSD17B13 by the compounds of the disclosure

| Molecule ID | Inhibition of 150 nM of HSD17B13 $IC_{50}$ (µM) | Inhibition of 50 nM of HSD17B13 $IC_{50}$ (µM) |
|---|---|---|
| 188 | | 0.28 |
| 187 | | 0.77 |
| 186 | | 1.83 |
| 185 | | 0.73 |
| 184 | | 0.15 |
| 163 | | 0.84 |
| 162 | | 0.08 |
| 183 | | 0.03 |
| 182 | | 0.02 |
| 161 | | 0.27 |
| 194 | | 0.09 |
| 181 | | 0.39 |
| 180 | | 0.16 |
| 179 | | 0.4 |
| 210 | | 0.93 |
| 178 | | 0.06 |
| 177 | | 0.04 |
| 176 | | 0.02 |
| 175 | | 0.28 |
| 193 | | 1.02 |
| 174 | | 0.24 |
| 192 | | 0.23 |
| 209 | | 3.44 |
| 208 | | >10.0 |
| 207 | | 0.18 |
| 62 | | 1.11 |
| 160 | | 0.18 |
| 159 | | 0.60 |
| 173 | | 0.03 |
| 64 | | 0.8 |
| 158 | | 0.36 |
| 157 | | 0.85 |
| 156 | | 0.26 |
| 206 | | 0.29 |
| 205 | | >10.0 |
| 189 | | 0.07 |
| 155 | | 0.46 |
| 154 | | 0.65 |
| 153 | | 1.79 |
| 152 | | 1.03 |
| 172 | | 0.14 |
| 171 | | 0.1 |
| 170 | | 0.35 |
| 169 | | 0.78 |
| 168 | | 0.33 |
| 167 | | 0.82 |
| 121 | | 0.22 |
| 120 | | 0.87 |
| 204 | | >10.0 |
| 191 | | 0.87 |
| 203 | | 1.05 |
| 151 | | 0.29 |
| 150 | | 0.40 |
| 119 | | 0.25 |
| 202 | | 0.35 |
| 201 | | 0.43 |
| 149 | | >10.0 |
| 148 | | 0.67 |
| 147 | | >10.0 |
| 166 | | 0.06 |
| 200 | | >10.0 |
| 146 | | 0.6 |
| 165 | | 0.11 |
| 211 | | 0.87 |
| 164 | | 0.9 |
| 214 | | >10.0 |
| 118 | | 0.3 |
| 114 | | 0.28 |
| 122 | | >10.0 |
| 113 | | >10.0 |
| 199 | | 5.15 |
| 112 | | >10.0 |
| 222 | | 2.17 |
| 111 | | 1.13 |
| 110 | | 0.84 |
| 109 | | 0.82 |
| 108 | | >10.0 |
| 107 | | 0.96 |
| 145 | | 0.21 |
| 106 | | >10.0 |
| 105 | | 4.28 |
| 144 | | 0.31 |
| 104 | | 8.65 |
| 61 | | 2.25 |
| 117 | | >10.0 |
| 103 | | >10.0 |
| 102 | | >10.0 |
| 143 | | 0.09 |
| 142 | | 0.54 |
| 137 | | 4.19 |
| 101 | | 1.23 |
| 100 | | 0.74 |
| 99 | | 2.72 |
| 116 | | >10.0 |
| 98 | | >10.0 |
| 97 | | 2.3 |
| 96 | | 1.74 |
| 95 | | 1.46 |
| 141 | | 0.36 |
| 95 | | 0.35 |
| 198 | | 0.40 |
| 115 | | 0.45 |
| 93 | | 0.60 |
| 92 | | 2.14 |
| 91 | | 0.92 |
| 90 | | 0.52 |
| 129 | | 4.33 |
| 197 | | 1.13 |
| 196 | | 0.63 |
| 89 | | 1.09 |
| 88 | | >10.0 |
| 140 | | 0.2 |
| 87 | | 1.13 |
| 86 | | 1.94 |
| 85 | | 0.84 |
| 212 | | >10.0 |
| 84 | | 1.04 |
| 83 | | 2.37 |
| 82 | | 0.84 |
| 139 | | 0.51 |
| 126 | | 1.75 |
| 81 | | 1.09 |
| 213 | | 2.24 |
| 125 | | 0.96 |
| 138 | | 0.02 |
| 190 | | 0.09 |
| 80 | | 0.36 |
| 79 | | 2.33 |
| 195 | | 3.31 |
| 124 | | 1.4 |
| 78 | | 1.34 |
| 77 | | 0.68 |
| 76 | | 1.70 |
| 216 | | 3.19 |
| 75 | | 1.87 |
| 74 | | 1.37 |

TABLE 63-continued

IC$_{50}$ values of inhibition of HSD17B13 by the compounds of the disclosure

| Molecule ID | Inhibition of 150 nM of HSD17B13 IC$_{50}$ (μM) | Inhibition of 50 nM of HSD17B13 IC$_{50}$ (μM) |
| --- | --- | --- |
| 123 | | 5.79 |
| 10 | | 0.67 |
| 49 | | 0.98 |
| 53 | | 0.31 |
| 52 | | 0.08 |
| 13A | | 1.31 |
| 60 | | >10.0 |
| 38 | | 0.45 |
| 39 | | 0.49 |
| 14A | | 4.28 |
| 41 | | 1.29 |
| 50 | | 0.12 |
| 51 | | 0.23 |
| 31 | | 0.46 |
| 32 | | 0.4 |
| 23A | | 0.99 |
| 34 | | 1.63 |
| 33 | | 0.82 |
| 8A | | 6.31 |
| 9A | | 1.20 |
| 48 | | 2.49 |
| 11 | | 1.09 |
| 59 | | >10.0 |
| 221 | | 6.40 |
| 57 | | 0.46 |
| 136 | | 1.13 |
| 220 | | >10.0 |
| 73 | | >10.0 |
| 54 | | 1.48 |
| 21A | | 1.85 |
| 15A | | 0.16 |
| 55 | | 0.18 |
| 42 | | 1.3 |
| 47 | | 1.83 |
| 56 | | 0.44 |
| 219 | | >10.0 |
| 127 | | 3.75 |
| 72 | | 7.05 |
| 22 | | 0.89 |
| 20A | | 1.56 |
| 40 | | 1.65 |
| 44 | | 0.53 |
| 71 | | 5.85 |
| 70 | | >10.0 |
| 45 | | 1.75 |
| 135 | | 1.91 |
| 58 | | 2.89 |
| 5A | | 1.52 |
| 130 | | >10.0 |
| 69 | | 2.59 |
| 22A | | 2.96 |
| 19A | | 0.99 |
| 23 | | 4.24 |
| 134 | | 1.41 |
| 43 | | 0.49 |
| 133 | | 1.45 |
| 132 | | 1.45 |
| 11A | | 1.19 |
| 46 | | 1.07 |
| 131 | | 1.82 |
| 12 | | 0.39 |
| 13 | | 0.94 |
| 68 | | 2.53 |
| 10A | | 1.46 |
| 217 | | 8.31 |
| 128 | | 5.69 |
| 67 | | 2.27 |
| 29 | | 0.47 |
| 30 | | 0.75 |
| 1A | | 0.53 |
| 18A | | 2.62 |
| 16A | | 3.64 |
| 16 | | 0.97 |
| 1 | | 1.75 |
| 7A | | 1.10 |
| 4A | | 0.55 |
| 36 | | 0.68 |
| 37 | | 0.78 |
| 24 | | 0.60 |
| 17 | | 0.96 |
| 12A | | 0.56 |
| 17A | | 3.1 |
| 66 | | 7.22 |
| 18 | | 2.48 |
| 14 | | 2.81 |
| 15 | | 0.26 |
| 218 | | 9.55 |
| 63 | | 3.68 |
| 6A | | 5.15 |
| 3A | | 1.3 |
| 2 | | 0.74 |
| 25 | | 0.53 |
| 19 | | 1.91 |
| 7 | | 3.09 |
| 215 | | 2.20 |
| 26 | | 1.2 |
| 9 | | |
| 28 | | 1.30 |
| 5 | | 0.85 |
| 21 | | 0.75 |
| 20 | 2.11 | |
| 8 | 3.23 | 1.61 |
| 4 | 4.70 | |
| 6 | 4.52 | |
| 27 | 0.47 | 1.06 |
| 3 | 1.31 | |
| 65 | >30.0 | |
| 35 | 2.78 | |
| 2A | 1.57 | 0.28 |
| 529 | | >10 |
| 505 | | 0.08 |
| 527 | | 0.99 |
| 526 | | 3.78 |
| 528 | | 0.09 |
| 502 | | 0.26 |
| 504 | | 0.06 |
| 503 | | 0.23 |
| 525 | | 6.51 |
| 439 | | 0.56 |
| 438 | | 0.05 |
| 437 | | 1.29 |
| 524 | | 9.33 |
| 523 | | >10 |
| 511 | | 0.05 |
| 255 | | >10 |
| 254 | | >10 |
| 436 | | 0.09 |
| 522 | | 0.61 |
| 501 | | 0.34 |
| 435 | | 0.11 |
| 534 | | 1.08 |
| 521 | | 0.02 |
| 500 | | 0.02 |
| 510 | | 0.02 |
| 520 | | 0.02 |
| 519 | | 1.35 |
| 434 | | 0.11 |
| 509 | | 0.01 |
| 476 | | >10 |
| 253 | | 4.27 |
| 475 | | 0.01 |
| 252 | | 0.01 |
| 517 | | 0.57 |
| 464 | | 0.01 |
| 489 | | 0.23 |
| 499 | | 0.03 |
| 508 | | 0.02 |
| 516 | | 0.20 |

TABLE 63-continued

IC$_{50}$ values of inhibition of HSD17B13 by the compounds of the disclosure

| Molecule ID | Inhibition of 150 nM of HSD17B13 IC$_{50}$ (µM) | Inhibition of 50 nM of HSD17B13 IC$_{50}$ (µM) |
|---|---|---|
| 498 | | 0.02 |
| 487 | | >10 |
| 497 | | 0.03 |
| 496 | | 0.02 |
| 474 | | 0.03 |
| 515 | | 0.03 |
| 482 | | 2.39 |
| 514 | | 0.02 |
| 513 | | 0.92 |
| 535 | | 0.05 |
| 495 | | 0.03 |
| 512 | | 0.09 |
| 486 | | >10 |
| 251 | | 0.65 |
| 250 | | 0.06 |
| 473 | | 0.03 |
| 507 | | 0.04 |
| 494 | | 0.02 |
| 432 | | 0.33 |
| 433 | | 0.73 |
| 506 | | 0.09 |
| 493 | | 0.09 |
| 431 | | 0.13 |
| 492 | | >10 |
| 430 | | 0.04 |
| 484 | | 4.98 |
| 429 | | 0.32 |
| 428 | | 0.02 |
| 427 | | 0.13 |
| 481 | | 1.42 |
| 455 | | 0.87 |
| 248 | | 0.30 |
| 249 | | 0.39 |
| 480 | | 0.40 |
| 490 | | 0.59 |
| 488 | | 0.11 |
| 472 | | 0.48 |
| 467 | | 0.99 |
| 456 | | 4.83 |
| 471 | | 0.28 |
| 536 | | 0.32 |
| 537 | | 0.15 |
| 485 | | >10 |
| 466 | | 0.60 |
| 454 | | 1.81 |
| 470 | | 0.42 |
| 483 | | 1.11 |
| 479 | | 0.26 |
| 282 | | 0.14 |
| 478 | | 1.41 |
| 280 | | 0.11 |
| 461 | | 0.04 |
| 538 | | 0.04 |
| 245 | | 1.08 |
| 244 | | 0.29 |
| 539 | | 0.74 |
| 243 | | 2.16 |
| 334 | | 2.39 |
| 458 | | 0.52 |
| 451 | | 1.96 |
| 281 | | 1.88 |
| 468 | | 0.19 |
| 453 | | 3.23 |
| 276 | | 2.62 |
| 247 | | 0.93 |
| 477 | | >10 |
| 469 | | 0.31 |
| 465 | | 0.61 |
| 279 | | 0.18 |
| 246 | | 0.30 |
| 452 | | 7.03 |
| 278 | | 2.00 |
| 277 | | 2.71 |
| 463 | | 0.05 |
| 462 | | 0.14 |
| 460 | | 0.03 |
| 450 | | 1.10 |
| 449 | | 0.97 |
| 275 | | 0.10 |
| 418 | | 0.07 |
| 540 | | 1.13 |
| 448 | | 0.14 |
| 447 | | 0.16 |
| 260 | | 0.02 |
| 332 | | 1.29 |
| 446 | | 0.27 |
| 459 | | >10 |
| 333 | | 0.74 |
| 407 | | 0.16 |
| 445 | | 0.23 |
| 457 | | 0.12 |
| 272 | | 0.43 |
| 443 | | 0.12 |
| 444 | | 0.17 |
| 442 | | 2.56 |
| 242 | | 0.07 |
| 420 | | 0.13 |
| 441 | | 2.19 |
| 440 | | 0.70 |
| 425 | | 0.27 |
| 331 | | 0.60 |
| 424 | | 1.14 |
| 423 | | 0.79 |
| 417 | | 0.10 |
| 330 | | 0.08 |
| 329 | | 1.68 |
| 422 | | 0.16 |
| 421 | | 0.36 |
| 274 | | 0.27 |
| 406 | | 0.23 |
| 416 | | 0.07 |
| 414 | | 0.25 |
| 419 | | 0.63 |
| 405 | | 0.16 |
| 328 | | 0.11 |
| 241 | | 0.03 |
| 551 | | 2.69 |
| 415 | | 0.05 |
| 552 | | 0.59 |
| 553 | | 2.08 |
| 413 | | 0.88 |
| 554 | | 2.35 |
| 555 | | >10 |
| 402 | | 0.36 |
| 327 | | 0.38 |
| 326 | | 0.06 |
| 410 | | 0.43 |
| 412 | | 0.11 |
| 411 | | 0.08 |
| 401 | | 0.35 |
| 550 | | 1.60 |
| 238 | | 0.68 |
| 556 | | 2.35 |
| 325 | | 0.18 |
| 237 | | 0.49 |
| 236 | | 0.74 |
| 235 | | 0.20 |
| 234 | | 0.41 |
| 557 | | 0.14 |
| 324 | | 0.04 |
| 404 | | 0.22 |
| 385 | | 0.04 |
| 558 | | 4.57 |
| 409 | | 0.04 |
| 541 | | 0.06 |
| 233 | | 1.32 |
| 386 | | 0.17 |
| 408 | | 2.47 |

TABLE 63-continued

IC$_{50}$ values of inhibition of HSD17B13 by the compounds of the disclosure

| Molecule ID | Inhibition of 150 nM of HSD17B13 IC$_{50}$ (µM) | Inhibition of 50 nM of HSD17B13 IC$_{50}$ (µM) |
| --- | --- | --- |
| 400 | | 0.23 |
| 399 | | 0.30 |
| 403 | | 0.11 |
| 384 | | 0.17 |
| 397 | | 2.97 |
| 398 | | 6.15 |
| 392 | | 0.08 |
| 391 | | 0.05 |
| 288 | | 0.19 |
| 396 | | 0.26 |
| 395 | | 9.17 |
| 379 | | 4.82 |
| 287 | | 0.06 |
| 290 | | 0.08 |
| 394 | | 0.26 |
| 387 | | 0.05 |
| 390 | | 0.07 |
| 383 | | 0.04 |
| 375 | | 2.40 |
| 382 | | 0.13 |
| 296 | | 0.17 |
| 389 | | 0.58 |
| 393 | | 1.23 |
| 388 | | 0.05 |
| 291 | | 0.08 |
| 381 | | 0.13 |
| 378 | | 0.76 |
| 377 | | 7.77 |
| 298 | | 0.06 |
| 518 | | 0.56 |
| 380 | | >10 |
| 376 | | 2.84 |
| 374 | | 2.49 |
| 363 | | 2.47 |
| 370 | | 0.27 |
| 371 | | 1.42 |
| 360 | | 0.59 |
| 359 | | 2.15 |
| 358 | | 0.46 |
| 357 | | 1.18 |
| 356 | | 2.16 |
| 353 | | 0.52 |
| 354 | | 0.51 |
| 339 | | 2.82 |
| 310 | | 0.68 |
| 323 | | 0.22 |
| 369 | | 0.11 |
| 368 | | 0.37 |
| 322 | | 0.30 |
| 321 | | 0.22 |
| 295 | | 0.10 |
| 319 | | 0.83 |
| 365 | | 0.16 |
| 364 | | 0.60 |
| 367 | | 0.38 |
| 366 | | 0.06 |
| 352 | | 0.70 |
| 373 | | 1.73 |
| 351 | | 0.51 |
| 320 | | 0.60 |
| 299 | | 0.10 |
| 362 | | 0.08 |
| 361 | | 0.30 |
| 355 | | 0.52 |
| 289 | | 0.08 |
| 542 | | 4.67 |
| 292 | | 0.22 |
| 343 | | 6.26 |
| 294 | | 0.09 |
| 350 | | 0.36 |
| 284 | | 0.34 |
| 344 | | 2.25 |
| 349 | | 1.41 |
| 318 | | 7.25 |
| 285 | | 0.03 |
| 543 | | 0.05 |
| 293 | | 0.13 |
| 286 | | 0.19 |
| 297 | | 0.11 |
| 544 | | 1.15 |
| 338 | | 4.26 |
| 342 | | 0.10 |
| 545 | | 4.85 |
| 348 | | 9.84 |
| 546 | | >10 |
| 347 | | >10 |
| 533 | | 0.68 |
| 547 | | 6.24 |
| 530 | | >10 |
| 337 | | 4.19 |
| 548 | | 9.28 |
| 345 | | 8.97 |
| 317 | | 4.03 |
| 230 | | 0.21 |
| 341 | | 0.07 |
| 340 | | 0.19 |
| 532 | | 5.20 |
| 336 | | 5.79 |
| 335 | | 4.47 |
| 549 | | 8.37 |
| 316 | | 5.96 |
| 309 | | 0.08 |
| 229 | | 1.40 |
| 223 | | 0.35 |
| 531 | | >10 |
| 315 | | 0.96 |
| 314 | | 5.52 |
| 271 | | 2.11 |
| 270 | | 1.39 |
| 273 | | 0.34 |
| 313 | | >10 |
| 228 | | 0.56 |
| 264 | | 9.78 |
| 312 | | 0.45 |
| 311 | | 0.19 |
| 308 | | 0.07 |
| 306 | | 0.03 |
| 307 | | 0.01 |
| 305 | | 7.85 |
| 304 | | >10 |
| 303 | | 3.06 |
| 302 | | 0.16 |
| 257 | | 7.13 |
| 301 | | 3.45 |
| 300 | | 0.14 |
| 269 | | 5.01 |
| 346 | | 7.03 |
| 283 | | 4.76 |
| 267 | | 9.44 |
| 232 | | 2.69 |
| 268 | | >10 |
| 266 | | 0.64 |
| 265 | | 0.08 |
| 263 | | 8.46 |
| 262 | | 0.98 |
| 227 | | 9.85 |
| 261 | | 6.87 |
| 258 | | 0.01 |
| 226 | | 8.05 |
| 225 | | 4.65 |
| 240 | | 0.11 |
| 259 | | 0.07 |
| 256 | | >10 |
| 239 | | 0.10 |
| 231 | | 0.03 |
| 224 | | >10 |

Example 113: Microsome Stability Assay

Compounds of the disclosure were screened in microsome stability assays. For the screen, test compounds were incubated at 37° C. with either human liver microsomes (Corning; #452117) or mouse liver microsomes (XenoTech; #M1000), pooled from multiple donors, at 1 µM in the presence of a NADPH regenerating system at 0.5 mg/mL microsomal protein. Positive controls included in the assay were testosterone (3A4 substrate), propafenone (2D6) and diclofenac (2C9). Samples were removed at different time points (0, 5, 10, 20, 30 and 60 minutes) and immediately mixed with cold acetonitrile containing internal standard (IS, 200 ng/mL tolbutamide and 200 ng/mL labetalol). Test compounds incubated with microsomes for 60 minutes without the NADPH regenerating system was also included. A single point for each test condition (n=1) was obtained, and samples were analyzed by LC/MS/MS. Disappearance of the test compound was assessed based on peak area ratios of analyte/IS (no standard curve). Results are reported in Table 64, below.

TABLE 64

Microsome Stability Assay Results for Exemplary Compounds of the Disclosure

| Compound Number | Microsome Stability Human liver microsomes $T\frac{1}{2}$ (minutes) | Microsome Stability Human liver microsomes Cl | Microsome Stability Human liver microsomes % Remaining @60 min | Microsome Stability Mouse liver microsomes $T\frac{1}{2}$ (minutes) | Microsome Stability Mouse liver microsomes Cl | Microsome Stability Mouse liver microsomes % Remaining @60 min |
|---|---|---|---|---|---|---|
| 51 | 60.3 | 23.0 (µL/min/mg) | 44.00% | 133.0 | 10.4 (µL/min/mg) | 73.50% |
| 17 | >145.0 | <9.6 (µL/min/mg) | 97.60% | 136.0 | 10.2 (µL/min/mg) | 70.60% |
| 15 | 45.9 | 30.2 (µL/min/mg) | 41.70% | 14.3 | 96.8 (µL/min/mg) | 5.60% |
| 9 | >145.0 | <9.6 (µL/min/mg) | 82.00% | 23.3 | 59.6 (µL/min/mg) | 16.80% |
| 1 | 103.0 | 13.4 (µL/min/mg) | 66.90% | 32.7 | 42.4 (µL/min/mg) | 29.00% |
| 12 | >145.0 | <9.6 (µL/min/mg) | 84.70% | 74.5 | 18.6 (µL/min/mg) | 56.90% |
| 190 | 8.07 | 172.0 (µL/min/mg) | 0.62% | 79.7 | 17.4 (µL/min/mg) | 59.10% |
| 50 | >145.0 | <9.6 (µL/min/mg) | 101.00% | >145.0 | <9.6 (µL/min/mg) | 97.70% |
| 52 | >145.0 | <9.6 (µL/min/mg) | 110.00% | >145.0 | <9.6 (µL/min/mg) | 125.00% |
| 138 | 77.9 | 17.8 (µL/min/mg) | 72.40% | >145.0 | <9.6 (µL/min/mg) | 97.40% |
| 2A | 2.7 | 515.0 (µL/min/mg) | 0.10% | | | |
| 35 | 21.9 | 63.4 (µL/min/mg) | 14.90% | | | |
| 65 | 11.8 | 118.0 (µL/min/mg) | 50.10% | | | |
| 3 | 6.39 | 217.0 (µL/min/mg) | 1.00% | | | |
| 27 | 2.71 | 511.0 (µL/min/mg) | 0.40% | | | |
| 21 | 128.33 | 10.8 (µL/min/mg) | 73.00% | | | |
| 5 | 26.65 | 52.0 (µL/min/mg) | 16.00% | | | |
| 28 | >145.0 | <9.6 (µL/min/mg) | 94.00% | | | |
| 26 | 22.21 | 62.4 (µL/min/mg) | 16.00% | | | |
| 215 | 3.35 | 414.0 (µL/min/mg) | 1.00% | | | |
| 7 | >145.0 | <9.6 (µL/min/mg) | 101.00% | | | |
| 19 | 68.6 | 20.2 (µL/min/mg) | 49.80% | | | |
| 25 | 5.22 | 265.0 (µL/min/mg) | 1.00% | | | |
| 2 | 12.6 | 110.0 (µL/min/mg) | 3.40% | | | |
| 14 | >145.0 | <9.6 (µL/min/mg) | 100.00% | | | |
| 18 | 42.0 | 33.0 (µL/min/mg) | 36.60% | | | |
| 24 | 10.6 | 131.0 (µL/min/mg) | 2.00% | | | |
| 37 | 15.0 | 92.4 (µL/min/mg) | 5.70% | | | |

TABLE 64-continued

Microsome Stability Assay Results for Exemplary Compounds of the Disclosure

| Compound Number | Microsome Stability Human liver microsomes T½ (minutes) | Microsome Stability Human liver microsomes Cl | Microsome Stability Human liver microsomes % Remaining @60 min | Microsome Stability Mouse liver microsomes T½ (minutes) | Microsome Stability Mouse liver microsomes Cl | Microsome Stability Mouse liver microsomes % Remaining @60 min |
|---|---|---|---|---|---|---|
| 36 | 11.0 | 126.0 (µL/min/mg) | 2.00% | | | |
| 4A | 8.86 | 156.0 (µL/min/mg) | 1.12% | | | |
| 7A | >145.0 | <9.6 (µL/min/mg) | 93.90% | | | |
| 16 | 30.7 | 45.2 (µL/min/mg) | 23.30% | | | |
| 1A | 7.87 | 176.0 (µL/min/mg) | 1.00% | | | |
| 13 | 10.1 | 138.0 (µL/min/mg) | 1.44% | | | |
| 43 | 34.8 | 39.8 (µL/min/mg) | 31.30% | | | |
| 134 | 3.38 | 410.0 (µL/min/mg) | 0.27% | | | |
| 19A | 15.6 | 88.6 (µL/min/mg) | 8.05% | | | |
| 252 | 126 | 11 (ul/min/mg) | 73.50% | 33.2 | 41.7 (ul/min/mg) | 28.60% |
| 490 | 6.83 | 203 (ul/min/mg) | 1% | 9.87 | 140 (ul/min/mg) | 1.60% |
| 260 | 29.5 | 46.9 (ul/min/mg) | 24.50% | >145 | <9.60 (ul/min/mg) | 81.70% |
| 272 | 114 | 12.1 (ul/min/mg) | 73.40% | 20.3 | 68.2 (ul/min/mg) | 13.10% |
| 441 | 52.5 | 26.4 (ul/min/mg) | 45% | 135 | 10.2 (ul/min/mg) | 74% |
| 241 | >145 | <9.60 (ul/min/mg) | 78% | 103 | 13.4 (ul/min/mg) | 64% |
| 327 | 87.7 | 15.8 (ul/min/mg) | 62% | 56.3 | 24.6 (ul/min/mg) | 46% |
| 401 | 2.99 | 463 (ul/min/mg) | 1.80% | 7.61 | 182 (ul/min/mg) | 4% |
| 235 | 2.53 | 547 (ul/min/mg) | 1% | 58.7 | 23.6 (ul/min/mg) | 50% |
| 234 | 3.76 | 369 (ul/min/mg) | 1% | 4.56 | 303 (ul/min/mg) | 1% |
| 557 | 3.17 | 437 (ul/min/mg) | 1% | 96.3 | 14.4 (ul/min/mg) | 65% |
| 385 | 2.15 | 643 (ul/min/mg) | 1% | 51.3 | 27 (ul/min/mg) | 43% |
| 387 | 12.3 | 112 (ul/min/mg) | 2.70% | 26.6 | 52 (ul/min/mg) | 21.60% |
| 390 | 9.15 | 151 (ul/min/mg) | 11% | 82.3 | 16.8 (ul/min/mg) | 62.80% |
| 388 | 9.26 | 150 (ul/min/mg) | 10% | 29.2 | 47.4 (ul/min/mg) | 24.60% |
| 291 | 25.5 | 54.5 (ul/min/mg) | 17.90% | 65 | 21.3 (ul/min/mg) | 52.20% |
| 298 | 3.08 | 450 (ul/min/mg) | 1% | 30.7 | 45.1 (ul/min/mg) | 26.50% |
| 370 | >145 | <9.60 (ul/min/mg) | 86.70% | >145 | <9.60 (ul/min/mg) | 99.10% |
| 360 | 4.36 | 318 (ul/min/mg) | 1% | 42.2 | 32.8 (ul/min/mg) | 36.20% |
| 358 | 9 | 154 (ul/min/mg) | 1% | 9 | 154 (ul/min/mg) | 1.01% |
| 353 | 39.1 | 35.4 (ul/min/mg) | 28.20% | 33.6 | 41.2 (ul/min/mg) | 28.90% |
| 369 | 45 | 30.8 (ul/min/mg) | 35.70% | >145 | <9.60 (ul/min/mg) | 95.30% |
| 368 | 59.3 | 23.4 (ul/min/mg) | 51.70% | 76.4 | 18.1 (ul/min/mg) | 56.20% |
| 295 | 6.26 | 221 (ul/min/mg) | 1% | 110 | 12.7 (ul/min/mg) | 69% |
| 366 | 31.3 | 44.2 (ul/min/mg) | 27.30% | >145 | <9.60 (ul/min/mg) | 87% |
| 352 | 14.8 | 93.5 (ul/min/mg) | 5.86% | >145 | <9.60 (ul/min/mg) | 88.70% |

TABLE 64-continued

Microsome Stability Assay Results for Exemplary Compounds of the Disclosure

| Compound Number | Microsome Stability Human liver microsomes T½ (minutes) | Microsome Stability Human liver microsomes Cl | Microsome Stability Human liver microsomes % Remaining @60 min | Microsome Stability Mouse liver microsomes T½ (minutes) | Microsome Stability Mouse liver microsomes Cl | Microsome Stability Mouse liver microsomes % Remaining @60 min |
|---|---|---|---|---|---|---|
| 351 | 8.84 | 157 (ul/min/mg) | 0.73% | >145 | <9.60 (ul/min/mg) | 83.70% |
| 299 | 20.8 | 66.8 (ul/min/mg) | 11% | 50.6 | 27.4 (ul/min/mg) | 43.50% |
| 362 | 90.7 | 15.3 (ul/min/mg) | 58.50% | 114 | 12.1 (ul/min/mg) | 70% |
| 361 | 82 | 17 (ul/min/mg) | 60.50% | 72.3 | 19.2 (ul/min/mg) | 52.90% |
| 289 | 23.1 | 59.9 (ul/min/mg) | 14.90% | 29.5 | 47 (ul/min/mg) | 22.70% |
| 294 | 2.15 | 643 (ul/min/mg) | 0.10% | 41.5 | 33.4 (ul/min/mg) | 33.80% |
| 284 | 141 | 9.82 (ul/min/mg) | 70.70% | >145 | <9.60 (ul/min/mg) | 76.40% |
| 285 | 10.1 | 137 (ul/min/mg) | 1.49% | 19.6 | 70.7 (ul/min/mg) | 11.20% |
| 543 | 3.81 | 364 (ul/min/mg) | 0.36% | 31.8 | 43.6 (ul/min/mg) | 25.30% |
| 293 | 6 | 231 (ul/min/mg) | 0.14% | 36.5 | 37.9 (ul/min/mg) | 33.80% |
| 286 | 32.3 | 42.9 (ul/min/mg) | 27.10% | 46.9 | 29.6 (ul/min/mg) | 38.20% |
| 297 | 9.30 | 149 (ul/min/mg) | 1.24% | 39.1 | 35.4 (ul/min/mg) | 36.10% |
| 533 | >145 | <9.60 (ul/min/mg) | 88.90% | >145 | <9.60 (ul/min/mg) | 90.20% |
| 230 | >145 | <9.60 (ul/min/mg) | 83.40% | >145 | <9.60 (ul/min/mg) | 94.70% |
| 341 | 10.5 | 132 (ul/min/mg) | 1.70% | 71.3 | 19.4 (ul/min/mg) | 54.30% |
| 223 | 93.7 | 14.8 (ul/min/mg) | 60.30% | >145 | <9.60 (ul/min/mg) | 83.80% |
| 273 | 105 | 13.2 (ul/min/mg) | 66.40% | 44.7 | 31 (ul/min/mg) | 39% |
| 228 | 84.5 | 16.4 (ul/min/mg) | 60.40% | >145 | <9.60 (ul/min/mg) | 76.60% |
| 312 | >145 | <9.60 (ul/min/mg) | 78.40% | >145 | <9.60 (ul/min/mg) | 96.90% |
| 311 | 132 | 10.5 (ul/min/mg) | 67.80% | >145 | <9.60 (ul/min/mg) | 105% |
| 306 | 19 | 72.9 (ul/min/mg) | 12.80% | 144 | 9.60 (ul/min/mg) | 70.90% |
| 307 | 9 | 154 (ul/min/mg) | 0.85% | >145 | <9.60 (ul/min/mg) | 96.20% |

Example 114: Counter Screen Assays

HSD17B1 Enzymatic Blocking Assay

To screen compounds of the disclosure for their ability to block HSD17B1 function, an enzymatic blocking assay was performed. For the assay, HSD17B1 activity was measured by detecting NADH formation from oxidation of Estradiol using a NADH Glo luminescence assay (Promega, #Cat. No. G9062). Compounds of the disclosure were evaluated in a dose titration assay where the compounds were titrated at 10-point dose curve using an Echo-555 liquid handling dispenser. HSD17B1 (SEQ ID NO: 2, expressed in mammalian cells) was added at a final concentration of 25 ng/well in a buffer containing 0.2M Tris-HCl, pH 7.5, into a low volume white 384-well assay plate. Compounds were incubated with the enzyme for 30 minutes at room temperature. The assay reaction was then initiated by addition of 25 µM Estradiol substrate (Sigma, catalog #E2758-250MG, CAS: 50-28-2) and 500 µM NAD co-factor, and the reaction mixture was incubated for 3 hours at room temperature. DMSO at a concentration of 0.5% was used as a negative control and a 'no substrate' control was used a positive control in the assay. Detection reagent was then added as per manufacturer's instructions, and the plate was subsequently incubated in the dark for 1 hour at room temperature, NADH generated was detected in the luminescence mode on the Envision Perkin Elmer plate reader. The $IC_{50}$ values were determined using Dotmatics analysis software.

As shown in Table 65, 59 of the 98 inhibitors tested in the enzymatic assay with HSD17B1 inhibited with $IC_{50}$ values from 2.04 µM to 28.8 µM. Thirty nine molecules tested did not demonstrate complete blockade and $IC_{50}$ values could not be determined.

TABLE 65

Results of HSD17B1 enzymatic blocking assay

| Compound Number | Inhibition of HSD17B1 IC$_{50}$ (µM) |
|---|---|
| 2 | >30.0 |
| 5 | >30.0 |
| 9 | >30.0 |
| 12A | >30.0 |
| 15 | >30.0 |
| 17 | >30.0 |
| 21 | >30.0 |
| 25 | >30.0 |
| 27 | >30.0 |
| 198 | >30.0 |
| 93 | 15.62 |
| 94 | 11.30 |
| 115 | 11.19 |
| 52 | 5.84 |
| 55 | 4.65 |
| 51 | 4.55 |
| 50 | 4.22 |
| 15A | 3.90 |
| 53 | 3.69 |
| 80 | 3.65 |
| 141 | 3.62 |
| 140 | 3.53 |
| 190 | 3.20 |
| 138 | 2.07 |
| 176 | 6.43 |
| 177 | 4.21 |
| 178 | 28.7 |
| 194 | 19.2 |
| 161 | 9.16 |
| 182 | 5.16 |
| 183 | 4.55 |
| 528 | 17.0 |
| 504 | 19.7 |
| 438 | 10.7 |
| 511 | 6.13 |
| 436 | 6.19 |
| 501 | >30 |
| 435 | 23.5 |
| 521 | 7.42 |
| 500 | 2.67 |
| 510 | 2.19 |
| 520 | 13.7 |
| 519 | 7.22 |
| 509 | 3.48 |
| 252 | 5.84 |
| 499 | 4.86 |
| 508 | 3.30 |
| 495 | 2.04 |
| 490 | >30 |
| 282 | >30 |
| 461 | 7.64 |
| 460 | 12.9 |
| 260 | 11.1 |
| 407 | 12.5 |
| 445 | 14.8 |
| 272 | >30 |
| 441 | >30 |
| 417 | 13.5 |
| 330 | >30 |
| 422 | 10.7 |
| 421 | 25.1 |
| 274 | 8.39 |
| 406 | 28.8 |
| 416 | 20.0 |
| 414 | 8.59 |
| 419 | >30 |
| 405 | >30 |
| 328 | 4.16 |
| 241 | 15.8 |
| 327 | 21.4 |
| 324 | >30 |
| 409 | >30 |
| 387 | >30 |
| 388 | >30 |
| 298 | >30 |
| 360 | >30 |
| 354 | >30 |
| 323 | >30 |
| 321 | >30 |
| 352 | >30 |
| 351 | >30 |
| 299 | >30 |
| 362 | >30 |
| 355 | >30 |
| 289 | >30 |
| 533 | >30 |
| 230 | >30 |
| 309 | 14.3 |
| 223 | >30 |
| 271 | 27.9 |
| 228 | 24.8 |
| 311 | >30 |
| 308 | 15.4 |
| 306 | 7.47 |
| 307 | 2.73 |
| 302 | >30 |
| 300 | 18.0 |

HSD17B2 Enzymatic Blocking Assay

To screen compounds of the disclosure for their ability to block HSD17B2 function, an enzymatic blocking assay was performed. For the assay, HSD17B2 activity was measured by detecting NADH formation from oxidation of Estradiol using a NADH Glo luminescence assay (Promega, #Cat. No. G9062). Compounds of the disclosure were evaluated in a dose titration assay where the compounds were titrated at 10-point dose curve using an Echo-555 liquid handling dispenser. HSD17B2 (SEQ ID NO: 3, expressed in mammalian cells) was added at a final concentration of 2 ng/µL in a buffer containing 50 mM Tris-HCl, pH 7.5, Pluronic F-127 0.05%, Tween20 0.01%, BSA 0.01% into a low volume white 384-well assay plate. Compounds were incubated with the enzyme for 15 min at 20° C. The assay reaction was then initiated by addition of 1.8 µM Estradiol substrate (Sigma, catalog #E2758-250MG, CAS: 50-28-2) and 650 µM NAD co-factor, and the reaction mixture was incubated for 45 min at 20° C. DMSO at a concentration of 0.5% was used as a negative control and a 'no substrate' control was used a positive control in the assay. Detection reagent was then added as per manufacturer's instructions, and the plate was subsequently incubated in the dark for 1 hour at room temperature, NADH generated was detected in the luminescence mode on the Envision Perkin Elmer plate reader. The IC$_{50}$ values were determined using Dotmatics analysis software.

As shown in Table 66, 101 of the 114 inhibitors tested in the enzymatic assay with HSD17B2 inhibited with IC$_{50}$ values from 2.27 µM to 72.7 µM. Thirteen molecules tested did not demonstrate complete blockade and IC$_{50}$ values could not be determined.

TABLE 66

Results of HSD17B2 enzymatic blocking assay

| Compound Number | Inhibition of HSD17B2 IC$_{50}$ (µM) |
|---|---|
| 198 | >100.0 |
| 63 | >100.0 |

TABLE 66-continued

Results of HSD17B2 enzymatic blocking assay

| Compound Number | Inhibition of HSD17B2 IC$_{50}$ (μM) |
|---|---|
| 46 | 38.09 |
| 19 | 33.63 |
| 12A | 23.67 |
| 26 | 22.65 |
| 24 | 20.55 |
| 94 | 18.77 |
| 25 | 18.18 |
| 27 | 16.76 |
| 138 | 16.07 |
| 12 | 15.60 |
| 5 | 15.35 |
| 1A | 14.50 |
| 14 | 14.23 |
| 19A | 13.21 |
| 3A | 13.2 |
| 44 | 12.84 |
| 22 | 12.76 |
| 28 | 12.59 |
| 21 | 11.99 |
| 4A | 11.65 |
| 15 | 11.16 |
| 115 | 10.96 |
| 17 | 10.93 |
| 93 | 10.68 |
| 53 | 10.67 |
| 140 | 10.67 |
| 55 | 9.15 |
| 80 | 8.91 |
| 190 | 8.71 |
| 51 | 8.71 |
| 52 | 8.69 |
| 9 | 8.48 |
| 2 | 8.02 |
| 141 | 7.30 |
| 43 | 6.59 |
| 15A | 6.33 |
| 50 | 5.16 |
| 20A | 2.27 |
| 176 | 28.3 |
| 177 | 14.6 |
| 178 | 64.0 |
| 194 | 17.4 |
| 161 | 8.22 |
| 182 | 10.3 |
| 183 | 9.61 |
| 528 | 23.2 |
| 504 | 39.4 |
| 438 | 23.5 |
| 511 | 16.2 |
| 436 | 27.3 |
| 501 | 46.0 |
| 435 | 59.4 |
| 521 | 29.2 |
| 500 | 14.8 |
| 510 | 5.53 |
| 520 | 25.3 |
| 519 | >100 |
| 509 | 11.9 |
| 252 | 19.3 |
| 499 | 9.80 |
| 508 | 45.8 |
| 495 | 19.7 |
| 490 | 16.1 |
| 282 | >100 |
| 461 | 45.4 |
| 460 | 25.0 |
| 260 | 32.1 |
| 407 | 69.2 |
| 445 | 42.9 |
| 272 | 29.7 |
| 441 | 11.2 |
| 417 | 47.9 |
| 330 | 22.1 |
| 422 | 17.3 |
| 421 | 11.3 |
| 274 | 9.16 |
| 406 | 54.0 |
| 416 | 14.8 |
| 414 | 17.5 |
| 419 | >100 |
| 405 | >100 |
| 328 | >100 |
| 241 | >100 |
| 327 | >100 |
| 324 | 56.4 |
| 409 | 29.7 |
| 387 | 27.7 |
| 388 | 25.8 |
| 298 | 30.9 |
| 360 | 23.1 |
| 354 | 29.3 |
| 323 | 35.5 |
| 321 | 8.32 |
| 352 | >100 |
| 351 | 65.4 |
| 299 | 22.6 |
| 362 | 27.5 |
| 355 | 37.6 |
| 289 | 29.4 |
| 533 | 72.7 |
| 230 | 40.7 |
| 309 | 22.6 |
| 223 | 28.6 |
| 271 | >100 |
| 228 | 28.0 |
| 311 | >100 |
| 308 | 16.9 |
| 306 | 17.3 |
| 307 | 8.98 |
| 302 | 23.0 |
| 300 | 10.2 |

HSD17B4 Enzymatic Blocking Assay

To screen compounds of the disclosure for their ability to block HSD17B4 function, an enzymatic blocking assay was performed. For the assay, HSD17B4 activity was measured by detecting NADH formation from oxidation of Estradiol using a NADH Glo luminescence assay (Promega, #Cat. No. G9062). Compounds of the disclosure were evaluated in a dose titration assay where the compounds were titrated at 10-point dose curve using an Echo-555 liquid handling dispenser. HSD17B4 (SEQ ID NO: 4, expressed in mammalian cells) was added at a final concentration of 2.5 ng/μL in a buffer containing 50 mM Tris-HCl, pH 7.5, Pluronic F-127 0.05%, Tween20 0.01%, BSA 0.01%, into a low volume white 384-well assay plate. Compounds were incubated with the enzyme for 15 min at 20° C. The assay reaction was then initiated by addition of 23.46 μM Estradiol substrate (Sigma, catalog #E2758-250MG, CAS: 50-28-2) and 1500 μM NAD co-factor, and the reaction mixture was incubated for 45 min at 20° C. DMSO at a concentration of 0.5% was used as a negative control and a 'no substrate' control was used a positive control in the assay. Detection reagent was then added as per manufacturer's instructions, and the plate was subsequently incubated in the dark for 1 hour at room temperature, NADH generated was detected in the luminescence mode on the Envision Perkin Elmer plate reader. The IC$_{50}$ values were determined using Dotmatics analysis software.

As shown in Table 67, 7 of the 15 inhibitors tested in the enzymatic assay with HSD17B4 inhibited with IC$_{50}$ values from 47.12 μM to 96.62 μM. Eight molecules tested did not demonstrate complete blockade and IC$_{50}$ values could not be determined.

TABLE 67

Results of HSD17B4 enzymatic blocking assay

| Compound Number | Inhibition of HSD17B4 IC$_{50}$ (µM) |
|---|---|
| 198 | >100.0 |
| 55 | >100.0 |
| 51 | >100.0 |
| 52 | >100.0 |
| 15A | >100.0 |
| 50 | >100.0 |
| 138 | >100.0 |
| 115 | >100.0 |
| 94 | 96.62 |
| 190 | 84.46 |
| 93 | 66.23 |
| 141 | 58.25 |
| 140 | 54.24 |
| 80 | 48.70 |
| 53 | 47.12 |

HSD17B10 Enzymatic Blocking Assay

To screen compounds of the disclosure for their ability to block HSD17B10 function, an enzymatic blocking assay was performed. For the assay, HSD17B10 activity was measured by detecting NADH formation from oxidation of Estradiol using a NADH Glo luminescence assay (Promega, #Cat. No. G9062). Compounds of the disclosure were evaluated in a dose titration assay where the compounds were titrated at 10-point dose curve using an Echo-555 liquid handling dispenser. HSD17B10 (Seq. ID NO: 5, expressed in mammalian cells) was added at a final concentration of 31.25 ng/well in a buffer containing 0.2M Tris-HCl, pH 7.5, into a low volume white 384-well assay plate. Compounds were incubated with the enzyme for 30 minutes at room temperature. The assay reaction was then initiated by addition of 25 µM Estradiol substrate (Sigma, catalog #E2758-250MG, CAS: 50-28-2) and 500 µM NAD co-factor, and the reaction mixture was incubated for 3 hours at room temperature. DMSO at a concentration of 0.5% was used as a negative control and a 'no substrate' control was used a positive control in the assay. Detection reagent was then added as per manufacturer's instructions, and the plate was subsequently incubated in the dark for 1 hour at room temperature, NADH generated was detected in the luminescence mode on the Envision Perkin Elmer plate reader. The IC$_{50}$ values were determined using Dotmatics analysis software.

As shown in Table 68, all of the compounds tested in the enzymatic assay with HSD17B10 did not demonstrate complete blockade and IC$_{50}$ values could not be determined.

TABLE 68

Results of HSD17B10 enzymatic blocking assay

| Compound Number | Inhibition of HSD17B10 IC$_{50}$ (µM) |
|---|---|
| 198 | >30.0 |
| 55 | >30.0 |
| 51 | >30.0 |
| 52 | >30.0 |
| 15A | >30.0 |
| 50 | >30.0 |
| 138 | >30.0 |
| 115 | >30.0 |
| 94 | >30.0 |
| 190 | >30.0 |
| 93 | >30.0 |
| 141 | >30.0 |
| 140 | >30.0 |
| 80 | >30.0 |
| 53 | >30.0 |

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

Protein Sequences:

```
HSD17B13-tag
Amino acids 2-272 HSD17B13 protein (amino acids 30-300 of
accession number NP_835236.2)
Amino acids 273-278 hexahistidine tag
                                                    (SEQ ID NO: 1)
MRRKSVAGEIVLITGAGHGIGRQTTYEFAKRQSILVLWDINKRGVEETAAECRKLGVTA

HAYVVDCSNREEIYRSLNQVKKEVGDVTIVVNNAGTVYPADLLSTKDEEITKTFEVNIL

GHFWITKALLPSMMERNHGHIVTVASVCGHEGIPYLIPYCSSKFAAVGFHRGLTSELQAL

GKTGIKTSCLCPVFVNTGFTKNPSTRLWPVLETDEVVRSLIDGILTNKKMIFVPSYINIFLR

LQKFLPERASAILNRMQNIQFEAVVGHKIKMKHHHHHH

HSD17B1-tag
Amino acids 1-328 HSD17B1 protein (amino acids 1-328 of
accession number P14061.3)
Amino acids 329-362 epitope tag
                                                    (SEQ ID NO: 2)
MARTVVLITGCSSGIGLHLAVRLASDPSQSFKVYATLRDLKTQGRLWEAARALACPPGS
```

-continued

LETLQLDVRDSKSVAAARERVTEGRVDVLVCNAGLGLLGPLEALGEDAVASVLDVNV

VGTVRMLQAFLPDMKRRGSGRVLVTGSVGGLMGLPFNDVYCASKFALEGLCESLAVL

LLPFGVHLSLIECGPVHTAFMEKVLGSPEEVLDRTDIHTFHRFYQYLAHSKQVFREAAQ

NPEEVAEVFLTALRAPKPTLRYFTTERFLPLLRMRLDDPSGSNYVTAMHREVFGDVPAK

AEAGAEAGGGAGPGAEDEAGRGAVGDPELGDPPAAPQSGPTRTRPLEQKLISEEDLAA

NDILDYKDDDDKV

HSD17B2-tag
Amino acids 1-387 HSD17B2 protein (amino acids 1-387 of
accession number P37059.1)
Amino acids 388-418 epitope tag
(SEQ ID NO: 3)
MSTFFSDTAWICLAVPTVLCGTVFCKYKKSSGQLWSWMVCLAGLCAVCLLILSPFWGLI

LFSVSCFLMYTYLSGQELLPVDQKAVLVTGGDCGLGHALCKYLDELGFTVFAGVLNEN

GPGAEELRRTCSPRLSVLQMDITKPVQIKDAYSKVAAMLQDRGLWAVINNAGVLGFPT

DGELLLMTDYKQCMAVNFFGTVEVTKTFLPLLRKSKGRLVNVSSMGGGAPMERLASY

GSSKAAVTMFSSVMRLELSKWGIKVASIQPGGFLTNIAGTSDKWEKLEKDILDHLPAEV

QEDYGQDYILAQRNFLLLINSLASKDFSPVLRDIQHAILAKSPFAYYTPGKGAYLWICLA

HYLPIGIYDYFAKRHFGQDKPMPRALRMPNYKKKATTRTRPLEQKLISEEDLAANDILD

YKDDDDKV

HSD17B4-tag
Amino acids 1-736 HSD17B4 protein (amino acids 1-736 of
accession number P51659.3)
Amino acids 737-767 epitope tag
(SEQ ID NO: 4)
MGSPLRFDGRVVLVTGAGAGLGRAYALAFAERGALVVVNDLGGDFKGVGKGSLAAD

KVVEEIRRRGGKAVANYDSVEEGEKVVKTALDAFGRIDVVVNNAGILRDRSFARISDED

WDIIHRVHLRGSFQVTRAAWEHMKKQKYGRIIMTSSASGIYGNFGQANYSAAKLGLLG

LANSLAIEGRKSNIHCNTIAPNAGSRMTQTVMPEDLVEALKPEYVAPLVLWLCHESCEE

NGGLFEVGAGWIGKLRWERTLGAIVRQKNHPMTPEAVKANWKKICDFENASKPQSIQE

STGSIIEVLSKIDSEGGVSANHTSRATSTATSGFAGAIGQKLPPFSYAYTELEAIMYALGV

GASIKDPKDLKFIYEGSSDFSCLPTFGVIIGQKSMMGGGLAEIPGLSINFAKVLHGEQYLE

LYKPLPRAGKLKCEAVVADVLDKGSGVVIIMDVYSYSEKELICHNQFSLFLVGSGGFGG

KRTSDKVKVAVAIPNRPPDAVLTDTTSLNQAALYRLSGDWNPLHIDPNFASLAGFDKPI

LHGLCTFGFSARRVLQQFADNDVSRFKAIKARFAKPVYPGQTLQTEMWKEGNRIHFQT

KVQETGDIVISNAYVDLAPTSGTSAKTPSEGGKLQSTFVFEEIGRRLKDIGPEVVKKVNA

VFEWHITKGGNIGAKWTIDLKSGSGKVYQGPAKGAADTTIILSDEDFMEVVLGKLDPQK

AFFSGRLKARGNIMLSQKLQMILKDYAKLTRTRPLEQKLISEEDLAANDILDYKDDDDK

V

HSD17B10-tag
Amino acids 1-261 HSD17B10 protein (amino acids 1-261 of
accession number Q99714.3)
Amino acids 262-292 epitope tag
(SEQ ID NO: 5)
MAAACRSVKGLVAVITGGASGLGLATAERLVGQGASAVLLDLPNSGGEAQAKKLGNN

CVFAPADVTSEKDVQTALALAKGKFGRVDVAVNCAGIAVASKTYNLKKGQTHTLEDF

QRVLDVNLMGTFNVIRLVAGEMGQNEPDQGGQRGVIINTASVAAFEGQVGQAAYSASK

GGIVGMTLPIARDLAPIGIRVMTIAPGLFGTPLLTSLPEKVCNFLASQVPFPSRLGDPAEY

AHLVQAIIENPFLNGEVIRLDGAIRMQPTRTRPLEQKLISEEDLAANDILDYKDDDDKV

-continued

HSD17B13
Amino acids 2-272 HSD17B13 protein (amino acids 30-300 of
accession number NP_835236.2)
(SEQ ID NO: 6)
MRRKSVAGEIVLITGAGHGIGRQTTYEFAKRQSILVLWDINKRGVEETAAECRKLGVTA

HAYVVDCSNREEIYRSLNQVKKEVGDVTIVVNNAGTVYPADLLSTKDEEITKTFEVNIL

GHFWITKALLPSMMERNHGHIVTVASVCGHEGIPYLIPYCSSKFAAVGFHRGLTSELQAL

GKTGIKTSCLCPVFVNTGFTKNPSTRLWPVLETDEVVRSLIDGILTNKKMIFVPSYINIFLR

LQKFLPERASAILNRMQNIQFEAVVGHKIKMK

HSD17B1
Amino acids 1-328 HSD17B1 protein (amino acids 1-328 of
accession number P14061.3)
(SEQ ID NO: 7)
MARTVVLITGCSSGIGLHLAVRLASDPSQSFKVYATLRDLKTQGRLWEAARALACPPGS

LETLQLDVRDSKSVAAARERVTEGRVDVLVCNAGLGLLGPLEALGEDAVASVLDVNV

VGTVRMLQAFLPDMKRRGSGRVLVTGSVGGLMGLPFNDVYCASKFALEGLCESLAVL

LLPFGVHLSLIECGPVHTAFMEKVLGSPEEVLDRTDIHTFHRFYQYLAHSKQVFREAAQ

NPEEVAEVFLTALRAPKPTLRYFTTERFLPLLRMRLDDPSGSNYVTAMHREVFGDVPAK

AEAGAEAGGGAGPGAEDEAGRGAVGDPELGDPPAAPQSGP

HSD17B2
Amino acids 1-387 HSD17B2 protein (amino acids 1-387 of
accession number P37059.1)
(SEQ ID NO: 8)
MSTFFSDTAWICLAVPTVLCGTVFCKYKKSSGQLWSWMVCLAGLCAVCLLILSPFWGLI

LFSVSCFLMYTYLSGQELLPVDQKAVLVTGGDCGLGHALCKYLDELGFTVFAGVLNEN

GPGAEELRRTCSPRLSVLQMDITKPVQIKDAYSKVAAMLQDRGLWAVINNAGVLGFPT

DGELLLMTDYKQCMAVNFFGTVEVTKTFLPLLRKSKGRLVNVSSMGGGAPMERLASY

GSSKAAVTMFSSVMRLELSKWGIKVASIQPGGFLTNIAGTSDKWEKLEKDILDHLPAEV

QEDYGQDYILAQRNFLLLINSLASKDFSPVLRDIQHAILAKSPFAYYTPGKGAYLWICLA

HYLPIGIYDYFAKRHFGQDKPMPRALRMPNYKKKAT

HSD17B4
Amino acids 1-736 HSD17B4 protein (amino acids 1-736 of
accession number P51659.3)
(SEQ ID NO: 9)
MGSPLRFDGRVVLVTGAGAGLGRAYALAFAERGALVVVNDLGGDFKGVGKGSLAAD

KVVEEIRRRGGKAVANYDSVEEGEKVVKTALDAFGRIDVVVNNAGILRDRSFARISDED

WDIIHRVHLRGSFQVTRAAWEHMKKQKYGRIIMTSSASGIYGNFGQANYSAAKLGLLG

LANSLAIEGRKSNIHCNTIAPNAGSRMTQTVMPEDLVEALKPEYVAPLVLWLCHESCEE

NGGLFEVGAGWIGKLRWERTLGAIVRQKNHPMTPEAVKANWKKICDFENASKPQSIQE

STGSIIEVLSKIDSEGGVSANHTSRATSTATSGFAGAIGQKLPPFSYAYTELEAIMYALGV

GASIKDPKDLKFIYEGSSDFSCLPTFGVIIGQKSMMGGGLAEIPGLSINFAKVLHGEQYLE

LYKPLPRAGKLKCEAVVADVLDKGSGVVIIMDVYSYSEKELICHNQFSLFLVGSGGFGG

KRTSDKVKVAVAIPNRPPDAVLTDTTSLNQAALYRLSGDWNPLHIDPNFASLAGFDKPI

LHGLCTFGFSARRVLQQFADNDVSRFKAIKARFAKPVYPGQTLQTEMWKEGNRIHFQT

KVQETGDIVISNAYVDLAPTSGTSAKTPSEGGKLQSTFVFEEIGRRLKDIGPEVVKKVNA

VFEWHITKGGNIGAKWTIDLKSGSGKVYQGPAKGAADTTIILSDEDFMEVVLGKLDPQK

AFFSGRLKARGNIMLSQKLQMILKDYAKL

HSD17B10
Amino acids 1-261 HSD17B10 protein (amino acids 1-261 of
accession number Q99714.3)

-continued (SEQ ID NO: 10)
MAAACRSVKGLVAVITGGASGLGLATAERLVGQGASAVLLDLPNSGGEAQAKKLGNN

CVFAPADVTSEKDVQTALALAKGKFGRVDVAVNCAGIAVASKTYNLKKGQTHTLEDF

QRVLDVNLMGTFNVIRLVAGEMGQNEPDQGGQRGVIINTASVAAFEGQVGQAAYSASK

GGIVGMTLPIARDLAPIGIRVMTIAPGLFGTPLLTSLPEKVCNFLASQVPFPSRLGDPAEY

AHLVQAIIENPFLNGEVIRLDGAIRMQP

What is claimed is:

1. A compound according to formula (II'):

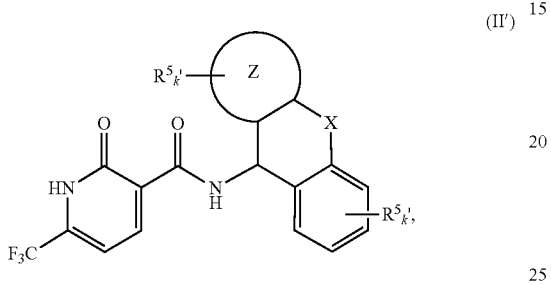

(II')

or a pharmaceutically acceptable salt thereof, wherein:
X is O or S;
Z is a 6-membered heterocycle comprising 1 to 2 N heteroatoms, or a $C_4$-$C_8$ cycloalkyl;
$R^5$ is independently at each occurrence $C_{1-3}$ alkyl, $C_{1-3}$ alkenyl, $C_{1-3}$ alkoxy, $C_{1-3}$ haloalkyl, halogen, —CN, or —OH; and
k and k' are independently from 0 to 2.

2. A compound of according to formula (II):

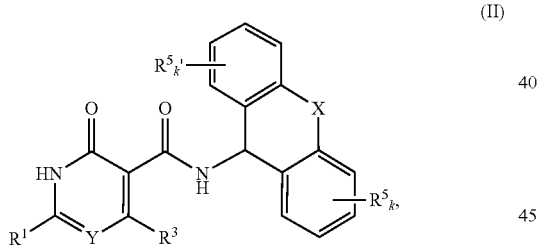

(II)

or a pharmaceutically acceptable salt thereof, wherein:
k and k' are independently from 0 to 4;
X is a bond, —$CH_2$—, —$CH_2$—$CH_2$—, —$CH_2$—O—, —CH=CH—, —(C=O)—, —O—, —$NR^\#$—, —S—, —(S=O)—, or —($SO_2$)—;
Y is N, —$CR^2$, or —$COR^2$;
$R^1$ is H, —$(CH_2)_{0-3}$—$NH_2$, —$(CH_2)_{0-3}NHR^\#$, —$(CH_2)_{0-3}$—$N(R^\#)_2$, $C_{1-4}$alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;
$R^2$ is H, halogen, —$(CH_2)_{0-3}$—$NH_2$, —$(CH_2)_{0-3}$—$NHR^\#$, —$(CH_2)_{0-3}$—$N(R^\#)_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl; and wherein:
when Y is N, at least one of $R^1$ and $R^3$ is not H, and when Y is $CR^2$, at least one of $R^1$, $R^2$, and $R^3$ is not H;

$R^5$ is independently at each occurrence halogen, —CN, =O, —OH, —$NH_2$, —$(CH_2)_{1-3}$—$OR^\#$, —NH—(C=O)—R*, —NH—(C=O)O—R*, —NH—($SO_2$)—R8, —$(CH_2)_{1-3}$-$NR^\#_2$, —$NHR^\#$, —$N(R^\#)_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with R*;

R* is halogen, —OH, $C_{1-3}$ alkyl, $C_{1-3}$ haloalkyl, phenyl, or benzyl, any of which is optionally substituted with a halogen; and $R^\#$is $C_{1-3}$ alkyl, $C_{1-3}$ haloalkyl, $C_{3-6}$ cycloalkyl, phenyl, or benzyl, any of which is optionally substituted with a halogen.

3. A compound according to any one of formula (IIa), formula (IIb), formula (IIc), and formula (IId)

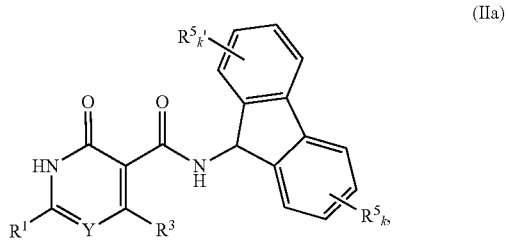

(IIa)

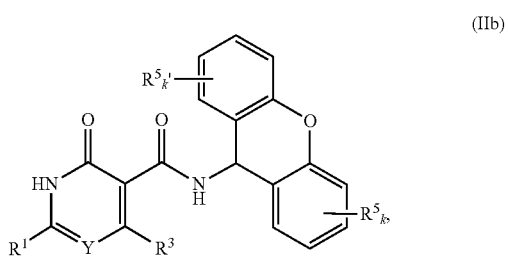

(IIb)

933

(IIc)

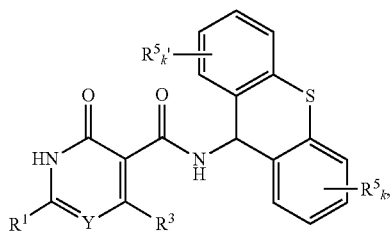

(IId)

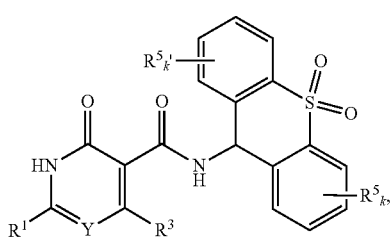

or a pharmaceutically acceptable salt thereof, wherein:

k and k' are independently from 0 to 4;

Y is N, —$CR^2$, or —$COR^2$;

$R^1$ is H, —$(CH_2)_{0-3}$—$NH_2$, —$(CH_2)_{0-3}$—$NHR^{\#}$, —$(CH_2)_{0-3}$—$N(R^{\#})_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groupls;

$R^2$ is H, halogen, —$(CH_2)_{0-3}$—$NH_2$, —$(CH_2)_{0-3}$—$NHR^{\#}$, —$(CH_2)_{0-3}$—$N(R^{\#})_2$, $C_{1-12}$ alkyl, $C_{1-12}$ alkenyl, $C_{6-12}$ aryl, $CH_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected fro O, N and S or combinations thereof, any of which is optionally substituted by one or more of —OH, $C_{1-4}$ alkyl, $C_{1-4}$ alkoxy, =O, phenyl, or benzyl;

$R^3$ is H, $C_{1-4}$ alkyl, or $C_{1-4}$ haloalkyl; and wherein:

when Y is N, at least one of $R^1$ and $R^3$ is not H, and when Y is $CR^2$, at least one of $R^1$, $R^2$, and $R^3$ is not H;

$R^5$ is independently at each occurrence halogen, —CN, =O, —OH, —$NH_2$, —$(CH_2)_{1-3}$—$OR^{\#}$, —NH(C=O)—$R^*$, —NH—(C=O)O—$R^*$, —NH—($SO_2$)—$R^*$, —$(CH_2)_{1-3}$—$NR^{\#}_2$, —$NHR^{\#}$, —$N(R^{\#})_2$, $C_{1-4}$ alkoxy, phenoxy, $C_{1-2}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ halalkoxy, $C_{6-12}$ aryl, a 3-7 membered heterocycle with 1 to 4 heteroatoms selected from O, N and S or combination thereof, or wherein two adjacent $R^5$ groups form a 5-7 membered ring that optionally contains 1 to 3 heteroatoms selected from O, N, and S; any of which is optionally substituted with $R^*$;

$R^*$ is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, $C_{3-6}$ cycloalkyl, phenyl, or benzyl, any of which is optionally substitued with a halogen.

934

4. A compound according to formula (V')

(V')

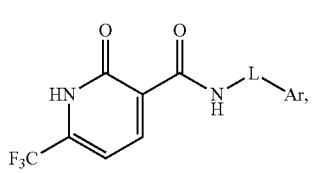

or a pharmaceutically acceptable salt thereof, wherein:

L is a bond, —$(CH_2)_n$—, —$(CHB)_n$—, —$CH_2CHB$—, or —$CHBCH_2$—;

wherein;

B is benzyl or $C_{1-12}$ alkyl optionally comprising 1-4 O atoms, either of which is optionally substituted by —OH or —$OCH_3$;

n is 1 or 2; and wherein: and Ar are as defined above.

when Ar is phenyl, phenyl is optionally substituted by one or more $R^7$ and not by $R^8$; when L is —$(CH_2)_n$—, Ar is phenyl, then at least one $R^7$ is a phenoxy that is optionally substituted with a halogen; and when L is —$(CHB)_n$—, B is $C_{1-4}$ alkyl, Ar is phenyl, then $R^7$ is present and is not —Cl, —F, —CN, $C_{1-4}$ alkyl, or $C_{1-4}$ alkoxy;

Ar is a phenyl, naphthyl, or a $C_4$—$C_8$ cycloalkyl, any of which is optionally substituted with one or more $R^{8 \text{ or Het}}$;

Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;

$R^7$ is independently at each occurrence halogen, —CN, =O, —OH, —$(CH_2)_{1-3}$—$OR^{\#}$, —NH—(C=O)—$R^*$, —NH—($SO_2$)—$R^*$, —$(CH_2)_{1-3}$—$NR^{\#}_2$, —$NHR^{\#}$, —$N(R^{\#})_2$, $C_{1-4}$alkoxy, phenoxy, $C_{1-12}$ alkyl, $C_{1-12}$ alkenyl, $C_{1-4}$ haloalkyl, or $C_{6-12}$ aryl, any of which is optionally substituted with $R^*$;

$R^8$ is independently at each occurrence halogen, —CN, =O, —OH, —$(CH_2)_{0-3}$—SH, —$(CH_2)_{0-3}$—$SR^*$, —($SO_2$)—$R^*$, —$NH_2$, —$(CH_2)_{1-3}$—$OR^{\#}$, —NH—(C=O)—$R^*$, —NH—($SO_2$)—$R^*$, —$(CH_2)_{1-3}$—$NR^{\#}_2$, —$NHR^{\#}$, or —$N(R^{\#})_2$, $C_{1-4}$ alkoxy, phenoxy, $C_{1-12}$ alkyl, $C_{1-12}$ alkenyl, $C_{1-12}$ alkynyl, $C_{1-4}$ haloalkyl, $C_{1-4}$ haloalkoxy, $C_{6-12}$ aryl, a 4-7 membered heterocycle with 1 to 4 heteroatoms selected from O, N and S or combinations thereof, or wherein two adjacent $R^8$ groups form a 5-7 membered ring that optionally contains 1 to 3 heteroatoms selected from O, N, and S; any of which is optionally substituted with $R^*$;

$R^*$ is halogen, —OH, $C_{1-3}$ alkyl, $C_{1-3}$ haloalkyl, phenyl, or benzyl, any of which is optionally substituted with a halogen; and $R^{\#}$ is $C_{1-3}$ alkyl, $C_{1-3}$ haloalkyl, $C_{3-6}$ cycloalkyl, phenyl, or benzyl, any of which is optionally substituted with a halogen.

5. A compound according to formula (VI):

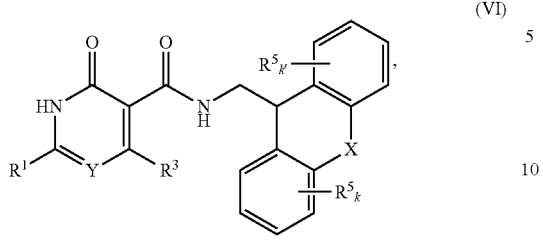

(VI)

or a pharmaceutically acceptable salt thereof, wherein:
k, k' are independently from 0 to 4;
X is a bond, —$CH_2$—, —$CH_2$—$CH_2$—, —$CH_2$—O—, —CH=CH—, —(C=O)—, —O—, —$NR^{\#}$—, —S—, —(S=O)—, or —($SO_2$)—,
Y is N, —$CR^2$, or —$COR^2$;
$R^1$ is H, —$(CH_2)_{0-3}$—$NH_2$, —$(CH_2)_{0-3}$—$NHR^{\#}$, —$(CH_2)_{0-3}$—$N(R^{\#})_2$, $C_{1-4}$ alkyl, $C_{1-4}$ haloalkyl, phenyl, benzyl, or —$(CH_2)_{0-3}$—X—$(CH_2)_{0-3}$-phenyl, wherein phenyl is optionally substituted with one or more $R^5$ groups;
$R^2$ is H, halogen, —$(CH_2)_{0-3}$—$NH_2$, —$(CH_2)_{0-3}$—$NHR^{\#}$, —$(CH_2)_{0-3}$—$N(R^{\#})_2$, $C_{1-12}$ alkyl, $C_{1-12}$ alkenyl, $C_{6-12}$ aryl, $C_{1-12}$ aralkyl, $C_{1-12}$ arylalkyl, $C_{1-4}$ haloalkyl, $C_{3-7}$ cycloalkyl, or a 5-7-membered heterocycle with 1 to 4 heteroatoms independently selected from O, N and S or combinations thereof, any of which is optionally substituted by one or more of —OH, $C_{1-4}$ alkyl, $C_{1-4}$ alkoxy, =O, phenyl, or benzyl;
$R^3$ is H, $C_{1-4}$ alkyl, or $C_{1-4}$ haloalkyl; and wherein:
when Y is N, at least one or $R^1$, and $R^3$ is not H, and when Y is $CR^2$, at least one of $R^1$, $R^2$, and $R^3$ is not H;
$R^5$ is independently at each occurrence halogen, —CN, =O, —OH, —$NH_2$, —$(CH_2)_{1-3}$—$OR^{\#}$, —NH—(C=O)—$R^*$, —NH—(C=O)O—$R^*$, —NH—($SO_2$)—$R^*$, —$(CH_2)_{1-3}$—$NR^{\#}_2$, —$NHR^{\#}$, —$N(R^{\#})_2$, $C_{1-4}$ alkoxy, phenoxy, $C_{1-12}$ alkyl, $C_{1-12}$ heteroalkyl comprising 1 to 3 hetero atoms selected from —O—, —S—, or —NH—, $C_{1-12}$ alkenyl, $C_{1-12}$ alkynyl, $C_{1-4}$ haloalkyl, $C_{1-4}$ haloalkoxy, $C_{6-12}$ aryl, a 3-7-membered heterocycle with 1 to 4 heteroatoms selected from O, N and S or combinations thereof, or wherein two adjacent $R^5$ groups form a 5-7 membered ring that optionally contains 1 to 3 heteroatoms selected from O, N, and S; any of which is optionally substituted with $R^*$;
$R^*$ is halogen, —OH, $C_{1-3}$ alkyl, $C_{1-3}$ haloalkyl, phenyl, or benzyl, any of which is optionally substituted with a halogen; and
$R^{\#}$ is $C_{1-3}$ alkyl, $C_{3-6}$ cycloalkyl, phenyl, or benzyl, any of which is optionally substituted with a halogen.

6. A compound according to formula (VII):

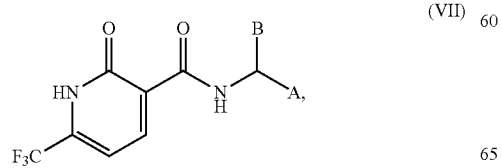

(VII)

or a pharmaceutically acceptable salt thereof, wherein:
A is A', A", $CR^4(Ar)_2$, or Ar;
wherein:

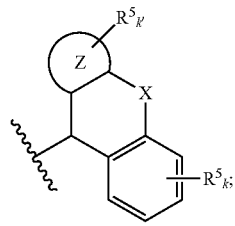

A' is

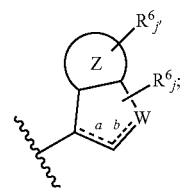

A" is
Z is phenyl, Het, or a $C_4$—$C_8$ cycloalkyl;
Ar is a phenyl, naphthyl, or a $C_4$—$C_8$ cycloalkyl, any of which is optionally substituted with one or more $R^8$ Het; and
Het is a 6-membered heterocycle comprising from 1 to 3 heteroatoms independently selected from N and O, wherein Het is optionally substituted with one or more of $C_{1-3}$ alkyl, $C_{1-3}$ alkenyl, halogen, —OH or =O;
wherein:
when A is phenyl, phenyl is optionally substituted by one or more $R^7$ and not by $R_8$; and
when B is $C_{1-4}$ alkyl, A is phenyl and $R^4$ is H, then $R^7$ is present and is not —Cl, —F, —CN, $C_{1-4}$ alkyl, or $C_{1-4}$ alkoxy;
$R^4$ is H, $C_{1-4}$ alkyl, or $C_{1-4}$ haloalkyl;
$R^6$ is independently at each occurrence halogen, —OH, =O, —CN, —$(CH_2)_{0-3}$—$NH_2$, —$(CH_2)_{0-3}$—$NHR^{\#}$, —$(CH_2)_{0-3}$—$N(R^{\#})_2$, —$(CH_2)_{0-3}$—$NHCOOR^{\#}$, —$(CH_2)_{0-3}$—$COOR^{\#}$, $C_{1-4}$ alkoxy, $C_{1-12}$ alkyl, $C_{1-12}$ alkenyl; $C_{1-4}$ haloalkyl, $C_{1-4}$ heteroalkyl with 1 or 2 methylene replaced with —O— or —S—, or $C_{6-12}$ aryl, any of which is optionally substituted with $R^*$;
j and j' are indenendently from 0 to 4;
a and b are independently a single bond or a double bonde;
W is =CH—, =C($R^6$)—, —$CH_2$, —CH($R^6$)—, —(C=O)—, —$CH_2CH_2$—, —CH($R^6$)—$CH_2$—, —O—, —O-13 $CH_2$—, —O—CH($R^6$)—, —(NH)—, —N($R^6$)—, —$CH_2$—NH—, —$CH_2$—N($R^6$)—, or —S—,
wherein:
when W is —$CH_2$—, or when W is —O—$CH_2$—, then A' is substituted with at least one $R^6$ which is not —OH;
$R^7$ is independently at each occurrence halogen, —CN, =O, —OH, —$(CH_2)_{1-3}$—$OR^{\#}$, —NH—(C=O)—$R^*$, —NH—($SO_2$)—$R^*$, —$(CH_2)_{1-3}$—$NR^{\#}_2$, —NHR#, —N(R#)$_2$, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;

R$^8$ is independently at each occurrence halogen, —CN, =O, —OH, —(CH$_2$)$_{0-3}$—SH, —(CH$_2$)$_{0-3}$—SR*, —(SO$_2$)—R*, —NH$_2$, —(CH$_2$)$_{1-3}$—OR#, —NH—(C=O)—R*, —(CH$_2$)$_{1-3}$—NR#$_2$, —NHR#, or —N(R#)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7 membered heterocycle with 1 to 4 heteroatoms selected from O, N and S or combinations thereof, or wherein two adjacent R$^8$ groups from a 5-7 membered ring that optionally contains 1 to 3 heteroatoms selected from O, N, and S; any of which is optionally substituted with R*;

R* is halogen, —OH, C$_{1-3}$ alkyl, C$_{1-3}$ haloalkyl, phenyl, or benzyl any of which is optionally substitued with a halogen;

R# is C$_{1-3}$ alkyl, C$_{1-3}$ haloalkyl, C$_{3-6}$ cycloalkyl, phenyl, or benzyl, any of which is optionally substituted wiht a halogen;

R$^5$ is independently at each occurrence halogen, —CN, =O, —OH, —NH$_2$, —(CH$_2$)$_{1-3}$—OR#, —NH—(C=O)—R*, —NH-13 (C=O)O—R*, —NH—(SO$_2$)—R*, —(CH$_2$)$_{1-3}$—NR#$_2$, —NHR#, —N(R#)$_2$, C$_{1-4}$ alkoxy, phenoxy, C$_{1-12}$ alkyl, C$_{1-12}$ heteroalkyl comprising 1 to 3 hetero atoms selected from —O—, —S—, or —NH—, C$_{1-12}$ alkenyl, C$_{1-12}$ alkynyl, C$_{1-4}$ haloalkyl, C$_{1-4}$ haloalkoxy, C$_{6-12}$ aryl, a 3-7-membered heterocycle with 1 to 4 heteroatoms selected from O, N and S or combinations thereof, or wherein two adjacent R$^5$ groups form a 5-7 membered ring that optionally contains 1 to 3 heteroatoms selected from O, N, and S; any of which is optionally substituted with R*;

k and k' are independently from 0 to 4;

X is a bond, —CH$_2$—, —CH$_2$—CH$_2$—, —CH$_2$—O—, —CH=CH—, —(C=O)—, —O—, —NR#—, —S—, —(S=O)—, or —(SO$_2$)—; and B is benzyl or C$_{1-12}$ alkyl optionally comprising 1-4 O atoms, either of which is optionally substituted by —OH or —OCH.

7. A compound according to formula (VIIa):

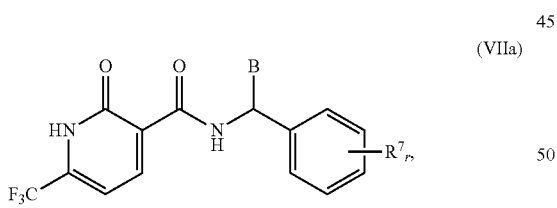

(VIIa)

or a pharmaceutically acceptable salt thereof, wherein:

r is from 1 to 4;

R$^7$ is independently at each occurrence halogen, —CN, =O, —OH, —(CH$_2$)$_{1-3}$—OR#, —NH—(C=O)—R*, —NH—(SO$_2$)—R*, —(CH$_2$)$_{1-3}$—NR#$_2$, —NHR#, —N(R#)$_2$, C$_{1-4}$ alkoxy, phenoxy, C$_{1-12}$ alkyl, C$_{1-12}$ alkenyl, C$_{1-4}$ haloalkyl, or C$_{6-12}$ aryl, any of which is optionally substituted with R*;

R* is halogen, —OH, C$_{1-3}$ alkyl, C$_{1-3}$ haloalkyl, phenyl, or benzyl, any of which is optionally substituted with a halogen; and R# is C$_{1-3}$ alkyl, C$_{1-3}$ haloalkyl, C$_{3-6}$ cycloalkyl, phenyl, or benzyl, any of which is optionally substituted with a halogen; and B is benzyl or C$_{1-12}$ alkyl optionally comprising 1-4 O atoms, either of which is optionally substituted by —OH or —OCH, wherein:

when B is C$_{1-4}$ alkyl, then R$^7$ is not —Cl, —F, —CN, C$_{1-4}$ alkyl, or C$_{1-4}$ alkoxy.

8. A compound according to formula (VIII):

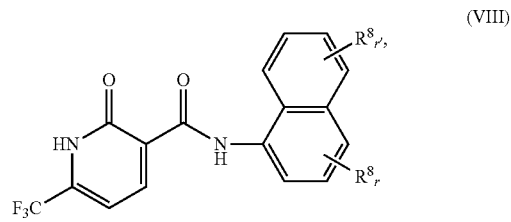

(VIII)

or a pharmaceutically acceptable salt thereof, wherein:

r and r' are independently from 0 to 4;

R$^8$ is independently at each occurrence halogen, —CN, =O, —OH, —(CH$_2$)$_{0-3}$—SH, —(CH$_2$)$_{0-3}$—SR*, —(SO$_2$)—R*, —NH$_2$, —(CH$_2$)$_{1-3}$—OR#, —NH—(C=O)—R*, —NH—(SO$_2$)—R*, —(CH$_2$)$_{1-3}$—NR#$_2$, —NHR#, or —N(R#)$_2$, C$_{1-4}$ alkoxy, phenoxy, C$_{1-12}$ alkyl, C$_{1-12}$ alkenyl, C$_{1-12}$ alkynyl, C$_{1-4}$ haloalkyl, C$_{1-4}$ haloalkoxy, C$_{6-12}$ aryl, a 4-7-membered heterocycle with 1 to 4 heteroatoms selected from O, N and S or combinations thereof, or wherein two adjacent R$^8$ groups form a 5-7 membered ring that optionally contains 1 to 3 heteroatoms selected from O, N, and S; any of which is optionally substituted with R*, R* is halogen, —OH, C$_{1-3}$ alkyl, C$_{1-3}$ haloalkyl, phenyl, or benzyl, any of which is optionally substituted with a halogen; and R# is C$_{1-3}$ alkyl, C$_{1-3}$ haloalkyl, C$_{3-6}$ cycloalkyl, phenyl, or benzyl, any of which is optionally substituted with a halogen.

9. A compound, wherein the compound is:

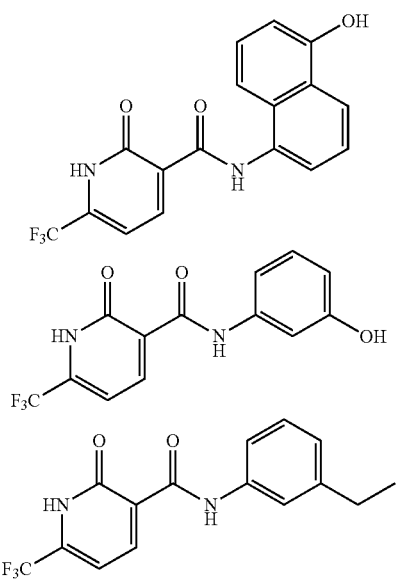

939
-continued
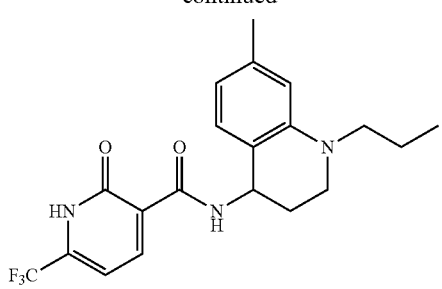
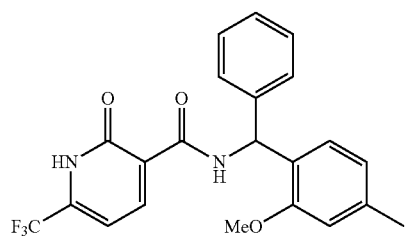
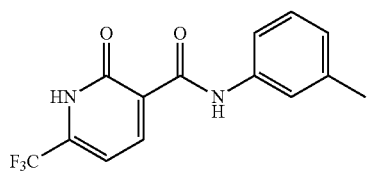
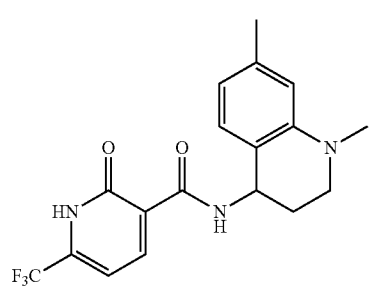
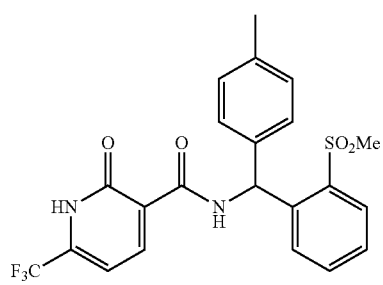
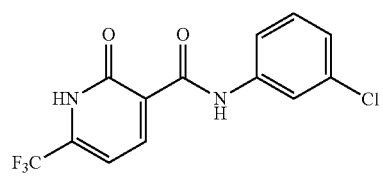
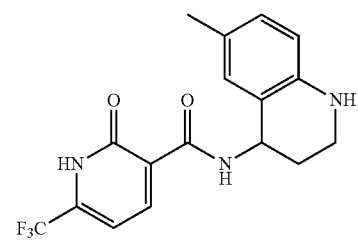
940
-continued
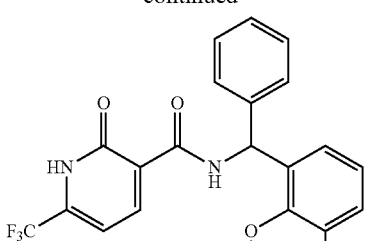
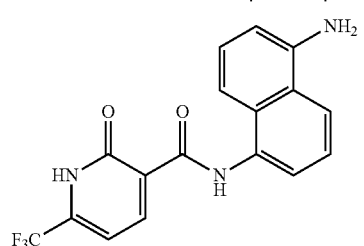
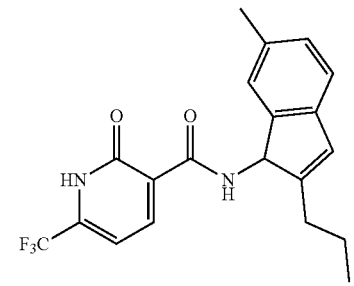
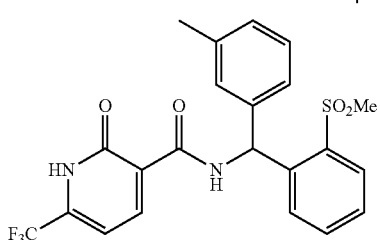
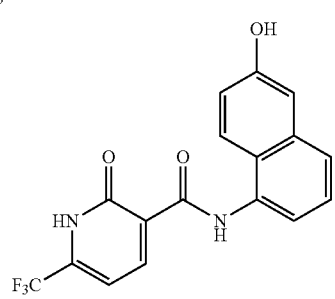
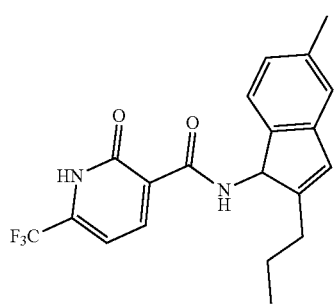

941
-continued
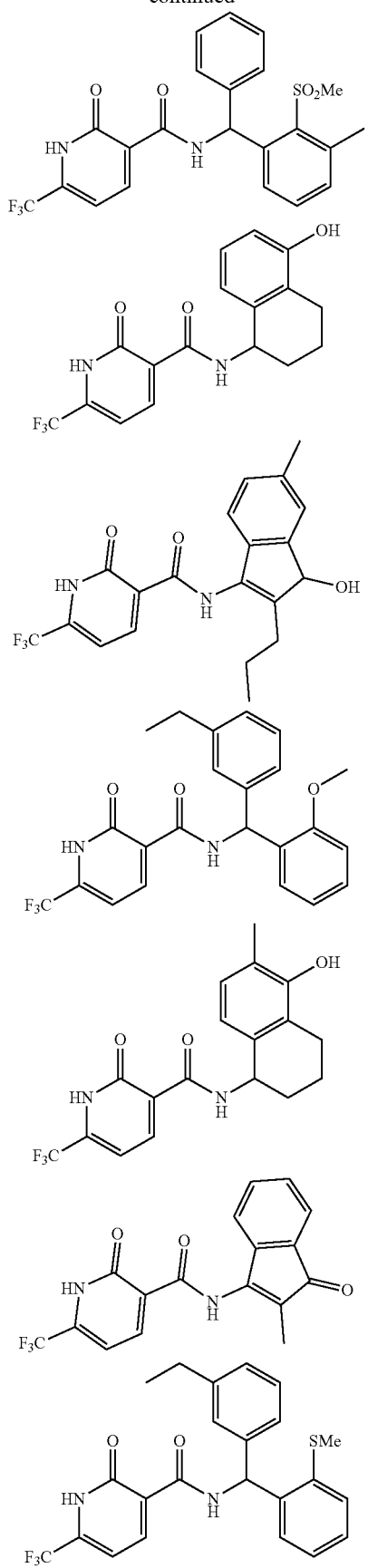
942
-continued
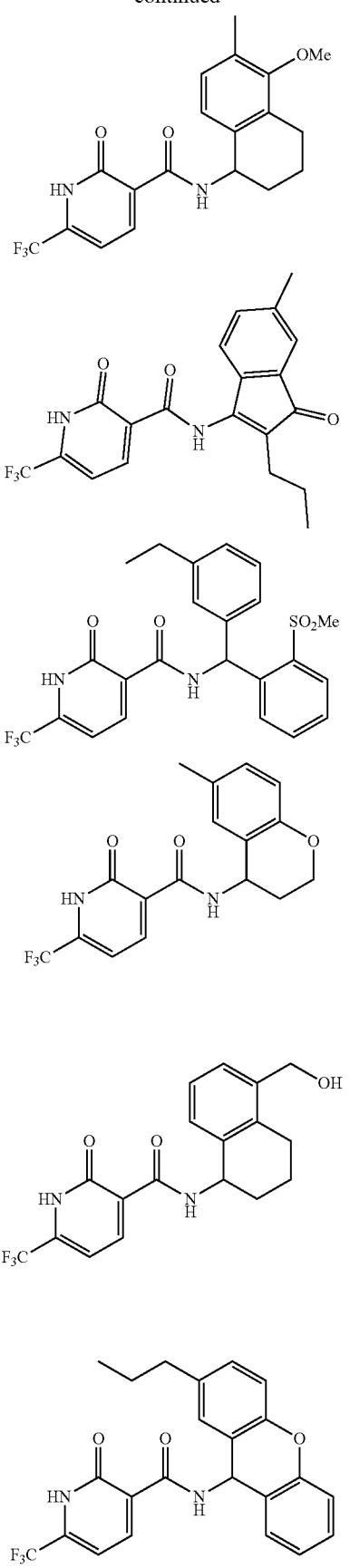

943
-continued
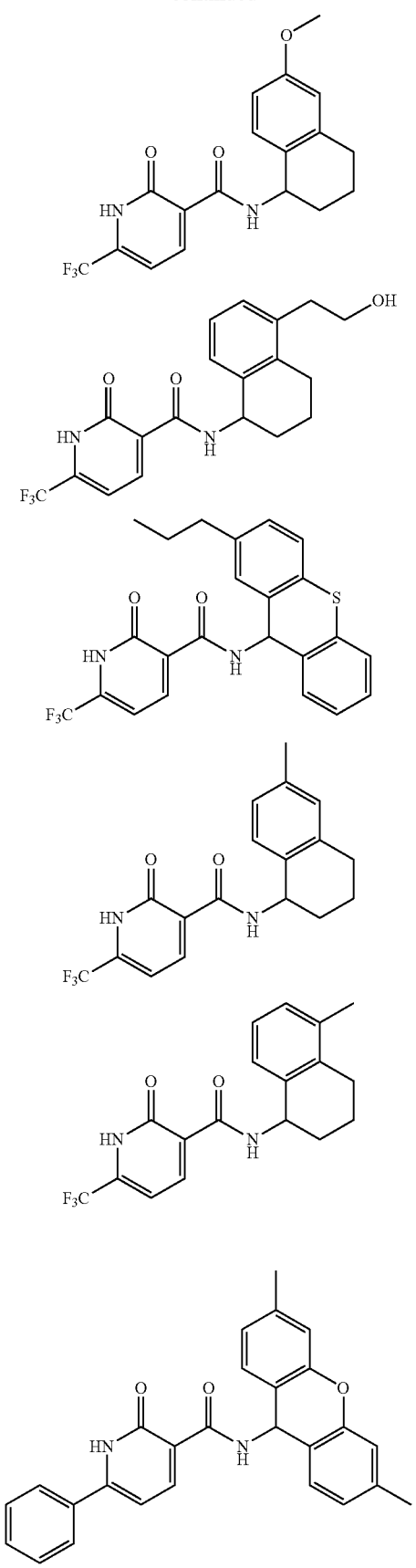
944
-continued
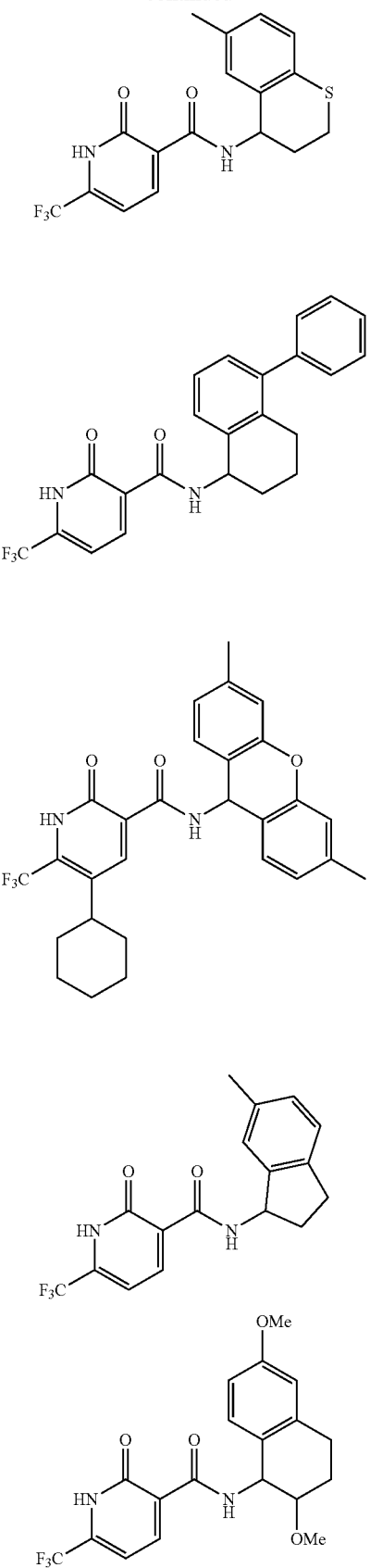

945
-continued
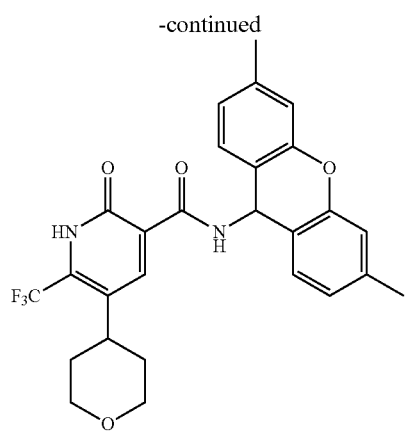
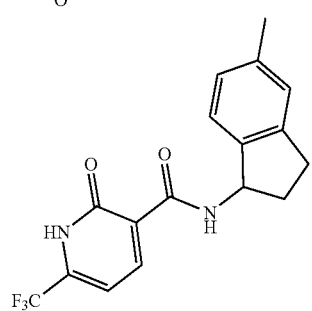
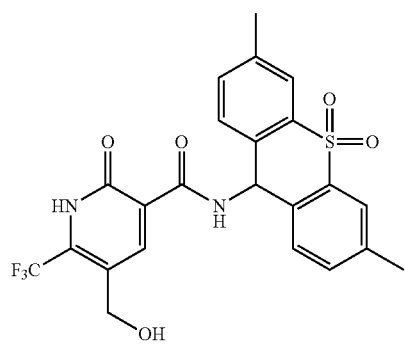
946
-continued
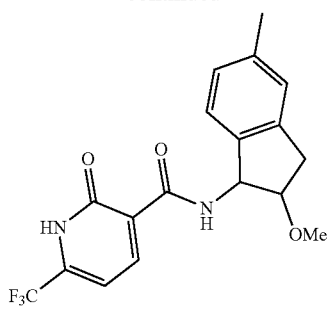
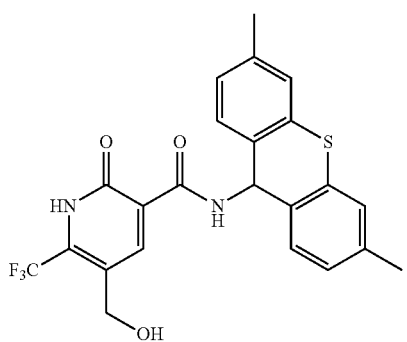
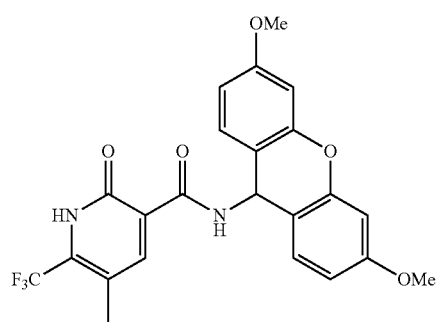
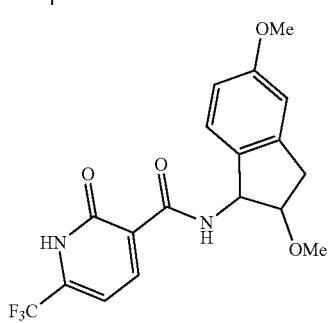
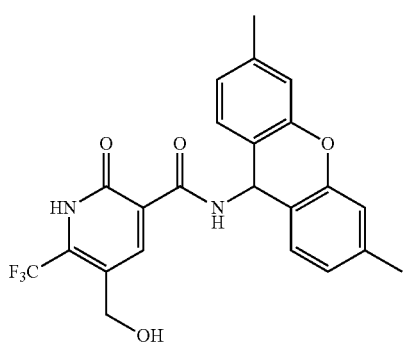

-continued
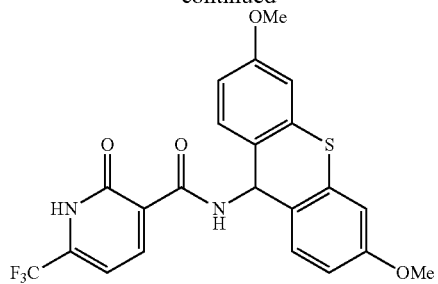
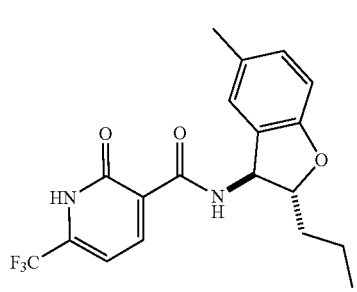
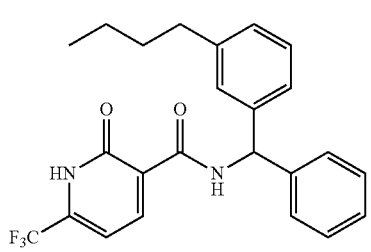
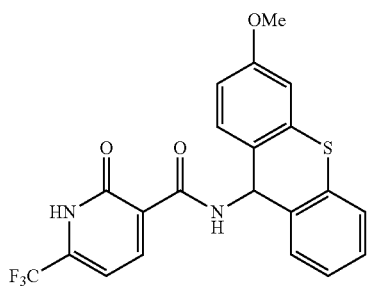
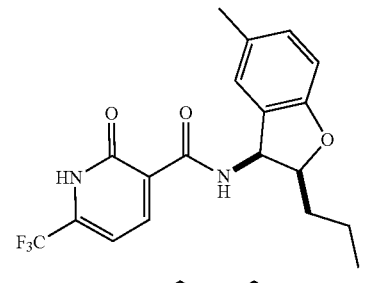
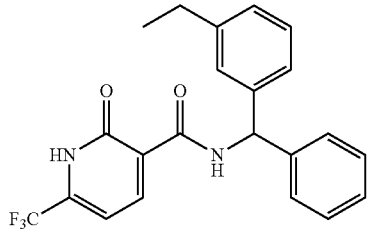
-continued
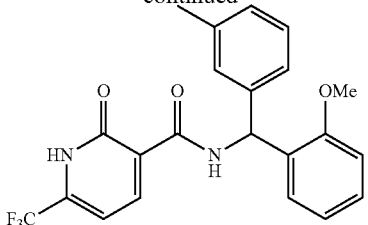
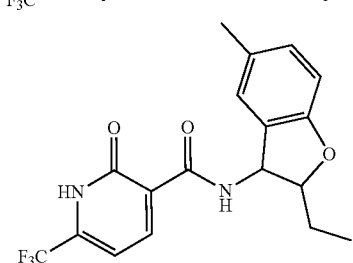
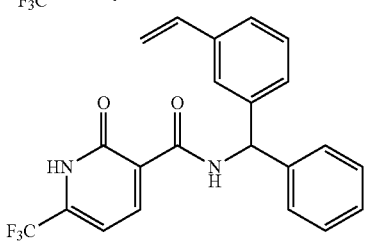
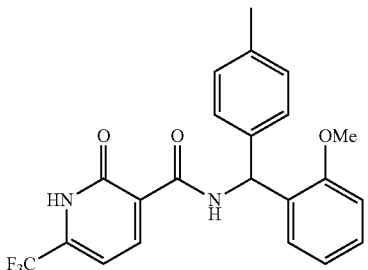
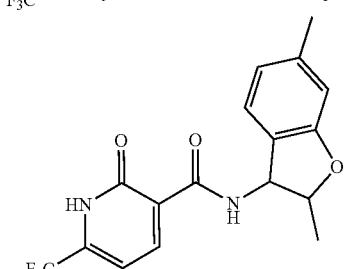
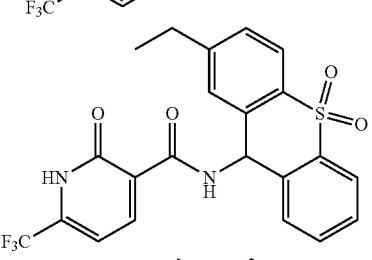
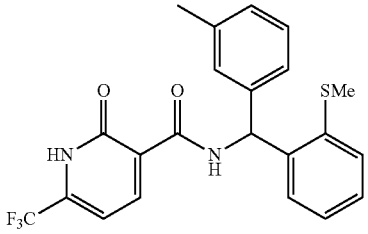

949
-continued
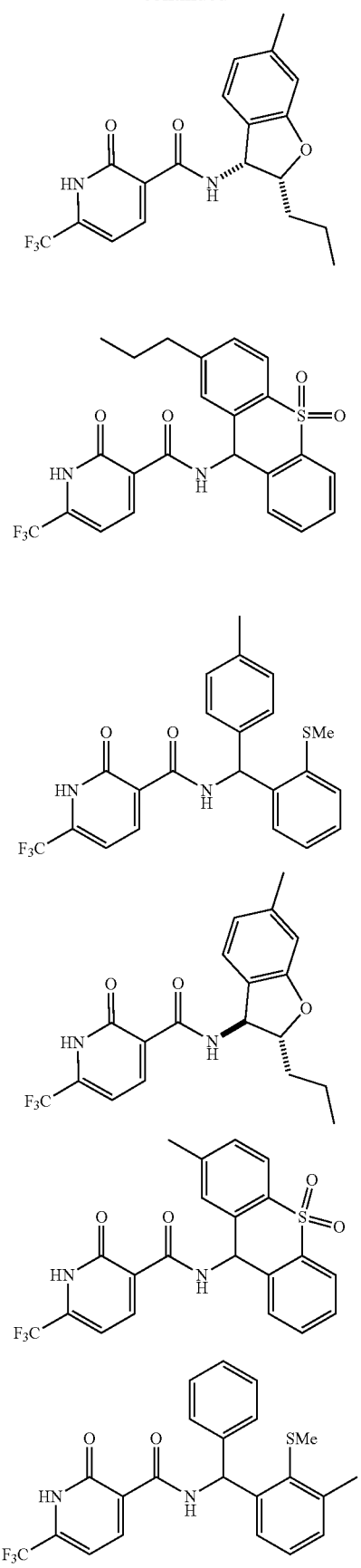
950
-continued
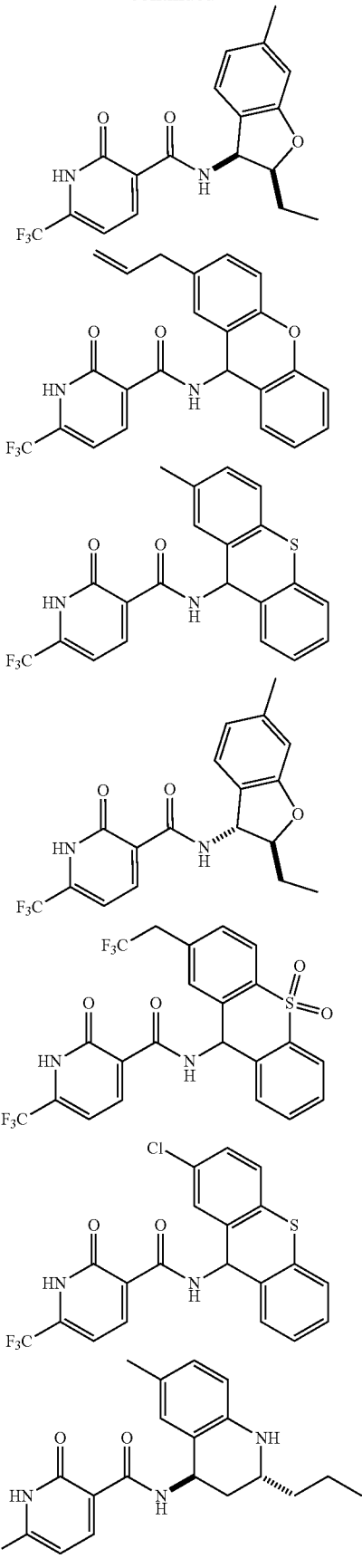

951
-continued
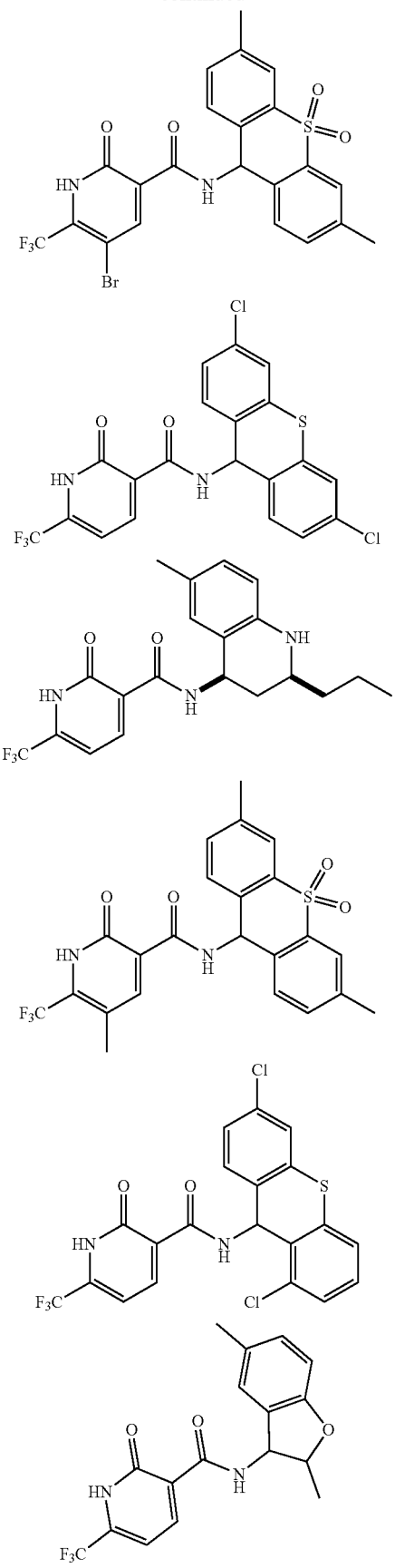
952
-continued
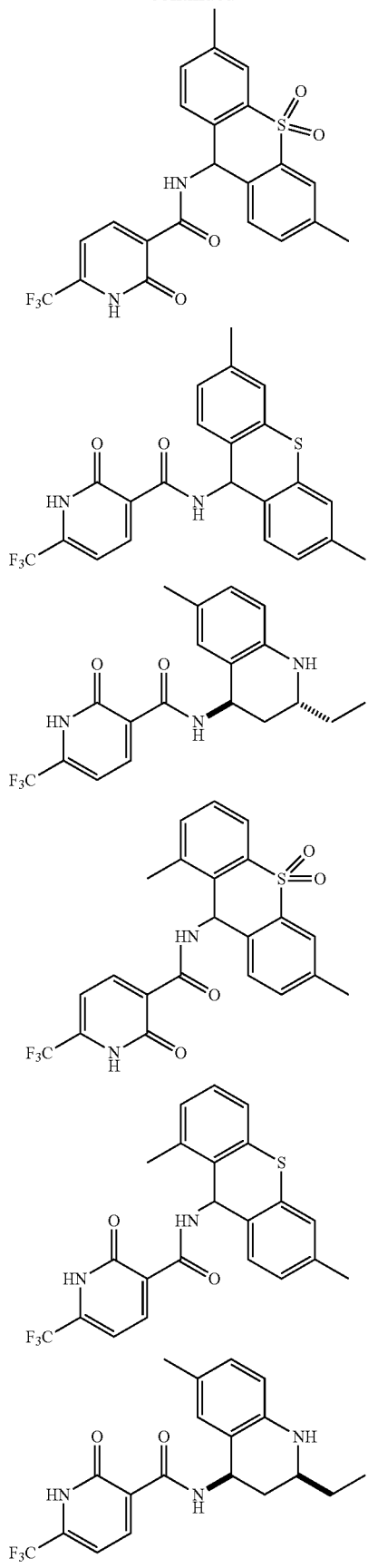

953
-continued
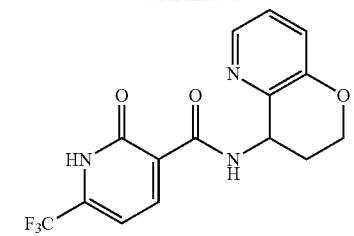
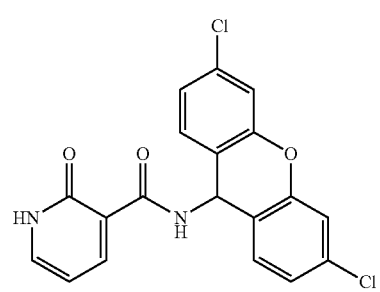
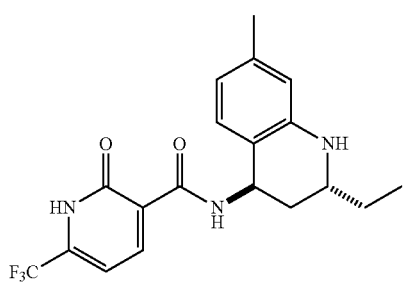
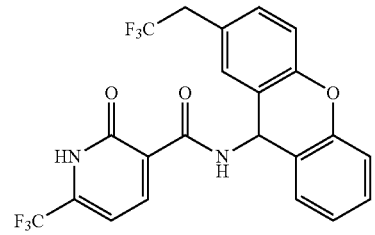
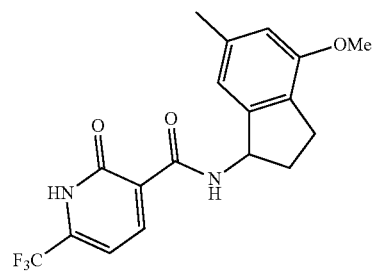
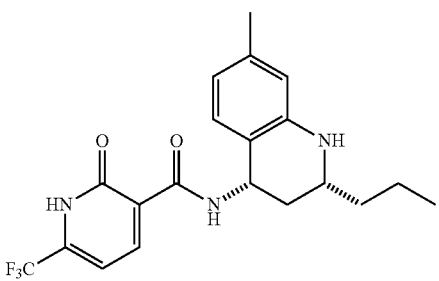
954
-continued
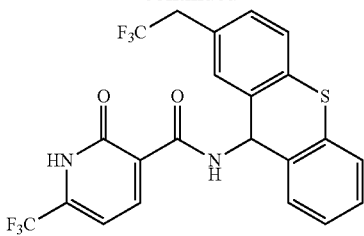
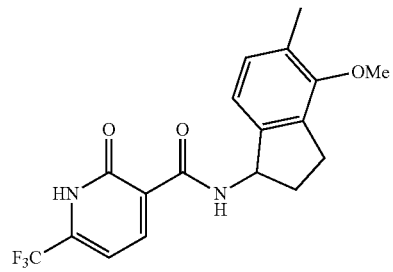
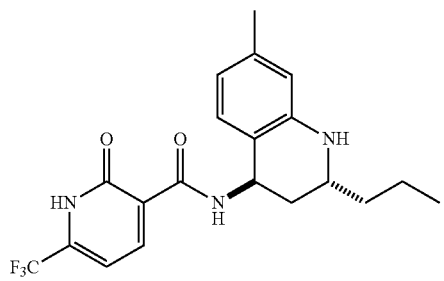
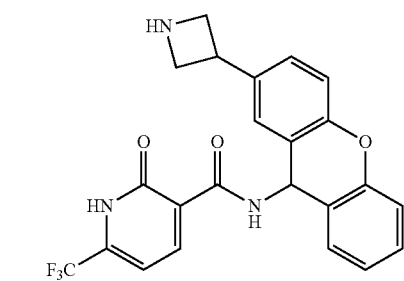
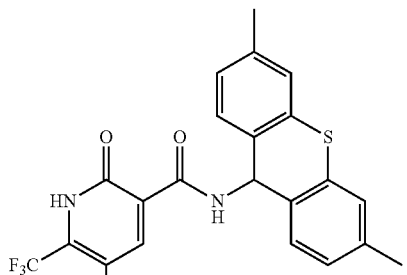
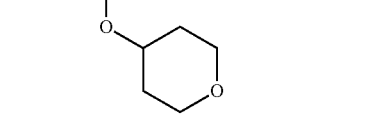
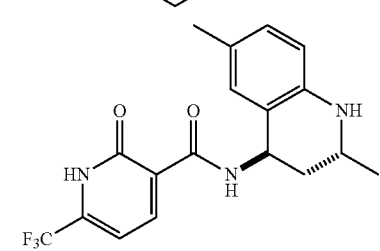

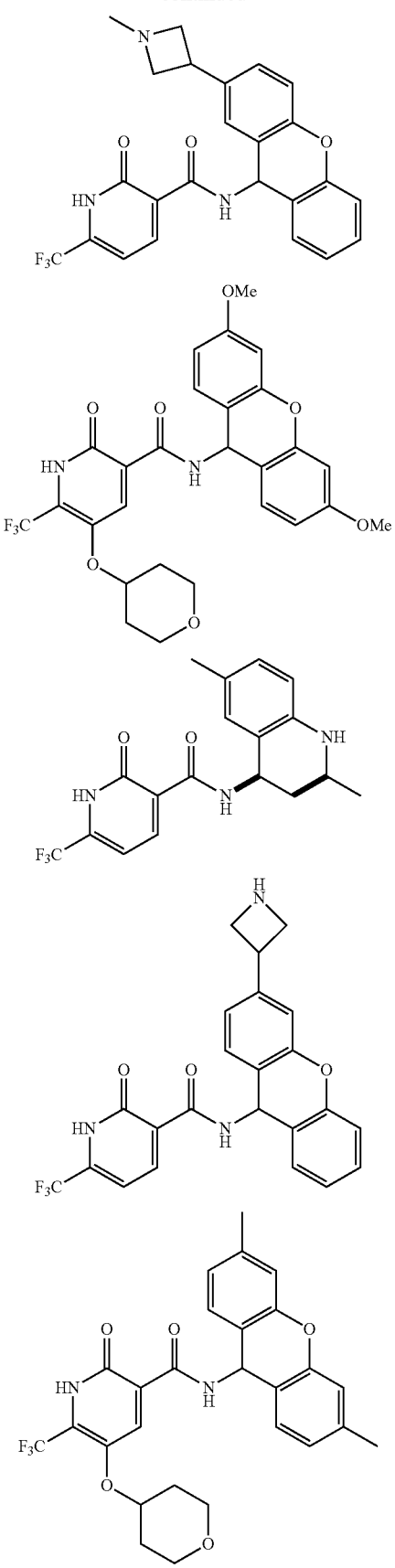
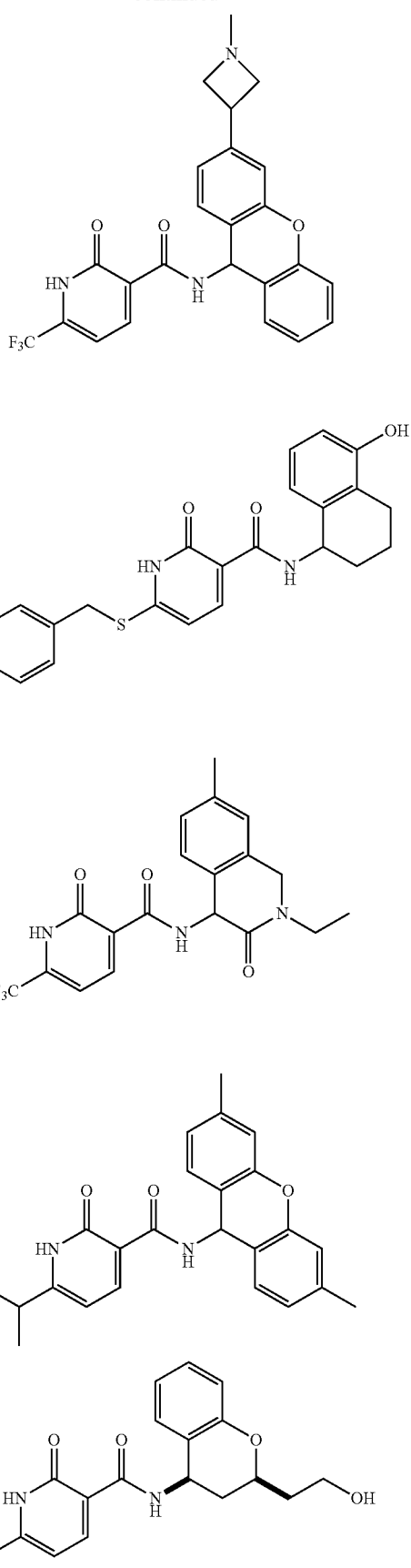

-continued
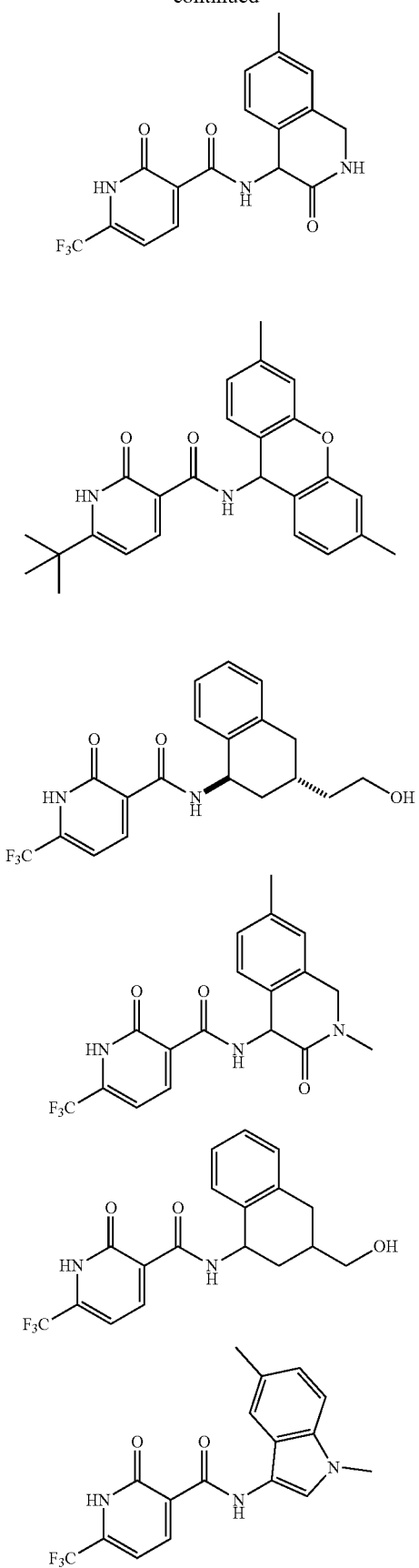
-continued
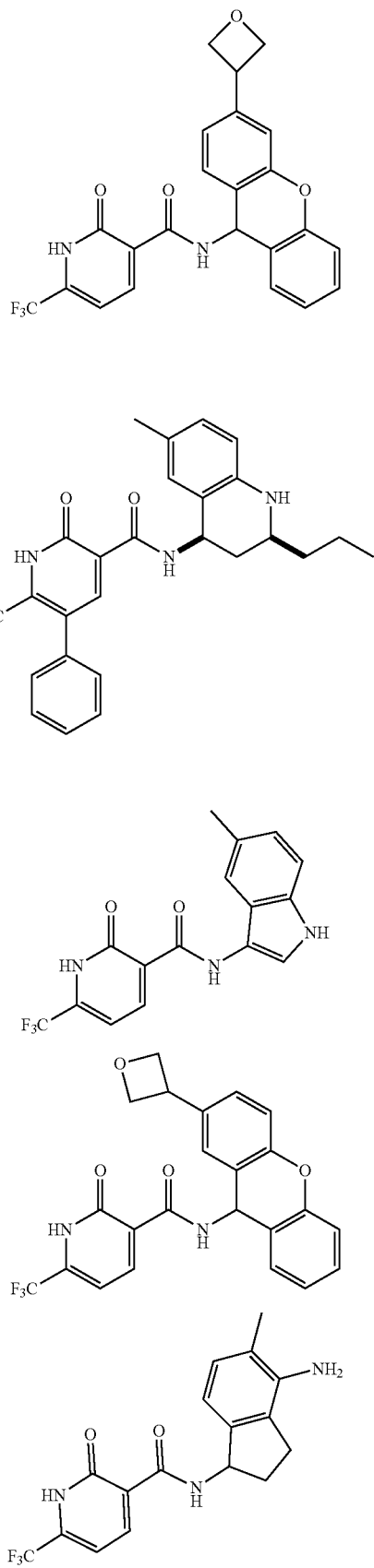

959
-continued
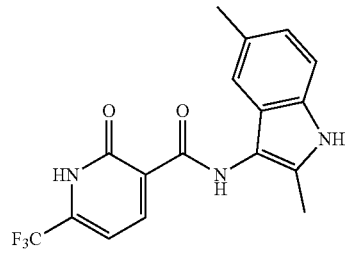
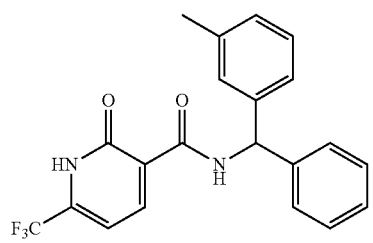
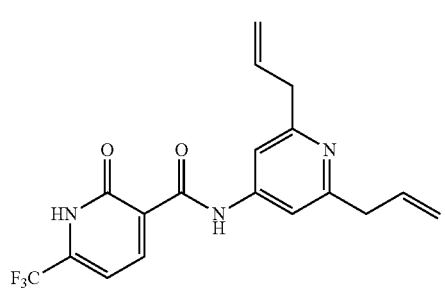
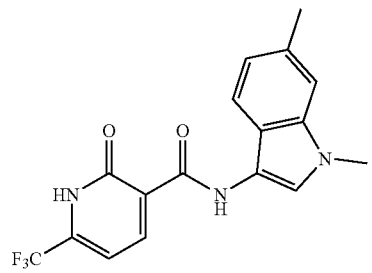
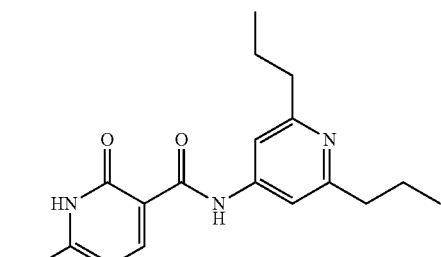
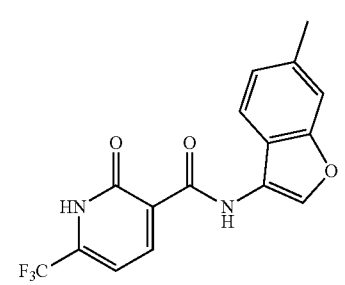
960
-continued
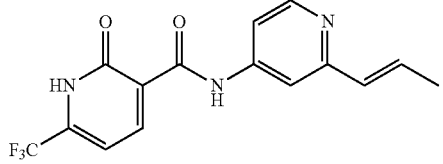
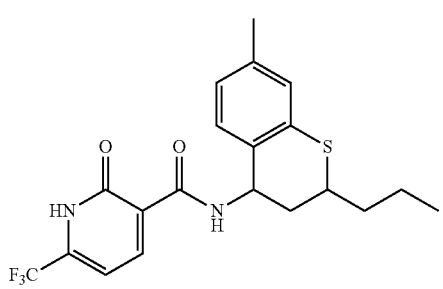
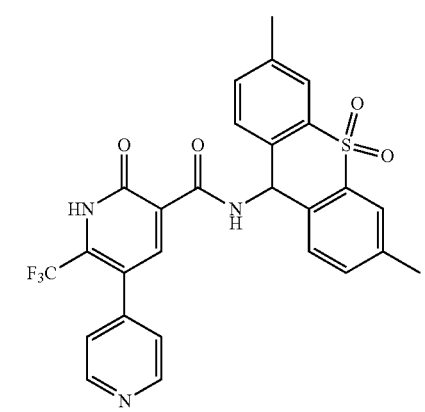
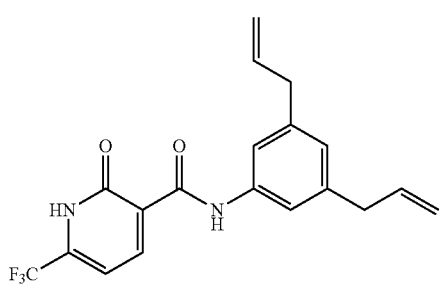
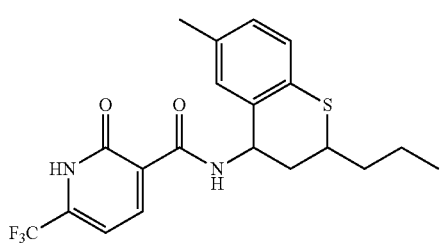

961
-continued
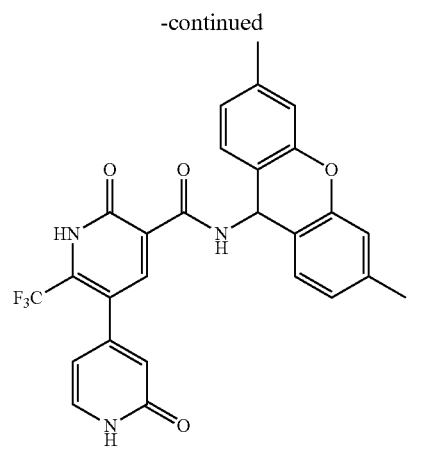
962
-continued
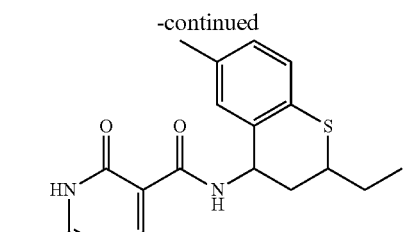
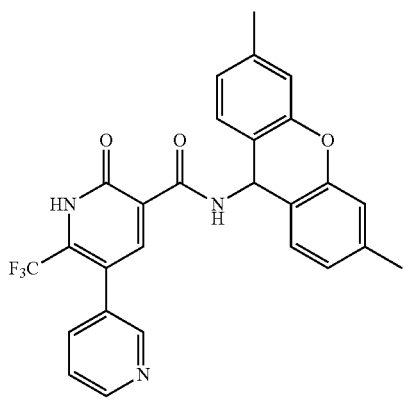
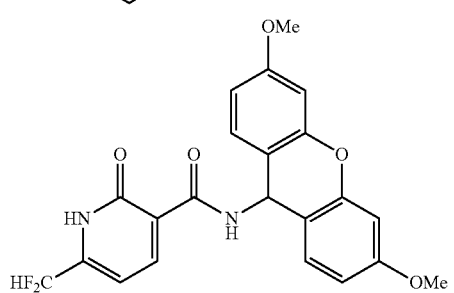
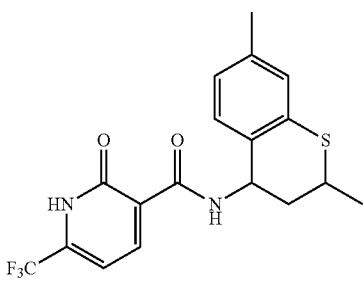
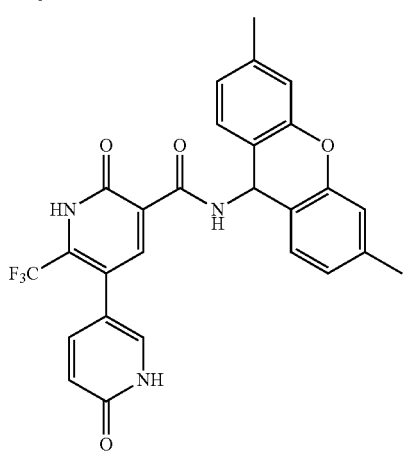

963
-continued
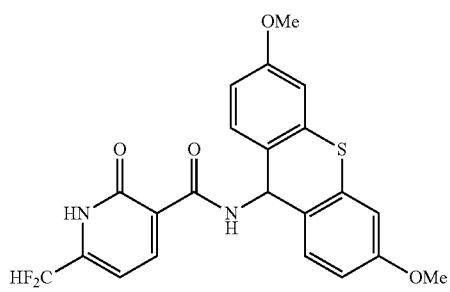
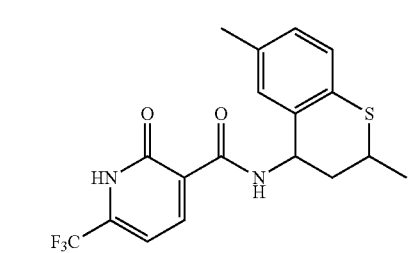
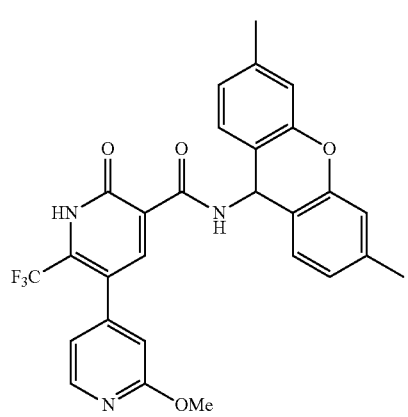
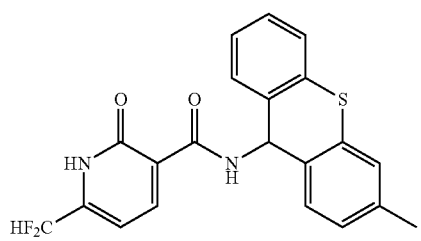
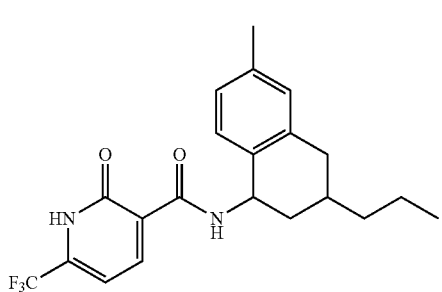
964
-continued
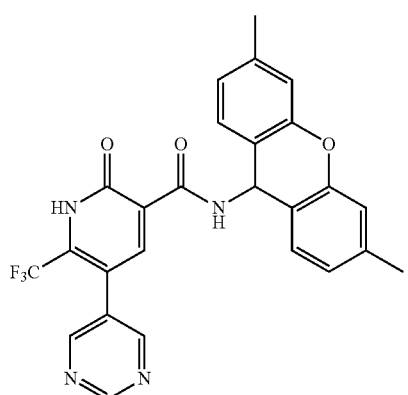
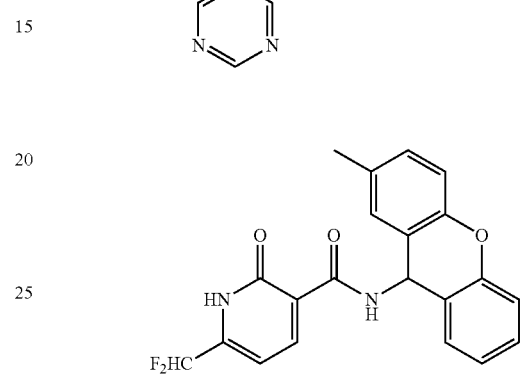
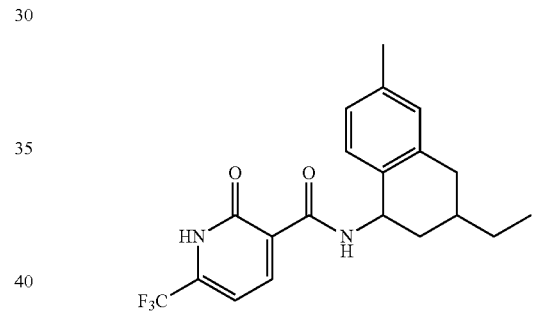
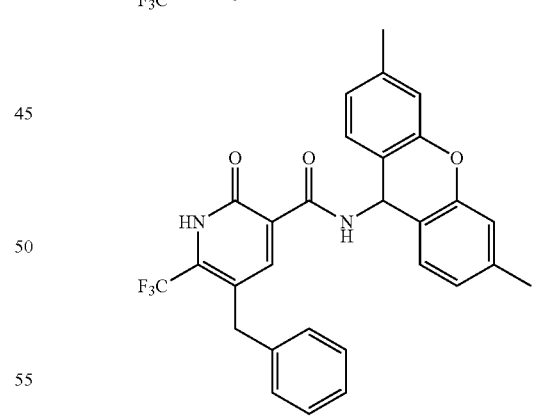
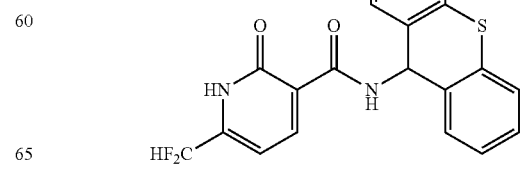

965
-continued
966
-continued
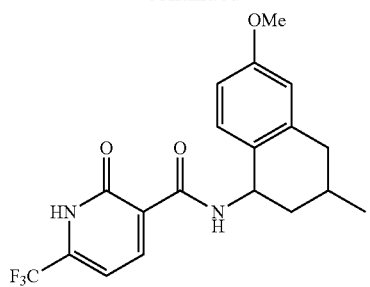
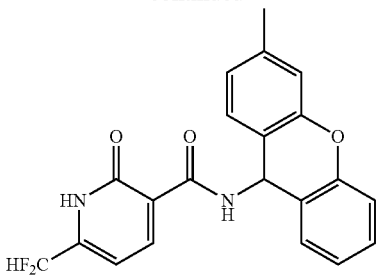

967
-continued
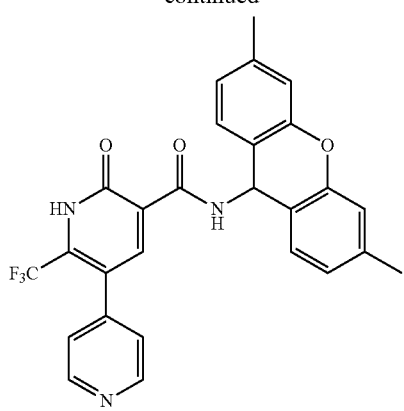
968
-continued
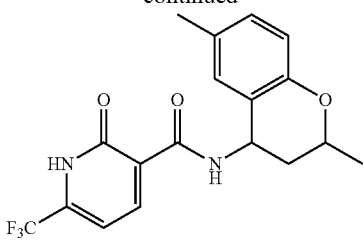
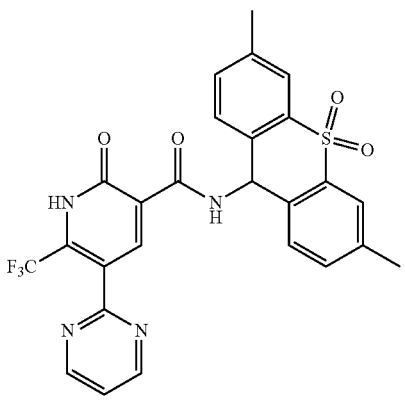
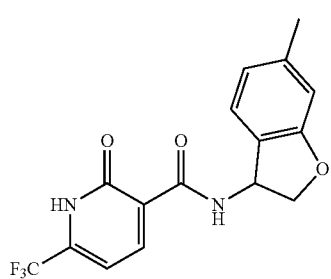
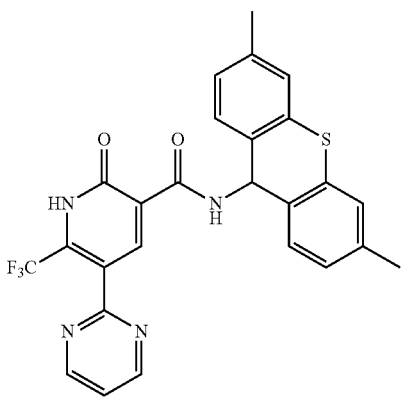
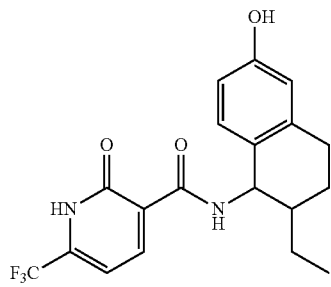

969
-continued
970
-continued
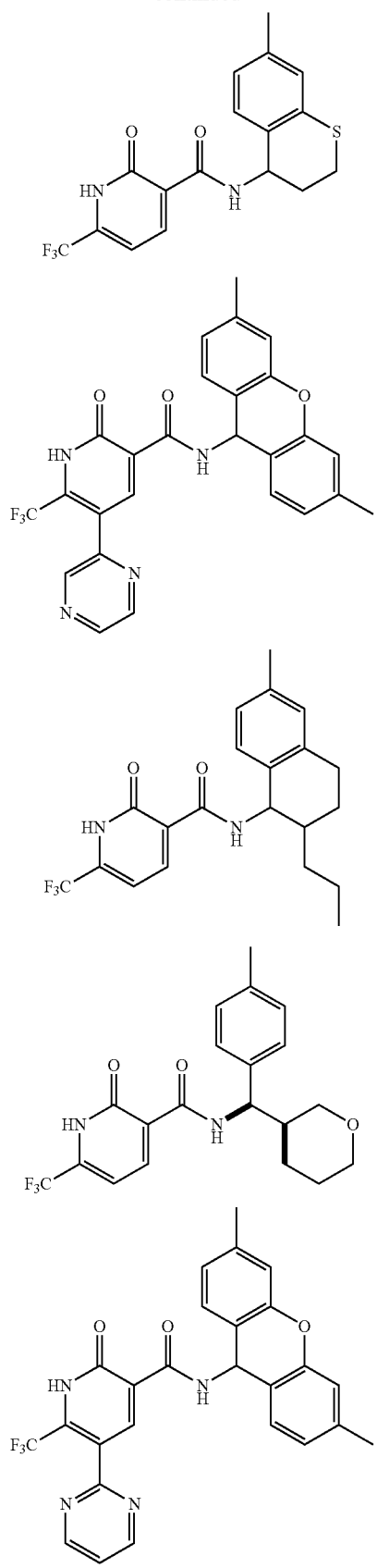
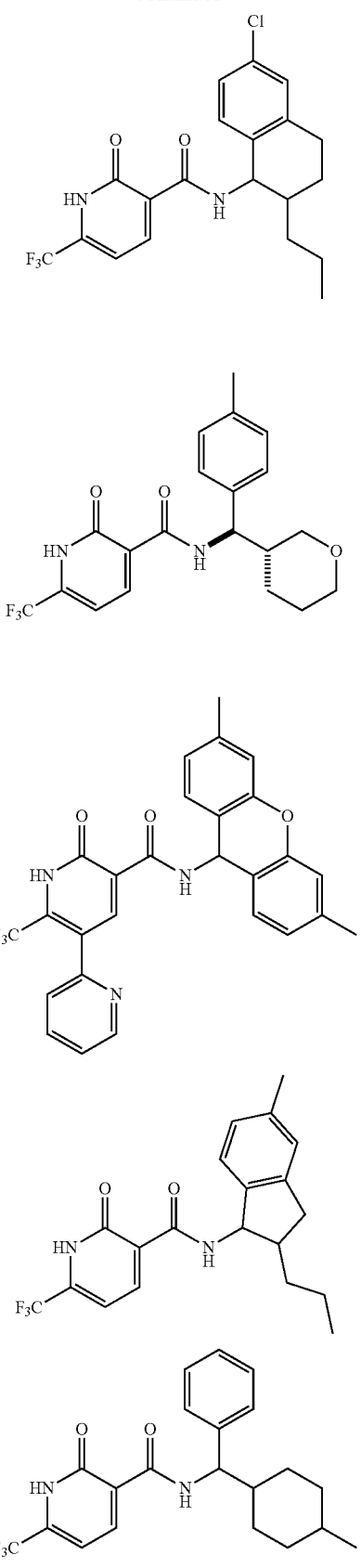

971 -continued
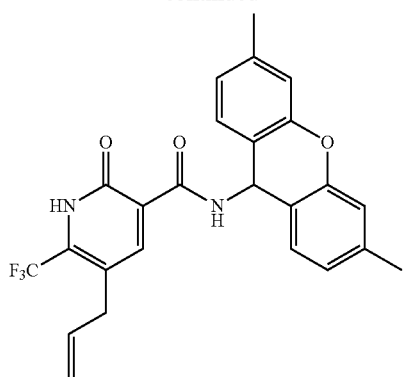
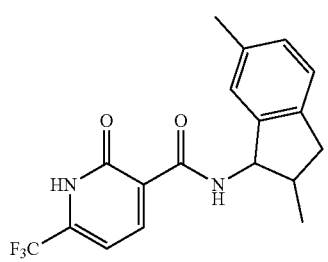
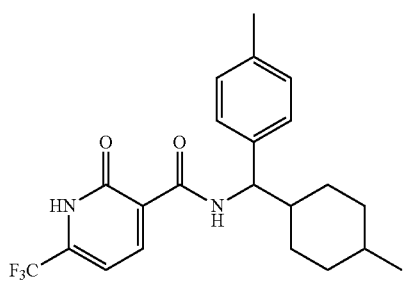
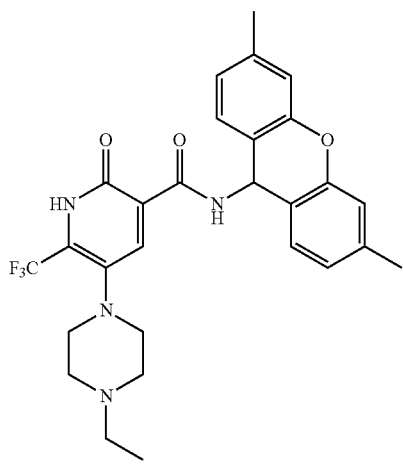
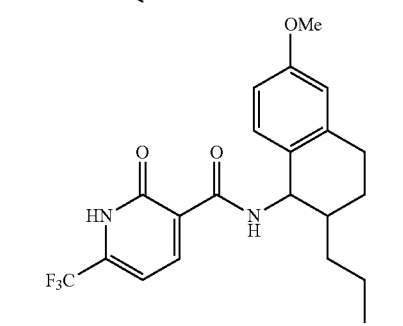
972 -continued
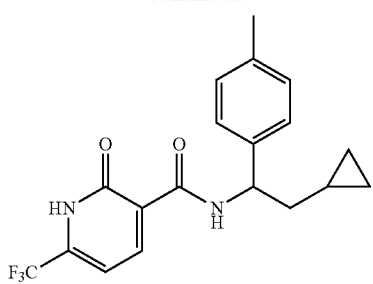
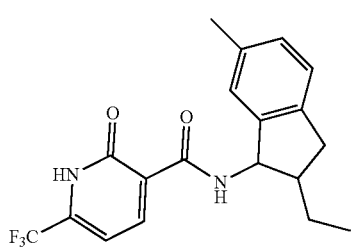
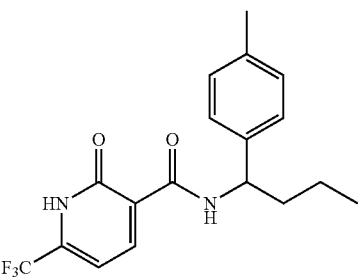

973
-continued
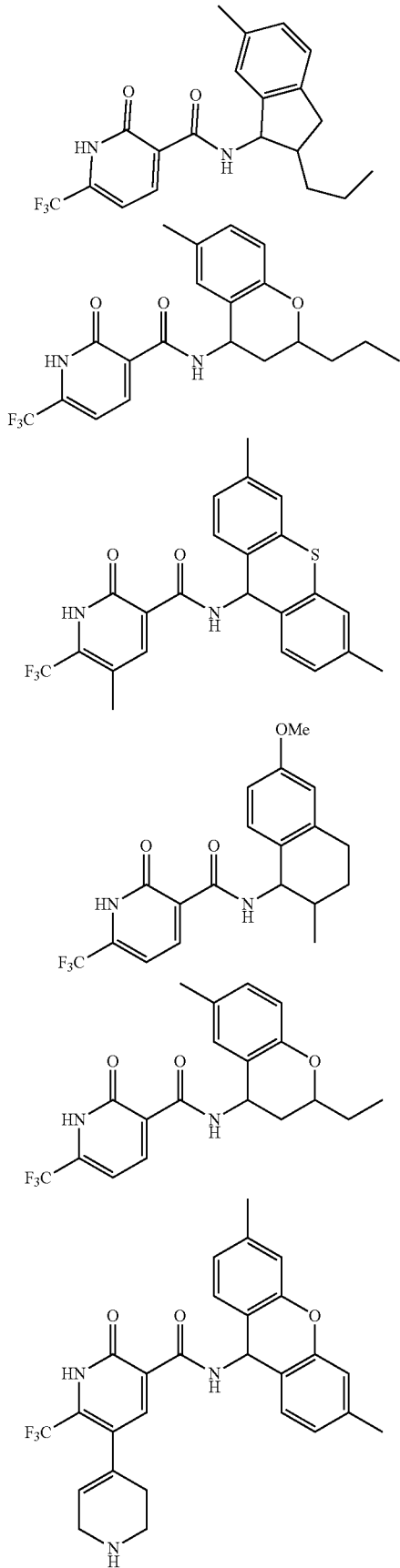
974
-continued
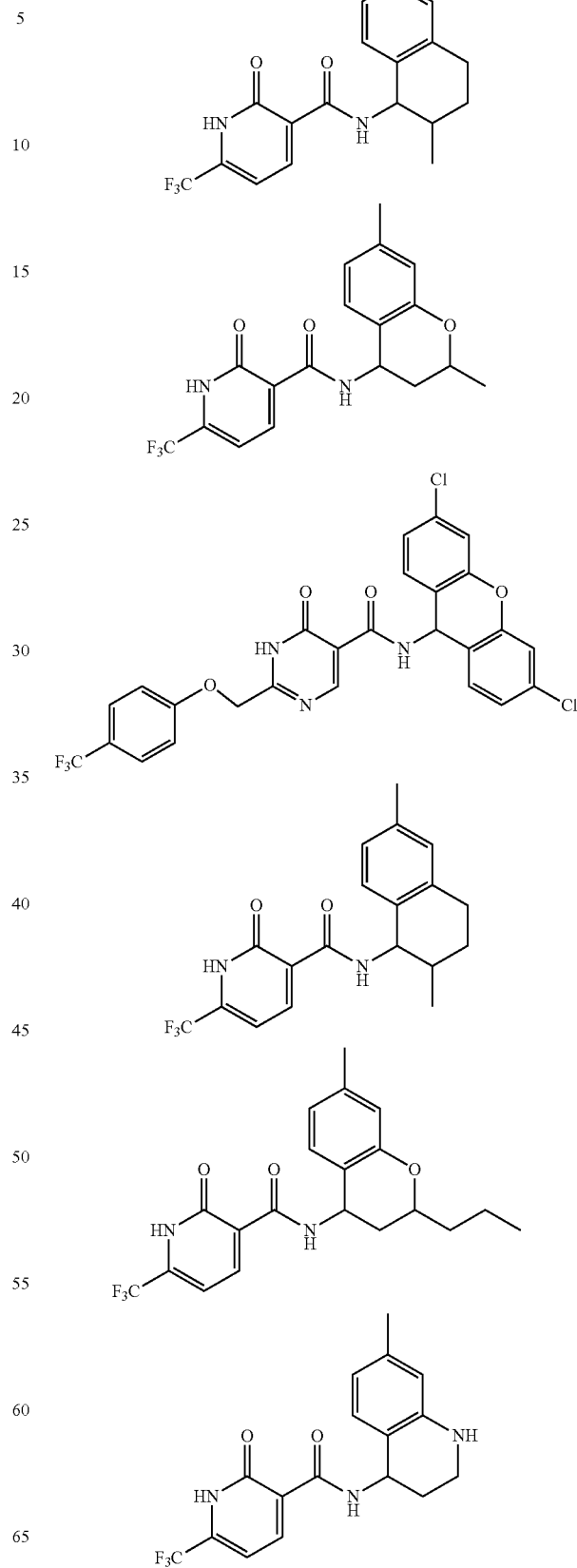

975
-continued
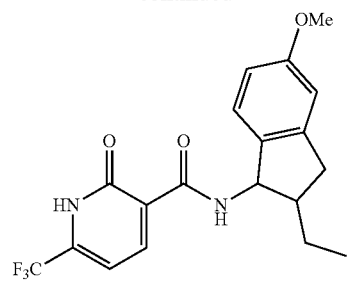
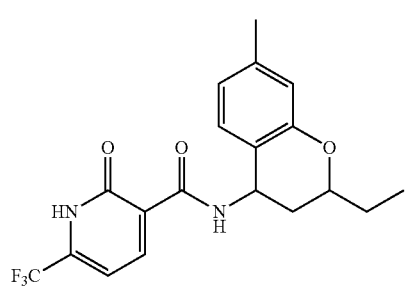
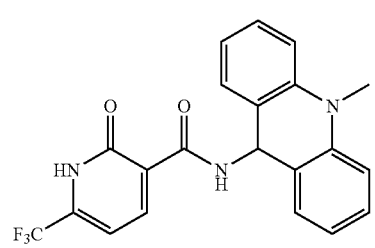
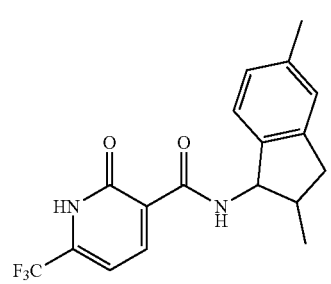
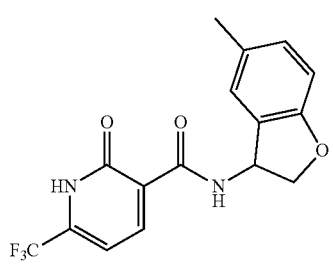
976
-continued
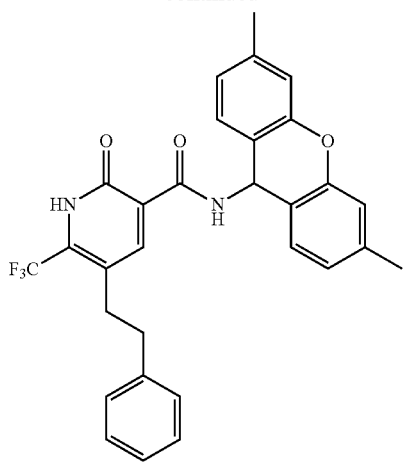
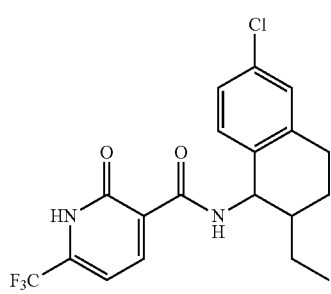
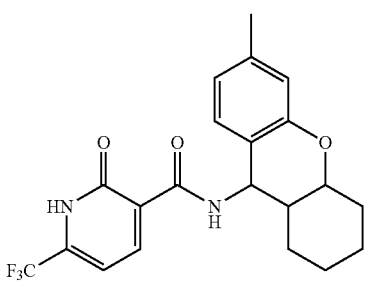
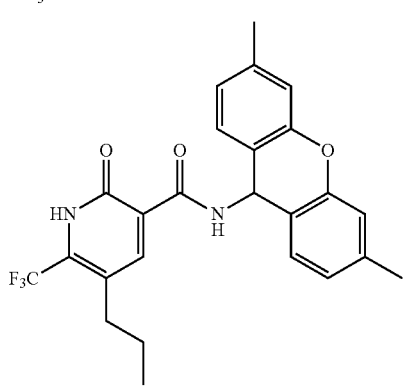
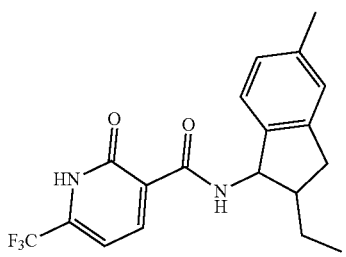

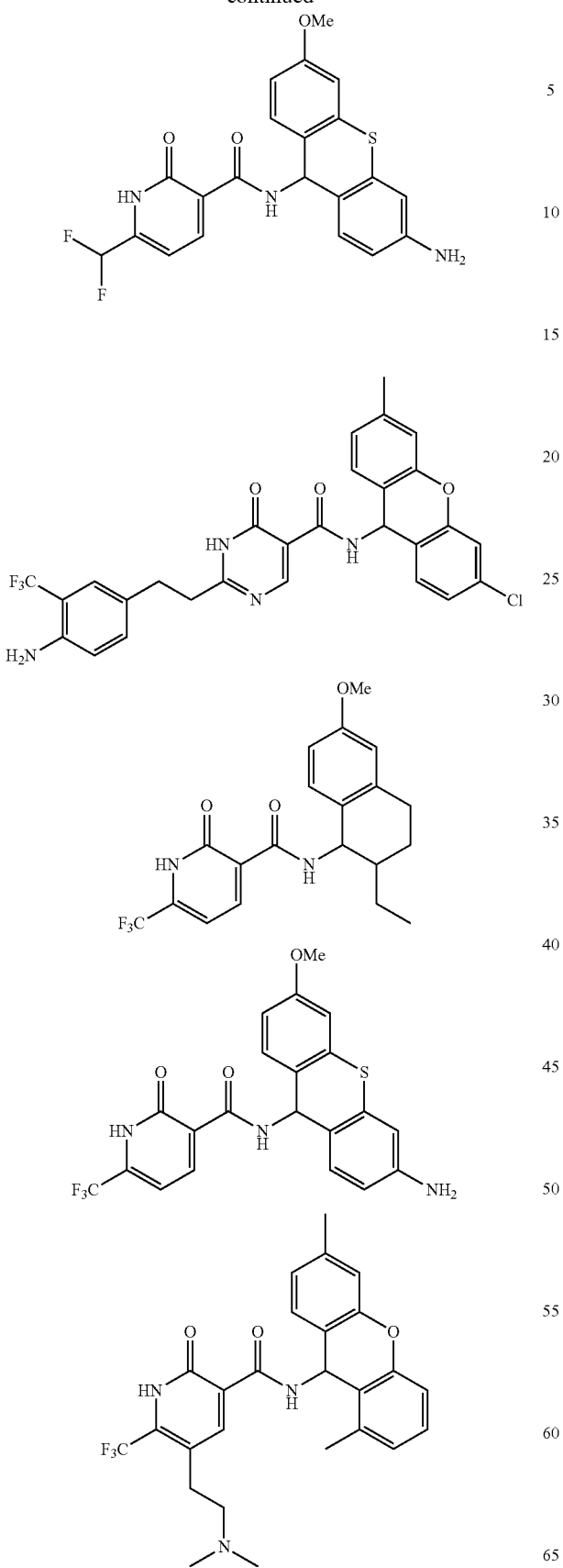
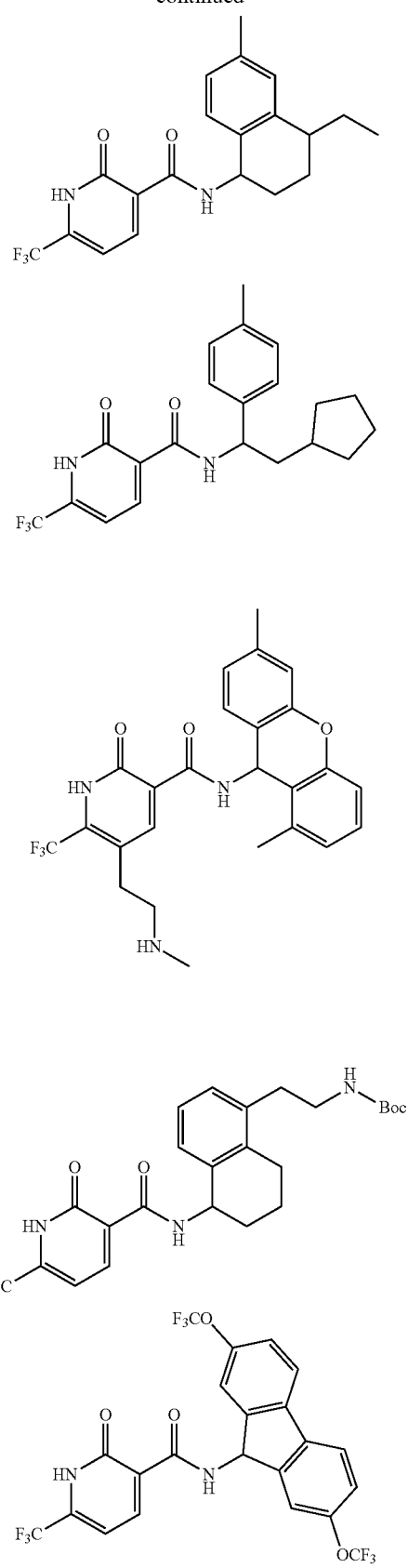

979
-continued

980
-continued

-continued
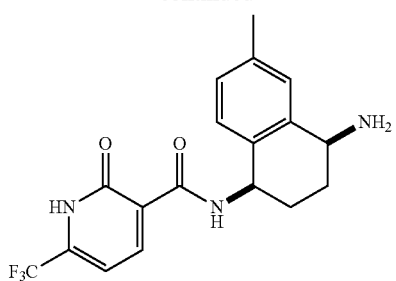
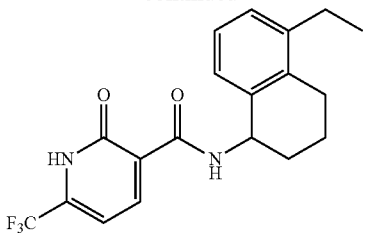
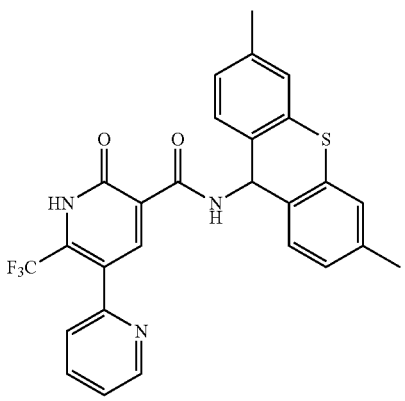
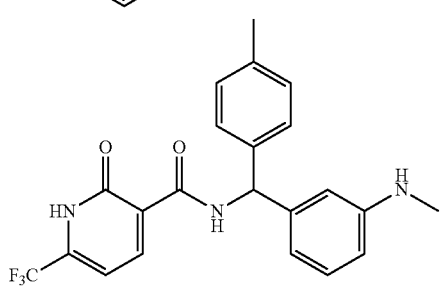
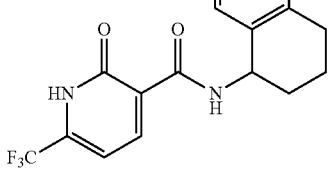
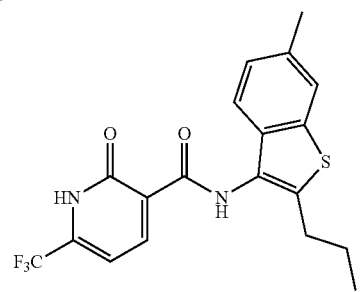
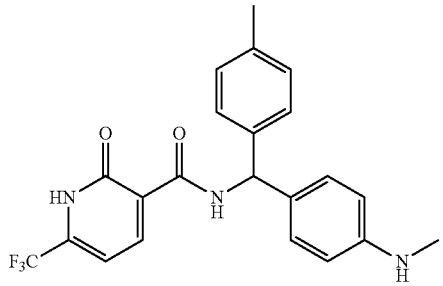

983
-continued
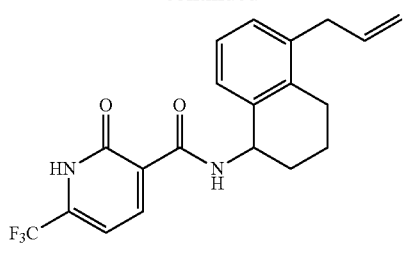
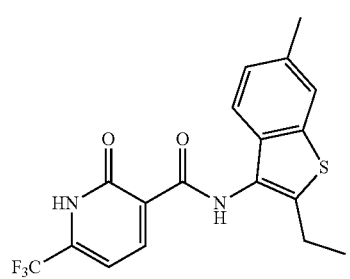
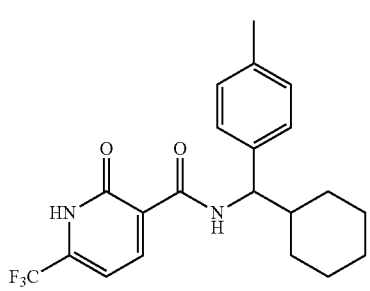
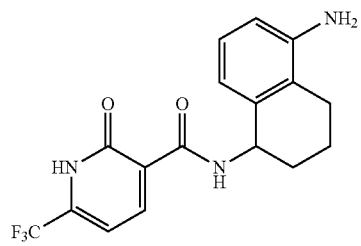
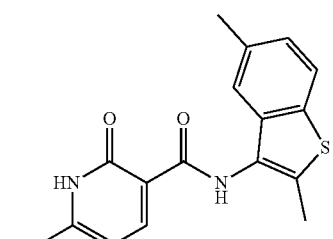
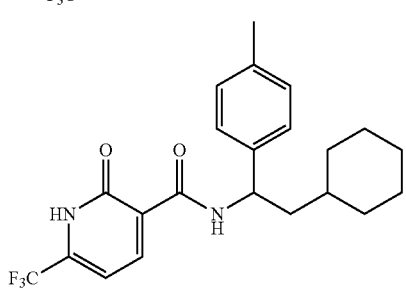
984
-continued
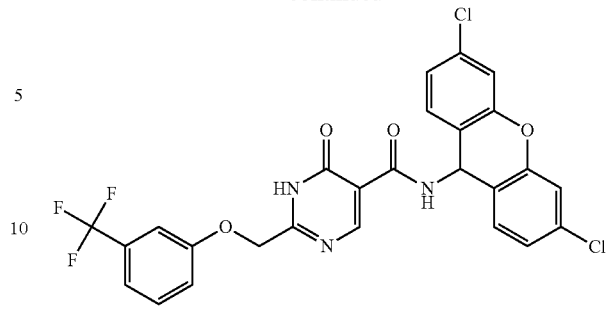
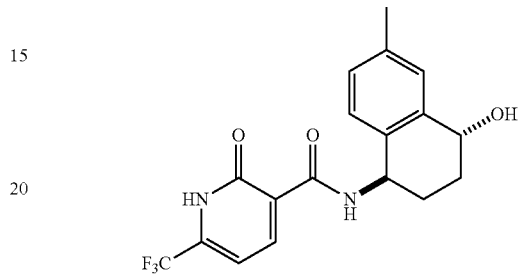
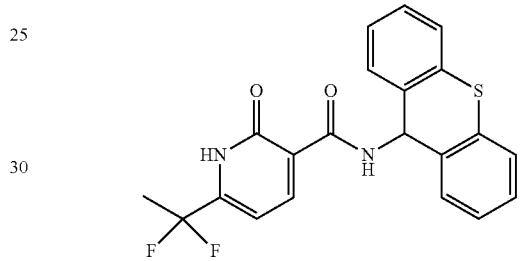
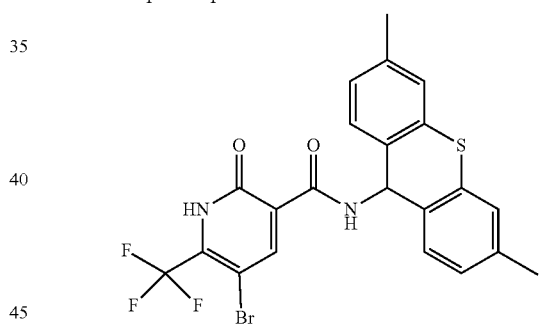
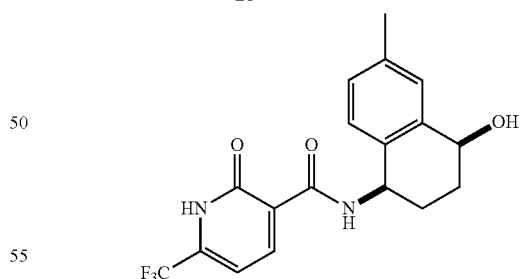
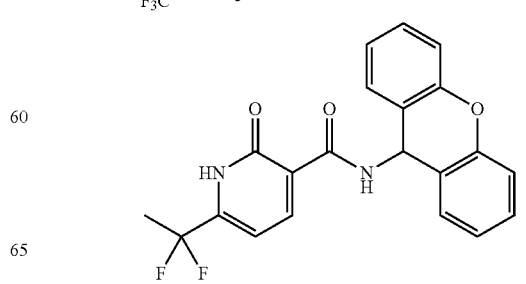

985
-continued
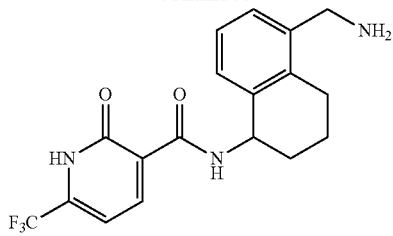
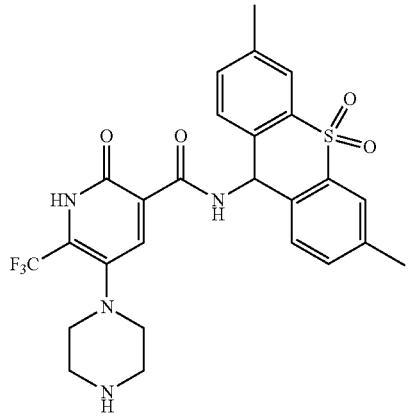
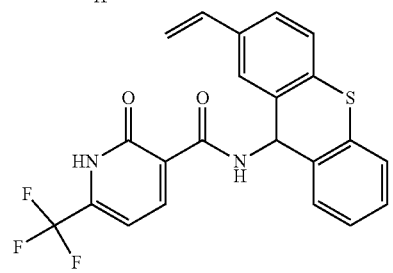
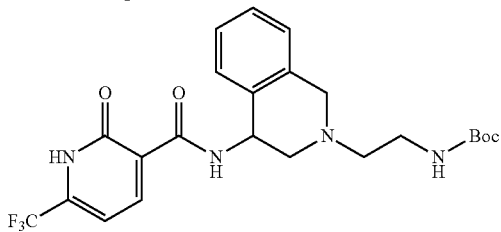
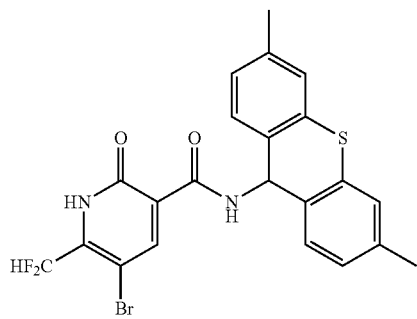
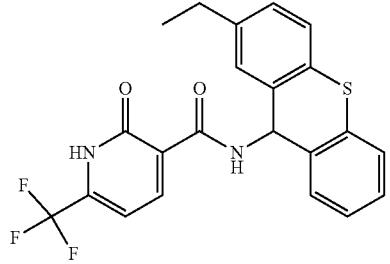
986
-continued
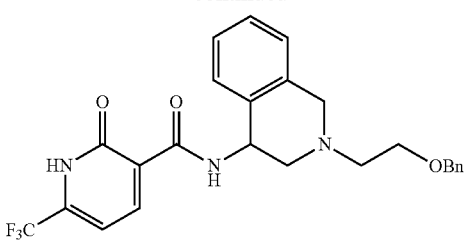
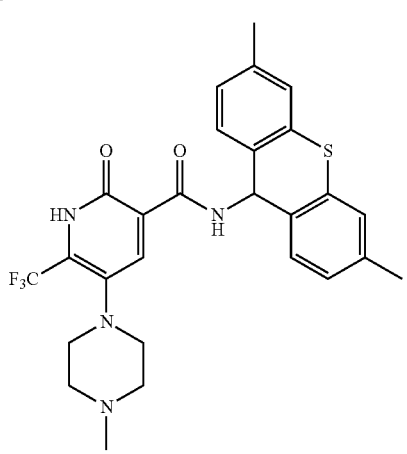
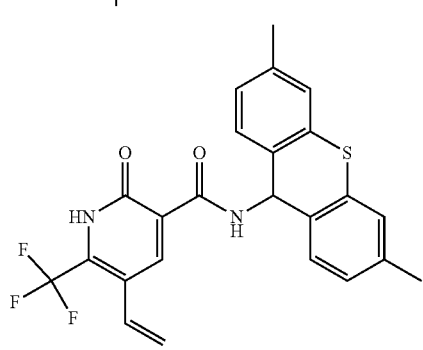
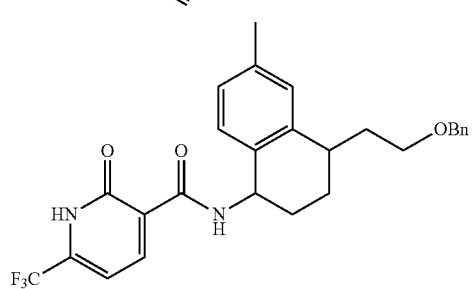
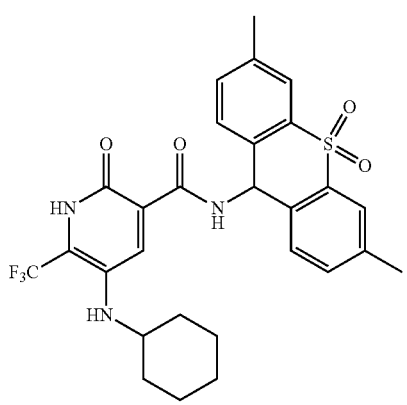

987
-continued
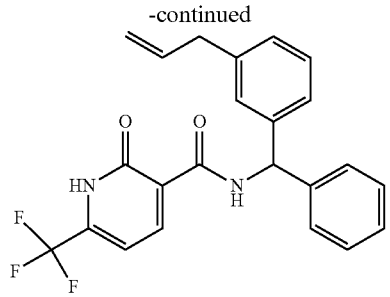
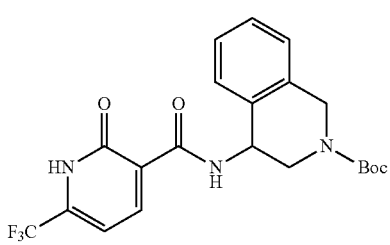
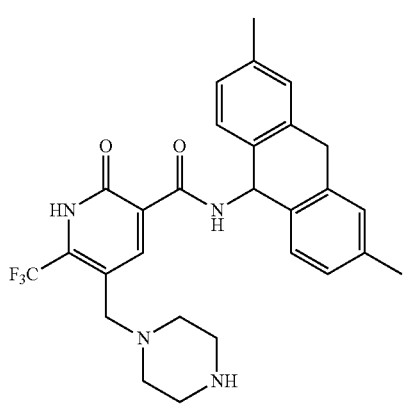
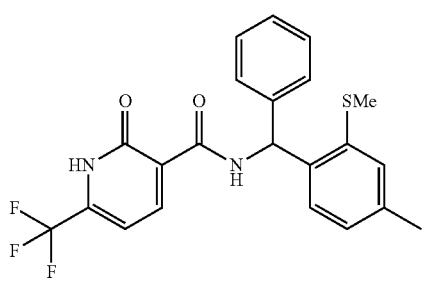
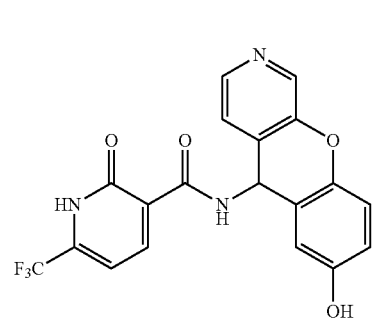
988
-continued
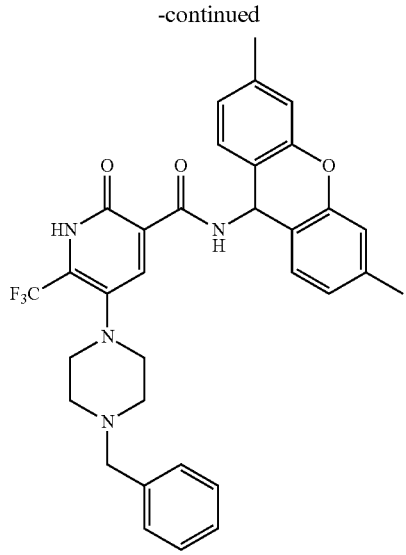
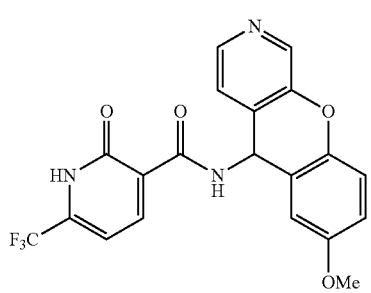
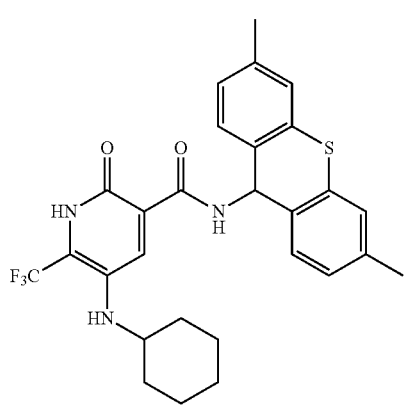
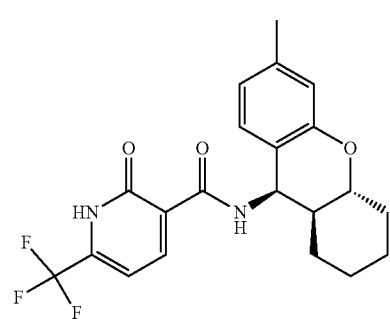

-continued
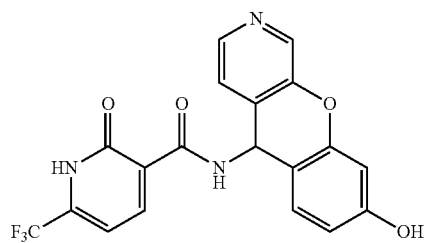
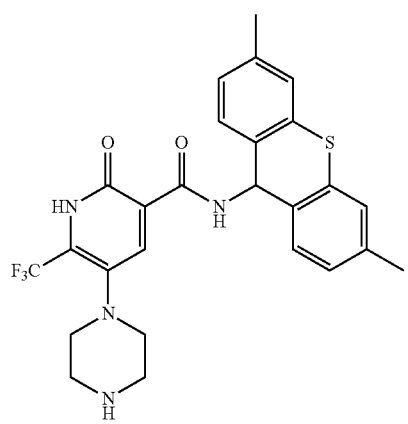
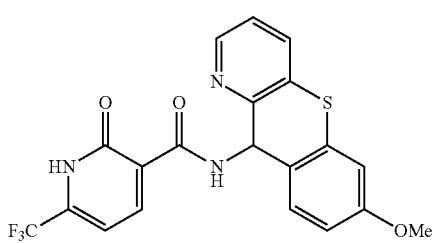
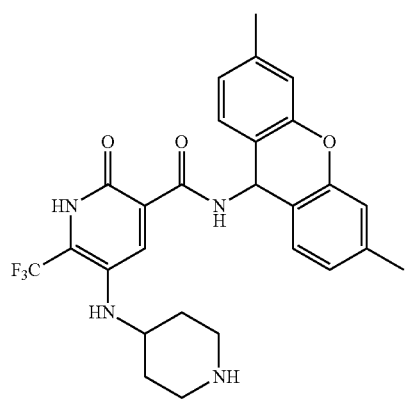
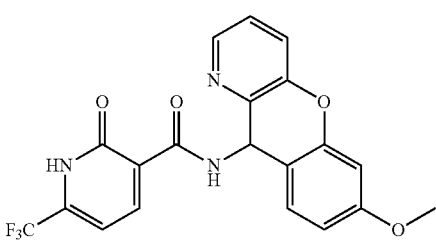
-continued
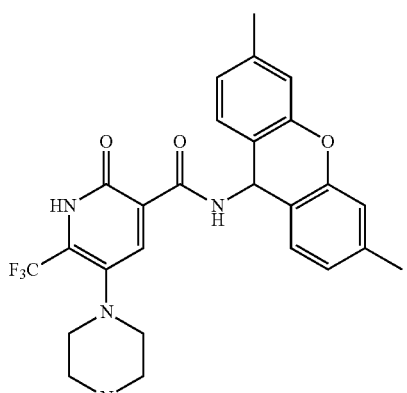
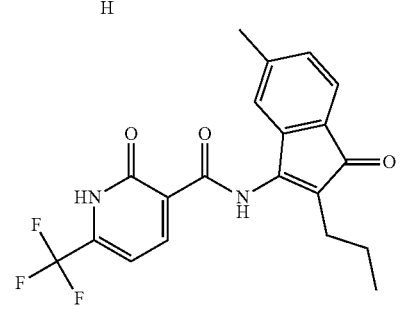
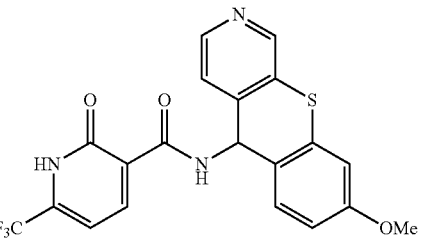
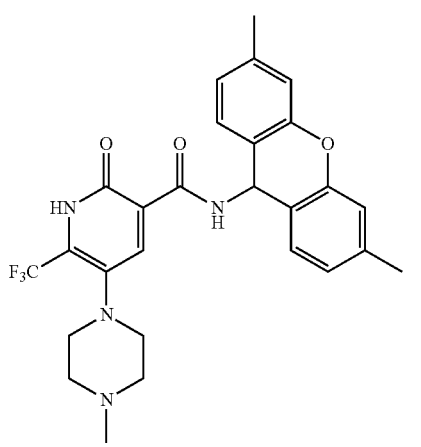
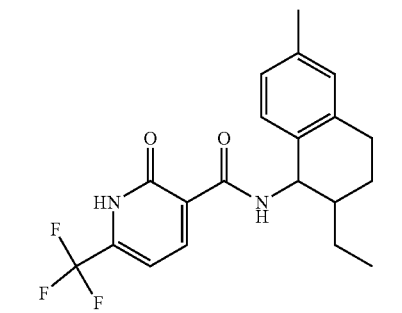

991
-continued
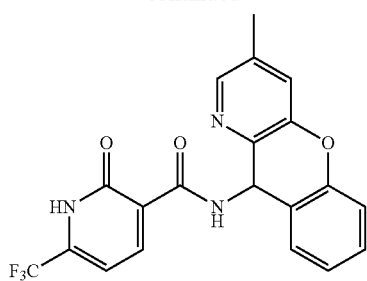
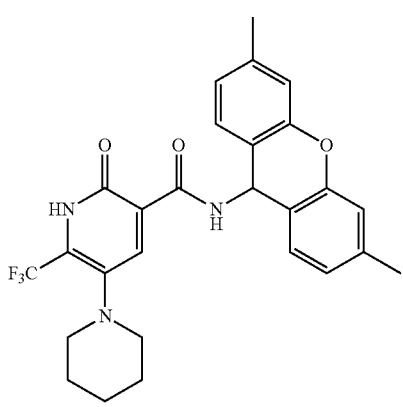
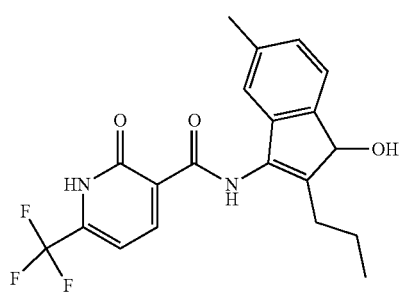
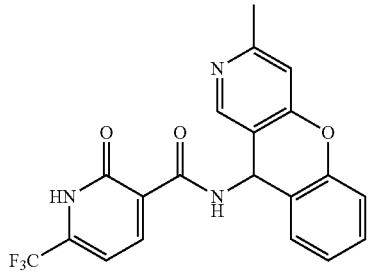
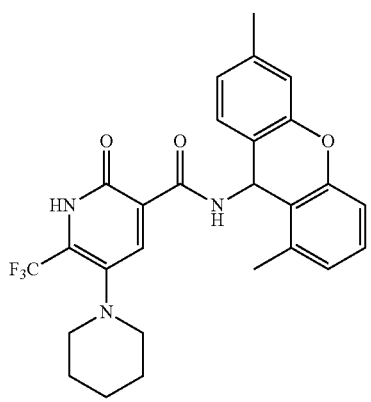
992
-continued
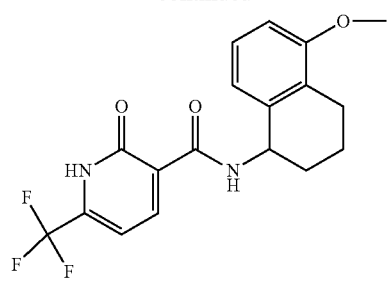
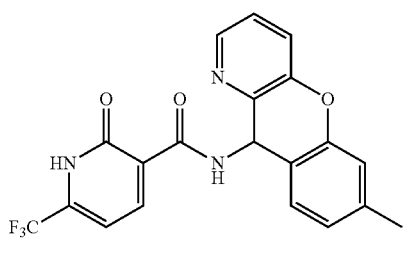
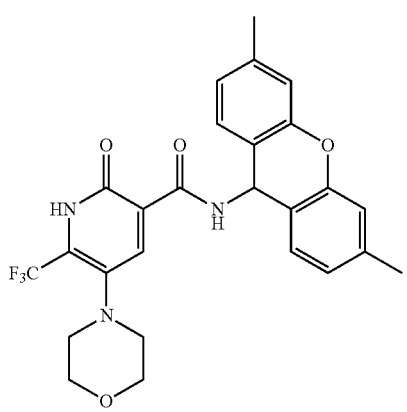
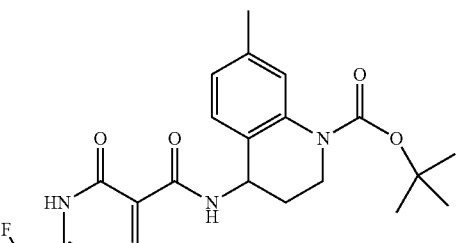
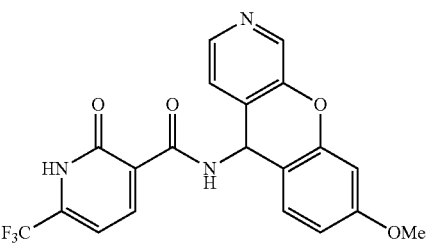

993
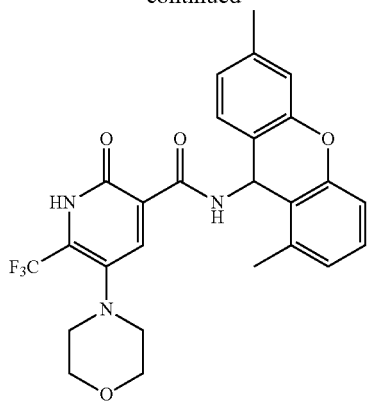
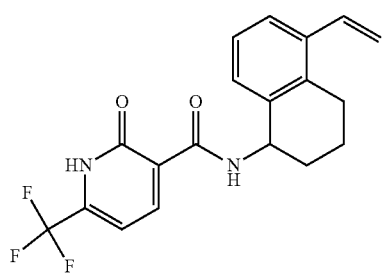
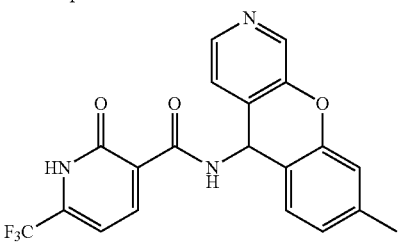
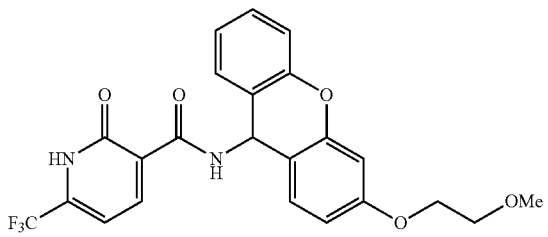
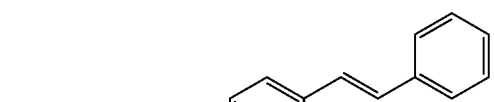
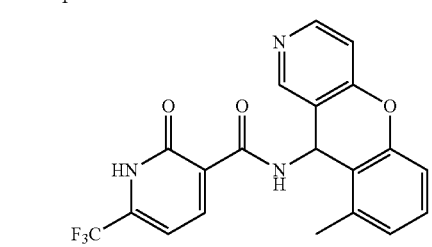
994
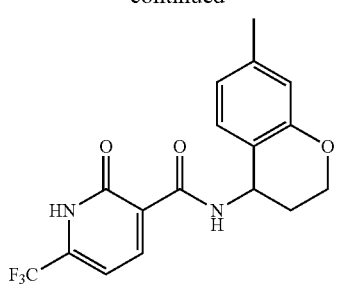
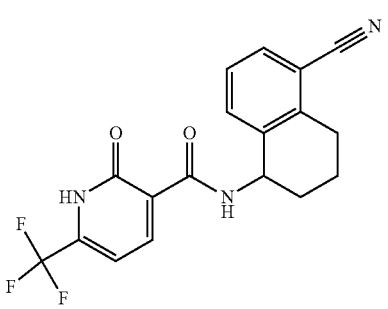
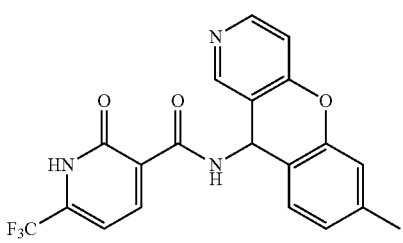
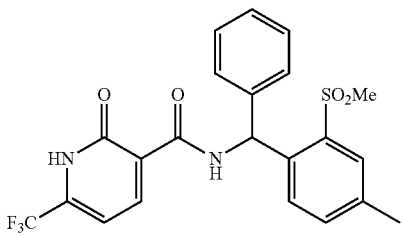
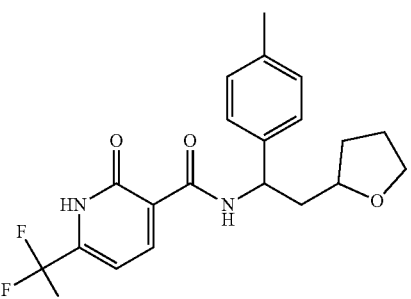
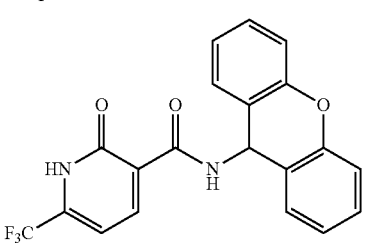

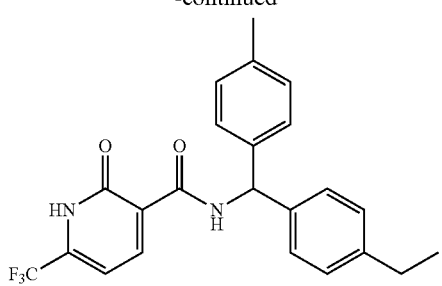
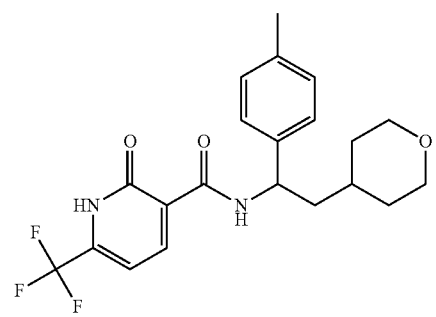
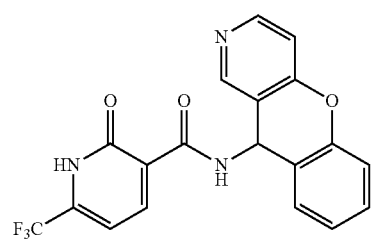
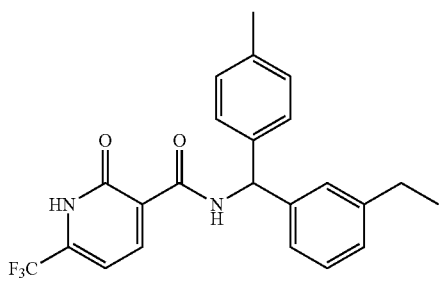
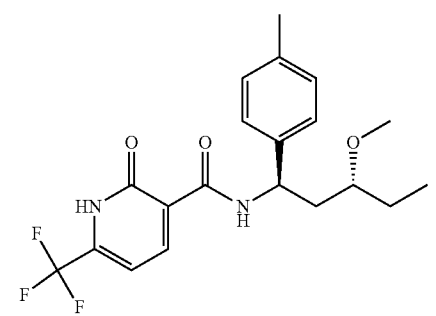
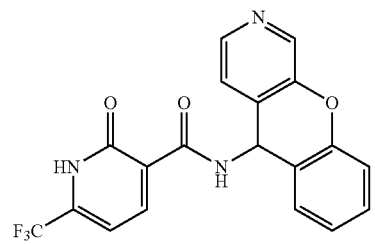
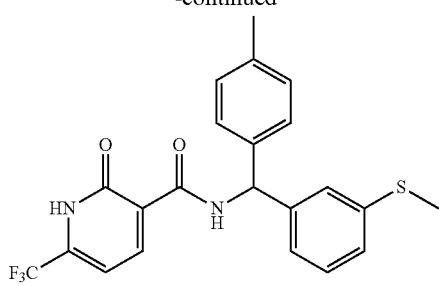
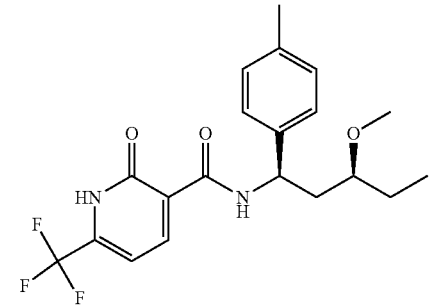
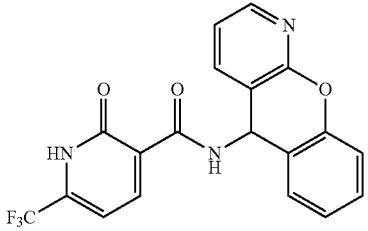
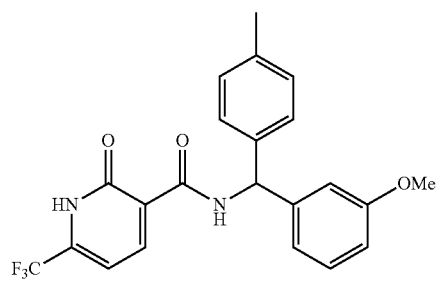
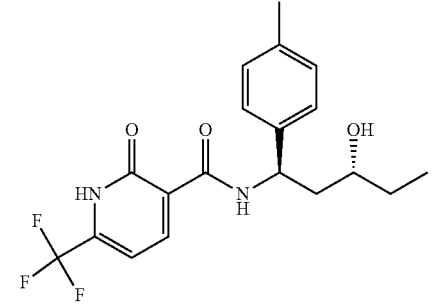
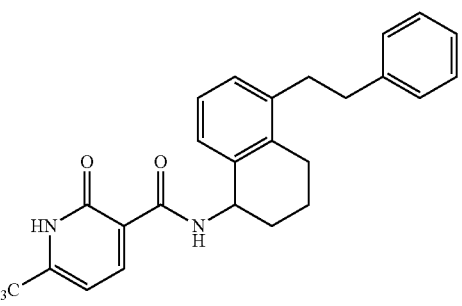

-continued
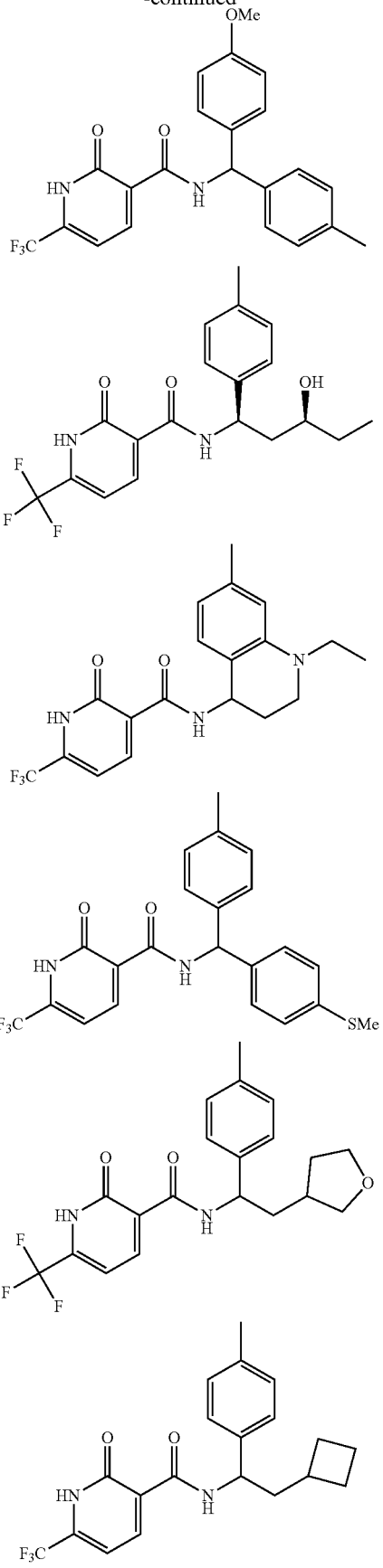
-continued
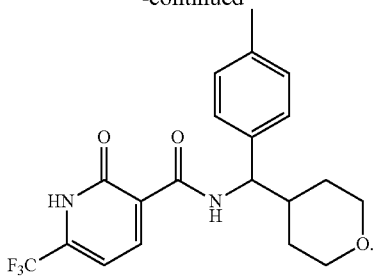
10. A compound, wherein the compound is:
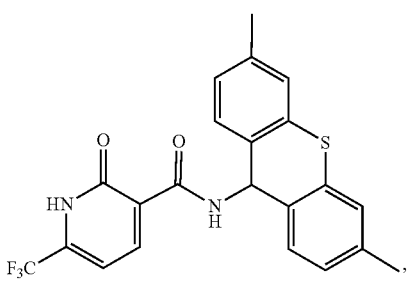
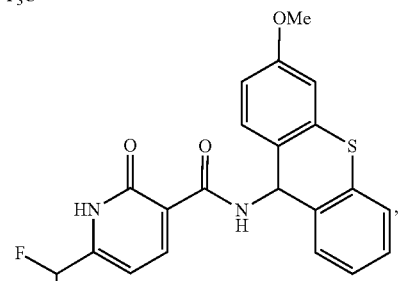
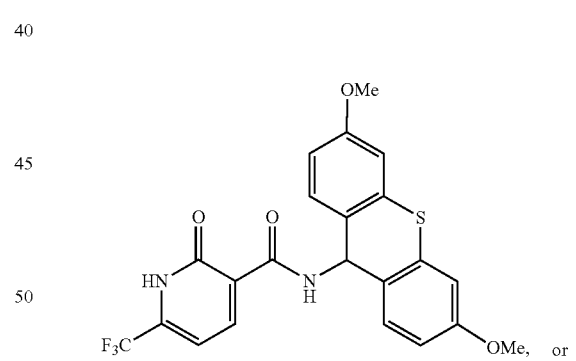
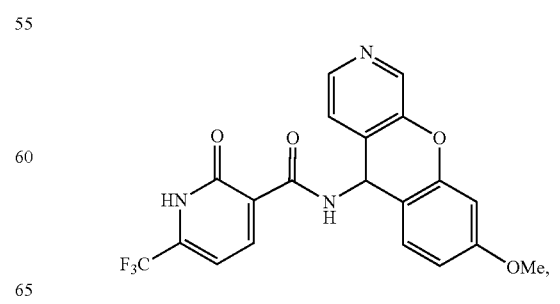
or a pharmaceutically acceptable salt thereof.

11. A compound, wherein the compound is:

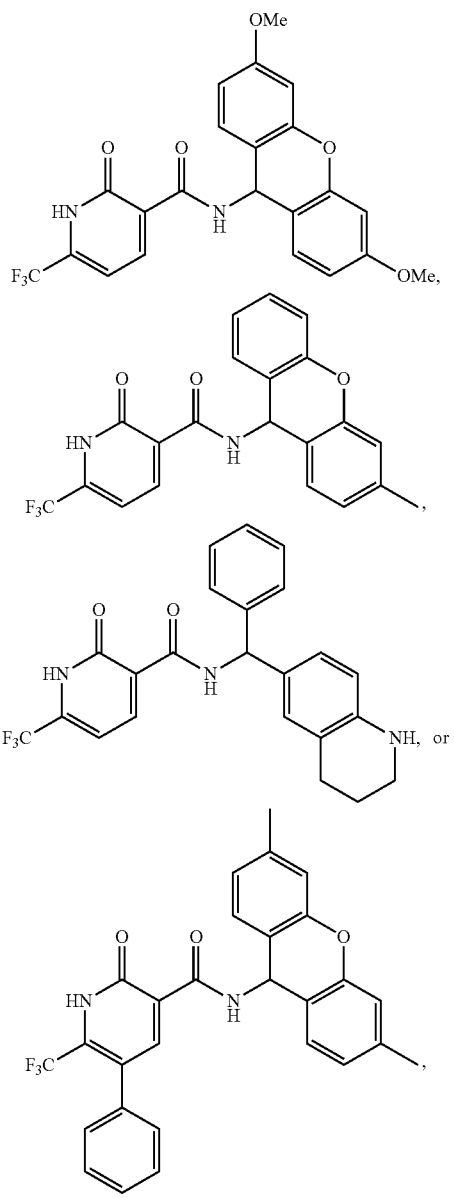

or a pharmaceutically acceptable salt thereof.

12. A compound according to:

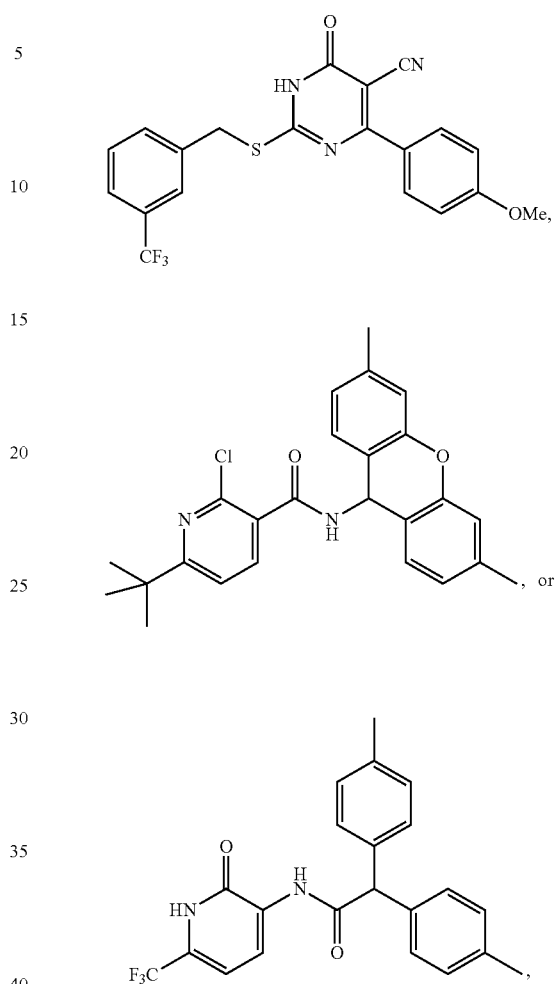

or a pharmaceutically acceptable salt thereof.

13. The pharmaceutical composition comprising the compound of any of any of claims 1, 2, 3, 4, 5, 7, 8, 9, 10-12 and a pharmaceutically acceptable carrier.

14. The pharmaceutical dosage form comprising the compound of any of any of claims 1, 2, 3, 4, 5, 7, 8, 9, 10-12 and a pharmaceutically acceptable carrier.

* * * * *

UNITED STATES PATENT AND TRADEMARK OFFICE
CERTIFICATE OF CORRECTION

PATENT NO. : 11,957,687 B2
APPLICATION NO. : 17/622454
DATED : April 16, 2024
INVENTOR(S) : Joseph Vacca Page 1 of 5

It is certified that error appears in the above-identified patent and that said Letters Patent is hereby corrected as shown below:

In the Claims

At Claim 1, at Column 931, Lines 15-25, please delete the following compound: 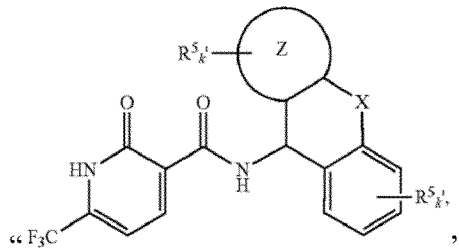 " and insert in its place the following compound: 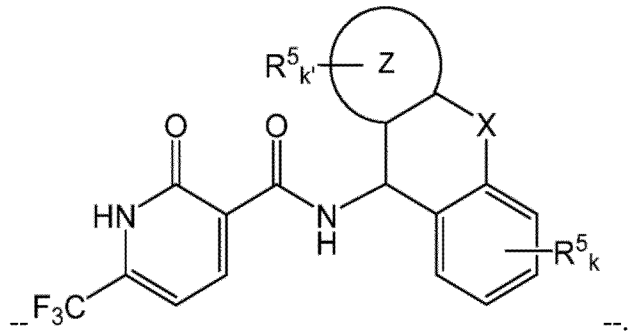 --.

At Claim 2, at Column 931, Line 34, please delete "of" after "compound".

At Claim 2, at Column 932, Lines 19-20, please delete "-NH-(SO$_2$)-R8," and insert -- -NH-(SO$_2$)-R*, --.

At Claim 2, at Column 932, Line 23, please insert -- C$_{1-12}$ alkenyl, -- after "-NH-,".

At Claim 3, at Column 933, Line 34, please delete "groupls" and insert -- groups --.

Signed and Sealed this
Sixteenth Day of July, 2024

*Katherine Kelly Vidal*

Katherine Kelly Vidal
*Director of the United States Patent and Trademark Office*

CERTIFICATE OF CORRECTION (continued)

At Claim 3, at Column 933, Line 39, please delete "fro" and insert -- from --.

At Claim 3, at Column 933, Line 50, please delete "-NHR#," and insert -- - NHR#, --.

At Claim 3, at Column 933, Line 50, please delete "-N(R#)$_2$," and insert -- -N(R#)$_2$, --.

At Claim 3, at Column 933, Line 54, please delete "$C_{1-4}$ halalkoxy" and insert -- $C_{1-4}$ haloalkoxy --.

At Claim 3, at Column 933, Line 56, please delete "combination" and insert -- combinations --.

At Claim 4, at Column 934, Line 21, please delete "and Ar are as defined above.".

At Claim 4, at Column 934, Line 34, please delete "or Het;" and insert -- or Het; --.

At Claim 5, at Column 935, Lines 4-13, please delete the following compound:

" 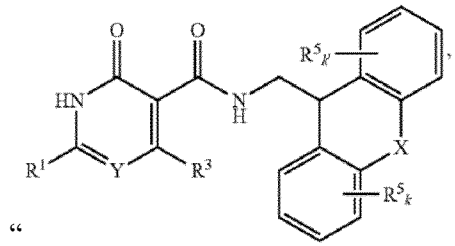 " and insert in its place the following compound:

-- 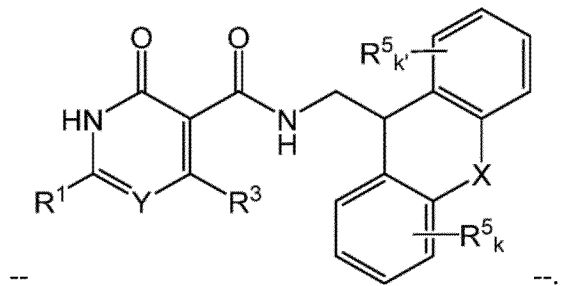 --.

At Claim 5, at Column 935, Line 15, please delete "k, k'" and insert -- k and k' --.

At Claim 5, at Column 935, Line 16, please delete "-CH$_2$" and insert -- -CH$_2$- --.

At Claim 5, at Column 935, Line 35, please delete "," after "R$^1$".

At Claim 5, at Column 935, Line 55, please insert -- $C_{1-3}$ haloalkyl, -- after "$C_{1-3}$ alkyl,".

At Claim 6, at Column 936, Line 32, please insert -- or -- after "R$^8$".

At Claim 6, at Column 936, Line 55, please delete "bonde" and insert -- bond --.

At Claim 6, at Column 936, Line 56, please delete "-CH$_2$" and insert -- -CH$_2$- --.

At Claim 6, at Column 936, Line 58, please delete "-O-13 CH$_2$-" and insert -- -O-CH$_2$- --.

At Claim 6, at Column 936, Line 63, please delete "A'" and insert -- A" --.

At Claim 6, at Column 937, Line 7, please add -- -NH-(SO$_2$)-R*, -- after "-NH-(C=O)-R*,".

At Claim 6, at Column 937, Line 20, please delete "wiht'" and insert -- with --.

At Claim 6, at Column 937, Line 24, please delete "-NH-13 (C=O)O-R*" and insert -- -NH-(C=O)O-R* --.

At Claim 6, at Column 937, Line 42, please delete "-OCH" and insert -- -OCH$_3$ --.

At Claim 7, at Column 938, Line 3, please delete "-OCH" and insert -- -OCH$_3$ --.

At Claim 9, at Column 956, Lines 58-67, please delete the following compound:

"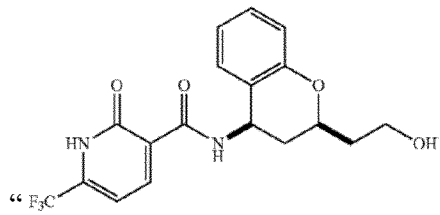 " and insert in its place the following compound:

--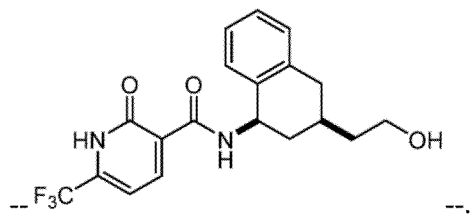--.

At Claim 9, at Column 965, Lines 41-52, please delete the following compound:

"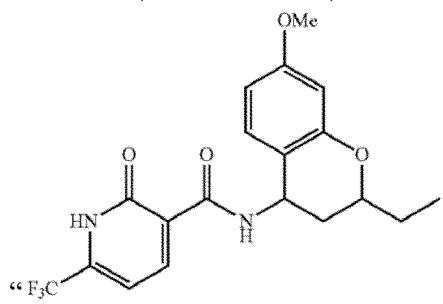 " and insert in its place the following compound:

--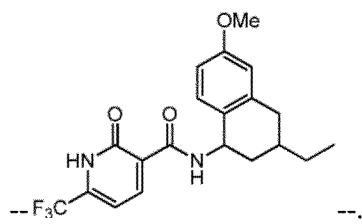--.

CERTIFICATE OF CORRECTION (continued)

At Claim 9, at Column 977, Lines 15-30, please delete the following compound:

" 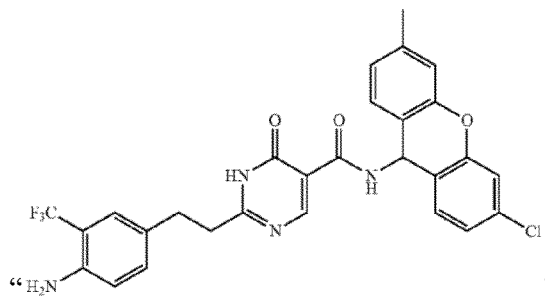 " and insert in its place the following compound:

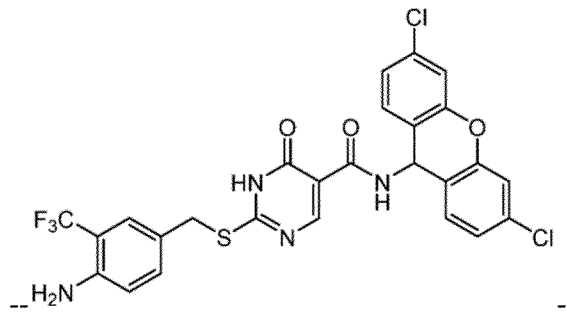 --.

At Claim 9, at Column 980, Lines 42-53, please delete the following compound:

" 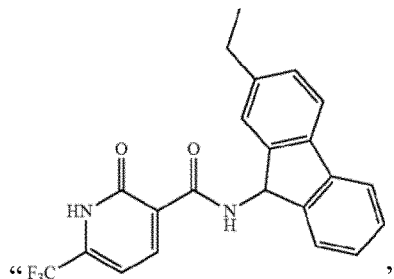 " and insert in its place the following compound:

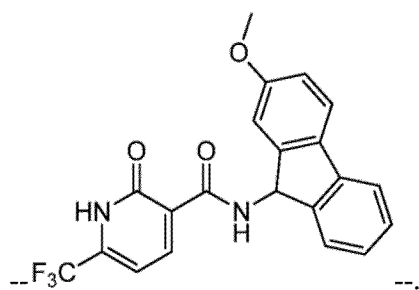 --.

At Claim 9, at Column 987, Lines 26-42, please delete the following compound:

" 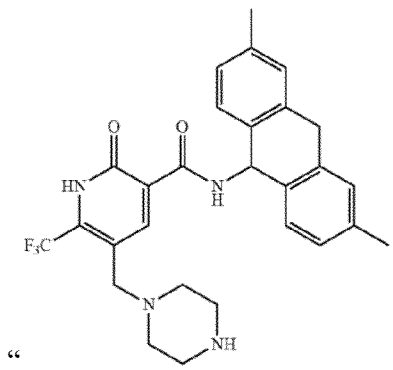 " and insert in its place the following compound:

-- 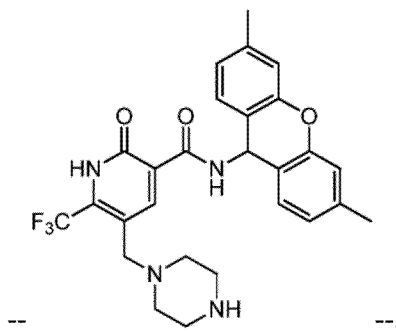 --.

At Claim 9, at Column 994, Lines 57-66 please delete the following compound:

" 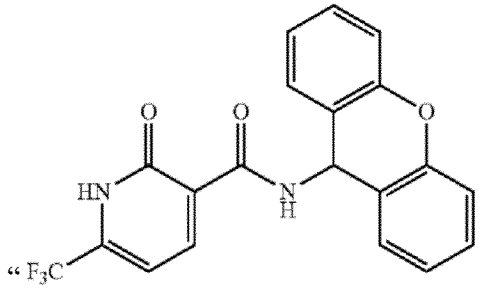 " and insert in its place the following compound:

-- 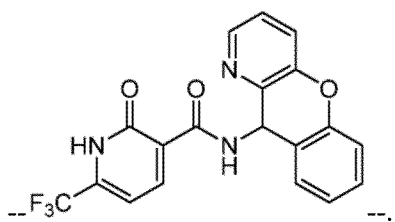 --.

At Claim 13, at Column 1000, Line 45, please delete "of any" after "compound".

At Claim 13, at Column 1000, Line 45, please insert -- 6, -- after "5,".

At Claim 14, at Column 1000, Line 48, please delete "of any" after "compound".

At Claim 14, at Column 1000, Line 48, please insert -- 6, -- after "5,".